US010695419B2

(12) United States Patent
Ciaramella et al.

(10) Patent No.: US 10,695,419 B2
(45) Date of Patent: Jun. 30, 2020

(54) HUMAN CYTOMEGALOVIRUS VACCINE

(71) Applicant: ModernaTX, Inc., Cambridge, MA (US)

(72) Inventors: Giuseppe Ciaramella, Sudbury, MA (US); Shinu John, Somerville, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

(21) Appl. No.: 16/389,545

(22) Filed: Apr. 19, 2019

(65) Prior Publication Data

US 2019/0314493 A1 Oct. 17, 2019

Related U.S. Application Data

(63) Continuation of application No. PCT/US2017/057748, filed on Oct. 20, 2017.

(60) Provisional application No. 62/548,184, filed on Aug. 21, 2017, provisional application No. 62/490,510, filed on Apr. 26, 2017, provisional application No. 62/490,541, filed on Apr. 26, 2017, provisional application No. 62/411,381, filed on Oct. 21, 2016.

(51) Int. Cl.

| | |
|---|---|
| ***A61K 39/245*** | (2006.01) |
| ***A61P 31/22*** | (2006.01) |
| *A61K 39/00* | (2006.01) |

(52) U.S. Cl.

CPC ............ *A61K 39/245* (2013.01); *A61P 31/22* (2018.01); *A61K 2039/53* (2013.01); *A61K 2039/6018* (2013.01); *C12N 2710/16134* (2013.01); *C12N 2710/16171* (2013.01)

(58) Field of Classification Search

None

See application file for complete search history.

(56) References Cited

U.S. PATENT DOCUMENTS

| | | | |
|---|---|---|---|
| 3,906,092 | A | 9/1975 | Hilleman et al. |
| 6,074,645 | A | 6/2000 | Diamond et al. |
| 6,162,620 | A | 12/2000 | Smith et al. |
| 6,207,161 | B1 | 3/2001 | Pande et al. |
| 6,448,389 | B1 | 9/2002 | Gonczol et al. |
| 6,500,419 | B1 | 12/2002 | Hone et al. |
| 6,514,948 | B1 | 2/2003 | Raz et al. |
| 6,713,070 | B1 | 3/2004 | Plachter et al. |
| 6,843,992 | B2 | 1/2005 | Diamond et al. |
| 7,001,890 | B1 | 2/2006 | Wagner et al. |
| 7,204,990 | B1 | 4/2007 | Kemble et al. |
| 7,387,782 | B2 | 6/2008 | Zaia et al. |
| 7,410,795 | B2 | 8/2008 | Hermanson et al. |
| 7,419,674 | B2 | 9/2008 | Chulay et al. |
| 8,173,362 | B2 | 5/2012 | Shenk et al. |
| 8,217,016 | B2 | 7/2012 | Hoerr et al. |
| 8,425,898 | B2 | 4/2013 | Sampson et al. |
| 8,673,317 | B2 | 3/2014 | Hermanson et al. |
| 8,710,200 | B2 | 4/2014 | Schrum et al. |
| 8,734,853 | B2 | 5/2014 | Sood et al. |
| 8,754,062 | B2 | 6/2014 | De Fougerolles et al. |
| 8,822,663 | B2 | 9/2014 | Schrum et al. |
| 8,877,206 | B2 | 11/2014 | Chen et al. |
| 8,999,380 | B2 | 4/2015 | Bancel et al. |
| 9,149,543 | B2 | 10/2015 | Hecker et al. |
| 9,221,891 | B2 | 12/2015 | Bancel et al. |
| 9,243,041 | B2 | 1/2016 | Weiner et al. |
| 9,283,287 | B2 | 3/2016 | Bancel et al. |
| 9,303,079 | B2 | 4/2016 | Bancel et al. |
| 9,464,124 | B2 | 10/2016 | Bancel et al. |
| 9,486,517 | B2 | 11/2016 | Becke et al. |
| 9,512,456 | B2 | 12/2016 | Wang et al. |
| 9,597,380 | B2 | 3/2017 | Chakraborty et al. |
| 9,764,026 | B2 | 9/2017 | Sampson et al. |
| 9,868,691 | B2 | 1/2018 | Benenato et al. |
| 9,872,900 | B2 | 1/2018 | Ciaramella et al. |
| 10,064,934 | B2 | 9/2018 | Ciaramella et al. |
| 10,064,935 | B2 | 9/2018 | Ciaramella et al. |
| 10,124,055 | B2 | 11/2018 | Ciaramella et al. |
| 10,207,010 | B2 | 2/2019 | Besin et al. |
| 10,273,269 | B2 | 4/2019 | Ciaramella |
| 10,449,244 | B2 | 10/2019 | Ciaramella et al. |
| 10,465,190 | B1 | 11/2019 | Chen et al. |
| 10,493,143 | B2 | 12/2019 | Ciaramella et al. |
| 10,526,629 | B2 | 1/2020 | Rabideau et al. |
| 2003/0092653 | A1 | 5/2003 | Kisich et al. |
| 2005/0032730 | A1 | 2/2005 | Von Der Mulbe et al. |
| 2005/0059624 | A1 | 3/2005 | Hoerr et al. |
| 2005/0170508 | A1 | 8/2005 | Huang et al. |
| 2005/0250723 | A1 | 11/2005 | Hoerr et al. |

(Continued)

FOREIGN PATENT DOCUMENTS

| | | |
|---|---|---|
| CA | 2473135 | 6/2003 |
| EP | 1026253 | 8/2000 |

(Continued)

OTHER PUBLICATIONS

Gerna and Lilleri, New Microbiologica, 2019, 42(1):1-20. (Year: 2019).*
U.S. Appl. No. 15/239,613, filed Aug. 17, 2016, Laska et al.
U.S. Appl. No. 16/036,318, filed Jul. 16, 2018, Ciaramella et al.
U.S. Appl. No. 16/048,154, filed Jul. 27, 2018, Ciaramella et al.
U.S. Appl. No. 16/144,394, filed Sep. 27, 2018, Ciaramella et al.
U.S. Appl. No. 15/748,773, filed Jan. 30, 2018, Ciaramella et al.
U.S. Appl. No. 15/155,986, filed May 16, 2016, Fritz.
U.S. Appl. No. 15/753,293, filed Feb. 17, 2018, Smith.
U.S. Appl. No. 15/753,297, filed Feb. 17, 2018, Thompson.
U.S. Appl. No. 15/748,782, filed Jan. 30, 2018, Mousavi et al.
U.S. Appl. No. 16/001,751, filed Jun. 6, 2018, Mousavi et al.
U.S. Appl. No. 15/156,249, filed May 16, 2016, Miracco.
U.S. Appl. No. 15/767,587, filed Apr. 11, 2018, Ciaramella.
U.S. Appl. No. 16/006,526, filed Jun. 12, 2018, Ciaramella.
U.S. Appl. No. 16/450,882, filed Jun. 24, 2019, Ciaramella.
U.S. Appl. No. 15/767,600, filed Apr. 11, 2018, Ciaramella et al.

(Continued)

*Primary Examiner* — Stacy B Chen

(74) *Attorney, Agent, or Firm* — Wolf, Greenfield & Sacks, P.C.

(57) ABSTRACT

The disclosure relates to HCMV ribonucleic acid (RNA) vaccines, as well as methods of using the vaccines and compositions comprising the vaccines.

24 Claims, 53 Drawing Sheets

Specification includes a Sequence Listing.

(56) References Cited

U.S. PATENT DOCUMENTS

| | | | |
|---|---|---|---|
| 2006/0172003 | A1 | 8/2006 | Meers et al. |
| 2007/0280929 | A1 | 12/2007 | Hoerr et al. |
| 2008/0025944 | A1 | 1/2008 | Hoerr et al. |
| 2008/0171711 | A1 | 7/2008 | Hoerr et al. |
| 2010/0112042 | A1 | 5/2010 | Polisky et al. |
| 2010/0203076 | A1 | 8/2010 | Fotin-Mleczek et al. |
| 2010/0239608 | A1 | 9/2010 | Von Der Mulbe et al. |
| 2010/0249208 | A1 | 9/2010 | Hecker et al. |
| 2010/0291156 | A1 | 11/2010 | Barner et al. |
| 2010/0305196 | A1 | 12/2010 | Probst et al. |
| 2011/0250225 | A1 | 10/2011 | Fotin-Mleczek et al. |
| 2011/0269950 | A1 | 11/2011 | Von Der Mulbe et al. |
| 2012/0009221 | A1 | 1/2012 | Hoerr et al. |
| 2012/0219573 | A1 | 8/2012 | Baumhof et al. |
| 2012/0263648 | A1 | 10/2012 | Shapiro et al. |
| 2013/0022538 | A1 | 1/2013 | Rossi |
| 2013/0102034 | A1 | 4/2013 | Schrum et al. |
| 2013/0121988 | A1 | 5/2013 | Hoerr et al. |
| 2013/0142818 | A1 | 6/2013 | Baumhof et al. |
| 2013/0158021 | A1 | 6/2013 | Dong et al. |
| 2013/0183355 | A1 | 7/2013 | Jain et al. |
| 2013/0195867 | A1 | 8/2013 | Hoerr et al. |
| 2013/0195967 | A1 | 8/2013 | Guild et al. |
| 2013/0195969 | A1 | 8/2013 | Geall et al. |
| 2013/0202684 | A1 | 8/2013 | Geall et al. |
| 2013/0243848 | A1 | 9/2013 | Lobovkina et al. |
| 2013/0245103 | A1 | 9/2013 | de Fougerolles et al. |
| 2013/0259923 | A1 | 10/2013 | Bancel et al. |
| 2013/0266640 | A1 | 10/2013 | de Fougerolles et al. |
| 2013/0295043 | A1 | 11/2013 | Kallen et al. |
| 2013/0336998 | A1 | 12/2013 | Kallen et al. |
| 2014/0037660 | A1 | 2/2014 | Folin-Mleczek et al. |
| 2014/0147432 | A1 | 5/2014 | Bancel et al. |
| 2014/0148502 | A1 | 5/2014 | Bancel et al. |
| 2014/0193482 | A1 | 7/2014 | Bancel et al. |
| 2014/0206752 | A1 | 7/2014 | Afeyan et al. |
| 2014/0206753 | A1 | 7/2014 | Guild et al. |
| 2014/0227346 | A1 | 8/2014 | Geall et al. |
| 2014/0271829 | A1 | 9/2014 | Lilja et al. |
| 2014/0308308 | A1 | 10/2014 | Anderson et al. |
| 2014/0348863 | A1 | 11/2014 | Bianchi et al. |
| 2014/0378538 | A1 | 12/2014 | Bancel |
| 2015/0051268 | A1 | 2/2015 | Bancel et al. |
| 2015/0141499 | A1 | 5/2015 | Bancel et al. |
| 2015/0307542 | A1 | 10/2015 | Roy et al. |
| 2015/0307850 | A1 | 10/2015 | Fu et al. |
| 2015/0315541 | A1 | 11/2015 | Bancel et al. |
| 2015/0322115 | A1 | 11/2015 | Wellnitz et al. |
| 2015/0335732 | A1 | 11/2015 | Sampson et al. |
| 2015/0359879 | A1 | 12/2015 | Wellnitz et al. |
| 2015/0376115 | A1 | 12/2015 | Ansell et al. |
| 2016/0024141 | A1 | 1/2016 | Issa et al. |
| 2016/0151284 | A1 | 1/2016 | Heyes et al. |
| 2016/0032273 | A1 | 2/2016 | Shahrokh et al. |
| 2016/0038612 | A1 | 2/2016 | Hoge et al. |
| 2016/0159864 | A1 | 6/2016 | Carfi et al. |
| 2016/0213771 | A1 | 7/2016 | Sampson et al. |
| 2016/0271272 | A1 | 9/2016 | Bancel et al. |
| 2016/0296619 | A1 | 10/2016 | Orlinger et al. |
| 2016/0317647 | A1 | 11/2016 | Ciaramella et al. |
| 2016/0331828 | A1 | 11/2016 | Ciaramella et al. |
| 2016/0376224 | A1 | 12/2016 | Du et al. |
| 2017/0065675 | A1 | 3/2017 | Bancel et al. |
| 2017/0119874 | A1 | 5/2017 | Lanzavecchia et al. |
| 2017/0130255 | A1 | 5/2017 | Wang et al. |
| 2017/0143848 | A1 | 5/2017 | Calias et al. |
| 2017/0202979 | A1 | 7/2017 | Chakraborty et al. |
| 2017/0239371 | A1 | 8/2017 | Guild et al. |
| 2017/0320916 | A1 | 11/2017 | Carfi et al. |
| 2017/0362278 | A1 | 12/2017 | Carfi et al. |
| 2018/0000953 | A1 | 1/2018 | Almarsson et al. |
| 2018/0002393 | A1 | 1/2018 | Bancel et al. |
| 2018/0237849 | A1 | 8/2018 | Thompson |
| 2018/0243225 | A1 | 8/2018 | Ciaramella |
| 2018/0243230 | A1 | 8/2018 | Smith |
| 2018/0271970 | A1 | 9/2018 | Ciaramella et al. |
| 2018/0273977 | A1 | 9/2018 | Mousavi et al. |
| 2018/0274009 | A1 | 9/2018 | Marquardt et al. |
| 2018/0280496 | A1 | 10/2018 | Ciaramella et al. |
| 2018/0289792 | A1 | 10/2018 | Ciaramella et al. |
| 2018/0303929 | A1 | 10/2018 | Ciaramella et al. |
| 2018/0311336 | A1 | 11/2018 | Ciaramella et al. |
| 2018/0312549 | A1 | 11/2018 | Ciaramella |
| 2018/0318409 | A1 | 11/2018 | Valiante et al. |
| 2018/0363019 | A1 | 12/2018 | Hoge |
| 2019/0002890 | A1 | 1/2019 | Martini et al. |
| 2019/0008938 | A1 | 1/2019 | Ciaramella et al. |
| 2019/0099481 | A1 | 4/2019 | Ciaramella et al. |
| 2019/0192646 | A1 | 6/2019 | Cohen et al. |
| 2019/0192653 | A1 | 6/2019 | Hoge et al. |
| 2019/0275170 | A1 | 9/2019 | Benenato et al. |
| 2019/0309337 | A1 | 10/2019 | Rabideau et al. |
| 2019/0314493 | A1 | 10/2019 | Ciaramella et al. |
| 2019/0336595 | A1 | 11/2019 | Ciaramella |
| 2019/0351040 | A1 | 11/2019 | Valiante et al. |

FOREIGN PATENT DOCUMENTS

| | | | |
|---|---|---|---|
| EP | 1083232 | | 2/2005 |
| EP | 1905844 | A2 | 2/2008 |
| EP | 2548960 | A1 | 1/2013 |
| EP | 3310384 | A1 | 4/2018 |
| WO | WO 1987/005326 | A1 | 9/1987 |
| WO | WO 1990/011092 | | 10/1990 |
| WO | WO 1993/014778 | | 8/1993 |
| WO | WO 1995/024485 | | 9/1995 |
| WO | WO 1995/026204 | | 10/1995 |
| WO | WO 1995/033835 | | 12/1995 |
| WO | WO 1998/033510 | A1 | 2/1998 |
| WO | WO 1999/033982 | | 7/1999 |
| WO | WO 2001/093836 | A2 | 12/2001 |
| WO | WO 2003/059381 | | 7/2003 |
| WO | WO 2004/058166 | A2 | 7/2004 |
| WO | WO 2004/076645 | A2 | 9/2004 |
| WO | WO 2005/007689 | A1 | 1/2005 |
| WO | WO 2005/009346 | | 2/2005 |
| WO | WO 2005/034979 | A2 | 4/2005 |
| WO | WO 2005/120152 | | 12/2005 |
| WO | WO 2005/120152 | A1 | 12/2005 |
| WO | WO 2006/056027 | A1 | 6/2006 |
| WO | WO 2006/071903 | | 7/2006 |
| WO | WO 2006/095259 | | 9/2006 |
| WO | WO 2007/095976 | A2 | 8/2007 |
| WO | WO 2007/146024 | A2 | 12/2007 |
| WO | WO 2008/052770 | A2 | 5/2008 |
| WO | WO 2009/030254 | A1 | 3/2009 |
| WO | WO 2009/030481 | A1 | 3/2009 |
| WO | WO 2009/095226 | | 8/2009 |
| WO | WO 2009/127230 | A1 | 10/2009 |
| WO | WO 2009/155535 | A2 | 12/2009 |
| WO | WO 2010/037408 | A1 | 4/2010 |
| WO | WO 2010/037539 | A1 | 4/2010 |
| WO | WO 2010/042877 | A1 | 4/2010 |
| WO | WO 2010/053572 | A2 | 5/2010 |
| WO | WO 2010/054406 | A1 | 5/2010 |
| WO | WO 2010/088927 | A1 | 8/2010 |
| WO | WO 2011/005799 | A2 | 1/2011 |
| WO | WO 2011/026641 | A9 | 3/2011 |
| WO | WO 2011/068810 | A1 | 6/2011 |
| WO | WO 2011/069529 | A1 | 6/2011 |
| WO | WO 2011/069586 | A1 | 6/2011 |
| WO | WO 2011/144358 | A1 | 11/2011 |
| WO | WO 2012/019630 | A1 | 2/2012 |
| WO | WO 2012/019780 | A1 | 2/2012 |
| WO | WO 2012/034025 | A1 | 3/2012 |
| WO | WO 2012/051211 | A2 | 4/2012 |
| WO | WO 2012/106377 | A2 | 8/2012 |
| WO | WO 2012/116714 | A1 | 9/2012 |
| WO | WO 2012/116715 | A1 | 9/2012 |
| WO | WO 2012/116810 | A1 | 9/2012 |
| WO | WO 2012/116811 | A1 | 9/2012 |
| WO | WO 2013/006838 | A1 | 1/2013 |
| WO | WO 2013/006842 | A2 | 1/2013 |
| WO | WO 2013/036465 | A2 | 3/2013 |

(56) References Cited

FOREIGN PATENT DOCUMENTS

| | | | |
|---|---|---|---|
| WO | WO 2013/055905 | A1 | 4/2013 |
| WO | WO 2013/068847 | A2 | 5/2013 |
| WO | WO 2013/090186 | A1 | 6/2013 |
| WO | WO 2013/096812 | A1 | 6/2013 |
| WO | WO 2013/102203 | A1 | 7/2013 |
| WO | WO 2013/120629 | A1 | 8/2013 |
| WO | WO 2013/185069 | A1 | 12/2013 |
| WO | WO 2014/018117 | A1 | 1/2014 |
| WO | WO 2014/068001 | A1 | 5/2014 |
| WO | WO 2014/089486 | A1 | 6/2014 |
| WO | WO 2014/152027 | A1 | 9/2014 |
| WO | WO 2014/152774 | A1 | 9/2014 |
| WO | WO 2014/152940 | A1 | 9/2014 |
| WO | WO 2014/160243 | A1 | 10/2014 |
| WO | WO 2014/172045 | A1 | 10/2014 |
| WO | WO 2014/182661 | A2 | 11/2014 |
| WO | WO 2015/024668 | A2 | 2/2015 |
| WO | WO 2015/061467 | A1 | 4/2015 |
| WO | WO 2015/082570 | A1 | 6/2015 |
| WO | WO 2015/089340 | A1 | 6/2015 |
| WO | WO 2015/095340 | A1 | 6/2015 |
| WO | WO 2015/110659 | A1 | 7/2015 |
| WO | WO 2015/161926 | A1 | 10/2015 |
| WO | WO 2015/165480 | A1 | 11/2015 |
| WO | WO 2015/170287 | A1 | 11/2015 |
| WO | WO 2015/181142 | A1 | 12/2015 |
| WO | WO 2015/199952 | A1 | 12/2015 |
| WO | WO 2016/004318 | A1 | 1/2016 |
| WO | WO 2016/037053 | A1 | 3/2016 |
| WO | WO 2016/067239 | A1 | 5/2016 |
| WO | WO 2016/092460 | A2 | 6/2016 |
| WO | WO 2016/116904 | A1 | 7/2016 |
| WO | WO 2016/116905 | A1 | 7/2016 |
| WO | WO 2016/130693 | A1 | 8/2016 |
| WO | WO 2016/133881 | A1 | 8/2016 |
| WO | WO 2016/164762 | A1 | 10/2016 |
| WO | WO 2017/070613 | A1 | 10/2016 |
| WO | WO 2016/184822 | A1 | 11/2016 |
| WO | WO 2016/201377 | A1 | 12/2016 |
| WO | WO 2016/203025 | A1 | 12/2016 |
| WO | WO 2017/015457 | A1 | 1/2017 |
| WO | WO 2017/019935 | A1 | 2/2017 |
| WO | WO 2017/020026 | A1 | 2/2017 |
| WO | WO 2017/153936 | | 3/2017 |
| WO | WO 2017/062513 | A1 | 4/2017 |
| WO | WO 2017/066789 | A1 | 4/2017 |
| WO | WO 2017/070601 | A1 | 4/2017 |
| WO | WO 2017/201340 | A1 | 11/2017 |
| WO | WO 2017/201342 | A1 | 11/2017 |
| WO | WO 2017/201347 | A1 | 11/2017 |
| WO | WO 2017/201349 | A1 | 11/2017 |
| WO | WO 2017/208191 | A1 | 12/2017 |
| WO | WO 2018/075980 | A1 | 4/2018 |
| WO | WO 2018/078053 | A1 | 5/2018 |
| WO | WO 2018/081459 | A1 | 5/2018 |
| WO | WO 2018/089851 | A1 | 5/2018 |
| WO | WO 2018/107088 | A1 | 6/2018 |
| WO | WO 2018/111967 | A1 | 6/2018 |
| WO | WO 2018/144082 | A1 | 8/2018 |
| WO | WO 2018/144778 | A1 | 8/2018 |
| WO | WO 2018/170245 | A1 | 9/2018 |
| WO | WO 2018/170256 | A1 | 9/2018 |
| WO | WO 2018/170260 | A1 | 9/2018 |
| WO | WO 2018/170270 | A1 | 9/2018 |
| WO | WO 2018/170347 | A1 | 9/2018 |
| WO | WO 2018/175783 | A1 | 9/2018 |
| WO | WO 2018/187590 | A2 | 10/2018 |
| WO | WO 2018/200737 | A1 | 11/2018 |
| WO | WO 2018/232355 | A1 | 12/2018 |
| WO | WO 2018/232357 | A1 | 12/2018 |
| WO | WO 2019/036670 | A1 | 2/2019 |
| WO | WO 2019/036682 | A1 | 2/2019 |
| WO | WO 2019/036683 | A1 | 2/2019 |
| WO | WO 2019/036685 | A1 | 2/2019 |
| WO | WO 2019/103993 | A1 | 5/2019 |
| WO | WO 2019/148101 | A1 | 8/2019 |
| WO | WO 2020/006242 | A1 | 1/2020 |

OTHER PUBLICATIONS

U.S. Appl. No. 16/023,013, filed Jun. 29, 2018, Ciaramella et al.
U.S. Appl. No. 15/769,710, filed Apr. 19, 2018, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.
U.S. Appl. No. 15/767,618, filed Apr. 11, 2018, Ciaramella et al.
U.S. Appl. No. 16/136,386, filed Sep. 20, 2018, Ciaramella et al.
U.S. Appl. No. 16/136,503, filed Sep. 20, 2018, Ciaramella et al.
U.S. Appl. No. 15/746,286, filed Jan. 19, 2018, Ciaramella et al.
U.S. Appl. No. 16/009,811, filed Jun. 15, 2018, Ciaramella et al.
U.S. Appl. No. 16/009,848, filed Jun. 15, 2018, Ciaramella et al.
U.S. Appl. No. 16/009,880, filed Jun. 15, 2018, Ciaramella et al.
U.S. Appl. No. 15/981,762, filed May 16, 2018, Bancel et al.
U.S. Appl. No. 15/387,263, filed Dec. 21, 2016, Chen et al.
U.S. Appl. No. 15/674,107, filed Aug. 10, 2017, Besin et al.
U.S. Appl. No. 16/229,509, filed Dec. 21, 2018, Besin et al.
U.S. Appl. No. 16/001,786, filed Jun. 6, 2018, Hoge et al.
U.S. Appl. No. 16/333,330, filed Mar. 14, 2019, Hoge et al.
U.S. Appl. No. 16/368,099, filed Mar. 28, 2019, Ciaramella et al.
U.S. Appl. No. 16/368,270, filed Mar. 28, 2019, Ciaramella et al.
U.S. Appl. No. 16/468,838, filed Jun. 12, 2019, Miracco.
U.S. Appl. No. 16/001,765, filed Jun. 6, 2018, Marquardt et al.
U.S. Appl. No. 16/348,943, filed May 10, 2019, Ciaramella.
U.S. Appl. No. 16/467,142, filed Jun. 6, 2019, Ciaramella et al.
U.S. Appl. No. 15/880,436, filed Jan. 25, 2018, Ciaramella.
U.S. Appl. No. 16/432,541, filed Jun. 5, 2019, Rabideau et al.
U.S. Appl. No. 16/362,366, filed Mar. 22, 2019, Ciaramella.
U.S. Appl. No. 16/302,607, filed Nov. 16, 2018, Benenato et al.
U.S. Appl. No. 16/131,793, filed Sep. 14, 2018, Ciaramella et al.
U.S. Appl. No. 16/180,076, filed Nov. 5, 2018, Cohen et al.
PCT/US2017/057748, Mar. 27, 2018, International Search Report and Written Opinion.
International Search Report and Written Opinion for Application No. PCT/US2017/057748, dated Mar. 27, 2018.
[No Author Listed], "Messenger RNA", Internet: Wikipedia. Jun. 19, 2013, XP002699196, Retrieved from the Internet: URL: http://en.wikipedia.org/wiki/Messenger RNA.
Archer, S.J., Induction of a T-cell specific antigen on bone marrow lymphocytes with thymus RNA. Immunology. Jan. 1978;34(1):123-9.
Ashley, D.M. et al., Bone marrow-generated dendritic cells pulsed with tumor extracts or tumor RNA induce antitumor immunity against central nervous system tumors. J Exp Med. Oct. 6, 1997; 186(7): 1177-82.
Bettinger, T. et al., Peptide-mediated RNA delivery: A novel approach for enhanced transfection of primary and post-mitotic cells. Nucleic Acids Res. Sep. 15, 2001;29(18):3882-91.
Bogers et al., Potent immune responses in rhesus macaques induced by nonviral delivery of a self-amplifying RNA vaccine expressing HIV type 1 envelope with a cationic nanoemulsion.J Infect Dis. Mar. 15, 2015;211(6):947-55. doi: 10.1093/infdis/jiu522. Epub Sep. 18, 2014.
Bonehill, A., et al., Single-step antigen loading and activation of dendritic cells by mRNA electroporation for the purpose of therapeutic vaccination in melanoma patients. Clin Cancer Res. May 2009; 15(10): 3366-3375.
Brito et al., A cationic nanoemulsion for the delivery of next-generation RNA vaccines. Mol Ther. Dec. 2014;22(12):2118-29. doi: 10.1038/mt.2014.133. Epub Jul. 16, 2014.
Conry, R.M. et al., Characterization of a messenger RNA polynucleotide vaccine vector. Cancer Res. Apr. 1, 1995;55 (7):1397-1400.
Cosman et al., ULBPs, Novel MHC Class I-Related Molecules, Bind to CMV Glycoprotein UL 16 and Stimulate NK Cytotoxicity through the NKG2D Receptor, Immunity,2001, vol. 14, No. vol. pp. 123-133.

(56) References Cited

OTHER PUBLICATIONS

Dahlman et al., In vivo endothelial siRNA delivery using polymeric nanoparticles with low molecular weight, Nature Nanotechnology, 2014, No. vol.#, pp. 1-8.
Davison. UL 128 [Human herpesvirus 5]. GenBank: AAR31335. Dep. Dec. 20, 2003.
Deering et al., Nucleic Acid Vaccines: Prospects for Non-Viral Delivery of mRNA Vaccines, Expert Opinion, 2014, vol. 11, No. 6, pp. 1-15.
Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.
Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.
Geall et al., Nonviral delivery of self-amplifying RNA vaccines. Proc Natl Acad Sci U S A. Sep. 4, 2012;109(36):14604-9. doi:10. 1073/pnas.1209367109. Epub Aug. 20, 2012.
Gilboa, E. et al., Cancer immunotherapy with mRNA-transfected dendritic cells. Immunol Rev. Jun. 2004;199:251-63.
Hajj et al., Tools for translation: non-viral materials for therapeutic mRNA delivery. Nat Rev Mat. Sep. 2017;2:17056.
Hecker, J.G. et al., Non-Viral DNA and mRNA Gene Delivery to the CNS Pre-Operatively for Neuroprotection and Following Neurotrauma. Molecular Therapy. 2004; 9, S258-S258.
Heiser, A. et al., Induction of polyclonal prostate cancer-specific CTL using dendritic cells transfected with amplified tumor RNA. J Immunol. Mar. 1, 2001; 166(5):2953-60.
Hoerr, I. et al., In vivo application of RNA leads to induction of specific cytotoxic T lymphocytes and antibodies. EurJ Immunol. Jan. 2000;30(1):1-7.
Hoerr, I. et al., Stabilized Messenger RNA (RNActiveTM) as a Tool for Innovative Gene Delivery. Tissue Engineering. Apr. 2007; 13(4): 865-925.
Hoerr, More than a messenger: A new class of drugs-mRNA-based therapeutics. Genetic Engineering & Biotechnology News. Jun. 18, 2013. http://www.genengnews.com/gen-articles/more-than-a-messenger-a-new-class-of-drugs-mrna-based-therapeutics/4916/ [last accessed Mar. 25, 2016].
Holtkamp, S. et al., Modification of antigen-encoding RNA increases stability, translational efficacy, and T-cell stimulatory capacity of dendritic cells. Blood. Dec. 15, 2006;108(13):4009-17.
Jirikowski, G.F., et al., Reversal of diabetes insipidus in Brattleboro Rats: Intrahypothalamic injection of vasopressin mRNA. Science. Feb. 1992; 255(5047): 996-998.
Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.
Kallen et al., A novel, disruptive vaccination technology: self-adjuvanted RNActive(®) vaccines. Hum Vaccin Immunother. Oct. 2013;9(10):2263-76. doi: 10.4161/hv.25181. Epub Jun. 4, 2013. Review.
Kanapathipillai, et al., Nanoparticle targeting of anti-cancer drugs that alter intracellular signaling or influence the tumor microenvironment, Adv. Drug Deliv. Rev. (2014), , pp. 1-12.
Kariko, K., et al., Generating the optimal mRNA for therapy: HPLC purification eliminates immune activation and improves translation of nucleoside-modified, protein-encoding mRNA, Nucleic Acids Research, Oxford University Press, GB, vol. 39, No. 21, Sep. 2, 2011 (Sep. 2, 2011), e142. doi: 10.1093/nar/gkr695. Epub Sep. 2, 2011.
Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.
Kisich et al., Antimycobacterial agent based on mRNA encoding human beta-defensin 2 enables primary macrophages to restrict growth of *Mycobacterium tuberculosis*.Infect Immun. Apr. 2001;69(4):2692-9.
Kozielski, Kristen L. et al., Bioreducible Cationic Polymer-Based Nanoparticles for Efficient and Environmentally Triggered Cytoplasmic siRNA Delivery to Primary Human Brain Cancer Cells, ACS Nano, 2014, vol. 8, 'No. 4',pp. 3232-3241.
Kreiter, S., et al., Intranodal vaccination with naked antigen-encoding RNA elicits potent prophylactic and therapeutic antitumoral immunity. Cancer Res. 2010; 70: 9031-9040.
Kreiter, S., et al., Tumor vaccination using messenger RNA: prospects of a future therapy. Curr Opinion in Immun. Jun. 2011; 23(3): 399-406.
Kuhn, A.N., et al., mRNA as a versatile tool for exogenous protein expression. Current Gene Therapy. Oct. 2012; 12 (5): 347-361.
Leitner, W.W. et al., DNA and RNA-based vaccines: principles, progress and prospects. Vaccine. Dec. 10, 1999;18 (9-10):765-77.
Li, L. et al., Overcoming obstacles to develop effective and safe siRNA therapeutics. Expert Opin Biol Ther. May 2009; 9(5): 609-19.
Lorenzi, J.C., et al., Intranasal vaccination with messenger RNA as a new approach in gene therapy: Use against tuberculosis. BMC Biotechnol. Oct. 2010; 10(77): 1-11.
Mackey et al., mRNA-based cancer vaccine: prevention of B16 melanoma progression and metastasis by systemic injection of MARTI1 mRNA histidylated lipopolyplexes, Cancer Gene Therapy, 2007, 14, pp. 802-814.
Magini et al., Self-Amplifying mRNA Vaccines Expressing Multiple Conserved Influenza Antigens Confer Protection against Homologous and Heterosubtypic Viral Challenge. PLoS One. Aug. 15, 2016;11(8):e0161193. doi: 10.1371/journal.pone.0161193. eCollection 2016.
Martinon, F. et al., Induction of virus-specific cytotoxic T lymphocytes in vivo by liposome-entrapped mRNA. EurJ Immunol. Jul. 1993;23(7):1719-22.
McVoy, Cytomegalovirus vaccines. Clin Infect Dis. Dec. 2013;57 Suppl 4:S196-9. doi: 10.1093/cid/cit587.
Midoux et al., Lipid-based mRNA vaccine delivery systems. Expert Rev Vaccines. Feb. 2015;14(2):221-34. doi: 10.1586/14760584. 2015.986104. Epub Dec. 26, 2014. Review.
Mitchell, DA et al., RNA transfected dendritic cells as cancer vaccines. Curr Opin Mal Ther. Apr. 2000;2(2):176-81.
Mitchell, DA et al., RNA-transfected dendritic cells in cancer immunotherapy. J Clin Invest. Nov. 2000;106 (9):1065-9.
Muller, M.R. et al., Transfection of dendritic cells with RNA induces CD4- and COB-mediated T cell immunity against breast carcinomas and reveals the immunodominance of presented T cell epitopes. J Immunol. Jun. 15, 2003;170(12):5892-6.
Pardi et al., Nucleoside-modified mRNA vaccines induce potent T follicular helper and germinal center B cell responses. J Exp Med. Jun. 4, 2018;215(6):1571-1588. doi: 10.1084/jem.20171450. Epub May 8, 2018.
Petsch et al., Protective efficacy of in vitro synthesized, specific mRNA vaccines against influenza A virus infection. Nat Biotechnol. Dec. 2012;30(12):1210-6. doi: 10.1038/nbt.2436. Epub Nov. 25, 2012.
Phua et al., Messenger RNA (mRNA) nanoparticle tumour vaccination. Nanoscale. Jul. 21, 2014;6(14):7715-29. doi: 10.1039/c4nr01346h. Review.
Pulford, B., et al., Liposome-siRNA-peptide complexes cross the blood-brain barrier and significantly decrease PrP'C on neuronal cells and PrP'RES in infected cell cultures. PLoS ONE. 201 O; 5(6): e11085.
Rabinovich, P.M., et al., Synthetic messenger RNA as a tool for gene therapy. Hum. Gene Ther. Oct. 2006; 17: 1027-1035.
Reap et al., Cellular and humoral immune responses to alphavirus replicon vaccines expressing cytomegalovirus pp65, IE1, and gB proteins. Clin Vaccine Immunol. Jun. 2007;14(6):748-55. Epub Apr. 18, 2007.
Rittig et al., Intradermal vaccinations with RNA coding for TAA generate CD8+ and CD4+ immune responses and induce clinical

(56) References Cited

OTHER PUBLICATIONS benefit in vaccinated patients. Mol Ther. May 2011;19(5):990-9. doi: 10.1038/mt.2010.289. Epub Dec. 28, 2010.
Sahin et al., mRNA-based therapeutics—developing a new class of drugs. Nat Rev Drug Discov. Oct. 2014;13(10):759-80. doi: 10.1038/nrd4278. Epub Sep. 19, 2014.
Schleiss et al., Additive Protection against Congenital Cytomegalovirus Conferred by Combined Glycoprotein B/pp65 Vaccination Using a Lymphocytic Choriomeningitis Virus Vector. Clin Vaccine Immunol. Jan. 5, 2017;24(1). pii: e00300-16. doi: 10.1128/CVI.00300-16. Print Jan. 2017.
Schmitt, W.E. et al., In vitro induction of a bladder cancer-specific T-cell response by mRNA-transfected dendritic cells. J Cancer Res Clin Oncol. 2001 ;127(3):203-6.
Schott, J.W., et al., Viral and non-viral approaches for transient delivery of mRNA and proteins. Current Gene Ther. 2011; 11 (5): 382-398.
Segura, J., et al., Monitoring gene therapy by external imaging of mRNA: Pilot study on murine erythropoietin. Ther Drug Monit. Oct. 2007; 29(5): 612-8.
Smits, E., et al., RNA-based gene transfer for adult stem cells and T cells. Leukemia. 2004; 18: 1898-1902.
Sohn, R.L., et al., In-vivo particle mediated delivery of mRNA to mammalian tissues: ballistic and biological effects. Wound Rep and Regen. Jul.-Aug. 2001; 287-296.
Stanton et al., Human herpesvirus 5 transgenic strain Merlin, complete genome. GenBank: GU179001. Dep. Dec. 13, 2009.
Strong, V.T. et al., Incorporation of beta-globin untranslated regions into a Sindbis virus vector for augmentation of heterologous mRNA expression. Gene Ther. Jun. 1997;4(6):624-7.
Sullenger, BA et al., Emerging clinical applications of RNA. Nature. Jul. 11, 2002;418(6894):252-8.
Sun et al., Human herpesvirus 5 isolate D-947 UL131A, UL130, and UL128 genes, complete cds. GenBank: GU568344. Dep. Apr. 20, 2010.
Tavernier, G., et al., mRNA as gene therapeutic: How to control protein expression. J. of Controlled Release. Mar. 2011; 150(3): 238-247.
Teufel, R. et al., Human peripheral blood mononuclear cells transfected with messenger RNA stimulate antigen-specific cytotoxic T-lymphocytes in vitro. Cell Mol Life Sci. Aug. 2005;62(15):1755-62.
Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015.103. Epub Jun. 8, 2015.
Tripathy et al., Long-term expression of erythropoietin in the systemic circulation of mice after intramuscular injection of a plasmid DNA vector, Proc. Natl. Acad. Sci. USA 93, 1996, pp. 10876-10880.
Uzgun, S., et al., PEGylation improves nanoparticle formation and transfection efficiency of messenger RNA. Pharm Res. Sep. 2011; 28(9); 2223-2232.
Van Den Bosch et al., Simultaneous activation of Viral Antigen-specific Memory CD4+ and CDS+ T-cells using mRNA-electroporated CD40-activaled autologous B-cells. J Immunother. Sep./Oct. 2006; 29, 512-23.
Vici et al., Immunologic treatments for precancerous lesions and uterine cervical cancer. J Exp Clin Cancer Res. Mar. 26, 2014; 33:29. doi: 10.1186/1756-9966-33-29.
Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.
Wen et al., Human cytomegalovirus gH/gL/UL128/UL130/UL131A complex elicits potently neutralizing antibodies in mice. Vaccine. Jun. 24, 2014;32(30):3796-804. doi: 10.1016/j.vaccine.2014.05.004. Epub May 14, 2014.
Wong et al., An mRNA vaccine for influenza. Nat Biotechnol. Dec. 2012;30(12):1202-4. doi: 10.1038/nbt.2439.
Yamamoto et al., Current prospects for mRNA gene delivery, European Journal of Pharmaceutics and Biopharmaceutics 71 (2009) 484-489.
YP_0181566. Davison et al., Human betaherpesvirus 5 (HHV-5; HCMB). Dep. Sep. 27, 2002, Updated Jul. 2, 2013.
YP_018555. Davison et al., Human betaherpesvirus 5 (HHV-5; HCMB). Dep. Sep. 27, 2002, Updated Jul. 2, 2013.
YP_018565. Davison et al., Human betaherpesvirus 5 (HHV-5; HCMB). Dep. Sep. 27, 2002, Updated Jul. 2, 2013.
YP_081514. Davison et al., Human betaherpesvirus 5 (HHV-5; HCMB). Dep. Sep. 27, 2002, Updated Jul. 2, 2013.
YP_081523. Davison et al., Human betaherpesvirus 5 (HHV-5; HCMB). Dep. Sep. 27, 2002, Updated Jul. 2, 2013.
Zhou, W.Z. et al., RNA melanoma vaccine: induction of antitumor immunity by human glycoprotein 100 mRNA immunization. Hum Gene Ther. Nov. 1, 1999;10(16):2719-24.
Schleiss, Cyotmegalovirus vaccines under clinical development. J Virus Erad. Oct. 5, 2016;2(4):198-207.
Anderson et al., Stability of mRNA/cationic lipid lipoplexes in human and rat cerebrospinal fluid: methods and evidence for nonviral mRNA gene delivery to the central nervous system. Hum Gene Ther. Feb. 10, 2003;14(3):191-202.
Andries et al., N(1)-methylpseudouridine-incorporated mRNA outperforms pseudouridine-incorporated mRNA by providing enhanced protein expression and reduced immunogenicity in mammalian cell lines and mice. J Control Release. Nov. 10, 2015;217:337-44. doi: 10.1016/j.jconrel.2015.08.051. Epub Sep. 3, 2015.
Chiuppesi et al., Vaccine-Derived Neutralizing Antibodies to the Human Cytomegalovirus gH/gL Pentamer Potently Block Primary Cytotrophoblast Infection. J Virol. Dec. 2015;89(23):11884-98. doi: 10.1128/JV1.01701-15. Epub Sep. 16, 2015.
Ernsting et al., Factors controlling the pharmacokinetics, biodistribution and intratumoral penetration of nanoparticles. J Control Release. Dec. 28, 2013;172(3):782-94. doi: 10.1016/j.jconrel.2013.09.013. Epub Sep. 25, 2013.
Ewert et al., Cationic liposome-nucleic acid complexes for gene delivery and silencing: pathways and mechanisms for plasmid DNA and siRNA. Top Curr Chem. 2010;296:191-226.
Gjetting et al., In vitro and in vivo effects of polyethylene glycol (PEG)-modified lipid in DOTAP/cholesterol-mediated gene transfection. Int J Nanomedicine. Aug. 9, 2010;5:371-83.
Hecker, Nonviral, cationic lipid-mediated delivery of mRNA. Methods Mol Biol. 2013;969:73-88. doi: 10.1007/978-1-62703-260-5_5.
Leroueil et al., Wide varieties of cationic nanoparticles induce defects in supported lipid bilayers. Nano Lett. Feb. 2008;8(2):420-4. doi: 10.1021/n10722929. Epub Jan. 25, 2008.
Lin et al., Lipid-based nanoparticles in the systemic delivery of siRNA. Nanomedicine (Lond). Jan. 2014;9(1):105-20. doi: 10.2217/nnm.13.192.
Pass et al., Vaccine prevention of maternal cytomegalovirus infection. N Engl J Med. Mar. 19, 2009;360(12):1191-9. doi: 10.1056/NEJMoa0804749.
Szebeni et al., Activation of complement by therapeutic liposomes and other lipid excipient-based therapeutic products: prediction and prevention. Adv Drug Deliv Rev. Sep. 16, 2011;63(12):1020-30. doi: 10.1016/j.addr.2011.06.017. Epub Jul. 14, 2011.
Szebeni et al., Complement activation as a bioequivalence issue relevant to the development of generic liposomes and other nanoparticulate drugs. Biochem Biophys Res Commun. Dec. 18, 2015;468(3):490-7. doi: 10.1016/j.bbrc.2015.06.177. Epub Jul. 14, 2015.
Szebeni, Complement activation-related pseudoallergy: a stress reaction in blood triggered by nanomedicines and biologicals. Mol Immunol. Oct. 2014;61(2):163-73. doi: 10.1016/j.molimm.2014.06.038. Epub Aug. 12, 2014.
Wussow et al., Human cytomegalovirus vaccine based on the envelope gH/gL pentamer complex. PLoS Pathog. Nov. 20, 2014;10(11):e1004524. doi: 10.1371/journal.ppat.1004524. eCollection Nov. 2014.
Xue et al., Lipid-Based Nanocarriers for RNA Delivery. Curr Pharm Des. 2015;21(22):3140-7.

(56) References Cited

OTHER PUBLICATIONS

Zou et al., Lipid-mediated delivery of RNA is more efficient than delivery of DNA in non-dividing cells. Int J Pharm. Apr. 15, 2010;389(1-2):232-43. doi: 10.1016/j.ijpharm.2010.01.019. Epub Jan. 18, 2010.

* cited by examiner

Adapted from Macagno et al., Journal of Virology, 2010.

| # doses | 1 | 3 | 3 | 3 | 1 | 3 | 3 | 3 | 2 | 3 | 1 | 3 | 3 |
|---|---|---|---|---|---|---|---|---|---|---|---|---|---|
| Penta. dose(µg) | 10 | 10 | 3.3 | 1 | 10 | 10 | 3.3 | 1 | 10 | 10 | 10 | 10 | - |
| Formulation | Pentamer (pre-mix, equimolar) | | | | Pentamer (post-mix, equimolar) | | | | Penta protein/ MF59 * | Pentamer (equal conc.) | Penta + gB(2µg) (equal conc.) | | Empty LNP |

| # doses | 1 | 2 | 2 | 2 | 1 | 2 |
|---|---|---|---|---|---|---|
| Pentamer dose (µg) | 10 | 1 | - | - | 10 | - |
| gB dose (µg) | - | - | 10 | 10 | 2 | - |
| Formulation | Pentamer pre-mix ( Equimolar) | | gB | gB / MF59 | gB+ Penta (Equal conc) | Empty |

* only received 2 doses

% IFNγ responses are plotted after background subtraction

% IFNγ responses are plotted after background subtraction

* outlier- didn't receive 2nd dose

Stimulation with Pentamer library

Pentamer: gB: pp65-IE1 (5:5:2)

Stimulation with pp65-IE1 peptide pool

Pentamer: gB: pp65-IE1 (1:1:1:1)

Stimulation with pp65-IE1 peptide pool

Weak T cell responses to pp65-IE1 in multivalent Vx. Potential interference

| # doses | 2 | 2 | 2 | 2 | 2 |
|---|---|---|---|---|---|
| Penta dose (µg) | 3 | 5 | 8 | 10 | - |
| gB dose (µg) | 7 | 5 | 2 | 2 | - |
| Formulation | Pentamer + gB + pp65-IE1 (2µg) | | | Pentamer + gB | Empty LNP |

| # doses | 2 | 2 | 2 | 2 | 2 |
|---|---|---|---|---|---|
| Penta dose (µg) | 3 | 5 | 8 | 10 | - |
| gB dose (µg) | 7 | 5 | 2 | 2 | - |
| Formulation | Pentamer + gB + pp65-IE1 (2µg) | | | Pentamer + gB | Empty LNP |

| | | | | | | | | | | | | |
|---|---|---|---|---|---|---|---|---|---|---|---|---|
| Pentamer dose, µg | 3 | 5 | 8 | 10 | - | | 3 | 5 | 8 | 10 | - | |
| gB dose, µg | 7 | 5 | 2 | 2 | - | | 7 | 5 | 2 | 2 | - | |
| Pp65-IE1 dose, ug | 2 | 2 | 2 | - | - | | 2 | 2 | 2 | - | - | |
| Formulation in MC3 | Pentamer+gB+pp65-IE1 | | | Pentamer+ gB | Empty LNP | Cytogam | Pentamer+gB+pp65-IE1 | | | Pentamer+ gB | Empty LNP | Cytogam |

| # doses | 1 | 2 | 2 | 2 | 2 | 2 | 2 | 2 | 2 | 2 | 2 |
|---|---|---|---|---|---|---|---|---|---|---|---|
| Penta dose (µg) | 8.8 | 8.8 | 2.9 | 1 | 8.6 | 2.9 | 1 | 8.8 | 2.9 | 1 | - |
| Formulation | Pentamer + gB | | | | Pentamer + gB + pp65-IE1 | | | Pentamer | | | Empty LNP |

| # doses | 1 | 2 | 2 | 2 | 2 | 2 | 2 | 2 | 2 | 2 | 2 |
|---|---|---|---|---|---|---|---|---|---|---|---|
| gB dose (µg) | 1.8 | 1.8 | 0.6 | 0.2 | 1.7 | 0.6 | 0.2 | 1.7 | 0.6 | 0.2 | - |
| Formulation | Pentamer + gB | | | | Pentamer + gB + pp65-IE1 | | | gB | | | Empty LNP |

| 1st and 2nd dose formulation Compound 25 | Pentamer (5μg) + gB (1μg) | | Pentamer (5μg) + gB (1μg) + pp65 phos mut (2μg) | | empty |
|---|---|---|---|---|---|
| mRNA chemistry | C1 | C2 | C1 | C2 | |

| 1st and 2nd dose formulation Compound 25 | Pentamer (5μg) + gB (1μg) | | Pentamer (5μg) + gB (1μg) + pp65 phos mut (2μg) | | empty |
|---|---|---|---|---|---|
| mRNA chemistry | C1 | C2 | C1 | C2 | |

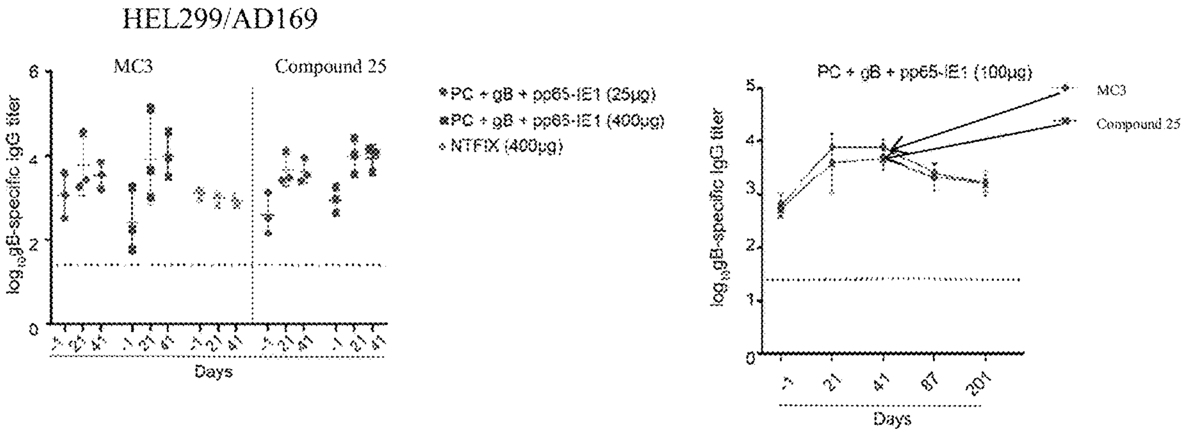
Fig. 47B
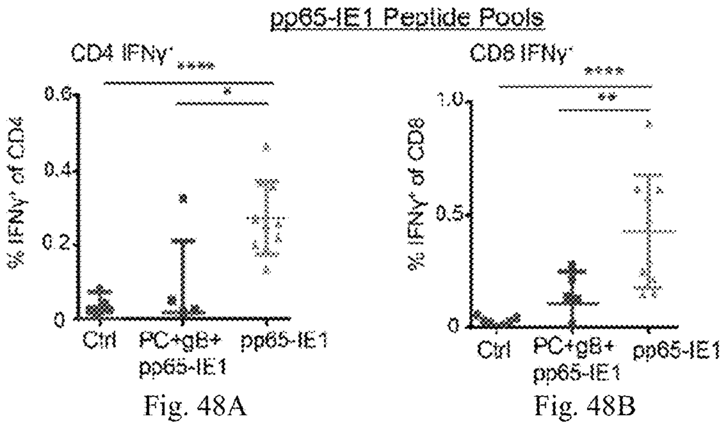
Fig. 48A
Fig. 48B
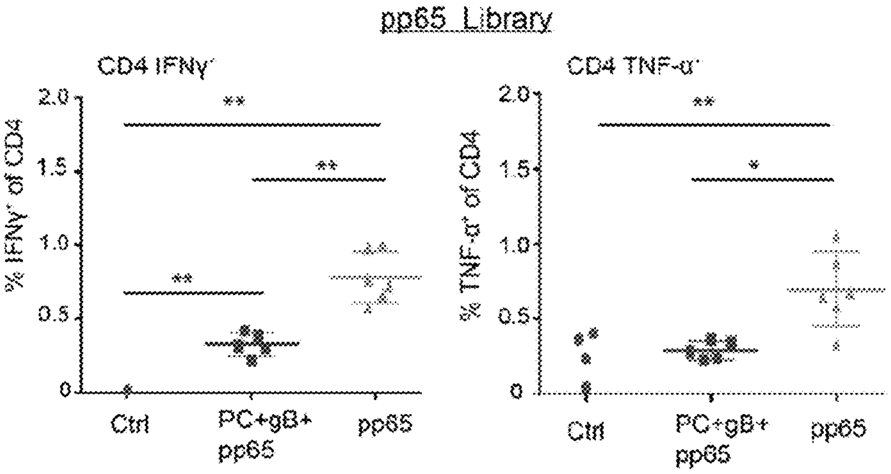
Fig. 48C pp65 Library PC Library

HUMAN CYTOMEGALOVIRUS VACCINE

RELATED APPLICATIONS

This application is a continuation of International Application No. PCT/US2017/057748, filed Oct. 20, 2017, which claims the benefit under 35 U.S.C. § 119(e) of U.S. Provisional Application Ser. No. 62/548,184, filed Aug. 21, 2017, entitled "Human Cytomegalovirus Vaccine," U.S. Provisional Application Ser. No. 62/490,510, filed Apr. 26, 2017, entitled "Human Cytomegalovirus Vaccine," U.S. Provisional Application Ser. No. 62/490,541, filed Apr. 26, 2017, entitled "Human Cytomegalovirus Vaccine," and U.S. Provisional Application No. 62/411,381, filed Oct. 21, 2016, entitled "Human Cytomegalovirus Vaccine," each of which is incorporated by reference herein in its entirety.

BACKGROUND

Human cytomegalovirus (HCMV) is a genus of viruses in the order Herpesvirales, in the family Herpesviridae, in the subfamily Betaherpesvirinae. There are currently eight species in this genus, which have been identified and classified for different mammals, including humans, monkeys, and rodents. The most studied genus is human cytomegalovirus, also known as human herpesvirus 5 (HHV-5), which is widely distributed in the human population. Diseases associated with HHV-5 include mononucleosis and pneumonias. All herpesviruses share a characteristic ability to remain latent within the body over long periods of time. Although they may be found throughout the body, CMV infections are frequently associated with the salivary glands in humans and other mammals. Other CMV viruses are found in several mammal species, but species isolated from animals differ from HCMV in terms of genomic structure, and have not been reported to cause human disease.

HCMV is endemic in most parts of the world. It is a ubiquitous large enveloped virus that infects 50 to 100% of the adult population worldwide. Although generally asymptomatic in immunocompetent hosts, HCMV infection is a major cause of morbidity and mortality in immunocompromised persons, such as infants following congenital or neonatal infections, transplant recipients, or AIDS patients.

Primary infection normally results in subclinical disease after which the virus becomes latent, retaining the capacity to reactivate at a later time. The virus is transmitted through body fluids, such as blood, saliva, urine, semen and breast milk. In particular, individuals with undeveloped or compromised immunity are highly sensitive to infection by HCMV. It is estimated that at least 60% of the US population has been exposed to CMV, with a prevalence of more than 90% in high-risk groups (e.g., unborn babies whose mothers become infected with CMV during the pregnancy or people with HIV).

In healthy individuals, HCMV typically causes an asymptomatic infection or produces mild, flulike symptoms. However, among two populations, HCMV is responsible for serious medical conditions. First, HCMV is a major cause of congenital defects in newborns infected in utero. Among congenitally infected newborns, 5-10% have major clinical symptoms at birth, such as microcephaly, intracranial calcifications, and hepatitis, as well as cytomegalic inclusion disease, which affects many tissues and organs including the central nervous system, liver, and retina and can lead to multi-organ failure and death. Other infants may be asymptomatic at birth, but later develop hearing loss or central nervous system abnormalities causing, in particular, poor intellectual performance and mental retardation. These pathologies are due in part to the ability of HCMV to enter and replicate in diverse cell types including epithelial cells, endothelial cells, smooth muscle cells, fibroblasts, neurons, and monocytes/macrophages.

The second population at risk are immunocompromised patients, such as those suffering from HIV infection and those undergoing transplantations. In this situation, the virus becomes an opportunistic pathogen and causes severe disease with high morbidity and mortality. The clinical disease causes a variety of symptoms including fever, pneumonia, hepatitis, encephalitis, myelitis, colitis, uveitis, retinitis, and neuropathy. Rarer manifestations of HCMV infections in immunocompetent individuals include Guillain-Barré syndrome, meningoencephalitis, pericarditis, myocarditis, thrombocytopenia, and hemolytic anemia. Moreover, HCMV infection increases the risk of organ graft loss through transplant vascular sclerosis and restenosis, and may increase atherosclerosis in transplant patients as well as in the general population. It is estimated that HCMV infection causes clinical disease in 75% of patients in the first year after transplantation.

There is currently no approved HCMV vaccine. Two candidate vaccines, Towne and gB/MF59, have completed phase II efficacy trials. The Towne vaccine appears protective against both infection and disease caused by challenge with pathogenic Toledo strain and also appears to be effective in preventing severe post-transplantation CMV disease. However, in a small phase II clinical trial, a low dose of Towne vaccine failed to show protection against infection of seronegative mothers who had children actively shedding CMV.

The gB/MF59 vaccine is a protein subunit vaccine comprised of a transmembrane-deleted version of HCMV gB protein, which induces high levels of fibroblast entry neutralizing antibodies in humans and has been shown to be safe and well tolerated in both adults and toddlers. A recent phase II double-blind placebo-controlled trial of the gB/MF59 vaccine revealed a 50% efficacy in inducing sterilizing immunity. As this vaccine induces potent antibody responses but very weak T-cell responses, the partial efficacy provided by the vaccine is thought to be primarily antibody-mediated. While this HCMV vaccine is the first to show any protective efficacy, its 50% protection falls short of the 80-90% desired for most vaccines.

In addition, antibody therapy has been used to control HCMV infection in immunocompromised individuals and to reduce the pathological consequences of maternal-fetal transmission, although such therapy is usually not sufficient to eradicate the virus. HCMV immunoglobulins (Igs) have been administered to transplant patients in association with immunosuppressive treatments for prophylaxis of HCMV disease with mixed results. Antibody therapy has also been used to control brief infection and prevent disease in newborns. However, these products are plasma derivatives with relatively low potency and have to be administered by intravenous infusion at very high doses in order to deliver sufficient amounts of neutralizing antibodies.

HCMV is the leading viral cause of neurodevelopmental abnormality and other birth defects in children and the costs to society are substantial. Although antiviral therapy is available, the treatment with antiviral agents is imperfect and development of a CMV vaccine is the most promising strategy for preventing CMV infection. Given that the health and economic benefits of effective HCMV vaccines are significant, the US Institute of Medicine and US National Vaccine Program Office has categorized development of a CMV vaccine as a highest priority, but no candidate vaccine is under consideration for licensure.

SUMMARY

In view of the lack of HCMV vaccines, there is a significant need for a vaccine that would be safe and effective in all patient populations to prevent and/or to treat HCMV infection. In particular, there is a need for a vaccine that would be safe and effective for immunocompromised, at-risk pregnant women, and infant patients to prevent or to reduce the severity and/or duration of HCMV. Provided herein is a ribonucleic acid (RNA) vaccine that builds on the knowledge that RNA (e.g., messenger RNA (mRNA)) can safely direct the body's cellular machinery to produce nearly any protein of interest, from native proteins to antibodies and other entirely novel protein constructs that can have therapeutic activity inside and outside of cells. The HCMV RNA vaccines of the present disclosure may be used to induce a balanced immune response against human cytomegalovirus comprising both cellular and humoral immunity, without many of the risks associated with DNA or attenuated virus vaccination.

The RNA vaccines may be utilized in various settings depending on the prevalence of the infection or the degree or level of unmet medical need. The RNA vaccines may be utilized to treat and/or prevent a HCMV of various genotypes, strains, and isolates. The RNA vaccines have superior properties in that they produce much larger antibody titers and produce responses earlier than commercially available anti-viral therapeutic treatments. While not wishing to be bound by theory, it is believed that the RNA vaccines, as mRNA polynucleotides, are better designed to produce the appropriate protein conformation upon translation as the RNA vaccines co-opt natural cellular machinery. Unlike traditional vaccines which are manufactured ex vivo and may trigger unwanted cellular responses, the RNA vaccines are presented to the cellular system in a more native fashion.

Various human cytomegalovirus amino acid sequences encompasses by the present disclosure are provided in Tables 2, 6, 7, 8, and 9 below. RNA vaccines as provided herein may include at least one RNA polynucleotide encoding at least one of the HCMV proteins provided in Tables 2, 6, 7, 8 or 9, or a fragment, homolog (e.g., having at least 80%, 85%, 90%, 95%, 98% or 99% identity) or derivative thereof.

Some embodiments of the present disclosure provide HCMV vaccines that include at least one ribonucleic acid (RNA) polynucleotide having an open reading frame encoding at least one HCMV antigenic polypeptide or an immunogenic fragment or epitope thereof. Some embodiments of the present disclosure provide HCMV vaccines that include at least one RNA polynucleotide having an open reading frame encoding two or more HCMV antigenic polypeptides or an immunogenic fragment or epitope thereof. Some embodiments of the present disclosure provide HCMV vaccines that include two or more RNA polynucleotides having an open reading frame encoding two or more HCMV antigenic polypeptides or immunogenic fragments or epitopes thereof. The one or more HCMV antigenic polypeptides may be encoded on a single RNA polynucleotide or may be encoded individually on multiple (e.g., two or more) RNA polynucleotides.

In some embodiments, an antigenic polypeptide is an HCMV glycoprotein. For example, a HCMV glycoprotein may be selected from HCMV gH, gL, gB, gO, gN, and gM and an immunogenic fragment or epitope thereof. In some embodiments, the antigenic polypeptide is a HCMV gH polypeptide. In some embodiments, the antigenic polypeptide is a HCMV gL polypeptide. In some embodiments, the antigenic polypeptide is a HCMV gB polypeptide. In some embodiments, the antigenic polypeptide is a HCMV gO polypeptide. In some embodiments, the antigenic polypeptide is a HCMV gN polypeptide. In some embodiments, the antigenic polypeptide is a HCMV gM polypeptide. In some embodiments, the HCMV glycoprotein is encoded by a nucleic acid sequence of SEQ ID NO: 1, SEQ ID NO:2, SEQ ID NO: 3, SEQ ID NO: 4, SEQ ID NO: 5, or SEQ ID NO:6.

In some embodiments, the HCMV glycoprotein is a variant gH polypeptide, a variant gL polypeptide, or a variant gB polypeptide. In some embodiments, the variant HCMV gH, gL, or gB polypeptide is a truncated polypeptide lacking one or more of the following domain sequences: (1) the hydrophobic membrane proximal domain, (2) the transmembrane domain, and (3) the cytoplasmic domain. In some embodiments, the truncated HCMV gH, gL, or gB polypeptide lacks the hydrophobic membrane proximal domain, the transmembrane domain, and the cytoplasmic domain. In some embodiments, the truncated HCMV gH, gL, or gB polypeptide comprises only the ectodomain sequence. In some embodiments, the HCMV truncated glycoprotein is encoded by a nucleic acid sequence of SEQ ID NO: 7, SEQ ID NO:8, SEQ ID NO: 9, SEQ ID NO: 10, SEQ ID NO: 11, or SEQ ID NO:12.

In some embodiments, an antigenic polypeptide is an HCMV protein selected from UL83, UL123, UL128, UL130 and UL131A or an immunogenic fragment or epitope thereof. In some embodiments, the antigenic polypeptide is a HCMV UL83 polypeptide. In some embodiments, the antigenic polypeptide is a HCMV UL123 polypeptide. In some embodiments, the antigenic polypeptide is a HCMV UL128 polypeptide. In some embodiments, the antigenic polypeptide is a HCMV UL130 polypeptide. In some embodiments, the antigenic polypeptide is a HCMV UL131A polypeptide. In some embodiments, the HCMV protein is encoded by a nucleic acid sequence of SEQ ID NO: 13, SEQ ID NO:14, SEQ ID NO: 15, SEQ ID NO: 16, SEQ ID NO: 17, or SEQ ID NO:18.

In some embodiments, the antigenic polypeptide comprises two or more HCMV proteins, fragments, or epitopes thereof. In some embodiments, the antigenic polypeptide comprises two or more glycoproteins, fragments, or epitopes thereof. In some embodiments, the antigenic polypeptide comprises at least one HCMV glycoprotein, fragment or epitope thereof and at least one other HCMV protein, fragment or epitope thereof. In some embodiments, the two or more HCMV polypeptides are encoded by a single RNA polynucleotide. In some embodiments, the two or more HCMV polypeptides are encoded by two or more RNA polynucleotides, for example, each HCMV polypeptide is encoded by a separate RNA polynucleotide. In some embodiments, the two or more HCMV glycoproteins can be any combination of HCMV gH, gL, gB, gO, gN, and gM polypeptides or immunogenic fragments or epitopes thereof. In some embodiments, the two or more glycoproteins can be any combination of HCMV gB and one or more HCMV polypeptides selected from gH, gL, gO, gN, and gM polypeptides or immunogenic fragments or epitopes thereof. In some embodiments, the two or more glycoproteins can be any combination of HCMV gH and one or more HCMV polypeptides selected from gL, gO, gN, and gM polypeptides or immunogenic fragments or epitopes thereof. In some embodiments, the two or more glycoproteins can be any combination of HCMV gL and one or more HCMV polypeptides selected from gB, gH, gO, gN, and gM polypeptides or immunogenic fragments or epitopes thereof. In some embodiments, the two or more HCMV glycoproteins are gB and gH. In some embodiments, the two or more HCMV glycoproteins are gB and gL. In some embodiments, the two or more HCMV glycoproteins are gH and gL. In some embodiments, the two or more HCMV glycoproteins are gB, gL, and gH. In some embodiments, the two or more HCMV proteins can be any combination of HCMV UL83, UL123, UL128, UL130, and UL131A polypeptides or immunogenic fragments or epitopes thereof. In some embodiments, the two or more HCMV glycoproteins are UL123 and UL130. In some embodiments, the two or more HCMV glycoproteins are UL123 and 131A. In some embodiments, the two or more HCMV glycoproteins are UL130 and 131A. In some embodiments, the two or more HCMV glycoproteins are UL 128, UL130 and 131A. In some embodiments, the two or more HCMV proteins can be any combination of HCMV gB, gH, gL, gO, gM, gN, UL83, UL123, UL128, UL130, and UL131A polypeptides or immunogenic fragments or epitopes thereof. In some embodiments, the two or more glycoproteins can be any combination of HCMV gH and one or more HCMV polypeptides selected from gL, UL128, UL130, and UL131A polypeptides or immunogenic fragments or epitopes thereof. In some embodiments, the two or more glycoproteins can be any combination of HCMV gL and one or more HCMV polypeptides selected from gH, UL128, UL130, and UL131A polypeptides or immunogenic fragments or epitopes thereof. In some embodiments, the two or more HCMV glycoproteins are gL, gH, UL 128, UL130 and 131A. In any of these embodiments in which the vaccine comprises two or more HCMV proteins, the HCMV gH may be a variant gH, such as any of the variant HCMV gH glycoproteins disclosed herein, for example, any of the variant HCMV gH disclosed in the preceding paragraphs and in the Examples. In any of these embodiments in which the vaccine comprises two or more HCMV proteins, the HCMV gB may be a variant gB, such as any of the variant HCMV gB glycoproteins disclosed herein, for example, any of the variant HCMV gB disclosed in the preceding paragraphs and in the Examples. In any of these embodiments in which the vaccine comprises two or more HCMV gL proteins, the HCMV gL may be a variant gL, such as any of the variant HCMV gL glycoproteins disclosed herein, for example, any of the variant HCMV gL disclosed in the preceding paragraphs and in the Examples.

In certain embodiments in which the HCMV vaccine includes two or more RNA polynucleotides having an open reading frame encoding two or more HCMV antigenic polypeptides or an immunogenic fragment or epitope thereof (either encoded by a single RNA polynucleotide or encoded by two or more RNA polynucleotides, for example, each protein encoded by a separate RNA polynucleotide), the two or more HCMV proteins are a variant gB, for example, any of the variant gB polypeptides disclosed herein in the preceding paragraphs, and a HCMV protein selected from gH, gL, gO, gM, gN, UL128, UL130, and UL131A polypeptides or immunogenic fragments or epitopes thereof. In some embodiments, the two or more HCMV proteins are a variant gH, for example, any of the variant gH polypeptides disclosed herein in the preceding paragraphs, and a HCMV protein selected from gH, gL, gO, gM, gN, UL128, UL130, and UL131A polypeptides or immunogenic fragments or epitopes thereof. In some embodiments, the two or more HCMV proteins are a variant gH, for example, any of the variant gH polypeptides disclosed herein in the preceding paragraphs, and a HCMV protein selected from gH, gL, gO, gM, gN, UL128, UL130, and UL131A polypeptides or immunogenic fragments or epitopes thereof. In some embodiments in which the variant HCMV proteins are variant HCMV gB, variant HCMV gL, and variant HCMV gH, the variant HCMV polypeptide is a truncated polypeptide selected from the following truncated polypeptides: lacks the hydrophobic membrane proximal domain; lacks the transmembrane domain; lacks the cytoplasmic domain; lacks two or more of the hydrophobic membrane proximal, transmembrane, and cytoplasmic domains; and comprises only the ectodomain.

In some embodiments, the HCMV vaccine includes multimeric RNA polynucleotides having an open reading frame encoding at least one HCMV antigenic polypeptide or an immunogenic fragment or epitope thereof. Some embodiments of the present disclosure provide HCMV vaccines that include at least one ribonucleic acid (RNA) polynucleotide having an open reading frame encoding at least one HCMV antigenic polypeptide or an immunogenic fragment or epitope thereof, wherein the 5'UTR of the RNA polynucleotide comprises a patterned UTR. In some embodiments, the patterned UTR has a repeating or alternating pattern, such as ABABAB or AABBAABBAABB or ABCABCABC or variants thereof repeated once, twice, or more than 3 times. In these patterns, each letter, A, B, or C represent a different UTR at the nucleotide level. In some embodiments, the 5'UTR of the RNA polynucleotide (e.g., a first nucleic acid) has regions of complementarity with a UTR of another RNA polynucleotide (a second nucleic acid). For example, UTR nucleotide sequences of two polynucleotides sought to be joined (e.g., in a multimeric molecule) can be modified to include a region of complementarity such that the two UTRs hybridize to form a multimeric molecule.

In some embodiments, the 5'UTR of an RNA polynucleotide encoding an HCMV antigenic polypeptide is modified to allow the formation of a multimeric sequence. In some embodiments, the 5'UTR of an RNA polynucleotide encoding an HCMV protein selected from UL128, UL130, UL131A1 is modified to allow the formation of a multimeric sequence. In some embodiments, the 5'UTR of an RNA polynucleotide encoding an HCMV glycoprotein is modified to allow the formation of a multimeric sequence. In some embodiments, the 5'UTR of an RNA polynucleotide encoding an HCMV glycoprotein selected from gH, gL, gB, gO, gM, and gN is modified to allow the formation of a multimeric sequence. In any of these embodiments, the multimer may be a dimer, a trimer, pentamer, hexamer, heptamer, octamer nonamer, or decamer. Thus, in some embodiments, the 5'UTR of an RNA polynucleotide encoding an HCMV protein selected from gH, gL, gB, gO, gM, gN, UL128, UL130, and UL131A1 is modified to allow the formation of a dimer. In some embodiments, the 5'UTR of an RNA polynucleotide encoding an HCMV protein selected from gH, gL, gB, gO, gM, gN, UL128, UL130, and UL131A1 is modified to allow the formation of a trimer. In some embodiments, the 5'UTR of an RNA polynucleotide encoding an HCMV protein selected from gH, gL, gB, gO, gM, gN, UL128, UL130, and UL131A1 is modified to allow the formation of a pentamer. Exemplary HCMV nucleic acids having modified 5'UTR sequence for the formation of a multimeric molecule (e.g., dimers, trimers, pentamers, etc) comprise SEQ ID Nos: 19-26.

In any of the above-described embodiments, the HCMV RNA polynucleotides may further comprise additional sequences, for example, one or more linker sequences or one or more sequence tags, such as FLAG-tag and histidine tag.

Some embodiments of the present disclosure provide HCMV vaccines that include at least one ribonucleic acid (RNA) polynucleotide having a single open reading frame encoding two or more (for example, two, three, four, five, or more) HCMV antigenic polypeptides or an immunogenic fragment or epitope thereof. Some embodiments of the present disclosure provide HCMV vaccines that include at least one ribonucleic acid (RNA) polynucleotide having more than one open reading frame, for example, two, three, four, five or more open reading frames encoding two, three, four, five or more HCMV antigenic polypeptides. In either of these embodiments, the at least one RNA polynucleotide may encode two or more HCMV antigenic polypeptides selected from gH, gB, gL, gO, gM, gN, UL83, UL123, UL128, UL130, UL131A, and fragments or epitopes thereof. In some embodiments, the at least one RNA polynucleotide encodes UL83 and UL123. In some embodiments, the at least one RNA polynucleotide encodes gH and gL. In some embodiments, the at least one RNA polynucleotide encodes UL128, UL130, and UL131A. In some embodiments, the at least one RNA polynucleotide encodes gH, gL, UL128, UL130, and UL131A. In some embodiments, in which the at least one RNA polynucleotide has a single open reading frame encoding two or more (for example, two, three, four, five, or more) HCMV antigenic polypeptides, the RNA polynucleotide further comprises additional sequence, for example, a linker sequence or a sequence that aids in the processing of the HCMV RNA transcripts or polypeptides, for example a cleavage site sequence. In some embodiments, the additional sequence may be a protease sequence, such as a furin sequence. In some embodiments, the additional sequence may be self-cleaving 2A peptide, such as a P2A, E2A, F2A, and T2A sequence. In some embodiments, the linker sequences and cleavage site sequences are interspersed between the sequences encoding HCMV polypeptides. In some embodiments, the RNA polynucleotide is encoded by SEQ ID NO: 27, SEQ ID NO: 28, SEQ ID NO: 29, SEQ ID NO: 30 or SEQ ID NO: 31.

In some embodiments, at least one RNA polynucleotide is encoded by at least one nucleic acid sequence selected from any of SEQ ID NOs: 1-31, 58, 60, 62, 64, 66, 68, 70, 72, 76, and 84-144 and homologs having at least 80% (e.g., 85%, 90%, 95%, 98%, 99%) identity with a nucleic acid sequence selected from SEQ ID NOs:1-31, 58, 60, 62, 64, 66, 68, 70, 72, 76, and 84-144. In some embodiments, at least one RNA polynucleotide is encoded by at least one nucleic acid sequence selected from any of SEQ ID NOs: 1-31, 58, 60, 62, 64, 66, 68, 70, 72, 76, and 84-144 and homologs having at least 90% (90%, 91%, 92%, 93%, 94%, 95%, 96%, 97%, 98%, 99%, 99.8% or 99.9%) identity with a nucleic acid sequence selected from SEQ ID NO:1-31, 58, 60, 62, 64, 66, 68, 70, 72, 76, and 84-144. In some embodiments, at least one RNA polynucleotide is encoded by at least one fragment of a nucleic acid sequence selected from any of SEQ ID NOs: 1-31, 58, 60, 62, 64, 66, 68, 70, 72, 76, and 84-144 and homologs having at least 80% (e.g., 85%, 90%, 95%, 98%, 99%) identity with a nucleic acid sequence selected from SEQ ID NO:1-31, 58, 60, 62, 64, 66, 68, 70, 72, 76, and 84-144.

In some embodiments, at least one RNA polynucleotide is encoded by at least one nucleic acid sequence selected from any of nucleic acids disclosed herein, or homologs having at least 80% (e.g., 85%, 90%, 95%, 98%, 99%) identity with a nucleic acid sequence disclosed herein.

In any of the above-described embodiments in the preceding paragraphs, the HCMV RNA polynucleotides may further comprise additional sequences, for example, one or more linker sequences or one or more sequence tags, such as FLAG-tag and histidine tag.

In some embodiments, at least one RNA polynucleotide encodes an antigenic polypeptide having at least 90% identity to the amino acid sequence of any of SEQ ID NOs: 32-52. In some embodiments, at least one RNA polynucleotide encodes an antigenic polypeptide having at least 95% identity to the amino acid sequence of any of SEQ ID NOs: 32-52. In some embodiments, at least one RNA polynucleotide encodes an antigenic polypeptide having at least 96% identity to the amino acid sequence of any of SEQ ID NOs:32-52. In some embodiments, at least one RNA polynucleotide encodes an antigenic polypeptide having at least 97% identity to the amino acid sequence of any of SEQ ID NOs: 32-52. In some embodiments, at least one RNA polynucleotide encodes an antigenic polypeptide having at least 98% identity to the amino acid sequence of SEQ ID NOs: 32-52. In some embodiments, at least one RNA polynucleotide encodes an antigenic polypeptide having at least 99% identity to the amino acid sequence of SEQ ID Nos: 32-52.

In some embodiments, the open reading from which the HCMV polypeptide is encoded is codon-optimized. In some embodiments, the at least one RNA polynucleotide encodes an antigenic protein of SEQ ID NO: 32, and wherein the RNA polynucleotide is codon optimized mRNA. In some embodiments, the at least one RNA polynucleotide encodes an antigenic protein of SEQ ID NO: 33, and wherein the RNA polynucleotide is codon optimized mRNA. In some embodiments, the at least one RNA polynucleotide encodes an antigenic protein of SEQ ID NO: 34, and wherein the RNA polynucleotide is codon optimized mRNA. In some embodiments, the at least one RNA polynucleotide encodes an antigenic protein of SEQ ID NO: 38, and wherein the RNA polynucleotide is codon optimized mRNA. In some embodiments, the at least one RNA polynucleotide encodes an antigenic protein of SEQ ID NO: 40, and wherein the RNA polynucleotide is codon optimized mRNA. In some embodiments, the at least one RNA polynucleotide encodes an antigenic protein of SEQ ID NO: 42, and wherein the RNA polynucleotide is codon optimized mRNA. In some embodiments, the at least one RNA polynucleotide encodes an antigenic protein of SEQ ID NO: 47, and wherein the RNA polynucleotide is codon optimized mRNA. In some embodiments, the at least one RNA polynucleotide encodes an antigenic protein of SEQ ID NO: 50, and wherein the RNA polynucleotide is codon optimized mRNA.

In some embodiments, the at least one RNA polynucleotide encodes an antigenic protein of SEQ ID NO: 32, and wherein the RNA polynucleotide has less than 80% identity to wild-type mRNA sequence. In some embodiments, the at least one RNA polynucleotide encodes an antigenic protein of SEQ ID NO: 32, and wherein the RNA polynucleotide has greater than 80% identity to wild-type mRNA sequence, but does not include wild-type mRNA sequence.

In some embodiments, the at least one RNA polynucleotide encodes an antigenic protein of SEQ ID NO: 33, and wherein the RNA polynucleotide has less than 80% identity to wild-type mRNA sequence. In some embodiments, the at least one RNA polynucleotide encodes an antigenic protein of SEQ ID NO: 33, and wherein the RNA polynucleotide has greater than 80% identity to wild-type mRNA sequence, but does not include wild-type mRNA sequence.

In some embodiments, the at least one RNA polynucleotide encodes an antigenic protein of SEQ ID NO: 34, and wherein the RNA polynucleotide has less than 80% identity to wild-type mRNA sequence. In some embodiments, the at least one RNA polynucleotide encodes an antigenic protein of SEQ ID NO: 34, and wherein the RNA polynucleotide has greater than 80% identity to wild-type mRNA sequence, but does not include wild-type mRNA sequence.

In some embodiments, the at least one RNA polynucleotide encodes an antigenic protein of SEQ ID NO: 38, and wherein the RNA polynucleotide has less than 80% identity to wild-type mRNA sequence. In some embodiments, the at least one RNA polynucleotide encodes an antigenic protein of SEQ ID NO: 38, and wherein the RNA polynucleotide has greater than 80% identity to wild-type mRNA sequence, but does not include wild-type mRNA sequence.

In some embodiments, the at least one RNA polynucleotide encodes an antigenic protein of SEQ ID NO: 40, and wherein the RNA polynucleotide has less than 80% identity to wild-type mRNA sequence. In some embodiments, the at least one RNA polynucleotide encodes an antigenic protein of SEQ ID NO: 40, and wherein the RNA polynucleotide has greater than 80% identity to wild-type mRNA sequence, but does not include wild-type mRNA sequence.

In some embodiments, the at least one RNA polynucleotide encodes an antigenic protein of SEQ ID NO: 42, and wherein the RNA polynucleotide has less than 80% identity to wild-type mRNA sequence. In some embodiments, the at least one RNA polynucleotide encodes an antigenic protein of SEQ ID NO: 42, and wherein the RNA polynucleotide has greater than 80% identity to wild-type mRNA sequence, but does not include wild-type mRNA sequence.

In some embodiments, the at least one RNA polynucleotide is encoded by a sequence selected from SEQ ID NO: 1-31 and 84-144 and includes at least one chemical modification.

In some embodiments, the HCMV vaccine is multivalent. In some embodiments, the RNA polynucleotide comprises a polynucleotide sequence derived from a virus strain or isolate selected from VR1814 VR6952, VR3480B1 (ganciclovir resistant), VR4760 (ganciclovir and foscarnet resistant), Towne, TB40/E, AD169, Merlin, and Toledo.

Some embodiments of the present disclosure provide a HCMV vaccine that includes at least one ribonucleic acid (RNA) polynucleotide having an open reading frame encoding at least one HCMV antigenic polypeptide or an immunogenic fragment thereof and at least one 5' terminal cap. In some embodiments, a 5' terminal cap is 7mG(5')ppp(5')NlmpNp.

Some embodiments of the present disclosure provide a HCMV vaccine that includes at least one ribonucleic acid (RNA) polynucleotide having an open reading frame encoding at least one HCMV antigenic polypeptide or an immunogenic fragment thereof, wherein the at least one ribonucleic acid (RNA) polynucleotide has at least one chemical modification. In some embodiments, the at least one ribonucleic acid (RNA) polynucleotide further comprises a second chemical modification. In some embodiments, the at least one ribonucleic acid (RNA) polynucleotide having at least one chemical modification has a 5' terminal cap. In some embodiments, the at least one chemical modification is selected from pseudouridine, N1-methylpseudouridine, N1-ethylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine.

Some embodiments of the present disclosure provide a HCMV vaccine that includes at least one ribonucleic acid (RNA) polynucleotide having an open reading frame encoding at least one HCMV antigenic polypeptide or an immunogenic fragment thereof, wherein at least 80% (e.g., 85%, 90%, 95%, 98%, 99%, 100%) of the uracil in the open reading frame have a chemical modification, optionally wherein the vaccine is formulated in a lipid nanoparticle. In some embodiments, 100% of the uracil in the open reading frame have a chemical modification. In some embodiments, a chemical modification is in the 5-position of the uracil. In some embodiments, a chemical modification is a N1-methyl pseudouridine.

Some embodiments of the present disclosure provide a HCMV vaccine that is formulated within a cationic lipid nanoparticle, also referred to herein as ionizable cationic lipid nanoparticles, ionizable lipid nanoparticles and lipid nanoparticles, which are used interchangeably. In some embodiments, the lipid nanoparticle comprises a cationic lipid, a PEG-modified lipid, a sterol and a non-cationic lipid. In some embodiments, the cationic lipid is an ionizable cationic lipid and the non-cationic lipid is a neutral lipid, and the sterol is a cholesterol. In some embodiments, the cationic lipid is selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319). In some embodiments, the lipid nanoparticle has a molar ratio of about 20-60% cationic lipid, about 5-25% non-cationic lipid, about 25-55% sterol, and about 0.5-15% PEG-modified lipid. In some embodiments, the nanoparticle has a polydiversity value of less than 0.4. In some embodiments, the nanoparticle has a net neutral charge at a neutral pH. In some embodiments, the nanoparticle has a mean diameter of 50-200 nm.

Some embodiments of the present disclosure provide methods of inducing an antigen specific immune response in a subject, comprising administering to the subject a HCMV RNA vaccine in an amount effective to produce an antigen specific immune response. In some embodiments, an antigen specific immune response comprises a T cell response or a B cell response. In some embodiments, an antigen specific immune response comprises a T cell response and a B cell response. In some embodiments, a method of producing an antigen specific immune response involves a single administration of the vaccine. In some embodiments, a method further includes administering to the subject a booster dose of the vaccine. In some embodiments, a vaccine is administered to the subject by intradermal or intramuscular injection.

Also provided herein are HCMV RNA vaccines for use in a method of inducing an antigen specific immune response in a subject, the method comprising administering the vaccine to the subject in an amount effective to produce an antigen specific immune response.

Further provided herein are uses of HCMV RNA vaccines in the manufacture of a medicament for use in a method of inducing an antigen specific immune response in a subject, the method comprising administering the vaccine to the subject in an amount effective to produce an antigen specific immune response.

Further provided herein are methods of preventing or treating HCMV infection comprising administering to a subject the vaccine of the present disclosure.

The HCMV vaccine disclosed herein may be formulated in an effective amount to produce an antigen specific immune response in a subject.

In some embodiments, an anti-HCMV antigenic polypeptide antibody titer produced in the subject is increased by at least 1 log relative to a control. In some embodiments, the anti-HCMV antigenic polypeptide antibody titer produced in the subject is increased by 1-3 log relative to a control. In some embodiments, an anti-HCMV antigenic polypeptide antibody titer produced in the subject is increased at least 2 times relative to a control. In some embodiments, the anti-HCMV antigenic polypeptide antibody titer produced in the subject is increased at least 5 times relative to a control. In some embodiments, the anti-HCMV antigenic polypeptide antibody titer produced in the subject is increased at least 10 times relative to a control. In some embodiments, the anti-HCMV antigenic polypeptide antibody titer produced in the subject is increased 2-10 times relative to a control.

In some embodiments, the control is an anti-HCMV antigenic polypeptide antibody titer produced in a subject who has not been administered HCMV vaccine.

In some embodiments, the control is an anti-HCMV antigenic polypeptide antibody titer produced in a subject who has been administered a live attenuated or inactivated HCMV vaccine.

In some embodiments, the control is an anti-HCMV antigenic polypeptide antibody titer produced in a subject who has been administered a recombinant or purified HCMV protein vaccine.

In some embodiments, the effective amount is a dose equivalent to an at least 2-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 4-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 10-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 100-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 1000-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to a 2-1000-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a total dose of 50-1000 μg. In some embodiments, the effective amount is a total dose of 100 μg. In some embodiments, the effective amount is a dose of 25 μg administered to the subject a total of two times. In some embodiments, the effective amount is a dose of 100 μg administered to the subject a total of two times. In some embodiments, the effective amount is a dose of 400 μg administered to the subject a total of two times. In some embodiments, the effective amount is a dose of 500 μg administered to the subject a total of two times.

Other aspects of the present disclosure provide methods of inducing an antigen specific immune response in a subject, including administering to a subject the HCMV vaccine disclosed herein in an effective amount to produce an antigen specific immune response in a subject.

In some embodiments, an anti-HCMV antigenic polypeptide antibody titer produced in the subject is increased by at least 1 log relative to a control. In some embodiments, an anti-HCMV antigenic polypeptide antibody titer produced in the subject is increased by 1-3 log relative to a control. In some embodiments, an anti-HCMV antigenic polypeptide antibody titer produced in the subject is increased at least 2 times relative to a control. In some embodiments, the anti-HCMV antigenic polypeptide antibody titer produced in the subject is increased at least 5 times relative to a control. In some embodiments, the anti-HCMV antigenic polypeptide antibody titer produced in the subject is increased at least 10 times relative to a control. In some embodiments, the anti-HCMV antigenic polypeptide antibody titer produced in the subject is increased 2-10 times relative to a control.

In some embodiments, the control is an anti-HCMV antigenic polypeptide antibody titer produced in a subject who has not been administered HCMV vaccine.

In some embodiments, the control is an anti-HCMV antigenic polypeptide antibody titer produced in a subject who has been administered a live attenuated or inactivated HCMV vaccine.

In some embodiments, the control is an anti-HCMV antigenic polypeptide antibody titer produced in a subject who has been administered a recombinant or purified HCMV protein vaccine.

In some embodiments, the effective amount is a dose equivalent to an at least 2-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant HCMV protein vaccine or a live attenuated HCMV vaccine.

In some embodiments, the effective amount is a dose equivalent to an at least 4-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 10-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 100-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 1000-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to a 2-1000-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a total dose of 50-1000 μg. In some embodiments, the effective amount is a total dose of 100 μg. In some embodiments, the effective amount is a dose of 25 μg administered to the subject a total of two times. In some embodiments, the effective amount is a dose of 100 μg administered to the subject a total of two times. In some embodiments, the effective amount is a dose of 400 μg administered to the subject a total of two times. In some embodiments, the effective amount is a dose of 500 μg administered to the subject a total of two times.

Other aspects of the present disclosure provide HCMV vaccines containing a signal peptide linked to a HCMV antigenic polypeptide.

In some embodiments, the HCMV antigenic polypeptide is a HCMV glycoprotein or an antigenic fragment thereof. In some embodiments, the HCMV antigenic polypeptide is a HCMV gB, gM, gN, gH, gL, gO, UL 83, UL123, UL128, UL130, or UL131A protein or an antigenic fragment or epitope thereof. In some embodiments, the HCMV glycoprotein is selected from HCMV gB, gM, gN, gH, gL, and gO.

In some embodiments, the HCMV glycoprotein is HCMV gH. In some embodiments, the HCMV glycoprotein is HCMV gL. In some embodiments, the HCMV glycoprotein is HCMV gB. In some embodiments, the HCMV protein is HCMV UL128. In some embodiments, the HCMV protein is HCMV UL130. In some embodiments, the HCMV protein is HCMV UL131A. In some embodiments, the HCMV protein is HCMV UL83. In some embodiments, the HCMV protein is HCMV UL123. In some embodiments, the HCMV glycoprotein is a variant HCMV gH polypeptide. In some embodiments, the HCMV glycoprotein is a variant HCMV gL polypeptide. In some embodiments, the HCMV glycoprotein is a variant HCMV gB polypeptide.

In some embodiments, the signal peptide is an IgE signal peptide. In some embodiments, the signal peptide is an IgE HC (Ig heavy chain epsilon-1) signal peptide. In some embodiments, the signal peptide has the amino acid sequence MDWTWILFLVAAATRVHS (SEQ ID NO: 53).

In some embodiments, the signal peptide is an IgGκ signal peptide. In some embodiments, the signal peptide has the amino acid sequence METPAQLLFLLLLWLPDTTG (SEQ ID NO: 54).

In some embodiments, the HCMV vaccine comprises at least one RNA polynucleotide encoding gH, gL, UL128, UL130, and UL131A, or antigenic fragments or epitopes thereof, and at least one RNA polynucleotide encoding gB, or an antigenic fragment or epitope thereof.

Further provided herein are uses of HCMV vaccines for prevention of congenital HCMV infection. Further provided herein are methods of administering HCMV vaccines to a women of child-bearing age.

Aspects of the invention relate to a human cytomegalovirus (HCMV) vaccine comprising: i) at least one RNA polynucleotide having one or more open reading frames encoding HCMV antigenic polypeptides gH, gL, UL128, UL130, and/or UL131A, or antigenic fragments or epitopes thereof; ii) an RNA polynucleotide having an open reading frame encoding HCMV antigenic polypeptide gB, or an antigenic fragment or epitope thereof; iii) an RNA polynucleotide having an open reading frame encoding HCMV antigenic polypeptide pp65, or an antigenic fragment or epitope thereof, and iv) a pharmaceutically acceptable carrier or excipient.

In some embodiments, the vaccine comprises: an RNA polynucleotide having an open reading frame encoding HCMV antigenic polypeptide gH, or an antigenic fragment or epitope thereof; an RNA polynucleotide having an open reading frame encoding HCMV antigenic polypeptide gL, or an antigenic fragment or epitope thereof; an RNA polynucleotide having an open reading frame encoding HCMV antigenic polypeptide UL128, or an antigenic fragment or epitope thereof; an RNA polynucleotide having an open reading frame encoding HCMV antigenic polypeptide UL130, or an antigenic fragment or epitope thereof; and an RNA polynucleotide having an open reading frame encoding HCMV antigenic polypeptide UL131A, or an antigenic fragment or epitope thereof.

In some embodiments, at least one RNA polynucleotide has an open reading frame encoding two or more HCMV antigenic polypeptides. In some embodiments, one or more of the open reading frames is codon-optimized. In some embodiments, the pp65 polypeptide contains a deletion of amino acids 435-438. In some embodiments, at least one RNA polynucleotide is encoded by at least one nucleic acid sequence selected from SEQ ID NOs: 58, 60, 62, 64, 66, 68, 70, and 84-144. In some embodiments, at least one of the RNA polynucleotides encodes an antigenic polypeptide having at least 90% identity to any of the amino acid sequences of SEQ ID NO: 59, SEQ ID NO: 61, SEQ ID NO: 63, SEQ ID NO: 65, SEQ ID NO: 67, SEQ ID NO: 69, SEQ ID NO: 71, and 80-83.

In some embodiments, at least one of the RNA polynucleotides encodes an antigenic polypeptide having at least 95% identity to any of the amino acid sequences of SEQ ID NO: 59, SEQ ID NO: 61, SEQ ID NO: 63, SEQ ID NO: 65, SEQ ID NO: 67, SEQ ID NO: 69, SEQ ID NO: 71, and 80-83. In some embodiments, at least one of the RNA polynucleotides encodes an antigenic polypeptide having at least 96% identity to any of the amino acid sequences of SEQ ID NO: 59, SEQ ID NO: 61, SEQ ID NO: 63, SEQ ID NO: 65, SEQ ID NO: 67, SEQ ID NO: 69, SEQ ID NO: 71, and 80-83. In some embodiments, at least 97% identity to any of the amino acid sequences of SEQ ID NO: 59, SEQ ID NO: 61, SEQ ID NO: 63, SEQ ID NO: 65, SEQ ID NO: 67, SEQ ID NO: 69, SEQ ID NO: 71, and 80-83. In some embodiments, at least 98% identity to any of the amino acid sequences SEQ ID NO: 59, SEQ ID NO: 61, SEQ ID NO: 63, SEQ ID NO: 65, SEQ ID NO: 67, SEQ ID NO: 69, SEQ ID NO: 71, and 80-83. In some embodiments, at least 99% identity to any of the amino acid sequences of SEQ ID NO: 59, SEQ ID NO: 61, SEQ ID NO: 63, SEQ ID NO: 65, SEQ ID NO: 67, SEQ ID NO: 69, SEQ ID NO: 71, and 80-83.

In some embodiments, at least one RNA polynucleotide encodes an antigenic protein of SEQ ID NOs: 59, 61, 63, 65, or 67 and the RNA polynucleotide has less than 80% identity to wild-type mRNA sequence or has greater than 80% identity to wild-type mRNA sequence, but does not include wild-type mRNA sequence. In some embodiments, at least one RNA polynucleotide encodes an antigenic protein of SEQ ID NO.: 69, and wherein the RNA polynucleotide has less than 80% identity to wild-type mRNA sequence or has greater than 80% identity to wild-type mRNA sequence, but does not include wild-type mRNA sequence. In some embodiments, at least one RNA polynucleotide encodes an antigenic protein of SEQ ID NO.: 71, and wherein the RNA polynucleotide has less than 80% identity to wild-type mRNA sequence or has greater than 80% identity to wild-type mRNA sequence, but does not include wild-type mRNA sequence.

In some embodiments, at least one RNA polynucleotide includes at least one chemical modification. In some embodiments, the vaccine is multivalent. In some embodiments, the RNA polynucleotide comprises a polynucleotide sequence derived from a virus strain or isolate selected from VR1814, VR6952, VR3480B1, VR4760, Towne, TB40/E, AD169, Merlin, and Toledo. In some embodiments, the HCMV vaccine further comprises a second chemical modification.

In some embodiments, the chemical modification is selected from the group consisting of pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, and 2'-O-methyl uridine.

In some embodiments, 80% of the uracil in the open reading frame have a chemical modification. In some embodiments, 100% of the uracil in the open reading frame have a chemical modification. In some embodiments, the chemical modification is in the 5-position of the uracil. In some embodiments, the chemical modification is N1-methylpseudouridine, N1-ethylpseudouridine. In some embodiments, the vaccine is formulated within a lipid nanoparticle. In some embodiments, the lipid nanoparticle comprises a cationic lipid, a PEG-modified lipid, a sterol and a non-cationic lipid. In some embodiments, the cationic lipid is an ionizable cationic lipid and the non-cationic lipid is a neutral lipid, and the sterol is a cholesterol. In some embodiments, the cationic lipid is selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319).

In some embodiments, the lipid nanoparticle has a molar ratio of about 20-60% cationic lipid, about 5-25% non-cationic lipid, about 25-55% sterol, and about 0.5-15% PEG-modified lipid. In some embodiments, the nanoparticle has a polydiversity value of less than 0.4. In some embodiments, the nanoparticle has a net neutral charge at a neutral pH. In some embodiments, the nanoparticle has a mean diameter of 50-200 nm.

Aspects of the invention relate to methods of inducing an antigen specific immune response in a subject, comprising administering any of the vaccines described herein to the subject in an effective amount to produce an antigen specific immune response. In some embodiments of methods described herein, the antigen specific immune response comprises a T cell response. In some embodiments of methods described herein, the antigen specific immune response comprises a B cell response. In some embodiments of methods described herein, the antigen specific immune response comprises a T cell response and a B cell response.

In some embodiments of methods described herein, the method of producing an antigen specific immune response involves a single administration of the vaccine. In some embodiments of methods described herein, methods further comprise administering a booster dose of the vaccine. In some embodiments of methods described herein, the vaccine is administered to the subject by intradermal or intramuscular injection.

Aspects of the invention relate to HCMV vaccines for use in a method of inducing an antigen specific immune response in a subject, the method comprising administering the vaccine to the subject in an effective amount to produce an antigen specific immune response.

Aspects of the invention relate to use of an HCMV vaccine described herein in the manufacture of a medicament for use in a method of inducing an antigen specific immune response in a subject, the method comprising administering the vaccine to the subject in an effective amount to produce an antigen specific immune response.

Aspects of the invention relate to methods of preventing or treating HCMV infection comprising administering to a subject any of the vaccines described herein.

Aspects of the invention relate to HCMV vaccines formulated in an effective amount to produce an antigen specific immune response in a subject. In some embodiments, an anti-HCMV antigenic polypeptide antibody titer produced in the subject is increased by at least 1 log relative to a control, or 1-3 log relative to a control. In some embodiments, an anti-HCMV antigenic polypeptide antibody titer produced in the subject is increased at least 2 times relative to a control, at least 5 times relative to a control, at least 10 times relative to a control, or 2-10 times relative to a control.

In some embodiments, the control is an anti-HCMV antigenic polypeptide antibody titer produced in a subject who has not been administered HCMV vaccine. In some embodiments, the control is an anti-HCMV antigenic polypeptide antibody titer produced in a subject who has been administered a live attenuated or inactivated HCMV vaccine. In some embodiments, the control is an anti-HCMV antigenic polypeptide antibody titer produced in a subject who has been administered a recombinant or purified HCMV protein vaccine.

In some embodiments, the effective amount is a dose equivalent to an at least 2-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 4-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 10-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 100-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 1000-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to a 2-1000-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a total dose of 50-1000 μg. In some embodiments, the effective amount is a total dose of 100 μg. In some embodiments, the effective amount is a dose of 25 μg administered to the subject a total of two times. In some embodiments, the effective amount is a dose of 100 μg administered to the subject a total of two times. In some embodiments, the effective amount is a dose of 400 μg administered to the subject a total of two times. In some embodiments, the effective amount is a dose of 500 μg administered to the subject a total of two times.

In some embodiments of methods disclosed herein, an anti-HCMV antigenic polypeptide antibody titer produced in the subject is increased by at least 1 log relative to a control or by 1-3 log relative to a control. In some embodiments of methods disclosed herein, an anti-HCMV antigenic polypeptide antibody titer produced in the subject is increased at least 2 times relative to a control, at least 5 times relative to a control, at least 10 times relative to a control, or 2-10 times relative to a control.

In some embodiments of methods disclosed herein, the control is an anti-HCMV antigenic polypeptide antibody titer produced in a subject who has not been administered HCMV vaccine. In some embodiments of methods disclosed herein, the control is an anti-HCMV antigenic polypeptide antibody titer produced in a subject who has been administered a live attenuated or inactivated HCMV vaccine. In some embodiments of methods disclosed herein, the control is an anti-HCMV antigenic polypeptide antibody titer produced in a subject who has been administered a recombinant or purified HCMV protein vaccine.

In some embodiments of methods disclosed herein, the effective amount is a dose equivalent to an at least 2-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant HCMV protein vaccine or a live attenuated HCMV vaccine.

In some embodiments of methods disclosed herein, the effective amount is a dose equivalent to an at least 4-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments of methods disclosed herein, the effective amount is a dose equivalent to an at least 10-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments of methods disclosed herein, the effective amount is a dose equivalent to an at least 100-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments of methods disclosed herein, the effective amount is a dose equivalent to an at least 1000-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments of methods disclosed herein, the effective amount is a dose equivalent to a 2-1000-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments of methods disclosed herein, the effective amount is a total dose of 50-1000 μg. In some embodiments of methods disclosed herein, the effective amount is a total dose of 100 μg. In some embodiments of methods disclosed herein, the effective amount is a dose of 25 μg administered to the subject a total of two times. In some embodiments of methods disclosed herein, the effective amount is a dose of 100 μg administered to the subject a total of two times. In some embodiments of methods disclosed herein, the effective amount is a dose of 400 μg administered to the subject a total of two times. In some embodiments of methods disclosed herein, the effective amount is a dose of 500 μg administered to the subject a total of two times.

Aspects of the invention relate to an HCMV vaccine, comprising: i) HCMV antigenic polypeptides gH, gL, UL128, UL130, and/or UL131A, or antigenic fragments or epitopes thereof; ii) HCMV antigenic polypeptide gB, or an antigenic fragment or epitope thereof; and iii) HCMV antigenic polypeptide pp65, or an antigenic fragment or epitope thereof.

In some embodiments, one or more of the HCMV antigenic polypeptides comprises a signal sequence linked to the HCMV antigenic polypeptide, optionally wherein the signal peptide is an IgE signal peptide. In some embodiments, the signal peptide is an IgE HC (Ig heavy chain epsilon-1) signal peptide. In some embodiments, the signal peptide has the amino acid sequence MDWTWILFLVAAATRVHS (SEQ ID NO: 53). In some embodiments, the signal peptide is an IgGκ signal peptide. In some embodiments, the signal peptide has the amino acid sequence METPAQLLFLLLLWLPDTTG (SEQ ID NO: 54). In some embodiments, the pp65 polypeptide contains a deletion of amino acids 435-438.

In some embodiments of methods disclosed herein, the subject is an immunocompromised organ transplant recipient. In some embodiments of methods disclosed herein, the transplant recipient is a hematopoietic cell transplant recipient or a solid organ transplant recipient.

Aspects of the invention relate to methods of treating an immunocompromised organ transplant recipient subject having a cytomegalovirus (CMV) infection, comprising administering to the subject a therapeutically effective amount of a human cytomegalovirus (HCMV) vaccine comprising: i) at least one RNA polynucleotide having one or more open reading frames encoding HCMV antigenic polypeptides gH, gL, UL128, UL130, and/or UL131A, or antigenic fragments or epitopes thereof; ii) an RNA polynucleotide having an open reading frame encoding HCMV antigenic polypeptide gB, or an antigenic fragment or epitope thereof; iii) an RNA polynucleotide having an open reading frame encoding HCMV antigenic polypeptide pp65, or an antigenic fragment or epitope thereof; and iv) a pharmaceutically acceptable carrier or excipient.

In some embodiments of methods disclosed herein, the vaccine comprises: an RNA polynucleotide having an open reading frame encoding HCMV antigenic polypeptide gH, or an antigenic fragment or epitope thereof; an RNA polynucleotide having an open reading frame encoding HCMV antigenic polypeptide gL, or an antigenic fragment or epitope thereof; an RNA polynucleotide having an open reading frame encoding HCMV antigenic polypeptide UL128, or an antigenic fragment or epitope thereof; an RNA polynucleotide having an open reading frame encoding HCMV antigenic polypeptide UL130, or an antigenic fragment or epitope thereof; and an RNA polynucleotide having an open reading frame encoding HCMV antigenic polypeptide UL131A, or an antigenic fragment or epitope thereof.

In some embodiments of methods disclosed herein, at least one RNA polynucleotide has an open reading frame encoding two or more HCMV antigenic polypeptides. In some embodiments of methods disclosed herein, one or more of the open reading frames is codon-optimized. In some embodiments of methods disclosed herein, the pp65 polypeptide contains a deletion of amino acids 435-438.

In some embodiments the nucleic acid vaccines described herein are chemically modified. In other embodiments the nucleic acid vaccines are unmodified.

Yet other aspects provide compositions for and methods of vaccinating a subject comprising administering to the subject a nucleic acid vaccine comprising one or more RNA polynucleotides having an open reading frame encoding a first antigenic polypeptide or a concatemeric polypeptide, wherein the RNA polynucleotide does not include a stabilization element, and wherein an adjuvant is not coformulated or co-administered with the vaccine.

In other aspects the invention is a composition for or method of vaccinating a subject comprising administering to the subject a nucleic acid vaccine comprising one or more RNA polynucleotides having an open reading frame encoding a first antigenic polypeptide wherein a dosage of between 10 ug/kg and 400 ug/kg of the nucleic acid vaccine is administered to the subject. In some embodiments the dosage of the RNA polynucleotide is 1-5 ug, 5-10 ug, 10-15 ug, 15-20 ug, 10-25 ug, 20-25 ug, 20-50 ug, 30-50 ug, 40-50 ug, 40-60 ug, 60-80 ug, 60-100 ug, 50-100 ug, 80-120 ug, 40-120 ug, 40-150 ug, 50-150 ug, 50-200 ug, 80-200 ug, 100-200 ug, 120-250 ug, 150-250 ug, 180-280 ug, 200-300 ug, 50-300 ug, 80-300 ug, 100-300 ug, 40-300 ug, 50-350 ug, 100-350 ug, 200-350 ug, 300-350 ug, 320-400 ug, 40-380 ug, 40-100 ug, 100-400 ug, 200-400 ug, or 300-400 ug per dose. In some embodiments, the nucleic acid vaccine is administered to the subject by intradermal or intramuscular injection. In some embodiments, the nucleic acid vaccine is administered to the subject on day zero. In some embodiments, a second dose of the nucleic acid vaccine is administered to the subject on day twenty one.

In some embodiments, a dosage of 25 micrograms of the RNA polynucleotide is included in the nucleic acid vaccine administered to the subject. In some embodiments, a dosage of 100 micrograms of the RNA polynucleotide is included in the nucleic acid vaccine administered to the subject. In some embodiments, a dosage of 50 micrograms of the RNA polynucleotide is included in the nucleic acid vaccine administered to the subject. In some embodiments, a dosage of 75 micrograms of the RNA polynucleotide is included in the nucleic acid vaccine administered to the subject. In some embodiments, a dosage of 150 micrograms of the RNA polynucleotide is included in the nucleic acid vaccine administered to the subject. In some embodiments, a dosage of 400 micrograms of the RNA polynucleotide is included in the nucleic acid vaccine administered to the subject. In some embodiments, a dosage of 200 micrograms of the RNA polynucleotide is included in the nucleic acid vaccine administered to the subject. In some embodiments, the RNA polynucleotide accumulates at a 100 fold higher level in the local lymph node in comparison with the distal lymph node. In other embodiments the nucleic acid vaccine is chemically modified and in other embodiments the nucleic acid vaccine is not chemically modified.

Aspects of the invention provide a nucleic acid vaccine comprising one or more RNA polynucleotides having an open reading frame encoding a first antigenic polypeptide or a concatemeric polypeptide, wherein the RNA polynucleotide does not include a stabilization element, and a pharmaceutically acceptable carrier or excipient, wherein an adjuvant is not included in the vaccine. In some embodiments, the stabilization element is a histone stem-loop. In some embodiments, the stabilization element is a nucleic acid sequence having increased GC content relative to wild type sequence.

Aspects of the invention provide nucleic acid vaccines comprising one or more RNA polynucleotides having an open reading frame encoding a first antigenic polypeptide, wherein the RNA polynucleotide is present in the formulation for in vivo administration to a host, which confers an antibody titer superior to the criterion for seroprotection for the first antigen for an acceptable percentage of human subjects. In some embodiments, the antibody titer produced by the mRNA vaccines of the invention is a neutralizing antibody titer. In some embodiments the neutralizing antibody titer is greater than a protein vaccine. In other embodiments the neutralizing antibody titer produced by the mRNA vaccines of the invention is greater than an adjuvanted protein vaccine. In yet other embodiments the neutralizing antibody titer produced by the mRNA vaccines of the invention is 1,000-10,000, 1,200-10,000, 1,400-10,000, 1,500-10,000, 1,000-5,000, 1,000-4,000, 1,800-10,000, 2000-10,000, 2,000-5,000, 2,000-3,000, 2,000-4,000, 3,000-5,000, 3,000-4,000, or 2,000-2,500. A neutralization titer is typically expressed as the highest serum dilution required to achieve a 50% reduction in the number of plaques.

In preferred aspects, vaccines of the invention (e.g., LNP-encapsulated mRNA vaccines) produce prophylactically- and/or therapeutically-efficacious levels, concentrations and/or titers of antigen-specific antibodies in the blood or serum of a vaccinated subject. As defined herein, the term antibody titer refers to the amount of antigen-specific antibody produces in s subject, e.g., a human subject. In exemplary embodiments, antibody titer is expressed as the inverse of the greatest dilution (in a serial dilution) that still gives a positive result. In exemplary embodiments, antibody titer is determined or measured by enzyme-linked immunosorbent assay (ELISA). In exemplary embodiments, antibody titer is determined or measured by neutralization assay, e.g., by microneutralization assay. In certain aspects, antibody titer measurement is expressed as a ratio, such as 1:40, 1:100, etc.

In exemplary embodiments of the invention, an efficacious vaccine produces an antibody titer of greater than 1:40, greater that 1:100, greater than 1:400, greater than 1:1000, greater than 1:2000, greater than 1:3000, greater than 1:4000, greater than 1:500, greater than 1:6000, greater than 1:7500, greater than 1:10000. In exemplary embodiments, the antibody titer is produced or reached by 10 days following vaccination, by 20 days following vaccination, by 30 days following vaccination, by 40 days following vaccination, or by 50 or more days following vaccination. In exemplary embodiments, the titer is produced or reached following a single dose of vaccine administered to the subject. In other embodiments, the titer is produced or reached following multiple doses, e.g., following a first and a second dose (e.g., a booster dose.)

In exemplary aspects of the invention, antigen-specific antibodies are measured in units of μg/ml or are measured in units of IU/L (International Units per liter) or mIU/ml (milli International Units per ml). In exemplary embodiments of the invention, an efficacious vaccine produces >0.5 μg/ml, >0.1 μg/ml, >0.2 μg/ml, >0.35 μg/ml, >0.5 μg/ml, >1 μg/ml, >2 μg/ml, >5 μg/ml or >10 μg/ml. In exemplary embodiments of the invention, an efficacious vaccine produces >10 mIU/ml, >20 mIU/ml, >50 mIU/ml, >100 mIU/ml, >200 mIU/ml, >500 mIU/ml or >1000 mIU/ml. In exemplary embodiments, the antibody level or concentration is produced or reached by 10 days following vaccination, by 20 days following vaccination, by 30 days following vaccination, by 40 days following vaccination, or by 50 or more days following vaccination. In exemplary embodiments, the level or concentration is produced or reached following a single dose of vaccine administered to the subject. In other embodiments, the level or concentration is produced or reached following multiple doses, e.g., following a first and a second dose (e.g., a booster dose.) In exemplary embodiments, antibody level or concentration is determined or measured by enzyme-linked immunosorbent assay (ELISA). In exemplary embodiments, antibody level or concentration is determined or measured by neutralization assay, e.g., by microneutralization assay.

Also provided are nucleic acid vaccines comprising one or more RNA polynucleotides having an open reading frame encoding a first antigenic polypeptide or a concatemeric polypeptide, wherein the RNA polynucleotide is present in a formulation for in vivo administration to a host for eliciting a longer lasting high antibody titer than an antibody titer elicited by an mRNA vaccine having a stabilizing element or formulated with an adjuvant and encoding the first antigenic polypeptide. In some embodiments, the RNA polynucleotide is formulated to produce a neutralizing antibodies within one week of a single administration. In some embodiments, the adjuvant is selected from a cationic peptide and an immunostimulatory nucleic acid. In some embodiments, the cationic peptide is protamine.

Aspects provide nucleic acid vaccines comprising one or more RNA polynucleotides having an open reading frame comprising at least one chemical modification or optionally no nucleotide modification, the open reading frame encoding a first antigenic polypeptide or a concatemeric polypeptide, wherein the RNA polynucleotide is present in the formulation for in vivo administration to a host such that the level of antigen expression in the host significantly exceeds a level of antigen expression produced by an mRNA vaccine having a stabilizing element or formulated with an adjuvant and encoding the first antigenic polypeptide.

Other aspects provide nucleic acid vaccines comprising one or more RNA polynucleotides having an open reading frame comprising at least one chemical modification or optionally no nucleotide modification, the open reading frame encoding a first antigenic polypeptide or a concatemeric polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Aspects of the invention also provide a unit of use vaccine, comprising between bug and 400 ug of one or more RNA polynucleotides having an open reading frame comprising at least one chemical modification or optionally no nucleotide modification, the open reading frame encoding a first antigenic polypeptide or a concatemeric polypeptide, and a pharmaceutically acceptable carrier or excipient, formulated for delivery to a human subject. In some embodiments, the vaccine further comprises a lipid nanoparticle.

Aspects of the invention provide methods of creating, maintaining or restoring antigenic memory to a virus in an individual or population of individuals comprising administering to said individual or population an antigenic memory booster nucleic acid vaccine comprising (a) at least one RNA polynucleotide, said polynucleotide comprising at least one chemical modification or optionally no nucleotide modification and two or more codon-optimized open reading frames, said open reading frames encoding a set of reference antigenic polypeptides, and (b) optionally a pharmaceutically acceptable carrier or excipient. In some embodiments, the vaccine is administered to the individual via a route selected from the group consisting of intramuscular administration, intradermal administration and subcutaneous administration. In some embodiments, the administering step comprises contacting a muscle tissue of the subject with a device suitable for injection of the composition. In some embodiments, the administering step comprises contacting a muscle tissue of the subject with a device suitable for injection of the composition in combination with electroporation.

Aspects of the invention provide methods of vaccinating a subject comprising administering to the subject a single dosage of between 25 ug/kg and 400 ug/kg of a nucleic acid vaccine comprising one or more RNA polynucleotides having an open reading frame encoding a first antigenic polypeptide or a concatemeric polypeptide in an effective amount to vaccinate the subject.

Other aspects provide nucleic acid vaccines comprising one or more RNA polynucleotides having an open reading frame comprising at least one chemical modification, the open reading frame encoding a first antigenic polypeptide or a concatemeric polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Other aspects provide nucleic acid vaccines comprising an LNP formulated RNA polynucleotide having an open reading frame comprising no nucleotide modifications (unmodified), the open reading frame encoding a first antigenic polypeptide or a concatemeric polypeptide, wherein the vaccine has at least 10 fold less RNA polynucleotide than is required for an unmodified mRNA vaccine not formulated in a LNP to produce an equivalent antibody titer. In some embodiments, the RNA polynucleotide is present in a dosage of 25-100 micrograms.

The data presented in the Examples demonstrate significant enhanced immune responses using the formulations of the invention. Surprisingly, in contrast to prior art reports that it was preferable to use chemically unmodified mRNA formulated in a carrier for the production of vaccines, it is described herein that chemically modified mRNA-LNP vaccines required a much lower effective mRNA dose than unmodified mRNA, i.e., tenfold less than unmodified mRNA when formulated in carriers other than LNP. Both the chemically modified and unmodified RNA vaccines of the invention produce better immune responses than mRNA vaccines formulated in a different lipid carrier.

In other aspects the invention encompasses a method of treating an elderly subject age 60 years or older comprising administering to the subject a nucleic acid vaccine comprising one or more RNA polynucleotides having an open reading frame encoding an antigenic polypeptide or a concatemeric polypeptide in an effective amount to vaccinate the subject.

In other aspects the invention encompasses a method of treating a young subject age 17 years or younger comprising administering to the subject a nucleic acid vaccine comprising one or more RNA polynucleotides having an open reading frame encoding an antigenic polypeptide or a concatemeric polypeptide in an effective amount to vaccinate the subject.

In other aspects the invention encompasses a method of treating an adult subject comprising administering to the subject a nucleic acid vaccine comprising one or more RNA polynucleotides having an open reading frame encoding an antigenic polypeptide or a concatemeric polypeptide in an effective amount to vaccinate the subject.

In some aspects the invention is a method of vaccinating a subject with a combination vaccine including at least two nucleic acid sequences encoding antigens wherein the dosage for the vaccine is a combined therapeutic dosage wherein the dosage of each individual nucleic acid encoding an antigen is a sub therapeutic dosage. In some embodiments, the combined dosage is 25 micrograms of the RNA polynucleotide in the nucleic acid vaccine administered to the subject. In some embodiments, the combined dosage is 100 micrograms of the RNA polynucleotide in the nucleic acid vaccine administered to the subject. In some embodiments the combined dosage is 50 micrograms of the RNA polynucleotide in the nucleic acid vaccine administered to the subject. In some embodiments, the combined dosage is 75 micrograms of the RNA polynucleotide in the nucleic acid vaccine administered to the subject. In some embodiments, the combined dosage is 150 micrograms of the RNA polynucleotide in the nucleic acid vaccine administered to the subject. In some embodiments, the combined dosage is 400 micrograms of the RNA polynucleotide in the nucleic acid vaccine administered to the subject. In some embodiments, the sub therapeutic dosage of each individual nucleic acid encoding an antigen is 1, 2, 3, 4, 5, 6, 7, 8, 9, 10, 11, 12, 13, 14, 15, 16, 17, 18, 19, or 20 micrograms. In other embodiments the nucleic acid vaccine is chemically modified and in other embodiments the nucleic acid vaccine is not chemically modified.

The RNA polynucleotide is one of SEQ ID NO: 58, 60, 62, 64, 66, 68, 70, and 84-144 and includes at least one chemical modification. In other embodiments the RNA polynucleotide is one of SEQ ID NO: 1 58, 60, 62, 64, 66, 68, 70, 84-144 and does not include any nucleotide modifications, or is unmodified.

Further aspects of the invention relate to methods of preventing or treating HCMV infection comprising administering to a subject a therapeutically effective amount of: (i) a first HCMV vaccine comprising an RNA polynucleotide having an open reading frame encoding HCMV antigenic polypeptide pp65, or an antigenic fragment or epitope thereof, and (ii) a second HCMV vaccine comprising at least one RNA polynucleotide having one or more open reading frames encoding HCMV antigenic polypeptides gH, gL, UL128, UL130, and/or UL131A, or antigenic fragments or epitopes thereof; an RNA polynucleotide having an open reading frame encoding HCMV antigenic polypeptide gB, or an antigenic fragment or epitope thereof; and an RNA polynucleotide having an open reading frame encoding HCMV antigenic polypeptide pp65, or an antigenic fragment or epitope thereof.

Further aspects of the invention relate to methods of treating an immunocompromised organ transplant recipient subject having a cytomegalovirus (CMV) infection, comprising administering to the subject a therapeutically effective amount of: (i) a first HCMV vaccine comprising an RNA polynucleotide having an open reading frame encoding HCMV antigenic polypeptide pp65, or an antigenic fragment or epitope thereof, and (ii) a second HCMV vaccine comprising at least one RNA polynucleotide having one or more open reading frames encoding HCMV antigenic polypeptides gH, gL, UL128, UL130, and/or UL131A, or antigenic fragments or epitopes thereof; an RNA polynucleotide having an open reading frame encoding HCMV antigenic polypeptide gB, or an antigenic fragment or epitope thereof; and an RNA polynucleotide having an open reading frame encoding HCMV antigenic polypeptide pp65, or an antigenic fragment or epitope thereof.

In some embodiments of methods described herein, the first HCMV vaccine is administered at least 1 week, at least 2 weeks, or at least 3 weeks prior to administering the second HCMV vaccine. In some embodiments of methods described herein, the pp65 polypeptide contains a deletion of amino acids 435-438.

In some embodiments of methods described herein, the second HCMV vaccine comprises: an RNA polynucleotide having an open reading frame encoding HCMV antigenic polypeptide gH, or an antigenic fragment or epitope thereof; an RNA polynucleotide having an open reading frame encoding HCMV antigenic polypeptide gL, or an antigenic fragment or epitope thereof; an RNA polynucleotide having an open reading frame encoding HCMV antigenic polypeptide UL128, or an antigenic fragment or epitope thereof; an RNA polynucleotide having an open reading frame encoding HCMV antigenic polypeptide UL130, or an antigenic fragment or epitope thereof; an RNA polynucleotide having an open reading frame encoding HCMV antigenic polypeptide UL131A, or an antigenic fragment or epitope thereof; an RNA polynucleotide having an open reading frame encoding HCMV antigenic polypeptide gB, or an antigenic fragment or epitope thereof; and an RNA polynucleotide having an open reading frame encoding HCMV antigenic polypeptide pp65, or an antigenic fragment or epitope thereof.

In some embodiments of methods described herein, one or more of the RNA polynucleotides in the first and/or second HCMV vaccines are codon optimized. In some embodiments of methods described herein, at least one of the RNA polynucleotides encodes an antigenic polypeptide having at least 90% identity to any of the amino acid sequences of SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 77, and SEQ ID NOs: 80-83.

In some embodiments of methods described herein, one or more of the RNA polynucleotides includes at least one chemical modification. In some embodiments of methods described herein, at least one chemical modification is selected from the group consisting of pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, and 2'-O-methyl uridine.

In some embodiments of methods described herein, the first and/or second HCMV vaccine is formulated within a lipid nanoparticle. In some embodiments of methods described herein, the lipid nanoparticle(s) comprise a molar ratio of 20-60% ionizable cationic lipid, 5-25% non-cationic lipid, 25-55% sterol, and 0.5-15% PEG-modified lipid. In some embodiments of methods described herein, the cationic lipid is selected from the group consisting of 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319).

In some embodiments of methods described herein, the first and/or second HCMV vaccine further comprises a pharmaceutically acceptable carrier or excipient. In some embodiments of methods described herein, the transplant recipient is a hematopoietic cell transplant recipient or a solid organ transplant recipient. In some embodiments of methods described herein, at least one RNA polynucleotide further encodes at least one 5' terminal cap, 7mG(5')ppp(5')NlmpNp.

Further aspects of the invention relate to a kit comprising: (i) a first HCMV vaccine comprising an RNA polynucleotide having an open reading frame encoding HCMV antigenic polypeptide pp65, or an antigenic fragment or epitope thereof, and (ii) a second HCMV vaccine comprising at least one RNA polynucleotide having one or more open reading frames encoding HCMV antigenic polypeptides gH, gL, UL128, UL130, and/or UL131A, or antigenic fragments or epitopes thereof; an RNA polynucleotide having an open reading frame encoding HCMV antigenic polypeptide gB, or an antigenic fragment or epitope thereof; and an RNA polynucleotide having an open reading frame encoding HCMV antigenic polypeptide pp65, or an antigenic fragment or epitope thereof.

In some embodiments of kits described herein, the first HCMV vaccine is administered at least 1 week, at least 2 weeks, or at least 3 weeks prior to administering the second HCMV vaccine. In some embodiments of methods described herein, the pp65 polypeptide contains a deletion of amino acids 435-438.

In some embodiments of kits described herein, the second HCMV vaccine comprises: an RNA polynucleotide having an open reading frame encoding HCMV antigenic polypeptide gH, or an antigenic fragment or epitope thereof; an RNA polynucleotide having an open reading frame encoding HCMV antigenic polypeptide gL, or an antigenic fragment or epitope thereof; an RNA polynucleotide having an open reading frame encoding HCMV antigenic polypeptide UL128, or an antigenic fragment or epitope thereof; an RNA polynucleotide having an open reading frame encoding HCMV antigenic polypeptide UL130, or an antigenic fragment or epitope thereof; an RNA polynucleotide having an open reading frame encoding HCMV antigenic polypeptide UL131A, or an antigenic fragment or epitope thereof; an RNA polynucleotide having an open reading frame encoding HCMV antigenic polypeptide gB, or an antigenic fragment or epitope thereof; and an RNA polynucleotide having an open reading frame encoding HCMV antigenic polypeptide pp65, or an antigenic fragment or epitope thereof.

In some embodiments of kits described herein, one or more of the RNA polynucleotides in the first and/or second HCMV vaccines are codon optimized. In some embodiments of kits described herein, at least one of the RNA polynucleotides encodes an antigenic polypeptide having at least 90% identity to any of the amino acid sequences of SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 77, and SEQ ID NOs: 80-83.

In some embodiments of kits described herein, one or more of the RNA polynucleotides includes at least one chemical modification. In some embodiments of kits described herein, at least one chemical modification is selected from the group consisting of pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, and 2'-O-methyl uridine.

In some embodiments of kits described herein, the first and/or second HCMV vaccine is formulated within a lipid nanoparticle. In some embodiments of kits described herein, the lipid nanoparticle(s) comprise a molar ratio of 20-60% ionizable cationic lipid, 5-25% non-cationic lipid, 25-55% sterol, and 0.5-15% PEG-modified lipid. In some embodiments of kits described herein, the cationic lipid is selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy) heptadecanedioate (L319).

In some embodiments of kits described herein, the first and/or second HCMV vaccine further comprises a pharmaceutically acceptable carrier or excipient. In some embodiments of kits described herein, at least one RNA polynucleotide further encodes at least one 5' terminal cap, 7mG(5')ppp(5')NlmpNp.

Kits described herein are for use in preventing or treating HCMV infection. In some embodiments of kits described herein, the subject is an immunocompromised organ transplant recipient. In some embodiments of kits described herein, the transplant recipient is a hematopoietic cell transplant recipient or a solid organ transplant recipient.

Further aspects of the invention relate to a human cytomegalovirus (HCMV) vaccine comprising: an RNA polynucleotide having an open reading frame encoding HCMV antigenic polypeptide pp65, or an antigenic fragment or epitope thereof, and a pharmaceutically acceptable carrier or excipient.

In some embodiments, the pp65 polypeptide contains a deletion of amino acids 435-438. In some embodiments, the RNA polynucleotide is codon optimized. In some embodiments, the RNA polynucleotide encodes an antigenic polypeptide having at least 90% identity to SEQ ID NO: 71 or SEQ ID NO: 82. In some embodiments, the RNA polynucleotide includes at least one chemical modification. In some embodiments, at least one chemical modification is selected from the group consisting of pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, and 2'-O-methyl uridine.

In some embodiments, the vaccine is formulated within a lipid nanoparticle. In some embodiments, the lipid nanoparticle(s) comprise a molar ratio of 20-60% ionizable cationic lipid, 5-25% non-cationic lipid, 25-55% sterol, and 0.5-15% PEG-modified lipid. In some embodiments, the cationic lipid is selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319). In some embodiments, the RNA polynucleotide further encodes at least one 5' terminal cap, 7mG(5')ppp(5')NlmpNp.

In some embodiments, the vaccine is for use in preventing or treating HCMV infection in a subject. In some embodiments, the subject is an immunocompromised organ transplant recipient. In some embodiments, the transplant recipient is a hematopoietic cell transplant recipient or a solid organ transplant recipient.

Aspects of the invention relate to a human cytomegalovirus (HCMV) vaccine comprising: an mRNA comprising an open reading frame (ORF) encoding a HCMV antigenic polypeptide pp65, or an antigenic fragment or epitope thereof, formulated within a lipid nanoparticle, wherein the lipid nanoparticle comprises an ionizable lipid, a PEG-modified lipid, a sterol and a non-cationic lipid.

In some embodiments, the HCMV vaccine further comprises an mRNA comprising an ORF encoding one or more HCMV antigenic polypeptides selected from gH, gL, UL128, UL130, and UL131A, or antigenic fragments or epitopes thereof.

In some embodiments, the HCMV vaccine further comprises an mRNA comprising two ORFs encoding two HCMV antigenic polypeptides selected from gH, gL, UL128, UL130, and UL131A, or antigenic fragments or epitopes thereof.

In some embodiments, the HCMV vaccine further comprises an mRNA comprising three ORFs encoding three HCMV antigenic polypeptides selected from gH, gL, UL128, UL130, and UL131A, or antigenic fragments or epitopes thereof.

In some embodiments, the HCMV vaccine further comprises an mRNA comprising four ORFs encoding four HCMV antigenic polypeptides selected from gH, gL, UL128, UL130, and UL131A, or antigenic fragments or epitopes thereof.

In some embodiments, the HCMV vaccine further comprises an mRNA comprising ORFs encoding each of HCMV antigenic polypeptides gH, gL, UL128, UL130, and UL131A, or antigenic fragments or epitopes thereof.

In some embodiments, the HCMV vaccine further comprises one or more mRNAs, each mRNA comprising an ORF encoding an HCMV antigenic polypeptide selected from gH, gL, UL128, UL130, and UL131A, or antigenic fragments or epitopes thereof.

In some embodiments, the HCMV vaccine further comprises two mRNAs, each mRNA comprising a different ORF encoding an HCMV antigenic polypeptide selected from gH, gL, UL128, UL130, and UL131A, or antigenic fragments or epitopes thereof.

In some embodiments, the HCMV vaccine further comprises three mRNAs, each mRNA comprising a different ORF encoding an HCMV antigenic polypeptide selected from gH, gL, UL128, UL130, and UL131A, or antigenic fragments or epitopes thereof.

In some embodiments, the HCMV vaccine further comprises four mRNAs, each mRNA comprising a different ORF encoding an HCMV antigenic polypeptide selected from gH, gL, UL128, UL130, and UL131A, or antigenic fragments or epitopes thereof.

In some embodiments, the HCMV vaccine further comprises five mRNAs, each mRNA comprising a different ORF encoding an HCMV antigenic polypeptide selected from gH, gL, UL128, UL130, and UL131A, or antigenic fragments or epitopes thereof.

In some embodiments, the HCMV vaccine further comprises an mRNA comprising an ORF encoding HCMV antigenic polypeptide gB, or an antigenic fragment or epitope thereof.

In some embodiments, the lipid nanoparticle has a molar ratio of about 20-60% ionizable lipid, about 5-25% non-cationic lipid, about 25-55% sterol, and about 0.5-15% PEG-modified lipid. In some embodiments, the ionizable lipid comprises Compound 25, a salt or a stereoisomer thereof, or any combination thereof.

In some embodiments, each mRNA is formulated in a separate lipid nanoparticle. In some embodiments, the mRNA comprising the ORF encoding the HCMV antigenic polypeptide pp65 is in a separate lipid nanoparticle than the other mRNA. In some embodiments, all of the mRNA other than the mRNA comprising the ORF encoding the HCMV antigenic polypeptide pp65 are formulated in the same lipid nanoparticle.

In some embodiments, the mRNA comprises a chemical modification. In some embodiments, the chemical modification is N1-methyl pseudouridine (m1Ψ). In some embodiments, each U in the mRNA is a N1-methyl pseudouridine (m1Ψ).

In some embodiments, the ORFs encoding the HCMV antigenic polypeptides are encoded by the following nucleic acid sequences: gH: SEQ ID NO: 87, gL: SEQ ID NO: 90, UL128: SEQ ID NO: 89, UL130: SEQ ID NO: 91, UL131A: SEQ ID NO: 144, gB: SEQ ID NO: 86, and pp65: SEQ ID NO: 92.

In some embodiments, the HCMV antigenic polypeptides have the following amino acid sequences: gH: SEQ ID NO: 59, gL: SEQ ID NO: 3, UL128: SEQ ID NO: 63, UL130: SEQ ID NO: 65, UL131A: SEQ ID NO: 67, gB: SEQ ID NO: 69, and pp65: SEQ ID NO: 71.

In some embodiments, the mRNA further comprises a UTR encoded by SEQ ID NO: 146 and/or SEQ ID NO: 147.

In some embodiments, anti-HCMV antigenic polypeptide antibody titer produced in the subject is increased by 1-3 log relative to a control. In some embodiments, anti-HCMV antigenic polypeptide antibody titer produced in the subject is increased 2-10 times relative to a control. In some embodiments, the control is an anti-HCMV antigenic polypeptide antibody titer produced in a subject who has not been administered HCMV vaccine, a subject who has been administered a live attenuated or inactivated HCMV vaccine, or a subject who has been administered a recombinant or purified HCMV protein vaccine.

In some embodiments, the mRNA is present in the lipid nanoparticle in a total dose selected from 50-1000 μg, 35-100 μg, or 25-50 μg.

In some embodiments, the ORFs encoding the HCMV antigenic polypeptides are encoded by the following nucleic acid sequences: gH: a sequence comprising at least 90%, 95% or 98% identity to SEQ ID NO: 87; gL: a sequence comprising at least 90%, 95% or 98% identity to SEQ ID NO: 90; UL128: a sequence comprising at least 90%, 95% or 98% identity to SEQ ID NO: 89; UL130: a sequence comprising at least 90%, 95% or 98% identity to SEQ ID NO: 91; UL131A: a sequence comprising at least 90%, 95% or 98% identity to SEQ ID NO: 144; gB: a sequence comprising at least 90%, 95% or 98% identity to SEQ ID NO: 86; and pp65: a sequence comprising at least 90%, 95% or 98% identity to SEQ ID NO: 92.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1A shows the gH/gL/gB complex that mediates the entry of hCMV into fibroblasts. FIG. 1B shows the pentameric complex containing gH/gL/UL128/UL130/UL131A. Such a pentameric complex mediates the entry of hCMV into epithelial cells, endothelial cells, monocytes, and dendritic cells. FIG. 1C, which is adapted from Macagno et al. (2010) J. Virology 84(2):1005-13 shows the hCMV pentameric complex (gH/gL/UL128/UL130/UL131A) further in complex with antibodies specific for the protein components of the pentameric complex: 8121 (anti-pentamer), 3G16 (anti-gH), 15D8 (anti-UL128), 7113 (anti-UL128/UL130/UL131A), and 10P3 (anti-gL).

FIG. 2A shows the surface expression of gH. FIG. 2B shows the surface expression of UL128/UL130/UL131A. FIG. 2C shows the surface expression of UL128. FIG. 2D shows the surface expression of the pentamer. The indicated subunits were detected by monoclonal antibodies. Data in bar graphs represent mean±standard deviation (s.d.).

FIGS. 10A and 10C show the results of a fluorescence-activated cell (FACS) sorting experiment detecting the surface expression of the pentameric complex using the 8121 (anti-pentamer) antibodies. Surface expression of the pentameric complex is indicated by the emerging fluorescent cell population. FIGS. 10B and 10D shows the quantification of the FACS experiment.

FIG. 18A depicts a graph showing anti-pentamer antibody titers. Equimolar and equal mass formulations of the pentameric mRNAs were compared and were found to be equally effective. FIG. 18B depicts a graph showing neutralizing titers measured on ARPE19 epithelial cells infected with hCMV strain VR1814. Equimolar and equal mass formulations of the pentameric mRNAs were compared and were found to be equally effective. Neutralizing titers were found to be approximately 25 fold higher than CytoGam®.

FIGS. 19A-C show that the depleting protein was either the pentamer or a gH/gL dimer. FIG. 19B and FIG. 19C depict graphs showing neutralization. FIG. 19B shows neutralization by sera from mice immunized with the pentamer or with a gH/gL dimer. FIG. 19C shows neutralization by CytoGam® combined with the pentamer or with a gH/gL.

FIG. 21A shows the pp65-IE1 peptide pool stimulated CD8 IFNγ response, as indicated by the emerging IFNγ+ cell population in FACS experiments. FIGS. 21B-

21C show the quantification of IFNγ response in splenocytes of mice immunized with different mRNA vaccine constructs.

Figure 22A:
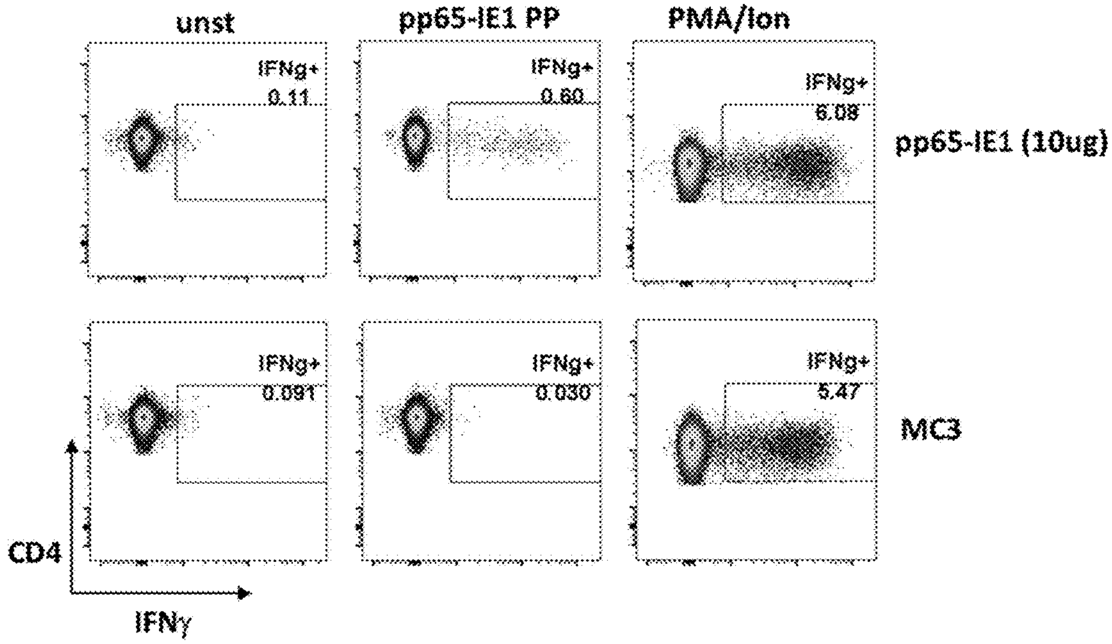
Figure 22B:
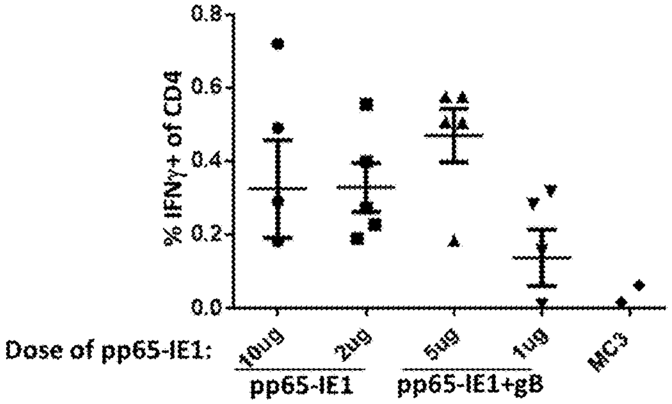
Figure 22C:
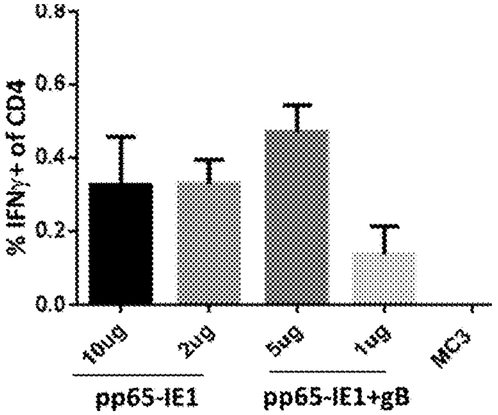

FIGS. 22A-22C show an analysis of the CD4 IFNγ responses in Balb/c mice splenic lymphocytes stimulated with a pp65-IE1 peptide pool. The mice were immunized with pp65-FE-1 or pp65-IE-1+gB mRNA vaccine constructs. pp65-IE1 mRNA induced specific CD4 IFNγ response. FIG. 22A shows the pp65-IE1 peptide pool stimulated CD4 IFNγ response, as indicated by the emerging IFNγ+ cell population in FACS experiments. FIGS. 22B-22C show the quantification of IFNγ response in splenocytes of mice immunized with different mRNA vaccine constructs.

Figure 23:
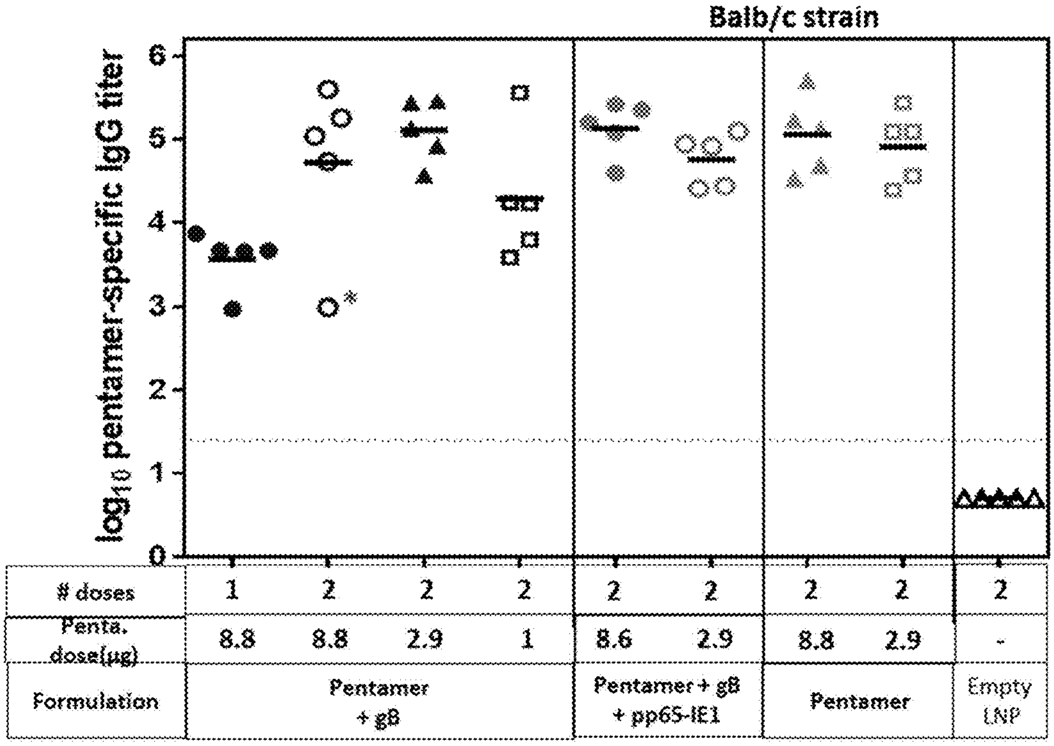

FIG. 23 is a graph showing that addition of other hCMV antigens (gB and/or pp65-1E1) does not interfere with the production of high titer pentamer-specific antibodies from the hCMV pentameric complex mRNA vaccine. Balb/c mice were vaccinated according to the vaccination schedule with indicated dosages of the mRNAs (lower panel). Mice serum IgG titers were assayed on day 41 post immunization on pentamer coated plates. Similar levels of pentamer-specific IgG titers were produced with addition of gB antigen and/or pp65-IE1 antigen.

Figure 24:
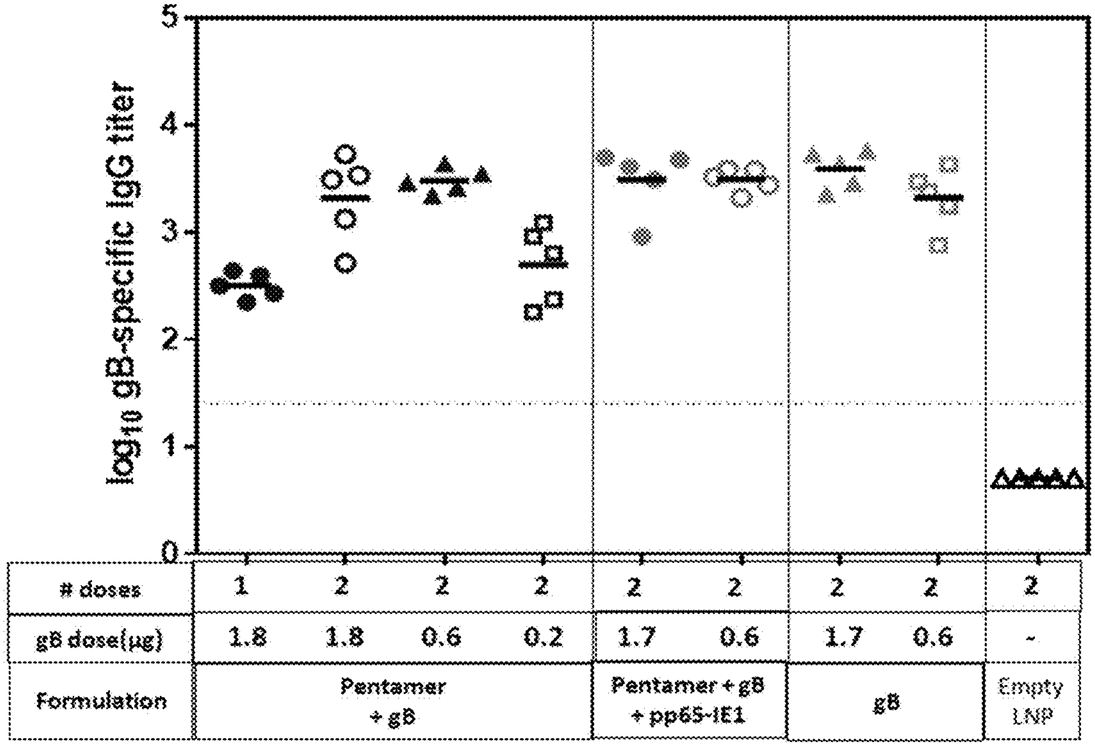

FIG. 24 is a graph showing that gB-specific antibody titers induced by gB mRNA vaccine were maintained in the presence of the hCMV pentamer and pp65-IE1. Balb/c mice were vaccinated according to the vaccination schedule with indicated dosages of the mRNAs (lower panel). Mice serum IgG titers were assayed on day 41 post immunization on gB coated plates. The presence of the pentamer and pp65-IE1 did not interfere with the induction of gB-specific IgG titer.

Figure 25A:
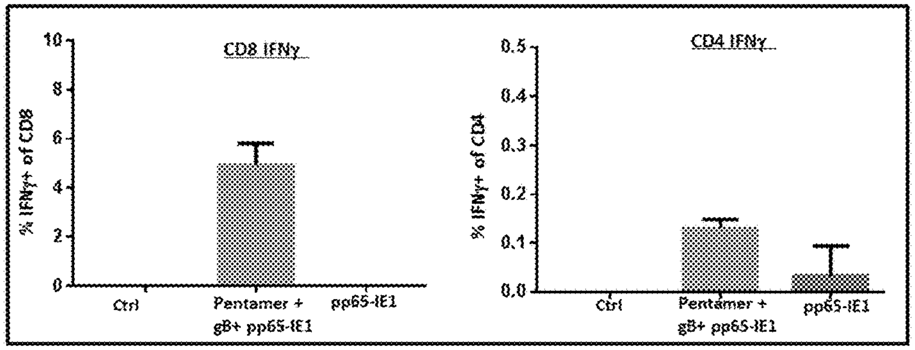
Figure 25B:
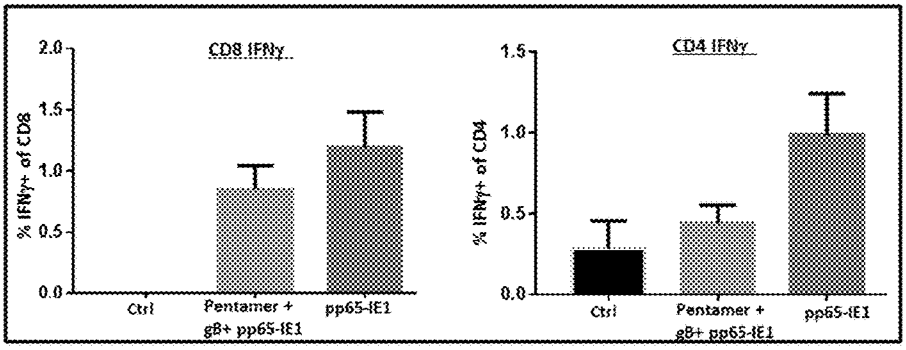
Figure 25C:
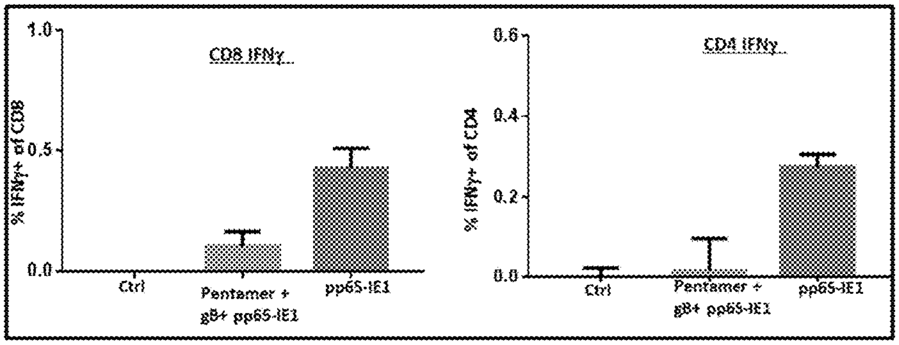

FIGS. 25A-25C are graphs showing the analysis of T cell responses in Balb/c mice splenic lymphocytes stimulated with a pentamer peptide library or a pp65-IE1 peptide pool. The mice were immunized with hCMV pentamer, gB, and pp65-IE1 mRNA vaccines. FIG. 25A shows the CD8 (left panel) and CD4 (right panel) response induced by a pentamer library. The mRNA vaccine used to immunize the mice was pentamer (5 μg):gB (5 μg): pp65-IE1 (2 μg). FIG. 25B shows the CD8 (left panel) and CD4 (right panel) response induced by a pp65-IE1 peptide pool. The mRNA vaccine used to immunize the mice was pentamer (1 μg):gB (1 μg): pp65-IE1 (1 μg). FIG. 25C shows the CD8 (left panel) and CD4 (right panel) response induced by a pp65-IE1 peptide pool. The mRNA vaccine used to immunize the mice was pentamer (5 μg):gB (5 μg): pp65-IE1 (2 μg).

Figure 26:
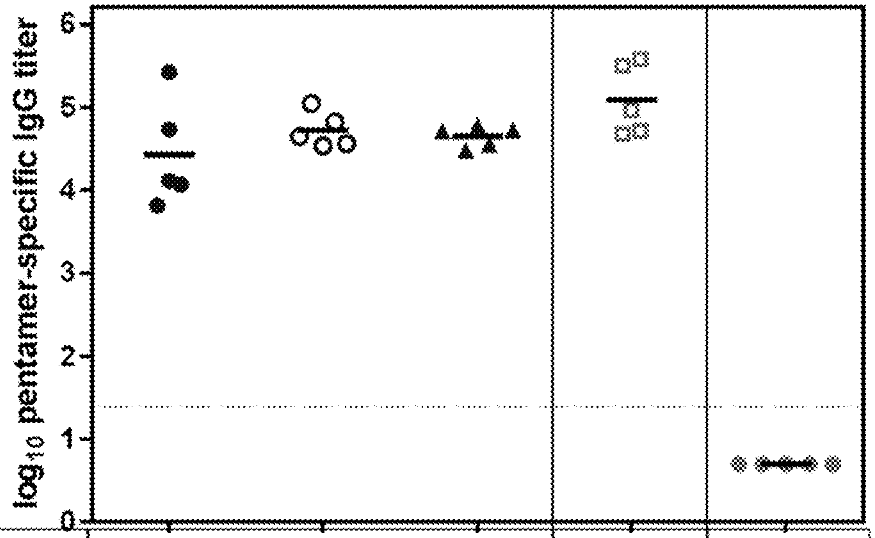

FIG. 26 shows an immunogenicity study of hCMV mRNA vaccines encoding the hCMV pentamer combined with gB or the pentamer combined with both gB and pp65-IE1. Balb/c mice were vaccinated intramuscularly according to the vaccination schedule with indicated dosages of the mRNAs (lower panel). Mice serum IgG titers were assayed on day 41 post immunization on pentamer coated plates. Similar levels of pentamer-specific IgG titers were produced with addition of gB and/or pp65-IE1.

Figure 27:
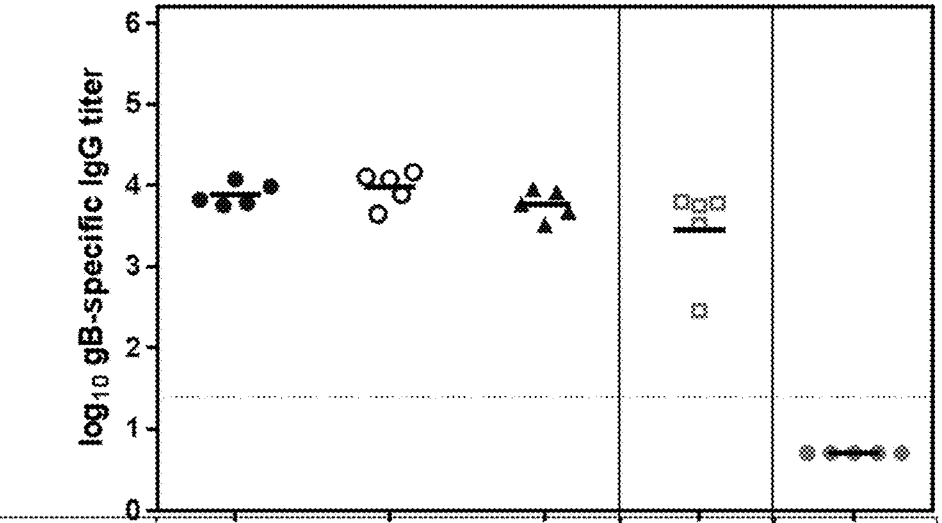

FIG. 27 shows an immunogenicity study of the hCMV mRNA vaccines encoding the hCMV pentamer combined with gB or the pentamer combined with gB and pp65-IE1. Balb/c mice were vaccinated intramuscularly according to the vaccination schedule with indicated dosages of the mRNAs (lower panel). Mice serum IgG titers were assayed on day 41 post immunization on gB coated plates. Similar levels of gB-specific IgG titers were produced with addition of the pentamer and/or pp65-IE1.

Figure 28:
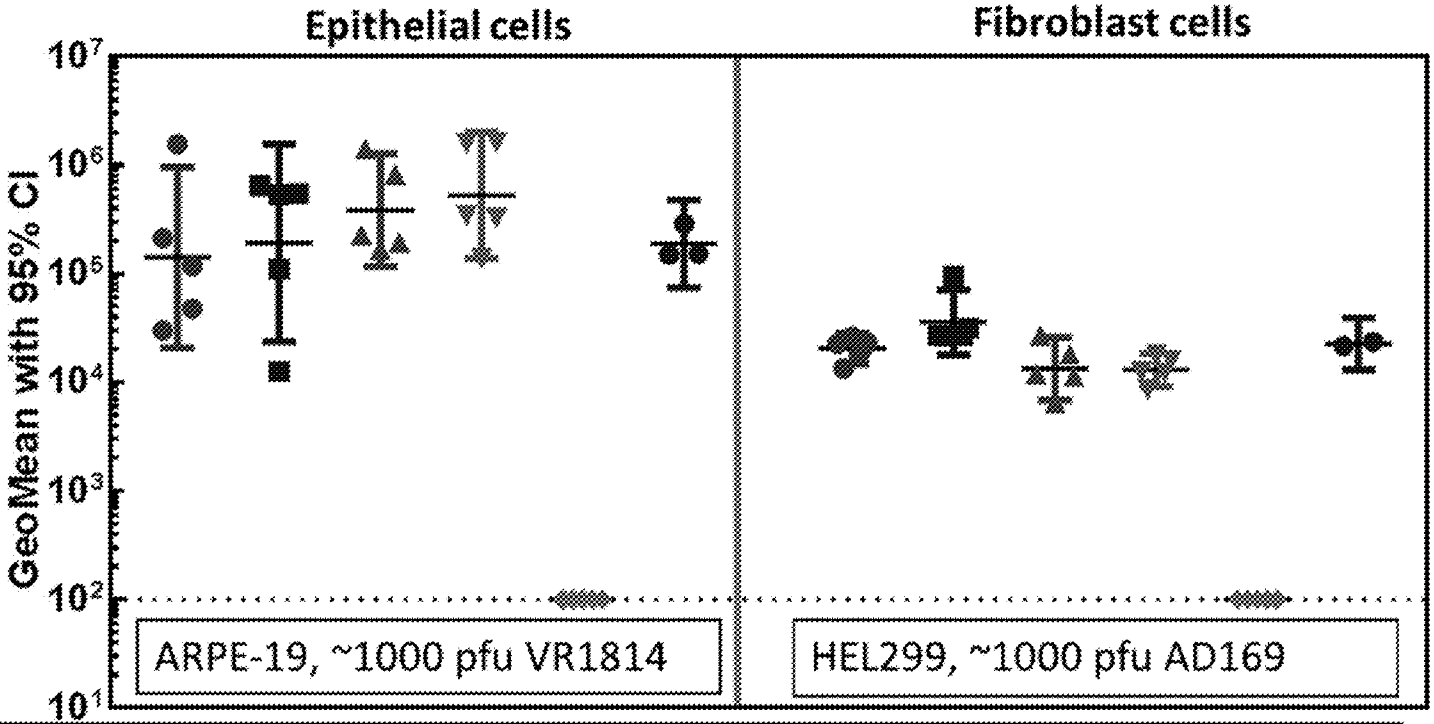

FIG. 28 depicts a graph showing the neutralizing antibody titers induced in mice by the hCMV mRNA vaccine constructs encoding the hCMV pentamer, gB, and pp65-IE1. Balb/c mice were vaccinated intramuscularly according to the vaccination schedule with indicated dosages of the mRNAs (lower panel). Neutralizing antibody titers in mice serum were measured at days 41 post immunization, with either ARPE-19 cells infected with ~1000 pfu of the hCMV VR1814 strain, or HEL200 cells infected with ~1000 pfu of the AD169 strain. The results show that the hCMV pentamer mRNA vaccine induced comparable or higher neutralization titers in mice that CytoGam®, which is a hyperimmune serum used clinically for prophylaxis of hCMV.

Figure 29:
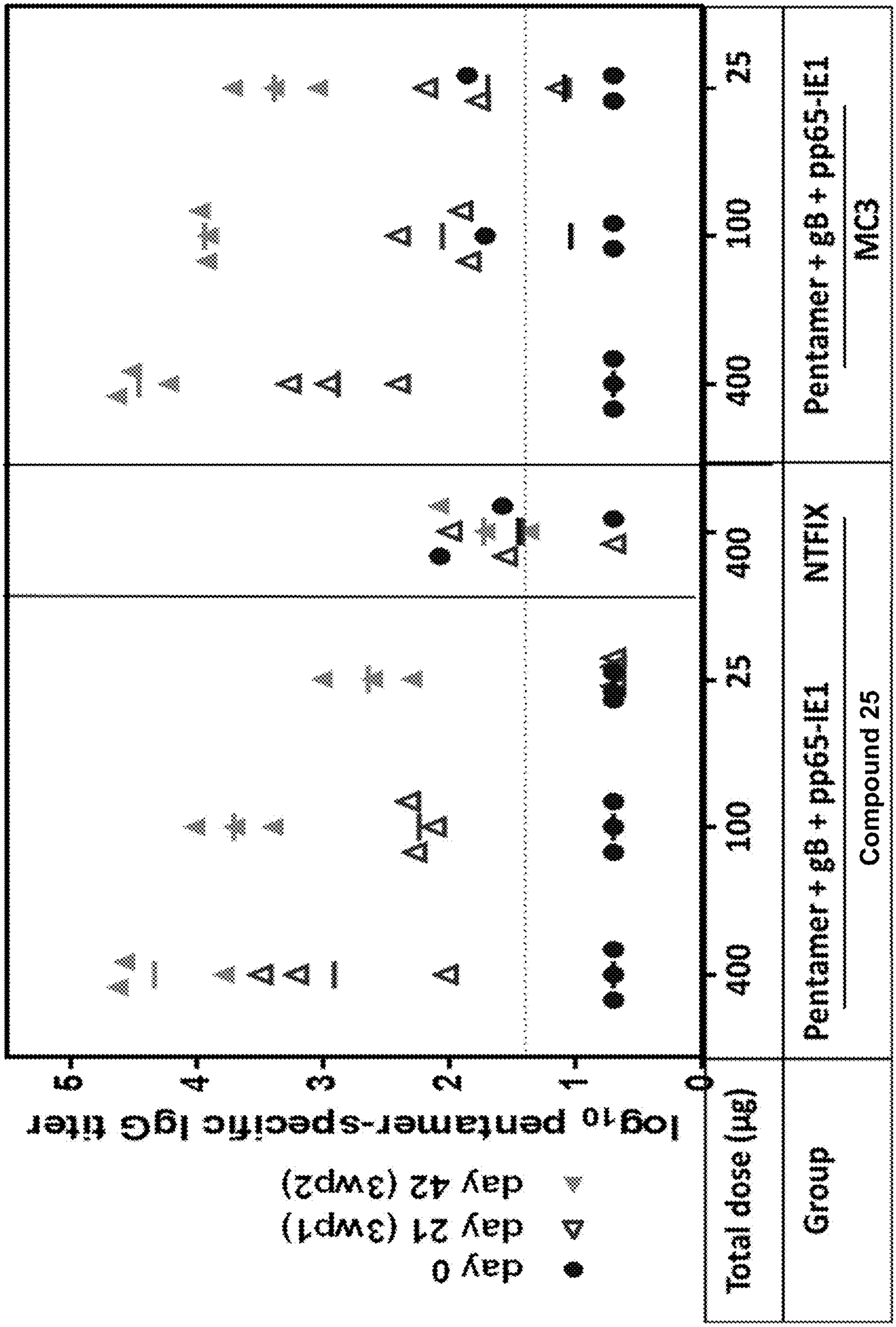

FIG. 29 is a graph showing the immunogenicity of hCMV mRNA vaccines formulated in lipid nanoparticles (Compound 25 and MC3). High titers of pentamer-specific antibodies were generated in Cynomolgus macaques following immunization with hCMV mRNA vaccines encoding the pentamer, gB, and pp65-IE1. Compound 25 formulation and MC3 formulation induced comparable antibody titers at high doses.

Figure 30A:
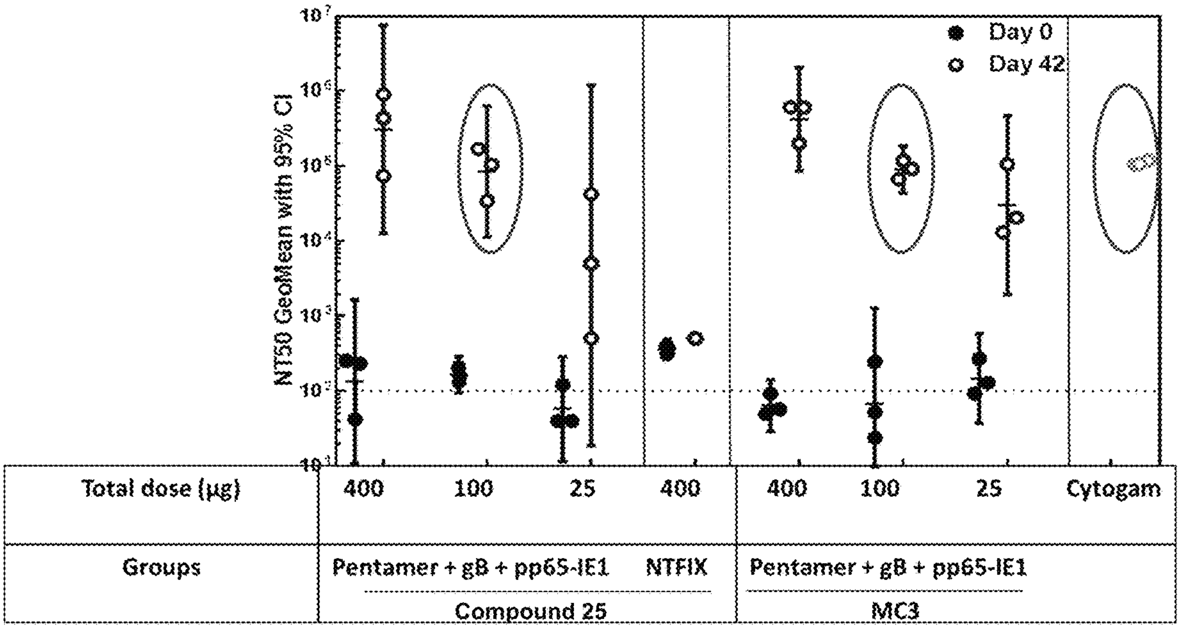
Figure 30B:
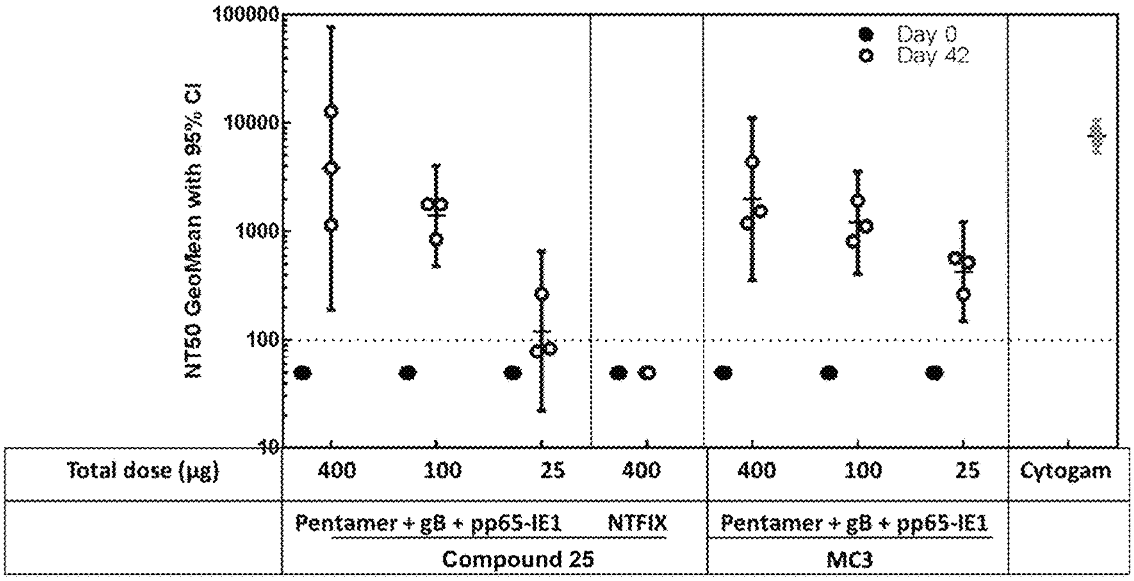

FIGS. 30A-30B is a graph showing an analysis of the neutralizing antibody titers induced by the hCMV mRNA vaccines formulated in lipid nanoparticles (Compound 25 and MC3). A 100 μg total dose of the mRNA vaccines formulated with Compound 25 lipids or MC3 lipids exhibited comparable ability to induce neutralizing antibodies against CMV infection as CytoGam®. FIG. 30A shows the results of neutralization assays performed on ARPE-19 epithelial cells infected with hCMV strain VR1814. FIG. 30B shows the results of neutralization assays performed on HEL299 fibroblast cells infected with hCMV strain AD169.

Figure 31A:
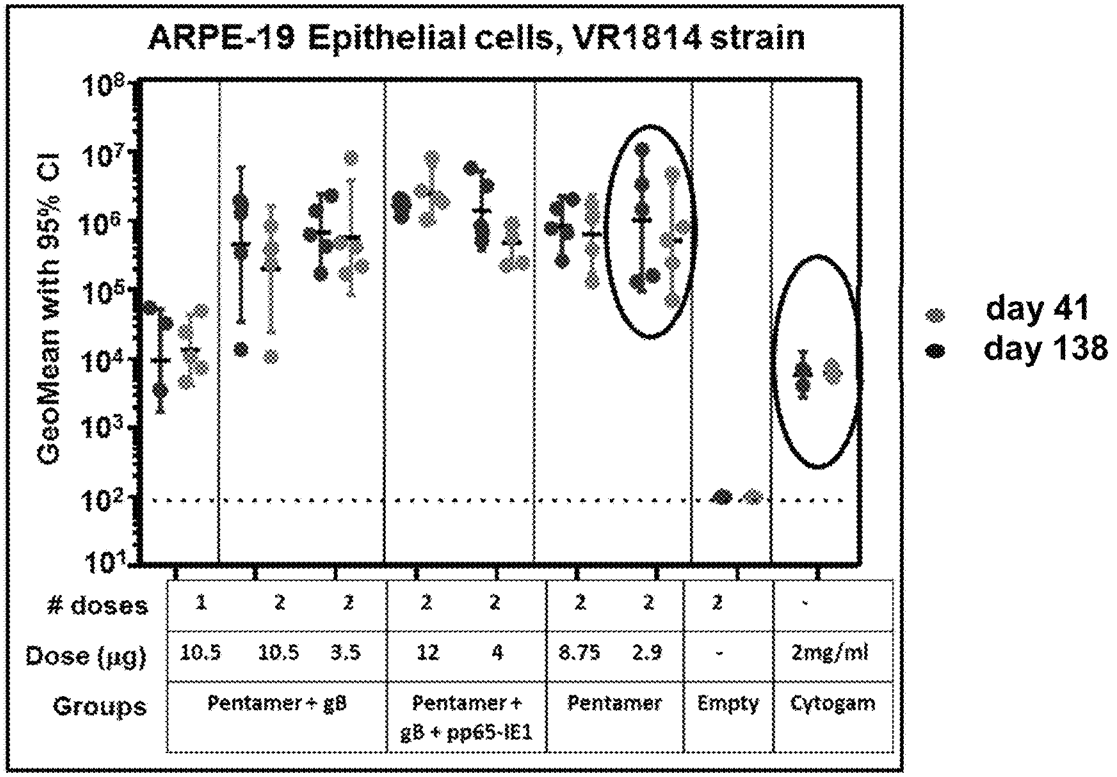
Figure 31B:
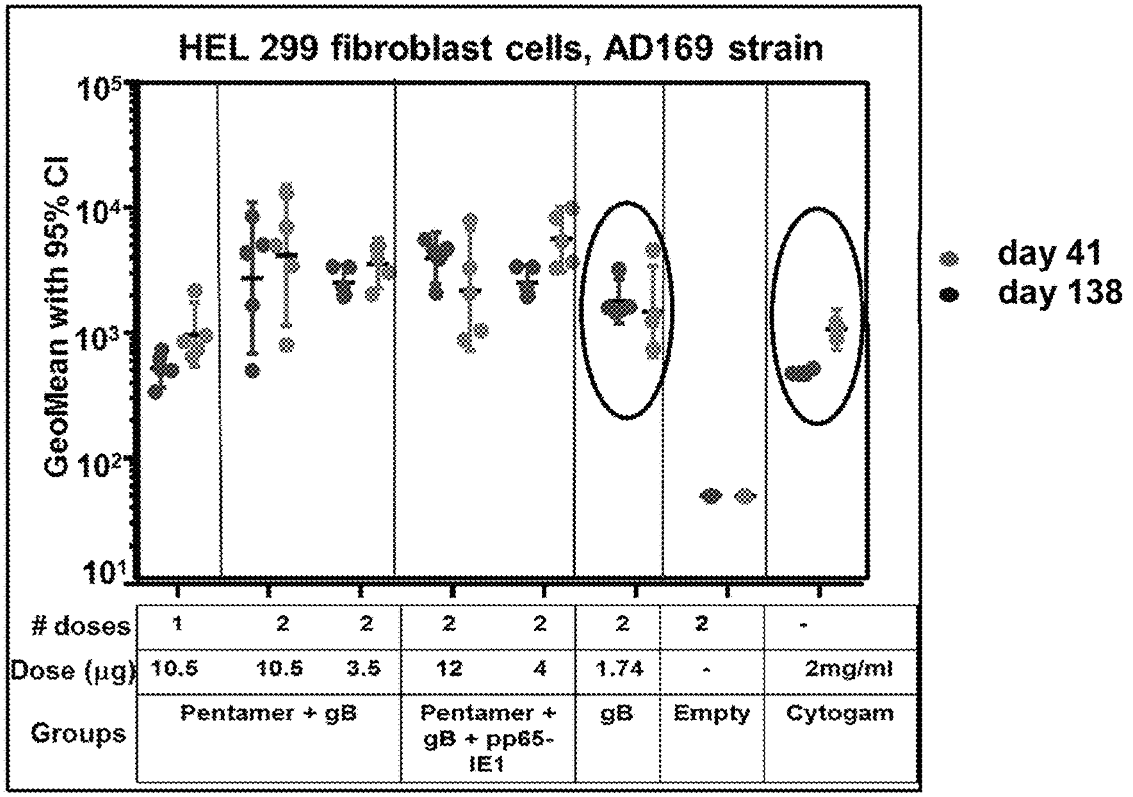

FIGS. 31A and 31B are graphs showing that low doses of hCMV mRNA vaccine encoding the pentamer, pentamer+gB, or pentamer+gB+pp65-IE1 formulated with MC3 lipids elicits neutralizing antibody titers that are higher or equivalent to CytoGam®. FIG. 31A shows the results of neutralization assays performed on ARPE-19 epithelial cells infected with hCMV strain VR1814. FIG. 31B shows the results of neutralization assays performed on HEL299 fibroblast cells infected with hCMV strain AD169.

Figure 32:
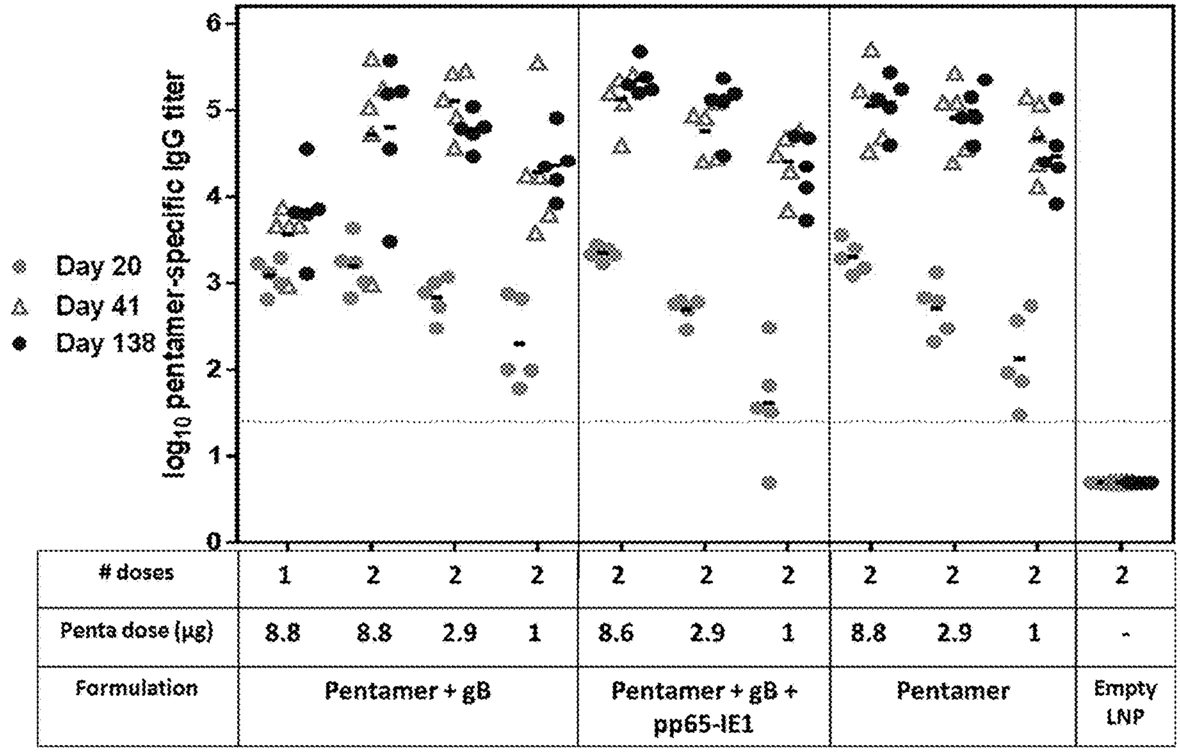

FIG. 32 is a graph showing that immunization with hCMV pentameric complex mRNA vaccine either alone or in combination with mRNAs encoding other antigens elicits similar levels of binding antibodies that are maintained over time.

Figure 33:
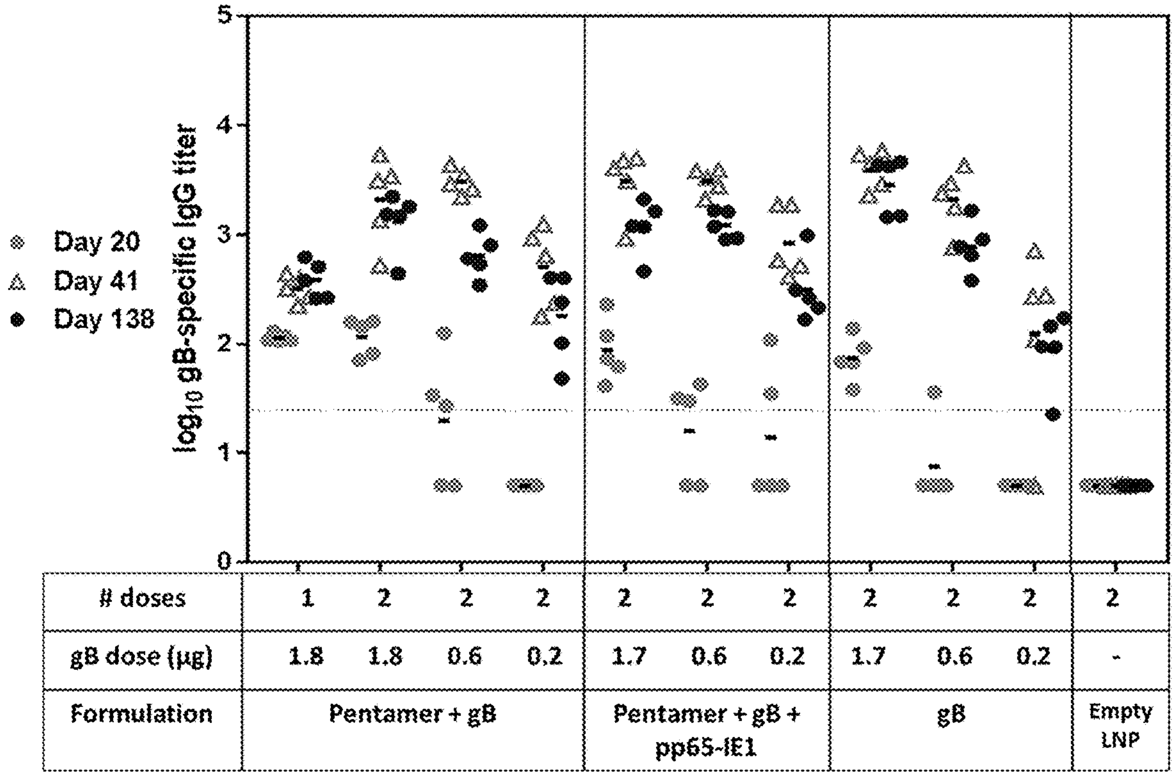

FIG. 33 is a graph showing the hCMV multivalent vaccine induced high titers of anti-gB antibodies in mice.

Figure 34A:
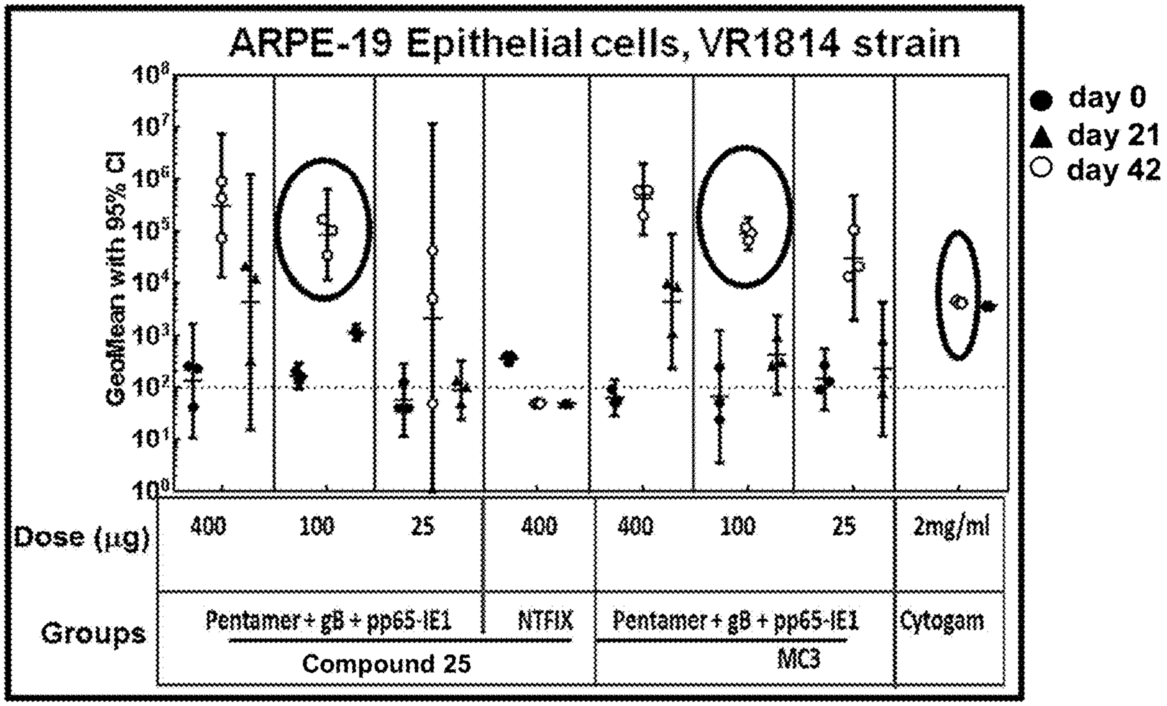
Figure 34B:
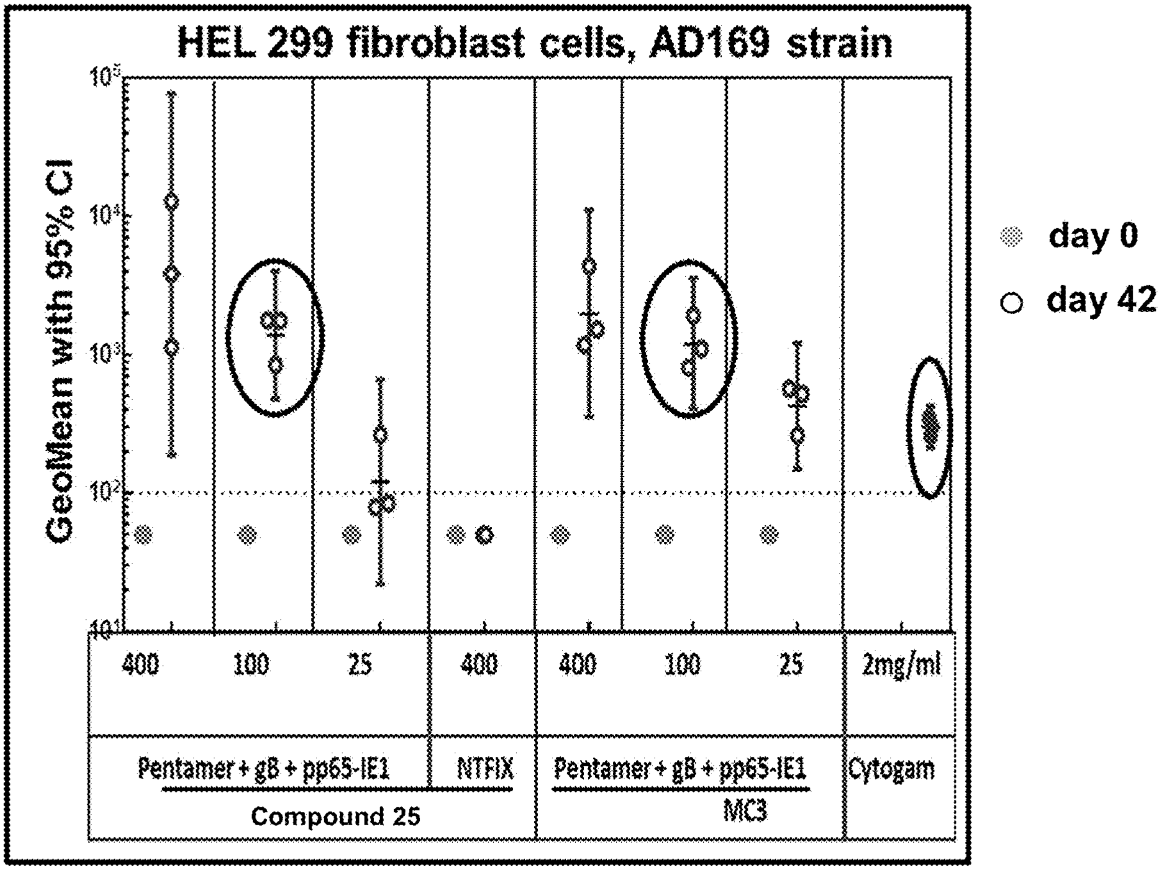

FIGS. 34A and 34B are graphs showing that immunization with multivalent hCMV vaccine in Cynomolgus macaques elicited potently neutralizing antibodies with either Compound 25 or MC3 lipid formulation. FIG. 34A shows the results of neutralization assays performed on ARPE-19 epithelial cells infected with hCMV strain VR1814. FIG. 34B shows the results of neutralization assays performed on HEL299 fibroblast cells infected with hCMV strain AD169.

Figure 35:
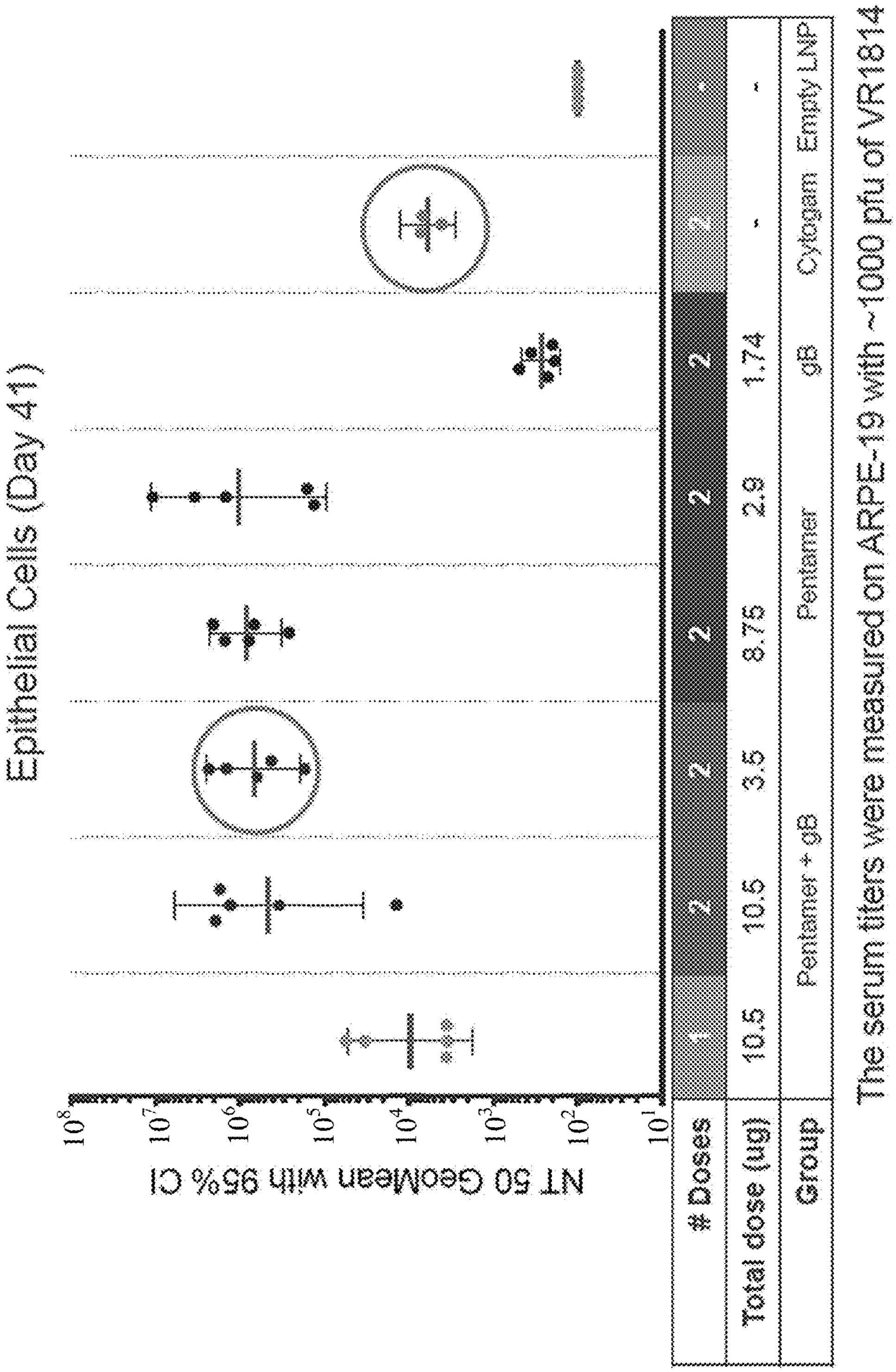

FIG. 35 is a graph showing that a 3 μg total dose of HCMV mRNA vaccine constructs encoding the pentameric complex elicited higher neutralization antibody titers than CytoGam®, a hyperimmune serum used clinically for prophylaxis of hCMV.

Figure 36:
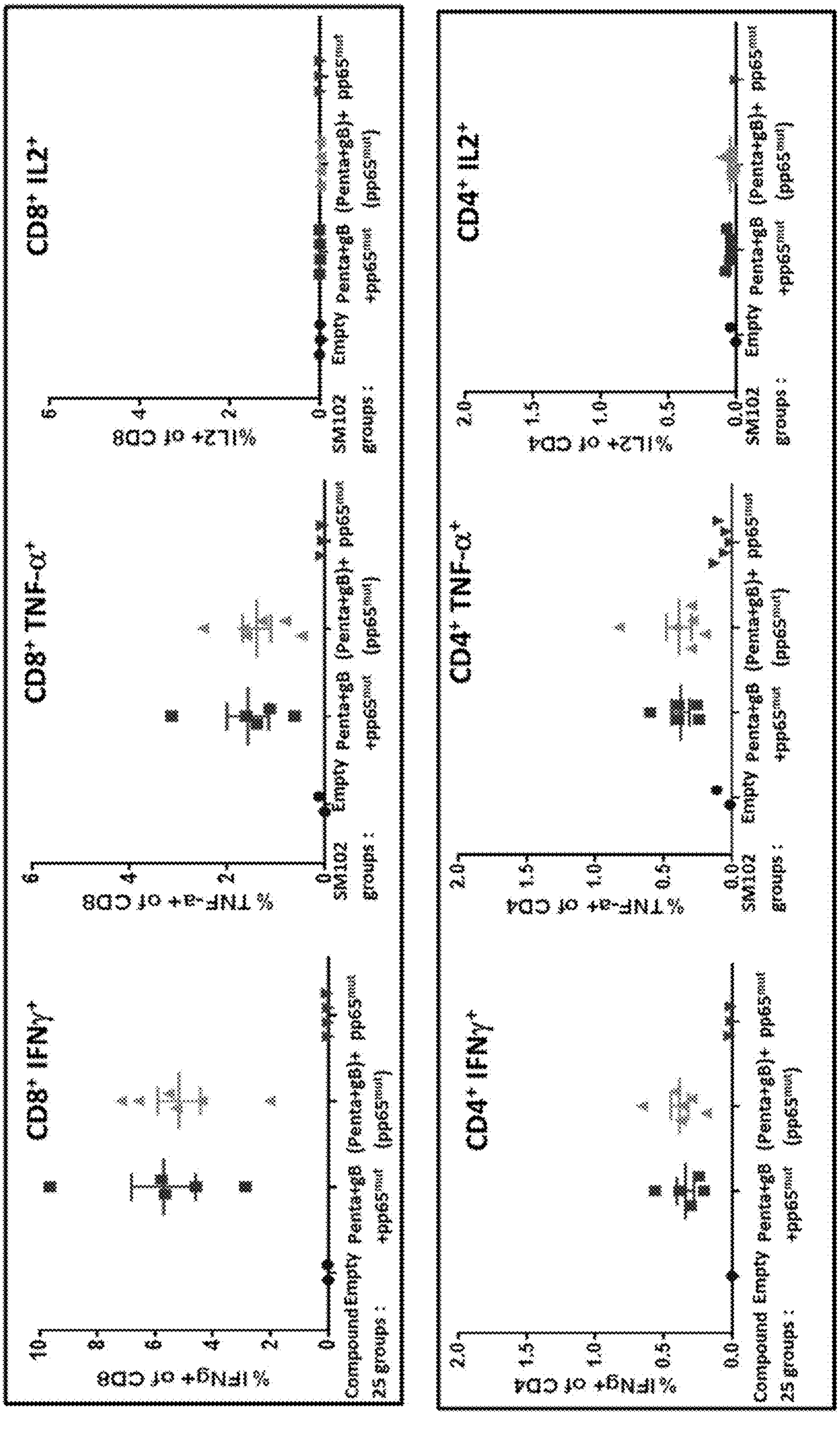

FIG. 36 depicts graphs showing the T cell response elicited by multivalent hCMV mRNA vaccine constructs encoding the pentamer, in mice. The mRNA vaccines constructs were formulated in Compound 25 lipid particles. Formulations tested included: mRNA encoding the pp65mut alone; mRNA encoding the pp65mut+mRNA encoding gB combined with mRNA encoding the pentamer; or mRNA encoding the pp65mut+mRNA encoding gB+the mRNA encoding the pentamer. A robust T cell response to the pentamer was elicited by the multivalent hCMV mRNA vaccine.

Figure 37A:
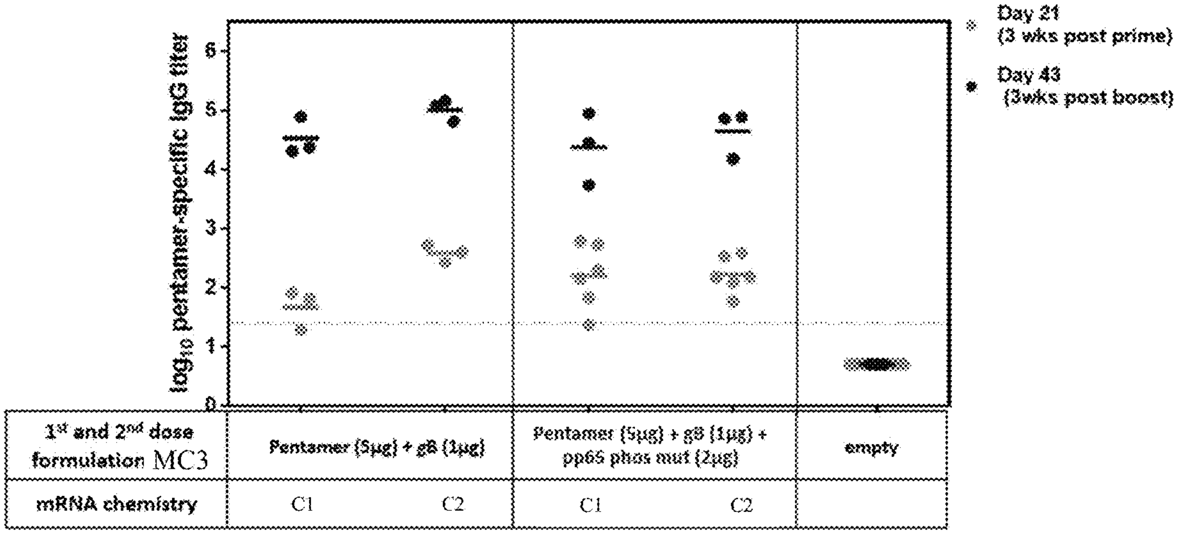
Figure 37B:
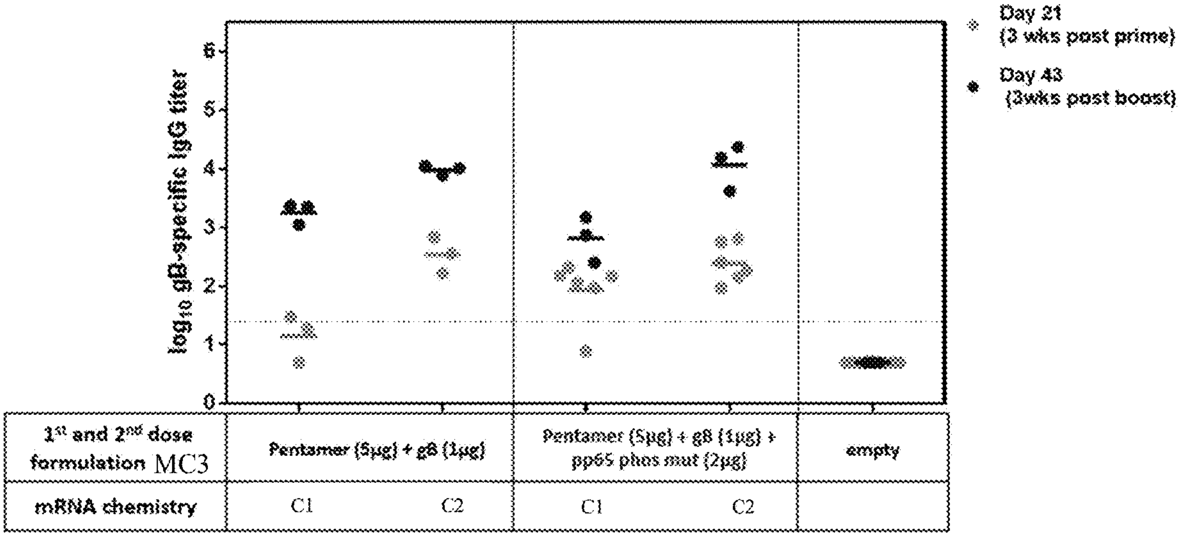

FIGS. 37A and 37B are graphs showing antibody titers elicited by hCMV mRNA vaccine constructs encoding hCMV pentamer (5 μg) and gB (1 μg), or constructs encoding hCMV pentamer (5 μg), gB (1 μg), and pp65mut (2 μg). The mRNA vaccine constructs were either unmodified (C1) or contained N1-methylpseudouridine chemical modification (C2) and were formulated in MC3 lipid particles. Mice were immunized with two doses (one primary dose and one booster dose on day 21 post primary dose) of the hCMV mRNA vaccines and sera were collected at days 21 and 43 post primary dose. The sera were analyzed on plates coated with hCMV pentamer (FIG. 37A) or gB (FIG. 37B). The hCMV mRNA vaccine constructs elicited antibody titers specific for hCMV pentmer and gB, and the antibody titers increased after the boost dose.

Figure 38A:
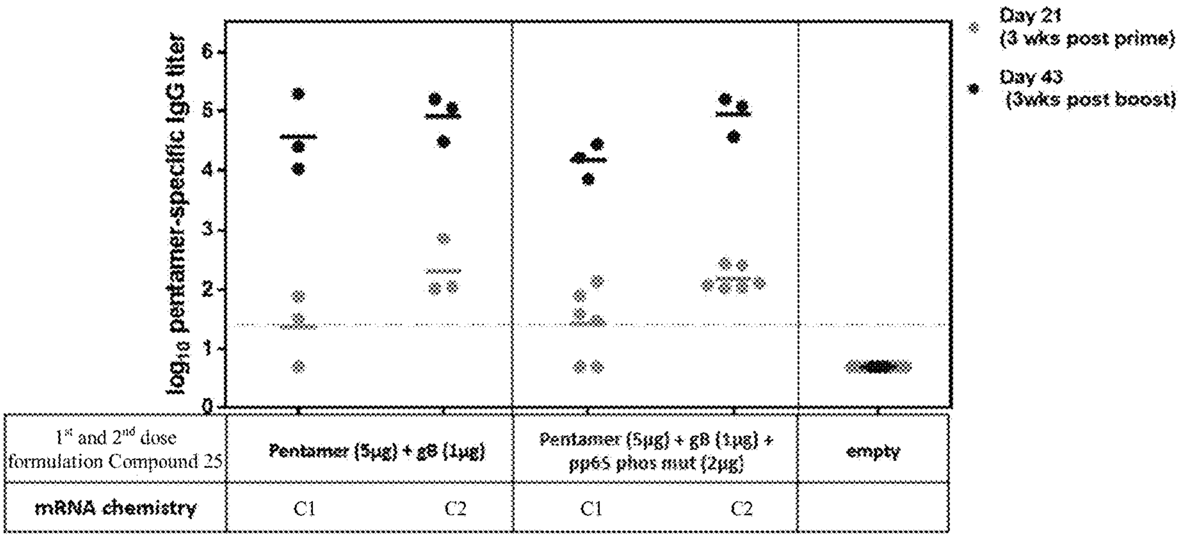
Figure 38B:
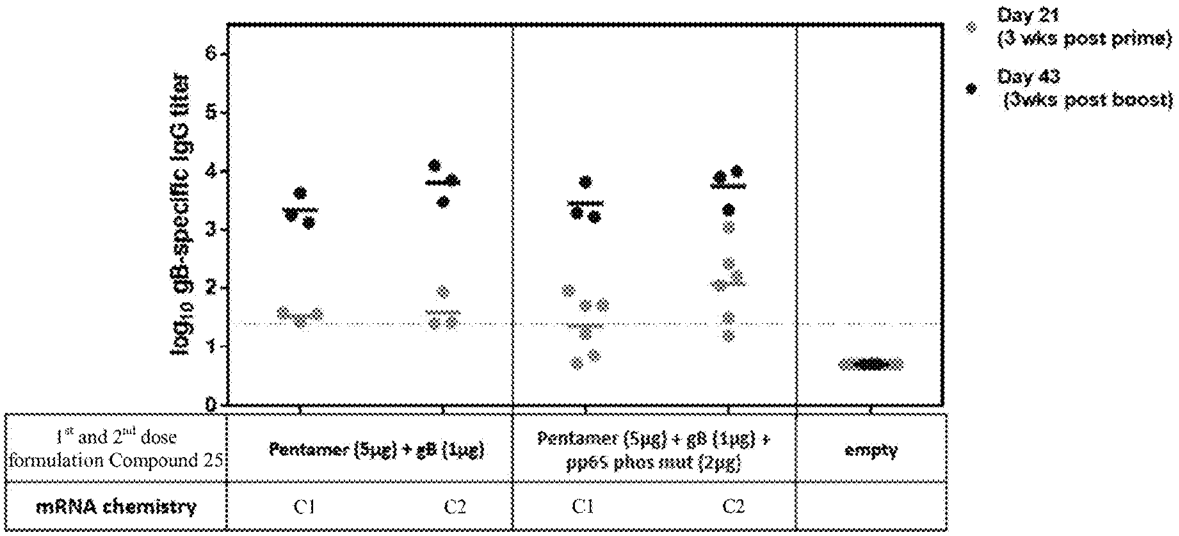

FIGS. 38A and 38B are graphs showing antibody titers elicited by hCMV mRNA vaccine constructs encoding hCMV pentamer (5 μg) and gB (1 μg), or constructs encoding hCMV pentamer (5 μg), gB (1 μg), and pp65mut (2 μg). The mRNA vaccine constructs were either unmodified (C1) or contained N1-methylpseudouridine chemical modification (C2), and were formulated in compound 25 lipid particles. Mice were immunized with two doses (one primary dose and one booster dose on day 21 post primary dose) of the hCMV mRNA vaccines and sera were collected at days 21 and 43 post primary. The sera were analyzed on plates coated with hCMV pentamer (FIG. 38A) or gB (FIG. 38B). The hCMV mRNA vaccine constructs elicited antibody titers specific for hCMV pentmer and gB and the antibody titers increased after the boost dose.

Figure 39A:
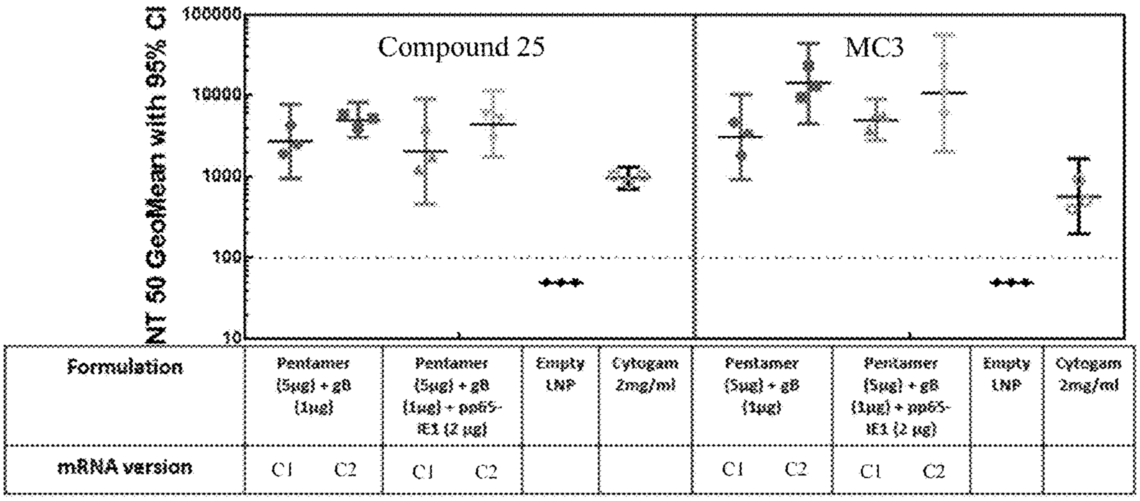
Figure 39B:
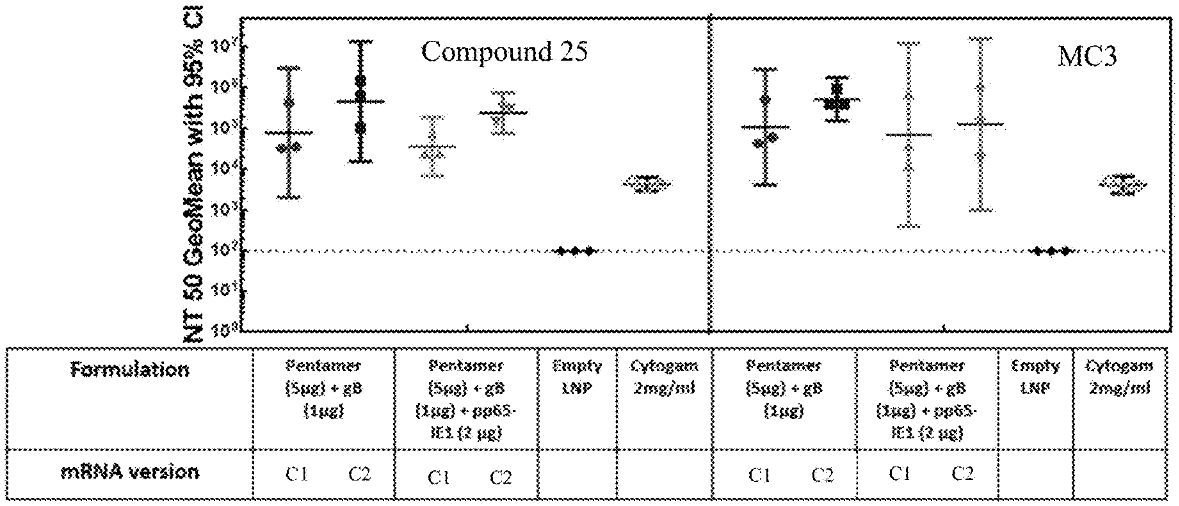

FIGS. 39A and 39B are graphs showing the neutralizing antibody titers against infection of hCMV in fibroblast cells (FIG. 39A) and epithelial cells (FIG. 39B). The mRNA vaccine constructs were either unmodified (C1) or contained N1-methylpseudouridine chemical modification (C2), and were formulated in either MC3 lipid particles or compound 25 lipid particles. Mice were immunized as described in FIGS. 37A and 37B. Mice sera were collected 20 days after the booster dose. The neutralizing antibody titers in the sera of immunized mice were measured on HEL299 cells infected with about 1000 pfu of hCMV AD169 strain (FIG. 39A) or were measured on ARPE-19 cells infected with about 1000 pfu of hCMV VR1814 strain (FIG. 39B). All mRNA vaccine constructs formulated with either MC3 or compound 25 lipid particles elicited neutralizing antibody titers against hCMV infection.

Figure 40A:
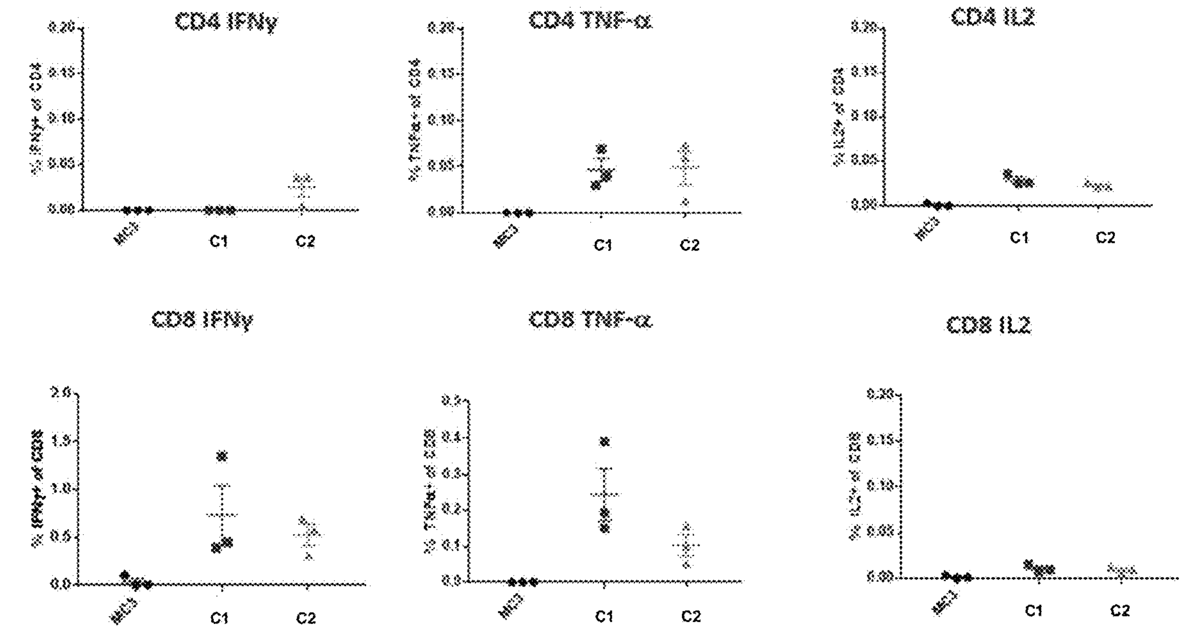
Figure 40B:
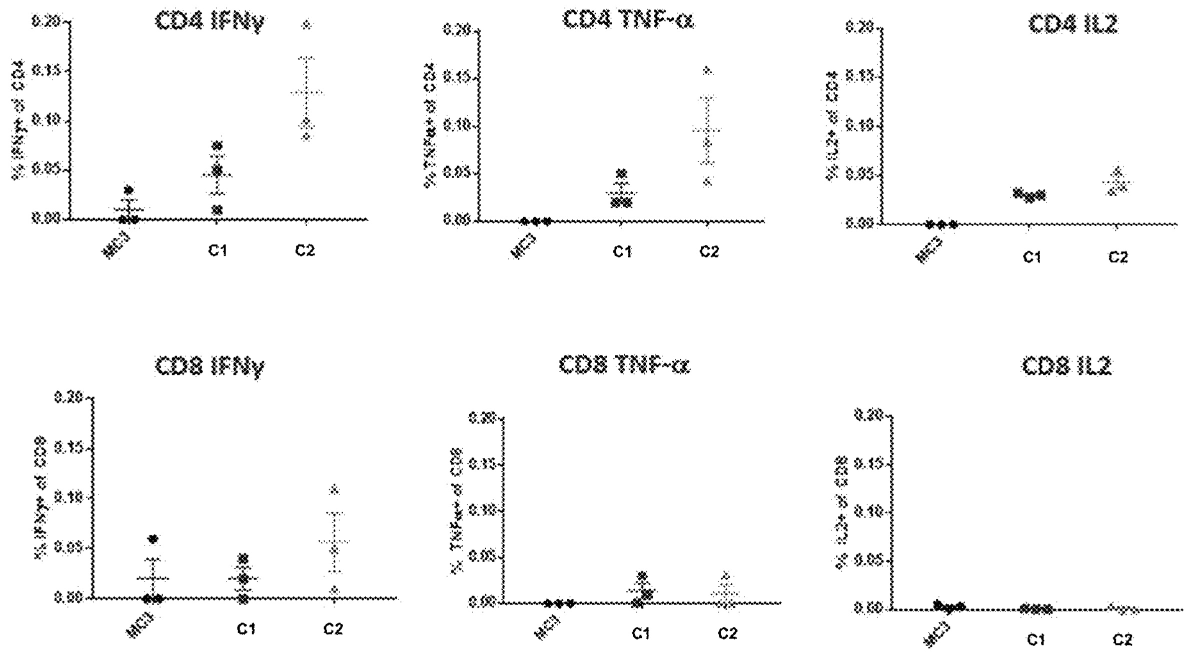
Figure 40C:
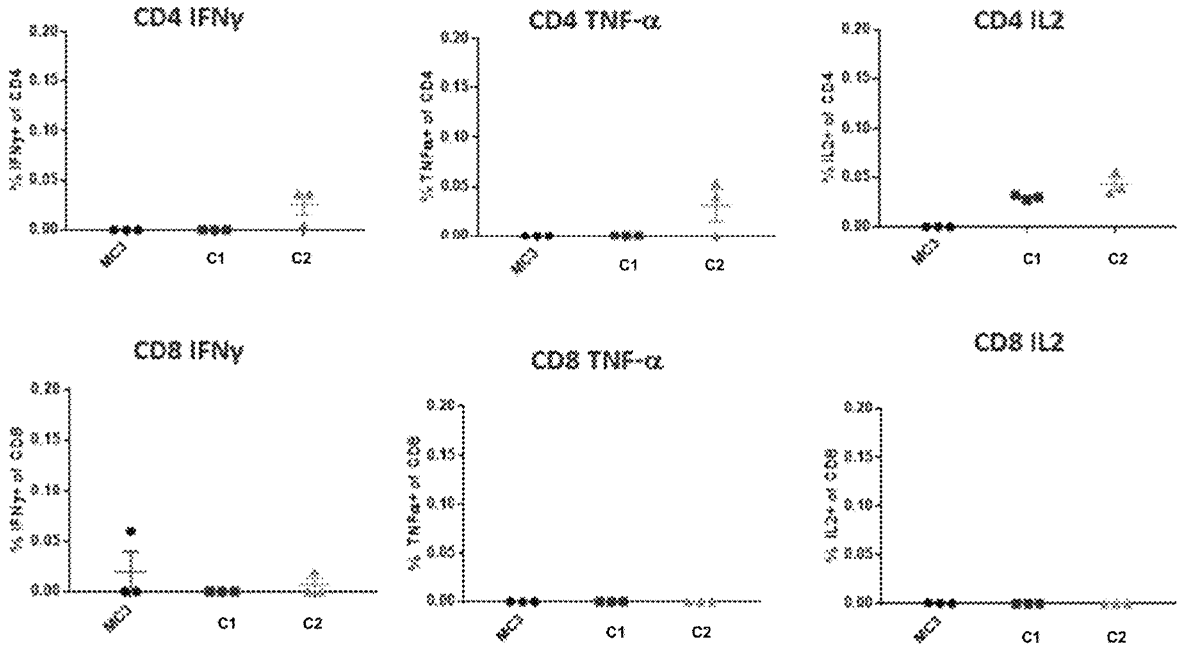

FIGS. 40A-40C are graphs showing T-cell responses (CD4+ T-cell response and CD8+ T-cell response) elicited by hCMV mRNA vaccine constructs encoding hCMV pentamer (5 μg), gB (1 μg), and pp65mut (2 μg). The mRNA vaccine constructs were either unmodified (C1) or contained N1-methylpseudouridine chemical modification (C2), and were formulated in MC3 lipid particles. FIG. 40A shows the T-cell responses elicited by the hCMV mRNA vaccine constructs against hCMV pentamer. FIG. 40B shows the T-cell responses elicited by the hCMV mRNA vaccine constructs against pp65. FIG. 40C shows the T-cell responses elicited by the hCMV mRNA vaccine constructs against gB.

Figure 41A:
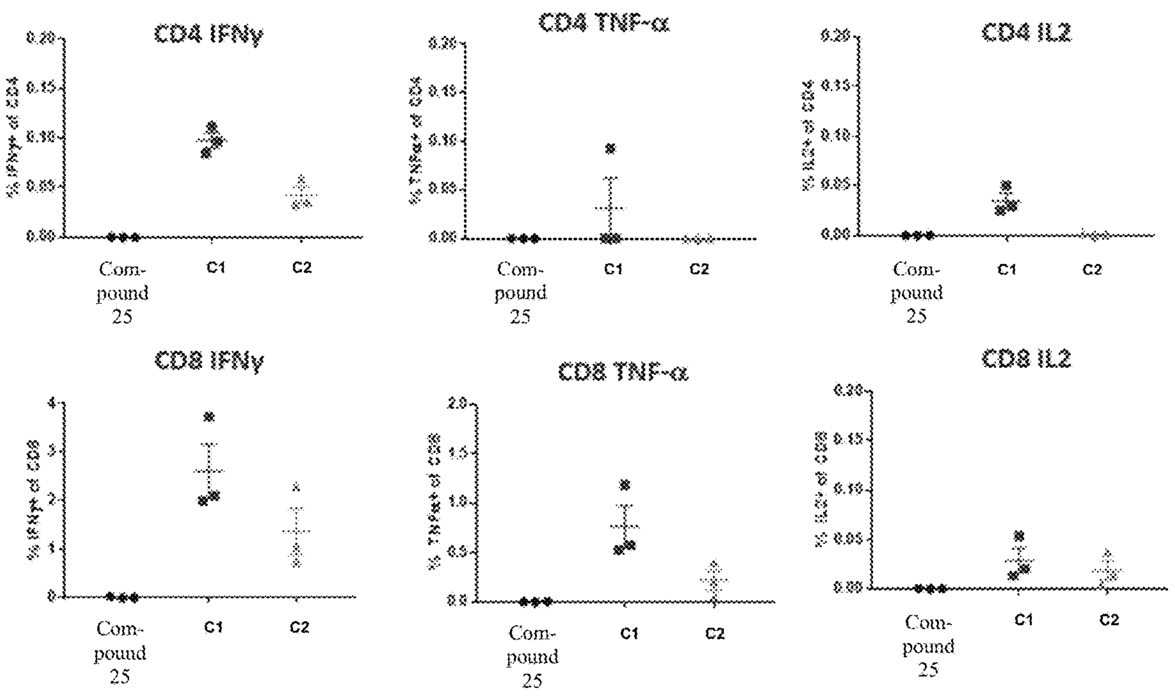
Figure 41B:
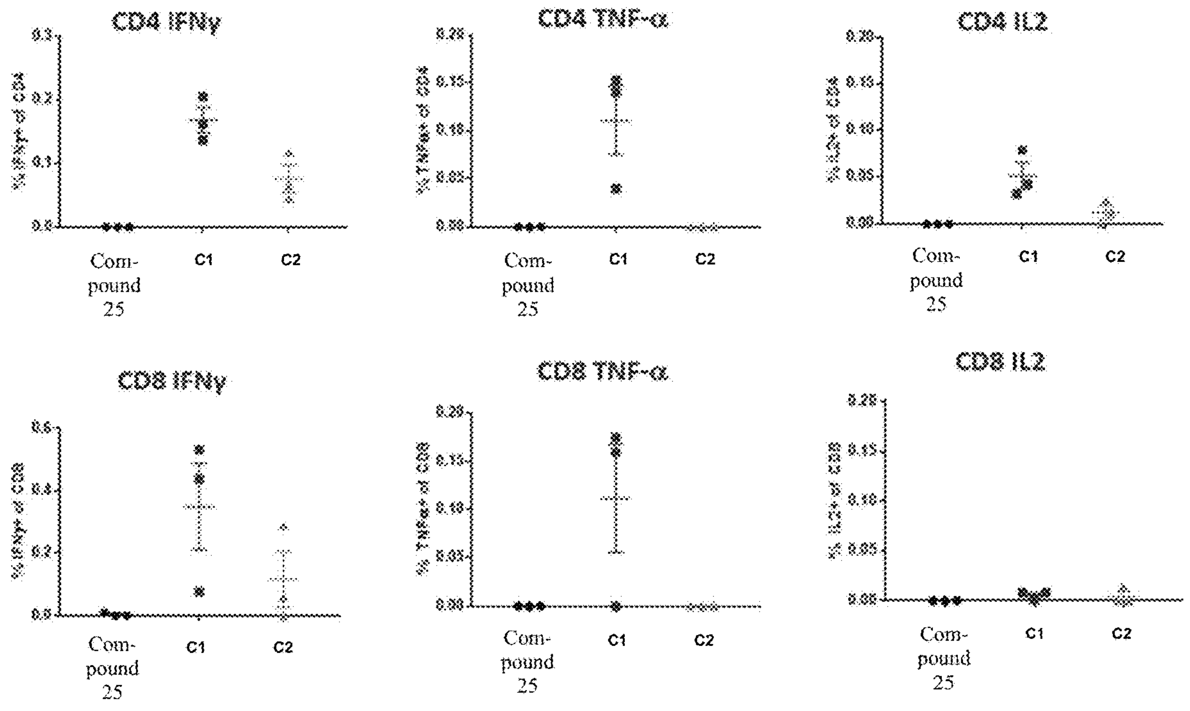
Figure 41C:
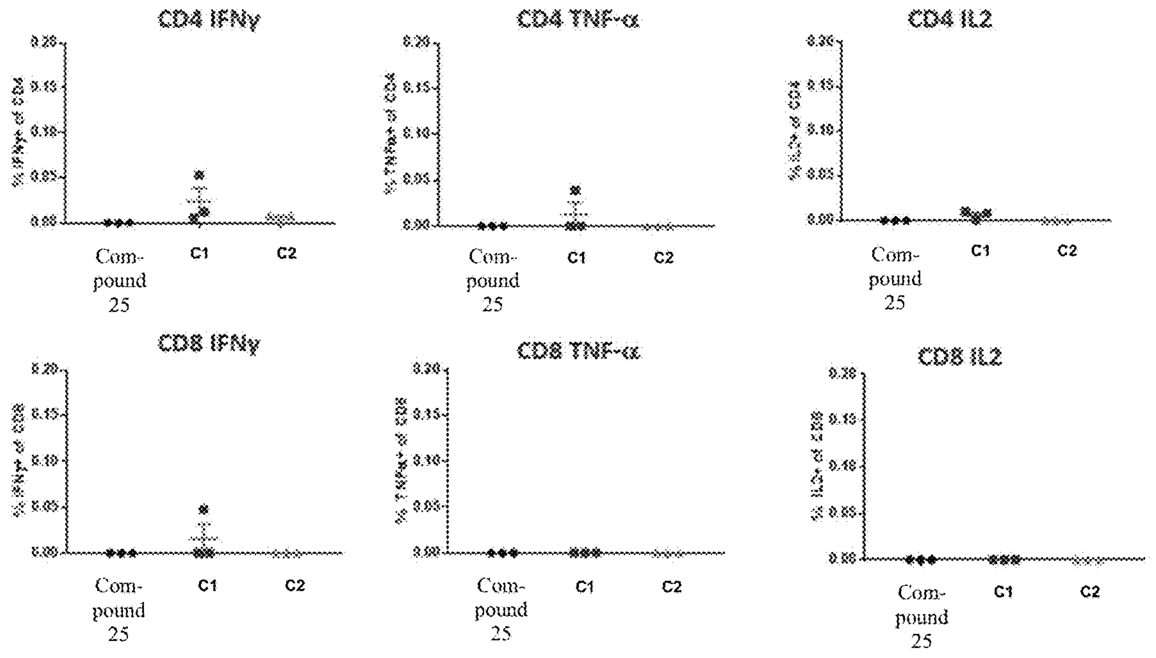

FIGS. 41A-41C are graphs showing T-cell responses (CD4+ T-cell response and CD8+ T-cell response) elicited by hCMV mRNA vaccine constructs encoding hCMV pentamer (5 μg), gB (1 μg), and pp65mut (2 μg). The mRNA vaccine constructs were either unmodified (C1) or contained N1-methylpseudouridine chemical modification (C2), and were formulated in compound 25 lipid particles. FIG. 41A shows the T-cell responses elicited by hCMV mRNA vaccine constructs against hCMV pentamer. FIG. 41B shows the T-cell responses elicited by the hCMV mRNA vaccine constructs against pp65. FIG. 41C shows the T-cell responses elicited by the hCMV mRNA vaccine constructs against gB.

Figure 42A:
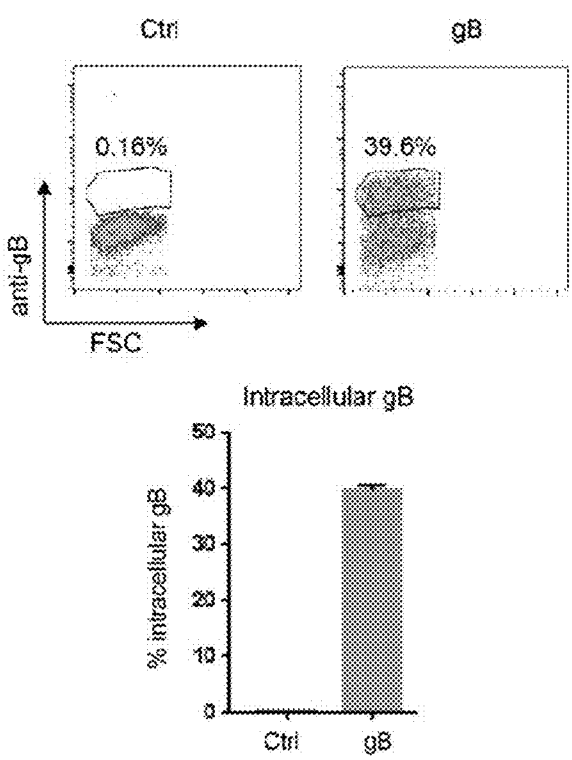
Figure 42B:
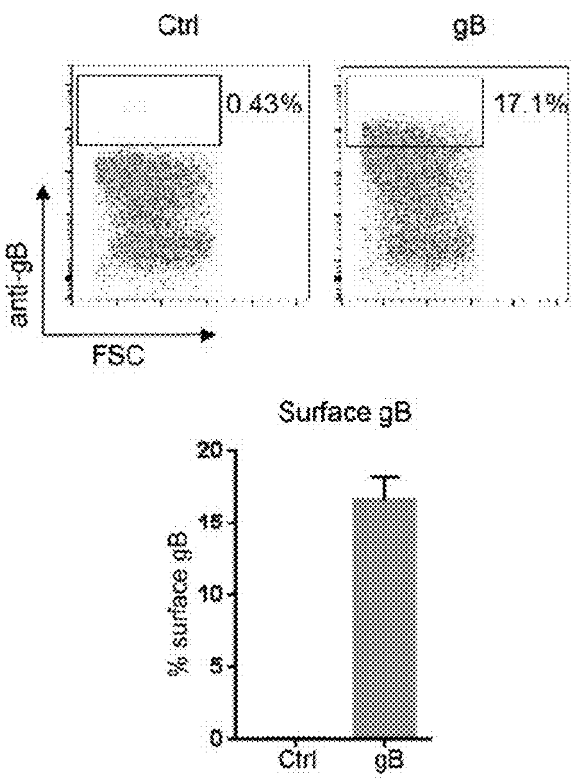
Figure 42C:
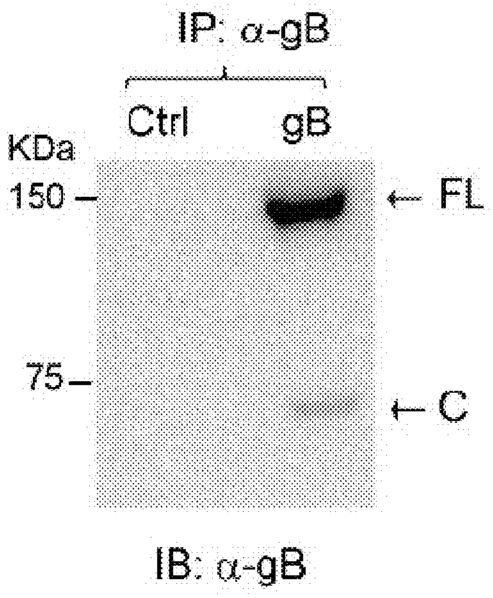

FIGS. 42A-42C show intracellular and cell surface expression analysis of gB by flow cytometry. HeLa cells were either untransfected (control) or transfected with gB mRNA; after 24 hr, the cells were either fixed and permeabilized or not fixed and stained with mouse monoclonal anti-gB antibody. Intracellular expression (FIG. 42A) and surface expression (FIG. 42B) were analyzed by flow cytometry. Representative flow cytometry plots (top) and bar graphs (bottom) depict percent intracellular gB expression. FIG. 42C depicts a Western blot showing expression of gB.

Figure 43A:
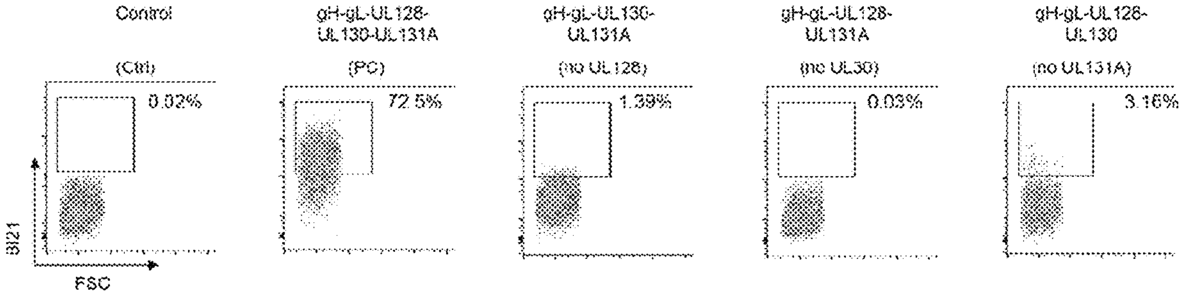
Figure 43B:
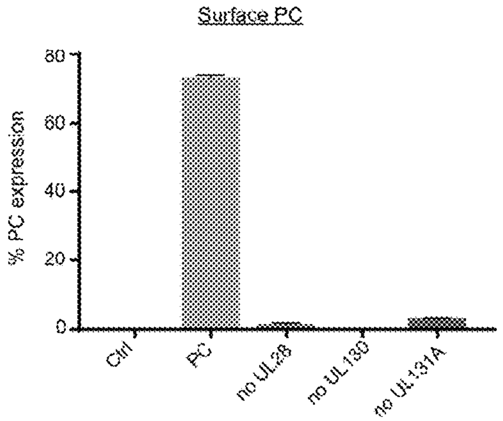

FIGS. 43A-43B are graphs showing expression of surface pentameric complex formation in cells transfected with the indicated mRNAs in equal mass ratios. HeLa cells were transfected with equal mass ratios of mRNAs for all five subunits of the pentametic complex or lacking one of the subunits, as indicated. Cell surface expression of the pentameric complex was analyzed by flow cytometry. FIG. 43A shows flow cytometry plots showing surface expression of the pentameric complex. FIG. 43B is a bar graph. The data in the bar graph represents mean±standard deviation.

Figure 44A:
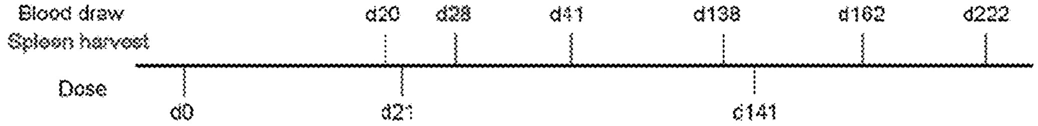
Figure 44B:
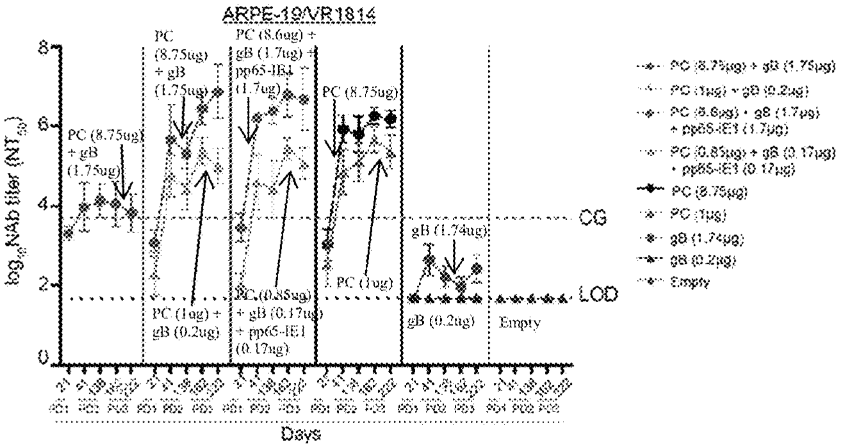
Figure 44C:
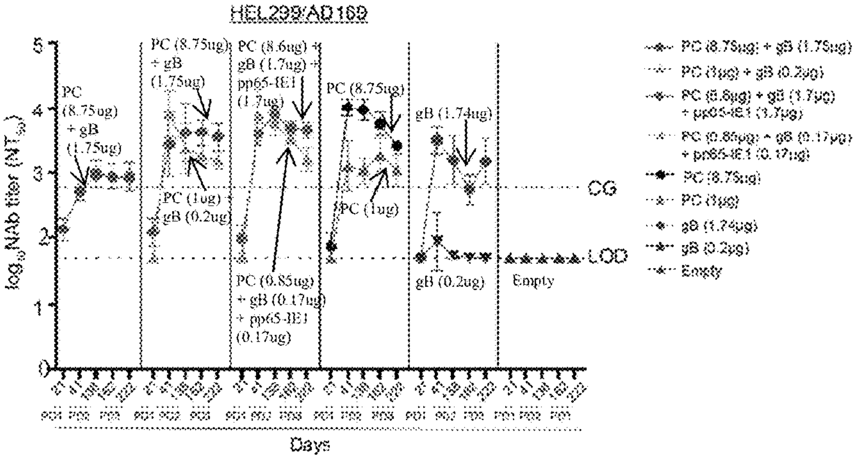
Figure 44D:
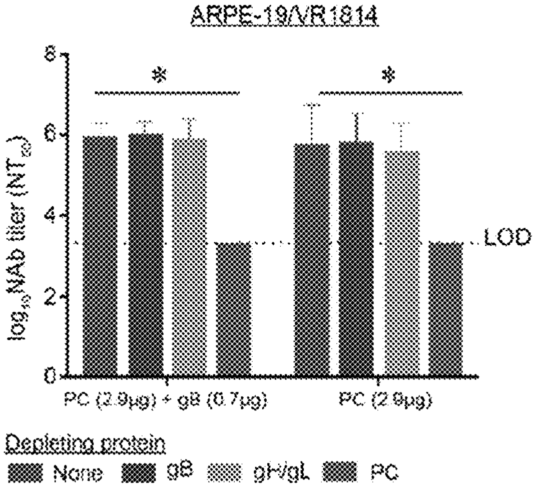
Figure 44E:
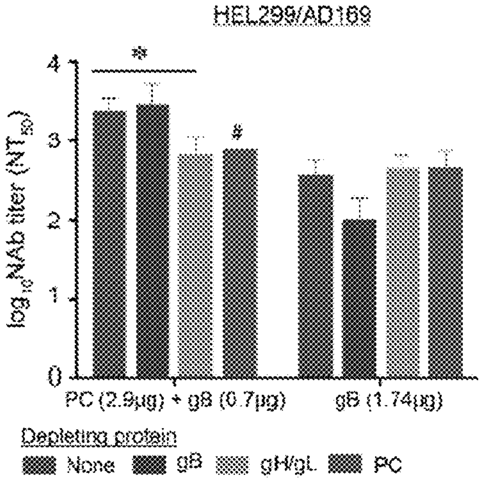

FIGS. 44A-44E demonstrate the neutralizing antibodies and specificity of antibodies in sera of mice immunized with the hCMV mRNA vaccines. FIG. 44A is a schematic of the vaccination regimen in mice showing days of dosing, blood draws, and spleen harvest. FIGS. 44B and 44C show neutralizing titers in sera from mice immunized with the indicated doses and mRNA groups. All mRNAs were present at equal mass in the various vaccine groups. Numbers in parentheses depict the dose of each antigen. PD1, PD2, and PD3 refer to postdose 1, postdose 2, and postdose 3, respectively. Shown are neutralization titers against VR1814 infection in ARPE-19 epithelial cells (FIG. 44B) and against AD169 infection in HEL299 fibroblast cells (FIG. 44C). FIGS. 44D and 44E show specificity of neutralizing antibodies in sera of mice immunized with hCMV mRNA vaccine. Mouse immune serum was preincubated with 5 μg of purified gB, gH/gL, or pentameric complex protein prior to performance of neutralization assays. Also shown are NT50 titers against epithelial (FIG. 44D) and fibroblast cell (FIG. 44E) infection. LOD refers to lower limit of detection; and CG refers to Cytogam. Results represent the mean±standard deviation in scatter and bar graphs. N=5 for all groups. Statistical analysis was done using the Kruskal-Wallis test and Dunn's multiple comparison test (*$p<0.05$).

Figure 45A:
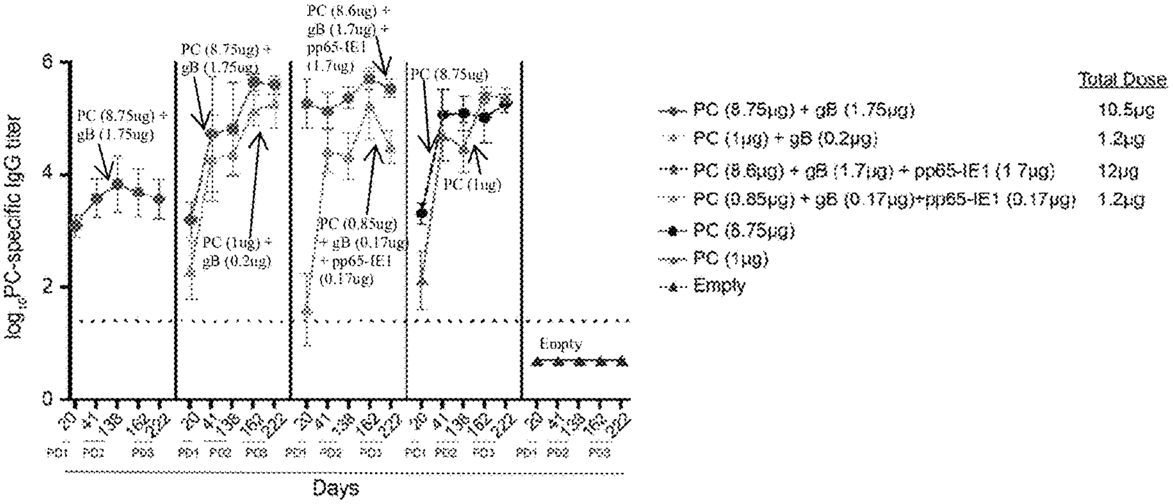
Figure 45B:
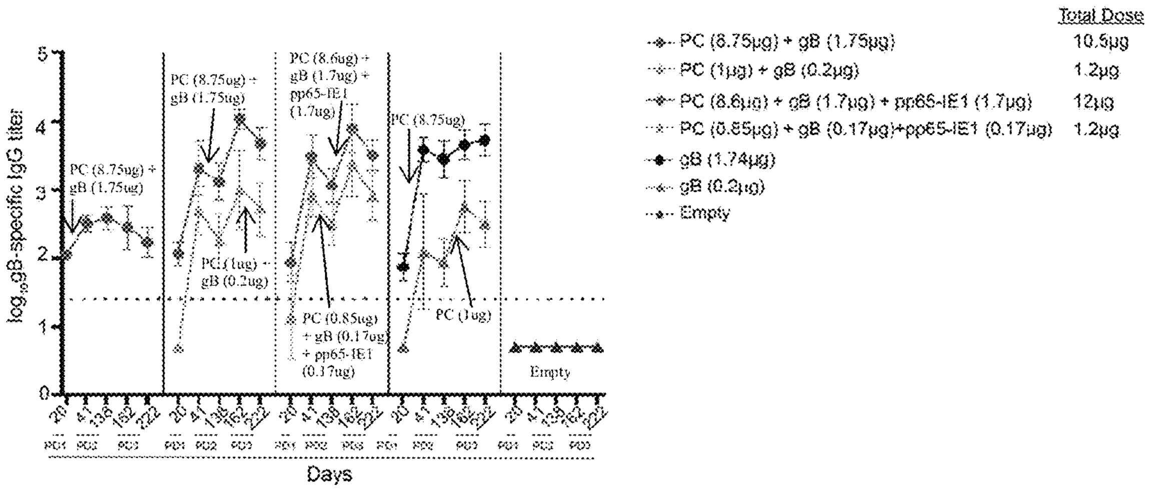

FIGS. 45A-45B are graphs showing antibody responses in mice immunized with hCMV multivalent mRNA vaccines. Anti-pentamer (FIG. 45A) and anti-gB (FIG. 45B) binding titers in sera from BALB/c mice immunized with the indicated doses and mRNA groups are shown. Numbers in parentheses indicate individual doses of each antigen. Also shown is the total dose of each vaccine. The dotted line represents positive cut-off values. N=5 for all groups.

Figure 46A:
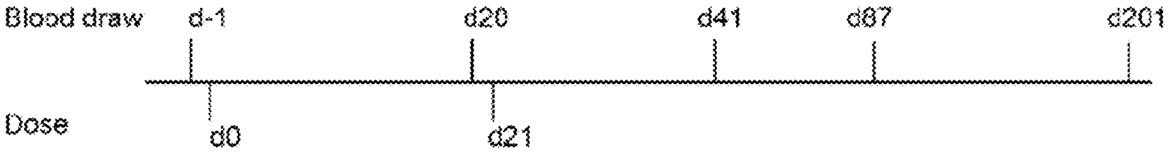

FIGS. 46A-46E demonstrate the neutralizing activity and specificity of antibodies in sera of non human primates (NHP) vaccinated with hCMV mRNA vaccine. FIG. 46A is a schematic of the vaccination regimen and blood draws in NHPs. Neutralizing titers are measured as described in FIGS. 44A-44E in the sera of NHPs that received two doses of the indicated vaccines. All mRNAs were present at equal mass in the various vaccine groups; the total dose is shown in parentheses. NT50 was measured on ARPE-19 cells infected with VR1814 strain (left, 400 μg and 25 μg dose; right, 100 μg dose, FIG. 46B) and HEL 299 cells infected with AD169 strain (left, 400 μg and 25 μg doses; right, 100 μg dose, FIG. 46C). Specificity of antibodies elicited by immunization of NHPs with HCMV antigens was assessed. NHP immune serum and Cytogam were preincubated with 5 μg of purified gB, g/gL, or the pentameric complex protein prior to performing neutralization assays. NT50 titers against epithelial (FIG. 46D) and fibroblast (FIG. 46E) cell infection are shown as mean±standard deviation, N=3, for each group. Statistical analysis was done using the Kruskal-Wallis test and Dunn's multiple comparison test (*p<0.05).

Figure 47A:
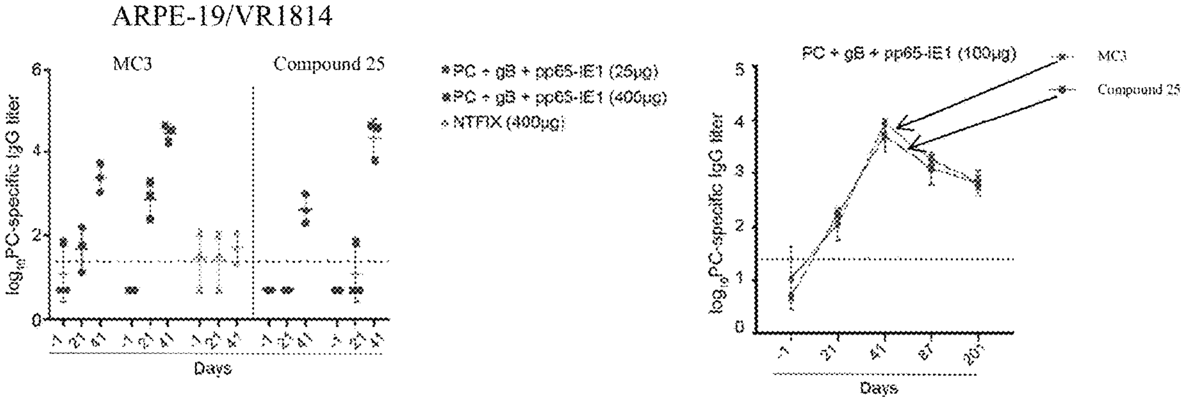

FIGS. 47A-47B show antibody responses in NHPs immunized with hCMV multivalent vaccines. Anti-pentameric complex (PC) (left, 400 μg and 25 μg doses; right, 100 μg dose. FIG. 47A) and anti-gB (left, 400 μg and 25 μg doses; right, 100 μg dose, FIG. 47B) binding titers in sera of NHPs immunized with the indicated doses of the various LNP/mRNA formulations are shown. The dotted line represents positive cut-off values. Results show mean±standard deviation, N=3, for each group.

Figure 48D:
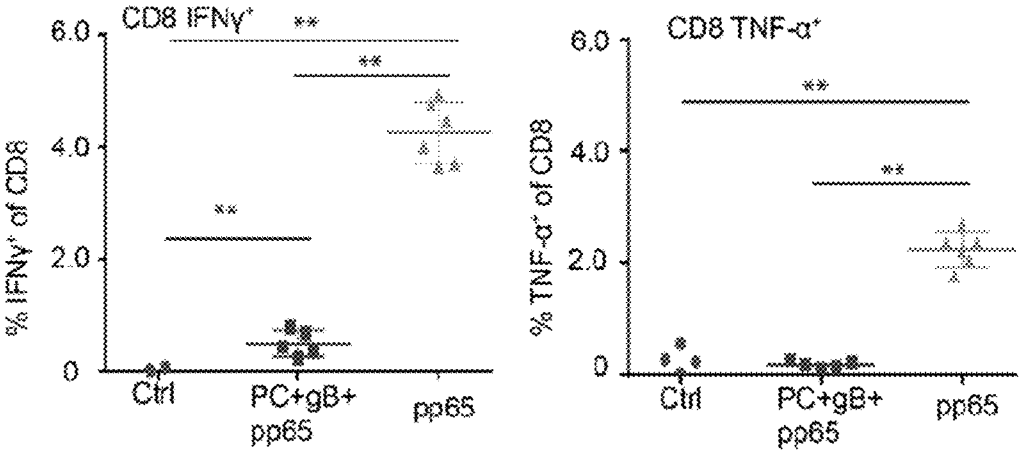
Figure 48E:
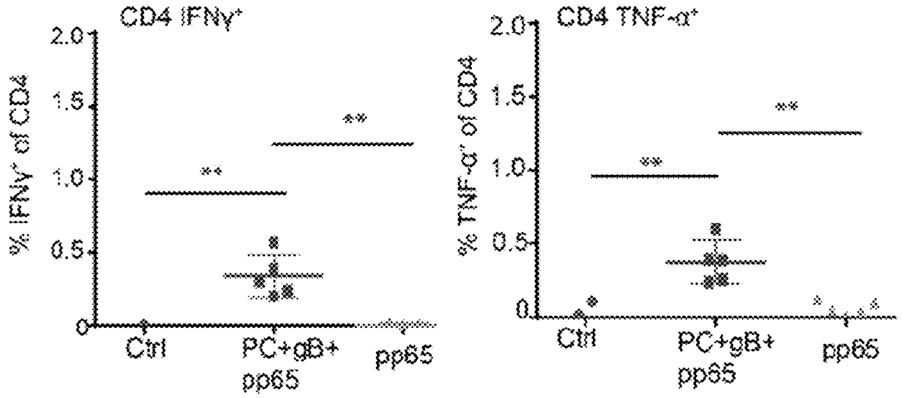
Figure 48F:
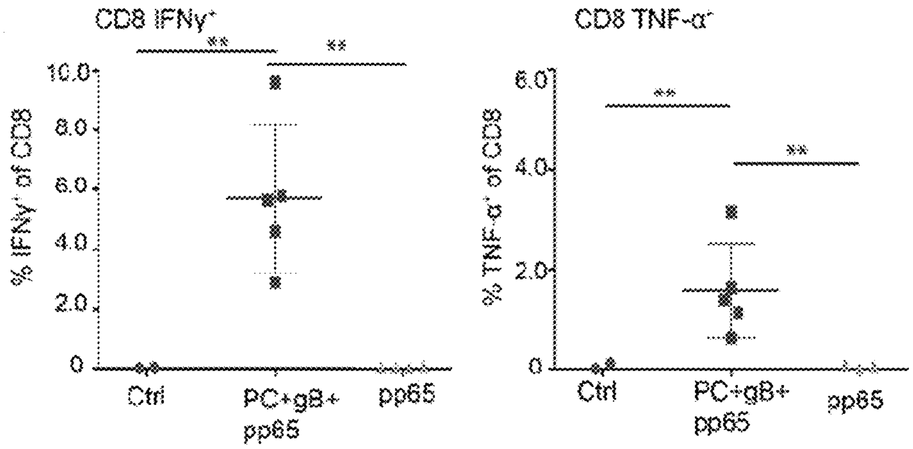

FIGS. 48A-48F show differential T cell responses to pp65 and the petameric complex in hCMV mRNA vaccine. FIGS. 48A and 48B show T cell responses to pp65-IE1. One week following boost, CD4 (FIG. 48A) and CD8 (FIG. 48B) T cells secreting IFNγ in response to pp65-IE1 peptide pools were measured by ICS and analyzed by flow cytometry. pp65-IE1 was present at a dose of 2 μg in both vaccine groups. FIGS. 48C and 48D show pp65-specific CD4 (FIG. 48C) and CD8 (FIG. 48D) T cell responses. FIGS. 48E and 48F show pentamer-specific CD4 (FIG. 48E) and CD8 (FIG. 48F) T cell responses. One week postboost, splenocytes from the indicated groups were stimulated either with pp65 (FIGS. 48C and 48D) or pentameric complex (PC) (FIGS. 48E and 48F) peptide libraries, and polyfunctional (IFNγ, TNF-α, IL-2) T cell responses were measured by ICS and analyzed by flow cytometry. Scatter plots represent mean±standard deviation. For FIGS. 48C-48E, the doses of pentameric complex, gB, and pp65 were 8 μg, 2 μg, and 2 μg, respectively, wherever applicable. N=5 for all groups. Statistical analysis was done using the two-tailed Mann-Whitney U test (*p<0.05, p<0.01, **p<0.0001).

Figure 49A:

FIGS. 49A-49E show that heterologous prime boost vaccine regimen restores pp65 specific T cell responses. FIG. 49A is a schematic of heterologous prime boost dosing schedule. FIGS. 49B-49E show pp65-specific (FIGS. 49B and 49C) and pentamer-specific (FIGS. 49D and 49E) T cell responses in mice vaccinated with the indicated hCMV mRNA antigens. Polyfunctional T cell responses were measured as described in FIGS. 48A-48F. Shown are pp65-specific CD4 (FIG. 49B) and CD8 (FIG. 49C) and pentameric complex (PC)-specific CD4 (FIG. 49D) and CD8 (FIG. 49E) T cell responses. Scatter plots represent mean±standard deviation, N=5, for all groups. Statistical analysis was done using the Kruskal-Wallis test and Dunn's multiple comparison test (*p<0.05, **p<0.01).

Figure 50A:
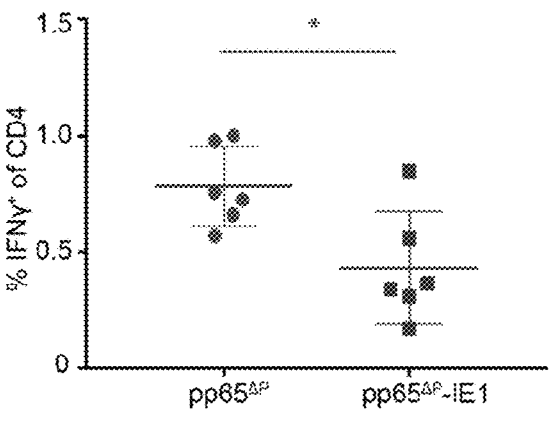
Figure 50B:
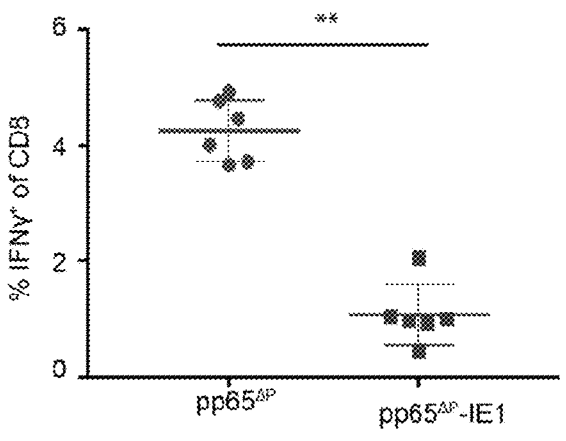

FIGS. 50A-50B show T cell responses in mice vaccinated with $pp65^{\Delta P}$ and $pp65^{\Delta P\text{-}IE1}$. CD4 (FIG. 50A) and CD8 T (FIG. 50B) cells secreting IFNγ in response to pp65 were measured by ICS and analyzed by Flow Cytometry. A 2 μg dose of mRNA was used for each vaccine group. Statistical analysis was done using the two-tailed Mann Whitney U test (*p<0.05, **p<0.01). N=5 for each group.

Figure 51A:
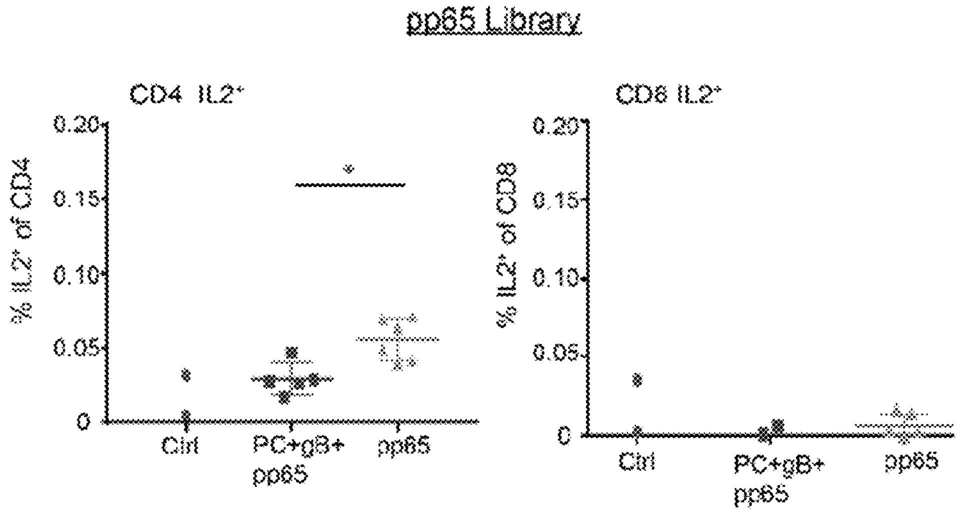
Figure 51B:
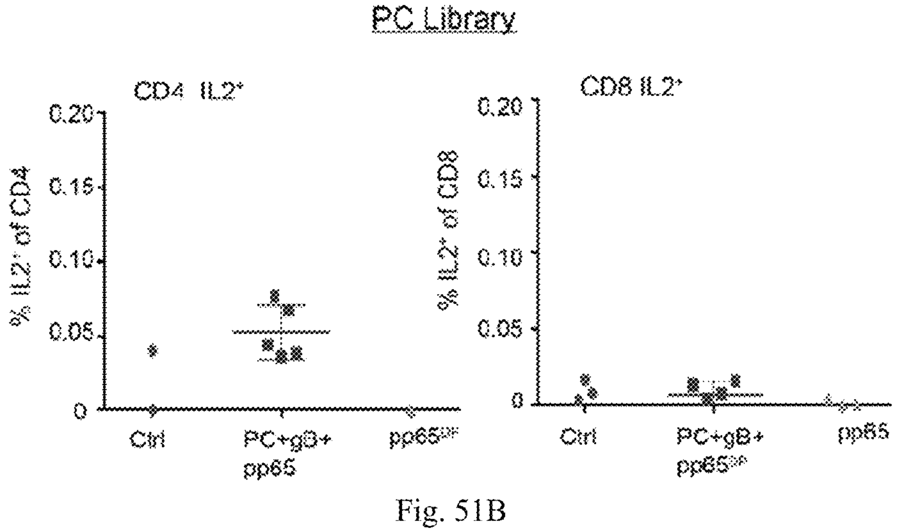
Figures 51C, 51D:
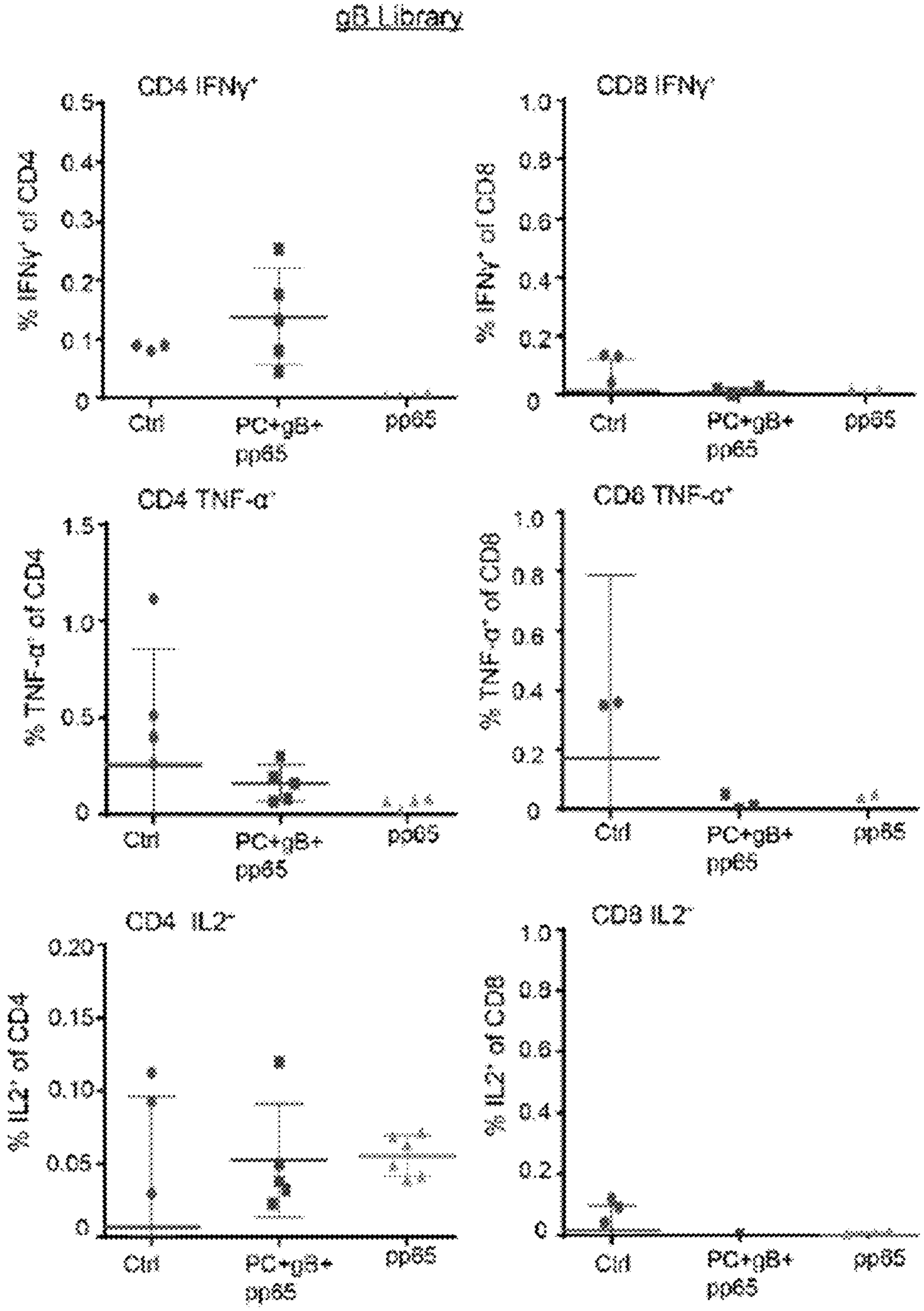

FIGS. 51A-51D show the T cell responses to various hCMV antigens. FIG. 51A shows pp65-specific CD4 and CD8 T cells that secrete IL2. FIG. 51B shows pentamer-specific T cells that secrete IL2. FIGS. 51C-51D show polyfunctional CD4 (FIG. 51C) and CD8 (FIG. 51D) T cell responses to gB antigen. T cell responses were measured as described in FIG. 5. Scatter plots represent mean±standard deviation, N=5, for all groups. Statistical analysis was done using the two-tailed Mann Whitney U test (*p<0.05).

Figure 52:
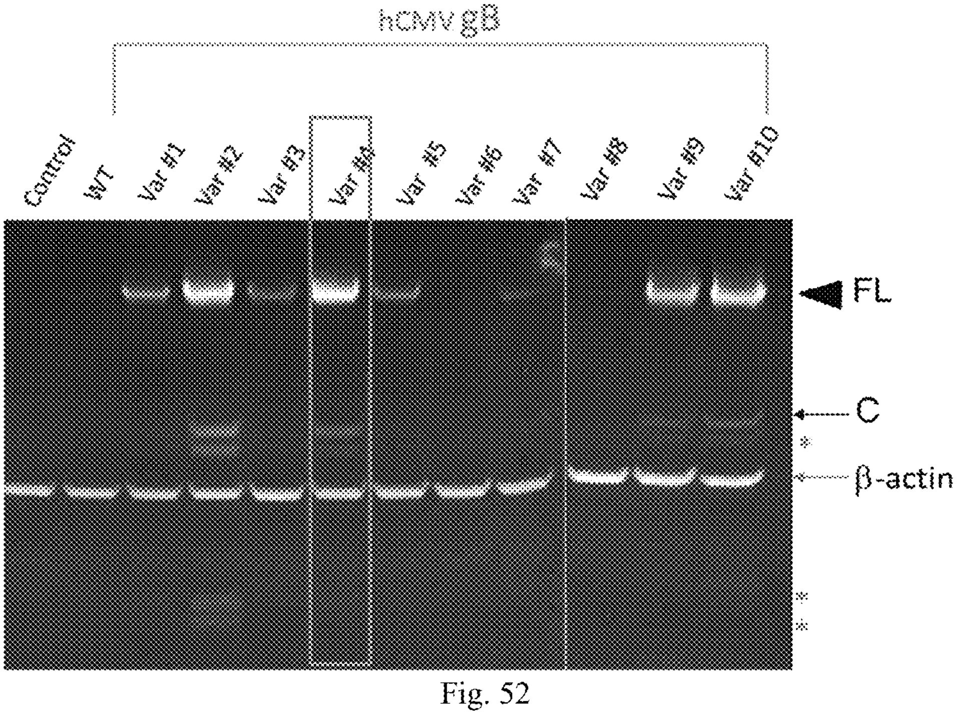

FIG. 52 shows the expression of gB in HEK 293 cells using codon-optimized gB mRNA variants. Compared to the wild type gB mRNA, several of the codon-optimized variants (Var #1-Var #4, Var #9, and Var #10) led to enhanced expression in HEK293 cells, among which Var #4 had the highest expression level. * indicates truncated proteins due to out of frame AUGs or background bands.

DETAILED DESCRIPTION

Embodiments of the present disclosure provide RNA (e.g., mRNA) vaccines that include polynucleotide encoding a human cytomegalovirus (HCMV) antigen. Demonstrated herein is an HCMV vaccine that elicits broad and durable neutralizing antibodies as well as robust T cell responses. The human cytomegalovirus (HCMV) is a ubiquitous double-stranded DNA virus belonging to the Herpes virus family. HCMV is made up of a DNA core, an outer capsid and covered by a lipid membrane (envelope) which incorporates virus specific glycoproteins. The diameter is around 150-200 nm. Genomes are linear and non-segmented, around 200 kb in length. Viral replication is nuclear, and is lysogenic. Replication is dsDNA bidirectional replication.

HCMV can infect a wide range of mammalian cells, which correlates with its ability to infect most organs and tissues. Entry into the host cell is achieved by attachment of the viral glycoproteins to host cell receptors, which mediates endocytosis. HCMV displays a broad host cell range, with the ability to infect several cell types, such as endothelial cells, epithelial cells, smooth muscle cells, fibroblasts, leukocytes, and dendritic cells. This broad cellular tropism suggests that HCMV may bind a number of receptors or a common surface molecule.

HCMV encodes several surface glycoproteins that are important for viral attachment and entry into different cell types. Entry into fibroblast cells is mediated by the core herpesvirus fusion machinery comprising gB and the gH/gL/gO ternary complex (Vanarsdall and Johnson, 2012; Vanarsdall et al., 2008, incorporated herein by reference). The pentameric complex (PC), composed of gH/gL/UL128/UL130/UL131A (Hahn et al., 2004; Ryckman et al., 2008; Wang and Shenk, 2005b, incorporated herein by reference), mediates entry into endothelial cells, epithelial cells, and myeloid cells. The majority of neutralizing antibodies are directed against envelope glycoproteins (Britt et al., 1990; Fouts et al., 2012; Macagno et al., 2010; Marshall et al., 1992, incorporated herein by reference), whereas robust T cell responses are directed against the tegument protein pp65 and nonstructural proteins such as 1E1 and 1E2 (Blanco-Lobo et al., 2016; Borysiewicz et al., 1988; Kern et al., 2002, incorporated herein by reference).

HCMV envelopment is very complicated and comprises more than 20 glycoproteins which may be the reason for broad cellular tropism of HCMV. HCMV particles contain at least four major glycoprotein complexes, all of which are involved in HCMV infection, which requires initial interaction with the cell surface through binding to heparin sulfate proteoglycans and possibly other surface receptors.

The gCI complex is comprised of dimeric molecules of the glycoprotein gB. Each 160-kDa monomer is cleaved to generate a 116-kDa surface unit linked by disulfide bonds to a 55-kDa transmembrane component. Some antibodies immunospecific for gB inhibit the attachment of virions to cells, whereas others block the fusion of infected cells, suggesting that the gB protein might execute multiple functions at the start of infection. Studies have confirmed that glycoprotein B (gB) facilitates HCMV entry into cells by binding receptors and mediating membrane fusion. Several cellular membrane proteins interact with gB, which interactions likely facilitate entry and activate cellular signaling pathways.

The gCII complex is the most abundant of the glycoprotein complexes and is a heterodimer consisting of glycoproteins gM and gN. The complex binds to heparan sulfate proteoglycans, suggesting it might contribute to the initial interaction of the virion with the cell surface. It may also perform a structural role during virion assembly/envelopment, similar to the gM-gN complex found in some α-herpesviruses.

The gCIII complex is a trimer comprised of glycoproteins gH, gL, gO which are covalently linked by disulfide bonds. All known herpesviruses encode gH-gL heterodimers, which mediate fusion of the virion envelope with the cell membrane. Antibodies specific for human CMV gH do not affect virus attachment but block penetration and cell-to-cell transmission. A gO-deficient mutant of HCMV (strain AD169) shows a significant growth defect.

HCMV proteins UL128, UL130, and UL131A assemble with gH and gL proteins to form a heterologous pentameric complex, designated gH/gL/UL128-131A, found on the surface of the HCMV. Natural variants and deletion and mutational analyses have implicated proteins of the gH/gL/UL128-131A complex with the ability to infect certain cell types, including for example, endothelial cells, epithelial cells, and leukocytes.

HCMV enters cells by fusing its envelope with either the plasma membrane (fibroblasts) or the endosomal membrane (epithelial and endothelial cells). HCMV initiates cell entry by attaching to the cell surface heparan sulfate proteoglycans using envelope glycoprotein M (gM) or gB. This step is followed by interaction with cell surface receptors that trigger entry or initiate intracellular signaling. The entry receptor function is provided by gH/gL glycoprotein complexes. Different gH/gL complexes are known to facilitate entry into epithelial cells, endothelial cells, or fibroblasts. For example, while entry into fibroblasts requires gH/gL heterodimer, entry into epithelial and endothelial cells requires the pentameric complex gH/gL/UL128/UL130/UL131 in addition to gH/gL. Thus, different gH/gL complexes engage distinct entry receptors on epithelial/endothelial cells and fibroblasts. Receptor engagement is followed by membrane fusion, a process mediated by gB and gH/gL. Early antibody studies have supported critical roles for both gB and gH/gL in HCMV entry. gB is essential for entry and cell spread. gB and gH/gL are necessary and sufficient for cell fusion and thus constitute the "core fusion machinery" of HCMV, which is conserved among other herpesviruses.

Thus, the four glycoprotein complexes play a crucial role in viral attachment, binding, fusion and entry into the host cell.

Studies involving the gH/gL/UL128-131A complex have shown that HCMV glycoproteins gB, gH, gL, gM, and gN, as well as UL128, UL130, and UL131A proteins, are antigenic and involved in the immunostimulatory response in a variety of cell types. Moreover, UL128, UL130, and UL131A genes are relatively conserved among HCMV isolates and therefore represent an attractive target for vaccination. Furthermore, recent studies have shown that antibodies to epitopes within the pentameric gH/gL/UL128-131 complex neutralize entry into endothelial, epithelial, and other cell types, thus blocking the ability of HCMV to infect several cell types.

HCMV envelope glycoprotein complexes (gCI, II, III, gH/gL/UL128-131A) represent major antigenic targets of antiviral immune responses. Embodiments of the present disclosure provide RNA (e.g., mRNA) vaccines that include polynucleotide encoding a HCMV antigen, in particular an HCMV antigen from one of the HCMV glycoprotein complexes. Embodiments of the present disclosure provide RNA (e.g., mRNA) vaccines that include at least one polynucleotide encoding at least one HCMV antigenic polypeptide. The HCMV RNA vaccines provided herein may be used to induce a balanced immune response, comprising both cellular and humoral immunity, without many of the risks associated with DNA vaccines and live attenuated vaccines.

The entire contents of International Application No. PCT/US2015/027400 (WO 2015/164674), entitled "Nucleic Acid Vaccines," is incorporated herein by reference.

HCMV Vaccine for Transplant Patients

Although HCMV infection is benign in most healthy adults, it can sometimes result in serious diseases, such as retinitis, in immunocompromised patients, e.g., an organ transplant recipient. An "immunocomprised patient" refers to a patient who does not have the ability to respond normally to an infection due to an impaired or weakened immune system. This inability to fight infection can be caused by a number of conditions including illness and disease (e.g., in some embodiments, diabetes, HIV), malnutrition, and drugs.

The control of HCMV infection in immunocomprised patients, e.g., organ transplant recipients who are receiving immunosuppressive drugs to suppress their adaptive immune systems, is associated with preserved cellular immune responses, e.g., T cell responses involving CD4+, CD8+, and NK T cells (Riddell et al., *Semin. Respir. Infect.* 10:199-208, 1995). HCMV antigens that elicit T cell responses (e.g., CD8+ responses) include, without limitation, the major tegument protein pp65, and the early-immediate proteins such as IE1 (e.g., in Khan et al., *J. Infect. Dis.* 185, 1025-1034, 2002). In some instances, T cell responses specific to the glycoprotein gB can be elicited (Borysiewicz et al., *J. Exp. Med.* 168, 919-931, 1988). CD4+ response is present in almost all individuals infected with HCMV. (Kern, F., et al., *J. Infect. Dis.* 185:1709-1716 (2002)).

In some embodiments, the immunocomprised patient is an organ transplant recipient. An "organ transplant recipient" refers to a subject who has received or will receive an organ transplant. As used herein, an "organ transplant" refers to the moving of an organ or tissue from a donor to a recipient. In some embodiments, a donor and a recipient are different subjects. In other embodiments, a donor and a recipient are the same subject. Donors and recipients can be human or non-human subjects. For example, in some embodiments, a donor and a recipient are both human subjects. In other embodiments, a donor is a non-human subject and a recipient subject is a human subject. In other embodiments, a donor is a human subject and a recipient is a non-human subject. In other embodiments, a donor and a recipient are both non-human subjects.

In some embodiments, the organ transplant recipient is a solid organ transplant (SOT) recipient. Solid organs/tissue that may be transplanted include, without limitation, heart, kidney, liver, lungs, pancreas, intestine, thymus, bones, tendons, cornea, skin, heart valves, nerves and veins. In some embodiments, the organ transplant recipient is a hematopoietic cell transplant (HCT) recipient. "Hematopoietic cell transplantation (HCT)" refers to the intravenous infusion of hematopoietic cells to a recipient. Hematopoietic cells may be from, e.g., bone marrow, peripheral blood, amniotic fluid, and umbilical cord blood. Bone marrow transplantation is a common type of hematopoietic stem cell transplantation. Hematopoietic cells can be transplanted from a donor to a recipient. The donor and recipient can be the same subject or different subjects.

The donor or recipient of a transplantation can be HCMV seropositive or seronegative. "Seropositive" means the individual (e.g., the transplant donor and/or the recipient) has had a past HCMV infection and HCMV IgG can be detected in his/her blood. Being "seropositive" does not necessarily mean that there is live, replicating HCMV in the blood of the subject. An individual who has not had a past HCMV infection does not have HCMV specific IgG in his/her blood, and is therefore "seronegative."

Without appropriate prophylactic measures, the seronegative recipient of an organ from a seropositive donor can be at high risk (>60%) of developing CMV disease. IgG detection can be used to diagnose donor seropositivity since donors generally have intact humoral responses. In some embodiments, the recipient is seropositive but the HCMV is latent, and the HCMV is reactivated after the transplantation.

"Latent," or "latency" refers to a phase in certain viruses' life cycles in which, after initial infection, proliferation of virus particles ceases. However, the viral genome is not fully eradicated. As a result, the virus can reactivate and begin producing large amounts of viral progeny without the host being infected by new outside virus. A virus can potentially stay within a host indefinitely. In some instances, a latent virus can be reactivated via external activators (i.e. sunlight, stress) to cause an acute infection.

Transplant recipients disclosed herein include subjects that are immunocompromised and subjects that are not immunocompromised. HCMV-associated diseases in organ transplant recipients can affect most organs of the body, and can result in, e.g., fever, pneumonia, hepatitis, encephalitis, myelitis, colitis, uveitis, retinitis, neuropathy, Guillain-Barre syndrome, meningoencephalitis, pericarditis, myocarditis, thrombocytopenia, hemolytic anemia, deadly pneumonitis, esophagitis, leukopenia, infections, and complications in organ transplant.

Aspects of the present disclosure provide safe and effective HCMV vaccines and methods to protect subjects, including immunocomprised organ transplant recipients, against HCMV infection. HCMV vaccines disclosed herein include RNA vaccines (e.g., mRNA vaccines) that encode at least one HCMV antigenic polypeptide, or an immunogenic fragment thereof. In some embodiments, the antigenic polypeptides or immunogenic fragments encoded by the HCMV RNA vaccine (e.g., mRNA vaccine) of the present disclosure are selected from gB, gH, gL, gO, gM, gN, UL83, UL123, UL128, UL130, UL131A, pp65 and 1E1 antigens. In some embodiments, the HCMV RNA vaccine (e.g., mRNA vaccine) comprises at least one RNA polynucleotide (e.g., mRNA) having one or more open reading frames encoding gH, gL, UL128, UL130, and/or UL131A, or antigenic fragments or epitopes thereof. In some embodiments, the HCMV RNA vaccine (e.g., mRNA vaccine) comprises at least one RNA polynucleotide (e.g., mRNA) having one or more open reading frames encoding gB, gH, gL, UL128, UL130, and/or UL131A, or antigenic fragments or epitopes thereof. In some embodiments, the HCMV RNA vaccine (e.g., mRNA vaccine) comprises at least one RNA polynucleotide (e.g., mRNA) having one or more open reading frames encodes gB, gH, gL, UL128, UL130, and UL131A, or antigenic fragments or epitopes thereof, and further comprises an RNA polynucleotide (e.g., mRNA) having an open reading frame encoding HCMV antigenic polypeptide pp65, or an antigenic fragment or epitope thereof. In some embodiments, the HCMV RNA vaccine (e.g., mRNA vaccine) comprises at least one RNA polynucleotide (e.g., mRNA) having one or more open reading frames encoding HCMV antigenic polypeptide pp65, or antigenic fragments or epitopes thereof. In some embodiments, the pp65 polypeptide sequence contains a deletion of amino acids 435-438. In some embodiments, a first HCMV vaccine and a second HCMV vaccine are administered. A first HCMV vaccine can comprise an RNA polynucleotide having an open reading frame encoding HCMV antigenic polypeptide pp65, or an antigenic fragment or epitope thereof, while a second HCMV vaccine can comprise at least one RNA polynucleotide having one or more open reading frames encoding HCMV antigenic polypeptides gH, gL, UL128, UL130, and/or UL131A, or antigenic fragments or epitopes thereof; an RNA polynucleotide having an open reading frame encoding HCMV antigenic polypeptide gB, or an antigenic fragment or epitope thereof; and an RNA polynucleotide having an open reading frame encoding HCMV antigenic polypeptide pp65, or an antigenic fragment or epitope thereof.

Within HCMV vaccines described herein, the various components can be formulated together or separately. In some embodiments, the RNA polynucleotides (e.g., mRNAs) encoding gB, gH, gL, UL128, UL130, UL131A, or antigenic fragments or epitopes thereof, may be formulated in one HCMV vaccine composition and can be formulated at equal ratios (e.g., at 1:1:1:1:1 ratio) or can be formulated at different ratios. In some embodiments, the RNA polynucleotides (e.g., mRNAs) ending pp65, or antigenic fragments or epitopes thereof, are formulated in a separate HCMV vaccine composition. In other embodiments, the RNA polynucleotides (e.g., mRNAs) encoding gB, gH, gL, UL128, UL130, UL131A, or antigenic fragments or epitopes thereof are formulated together with the RNA polynucleotides (e.g., mRNAs) ending pp65, or antigenic fragments or epitopes thereof.

HCMV vaccines described herein can be administered to donors and/or recipients of organ transplant. Donors and/or recipients can be seronegative or seropositive. In some embodiments, the HCMV mRNA vaccines of the present disclosure are administered to: seronegative recipients receiving a transplant from a seropositive donor; seronegative recipients receiving a transplantation from a seronegative donor; or seropositive recipients receiving a transplant from a seropositive or seronegative donor. The HCMV mRNA vaccines of the present disclosure may also be administered to transplant donors, either seronegative or seropositive, to prevent or treat HCMV.

HCMV mRNA vaccines described herein may be administered to transplant recipients or donors before or after the transplantation. If given before transplantation, it may be given, e.g., 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 4 months, 5 months, 6 months, or more before the transplantation. If give after the transplantation, it may be given, e.g., 1 day, 2 days, 3 days, 4 days, 5 days, 6 days, 7 days, 8 days, 9 days, 10 days, 2 weeks, 3 weeks, 4 weeks, 5 weeks, 6 weeks, 7 weeks, 8 weeks, 3 months, 4 months, 6 months, or more after the transplantation. The dosage of the HCMV mRNA vaccines may include any of the dosages described herein. Booster doses may also be given after one or two primary doses. In some embodiments, two primary doses are given at 0 and 1 month, and a booster dose is given at 6 months.

In some embodiments, in which two HCMV vaccines are administered, the two HCMV vaccines may be administered simultaneously or sequentially. For example, in some embodiments, a first HCMV vaccine comprising an RNA polynucleotide having an open reading frame encoding HCMV antigenic polypeptide pp65, or an antigenic fragment or epitope thereof is administered before a second HCMV vaccine comprising at least one RNA polynucleotide having one or more open reading frames encoding HCMV antigenic polypeptides gH, gL, UL128, UL130, and/or UL131A, or antigenic fragments or epitopes thereof; an RNA polynucleotide having an open reading frame encoding HCMV antigenic polypeptide gB, or an antigenic fragment or epitope thereof; and an RNA polynucleotide having an open reading frame encoding HCMV antigenic polypeptide pp65, or an antigenic fragment or epitope thereof. For example, the first HCMV vaccine can be administered at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days before the second vaccine. In some embodiments, the first HCMV vaccine is administered at least 1, 2, 3, or 4 weeks before the second HCMV vaccine. In some embodiments, the first HCMV vaccine is administered at least 1, 2, or 3 weeks before the second HCMV vaccine.

In some embodiments, HCMV mRNA vaccines described herein may be given in combination with other antiviral drugs, e.g., Ganciclovir and derivatives, CMV-CTL, HCMV specific antibodies, Brincidofovir, or Letermovir.

It has been discovered that the mRNA vaccines described herein are superior to current vaccines in several ways. First, the lipid nanoparticle (LNP) delivery is superior to other formulations including liposome or protamine based approachs described in the literature and no additional adjuvants are to be necessary. The use of LNPs enables the effective delivery of chemically modified or unmodified (no nucleotide modifications) mRNA vaccines. Both modified and unmodified LNP formulated mRNA vaccines are superior to conventional vaccines by a significant degree. In some embodiments the mRNA vaccines of the invention are superior to conventional vaccines by a factor of at least 10 fold, 20 fold, 40 fold, 50 fold, 100 fold, 500 fold or 1,000 fold.

Although attempts have been made to produce functional RNA vaccines, including mRNA vaccines and self-replicating RNA vaccines, the therapeutic efficacy of these RNA vaccines have not yet been fully established. Quite surprisingly, the inventors have discovered, according to aspects of the invention a class of formulations for delivering mRNA vaccines in vivo that results in significantly enhanced, and in many respects synergistic, immune responses including enhanced antigen generation and functional antibody production with neutralization capability. These results can be achieved even when significantly lower doses of the mRNA are administered in comparison with mRNA doses used in other classes of lipid based formulations. The formulations of the invention have demonstrated significant unexpected immune responses sufficient to establish the efficacy of functional mRNA vaccines as prophylactic and therapeutic agents. Additionally, self-replicating RNA vaccines rely on viral replication pathways to deliver enough RNA to a cell to produce an immunogenic response. The formulations of the invention do not require viral replication to produce enough protein to result in a strong immune response. Thus, the mRNA of the invention are not self-replicating RNA and do not include components necessary for viral replication.

Nucleic Acids/Polynucleotides

Human cytomegalovirus (HCMV) vaccines, as provided herein, comprise at least one (one or more) ribonucleic acid (RNA) polynucleotide having an open reading frame encoding at least one HCMV antigenic polypeptide. The term "nucleic acid," in its broadest sense, includes any compound and/or substance that comprises a polymer of nucleotides. These polymers are referred to as polynucleotides.

In some embodiments, at least one RNA polynucleotide of a HCMV vaccine is encoded by at least one nucleic acid sequence selected from any of SEQ ID NOs: 1-31, 58, 60, 62, 64, 66, 68, 70, and 80-83. In some embodiments, at least one RNA polynucleotide of a HCMV vaccine is encoded by at least one fragment of a nucleic acid sequence selected from any of SEQ ID NOs: 1-31, 58, 60, 62, 64, 66, 68, 70, and 80-83.

In some embodiments, an RNA vaccine comprises an RNA polynucleotide having an open reading frame encoded by SEQ ID NO:58, or an antigenic fragment or epitope thereof; an RNA polynucleotide having an open reading frame encoded by SEQ ID NO:60, or an antigenic fragment or epitope thereof; an RNA polynucleotide having an open reading frame encoded by SEQ ID NO:62, or an antigenic fragment or epitope thereof; an RNA polynucleotide having an open reading frame encoded by SEQ ID NO:64, or an antigenic fragment or epitope thereof; an RNA polynucleotide having an open reading frame encoded by SEQ ID NO:66, or an antigenic fragment or epitope thereof, and an RNA polynucleotide having an open reading frame encoded by SEQ ID NO:68, or an antigenic fragment or epitope thereof. In some embodiments, an RNA vaccine also comprises an RNA polynucleotide having an open reading frame encoded by SEQ ID NO:70, or an antigenic fragment or epitope thereof.

In some embodiments, an RNA vaccine comprises an RNA polynucleotide having an open reading frame encoded by SEQ ID NO:90, or an antigenic fragment or epitope thereof; an RNA polynucleotide having an open reading frame encoded by SEQ ID NO:91, or an antigenic fragment or epitope thereof; an RNA polynucleotide having an open reading frame encoded by SEQ ID NO:144, or an antigenic fragment or epitope thereof; an RNA polynucleotide having an open reading frame encoded by SEQ ID NO:87, or an antigenic fragment or epitope thereof; an RNA polynucleotide having an open reading frame encoded by SEQ ID NO:89, or an antigenic fragment or epitope thereof; an RNA polynucleotide having an open reading frame encoded by SEQ ID NO:86, or an antigenic fragment or epitope thereof; and/or an RNA polynucleotide having an open reading frame encoded by SEQ ID NO:92, or an antigenic fragment or epitope thereof.

It should be appreciated that open reading frame sequences can be combined with multiple different regulatory sequences, such as untranslated regions (UTRs). ORFs described herein can be linked to different UTRs. In some embodiments, a 5' UTR sequence comprises SEQ ID NO: 146. In some embodiments, a 3'UTR sequence comprises SEQ ID NO:147.

In some embodiments, an RNA vaccine comprises an RNA polynucleotide having an open reading frame encoded by SEQ ID NO:90, or an antigenic fragment or epitope thereof, with a 5' UTR sequence comprising SEQ ID NO: 146 and/or a 3'UTR sequence comprising SEQ ID NO: 147; an RNA polynucleotide having an open reading frame encoded by SEQ ID NO:91, or an antigenic fragment or epitope thereof, with a 5' UTR sequence comprising SEQ ID NO: 146 and/or a 3'UTR sequence comprising SEQ ID NO: 147; an RNA polynucleotide having an open reading frame encoded by SEQ ID NO:144, or an antigenic fragment or epitope thereof, with a 5' UTR sequence comprising SEQ ID NO: 146 and/or a 3'UTR sequence comprising SEQ ID NO: 147; an RNA polynucleotide having an open reading frame encoded by SEQ ID NO:87, or an antigenic fragment or epitope thereof, with a 5' UTR sequence comprising SEQ ID NO: 146 and/or a 3'UTR sequence comprising SEQ ID NO: 147; an RNA polynucleotide having an open reading frame encoded by SEQ ID NO:89, or an antigenic fragment or epitope thereof, with a 5' UTR sequence comprising SEQ ID NO: 146 and/or a 3'UTR sequence comprising SEQ ID NO: 147; an RNA polynucleotide having an open reading frame encoded by SEQ ID NO:86, or an antigenic fragment or epitope thereof, with a 5' UTR sequence comprising SEQ ID NO: 146 and/or a 3'UTR sequence comprising SEQ ID NO: 147; and/or an RNA polynucleotide having an open reading frame encoded by SEQ ID NO:92, or an antigenic fragment or epitope thereof, with a 5' UTR sequence comprising SEQ ID NO: 146 and/or a 3'UTR sequence comprising SEQ ID NO: 147.

In some embodiments, a transplant donor or recipient is administered an RNA vaccine composition comprising an RNA polynucleotide having an open reading frame encoded by SEQ ID NO:58, or an antigenic fragment or epitope thereof; an RNA polynucleotide having an open reading frame encoded by SEQ ID NO:60, or an antigenic fragment or epitope thereof; an RNA polynucleotide having an open reading frame encoded by SEQ ID NO:62, or an antigenic fragment or epitope thereof; an RNA polynucleotide having an open reading frame encoded by SEQ ID NO:64, or an antigenic fragment or epitope thereof; an RNA polynucleotide having an open reading frame encoded by SEQ ID NO:66, or an antigenic fragment or epitope thereof, and an RNA polynucleotide having an open reading frame encoded by SEQ ID NO:68, or an antigenic fragment or epitope thereof. In some embodiments, the transplant donor or recipient is also administered an RNA polynucleotide having an open reading frame encoded by SEQ ID NO:70, or an antigenic fragment or epitope thereof. The RNA polynucleotide having an open reading frame encoded by SEQ ID NO:70, or an antigenic fragment or epitope thereof can be formulated together or separately with the other RNA polynucleotides administered to the transplant donor or recipient and can be administered either together or separately from the other RNA polynucleotides administered to the transplant donor or recipient.

In some embodiments, a transplant donor or recipient is only administered an RNA polynucleotide having an open reading frame encoded by SEQ ID NO:70, or an antigenic fragment or epitope thereof.

Nucleic acids (also referred to as polynucleotides) may be or may include, for example, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or chimeras or combinations thereof.

In some embodiments, polynucleotides of the present disclosure function as messenger RNA (mRNA). "Messenger RNA" (mRNA) refers to any polynucleotide that encodes a (at least one) polypeptide (a naturally-occurring, non-naturally-occurring, or modified polymer of amino acids) and can be translated to produce the encoded polypeptide in vitro, in vivo, in situ or ex vivo. In some preferred embodiments, an mRNA is translated in vivo. The skilled artisan will appreciate that, except where otherwise noted, polynucleotide sequences set forth in the instant application will recite "T"s in a representative DNA sequence but where the sequence represents RNA (e.g., mRNA), the "T"s would be substituted for "U"s. Thus, any of the RNA polynucleotides encoded by a DNA identified by a particular sequence identification number may also comprise the corresponding RNA (e.g., mRNA) sequence encoded by the DNA, where each "T" of the DNA sequence is substituted with "U." One of ordinary skill in the art would understand how to identify an mRNA sequence based on the corresponding DNA sequence.

The basic components of an mRNA molecule typically include at least one coding region, a 5' untranslated region (UTR), a 3' UTR, a 5' cap and a poly-A tail. Polynucleotides of the present disclosure may function as mRNA but can be distinguished from wild-type mRNA in their functional and/or structural design features which serve to overcome existing problems of effective polypeptide expression using nucleic-acid based therapeutics.

Some embodiments of the present disclosure provide HCMV vaccines that include at least one ribonucleic acid (RNA) polynucleotide having an open reading frame encoding at least one HCMV antigenic polypeptide or an immunogenic fragment or epitope thereof. Some embodiments of the present disclosure provide HCMV vaccines that include at least one RNA polynucleotide having an open reading frame encoding two or more HCMV antigenic polypeptides or an immunogenic fragment or epitope thereof. Some embodiments of the present disclosure provide HCMV vaccines that include two or more RNA polynucleotides having an open reading frame encoding two or more HCMV antigenic polypeptides or immunogenic fragments or epitopes thereof. The one or more HCMV antigenic polypeptides may be encoded on a single RNA polynucleotide or may be encoded individually on multiple (e.g., two or more) RNA polynucleotides.

Some embodiments of the present disclosure provide HCMV vaccines that include at least one ribonucleic acid (RNA) polynucleotide having a single open reading frame encoding two or more (for example, two, three, four, five, or more) HCMV antigenic polypeptides or an immunogenic fragment or epitope thereof. Some embodiments of the present disclosure provide HCMV vaccines that include at least one ribonucleic acid (RNA) polynucleotide having more than one open reading frame, for example, two, three, four, five or more open reading frames encoding two, three, four, five or more HCMV antigenic polypeptides. In either of these embodiments, the at least one RNA polynucleotide may encode two or more HCMV antigenic polypeptides selected from gH, gB, gL, gO, gM, gN, UL83, UL123, UL128, UL130, UL131A, and fragments or epitopes thereof. In some embodiments, the at least one RNA polynucleotide encodes UL83 and UL123. In some embodiments, the at least one RNA polynucleotide encodes gH and gL. In some embodiments, the at least one RNA polynucleotide encodes UL128, UL130, and UL131A. In some embodiments, the at least one RNA polynucleotide encodes gH, gL, UL128, UL130, and UL131A.

In some embodiments, a vaccine comprises an RNA polynucleotide having an open reading frame encoding HCMV antigenic polypeptide gH, or an antigenic fragment or epitope thereof; an RNA polynucleotide having an open reading frame encoding HCMV antigenic polypeptide gL, or an antigenic fragment or epitope thereof; an RNA polynucleotide having an open reading frame encoding HCMV antigenic polypeptide UL128, or an antigenic fragment or epitope thereof; an RNA polynucleotide having an open reading frame encoding HCMV antigenic polypeptide UL130, or an antigenic fragment or epitope thereof; an RNA polynucleotide having an open reading frame encoding HCMV antigenic polypeptide UL131A, or an antigenic fragment or epitope thereof; and an RNA polynucleotide having an open reading frame encoding HCMV antigenic polypeptide gB, or an antigenic fragment or epitope thereof. In some embodiments, the vaccine also comprises an RNA polynucleotide having an open reading frame encoding HCMV antigenic polypeptide pp65, or an antigenic fragment or epitope thereof. In some embodiments, the pp65 polypeptide encoded by the RNA polynucleotide contains a deletion of amino acids 435-438. In some embodiments, the pp65 polypeptide encoded by the RNA polynucleotide comprises SEQ ID NO:71. In some embodiments, the pp65 polypeptide is part of a fusion protein. In some embodiments, pp65 polypeptide, or a fragment thereof, is fused to 1E1 or a fragment thereof.

In some embodiments, in which the at least one RNA polynucleotide has a single open reading frame encoding two or more (for example, two, three, four, five, or more) HCMV antigenic polypeptides, the RNA polynucleotide may further comprise additional sequence, for example, a linker sequence or a sequence that aids in the processing of the HCMV RNA transcripts or polypeptides, for example a cleavage site sequence. In some embodiments, the additional sequence may be a protease sequence, such as a furin sequence. Furin, also referred to as PACE (paired basic amino acid cleaving enzyme), is a calcium-dependent serine endoprotease that cleaves precursor proteins into biologically active products at paired basic amino acid processing sites. Some of its substrates include the following: proparathyroid hormone, transforming growth factor beta 1 precursor, proalbumin, pro-beta-secretase, membrane type-1 matrix metalloproteinase, beta subunit of pro-nerve growth factor, and von Willebrand factor. The envelope proteins of certain viruses must be cleaved by furin in order to become fully functional, while some viruses require furin processing during their entry into host cells. T cells require furin to maintain peripheral immune tolerance. In some embodiments, the additional sequence may be self-cleaving 2A peptide, such as a P2A, E2A, F2A, and T2A sequence. In some embodiments, the linker sequences and cleavage site sequences are interspersed between the sequences encoding HCMV polypeptides. 2A peptides are "self-cleaving" small peptides, approximately 18-22 amino acids in length. Ribosomes skip the synthesis of a glycyl-prolyl peptide bond at the C-terminus of a 2A peptide, resulting in the cleavage of the 2A peptide and its immediate downstream peptide. They are frequently used in biomedical research to allow for the simultaneous expression of more than one gene in cells using a single plasmid. There are a number of 2A peptides, including the following: foot-and-mouth disease virus (FMDV) 2A (F2A), equine rhinitis A virus (ERAV) 2A (E2A), porcine teschovirus-1 2A (P2A), and Thoseaasigna virus 2A (T2A). T2A has the highest cleavage efficiency (close to 100%), followed by E2A, P2A, and F2A. Amino acid sequences are the following: P2A:(GSG)ATNF-SLLKQAGDVEENPGP (SEQ ID NO: 153); T2A: (GSG) EGRGSLLTCGDVEENPGP (SEQ ID NO: 154); E2A: (GSG)QCTNYALLKLAGDVESNPGP (SEQ ID NO: 155); F2A: (GSG)VKQTLNFDLLKLAGDVESNPGP (SEQ ID NO: 156). In some embodiments, the linker sequences and cleavage site sequences are interspersed between the sequences encoding HCMV polypeptides. In some embodiments, the RNA polynucleotide is encoded by SEQ ID NO: 27, SEQ ID NO: 28, SEQ ID NO: 29, SEQ ID NO: 30 or SEQ ID NO: 31.

In some embodiments, a RNA polynucleotide of a HCMV vaccine encodes 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9 or 9-10 antigenic polypeptides. In some embodiments, a RNA polynucleotide of a HCMV vaccine encodes at least 10, 20, 30, 40, 50, 60, 70, 80, 90 or 100 antigenic polypeptides. In some embodiments, a RNA polynucleotide of a HCMV vaccine encodes at least 100 or at least 200 antigenic polypeptides. In some embodiments, a RNA polynucleotide of a HCMV vaccine encodes 1-10, 5-15, 10-20, 15-25, 20-30, 25-35, 30-40, 35-45, 40-50, 1-50, 1-100, 2-50 or 2-100 antigenic polypeptides.

Polynucleotides of the present disclosure, in some embodiments, are codon optimized. Codon optimization methods are known in the art and may be used as provided herein. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g. glycosylation sites); add, remove or shuffle protein domains; insert or delete restriction sites; modify ribosome binding sites and mRNA degradation sites; adjust translational rates to allow the various domains of the protein to fold properly; or to reduce or eliminate problem secondary structures within the polynucleotide. Codon optimization tools, algorithms and services are known in the art—non-limiting examples include services from GeneArt (Life Technologies), DNA2.0 (Menlo Park Calif.) and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 90% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 85% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 80% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 75% sequence identity to a naturally-occurring or wild-type sequence (e.g., a naturally-occurring or wild-type mRNA sequence encoding a polypeptide or protein of interest (e.g., an antigenic protein or polypeptide.

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares between 65% and 75 or about 80% sequence identity to a naturally-occurring or wild-type sequence (e.g., a naturally-occurring or wild-type mRNA sequence encoding a polypeptide or protein of interest (e.g., an antigenic protein or polypeptide.

The skilled artisan will appreciate that, except where otherwise noted, polynucleotide sequences set forth in the instant application will recite "T"s in a representative DNA sequence but where the sequence represents RNA, the "T"s would be substituted for "U"s.

Antigens/Antigenic Polypeptides

In some embodiments, an antigenic polypeptide is an HCMV glycoprotein. For example, a HCMV glycoprotein may be HCMV gB, gH, gL, gO, gN, or gM or an immunogenic fragment or epitope thereof. In some embodiments, the antigenic polypeptide is a HCMV gH polypeptide. In some embodiments, the antigenic polypeptide is a HCMV gL polypeptide. In some embodiments, the antigenic polypeptide is a HCMV gB polypeptide. In some embodiments, the antigenic polypeptide is a HCMV gO polypeptide. In some embodiments, the antigenic polypeptide is a HCMV gN polypeptide. In some embodiments, the antigenic polypeptide is a HCMV gM polypeptide. In some embodiments, the antigenic polypeptide is a HCMV gC polypeptide. In some embodiments, the antigenic polypeptide is a HCMV gN polypeptide. In some embodiments, the antigenic polypeptide is a HCMV gM polypeptide.

In some embodiments, an antigenic polypeptide is a HCMV protein selected from UL83, UL123, UL128, UL130, and UL131A or an immunogenic fragment or epitope thereof. In some embodiments, the antigenic polypeptide is a HCMV UL83 polypeptide. In some embodiments, the antigenic polypeptide is a HCMV UL123 polypeptide. In some embodiments, the antigenic polypeptide is a HCMV UL128 polypeptide. In some embodiments, the antigenic polypeptide is a HCMV UL130 polypeptide. In some embodiments, the antigenic polypeptide is a HCMV UL131A polypeptide.

In some embodiments, the antigenic HCMV polypeptide comprises two or more HCMV polypeptides. The two or more HCMV polypeptides can be encoded by a single RNA polynucleotide or can be encoded by two or more RNA polynucleotides, for example, each glycoprotein encoded by a separate RNA polynucleotide. In some embodiments, the two or more HCMV polypeptides can be any combination of HCMV gH, gL, gB, gO, gN, gM, UL83, UL123, UL128, UL130, and UL131A polypeptides or immunogenic fragments or epitopes thereof. In some embodiments, the two or more HCMV polypeptides can be any combination of HCMV gH and a polypeptide selected from gL, gB, gO, gN, gM, UL83, UL123, UL128, UL130, and UL polypeptides or immunogenic fragments or epitopes thereof. In some embodiments, the two or more HCMV polypeptides can be any combination of HCMV gB and a polypeptide selected from gH, gL, gO, gN, gM, UL83, UL123, UL128, UL130, and UL131A polypeptides or immunogenic fragments or epitopes thereof. In some embodiments, the two or more HCMV polypeptides can be any combination of HCMV gL and a polypeptide selected from gH, gB, gO, gN, gM, UL83, UL123, UL128, UL130, and UL131A polypeptides or immunogenic fragments or epitopes thereof. In some embodiments, the two or more HCMV polypeptides can be any combination of HCMV gH, gL and a polypeptide selected from gB, gO, gN, gM, UL83, UL123, UL128, UL130, and UL131A polypeptides or immunogenic fragments or epitopes thereof. In some embodiments, the two or more HCMV polypeptides can be any combination of HCMV gH, gL, and a glycoprotein selected from gB, gH, gK, gL, gC, gN, and gM polypeptides or immunogenic fragments or epitopes thereof. In some embodiments, the two or more HCMV polypeptides can be any combination of HCMV gH, gL, and a polypeptide selected from UL83, UL123, UL128, UL130, and UL131A polypeptides or immunogenic fragments or epitopes thereof. In some embodiments, the two or more HCMV polypeptides are UL128, UL130, and UL131A. In some embodiments, the two or more HCMV polypeptides are gH and gL. In some embodiments, the two or more HCMV polypeptides are gH, gL, UL128, UL130, and UL131A. In some embodiments, the two or more HCMV polypeptides are gB, gH, gL, UL128, UL130, and UL131A.

HCMV vaccines described herein can further include the HCMV tegument protein pp65. This protein is a target antigen for HCMV-specific cytotoxic T lymphocytes (CTL) responses. (Mclaughlin-Taylor et al., *J. Med. Virol.* 43:103-110 (1994)).

Pp65 is the major constituent of extracellular virus particles and is the major tegument protein responsible for modulating/evading the host cell immune response during HCMV infections (e.g., in McLaughlin-Taylor et al., *J Med Virol* 1994, 43: 103-110). Further, pp65 is implicated in counteracting both innate and adaptive immune responses during HCMV infections (e.g., in Kalejta et al., J Gen Virol 2006, 87: 1763-1779). Pp65's role in immune evasion is largely attributable to its targeting of both humoral and cellular immunity as well as serving as the dominant target antigen of cytotoxic T lymphocytes (e.g., in McLaughlin-Taylor et al., *J Med Virol* 1994, 43: 103-110). Further, pp65 mediates the phosphorylation of viral immediate-early proteins (IE), produced abundantly early after infection, which blocks their presentation to the major histocompatibility complex class I molecules (Gilbert et al., *Nature,* 383:720-722, 1996). pp65 also plays a role in immune evasion during HCMV infections through the inhibition of natural killer cell cytotoxicity (e.g., in Arnon et al., *Nat Immunol* 2005, 6: 515-523) and/or attenuation of the interferon response (e.g., in Abate et al., *J Virol* 2004, 78: 10995-11006). It has also been shown that a pp65-IE1 fusion protein is able to induce both cellular and humoral immune response against HCMV (Reap et al., *Clin Vaccine Immunol*, vol. 14 no. 6 748-755, 2007; Lilja et al., *Vaccine*, November 19; 30(49), 2002).

Embodiments of the present disclosure provide RNA (e.g., mRNA) vaccines that include polynucleotides encoding a HCMV structural protein, e.g., pp65, or a pp654E1 fusion protein, for eliciting protective immunity against CMV infection. Tables 8 and 9 provide nucleic acid and protein sequences for pp65 and fusion proteins encompassing pp65. In some embodiments, a pp65 RNA polynucleotide is encoded by a sequence within Table 8 Table 9, or Table 13. In some embodiments, a pp65 RNA polynucleotide is encoded by SEQ ID NO:70 or SEQ ID NO: 93. In some embodiments, the RNA polynucleotide encodes a pp65 protein provided in Table 8 or Table 9. In some embodiments, the pp65 protein comprises SEQ ID NO:71. In some embodiments, the pp65 polypeptide is part of a fusion protein. In some embodiments, pp65 polypeptide, or a fragment thereof, is fused to IE1 or a fragment thereof.

The present disclosure includes variant HCMV antigenic polypeptides. In some embodiments, the variant HCMV antigenic polypeptide is a variant pp65 polypeptide. In some embodiments, a variant pp65 polypeptide contains a deletion of amino acids 435-438 relative to the wild type pp65 sequence. The variant pp65 polypeptide can comprise SEQ ID NO:71. A pp65 protein with a deletion of amino acids 435-438 is also referred to herein as "pp65mut" or "$pp65^{\Delta P}$." In some embodiments, pp65mut is encoded by a polynucleotide comprising the nucleotide sequence of SEQ ID NO: 92. In some embodiments, the variant pp65 polypeptide is part of a fusion protein. In some embodiments, a variant pp65 polypeptide, or a fragment thereof, is fused to 1E1 or a fragment thereof.

The use of pp65, including variant forms of pp65, in vaccine compositions is described in and incorporated by reference from: U.S. Pat. Nos. 7,387,782, 7,025,969, 6,133,433, 6,207,161, 6,074,645, 6,251,399, 6,727,093, 6,726,910, 6,843,992, 6,544,521, 6,951,651, 8,580,276, 7,163,685, 6,242,567, 6,835,383, 6,156,317, 6,562,345, 8,673,317, 8,278,093, 7,888,112, 9,180,162, 7,410,795, 6,579,970, 7,202,331, 8,029,796, 8,425,898, US 2015-0335732, US 2016-0213771, WO 2015/047901, US 2012-0213818, US 2014-0127216, 7,041,442, 8,617,560, 7,976,845, US 2015-0273051, US 2015-0174237, 6,448,389, WO 2015/082570, 7,419,674, US 2014-0308308, and US 2013-0202708, which are incorporated by reference herein in their entireties.

The present disclosure includes variant HCMV antigenic polypeptides. In some embodiments, the variant HCMV antigenic polypeptide is a variant HCMV gH polypeptide. In some embodiments, the variant HCMV antigenic polypeptide is a variant HCMV gL polypeptide. In some embodiments, the variant HCMV antigenic polypeptide is a variant HCMV gB polypeptide. The variant HCMV polypeptides are designed to expedite passage of the antigenic polypeptide through the ER/golgi, leading to increased surface expression of the antigen. In some embodiments, the variant HCMV polypeptides are truncated to delete one or more of the following domains: hydrophobic membrane proximal domain, transmembrane domain, and cytoplasmic domain. In some embodiments, the variant HCMV polypeptides are truncated to include only the ectodomain sequence. For example, the variant HCMV polypeptide can be a truncated HCMV gH polypeptide, truncated HCMV gB polypeptide, or truncated HCMV gL polypeptide comprising at least amino acids 1-124, including, for example, amino acids 1-124, 1-140, 1-160, 1-200, 1-250, 1-300, 1-350, 1-360, 1-400, 1-450, 1-500, 1-511, 1-550, and 1-561, as well as polypeptide fragments having fragment sizes within the recited size ranges.

In some embodiments, a HCMV antigenic polypeptide is longer than 25 amino acids and shorter than 50 amino acids. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. Polypeptides may also comprise single chain or multichain polypeptides such as antibodies or insulin and may be associated or linked. Most commonly, disulfide linkages are found in multichain polypeptides. The term polypeptide may also apply to amino acid polymers in which at least one amino acid residue is an artificial chemical analogue of a corresponding naturally-occurring amino acid.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants possess at least 50% identity to a native or reference sequence. In some embodiments, variants share at least 80%, or at least 90% identity with a native or reference sequence.

In some embodiments "variant mimics" are provided. As used herein, the term "variant mimic" is one which contains at least one amino acid that would mimic an activated sequence. For example, glutamate may serve as a mimic for phosphoro-threonine and/or phosphoro-serine. Alternatively, variant mimics may result in deactivation or in an inactivated product containing the mimic, for example, phenylalanine may act as an inactivating substitution for tyrosine; or alanine may act as an inactivating substitution for serine.

"Orthologs" refers to genes in different species that evolved from a common ancestral gene by speciation. Normally, orthologs retain the same function in the course of evolution. Identification of orthologs is critical for reliable prediction of gene function in newly sequenced genomes.

"Analogs" is meant to include polypeptide variants which differ by one or more amino acid alterations, for example, substitutions, additions or deletions of amino acid residues that still maintain one or more of the properties of the parent or starting polypeptide.

The present disclosure provides several types of compositions that are polynucleotide or polypeptide based, including variants and derivatives. These include, for example, substitutional, insertional, deletion and covalent variants and derivatives. The term "derivative" is used synonymously with the term "variant" but generally refers to a molecule that has been modified and/or changed in any way relative to a reference molecule or starting molecule.

As such, polynucleotides encoding peptides or polypeptides containing substitutions, insertions and/or additions, deletions and covalent modifications with respect to reference sequences, in particular the polypeptide sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to polypeptides are those that have at least one amino acid residue in a native or starting sequence removed and a different amino acid inserted in its place at the same position. Substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Features" when referring to polypeptide or polynucleotide are defined as distinct amino acid sequence-based or nucleotide-based components of a molecule respectively. Features of the polypeptides encoded by the polynucleotides include surface manifestations, local conformational shape, folds, loops, half-loops, domains, half-domains, sites, termini or any combination thereof.

As used herein when referring to polypeptides the term "domain" refers to a motif of a polypeptide having one or more identifiable structural or functional characteristics or properties (e.g., binding capacity, serving as a site for protein-protein interactions).

As used herein when referring to polypeptides the terms "site" as it pertains to amino acid based embodiments is used synonymously with "amino acid residue" and "amino acid side chain." As used herein when referring to polynucleotides the terms "site" as it pertains to nucleotide based embodiments is used synonymously with "nucleotide." A site represents a position within a peptide or polypeptide or polynucleotide that may be modified, manipulated, altered, derivatized or varied within the polypeptide or polynucleotide based molecules.

As used herein the terms "termini" or "terminus" when referring to polypeptides or polynucleotides refers to an extremity of a polypeptide or polynucleotide respectively. Such extremity is not limited only to the first or final site of the polypeptide or polynucleotide but may include additional amino acids or nucleotides in the terminal regions. Polypeptide-based molecules may be characterized as having both an N-terminus (terminated by an amino acid with a free amino group (NH2)) and a C-terminus (terminated by an amino acid with a free carboxyl group (COOH)). Proteins are in some cases made up of multiple polypeptide chains brought together by disulfide bonds or by non-covalent forces (multimers, oligomers). These proteins have multiple N- and C-termini. Alternatively, the termini of the polypeptides may be modified such that they begin or end, as the case may be, with a non-polypeptide based moiety such as an organic conjugate.

As recognized by those skilled in the art, protein fragments, functional protein domains, and homologous proteins are also considered to be within the scope of polypeptides of interest. For example, provided herein is any protein fragment (meaning a polypeptide sequence at least one amino acid residue shorter than a reference polypeptide sequence but otherwise identical) of a reference protein 10, 20, 30, 40, 50, 60, 70, 80, 90, 100 or greater than 100 amino acids in length. In another example, any protein that includes a stretch of 20, 30, 40, 50, or 100 amino acids which are 40%, 50%, 60%, 70%, 80%, 90%, 95%, or 100% identical to any of the sequences described herein can be utilized in accordance with the disclosure. In some embodiments, a polypeptide includes 2, 3, 4, 5, 6, 7, 8, 9, 10, or more mutations as shown in any of the sequences provided or referenced herein.

Polypeptide or polynucleotide molecules of the present disclosure may share a certain degree of sequence similarity or identity with the reference molecules (e.g., reference polypeptides or reference polynucleotides), for example, with art-described molecules (e.g., engineered or designed molecules or wild-type molecules). The term "identity" as known in the art, refers to a relationship between the sequences of two or more polypeptides or polynucleotides, as determined by comparing the sequences. In the art, identity also means the degree of sequence relatedness between them as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related peptides can be readily calculated by known methods. "% identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", *Nucleic* Acids Res. 25:3389-3402). Another popular local alignment technique is based on the Smith-Waterman algorithm (Smith, T. F. & Waterman, M. S. (1981) "Identification of common molecular subsequences." J. Mol. Biol. 147:195-197.) A general global alignment technique based on dynamic programming is the Needleman-Wunsch algorithm (Needleman, S. B. & Wunsch, C. D. (1970) "A general method applicable to the search for similarities in the amino acid sequences of two proteins." J. Mol. Biol. 48:443-453.). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm. Other tools are described herein, specifically in the definition of "identity" below.

As used herein, the term "homology" refers to the overall relatedness between polymeric molecules, e.g. between nucleic acid molecules (e.g. DNA molecules and/or RNA molecules) and/or between polypeptide molecules. Polymeric molecules (e.g. nucleic acid molecules (e.g. DNA molecules and/or RNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity or identity is a quantitative term that defines the degree of sequence match between two compared sequences. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). Two polynucleotide sequences are considered homologous if the polypeptides they encode are at least 50%, 60%, 70%, 80%, 90%, 95%, or even 99% for at least one stretch of at least, 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. Two protein sequences are considered homologous if the proteins are at least 50%, 60%, 70%, 80%, or 90% identical for at least one stretch of at least 20 amino acids.

Homology implies that the compared sequences diverged in evolution from a common origin. The term "homolog" refers to a first amino acid sequence or nucleic acid sequence (e.g., gene (DNA or RNA) or protein sequence) that is related to a second amino acid sequence or nucleic acid sequence by descent from a common ancestral sequence. The term "homolog" may apply to the relationship between genes and/or proteins separated by the event of speciation or to the relationship between genes and/or proteins separated by the event of genetic duplication. "Orthologs" are genes (or proteins) in different species that evolved from a common ancestral gene (or protein) by speciation. Typically, orthologs retain the same function in the course of evolution. "Paralogs" are genes (or proteins) related by duplication within a genome. Orthologs retain the same function in the course of evolution, whereas paralogs evolve new functions, even if these are related to the original one.

The term "identity" refers to the overall relatedness between polymeric molecules, for example, between polynucleotide molecules (e.g. DNA molecules and/or RNA molecules) and/or between polypeptide molecules. Calculation of the percent identity of two polynucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleic acid sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleic acid sequences can be determined using the algorithm of Meyers and Miller (*CABIOS,* 1989, 4:11-17), which has been incorporated into the ALIGN program (version 2.0) using a PAM120 weight residue table, a gap length penalty of 12 and a gap penalty of 4. The percent identity between two nucleic acid sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Altschul, S. F. et al., *J. Molec. Biol.,* 215, 403 (1990)).

In some embodiments, the polypeptides further comprise additional sequences or functional domains. For example, the HCMV polypeptides of the present disclosure may comprise one or more linker sequences. In some embodiments, the HCMV of the present invention may comprise a polypeptide tag, such as an affinity tag (chitin binding protein (CBP), maltose binding protein (MBP), glutathione-S-transferase (GST), SBP-tag, Strep-tag, AviTag, Calmodulin-tag); solubilization tag; chromatography tag (polyanionic amino acid tag, such as FLAG-tag); epitope tag (short peptide sequences that bind to high-affinity antibodies, such as V5-tag, Myc-tag, VSV-tag, Xpress tag, E-tag, S-tag, and HA-tag); fluorescence tag (e.g., GFP). In some embodiments, the HCMV of the present invention may comprise an amino acid tag, such as one or more lysines, histidines, or glutamates, which can be added to the polypeptide sequences (e.g., at the N-terminal or C-terminal ends). Lysines can be used to increase peptide solubility or to allow for biotinylation. Protein and amino acid tags are peptide sequences genetically grafted onto a recombinant protein. Sequence tags are attached to proteins for various purposes, such as peptide purification, identification, or localization, for use in various applications including, for example, affinity purification, protein array, western blotting, immunofluorescence, and immunoprecipitation. Such tags are subsequently removable by chemical agents or by enzymatic means, such as by specific proteolysis or intein splicing.

Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

Multiprotein and Multicomponent Vaccines

The present disclosure encompasses HCMV vaccines, e.g., vaccines against human cytomegalovirus, comprising multiple RNA (e.g., mRNA) polynucleotides, each encoding a single antigenic polypeptide, as well as HCMV vaccines comprising a single RNA polynucleotide encoding more than one antigenic polypeptide (e.g., as a fusion polypeptide). Thus, it should be understood that a vaccine composition comprising a RNA polynucleotide having an open reading frame encoding a first HCMV antigenic polypeptide and a RNA polynucleotide having an open reading frame encoding a second HCMV antigenic polypeptide encompasses (a) vaccines that comprise a first RNA polynucleotide encoding a first HCMV antigenic polypeptide and a second RNA polynucleotide encoding a second HCMV antigenic polypeptide, and (b) vaccines that comprise a single RNA polynucleotide encoding a first and second HCMV antigenic polypeptide (e.g., as a fusion polypeptide). HCMV RNA vaccines of the present disclosure, in some embodiments, comprise 2-10 (e.g., 2, 3, 4, 5, 6, 7, 8, 9 or 10), or more, RNA polynucleotides having an open reading frame, each of which encodes a different HCMV antigenic polypeptide (or a single RNA polynucleotide encoding 2-10, or more, different HCMV antigenic polypeptides). In some embodiments, an HCMV RNA vaccine comprises a RNA polynucleotide having an open reading frame encoding an HCMV glycoprotein. In some embodiments, an HCMV RNA vaccine comprises a RNA polynucleotide having an open reading frame encoding an HCMV glycoprotein B (gB), a RNA polynucleotide having an open reading frame encoding an HCMV glycoprotein M (gM), a RNA polynucleotide having an open reading frame encoding an HCMV glyprotein N (gN), a RNA polynucleotide having an open reading frame encoding an HCMV glycoprotein H (gH), a RNA polynucleotide having an open reading frame encoding an HCMV glycoprotein L (gL), and a RNA polynucleotide having an open reading frame encoding an HCMV glycoprotein 0 (gO). In some embodiments, an HCMV RNA vaccine comprises a RNA polynucleotide having an open reading frame encoding an HCMV gB protein. In some embodiments, an HCMV RNA vaccine comprises a RNA polynucleotide having an open reading frame encoding an HCMV UL128 protein. In some embodiments, an HCMV RNA vaccine comprises a RNA polynucleotide having an open reading frame encoding an HCMV UL130 protein. In some embodiments, an HCMV RNA vaccine comprises a RNA polynucleotide having an open reading frame encoding an HCMV UL131 protein. In some embodiments, an HCMV RNA vaccine comprises a RNA polynucleotide having an open reading frame encoding an HCMV pp65 protein. In some embodiments, the pp65 protein contains a deletion of amino acids 435-438. In some embodiments, an HCMV RNA vaccine comprises a RNA polynucleotide having an open reading frame encoding an HCMV gM and gN proteins. In some embodiments, an HCMV RNA vaccine comprises a RNA polynucleotide having an open reading frame encoding an HCMV gH, gL, and gO proteins. In some embodiments, an HCMV RNA vaccine comprises a RNA polynucleotide having an open reading frame encoding an HCMV gH, gL, UL128, UL130, and UL131A proteins. In some embodiments, an HCMV RNA vaccine comprises RNA polynucleotides having one or more open reading frames encoding an HCMV UL83, UL128, UL123, UL130, or UL131A protein. In some embodiments, the HCMV RNA vaccine further comprises a RNA polynucleotide having an open reading frame encoding one or more (e.g., 2, 3, 4, 5, 6 or 7) HCMV proteins.

In some embodiments, an HCMV RNA vaccine comprises RNA polynucleotides having one or more open reading frames encoding HCMV gH, gL, UL128, UL130, and UL131A proteins, or fragments thereof, and an HCMV gB protein, or fragment thereof.

In some embodiments, an HCMV RNA vaccine comprises an RNA polynucleotide having an open reading frame encoding a gH protein or a fragment thereof, an RNA polynucleotide having an open reading frame encoding a gL protein or a fragment thereof, an RNA polynucleotide having an open reading frame encoding a UL128 protein or a fragment thereof, an RNA polynucleotide having an open reading frame encoding a UL130 protein or a fragment thereof, an RNA polynucleotide having an open reading frame encoding a UL131A protein or a fragment thereof, and an an RNA polynucleotide having an open reading frame encoding a gB protein, or a fragment thereof. In some embodiments, an HCMV RNA vaccine also comprises an RNA polynucleotide having an open reading frame encoding a pp65 protein or a fragment thereof. In some embodiments, the pp65 polypeptide contains a deletion of amino acids 435-438.

In some embodiments, a RNA polynucleotide encodes an HCMV antigenic polypeptide fused to a signal peptide (e.g., SEQ ID NO: 53 or 54). The signal peptide may be fused at the N-terminus or the C-terminus of the antigenic polypeptide.

Signal Peptides

In some embodiments, antigenic polypeptides encoded by HCMV nucleic acids comprise a signal peptide. Signal peptides, comprising the N-terminal 15-60 amino acids of proteins, are typically needed for the translocation across the membrane on the secretory pathway and thus universally control the entry of most proteins both in eukaryotes and prokaryotes to the secretory pathway. Signal peptides generally include three regions: an N-terminal region of differing length, which usually comprises positively charged amino acids, a hydrophobic region, and a short carboxy-terminal peptide region. In eukaryotes, the signal peptide of a nascent precursor protein (pre-protein) directs the ribosome to the rough endoplasmic reticulum (ER) membrane and initiates the transport of the growing peptide chain across it. The signal peptide is not responsible for the final destination of the mature protein, however. Secretory proteins devoid of further address tags in their sequence are by default secreted to the external environment. Signal peptides are cleaved from precursor proteins by an endoplasmic reticulum (ER)-resident signal peptidase or they remain uncleaved and function as a membrane anchor. During recent years, a more advanced view of signal peptides has evolved, showing that the functions and immunodorminance of certain signal peptides are much more versatile than previously anticipated.

HCMV vaccines of the present disclosure may comprise, for example, RNA polynucleotides encoding an artificial signal peptide, wherein the signal peptide coding sequence is operably linked to and is in frame with the coding sequence of the HCMV antigenic polypeptide. Thus, HCMV vaccines of the present disclosure, in some embodiments, produce an antigenic polypeptide comprising a HCMV antigenic polypeptide fused to a signal peptide. In some embodiments, a signal peptide is fused to the N-terminus of the HCMV antigenic polypeptide. In some embodiments, a signal peptide is fused to the C-terminus of the HCMV antigenic polypeptide.

In some embodiments, the signal peptide fused to the HCMV antigenic polypeptide is an artificial signal peptide. In some embodiments, an artificial signal peptide fused to the HCMV antigenic polypeptide encoded by the HCMV RNA vaccine is obtained from an immunoglobulin protein, e.g., an IgE signal peptide or an IgG signal peptide. In some embodiments, a signal peptide fused to the HCMV antigenic polypeptide encoded by an HCMV mRNA vaccine is an Ig heavy chain epsilon-1 signal peptide (IgE HC SP) having the sequence of: MDWTWILFLVAAATRVHS (SEQ ID NO: 53). In some embodiments, a signal peptide fused to a HCMV antigenic polypeptide encoded by the HCMV RNA vaccine is an $IgG_k$ chain V-III region HAH signal peptide ($IgG_k$ SP) having the sequence of METPAQLLFLLLLWLP-DTTG (SEQ ID NO: 54). In some embodiments, a signal peptide fused to the HCMV antigenic polypeptide encoded by an HCMV RNA vaccine has an amino acid sequence set forth in SEQ ID NO: 53 or SEQ ID NO: 54. The examples disclosed herein are not meant to be limiting and any signal peptide that is known in the art to facilitate targeting of a protein to ER for processing and/or targeting of a protein to the cell membrane may be used in accordance with the present disclosure.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide may have a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

Non-limiting examples of HCMV antigenic polypeptides fused to signal peptides, which are encoded by the HCMV RNA vaccine of the present disclosure, may be found in Table 2, SEQ ID NOs: 32-52.

A signal peptide is typically cleaved from the nascent polypeptide at the cleavage junction during ER processing. The mature HCMV antigenic polypeptide produce by HCMV RNA vaccine of the present disclosure typically does not comprise a signal peptide.

Chemical Modifications

HCMV RNA vaccines of the present disclosure comprise, in some embodiments, at least one ribonucleic acid (RNA) polynucleotide having an open reading frame encoding at least one HCMV antigenic polypeptide, or an immunogenic fragment thereof, that comprises at least one chemical modification.

The terms "chemical modification" and "chemically modified" refer to modification with respect to adenosine (A), guanosine (G), uridine (U), thymidine (T) or cytidine (C) ribonucleosides or deoxyribnucleosides in at least one of their position, pattern, percent or population. Generally, these terms do not refer to the ribonucleotide modifications in naturally occurring 5'-terminal mRNA cap moieties. With respect to a polypeptide, the term "modification" refers to a modification relative to the canonical set 20 amino acids. Polypeptides, as provided herein, are also considered "modified" of they contain amino acid substitutions, insertions or a combination of substitutions and insertions.

Polynucleotides (e.g., RNA polynucleotides, such as mRNA polynucleotides), in some embodiments, comprise various (more than one) different modifications. In some embodiments, a particular region of a polynucleotide contains one, two or more (optionally different) nucleoside or nucleotide modifications. In some embodiments, a modified RNA polynucleotide (e.g., a modified mRNA polynucleotide), introduced to a cell or organism, exhibits reduced degradation in the cell or organism, respectively, relative to an unmodified polynucleotide. In some embodiments, a modified RNA polynucleotide (e.g., a modified mRNA polynucleotide), introduced into a cell or organism, may exhibit reduced immunogenicity in the cell or organism, respectively (e.g., a reduced innate response).

Modifications of polynucleotides include, without limitation, those described herein. Polynucleotides (e.g., RNA polynucleotides, such as mRNA polynucleotides) may comprise modifications that are naturally-occurring, non-naturally-occurring or the polynucleotide may comprise a combination of naturally-occurring and non-naturally-occurring modifications. Polynucleotides may include any useful modification, for example, of a sugar, a nucleobase, or an internucleoside linkage (e.g., to a linking phosphate, to a phosphodiester linkage or to the phosphodiester backbone).

Polynucleotides (e.g., RNA polynucleotides, such as mRNA polynucleotides), in some embodiments, comprise non-natural modified nucleotides that are introduced during synthesis or post-synthesis of the polynucleotides to achieve desired functions or properties. The modifications may be present on an internucleotide linkages, purine or pyrimidine bases, or sugars. The modification may be introduced with chemical synthesis or with a polymerase enzyme at the terminal of a chain or anywhere else in the chain. Any of the regions of a polynucleotide may be chemically modified.

The present disclosure provides for modified nucleosides and nucleotides of a polynucleotide (e.g., RNA polynucleotides, such as mRNA polynucleotides). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A nucleotide" refers to a nucleoside, including a phosphate group. Modified nucleotides may by synthesized by any useful method, such as, for example, chemically, enzymatically, or recombinantly, to include one or more modified or non-natural nucleosides. Polynucleotides may comprise a region or regions of linked nucleosides. Such regions may have variable backbone linkages. The linkages may be standard phosphodiester linkages, in which case the polynucleotides would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleotide inosine and adenine, cytosine or uracil. Any combination of base/sugar or linker may be incorporated into polynucleotides of the present disclosure.

Modifications of polynucleotides (e.g., RNA polynucleotides, such as mRNA polynucleotides) that are useful in the vaccines of the present disclosure include, but are not limited to the following: 2-methylthio-N6-(cis-hydroxyisopentenyl)adenosine; 2-methylthio-N6-methyladenosine; 2-methylthio-N6-threonyl carbamoyladenosine; N6-glycinylcarbamoyladenosine; N6-isopentenyladenosine; N6-methyladenosine; N6-threonylcarbamoyladenosine; 1,2'-O-dimethyladenosine; 1-methyladenosine; 2'-O-methyladenosine; 2'-O-ribosyladenosine (phosphate); 2-methyladenosine; 2-methylthio-N6 isopentenyladenosine; 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl)adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalylcarbamoyladenosine; N6-methyl-N6-threonylcarbamoyladenosine; 2-methyladenosine; 2-methylthio-N6-isopentenyladenosine; 7-deaza-adenosine; N1-methyl-adenosine; N6,N6 (dimethyl)adenine; N6-cis-hydroxy-isopentenyl-adenosine; α-thio-adenosine; 2 (amino)adenine; 2 (aminopropyl)adenine; 2 (methylthio) N6 (isopentenyl)adenine; 2-(alkyl)adenine; 2-(aminoalkyl)adenine; 2-(aminopropyl)adenine; 2-(halo)adenine; 2-(halo) adenine; 2-(propyl)adenine; 2'-Amino-2'-deoxy-ATP; 2'-Azido-2'-deoxy-ATP; 2'-Deoxy-2'-a-aminoadenosine TP; 2'-Deoxy-2'-a-azidoadenosine TP; 6 (alkyl)adenine; 6 (methyl)adenine; 6-(alkyl)adenine; 6-(methyl)adenine; 7 (deaza)adenine; 8 (alkenyl)adenine; 8 (alkynyl)adenine; 8 (amino)adenine; 8 (thioalkyl)adenine; 8-(alkenyl)adenine; 8-(alkyl)adenine; 8-(alkynyl)adenine; 8-(amino)adenine; 8-(halo)adenine; 8-(hydroxyl)adenine; 8-(thioalkyl)adenine; 8-(thiol)adenine; 8-azido-adenosine; aza adenine; deaza adenine; N6 (methyl)adenine; N6-(isopentyl)adenine; 7-deaza-8-aza-adenosine; 7-methyladenine; 1-Deazaadenosine TP; 2'Fluoro-N6-Bz-deoxyadenosine TP; 2'-OMe-2-Amino-ATP; 2'O-methyl-N6-Bz-deoxyadenosine TP; 2'-a-Ethynyladenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2',2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; α-thio-cytidine; 2-(thio)cytosine; 2'-Amino-2'-deoxy-CTP; 2'-Azido-2'-deoxy-CTP; 2'-Deoxy-2'-a-aminocytidine TP; 2'-Deoxy-2'-a-azidocytidine TP; 3 (deaza) 5 (aza)cytosine; 3 (methyl)cytosine; 3-(alkyl)cytosine; 3-(deaza) 5 (aza)cytosine; 3-(methyl)cytidine; 4,2'-O-dimethylcytidine; 5 (halo)cytosine; 5 (methyl)cytosine; 5 (propynyl)cytosine; 5 (trifluoromethyl)cytosine; 5-(alkyl) cytosine; 5-(alkynyl)cytosine; 5-(halo)cytosine; 5-(propynyl)cytosine; 5-(trifluoromethyl)cytosine; 5-bromo-cytidine; 5-iodo-cytidine; 5-propynyl cytosine; 6-(azo)cytosine; 6-aza-cytidine; aza cytosine; deaza cytosine; N4 (acetyl) cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl)cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-Acetyl-cytidine TP; 2'O-methyl-N4-Bz-cytidine TP; 2'-a-Ethynylcytidine TP; 2'-a-Trifluoromethylcytidine TP; 2'-b-Ethynylcytidine TP; 2'-b-Trifluoromethylcytidine TP; 2'-Deoxy-2',2'-difluorocytidine TP; 2'-Deoxy-2'-a-mercaptocytidine TP; 2'-Deoxy-2'-a-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl)cytidine TP; 3'-Ethynylcytidine TP; 4'-Azidocytidine TP; 4'-Carbocyclic cytidine TP; 4'-Ethynylcytidine TP; 5-(1-Propynyl)ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; α-thio-guanosine; 2 (propyl)guanine; 2-(alkyl)guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl)guanine; 6-(alkyl)guanine; 6-(methyl)guanine; 6-methyl-guanosine; 7 (alkyl)guanine; 7 (deaza)guanine; 7 (methyl)guanine; 7-(alkyl)guanine; 7-(deaza)guanine; 7-(methyl)guanine; 8 (alkyl)guanine; 8 (alkynyl)guanine; 8 (halo)guanine; 8 (thioalkyl)guanine; 8-(alkenyl)guanine; 8-(alkyl)guanine; 8-(alkynyl)guanine; 8-(amino)guanine; 8-(halo)guanine; 8-(hydroxyl)guanine; 8-(thioalkyl)guanine; 8-(thiol)guanine; aza guanine; deaza guanine; N (methyl)guanine; N-(methyl)guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a- mercaptoguanosine TP; 2'-Deoxy-2'-a-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homo-guanosine TP; 8-bromo-guanosine TP; 9-Deazaguanosine TP; N2-isobutyl-guanosine TP; 1-methylinosine; Inosine; 1,2'-O-dimethylinosine; 2'-O-methylinosine; 7-methylinosine; 2'-O-methylinosine; Epoxyqueuosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl)uridine; 1-methyl-3-(3-amino-5-carboxypropyl)pseudouridine; 1-methylpseduouridine; 1-methyl-pseudouridine; 2'-O-methyluridine; 2'-O-methylpseudouridine; 2'-O-methyluridine; 2-thio-2'-O-methyluridine; 3-(3-amino-3-carboxypropyl)uridine; 3,2'-O-dimethyluridine; 3-Methyl-pseudo-Uridine TP; 4-thiouridine; 5-(carboxyhydroxymethyl)uridine; 5-(carboxyhydroxymethyl)uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethylaminomethyl-2-thiouridine; 5-carboxymethylaminomethyluridine; 5-carboxymethylaminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methoxyuridine; 5-methyl-2-thiouridine; 5-methylaminomethyl-2-selenouridine; 5-methylaminomethyl-2-thiouridine; 5-methylaminomethyluridine; 5-Methyldihydrouridine; 5-Oxyacetic acid-Uridine TP; 5-Oxyacetic acid-methyl ester-Uridine TP; N1-methyl-pseudo-uridine; N1-ethyl-pseudo-uridine; uridine 5-oxyacetic acid; uridine 5-oxyacetic acid methyl ester; 3-(3-Amino-3-carboxypropyl)-Uridine TP; 5-(iso-Pentenylaminomethyl)-2-thiouridine TP; 5-(iso-Pentenylaminomethyl)-2'-O-methyluridine TP; 5-(iso-Pentenylaminomethyl)uridine TP; 5-propynyl uracil; α-thio-uridine; 1 (aminoalkylamino-carbonylethylenyl)-2 (thio)-pseudouracil; 1 (aminoalkylaminocarbonylethylenyl)-2,4-(dithio)pseudouracil; 1 (aminoalkylaminocarbonylethylenyl)-4 (thio)pseudouracil; 1 (aminoalkylaminocarbonylethylenyl)-pseudouracil; 1 (aminocarbonylethylenyl)-2(thio)-pseudouracil; 1 (aminocarbonylethylenyl)-2,4-(dithio)pseudouracil; 1 (aminocarbonylethylenyl)-4 (thio)pseudouracil; 1 (aminocarbonylethylenyl)-pseudouracil; 1 substituted 2(thio)-pseudouracil; 1 substituted 2,4-(dithio)pseudouracil; 1 substituted 4 (thio) pseudouracil; 1 substituted pseudouracil; 1-(aminoalkylamino-carbonylethylenyl)-2-(thio)-pseudouracil; 1-Methyl-3-(3-amino-3-carboxypropyl) pseudouridine TP; 1-Methyl-3-(3-amino-3-carboxypropyl)pseudo-UTP; 1-Methyl-pseudo-UTP; 2 (thio)pseudouracil; 2' deoxy uridine; 2' fluorouridine; 2-(thio)uracil; 2,4-(dithio)psuedouracil; 2' methyl, 2'amino, 2'azido, 2'fluro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl)uracil; 4 (thio)pseudouracil; 4-(thio)pseudouracil; 4-(thio)uracil; 4-thiouracil; 5 (1,3-diazole-1-alkyl)uracil; 5 (2-aminopropyl)uracil; 5 (aminoalkyl)uracil; 5 (dimethylaminoalkyl)uracil; 5 (guanidiniumalkyl)uracil; 5 (methoxycarbonylmethyl)-2-(thio)uracil; 5 (methoxycarbonyl-methyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methylaminomethyl)-2,4 (dithio)uracil; 5 (methylaminomethyl)-4 (thio) uracil; 5 (propynyl)uracil; 5 (trifluoromethyl)uracil; 5-(2-aminopropyl)uracil; 5-(alkyl)-2-(thio)pseudouracil; 5-(alkyl)-2,4 (dithio)pseudouracil; 5-(alkyl)-4 (thio) pseudouracil; 5-(alkyl)pseudouracil; 5-(alkyl)uracil; 5-(alkynyl)uracil; 5-(allylamino)uracil; 5-(cyanoalkyl)uracil; 5-(dialkylaminoalkyl)uracil; 5-(dimethylaminoalkyl) uracil; 5-(guanidiniumalkyl)uracil; 5-(halo)uracil; 5-(1,3-diazole-1-alkyl)uracil; 5-(methoxy)uracil; 5-(methoxycarbonylmethyl)-2-(thio)uracil; 5-(methoxycarbonyl-methyl)uracil; 5-(methyl) 2(thio)uracil; 5-(methyl) 2,4 (dithio)uracil; 5-(methyl) 4 (thio)uracil; 5-(methyl)-2-(thio)pseudouracil; 5-(methyl)-2,4 (dithio)pseudouracil; 5-(methyl)-4 (thio)pseudouracil; 5-(methyl)pseudouracil; 5-(methylaminomethyl)-2 (thio)uracil; 5-(methylaminomethyl)-2,4(dithio)uracil; 5-(methylaminomethyl)-4-(thio) uracil; 5-(propynyl)uracil; 5-(trifluoromethyl)uracil; 5-aminoallyl-uridine; 5-bromo-uridine; 5-iodo-uridine; 5-uracil; 6 (azo)uracil; 6-(azo)uracil; 6-aza-uridine; allyamino-uracil; aza uracil; deaza uracil; N3 (methyl)uracil; Pseudo-UTP-1-2-ethanoic acid; Pseudouracil; 4-Thio-pseudo-UTP; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (±)1-(2-Hydroxypropyl)pseudouridine TP; (2R)-1-(2-Hydroxypropyl)pseudouridine TP; (2S)-1-(2-Hydroxypropyl) pseudouridine TP; (E)-5-(2-Bromo-vinyl)ara-uridine TP; (E)-5-(2-Bromo-vinyl)uridine TP; (Z)-5-(2-Bromo-vinyl) ara-uridine TP; (Z)-5-(2-Bromo-vinyl)uridine TP; 1-(2,2,2-Trifluoroethyl)-pseudo-UTP; 1-(2,2,3,3,3-Pentafluoropropyl)pseudouridine TP; 1-(2,2-Diethoxyethyl)pseudouridine TP; 1-(2,4,6-Trimethylbenzyl)pseudouridine TP; 1-(2,4,6-Trimethyl-benzyl)pseudo-UTP; 1-(2,4,6-Trimethyl-phenyl) pseudo-UTP; 1-(2-Amino-2-carboxyethyl)pseudo-UTP; 1-(2-Amino-ethyl)pseudo-UTP; 1-(2-Hydroxyethyl) pseudouridine TP; 1-(2-Methoxyethyl)pseudouridine TP; 1-(3,4-Bis-trifluoromethoxybenzyl)pseudouridine TP; 1-(3,4-Dimethoxybenzyl)pseudouridine TP; 1-(3-Amino-3-carboxypropyl)pseudo-UTP; 1-(3-Amino-propyl)pseudo-UTP; 1-(3-Cyclopropyl-prop-2-ynyl)pseudouridine TP; 1-(4-Amino-4-carboxybutyl)pseudo-UTP; 1-(4-Amino-benzyl) pseudo-UTP; 1-(4-Amino-butyl)pseudo-UTP; 1-(4-Amino-phenyl)pseudo-UTP; 1-(4-Azidobenzyl)pseudouridine TP; 1-(4-Bromobenzyl)pseudouridine TP; 1-(4-Chlorobenzyl) pseudouridine TP; 1-(4-Fluorobenzyl)pseudouridine TP; 1-(4-Iodobenzyl)pseudouridine TP; 1-(4-Methanesulfonyl-benzyl)pseudouridine TP; 1-(4-Methoxybenzyl)pseudouridine TP; 1-(4-Methoxy-benzyl)pseudo-UTP; 1-(4-Methoxy-phenyl)pseudo-UTP; 1-(4-Methylbenzyl)pseudouridine TP; 1-(4-Methyl-benzyl)pseudo-UTP; 1-(4-Nitrobenzyl) pseudouridine TP; 1-(4-Nitro-benzyl)pseudo-UTP; 1(4-Nitro-phenyl)pseudo-UTP; 1-(4-Thiomethoxybenzyl) pseudouridine TP; 1-(4-Trifluoromethoxybenzyl) pseudouridine TP; 1-(4-Trifluoromethylbenzyl) pseudouridine TP; 1-(5-Amino-pentyl)pseudo-UTP; 1-(6-Amino-hexyl)pseudo-UTP; 1,6-Dimethyl-pseudo-UTP; 1-[3-(2-{2-[2-(2-Aminoethoxy)-ethoxy]-ethoxy}-ethoxy)-propionyl]pseudouridine TP; 1-{3-[2-(2-Aminoethoxy)-ethoxy]-propionyl}pseudouridine TP; 1-Acetylpseudouridine TP; 1-Alkyl-6-(1-propynyl)-pseudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinylpseudouridine TP; 1-Butyl-pseudo-UTP; 1-Cyanomethylpseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooctylmethyl-pseudo-UTP; 1-Cyclooctyl-pseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethylpseudouridine TP; 1-Methoxymethylpseudouridine TP; 1-Methyl-6-(2,2,2-Trifluoroethyl)pseudo-UTP; 1-Methyl-6-(4-morpholino)-pseudo-UTP; 1-Methyl-6-(4-thiomorpholino)-pseudo-UTP; 1-Methyl-6-(substituted phenyl) pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyano-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6-tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouridine TP; 1-Trifluoromethyl-pseudo-UTP; 1-Vinylpseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-2'-a-mercaptouridine TP; 2'-Deoxy-2'-a-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl)uridine TP; 3-Alkyl-pseudo-UTP; 4'-Azidouridine TP; 4'-Carbocyclic uridine TP; 4'-Ethynyluridine TP; 5-(1-Propynyl)ara-uridine TP; 5-(2-Furanyl)uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Phenyl-pseudo-UTP; 6-Propyl-pseudo-UTP; 6-tert-Butyl-pseudo-UTP; 6-Trifluoromethoxy-pseudo-UTP; 6-Trifluoromethyl-pseudo-UTP; Alpha-thio-pseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2(2-ethoxy)-ethoxy}-ethoxy]-ethoxy)-ethoxy}]propionic acid; Pseudouridine TP 1-[3-{2-(2-[2-ethoxy]-ethoxy)-ethoxy}]propionic acid; Pseudouridine TP 1-[3-{2-(2-ethoxy)-ethoxy}]propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino)purine; 1-(aza)-2-(thio)-3-(aza)-phenoxazin-1-yl: 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino)purine; 2,4,5-(trimethyl)phenyl; 2' methyl, 2'amino, 2'azido, 2'fluro-cytidine; 2' methyl, 2'amino, 2'azido, 2'fluro-adenine; 2'methyl, 2'amino, 2'azido, 2'fluro-uridine; 2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl) isocarbostyrilyl; 3-(methyl)isocarbostyrilyl; 4-(fluoro)-6-(methyl)benzimidazole; 4-(methyl)benzimidazole; 4-(methyl)indolyl; 4,6-(dimethyl)indolyl; 5 nitroindole; 5 substituted pyrimidines; 5-(methyl)isocarbostyrilyl; 5-nitroindole; 6-(aza)pyrimidine; 6-(azo)thymine; 6-(methyl)-7-(aza)indolyl; 6-chloro-purine; 6-phenyl-pyrrolo-pyrimidin-2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazinl-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkyl-hydroxy)-1,3-

(diaza)-2-(oxo)-phenthiazin-1-yl; 7-(guanidiniumalkylhydroxy)-1,3-(diaza)-2-(oxo)-phenoxazin-1-yl; 7-(propynyl)isocarbostyrilyl; 7-(propynyl)isocarbostyrilyl, propynyl-7-(aza)indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-substituted purines; N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nubularine; O6-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza)indolyl; Pyrenyl; pyridopyrimidin-3-yl; pyridopyrimidin-3-yl, 2-oxo-7-amino-pyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl)uridine TP; and N6-(19-Amino-pentaoxanonadecyl)adenosine TP.

In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of pseudouridine (ψ), N1-methylpseudouridine ($m^1ψ$), N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine. In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of 1-methyl-pseudouridine ($m^1ψ$), 5-methoxy-uridine ($mo^5U$), 5-methyl-cytidine ($m^5C$), pseudouridine (ψ), α-thio-guanosine and α-thio-adenosine. In some embodiments, polynucleotides includes a combination of at least two (e.g., 2, 3, 4 or more) of the aforementioned modified nucleobases.

In some embodiments, polynucleotides (e.g., RNA polynucleotides, such as mRNA polynucleotides) comprise pseudouridine (ψ) and 5-methyl-cytidine ($m^5C$). In some embodiments, polynucleotides (e.g., RNA polynucleotides, such as mRNA polynucleotides) comprise 1-methyl-pseudouridine ($m^1ψ$). In some embodiments, polynucleotides (e.g., RNA polynucleotides, such as mRNA polynucleotides) comprise 1-methyl-pseudouridine ($m^1ψ$) and 5-methyl-cytidine ($m^5C$). In some embodiments, polynucleotides (e.g., RNA polynucleotides, such as mRNA polynucleotides) comprise 2-thiouridine ($s^2U$). In some embodiments, polynucleotides (e.g., RNA polynucleotides, such as mRNA polynucleotides) comprise 2-thiouridine and 5-methyl-cytidine ($m^5C$). In some embodiments, polynucleotides (e.g., RNA polynucleotides, such as mRNA polynucleotides) comprise methoxy-uridine ($mo^5U$). In some embodiments, polynucleotides (e.g., RNA polynucleotides, such as mRNA polynucleotides) comprise 5-methoxy-uridine ($mo^5U$) and 5-methyl-cytidine ($m^5C$). In some embodiments, polynucleotides (e.g., RNA polynucleotides, such as mRNA polynucleotides) comprise 2'-O-methyl uridine. In some embodiments polynucleotides (e.g., RNA polynucleotides, such as mRNA polynucleotides) comprise 2'-O-methyl uridine and 5-methyl-cytidine ($m^5C$). In some embodiments, polynucleotides (e.g., RNA polynucleotides, such as mRNA polynucleotides) comprise N6-methyl-adenosine ($m^6A$). In some embodiments, polynucleotides (e.g., RNA polynucleotides, such as mRNA polynucleotides) comprise N6-methyl-adenosine ($m^6A$) and 5-methyl-cytidine ($m^5C$).

In some embodiments, polynucleotides (e.g., RNA polynucleotides, such as mRNA polynucleotides) are uniformly modified (e.g., fully modified, modified throughout the entire sequence) for a particular modification. For example, a polynucleotide can be uniformly modified with 5-methyl-cytidine ($m^5C$), meaning that all cytosine residues in the mRNA sequence are replaced with 5-methyl-cytidine ($m^5C$). Similarly, a polynucleotide can be uniformly modified for any type of nucleoside residue present in the sequence by replacement with a modified residue such as those set forth above.

Exemplary nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), and 2-thio-5-methyl-cytidine.

In some embodiments, a modified nucleobase is a modified uridine. Exemplary nucleobases and In some embodiments, a modified nucleobase is a modified cytosine. nucleosides having a modified uridine include 5-cyano uridine, and 4'-thio uridine.

In some embodiments, a modified nucleobase is a modified adenine. Exemplary nucleobases and nucleosides having a modified adenine include 7-deaza-adenine, 1-methyl-adenosine (m1A), 2-methyl-adenine (m2A), and N6-methyl-adenosine (m6A).

In some embodiments, a modified nucleobase is a modified guanine. Exemplary nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine.

The polynucleotides of the present disclosure may be partially or fully modified along the entire length of the molecule. For example, one or more or all or a given type of nucleotide (e.g., purine or pyrimidine, or any one or more or all of A, G, U, C) may be uniformly modified in a polynucleotide of the invention, or in a given predetermined sequence region thereof (e.g., in the mRNA including or excluding the polyA tail). In some embodiments, all nucleotides X in a polynucleotide of the present disclosure (or in a given sequence region thereof) are modified nucleotides, wherein X may any one of nucleotides A, G, U, C, or any one of the combinations A+G, A+U, A+C, G+U, G+C, U+C, A+G+U, A+G+C, G+U+C or A+G+C.

The polynucleotide may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The polynucleotides may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the polynucleotides may contain a modified pyrimidine such as a modified uracil or cytosine. In some embodiments, at least 5%, at least 10%, at least 25%, at least 50%, at least 80%, at least 90% or 100% of the uracil in the polynucleotide is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the polynucleotide is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures). In some embodiments a codon optimized RNA may, for instance, be one in which the levels of G/C are enhanced. The G/C-content of nucleic acid molecules may influence the stability of the RNA. RNA having an increased amount of guanine (G) and/or cytosine (C) residues may be functionally more stable than nucleic acids containing a large amount of adenine (A) and thymine (T) or uracil (U) nucleotides. WO02/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Thus, in some embodiments, the RNA (e.g., mRNA) vaccines comprise a 5'UTR element, an optionally codon optimized open reading frame, and a 3'UTR element, a poly(A) sequence and/or a polyadenylation signal wherein the RNA is not chemically modified.

In some embodiments, the modified nucleobase is a modified uracil. Exemplary nucleobases and nucleosides having a modified uracil include pseudouridine (ψ), pyridin-4-one ribonucleoside, 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho5U), 5-aminoallyl-uridine, 5-halo-uridine (e.g., 5-iodo-uridineor 5-bromo-uridine), 3-methyl-uridine (m3U), 5-methoxy-uridine (mo5U), uridine 5-oxyacetic acid (cmo5U), uridine 5-oxyacetic acid methyl ester (mcmo5U), 5-carboxymethyl-uridine (cm5U), 1-carboxymethyl-pseudouridine, 5-carboxyhydroxymethyl-uridine (chm5U), 5-carboxyhydroxymethyl-uridine methyl ester (mchm5U), 5-methoxycarbonylmethyl-uridine (mcm5U), 5-methoxycarbonylmethyl-2-thio-uridine (mcm5s2U), 5-aminomethyl-2-thio-uridine (nm5s2U), 5-methylaminomethyl-uridine (mnm5U), 5-methylaminomethyl-2-thio-uridine (mnm5s2U), 5-methylaminomethyl-2-seleno-uridine (mnm5se2U), 5-carbamoylmethyluridine (ncm5U), 5-carboxymethylaminomethyl-uridine (cmnm5U), 5-carboxymethylaminomethyl-2-thio-uridine (cmnm5s2U), 5-propynyl-uridine, 1-propynyl-pseudouridine, 5-taurinomethyl-uridine (τm5U), 1-taurinomethyl-pseudouridine, 5-taurinomethyl-2-thio-uridine(τm5s2U), 1-taurinomethyl-4-thio-pseudouridine, 5-methyl-uridine (m5U, i.e., having the nucleobase deoxythymine), 1-methyl-pseudouridine (m1ψ), 5-methyl-2-thio-uridine (m5s2U), 1-methyl-4-thio-pseudouridine (m1s4ψ), 4-thio-1-methyl-pseudouridine, 3-methyl-pseudouridine (m3ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m5D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, N1-ethyl-pseudouridine 3-(3-amino-3-carboxypropyl)uridine (acp3U), 1-methyl-3-(3-amino-3-carboxypropyl)pseudouridine (acp3ψ), 5-(isopentenylaminomethyl)uridine (inm5U), 5-(isopentenylaminomethyl)-2-thio-uridine (inm5s2U), α-thio-uridine, 2'-O-methyl-uridine (Um), 5,2'-O-dimethyl-uridine (m5Um), 2'-O-methyl-pseudouridine (ψm), 2-thio-2'-O-methyl-uridine (s2Um), 5-methoxycarbonylmethyl-2'-O-methyl-uridine (mcm5Um), 5-carbamoylmethyl-2'-O-methyl-uridine (ncm5Um), 5-carboxymethylaminomethyl-2'-O-methyl-uridine (cmnm5Um), 3,2'-O-dimethyl-uridine (m3Um), and 5-(isopentenylaminomethyl)-2'-O-methyl-uridine (inm5Um), 1-thio-uridine, deoxythymidine, 2'-F-ara-uridine, 2'-F-uridine, 2'-OH-ara-uridine, 5-(2-carbomethoxyvinyl) undine, and 5-[3-(1-E-propenylamino)] uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine (m3C), N4-acetyl-cytidine (ac4C), 5-formylcytidine (f5C), N4-methyl-cytidine (m4C), 5-methyl-cytidine (m5C), 5-halo-cytidine (e.g., 5-iodo-cytidine), 5-hydroxymethyl-cytidine (hm5C), 1-methyl-pseudoisocytidine, pyrrolo-cytidine, pyrrolo-pseudoisocytidine, 2-thio-cytidine (s2C), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine (k2C), α-thio-cytidine, 2'-O-methyl-cytidine (Cm), 5,2'-O-dimethylcytidine (m5Cm), N4-acetyl-2'-O-methyl-cytidine (ac4Cm), N4,2'-O-dimethylcytidine (m4Cm), 5-formyl-2'-

O-methyl-cytidine (f5Cm), N4,N4,2'-O-dimethylcytidine (m42Cm), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include 2-amino-purine, 2, 6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine (m1A), 2-methyl-adenine (m2A), N6-methyl-adenosine (m6A), 2-methylthio-N6-methyl-adenosine (ms2m6A), N6-isopentenyl-adenosine (i6A), 2-methylthio-N6-isopentenyl-adenosine (ms2i6A), N6-(cis-hydroxyisopentenyl)adenosine (io6A), 2-methylthio-N6-(cis-hydroxyisopentenyl) adenosine (ms2io6A), N6-glycinylcarbamoyl-adenosine (g6A), N6-threonylcarbamoyl-adenosine (t6A), N6-methyl-N6-threonylcarbamoyl-adenosine (m6t6A), 2-methylthio-N6-threonylcarbamoyl-adenosine (ms2g6A), N6,N6-dimethyl-adenosine (m62A), N6-hydroxynorvalylcarbamoyl-adenosine (hn6A), 2-methylthio-N6-hydroxynorvalylcarbamoyl-adenosine (ms2hn6A), N6-acetyl-adenosine (ac6A), 7-methyl-adenine, 2-methylthio-adenine, 2-methoxy-adenine, α-thio-adenosine, 2'-O-methyl-adenosine (Am), N6,2'-O-dimethyl-adenosine (m6Am), N6,N6,2'-O-dimethyl-adenosine (m62Am), 1,2'-O-dimethyl-adenosine (ml Am), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include inosine (I), 1-methyl-inosine (m1D, wyosine (imG), methylwyosine (mimG), 4-demethyl-wyosine (imG-14), isowyosine (imG2), wybutosine (yW), peroxywybutosine (o2yW), hydroxywybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine (preQ0), 7-aminomethyl-7-deaza-guanosine (preQ1), archaeosine (G+), 7-deaza-8-aza-guanosine, 6-thio-guanosine, 6-thio-7-deaza-guanosine, 6-thio-7-deaza-8-aza-guanosine, 7-methyl-guanosine (m7G), 6-thio-7-methyl-guanosine, 7-methyl-inosine, 6-methoxy-guanosine, 1-methyl-guanosine (m1G), N2-methyl-guanosine (m2G), N2,N2-dimethyl-guanosine (m22G), N2,7-dimethyl-guanosine (m2,7G), N2,N2,7-dimethyl-guanosine (m2,2,7G), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine (m2Gm), N2,N2-dimethyl-2'-O-methyl-guanosine (m22Gm), 1-methyl-2'-O-methyl-guanosine (ml Gm), N2,7-dimethyl-2'-O-methyl-guanosine (m2,7Gm), 2'-O-methyl-inosine (Im), 1,2'-O-dimethyl-inosine (m1Im), 2'-O-ribosylguanosine (phosphate) (Gr(p)), 1-thio-guanosine, O6-methyl-guanosine, 2'-F-ara-guanosine, and 2'-F-guanosine.

In Vitro Transcription of RNA (e.g., mRNA)

HCMV vaccines of the present disclosure comprise at least one RNA polynucleotide, such as a mRNA (e.g., modified mRNA). mRNA, for example, is transcribed in vitro from template DNA, referred to as an "in vitro transcription template." In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

A "5' untranslated region" (UTR) refers to a region of an mRNA that is directly upstream (i.e., 5') from the start codon (i.e., the first codon of an mRNA transcript translated by a ribosome) that does not encode a polypeptide.

A "3' untranslated region" (UTR) refers to a region of an mRNA that is directly downstream (i.e., 3') from the stop codon (i.e., the codon of an mRNA transcript that signals a termination of translation) that does not encode a polypeptide.

An "open reading frame" is a continuous stretch of DNA beginning with a start codon (e.g., methionine (ATG)), and ending with a stop codon (e.g., TAA, TAG or TGA) and encodes a polypeptide.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, export of the mRNA from the nucleus and translation.

In some embodiments, a polynucleotide includes 200 to 3,000 nucleotides. For example, a polynucleotide may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides).

Methods of Treatment

Provided herein are compositions (e.g., pharmaceutical compositions), methods, kits and reagents for prevention and/or treatment of HCMV in humans and other mammals. HCMV RNA vaccines can be used as therapeutic or prophylactic agents. They may be used in medicine to prevent and/or treat infectious disease. In exemplary aspects, the HCMV RNA vaccines of the invention are used to provide prophylactic protection from human cytomegalovirus infection and may be particularly useful for prevention and/or treatment of immunocompromised and infant patients to prevent or to reduce the severity and/or duration of the clinical manifestation of the cytomegalovirus infection. In some embodiments, vaccines described herein reduce or prevent congenital transmission of HCMV from mother to child.

Broad Spectrum Vaccines

HCMV RNA (e.g., mRNA) vaccines can be used as therapeutic or prophylactic agents. It is envisioned that there may be situations where persons are at risk for infection with more than one betacoronovirus, for example, at risk for infection with HCMV. RNA (e.g., mRNA) therapeutic vaccines are particularly amenable to combination vaccination approaches due to a number of factors including, but not limited to, speed of manufacture, ability to rapidly tailor vaccines to accommodate perceived geographical threat, and the like. Moreover, because the vaccines utilize the human body to produce the antigenic protein, the vaccines are amenable to the production of larger, more complex antigenic proteins, allowing for proper folding, surface expression, antigen presentation, etc. in the human subject. To protect against more than one HCMV strain, a combination vaccine can be administered that includes RNA encoding at least one antigenic polypeptide of a first HCMV and further includes RNA encoding at least one antigenic polypeptide of a second HCMV. RNAs (mRNAs) can be co-formulated, for example, in a single LNP or can be formulated in separate LNPs destined for co-administration.

A method of eliciting an immune response in a subject against a HCMV is provided in aspects of the invention. The method involves administering to the subject a HCMV RNA vaccine comprising at least one RNA polynucleotide having an open reading frame encoding at least one HCMV antigenic polypeptide or an immunogenic fragment thereof, thereby inducing in the subject an immune response specific to HCMV antigenic polypeptide or an immunogenic fragment thereof, wherein anti-antigenic polypeptide antibody titer in the subject is increased following vaccination relative to anti-antigenic polypeptide antibody titer in a subject vaccinated with a prophylactically effective dose of a traditional vaccine against the HCMV. An "anti-antigenic polypeptide antibody" is a serum antibody the binds specifically to the antigenic polypeptide.

A prophylactically effective dose is a therapeutically effective dose that prevents infection with the virus at a clinically acceptable level. In some embodiments the therapeutically effective dose is a dose listed in a package insert for the vaccine. A traditional vaccine, as used herein, refers to a vaccine other than the mRNA vaccines of the invention. For instance, a traditional vaccine includes but is not limited to live microorganism vaccines, killed microorganism vaccines, subunit vaccines, protein antigen vaccines, DNA vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA).

In some embodiments the anti-antigenic polypeptide antibody titer in the subject is increased 1 log to 10 log following vaccination relative to anti-antigenic polypeptide antibody titer in a subject vaccinated with a prophylactically effective dose of a traditional vaccine against the HCMV.

In some embodiments the anti-antigenic polypeptide antibody titer in the subject is increased 1 log following vaccination relative to anti-antigenic polypeptide antibody titer in a subject vaccinated with a prophylactically effective dose of a traditional vaccine against the HCMV.

In some embodiments the anti-antigenic polypeptide antibody titer in the subject is increased 2 log following vaccination relative to anti-antigenic polypeptide antibody titer in a subject vaccinated with a prophylactically effective dose of a traditional vaccine against the HCMV.

In some embodiments the anti-antigenic polypeptide antibody titer in the subject is increased 3 log following vaccination relative to anti-antigenic polypeptide antibody titer in a subject vaccinated with a prophylactically effective dose of a traditional vaccine against the HCMV.

In some embodiments the anti-antigenic polypeptide antibody titer in the subject is increased 5 log following vaccination relative to anti-antigenic polypeptide antibody titer in a subject vaccinated with a prophylactically effective dose of a traditional vaccine against the HCMV.

In some embodiments the anti-antigenic polypeptide antibody titer in the subject is increased 10 log following vaccination relative to anti-antigenic polypeptide antibody titer in a subject vaccinated with a prophylactically effective dose of a traditional vaccine against the HCMV.

A method of eliciting an immune response in a subject against a HCMV is provided in other aspects of the invention. The method involves administering to the subject a HCMV RNA vaccine comprising at least one RNA polynucleotide having an open reading frame encoding at least one HCMV antigenic polypeptide or an immunogenic fragment thereof, thereby inducing in the subject an immune response specific to HCMV antigenic polypeptide or an immunogenic fragment thereof, wherein the immune response in the subject is equivalent to an immune response in a subject vaccinated with a traditional vaccine against the HCMV at 2 times to 100 times the dosage level relative to the RNA vaccine.

In some embodiments the immune response in the subject is equivalent to an immune response in a subject vaccinated with a traditional vaccine at twice the dosage level relative to the HCMV RNA vaccine.

In some embodiments the immune response in the subject is equivalent to an immune response in a subject vaccinated with a traditional vaccine at three times the dosage level relative to the HCMV RNA vaccine.

In some embodiments the immune response in the subject is equivalent to an immune response in a subject vaccinated with a traditional vaccine at 4 times the dosage level relative to the HCMV RNA vaccine.

In some embodiments the immune response in the subject is equivalent to an immune response in a subject vaccinated with a traditional vaccine at 5 times the dosage level relative to the HCMV RNA vaccine.

In some embodiments the immune response in the subject is equivalent to an immune response in a subject vaccinated with a traditional vaccine at 10 times the dosage level relative to the HCMV RNA vaccine.

In some embodiments the immune response in the subject is equivalent to an immune response in a subject vaccinated with a traditional vaccine at 50 times the dosage level relative to the HCMV RNA vaccine.

In some embodiments the immune response in the subject is equivalent to an immune response in a subject vaccinated with a traditional vaccine at 100 times the dosage level relative to the HCMV RNA vaccine.

In some embodiments the immune response in the subject is equivalent to an immune response in a subject vaccinated with a traditional vaccine at 10 times to 1000 times the dosage level relative to the HCMV RNA vaccine.

In some embodiments the immune response in the subject is equivalent to an immune response in a subject vaccinated with a traditional vaccine at 100 times to 1000 times the dosage level relative to the HCMV RNA vaccine.

In other embodiments the immune response is assessed by determining anti-antigenic polypeptide antibody titer in the subject.

In other aspects the invention is a method of eliciting an immune response in a subject against a HCMV by administering to the subject a HCMV RNA vaccine comprising at least one RNA polynucleotide having an open reading frame encoding at least one HCMV antigenic polypeptide or an immunogenic fragment thereof, thereby inducing in the subject an immune response specific to HCMV antigenic polypeptide or an immunogenic fragment thereof, wherein the immune response in the subject is induced 2 days to 10 weeks earlier relative to an immune response induced in a subject vaccinated with a prophylactically effective dose of a traditional vaccine against the HCMV. In some embodiments the immune response in the subject is induced in a subject vaccinated with a prophylactically effective dose of a traditional vaccine at 2 times to 100 times the dosage level relative to the RNA vaccine.

In some embodiments the immune response in the subject is induced 2 days earlier relative to an immune response induced in a subject vaccinated with a prophylactically effective dose of a traditional vaccine.

In some embodiments the immune response in the subject is induced 3 days earlier relative to an immune response induced in a subject vaccinated a prophylactically effective dose of a traditional vaccine.

In some embodiments the immune response in the subject is induced 1 week earlier relative to an immune response induced in a subject vaccinated with a prophylactically effective dose of a traditional vaccine.

In some embodiments the immune response in the subject is induced 2 weeks earlier relative to an immune response induced in a subject vaccinated with a prophylactically effective dose of a traditional vaccine.

In some embodiments the immune response in the subject is induced 3 weeks earlier relative to an immune response induced in a subject vaccinated with a prophylactically effective dose of a traditional vaccine.

In some embodiments the immune response in the subject is induced 5 weeks earlier relative to an immune response induced in a subject vaccinated with a prophylactically effective dose of a traditional vaccine.

In some embodiments the immune response in the subject is induced 10 weeks earlier relative to an immune response induced in a subject vaccinated with a prophylactically effective dose of a traditional vaccine.

A method of eliciting an immune response in a subject against a HCMV by administering to the subject a HCMV RNA vaccine having an open reading frame encoding a first antigenic polypeptide, wherein the RNA polynucleotide does not include a stabilization element, and wherein an adjuvant is not coformulated or co-administered with the vaccine is also provided herein.

Standard of Care for CMV Prevention and Treatment

A variety of approaches to preventing and/or treating CMV, including immunization strategies, have previously been pursued or are currently being pursued, some of which are summarized below. However, all of these approaches have drawbacks and limitations. (Schleiss et al. (2008), *Curr Top Microbiol Immunol.* 325:361-382).

Ganciclovir and Valganciclovir

In some embodiments, Ganciclovir or Valganciclovir is the standard of care therapy for treatment or prevention of CMV infections (Reusser P. et al. (2000); 130(4):101-12; Biron et al. (2006) *Antiviral Research* 71:154-163).

Ganciclovir (marketed as CYTOVENE® and ZIRGAN®) and Valganciclovir (a prodrug form of Ganciclovir marketed as VALCYTE®) are antiviral medications developed by Hoffmann-La Roche to treat CMV infection. They are analogues of 2'-deoxy-guanosine, which competitively inhibits dGTP incorporation into DNA and, in turn, viral replication (Sugawara M et al., *J Pharm Sci.* 2000; 89(6): 781-9). CYTOVENE-1V (ganciclovir sodium for injection) is FDA approved "for use only in the treatment of cytomegalovirus (CMV) retinitis in immunocompromised patients and for the prevention of CMV disease in transplant patients at risk for CMV disease." (FDA Label, 1/31/2006, page 1.)

The recommended dose regimen for CYTOVENE-IV for treatment of CMV retinitis for patients with normal renal function includes an induction phase of 5 mg/kg (administered intravenously over an hour) every 12 hours for 14-21 days, followed by a maintenance phase of 5 mg/kg (administered intravenously over an hour) once daily seven days a week or 6 mg/kg once daily five days a week. (Id., page 22.) For prevention of CMV in transplant patients with normal renal function, the recommended dose regimen includes 5 mg/kg (administered intravenously over an hour) every 12 hours for 7-14 days; then 5 mg/kg once daily seven days a week or 6 mg/kg once daily five days a week. (Id.)

In a study involving heart transplant patients, at 120 days post-transplant, the incidence of CMV in seropositive subjects was 9% in subjects receiving treatment compared to 46% in subjects receiving a placebo. (Biron et al. (2006) *Antiviral Research* 71:154-163, page 157.) In a study involving bone marrow transplant subjects, at 100 days post-transplant the incidence of CMV in treated subjects was 3% compared to 43% in subjects treated with a placebo. (Id.)

One form of Ganciclovir that is marketed by Bausch and Lomb, ZIRGAN®, is in the form of an ophthalmic gel, which is FDA approved for treatment of acute herpetic keratitis (dendritic ulcers.) (FDA label, 9/15/2009, page 4; Wilhelmus K R et al., 2010, *Cochrane Database Syst Rev* 12: CD002898).

VALCYTE® (valganciclovir hydrochloride) in tablet form is FDA approved in adult patients for treatment of CMV retinitis in patients with acquired immunodeficiency syndrome (AIDS) and prevention of CMV disease in kidney, heart, and kidney-pancreas transplant patients at high risk. (FDA label, 4/23/2015, page 1.) The dose regimen for VALCYTE® is shown in the following table, as depicted on the FDA label dated Apr. 23, 2015:

TABLE 1

| Dose regimen for VALCYTE ®<br>DOSAGE AND ADMINISTRATION | |
|---|---|
| Adult Dosage (2.2) | |
| Treatment of CMV retinitis | Induction: 900 mg (two 450 mg tablets) twice a day for 21 days<br>Maintenance: 900 mg (two 450 mg tablets) once a day |
| Prevention of CMV disease in heart or kidney-pancreas transplant patients | 900 mg (two 450 mg tablets) once a day within 10 days of transplantation until 100 days post-transplantation |
| Prevention of CMV disease in kidney transplant patients | 900 mg (two 450 mg tablets) once a day within 10 days of tansplantation until 200 days post-transplantation |
| Pediatric Dosage (2.3) | |
| Prevention of CMV disease in kidney transplant patients 4 months to 16 years of age | Dose once a day within 10 days of transplantation until 200 days post-transplantation according to dosage algorithm (note the calculation of creatinine clearance using a modified Schwartz formula in children) |
| Prevention of CMV disease in heart transplant patients 1 month to 16 years of age | Dose once a day within 10 days of transplantation until 100 days post-transplantation according to dosage algorithm (note the calculation of creatinine clearance using a modified Schwartz formula in children) |

An oral form of Ganciclovir was found to have low bioavailability. (Biron et al. (2006) *Antiviral Research* 71:154-163.) Valganciclovir was reported to have better bioavailability than Ganciclovir. (Pescovitz M D et al., *Antimicrob Agents Chemother.* 2000; 44(10):2811-5; Biron et al. (2006) *Antiviral Research* 71:154-163.)

Adverse side effects associated with Ganciclovir and Valganciclovir include: fever, rash, diarrhea, and hematologic effects (such as neutropenia, anemia, and thrombocytopenia), as well as potential reproductive toxicity. Ganciclovir was also found to affect fertility and to be carcinogenic and teratogenic in animal studies. (Biron et al. (2006) *Antiviral Research* 71:154-163.) Phase 3 clinical trials involving treatment of CMV infection with Ganciclovir or Valganciclovir include trials associated with clinicaltrials.gov identifier numbers: NCT00000143, NCT00000136, NCT00000134, NCT00497796, NCT00227370, NCT00466817, and NCT00294515. Results of clinical trials involving Ganciclovir or Valganciclovir are summarized in Biron et al. (2006) *Antiviral Research* 71:154-163, incorporated by reference herein in its entirety.

Experimental Vaccines in Development for CMV

TransVax™ (Also Known as ASP0113 and VCL-CB01)

TransVax™ is a CMV vaccine being developed by Vical Incorporated and Astellas Pharma Inc. (Smith et al. (2013) *Vaccines* 1(4):398-414.) TransVax™ is a bivalent DNA vaccine containing plasmids encoding CMV pp65 and gB antigens formulated in CRL1005 poloxamer and benzalkonium. (Id.; Kharfan-Dabaja et al. (2012) *Lancet Infect Dis* 12:290-99). The pp65 antigen induces cytotoxic T cell response, conferring cellular immunity, while the gB antigen elicits both cellular immunity and antigen-specific antibody production. Accordingly, the vaccine is intended to induce both cellular and humoral immune responses. The pp65 and gB sequences are modified from wild type protein sequences through deletions and codon optimization, as described on pages 402-403 of Smith et al. (2013) *Vaccines* 1(4):398-414, incorporated by reference herein in its entirety.

TransVax™ has received orphan drug designation in the United States and Europe for hematopoietic stem cell transplantation (HSCT), e.g., bone marrow transplantation, and solid organ transplantation (SOT) patients.

In a Phase 1 clinical trial, 37.5% and 50% of $CMV^-$ subjects, who were dosed with 1 mg and 5 mg, respectively, of the vaccine, demonstrated antibody or T-cell responses. (Page 406 of Smith et al. (2013) *Vaccines* 1(4):398-414.) A Phase 2 clinical trial was conducted in patients undergoing allogenic haemopoietic stem cell transplantation (ClinicalTrials.gov identifier number NCT00285259) (Kharfan-Dabaja et al. (2012) *Lancet Infect Dis* 12:290-99). Transplant patients received the experimental vaccine four times, including once before the transplantation. (Id., page 292.) The dose before transplantation was administered between 3-5 days before transplantation, while the doses after transplantation were administered between 21-42 days after transplantation, and at 84 and 196 days after transplantation. (Id.) Endpoints included assessment of safety and reduction in cytomegalovirus viraemia. (Id.) The incidence of cytomegalovirus viraemia was found to be lower in patients who received the vaccine compared to placebo (32.5% (vaccine group) compared to 61.8% (placebo); Table 2, on page 294 of Kharfan-Dabaja et al.). The vaccine was also reported to be well-tolerated and safe. (Id., page 295.) However, after vaccine treatment, rates of viraemia necessitation anti-viral treatment resembled those of placebo controls. (Id., page 296.)

TransVax™ is currently being tested in a Phase 3 clinical trial for treatment of hematopoietic cell transplant (HCT) patients, accorded ClinicalTrials.gov identifier number NCT01877655. The endpoint for the trial is mortality and end organ disease (EOD) 1 year after transplant. The estimated enrollment is 500 and the vaccine is administered by intramuscular injection. TransVax™ is also currently being tested in a Phase 2 clinical trial in CMV-Seronegative kidney transplant recipients receiving an organ from a CMV-Seropositive donor, accorded ClinicalTrials.gov identifier number NCT01974206. The primary outcome being measured in this trial is incidence of CMV viremia one year after first administration of the drug. The enrollment is 150 and the vaccine is administered by intramuscular injection. Subjects included in the trial also received ganciclovir or valganciclovir from within ten days up transplant through randomization.

Clinical trials involving TransVax™ are found at the ClinicalTrials.gov website with the following ClinicalTrials.gov identifier numbers: NCT02103426, NCT01877655, NCT01974206, and NCT01903928.

US patents and published applications that are assigned to Vical Inc. and relate to CMV include: U.S. Pat. Nos. 8,673,317, 9,180,162, 8,278,093, 7,888,112, 7,410,795, which are incorporated by reference herein in their entireties.

Experimental Vaccines in Development by City of Hope/National Cancer Institute/Helocyte Several experimental CMV vaccines are being developed by City of Hope and its licensee Helocyte. US patents and published applications that are assigned to City of Hope and relate to CMV include: U.S. Pat. Nos. 7,387,782, 7,025,969, 6,133,433, 6,207,161, 6,074,645, 6,251,399, 6,727,093, 6,726,910, 6,843,992, 6,544,521, 6,951,651, 8,580,276, 7,163,685, 6,242,567, 6,835,383, 6,156,317, 6,562,345, US 2014-0065181 and US 2015-0216965, which are incorporated by reference herein in their entireties.

i) CMVPepVax

CMVPepVax is an experimental vaccine being developed by City of Hope Medical Center, National Cancer Institute, and Helocyte, Inc. The vaccine includes a pp65 T-cell epitope and a tetanus T-helper epitope in the form of a chimeric peptide, and also includes the adjuvant PF03512676. (Nakamura R et al., *Lancet Heamatology* (2016) February; 3(2):e87-98).

CMVPepVax was tested in a Phase 1b clinical trial on CMV-seropositive patients who were undergoing haemopoietic stem-cell transplantation (HCT). (Id.) The vaccine was administered on days 28 and 56 through subcutaneous administration. (Id.) It was reported that patients receiving the vaccine showed improved relapse-free survival. (Id.) This clinical trial was accorded ClinicalTrials.gov identifier number NCT01588015. CMVPepVax is currently being tested in a Phase 2 clinical trial to measure efficacy in reducing the frequency of Cytomegalovirus events in patients with hematologic malignancies undergoing donor stem cell transplant, accorded ClinicalTrials.gov identifier number NCT02396134.

ii) CMV-MVA Triplex

CMV-MVA-Triplex is an experimental CMV vaccine being developed by City of Hope Medical Center, National Cancer Institute, and Helocyte, Inc. (formerly DiaVax Biosciences). This vaccine consists of an inactivated Modified Vaccinia Ankara (MVA) viral vector that encodes the CMV antigens UL83 (pp65), UL123 (1E1) and UL122 (1E2). (NCI Drug Dictionary.)

CMV-MVA Triplex is currently being tested in a Phase 2 clinical trial investigating efficacy in reducing CMV complications in patients previously infected with CMV and undergoing donor hematopoietic cell transplant. This trial has been accorded ClinicalTrials.gov identifier number NCT02506933. A Phase 1 clinical trial in healthy volunteers with or without previous exposure to CMV is also ongoing (ClinicalTrials.gov identifier No. NCT01941056).

iii) Pentamer

City of Hope and Helocyte, Inc. are also pursuing a pentameric vaccine using a Modified Vaccinia Ankara (MVA) viral vector that encodes the five CMV pentameric subunits. This vaccine is still in preclinical development. (Wussow et al. (2014) PLoS Pathog 10(11): e1004524. doi: 10.1371/journal.ppat.1004524).

gB/MF59

This experimental vaccine, originally developed in the 1990s combines the gB antigen with the MF59 adjuvant. (Pass et al. (2009) *J Clin Virol* 46(Suppl 4):S73-S76.) Several clinical trials that were conducted in the 1990s, sponsored by Chiron Corporation, indicated that the vaccine was safe. (Id., page 2.) Sanofi Pasteur later obtained the rights to this vaccine. (Id.)

A Phase 2 clinical trial was conducted in postpartum females starting in 1999 (with enrollment completed in 2006) using the endpoint of time to CMV infection. (Id., page 3.) Subjects were administered the vaccine at 0, 1, and 6 months. (Rieder et al. (2014) *Clin Microbiol Infect* 20 (Suppl. 5):95-102, page 98). Infection with CMV was diagnosed in 8% of vaccine-treated subjects compared to 14% of placebo-treated subjects, respectively (corresponding to 43% efficacy). Results indicated a 50% reduction in rate of CMV infection in subjects treated with the vaccine (3.3% in test subjects compared to 6.6% in placebo-treated subjects). (Id.; Pass et al. (2009) *J Clin Virol* 46(Suppl 4):S73-S76., page 4.). The 50% reduction in rate of CMV infection has been described as "lower than wished for from a clinical perspective." (Rieder et al. (2014) *Clin Microbiol Infect* 20 (Suppl. 5):95-102, page 98.)

A Phase 2 clinical trial has also been conducted with gB/MF59 in kidney and liver transplant patients. (Id., page 100.) It was reported that "high gB-antibody titres correlated with shorter duration of viraemia" and that "duration of viraemia and number of days of ganciclovir treatment were reduced." (Id.)

Clinical trials involving gB/MF59 are found at the ClinicalTrials.gov website with the following ClinicalTrials.gov identifier numbers: NCT00133497, NCT00815165, and NCT00125502.

US 2009-0104227, assigned to Sanofi Pasteur SA, is incorporated by reference herein in its entirety.

gB/AS01

GlaxoSmithKline is developing an experimental vaccine that includes the gB antigen combined with the AS01 adjuvant. (McVoy (2013) *Clinical Infectious Diseases* 57(S4):S196-9, page S197.) This vaccine is referred to as GSK1492903A. Clinical trials involving GSK1492903A are found at the ClinicalTrials.gov website with the following ClinicalTrials.gov identifier numbers: NCT00435396 and NCT01357915.

WO 2016/067239 and WO 2015/181142, filed by GlaxoSmithKline Biologicals SA, are incorporated by reference herein in their entireties.

Towne Vaccine

The CMV Towne vaccine is a live attenuated vaccine. (McVoy (2013) *Clinical Infectious Diseases* 57(S4):S196-9, page S197.) This vaccine was not successful in protecting against primary maternal infection, at least when administered at a low dose. (Id.) In a trial involving kidney transplant subjects, treatment with this vaccine resulted in reduction of severe disease, while only having a minimal impact on mild disease. (Plotkin et al. (1994) *Transplantation* 58(11):1176-8.)

Live attenuated vaccines in which sections of the Towne genome have been replaced with sequence from other "low-passage" strains have also been developed, referred to as "Towne-Toledo chimeras," which were found to be well-tolerated in a Phase 1 clinical trial. (McVoy (2013) *Clinical Infectious Diseases* 57(S4):S196-9, page S197; Heineman et al. (2006) *The Journal of Infectious Diseases* 193:1350-60.) Chimeric viral genomes including portions of the Towne genome are described in and incorporated by reference from U.S. Pat. No. 7,204,990, incorporated by reference herein in its entirety.

Another approach that is being explored involves co-administering the Towne vaccine with the adjuvant recombinant interleukin-12 (rhIL-12) (Jacobson et al. (2006) *Vaccine* 24:5311-9.)

CMV-CTL

CMV Targeted T-Cell Program (CMV-CTL) represents a cellular immunotherapy approach being developed by Atara Biotherapeutics.

A Phase 1 clinical trial used CMV pp65 or pp65/IE1 peptide mixes to pulse monocytes to expand CMV CTL and investigated the immunologic effects. (Bao et al. (2012) *J Immunother* 35(3):293-298). CMV specific immune responses were observed in approximately 70% of subjects receiving CTL. (Id., page 5.)

A Phase 2 clinical trial is currently ongoing, investigating third party donor derived CMVpp65 specific T-cells for the treatment of CMV infection or persistent CMV viremia after allogeneic hematopoietic stem cell transplantation. This trial was assigned ClinicalTrials.gov identifier number NCT02136797. A second Phase 2 clinical trial is also ongoing, investigating primary transplant donor derived CMVpp65 specific T-cells for the treatment of CMV infection or persistent CMV viremia after allogeneic hematopoietic stem cell transplantation. This trial was assigned ClinicalTrials.gov identifier number NCT01646645.

Monoclonal Abs

Novartis

CSJ148, being developed by Novartis, represents a combination of two monoclonal antibodies that target gB and the CMV pentameric complex. (Dole et al. (2016) *Antimicrob Agents Chemother*. April 22; 60(5):2881-7). The two antibodies are known as LJP538 and LJP539. (Id.) LJP538, LJP539, and CSJ148 were found to be safe when administered intravenously to healthy volunteers and revealed expected pharmacokinetics for IgG. (Id.) CSJ148 is currently in a Phase 2 clinical trial investigating efficacy and safety in stem cell transplant patients (ClinicalTrials.gov identifier number NCT02268526).

Theraclone

TCN-202 is a fully human monoclonal antibody being developed by Theraclone for treatment of CMV infection. TCN-202 was found to be safe and well-tolerated in a Phase 1 clinical trial (ClinicalTrial.gov identifier number NCT01594437). A Phase 2 study was initiated in 2013 to investigate efficacy in kidney transplant recipients. (Theraclone Press Release, Sep. 10, 2013.)

Brincidofovir

Brincidofovir (CMX001) is an experimental lipid-nucleotide conjugate being developed by Chimerix, Durham, N.C., for treatment of DNA viruses including CMV. Brincidofovir received Fast Track designation from the FDA for CMV.

Results from a Phase 3 clinical trial (called "SUPPRESS") investigating prevention of CMV in subjects undergoing hematopoietic cell transplantation (HCT) were announced in February, 2016. (Chimerix Press Release, Feb. 20, 2016.) It was reported that the trial failed to meet its primary endpoint of preventing CMV at week 24, although an anti-viral effect was observed during the treatment phase. (Id.) The trial involved 452 subjects undergoing HCT who were administered Brincidofovir twice a week for up to fourteen weeks. (Id.) It was speculated that increased use of immunosteroids, such as corticosteroids, for treatment of graft versus host disease (GVHD), after treatment with Brincidofovir, may have contributed to failure to reach the primary endpoint of the trial. (Id.) Other. Phase 3 trials were terminated based on the results of the SUPPRESS trial, but Chimerix has indicated that they intend to pursue further Phase 2 trials in subjects undergoing kidney transplants. (Id.)

Information about clinical trials associated with Brincidofovir are found at the ClinicalTrials.gov website, including identifier numbers: NCT02087306, NCT02271347, NCT02167685, NCT02596997, NCT02439970, NCT00793598, NCT01769170, NCT00780182, NCT01241344, NCT00942305, NCT02420080, NCT02439957, NCT01143181, and NCT01610765.

V160

V160 is an experimental CMV vaccine being developed by Merck, which is based on the attenuated AD169 strain. V160 is currently being tested in a Phase 1 clinical trial evaluating a three dose regimen testing several formulations in healthy adults. This trial was assigned the ClinicalTrials.gov identifier number NCT01986010.

Merck is also pursuing vaccines that target the CMV pentameric complex. (Loughney et al. (2015) jbc.M115.652230.) US patents and published applications assigned to Merck Sharp & Dohme Corp include: US 2014-0220062 and US 2015-0307850, which are incorporated by reference herein in their entireties.

Letermovir

Letermovir (AIC246) is an antiviral drug being developed by Merck for the treatment of CMV infections (Chemaly et al. (2014) *New England Journal of Medicine,* 370; 19, May 8, 2014, Verghese et al. (2013) *Drugs Future*. May; 38(5): 291-298). It was tested in a Phase IIb clinical trial investigating prevention of CMV in HSCT recipients, corresponding to ClinicalTrials.gov identifier number NCT01063829, and was found to reduce the incidence of CMV infection in transplant subjects.

Redvax GmbH/Pfizer

A preclinical candidate targeting CMV was developed by Redvax GmbH, which spun out from Redbiotec AG. This candidate is now being pursued by Pfizer Inc.

Patents and patent publications assigned to Redvax GmbH or Pfizer and related to CMV include: US 2015-0322115, WO 2015/170287, US 2015-0359879, and WO 2014/068001, incorporated by reference herein in their entireties.

Therapeutic and Prophylactic Compositions

Provided herein are compositions (e.g., pharmaceutical compositions), methods, kits and reagents for prevention, treatment or diagnosis of HCMV in humans. HCMV RNA vaccines can be used as therapeutic or prophylactic agents. They may be used in medicine to prevent and/or treat infectious disease. In some embodiments, the HCMV vaccines of the invention can be envisioned for use in the priming of immune effector cells, for example, to activate peripheral blood mononuclear cells (PBMCs) ex vivo, which are then infused (re-infused) into a subject.

In exemplary embodiments, one or more HCMV vaccine containing RNA polynucleotides as described herein can be administered to a subject (e.g., a mammalian subject, such as a human subject), and the RNA polynucleotides are translated in vivo to produce an antigenic polypeptide. In some embodiments, the subject is an organ donor or an organ recipient. For example, the subject can be an immunocompromised organ transplant recipient. In some embodiments, the transplant recipient is a hematopoietic cell transplant recipient or a solid organ transplant recipient. In some embodiments, the subject is a woman of child-bearing age. In some embodiments, vaccines described herein reduce or prevent congenital transmission of HCMV from a mother to a child. (Pass et al. (2014) *J Ped Infect Dis* 3 (suppl 1): S2-S6.)

The HCMV RNA vaccines may be induced for translation of a polypeptide (e.g., antigen or immunogen) in a cell, tissue or organism. In exemplary embodiments, such translation occurs in vivo, although there can be envisioned embodiments where such translation occurs ex vivo, in culture or in vitro. In exemplary embodiments, the cell, tissue or organism is contacted with an effective amount of a composition containing a HCMV RNA vaccine that contains a polynucleotide that has at least one a translatable region encoding an antigenic polypeptide.

An "effective amount" of one or more HCMV RNA vaccines is provided based, at least in part, on the target tissue, target cell type, means of administration, physical characteristics of the polynucleotide (e.g., size, and extent of modified nucleosides) and other components of the HCMV RNA vaccine, and other determinants. In general, an effective amount of one or more HCMV RNA vaccine compositions provides an induced or boosted immune response as a function of antigen production in the cell, preferably more efficient than a composition containing a corresponding unmodified polynucleotide encoding the same antigen or a peptide antigen. Increased antigen production may be demonstrated by increased cell transfection (the percentage of cells transfected with the RNA vaccine), increased protein translation from the polynucleotide, decreased nucleic acid degradation (as demonstrated, for example, by increased duration of protein translation from a modified polynucleotide), or altered antigen specific immune response of the host cell.

In some embodiments, RNA vaccines (including polynucleotides their encoded polypeptides) in accordance with the present disclosure may be used for treatment of HCMV.

HCMV RNA vaccines may be administered prophylactically or therapeutically as part of an active immunization scheme to healthy individuals or early in infection during the incubation phase or during active infection after onset of symptoms. In some embodiments, the amount of RNA vaccines of the present disclosure provided to a cell, a tissue or a subject may be an amount effective for immune prophylaxis.

HCMV RNA vaccines may be administrated with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In exemplary embodiments, the time of administration between the initial administration of the prophylactic composition and the booster may be, but is not limited to, 1 week, 2 weeks, 3 weeks, 1 month, 2 months, 3 months, 6 months or 1 year.

In some embodiments, HCMV RNA vaccines may be administered intramuscularly or intradermally, similarly to the administration of inactivated vaccines known in the art.

The HCMV RNA vaccines may be utilized in various settings depending on the prevalence of the infection or the degree or level of unmet medical need. As a non-limiting example, the RNA vaccines may be utilized to treat and/or prevent a variety of infectious disease. RNA vaccines have superior properties in that they produce much larger antibody titers and produce responses early than commercially available anti-virals.

Provided herein are pharmaceutical compositions including HCMV RNA vaccines and RNA vaccine compositions and/or complexes optionally in combination with one or more pharmaceutically acceptable excipients.

HCMV RNA vaccines may be formulated or administered alone or in conjunction with one or more other components. For instance, HCMV RNA vaccines (vaccine compositions) may comprise other components including, but not limited to, adjuvants. In some embodiments, HCMV RNA vaccines do not include an adjuvant (they are adjuvant free).

HCMV RNA vaccines may be formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

In some embodiments, HCMV RNA vaccines are administered to humans, human patients or subjects. For the purposes of the present disclosure, the phrase "active ingredient" generally refers to the RNA vaccines or the polynucleotides contained therein, for example, RNA polynucleotides (e.g., mRNA polynucleotides) encoding antigenic polypeptides.

Formulations of the vaccine compositions described herein may be prepared by any method known or hereafter developed in the art of pharmacology. In general, such preparatory methods include the step of bringing the active ingredient (e.g., mRNA polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

HCMV RNA vaccines can be formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with HCMV RNA vaccines (e.g., for transplantation into a subject), hyaluronidase, nanoparticle mimics and combinations thereof.

Stabilizing Elements

Naturally-occurring eukaryotic mRNA molecules have been found to contain stabilizing elements, including, but not limited to untranslated regions (UTR) at their 5'-end (5'UTR) and/or at their 3'-end (3'UTR), in addition to other structural features, such as a 5'-cap structure or a 3'-poly(A) tail. Both the 5'UTR and the 3'UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing. The 3'-poly(A) tail is typically a stretch of adenine nucleotides added to the 3'-end of the transcribed mRNA. It can comprise up to about 400 adenine nucleotides. In some embodiments the length of the 3'-poly(A) tail may be an essential element with respect to the stability of the individual mRNA.

In some embodiments the RNA vaccine may include one or more stabilizing elements. Stabilizing elements may include for instance a histone stem-loop. A stem-loop binding protein (SLBP), a 32 kDa protein has been identified. It is associated with the histone stem-loop at the 3'-end of the histone messages in both the nucleus and the cytoplasm. Its expression level is regulated by the cell cycle; it is peaks during the S-phase, when histone mRNA levels are also elevated. The protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, the RNA vaccines include a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. Luciferase, GFP, EGFP, β-Galactosidase, EGFP), or a marker or selection protein (e.g. alpha-Globin, Galactokinase and Xanthine: guanine phosphoribosyl transferase (GPT)).

In some embodiments, the combination of a poly(A) sequence or polyadenylation signal and at least one histone stem-loop, even though both represent alternative mechanisms in nature, acts synergistically to increase the protein expression beyond the level observed with either of the individual elements. It has been found that the synergistic effect of the combination of poly(A) and at least one histone stem-loop does not depend on the order of the elements or the length of the poly(A) sequence.

In some embodiments, the RNA vaccine does not comprise a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. Ideally, the inventive nucleic acid does not include an intron.

In some embodiments, the RNA vaccine may or may not contain a enhancer and/or promoter sequence, which may be modified or unmodified or which may be activated or inactivated. In some embodiments, the histone stem-loop is generally derived from histone genes, and includes an intramolecular base pairing of two neighbored partially or entirely reverse complementary sequences separated by a spacer, consisting of a short sequence, which forms the loop of the structure. The unpaired loop region is typically unable to base pair with either of the stem loop elements. It occurs more often in RNA, as is a key component of many RNA secondary structures, but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides.

In other embodiments the RNA vaccine may have one or more AU-rich sequences removed. These sequences, sometimes referred to as AURES are destabilizing sequences found in the 3'UTR. The AURES may be removed from the RNA vaccines. Alternatively the AURES may remain in the RNA vaccine.

Nanoparticle Formulations

In some embodiments, HCMV RNA vaccines are formulated in a nanoparticle. In some embodiments, HCMV RNA vaccines are formulated in a lipid nanoparticle. In some embodiments, HCMV RNA vaccines are formulated in a lipid-polycation complex, referred to as a lipid nanoparticle. The formation of the lipid nanoparticle may be accomplished by methods known in the art and/or as described in U.S. Pub. No. 20120178702, herein incorporated by reference in its entirety. As a non-limiting example, the polycation may include a cationic peptide or a polypeptide such as, but not limited to, polylysine, polyornithine and/or polyarginine and the cationic peptides described in International Pub. No. WO2012013326 or US Patent Pub. No. US20130142818; each of which is herein incorporated by reference in its entirety. In some embodiments, HCMV RNA vaccines are formulated in a lipid nanoparticle that includes a non-cationic lipid such as, but not limited to, cholesterol or dioleoyl phosphatidylethanolamine (DOPE).

A lipid nanoparticle formulation may be influenced by, but not limited to, the selection of the ionizable lipid component, the degree of ionizable lipid saturation, the nature of the PEGylation, ratio of all components and biophysical parameters such as size. In one example by Semple et al. (*Nature Biotech.* 2010 28:172-176; herein incorporated by reference in its entirety), the lipid nanoparticle formulation is composed of 57.1% cationic lipid, 7.1% dipalmitoylphosphatidylcholine, 34.3% cholesterol, and 1.4% PEG-c-DMA. As another example, changing the composition of the cationic lipid can more effectively deliver siRNA to various antigen presenting cells (Basha et al. *Mol Ther.* 2011 19:2186-2200; herein incorporated by reference in its entirety).

In some embodiments, lipid nanoparticle formulations may comprise 35 to 45% ionizable cationic lipid, 40% to 50% ionizable cationic lipid, 50% to 60% ionizable cationic lipid and/or 55% to 65% ionizable cationic lipid. In some embodiments, the ratio of lipid to RNA (e.g., mRNA) in lipid nanoparticles may be 5:1 to 20:1, 10:1 to 25:1, 15:1 to 30:1 and/or at least 30:1.

In some embodiments, the ratio of PEG in the lipid nanoparticle formulations may be increased or decreased and/or the carbon chain length of the PEG lipid may be modified from C14 to C18 to alter the pharmacokinetics and/or biodistribution of the lipid nanoparticle formulations. As a non-limiting example, lipid nanoparticle formulations may contain 0.5% to 3.0%, 1.0% to 3.5%, 1.5% to 4.0%, 2.0% to 4.5%, 2.5% to 5.0% and/or 3.0% to 6.0% of the lipid molar ratio of PEG-c-DOMG (R-3-[(ω-methoxy-poly(ethyleneglycol)2000)carbamoyl)]-1,2-dimyristyloxypropyl-3-amine) (also referred to herein as PEG-DOMG) as compared to the cationic lipid, DSPC and cholesterol. In some embodiments, the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In some embodiments, a HCMV RNA vaccine formulation is a nanoparticle that comprises at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In some embodiments, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in US Patent Publication No. US20130150625, herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-[(9Z,12Z)-octadeca-9,12-dien-1-yloxy]methyl propan-1-ol (Compound 4 in US20130150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino)butanoyl)oxy)heptadecanedioate (L319), and further comprise a neutral lipid, a sterol and a molecule capable of reducing particle aggregation, for example a PEG or PEG-modified lipid.

In some embodiments, a lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy) heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of 20-60% ionizable cationic lipid: 5-25% neutral lipid: 25-55% sterol; 0.5-15% PEG-lipid.

In some embodiments, a lipid nanoparticle formulation includes 25% to 75% on a molar basis of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), e.g., 35 to 65%, 45 to 65%, 60%, 57.5%, 50% or 40% on a molar basis.

In some embodiments, a lipid nanoparticle formulation includes 0.5% to 15% on a molar basis of the neutral lipid, e.g., 3 to 12%, 5 to 10% or 15%, 10%, or 7.5% on a molar basis. Examples of neutral lipids include, without limitation, DSPC, POPC, DPPC, DOPE and SM. In some embodiments, the formulation includes 5% to 50% on a molar basis of the sterol (e.g., 15 to 45%, 20 to 40%, 40%, 38.5%, 35%, or 31% on a molar basis. A non-limiting example of a sterol is cholesterol. In some embodiments, a lipid nanoparticle formulation includes 0.5% to 20% on a molar basis of the PEG or PEG-modified lipid (e.g., 0.5 to 10%, 0.5 to 5%, 1.5%, 0.5%, 1.5%, 3.5%, or 5% on a molar basis. In some embodiments, a PEG or PEG modified lipid comprises a PEG molecule of an average molecular weight of 2,000 Da. In some embodiments, a PEG or PEG modified lipid comprises a PEG molecule of an average molecular weight of less than 2,000, for example around 1,500 Da, around 1,000 Da, or around 500 Da. Non-limiting examples of PEG-modified lipids include PEG-distearoyl glycerol (PEG-DMG) (also referred herein as PEG-C14 or C14-PEG), PEG-cDMA (further discussed in Reyes et al. *J. Controlled Release,* 107, 276-287 (2005) the contents of which are herein incorporated by reference in its entirety).

In some embodiments, lipid nanoparticle formulations include 25-75% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 0.5-15% of the neutral lipid, 5-50% of the sterol, and 0.5-20% of the PEG or PEG-modified lipid on a molar basis.

In some embodiments, lipid nanoparticle formulations include 35-65% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 3-12% of the neutral lipid, 15-45% of the sterol, and 0.5-10% of the PEG or PEG-modified lipid on a molar basis.

In some embodiments, lipid nanoparticle formulations include 45-65% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 5-10% of the neutral lipid, 25-40% of the sterol, and 0.5-10% of the PEG or PEG-modified lipid on a molar basis.

In some embodiments, lipid nanoparticle formulations include 60% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 7.5% of the neutral lipid, 31% of the sterol, and 1.5% of the PEG or PEG-modified lipid on a molar basis.

In some embodiments, lipid nanoparticle formulations include 50% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 10% of the neutral lipid, 38.5% of the sterol, and 1.5% of the PEG or PEG-modified lipid on a molar basis.

In some embodiments, lipid nanoparticle formulations include 50% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 10% of the neutral lipid, 35% of the sterol, 4.5% or 5% of the PEG or PEG-modified lipid, and 0.5% of the targeting lipid on a molar basis.

In some embodiments, lipid nanoparticle formulations include 40% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 15% of the neutral lipid, 40% of the sterol, and 5% of the PEG or PEG-modified lipid on a molar basis.

In some embodiments, lipid nanoparticle formulations include 57.2% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 7.1% of the neutral lipid, 34.3% of the sterol, and 1.4% of the PEG or PEG-modified lipid on a molar basis.

In some embodiments, lipid nanoparticle formulations include 57.5% of a cationic lipid selected from the PEG lipid is PEG-cDMA (PEG-cDMA is further discussed in Reyes et al. (J. Controlled Release, 107, 276-287 (2005), the contents of which are herein incorporated by reference in its entirety), 7.5% of the neutral lipid, 31.5% of the sterol, and 3.5% of the PEG or PEG-modified lipid on a molar basis.

In some embodiments, lipid nanoparticle formulations consists essentially of a lipid mixture in molar ratios of 20-70% ionizable cationic lipid: 5-45% neutral lipid: 20-55% cholesterol: 0.5-15% PEG-modified lipid. In some embodiments, lipid nanoparticle formulations consists essentially of a lipid mixture in a molar ratio of 20-60% ionizable cationic lipid: 5-25% neutral lipid: 25-55% cholesterol: 0.5-15% PEG-modified lipid.

In some embodiments, the molar lipid ratio is 50/10/38.5/1.5 (mol % ionizable cationic lipid/neutral lipid, e.g., DSPC/Chol/PEG-modified lipid, e.g., PEG-DMG, PEG-DSG or PEG-DPG), 57.2/7.1134.3/1.4 (mol % ionizable cationic lipid/neutral lipid, e.g., DPPC/Chol/PEG-modified lipid, e.g., PEG-cDMA), 40/15/40/5 (mol % ionizable cationic lipid/neutral lipid, e.g., DSPC/Chol/PEG-modified lipid, e.g., PEG-DMG), 50/10/35/4.5/0.5 (mol % ionizable cationic lipid/neutral lipid, e.g., DSPC/Chol/PEG-modified lipid, e.g., PEG-DSG), 50/10/35/5 (ionizable cationic lipid/neutral lipid, e.g., DSPC/Chol/PEG-modified lipid, e.g., PEG-DMG), 40/10/40/10 (mol % ionizable cationic lipid/neutral lipid, e.g., DSPC/Chol/PEG-modified lipid, e.g., PEG-DMG or PEG-cDMA), 35/15/40/10 (mol % ionizable cationic lipid/neutral lipid, e.g., DSPC/Chol/PEG-modified lipid, e.g., PEG-DMG or PEG-cDMA) or 52/13/30/5 (mol % ionizable cationic lipid/neutral lipid, e.g., DSPC/Chol/PEG-modified lipid, e.g., PEG-DMG or PEG-cDMA).

Non-limiting examples of lipid nanoparticle compositions and methods of making them are described, for example, in Semple et al. (2010) *Nat. Biotechnol.* 28:172-176; Jayarama et al. (2012), *Angew. Chem. Int. Ed.,* 51: 8529-8533; and Maier et al. (2013) *Molecular Therapy* 21, 1570-1578 (the contents of each of which are incorporated herein by reference in their entirety).

In some embodiments, lipid nanoparticle formulations may comprise a ionizable cationic lipid, a PEG lipid and a structural lipid and optionally comprise a non-cationic lipid. As a non-limiting example, a lipid nanoparticle may comprise 40-60% of ionizable cationic lipid, 5-15% of a non-cationic lipid, 1-2% of a PEG lipid and 30-50% of a structural lipid. As another non-limiting example, the lipid nanoparticle may comprise 50% ionizable cationic lipid, 10% non-cationic lipid, 1.5% PEG lipid and 38.5% structural lipid. As yet another non-limiting example, a lipid nanoparticle may comprise 55% ionizable cationic lipid, 10% non-cationic lipid, 2.5% PEG lipid and 32.5% structural lipid. In some embodiments, the ionizable cationic lipid may be any cationic lipid described herein such as, but not limited to, DLin-KC2-DMA, DLin-MC3-DMA and L319.

In some embodiments, the lipid nanoparticle formulations described herein may be 4 component lipid nanoparticles. The lipid nanoparticle may comprise a ionizable cationic lipid, a non-cationic lipid, a PEG lipid and a structural lipid. As a non-limiting example, the lipid nanoparticle may comprise 40-60% of ionizable cationic lipid, 5-15% of a non-cationic lipid, 1-2% of a PEG lipid and 30-50% of a structural lipid. As another non-limiting example, the lipid nanoparticle may comprise 50% ionizable cationic lipid, 10% non-cationic lipid, 1.5% PEG lipid and 38.5% structural lipid. As yet another non-limiting example, the lipid nanoparticle may comprise 55% ionizable cationic lipid, 10% non-cationic lipid, 2.5% PEG lipid and 32.5% structural lipid. In some embodiments, the ionizable cationic lipid may be any cationic lipid described herein such as, but not limited to, DLin-KC2-DMA, DLin-MC3-DMA and L319.

In some embodiments, the lipid nanoparticle formulations described herein may comprise a ionizable cationic lipid, a non-cationic lipid, a PEG lipid and a structural lipid. As a non-limiting example, the lipid nanoparticle comprise 50% of the cationic lipid DLin-KC2-DMA, 10% of the non-cationic lipid DSPC, 1.5% of the PEG lipid PEG-DOMG and 38.5% of the structural lipid cholesterol. As a non-limiting example, the lipid nanoparticle comprise 50% of the cationic lipid DLin-MC3-DMA, 10% of the non-cationic lipid DSPC, 1.5% of the PEG lipid PEG-DOMG and 38.5% of the structural lipid cholesterol. As a non-limiting example, the lipid nanoparticle comprise 50% of the cationic lipid DLin-MC3-DMA, 10% of the non-cationic lipid DSPC, 1.5% of the PEG lipid PEG-DMG and 38.5% of the structural lipid cholesterol. As yet another non-limiting example, the lipid nanoparticle comprise 55% of the cationic lipid L319, 10% of the non-cationic lipid DSPC, 2.5% of the PEG lipid PEG-DMG and 32.5% of the structural lipid cholesterol.

Relative amounts of the active ingredient, the pharmaceutically acceptable excipient, and/or any additional ingredients in a vaccine composition may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, the RNA vaccine composition may comprise the polynucleotide described herein, formulated in a lipid nanoparticle comprising MC3, Cholesterol, DSPC and PEG2000-DMG, the buffer trisodium citrate, sucrose and water for injection. As a non-limiting example, the composition comprises: 2.0 mg/mL of drug substance (e.g., polynucleotides encoding H10N8 influenza virus), 21.8 mg/mL of MC3, 10.1 mg/mL of cholesterol, 5.4 mg/mL of DSPC, 2.7 mg/mL of PEG2000-DMG, 5.16 mg/mL of trisodium citrate, 71 mg/mL of sucrose and 1.0 mL of water for injection.

In some embodiments, a nanoparticle (e.g., a lipid nanoparticle) has a mean diameter of 10-500 nm, 20-400 nm, 30-300 nm, 40-200 nm. In some embodiments, a nanoparticle (e.g., a lipid nanoparticle) has a mean diameter of 50-150 nm, 50-200 nm, 80-100 nm or 80-200 nm.

Liposomes, Lipoplexes, and Lipid Nanoparticles

The RNA vaccines of the invention can be formulated using one or more liposomes, lipoplexes, or lipid nanoparticles. In some embodiments, the RNA vaccine comprises one or more RNA polynucleotides comprising one or more open reading frames encoding one or more of HCMV antigenic polypeptides gB, gH, gL, UL128, UL130, UL131, and pp65. In some embodiments, all of the RNA polynucleotide components of the vaccine are formulated in the same liposome, lipoplex or lipid nanoparticle. In other embodiments, one or more of the RNA polynucleotide components of the vaccine are formulated in different liposomes, lipoplexes or lipid nanoparticles. In other embodiments, each of RNA polynucleotide components of the vaccine is formulated in a different liposome, lipoplex or lipid nanoparticle. In some embodiments, an RNA vaccine comprises RNA polynucleotides encoding gB, gH, gL, UL128, UL130 and UL131. The RNA polynucleotides encoding gB, gH, gL, UL128, UL130 and UL131 can be formulated in one or more liposomes, lipoplexes, or lipid nanoparticles. In certain embodiments, RNA polynucleotides encoding gB, gH, gL, UL128, UL130 and UL131 are all included in the same liposome, lipoplexe, or lipid nanoparticle. In some embodiments, an RNA vaccine further comprises an RNA polynucleotide encoding pp65. In some embodiments, the pp65 polypeptide contains a deletion of amino acids 435-438. The RNA polynucleotide encoding pp65 can be formulated with the other RNA components of the vaccine or separately from the other RNA components of the vaccine. In some embodiments, an RNA polynucleotide encoding pp65 is formulated in a separate vaccine. In some embodiments, RNA polynucleotides encoding gB, gH, gL, UL128, UL130 and UL131 are all included in the same liposome, lipoplexe, or lipid nanoparticle, while an RNA polynucleotide encoding pp65 is formulated in a separate liposome, lipoplexe, or lipid nanoparticle. When RNA polynucleotides are formulated in separate liposomes, lipoplexes, or lipid nanoparticles, they can be administered together or separately. In some embodiments, a liposome, lipoplexe, or lipid nanoparticle comprising an RNA polynucleotide encoding pp65 is administered before a liposome, lipoplexe, or lipid nanoparticle comprising RNA polynucleotides encoding gB, gH, gL, UL128, UL130, and UL131. In some embodiments, a liposome, lipoplexe, or lipid nanoparticle comprising an RNA polynucleotide encoding pp65 is administered before a liposome, lipoplexe, or lipid nanoparticle comprising RNA polynucleotides encoding gB, gH, gL, UL128, UL130, UL131, and pp65.

In some embodiments, pharmaceutical compositions of RNA vaccines include liposomes. Liposomes are artificially-prepared vesicles which may primarily be composed of a lipid bilayer and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

The formation of liposomes may depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

As a non-limiting example, liposomes such as synthetic membrane vesicles may be prepared by the methods, apparatus and devices described in US Patent Publication No. US20130177638, US20130177637, US20130177636, US20130177635, US20130177634, US20130177633, US20130183375, US20130183373 and US20130183372, the contents of each of which are herein incorporated by reference in its entirety.

In some embodiments, pharmaceutical compositions described herein may include, without limitation, liposomes such as those formed from 1,2-dioleyloxy-N,N-dimethylaminopropane (DODMA) liposomes, DiLa2 liposomes from Marina Biotech (Bothell, Wash.), 1,2-dilinoleyloxy-3-dimethylaminopropane (DLin-DMA), 2,2-dilinoleyl-4-(2-dimethylaminoethyl)[1,3]-dioxolane (DLin-KC2-DMA), and MC3 (US20100324120; herein incorporated by reference in its entirety) and liposomes which may deliver small molecule drugs such as, but not limited to, DOXIL® from Janssen Biotech, Inc. (Horsham, Pa.).

In some embodiments, pharmaceutical compositions described herein may include, without limitation, liposomes such as those formed from the synthesis of stabilized plasmid-lipid particles (SPLP) or stabilized nucleic acid lipid particle (SNALP) that have been previously described and shown to be suitable for oligonucleotide delivery in vitro and in vivo (see Wheeler et al. Gene Therapy. 1999 6:271-281; Zhang et al. Gene Therapy. 1999 6:1438-1447; Jeffs et al. Pharm Res. 2005 22:362-372; Morrissey et al., Nat Biotechnol. 2005 2:1002-1007; Zimmermann et al., Nature. 2006 441:111-114; Heyes et al. J Contr Rel. 2005 107:276-287; Semple et al. Nature Biotech. 2010 28:172-176; Judge et al. J Clin Invest. 2009 119:661-673; deFougerolles Hum Gene Ther. 2008 19:125-132; U.S. Patent Publication No US20130122104; all of which are incorporated herein in their entireties). The original manufacture method by Wheeler et al. was a detergent dialysis method, which was later improved by Jeffs et al. and is referred to as the spontaneous vesicle formation method. The liposome formulations are composed of 3 to 4 lipid components in addition to the polynucleotide. As an example a liposome can contain, but is not limited to, 55% cholesterol, 20% disteroylphosphatidyl choline (DSPC), 10% PEG-S-DSG, and 15% 1,2-dioleyloxy-N,N-dimethylaminopropane (DODMA), as described by Jeffs et al. As another example, certain liposome formulations may contain, but are not limited to, 48% cholesterol, 20% DSPC, 2% PEG-c-DMA, and 30% cationic lipid, where the cationic lipid can be 1,2-distearloxy-N,N-dimethylaminopropane (DSDMA), DODMA, DLin-DMA, or 1,2-dilinolenyloxy-3-dimethylaminopropane (DLenDMA), as described by Heyes et al.

In some embodiments, liposome formulations may comprise from about 25.0% cholesterol to about 40.0% cholesterol, from about 30.0% cholesterol to about 45.0% cholesterol, from about 35.0% cholesterol to about 50.0% cholesterol and/or from about 48.5% cholesterol to about 60% cholesterol. In a preferred embodiment, formulations may comprise a percentage of cholesterol selected from the group consisting of 28.5%, 31.5%, 33.5%, 36.5%, 37.0%, 38.5%, 39.0% and 43.5%. In some embodiments, formulations may comprise from about 5.0% to about 10.0% DSPC and/or from about 7.0% to about 15.0% DSPC.

In some embodiments, pharmaceutical compositions may include liposomes which may be formed to deliver polynucleotides which may encode at least one immunogen (antigen) or any other polypeptide of interest. The RNA vaccine may be encapsulated by the liposome and/or it may be contained in an aqueous core which may then be encapsulated by the liposome (see International Pub. Nos. WO2012031046, WO2012031043, WO2012030901 and WO2012006378 and US Patent Publication No. US20130189351, US20130195969 and US20130202684; the contents of each of which are herein incorporated by reference in their entirety).

In another embodiment, liposomes may be formulated for targeted delivery. As a non-limiting example, the liposome may be formulated for targeted delivery to the liver. The liposome used for targeted delivery may include, but is not limited to, the liposomes described in and methods of making liposomes described in US Patent Publication No. US20130195967, the contents of which are herein incorporated by reference in its entirety.

In another embodiment, the polynucleotide which may encode an immunogen (antigen) may be formulated in a cationic oil-in-water emulsion where the emulsion particle comprises an oil core and a cationic lipid which can interact with the polynucleotide anchoring the molecule to the emulsion particle (see International Pub. No. WO2012006380; herein incorporated by reference in its entirety).

In some embodiments, the RNA vaccines may be formulated in a water-in-oil emulsion comprising a continuous hydrophobic phase in which the hydrophilic phase is dispersed. As a non-limiting example, the emulsion may be made by the methods described in International Publication No. WO201087791, the contents of which are herein incorporated by reference in its entirety.

In another embodiment, the lipid formulation may include at least cationic lipid, a lipid which may enhance transfection and a least one lipid which contains a hydrophilic head group linked to a lipid moiety (International Pub. No. WO2011076807 and U.S. Pub. No. 20110200582; the contents of each of which is herein incorporated by reference in their entirety). In another embodiment, the polynucleotides encoding an immunogen may be formulated in a lipid vesicle which may have crosslinks between functionalized lipid bilayers (see U.S. Pub. No. 20120177724, the contents of which is herein incorporated by reference in its entirety).

In some embodiments, the polylnucleotides may be formulated in a lipsome as described in International Patent Publication No. WO2013086526, the contents of which is herein incorporated by reference in its entirety. The RNA vaccines may be encapsulated in a liposome using reverse pH gradients and/or optimized internal buffer compositions as described in International Patent Publication No. WO2013086526, the contents of which is herein incorporated by reference in its entirety.

In some embodiments, the RNA vaccine pharmaceutical compositions may be formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. Cancer Biology & Therapy 2006 5(12)1708-1713); herein incorporated by reference in its entirety) and hyaluronan-coated liposomes (Quiet Therapeutics, Israel).

In some embodiments, the cationic lipid may be a low molecular weight cationic lipid such as those described in US Patent Application No. 20130090372, the contents of which are herein incorporated by reference in its entirety.

In some embodiments, the RNA vaccines may be formulated in a lipid vesicle which may have crosslinks between functionalized lipid bilayers.

In some embodiments, the RNA vaccines may be formulated in a liposome comprising a cationic lipid. The liposome may have a molar ratio of nitrogen atoms in the cationic lipid to the phophates in the RNA (N:P ratio) of between 1:1 and 20:1 as described in International Publication No. WO2013006825, herein incorporated by reference in its entirety. In another embodiment, the liposome may have a N:P ratio of greater than 20:1 or less than 1:1.

In some embodiments, the RNA vaccines may be formulated in a lipid-polycation complex. The formation of the lipid-polycation complex may be accomplished by methods known in the art and/or as described in U.S. Pub. No. 20120178702, herein incorporated by reference in its entirety. As a non-limiting example, the polycation may include a cationic peptide or a polypeptide such as, but not limited to, polylysine, polyornithine and/or polyarginine and the cationic peptides described in International Pub. No. WO2012013326 or US Patent Pub. No. US20130142818; each of which is herein incorporated by reference in its entirety. In another embodiment, the RNA vaccines may be formulated in a lipid-polycation complex which may further include a non-cationic lipid such as, but not limited to, cholesterol or dioleoyl phosphatidylethanolamine (DOPE).

In some embodiments, the RNA vaccines may be formulated in an aminoalcohol lipidoid. Aminoalcohol lipidoids which may be used in the present invention may be prepared by the methods described in U.S. Pat. No. 8,450,298, herein incorporated by reference in its entirety.

The liposome formulation may be influenced by, but not limited to, the selection of the cationic lipid component, the degree of cationic lipid saturation, the nature of the PEGylation, ratio of all components and biophysical parameters such as size. In one example by Semple et al. (Semple et al. Nature Biotech. 2010 28:172-176; herein incorporated by reference in its entirety), the liposome formulation was composed of 57.1% cationic lipid, 7.1% dipalmitoylphosphatidylcholine, 34.3% cholesterol, and 1.4% PEG-c-DMA. As another example, changing the composition of the cationic lipid could more effectively deliver siRNA to various antigen presenting cells (Basha et al. *Mol Ther.* 2011 19:2186-2200; herein incorporated by reference in its entirety). In some embodiments, liposome formulations may comprise from about 35 to about 45% cationic lipid, from about 40% to about 50% cationic lipid, from about 50% to about 60% cationic lipid and/or from about 55% to about 65% cationic lipid. In some embodiments, the ratio of lipid to mRNA in liposomes may be from about 5:1 to about 20:1, from about 10:1 to about 25:1, from about 15:1 to about 30:1 and/or at least 30:1.

In some embodiments, the ratio of PEG in the lipid nanoparticle (LNP) formulations may be increased or decreased and/or the carbon chain length of the PEG lipid may be modified from C14 to C18 to alter the pharmacokinetics and/or biodistribution of the LNP formulations. As a non-limiting example, LNP formulations may contain from about 0.5% to about 3.0%, from about 1.0% to about 3.5%, from about 1.5% to about 4.0%, from about 2.0% to about 4.5%, from about 2.5% to about 5.0% and/or from about 3.0% to about 6.0% of the lipid molar ratio of PEG-c-DOMG (R-3-[(ω-methoxy-poly(ethyleneglycol)2000)carbamoyl)]-1,2-dimyristyloxypropyl-3-amine) (also referred to herein as PEG-DOMG) as compared to the cationic lipid, DSPC and cholesterol. In another embodiment the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In some embodiments, the RNA vaccines may be formulated in a lipid nanoparticle such as those described in International Publication No. WO2012170930, the contents of which is herein incorporated by reference in its entirety.

In some embodiments, the RNA vaccine formulation comprising the polynucleotide is a nanoparticle which may comprise at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In another aspect, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in US Patent Publication No. US20130150625, herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US20130150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino)butanoyl)oxy)heptadecanedioate (L319), and further comprise a neutral lipid, a sterol and a molecule capable of reducing particle aggregation, for example a PEG or PEG-modified lipid.

In some embodiments, the lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy) heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of about 20-60% cationic lipid: 5-25% neutral lipid: 25-55% sterol; 0.5-15% PEG-lipid.

In some embodiments, the formulation includes from about 25% to about 75% on a molar basis of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), e.g., from about 35 to about 65%, from about 45 to about 65%, about 60%, about 57.5%, about 50% or about 40% on a molar basis.

In some embodiments, the formulation includes from about 0.5% to about 15% on a molar basis of the neutral lipid e.g., from about 3 to about 12%, from about 5 to about 10% or about 15%, about 10%, or about 7.5% on a molar basis. Exemplary neutral lipids include, but are not limited to, DSPC, POPC, DPPC, DOPE and SM. In some embodiments, the formulation includes from about 5% to about 50% on a molar basis of the sterol (e.g., about 15 to about 45%, about 20 to about 40%, about 40%, about 38.5%, about 35%, or about 31% on a molar basis. An exemplary sterol is cholesterol. In some embodiments, the formulation includes from about 0.5% to about 20% on a molar basis of the PEG or PEG-modified lipid (e.g., about 0.5 to about 10%, about 0.5 to about 5%, about 1.5%, about 0.5%, about 1.5%, about 3.5%, or about 5% on a molar basis. In some embodiments, the PEG or PEG modified lipid comprises a PEG molecule of an average molecular weight of 2,000 Da. In other embodiments, the PEG or PEG modified lipid comprises a PEG molecule of an average molecular weight of less than 2,000, for example around 1,500 Da, around 1,000 Da, or around 500 Da. Exemplary PEG-modified lipids include, but are not limited to, PEG-distearoyl glycerol (PEG-DMG) (also referred herein as PEG-C14 or C14-PEG), PEG-cDMA (further discussed in Reyes et al. *J. Controlled Release,* 107, 276-287 (2005) the contents of which are herein incorporated by reference in its entirety)

In some embodiments, the formulations of the inventions include 25-75% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 0.5-15% of the neutral lipid, 5-50% of the sterol, and 0.5-20% of the PEG or PEG-modified lipid on a molar basis.

In some embodiments, the formulations of the inventions include 35-65% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 3-12% of the neutral lipid, 15-45% of the sterol, and 0.5-10% of the PEG or PEG-modified lipid on a molar basis.

In some embodiments, the formulations of the inventions include 45-65% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 5-10% of the neutral lipid, 25-40% of the sterol, and 0.5-10% of the PEG or PEG-modified lipid on a molar basis.

In some embodiments, the formulations of the inventions include about 60% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.5% of the neutral lipid, about 31% of the sterol, and about 1.5% of the PEG or PEG-modified lipid on a molar basis.

In some embodiments, the formulations of the inventions include about 50% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 38.5% of the sterol, and about 1.5% of the PEG or PEG-modified lipid on a molar basis.

In some embodiments, the formulations of the inventions include about 50% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 35% of the sterol, about 4.5% or about 5% of the PEG or PEG-modified lipid, and about 0.5% of the targeting lipid on a molar basis.

In some embodiments, the formulations of the inventions include about 40% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 15% of the neutral lipid, about 40% of the sterol, and about 5% of the PEG or PEG-modified lipid on a molar basis.

In some embodiments, the formulations of the inventions include about 57.2% of a cationic lipid selected from 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.1% of the neutral lipid, about 34.3% of the sterol, and about 1.4% of the PEG or PEG-modified lipid on a molar basis.

In some embodiments, the formulations of the inventions include about 57.5% of a cationic lipid selected from the PEG lipid is PEG-cDMA (PEG-cDMA is further discussed in Reyes et al. (*J. Controlled Release,* 107, 276-287 (2005), the contents of which are herein incorporated by reference in its entirety), about 7.5% of the neutral lipid, about 31.5% of the sterol, and about 3.5% of the PEG or PEG-modified lipid on a molar basis.

In preferred embodiments, lipid nanoparticle formulation consists essentially of a lipid mixture in molar ratios of about 20-70% ionizable cationic lipid: 5-45% neutral lipid: 20-55% cholesterol: 0.5-15% PEG-modified lipid; more preferably in a molar ratio of about 20-60% ionizable cationic lipid: 5-25% neutral lipid: 25-55% cholesterol: 0.5-15% PEG-modified lipid.

In particular embodiments, the molar lipid ratio is approximately 50/10/38.5/1.5 (mol % cationic lipid/neutral lipid, e.g., DSPC/Chol/PEG-modified lipid, e.g., PEG-DMG, PEG-DSG or PEG-DPG), 57.2/7.1134.3/1.4 (mol % cationic lipid/neutral lipid, e.g., DPPC/Chol/PEG-modified lipid, e.g., PEG-cDMA), 40/15/40/5 (mol % cationic lipid/neutral lipid, e.g., DSPC/Chol/PEG-modified lipid, e.g., PEG-DMG), 50/10/35/4.5/0.5 (mol % cationic lipid/neutral lipid, e.g., DSPC/Choi/PEG-modified lipid, e.g., PEG-DSG), 50/10/35/5 (cationic lipid/neutral lipid, e.g., DSPC/Choi/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/10 (mol % cationic lipid/neutral lipid, e.g., DSPC/Chol/PEG-modified lipid, e.g., PEG-DMG or PEG-cDMA) or 52/13/30/5 (mol % cationic lipid/neutral lipid, e.g., DSPC/Choi/PEG-modified lipid, e.g., PEG-DMG or PEG-cDMA).

Exemplary lipid nanoparticle compositions and methods of making same are described, for example, in Semple et al. (2010) Nat. Biotechnol. 28:172-176; Jayarama et al. (2012), Angew. Chem. Int. Ed., 51: 8529-8533; and Maier et al. (2013) *Molecular Therapy* 21, 1570-1578 (the contents of each of which are incorporated herein by reference in their entirety).

In some embodiments, the lipid nanoparticle formulations described herein may comprise a ionizable cationic lipid, a PEG lipid and a structural lipid and optionally comprise a non-cationic lipid. As a non-limiting example, the lipid nanoparticle may comprise about 40-60% of ionizable cationic lipid, about 5-15% of a non-cationic lipid, about 1-2% of a PEG lipid and about 30-50% of a structural lipid. As another non-limiting example, the lipid nanoparticle may comprise about 50% ionizable cationic lipid, about 10% non-cationic lipid, about 1.5% PEG lipid and about 38.5% structural lipid. As yet another non-limiting example, the lipid nanoparticle may comprise about 55% ionizable cationic lipid, about 10% non-cationic lipid, about 2.5% PEG lipid and about 32.5% structural lipid. In some embodiments, the ionizable cationic lipid may be any cationic lipid described herein such as, but not limited to, DLin-KC2-DMA, DLin-MC3-DMA and L319.

In some embodiments, the lipid nanoparticle formulations described herein may be 4 component lipid nanoparticles. The lipid nanoparticle may comprise a ionizable cationic lipid, a non-cationic lipid, a PEG lipid and a structural lipid. As a non-limiting example, the lipid nanoparticle may comprise about 40-60% of cationic lipid, about 5-15% of a non-cationic lipid, about 1-2% of a PEG lipid and about 30-50% of a structural lipid. As another non-limiting example, the lipid nanoparticle may comprise about 50% cationic lipid, about 10% non-cationic lipid, about 1.5% PEG lipid and about 38.5% structural lipid. As yet another non-limiting example, the lipid nanoparticle may comprise about 55% cationic lipid, about 10% non-cationic lipid, about 2.5% PEG lipid and about 32.5% structural lipid. In some embodiments, the cationic lipid may be any cationic lipid described herein such as, but not limited to, DLin-KC2-DMA, DLin-MC3-DMA and L319.

In some embodiments, the lipid nanoparticle formulations described herein may comprise a cationic lipid, a non-cationic lipid, a PEG lipid and a structural lipid. As a non-limiting example, the lipid nanoparticle comprise about 50% of the cationic lipid DLin-KC2-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DMG and about 38.5% of the structural lipid cholesterol. As yet another non-limiting example, the lipid nanoparticle comprise about 55% of the cationic lipid L319, about 10% of the non-cationic lipid DSPC, about 2.5% of the PEG lipid PEG-DMG and about 32.5% of the structural lipid cholesterol.

In some embodiments, the cationic lipid may be selected from, but not limited to, a cationic lipid described in International Publication Nos. WO2012040184, WO2011153120, WO2011149733, WO2011090965, WO2011043913, WO2011022460, WO2012061259, WO2012054365, WO2012044638, WO2010080724, WO201021865, WO2008103276, WO2013086373 and WO2013086354, U.S. Pat. Nos. 7,893,302, 7,404,969, 8,283,333, and 8,466,122 and US Patent Publication No. US20100036115, US20120202871, US20130064894, US20130129785, US20130150625, US20130178541 and US20130225836; the contents of each of which are herein incorporated by reference in their entirety. In another embodiment, the cationic lipid may be selected from, but not limited to, formula A described in International Publication Nos. WO2012040184, WO2011153120, WO2011149733, WO2011090965, WO2011043913, WO2011022460, WO2012061259, WO2012054365, WO2012044638 and WO2013116126 or US Patent Publication No. US20130178541 and US20130225836; the contents of each of which is herein incorporated by reference in their entirety. In yet another embodiment, the cationic lipid may be selected from, but not limited to, formula CLI-CLXXIX of International Publication No. WO2008103276, formula CLI-CLXXIX of U.S. Pat. No. 7,893,302, formula CLI-CLXXXXII of U.S. Pat. No. 7,404,969 and formula I-VI of US Patent Publication No. US20100036115, formula I of US Patent Publication No US20130123338; each of which is herein incorporated by reference in their entirety. As a non-limiting example, the cationic lipid may be selected from (20Z,23Z)—N,N-dimethylnonacosa-20,23-dien-10-amine, (17Z,20Z)—N,N-dimemylhexacosa-17,20-dien-9-amine, (1Z,19Z)—N5N-dimethylpentacosa-1 6, 19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21 Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21 Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl]pyrrolidine, (20Z)—N,N-dimethylheptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, (13Z,16Z)—N,N-dimethyl-3-nonyldocosa-13,16-dien-1-amine, N,N-dimethyl-1-[(1S,2R)-2-octylcyclopropyl]eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine,N,N-dimethyl-1-[(1S,2S)-2-{[(1R,2R)-2-pentylcyclopropyl]methyl}cyclopropyl]nonadecan-10-amine,N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl]heptyl}dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl]ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy)propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11 Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentylcyclopropyl]methyl)cyclopropyl]octyl}oxy)propan-2-amine, N,N-dimethyl-1-([8-(2-oclylcyclopropyl)octyl]oxy}-3-(octyloxy)propan-2-amine and (11E,20Z,23Z)—N,N-dimethylnonacosa-11,20,2-trien-10-amine or a pharmaceutically acceptable salt or stereoisomer thereof.

In some embodiments, the lipid may be a cleavable lipid such as those described in International Publication No. WO2012170889, herein incorporated by reference in its entirety.

In another embodiment, the lipid may be a cationic lipid such as, but not limited to, Formula (I) of U.S. Patent Application No. US20130064894, the contents of which are herein incorporated by reference in its entirety.

In some embodiments, the cationic lipid may be synthesized by methods known in the art and/or as described in International Publication Nos. WO2012040184, WO2011153120, WO2011149733, WO2011090965, WO2011043913, WO2011022460, WO2012061259, WO2012054365, WO2012044638, WO2010080724, WO201021865, WO2013086373 and WO2013086354; the contents of each of which are herein incorporated by reference in their entirety.

In another embodiment, the cationic lipid may be a trialkyl cationic lipid. Non-limiting examples of trialkyl cationic lipids and methods of making and using the trialkyl cationic lipids are described in International Patent Publication No. WO2013126803, the contents of which are herein incorporated by reference in its entirety.

In some embodiments, the LNP formulations of the RNA vaccines may contain PEG-c-DOMG at 3% lipid molar ratio. In another embodiment, the LNP formulations RRNA vaccines may contain PEG-c-DOMG at 1.5% lipid molar ratio.

In some embodiments, the pharmaceutical compositions of the RNA vaccines may include at least one of the PEGylated lipids described in International Publication No. WO2012099755, the contents of which is herein incorporated by reference in its entirety.

In some embodiments, the LNP formulation may contain PEG-DMG 2000 (1,2-dimyristoyl-sn-glycero-3-phophoethanolamine-N-[methoxy(polyethylene glycol)-2000). In some embodiments, the LNP formulation may contain PEG-DMG 2000, a cationic lipid known in the art and at least one other component. In another embodiment, the LNP formulation may contain PEG-DMG 2000, a cationic lipid known in the art, DSPC and cholesterol. As a non-limiting example, the LNP formulation may contain PEG-DMG 2000, DLin-DMA, DSPC and cholesterol. As another non-limiting example the LNP formulation may contain PEG-DMG 2000, DLin-DMA, DSPC and cholesterol in a molar ratio of 2:40:10:48 (see e.g., Geall et al., Nonviral delivery of self-amplifying RNA vaccines, PNAS 2012; PMID: 22908294; herein incorporated by reference in its entirety).

In some embodiments, the LNP formulation may be formulated by the methods described in International Publication Nos. WO2011127255 or WO2008103276, the contents of each of which is herein incorporated by reference in their entirety. As a non-limiting example, the RNA vaccines described herein may be encapsulated in LNP formulations as described in WO2011127255 and/or WO2008103276; each of which is herein incorporated by reference in their entirety.

In some embodiments, the RNA vaccines described herein may be formulated in a nanoparticle to be delivered by a parenteral route as described in U.S. Pub. No. US20120207845; the contents of which are herein incorporated by reference in its entirety.

In some embodiments, the RNA vaccines may be formulated in a lipid nanoparticle made by the methods described in US Patent Publication No US20130156845 or International Publication No WO2013093648 or WO2012024526, each of which is herein incorporated by reference in its entirety.

The lipid nanoparticles described herein may be made in a sterile environment by the system and/or methods described in US Patent Publication No. US20130164400, herein incorporated by reference in its entirety.

In some embodiments, the LNP formulation may be formulated in a nanoparticle such as a nucleic acid-lipid particle described in U.S. Pat. No. 8,492,359, the contents of which are herein incorporated by reference in its entirety. As a non-limiting example, the lipid particle may comprise one or more active agents or therapeutic agents; one or more cationic lipids comprising from about 50 mol % to about 85 mol % of the total lipid present in the particle; one or more non-cationic lipids comprising from about 13 mol % to about 49.5 mol % of the total lipid present in the particle; and one or more conjugated lipids that inhibit aggregation of particles comprising from about 0.5 mol % to about 2 mol % of the total lipid present in the particle. The nucleic acid in the nanoparticle may be the polynucleotides described herein and/or are known in the art.

In some embodiments, the LNP formulation may be formulated by the methods described in International Publication Nos. WO2011127255 or WO2008103276, the contents of each of which are herein incorporated by reference in their entirety. As a non-limiting example, modified RNA described herein may be encapsulated in LNP formulations as described in WO2011127255 and/or WO2008103276; the contents of each of which are herein incorporated by reference in their entirety.

In some embodiments, LNP formulations described herein may comprise a polycationic composition. As a non-limiting example, the polycationic composition may be selected from formula 1-60 of US Patent Publication No. US20050222064; the content of which is herein incorporated by reference in its entirety. In another embodiment, the LNP formulations comprising a polycationic composition may be used for the delivery of the modified RNA described herein in vivo and/or in vitro.

In some embodiments, the LNP formulations described herein may additionally comprise a permeability enhancer molecule. Non-limiting permeability enhancer molecules are described in US Patent Publication No. US20050222064; the content of which is herein incorporated by reference in its entirety.

In some embodiments, the RNA vaccine pharmaceutical compositions may be formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. Cancer Biology & Therapy 2006 5(12)1708-1713); herein incorporated by reference in its entirety) and hyaluronan-coated liposomes (Quiet Therapeutics, Israel).

In some embodiments, the RNA vaccines may be formulated in a lyophilized gel-phase liposomal composition as described in US Publication No. US2012060293, herein incorporated by reference in its entirety.

The nanoparticle formulations may comprise a phosphate conjugate. The phosphate conjugate may increase in vivo circulation times and/or increase the targeted delivery of the nanoparticle. Phosphate conjugates for use with the present invention may be made by the methods described in International Application No. WO2013033438 or US Patent Publication No. US20130196948, the contents of each of which are herein incorporated by reference in its entirety. As a non-limiting example, the phosphate conjugates may include a compound of any one of the formulas described in International Application No. WO2013033438, herein incorporated by reference in its entirety.

The nanoparticle formulation may comprise a polymer conjugate. The polymer conjugate may be a water soluble conjugate. The polymer conjugate may have a structure as described in U.S. Patent Application No. 20130059360, the contents of which are herein incorporated by reference in its entirety. In one aspect, polymer conjugates with the polynucleotides of the present invention may be made using the methods and/or segmented polymeric reagents described in U.S. Patent Application No. 20130072709, herein incorporated by reference in its entirety. In another aspect, the polymer conjugate may have pendant side groups comprising ring moieties such as, but not limited to, the polymer conjugates described in US Patent Publication No. US20130196948, the contents of which is herein incorporated by reference in its entirety.

The nanoparticle formulations may comprise a conjugate to enhance the delivery of nanoparticles of the present invention in a subject. Further, the conjugate may inhibit phagocytic clearance of the nanoparticles in a subject. In one aspect, the conjugate may be a "self" peptide designed from the human membrane protein CD47 (e.g., the "self" particles described by Rodriguez et al (*Science* 2013 339, 971-975), herein incorporated by reference in its entirety). As shown by Rodriguez et al. the self peptides delayed macrophage-mediated clearance of nanoparticles which enhanced delivery of the nanoparticles. In another aspect, the conjugate may be the membrane protein CD47 (e.g., see Rodriguez et al. *Science* 2013 339, 971-975, herein incorporated by reference in its entirety). Rodriguez et al. showed that, similarly to "self" peptides, CD47 can increase the circulating particle ratio in a subject as compared to scrambled peptides and PEG coated nanoparticles.

In some embodiments, the RNA vaccines of the present invention are formulated in nanoparticles which comprise a conjugate to enhance the delivery of the nanoparticles of the present invention in a subject. The conjugate may be the CD47 membrane or the conjugate may be derived from the CD47 membrane protein, such as the "self" peptide described previously. In another aspect the nanoparticle may comprise PEG and a conjugate of CD47 or a derivative thereof. In yet another aspect, the nanoparticle may comprise both the "self" peptide described above and the membrane protein CD47.

In another aspect, a "self" peptide and/or CD47 protein may be conjugated to a virus-like particle or pseudovirion, as described herein for delivery of the RNA vaccines of the present invention.

In another embodiment, RNA vaccine pharmaceutical compositions comprising the polynucleotides of the present invention and a conjugate which may have a degradable linkage. Non-limiting examples of conjugates include an aromatic moiety comprising an ionizable hydrogen atom, a spacer moiety, and a water-soluble polymer. As a non-limiting example, pharmaceutical compositions comprising a conjugate with a degradable linkage and methods for delivering such pharmaceutical compositions are described in US Patent Publication No. US20130184443, the contents of which are herein incorporated by reference in its entirety.

The nanoparticle formulations may be a carbohydrate nanoparticle comprising a carbohydrate carrier and a RNA vaccine. As a non-limiting example, the carbohydrate carrier may include, but is not limited to, an anhydride-modified phytoglycogen or glycogen-type material, phtoglycogen octenyl succinate, phytoglycogen beta-dextrin, anhydride-modified phytoglycogen beta-dextrin. (See e.g., International Publication No. WO2012109121; the contents of which are herein incorporated by reference in its entirety).

Nanoparticle formulations of the present invention may be coated with a surfactant or polymer in order to improve the delivery of the particle. In some embodiments, the nanoparticle may be coated with a hydrophilic coating such as, but not limited to, PEG coatings and/or coatings that have a neutral surface charge. The hydrophilic coatings may help to deliver nanoparticles with larger payloads such as, but not limited to, RNA vaccines within the central nervous system. As a non-limiting example nanoparticles comprising a hydrophilic coating and methods of making such nanoparticles are described in US Patent Publication No. US20130183244, the contents of which are herein incorporated by reference in its entirety.

In some embodiments, the lipid nanoparticles of the present invention may be hydrophilic polymer particles. Non-limiting examples of hydrophilic polymer particles and methods of making hydrophilic polymer particles are described in US Patent Publication No. US20130210991, the contents of which are herein incorporated by reference in its entirety.

In another embodiment, the lipid nanoparticles of the present invention may be hydrophobic polymer particles.

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

In some embodiments, the internal ester linkage may be located on either side of the saturated carbon.

In some embodiments, an immune response may be elicited by delivering a lipid nanoparticle which may include a nanospecies, a polymer and an immunogen. (U.S. Publication No. 20120189700 and International Publication No. WO2012099805; each of which is herein incorporated by reference in their entirety). The polymer may encapsulate the nanospecies or partially encapsulate the nanospecies. The immunogen may be a recombinant protein, a modified RNA and/or a polynucleotide described herein. In some embodiments, the lipid nanoparticle may be formulated for use in a vaccine such as, but not limited to, against a pathogen.

Lipid nanoparticles may be engineered to alter the surface properties of particles so the lipid nanoparticles may penetrate the mucosal barrier. Mucus is located on mucosal tissue such as, but not limited to, oral (e.g., the buccal and esophageal membranes and tonsil tissue), ophthalmic, gastrointestinal (e.g., stomach, small intestine, large intestine, colon, rectum), nasal, respiratory (e.g., nasal, pharyngeal, tracheal and bronchial membranes), genital (e.g., vaginal, cervical and urethral membranes). Nanoparticles larger than 10-200 nm which are preferred for higher drug encapsulation efficiency and the ability to provide the sustained delivery of a wide array of drugs have been thought to be too large to rapidly diffuse through mucosal barriers. Mucus is continuously secreted, shed, discarded or digested and recycled so most of the trapped particles may be removed from the mucosla tissue within seconds or within a few hours. Large polymeric nanoparticles (200 nm-500 nm in diameter) which have been coated densely with a low molecular weight polyethylene glycol (PEG) diffused through mucus only 4 to 6-fold lower than the same particles diffusing in water (Lai et al. PNAS 2007 104(5):1482-487; Lai et al. Adv Drug Deliv Rev. 2009 61(2): 158-171; each of which is herein incorporated by reference in their entirety). The transport of nanoparticles may be determined using rates of permeation and/or fluorescent microscopy techniques including, but not limited to, fluorescence recovery after photobleaching (FRAP) and high resolution multiple particle tracking (MPT). As a non-limiting example, compositions which can penetrate a mucosal barrier may be made as described in U.S. Pat. No. 8,241,670 or International Patent Publication No. WO2013110028, the contents of each of which are herein incorporated by reference in its entirety.

The lipid nanoparticle engineered to penetrate mucus may comprise a polymeric material (i.e. a polymeric core) and/or a polymer-vitamin conjugate and/or a tri-block co-polymer. The polymeric material may include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates. The polymeric material may be biodegradable and/or biocompatible. Non-limiting examples of biocompatible polymers are described in International Patent Publication No. WO2013116804, the contents of which are herein incorporated by reference in its entirety. The polymeric material may additionally be irradiated. As a non-limiting example, the polymeric material may be gamma irradiated (See e.g., International App. No. WO201282165, herein incorporated by reference in its entirety). Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly (lactic acid-co-glycolic acid) (PLGA), poly(L-lactic acid-co-glycolic acid) (PLLGA), poly(D,L-lactide) (PDLA), poly (L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly (ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth) acrylate) (PMMA), poly(ethyl(meth)acrylate), poly(butyl (meth)acrylate), poly(isobutyl(meth)acrylate), poly(hexyl (meth)acrylate), poly(isodecyl(meth)acrylate), poly(lauryl (meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho)esters, poly(butyric acid), poly(valeric acid), poly(lactide-co-caprolactone), PEG-PLGA-PEG and trimethylene carbonate, polyvinylpyrrolidone. The lipid nanoparticle may be coated or associated with a co-polymer such as, but not limited to, a block co-polymer (such as a branched polyether-polyamide block copolymer described in International Publication No. WO2013012476, herein incorporated by reference in its entirety), and (poly(ethylene glycol))-(poly(propylene oxide))-(poly(ethylene glycol)) triblock copolymer (see e.g., US Publication 20120121718 and US Publication 20100003337 and U.S. Pat. No. 8,263,665; each of which is herein incorporated by reference in their entirety). The co-polymer may be a polymer that is generally regarded as safe (GRAS) and the formation of the lipid nanoparticle may be in such a way that no new chemical entities are created. For example, the lipid nanoparticle may comprise poloxamers coating PLGA nanoparticles without forming new chemical entities which are still able to rapidly penetrate human mucus (Yang et al. Angew. Chem. Int. Ed. 2011 50:2597-2600; the contents of which are herein incorporated by reference in its entirety). A non-limiting scalable method to produce nanoparticles which can penetrate human mucus is described by Xu et al. (See e.g., J Control Release 2013, 170(2):279-86; the contents of which are herein incorporated by reference in its entirety).

The vitamin of the polymer-vitamin conjugate may be vitamin E. The vitamin portion of the conjugate may be substituted with other suitable components such as, but not limited to, vitamin A, vitamin E, other vitamins, cholesterol, a hydrophobic moiety, or a hydrophobic component of other surfactants (e.g., sterol chains, fatty acids, hydrocarbon chains and alkylene oxide chains).

The lipid nanoparticle engineered to penetrate mucus may include surface altering agents such as, but not limited to, polynucleotides, anionic proteins (e.g., bovine serum albumin), surfactants (e.g., cationic surfactants such as for example dimethyldioctadecylammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4 dornase alfa, neltenexine, erdosteine) and various DNases including rhDNase. The surface altering agent may be embedded or enmeshed in the particle's surface or disposed (e.g., by coating, adsorption, covalent linkage, or other process) on the surface of the lipid nanoparticle. (see e.g., US Publication 20100215580 and US Publication 20080166414 and US20130164343; the contents of each of which is herein incorporated by reference in their entirety).

In some embodiments, the mucus penetrating lipid nanoparticles may comprise at least one polynucleotide described herein. The polynucleotide may be encapsulated in the lipid nanoparticle and/or disposed on the surface of the particle. The polynucleotide may be covalently coupled to the lipid nanoparticle. Formulations of mucus penetrating lipid nanoparticles may comprise a plurality of nanoparticles. Further, the formulations may contain particles which may interact with the mucus and alter the structural and/or adhesive properties of the surrounding mucus to decrease mucoadhesion which may increase the delivery of the mucus penetrating lipid nanoparticles to the mucosal tissue.

In another embodiment, the mucus penetrating lipid nanoparticles may be a hypotonic formulation comprising a mucosal penetration enhancing coating. The formulation may be hypotonice for the epithelium to which it is being delivered. Non-limiting examples of hypotonic formulations may be found in International Patent Publication No. WO2013110028, the contents of which are herein incorporated by reference in its entirety.

In some embodiments, in order to enhance the delivery through the mucosal barrier the RNA vaccine formulation may comprise or be a hypotonic solution. Hypotonic solutions were found to increase the rate at which mucoinert particles such as, but not limited to, mucus-penetrating particles, were able to reach the vaginal epithelial surface (See e.g., Ensign et al. Biomaterials 2013 34(28):6922-9; the contents of which is herein incorporated by reference in its entirety).

In some embodiments, the RNA vaccine is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, Mass.), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293 Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in its entirety).

In some embodiments such formulations may also be constructed or compositions altered such that they passively or actively are directed to different cell types in vivo, including but not limited to hepatocytes, immune cells, tumor cells, endothelial cells, antigen presenting cells, and leukocytes (Akinc et al. Mol Ther. 2010 18:1357-1364; Song et al., Nat Biotechnol. 2005 23:709-717; Judge et al., J Clin Invest. 2009 119:661-673; Kaufmann et al., Microvasc Res 2010 80:286-293; Santel et al., Gene Ther 2006 13:1222-1234; Santel et al., Gene Ther 2006 13:1360-1370; Gutbier et al., Pulm Pharmacol. Ther. 2010 23:334-344; Basha et al., Mol. Ther. 2011 19:2186-2200; Fenske and Cullis, Expert Opin Drug Deliv. 2008 5:25-44; Peer et al., Science. 2008 319:627-630; Peer and Lieberman, Gene Ther. 2011 18:1127-1133; all of which are incorporated herein by reference in its entirety). One example of passive targeting of formulations to liver cells includes the DLin-DMA, DLin-KC2-DMA and DLin-MC3-DMA-based lipid nanoparticle formulations which have been shown to bind to apolipoprotein E and promote binding and uptake of these formulations into hepatocytes in vivo (Akinc et al. Mol Ther. 2010 18:1357-1364; herein incorporated by reference in its entirety). Formulations can also be selectively targeted through expression of different ligands on their surface as exemplified by, but not limited by, folate, transferrin, N-acetylgalactosamine (GalNAc), and antibody targeted approaches (Kolhatkar et al., Curr Drug Discov Technol.

2011 8:197-206; Musacchio and Torchilin, Front Biosci. 2011 16:1388-1412; Yu et al., Mol Membr Biol. 2010 27:286-298; Patil et al., Crit Rev Ther Drug Carrier Syst. 2008 25:1-61; Benoit et al., Biomacromolecules. 2011 12:2708-2714; Zhao et al., Expert Opin Drug Deliv. 2008 5:309-319; Akinc et al., Mol Ther. 2010 18:1357-1364; Srinivasan et al., Methods Mol Biol. 2012 820:105-116; Ben-Arie et al., Methods Mol Biol. 2012 757:497-507; Peer 2010 J Control Release. 20:63-68; Peer et al., Proc Natl Acad Sci USA. 2007 104:4095-4100; Kim et al., Methods Mol Biol. 2011 721:339-353; Subramanya et al., Mol Ther. 2010 18:2028-2037; Song et al., Nat Biotechnol. 2005 23:709-717; Peer et al., Science. 2008 319:627-630; Peer and Lieberman, Gene Ther. 2011 18:1127-1133; all of which are incorporated herein by reference in its entirety).

In some embodiments, the RNA vaccine is formulated as a solid lipid nanoparticle. A solid lipid nanoparticle (SLN) may be spherical with an average diameter between 10 to 1000 nm. SLN possess a solid lipid core matrix that can solubilize lipophilic molecules and may be stabilized with surfactants and/or emulsifiers. In a further embodiment, the lipid nanoparticle may be a self-assembly lipid-polymer nanoparticle (see Zhang et al., ACS Nano, 2008, 2 (8), pp 1696-1702; the contents of which are herein incorporated by reference in its entirety). As a non-limiting example, the SLN may be the SLN described in International Patent Publication No. WO2013105101, the contents of which are herein incorporated by reference in its entirety. As another non-limiting example, the SLN may be made by the methods or processes described in International Patent Publication No. WO2013105101, the contents of which are herein incorporated by reference in its entirety.

Liposomes, lipoplexes, or lipid nanoparticles may be used to improve the efficacy of polynucleotides directed protein production as these formulations may be able to increase cell transfection by the RNA vaccine; and/or increase the translation of encoded protein. One such example involves the use of lipid encapsulation to enable the effective systemic delivery of polyplex plasmid DNA (Heyes et al., Mol Ther. 2007 15:713-720; herein incorporated by reference in its entirety). The liposomes, lipoplexes, or lipid nanoparticles may also be used to increase the stability of the polynucleotide.

In some embodiments, the RNA vaccines of the present invention can be formulated for controlled release and/or targeted delivery. As used herein, "controlled release" refers to a pharmaceutical composition or compound release profile that conforms to a particular pattern of release to effect a therapeutic outcome. In some embodiments, the RRNA vaccines may be encapsulated into a delivery agent described herein and/or known in the art for controlled release and/or targeted delivery. As used herein, the term "encapsulate" means to enclose, surround or encase. As it relates to the formulation of the compounds of the invention, encapsulation may be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the invention may be enclosed, surrounded or encased within the delivery agent. "Partially encapsulation" means that less than 10, 10, 20, 30, 40 50 or less of the pharmaceutical composition or compound of the invention may be enclosed, surrounded or encased within the delivery agent. Advantageously, encapsulation may be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the invention are encapsulated in the delivery agent.

In some embodiments, the controlled release formulation may include, but is not limited to, tri-block co-polymers. As a non-limiting example, the formulation may include two different types of tri-block co-polymers (International Pub. No. WO2012131104 and WO2012131106; the contents of each of which is herein incorporated by reference in its entirety).

In another embodiment, the RNA vaccines may be encapsulated into a lipid nanoparticle or a rapidly eliminated lipid nanoparticle and the lipid nanoparticles or a rapidly eliminated lipid nanoparticle may then be encapsulated into a polymer, hydrogel and/or surgical sealant described herein and/or known in the art. As a non-limiting example, the polymer, hydrogel or surgical sealant may be PLGA, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TISSELL® (Baxter International, Inc Deerfield, Ill.), PEG-based sealants, and COSEAL® (Baxter International, Inc Deerfield, Ill.).

In another embodiment, the lipid nanoparticle may be encapsulated into any polymer known in the art which may form a gel when injected into a subject. As another non-limiting example, the lipid nanoparticle may be encapsulated into a polymer matrix which may be biodegradable.

In some embodiments, the RNA vaccine formulation for controlled release and/or targeted delivery may also include at least one controlled release coating. Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, EUDRAGIT RL®, EUDRAGIT RS® and cellulose derivatives such as ethylcellulose aqueous dispersions (AQUACOAT® and SURELEASE®).

In some embodiments, the RNA vaccine controlled release and/or targeted delivery formulation may comprise at least one degradable polyester which may contain polycationic side chains. Degradeable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

In some embodiments, the RNA vaccine controlled release and/or targeted delivery formulation comprising at least one polynucleotide may comprise at least one PEG and/or PEG related polymer derivatives as described in U.S. Pat. No. 8,404,222, herein incorporated by reference in its entirety.

In another embodiment, the RNA vaccine controlled release delivery formulation comprising at least one polynucleotide may be the controlled release polymer system described in US20130130348, herein incorporated by reference in its entirety.

In some embodiments, the RNA vaccines of the present invention may be encapsulated in a therapeutic nanoparticle, referred to herein as "therapeutic nanoparticle RRNA vaccines." Therapeutic nanoparticles may be formulated by methods described herein and known in the art such as, but not limited to, International Pub Nos. WO2010005740, WO2010030763, WO2010005721, WO2010005723, WO2012054923, US Pub. Nos. US20110262491, U520100104645, U520100087337, U520100068285, US20110274759, U520100068286, US20120288541, US20130123351 and US20130230567 and U.S. Pat. Nos. 8,206,747, 8,293,276, 8,318,208 and 8,318,211; the contents of each of which are herein incorporated by reference in their entirety. In another embodiment, therapeutic polymer nanoparticles may be identified by the methods described in US Pub No. US20120140790, the contents of which is herein incorporated by reference in its entirety.

In some embodiments, the therapeutic nanoparticle RNA vaccine may be formulated for sustained release. As used herein, "sustained release" refers to a pharmaceutical composition or compound that conforms to a release rate over a specific period of time. The period of time may include, but is not limited to, hours, days, weeks, months and years. As a non-limiting example, the sustained release nanoparticle may comprise a polymer and a therapeutic agent such as, but not limited to, the polynucleotides of the present invention (see International Pub No. 2010075072 and US Pub No. US20100216804, US20110217377 and US20120201859, each of which is herein incorporated by reference in their entirety). In another non-limiting example, the sustained release formulation may comprise agents which permit persistent bioavailability such as, but not limited to, crystals, macromolecular gels and/or particulate suspensions (see US Patent Publication No US20130150295, the contents of which is herein incorporated by reference in its entirety).

In some embodiments, the therapeutic nanoparticle RNA vaccines may be formulated to be target specific. As a non-limiting example, the therapeutic nanoparticles may include a corticosteroid (see International Pub. No. WO2011084518; herein incorporated by reference in its entirety). As a non-limiting example, the therapeutic nanoparticles may be formulated in nanoparticles described in International Pub No. WO2008121949, WO2010005726, WO2010005725, WO2011084521 and US Pub No. US20100069426, US20120004293 and US20100104655, each of which is herein incorporated by reference in their entirety.

In some embodiments, the nanoparticles of the present invention may comprise a polymeric matrix. As a non-limiting example, the nanoparticle may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

In some embodiments, the therapeutic nanoparticle comprises a diblock copolymer. In some embodiments, the diblock copolymer may include PEG in combination with a polymer such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof. In another embodiment, the diblock copolymer may comprise the diblock copolymers described in European Patent Publication No. the contents of which are herein incorporated by reference in its entirety. In yet another embodiment, the diblock copolymer may be a high-X diblock copolymer such as those described in International Patent Publication No. WO2013120052, the contents of which are herein incorporated by reference in its entirety.

As a non-limiting example the therapeutic nanoparticle comprises a PLGA-PEG block copolymer (see US Pub. No. US20120004293 and U.S. Pat. No. 8,236,330, each of which is herein incorporated by reference in their entirety). In another non-limiting example, the therapeutic nanoparticle is a stealth nanoparticle comprising a diblock copolymer of PEG and PLA or PEG and PLGA (see U.S. Pat. No. 8,246,968 and International Publication No. WO2012166923, the contents of each of which are herein incorporated by reference in its entirety). In yet another non-limiting example, the therapeutic nanoparticle is a stealth nanoparticle or a target-specific stealth nanoparticle as described in US Patent Publication No. US20130172406, the contents of which are herein incorporated by reference in its entirety.

In some embodiments, the therapeutic nanoparticle may comprise a multiblock copolymer (See e.g., U.S. Pat. Nos. 8,263,665 and 8,287,910 and US Patent Pub. No. US20130195987; the contents of each of which are herein incorporated by reference in its entirety).

In yet another non-limiting example, the lipid nanoparticle comprises the block copolymer PEG-PLGA-PEG (see e.g., the thermosensitive hydrogel (PEG-PLGA-PEG) was used as a TGF-beta1 gene delivery vehicle in Lee et al. Thermosensitive Hydrogel as a Tgf-β1 Gene Delivery Vehicle Enhances Diabetic Wound Healing. Pharmaceutical Research, 2003 20(12): 1995-2000; as a controlled gene delivery system in Li et al. Controlled Gene Delivery System Based on Thermosensitive Biodegradable Hydrogel. Pharmaceutical Research 2003 20(6):884-888; and Chang et al., Non-ionic amphiphilic biodegradable PEG-PLGA-PEG copolymer enhances gene delivery efficiency in rat skeletal muscle. J Controlled Release. 2007 118:245-253; each of which is herein incorporated by reference in its entirety). The RNA vaccines of the present invention may be formulated in lipid nanoparticles comprising the PEG-PLGA-PEG block copolymer.

In some embodiments, the therapeutic nanoparticle may comprise a multiblock copolymer (See e.g., U.S. Pat. Nos. 8,263,665 and 8,287,910 and US Patent Pub. No. US20130195987; the contents of each of which are herein incorporated by reference in its entirety).

In some embodiments, the block copolymers described herein may be included in a polyion complex comprising a non-polymeric micelle and the block copolymer. (See e.g., U.S. Pub. No. 20120076836; herein incorporated by reference in its entirety).

In some embodiments, the therapeutic nanoparticle may comprise at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly (acrylic acid), poly(methacrylic acid), polycyanoacrylates and combinations thereof.

In some embodiments, the therapeutic nanoparticles may comprise at least one poly(vinyl ester) polymer. The poly (vinyl ester) polymer may be a copolymer such as a random copolymer. As a non-limiting example, the random copolymer may have a structure such as those described in International Application No. WO2013032829 or US Patent Publication No US20130121954, the contents of which are herein incorporated by reference in its entirety. In one aspect, the poly(vinyl ester) polymers may be conjugated to the polynucleotides described herein. In another aspect, the poly(vinyl ester) polymer which may be used in the present invention may be those described in, herein incorporated by reference in its entirety.

In some embodiments, the therapeutic nanoparticle may comprise at least one diblock copolymer. The diblock copolymer may be, but it not limited to, a poly(lactic) acid-poly (ethylene)glycol copolymer (see e.g., International Patent Publication No. WO2013044219; herein incorporated by reference in its entirety). As a non-limiting example, the therapeutic nanoparticle may be used to treat cancer (see International publication No. WO2013044219; herein incorporated by reference in its entirety).

In some embodiments, the therapeutic nanoparticles may comprise at least one cationic polymer described herein and/or known in the art.

In some embodiments, the therapeutic nanoparticles may comprise at least one amine-containing polymer such as, but not limited to polylysine, polyethylene imine, poly(amidoamine) dendrimers, poly(beta-amino esters) (See e.g., U.S. Pat. No. 8,287,849; herein incorporated by reference in its entirety) and combinations thereof.

In another embodiment, the nanoparticles described herein may comprise an amine cationic lipid such as those described in International Patent Application No. WO2013059496, the contents of which are herein incorporated by reference in its entirety. In one aspect the cationic lipids may have an amino-amine or an amino-amide moiety.

In some embodiments, the therapeutic nanoparticles may comprise at least one degradable polyester which may contain polycationic side chains. Degradeable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

In another embodiment, the therapeutic nanoparticle may include a conjugation of at least one targeting ligand. The targeting ligand may be any ligand known in the art such as, but not limited to, a monoclonal antibody. (Kirpotin et al, Cancer Res. 2006 66:6732-6740; herein incorporated by reference in its entirety).

In some embodiments, the therapeutic nanoparticle may be formulated in an aqueous solution which may be used to target cancer (see International Pub No. WO2011084513 and US Pub No. US20110294717, each of which is herein incorporated by reference in their entirety).

In some embodiments, the therapeutic nanoparticle RNA vaccines, e.g., therapeutic nanoparticles comprising at least one RNA vaccine may be formulated using the methods described by Podobinski et al in U.S. Pat. No. 8,404,799, the contents of which are herein incorporated by reference in its entirety.

In some embodiments, the RNA vaccines may be encapsulated in, linked to and/or associated with synthetic nanocarriers. Synthetic nanocarriers include, but are not limited to, those described in International Pub. Nos. WO2010005740, WO2010030763, WO201213501, WO2012149252, WO2012149255, WO2012149259, WO2012149265, WO2012149268, WO2012149282, WO2012149301, WO2012149393, WO2012149405, WO2012149411, WO2012149454 and WO2013019669, and US Pub. Nos. US20110262491, US20100104645, US20100087337 and US20120244222, each of which is herein incorporated by reference in their entirety. The synthetic nanocarriers may be formulated using methods known in the art and/or described herein. As a non-limiting example, the synthetic nanocarriers may be formulated by the methods described in International Pub Nos. WO2010005740, WO2010030763 and WO201213501 and US Pub. Nos. US20110262491, US20100104645, US20100087337 and U52012024422, each of which is herein incorporated by reference in their entirety. In another embodiment, the synthetic nanocarrier formulations may be lyophilized by methods described in International Pub. No. WO2011072218 and U.S. Pat. No. 8,211,473; the content of each of which is herein incorporated by reference in their entirety. In yet another embodiment, formulations of the present invention, including, but not limited to, synthetic nanocarriers, may be lyophilized or reconstituted by the methods described in US Patent Publication No. US20130230568, the contents of which are herein incorporated by reference in its entirety.

In some embodiments, the synthetic nanocarriers may contain reactive groups to release the polynucleotides described herein (see International Pub. No. WO20120952552 and US Pub No. US20120171229, each of which is herein incorporated by reference in their entirety).

In some embodiments, the synthetic nanocarriers may contain an immunostimulatory agent to enhance the immune response from delivery of the synthetic nanocarrier. As a non-limiting example, the synthetic nanocarrier may comprise a Th1 immunostimulatory agent which may enhance a Th1-based response of the immune system (see International Pub No. WO2010123569 and US Pub. No. US20110223201, each of which is herein incorporated by reference in its entirety).

In some embodiments, the synthetic nanocarriers may be formulated for targeted release. In some embodiments, the synthetic nanocarrier is formulated to release the polynucleotides at a specified pH and/or after a desired time interval. As a non-limiting example, the synthetic nanoparticle may be formulated to release the RNA vaccines after 24 hours and/or at a pH of 4.5 (see International Pub. Nos. WO2010138193 and WO2010138194 and US Pub Nos. US20110020388 and US20110027217, each of which is herein incorporated by reference in their entireties).

In some embodiments, the synthetic nanocarriers may be formulated for controlled and/or sustained release of the polynucleotides described herein. As a non-limiting example, the synthetic nanocarriers for sustained release may be formulated by methods known in the art, described herein and/or as described in International Pub No. WO2010138192 and US Pub No. 20100303850, each of which is herein incorporated by reference in their entirety.

In some embodiments, the RNA vaccine may be formulated for controlled and/or sustained release wherein the formulation comprises at least one polymer that is a crystalline side chain (CYSC) polymer. CYSC polymers are described in U.S. Pat. No. 8,399,007, herein incorporated by reference in its entirety.

In some embodiments, the synthetic nanocarrier may be formulated for use as a vaccine. In some embodiments, the synthetic nanocarrier may encapsulate at least one polynucleotide which encode at least one antigen. As a non-limiting example, the synthetic nanocarrier may include at least one antigen and an excipient for a vaccine dosage form (see International Pub No. WO2011150264 and US Pub No. US20110293723, each of which is herein incorporated by reference in their entirety). As another non-limiting example, a vaccine dosage form may include at least two synthetic nanocarriers with the same or different antigens and an excipient (see International Pub No. WO2011150249 and US Pub No. US20110293701, each of which is herein incorporated by reference in their entirety). The vaccine dosage form may be selected by methods described herein, known in the art and/or described in International Pub No. WO2011150258 and US Pub No. US20120027806, each of which is herein incorporated by reference in their entirety).

In some embodiments, the synthetic nanocarrier may comprise at least one polynucleotide which encodes at least one adjuvant. As non-limiting example, the adjuvant may comprise dimethyldioctadecylammonium-bromide, dimethyldioctadecylammonium-chloride, dimethyldioctadecylammonium-phosphate or dimethyldioctadecylammonium-acetate (DDA) and an apolar fraction or part of said apolar fraction of a total lipid extract of a mycobacterium (See e.g, U.S. Pat. No. 8,241,610; herein incorporated by reference in its entirety). In another embodiment, the synthetic nanocarrier may comprise at least one polynucleotide and an adjuvant. As a non-limiting example, the synthetic nanocarrier comprising and adjuvant may be formulated by the methods described in International Pub No. WO2011150240 and US Pub No. US20110293700, each of which is herein incorporated by reference in its entirety.

In some embodiments, the synthetic nanocarrier may encapsulate at least one polynucleotide which encodes a peptide, fragment or region from a virus. As a non-limiting example, the synthetic nanocarrier may include, but is not limited to, the nanocarriers described in International Pub No. WO2012024621, WO201202629, WO2012024632 and US Pub No. US20120064110, US20120058153 and US20120058154, each of which is herein incorporated by reference in their entirety.

In some embodiments, the synthetic nanocarrier may be coupled to a polynucleotide which may be able to trigger a humoral and/or cytotoxic T lymphocyte (CTL) response (See e.g., International Publication No. WO2013019669, herein incorporated by reference in its entirety).

In some embodiments, the RNA vaccine may be encapsulated in, linked to and/or associated with zwitterionic lipids. Non-limiting examples of zwitterionic lipids and methods of using zwitterionic lipids are described in US Patent Publication No. US20130216607, the contents of which are herein incorporated by reference in its entirety. In one aspect, the zwitterionic lipids may be used in the liposomes and lipid nanoparticles described herein.

In some embodiments, the RNA vaccine may be formulated in colloid nanocarriers as described in US Patent Publication No. US20130197100, the contents of which are herein incorporated by reference in its entirety.

In some embodiments, the nanoparticle may be optimized for oral administration. The nanoparticle may comprise at least one cationic biopolymer such as, but not limited to, chitosan or a derivative thereof. As a non-limiting example, the nanoparticle may be formulated by the methods described in U.S. Pub. No. 20120282343; herein incorporated by reference in its entirety.

In some embodiments, LNPs comprise the lipid KL52 (an amino-lipid disclosed in U.S. Application Publication No. 2012/0295832 expressly incorporated herein by reference in its entirety). Activity and/or safety (as measured by examining one or more of ALT/AST, white blood cell count and cytokine induction) of LNP administration may be improved by incorporation of such lipids. LNPs comprising KL52 may be administered intravenously and/or in one or more doses. In some embodiments, administration of LNPs comprising KL52 results in equal or improved mRNA and/or protein expression as compared to LNPs comprising MC3.

In some embodiments, RNA vaccine may be delivered using smaller LNPs. Such particles may comprise a diameter from below 0.1 um up to 100 nm such as, but not limited to, less than 0.1 um, less than 1.0 um, less than 5 um, less than 10 um, less than 15 um, less than 20 um, less than 25 um, less than 30 um, less than 35 um, less than 40 um, less than 50 urn, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, and less than 975 um.

In another embodiment, RNA vaccines may be delivered using smaller LNPs which may comprise a diameter from about 1 nm to about 100 nm, from about 1 nm to about 10 nm, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nM, from about 20 to about 50 nm, from about 30 to about 50 nm, from about 40 to about 50 nm, from about 20 to about 60 nm, from about 30 to about 60 nm, from about 40 to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm and/or from about 70 to about 90 nm.

In some embodiments, such LNPs are synthesized using methods comprising microfluidic mixers. Exemplary microfluidic mixers may include, but are not limited to a slit interdigitial micromixer including, but not limited to those manufactured by Microinnova (Allerheiligen bei Wildon, Austria) and/or a staggered herringbone micromixer (SHM) (Zhigaltsev, I. V. et al., Bottom-up design and synthesis of limit size lipid nanoparticle systems with aqueous and triglyceride cores using millisecond microfluidic mixing have been published (Langmuir. 2012. 28:3633-40; Belliveau, N. M. et al., Microfluidic synthesis of highly potent limit-size lipid nanoparticles for in vivo delivery of siRNA. Molecular Therapy-Nucleic Acids. 2012. 1:e37; Chen, D. et al., Rapid discovery of potent siRNA-containing lipid nanoparticles enabled by controlled microfluidic formulation. J Am Chem Soc. 2012. 134(16):6948-51; each of which is herein incorporated by reference in its entirety). In some embodiments, methods of LNP generation comprising SHM, further comprise the mixing of at least two input streams wherein mixing occurs by microstructure-induced chaotic advection (MICA). According to this method, fluid streams flow through channels present in a herringbone pattern causing rotational flow and folding the fluids around each other. This method may also comprise a surface for fluid mixing wherein the surface changes orientations during fluid cycling. Methods of generating LNPs using SHM include those disclosed in U.S. Application Publication Nos. 2004/0262223 and 2012/0276209, each of which is expressly incorporated herein by reference in their entirety.

In some embodiments, the RNA vaccine of the present invention may be formulated in lipid nanoparticles created using a micromixer such as, but not limited to, a Slit Interdigital Microstructured Mixer (SIMM-V2) or a Standard Slit Interdigital Micro Mixer (SSIMM) or Caterpillar (CPMM) or Impinging-jet (IJMM) from the Institut für Mikrotechnik Mainz GmbH, Mainz Germany).

In some embodiments, the RNA vaccines of the present invention may be formulated in lipid nanoparticles created using microfluidic technology (see Whitesides, George M. The Origins and the Future of Microfluidics. Nature, 2006 442: 368-373; and Abraham et al. Chaotic Mixer for Microchannels. Science, 2002 295: 647-651; each of which is herein incorporated by reference in its entirety). As a non-limiting example, controlled microfluidic formulation includes a passive method for mixing streams of steady pressure-driven flows in micro channels at a low Reynolds number (See e.g., Abraham et al. Chaotic Mixer for Microchannels. Science, 2002 295: 647-651; which is herein incorporated by reference in its entirety).

In some embodiments, the RNA vaccines of the present invention may be formulated in lipid nanoparticles created using a micromixer chip such as, but not limited to, those from Harvard Apparatus (Holliston, Mass.) or Dolomite Microfluidics (Royston, UK). A micromixer chip can be used for rapid mixing of two or more fluid streams with a split and recombine mechanism.

In some embodiments, the RNA vaccines of the invention may be formulated for delivery using the drug encapsulating microspheres described in International Patent Publication No. WO2013063468 or U.S. Pat. No. 8,440,614, each of which is herein incorporated by reference in its entirety. The microspheres may comprise a compound of the formula (I), (II), (III), (IV), (V) or (VI) as described in International Patent Publication No. WO2013063468, the contents of which are herein incorporated by reference in its entirety. In another aspect, the amino acid, peptide, polypeptide, lipids (APPL) are useful in delivering the RNA vaccines of the invention to cells (see International Patent Publication No. WO2013063468, the contents of which is herein incorporated by reference in its entirety).

In some embodiments, the RNA vaccines of the invention may be formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles may have a diameter from about 10 to 500 nm.

In some embodiments, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In one aspect, the lipid nanoparticle may be a limit size lipid nanoparticle described in International Patent Publication No. WO2013059922, the contents of which are herein incorporated by reference in its entirety. The limit size lipid nanoparticle may comprise a lipid bilayer surrounding an aqueous core or a hydrophobic core; where the lipid bilayer may comprise a phospholipid such as, but not limited to, diacylphosphatidylcholine, a diacylphosphatidylethanolamine, a ceramide, a sphingomyelin, a dihydrosphingomyelin, a cephalin, a cerebroside, a C8-C20 fatty acid diacylphophatidylcholine, and 1-palmitoyl-2-oleoyl phosphatidylcholine (POPC). In another aspect the limit size lipid nanoparticle may comprise a polyethylene glycol-lipid such as, but not limited to, DLPE-PEG, DMPE-PEG, DPPC-PEG and DSPE-PEG.

In some embodiments, the RNA vaccines may be delivered, localized and/or concentrated in a specific location using the delivery methods described in International Patent Publication No. WO2013063530, the contents of which are herein incorporated by reference in its entirety. As a non-limiting example, a subject may be administered an empty polymeric particle prior to, simultaneously with or after delivering the RNA vaccines to the subject. The empty polymeric particle undergoes a change in volume once in contact with the subject and becomes lodged, embedded, immobilized or entrapped at a specific location in the subject.

In some embodiments, the RNA vaccines may be formulated in an active substance release system (See e.g., US Patent Publication No. US20130102545, the contents of which is herein incorporated by reference in its entirety). The active substance release system may comprise 1) at least one nanoparticle bonded to an oligonucleotide inhibitor strand which is hybridized with a catalytically active nucleic acid and 2) a compound bonded to at least one substrate molecule bonded to a therapeutically active substance (e.g., polynucleotides described herein), where the therapeutically active substance is released by the cleavage of the substrate molecule by the catalytically active nucleic acid.

In some embodiments, the RNA vaccines may be formulated in a nanoparticle comprising an inner core comprising a non-cellular material and an outer surface comprising a cellular membrane. The cellular membrane may be derived from a cell or a membrane derived from a virus. As a non-limiting example, the nanoparticle may be made by the methods described in International Patent Publication No. WO2013052167, herein incorporated by reference in its entirety. As another non-limiting example, the nanoparticle described in International Patent Publication No.

WO2013052167, herein incorporated by reference in its entirety, may be used to deliver the RNA vaccines described herein.

In some embodiments, the RNA vaccines may be formulated in porous nanoparticle-supported lipid bilayers (protocells). Protocells are described in International Patent Publication No. WO2013056132, the contents of which are herein incorporated by reference in its entirety.

In some embodiments, the RNA vaccines described herein may be formulated in polymeric nanoparticles as described in or made by the methods described in U.S. Pat. Nos. 8,420,123 and 8,518,963 and European Patent No. EP2073848B1, the contents of each of which are herein incorporated by reference in their entirety. As a non-limiting example, the polymeric nanoparticle may have a high glass transition temperature such as the nanoparticles described in or nanoparticles made by the methods described in U.S. Pat. No. 8,518,963, the contents of which are herein incorporated by reference in its entirety. As another non-limiting example, the polymer nanoparticle for oral and parenteral formulations may be made by the methods described in European Patent No. EP2073848B1, the contents of which are herein incorporated by reference in its entirety.

In another embodiment, the RNA vaccines described herein may be formulated in nanoparticles used in imaging. The nanoparticles may be liposome nanoparticles such as those described in US Patent Publication No US20130129636, herein incorporated by reference in its entirety. As a non-limiting example, the liposome may comprise gadolinium(III)2-{4,7-bis-carboxymethyl-10-[(N, N-distearylamidomethyl-N'-amido-methyl]-1,4,7,10-tetra-azacyclododec-1-yl}-acetic acid and a neutral, fully saturated phospholipid component (see e.g., US Patent Publication No US20130129636, the contents of which is herein incorporated by reference in its entirety).

In some embodiments, the nanoparticles which may be used in the present invention are formed by the methods described in U.S. Patent Application No. US20130130348, the contents of which is herein incorporated by reference in its entirety.

The nanoparticles of the present invention may further include nutrients such as, but not limited to, those which deficiencies can lead to health hazards from anemia to neural tube defects (see e.g, the nanoparticles described in International Patent Publication No WO2013072929, the contents of which is herein incorporated by reference in its entirety). As a non-limiting example, the nutrient may be iron in the form of ferrous, ferric salts or elemental iron, iodine, folic acid, vitamins or micronutrients.

In some embodiments, the RNA vaccines of the present invention may be formulated in a swellable nanoparticle. The swellable nanoparticle may be, but is not limited to, those described in U.S. Pat. No. 8,440,231, the contents of which is herein incorporated by reference in its entirety. As a non-limiting embodiment, the swellable nanoparticle may be used for delivery of the RNA vaccines of the present invention to the pulmonary system (see e.g., U.S. Pat. No. 8,440,231, the contents of which is herein incorporated by reference in its entirety).

The RNA vaccines of the present invention may be formulated in polyanhydride nanoparticles such as, but not limited to, those described in U.S. Pat. No. 8,449,916, the contents of which is herein incorporated by reference in its entirety.

The nanoparticles and microparticles of the present invention may be geometrically engineered to modulate macrophage and/or the immune response. In one aspect, the geometrically engineered particles may have varied shapes, sizes and/or surface charges in order to incorporated the polynucleotides of the present invention for targeted delivery such as, but not limited to, pulmonary delivery (see e.g., International Publication No WO2013082111, the contents of which is herein incorporated by reference in its entirety). Other physical features the geometrically engineering particles may have include, but are not limited to, fenestrations, angled arms, asymmetry and surface roughness, charge which can alter the interactions with cells and tissues. As a non-limiting example, nanoparticles of the present invention may be made by the methods described in International Publication No WO2013082111, the contents of which is herein incorporated by reference in its entirety.

In some embodiments, the nanoparticles of the present invention may be water soluble nanoparticles such as, but not limited to, those described in International Publication No. WO2013090601, the contents of which is herein incorporated by reference in its entirety. The nanoparticles may be inorganic nanoparticles which have a compact and zwitterionic ligand in order to exhibit good water solubility. The nanoparticles may also have small hydrodynamic diameters (HD), stability with respect to time, pH, and salinity and a low level of non-specific protein binding.

In some embodiments the nanoparticles of the present invention may be developed by the methods described in US Patent Publication No. US20130172406, the contents of which are herein incorporated by reference in its entirety.

In some embodiments, the nanoparticles of the present invention are stealth nanoparticles or target-specific stealth nanoparticles such as, but not limited to, those described in US Patent Publication No. US20130172406; the contents of which is herein incorporated by reference in its entirety. The nanoparticles of the present invention may be made by the methods described in US Patent Publication No. US20130172406, the contents of which are herein incorporated by reference in its entirety.

In another embodiment, the stealth or target-specific stealth nanoparticles may comprise a polymeric matrix. The polymeric matrix may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates or combinations thereof.

In some embodiments, the nanoparticle may be a nanoparticle-nucleic acid hybrid structure having a high density nucleic acid layer. As a non-limiting example, the nanoparticle-nucleic acid hybrid structure may made by the methods described in US Patent Publication No. US20130171646, the contents of which are herein incorporated by reference in its entirety. The nanoparticle may comprise a nucleic acid such as, but not limited to, polynucleotides described herein and/or known in the art.

At least one of the nanoparticles of the present invention may be embedded in the core a nanostructure or coated with a low density porous 3-D structure or coating which is capable of carrying or associating with at least one payload within or on the surface of the nanostructure. Non-limiting examples of the nanostructures comprising at least one nanoparticle are described in International Patent Publication No. WO2013123523, the contents of which are herein incorporated by reference in its entirety.

In some embodiments the RNA (e.g., mRNA) vaccine may be associated with a cationic or polycationic compounds, including protamine, nucleoline, spermine or spermidine, or other cationic peptides or proteins, such as poly-L-lysine (PLL), polyarginine, basic polypeptides, cell penetrating peptides (CPPs), including HIV-binding peptides, HIV-1 Tat (HIV), Tat-derived peptides, Penetratin, $VP^{22}$ derived or analog peptides, Pestivirus Erns, HSV, $VP^{22}$ (Herpes simplex), MAP, KALA or protein transduction domains (Pills), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila* antennapedia), pAntp, pIsl, FGF, Lactoferrin, Transportan, Buforin-2, Bac715-24, SynB, SynB(1), pVEC, hCT-derived peptides, SAP, histones, cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristooxypropyl dimethyl hydroxyethyl ammonium bromide, DOTAP: dioleoyloxy-3-(trimethylammonio)propane, DC-6-14: O,O-ditetradecanoyl-N-.alpha.-trimethylammonioacetyl)diethanolamine chloride, CLIP 1: rac-[(2,3-dioctadecyloxypropyl)(2-hydroxyethyl)]-dimethylammonium chloride, CLIP6: rac-[2(2,3-dihexadecyloxypropyloxymethyloxy)ethyl]-trimethylammonium, CLIP9: rac-[2(2,3-dihexadecyloxypropyloxysuccinyloxy)ethyl]-trimethylammo-nium, oligofectamine, or cationic or polycationic polymers, e.g. modified polyaminoacids, such as beta-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified amidoamines such as pAMAM (poly(amidoamine)), etc., modified polybetaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole), etc.

In other embodiments the RNA (e.g., mRNA) vaccine is not associated with a cationic or polycationic compounds.

In some embodiments, a nanoparticle comprises compounds of Formula (I):

(I)

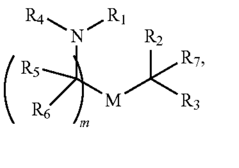

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —$CQ(R)_2$, and unsubstituted $C_{1-6}$ alkyl, where Q is selected from a carbocycle, heterocycle, —OR, —$O(CH_2)_nN(R)_2$, —C(O)OR, —OC(O)R, —$CX_3$, —$CX_2H$, —$CXH_2$, —CN, —$N(R)_2$, —C(O)$N(R)_2$, —N(R)C(O)R, —N(R)S$(O)_2$R, —N(R)C(O)$N(R)_2$, —N(R)C(S)$N(R)_2$, —N(R)$R_8$, —$O(CH_2)_n$OR, —N(R)C(=$NR_9$)$N(R)_2$, —N(R)C(=$CHR_9$)$N(R)_2$, —OC(O)$N(R)_2$, —N(R)C(O)OR, —N(OR)C(O)R, —N(OR)S$(O)_2$R, —N(OR)C(O)OR, —N(OR)C(O)$N(R)_2$, —N(OR)C(S)$N(R)_2$, —N(OR)C(=$NR_9$)$N(R)_2$, —N(OR)C(=$CHR_9$)$N(R)_2$, —C(=$NR_9$)$N(R)_2$, —C(=$NR_9$)R, —C(O)N(R)OR, and —C(R)$N(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—,

—N(R')C(O)—, —C(O)—, —C(S)—, —C(S)S—, —SC(S)—, —CH(OH)—, —P(O)(OR')O—, —S$(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S$(O)_2$R, —S$(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —$(CH_2)_n$Q, —$(CH_2)_n$CHQR, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —N(R)C(=$NR_9$)$N(R)_2$, —N(R)C(=$CHR_9$)$N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —N(OR)C(=$NR_9$)$N(R)_2$, —N(OR)C(=$CHR_9$)$N(R)_2$, —C(=$NR_9$)$N(R)_2$, —C(=$NR_9$)R, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —N(R)C(=$NR_9$)$N(R)_2$, —N(R)C(=$CHR_9$)$N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —N(OR)C(=$NR_9$)$N(R)_2$, —N(OR)C(=$CHR_9$)$N(R)_2$, —C(=$NR_9$)R, —C(O)N(R)OR, and —C(=$NR_9$)$N(R)_2$, and each n is independently selected from 1, 2, 3, 4, and 5; and when Q is a 5- to 14-membered heterocycle and (i) $R_4$ is —$(CH_2)_nQ$ in which n is 1 or 2, or (ii) $R_4$ is —$(CH_2)_nCHQR$ in which n is 1, or (iii) $R_4$ is —CHQR, and —$CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —N(R)C(=$NR_9$)$N(R)_2$, —N(R)C(=$CHR_9$)$N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —N(OR)C(=$NR_9$)$N(R)_2$, —N(OR)C(=$CHR_9$)$N(R)_2$, —C(=$NR_9$)R, —C(O)N(R)OR, and —C(=$NR_9$)$N(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_nQ$ or —$(CH_2)_nCHQR$, where Q is —$N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_nQ$, —$(CH_2)_nCHQR$, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

(IA)

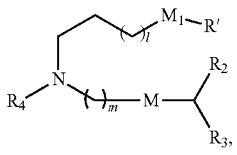

or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_nQ$, in which Q is OH, —NHC(S)N$(R)_2$, —NHC(O)N$(R)_2$, —N(R)C(O)R, —N(R)$S(O)_2R$, —N(R)$R_8$, —NHC(═$NR_9$)N(R)z, —NHC(═$CHR_9$)N$(R)_2$, —OC(O)N$(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II):

(II)

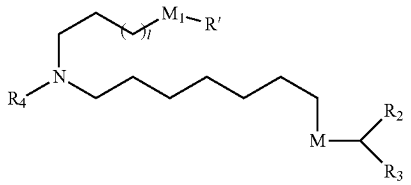

or a salt or isomer thereof, wherein 1 is selected from 1, 2, 3, 4, and 5; $M_1$ is a bond or M'; $R_4$ is unsubstituted $C_{1-3}$ alkyl, or —$(CH_2)_nQ$, in which n is 2, 3, or 4, and Q is OH, —NHC(S)N$(R)_2$, —NHC(O)N$(R)_2$, —N(R)C(O)R, —N(R)$S(O)_2R$, —N(R)$R_8$, —NHC(═$NR_9$)N$(R)_2$, —NHC(═$CHR_9$)N$(R)_2$, —OC(O)N$(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IIa), (IIb), (IIc), or (IIe):

(IIa)

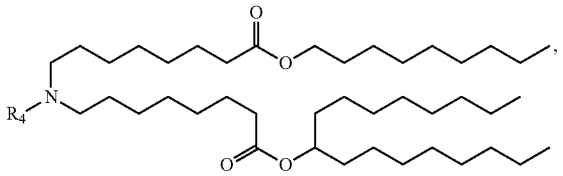

(IIb)

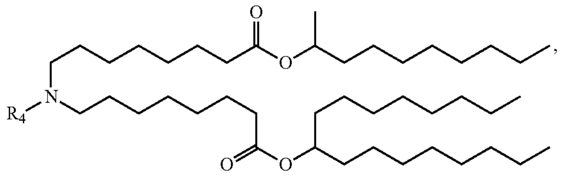

(IIc)

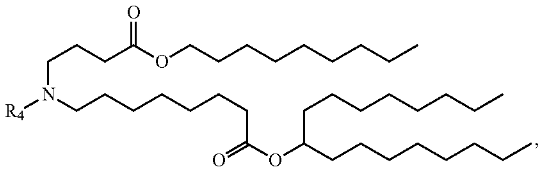

or (IIe)

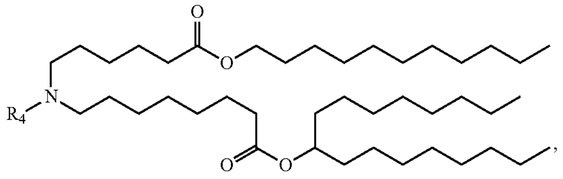

or a salt or isomer thereof, wherein $R_4$ is as described herein.

In some embodiments, a subset of compounds of Formula (I) includes those of Formula (IId):

(IId)

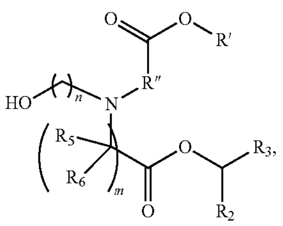

or a salt or isomer thereof, wherein n is 2, 3, or 4; and m, R', R'', and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, a subset of compounds of Formula (I) includes those of Formula (IIa), (IIb), (IIc), or (IIe):

(IIa)

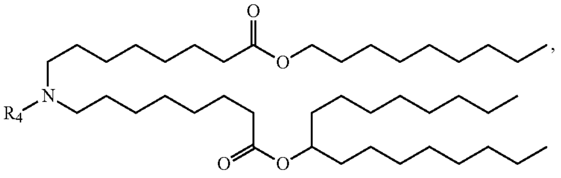

(IIb)

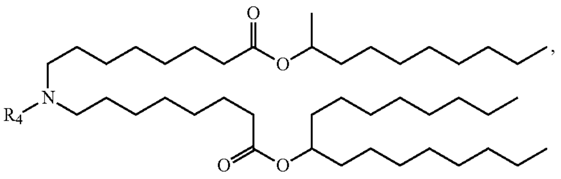

(IIc)

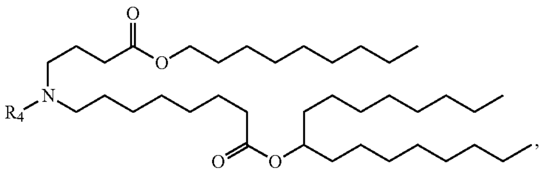

or (IIe)

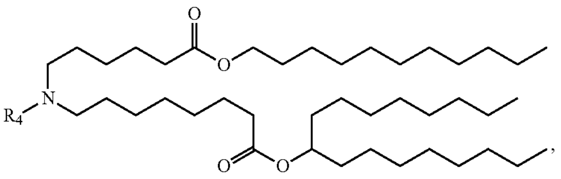

or a salt or isomer thereof, wherein $R_4$ is as described herein.

In some embodiments, a subset of compounds of Formula (I) includes those of Formula (IId):

(IId)

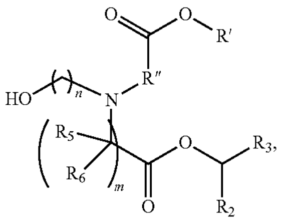

or a salt or isomer thereof, wherein n is 2, 3, or 4; and m, R', R'', and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, the compound of Formula (I) is selected from the group consisting of:
(Compound 1)
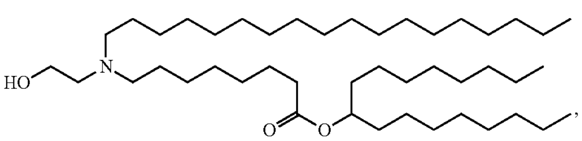,
(Compound 2)
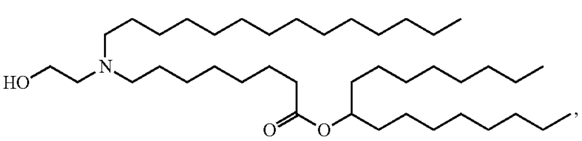,
(Compound 3)
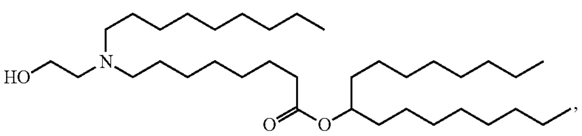,
(Compound 4)
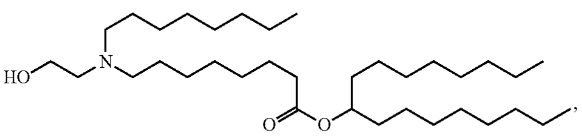,
(Compound 5)
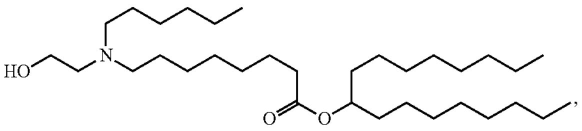,
(Compound 6)
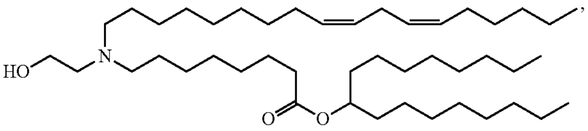,
(Compound 7)
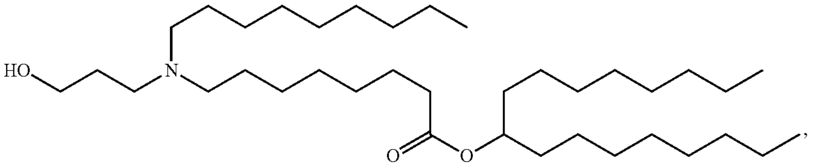,
(Compound 8)
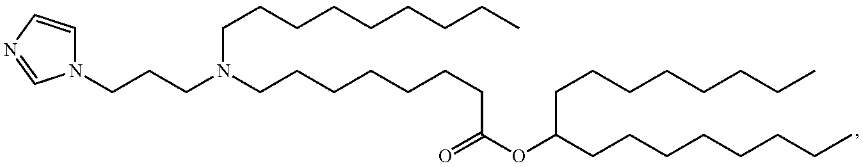,
(Compound 9)
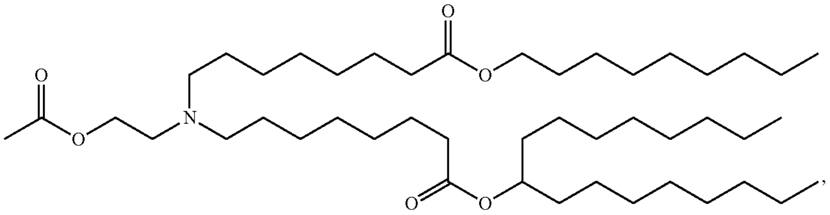,
(Compound 10)
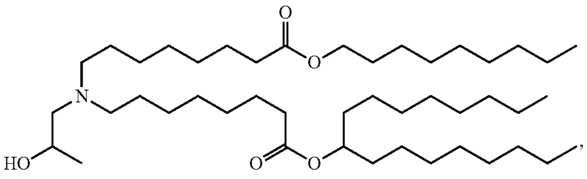,
(Compound 11)
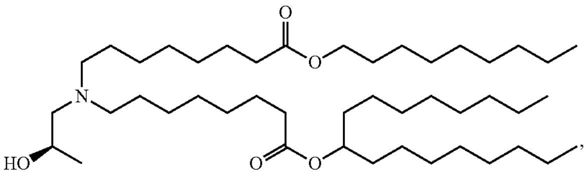,
(Compound 12)
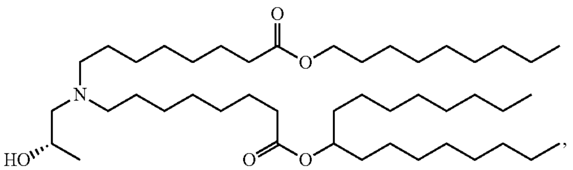,
(Compound 13)
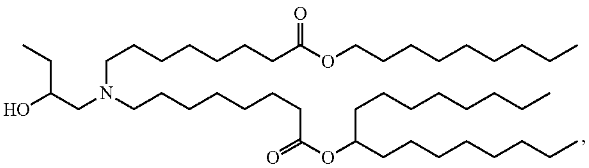, -continued
(Compound 14)
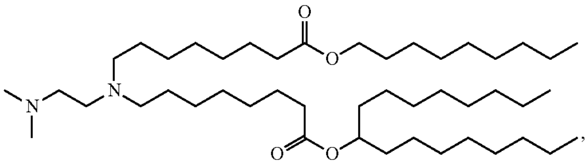
,
(Compound 15)
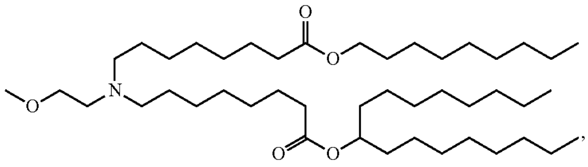
,
(Compound 16)
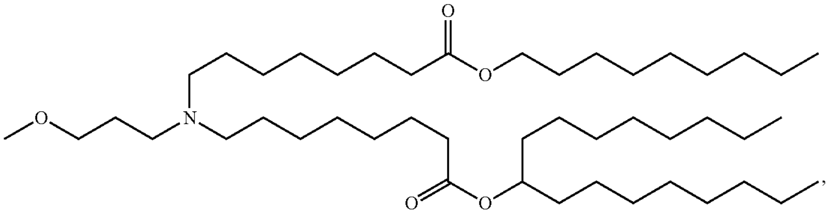
,
(Compound 17)
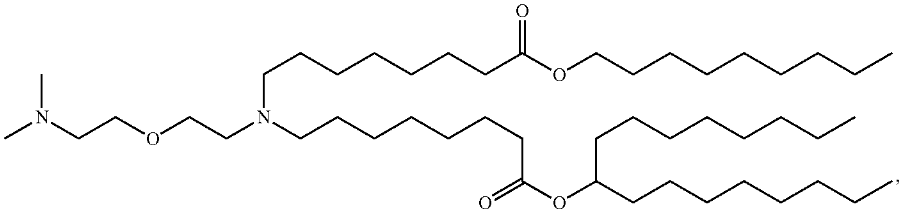
,
(Compound 18)
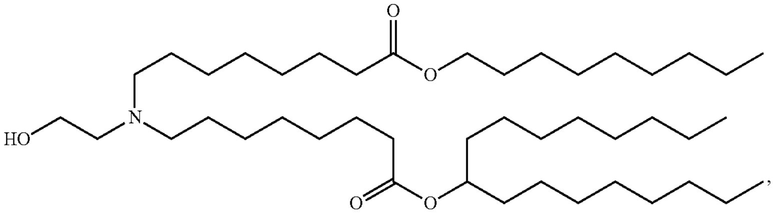
,
(Compound 19)
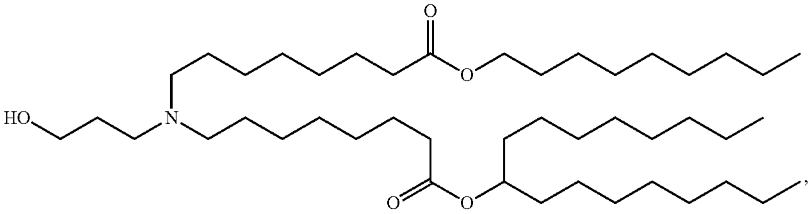
,
(Compound 20)
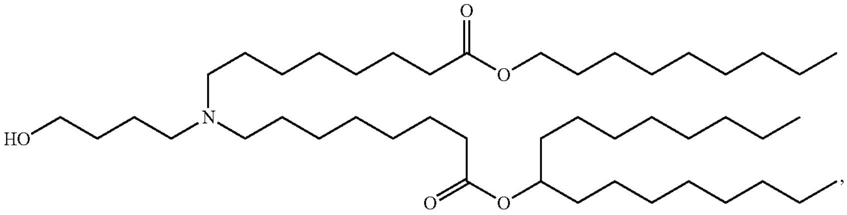
,
(Compound 21)
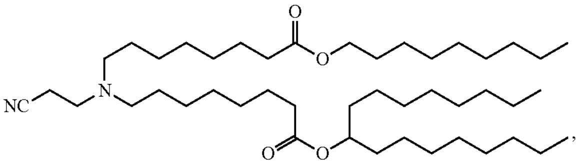
,
(Compound 22)
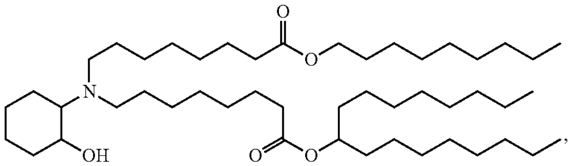
, -continued
(Compound 23)
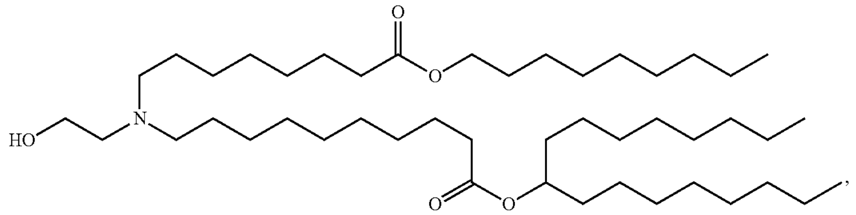
(Compound 24)
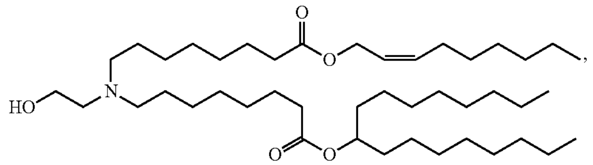
(Compound 25)
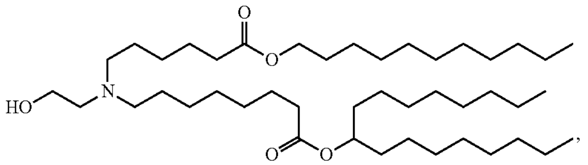
(Compound 26)
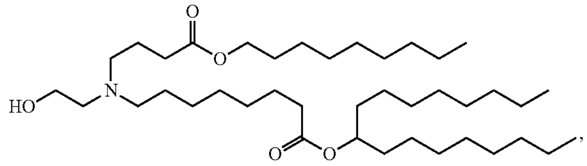
(Compound 27)
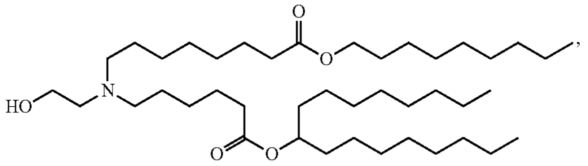
(Compound 28)
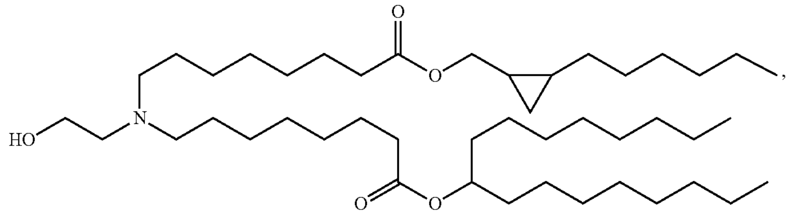
(Compound 29)
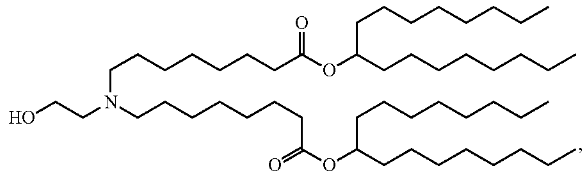
(Compound 30)
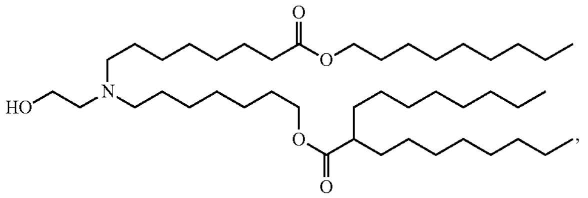
(Compound 31)
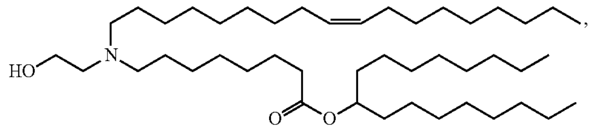
(Compound 32)
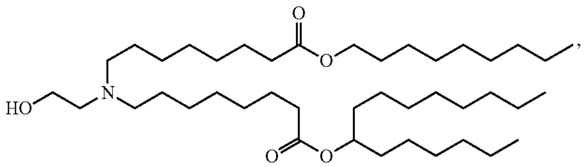
(Compound 33)
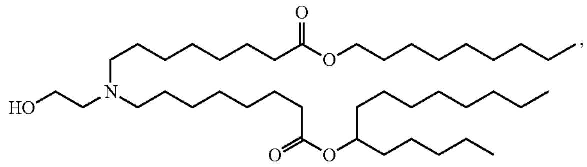
(Compound 34)
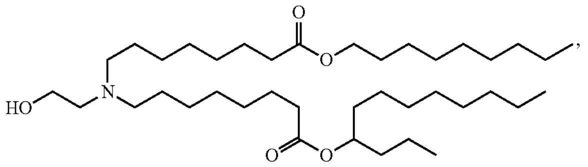

-continued
(Compound 35)
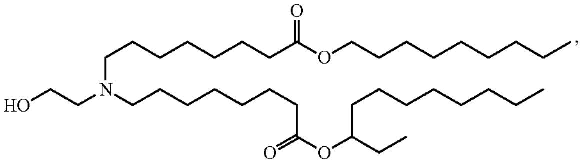
(Compound 36)
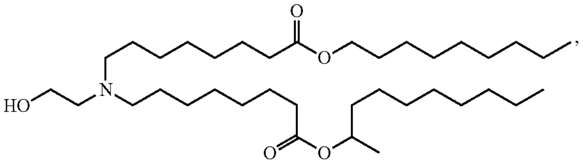
(Compound 37)
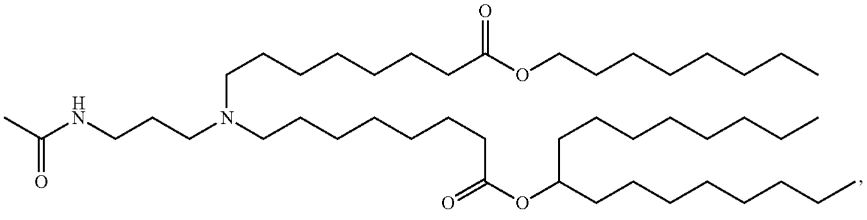
(Compound 38)
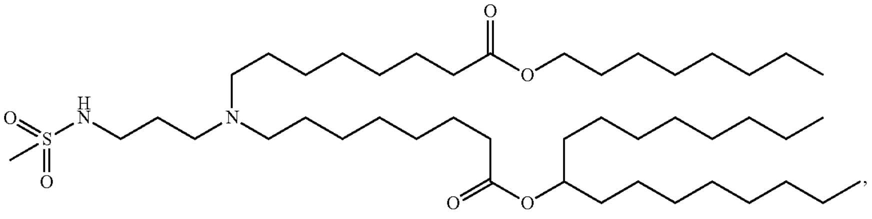
(Compound 39)
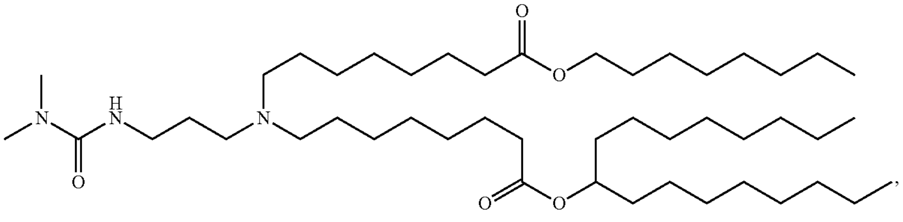
(Compound 40)
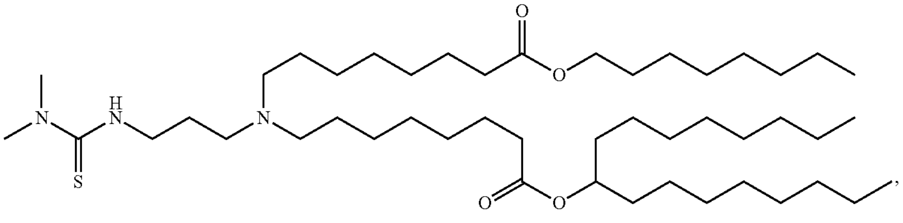
(Compound 41)
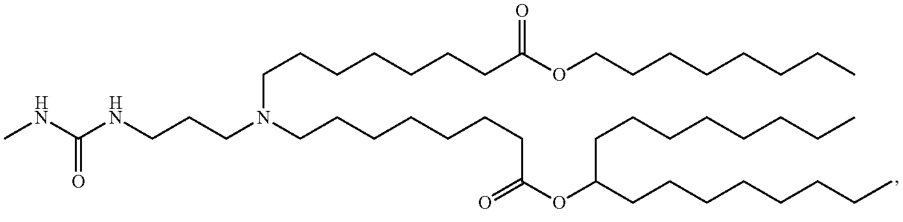
(Compound 42)
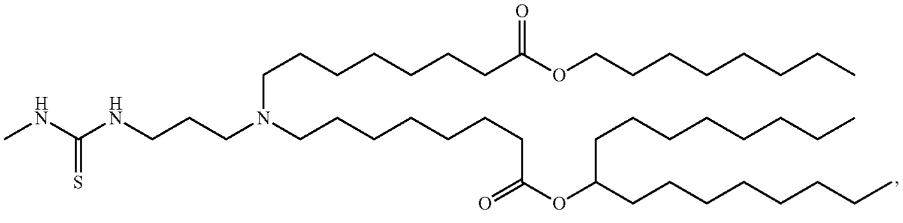

-continued
(Compound 43)
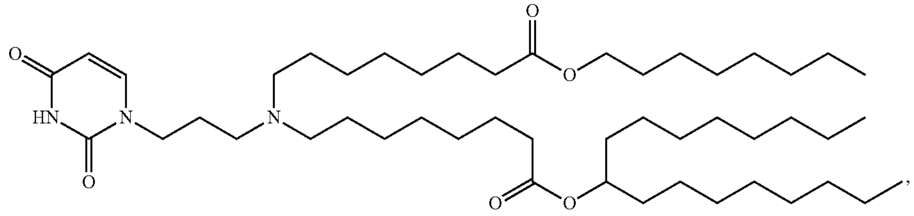
(Compound 44)
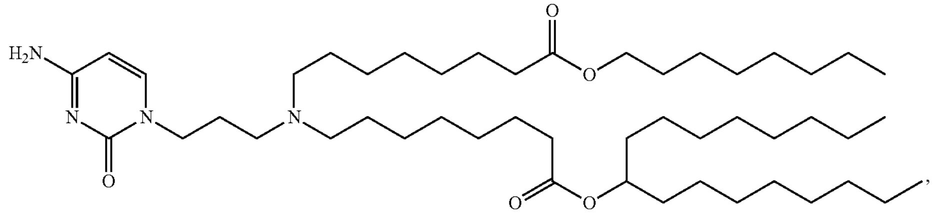
(Compound 45)
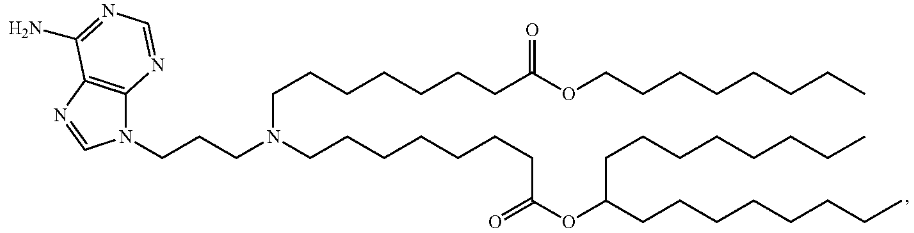
(Compound 46)
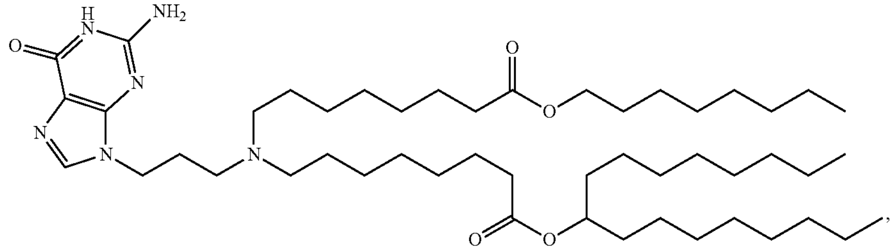
(Compound 47)
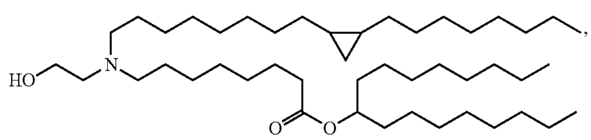
(Compound 48)
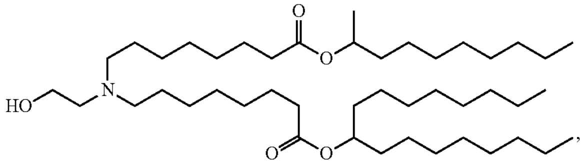
(Compound 49)
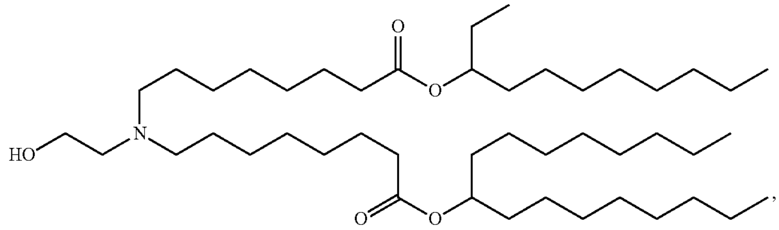
(Compound 50)
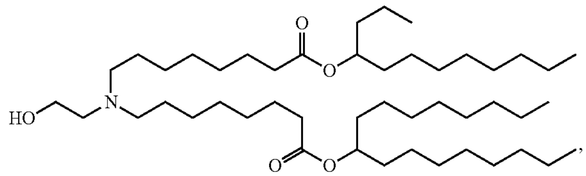
(Compound 51)
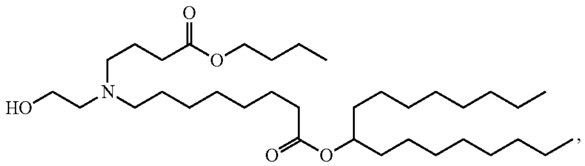

-continued
(Compound 52)
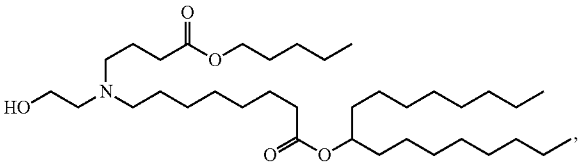
,
(Compound 53)
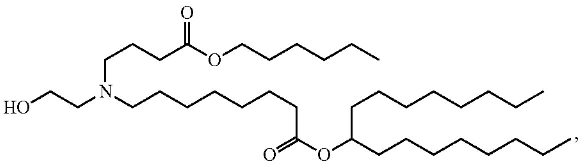
,
(Compound 54)
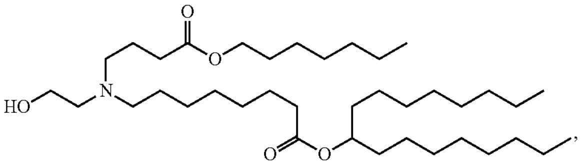
,
(Compound 55)
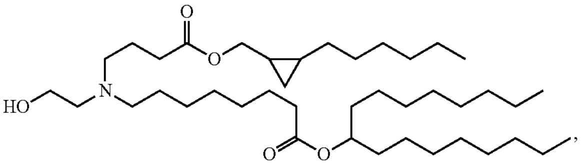
,
(Compound 56)
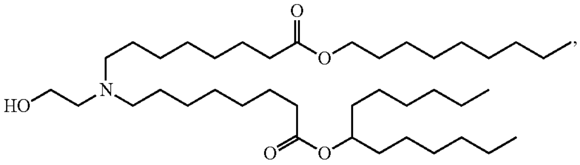
,
(Compound 57)
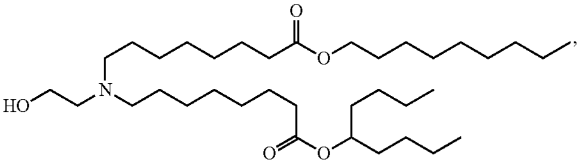
,
(Compound 58)
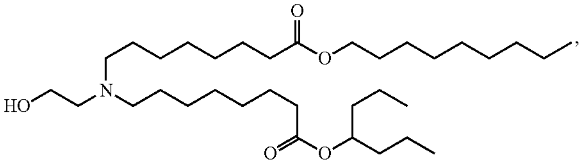
,
(Compound 59)
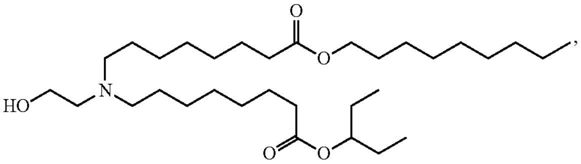
,
(Compound 60)
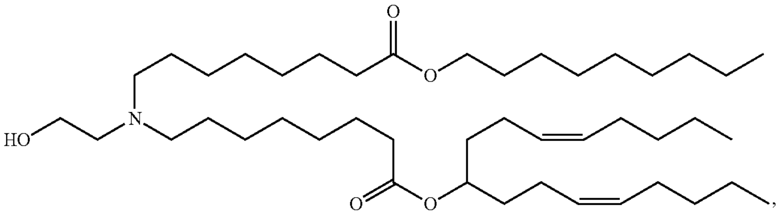
, and
(Compound 61)
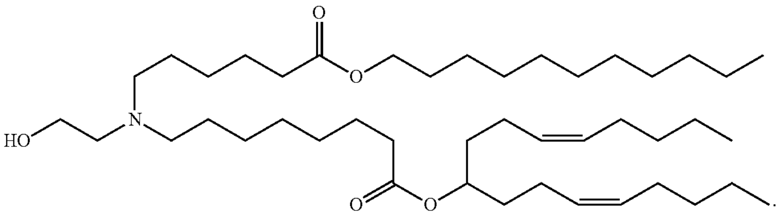
.

In further embodiments, the compound of Formula (I) is selected from the group consisting of:
(Compound 62)
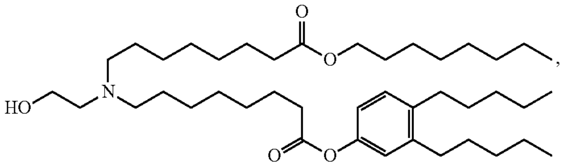
,
(Compound 63)
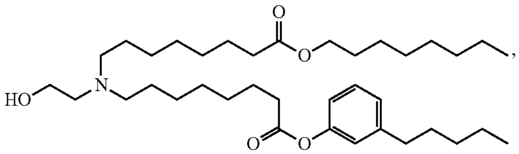
, and
(Compound 64)
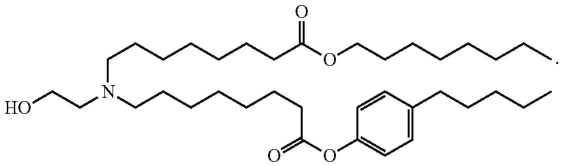
.
In some embodiments, the compound of Formula (I) is selected from the group consisting of:
(Compound 65)
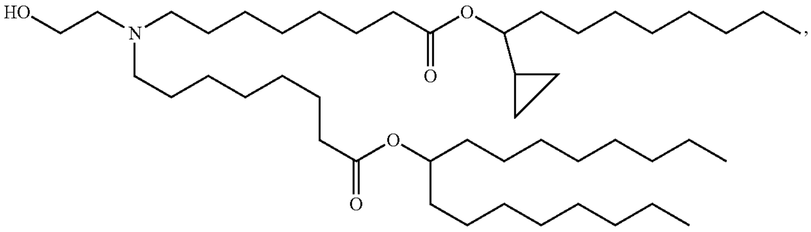
,
(Compound 66)
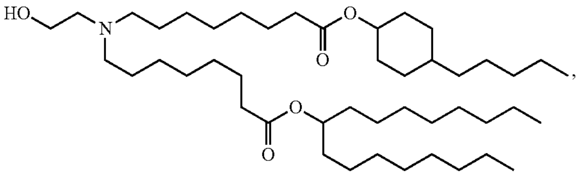
,
(Compound 67)
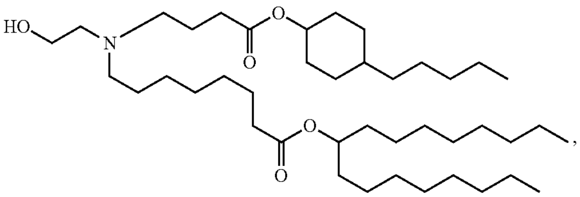
,
(Compound 68)
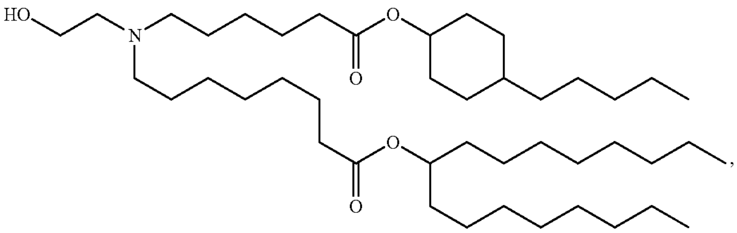
, -continued
(Compound 69)
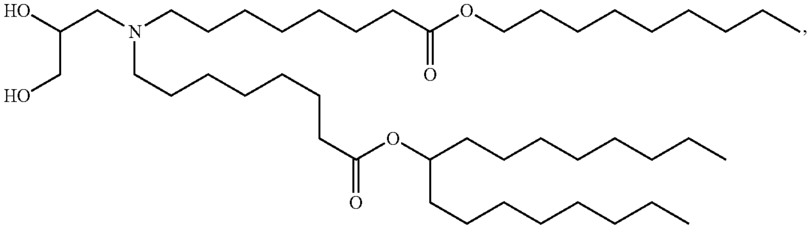
(Compound 70)
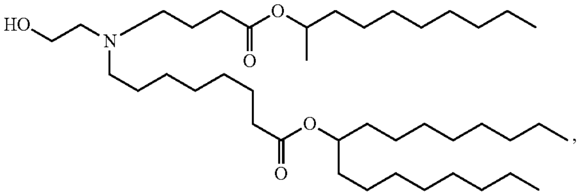
(Compound 71)
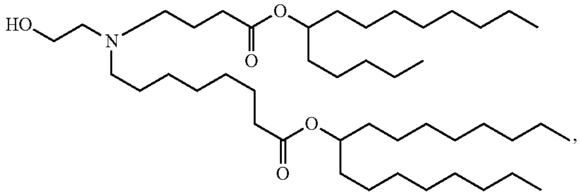
(Compound 72)
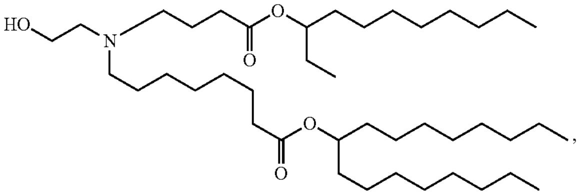
(Compound 73)
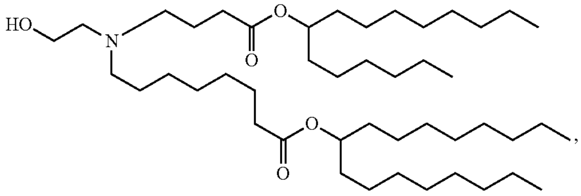
(Compound 74)
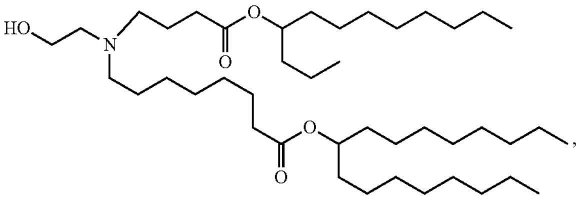
(Compound 75)
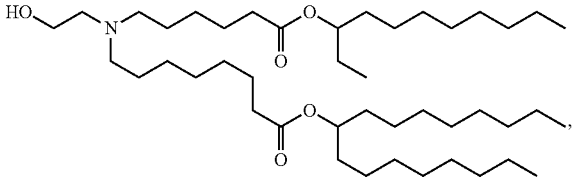
(Compound 76)
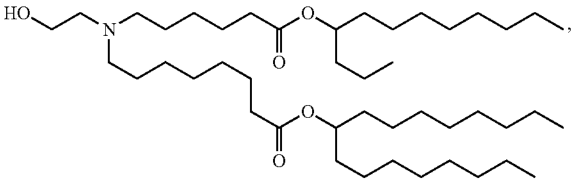
(Compound 77)
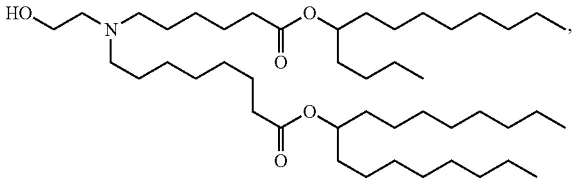
(Compound 78)
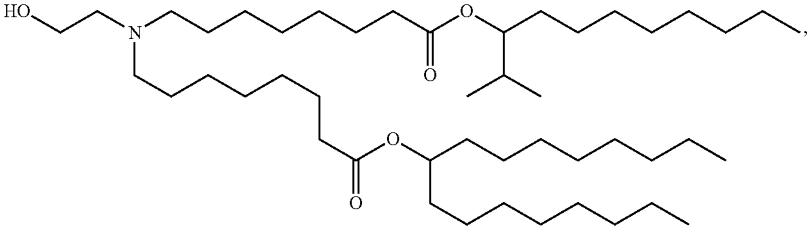
(Compound 79)
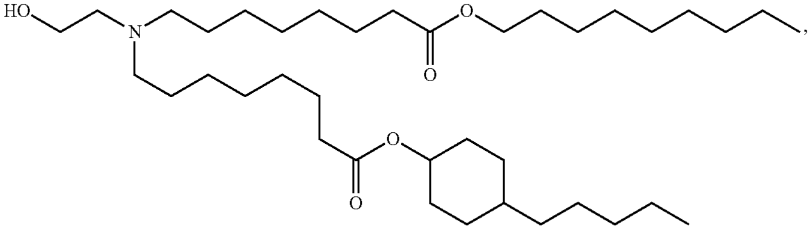

-continued
(Compound 80)
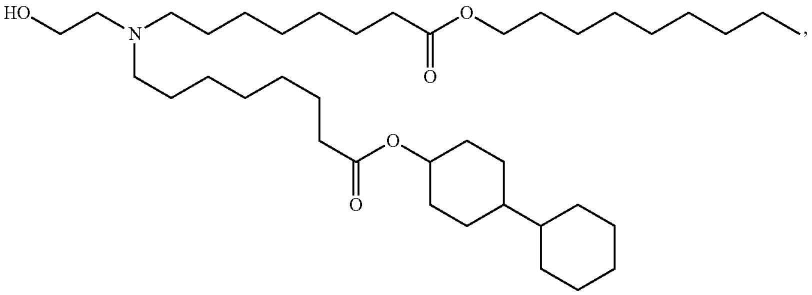
(Compound 81)
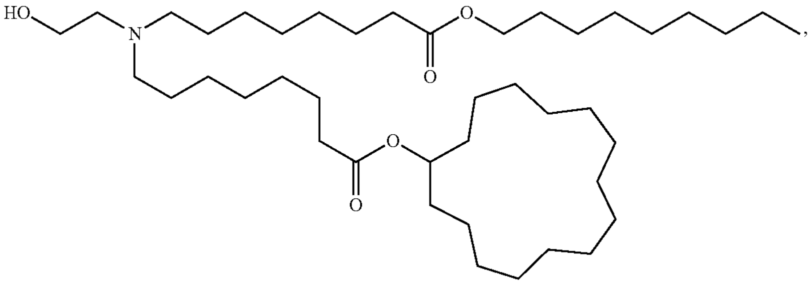
(Compound 82)
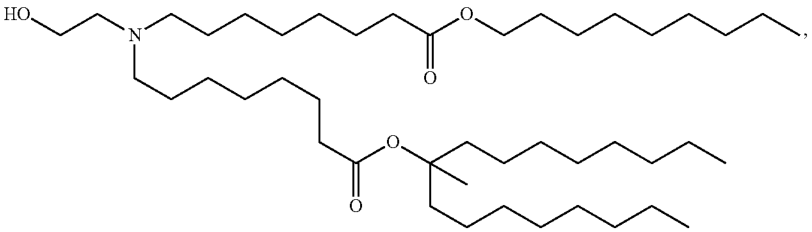
(Compound 83)
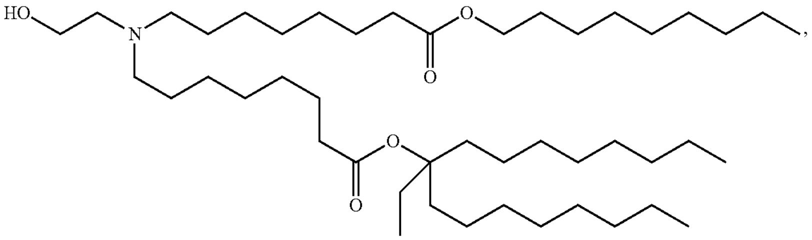
(Compound 84)
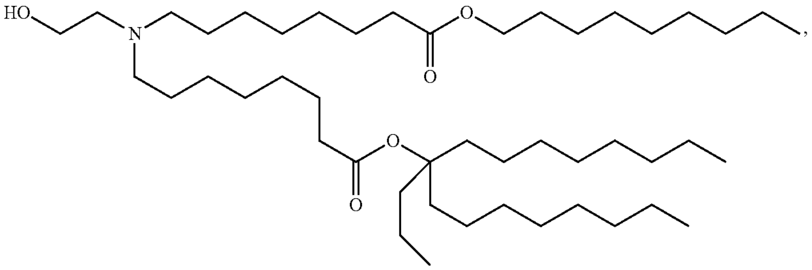
(Compound 85)
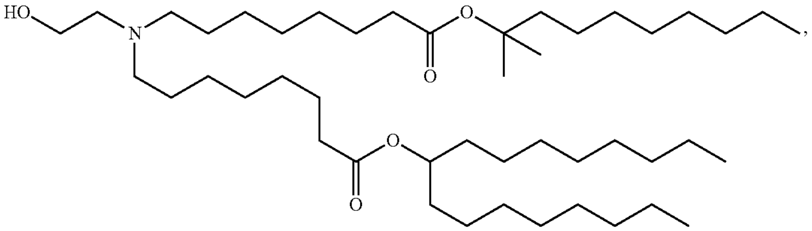

-continued
(Compound 86)
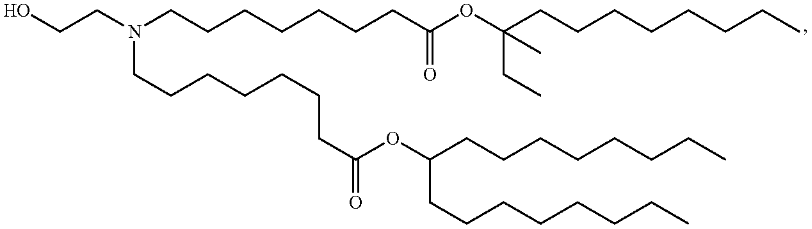
(Compound 87)
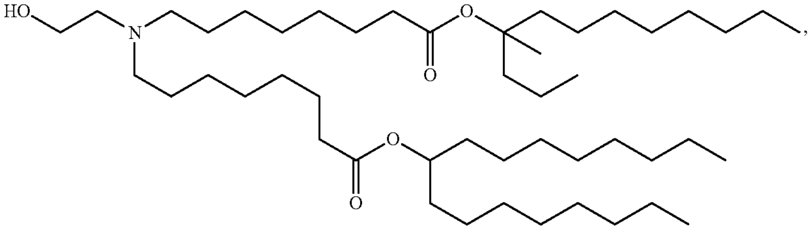
(Compound 88)
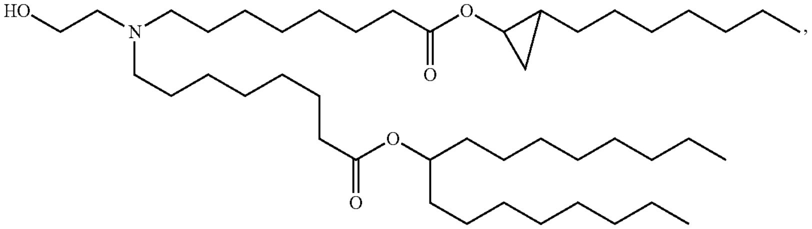
(Compound 89)
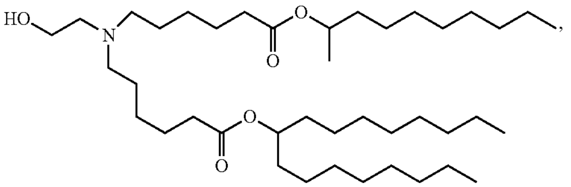
(Compound 90)
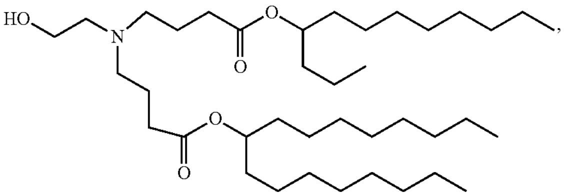
(Compound 91)
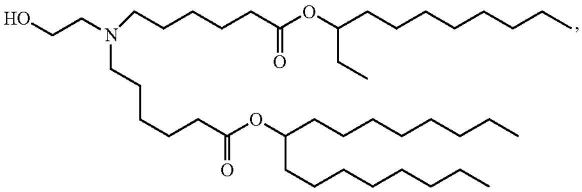
(Compound 92)
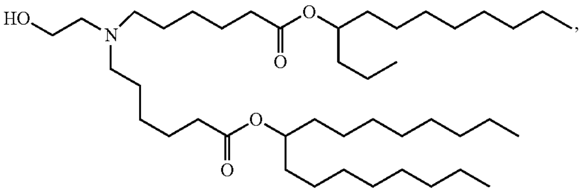
(Compound 93)
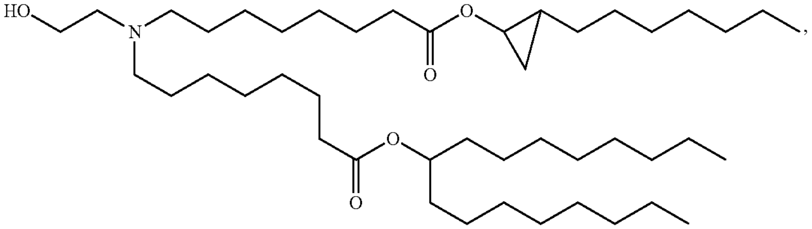
(Compound 94)
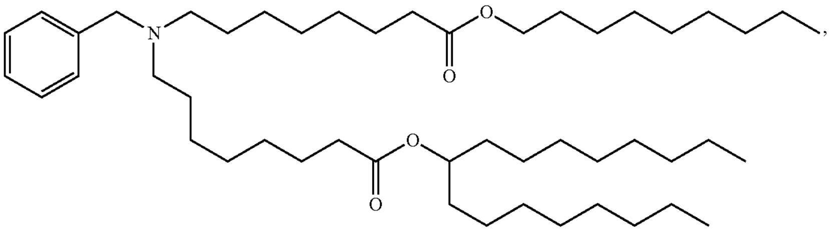

-continued
(Compound 95)
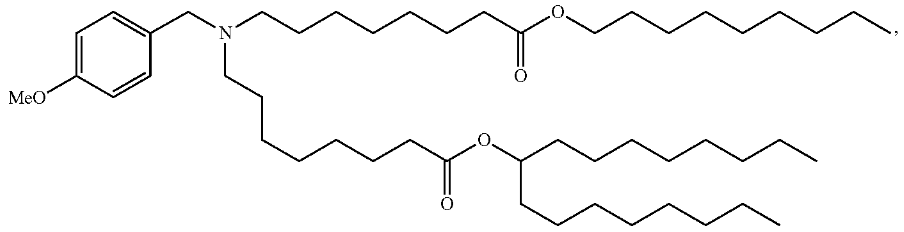
(Compound 96)
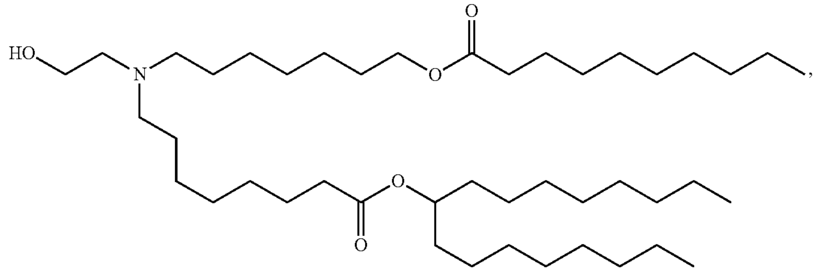
(Compound 97)
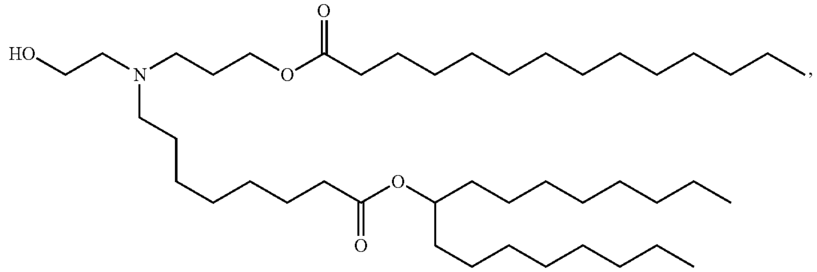
(Compound 98)
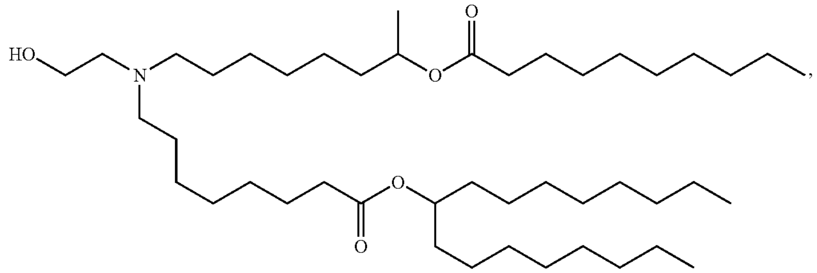
(Compound 99)
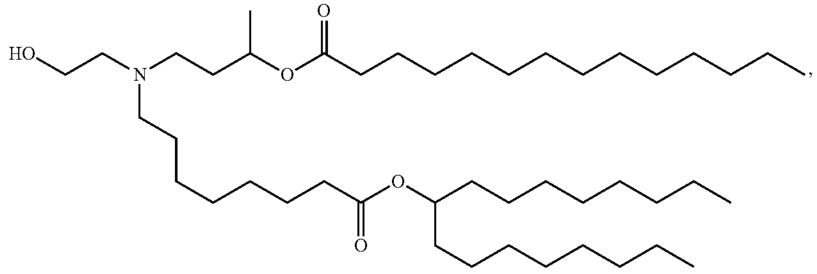

-continued
(Compound 100)
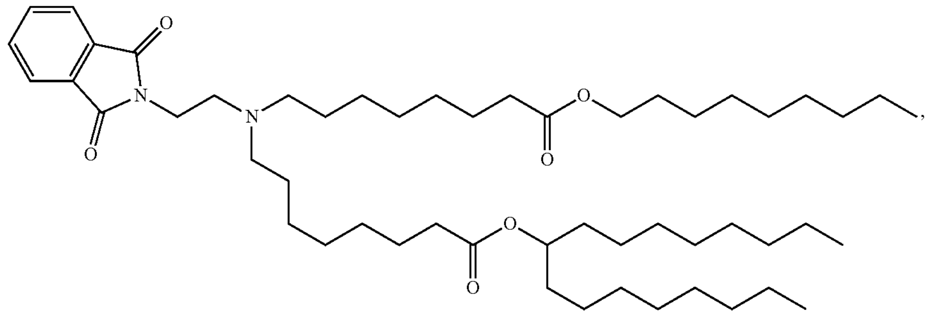
(Compound 101)
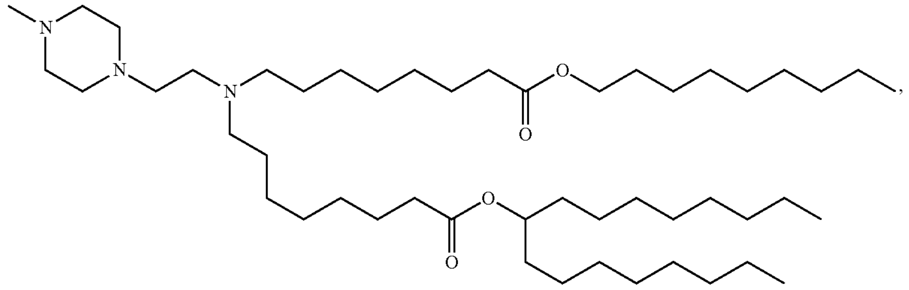
(Compound 102)
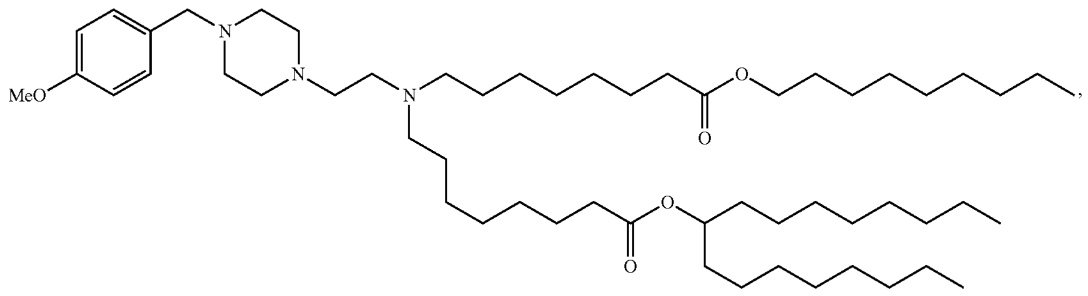
(Compound 103)
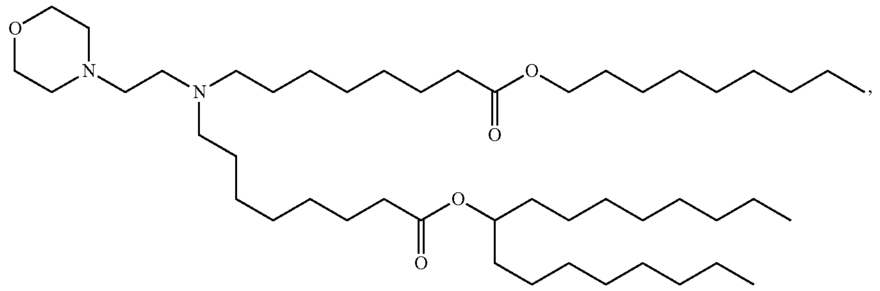
(Compound 104)
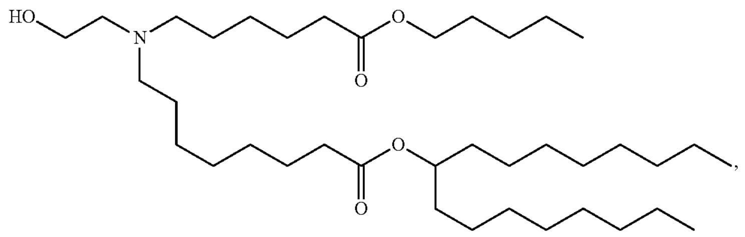

-continued
(Compound 105)
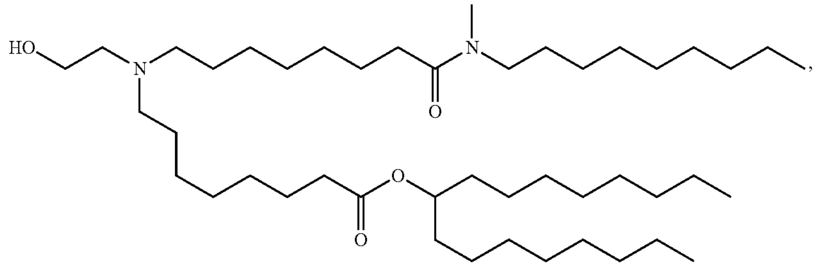
(Compound 106)
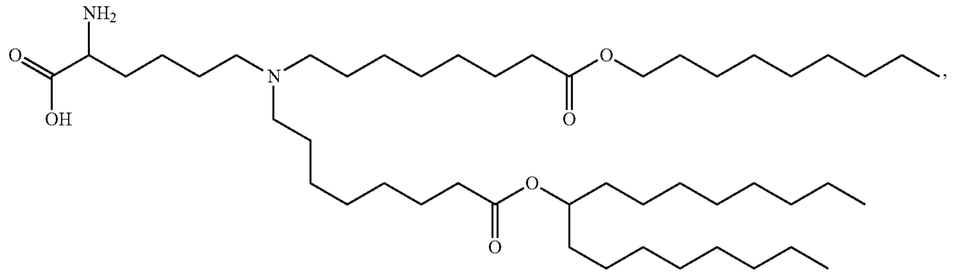
(Compound 107)
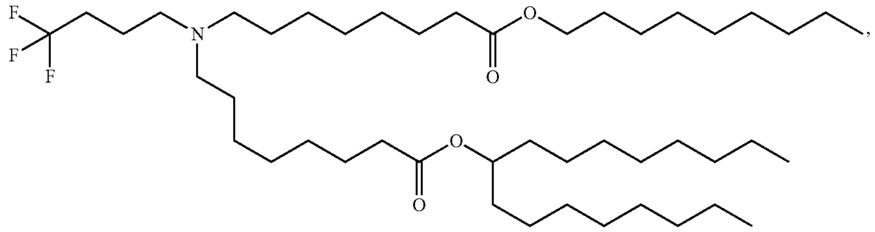
(Compound 108)
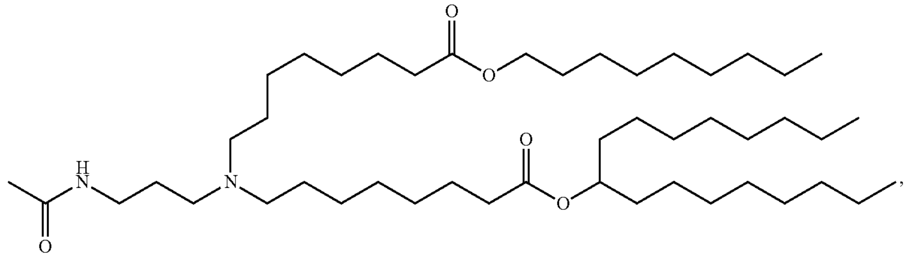
(Compound 109)
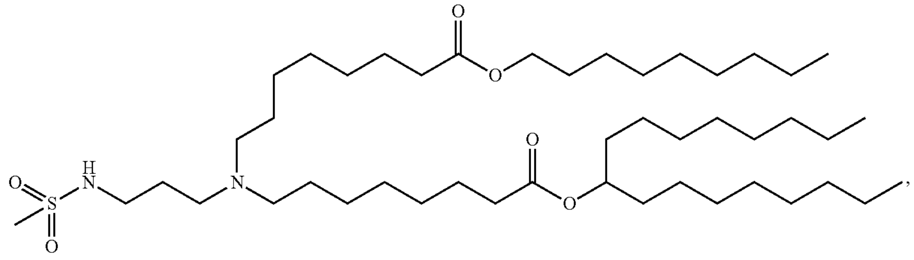
(Compound 110)
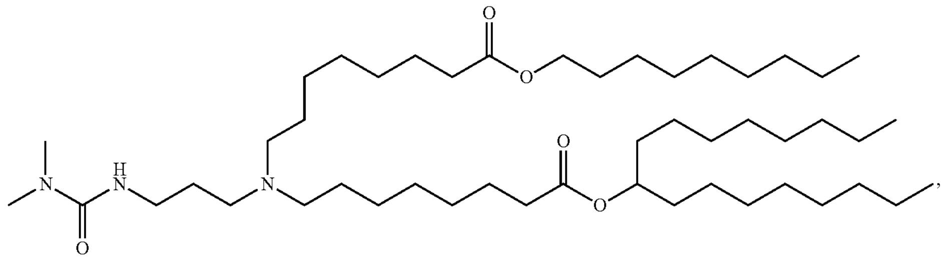

-continued
(Compound 111)
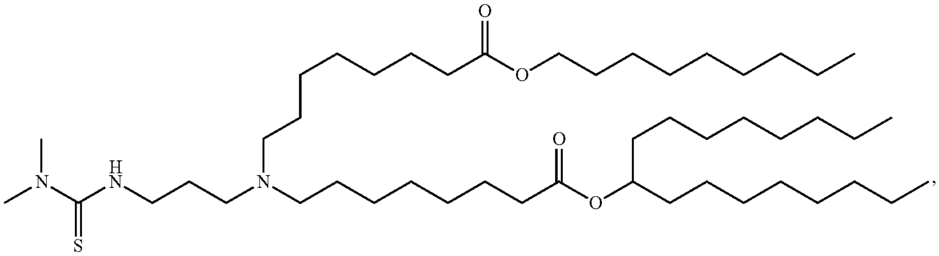
,
(Compound 112)
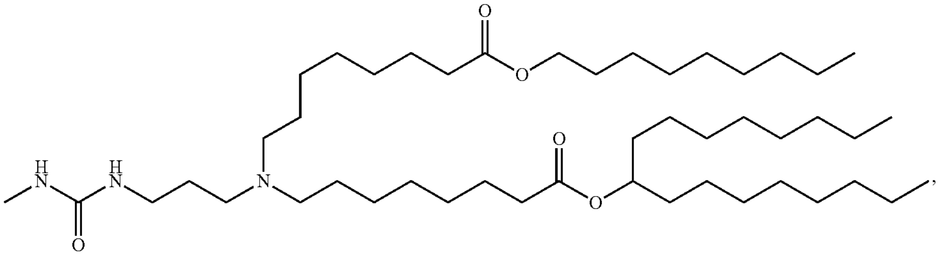
,
(Compound 113)
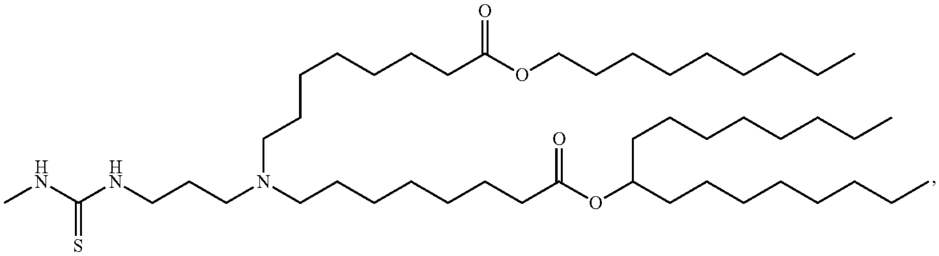
,
(Compound 114)
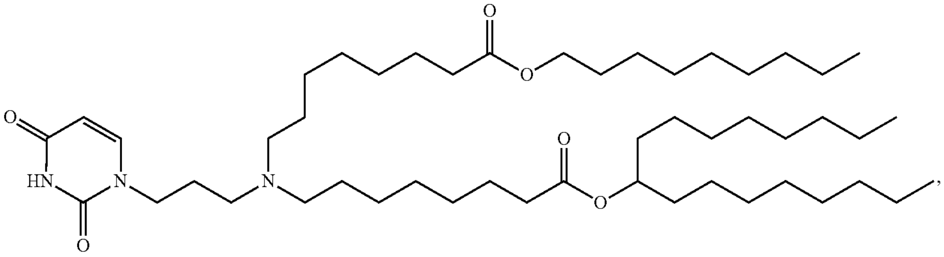
,
(Compound 115)
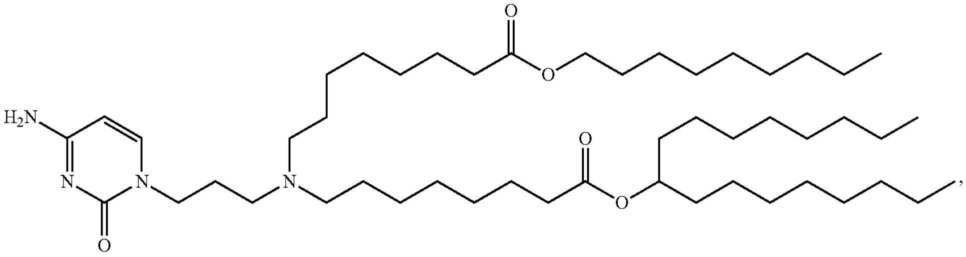
,
(Compound 116)
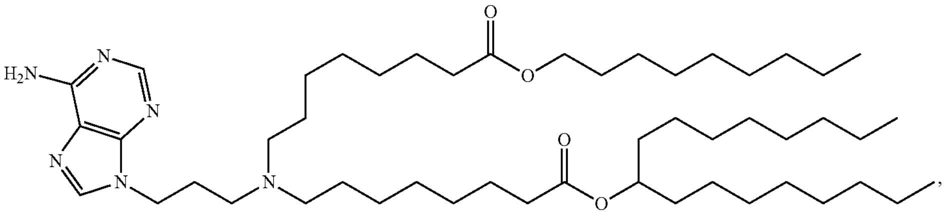
, -continued
(Compound 117)
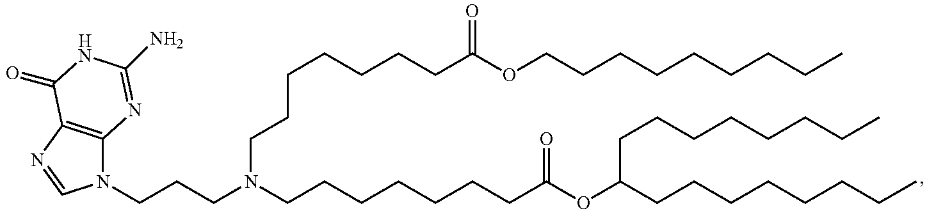
(Compound 118)
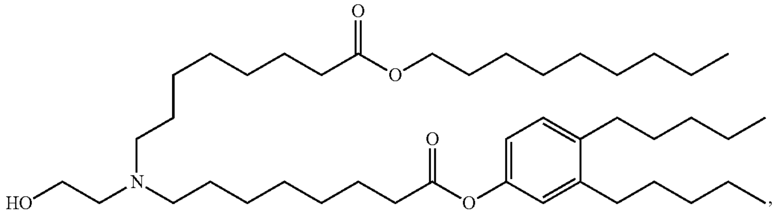
(Compound 119)
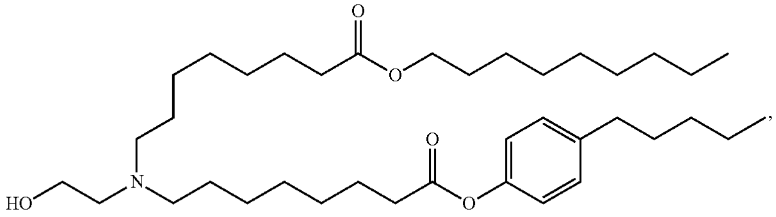
(Compound 120)
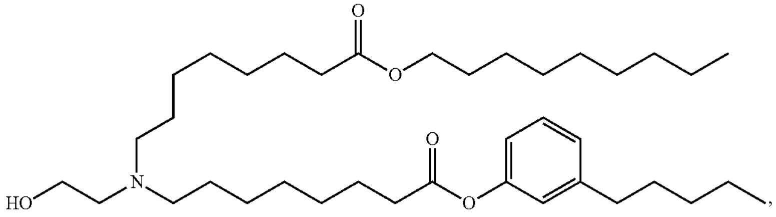
(Compound 121)
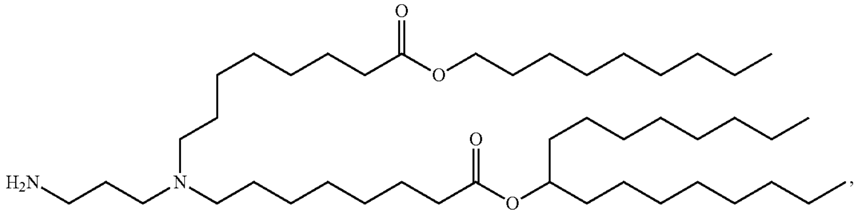
(Compound 122)
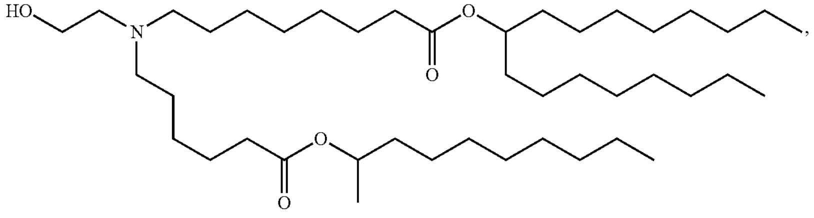
(Compound 123)
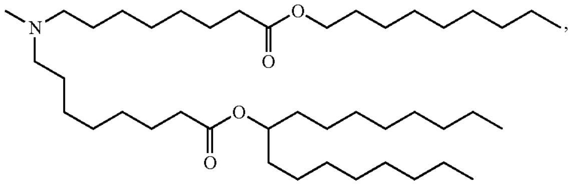
(Compound 124)
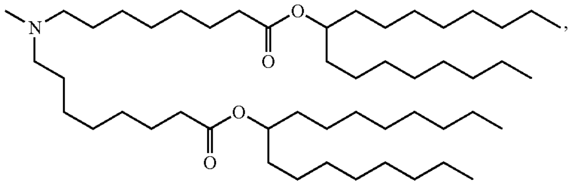

-continued
(Compound 125)
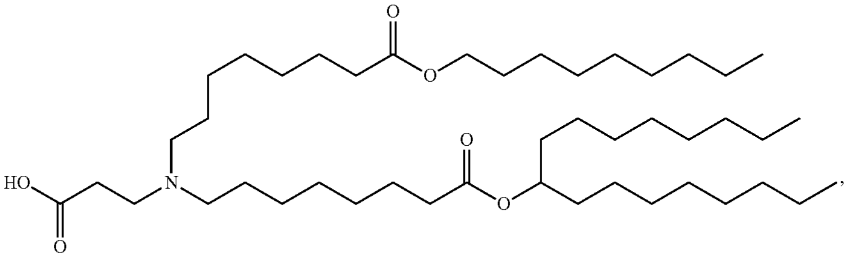
,
(Compound 126)
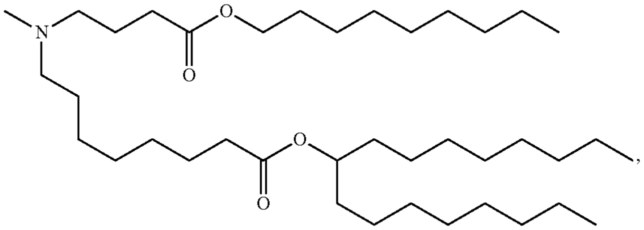
,
(Compound 127)
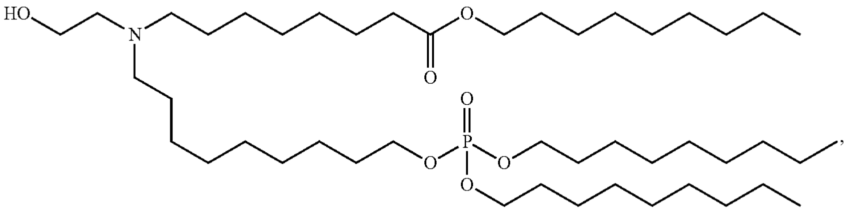
,
(Compound 128)
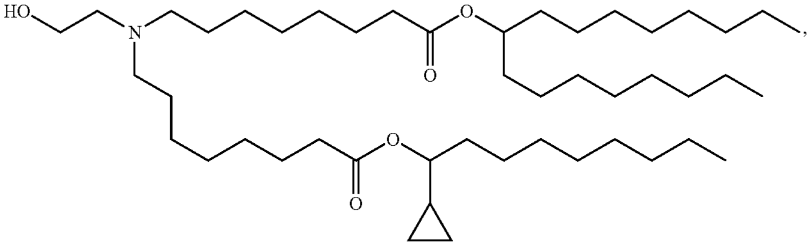
,
(Compound 129)
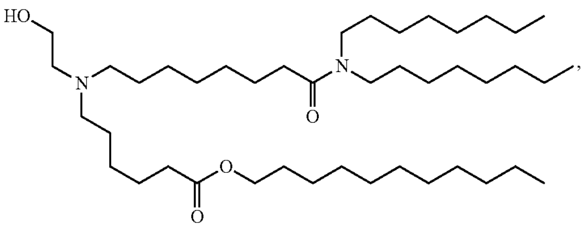
,
(Compound 130)
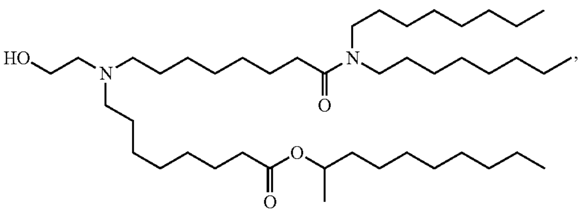
,
(Compound 131)
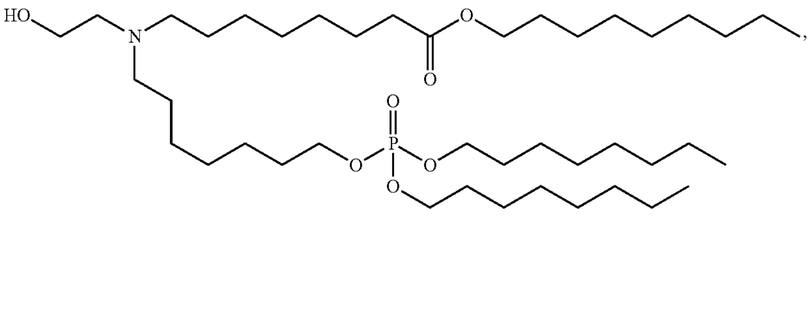
, -continued
(Compound 132)
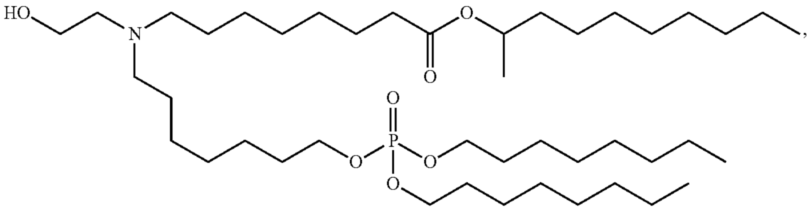
(Compound 133)
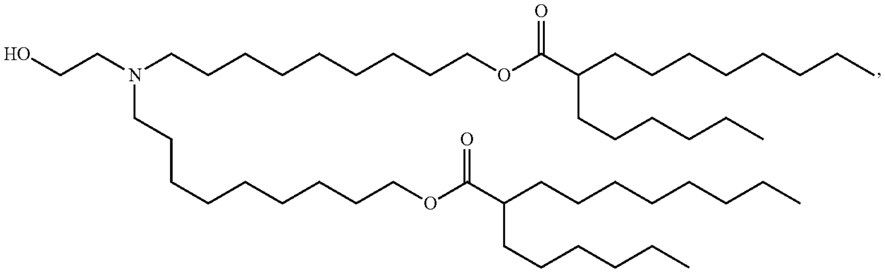
(Compound 134)
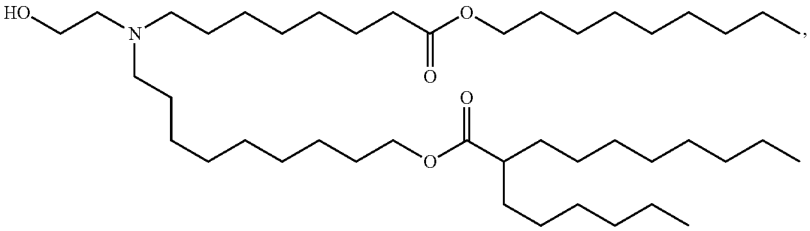
(Compound 135)
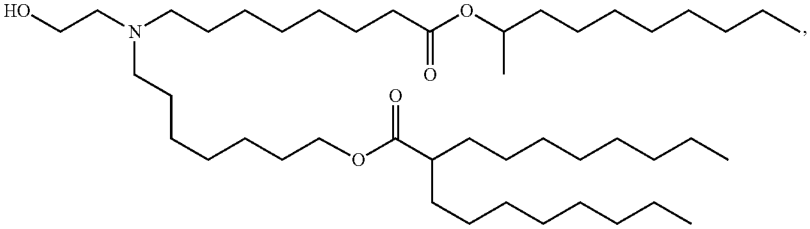
(Compound 136)
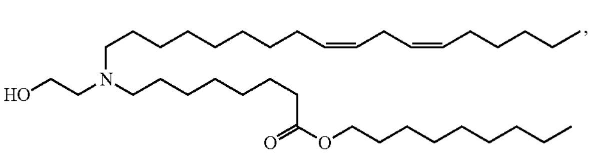
(Compound 137)
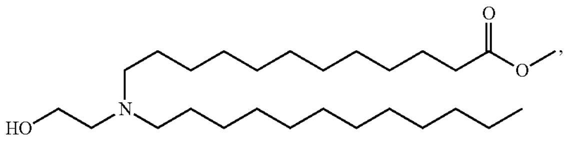
(Compound 138)
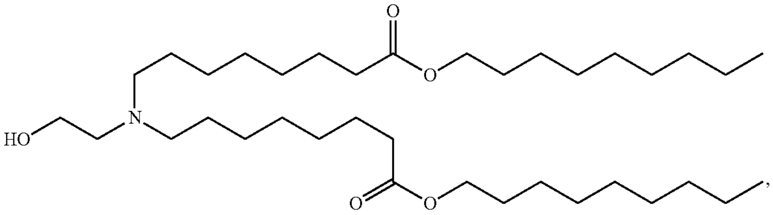
(Compound 139)
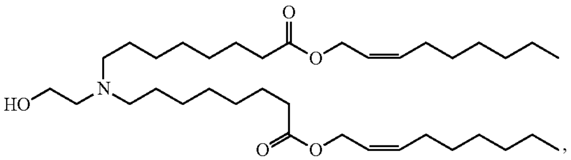
(Compound 140)
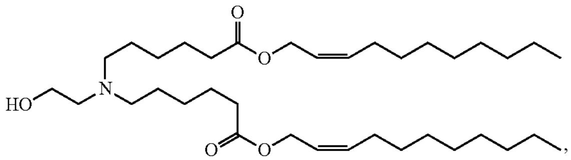

-continued
(Compound 141)
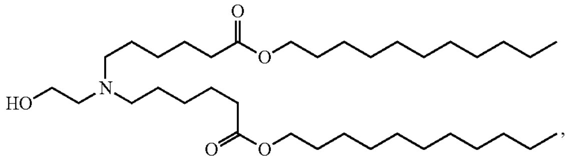
(Compound 142)
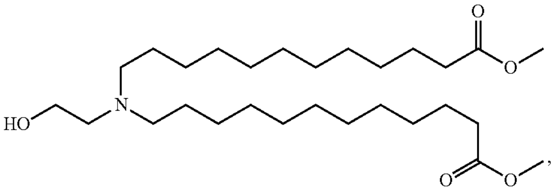
(Compound 143)
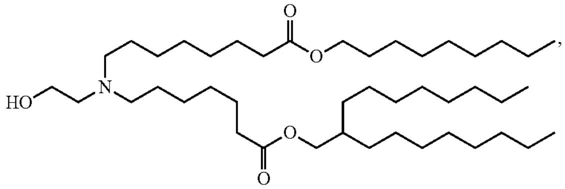
(Compound 144)
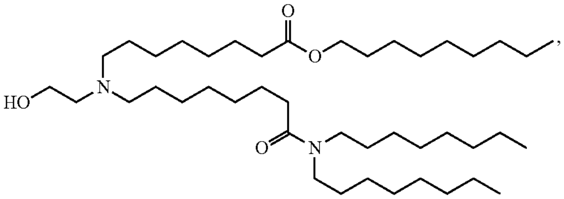
(Compound 145)
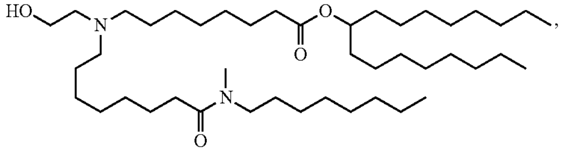
(Compound 146)
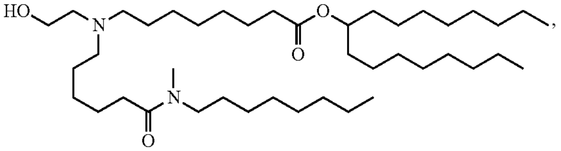
(Compound 147)
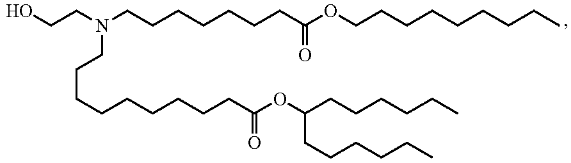
(Compound 148)
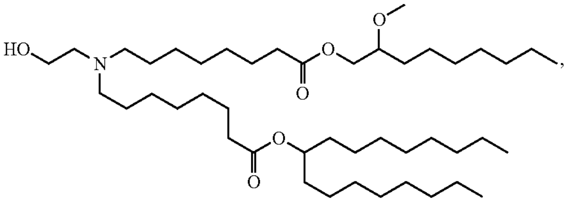
(Compound 149)
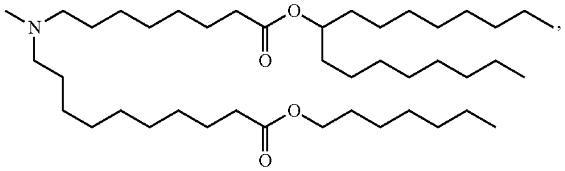
(Compound 150)
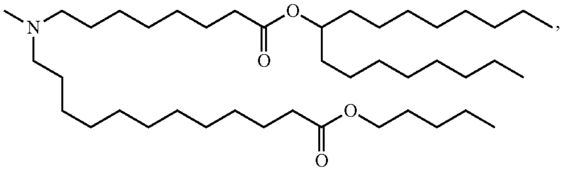
(Compound 151)
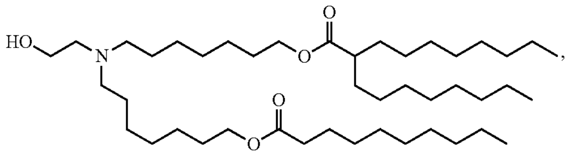
(Compound 152)
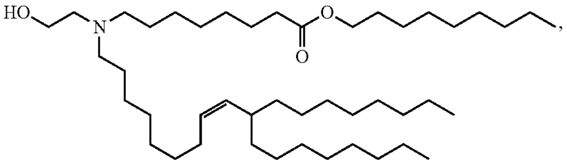
(Compound 153)
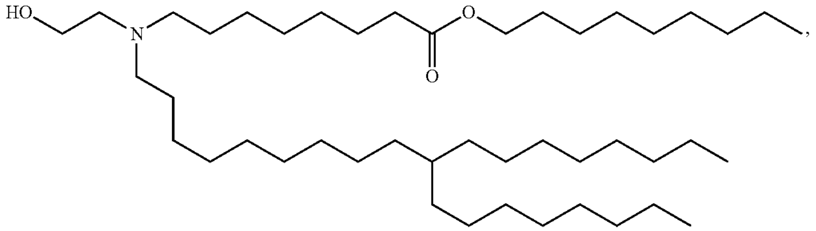

-continued
(Compound 154)
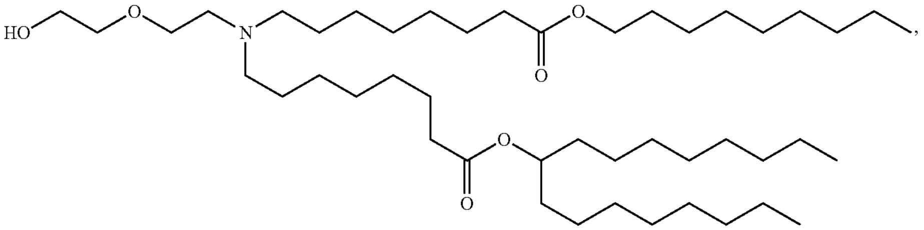
(Compound 155)
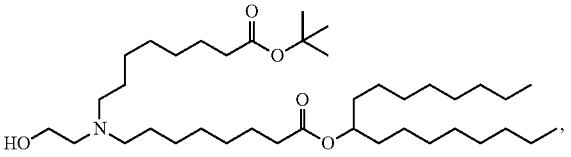
(Compound 156)
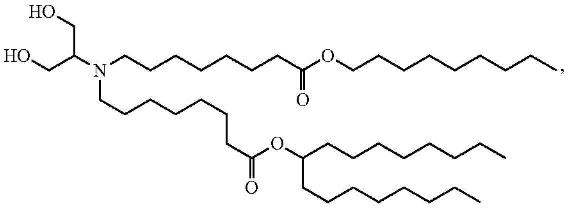
(Compound 157)
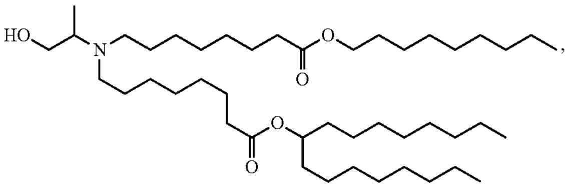
(Compound 158)
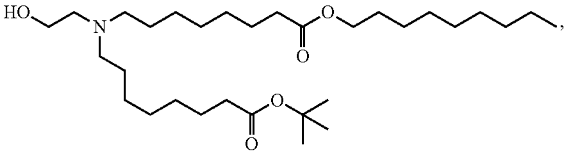
(Compound 159)
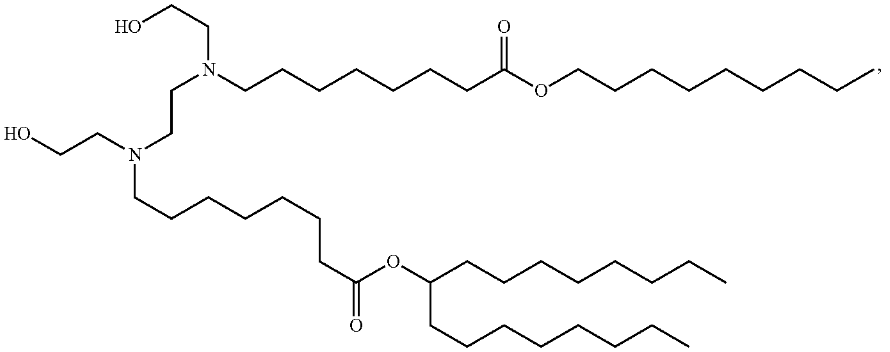
(Compound 160)
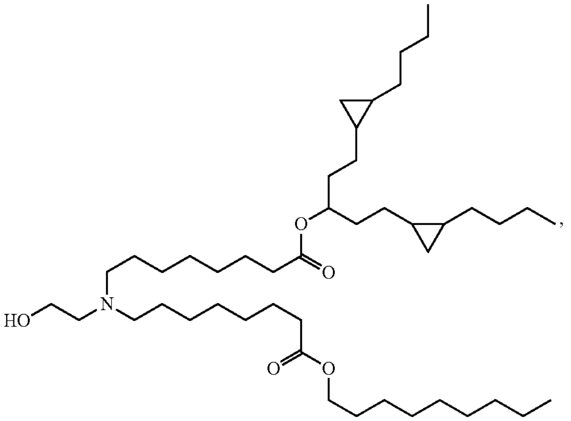
(Compound 161)
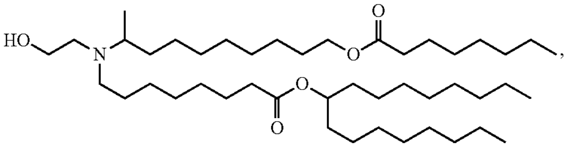

-continued
(Compound 162)
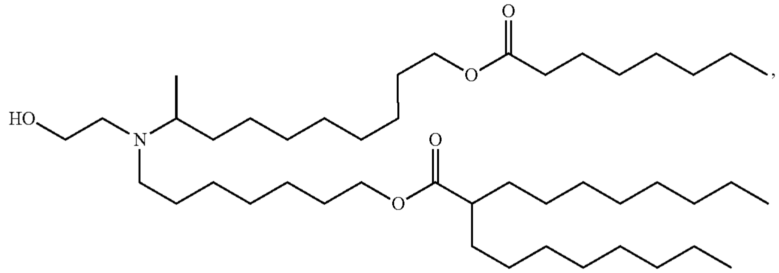
(Compound 163)
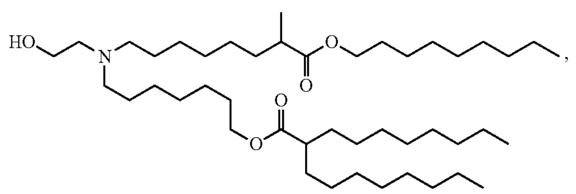
(Compound 164)
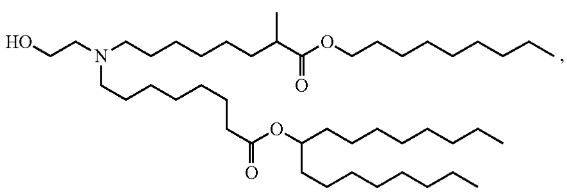
(Compound 165)
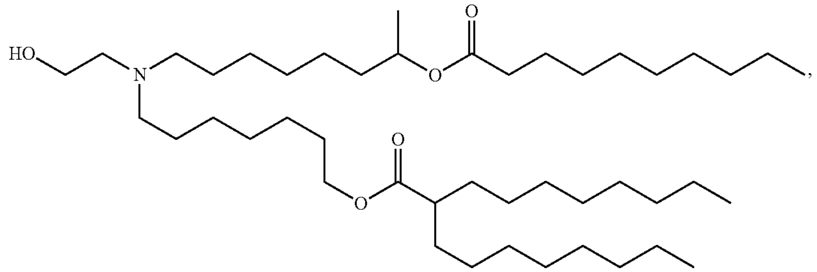
(Compound 166)
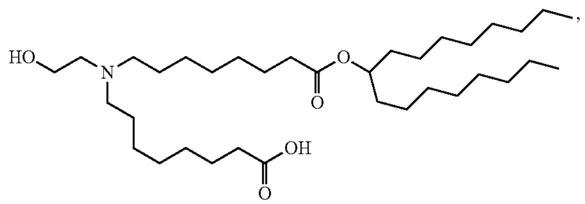
(Compound 167)
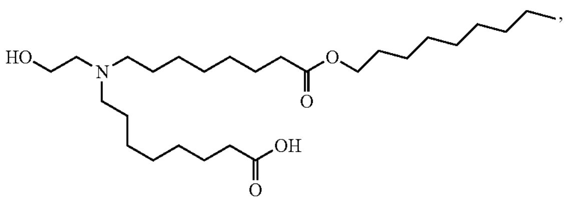
(Compound 168)
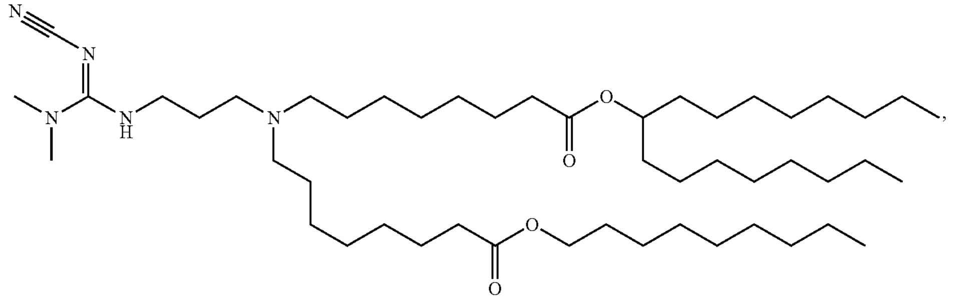
(Compound 169)
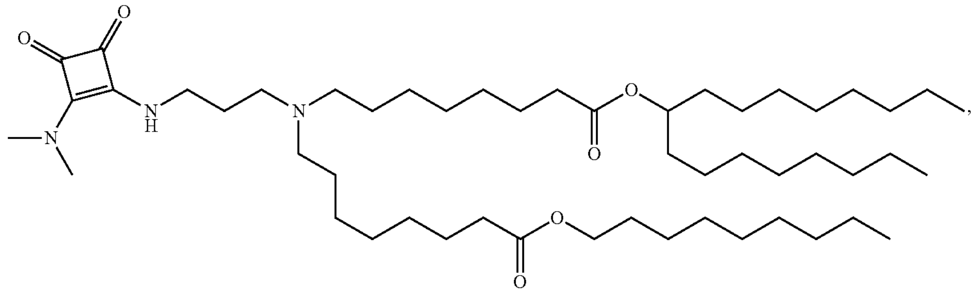

-continued
(Compound 170)
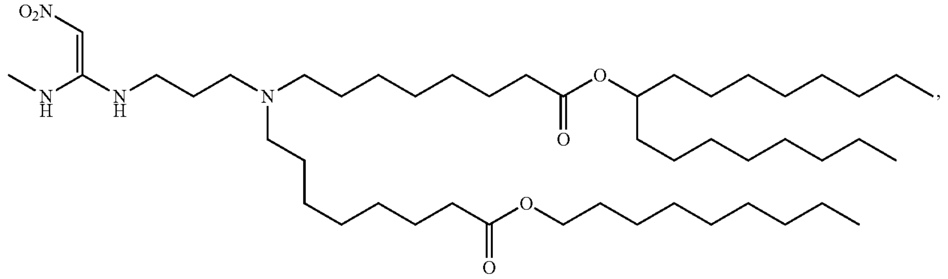
(Compound 171)
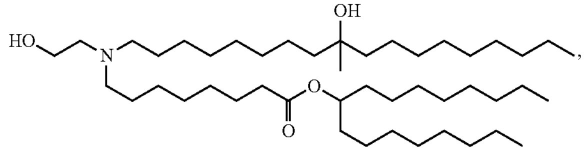
(Compound 172)
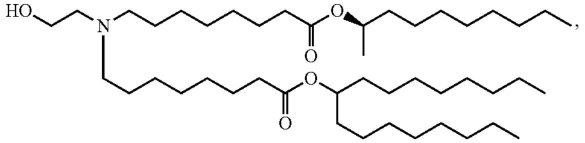
(Compound 173)
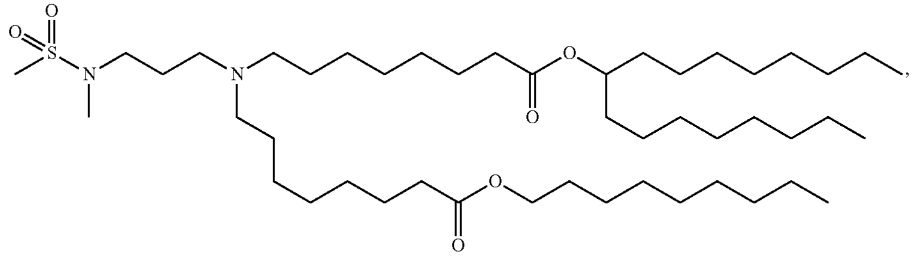
(Compound 174)
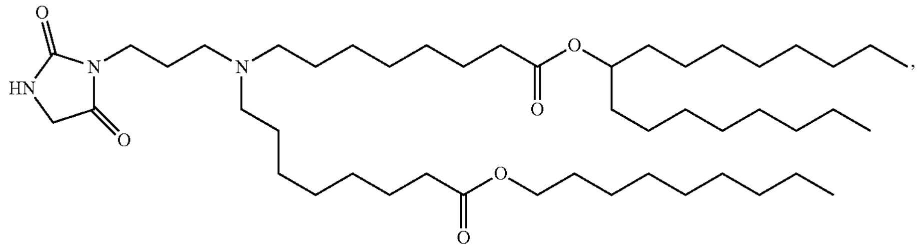
(Compound 175)
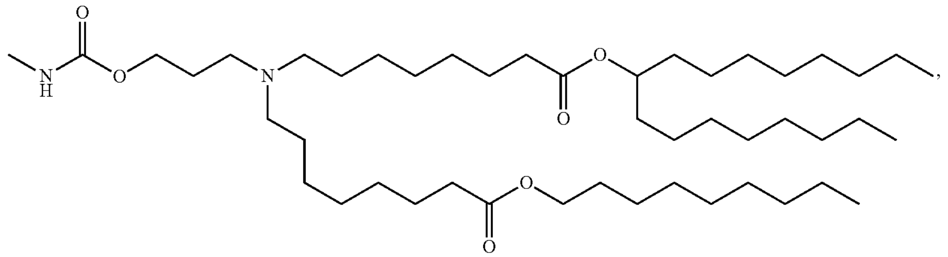
(Compound 176)
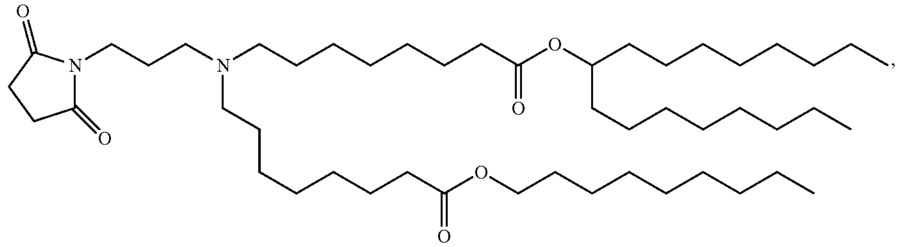

-continued
(Compound 177)
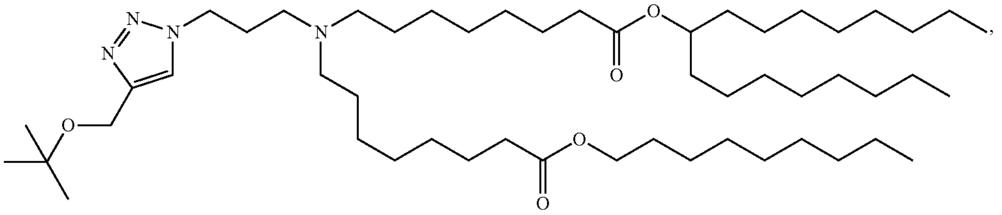
(Compound 178)
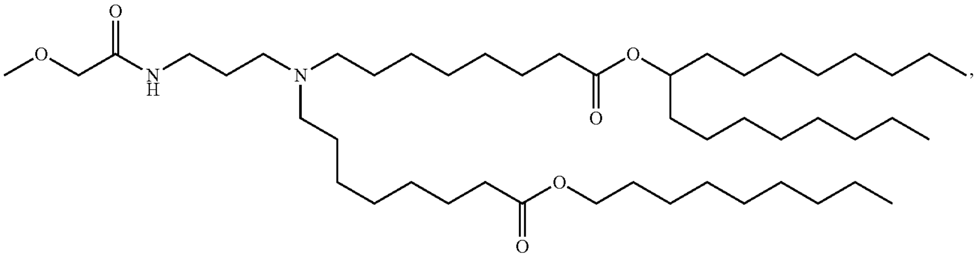
(Compound 179)
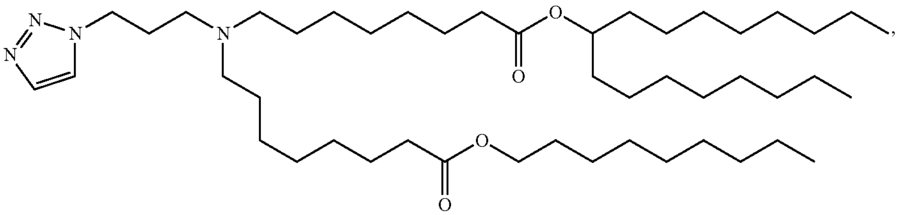
(Compound 180)
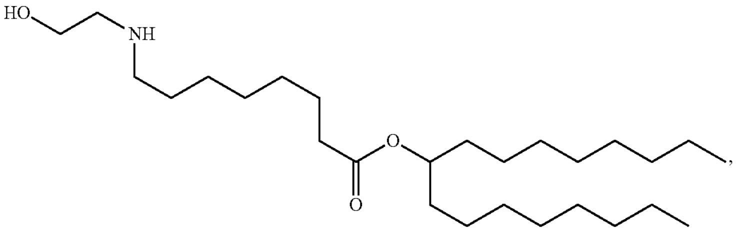
(Compound 181)
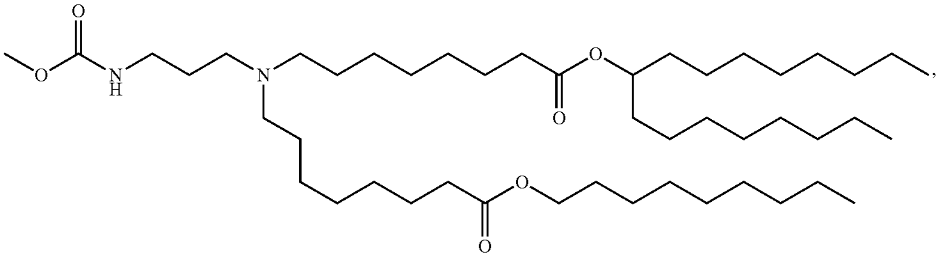
(Compound 182)
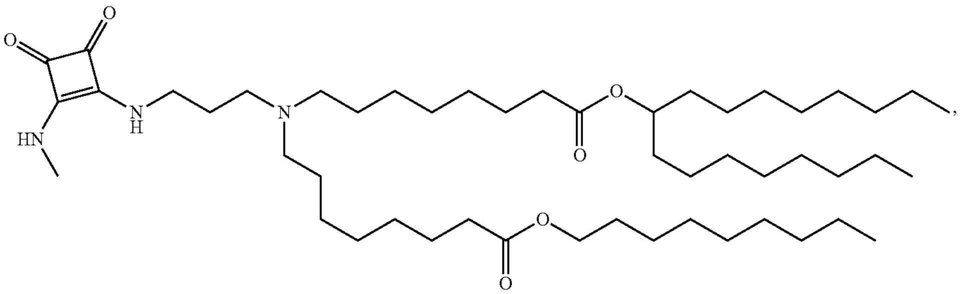

-continued
(Compound 183)
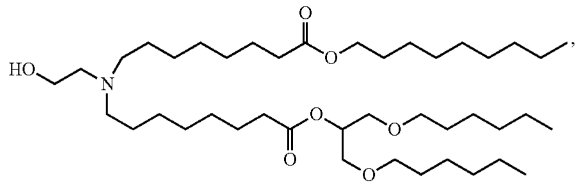
,
(Compound 184)
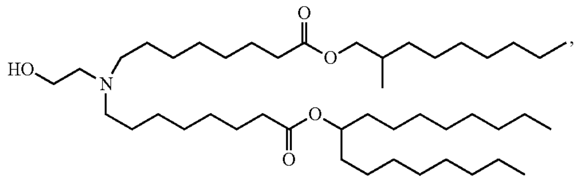
,
(Compound 185)
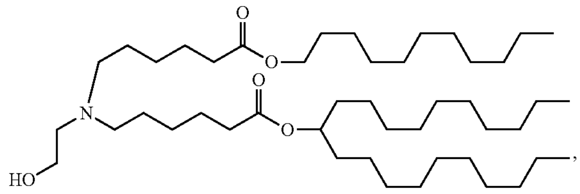
,
(Compound 186)
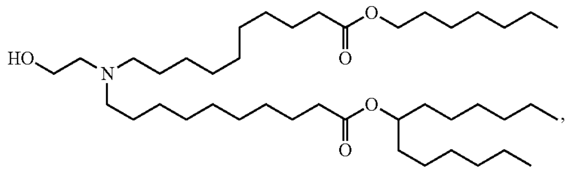
,
(Compound 187)
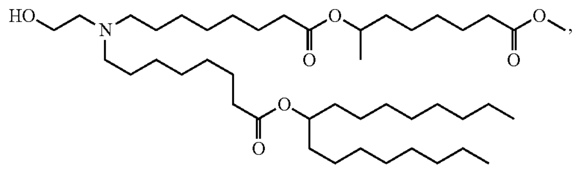
,
(Compound 188)
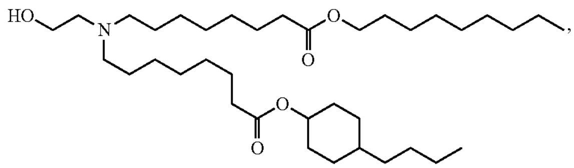
,
(Compound 189)
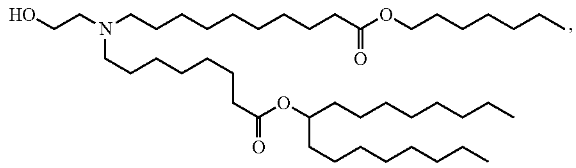
,
(Compound 190)
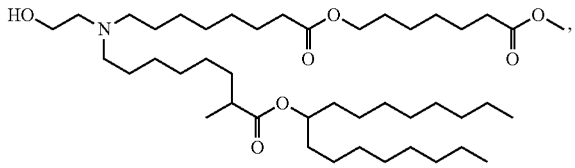
,
(Compound 191)
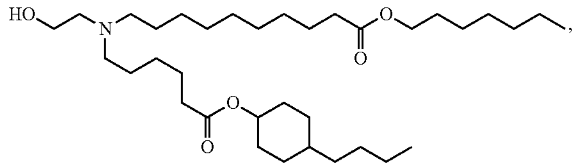
,
(Compound 192)
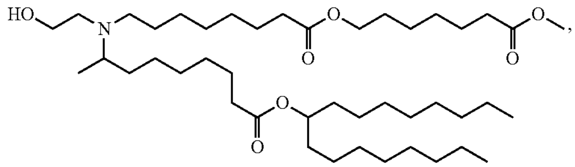
,
(Compound 193)
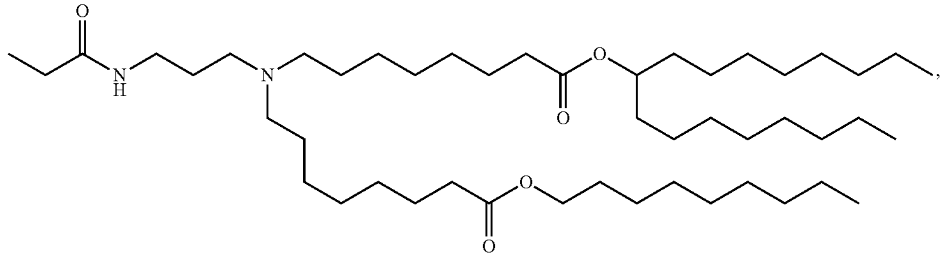
,
(Compound 194)
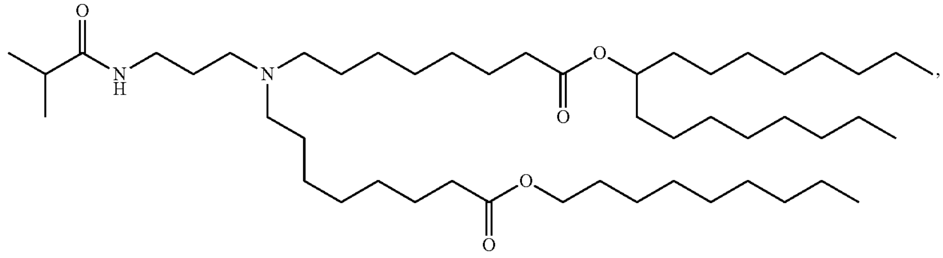
, -continued
(Compound 195)
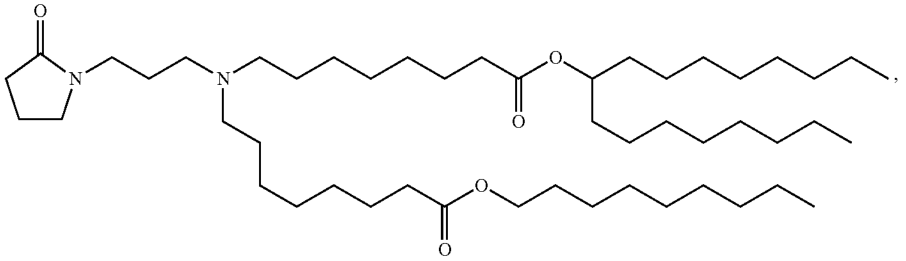
(Compound 196)
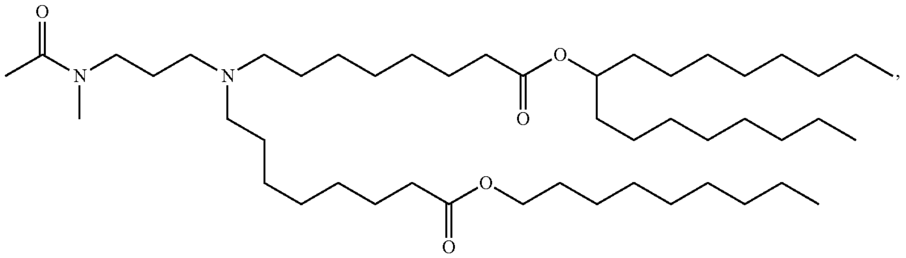
(Compound 197)
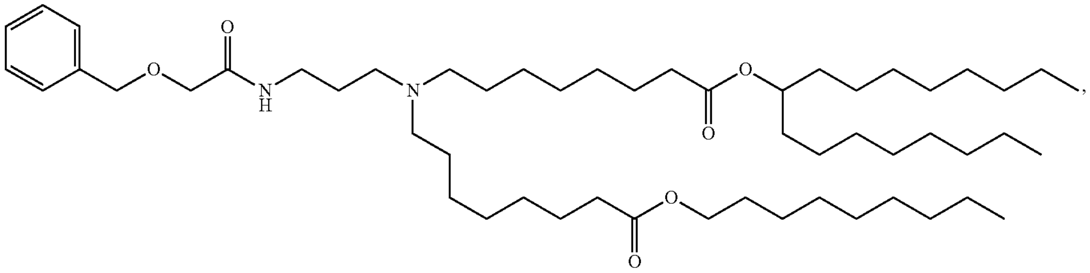
(Compound 198)
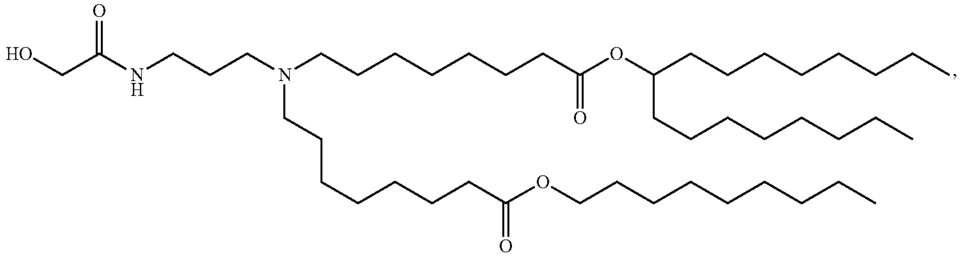
(Compound 199)
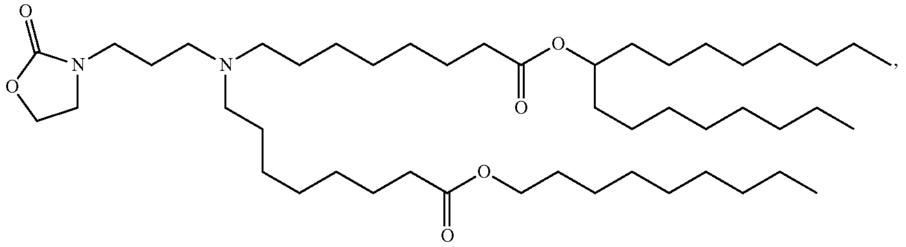
(Compound 200)
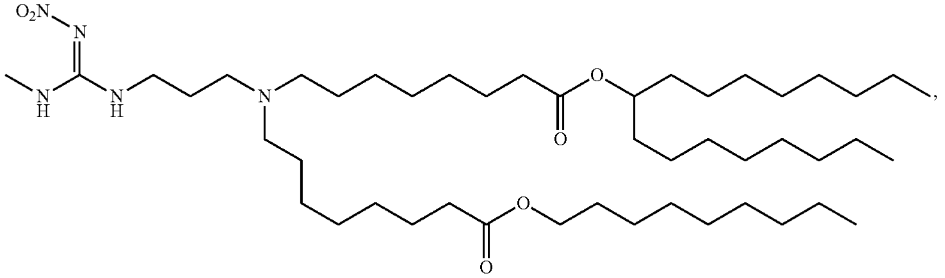

-continued
(Compound 201)
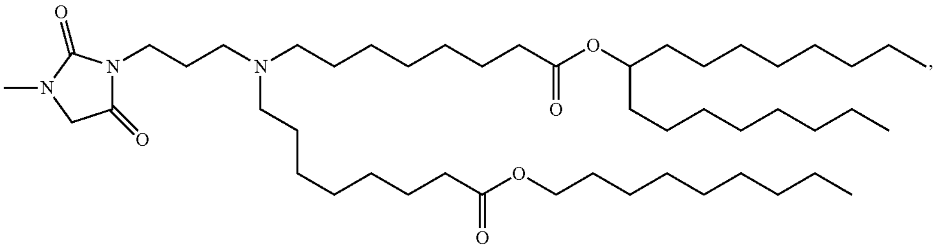
(Compound 202)
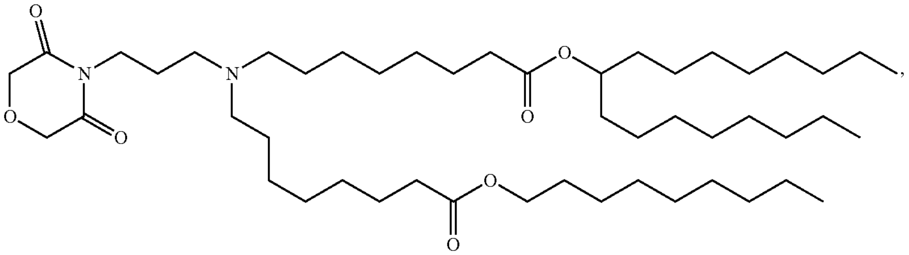
(Compound 203)
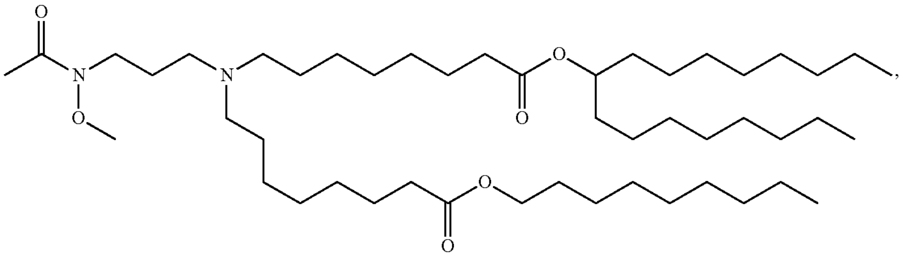
(Compound 204)
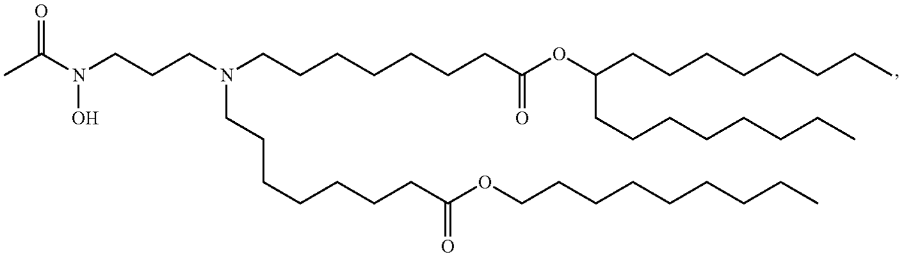
(Compound 205)
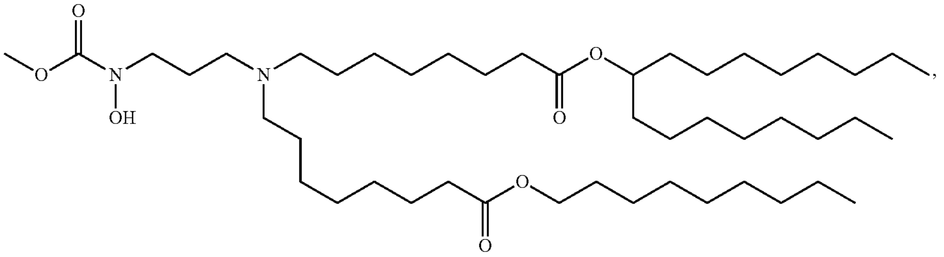
(Compound 206)
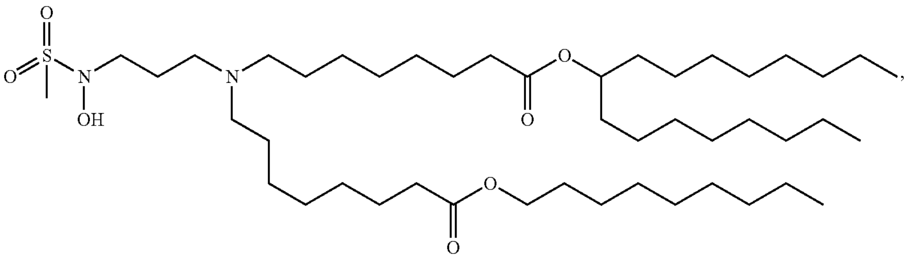

-continued
(Compound 207)
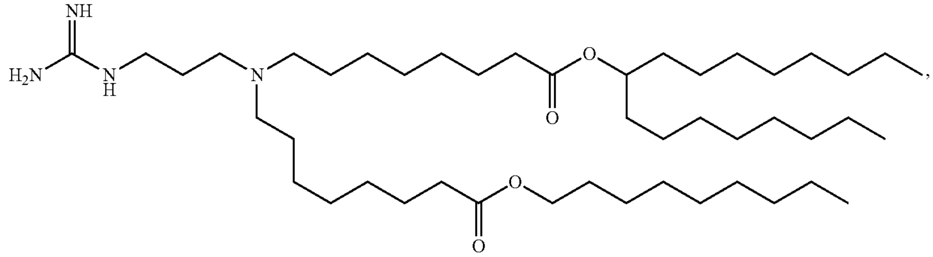
,
(Compound 208)
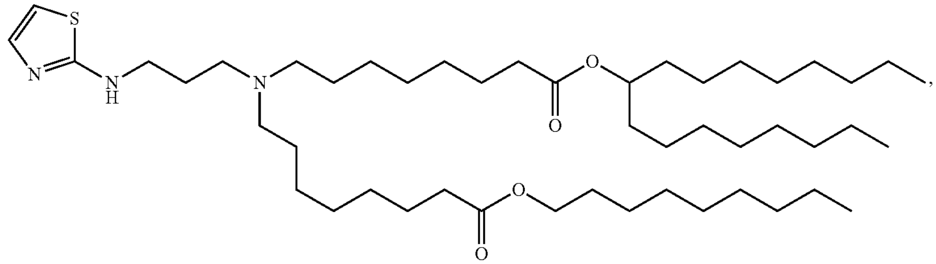
,
(Compound 209)
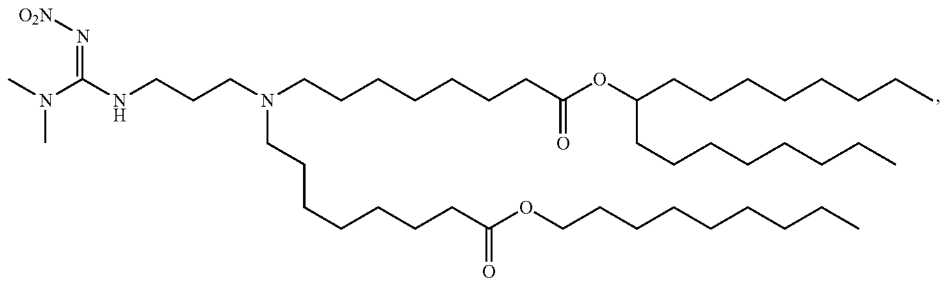
,
(Compound 210)
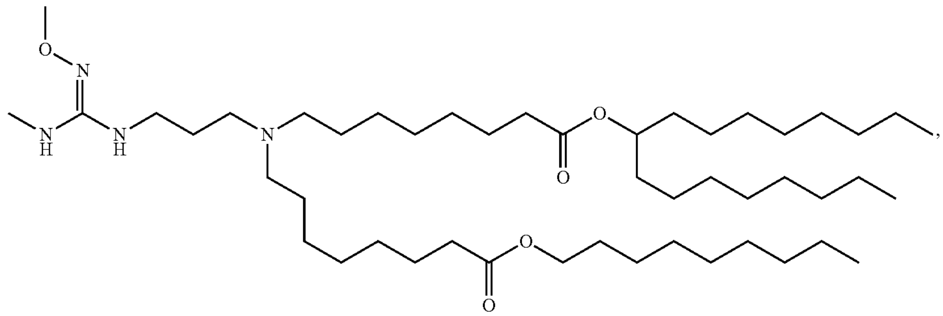
,
(Compound 211)
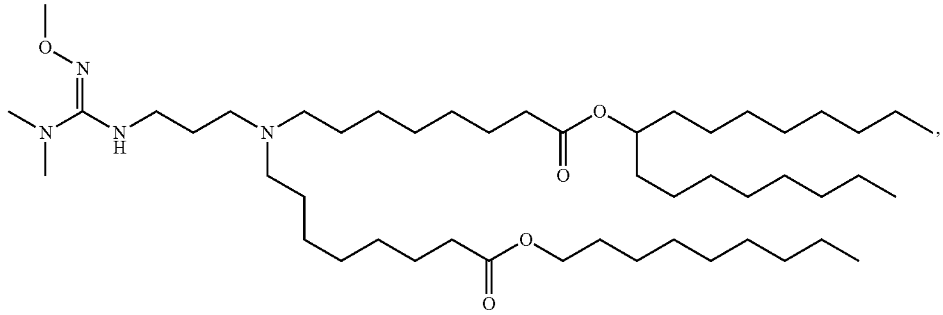
, -continued
(Compound 212)
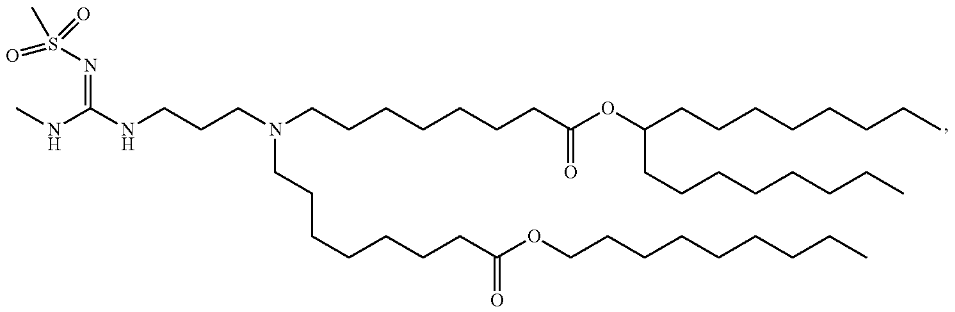
(Compound 213)
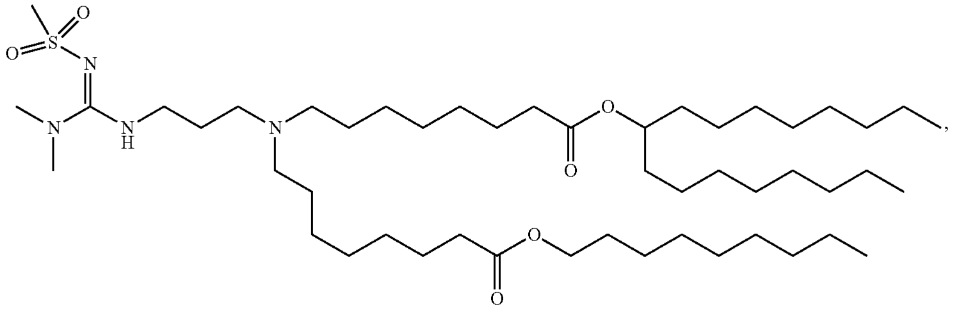
(Compound 214)
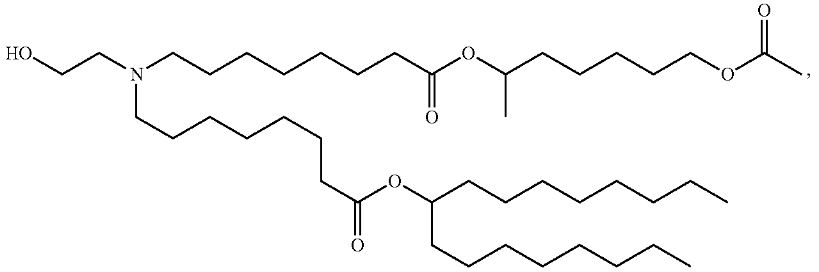
(Compound 215)
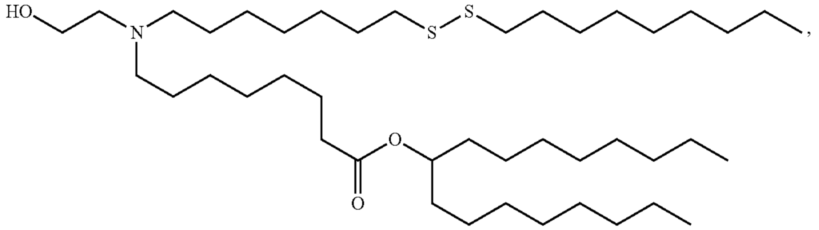
(Compound 216)
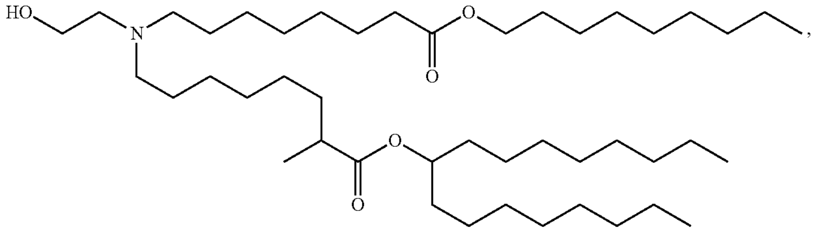
(Compound 217)
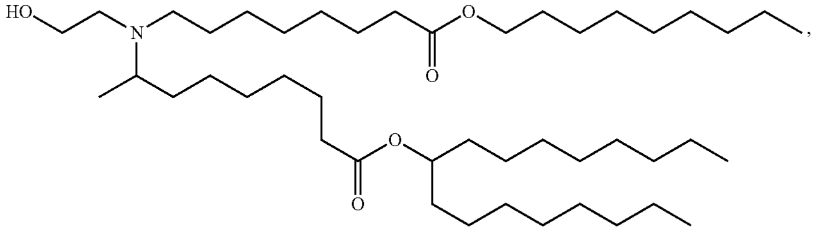

-continued
(Compound 218)
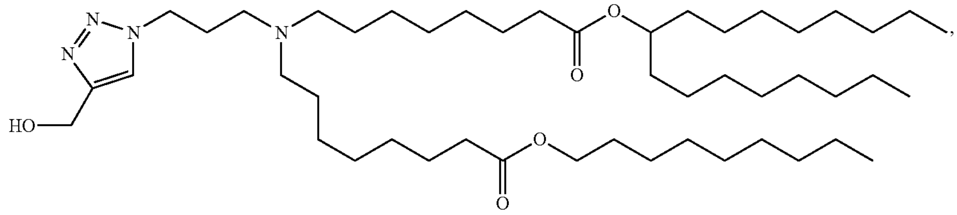
,
(Compound 219)
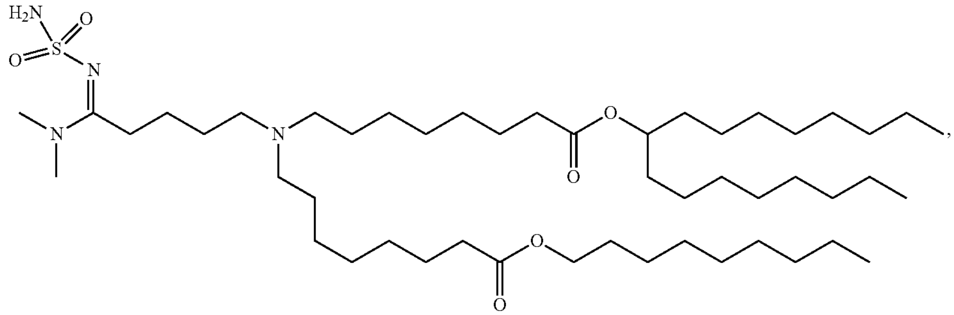
,
(Compound 220)
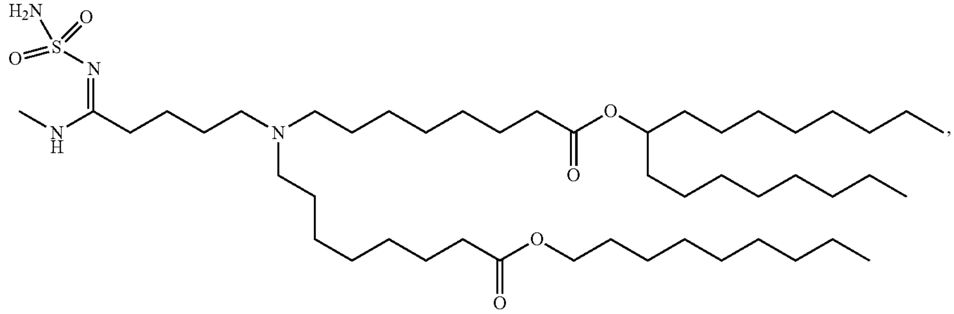
,
(Compound 221)
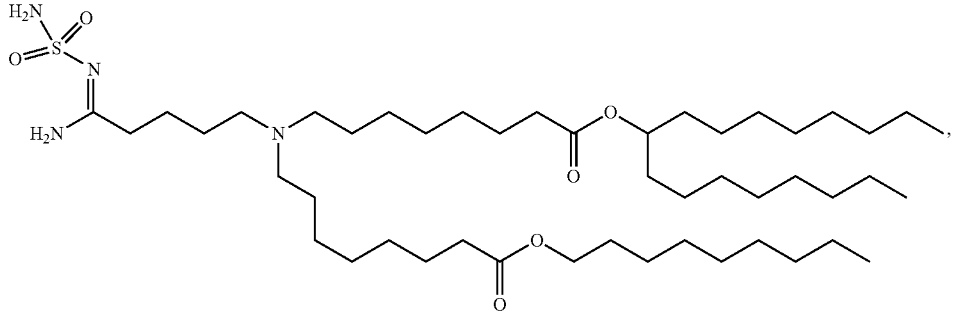
,
(Compound 222)
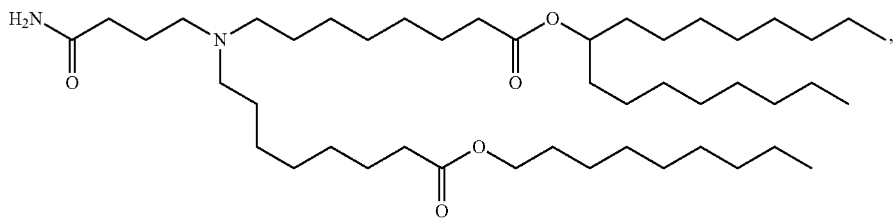
,
(Compound 223)
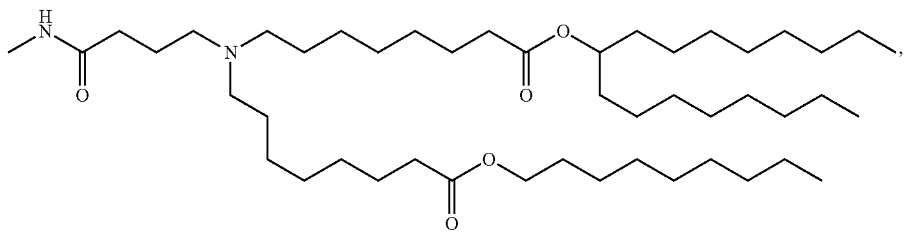
, -continued
(Compound 224)
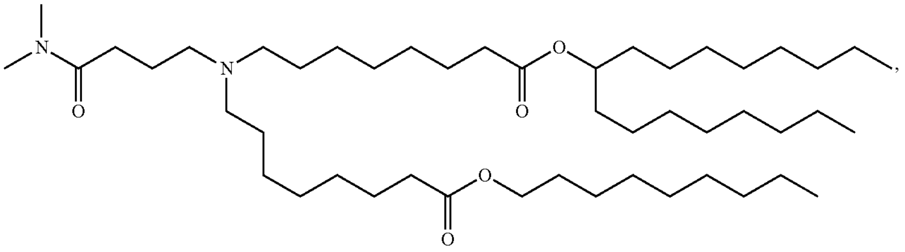
(Compound 225)
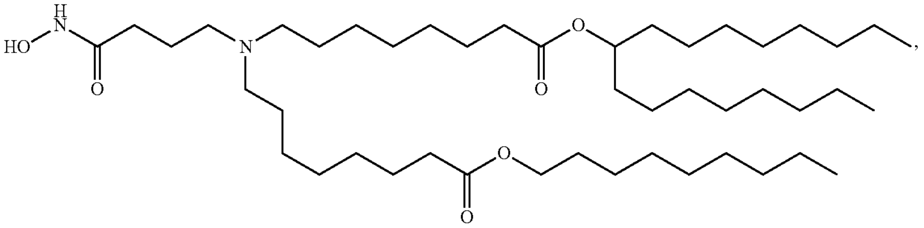
(Compound 226)
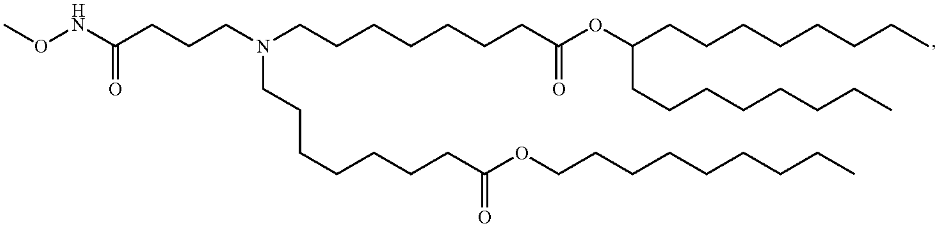
(Compound 227)
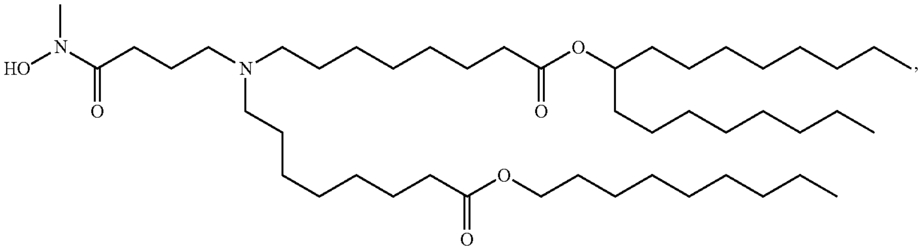
(Compound 228)
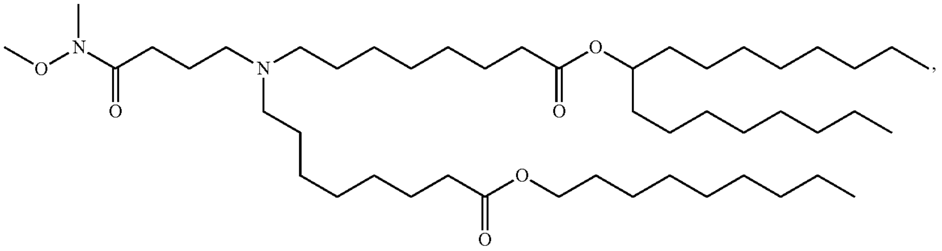
(Compound 229)
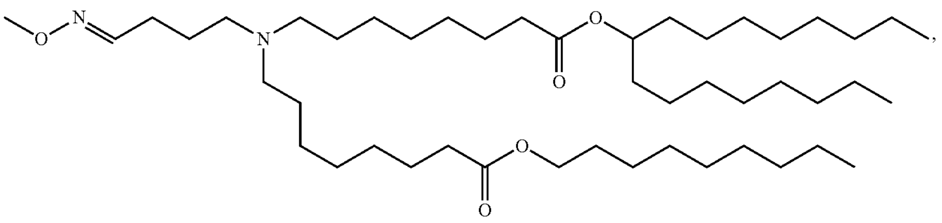

-continued
(Compound 230)
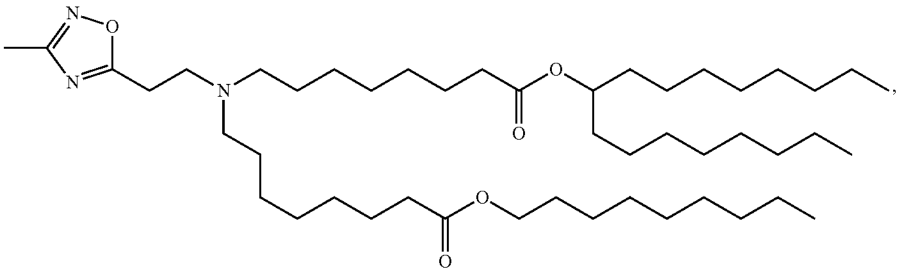
(Compound 231)
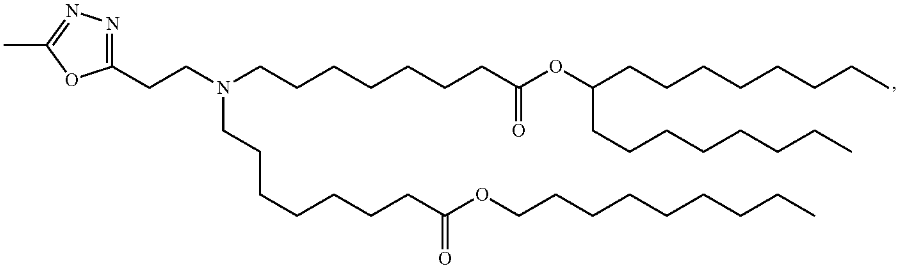
(Compound 232)
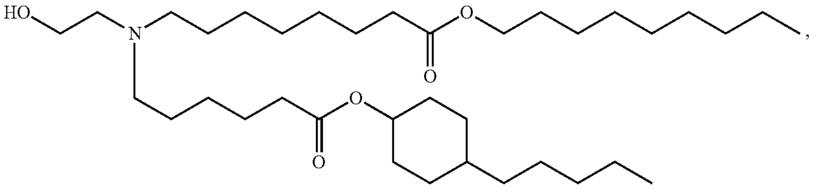
and salts and isomers thereof.
In some embodiments, a nanoparticle comprises the following compound:
(Compound 233)
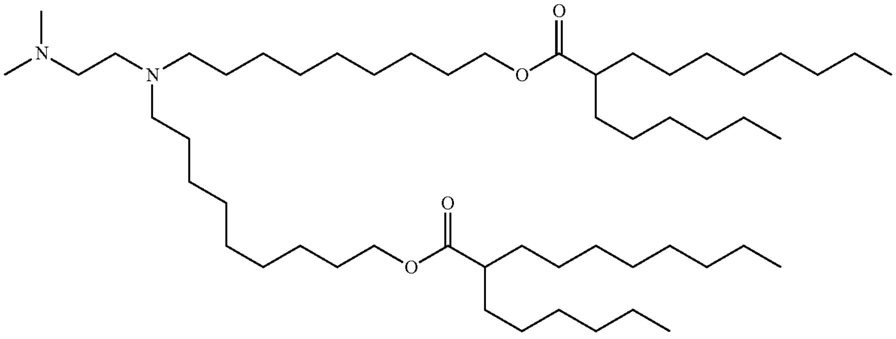
or salts and isomers thereof.

In some embodiments, the disclosure features a nanoparticle composition including a lipid component comprising a compound as described herein (e.g., a compound according to Formula (I), (IA), (II), (IIa), (IIb), (IIc), (IId) or (IIe)).

In some embodiments, a cationic lipid is an ionizable cationic lipid and the non-cationic lipid is a neutral lipid, and the sterol is a cholesterol. In some embodiments, a cationic lipid is selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate (L319), (12Z,15Z)—N,N-dimethyl-2-nonylhenicosa-12,15-dien-1-amine (L608), and N,N-dimethyl-1-[(1S,2R)-2-octylcyclopropyl]heptadecan-8-amine (L530).

In some embodiments, the lipid is (L608)

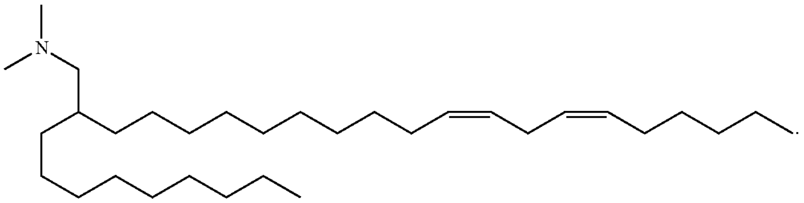

In some embodiments, the lipid is (L530)

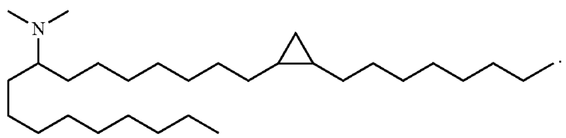

Multimeric Complexes

The RNA vaccines described herein can be assembled as multimeric complexes having non-covalent (e.g., hydrogen bonds) linkages between mRNA molecules. These types of multimeric structures allow for uniform distribution of the mRNA in a therapeutic composition. When multiple nucleic acids such as RNA are formulated, for instance, in a lipid based formulation, a relatively uniform distribution of the total nucleic acid through the formulation may be achieved. However, the distribution of a particular nucleic acid with respect to the other nucleic acids in the mixture is not uniform. For instance when the nucleic acid mixture is composed of two distinct mRNA sequences, some of the lipid particles or other formulatory agents will house a single mRNA sequence, while others will house the other mRNA sequence and a few will house both of the mRNA sequences. In a therapeutic context this uneven distribution of mRNA is undesirable because the dosage of the mRNA being delivered to a patient will vary from administration to administration. Quite surprisingly, the multimeric structures described herein have enabled the production of formulations having nucleic acids with a uniform distribution throughout the formulation. It was surprising that a non-covalent interaction between the individual nucleic acids would be capable of producing such a uniform distribution of the nucleic acids in a formulation. Additionally, the multimeric nucleic acid complexes do not interfere with activity such as mRNA expression activity.

In some embodiments the multimeric structures of the RNA polynucleotides making up the vaccine are uniformly distributed throughout a composition such as a lipid nanoparticle. Uniformly distributed, as used herein in the context of multiple nucleic acids (each having a unique nucleotide sequence), refers to the distribution of each of the nucleic acids relative to one another in the formulation. Distribution of the nucleic acids in a formulation may be assessed using methods known in the art. A nucleic acid is uniformly distributed relative to another nucleic acid if the nucleic acid is associated in proximity within a particular area of the formulation to the other nucleic acid at an approximately 1:1 ratio. In some embodiments the nucleic acid is uniformly distributed relative to another nucleic acid if the nucleic acid is positioned within a particular area of the formulation to the other nucleic acid at an approximately 1:1.1, 1:1.2, 1:1.3, 1:1.4, 1:1.5, 1:1.6, 1:1.7, 1:1.8, 1:1.9, or 1:2 ratio.

A multimeric structure as used herein is series of at least nucleic acids linked together to form a multimeric structure. In some embodiments a multimeric structure is composed of 2 or more, 3 or more, 4 or more, 5 or more 6 or more 7 or more, 8 or more, 9 or more nucleic acids. In other embodiments the multimeric structure is composed of 1000 or less, 900 or less, 500 or less, 100 or less, 75 or less, 50 or less, 40 or less, 30 or less, 20 or less or 100 or less nucleic acids. In yet other embodiments a multimeric structure has 3-100, 5-100, 10-100, 15-100, 20-100, 25-100, 30-100, 35-100, 40-100, 45-100, 50-100, 55-100, 60-100, 65-100, 70-100, 75-100, 80-100, 90-100, 5-50, 10-50, 15-50, 20-50, 25-50, 30-50, 35-50, 40-50, 45-50, 100-150, 100-200, 100-300, 100-400, 100-500, 50-500, 50-800, 50-1,000, or 100-1,000 nucleic acids. In preferred embodiments a multimeric structure is composed of 3-5 nucleic acids.

In some embodiments the upper limit on the number of nucleic acids in a multimeric structure depends on the length of dimerizable region. A greater than 20-nucleotide space between mRNAs can provide specificity and enough force to keep the multi-mRNA complex intact for downstream processing and is thus preferred in some embodiments. In some embodiments 4-5 nucleic acids in a multimeric structure may be desirable for vaccines.

The multimeric structures may be self-assembling multimeric mRNA structures composed of a first mRNA having a first linking region comprised of a part A and a part B and a second mRNA having a second linking region comprised of a part C and a part D, wherein at least part A of the first and at least part C of the second linking regions are complementary to one another. Preferably the nucleic acids are linked to one another through a non-covalent bond in the linking regions. The following is an exemplary linking region, wherein X is any nucleic acid sequence of 0-100 nucleotides and A and B are complementary parts, which are complementary to one or more other nucleic acids.

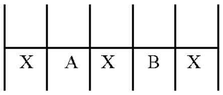

A linking region, as used herein, refers to a nucleic acid sequence having one or more regions or parts that are complementary to one or more regions of other linking regions. A pair of linking regions, each having one complementary region, may be at least 70% complementary to one another. In some embodiments a pair of linking regions are at least 75%, 80%, 85%, 90%, 95%, 96%, 97%, 98%, 99% or 100% complementary to one another. A linking region may be composed of sub-parts, optionally referred to as parts A, B, C, D, . . . , which have shorter regions of complementarity between one another, such that the sub-parts may be complementary with other sub-parts. For instance, a simple multimeric structure of two mRNAs can each have a linking region with a single region of complementarity. The two linking regions are able to form non-covalent interactions with one another through base pairing. More complex multimeric structures are also contemplated wherein a linking region of each nucleic acid has at least two parts, each part having complementarity with a part on another nucleic acid linking region. Linking regions having multiple parts with different complementarity enables the production of larger multimeric complexes of 3, 4, 5 or more nucleic acids.

The linking regions in some embodiments are 5-100 nucleotides in length. In other embodiments the linking regions are 10-25 nucleotides in length.

As used herein, the term "region of complementarity" refers to a region on a first nucleic acid strand that is substantially complementary to a second region on a second nucleic acid strand. Generally, two nucleic acids sharing a region of complementarity are capable, under suitable conditions, of hybridizing (e.g., via nucleic acid base pairing) to form a duplex structure. A region of complementarity can vary in size. In some embodiments, a region of complementarity ranges in length from about 2 base pairs to about 100 base pairs. In some embodiments, a region of complementarity ranges in length from about 5 base pairs to about 75 base pairs. In some embodiments, a region of complementarity ranges in length from about 10 base pairs to about 50 base pairs. In some embodiments, a region of complementarity ranges in length from about 20 base pairs to about 30 base pairs.

The number of nucleic acid bases shared between two nucleic acids across a region of complementarity can vary. In some embodiments, two nucleic acids share 100% complementary base pairs (e.g., no mismatches) across a region of complementarity. In some embodiments, two nucleic acids share at least 99.9%, at least 95%, at least 90%, at least 85%, at least 80%, at least 75% or at least 70% complementary base pairs across a region of complementarity. In some embodiments, a region of complementarity shared between two nucleic acids includes at least 1, at least 2, at least 3, at least 4, at least 5, at least 6, at least 7, at least 8, at least 9, or at least 10 base pair mismatches. In some embodiments, a region of complementarity shared between two nucleic acids includes more than 10 base pair mismatches.

As used herein, the term "non-covalent bond" refers to a chemical interaction (e.g., joining) between molecules that does not involve the sharing of electrons. Generally, non-covalent bonds are formed via electromagnetic interactions between charged molecules. Examples of non-covalent bonds include, but are not limited to, ionic bonds, hydrogen bonds, halogen bonds, Van der Waals forces (e.g., dipole-dipole interactions, London dispersion forces, etc.), π-effects (π-π interactions, cation-π interactions, anion-π interactions), and hydrophobic effect.

In some embodiments, at least one non-covalent bond formed between the nucleic acid molecules (e.g., mRNA molecules) of a multimeric molecule is a result of Watson-Crick base-pairing. The term "Watson-Crick base-pairing", or "base-pairing" refers to the formation of hydrogen bonds between specific pairs of nucleotide bases ("complementary base pairs"). For example, two hydrogen bonds form between adenine (A) and uracil (U), and three hydrogen bonds form between guanine (G) and cytosine (C). One method of assessing the strength of bonding between two polynucleotides is by quantifying the percentage of bonds formed between the guanine and cytosine bases of the two polynucleotides ("GC content"). In some embodiments, the GC content of bonding between two nucleic acids of a multimeric molecule (e.g., a multimeric mRNA molecule) is at least 10%, at least 20%, at least 30%, at least 40%, or at least 50%. In some embodiments, the GC content of bonding between two nucleic acids of a multimeric molecule (e.g., a multimeric mRNA molecule) is between 10% and 70%, about 20% to about 60%, or about 30% to about 60%. The formation of a nucleic acid duplex via bonding of complementary base pairs can also be referred to as "hybridization".

In some embodiments, two nucleic acid molecules (e.g., mRNA molecules) hybridize to form a multimeric molecule. Hybridization can result from the formation of at least 1, at least 2, at least 3, at least 4, at least 5, at least 6, at least 7, at least 8, at least 9, or at least 10 non-covalent bonds between two polynucleotides (e.g., mRNA molecules). In some embodiments, between about 2 non-covalent bonds and about 10 non-covalent bonds are formed between two nucleic acid molecules. In some embodiments, between about 5 and about 15 non-covalent bonds are formed between two nucleic acid molecules. In some embodiments, between about 10 and about 20 non-covalent bonds are formed between two nucleic acid molecules. In some embodiments, between about 15 and about 30 non-covalent bonds are formed between two nucleic acid molecules. In some embodiments, between about 20 and about 50 non-covalent bonds are formed between two nucleic acid molecules. In some embodiments, the number of non-covalent bonds formed between two nucleic acid molecules (e.g., mRNA molecules) is 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 non-covalent bonds.

In some embodiments the self-assembling multimeric mRNA structure is comprised of at least 2-100 mRNAs each mRNA having a linking region and a stabilizing nucleic acid, wherein the stabilizing nucleic acid has a nucleotide sequence with regions complementary to each linking region. A stabilizing nucleic acid as used herein is any nucleic acid that has multiple linking regions and is capable of forming non-covalent interactions with at least 2, but more preferably, 3, 4, 5, 6,7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 other nucleic acids. For instance the stabilizing nucleic acid may have the following structure: $L_1X_1L_2X_2L_3X_3L_4X_4L_5X_5L_6X_6$ wherein L is a nucleic acid sequence complementary to a linking region and wherein x is any nucleic acid sequence 0-50 nucleotides in length. Such a structure may look like the following:

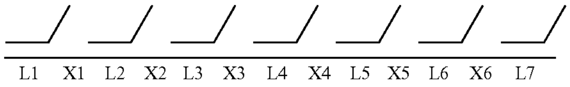

In some embodiments, a multimeric mRNA molecule comprises a first mRNA and a second mRNA, wherein the first mRNA and the second mRNA are non-covalently linked to one another through a splint. As used herein, the term "splint" refers to an oligonucleotide having a first region of complementarity with the first nucleic acid and a second region of complementarity with the second nucleic acid. A splint can be a DNA oligonucleotide or an RNA oligonucleotide. In some embodiments, a splint comprises one or more modified oligonucleotides. In some embodiments, a splint is non-covalently linked to a 5'UTR of an mRNA. In some embodiments, a splint is non-covalently linked to a 3'UTR of an mRNA.

In some embodiments, non-covalent bonds between nucleic acid molecules (e.g., mRNA molecules) are formed in a non-coding region of each molecule. As used herein, the term "non-coding region" refers to a location of a polynucleotide (e.g., an mRNA) that is not translated into a protein. Examples of non-coding regions include regulatory regions (e.g., DNA binding domains, promoter sequences, enhancer sequences), and untranslated regions (e.g., 5'UTR, 3'UTR). In some embodiments, the non-coding region is an untranslated region (UTR).

By definition, wild type untranslated regions (UTRs) of a gene are transcribed but not translated. In mRNA, the 5'UTR starts at the transcription start site and continues to the start codon but does not include the start codon; whereas, the 3'UTR starts immediately following the stop codon and continues until the transcriptional termination signal.

Natural 5'UTRs bear features which play roles in translation initiation. They harbor signatures like Kozak sequences which are commonly known to be involved in the process by which the ribosome initiates translation of many genes. Kozak sequences have the consensus CCR(A/G) CCAUGG, where R is a purine (adenine or guanine) three bases upstream of the start codon (AUG), which is followed by another 'G'. 5'UTR also have been known to form secondary structures which are involved in elongation factor binding.

It should be understood that any UTR from any gene may be incorporated into the regions of the polynucleotide. Furthermore, multiple wild-type UTRs of any known gene may be utilized. It is also within the scope of the present invention to provide artificial UTRs which are not variants of wild type regions. These UTRs or portions thereof may be placed in the same orientation as in the transcript from which they were selected or may be altered in orientation or location. Hence a 5' or 3' UTR may be inverted, shortened, lengthened, made with one or more other 5' UTRs or 3' UTRs. As used herein, the term "altered" as it relates to a UTR sequence, means that the UTR has been changed in some way in relation to a reference sequence. For example, a 3' or 5' UTR may be altered relative to a wild type or native UTR by the change in orientation or location as taught above or may be altered by the inclusion of additional nucleotides, deletion of nucleotides, swapping or transposition of nucleotides. Any of these changes producing an "altered" UTR (whether 3' or 5') comprise a variant UTR.

In some embodiments, a double, triple or quadruple UTR such as a 5' or 3' UTR may be used. As used herein, a "double" UTR is one in which two copies of the same UTR are encoded either in series or substantially in series.

It is also within the scope of the present invention to have patterned UTRs. As used herein "patterned UTRs" are those UTRs which reflect a repeating or alternating pattern, such as ABABAB or AABBAABBAABB or ABCABCABC or variants thereof repeated once, twice, or more than 3 times. In these patterns, each letter, A, B, or C represent a different UTR at the nucleotide level.

In some embodiments, flanking regions are selected from a family of transcripts whose proteins share a common function, structure, feature of property. For example, polypeptides of interest may belong to a family of proteins which are expressed in a particular cell, tissue or at some time during development. The UTRs from any of these genes may be swapped for any other UTR of the same or different family of proteins to create a new polynucleotide. As used herein, a "family of proteins" is used in the broadest sense to refer to a group of two or more polypeptides of interest which share at least one function, structure, feature, localization, origin, or expression pattern. The untranslated region may also include translation enhancer elements (TEE).

In some embodiments, an UTR of a polynucleotide (e.g., a first nucleic acid) of the present invention is engineered or modified to have regions of complementarity with an UTR of another polynucleotide (a second nucleic acid). For example, UTR nucleotide sequences of two polynucleotides sought to be joined (e.g., in a multimeric molecule) can be modified to include a region of complementarity such that the two UTRs hybridize to form a multimeric molecule.

In some embodiments, the 5'UTR of an RNA polynucleotide encoding an HCMV antigenic polypeptide is modified to allow the formation of a multimeric sequence. In some embodiments, the 5'UTR of an RNA polynucleotide encoding an HCMV protein selected from gH, gL, gB, gO, gM, gM, UL128, UL130, UL131A1 is modified to allow the formation of a multimeric sequence. In some embodiments, the 5'UTR of an RNA polynucleotide encoding an HCMV protein selected from UL128, UL130, UL131A1 is modified to allow the formation of a multimeric sequence. In some embodiments, the 5'UTR of an RNA polynucleotide encoding an HCMV glycoprotein is modified to allow the formation of a multimeric sequence. In some embodiments, the 5'UTR of an RNA polynucleotide encoding an HCMV glycoprotein selected from gH, gL, gB, gO, gM, and gM is modified to allow the formation of a multimeric sequence. In any of these embodiments, the multimer may be a dimer, a trimer, pentamer, hexamer, heptamer, octamer nonamer, or decamer. In any of these embodiments, the multimer may be a homogenous multimer, that is, it may comprise dimers, trimers, pentamers etc having sequence encoding the same HCMV antigenic polypeptide. In any of these embodiments, the multimer may be a heterogeneous multimer comprising dimers, trimers, pentamers etc having sequence encoding different HCMV antigenic polypeptides, for example two different antigenic polypeptides, three different antigenic polypeptides, four different antigenic polypeptide, five different antigenic polypeptides, etc. Exemplary HCMV nucleic acids having modified 5'UTR sequence for the formation of a multimeric molecule (e.g., dimers, trimers, pentamers, etc) comprise SEQ ID Nos: 19-26.

In some embodiments the RNA vaccine may be associated with a cationic or polycationic compounds, including protamine, nucleoline, spermine or spermidine, or other cationic peptides or proteins, such as poly-L-lysine (PLL), polyarginine, basic polypeptides, cell penetrating peptides (CPPs), including HIV-binding peptides, HIV-1 Tat (HIV), Tat-derived peptides, Penetratin, $VP^{22}$ derived or analog peptides, Pestivirus Erns, HSV, $VP^{22}$ (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila* antennapedia), pAntp, pIsl, FGF, Lactoferrin, Transportan, Buforin-2, Bac715-24, SynB, SynB(1), pVEC, hCT-derived peptides, SAP, histones, cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristooxypropyl dimethyl hydroxyethyl ammonium bromide, DOTAP: dioleoyloxy-3-(trimethylammonio)propane, DC-6-14: O,O-ditetradecanoyl-N-.alpha.-trimethylammonioacetyl)diethanolamine chloride, CLIP 1: rac-[(2,3-dioctadecyloxypropyl)(2-hydroxyethyl)]-dimethylammonium chloride, CLIP6: rac-[2(2,3-dihexadecyloxypropyloxymethyloxy)ethyl]-trimethylammonium, CLIP9: rac-[2(2,3-dihexadecyloxypropyloxysuccinyloxy)ethyl]-trimethylammo-nium, oligofectamine, or cationic or polycationic polymers, e.g. modified polyaminoacids, such as beta-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified amidoamines such as pAMAM (poly(amidoamine)), etc., modified polybetaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole); etc.

In other embodiments the RNA vaccine is not associated with a cationic or polycationic compounds.

Modes of Vaccine Administration

HCMV RNA vaccines may be administered by any route which results in a therapeutically effective outcome. These include, but are not limited, to intradermal, intramuscular, and/or subcutaneous administration. The present disclosure provides methods comprising administering RNA vaccines to a subject in need thereof. The exact amount required will vary from subject to subject, depending on the species, age, and general condition of the subject, the severity of the disease, the particular composition, its mode of administration, its mode of activity, and the like. HCMV RNA vaccines compositions are typically formulated in dosage unit form for ease of administration and uniformity of dosage. It will be understood, however, that the total daily usage of HCMV RNA vaccines compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, HCMV RNA vaccines compositions may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see e.g., the range of unit doses described in International Publication No WO2013078199, herein incorporated by reference in its entirety). The desired dosage may be delivered three times a day, two times a day, once a day, every other day, every third day, every week, every two weeks, every three weeks, every four weeks, every 2 months, every three months, every 6 months, etc. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In exemplary embodiments, HCMV RNA vaccines compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

In some embodiments, HCMV RNA vaccine compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, HCMV RNA vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, a HCMV RNA vaccine composition may be administered three or four times.

In some embodiments, HCMV RNA vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.010 mg, 0.025 mg, 0.100 mg or 0.400 mg.

In some embodiments the RNA vaccine for use in a method of vaccinating a subject is administered to the subject in a single dosage of between 10 μg/kg and 400 μg/kg of the nucleic acid vaccine in an effective amount to vaccinate the subject. In some embodiments the RNA vaccine for use in a method of vaccinating a subject is administered to the subject in a single dosage of between 10 μg and 400 μg of the nucleic acid vaccine in an effective amount to vaccinate the subject. In some embodiments, an HCMV RNA (e.g., mRNA) vaccine for use in a method of vaccinating a subject is administered to the subject in a single dosage of 10 μg. In some embodiments, an HCMV RNA vaccine for use in a method of vaccinating a subject is administered to the subject in a single dosage of 2 μg. In some embodiments, an HCMV RNA vaccine for use in a method of vaccinating a subject is administered to the subject in two dosages of 10 μg. In some embodiments, an HCMV RNA vaccine for use in a method of vaccinating a subject is administered the subject two dosages of 2 μg.

HCMV vaccines described herein can contain multiple RNA polynucleotides. The RNA polynucleotides can be present in equal or different amounts within the vaccine. For example, a vaccine can comprise: an RNA polynucleotide having an open reading frame encoding HCMV antigenic polypeptide gH, or an antigenic fragment or epitope thereof; an RNA polynucleotide having an open reading frame encoding HCMV antigenic polypeptide gL, or an antigenic fragment or epitope thereof; an RNA polynucleotide having an open reading frame encoding HCMV antigenic polypeptide UL128, or an antigenic fragment or epitope thereof; an RNA polynucleotide having an open reading frame encoding HCMV antigenic polypeptide UL130, or an antigenic fragment or epitope thereof; an RNA polynucleotide having an open reading frame encoding HCMV antigenic polypeptide UL131A, or an antigenic fragment or epitope thereof; and/or an RNA polynucleotide having an open reading frame encoding HCMV antigenic polypeptide gB, or an antigenic fragment or epitope thereof. In some embodiments, the ratio of gH-gL-UL128-UL130-UL131A is approximately 1:1:1:1:1. In other embodiments, the ratio of gH-gL-UL128-UL130-UL131A is approximately 4:2:1:1:1. In some embodiments, the ratio of gB-gH-gL-UL128-UL130-UL131A is approximately 1:1:1:1:1:1. In some embodiments, the vaccine comprises an equimolar concentration of gH, gL, UL128, UL130, and UL131A. In some embodiments, the vaccine comprises an equimolar concentration of gB, gH, gL, UL128, UL130, and UL131A. In some embodiments, the vaccine comprises an equal mass of gH, gL, UL128, UL130, and UL131A. In some embodiments, the vaccine comprises an equal mass of gB, gH, gL, UL128, UL130, and UL131A.

An HCMV RNA vaccine pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

HCMV RNA Vaccine Formulations and Methods of Use

Some aspects of the present disclosure provide formulations of one or more HCMV RNA (e.g., mRNA) vaccines, wherein the HCMV RNA vaccines are formulated in an effective amount to produce an antigen specific immune response in a subject (e.g., production of antibodies specific to an anti-HCMV antigenic polypeptide). "An effective amount" is a dose of an HCMV RNA (e.g., mRNA) vaccine effective to produce an antigen-specific immune response. Also provided herein are methods of inducing an antigen-specific immune response in a subject.

In some embodiments, the antigen-specific immune response is characterized by measuring an anti-HCMV antigenic polypeptide antibody titer produced in a subject administered an HCMV RNA (e.g., mRNA) vaccine as provided herein. An antibody titer is a measurement of the amount of antibodies within a subject, for example, antibodies that are specific to a particular antigen (e.g., an anti-HCMV antigenic polypeptide) or epitope of an antigen. Antibody titer is typically expressed as the inverse of the greatest dilution that provides a positive result. Enzyme-linked immunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by the HCMV RNA vaccine.

In some embodiments, an anti-HCMV antigenic polypeptide antibody titer produced in a subject is increased by at least 1 log relative to a control. For example, anti-HCMV antigenic polypeptide antibody titer produced in a subject may be increased by at least 1.5, at least 2, at least 2.5, or at least 3 log relative to a control. In some embodiments, the anti-HCMV antigenic polypeptide antibody titer produced in the subject is increased by 1, 1.5, 2, 2.5 or 3 log relative to a control. In some embodiments, the anti-HCMV antigenic polypeptide antibody titer produced in the subject is increased by 1-3 log relative to a control. For example, the anti-HCMV antigenic polypeptide antibody titer produced in a subject may be increased by 1-1.5, 1-2, 1-2.5, 1-3, 1.5-2, 1.5-2.5, 1.5-3, 2-2.5, 2-3, or 2.5-3 log relative to a control.

In some embodiments, the anti-HCMV antigenic polypeptide antibody titer produced in a subject is increased at least 2 times relative to a control. For example, the anti-HCMV antigenic polypeptide antibody titer produced in a subject may be increased at least 3 times, at least 4 times, at least 5 times, at least 6 times, at least 7 times, at least 8 times, at least 9 times, or at least 10 times relative to a control. In some embodiments, the anti-HCMV antigenic polypeptide antibody titer produced in the subject is increased 2, 3, 4, 5,6, 7, 8, 9, or 10 times relative to a control. In some embodiments, the anti-HCMV antigenic polypeptide antibody titer produced in a subject is increased 2-10 times relative to a control. For example, the anti-HCMV antigenic polypeptide antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 times relative to a control.

A control, in some embodiments, is the anti-HCMV antigenic polypeptide antibody titer produced in a subject who has not been administered an HCMV RNA (e.g., mRNA) vaccine. In some embodiments, a control is an anti-HCMV antigenic polypeptide antibody titer produced in a subject who has been administered a live attenuated HCMV vaccine. An attenuated vaccine is a vaccine produced by reducing the virulence of a viable (live). An attenuated virus is altered in a manner that renders it harmless or less virulent relative to live, unmodified virus. In some embodiments, a control is an anti-HCMV antigenic polypeptide antibody titer produced in a subject administered inactivated HCMV vaccine. In some embodiments, a control is an anti-HCMV antigenic polypeptide antibody titer produced in a subject administered a recombinant or purified HCMV protein vaccine. Recombinant protein vaccines typically include protein antigens that either have been produced in a heterologous expression system (e.g., bacteria or yeast) or purified from large amounts of the pathogenic organism.

In some embodiments, an effective amount of an HCMV RNA (e.g., mRNA) vaccine is a dose that is reduced compared to the standard of care dose of a recombinant HCMV protein vaccine. A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified HCMV protein vaccine, or a live attenuated or inactivated HCMV vaccine, that a physician/clinician or other medical professional would administer to a subject to treat or prevent HCMV, or an HCMV-related condition, while following the standard of care guideline for treating or preventing HCMV, or an HCMV-related condition.

In some embodiments, the anti-HCMV antigenic polypeptide antibody titer produced in a subject administered an effective amount of an HCMV RNA vaccine is equivalent to an anti-HCMV antigenic polypeptide antibody titer produced in a control subject administered a standard of care dose of a recombinant or purified HCMV protein vaccine or a live attenuated or inactivated HCMV vaccine.

In some embodiments, an effective amount of an HCMV RNA (e.g., mRNA) vaccine is a dose equivalent to an at least 2-fold reduction in a standard of care dose of a recombinant or purified HCMV protein vaccine. For example, an effective amount of an HCMV RNA vaccine may be a dose equivalent to an at least 3-fold, at least 4-fold, at least 5-fold, at least 6-fold, at least 7-fold, at least 8-fold, at least 9-fold, or at least 10-fold reduction in a standard of care dose of a recombinant or purified HCMV protein vaccine. In some embodiments, an effective amount of an HCMV RNA vaccine is a dose equivalent to an at least at least 100-fold, at least 500-fold, or at least 1000-fold reduction in a standard of care dose of a recombinant or purified HCMV protein vaccine. In some embodiments, an effective amount of an HCMV RNA vaccine is a dose equivalent to a 2-, 3-, 4-, 5-, 6-, 7-, 8-, 9-, 10-, 20-, 50-, 100-, 250-, 500-, or 1000-fold reduction in a standard of care dose of a recombinant or purified HCMV protein vaccine. In some embodiments, the anti-HCMV antigenic polypeptide antibody titer produced in a subject administered an effective amount of an HCMV RNA vaccine is equivalent to an anti-HCMV antigenic polypeptide antibody titer produced in a control subject administered the standard of care dose of a recombinant or protein HCMV protein vaccine or a live attenuated or inactivated HCMV vaccine. In some embodiments, an effective amount of an HCMV RNA (e.g., mRNA) vaccine is a dose equivalent to a 2-fold to 1000-fold (e.g., 2-fold to 100-fold, 10-fold to 1000-fold) reduction in the standard of care dose of a recombinant or purified HCMV protein vaccine, wherein the anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount of an HCMV RNA (e.g., mRNA) vaccine is a dose equivalent to a 2 to 1000-, 2 to 900-, 2 to 800-, 2 to 700-, 2 to 600-, 2 to 500-, 2 to 400-, 2 to 300-, 2 to 200-, 2 to 100-, 2 to 90-, 2 to 80-, 2 to 70-, 2 to 60-, 2 to 50-, 2 to 40-, 2 to 30-, 2 to 20-, 2 to 10-, 2 to 9-, 2 to 8-, 2 to 7-, 2 to 6-, 2 to 5-, 2 to 4-, 2 to 3-, 3 to 1000-, 3 to 900-, 3 to 800-, 3 to 700-, 3 to 600-, 3 to 500-, 3 to 400-, 3 to 3 to 00-, 3 to 200-, 3 to 100-, 3 to 90-, 3 to 80-, 3 to 70-, 3 to 60-, 3 to 50-, 3 to 40-, 3 to 30-, 3 to 20-, 3 to 10-, 3 to 9-, 3 to 8-, 3 to 7-, 3 to 6-, 3 to 5-, 3 to 4-, 4 to 1000-, 4 to 900-, 4 to 800-, 4 to 700-, 4 to 600-, 4 to 500-, 4 to 400-, 4 to 4 to 00-, 4 to 200-, 4 to 100-, 4 to 90-, 4 to 80-, 4 to 70-, 4 to 60-, 4 to 50-, 4 to 40-, 4 to 30-, 4 to 20-, 4 to 10-, 4 to 9-, 4 to 8-, 4 to 7-, 4 to 6-, 4 to 5-, 4 to 4-, 5 to 1000-, 5 to 900-, 5 to 800-, 5 to 700-, 5 to 600-, 5 to 500-, 5 to 400-, 5 to 300-, 5 to 200-, 5 to 100-, 5 to 90-, 5 to 80-, 5 to 70-, 5 to 60-, 5 to 50-, 5 to 40-, 5 to 30-, 5 to 20-, 5 to 10-, 5 to 9-, 5 to 8-, 5 to 7-, 5 to 6-, 6 to 1000-, 6 to 900-, 6 to 800-, 6 to 700-, 6 to 600-, 6 to 500-, 6 to 400-, 6 to 300-, 6 to 200-, 6 to 100-, 6 to 90-, 6 to 80-, 6 to 70-, 6 to 60-, 6 to 50-, 6 to 40-, 6 to 30-, 6 to 20-, 6 to 10-, 6 to 9-, 6 to 8-, 6 to 7-, 7 to 1000-, 7 to 900-, 7 to 800-, 7 to 700-, 7 to 600-, 7 to 500-, 7 to 400-, 7 to 300-, 7 to 200-, 7 to 100-, 7 to 90-, 7 to 80-, 7 to 70-, 7 to 60-, 7 to 50-, 7 to 40-, 7 to 30-, 7 to 20-, 7 to 10-, 7 to 9-, 7 to 8-, 8 to 1000-, 8 to 900-, 8 to 800-, 8 to 700-, 8 to 600-, 8 to 500-, 8 to 400-, 8 to 300-, 8 to 200-, 8 to 100-, 8 to 90-, 8 to 80-, 8 to 70-, 8 to 60-, 8 to 50-, 8 to 40-, 8 to 30-, 8 to 20-, 8 to 10-, 8 to 9-, 9 to 1000-, 9 to 900-, 9 to 800-, 9 to 700-, 9 to 600-, 9 to 500-, 9 to 400-, 9 to 300-, 9 to 200-, 9 to 100-, 9 to 90-, 9 to 80-, 9 to 70-, 9 to 60-, 9 to 50-, 9 to 40-, 9 to 30-, 9 to 20-, 9 to 10-, 10 to 1000-, 10 to 900-, 10 to 800-, 10 to 700-, 10 to 600-, 10 to 500-, 10 to 400-, 10 to 300-, 10 to 200-, 10 to 100-, 10 to 90-, 10 to 80-, 10 to 70-, 10 to 60-, 10 to 50-, 10 to 40-, 10 to 30-, 10 to 20-, 20 to 1000-, 20 to 900-, 20 to 800-, 20 to 700-, 20 to 600-, 20 to 500-, 20 to 400-, 20 to 300-, 20 to 200-, 20 to 100-, 20 to 90-, 20 to 80-, 20 to 70-, 20 to 60-, 20 to 50-, 20 to 40-, 20 to 30-, 30 to 1000-, 30 to 900-, 30 to 800-, 30 to 700-, 30 to 600-, 30 to 500-, 30 to 400-, 30 to 300-, 30 to 200-, 30 to 100-, 30 to 90-, 30 to 80-, 30 to 70-, 30 to 60-, 30 to 50-, 30 to 40-, 40 to 1000-, 40 to 900-, 40 to 800-, 40 to 700-, 40 to 600-, 40 to 500-, 40 to 400-, 40 to 300-, 40 to 200-, 40 to 100-, 40 to 90-, 40 to 80-, 40 to 70-, 40 to 60-, 40 to 50-, 50 to 1000-, 50 to 900-, 50 to 800-, 50 to 700-, 50 to 600-, 50 to 500-, 50 to 400-, 50 to 300-, 50 to 200-, 50 to 100-, 50 to 90-, 50 to 80-, 50 to 70-, 50 to 60-, 60 to 1000-, 60 to 900-, 60 to 800-, 60 to 700-, 60 to 600-, 60 to 500-, 60 to 400-, 60 to 300-, 60 to 200-, 60 to 100-, 60 to 90-, 60 to 80-, 60 to 70-, 70 to 1000-, 70 to 900-, 70 to 800-, 70 to 700-, 70 to 600-, 70 to 500-, 70 to 400-, 70 to 300-, 70 to 200-, 70 to 100-, 70 to 90-, 70 to 80-, 80 to 1000-, 80 to 900-, 80 to 800-, 80 to 700-, 80 to 600-, 80 to 500-, 80 to 400-, 80 to 300-, 80 to 200-, 80 to 100-, 80 to 90-, 90 to 1000-, 90 to 900-, 90 to 800-, 90 to 700-, 90 to 600-, 90 to 500-, 90 to 400-, 90 to 300-, 90 to 200-, 90 to 100-, 100 to 1000-, 100 to 900-, 100 to 800-, 100 to 700-, 100 to 600-, 100 to 500-, 100 to 400-, 100 to 300-, 100 to 200-, 200 to 1000-, 200 to 900-, 200 to 800-, 200 to 700-, 200 to 600-, 200 to 500-, 200 to 400-, 200 to 300-, 300 to 1000-, 300 to 900-, 300 to 800-, 300 to 700-, 300 to 600-, 300 to 500-, 300 to 400-, 400 to 1000-, 400 to 900-, 400 to 800-, 400 to 700-, 400 to 600-, 400 to 500-, 500 to 1000-, 500 to 900-, 500 to 800-, 500 to 700-, 500 to 600-, 600 to 1000-, 600 to 900-, 600 to 800-, 600 to 700-, 700 to 1000-, 700 to 900-, 700 to 800-, 800 to 1000-, 800 to 900-, or 900 to 1000-fold reduction in the standard of care dose of a recombinant HCMV protein vaccine. In some embodiments, such as the foregoing, the anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine. In some embodiments, the effective amount is a dose equivalent to (or equivalent to an at least) 2-, 3-, 4-, 5-, 6-, 7-, 8-, 9-, 10-, 20-, 30-, 40-, 50-, 60-, 70-, 80-, 90-, 100-, 110-, 120-, 130-, 140-, 150-, 160-, 170-, 1280-, 190-, 200-, 210-, 220-, 230-, 240-, 250-, 260-, 270-, 280-, 290-, 300-, 310-, 320-, 330-, 340-, 350-, 360-, 370-, 380-, 390-, 400-, 410-, 420-, 430-, 440-, 450-, 4360-, 470-, 480-, 490-, 500-, 510-, 520-, 530-, 540-, 550-, 560-, 5760-, 580-, 590-, 600-, 610-, 620-, 630-, 640-, 650-, 660-, 670-, 680-, 690-, 700-, 710-, 720-, 730-, 740-, 750-, 760-, 770-, 780-, 790-, 800-, 810-, 820-, 830-, 840-, 850-, 860-, 870-, 880-, 890-, 900-, 910-, 920-, 930-, 940-, 950-, 960-, 970-, 980-, 990-, or 1000-fold reduction in the standard of care dose of a recombinant HCMV protein vaccine. In some embodiments, such as the foregoing, an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount of an HCMV RNA (e.g., mRNA) vaccine is a total dose of 50-1000 μg. In some embodiments, the effective amount of an HCMV RNA (e.g., mRNA) vaccine is a total dose of 50-1000, 50-900, 50-800, 50-700, 50-600, 50-500, 50-400, 50-300, 50-200, 50-100, 50-90, 50-80, 50-70, 50-60, 60-1000, 60-900, 60-800, 60-700, 60-600, 60-500, 60-400, 60-300, 60-200, 60-100, 60-90, 60-80, 60-70, 70-1000, 70-900, 70-800, 70-700, 70-600, 70-500, 70-400, 70-300, 70-200, 70-100, 70-90, 70-80, 80-1000, 80-900, 80-800, 80-700, 80-600, 80-500, 80-400, 80-300, 80-200, 80-100, 80-90, 90-1000, 90-900, 90-800, 90-700, 90-600, 90-500, 90-400, 90-300, 90-200, 90-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-900, 600-700, 700-1000, 700-900, 700-800, 800-1000, 800-900, or 900-1000 μg. In some embodiments, the effective amount of an HCMV RNA (e.g., mRNA) vaccine is a total dose of 50, 100, 150, 200, 250, 300, 350, 400, 450, 500, 550, 600, 650, 700, 750, 800, 850, 900, 950 or 1000 μg.

In some embodiments, the effective amount is a dose of 25-500 μg administered to the subject a total of two times. In some embodiments, the effective amount of an HCMV RNA (e.g., mRNA) vaccine is a dose of 25-500, 25-400, 25-300, 25-200, 25-100, 25-50, 50-500, 50-400, 50-300, 50-200, 50-100, 100-500, 100-400, 100-300, 100-200, 150-500, 150-400, 150-300, 150-200, 200-500, 200-400, 200-300, 250-500, 250-400, 250-300, 300-500, 300-400, 350-500, 350-400, 400-500 or 450-500 μg administered to the subject a total of two times. In some embodiments, the effective amount of an HCMV RNA (e.g., mRNA) vaccine is a total dose of 25, 50, 100, 150, 200, 250, 300, 350, 400, 450, or 500 μg administered to the subject a total of two times.

In some embodiments, the antigen specific immune response induced by the HCMV RNA vaccines in a subject is the production of antibodies specific to an anti-HCMV antigenic polypeptide. In some embodiments, such antibodies are capable of neutralizing HCMV in an infected host. In some embodiments, the antigen specific immune response induced by the HCMV RNA vaccines in a subject is antigen-specific T-cell response. Such T-cell response may provide immunity to the immunized animal (e.g., mice or human) against fution HCMV infenctions.

Kits

The present disclosure also provides any of the above-mentioned compositions in kits. Aspects of the disclosure relate to kits comprising one or more HCMV vaccines. In some aspects, a kit comprises: (i) an HCMV vaccine comprising an RNA polynucleotide having an open reading frame encoding HCMV antigenic polypeptide pp65, or an antigenic fragment or epitope thereof, and/or (ii) an HCMV vaccine comprising at least one RNA polynucleotide having one or more open reading frames encoding HCMV antigenic polypeptides gH, gL, UL128, UL130, and/or UL131A, or antigenic fragments or epitopes thereof; an RNA polynucleotide having an open reading frame encoding HCMV antigenic polypeptide gB, or an antigenic fragment or epitope thereof; and an RNA polynucleotide having an open reading frame encoding HCMV antigenic polypeptide pp65, or an antigenic fragment or epitope thereof.

In certain embodiments, instructions are provided for administering the one or more HCMV vaccines. The kit can include a description of use of the composition(s) for participation in any biological or chemical mechanism disclosed herein. The kits can further include a description of activity of the condition in treating the pathology, as opposed to the symptoms of the condition. That is, the kit can include a description of use of the compositions as discussed herein. The kit also can include instructions for use of a combination of two or more compositions of the invention, or instruction for use of a combination of a composition of the invention and other products. Instructions also may be provided for administering the composition by any suitable technique as previously described.

The kits described herein may also contain one or more containers, which may contain the composition and other ingredients as previously described. The kits also may contain instructions for mixing, diluting, and/or administering or applying the compositions of the invention in some cases. The compositions of the kit may be provided as any suitable form.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Example 1: Manufacture of Polynucleotides

According to the present disclosure, the manufacture of polynucleotides and or parts or regions thereof may be accomplished utilizing the methods taught in International Application WO2014/152027 entitled "Manufacturing Methods for Production of RNA Transcripts", the contents of which is incorporated herein by reference in its entirety.

Purification methods may include those taught in International Application WO2014/152030 and WO2014/152031, each of which is incorporated herein by reference in its entirety.

Detection and characterization methods of the polynucleotides may be performed as taught in WO2014/144039, which is incorporated herein by reference in its entirety.

Characterization of the polynucleotides of the disclosure may be accomplished using a procedure selected from the group consisting of polynucleotide mapping, reverse transcriptase sequencing, charge distribution analysis, and detection of RNA impurities, wherein characterizing comprises determining the RNA transcript sequence, determining the purity of the RNA transcript, or determining the charge heterogeneity of the RNA transcript. Such methods are taught in, for example, WO2014/144711 and WO2014/144767, the contents of each of which is incorporated herein by reference in its entirety.

Example 2: Chimeric Polynucleotide Synthesis

Introduction

According to the present disclosure, two regions or parts of a chimeric polynucleotide may be joined or ligated using triphosphate chemistry.

According to this method, a first region or part of 100 nucleotides or less is chemically synthesized with a 5' monophosphate and terminal 3'desOH or blocked OH. If the region is longer than 80 nucleotides, it may be synthesized as two strands for ligation.

If the first region or part is synthesized as a non-positionally modified region or part using in vitro transcription (IVT), conversion the 5'monophosphate with subsequent capping of the 3' terminus may follow.

Monophosphate protecting groups may be selected from any of those known in the art.

The second region or part of the chimeric polynucleotide may be synthesized using either chemical synthesis or IVT methods. IVT methods may include an RNA polymerase that can utilize a primer with a modified cap. Alternatively, a cap of up to 130 nucleotides may be chemically synthesized and coupled to the IVT region or part.

It is noted that for ligation methods, ligation with DNA T4 ligase, followed by treatment with DNAse should readily avoid concatenation.

The entire chimeric polynucleotide need not be manufactured with a phosphate-sugar backbone. If one of the regions or parts encodes a polypeptide, then it is preferable that such region or part comprise a phosphate-sugar backbone.

Ligation is then performed using any known click chemistry, orthoclick chemistry, solulink, or other bioconjugate chemistries known to those in the art.

Synthetic Route

The chimeric polynucleotide is made using a series of starting segments. Such segments include:

(a) Capped and protected 5' segment comprising a normal 3'OH (SEG. 1)

(b) 5' triphosphate segment which may include the coding region of a polypeptide and comprising a normal 3'OH (SEG. 2)

(c) 5' monophosphate segment for the 3' end of the chimeric polynucleotide (e.g., the tail) comprising cordycepin or no 3'OH (SEG. 3)

After synthesis (chemical or NT), segment 3 (SEG. 3) is treated with cordycepin and then with pyrophosphatase to create the 5'monophosphate.

Segment 2 (SEG. 2) is then ligated to SEG. 3 using RNA ligase. The ligated polynucleotide is then purified and treated with pyrophosphatase to cleave the diphosphate. The treated SEG.2-SEG. 3 construct is then purified and SEG. 1 is ligated to the 5' terminus. A further purification step of the chimeric polynucleotide may be performed.

Where the chimeric polynucleotide encodes a polypeptide, the ligated or joined segments may be represented as: 5'UTR (SEG. 1), open reading frame or ORF (SEG. 2) and 3'UTR+PolyA (SEG. 3).

The yields of each step may be as much as 90-95%.

Example 3: PCR for cDNA Production

PCR procedures for the preparation of cDNA are performed using 2x KAPA HIFI™ HotStart ReadyMix by Kapa Biosystems (Woburn, Mass.). This system includes 2x KAPA ReadyMix12.5 μl; Forward Primer (10 μM) 0.75 μl; Reverse Primer (10 μM) 0.75 μl; Template cDNA—100 ng; and $dH_2O$ diluted to 25.0 μl. The reaction conditions are at 95° C. for 5 min. and 25 cycles of 98° C. for 20 sec, then 58° C. for 15 sec, then 72° C. for 45 sec, then 72° C. for 5 min. then 4° C. to termination.

The reaction is cleaned up using Invitrogen's PURELINK™ PCR Micro Kit (Carlsbad, Calif.) per manufacturer's instructions (up to 5 μg). Larger reactions will require a cleanup using a product with a larger capacity. Following the cleanup, the cDNA is quantified using the NANODROP™ and analyzed by agarose gel electrophoresis to confirm the cDNA is the expected size. The cDNA is then submitted for sequencing analysis before proceeding to the in vitro transcription reaction.

Example 4: In Vitro Transcription (IVT)

The in vitro transcription reaction generates polynucleotides containing uniformly modified polynucleotides. Such uniformly modified polynucleotides may comprise a region or part of the polynucleotides of the disclosure. The input nucleotide triphosphate (NTP) mix is made in-house using natural and un-natural NTPs.

A typical in vitro transcription reaction includes the following:

| | | |
|---|---|---|
| 1 | Template cDNA | 1.0 μg |
| 2 | 10x transcription buffer (400 mM Tris-HCl pH 8.0, 190 mM $MgCl_2$, 50 mM DTT, 10 mM Spermidine) | 2.0 μl |
| 3 | Custom NTPs (25 mM each) | 7.2 μl |
| 4 | RNase Inhibitor | 20 U |
| 5 | T7 RNA polymerase | 3000 U |
| 6 | $dH_20$ | Up to 20.0 μl. and |
| 7 | Incubation at 37° C. for 3 hr-5 hrs. | |

The crude IVT mix may be stored at 4° C. overnight for cleanup the next day. 1 U of RNase-free DNase is then used to digest the original template. After 15 minutes of incubation at 37° C., the mRNA is purified using Ambion's MEGACLEAR™ Kit (Austin, Tex.) following the manufacturer's instructions. This kit can purify up to 500 μg of RNA. Following the cleanup, the RNA is quantified using the NanoDrop and analyzed by agarose gel electrophoresis to confirm the RNA is the proper size and that no degradation of the RNA has occurred.

Example 5: Enzymatic Capping

Capping of a polynucleotide is performed as follows where the mixture includes: NT RNA 60 μg-180 μg and $dH_2O$ up to 72 μl. The mixture is incubated at 65° C. for 5 minutes to denature RNA, and then is transferred immediately to ice.

The protocol then involves the mixing of 10x Capping Buffer (0.5 M Tris-HCl (pH 8.0), 60 mM KCl, 12.5 mM $MgCl_2$) (10.0 μl); 20 mM GTP (5.0 μl); 20 mM S-Adenosyl Methionine (2.5 μl); RNase Inhibitor (100 U); 2'-O-Methyltransferase (400U); Vaccinia capping enzyme (Guanylyl transferase) (40 U); $dH_2O$ (Up to 28 μl); and incubation at 37° C. for 30 minutes for 60 μg RNA or up to 2 hours for 180 μg of RNA.

The polynucleotide is then purified using Ambion's MEGACLEAR™ Kit (Austin, Tex.) following the manufacturer's instructions. Following the cleanup, the RNA is quantified using the NANODROP™ (ThermoFisher, Waltham, Mass.) and analyzed by agarose gel electrophoresis to confirm the RNA is the proper size and that no degradation of the RNA has occurred. The RNA product may also be sequenced by running a reverse-transcription-PCR to generate the cDNA for sequencing.

Example 6: PolyA Tailing Reaction

Without a poly-T in the cDNA, a poly-A tailing reaction must be performed before cleaning the final product. This is done by mixing Capped NT RNA (100 μl); RNase Inhibitor (20 U); 10x Tailing Buffer (0.5 M Tris-HCl (pH 8.0), 2.5 M NaCl, 100 mM $MgCl_2$)(12.0 μl); 20 mM ATP (6.0 μl); Poly-A Polymerase (20 U); $dH_2O$ up to 123.5 μl and incubation at 37° C. for 30 min. If the poly-A tail is already in the transcript, then the tailing reaction may be skipped and proceed directly to cleanup with Ambion's MEGACLEAR™ kit (Austin, Tex.) (up to 500 μg). Poly-A Polymerase is preferably a recombinant enzyme expressed in yeast.

It should be understood that the processivity or integrity of the polyA tailing reaction may not always result in an exact size polyA tail. Hence polyA tails of approximately between 40-200 nucleotides, e.g, about 40, 50, 60, 70, 80, 90, 91, 92, 93, 94, 95, 96, 97, 98, 99, 100, 101, 102, 103, 104, 105, 106, 107, 108, 109, 110, 150-165, 155, 156, 157, 158, 159, 160, 161, 162, 163, 164 or 165 are within the scope of the invention.

Example 7: Natural 5' Caps and 5' Cap Analogues

5'-capping of polynucleotides may be completed concomitantly during the in vitro-transcription reaction using the following chemical RNA cap analogs to generate the 5'-guanosine cap structure according to manufacturer protocols: 3'-O-Me-m7G(5)ppp(5') G [the ARCA cap];G(5')ppp(5')A; G(5')ppp(5')G; m7G(5')ppp(5')A; m7G(5')ppp(5')G (New England BioLabs, Ipswich, Mass.). 5'-capping of modified RNA may be completed post-transcriptionally using a Vaccinia Virus Capping Enzyme to generate the "Cap 0" structure: m7G(5')ppp(5')G (New England BioLabs, Ipswich, Mass.). Cap 1 structure may be generated using both Vaccinia Virus Capping Enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes are preferably derived from a recombinant source.

When transfected into mammalian cells, the modified mRNAs have a stability of between 12-18 hours or more than 18 hours, e.g., 24, 36, 48, 60, 72 or greater than 72 hours.

Example 8: Capping Assays

A. Protein Expression Assay

Polynucleotides encoding a polypeptide, containing any of the caps taught herein can be transfected into cells at equal concentrations. 6, 12, 24 and 36 hours post-transfection the amount of protein secreted into the culture medium can be assayed by ELISA. Synthetic polynucleotides that secrete higher levels of protein into the medium would correspond to a synthetic polynucleotide with a higher translationally-competent Cap structure.

B. Purity Analysis Synthesis

Polynucleotides encoding a polypeptide, containing any of the caps taught herein can be compared for purity using denaturing Agarose-Urea gel electrophoresis or HPLC analysis. Polynucleotides with a single, consolidated band by electrophoresis correspond to the higher purity product compared to polynucleotides with multiple bands or streaking bands. Synthetic polynucleotides with a single HPLC peak would also correspond to a higher purity product. The capping reaction with a higher efficiency would provide a more pure polynucleotide population.

C. Cytokine Analysis

Polynucleotides encoding a polypeptide, containing any of the caps taught herein can be transfected into cells at multiple concentrations. 6, 12, 24 and 36 hours post-transfection the amount of pro-inflammatory cytokines such as TNF-alpha and IFN-beta secreted into the culture medium can be assayed by ELISA. Polynucleotides resulting in the secretion of higher levels of pro-inflammatory cytokines into the medium would correspond to a polynucleotides containing an immune-activating cap structure.

D. Capping Reaction Efficiency

Polynucleotides encoding a polypeptide, containing any of the caps taught herein can be analyzed for capping reaction efficiency by LC-MS after nuclease treatment. Nuclease treatment of capped polynucleotides would yield a mixture of free nucleotides and the capped 5'-5-triphosphate cap structure detectable by LC-MS. The amount of capped product on the LC-MS spectra can be expressed as a percent of total polynucleotide from the reaction and would correspond to capping reaction efficiency. The cap structure with higher capping reaction efficiency would have a higher amount of capped product by LC-MS.

Example 9: Agarose Gel Electrophoresis of Modified RNA or RT PCR Products

Individual polynucleotides (200-400 ng in a 20 μl volume) or reverse transcribed PCR products (200-400 ng) are loaded into a well on a non-denaturing 1.2% Agarose E-Gel (Invitrogen, Carlsbad, Calif.) and run for 12-15 minutes according to the manufacturer protocol.

Example 10: Nanodrop Modified RNA Quantification and UV Spectral Data

Modified polynucleotides in TE buffer (1 μl) are used for Nanodrop UV absorbance readings to quantitate the yield of each polynucleotide from an chemical synthesis or in vitro transcription reaction.

Example 11: Formulation of Modified mRNA Using Lipidoids

Polynucleotides are formulated for in vitro experiments by mixing the polynucleotides with the lipidoid at a set ratio prior to addition to cells. In vivo formulation may require the addition of extra ingredients to facilitate circulation throughout the body. To test the ability of these lipidoids to form particles suitable for in vivo work, a standard formulation process used for siRNA-lipidoid formulations may used as a starting point. After formation of the particle, polynucleotide is added and allowed to integrate with the complex. The encapsulation efficiency is determined using a standard dye exclusion assays.

Example 12: hCMV Vaccine—hCMV Glycoprotein Sequences

A hCMV vaccine may comprise, for example, at least one RNA polynucleotide encoded by at least one of the following sequences or by at least one fragment or epitope of the following sequences. In some embodiments, a hCMV vaccine may comprise at least one RNA polynucleotide comprising one of the mRNA sequences listed below or at least one fragment of one of the sequences listed below.

Throughout all of the Examples described herein, each of the sequences described herein can be a chemically modified sequence or an unmodified sequence which includes no nucleotide modifications.

Throughout all of the Examples described herein, open reading frame sequences can be linked to different 5' and 3'UTRs.

Examples of UTR sequences include:

```
5′ UTR coding sequence:
                                        (SEQ ID NO: 145)
TCAAGCTTTTGGACCCTCGTACAGAAGCTAATACGACTCACTATAGGG
AAATAAGAGAGAAAAGAAGAGTAAGAAGAAATATAAGAGCCACC
```

```
5′ UTR (without promoter) coding sequence:
                                        (SEQ ID NO: 146)
GGGAAATAAGAGAGAAAAGAAGAGTAAGAAGAAATATAAGAGCCACC
```

```
3′ UTR coding sequence:
                                        (SEQ ID NO: 147)
TGATAATAGGCTGGAGCCTCGGTGGCCATGCTTCTTGCCCCTTGGGCC
TCCCCCCAGCCCCTCCTCCCCTTCCTGCACCCGTACCCCCGTGGTCTT
TGAATAAAGTCTGAGTGGGCGGC.
```

5'UTR is bolded
3'UTR is underlined hCMV-gH: hCMV, glycoprotein H (Merlin Strain)

(SEQ ID NO: 1)

TCAAGCTTTTGGACCCTCGTACAGAAGCTAATACGACTCACTATAGGGAAATAAGAGAGAAA

AGAAGAGTAAGAAGAAATATAAGAGCCACCATGCGGCCAGGCCTCCCCTCCTACCTCATCAT

CCTCGCCGTCTGTCTCTTCAGCCACCTACTTTCGTCACGATATGGCGCAGAAGCCGTATCCG

AACCGCTGGACAAAGCGTTTCACCTACTGCTCAACACCTACGGGAGACCCATCCGCTTCCTG

CGTGAAAATACCACCCAGTGTACCTACAACAGCAGCCTCCGTAACAGCACGGTCGTCAGGGA

AAACGCCATCAGTTTCAACTTTTTCCAAAGCTATAATCAATACTATGTATTCCATATGCCTC

GATGTCTTTTTGCGGGTCCTCTGGCGGAGCAGTTTCTGAACCAGGTAGATCTGACCGAAACC

CTGGAAAGATACCAACAGAGACTTAACACTTACGCGCTGGTATCCAAAGACCTGGCCAGCTA

CCGATCTTTTTCGCAGCAGCTAAAGGCACAAGACAGCCTAGGTGAACAGCCCACCACTGTGC

CACCGCCCATTGACCTGTCAATACCTCACGTTTGGATGCCACCGCAAACCACTCCACACGGC

TGGACAGAATCACATACCACCTCAGGACTACACCGACCACACTTTAACCAGACCTGTATCCT

CTTTGATGGACACGATCTACTATTCAGCACCGTCACACCTTGTTTGCACCAAGGCTTTTACC

TCATCGACGAACTACGTTACGTTAAAATAACACTGACCGAGGACTTCTTCGTAGTTACGGTG

TCCATAGACGACGACACACCCATGCTGCTTATCTTCGGCCATCTTCCACGCGTACTTTTCAA

AGCGCCCTATCAACGCGACAACTTTATACTACGACAAACTGAAAAACACGAGCTCCTGGTGC

TAGTTAAGAAAGATCAACTGAACCGTCACTCTTATCTCAAAGACCCGGACTTTCTTGACGCC

GCACTTGACTTCAACTACCTAGACCTCAGCGCACTACTACGTAACAGCTTTCACCGTTACGC

CGTGGATGTACTCAAGAGCGGTCGATGTCAGATGCTGGACCGCCGCACGGTAGAAATGGCCT

TCGCCTACGCATTAGCACTGTTCGCAGCAGCCCGACAAGAAGAGGCCGGCGCCCAAGTCTCC

-continued

GTCCCACGGGCCCTAGACCGCCAGGCCGCACTCTTACAAATACAAGAATTTATGATCACCTG

CCTCTCACAAACACCACCACGCACCACGTTGCTGCTGTATCCCACGGCCGTGGACCTGGCCA

AACGAGCCCTTTGGACACCGAATCAGATCACCGACATCACCAGCCTCGTACGCCTGGTCTAC

ATACTCTCTAAACAGAATCAGCAACATCTCATCCCCCAATGGGCACTACGACAGATCGCCGA

CTTTGCCCTAAAACTACACAAAACGCACCTGGCCTCTTTTCTTTCAGCCTTCGCACGCCAAG

AACTCTACCTCATGGGCAGCCTCGTCCACTCCATGCTGGTACATACGACGGAGAGACGCGAA

ATCTTCATCGTAGAAACGGGCCTCTGTTCATTGGCCGAGCTATCACACTTTACGCAGTTGTT

AGCTCATCCACACCACGAATACCTCAGCGACCTGTACACACCCTGTTCCAGTAGCGGGCGAC

GCGATCACTCGCTCGAACGCCTCACGCGTCTCTTCCCCGATGCCACCGTCCCCGCTACCGTT

CCCGCCGCCCTCTCCATCCTATCTACCATGCAACCAAGCACGCTGGAAACCTTCCCCGACCT

GTTTTGCTTGCCGCTCGGCGAATCCTTCTCCGCGCTGACCGTCTCCGAACACGTCAGTTATA

TCGTAACAAACCAGTACCTGATCAAAGGTATCTCCTACCCTGTCTCCACCACCGTCGTAGGC

CAGAGCCTCATCATCACCCAGACGGACAGTCAAACTAAATGCGAACTGACGCGCAACATGCA

TACCACACACAGCATCACAGTGGCGCTCAACATTTCGCTAGAAAACTGCGCCTTTTGCCAAA

GCGCCCTGCTAGAATACGACGACACGCAAGGCGTCATCAACATCATGTACATGCACGACTCG

GACGACGTCCTTTTCGCCCTGGATCCCTACAACGAAGTGGTGGTCTCATCTCCGCGAACTCA

CTACCTCATGCTTTTGAAAAACGGTACGGTACTAGAAGTAACTGACGTCGTCGTGGACGCCA

CCGACAGTCGTCTCCTCATGATGTCCGTCTACGCGCTATCGGCCATCATCGGCATCTATCTG

CTCTACCGCATGCTCAAGACATGCTGATAATAGGCTGGAGCCTCGGTGGCCATGCTTCTTGC

CCCTTGGGCCTCCCCCCAGCCCCTCCTCCCCTTCCTGCACCCGTACCCCCGTGGTCTTTGAA

TAAAGTCTGAGTGGGCGGC hCMV-gH: hCMV, glycoprotein H (Merlin Strain) mRNA (SEQ ID NO: 158)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGCGGCCAGGCCUCCCCUCCUACCUCAUCAU

CCUCGCCGUCUGUCUCUUCAGCCACCUACUUUCGUCACGAUAUGGCGCAGAAGCCGUAUCCG

AACCGCUGGACAAAGCGUUUCACCUACUGCUCAACACCUACGGGAGACCCAUCCGCUUCCUG

CGUGAAAAUACCACCCAGUGUACCUACAACAGCAGCCUCCGUAACAGCACGGUCGUCAGGGA

AAACGCCAUCAGUUUCAACUUUUUCCAAAGCUAUAAUCAAUACUAUGUAUUCCAUAUGCCUC

GAUGUCUUUUUGCGGGUCCUCUGGCGGAGCAGUUUCUGAACCAGGUAGAUCUGACCGAAACC

CUGGAAAGAUACCAACAGAGACUUAACACUUACGCGCUGGUAUCCAAAGACCUGGCCAGCUA

CCGAUCUUUUUCGCAGCAGCUAAAGGCACAAGACAGCCUAGGUGAACAGCCCACCACUGUGC

CACCGCCCAUUGACCUGUCAAUACCUCACGUUUGGAUGCCACCGCAAACCACUCCACACGGC

UGGACAGAAUCACAUACCACCUCAGGACUACACCGACCACACUUUAACCAGACCUGUAUCCU

CUUUGAUGGACACGAUCUACUAUUCAGCACCGUCACACCUUGUUUGCACCAAGGCUUUUACC

UCAUCGACGAACUACGUUACGUUAAAAUAACACUGACCGAGGACUUCUUCGUAGUUACGGUG

UCCAUAGACGACGACACACCCAUGCUGCUUAUCUUCGGCCAUCUUCCACGCGUACUUUUCAA

AGCGCCCUAUCAACGCGACAACUUUAUACUACGACAAACUGAAAAACACGAGCUCCUGGUGC

UAGUUAAGAAAGAUCAACUGAACCGUCACUCUUAUCUCAAAGACCCGGACUUUCUUGACGCC

GCACUUGACUUCAACUACCUAGACCUCAGCGCACUACUACGUAACAGCUUUCACCGUUACGC

CGUGGAUGUACUCAAGAGCGGUCGAUGUCAGAUGCUGGACCGCCGCACGGUAGAAAUGGCCU

UCGCCUACGCAUUAGCACUGUUCGCAGCAGCCCGACAAGAAGAGGCCGGCGCCCAAGUCUCC

-continued

GUCCCACGGGCCCUAGACCGCCAGGCCGCACUCUUACAAAUACAAGAAUUUAUGAUCACCUG

CCUCUCACAAACACCACCACGCACCACGUUGCUGCUGUAUCCCACGGCCGUGGACCUGGCCA

AACGAGCCCUUUGGACACCGAAUCAGAUCACCGACAUCACCAGCCUCGUACGCCUGGUCUAC

AUACUCUCUAAACAGAAUCAGCAACAUCUCAUCCCCCAAUGGGCACUACGACAGAUCGCCGA

CUUUGCCCUAAAACUACACAAAACGCACCUGGCCUCUUUUCUUUCAGCCUUCGCACGCCAAG

AACUCUACCUCAUGGGCAGCCUCGUCCACUCCAUGCUGGUACAUACGACGGAGAGACGCGAA

AUCUUCAUCGUAGAAACGGGCCUCUGUUCAUUGGCCGAGCUAUCACACUUUACGCAGUUGUU

AGCUCAUCCACACCACGAAUACCUCAGCGACCUGUACACACCCUGUUCCAGUAGCGGGCGAC

GCGAUCACUCGCUCGAACGCCUCACGCGUCUCUUCCCCGAUGCCACCGUCCCCGCUACCGUU

CCCGCCGCCCUCUCCAUCCUAUCUACCAUGCAACCAAGCACGCUGGAAACCUUCCCCGACCU

GUUUUGCUUGCCGCUCGGCGAAUCCUUCUCCGCGCUGACCGUCUCCGAACACGUCAGUUAUA

UCGUAACAAACCAGUACCUGAUCAAAGGUAUCUCCUACCCUGUCUCCACCACCGUCGUAGGC

CAGAGCCUCAUCAUCACCCAGACGGACAGUCAAACUAAAUGCGAACUGACGCGCAACAUGCA

UACCACACACAGCAUCACAGUGGCGCUCAACAUUUCGCUAGAAAACUGCGCCUUUUGCCAAA

GCGCCCUGCUAGAAUACGACGACACGCAAGGCGUCAUCAACAUCAUGUACAUGCACGACUCG

GACGACGUCCUUUUCGCCCUGGAUCCCUACAACGAAGUGGUGGUCUCAUCUCCGCGAACUCA

CUACCUCAUGCUUUUGAAAAACGGUACGGUACUAGAAGUAACUGACGUCGUCGUGGACGCCA

CCGACAGUCGUCUCCUCAUGAUGUCCGUCUACGCGCUAUCGGCCAUCAUCGGCAUCUAUCUG

CUCUACCGCAUGCUCAAGACAUGCUGAUAAUAGGCUGGAGCCUCGGUGGCCAUGCUUCUUGC

CCCUUGGGCCUCCCCCCAGCCCCUCCUCCCCUUCCUGCACCCGUACCCCCGUGGUCUUUGAA

UAAAGUCUGAGUGGGCGGC hCMV-gHFLAG, hCMV glycoproteinH-FLAG tag (SEQ ID NO: 2)

TCAAGCTTTTGGACCCTCGTACAGAAGCTAATACGACTCACTATAGGGAAATAAGAGAGAAA

AGAAGAGTAAGAAGAAATATAAGAGCCACCATGCGGCCAGGCCTCCCCTCCTACCTCATCAT

CCTCGCCGTCTGTCTCTTCAGCCACCTACTTTCGTCACGATATGGCGCAGAAGCCGTATCCG

AACCGCTGGACAAAGCGTTTCACCTACTGCTCAACACCTACGGGAGACCCATCCGCTTCCTG

CGTGAAAATACCACCCAGTGTACCTACAACAGCAGCCTCCGTAACAGCACGGTCGTCAGGGA

AAACGCCATCAGTTTCAACTTTTTCCAAAGCTATAATCAATACTATGTATTCCATATGCCTC

GATGTCTTTTTGCGGGTCCTCTGGCGGAGCAGTTTCTGAACCAGGTAGATCTGACCGAAACC

CTGGAAAGATACCAACAGAGACTTAACACTTACGCGCTGGTATCCAAAGACCTGGCCAGCTA

CCGATCTTTTTCGCAGCAGCTAAAGGCACAAGACAGCCTAGGTGAACAGCCCACCACTGTGC

CACCGCCCATTGACCTGTCAATACCTCACGTTTGGATGCCACCGCAAACCACTCCACACGGC

TGGACAGAATCACATACCACCTCAGGACTACACCGACCACACTTTAACCAGACCTGTATCCT

CTTTGATGGACACGATCTACTATTCAGCACCGTCACACCTTGTTTGCACCAAGGCTTTTACC

TCATCGACGAACTACGTTACGTTAAAATAACACTGACCGAGGACTTCTTCGTAGTTACGGTG

TCCATAGACGACGACACACCCATGCTGCTTATCTTCGGCCATCTTCCACGCGTACTTTTCAA

AGCGCCCTATCAACGCGACAACTTTATACTACGACAAACTGAAAAACACGAGCTCCTGGTGC

TAGTTAAGAAAGATCAACTGAACCGTCACTCTTATCTCAAAGACCCGGACTTTCTTGACGCC

GCACTTGACTTCAACTACCTAGACCTCAGCGCACTACTACGTAACAGCTTTCACCGTTACGC

CGTGGATGTACTCAAGAGCGGTCGATGTCAGATGCTGGACCGCCGCACGGTAGAAATGGCCT

-continued

TCGCCTACGCATTAGCACTGTTCGCAGCAGCCCGACAAGAAGAGGCCGGCGCCCAAGTCTCC

GTCCCACGGGCCCTAGACCGCCAGGCCGCACTCTTACAAATACAAGAATTTATGATCACCTG

CCTCTCACAAACACCACCACGCACCACGTTGCTGCTGTATCCCACGGCCGTGGACCTGGCCA

AACGAGCCCTTTGGACACCGAATCAGATCACCGACATCACCAGCCTCGTACGCCTGGTCTAC

ATACTCTCTAAACAGAATCAGCAACATCTCATCCCCCAATGGGCACTACGACAGATCGCCGA

CTTTGCCCTAAAACTACACAAAACGCACCTGGCCTCTTTTCTTTCAGCCTTCGCACGCCAAG

AACTCTACCTCATGGGCAGCCTCGTCCACTCCATGCTGGTACATACGACGGAGAGACGCGAA

ATCTTCATCGTAGAAACGGGCCTCTGTTCATTGGCCGAGCTATCACACTTTACGCAGTTGTT

AGCTCATCCACACCACGAATACCTCAGCGACCTGTACACACCCTGTTCCAGTAGCGGGCGAC

GCGATCACTCGCTCGAACGCCTCACGCGTCTCTTCCCCGATGCCACCGTCCCCGCTACCGTT

CCCGCCGCCCTCTCCATCCTATCTACCATGCAACCAAGCACGCTGGAAACCTTCCCCGACCT

GTTTTGCTTGCCGCTCGGCGAATCCTTCTCCGCGCTGACCGTCTCCGAACACGTCAGTTATA

TCGTAACAAACCAGTACCTGATCAAAGGTATCTCCTACCCTGTCTCCACCACCGTCGTAGGC

CAGAGCCTCATCATCACCCAGACGGACAGTCAAACTAAATGCGAACTGACGCGCAACATGCA

TACCACACACAGCATCACAGTGGCGCTCAACATTTCGCTAGAAAACTGCGCCTTTTGCCAAA

GCGCCCTGCTAGAATACGACGACACGCAAGGCGTCATCAACATCATGTACATGCACGACTCG

GACGACGTCCTTTTCGCCCTGGATCCCTACAACGAAGTGGTGGTCTCATCTCCGCGAACTCA

CTACCTCATGCTTTTGAAAAACGGTACGGTACTAGAAGTAACTGACGTCGTCGTGGACGCCA

CCGACAGTCGTCTCCTCATGATGTCCGTCTACGCGCTATCGGCCATCATCGGCATCTATCTG

CTCTACCGCATGCTCAAGACATGCGATTACAAGGACGATGACGATAAGTGATGATAATAGGC

TGGAGCCTCGGTGGCCATGCTTCTTGCCCCTTGGGCCTCCCCCCAGCCCCTCCTCCCCTTCC

TGCACCCGTACCCCCGTGGTCTTTGAATAAAGTCTGAGTGGGCGGC hCMV-gHFLAG, hCMV glycoproteinH-FLAG tag mRNA (SEQ ID NO: 159)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGCGGCCAGGCCUCCCCUCCUACCUCAUCAU

CCUCGCCGUCUGUCUCUUCAGCCACCUACUUUCGUCACGAUAUGGCGCAGAAGCCGUAUCCG

AACCGCUGGACAAAGCGUUUCACCUACUGCUCAACACCUACGGGAGACCCAUCCGCUUCCUG

CGUGAAAAUACCACCCAGUGUACCUACAACAGCAGCCUCCGUAACAGCACGGUCGUCAGGGA

AAACGCCAUCAGUUUCAACUUUUUCCAAAGCUAUAAUCAAUACUAUGUAUUCCAUAUGCCUC

GAUGUCUUUUUGCGGGUCCUCUGGCGGAGCAGUUUCUGAACCAGGUAGAUCUGACCGAAACC

CUGGAAAGAUACCAACAGAGACUUAACACUUACGCGCUGGUAUCCAAAGACCUGGCCAGCUA

CCGAUCUUUUUCGCAGCAGCUAAAGGCACAAGACAGCCUAGGUGAACAGCCCACCACUGUGC

CACCGCCCAUUGACCUGUCAAUACCUCACGUUUGGAUGCCACCGCAAACCACUCCACACGGC

UGGACAGAAUCACAUACCACCUCAGGACUACACCGACCACACUUUAACCAGACCUGUAUCCU

CUUUGAUGGACACGAUCUACUAUUCAGCACCGUCACACCUUGUUUGCACCAAGGCUUUUACC

UCAUCGACGAACUACGUUACGUUAAAAUAACACUGACCGAGGACUUCUUCGUAGUUACGGUG

UCCAUAGACGACGACACACCCAUGCUGCUUAUCUUCGGCCAUCUUCCACGCGUACUUUUCAA

AGCGCCCUAUCAACGCGACAACUUUAUACUACGACAAACUGAAAAACACGAGCUCCUGGUGC

UAGUUAAGAAAGAUCAACUGAACCGUCACUCUUAUCUCAAAGACCCGGACUUUCUUGACGCC

GCACUUGACUUCAACUACCUAGACCUCAGCGCACUACUACGUAACAGCUUUCACCGUUACGC

CGUGGAUGUACUCAAGAGCGGUCGAUGUCAGAUGCUGGACCGCCGCACGGUAGAAAUGGCCU

-continued

UCGCCUACGCAUUAGCACUGUUCGCAGCAGCCCGACAAGAAGAGGCCGGCGCCCAAGUCUCC

GUCCCACGGGCCCUAGACCGCCAGGCCGCACUCUUACAAAUACAAGAAUUUAUGAUCACCUG

CCUCUCACAAACACCACCACGCACCACGUUGCUGCUGUAUCCCACGGCCGUGGACCUGGCCA

AACGAGCCCUUUGGACACCGAAUCAGAUCACCGACAUCACCAGCCUCGUACGCCUGGUCUAC

AUACUCUCUAAACAGAAUCAGCAACAUCUCAUCCCCCAAUGGGCACUACGACAGAUCGCCGA

CUUUGCCCUAAAACUACACAAAACGCACCUGGCCUCUUUUCUUUCAGCCUUCGCACGCCAAG

AACUCUACCUCAUGGGCAGCCUCGUCCACUCCAUGCUGGUACAUACGACGGAGAGACGCGAA

AUCUUCAUCGUAGAAACGGGCCUCUGUUCAUUGGCCGAGCUAUCACACUUUACGCAGUUGUU

AGCUCAUCCACACCACGAAUACCUCAGCGACCUGUACACACCCUGUUCCAGUAGCGGGCGAC

GCGAUCACUCGCUCGAACGCCUCACGCGUCUCUUCCCCGAUGCCACCGUCCCCGCUACCGUU

CCCGCCGCCCUCUCCAUCCUAUCUACCAUGCAACCAAGCACGCUGGAAACCUUCCCCGACCU

GUUUUGCUUGCCGCUCGGCGAAUCCUUCUCCGCGCUGACCGUCUCCGAACACGUCAGUUAUA

UCGUAACAAACCAGUACCUGAUCAAAGGUAUCUCCUACCCUGUCUCCACCACCGUCGUAGGC

CAGAGCCUCAUCAUCACCCAGACGGACAGUCAAACUAAAUGCGAACUGACGCGCAACAUGCA

UACCACACACAGCAUCACAGUGGCGCUCAACAUUUCGCUAGAAAACUGCGCCUUUUGCCAAA

GCGCCCUGCUAGAAUACGACGACACGCAAGGCGUCAUCAACAUCAUGUACAUGCACGACUCG

GACGACGUCCUUUUCGCCCUGGAUCCCUACAACGAAGUGGUGGUCUCAUCUCCGCGAACUCA

CUACCUCAUGCUUUUGAAAAACGGUACGGUACUAGAAGUAACUGACGUCGUCGUGGACGCCA

CCGACAGUCGUCUCCUCAUGAUGUCCGUCUACGCGCUAUCGGCCAUCAUCGGCAUCUAUCUG

CUCUACCGCAUGCUCAAGACAUGCGAUUACAAGGACGAUGACGAUAAGUGAUGAUAAUAGGC

UGGAGCCUCGGUGGCCAUGCUUCUUGCCCCUUGGGCCUCCCCCCAGCCCCUCCUCCCCUUCC

UGCACCCGUACCCCCGUGGUCUUUGAAUAAAGUCUGAGUGGGCGGC hCMV-gL, hCMV glycoprotein L (SEQ ID NO: 3)

TCAAGCTTTTGGACCCTCGTACAGAAGCTAATACGACTCACTATAGGGAAATAAGAGAGAAA

AGAAGAGTAAGAAGAAATATAAGAGCCACCATGTGCCGCCGCCCGGATTGCGGCTTCTCTTT

CTCACCTGGACCGGTGATACTGCTGTGGTGTTGCCTTCTGCTGCCCATTGTTTCCTCAGCCG

CCGTCAGCGTCGCTCCTACCGCCGCCGAGAAAGTCCCCGCGGAGTGCCCCGAACTAACGCGC

CGATGCTTGTTGGGTGAGGTGTTTGAGGGTGACAAGTATGAAAGTTGGCTGCGCCCGTTGGT

GAATGTTACCGGGCGCGATGGCCCGCTATCGCAACTTATCCGTTACCGTCCCGTTACGCCGG

AGGCCGCCAACTCCGTGCTGTTGGACGAGGCTTTCCTGGACACTCTGGCCCTGCTGTACAAC

AATCCGGATCAATTGCGGGCCCTGCTGACGCTGTTGAGCTCGGACACAGCGCCGCGCTGGAT

GACGGTGATGCGCGGCTACAGCGAGTGCGGCGATGGCTCGCCGGCCGTGTACACGTGCGTGG

ACGACCTGTGCCGCGGCTACGACCTCACGCGACTGTCATACGGGCGCAGCATCTTCACGGAA

CACGTGTTAGGCTTCGAGCTGGTGCCACCGTCTCTCTTTAACGTGGTGGTGGCCATACGCAA

CGAAGCCACGCGTACCAACCGCGCCGTGCGTCTGCCCGTGAGCACCGCTGCCGCGCCCGAGG

GCATCACGCTCTTTTACGGCCTGTACAACGCAGTGAAGGAATTCTGCCTGCGTCACCAGCTG

GACCCGCCGCTGCTACGCCACCTAGATAAATACTACGCCGGACTGCCGCCCGAGCTGAAGCA

GACGCGCGTCAACCTGCCGGCTCACTCGCGCTATGGCCCTCAAGCAGTGGATGCTCGCTGAT

-continued

AATAGGCTGGAGCCTCGGTGGCCATGCTTCTTGCCCCTTGGGCCTCCCCCCAGCCCCTCCTC

CCCTTCCTGCACCCGTACCCCCGTGGTCTTTGAATAAAGTCTGAGTGGGCGGC hCMV-gL, hCMV glycoprotein L mRNA (SEQ ID NO: 160)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGUGCCGCCGCCCGGAUUGCGGCUUCUCUUU

CUCACCUGGACCGGUGAUACUGCUGUGGUGUUGCCUUCUGCUGCCCAUUGUUUCCUCAGCCG

CCGUCAGCGUCGCUCCUACCGCCGCCGAGAAAGUCCCCGCGGAGUGCCCCGAACUAACGCGC

CGAUGCUUGUUGGGUGAGGUGUUUGAGGGUGACAAGUAUGAAAGUUGGCUGCGCCCGUUGGU

GAAUGUUACCGGGCGCGAUGGCCCGCUAUCGCAACUUAUCCGUUACCGUCCCGUUACGCCGG

AGGCCGCCAACUCCGUGCUGUUGGACGAGGCUUUCCUGGACACUCUGGCCCUGCUGUACAAC

AAUCCGGAUCAAUUGCGGGCCCUGCUGACGCUGUUGAGCUCGGACACAGCGCCGCGCUGGAU

GACGGUGAUGCGCGGCUACAGCGAGUGCGGCGAUGGCUCGCCGGCCGUGUACACGUGCGUGG

ACGACCUGUGCCGCGGCUACGACCUCACGCGACUGUCAUACGGGCGCAGCAUCUUCACGGAA

CACGUGUUAGGCUUCGAGCUGGUGCCACCGUCUCUCUUUAACGUGGUGGUGGCCAUACGCAA

CGAAGCCACGCGUACCAACCGCGCCGUGCGUCUGCCCGUGAGCACCGCUGCCGCGCCCGAGG

GCAUCACGCUCUUUUACGGCCUGUACAACGCAGUGAAGGAAUUCUGCCUGCGUCACCAGCUG

GACCCGCCGCUGCUACGCCACCUAGAUAAAUACUACGCCGGACUGCCGCCCGAGCUGAAGCA

GACGCGCGUCAACCUGCCGGCUCACUCGCGCUAUGGCCCUCAAGCAGUGGAUGCUCGCUGAU

AAUAGGCUGGAGCCUCGGUGGCCAUGCUUCUUGCCCCUUGGGCCUCCCCCCAGCCCCUCCUC

CCCUUCCUGCACCCGUACCCCCGUGGUCUUUGAAUAAAGUCUGAGUGGGCGGC hCMV-gLFLAG, glycoprotein L-FLAG (SEQ ID NO: 4)

TCAAGCTTTTGGACCCTCGTACAGAAGCTAATACGACTCACTATAGGGAAATAAGAGAGAAA

AGAAGAGTAAGAAGAAATATAAGAGCCACCATGTGCCGCCGCCCGGATTGCGGCTTCTCTTT

CTCACCTGGACCGGTGATACTGCTGTGGTGTTGCCTTCTGCTGCCCATTGTTTCCTCAGCCG

CCGTCAGCGTCGCTCCTACCGCCGCCGAGAAAGTCCCCGCGGAGTGCCCCGAACTAACGCGC

CGATGCTTGTTGGGTGAGGTGTTTGAGGGTGACAAGTATGAAAGTTGGCTGCGCCCGTTGGT

GAATGTTACCGGGCGCGATGGCCCGCTATCGCAACTTATCCGTTACCGTCCCGTTACGCCGG

AGGCCGCCAACTCCGTGCTGTTGGACGAGGCTTTCCTGGACACTCTGGCCCTGCTGTACAAC

AATCCGGATCAATTGCGGGCCCTGCTGACGCTGTTGAGCTCGGACACAGCGCCGCGCTGGAT

GACGGTGATGCGCGGCTACAGCGAGTGCGGCGATGGCTCGCCGGCCGTGTACACGTGCGTGG

ACGACCTGTGCCGCGGCTACGACCTCACGCGACTGTCATACGGGCGCAGCATCTTCACGGAA

CACGTGTTAGGCTTCGAGCTGGTGCCACCGTCTCTCTTTAACGTGGTGGTGGCCATACGCAA

CGAAGCCACGCGTACCAACCGCGCCGTGCGTCTGCCCGTGAGCACCGCTGCCGCGCCCGAGG

GCATCACGCTCTTTTACGGCCTGTACAACGCAGTGAAGGAATTCTGCCTGCGTCACCAGCTG

GACCCGCCGCTGCTACGCCACCTAGATAAATACTACGCCGGACTGCCGCCCGAGCTGAAGCA

GACGCGCGTCAACCTGCCGGCTCACTCGCGCTATGGCCCTCAAGCAGTGGATGCTCGCGATT

ACAAGGACGATGACGATAAGTGATGATAATAGGCTGGAGCCTCGGTGGCCATGCTTCTTGCC

CCTTGGGCCTCCCCCCAGCCCCTCCTCCCCTTCCTGCACCCGTACCCCCGTGGTCTTTGAAT

AAAGTCTGAGTGGGCGGC

-continued hCMV-gLFLAG, glycoprotein L-FLAG mRNA
(SEQ ID NO: 161)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGUGCCGCCGCCCGGAUUGCGGCUUCUCUUU

CUCACCUGGACCGGUGAUACUGCUGUGGUGUUGCCUUCUGCUGCCCAUUGUUUCCUCAGCCG

CCGUCAGCGUCGCUCCUACCGCCGCCGAGAAAGUCCCCGCGGAGUGCCCCGAACUAACGCGC

CGAUGCUUGUUGGGUGAGGUGUUUGAGGGUGACAAGUAUGAAAGUUGGCUGCGCCCGUUGGU

GAAUGUUACCGGGCGCGAUGGCCCGCUAUCGCAACUUAUCCGUUACCGUCCCGUUACGCCGG

AGGCCGCCAACUCCGUGCUGUUGGACGAGGCUUUCCUGGACACUCUGGCCCUGCUGUACAAC

AAUCCGGAUCAAUUGCGGGCCCUGCUGACGCUGUUGAGCUCGGACACAGCGCCGCGCUGGAU

GACGGUGAUGCGCGGCUACAGCGAGUGCGGCGAUGGCUCGCCGGCCGUGUACACGUGCGUGG

ACGACCUGUGCCGCGGCUACGACCUCACGCGACUGUCAUACGGGCGCAGCAUCUUCACGGAA

CACGUGUUAGGCUUCGAGCUGGUGCCACCGUCUCUCUUUAACGUGGUGGUGGCCAUACGCAA

CGAAGCCACGCGUACCAACCGCGCCGUGCGUCUGCCCGUGAGCACCGCUGCCGCGCCCGAGG

GCAUCACGCUCUUUUACGGCCUGUACAACGCAGUGAAGGAAUUCUGCCUGCGUCACCAGCUG

GACCCGCCGCUGCUACGCCACCUAGAUAAAUACUACGCCGGACUGCCGCCCGAGCUGAAGCA

GACGCGCGUCAACCUGCCGGCUCACUCGCGCUAUGGCCCUCAAGCAGUGGAUGCUCGCGAUU

ACAAGGACGAUGACGAUAAGUGAUGAUAAUAGGCUGGAGCCUCGGUGGCCAUGCUUCUUGCC

CCUUGGGCCUCCCCCCAGCCCCUCCUCCCCUUCCUGCACCCGUACCCCCGUGGUCUUUGAAU

AAAGUCUGAGUGGGCGGC hCMV gB, hCMV glycoprotein B
(SEQ ID NO: 5)

TCAAGCTTTTGGACCCTCGTACAGAAGCTAATACGACTCACTATAGGGAAATAAGAGAGAAA

AGAAGAGTAAGAAGAAATATAAGAGCCACCATGGAATCCAGGATCTGGTGCCTGGTAGTCTG

CGTTAACTTGTGTATCGTCTGTCTGGGTGCTGCGGTTTCCTCATCTTCTACTCGTGGAACTT

CTGCTACTCACAGTCACCATTCCTCTCATACGACGTCTGCTGCTCACTCTCGATCCGGTTCA

GTCTCTCAACGCGTAACTTCTTCCCAAACGGTCAGCCATGGTGTTAACGAGACCATCTACAA

CACTACCCTCAAGTACGGAGATGTGGTGGGGGTCAATACCACCAAGTACCCCTATCGCGTGT

GTTCTATGGCCCAGGGTACGGATCTTATTCGCTTTGAACGTAATATCGTCTGCACCTCGATG

AAGCCCATCAATGAAGACCTGGACGAGGGCATCATGGTGGTCTACAAACGCAACATCGTCGC

GCACACCTTTAAGGTACGAGTCTACCAGAAGGTTTTGACGTTTCGTCGTAGCTACGCTTACA

TCCACACCACTTATCTGCTGGGCAGCAACACGGAATACGTGGCGCCTCCTATGTGGGAGATT

CATCATATCAACAGCCACAGTCAGTGCTACAGTTCCTACAGCCGCGTTATAGCAGGCACGGT

TTTCGTGGCTTATCATAGGGACAGCTATGAAAACAAAACCATGCAATTAATGCCCGACGATT

ATTCCAACACCCACAGTACCCGTTACGTGACGGTCAAGGATCAATGGCACAGCCGCGGCAGC

ACCTGGCTCTATCGTGAGACCTGTAATCTGAATTGTATGGTGACCATCACTACTGCGCGCTC

CAAATATCCTTATCATTTTTTCGCCACTTCCACGGGTGACGTGGTTGACATTTCTCCTTTCT

ACAACGGAACCAATCGCAATGCCAGCTACTTTGGAGAAAACGCCGACAAGTTTTTCATTTTT

CCGAACTACACTATCGTCTCCGACTTTGGAAGACCGAATTCTGCGTTAGAGACCCACAGGTT

GGTGGCTTTTCTTGAACGTGCGGACTCGGTGATCTCCTGGGATATACAGGACGAAAAGAATG

TCACTTGTCAACTCACTTTCTGGGAAGCCTCGGAACGCACCATTCGTTCCGAAGCCGAGGAC

TCGTATCACTTTTCTTCTGCCAAAATGACCGCCACTTTCTTATCTAAGAAGCAAGAGGTGAA

-continued

CATGTCCGACTCTGCGCTGGACTGCGTACGTGATGAGGCTATAAATAAGTTACAGCAGATTT

TCAATACTTCATACAATCAAACATATGAAAAATATGGAAACGTGTCCGTCTTTGAAACCACT

GGTGGTTTGGTAGTGTTCTGGCAAGGTATCAAGCAAAAATCTCTGGTGGAACTCGAACGTTT

GGCCAACCGCTCCAGTCTGAATCTTACTCATAATAGAACCAAAAGAAGTACAGATGGCAACA

ATGCAACTCATTTATCCAACATGGAATCGGTGCACAATCTGGTCTACGCCCAGCTGCAGTTC

ACCTATGACACGTTGCGCGGTTACATCAACCGGGCGCTGGCGCAAATCGCAGAAGCCTGGTG

TGTGGATCAACGGCGCACCCTAGAGGTCTTCAAGGAACTCAGCAAGATCAACCCGTCAGCCA

TTCTCTCGGCCATTTACAACAAACCGATTGCCGCGCGTTTCATGGGTGATGTCTTGGGCCTG

GCCAGCTGCGTGACCATCAACCAAACCAGCGTCAAGGTGCTGCGTGATATGAACGTGAAGGA

GTCGCCAGGACGCTGCTACTCACGACCCGTGGTCATCTTTAATTTCGCCAACAGCTCGTACG

TGCAGTACGGTCAACTGGGCGAGGACAACGAAATCCTGTTGGGCAACCACCGCACTGAGGAA

TGTCAGCTTCCCAGCCTCAAGATCTTCATCGCCGGGAACTCGGCCTACGAGTACGTGGACTA

CCTCTTCAAACGCATGATTGACCTCAGCAGTATCTCCACCGTCGACAGCATGATCGCCCTGG

ATATCGACCCGCTGGAAAATACCGACTTCAGGGTACTGGAACTTTACTCGCAGAAAGAGCTG

CGTTCCAGCAACGTTTTTGACCTCGAAGAGATCATGCGCGAATTCAACTCGTACAAGCAGCG

GGTAAAGTACGTGGAGGACAAGGTAGTCGACCCGCTACCGCCCTACCTCAAGGGTCTGGACG

ACCTCATGAGCGGCCTGGGCGCCGCGGGAAAGGCCGTTGGCGTAGCCATTGGGGCCGTGGGT

GGCGCGGTGGCCTCCGTGGTCGAAGGCGTTGCCACCTTCCTCAAAAACCCCTTCGGAGCGTT

CACCATCATCCTCGTGGCCATAGCTGTAGTCATTATCACTTATTTGATCTATACTCGACAGC

GGCGTTTGTGCACGCAGCCGCTGCAGAACCTCTTTCCCTATCTGGTGTCCGCCGACGGGACC

ACCGTGACGTCGGGCAGCACCAAAGACACGTCGTTACAGGCTCCGCCTTCCTACGAGGAAAG

TGTTTATAATTCTGGTCGCAAAGGACCGGGACCACCGTCGTCTGATGCATCCACGGCGGCTC

CGCCTTACACCAACGAGCAGGCTTACCAGATGCTTCTGGCCCTGGCCCGTCTGGACGCAGAG

CAGCGAGCGCAGCAGAACGGTACAGATTCTTTGGACGGACGGACTGGCACGCAGGACAAGGG

ACAGAAGCCCAACCTACTAGACCGACTGCGACATCGCAAAAACGGCTACCGACACTTGAAAG

ACTCTGACGAAGAAGAGAACGTCTGATAATAGGCTGGAGCCTCGGTGGCCATGCTTCTTGCC

CCTTGGGCCTCCCCCCAGCCCCTCCTCCCCTTCCTGCACCCGTACCCCCGTGGTCTTTGAAT

AAAGTCTGAGTGGGCGGC hCMV_gB, hCMV glycoprotein B mRNA (SEQ ID NO: 162)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGGAAUCCAGGAUCUGGUGCCUGGUAGUCUG

CGUUAACUUGUGUAUCGUCUGUCUGGGUGCUGCGGUUUCCUCAUCUUCUACUCGUGGAACUU

CUGCUACUCACAGUCACCAUUCCUCUCAUACGACGUCUGCUGCUCACUCUCGAUCCGGUUCA

GUCUCUCAACGCGUAACUUCUUCCCAAACGGUCAGCCAUGGUGUUAACGAGACCAUCUACAA

CACUACCCUCAAGUACGGAGAUGUGGUGGGGGUCAAUACCACCAAGUACCCCUAUCGCGUGU

GUUCUAUGGCCCAGGGUACGGAUCUUAUUCGCUUUGAACGUAAUAUCGUCUGCACCUCGAUG

AAGCCCAUCAAUGAAGACCUGGACGAGGGCAUCAUGGUGGUCUACAAACGCAACAUCGUCGC

GCACACCUUUAAGGUACGAGUCUACCAGAAGGUUUUGACGUUUCGUCGUAGCUACGCUUACA

UCCACACCACUUAUCUGCUGGGCAGCAACACGGAAUACGUGGCGCCUCCUAUGUGGGAGAUU

CAUCAUAUCAACAGCCACAGUCAGUGCUACAGUUCCUACAGCCGCGUUAUAGCAGGCACGGU

UUUCGUGGCUUAUCAUAGGGACAGCUAUGAAAACAAAACCAUGCAAUUAAUGCCCGACGAUU

-continued

AUUCCAACACCCACAGUACCCGUUACGUGACGGUCAAGGAUCAAUGGCACAGCCGCGGCAGC

ACCUGGCUCUAUCGUGAGACCUGUAAUCUGAAUUGUAUGGUGACCAUCACUACUGCGCGCUC

CAAAUAUCCUUAUCAUUUUUUCGCCACUUCCACGGGUGACGUGGUUGACAUUUCUCCUUUCU

ACAACGGAACCAAUCGCAAUGCCAGCUACUUUGGAGAAAACGCCGACAAGUUUUUCAUUUUU

CCGAACUACACUAUCGUCUCCGACUUUGGAAGACCGAAUUCUGCGUUAGAGACCCACAGGUU

GGUGGCUUUUCUUGAACGUGCGGACUCGGUGAUCUCCUGGGAUAUACAGGACGAAAAGAAUG

UCACUUGUCAACUCACUUUCUGGGAAGCCUCGGAACGCACCAUUCGUUCCGAAGCCGAGGAC

UCGUAUCACUUUUCUUCUGCCAAAAUGACCGCCACUUUCUUAUCUAAGAAGCAAGAGGUGAA

CAUGUCCGACUCUGCGCUGGACUGCGUACGUGAUGAGGCUAUAAAUAAGUUACAGCAGAUUU

UCAAUACUUCAUACAAUCAAACAUAUGAAAAAUAUGGAAACGUGUCCGUCUUUGAAACCACU

GGUGGUUUGGUAGUGUUCUGGCAAGGUAUCAAGCAAAAAUCUCUGGUGGAACUCGAACGUUU

GGCCAACCGCUCCAGUCUGAAUCUUACUCAUAAUAGAACCAAAAGAAGUACAGAUGGCAACA

AUGCAACUCAUUUAUCCAACAUGGAAUCGGUGCACAAUCUGGUCUACGCCCAGCUGCAGUUC

ACCUAUGACACGUUGCGCGGUUACAUCAACCGGGCGCUGGCGCAAAUCGCAGAAGCCUGGUG

UGUGGAUCAACGGCGCACCCUAGAGGUCUUCAAGGAACUCAGCAAGAUCAACCCGUCAGCCA

UUCUCUCGGCCAUUUACAACAAACCGAUUGCCGCGCGUUUCAUGGGUGAUGUCUUGGGCCUG

GCCAGCUGCGUGACCAUCAACCAAACCAGCGUCAAGGUGCUGCGUGAUAUGAACGUGAAGGA

GUCGCCAGGACGCUGCUACUCACGACCCGUGGUCAUCUUUAAUUUCGCCAACAGCUCGUACG

UGCAGUACGGUCAACUGGGCGAGGACAACGAAAUCCUGUUGGGCAACCACCGCACUGAGGAA

UGUCAGCUUCCCAGCCUCAAGAUCUUCAUCGCCGGGAACUCGGCCUACGAGUACGUGGACUA

CCUCUUCAAACGCAUGAUUGACCUCAGCAGUAUCUCCACCGUCGACAGCAUGAUCGCCCUGG

AUAUCGACCCGCUGGAAAAUACCGACUUCAGGGUACUGGAACUUUACUCGCAGAAAGAGCUG

CGUUCCAGCAACGUUUUUGACCUCGAAGAGAUCAUGCGCGAAUUCAACUCGUACAAGCAGCG

GGUAAAGUACGUGGAGGACAAGGUAGUCGACCCGCUACCGCCCUACCUCAAGGGUCUGGACG

ACCUCAUGAGCGGCCUGGGCGCCGCGGGAAAGGCCGUUGGCGUAGCCAUUGGGGCCGUGGGU

GGCGCGGUGGCCUCCGUGGUCGAAGGCGUUGCCACCUUCCUCAAAAACCCCUUCGGAGCGUU

CACCAUCAUCCUCGUGGCCAUAGCUGUAGUCAUUAUCACUUAUUUGAUCUAUACUCGACAGC

GGCGUUUGUGCACGCAGCCGCUGCAGAACCUCUUUCCCUAUCUGGUGUCCGCCGACGGGACC

ACCGUGACGUCGGGCAGCACCAAAGACACGUCGUUACAGGCUCCGCCUUCCUACGAGGAAAG

UGUUUAUAAUUCUGGUCGCAAAGGACCGGGACCACCGUCGUCUGAUGCAUCCACGGCGGCUC

CGCCUUACACCAACGAGCAGGCUUACCAGAUGCUUCUGGCCCUGGCCCGUCUGGACGCAGAG

CAGCGAGCGCAGCAGAACGGUACAGAUUCUUUGGACGGACGGACUGGCACGCAGGACAAGGG

ACAGAAGCCCAACCUACUAGACCGACUGCGACAUCGCAAAAACGGCUACCGACACUUGAAAG

ACUCUGACGAAGAAGAGAACGUCUGAUAAUAGGCUGGAGCCUCGGUGGCCAUGCUUCUUGCC

CCUUGGGCCUCCCCCCAGCCCCUCCUCCCCUUCCUGCACCCGUACCCCCGUGGUCUUUGAAU

AAAGUCUGAGUGGGCGGC hCMV gBFLAG, hCMV glycoproteinB-FLAG (SEQ ID NO: 6)

TCAAGCTTTTGGACCCTCGTACAGAAGCTAATACGACTCACTATAGGGAAATAAGAGAGAAA

AGAAGAGTAAGAAGAAATATAAGAGCCACCATGGAATCCAGGATCTGGTGCCTGGTAGTCTG

CGTTAACTTGTGTATCGTCTGTCTGGGTGCTGCGGTTTCCTCATCTTCTACTCGTGGAACTT

-continued
CTGCTACTCACAGTCACCATTCCTCTCATACGACGTCTGCTGCTCACTCTCGATCCGGTTCA
GTCTCTCAACGCGTAACTTCTTCCCAAACGGTCAGCCATGGTGTTAACGAGACCATCTACAA
CACTACCCTCAAGTACGGAGATGTGGTGGGGGTCAATACCACCAAGTACCCCTATCGCGTGT
GTTCTATGGCCCAGGGTACGGATCTTATTCGCTTTGAACGTAATATCGTCTGCACCTCGATG
AAGCCCATCAATGAAGACCTGGACGAGGGCATCATGGTGGTCTACAAACGCAACATCGTCGC
GCACACCTTTAAGGTACGAGTCTACCAGAAGGTTTTGACGTTTCGTCGTAGCTACGCTTACA
TCCACACCACTTATCTGCTGGGCAGCAACACGGAATACGTGGCGCCTCCTATGTGGGAGATT
CATCATATCAACAGCCACAGTCAGTGCTACAGTTCCTACAGCCGCGTTATAGCAGGCACGGT
TTTCGTGGCTTATCATAGGGACAGCTATGAAAACAAAACCATGCAATTAATGCCCGACGATT
ATTCCAACACCCACAGTACCCGTTACGTGACGGTCAAGGATCAATGGCACAGCCGCGGCAGC
ACCTGGCTCTATCGTGAGACCTGTAATCTGAATTGTATGGTGACCATCACTACTGCGCGCTC
CAAATATCCTTATCATTTTTTCGCCACTTCCACGGGTGACGTGGTTGACATTTCTCCTTTCT
ACAACGGAACCAATCGCAATGCCAGCTACTTTGGAGAAAACGCCGACAAGTTTTTCATTTTT
CCGAACTACACTATCGTCTCCGACTTTGGAAGACCGAATTCTGCGTTAGAGACCCACAGGTT
GGTGGCTTTTCTTGAACGTGCGGACTCGGTGATCTCCTGGGATATACAGGACGAAAAGAATG
TCACTTGTCAACTCACTTTCTGGGAAGCCTCGGAACGCACCATTCGTTCCGAAGCCGAGGAC
TCGTATCACTTTTCTTCTGCCAAAATGACCGCCACTTTCTTATCTAAGAAGCAAGAGGTGAA
CATGTCCGACTCTGCGCTGGACTGCGTACGTGATGAGGCTATAAATAAGTTACAGCAGATTT
TCAATACTTCATACAATCAAACATATGAAAAATATGGAAACGTGTCCGTCTTTGAAACCACT
GGTGGTTTGGTAGTGTTCTGGCAAGGTATCAAGCAAAAATCTCTGGTGGAACTCGAACGTTT
GGCCAACCGCTCCAGTCTGAATCTTACTCATAATAGAACCAAAAGAAGTACAGATGGCAACA
ATGCAACTCATTTATCCAACATGGAATCGGTGCACAATCTGGTCTACGCCCAGCTGCAGTTC
ACCTATGACACGTTGCGCGGTTACATCAACCGGGCGCTGGCGCAAATCGCAGAAGCCTGGTG
TGTGGATCAACGGCGCACCCTAGAGGTCTTCAAGGAACTCAGCAAGATCAACCCGTCAGCCA
TTCTCTCGGCCATTTACAACAAACCGATTGCCGCGCGTTTCATGGGTGATGTCTTGGGCCTG
GCCAGCTGCGTGACCATCAACCAAACCAGCGTCAAGGTGCTGCGTGATATGAACGTGAAGGA
GTCGCCAGGACGCTGCTACTCACGACCCGTGGTCATCTTTAATTTCGCCAACAGCTCGTACG
TGCAGTACGGTCAACTGGGCGAGGACAACGAAATCCTGTTGGGCAACCACCGCACTGAGGAA
TGTCAGCTTCCCAGCCTCAAGATCTTCATCGCCGGGAACTCGGCCTACGAGTACGTGGACTA
CCTCTTCAAACGCATGATTGACCTCAGCAGTATCTCCACCGTCGACAGCATGATCGCCCTGG
ATATCGACCCGCTGGAAAATACCGACTTCAGGGTACTGGAACTTTACTCGCAGAAAGAGCTG
CGTTCCAGCAACGTTTTTGACCTCGAAGAGATCATGCGCGAATTCAACTCGTACAAGCAGCG
GGTAAAGTACGTGGAGGACAAGGTAGTCGACCCGCTACCGCCCTACCTCAAGGGTCTGGACG
ACCTCATGAGCGGCCTGGGCGCCGCGGGAAAGGCCGTTGGCGTAGCCATTGGGGCCGTGGGT
GGCGCGGTGGCCTCCGTGGTCGAAGGCGTTGCCACCTTCCTCAAAAACCCCTTCGGAGCGTT
CACCATCATCCTCGTGGCCATAGCTGTAGTCATTATCACTTATTTGATCTATACTCGACAGC
GGCGTTTGTGCACGCAGCCGCTGCAGAACCTCTTTCCCTATCTGGTGTCCGCCGACGGGACC
ACCGTGACGTCGGGCAGCACCAAAGACACGTCGTTACAGGCTCCGCCTTCCTACGAGGAAAG
TGTTTATAATTCTGGTCGCAAAGGACCGGGACCACCGTCGTCTGATGCATCCACGGCGGCTC
CGCCTTACACCAACGAGCAGGCTTACCAGATGCTTCTGGCCCTGGCCCGTCTGGACGCAGAG
CAGCGAGCGCAGCAGAACGGTACAGATTCTTTGGACGGACGGACTGGCACGCAGGACAAGGG -continued

ACAGAAGCCCAACCTACTAGACCGACTGCGACATCGCAAAAACGGCTACCGACACTTGAAAG

ACTCTGACGAAGAAGAGAACGTCGATTACAAGGACGATGACGATAAGTGATAATAGGCTGGA

GCCTCGGTGGCCATGCTTCTTGCCCCTTGGGCCTCCCCCCAGCCCCTCCTCCCCTTCCTGCA

CCCGTACCCCCGTGGTCTTTGAATAAAGTCTGAGTGGGCGGC hCMV gBFLAG, hCMV glycoproteinB-FLAG mRNA (SEQ ID NO: 163)

TCAAGCUUUUGGACCCUCGUACAGAAGCUAAUACGACUCACUAUAGGGAAAUAAGAGAGAAA

AGAAGAGUAAGAAGAAAUAUAAGAGCCACCAUGGAAUCCAGGAUCUGGUGCCUGGUAGUCUG

CGUUAACUUGUGUAUCGUCUGUCUGGGUGCUGCGGUUUCCUCAUCUUCUACUCGUGGAACUU

CUGCUACUCACAGUCACCAUUCCUCUCAUACGACGUCUGCUGCUCACUCUCGAUCCGGUUCA

GUCUCUCAACGCGUAACUUCUUCCCAAACGGUCAGCCAUGGUGUUAACGAGACCAUCUACAA

CACUACCCUCAAGUACGGAGAUGUGGUGGGGGUCAAUACCACCAAGUACCCCUAUCGCGUGU

GUUCUAUGGCCCAGGGUACGGAUCUUAUUCGCUUUGAACGUAAUAUCGUCUGCACCUCGAUG

AAGCCCAUCAAUGAAGACCUGGACGAGGGCAUCAUGGUGGUCUACAAACGCAACAUCGUCGC

GCACACCUUUAAGGUACGAGUCUACCAGAAGGUUUUGACGUUUCGUCGUAGCUACGCUUACA

UCCACACCACUUAUCUGCUGGGCAGCAACACGGAAUACGUGGCGCCUCCUAUGUGGGAGAUU

CAUCAUAUCAACAGCCACAGUCAGUGCUACAGUUCCUACAGCCGCGUUAUAGCAGGCACGGU

UUUCGUGGCUUAUCAUAGGGACAGCUAUGAAAACAAAACCAUGCAAUUAAUGCCCGACGAUU

AUUCCAACACCCACAGUACCCGUUACGUGACGGUCAAGGAUCAAUGGCACAGCCGCGGCAGC

ACCUGGCUCUAUCGUGAGACCUGUAAUCUGAAUUGUAUGGUGACCAUCACUACUGCGCGCUC

CAAAUAUCCUUAUCAUUUUUUCGCCACUUCCACGGGUGACGUGGUUGACAUUUCUCCUUUCU

ACAACGGAACCAAUCGCAAUGCCAGCUACUUUGGAGAAAACGCCGACAAGUUUUUCAUUUUU

CCGAACUACACUAUCGUCUCCGACUUUGGAAGACCGAAUUCUGCGUUAGAGACCCACAGGUU

GGUGGCUUUUCUUGAACGUGCGGACUCGGUGAUCUCCUGGGAUAUACAGGACGAAAAGAAUG

UCACUUGUCAACUCACUUUCUGGGAAGCCUCGGAACGCACCAUUCGUUCCGAAGCCGAGGAC

UCGUAUCACUUUUCUUCUGCCAAAAUGACCGCCACUUUCUUAUCUAAGAAGCAAGAGGUGAA

CAUGUCCGACUCUGCGCUGGACUGCGUACGUGAUGAGGCUAUAAAUAAGUUACAGCAGAUUU

UCAAUACUUCAUACAAUCAAACAUAUGAAAAAUAUGGAAACGUGUCCGUCUUUGAAACCACU

GGUGGUUUGGUAGUGUUCUGGCAAGGUAUCAAGCAAAAAUCUCUGGUGGAACUCGAACGUUU

GGCCAACCGCUCCAGUCUGAAUCUUACUCAUAAUAGAACCAAAAGAAGUACAGAUGGCAACA

AUGCAACUCAUUUAUCCAACAUGGAAUCGGUGCACAAUCUGGUCUACGCCCAGCUGCAGUUC

ACCUAUGACACGUUGCGCGGUUACAUCAACCGGGCGCUGGCGCAAAUCGCAGAAGCCUGGUG

UGUGGAUCAACGGCGCACCCUAGAGGUCUUCAAGGAACUCAGCAAGAUCAACCCGUCAGCCA

UUCUCUCGGCCAUUUACAACAAACCGAUUGCCGCGCGUUUCAUGGGUGAUGUCUUGGGCCUG

GCCAGCUGCGUGACCAUCAACCAAACCAGCGUCAAGGUGCUGCGUGAUAUGAACGUGAAGGA

GUCGCCAGGACGCUGCUACUCACGACCCGUGGUCAUCUUUAAUUUCGCCAACAGCUCGUACG

UGCAGUACGGUCAACUGGGCGAGGACAACGAAAUCCUGUUGGGCAACCACCGCACUGAGGAA

UGUCAGCUUCCCAGCCUCAAGAUCUUCAUCGCCGGGAACUCGGCCUACGAGUACGUGGACUA

CCUCUUCAAACGCAUGAUUGACCUCAGCAGUAUCUCCACCGUCGACAGCAUGAUCGCCCUGG

AUAUCGACCCGCUGGAAAAUACCGACUUCAGGGUACUGGAACUUUACUCGCAGAAAGAGCUG

CGUUCCAGCAACGUUUUUGACCUCGAAGAGAUCAUGCGCGAAUUCAACUCGUACAAGCAGCG

-continued

GGUAAAGUACGUGGAGGACAAGGUAGUCGACCCGCUACCGCCCUACCUCAAGGGUCUGGACG

ACCUCAUGAGCGGCCUGGGCGCCGCGGGAAAGGCCGUUGGCGUAGCCAUUGGGGCCGUGGGU

GGCGCGGUGGCCUCCGUGGUCGAAGGCGUUGCCACCUUCCUCAAAAACCCCUUCGGAGCGUU

CACCAUCAUCCUCGUGGCCAUAGCUGUAGUCAUUAUCACUUAUUUGAUCUAUACUCGACAGC

GGCGUUUGUGCACGCAGCCGCUGCAGAACCUCUUUCCCUAUCUGGUGUCCGCCGACGGGACC

ACCGUGACGUCGGGCAGCACCAAAGACACGUCGUUACAGGCUCCGCCUUCCUACGAGGAAAG

UGUUUAUAAUUCUGGUCGCAAAGGACCGGGACCACCGUCGUCUGAUGCAUCCACGGCGGCUC

CGCCUUACACCAACGAGCAGGCUUACCAGAUGCUUCUGGCCCUGGCCCGUCUGGACGCAGAG

CAGCGAGCGCAGCAGAACGGUACAGAUUCUUUGGACGGACGGACUGGCACGCAGGACAAGGG

ACAGAAGCCCAACCUACUAGACCGACUGCGACAUCGCAAAAACGGCUACCGACACUUGAAAG

ACUCUGACGAAGAAGAGAACGUCGAUUACAAGGACGAUGACGAUAAGUGAUAAUAGGCUGGA

GCCUCGGUGGCCAUGCUUCUUGCCCCUUGGGCCUCCCCCCAGCCCCUCCUCCCCUUCCUGCA

CCCGUACCCCCGUGGUCUUUGAAUAAAGUCUGAGUGGGCGGC

Example 13: hCMV Vaccine—hCMV Variant Glycoprotein Sequences

A hCMV vaccine may comprise, for example, at least one RNA polynucleotide encoded by at least one of the following sequences or by at least one fragment or epitope of the following sequences. In some embodiments, a hCMV vaccine may comprise at least one RNA polynucleotide comprising at least one of the mRNA sequences listed below or at least one fragment of the mRNA sequences listed below.

hCMV-gHtrunc, hCMV glycoproteinH (Ectodomain)

(SEQ ID NO: 7)

TCAAGCTTTTGGACCCTCGTACAGAAGCTAATACGACTCACTATAGGGAAATAAGAGAGAAA

AGAAGAGTAAGAAGAAATATAAGAGCCACCATGCGGCCAGGCCTCCCCTCCTACCTCATCAT

CCTCGCCGTCTGTCTCTTCAGCCACCTACTTTCGTCACGATATGGCGCAGAAGCCGTATCCG

AACCGCTGGACAAAGCGTTTCACCTACTGCTCAACACCTACGGGAGACCCATCCGCTTCCTG

CGTGAAAATACCACCCAGTGTACCTACAACAGCAGCCTCCGTAACAGCACGGTCGTCAGGGA

AAACGCCATCAGTTTCAACTTTTTCCAAAGCTATAATCAATACTATGTATTCCATATGCCTC

GATGTCTTTTTGCGGGTCCTCTGGCGGAGCAGTTTCTGAACCAGGTAGATCTGACCGAAACC

CTGGAAAGATACCAACAGAGACTTAACACTTACGCGCTGGTATCCAAAGACCTGGCCAGCTA

CCGATCTTTTTCGCAGCAGCTAAAGGCACAAGACAGCCTAGGTGAACAGCCCACCACTGTGC

CACCGCCCATTGACCTGTCAATACCTCACGTTTGGATGCCACCGCAAACCACTCCACACGGC

TGGACAGAATCACATACCACCTCAGGACTACACCGACCACACTTTAACCAGACCTGTATCCT

CTTTGATGGACACGATCTACTATTCAGCACCGTCACACCTTGTTTGCACCAAGGCTTTTACC

TCATCGACGAACTACGTTACGTTAAAATAACACTGACCGAGGACTTCTTCGTAGTTACGGTG

TCCATAGACGACGACACACCCATGCTGCTTATCTTCGGCCATCTTCCACGCGTACTTTTCAA

AGCGCCCTATCAACGCGACAACTTTATACTACGACAAACTGAAAAACACGAGCTCCTGGTGC

TAGTTAAGAAAGATCAACTGAACCGTCACTCTTATCTCAAAGACCCGGACTTTCTTGACGCC

GCACTTGACTTCAACTACCTAGACCTCAGCGCACTACTACGTAACAGCTTTCACCGTTACGC

CGTGGATGTACTCAAGAGCGGTCGATGTCAGATGCTGGACCGCCGCACGGTAGAAATGGCCT

TCGCCTACGCATTAGCACTGTTCGCAGCAGCCCGACAAGAAGAGGCCGGCGCCCAAGTCTCC

GTCCCACGGGCCCTAGACCGCCAGGCCGCACTCTTACAAATACAAGAATTTATGATCACCTG

CCTCTCACAAACACCACCACGCACCACGTTGCTGCTGTATCCCACGGCCGTGGACCTGGCCA

AACGAGCCCTTTGGACACCGAATCAGATCACCGACATCACCAGCCTCGTACGCCTGGTCTAC

-continued

ATACTCTCTAAACAGAATCAGCAACATCTCATCCCCCAATGGGCACTACGACAGATCGCCGA

CTTTGCCCTAAAACTACACAAAACGCACCTGGCCTCTTTTCTTTCAGCCTTCGCACGCCAAG

AACTCTACCTCATGGGCAGCCTCGTCCACTCCATGCTGGTACATACGACGGAGAGACGCGAA

ATCTTCATCGTAGAAACGGGCCTCTGTTCATTGGCCGAGCTATCACACTTTACGCAGTTGTT

AGCTCATCCACACCACGAATACCTCAGCGACCTGTACACACCCTGTTCCAGTAGCGGGCGAC

GCGATCACTCGCTCGAACGCCTCACGCGTCTCTTCCCCGATGCCACCGTCCCCGCTACCGTT

CCCGCCGCCCTCTCCATCCTATCTACCATGCAACCAAGCACGCTGGAAACCTTCCCCGACCT

GTTTTGCTTGCCGCTCGGCGAATCCTTCTCCGCGCTGACCGTCTCCGAACACGTCAGTTATA

TCGTAACAAACCAGTACCTGATCAAAGGTATCTCCTACCCTGTCTCCACCACCGTCGTAGGC

CAGAGCCTCATCATCACCCAGACGGACAGTCAAACTAAATGCGAACTGACGCGCAACATGCA

TACCACACACAGCATCACAGTGGCGCTCAACATTTCGCTAGAAAACTGCGCCTTTTGCCAAA

GCGCCCTGCTAGAATACGACGACACGCAAGGCGTCATCAACATCATGTACATGCACGACTCG

GACGACGTCCTTTTCGCCCTGGATCCCTACAACGAAGTGGTGGTCTCATCTCCGCGAACTCA

CTACCTCATGCTTTTGAAAAACGGTACGGTACTAGAAGTAACTGACGTCGTCGTGGACGCCA

CCGACTGATAATAGGCTGGAGCCTCGGTGGCCATGCTTCTTGCCCCTTGGGCCTCCCCCCAG

CCCCTCCTCCCCTTCCTGCACCCGTACCCCCGTGGTCTTTGAATAAAGTCTGAGTGGGCGGC hCMV-gHtrunc, hCMV glycoproteinH (Ectodomain) mRNA (SEQ ID NO: 164)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGCGGCCAGGCCUCCCCUCCUACCUCAUCAU

CCUCGCCGUCUGUCUCUUCAGCCACCUACUUUCGUCACGAUAUGGCGCAGAAGCCGUAUCCG

AACCGCUGGACAAAGCGUUUCACCUACUGCUCAACACCUACGGGAGACCCAUCCGCUUCCUG

CGUGAAAAUACCACCCAGUGUACCUACAACAGCAGCCUCCGUAACAGCACGGUCGUCAGGGA

AAACGCCAUCAGUUUCAACUUUUUCCAAAGCUAUAAUCAAUACUAUGUAUUCCAUAUGCCUC

GAUGUCUUUUUGCGGGUCCUCUGGCGGAGCAGUUUCUGAACCAGGUAGAUCUGACCGAAACC

CUGGAAAGAUACCAACAGAGACUUAACACUUACGCGCUGGUAUCCAAAGACCUGGCCAGCUA

CCGAUCUUUUUCGCAGCAGCUAAAGGCACAAGACAGCCUAGGUGAACAGCCCACCACUGUGC

CACCGCCCAUUGACCUGUCAAUACCUCACGUUUGGAUGCCACCGCAAACCACUCCACACGGC

UGGACAGAAUCACAUACCACCUCAGGACUACACCGACCACACUUUAACCAGACCUGUAUCCU

CUUUGAUGGACACGAUCUACUAUUCAGCACCGUCACACCUUGUUUGCACCAAGGCUUUUACC

UCAUCGACGAACUACGUUACGUUAAAAUAACACUGACCGAGGACUUCUUCGUAGUUACGGUG

UCCAUAGACGACGACACACCCAUGCUGCUUAUCUUCGGCCAUCUUCCACGCGUACUUUUCAA

AGCGCCCUAUCAACGCGACAACUUUAUACUACGACAAACUGAAAAACACGAGCUCCUGGUGC

UAGUUAAGAAAGAUCAACUGAACCGUCACUCUUAUCUCAAAGACCCGGACUUUCUUGACGCC

GCACUUGACUUCAACUACCUAGACCUCAGCGCACUACUACGUAACAGCUUUCACCGUUACGC

CGUGGAUGUACUCAAGAGCGGUCGAUGUCAGAUGCUGGACCGCCGCACGGUAGAAAUGGCCU

UCGCCUACGCAUUAGCACUGUUCGCAGCAGCCCGACAAGAAGAGGCCGGCGCCCAAGUCUCC

GUCCCACGGGCCCUAGACCGCCAGGCCGCACUCUUACAAAUACAAGAAUUUAUGAUCACCUG

CCUCUCACAAACACCACCACGCACCACGUUGCUGCUGUAUCCCACGGCCGUGGACCUGGCCA

AACGAGCCCUUUGGACACCGAAUCAGAUCACCGACAUCACCAGCCUCGUACGCCUGGUCUAC

AUACUCUCUAAACAGAAUCAGCAACAUCUCAUCCCCCAAUGGGCACUACGACAGAUCGCCGA

CUUUGCCCUAAAACUACACAAAACGCACCUGGCCUCUUUUCUUUCAGCCUUCGCACGCCAAG

-continued

AACUCUACCUCAUGGGCAGCCUCGUCCACUCCAUGCUGGUACAUACGACGGAGAGACGCGAA

AUCUUCAUCGUAGAAACGGGCCUCUGUUCAUUGGCCGAGCUAUCACACUUUACGCAGUUGUU

AGCUCAUCCACACCACGAAUACCUCAGCGACCUGUACACACCCUGUUCCAGUAGCGGGCGAC

GCGAUCACUCGCUCGAACGCCUCACGCGUCUCUUCCCCGAUGCCACCGUCCCCGCUACCGUU

CCCGCCGCCCUCUCCAUCCUAUCUACCAUGCAACCAAGCACGCUGGAAACCUUCCCCGACCU

GUUUUGCUUGCCGCUCGGCGAAUCCUUCUCCGCGCUGACCGUCUCCGAACACGUCAGUUAUA

UCGUAACAAACCAGUACCUGAUCAAAGGUAUCUCCUACCCUGUCUCCACCACCGUCGUAGGC

CAGAGCCUCAUCAUCACCCAGACGGACAGUCAAACUAAAUGCGAACUGACGCGCAACAUGCA

UACCACACACAGCAUCACAGUGGCGCUCAACAUUUCGCUAGAAAACUGCGCCUUUUGCCAAA

GCGCCCUGCUAGAAUACGACGACACGCAAGGCGUCAUCAACAUCAUGUACAUGCACGACUCG

GACGACGUCCUUUUCGCCCUGGAUCCCUACAACGAAGUGGUGGUCUCAUCUCCGCGAACUCA

CUACCUCAUGCUUUUGAAAAACGGUACGGUACUAGAAGUAACUGACGUCGUCGUGGACGCCA

CCGACUGAUAAUAGGCUGGAGCCUCGGUGGCCAUGCUUCUUGCCCCUUGGGCCUCCCCCCAG

CCCCUCCUCCCCUUCCUGCACCCGUACCCCCGUGGUCUUUGAAUAAAGUCUGAGUGGGCGGC hCMV-gHtruncFLAG, glycoprotein H Ectodomain (SEQ ID NO: 8)

TCAAGCTTTTGGACCCTCGTACAGAAGCTAATACGACTCACTATAGGGAAATAAGAGAGAAA

AGAAGAGTAAGAAGAAATATAAGAGCCACCATGCGGCCAGGCCTCCCCTCCTACCTCATCAT

CCTCGCCGTCTGTCTCTTCAGCCACCTACTTTCGTCACGATATGGCGCAGAAGCCGTATCCG

AACCGCTGGACAAAGCGTTTCACCTACTGCTCAACACCTACGGGAGACCCATCCGCTTCCTG

CGTGAAAATACCACCCAGTGTACCTACAACAGCAGCCTCCGTAACAGCACGGTCGTCAGGGA

AAACGCCATCAGTTTCAACTTTTTCCAAAGCTATAATCAATACTATGTATTCCATATGCCTC

GATGTCTTTTTGCGGGTCCTCTGGCGGAGCAGTTTCTGAACCAGGTAGATCTGACCGAAACC

CTGGAAAGATACCAACAGAGACTTAACACTTACGCGCTGGTATCCAAAGACCTGGCCAGCTA

CCGATCTTTTTCGCAGCAGCTAAAGGCACAAGACAGCCTAGGTGAACAGCCCACCACTGTGC

CACCGCCCATTGACCTGTCAATACCTCACGTTTGGATGCCACCGCAAACCACTCCACACGGC

TGGACAGAATCACATACCACCTCAGGACTACACCGACCACACTTTAACCAGACCTGTATCCT

CTTTGATGGACACGATCTACTATTCAGCACCGTCACACCTTGTTTGCACCAAGGCTTTTACC

TCATCGACGAACTACGTTACGTTAAAATAACACTGACCGAGGACTTCTTCGTAGTTACGGTG

TCCATAGACGACGACACACCCATGCTGCTTATCTTCGGCCATCTTCCACGCGTACTTTTCAA

AGCGCCCTATCAACGCGACAACTTTATACTACGACAAACTGAAAAACACGAGCTCCTGGTGC

TAGTTAAGAAAGATCAACTGAACCGTCACTCTTATCTCAAAGACCCGGACTTTCTTGACGCC

GCACTTGACTTCAACTACCTAGACCTCAGCGCACTACTACGTAACAGCTTTCACCGTTACGC

CGTGGATGTACTCAAGAGCGGTCGATGTCAGATGCTGGACCGCCGCACGGTAGAAATGGCCT

TCGCCTACGCATTAGCACTGTTCGCAGCAGCCCGACAAGAAGAGGCCGGCGCCCAAGTCTCC

GTCCCACGGGCCCTAGACCGCCAGGCCGCACTCTTACAAATACAAGAATTTATGATCACCTG

CCTCTCACAAACACCACCACGCACCACGTTGCTGCTGTATCCCACGGCCGTGGACCTGGCCA

AACGAGCCCTTTGGACACCGAATCAGATCACCGACATCACCAGCCTCGTACGCCTGGTCTAC

ATACTCTCTAAACAGAATCAGCAACATCTCATCCCCCAATGGGCACTACGACAGATCGCCGA

CTTTGCCCTAAAACTACACAAAACGCACCTGGCCTCTTTTCTTTCAGCCTTCGCACGCCAAG

AACTCTACCTCATGGGCAGCCTCGTCCACTCCATGCTGGTACATACGACGGAGAGACGCGAA

-continued

ATCTTCATCGTAGAAACGGGCCTCTGTTCATTGGCCGAGCTATCACACTTTACGCAGTTGTT

AGCTCATCCACACCACGAATACCTCAGCGACCTGTACACACCCTGTTCCAGTAGCGGGCGAC

GCGATCACTCGCTCGAACGCCTCACGCGTCTCTTCCCCGATGCCACCGTCCCCGCTACCGTT

CCCGCCGCCCTCTCCATCCTATCTACCATGCAACCAAGCACGCTGGAAACCTTCCCCGACCT

GTTTTGCTTGCCGCTCGGCGAATCCTTCTCCGCGCTGACCGTCTCCGAACACGTCAGTTATA

TCGTAACAAACCAGTACCTGATCAAAGGTATCTCCTACCCTGTCTCCACCACCGTCGTAGGC

CAGAGCCTCATCATCACCCAGACGGACAGTCAAACTAAATGCGAACTGACGCGCAACATGCA

TACCACACACAGCATCACAGTGGCGCTCAACATTTCGCTAGAAAACTGCGCCTTTTGCCAAA

GCGCCCTGCTAGAATACGACGACACGCAAGGCGTCATCAACATCATGTACATGCACGACTCG

GACGACGTCCTTTTCGCCCTGGATCCCTACAACGAAGTGGTGGTCTCATCTCCGCGAACTCA

CTACCTCATGCTTTTGAAAAACGGTACGGTACTAGAAGTAACTGACGTCGTCGTGGACGCCA

CCGACGATTACAAGGACGATGACGATAAGTGATGATAATAGGCTGGAGCCTCGGTGGCCATG

CTTCTTGCCCCTTGGGCCTCCCCCCAGCCCCTCCTCCCCTTCCTGCACCCGTACCCCCGTGG

TCTTTGAATAAAGTCTGAGTGGGCGGC hCMV-gHtruncFLAG, glycoprotein H Ectodomain mRNA (SEQ ID NO: 165)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGCGGCCAGGCCUCCCCUCCUACCUCAUCAU

CCUCGCCGUCUGUCUCUUCAGCCACCUACUUUCGUCACGAUAUGGCGCAGAAGCCGUAUCCG

AACCGCUGGACAAAGCGUUUCACCUACUGCUCAACACCUACGGGAGACCCAUCCGCUUCCUG

CGUGAAAAUACCACCCAGUGUACCUACAACAGCAGCCUCCGUAACAGCACGGUCGUCAGGGA

AAACGCCAUCAGUUUCAACUUUUUCCAAAGCUAUAAUCAAUACUAUGUAUUCCAUAUGCCUC

GAUGUCUUUUUGCGGGUCCUCUGGCGGAGCAGUUUCUGAACCAGGUAGAUCUGACCGAAACC

CUGGAAAGAUACCAACAGAGACUUAACACUUACGCGCUGGUAUCCAAAGACCUGGCCAGCUA

CCGAUCUUUUUCGCAGCAGCUAAAGGCACAAGACAGCCUAGGUGAACAGCCCACCACUGUGC

CACCGCCCAUUGACCUGUCAAUACCUCACGUUUGGAUGCCACCGCAAACCACUCCACACGGC

UGGACAGAAUCACAUACCACCUCAGGACUACACCGACCACACUUUAACCAGACCUGUAUCCU

CUUUGAUGGACACGAUCUACUAUUCAGCACCGUCACACCUUGUUUGCACCAAGGCUUUUACC

UCAUCGACGAACUACGUUACGUUAAAAUAACACUGACCGAGGACUUCUUCGUAGUUACGGUG

UCCAUAGACGACGACACACCCAUGCUGCUUAUCUUCGGCCAUCUUCCACGCGUACUUUUCAA

AGCGCCCUAUCAACGCGACAACUUUAUACUACGACAAACUGAAAAACACGAGCUCCUGGUGC

UAGUUAAGAAAGAUCAACUGAACCGUCACUCUUAUCUCAAAGACCCGGACUUUCUUGACGCC

GCACUUGACUUCAACUACCUAGACCUCAGCGCACUACUACGUAACAGCUUUCACCGUUACGC

CGUGGAUGUACUCAAGAGCGGUCGAUGUCAGAUGCUGGACCGCCGCACGGUAGAAAUGGCCU

UCGCCUACGCAUUAGCACUGUUCGCAGCAGCCCGACAAGAAGAGGCCGGCGCCCAAGUCUCC

GUCCCACGGGCCCUAGACCGCCAGGCCGCACUCUUACAAAUACAAGAAUUUAUGAUCACCUG

CCUCUCACAAACACCACCACGCACCACGUUGCUGCUGUAUCCCACGGCCGUGGACCUGGCCA

AACGAGCCCUUUGGACACCGAAUCAGAUCACCGACAUCACCAGCCUCGUACGCCUGGUCUAC

AUACUCUCUAAACAGAAUCAGCAACAUCUCAUCCCCCAAUGGGCACUACGACAGAUCGCCGA

CUUUGCCCUAAAACUACACAAAACGCACCUGGCCUCUUUUCUUUCAGCCUUCGCACGCCAAG

AACUCUACCUCAUGGGCAGCCUCGUCCACUCCAUGCUGGUACAUACGACGGAGAGACGCGAA

AUCUUCAUCGUAGAAACGGGCCUCUGUUCAUUGGCCGAGCUAUCACACUUUACGCAGUUGUU

-continued

AGCUCAUCCACACCACGAAUACCUCAGCGACCUGUACACACCCUGUUCCAGUAGCGGGCGAC

GCGAUCACUCGCUCGAACGCCUCACGCGUCUCUUCCCCGAUGCCACCGUCCCCGCUACCGUU

CCCGCCGCCCUCUCCAUCCUAUCUACCAUGCAACCAAGCACGCUGGAAACCUUCCCCGACCU

GUUUUGCUUGCCGCUCGGCGAAUCCUUCUCCGCGCUGACCGUCUCCGAACACGUCAGUUAUA

UCGUAACAAACCAGUACCUGAUCAAAGGUAUCUCCUACCCUGUCUCCACCACCGUCGUAGGC

CAGAGCCUCAUCAUCACCCAGACGGACAGUCAAACUAAAUGCGAACUGACGCGCAACAUGCA

UACCACACACAGCAUCACAGUGGCGCUCAACAUUUCGCUAGAAAACUGCGCCUUUUGCCAAA

GCGCCCUGCUAGAAUACGACGACACGCAAGGCGUCAUCAACAUCAUGUACAUGCACGACUCG

GACGACGUCCUUUUCGCCCUGGAUCCCUACAACGAAGUGGUGGUCUCAUCUCCGCGAACUCA

CUACCUCAUGCUUUUGAAAAACGGUACGGUACUAGAAGUAACUGACGUCGUCGUGGACGCCA

CCGACGAUUACAAGGACGAUGACGAUAAGUGAUGAUAAUAGGCUGGAGCCUCGGUGGCCAUG

CUUCUUGCCCCUUGGGCCUCCCCCCAGCCCCUCCUCCCCUUCCUGCACCCGUACCCCCGUGG

UCUUUGAAUAAAGUCUGAGUGGGCGGC hCMVgHtrunc6XHis, glycoprotein H Ectodomain-6XHis tag (SEQ ID NO: 9)

TCAAGCTTTTGGACCCTCGTAGAGAAGCTAATACGACTCACTATAGGGAAATAAGAGAGAAA

AGAAGAGTAAGAAGAAATATAAGAGCCACCATGCGGCCAGGCCTCCCCTCCTACCTCATCAT

CCTCGCCGTCTGTCTCTTCAGCCACCTACTTTCGTCACGATATGGCGCAGAAGCCGTATCCG

AACCGCTGGACAAAGCGTTTCACCTACTGCTCAACACCTACGGGAGACCCATCCGCTTCCTG

CGTGAAAATACCACCCAGTGTACCTACAACAGCAGCCTCCGTAACAGCACGGTCGTCAGGGA

AAACGCCATCAGTTTCAACTTTTTCCAAAGCTATAATCAATACTATGTATTCCATATGCCTC

GATGTCTTTTTGCGGGTCCTCTGGCGGAGCAGTTTCTGAACCAGGTAGATCTGACCGAAACC

CTGGAAAGATACCAACAGAGACTTAACACTTACGCGCTGGTATCCAAAGACCTGGCCAGCTA

CCGATCTTTTTCGCAGCAGCTAAAGGCACAAGACAGCCTAGGTGAACAGCCCACCACTGTGC

CACCGCCCATTGACCTGTCAATACCTCACGTTTGGATGCCACCGCAAACCACTCCACACGGC

TGGACAGAATCACATACCACCTCAGGACTACACCGACCACACTTTAACCAGACCTGTATCCT

CTTTGATGGACACGATCTACTATTCAGCACCGTCACACCTTGTTTGCACCAAGGCTTTTACC

TCATCGACGAACTACGTTACGTTAAAATAACACTGACCGAGGACTTCTTCGTAGTTACGGTG

TCCATAGACGACGACACACCCATGCTGCTTATCTTCGGCCATCTTCCACGCGTACTTTTCAA

AGCGCCCTATCAACGCGACAACTTTATACTACGACAAACTGAAAAACACGAGCTCCTGGTGC

TAGTTAAGAAAGATCAACTGAACCGTCACTCTTATCTCAAAGACCCGGACTTTCTTGACGCC

GCACTTGACTTCAACTACCTAGACCTCAGCGCACTACTACGTAACAGCTTTCACCGTTACGC

CGTGGATGTACTCAAGAGCGGTCGATGTCAGATGCTGGACCGCCGCACGGTAGAAATGGCCT

TCGCCTACGCATTAGCACTGTTCGCAGCAGCCCGACAAGAAGAGGCCGGCGCCCAAGTCTCC

GTCCCACGGGCCCTAGACCGCCAGGCCGCACTCTTACAAATACAAGAATTTATGATCACCTG

CCTCTCACAAACACCACCACGCACCACGTTGCTGCTGTATCCCACGGCCGTGGACCTGGCCA

AACGAGCCCTTTGGACACCGAATCAGATCACCGACATCACCAGCCTCGTACGCCTGGTCTAC

ATACTCTCTAAACAGAATCAGCAACATCTCATCCCCCAATGGGCACTACGACAGATCGCCGA

CTTTGCCCTAAAACTACACAAAACGCACCTGGCCTCTTTTCTTTCAGCCTTCGCACGCCAAG

AACTCTACCTCATGGGCAGCCTCGTCCACTCCATGCTGGTACATACGACGGAGAGACGCGAA

ATCTTCATCGTAGAAACGGGCCTCTGTTCATTGGCCGAGCTATCACACTTTACGCAGTTGTT

-continued

AGCTCATCCACACCACGAATACCTCAGCGACCTGTACACACCCTGTTCCAGTAGCGGGCGAC

GCGATCACTCGCTCGAACGCCTCACGCGTCTCTTCCCCGATGCCACCGTCCCCGCTACCGTT

CCCGCCGCCCTCTCCATCCTATCTACCATGCAACCAAGCACGCTGGAAACCTTCCCCGACCT

GTTTTGCTTGCCGCTCGGCGAATCCTTCTCCGCGCTGACCGTCTCCGAACACGTCAGTTATA

TCGTAACAAACCAGTACCTGATCAAAGGTATCTCCTACCCTGTCTCCACCACCGTCGTAGGC

CAGAGCCTCATCATCACCCAGACGGACAGTCAAACTAAATGCGAACTGACGCGCAACATGCA

TACCACACACAGCATCACAGTGGCGCTCAACATTTCGCTAGAAAACTGCGCCTTTTGCCAAA

GCGCCCTGCTAGAATACGACGACACGCAAGGCGTCATCAACATCATGTACATGCACGACTCG

GACGACGTCCTTTTCGCCCTGGATCCCTACAACGAAGTGGTGGTCTCATCTCCGCGAACTCA

CTACCTCATGCTTTTGAAAAACGGTACGGTACTAGAAGTAACTGACGTCGTCGTGGACGCCA

CCGACCACCATCACCACCATCACTGATGATAATAGGCTGGAGCCTCGGTGGCCATGCTTCTT

GCCCCTTGGGCCTCCCCCCAGCCCCTCCTCCCCTTCCTGCACCCGTACCCCCGTGGTCTTTG

AATAAAGTCTGAGTGGGCGGC hCMVgHtrunc6XHis, glycoprotein H Ectodomain-6XHis tag mRNA (SEQ ID NO: 166)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGCGGCCAGGCCUCCCCUCCUACCUCAUCAU

CCUCGCCGUCUGUCUCUUCAGCCACCUACUUUCGUCACGAUAUGGCGCAGAAGCCGUAUCCG

AACCGCUGGACAAAGCGUUUCACCUACUGCUCAACACCUACGGGAGACCCAUCCGCUUCCUG

CGUGAAAAUACCACCCAGUGUACCUACAACAGCAGCCUCCGUAACAGCACGGUCGUCAGGGA

AAACGCCAUCAGUUUCAACUUUUUCCAAAGCUAUAAUCAAUACUAUGUAUUCCAUAUGCCUC

GAUGUCUUUUUGCGGGUCCUCUGGCGGAGCAGUUUCUGAACCAGGUAGAUCUGACCGAAACC

CUGGAAAGAUACCAACAGAGACUUAACACUUACGCGCUGGUAUCCAAAGACCUGGCCAGCUA

CCGAUCUUUUUCGCAGCAGCUAAAGGCACAAGACAGCCUAGGUGAACAGCCCACCACUGUGC

CACCGCCCAUUGACCUGUCAAUACCUCACGUUUGGAUGCCACCGCAAACCACUCCACACGGC

UGGACAGAAUCACAUACCACCUCAGGACUACACCGACCACACUUUAACCAGACCUGUAUCCU

CUUUGAUGGACACGAUCUACUAUUCAGCACCGUCACACCUUGUUUGCACCAAGGCUUUUACC

UCAUCGACGAACUACGUUACGUUAAAAUAACACUGACCGAGGACUUCUUCGUAGUUACGGUG

UCCAUAGACGACGACACACCCAUGCUGCUUAUCUUCGGCCAUCUUCCACGCGUACUUUUCAA

AGCGCCCUAUCAACGCGACAACUUUAUACUACGACAAACUGAAAAACACGAGCUCCUGGUGC

UAGUUAAGAAAGAUCAACUGAACCGUCACUCUUAUCUCAAAGACCCGGACUUUCUUGACGCC

GCACUUGACUUCAACUACCUAGACCUCAGCGCACUACUACGUAACAGCUUUCACCGUUACGC

CGUGGAUGUACUCAAGAGCGGUCGAUGUCAGAUGCUGGACCGCCGCACGGUAGAAAUGGCCU

UCGCCUACGCAUUAGCACUGUUCGCAGCAGCCCGACAAGAAGAGGCCGGCGCCCAAGUCUCC

GUCCCACGGGCCCUAGACCGCCAGGCCGCACUCUUACAAAUACAAGAAUUUAUGAUCACCUG

CCUCUCACAAACACCACCACGCACCACGUUGCUGCUGUAUCCCACGGCCGUGGACCUGGCCA

AACGAGCCCUUUGGACACCGAAUCAGAUCACCGACAUCACCAGCCUCGUACGCCUGGUCUAC

AUACUCUCUAAACAGAAUCAGCAACAUCUCAUCCCCCAAUGGGCACUACGACAGAUCGCCGA

CUUUGCCCUAAAACUACACAAAACGCACCUGGCCUCUUUUCUUUCAGCCUUCGCACGCCAAG

AACUCUACCUCAUGGGCAGCCUCGUCCACUCCAUGCUGGUACAUACGACGGAGAGACGCGAA

AUCUUCAUCGUAGAAACGGGCCUCUGUUCAUUGGCCGAGCUAUCACACUUUACGCAGUUGUU

AGCUCAUCCACACCACGAAUACCUCAGCGACCUGUACACACCCUGUUCCAGUAGCGGGCGAC

-continued

GCGAUCACUCGCUCGAACGCCUCACGCGUCUCUUCCCCGAUGCCACCGUCCCCGCUACCGUU

CCCGCCGCCCUCUCCAUCCUAUCUACCAUGCAACCAAGCACGCUGGAAACCUUCCCCGACCU

GUUUUGCUUGCCGCUCGGCGAAUCCUUCUCCGCGCUGACCGUCUCCGAACACGUCAGUUAUA

UCGUAACAAACCAGUACCUGAUCAAAGGUAUCUCCUACCCUGUCUCCACCACCGUCGUAGGC

CAGAGCCUCAUCAUCACCCAGACGGACAGUCAAACUAAAUGCGAACUGACGCGCAACAUGCA

UACCACACACAGCAUCACAGUGGCGCUCAACAUUUCGCUAGAAAACUGCGCCUUUUGCCAAA

GCGCCCUGCUAGAAUACGACGACACGCAAGGCGUCAUCAACAUCAUGUACAUGCACGACUCG

GACGACGUCCUUUUCGCCCUGGAUCCCUACAACGAAGUGGUGGUCUCAUCUCCGCGAACUCA

CUACCUCAUGCUUUUGAAAAACGGUACGGUACUAGAAGUAACUGACGUCGUCGUGGACGCCA

CCGACCACCAUCACCACCAUCACUGAUGAUAAUAGGCUGGAGCCUCGGUGGCCAUGCUUCUU

GCCCCUUGGGCCUCCCCCCAGCCCCUCCUCCCCUUCCUGCACCCGUACCCCCGUGGUCUUUG

AAUAAAGUCUGAGUGGGCGGC hCMV TrgB, glycoprotein B (ectodomain)

(SEQ ID NO: 10)

TCAAGCTTTTGGACCCTCGTAGAGAAGCTAATACGACTCACTATAGGGAAATAAGAGAGAAA

AGAAGAGTAAGAAGAAATATAAGAGCCACCATGGAATCCAGGATCTGGTGCCTGGTAGTCTG

CGTTAACTTGTGTATCGTCTGTCTGGGTGCTGCGGTTTCCTCATCTTCTACTCGTGGAACTT

CTGCTACTCACAGTCACCATTCCTCTCATACGACGTCTGCTGCTCACTCTCGATCCGGTTCA

GTCTCTCAACGCGTAACTTCTTCCCAAACGGTCAGCCATGGTGTTAACGAGACCATCTACAA

CACTACCCTCAAGTACGGAGATGTGGTGGGGGTCAATACCACCAAGTACCCCTATCGCGTGT

GTTCTATGGCCCAGGGTACGGATCTTATTCGCTTTGAACGTAATATCGTCTGCACCTCGATG

AAGCCCATCAATGAAGACCTGGACGAGGGCATCATGGTGGTCTACAAACGCAACATCGTCGC

GCACACCTTTAAGGTACGAGTCTACCAGAAGGTTTTGACGTTTCGTCGTAGCTACGCTTACA

TCCACACCACTTATCTGCTGGGCAGCAACACGGAATACGTGGCGCCTCCTATGTGGGAGATT

CATCATATCAACAGCCACAGTCAGTGCTACAGTTCCTACAGCCGCGTTATAGCAGGCACGGT

TTTCGTGGCTTATCATAGGGACAGCTATGAAAACAAAACCATGCAATTAATGCCCGACGATT

ATTCCAACACCCACAGTACCCGTTACGTGACGGTCAAGGATCAATGGCACAGCCGCGGCAGC

ACCTGGCTCTATCGTGAGACCTGTAATCTGAATTGTATGGTGACCATCACTACTGCGCGCTC

CAAATATCCTTATCATTTTTTCGCCACTTCCACGGGTGACGTGGTTGACATTTCTCCTTTCT

ACAACGGAACCAATCGCAATGCCAGCTACTTTGGAGAAAACGCCGACAAGTTTTTCATTTTT

CCGAACTACACTATCGTCTCCGACTTTGGAAGACCGAATTCTGCGTTAGAGACCCACAGGTT

GGTGGCTTTTCTTGAACGTGCGGACTCGGTGATCTCCTGGGATATACAGGACGAAAAGAATG

TCACTTGTCAACTCACTTTCTGGGAAGCCTCGGAACGCACCATTCGTTCCGAAGCCGAGGAC

TCGTATCACTTTTCTTCTGCCAAAATGACCGCCACTTTCTTATCTAAGAAGCAAGAGGTGAA

CATGTCCGACTCTGCGCTGGACTGCGTACGTGATGAGGCTATAAATAAGTTACAGCAGATTT

TCAATACTTCATACAATCAAACATATGAAAAATATGGAAACGTGTCCGTCTTTGAAACCACT

GGTGGTTTGGTAGTGTTCTGGCAAGGTATCAAGCAAAAATCTCTGGTGGAACTCGAACGTTT

GGCCAACCGCTCCAGTCTGAATCTTACTCATAATAGAACCAAAAGAAGTACAGATGGCAACA

ATGCAACTCATTTATCCAACATGGAATCGGTGCACAATCTGGTCTACGCCCAGCTGCAGTTC

ACCTATGACACGTTGCGCGGTTACATCAACCGGGCGCTGGCGCAAATCGCAGAAGCCTGGTG

TGTGGATCAACGGCGCACCCTAGAGGTCTTCAAGGAACTCAGCAAGATCAACCCGTCAGCCA

-continued

TTCTCTCGGCCATTTACAACAAACCGATTGCCGCGCGTTTCATGGGTGATGTCTTGGGCCTG

GCCAGCTGCGTGACCATCAACCAAACCAGCGTCAAGGTGCTGCGTGATATGAACGTGAAGGA

GTCGCCAGGACGCTGCTACTCACGACCCGTGGTCATCTTTAATTTCGCCAACAGCTCGTACG

TGCAGTACGGTCAACTGGGCGAGGACAACGAAATCCTGTTGGGCAACCACCGCACTGAGGAA

TGTCAGCTTCCCAGCCTCAAGATCTTCATCGCCGGGAACTCGGCCTACGAGTACGTGGACTA

CCTCTTCAAACGCATGATTGACCTCAGCAGTATCTCCACCGTCGACAGCATGATCGCCCTGG

ATATCGACCCGCTGGAAAATACCGACTTCAGGGTACTGGAACTTTACTCGCAGAAAGAGCTG

CGTTCCAGCAACGTTTTTGACCTCGAAGAGATCATGCGCGAATTCAACTCGTACAAGCAGTG

ATAATAGGCTGGAGCCTCGGTGGCCATGCTTCTTGCCCCTTGGGCCTCCCCCCAGCCCCTCC

TCCCCTTCCTGCACCCGTACCCCCGTGGTCTTTGAATAAAGTCTGAGTGGGCGGC hCMV TrgB, glycoprotein B (ectodomain) mRNA (SEQ ID NO: 167)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGGAAUCCAGGAUCUGGUGCCUGGUAGUCUG

CGUUAACUUGUGUAUCGUCUGUCUGGGUGCUGCGGUUUCCUCAUCUUCUACUCGUGGAACUU

CUGCUACUCACAGUCACCAUUCCUCUCAUACGACGUCUGCUGCUCACUCUCGAUCCGGUUCA

GUCUCUCAACGCGUAACUUCUUCCCAAACGGUCAGCCAUGGUGUUAACGAGACCAUCUACAA

CACUACCCUCAAGUACGGAGAUGUGGUGGGGGUCAAUACCACCAAGUACCCCUAUCGCGUGU

GUUCUAUGGCCCAGGGUACGGAUCUUAUUCGCUUUGAACGUAAUAUCGUCUGCACCUCGAUG

AAGCCCAUCAAUGAAGACCUGGACGAGGGCAUCAUGGUGGUCUACAAACGCAACAUCGUCGC

GCACACCUUUAAGGUACGAGUCUACCAGAAGGUUUUGACGUUUCGUCGUAGCUACGCUUACA

UCCACACCACUUAUCUGCUGGGCAGCAACACGGAAUACGUGGCGCCUCCUAUGUGGGAGAUU

CAUCAUAUCAACAGCCACAGUCAGUGCUACAGUUCCUACAGCCGCGUUAUAGCAGGCACGGU

UUUCGUGGCUUAUCAUAGGGACAGCUAUGAAAACAAAACCAUGCAAUUAAUGCCCGACGAUU

AUUCCAACACCCACAGUACCCGUUACGUGACGGUCAAGGAUCAAUGGCACAGCCGCGGCAGC

ACCUGGCUCUAUCGUGAGACCUGUAAUCUGAAUUGUAUGGUGACCAUCACUACUGCGCGCUC

CAAAUAUCCUUAUCAUUUUUUCGCCACUUCCACGGGUGACGUGGUUGACAUUUCUCCUUUCU

ACAACGGAACCAAUCGCAAUGCCAGCUACUUUGGAGAAAACGCCGACAAGUUUUUCAUUUUU

CCGAACUACACUAUCGUCUCCGACUUUGGAAGACCGAAUUCUGCGUUAGAGACCCACAGGUU

GGUGGCUUUUCUUGAACGUGCGGACUCGGUGAUCUCCUGGGAUAUACAGGACGAAAAGAAUG

UCACUUGUCAACUCACUUUCUGGGAAGCCUCGGAACGCACCAUUCGUUCCGAAGCCGAGGAC

UCGUAUCACUUUUCUUCUGCCAAAAUGACCGCCACUUUCUUAUCUAAGAAGCAAGAGGUGAA

CAUGUCCGACUCUGCGCUGGACUGCGUACGUGAUGAGGCUAUAAAUAAGUUACAGCAGAUUU

UCAAUACUUCAUACAAUCAAACAUAUGAAAAAUAUGGAAACGUGUCCGUCUUUGAAACCACU

GGUGGUUUGGUAGUGUUCUGGCAAGGUAUCAAGCAAAAAUCUCUGGUGGAACUCGAACGUUU

GGCCAACCGCUCCAGUCUGAAUCUUACUCAUAAUAGAACCAAAAGAAGUACAGAUGGCAACA

AUGCAACUCAUUUAUCCAACAUGGAAUCGGUGCACAAUCUGGUCUACGCCCAGCUGCAGUUC

ACCUAUGACACGUUGCGCGGUUACAUCAACCGGGCGCUGGCGCAAAUCGCAGAAGCCUGGUG

UGUGGAUCAACGGCGCACCCUAGAGGUCUUCAAGGAACUCAGCAAGAUCAACCCGUCAGCCA

UUCUCUCGGCCAUUUACAACAAACCGAUUGCCGCGCGUUUCAUGGGUGAUGUCUUGGGCCUG

GCCAGCUGCGUGACCAUCAACCAAACCAGCGUCAAGGUGCUGCGUGAUAUGAACGUGAAGGA

GUCGCCAGGACGCUGCUACUCACGACCCGUGGUCAUCUUUAAUUUCGCCAACAGCUCGUACG

-continued

UGCAGUACGGUCAACUGGGCGAGGACAACGAAAUCCUGUUGGGCAACCACCGCACUGAGGAA

UGUCAGCUUCCCAGCCUCAAGAUCUUCAUCGCCGGGAACUCGGCCUACGAGUACGUGGACUA

CCUCUUCAAACGCAUGAUUGACCUCAGCAGUAUCUCCACCGUCGACAGCAUGAUCGCCCUGG

AUAUCGACCCGCUGGAAAAUACCGACUUCAGGGUACUGGAACUUUACUCGCAGAAAGAGCUG

CGUUCCAGCAACGUUUUUGACCUCGAAGAGAUCAUGCGCGAAUUCAACUCGUACAAGCAGUG

AUAAUAGGCUGGAGCCUCGGUGGCCAUGCUUCUUGCCCCUUGGGCCUCCCCCCAGCCCCUCC

UCCCCUUCCUGCACCCGUACCCCCGUGGUCUUUGAAUAAAGUCUGAGUGGGCGGC hCMV TrgBFLAG, hCMV glycoproteinB ectodomain-FLAG (SEQ ID NO: 11)

TCAAGCTTTTGGACCCTCGTACAGAAGCTAATACGACTCACTATAGGGAAATAAGAGAGAAA

AGAAGAGTAAGAAGAAATATAAGAGCCACCATGGAATCCAGGATCTGGTGCCTGGTAGTCTG

CGTTAACTTGTGTATCGTCTGTCTGGGTGCTGCGGTTTCCTCATCTTCTACTCGTGGAACTT

CTGCTACTCACAGTCACCATTCCTCTCATACGACGTCTGCTGCTCACTCTCGATCCGGTTCA

GTCTCTCAACGCGTAACTTCTTCCCAAACGGTCAGCCATGGTGTTAACGAGACCATCTACAA

CACTACCCTCAAGTACGGAGATGTGGTGGGGGTCAATACCACCAAGTACCCCTATCGCGTGT

GTTCTATGGCCCAGGGTACGGATCTTATTCGCTTTGAACGTAATATCGTCTGCACCTCGATG

AAGCCCATCAATGAAGACCTGGACGAGGGCATCATGGTGGTCTACAAACGCAACATCGTCGC

GCACACCTTTAAGGTACGAGTCTACCAGAAGGTTTTGACGTTTCGTCGTAGCTACGCTTACA

TCCACACCACTTATCTGCTGGGCAGCAACACGGAATACGTGGCGCCTCCTATGTGGGAGATT

CATCATATCAACAGCCACAGTCAGTGCTACAGTTCCTACAGCCGCGTTATAGCAGGCACGGT

TTTCGTGGCTTATCATAGGGACAGCTATGAAAACAAAACCATGCAATTAATGCCCGACGATT

ATTCCAACACCCACAGTACCCGTTACGTGACGGTCAAGGATCAATGGCACAGCCGCGGCAGC

ACCTGGCTCTATCGTGAGACCTGTAATCTGAATTGTATGGTGACCATCACTACTGCGCGCTC

CAAATATCCTTATCATTTTTTCGCCACTTCCACGGGTGACGTGGTTGACATTTCTCCTTTCT

ACAACGGAACCAATCGCAATGCCAGCTACTTTGGAGAAAACGCCGACAAGTTTTTCATTTTT

CCGAACTACACTATCGTCTCCGACTTTGGAAGACCGAATTCTGCGTTAGAGACCCACAGGTT

GGTGGCTTTTCTTGAACGTGCGGACTCGGTGATCTCCTGGGATATACAGGACGAAAAGAATG

TCACTTGTCAACTCACTTTCTGGGAAGCCTCGGAACGCACCATTCGTTCCGAAGCCGAGGAC

TCGTATCACTTTTCTTCTGCCAAAATGACCGCCACTTTCTTATCTAAGAAGCAAGAGGTGAA

CATGTCCGACTCTGCGCTGGACTGCGTACGTGATGAGGCTATAAATAAGTTACAGCAGATTT

TCAATACTTCATACAATCAAACATATGAAAAATATGGAAACGTGTCCGTCTTTGAAACCACT

GGTGGTTTGGTAGTGTTCTGGCAAGGTATCAAGCAAAAATCTCTGGTGGAACTCGAACGTTT

GGCCAACCGCTCCAGTCTGAATCTTACTCATAATAGAACCAAAAGAAGTACAGATGGCAACA

ATGCAACTCATTTATCCAACATGGAATCGGTGCACAATCTGGTCTACGCCCAGCTGCAGTTC

ACCTATGACACGTTGCGCGGTTACATCAACCGGGCGCTGGCGCAAATCGCAGAAGCCTGGTG

TGTGGATCAACGGCGCACCCTAGAGGTCTTCAAGGAACTCAGCAAGATCAACCCGTCAGCCA

TTCTCTCGGCCATTTACAACAAACCGATTGCCGCGCGTTTCATGGGTGATGTCTTGGGCCTG

GCCAGCTGCGTGACCATCAACCAAACCAGCGTCAAGGTGCTGCGTGATATGAACGTGAAGGA

GTCGCCAGGACGCTGCTACTCACGACCCGTGGTCATCTTTAATTTCGCCAACAGCTCGTACG

TGCAGTACGGTCAACTGGGCGAGGACAACGAAATCCTGTTGGGCAACCACCGCACTGAGGAA

TGTCAGCTTCCCAGCCTCAAGATCTTCATCGCCGGGAACTCGGCCTACGAGTACGTGGACTA

-continued

CCTCTTCAAACGCATGATTGACCTCAGCAGTATCTCCACCGTCGACAGCATGATCGCCCTGG

ATATCGACCCGCTGGAAAATACCGACTTCAGGGTACTGGAACTTTACTCGCAGAAAGAGCTG

CGTTCCAGCAACGTTTTTGACCTCGAAGAGATCATGCGCGAATTCAACTCGTACAAGCAGGA

TTACAAGGACGATGACGATAAGTGATAATAGGCTGGAGCCTCGGTGGCCATGCTTCTTGCCC

CTTGGGCCTCCCCCCAGCCCCTCCTCCCCTTCCTGCACCCGTACCCCCGTGGTCTTTGAATA

AAGTCTGAGTGGGCGGC hCMV TrgBFLAG, hCMV glycoproteinB ectodomain-FLAG mRNA
(SEQ ID NO: 168)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGGAAUCCAGGAUCUGGUGCCUGGUAGUCUG

CGUUAACUUGUGUAUCGUCUGUCUGGGUGCUGCGGUUUCCUCAUCUUCUACUCGUGGAACUU

CUGCUACUCACAGUCACCAUUCCUCUCAUACGACGUCUGCUGCUCACUCUCGAUCCGGUUCA

GUCUCUCAACGCGUAACUUCUUCCCAAACGGUCAGCCAUGGUGUUAACGAGACCAUCUACAA

CACUACCCUCAAGUACGGAGAUGUGGUGGGGGUCAAUACCACCAAGUACCCCUAUCGCGUGU

GUUCUAUGGCCCAGGGUACGGAUCUUAUUCGCUUUGAACGUAAUAUCGUCUGCACCUCGAUG

AAGCCCAUCAAUGAAGACCUGGACGAGGGCAUCAUGGUGGUCUACAAACGCAACAUCGUCGC

GCACACCUUUAAGGUACGAGUCUACCAGAAGGUUUUGACGUUUCGUCGUAGCUACGCUUACA

UCCACACCACUUAUCUGCUGGGCAGCAACACGGAAUACGUGGCGCCUCCUAUGUGGGAGAUU

CAUCAUAUCAACAGCCACAGUCAGUGCUACAGUUCCUACAGCCGCGUUAUAGCAGGCACGGU

UUUCGUGGCUUAUCAUAGGGACAGCUAUGAAAACAAAACCAUGCAAUUAAUGCCCGACGAUU

AUUCCAACACCCACAGUACCCGUUACGUGACGGUCAAGGAUCAAUGGCACAGCCGCGGCAGC

ACCUGGCUCUAUCGUGAGACCUGUAAUCUGAAUUGUAUGGUGACCAUCACUACUGCGCGCUC

CAAAUAUCCUUAUCAUUUUUUCGCCACUUCCACGGGUGACGUGGUUGACAUUUCUCCUUUCU

ACAACGGAACCAAUCGCAAUGCCAGCUACUUUGGAGAAAACGCCGACAAGUUUUUCAUUUUU

CCGAACUACACUAUCGUCUCCGACUUUGGAAGACCGAAUUCUGCGUUAGAGACCCACAGGUU

GGUGGCUUUUCUUGAACGUGCGGACUCGGUGAUCUCCUGGGAUAUACAGGACGAAAAGAAUG

UCACUUGUCAACUCACUUUCUGGGAAGCCUCGGAACGCACCAUUCGUUCCGAAGCCGAGGAC

UCGUAUCACUUUUCUUCUGCCAAAAUGACCGCCACUUUCUUAUCUAAGAAGCAAGAGGUGAA

CAUGUCCGACUCUGCGCUGGACUGCGUACGUGAUGAGGCUAUAAAUAAGUUACAGCAGAUUU

UCAAUACUUCAUACAAUCAAACAUAUGAAAAAUAUGGAAACGUGUCCGUCUUUGAAACCACU

GGUGGUUUGGUAGUGUUCUGGCAAGGUAUCAAGCAAAAAUCUCUGGUGGAACUCGAACGUUU

GGCCAACCGCUCCAGUCUGAAUCUUACUCAUAAUAGAACCAAAAGAAGUACAGAUGGCAACA

AUGCAACUCAUUUAUCCAACAUGGAAUCGGUGCACAAUCUGGUCUACGCCCAGCUGCAGUUC

ACCUAUGACACGUUGCGCGGUUACAUCAACCGGGCGCUGGCGCAAAUCGCAGAAGCCUGGUG

UGUGGAUCAACGGCGCACCCUAGAGGUCUUCAAGGAACUCAGCAAGAUCAACCCGUCAGCCA

UUCUCUCGGCCAUUUACAACAAACCGAUUGCCGCGCGUUUCAUGGGUGAUGUCUUGGGCCUG

GCCAGCUGCGUGACCAUCAACCAAACCAGCGUCAAGGUGCUGCGUGAUAUGAACGUGAAGGA

GUCGCCAGGACGCUGCUACUCACGACCCGUGGUCAUCUUUAAUUUCGCCAACAGCUCGUACG

UGCAGUACGGUCAACUGGGCGAGGACAACGAAAUCCUGUUGGGCAACCACCGCACUGAGGAA

UGUCAGCUUCCCAGCCUCAAGAUCUUCAUCGCCGGGAACUCGGCCUACGAGUACGUGGACUA

CCUCUUCAAACGCAUGAUUGACCUCAGCAGUAUCUCCACCGUCGACAGCAUGAUCGCCCUGG

AUAUCGACCCGCUGGAAAAUACCGACUUCAGGGUACUGGAACUUUACUCGCAGAAAGAGCUG

-continued

CGUUCCAGCAACGUUUUUGACCUCGAAGAGAUCAUGCGCGAAUUCAACUCGUACAAGCAGGA

UUACAAGGACGAUGACGAUAAGUGAUAAUAGGCUGGAGCCUCGGUGGCCAUGCUUCUUGCCC

CUUGGGCCUCCCCCCAGCCCCUCCUCCCCUUCCUGCACCCGUACCCCCGUGGUCUUUGAAUA

AAGUCUGAGUGGGCGGC hCMV-TrgB6XHis, hCMV glycoprotein ectodomain-6XHis tag
(SEQ ID NO: 12)

TCAAGCTTTTGGACCCTCGTACAGAAGCTAATACGACTCACTATAGGGAAATAAGAGAGAAA

AGAAGAGTAAGAAGAAATATAAGAGCCACCATGGAATCCAGGATCTGGTGCCTGGTAGTCTG

CGTTAACTTGTGTATCGTCTGTCTGGGTGCTGCGGTTTCCTCATCTTCTACTCGTGGAACTT

CTGCTACTCACAGTCACCATTCCTCTCATACGACGTCTGCTGCTCACTCTCGATCCGGTTCA

GTCTCTCAACGCGTAACTTCTTCCCAAACGGTCAGCCATGGTGTTAACGAGACCATCTACAA

CACTACCCTCAAGTACGGAGATGTGGTGGGGGTCAATACCACCAAGTACCCCTATCGCGTGT

GTTCTATGGCCCAGGGTACGGATCTTATTCGCTTTGAACGTAATATCGTCTGCACCTCGATG

AAGCCCATCAATGAAGACCTGGACGAGGGCATCATGGTGGTCTACAAACGCAACATCGTCGC

GCACACCTTTAAGGTACGAGTCTACCAGAAGGTTTTGACGTTTCGTCGTAGCTACGCTTACA

TCCACACCACTTATCTGCTGGGCAGCAACACGGAATACGTGGCGCCTCCTATGTGGGAGATT

CATCATATCAACAGCCACAGTCAGTGCTACAGTTCCTACAGCCGCGTTATAGCAGGCACGGT

TTTCGTGGCTTATCATAGGGACAGCTATGAAAACAAAACCATGCAATTAATGCCCGACGATT

ATTCCAACACCCACAGTACCCGTTACGTGACGGTCAAGGATCAATGGCACAGCCGCGGCAGC

ACCTGGCTCTATCGTGAGACCTGTAATCTGAATTGTATGGTGACCATCACTACTGCGCGCTC

CAAATATCCTTATCATTTTTTCGCCACTTCCACGGGTGACGTGGTTGACATTTCTCCTTTCT

ACAACGGAACCAATCGCAATGCCAGCTACTTTGGAGAAAACGCCGACAAGTTTTTCATTTTT

CCGAACTACACTATCGTCTCCGACTTTGGAAGACCGAATTCTGCGTTAGAGACCCACAGGTT

GGTGGCTTTTCTTGAACGTGCGGACTCGGTGATCTCCTGGGATATACAGGACGAAAAGAATG

TCACTTGTCAACTCACTTTCTGGGAAGCCTCGGAACGCACCATTCGTTCCGAAGCCGAGGAC

TCGTATCACTTTTCTTCTGCCAAAATGACCGCCACTTTCTTATCTAAGAAGCAAGAGGTGAA

CATGTCCGACTCTGCGCTGGACTGCGTACGTGATGAGGCTATAAATAAGTTACAGCAGATTT

TCAATACTTCATACAATCAAACATATGAAAAATATGGAAACGTGTCCGTCTTTGAAACCACT

GGTGGTTTGGTAGTGTTCTGGCAAGGTATCAAGCAAAAATCTCTGGTGGAACTCGAACGTTT

GGCCAACCGCTCCAGTCTGAATCTTACTCATAATAGAACCAAAAGAAGTACAGATGGCAACA

ATGCAACTCATTTATCCAACATGGAATCGGTGCACAATCTGGTCTACGCCCAGCTGCAGTTC

ACCTATGACACGTTGCGCGGTTACATCAACCGGGCGCTGGCGCAAATCGCAGAAGCCTGGTG

TGTGGATCAACGGCGCACCCTAGAGGTCTTCAAGGAACTCAGCAAGATCAACCCGTCAGCCA

TTCTCTCGGCCATTTACAACAAACCGATTGCCGCGCGTTTCATGGGTGATGTCTTGGGCCTG

GCCAGCTGCGTGACCATCAACCAAACCAGCGTCAAGGTGCTGCGTGATATGAACGTGAAGGA

GTCGCCAGGACGCTGCTACTCACGACCCGTGGTCATCTTTAATTTCGCCAACAGCTCGTACG

TGCAGTACGGTCAACTGGGCGAGGACAACGAAATCCTGTTGGGCAACCACCGCACTGAGGAA

TGTCAGCTTCCCAGCCTCAAGATCTTCATCGCCGGGAACTCGGCCTACGAGTACGTGGACTA

CCTCTTCAAACGCATGATTGACCTCAGCAGTATCTCCACCGTCGACAGCATGATCGCCCTGG

ATATCGACCCGCTGGAAAATACCGACTTCAGGGTACTGGAACTTTACTCGCAGAAAGAGCTG

CGTTCCAGCAACGTTTTTGACCTCGAAGAGATCATGCGCGAATTCAACTCGTACAAGCAGCA

-continued

CCATCACCACCATCACTGATAATAGGCTGGAGCCTCGGTGGCCATGCTTCTTGCCCCTTGGG

CCTCCCCCCAGCCCCTCCTCCCCTTCCTGCACCCGTACCCCCGTGGTCTTTGAATAAAGTCT

GAGTGGGCGGC hCMV-TrgB6XHis, hCMV glycoprotein ectodomain-6XHis tag mRNA
(SEQ ID NO: 169)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGGAAUCCAGGAUCUGGUGCCUGGUAGUCUG

CGUUAACUUGUGUAUCGUCUGUCUGGGUGCUGCGGUUUCCUCAUCUUCUACUCGUGGAACUU

CUGCUACUCACAGUCACCAUUCCUCUCAUACGACGUCUGCUGCUCACUCUCGAUCCGGUUCA

GUCUCUCAACGCGUAACUUCUUCCCAAACGGUCAGCCAUGGUGUUAACGAGACCAUCUACAA

CACUACCCUCAAGUACGGAGAUGUGGUGGGGGUCAAUACCACCAAGUACCCCUAUCGCGUGU

GUUCUAUGGCCCAGGGUACGGAUCUUAUUCGCUUUGAACGUAAUAUCGUCUGCACCUCGAUG

AAGCCCAUCAAUGAAGACCUGGACGAGGGCAUCAUGGUGGUCUACAAACGCAACAUCGUCGC

GCACACCUUUAAGGUACGAGUCUACCAGAAGGUUUUGACGUUUCGUCGUAGCUACGCUUACA

UCCACACCACUUAUCUGCUGGGCAGCAACACGGAAUACGUGGCGCCUCCUAUGUGGGAGAUU

CAUCAUAUCAACAGCCACAGUCAGUGCUACAGUUCCUACAGCCGCGUUAUAGCAGGCACGGU

UUUCGUGGCUUAUCAUAGGGACAGCUAUGAAAACAAAACCAUGCAAUUAAUGCCCGACGAUU

AUUCCAACACCCACAGUACCCGUUACGUGACGGUCAAGGAUCAAUGGCACAGCCGCGGCAGC

ACCUGGCUCUAUCGUGAGACCUGUAAUCUGAAUUGUAUGGUGACCAUCACUACUGCGCGCUC

CAAAUAUCCUUAUCAUUUUUUCGCCACUUCCACGGGUGACGUGGUUGACAUUUCUCCUUUCU

ACAACGGAACCAAUCGCAAUGCCAGCUACUUUGGAGAAAACGCCGACAAGUUUUUCAUUUUU

CCGAACUACACUAUCGUCUCCGACUUUGGAAGACCGAAUUCUGCGUUAGAGACCCACAGGUU

GGUGGCUUUUCUUGAACGUGCGGACUCGGUGAUCUCCUGGGAUAUACAGGACGAAAAGAAUG

UCACUUGUCAACUCACUUUCUGGGAAGCCUCGGAACGCACCAUUCGUUCCGAAGCCGAGGAC

UCGUAUCACUUUUCUUCUGCCAAAAUGACCGCCACUUUCUUAUCUAAGAAGCAAGAGGUGAA

CAUGUCCGACUCUGCGCUGGACUGCGUACGUGAUGAGGCUAUAAAUAAGUUACAGCAGAUUU

UCAAUACUUCAUACAAUCAAACAUAUGAAAAAUAUGGAAACGUGUCCGUCUUUGAAACCACU

GGUGGUUUGGUAGUGUUCUGGCAAGGUAUCAAGCAAAAAUCUCUGGUGGAACUCGAACGUUU

GGCCAACCGCUCCAGUCUGAAUCUUACUCAUAAUAGAACCAAAAGAAGUACAGAUGGCAACA

AUGCAACUCAUUUAUCCAACAUGGAAUCGGUGCACAAUCUGGUCUACGCCCAGCUGCAGUUC

ACCUAUGACACGUUGCGCGGUUACAUCAACCGGGCGCUGGCGCAAAUCGCAGAAGCCUGGUG

UGUGGAUCAACGGCGCACCCUAGAGGUCUUCAAGGAACUCAGCAAGAUCAACCCGUCAGCCA

UUCUCUCGGCCAUUUACAACAAACCGAUUGCCGCGCGUUUCAUGGGUGAUGUCUUGGGCCUG

GCCAGCUGCGUGACCAUCAACCAAACCAGCGUCAAGGUGCUGCGUGAUAUGAACGUGAAGGA

GUCGCCAGGACGCUGCUACUCACGACCCGUGGUCAUCUUUAAUUUCGCCAACAGCUCGUACG

UGCAGUACGGUCAACUGGGCGAGGACAACGAAAUCCUGUUGGGCAACCACCGCACUGAGGAA

UGUCAGCUUCCCAGCCUCAAGAUCUUCAUCGCCGGGAACUCGGCCUACGAGUACGUGGACUA

CCUCUUCAAACGCAUGAUUGACCUCAGCAGUAUCUCCACCGUCGACAGCAUGAUCGCCCUGG

AUAUCGACCCGCUGGAAAAUACCGACUUCAGGGUACUGGAACUUUACUCGCAGAAAGAGCUG

CGUUCCAGCAACGUUUUUGACCUCGAAGAGAUCAUGCGCGAAUUCAACUCGUACAAGCAGCA

-continued

CCAUCACCACCAUCACUGAUAAUAGGCUGGAGCCUCGGUGGCCAUGCUUCUUGCCCCUUGGG

CCUCCCCCCAGCCCCUCCUCCCCUUCCUGCACCCGUACCCCCGUGGUCUUUGAAUAAAGUCU

GAGUGGGCGGC

Example 14: hCMV Vaccine—hCMV UL Sequences

A hCMV vaccine may comprise, for example, at least one RNA polynucleotide encoded by at least one of the following sequences or by at least one fragment or epitope of the following sequences. In some embodiments, a hCMV vaccine may comprise at least one RNA polynucleotide comprising at least one of the mRNA sequences listed below or at least one fragment of the mRNA sequences listed below.

hCMV UL128

(SEQ ID NO: 13)

TCAAGCTTTTGGACCCTCGTACAGAAGCTAATACGACTCACTATAGGGAAATAAGAGAGAAA

AGAAGAGTAAGAAGAAATATAAGAGCCACCATGAGTCCCAAAGATCTGACGCCGTTCTTGAC

GGCGTTGTGGCTGCTATTGGGTCACAGCCGCGTGCCGCGGGTGCGCGCAGAAGAATGTTGCG

AATTCATAAACGTCAACCACCCGCCGGAACGCTGTTACGATTTCAAAATGTGCAATCGCTTC

ACCGTCGCGCTGCGGTGTCCGGACGGCGAAGTCTGCTACAGTCCCGAGAAAACGGCTGAGAT

TCGCGGGATCGTCACCACCATGACCCATTCATTGACACGCCAGGTCGTACACAACAAACTGA

CGAGCTGCAACTACAATCCGTTATACCTCGAAGCTGACGGGCGAATACGCTGCGGCAAAGTA

AACGACAAGGCGCAGTACCTGCTGGGCGCCGCTGGCAGCGTTCCCTATCGATGGATCAATCT

GGAATACGACAAGATAACCCGGATCGTGGGCCTGGATCAGTACCTGGAGAGCGTTAAGAAAC

ACAAACGGCTGGATGTGTGCCGCGCTAAAATGGGCTATATGCTGCAGTGATAATAGGCTGGA

GCCTCGGTGGCCATGCTTCTTGCCCCTTGGGCCTCCCCCCAGCCCCTCCTCCCCTTCCTGCA

CCCGTACCCCCGTGGTCTTTGAATAAAGTCTGAGTGGGCGGC hCMV UL128 mRNA (SEQ ID NO: 170)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGAGUCCCAAAGAUCUGACGCCGUUCUUGAC

GGCGUUGUGGCUGCUAUUGGGUCACAGCCGCGUGCCGCGGGUGCGCGCAGAAGAAUGUUGCG

AAUUCAUAAACGUCAACCACCCGCCGGAACGCUGUUACGAUUUCAAAAUGUGCAAUCGCUUC

ACCGUCGCGCUGCGGUGUCCGGACGGCGAAGUCUGCUACAGUCCCGAGAAAACGGCUGAGAU

UCGCGGGAUCGUCACCACCAUGACCCAUUCAUUGACACGCCAGGUCGUACACAACAAACUGA

CGAGCUGCAACUACAAUCCGUUAUACCUCGAAGCUGACGGGCGAAUACGCUGCGGCAAAGUA

AACGACAAGGCGCAGUACCUGCUGGGCGCCGCUGGCAGCGUUCCCUAUCGAUGGAUCAAUCU

GGAAUACGACAAGAUAACCCGGAUCGUGGGCCUGGAUCAGUACCUGGAGAGCGUUAAGAAAC

ACAAACGGCUGGAUGUGUGCCGCGCUAAAAUGGGCUAUAUGCUGCAGUGAUAAUAGGCUGGA

GCCUCGGUGGCCAUGCUUCUUGCCCCUUGGGCCUCCCCCCAGCCCCUCCUCCCCUUCCUGCA

CCCGUACCCCCGUGGUCUUUGAAUAAAGUCUGAGUGGGCGGC hCMV-128FLAG, UL128-FLAG tag (SEQ ID NO: 14)

TCAAGCTTTTGGACCCTCGTACAGAAGCTAATACGACTCACTATAGGGAAATAAGAGAGAAA

AGAAGAGTAAGAAGAAATATAAGAGCCACCATGAGTCCCAAAGATCTGACGCCGTTCTTGAC

GGCGTTGTGGCTGCTATTGGGTCACAGCCGCGTGCCGCGGGTGCGCGCAGAAGAATGTTGCG

AATTCATAAACGTCAACCACCCGCCGGAACGCTGTTACGATTTCAAAATGTGCAATCGCTTC

ACCGTCGCGCTGCGGTGTCCGGACGGCGAAGTCTGCTACAGTCCCGAGAAAACGGCTGAGAT

TCGCGGGATCGTCACCACCATGACCCATTCATTGACACGCCAGGTCGTACACAACAAACTGA

-continued

CGAGCTGCAACTACAATCCGTTATACCTCGAAGCTGACGGGCGAATACGCTGCGGCAAAGTA

AACGACAAGGCGCAGTACCTGCTGGGCGCCGCTGGCAGCGTTCCCTATCGATGGATCAATCT

GGAATACGACAAGATAACCCGGATCGTGGGCCTGGATCAGTACCTGGAGAGCGTTAAGAAAC

ACAAACGGCTGGATGTGTGCCGCGCTAAAATGGGCTATATGCTGCAGGATTACAAGGACGAT

GACGATAAGTGATAATAGGCTGGAGCCTCGGTGGCCATGCTTCTTGCCCCTTGGGCCTCCCC

CCAGCCCCTCCTCCCCTTCCTGCACCCGTACCCCCGTGGTCTTTGAATAAAGTCTGAGTGGG

CGGC hCMV-128FLAG, UL128-FLAG tag mRNA (SEQ ID NO: 171)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGAGUCCCAAAGAUCUGACGCCGUUCUUGAC

GGCGUUGUGGCUGCUAUUGGGUCACAGCCGCGUGCCGCGGGUGCGCGCAGAAGAAUGUUGCG

AAUUCAUAAACGUCAACCACCCGCCGGAACGCUGUUACGAUUUCAAAAUGUGCAAUCGCUUC

ACCGUCGCGCUGCGGUGUCCGGACGGCGAAGUCUGCUACAGUCCCGAGAAAACGGCUGAGAU

UCGCGGGAUCGUCACCACCAUGACCCAUUCAUUGACACGCCAGGUCGUACACAACAAACUGA

CGAGCUGCAACUACAAUCCGUUAUACCUCGAAGCUGACGGGCGAAUACGCUGCGGCAAAGUA

AACGACAAGGCGCAGUACCUGCUGGGCGCCGCUGGCAGCGUUCCCUAUCGAUGGAUCAAUCU

GGAAUACGACAAGAUAACCCGGAUCGUGGGCCUGGAUCAGUACCUGGAGAGCGUUAAGAAAC

ACAAACGGCUGGAUGUGUGCCGCGCUAAAAUGGGCUAUAUGCUGCAGGAUUACAAGGACGAU

GACGAUAAGUGAUAAUAGGCUGGAGCCUCGGUGGCCAUGCUUCUUGCCCCUUGGGCCUCCCC

CCAGCCCCUCCUCCCCUUCCUGCACCCGUACCCCCGUGGUCUUUGAAUAAAGUCUGAGUGGG

CGGC hCMV-UL130

(SEQ ID NO: 15)

TCAAGCTTTTGGACCCTCGTACAGAAGCTAATACGACTCACTATAGGGAAATAAGAGAGAAA

AGAAGAGTAAGAAGAAATATAAGAGCCACCATGCTGCGGCTTCTGCTTCGTCACCACTTTCA

CTGCCTGCTTCTGTGCGCGGTTTGGGCAACGCCCTGTCTGGCGTCTCCGTGGTCGACGCTAA

CAGCAAACCAGAATCCGTCCCCGCCATGGTCTAAACTGACGTATTCCAAACCGCATGACGCG

GCGACGTTTTACTGTCCTTTTCTCTATCCCTCGCCCCCACGATCCCCCTTGCAATTCTCGGG

GTTCCAGCGGGTATCAACGGGTCCCGAGTGTCGCAACGAGACCCTGTATCTGCTGTACAACC

GGGAAGGCCAGACCTTGGTGGAGAGAAGCTCCACCTGGGTGAAAAAGGTGATCTGGTACCTG

AGCGGTCGGAACCAAACCATCCTCCAACGGATGCCCCGAACGGCTTCGAAACCGAGCGACGG

AAACGTGCAGATCAGCGTGGAAGACGCCAAGATTTTTGGAGCGCACATGGTGCCCAAGCAGA

CCAAGCTGCTACGCTTCGTCGTCAACGATGGCACACGTTATCAGATGTGTGTGATGAAGCTG

GAGAGCTGGGCTCACGTCTTCCGGGACTACAGCGTGTCTTTTCAGGTGCGATTGACGTTCAC

CGAGGCCAATAACCAGACTTACACCTTCTGCACCCATCCCAATCTCATCGTTTGATAATAGG

CTGGAGCCTCGGTGGCCATGCTTCTTGCCCCTTGGGCCTCCCCCCAGCCCCTCCTCCCCTTC

CTGCACCCGTACCCCCGTGGTCTTTGAATAAAGTCTGAGTGGGCGGC hCMV-UL130 mRNA (SEQ ID NO: 172)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGCUGCGGCUUCUGCUUCGUCACCACUUUCA

CUGCCUGCUUCUGUGCGCGGUUUGGGCAACGCCCUGUCUGGCGUCUCCGUGGUCGACGCUAA

-continued

CAGCAAACCAGAAUCCGUCCCCGCCAUGGUCUAAACUGACGUAUUCCAAACCGCAUGACGCG

GCGACGUUUUACUGUCCUUUUCUCUAUCCCUCGCCCCCACGAUCCCCCUUGCAAUUCUCGGG

GUUCCAGCGGGUAUCAACGGGUCCCGAGUGUCGCAACGAGACCCUGUAUCUGCUGUACAACC

GGGAAGGCCAGACCUUGGUGGAGAGAAGCUCCACCUGGGUGAAAAAGGUGAUCUGGUACCUG

AGCGGUCGGAACCAAACCAUCCUCCAACGGAUGCCCCGAACGGCUUCGAAACCGAGCGACGG

AAACGUGCAGAUCAGCGUGGAAGACGCCAAGAUUUUUGGAGCGCACAUGGUGCCCAAGCAGA

CCAAGCUGCUACGCUUCGUCGUCAACGAUGGCACACGUUAUCAGAUGUGUGUGAUGAAGCUG

GAGAGCUGGGCUCACGUCUUCCGGGACUACAGCGUGUCUUUUCAGGUGCGAUUGACGUUCAC

CGAGGCCAAUAACCAGACUUACACCUUCUGCACCCAUCCCAAUCUCAUCGUUUGAUAAUAGG

CUGGAGCCUCGGUGGCCAUGCUUCUUGCCCCUUGGGCCUCCCCCCAGCCCCUCCUCCCCUUC

CUGCACCCGUACCCCCGUGGUCUUUGAAUAAAGUCUGAGUGGGCGGC hCMV-UL130FLAG, UL130-FLAG tag (SEQ ID NO: 16)

TCAAGCTTTTGGACCCTCGTACAGAAGCTAATACGACTCACTATAGGGAAATAAGAGAGAAA

AGAAGAGTAAGAAGAAATATAAGAGCCACCATGCTGCGGCTTCTGCTTCGTCACCACTTTCA

CTGCCTGCTTCTGTGCGCGGTTTGGGCAACGCCCTGTCTGGCGTCTCCGTGGTCGACGCTAA

CAGCAAACCAGAATCCGTCCCCGCCATGGTCTAAACTGACGTATTCCAAACCGCATGACGCG

GCGACGTTTTACTGTCCTTTTCTCTATCCCTCGCCCCCACGATCCCCCTTGCAATTCTCGGG

GTTCCAGCGGGTATCAACGGGTCCCGAGTGTCGCAACGAGACCCTGTATCTGCTGTACAACC

GGGAAGGCCAGACCTTGGTGGAGAGAAGCTCCACCTGGGTGAAAAAGGTGATCTGGTACCTG

AGCGGTCGGAACCAAACCATCCTCCAACGGATGCCCCGAACGGCTTCGAAACCGAGCGACGG

AAACGTGCAGATCAGCGTGGAAGACGCCAAGATTTTTGGAGCGCACATGGTGCCCAAGCAGA

CCAAGCTGCTACGCTTCGTCGTCAACGATGGCACACGTTATCAGATGTGTGTGATGAAGCTG

GAGAGCTGGGCTCACGTCTTCCGGGACTACAGCGTGTCTTTTCAGGTGCGATTGACGTTCAC

CGAGGCCAATAACCAGACTTACACCTTCTGCACCCATCCCAATCTCATCGTTGATTACAAGG

ACGATGACGATAAGTGATGATAATAGGCTGGAGCCTCGGTGGCCATGCTTCTTGCCCCTTGG

GCCTCCCCCCAGCCCCTCCTCCCCTTCCTGCACCCGTACCCCCGTGGTCTTTGAATAAAGTC

TGAGTGGGCGGC hCMV-UL130FLAG, UL130-FLAG tag mRNA (SEQ ID NO: 173)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGCUGCGGCUUCUGCUUCGUCACCACUUUCA

CUGCCUGCUUCUGUGCGCGGUUUGGGCAACGCCCUGUCUGGCGUCUCCGUGGUCGACGCUAA

CAGCAAACCAGAAUCCGUCCCCGCCAUGGUCUAAACUGACGUAUUCCAAACCGCAUGACGCG

GCGACGUUUUACUGUCCUUUUCUCUAUCCCUCGCCCCCACGAUCCCCCUUGCAAUUCUCGGG

GUUCCAGCGGGUAUCAACGGGUCCCGAGUGUCGCAACGAGACCCUGUAUCUGCUGUACAACC

GGGAAGGCCAGACCUUGGUGGAGAGAAGCUCCACCUGGGUGAAAAAGGUGAUCUGGUACCUG

AGCGGUCGGAACCAAACCAUCCUCCAACGGAUGCCCCGAACGGCUUCGAAACCGAGCGACGG

AAACGUGCAGAUCAGCGUGGAAGACGCCAAGAUUUUUGGAGCGCACAUGGUGCCCAAGCAGA

CCAAGCUGCUACGCUUCGUCGUCAACGAUGGCACACGUUAUCAGAUGUGUGUGAUGAAGCUG

GAGAGCUGGGCUCACGUCUUCCGGGACUACAGCGUGUCUUUUCAGGUGCGAUUGACGUUCAC

CGAGGCCAAUAACCAGACUUACACCUUCUGCACCCAUCCCAAUCUCAUCGUUGAUUACAAGG

ACGAUGACGAUAAGUGAUGAUAAUAGGCUGGAGCCUCGGUGGCCAUGCUUCUUGCCCCUUGG

-continued

GCCUCCCCCCAGCCCCUCCUCCCCUUCCUGCACCCGUACCCCCGUGGUCUUUGAAUAAAGUC

UGAGUGGGCGGC hCMV-UL131A (SEQ ID NO: 17)

TCAAGCTTTTGGACCCTCGTACAGAAGCTAATACGACTCACTATAGGGAAATAAGAGAGAAA

AGAAGAGTAAGAAGAAATATAAGAGCCACCATGCGGCTGTGTCGGGTGTGGCTGTCTGTTTG

TCTGTGCGCCGTGGTGCTGGGTCAGTGCCAGCGGGAAACCGCGGAAAAAAACGATTATTACC

GAGTACCGCATTACTGGGACGCGTGCTCTCGCGCGCTGCCCGACCAAACCCGTTACAAGTAT

GTGGAACAGCTCGTGGACCTCACGTTGAACTACCACTACGATGCGAGCCACGGCTTGGACAA

CTTTGACGTGCTCAAGAGAATCAACGTGACCGAGGTGTCGTTGCTCATCAGCGACTTTAGAC

GTCAGAACCGTCGCGGCGGCACCAACAAAAGGACCACGTTCAACGCCGCCGGTTCGCTGGCG

CCACACGCCCGGAGCCTCGAGTTCAGCGTGCGGCTCTTTGCCAACTGATAATAGGCTGGAGC

CTCGGTGGCCATGCTTCTTGCCCCTTGGGCCTCCCCCCAGCCCCTCCTCCCCTTCCTGCACC

CGTACCCCCGTGGTCTTTGAATAAAGTCTGAGTGGGCGGC hCMV-UL131A mRNA (SEQ ID NO: 174)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGCGGCUGUGUCGGGUGUGGCUGUCUGUUUG

UCUGUGCGCCGUGGUGCUGGGUCAGUGCCAGCGGGAAACCGCGGAAAAAAACGAUUAUUACC

GAGUACCGCAUUACUGGGACGCGUGCUCUCGCGCGCUGCCCGACCAAACCCGUUACAAGUAU

GUGGAACAGCUCGUGGACCUCACGUUGAACUACCACUACGAUGCGAGCCACGGCUUGGACAA

CUUUGACGUGCUCAAGAGAAUCAACGUGACCGAGGUGUCGUUGCUCAUCAGCGACUUUAGAC

GUCAGAACCGUCGCGGCGGCACCAACAAAAGGACCACGUUCAACGCCGCCGGUUCGCUGGCG

CCACACGCCCGGAGCCUCGAGUUCAGCGUGCGGCUCUUUGCCAACUGAUAAUAGGCUGGAGC

CUCGGUGGCCAUGCUUCUUGCCCCUUGGGCCUCCCCCCAGCCCCUCCUCCCCUUCCUGCACC

CGUACCCCCGUGGUCUUUGAAUAAAGUCUGAGUGGGCGGC hCMV-UL131AFLAG, UL131A-FLAG (SEQ ID NO: 18)

TCAAGCTTTTGGACCCTCGTACAGAAGCTAATACGACTCACTATAGGGAAATAAGAGAGAAA

AGAAGAGTAAGAAGAAATATAAGAGCCACCATGCGGCTGTGTCGGGTGTGGCTGTCTGTTTG

TCTGTGCGCCGTGGTGCTGGGTCAGTGCCAGCGGGAAACCGCGGAAAAAAACGATTATTACC

GAGTACCGCATTACTGGGACGCGTGCTCTCGCGCGCTGCCCGACCAAACCCGTTACAAGTAT

GTGGAACAGCTCGTGGACCTCACGTTGAACTACCACTACGATGCGAGCCACGGCTTGGACAA

CTTTGACGTGCTCAAGAGAATCAACGTGACCGAGGTGTCGTTGCTCATCAGCGACTTTAGAC

GTCAGAACCGTCGCGGCGGCACCAACAAAAGGACCACGTTCAACGCCGCCGGTTCGCTGGCG

CCACACGCCCGGAGCCTCGAGTTCAGCGTGCGGCTCTTTGCCAACGATTACAAGGACGATGA

CGATAAGTGATGATAATAGGCTGGAGCCTCGGTGGCCATGCTTCTTGCCCCTTGGGCCTCCC

CCCAGCCCCTCCTCCCCTTCCTGCACCCGTACCCCCGTGGTCTTTGAATAAAGTCTGAGTGG

GCGGC hCMV-UL131AFLAG, UL131A-FLAG mRNA (SEQ ID NO: 175)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGCGGCUGUGUCGGGUGUGGCUGUCUGUUUG

UCUGUGCGCCGUGGUGCUGGGUCAGUGCCAGCGGGAAACCGCGGAAAAAAACGAUUAUUACC

-continued

GAGUACCGCAUUACUGGGACGCGUGCUCUCGCGCGCUGCCCGACCAAACCCGUUACAAGUAU

GUGGAACAGCUCGUGGACCUCACGUUGAACUACCACUACGAUGCGAGCCACGGCUUGGACAA

CUUUGACGUGCUCAAGAGAAUCAACGUGACCGAGGUGUCGUUGCUCAUCAGCGACUUUAGAC

GUCAGAACCGUCGCGGCGGCACCAACAAAAGGACCACGUUCAACGCCGCCGGUUCGCUGGCG

CCACACGCCCGGAGCCUCGAGUUCAGCGUGCGGCUCUUUGCCAACGAUUACAAGGACGAUGA

CGAUAAGUGAUGAUAAUAGGCUGGAGCCUCGGUGGCCAUGCUUCUUGCCCCUUGGGCCUCCC

CCCAGCCCCUCCUCCCCUUCCUGCACCCGUACCCCCGUGGUCUUUGAAUAAAGUCUGAGUGG

GCGGC

Example 15: hCMV Vaccine—hCMV UL Multimeric Sequences

A hCMV vaccine may comprise, for example, at least one RNA polynucleotide encoded by at least one of the following sequences or by at least one fragment or epitope of the following sequences. In some embodiments, a hCMV vaccine may comprise at least one RNA polynucleotide comprising at least one of the mRNA sequences listed below or at least one fragment of the mRNA sequences listed below.

hCMV gH penta (SEQ ID NO: 19)

TCAAGCTTTTGGACCCTCGTACAGAAGCTAATACGACTCACTATAGGGACAGACGAGAGAGA

AGCACGCCAATTCTGCCTGCTTAAGCCATGCGGCCAGGCCTCCCCTCCTACCTCATCATCCT

CGCCGTCTGTCTCTTCAGCCACCTACTTTCGTCACGATATGGCGCAGAAGCCGTATCCGAAC

CGCTGGACAAAGCGTTTCACCTACTGCTCAACACCTACGGGAGACCCATCCGCTTCCTGCGT

GAAAATACCACCCAGTGTACCTACAACAGCAGCCTCCGTAACAGCACGGTCGTCAGGGAAAA

CGCCATCAGTTTCAACTTTTTCCAAAGCTATAATCAATACTATGTATTCCATATGCCTCGAT

GTCTTTTTGCGGGTCCTCTGGCGGAGCAGTTTCTGAACCAGGTAGATCTGACCGAAACCCTG

GAAAGATACCAACAGAGACTTAACACTTACGCGCTGGTATCCAAAGACCTGGCCAGCTACCG

ATCTTTTTCGCAGCAGCTAAAGGCACAAGACAGCCTAGGTGAACAGCCCACCACTGTGCCAC

CGCCCATTGACCTGTCAATACCTCACGTTTGGATGCCACCGCAAACCACTCCACACGGCTGG

ACAGAATCACATACCACCTCAGGACTACACCGACCACACTTTAACCAGACCTGTATCCTCTT

TGATGGACACGATCTACTATTCAGCACCGTCACACCTTGTTTGCACCAAGGCTTTTACCTCA

TCGACGAACTACGTTACGTTAAAATAACACTGACCGAGGACTTCTTCGTAGTTACGGTGTCC

ATAGACGACGACACACCCATGCTGCTTATCTTCGGCCATCTTCCACGCGTACTTTTCAAAGC

GCCCTATCAACGCGACAACTTTATACTACGACAAACTGAAAAACACGAGCTCCTGGTGCTAG

TTAAGAAAGATCAACTGAACCGTCACTCTTATCTCAAAGACCCGGACTTTCTTGACGCCGCA

CTTGACTTCAACTACCTAGACCTCAGCGCACTACTACGTAACAGCTTTCACCGTTACGCCGT

GGATGTACTCAAGAGCGGTCGATGTCAGATGCTGGACCGCCGCACGGTAGAAATGGCCTTCG

CCTACGCATTAGCACTGTTCGCAGCAGCCCGACAAGAAGAGGCCGGCGCCCAAGTCTCCGTC

CCACGGGCCCTAGACCGCCAGGCCGCACTCTTACAAATACAAGAATTTATGATCACCTGCCT

CTCACAAACACCACCACGCACCACGTTGCTGCTGTATCCCACGGCCGTGGACCTGGCCAAAC

GAGCCCTTTGGACACCGAATCAGATCACCGACATCACCAGCCTCGTACGCCTGGTCTACATA

CTCTCTAAACAGAATCAGCAACATCTCATCCCCCAATGGGCACTACGACAGATCGCCGACTT

TGCCCTAAAACTACACAAAACGCACCTGGCCTCTTTTCTTTCAGCCTTCGCACGCCAAGAAC

TCTACCTCATGGGCAGCCTCGTCCACTCCATGCTGGTACATACGACGGAGAGACGCGAAATC

TTCATCGTAGAAACGGGCCTCTGTTCATTGGCCGAGCTATCACACTTTACGCAGTTGTTAGC

TCATCCACACCACGAATACCTCAGCGACCTGTACACACCCTGTTCCAGTAGCGGGCGACGCG

-continued

ATCACTCGCTCGAACGCCTCACGCGTCTCTTCCCCGATGCCACCGTCCCCGCTACCGTTCCC

GCCGCCCTCTCCATCCTATCTACCATGCAACCAAGCACGCTGGAAACCTTCCCCGACCTGTT

TTGCTTGCCGCTCGGCGAATCCTTCTCCGCGCTGACCGTCTCCGAACACGTCAGTTATATCG

TAACAAACCAGTACCTGATCAAAGGTATCTCCTACCCTGTCTCCACCACCGTCGTAGGCCAG

AGCCTCATCATCACCCAGACGGACAGTCAAACTAAATGCGAACTGACGCGCAACATGCATAC

CACACACAGCATCACAGTGGCGCTCAACATTTCGCTAGAAAACTGCGCCTTTTGCCAAAGCG

CCCTGCTAGAATACGACGACACGCAAGGCGTCATCAACATCATGTACATGCACGACTCGGAC

GACGTCCTTTTCGCCCTGGATCCCTACAACGAAGTGGTGCTCTCATCTCCCCGAACTCACTA

CCTCATGCTTTTGAAAAACGCTACCGTACTAGAAGTAACTGACGTCGTCGTGGACGCCACCG

ACAGTCGTCTCCTCATGATGTCCGTCTACGCGCTATCGGCCATCATCGGCATCTATCTGCTC

TACCGCATGCTCAAaACATGCTGATAATAGGCTGGAGCCTCGGTGGCCATGCTTCTTGCCCC

TTGGGCCTCCCCCCAGCCCCTCCTCCCCTTCCTGCACCCGTACCCCCGTGGTCTTTGAATAA

AGTCTGAGTGGGCGGC hCMV gH penta mRNA (SEQ ID NO: 176)

UCAAGCUUUUGGACCCUCGUACAGAAGCUAAUACGACUCACUAUAGGGACAGACGAGAGAGA

AGCACGCCAAUUCUGCCUGCUUAAGCCAUGCGGCCAGGCCUCCCCUCCUACCUCAUCAUCCU

CGCCGUCUGUCUCUUCAGCCACCUACUUUCGUCACGAUAUGGCGCACAAGCCGUAUCCGAAC

CGCUGGACAAAGCGUUUCACCUACUGCUCAACACCUACGGGAGACCCAUCCGCUUCCUGCGU

GAAAAUACCACCCAGUGUACCUACAACAGCAGCCUCCGUAACAGCACGGUCGUCAGGGAAAA

CGCCAUCAGUUUCAACUUUUUCCAAAGCUAUAAUCAAUACUAUGUAUUCCAUAUGCCUCGAU

GUCUUUUUGCGGGUCCUCUGGCGGAGCACUUUCUGAACCACGUACAUCUGACCGAAACCCUG

GAAAGAUACCAACAGAGACUUAACACUUACCCGCUGGUAUCCAAAGACCUGGCCAGCUACCG

AUCUUUUUCGCAGCAGCUAAAGGCACAAGACAGCCUAGGUGAACAGCCCACCACUGUGCCAC

CGCCCAUUGACCUGUCAAUACCUCACGUUUGGAUGCCACCGCAAACCACUCCACACGGCUGG

ACAGAAUCACAUACCACCUCAGGACUACACCGACCACACUUUAACCAGACCUGUAUCCUCUU

UGAUGGACACGAUCUACUAUUCAGCACCGUCACACCUUGUUUGCACCAAGGCUUUUACCUCA

UCGACGAACUACGUUACGUUAAAAUAACACUGACCGAGGACUUCUUCGUAGUUACGGUGUCC

AUAGACGACGACACACCCAUGCUGCUUAUCUUCGGCCAUCUUCCACGCGUACUUUUCAAAGC

GCCCUAUCAACGCGACAACUUUAUACUACGACAAACUGAAAAACACGAGCUCCUGGUGCUAG

UUAAGAAAGAUCAACUGAACCGUCACUCUUAUCUCAAAGACCCGGACUUUCUUGACGCCGCA

CUUGACUUCAACUACCUAGACCUCAGCGCACUACUACGUAACAGCUUUCACCGUUACGCCGU

GGAUGUACUCAAGAGCCGUCCAUGUCAGAUGCUGGACCGCCGCACGGUAGAAAUGGCCUUCG

CCUACGCAUUAGCACUGUUCGCAGCAGCCCGAaAAaAAGAGGCCGGCGCCGAAGUCUCCGUC

CCACGGCCCCUAGACCGCCAGGCCGCACUCUUACAAAUACAAGAAUUUAUGAUCACCUGCCU

CUCACAAACACCACCACGCACCACGUUGCUGCUGUAUCCCACGGCCGUGGACCUGGCCAAAC

GAGCCCUUUGGACACCGAAUCAGAUCACCGACAUCACCAGCCUCGUACGCCUGGUCUACAUA

CUCUCUAAACAGAAUCAGCAACAUCUCAUCCCCCAAUGGGCACUACGACAGAUCGCCGACUU

UGCCCUAAAACUACACAAAACGCACCUGGCCUCUUUUCUUUCAGCCUUCGCACGCCAAGAAC

UCUACCUCAUGGGCAGCCUCGUCCACUCCAUGCUGGUACAUACGACGGAGAGACGCGAAAUC

UUCAUCGUAGAAACGGGCCUCUGUUCAUUGGCCGAGCUAUCACACUUUACGCAGUUGUUAGC

-continued

UCAUCCACACCACGAAUACCUCAGCGACCUGUACACACCCUGUUCCAGUAGCGGGCGACGCG

AUCACUCGCUCGAACGCCUCACGCGUCUCUUCCCCGAUGCCACCGUCCCCGCUACCGUUCCC

GCCGCCCUCUCCAUCCUAUCUACCAUGCAACCAAGCACGCUGGAAACCUUCCCCGACCUGUU

UUGCUUGCCGCUCGGCGAAUCCUUCUCCGCGCUGACCGUCUCCGAACACGUCAGUUAUAUCG

UAACAAACCAGUACCUGAUCAAAGGUAUCUCCUACCCUGUCUCCACCACCGUCGUAGGCCAG

AGCCUCAUCAUCACCCAGACGGACAGUCAAACUAAAUGCGAACUGACGCGCAACAUGCAUAC

CACACACAGCAUCACAGUGGCGCUCAACAUUUCGCUAGAAAACUGCGCCUUUUGCCAAAGCG

CCCUGCUAGAAUACGACGACACGaAAGGCGUCAUCAACAUCAUGUACAUGCACGACUCGGAC

GACGUCCUUUUCGCCCUGGAUCCCUACAACGAAGUGGUGGUCUCAUCUCCGCGAACUCACUA

CCUCAUGCUUUUGAAAAACGGUACGGUACUAGAAGUAACUGACGUCGUCGUGGACGCCACCG

ACAGUCGUCUCCUCAUGAUGUCCGUCUACGCGCUAUCGGCCAUCAUCGGCAUCUAUCUGCUC

UACCGCAUGCUCAAGACAUGCUGAUAAUAGGCUGGAGCCUCGGUGGCCAUGCUUCUUGCCCC

UUGGGCCUCCCCCCAGCCCCUCCUCCCCUUCCUGCACCCGUACCCCGUGGUCUUUGAAUAA

AGUCUGAGUGGGCGGC hCMV gL penta (SEQ ID NO: 20)

TCAAGCTTTTGGACCCTCGTACAGAAGCTAATACGACTCACTATAGGGCTTAAGCAGGCAGA

ATTGGCCCTTAGCCTGTACCAGCCGAACCATGTGCCGCCGCCCGGATTGCGGCTTCTCTTTC

TCACCTGGACCGGTGATACTGCTGTGGTGTTGCCTTCTGCTGCCCATTGTTTCCTCAGCCGC

CGTCAGCGTCGCTCCTACCGCCGCCGAGAAAGTCCCCGCGGAGTGCCCCGAACTAACGCGCC

GATGCTTGTTGGGTGAGGTGTTTGAGGGTGACAAGTATGAAAGTTGGCTGCGCCCGTTGGTG

AATGTTACCGGGCGCGATGGCCCGCTATCGCAACTTATCCGTTACCGTCCCGTTACGCCGGA

GGCCGCCAACTCCGTGCTGTTGGACGAGGCTTTCCTGGACACTCTGGCCCTGCTGTACAACA

ATCCGGATCAATTGCGGGCCCTGCTGACGCTGTTGAGCTCGGACACAGCGCCGCGCTGGATG

ACGGTGATGCGCGGCTACAGCGAGTGACGCGATGGCTCGCCGGCCGTGTACACGTGCGTGGA

CGACCTGTGCCGCGGCTACGACCTCACGCGACTGTCATACGGGCGCAGCATCTTCACGGAAC

ACGTGTTAGGCTTCGAGCTGGTGCCACCGTCTCTCTTTAACGTGGTGGTGGCCATACGCAAC

GAAGCCACGCGTACCAACCGCGCCGTGCGTCTGCCCGTGAGCACCGCTGCCGCGCCCGAGGG

CATCACGCTCTTTTACGGCCTGTACAACGCAGTGAAGGAATTCTGCCTGCGTCACCAGCTGG

ACCCGCCGCTGCTACGCCACCTAGATAAATACTACGCCGGACTGCCGCCCGAGCTGAAGCAG

ACGCGCGTCAACCTGCCGGCTCACTCGCGCTATGGCCCTCAAGCAGTGGATGCTCGCTGATA

ATAGGCTGGAGCCTCGGTGGCCATGCTTCTTGCCCCTTGGGCCTCCCCCCAGCCCCTCCTCC

CCTTCCTGCACCCGTACCCCGTGGTCTTTGAATAAAGTCTGAGTGGGCGGC hCMV gL penta mRNA (SEQ ID NO: 177)

UCAAGCUUUUGGACCCUCGUACAGAAGCUAAUACGACUCACUAUAGGGCUUAAGCAGGCAGA

AUUGGCCCUUAGCCUGUACCAGCCGAACCAUGUGCCGCCGCCCGGAUUGCGGCUUCUCUUUC

UCACCUGGACCGGUGAUACUGCUGUGGUGUUGCCUUCUGCUGCCCAUUGUUUCCUCAGCCGC

CGUCAGCGUCGCUCCUACCGCCGCCGAGAAAGUCCCCGCGGAGUGCCCCGAACUAACGCGCC

GAUGCUUGUUGGGUGAGGUGUUUGAGGGUGACAAGUAUGAAAGUUGGCUGCGCCCGUUGGUG

AAUGUUACCGGGCGCGAUGGCCCGCUAUCGCAACUUAUCCGUUACCGUCCCGUUACGCCGGA

GGCCGCCAACUCCGUGCUGUUGGACGAGGCUUUCCUGGACACUCUGGCCCUGCUGUACAACA

AUCCGGAUCAAUUGCGGGCCCUGCUGACGCUGUUGAGCUCGGACACAGCGCCGCGCUGGAUG

-continued

ACGCUGAUGCGCGGCUACAGCGAGUGCGGCGAUGGCUCGCCGGCCGUGUACACGUGCGUGGA

CGACCUGUGCCGCGGCUACGACCUCACGCGACUGUCAUACGGGCGCAGCAUCUUCACGGAAC

ACGUGUUAGGCUUCGAGCUGGUGCCACCGUCUCUCUUUAACGUGGUGGUGGCCAUACGCAAC

GAAGCCACGCGUACCAACCGCGCCGUGCGUCUGCCCGUGAGCACCGCUGCCGCGCCCGAGGG

CAUCACGCUGCUUUACGGCCUGUACAACGCAGUGAAGGAAUUCUGCCUGCGUCACCAGCUGG

ACCCGCCGCUGCUACGCCACCUAGAUAAAUACUACGCCGGAEUGCCGCCCGAGCUGAAGCAG

ACGCGCGUCAACCUGCCGGCUCACUCGCGCUAUGGCCCUCAAGCAGUGGAUGCUCGCUGAUA

AUAGGCUGGAGCCUCGGUGGCCAUGCUUCUUGCCCCUUGGGCCUCCCCCCAGCCCCUCCUCC

CCUUCCUGCACCCGUACCCCCGUGGUCUUUGAAUAAAGUCUGAGUGGGCGGC hCMV gL dimer (SEQ ID NO: 21)

TCAAGCTTTTGGACCCTCGTACAGAAGCTAATACGACTCACTATAGGGTGGCTCTTATATTT

CTTCTTACTCTTCTTTTCTCTCTTATTTCCATGTGCCGCCGCCCGGATTGCGGCTTCTCTTT

CTCACCTGGACCGGTGATACTGCTGTGGTGTTGCCTTCTGCTGCCCATTGTTTCCTCAGCCG

CCGTCAGCGTCGCTCCTACCGCCGCCGAGAAAGTCCCCGCGGAGTGCCCCGAACTAACGCGC

CGATGCTTGTTGGGTGAGGTGTTTGAGGGTGACAAGTATGAAAGTTGGCTGCGCCCGTTGGT

GAATGTTACCGGGCGCGATGGCCCGCTATCGCAACTTATCCGTTACCGTCCCGTTACGCCGG

AGGCCGCCAACTCCGTGCTGTTGGACGAGGCTTTCCTGGACACTCTGGCCCTGCTGTACAAC

AATCCGGATCAATTGCGGGCCCTGCTGACGCTGTTGAGCTCGGACACAGCGCCGCGCTGGAT

GACGGTGATGCGCGGCTACAGCGAGTGCGGCGATGGCTCGCCGGCCGTGTACACGTGCGTGG

ACGACCTGTGCCGCGGCTACGACCTCACGCGACTGTCNTACGGGCGCAGCATCTTCACGGAA

CACGTGTTAGGCTTCGAGCTGGTGCCACCGTCTCTCTTTAACGTGGTGGTGGCCATACGCAA

CGAAGCCACGCGTACCAACCGCGCCGTGCGTCTGCCCGTGAGCACCGCTGCCGCGCCCGAGG

GCATCACGCTCTTTTACGGCCTGTACAACGCAGTGAAGGAATTCTGCCTGCGTCACCAGCTG

GACCCGCCGCTGCTACGCCACCTAGATAAATACTACGCCGGACTGCCGCCCGAGCTGAAGCA

GACGCGCGTCAACCTGCCGGCTCACTCGCGCTATGGCCCTCAAGCAGTGGATGCTCGCTGAT

AATAGGCTGGAGCCTCGGTGGCCATGCTTCTTGCCCCTTGGGCCTCCCCCCAGCCCCTCCTC

CCCTTCCTGCACCCGTACCCCCGTGGTCTTTGAATAAAGTCTGAGTGGGCGGC hCMV gL dimer mRNA (SEQ ID NO: 178)

UCAAGCUUUUGGACCCUCGUACAGAAGCUAAUACGACUCACUAUAGGGUGGCUCUUAUAUUU

CUUCUUACUCUUCUUUUCUCUCUUAUUUCCAUGUGCCGCCGCCCGGAUUGCGGCUUCUCUUU

CUCACCUGGACCGGUGAUACUGCUGUGGUGUUGCCUUCUGCUGCCCAUUGUUUCCUCAGCCG

CCGUCAGCGUCGCUCCUACCGCCGCCGAGAAAGUCCCCGCGGAGAGCCCCGAACUAACGCGC

CGAUGCUUGUUGGGUGAGGUGUUUGAGGGUGACAAGUAUGAAAGUUGGCUGCGCCCGUUGGU

GAAUGUUACCGGGCGCGAUGGCCCGCUAUCGCAACUUAUCCGUUACCGUCCCGUUACGCCGG

AGGCCGCCAACUCCGUGCUGUUGGACGAGGCUUUCCUGGACACUCUGGCCCUGCUGUACAAC

AAUCCGGAUCAAUUGCGGGCCCUGCUGACGCUGUUGAGCUCGGACACAGCGCCGCGCUGGAU

GACGGUGAUGCGCGGCUACAGCGAGUGCGGCGAUGGCUCGCCGGCCGUGUACACGUGCGUGG

ACGACCUGUGCCGCGGCUACGACCUCACGCGACUGUCAUACGGGCGCAGCAUCUUCACGGAA

CACGUGUUAGGCUUCGAGCUGGUGCCACCGUCUCUCUUUAACGUGGUGGUGGCCAUACGCAA

CGAAGCCACGCGUACCAACCGCGCCGUGCGUCUGCCCGUGAGCACCGCUGCCGCGCCCGAGG

-continued

GCAUCACGCUCUUUUACGGCCUGUACAACGCAGUGAAGGAAUUCUGCCUGCGUCACCAGCUG

GACCCGCCGCUGCUACGCCACCUAGAUAAAUACUACGCCGGACUGCCGCCCGAGCUGAAGCA

GACGCGCGUCAACCUGCCGGCUCACUCGCGCUAUGGCCCUCAAGCAGUGGAUGCUCGCUGAU

AAUAGGCUGGAGCCUCGGUGGCCAUGCUUCUUGCCCCUUGGGCCUCCCCCCAGCCCCUCCUC

CCCUUCCUGCACCCGUACCCCCGUGGUCUUUGAAUAAAGUCUGAGUGGGCGGC hCMV UL128 penta (SEQ ID NO: 22)

TCAAGCTTTTGGACCCTCGTACAGAAGCTAATACGACTCACTATAGGGTTCGGCTGGTACAG

GCTAACCAGAAGACAGATAAGAGCCTCCATGAGTCCCAAAGATCTGACGCCGTTCTTGACGG

CGTTGTGGCTGCTATTGGGTCACAGCCGCGTGCCGCGGGTGCGCGCAaAAGAATGTTGCGAA

TTCATAAACGTCAACCACCCGCCGGAACGCTGTTACGATTTCAAAATGTGCAATCGCTTCAC

CGTCGCGCTGCCGTGTCCGGACCGCGAAGTCTGCTACAGTCCCGAGAAAACCGCTGAGATTC

GCGGGATCGTCACCACCATGACCCATTCATTGACACGCCAGGTCGTACACAACAAACTGACG

AGCTGCAACTACAATCCGTTATACCTCGAAGCTGACGGGCGAATACGCTGCGGCAAAGTAAA

CGACAAGGCGCAGTACCTGCTGGGCGCCGCTGGCAGCGTTCCCTATCGATGGATCAATCTGG

AATACGACAAGATAACCCGGATCGTGGGCCTGGATCAGTACCTGGAGAGCGTTAAGAAACAC

AAACGGCTGGATGTGTGCCGCGCTAAAATGGGCTATATGCTGCAGTGATAATAGGCTGGAGC

CTCGGTGGCCATGCTTCTTGCCCCTTGGGCCTCCCCCCAGCCCCTCCTCCCCTTCCTGCACC

CGTACCCCCGTGGTCTTTGAATAAAGTCTGAGTGGGCGGC hCMV UL128 penta mRNA (SEQ ID NO: 179)

UCAAGCUUUUGGACCCUCGUACAGAAGCUAAUACGACUCACUAUAGGGUUCGGCUGGUACAG

GCUAACCAGAAGACAGAUAAGAGCCUCCAUGAGUCCCAAAGAUCUGACGCCGUUCUUGACGG

CGUUGUGGCUGCUAUUGGGUCACAGCCGCGUGCCGCGGGUGCGCGCAGAAGAAUGUUGCGAA

UUCAUAAACGUCAACCACCCGCCGGAACGCUGUUACGAUUUCAAAAUGUGCAAUCGCUUCAC

CGUCGCGCUGCGGUGUCCGGACGGCGAAGUCUGCUACAGUCCCGAGAAAACGGCUGAGAUUC

GCGGGAUCGUCACCACCAUGACCCAUUCAUUGACACGCCAGGUCGUACAaAAaAAACUGACG

AGCUGCAACUACAAUCCGUUAUACCUCGAAGCUGACGGGCGAAUACGCUGCGGCAAAGUAAA

CGACAAGGCGCAGUACCUGCUGGGCGCCGCUGGCAGCGUUCCCUAUCGAUGGAUCAAUCUGG

AAUACGACAAGAUAACCCGGAUCCUGGGCCUGGAUCAGUACCUGGAGAGCGUUAAGAAACAC

AAACCGCUGGAUGUGUGCCGCGCUAAAAUGGGCUAUAUGCUGCAGUGAUAAUAGGCUGGAGC

CUCGGUGGCCAUGCUUCUUGCCCCUUGGGCCUCCCCCCAGCCCCUCCUCCCCUUCCUGCACC

CGUACCCCCGUGGUCUUUGAAUAAAGUCUGAGUGGGCGGC hCMV-UL130 penta (SEQ ID NO: 23)

TCAAGCTTTTGGACCCTCGTACAGAAGCTAATACGACTCACTATAGGGAGGCTCTTATCTGT

CTTCTCAGTCCGAATTCGAAGTACGGCTACCATGCTGCGGCTTCTGCTTCGTCACCACTTTC

ACTGCCTGCTTCTGTGCGCGGTTTGGGCAACGCCCTGTCTGGCGTCTCCGTGGTCGACGCTA

ACAGCAAACCAGAATCCGTCCCCGCCATGGTCTAAACTGACGTATTCCAAACCGCATGACGC

GGCGACGTTTTACTGTCCTTTTCTCTATCCCTCGCCCCCACGATCCCCCTTGCAATTCTCGG

CGGGAAGGCCAGACCTTGGTGGAGAGAAGCTCCACCTGGGTGAAAAAGGTGATCTGGTACCT

GAGCGGTCGGAACCAAACCATCCTCCAACGGATGCCCCGAACGGCTTCGAAACCGAGCGACG

GAAACGTGCAGATCAGCGTGGAAGACGCCAAGATTTTTGGAGCGCACATGGTGCCCAAGCAG

ACCAAGCTGCTACGCTTCGTCGTCAACGATGGCACACGTTATCAGATGTGTGTGATGAAGCT

-continued

GGAGAGCTGGGCTCACGTCTTCCGGGACTACAGCGTGTCTTTTCAGGTGCGATTGACGTTCA

CCGAGGCCAATAACCAGACTTACACCTTCTGCACCCATCCCAATCTCATCGTTTGATAATAG

GCTGGAGCCTCGGTGGCCATGCTTCTTGCCCCTTGGGCCTCCCCCCAGCCCCTCCTCCCCTT

CCTGCACCCGTACCCCCGTGGTCTTTGAATAAAGTCTGAGTGGGCGGC hCMV-UL130 penta mRNA (SEQ ID NO: 180)

UCAAGCUUUUGGACCCUCGUACAGAAGCUAAUACGACUCACUAUAGGGAGGCUCUUAUCUGU

CUUCUCAGUCCGAAUUCGAAGUACGGCUACCAUGCUGCGGCUUCUGCUUCGUCACCACUUUC

ACUGCCUGCUUCUGUGCGCGGUUUGGGCAACGCCCUGUCUGGCGUCUCCGUGGUCGACGCUA

ACAGCAAACCAGAAUCCGUCCCCGCCAUGGUCUAAACUGACGUAUUCCAAACCGCAUGACGC

GGCGACGUUUUACUGUCCUUUUCUCUAUCCCUCGCCCCCACGAUCCCCCUUGCAAUUCUCGG

GGUUCCAGCGGGUAUCAACGGGUCCCGAGUGUCGCAACGAGACCCUGUAUCUGCUGUACAAC

CGGGAAGGCCAGACCUUGGUGGAGAGAAGCUCCACCUGGGUGAAAAAGGUGAUCUGGUACCU

GAGCGGUCGGAACCAAACCAUCCUCCAACGGAUGCCCCGAACGGCUUCGAAACCGAGCGACG

GAAACGUGCAGAUCAGCGUGGAAGACGCCAAGAUUUUUGGAGCGCACAUGGUGCCCAAGCAG

ACCAAGCUGCUACGCUUCGUCGUCAACGAUGGCACACGUUAUCAGAUGUGUGUGAUGAAGCU

GGAGAGCUGGGCUCACGUCUUCCGGGACUACAGCGUGUCUUUUCAGGUGCGAUUGACGUUCA

CCGAGGCCAAUAACCAGACUUACACCUUCUGCACCCAUCCCAAUCUCAUCGUUUGAUAAUAG

GCUGGAGCCUCGGUGGCCAUGCUUCUUGCCCCUUGGGCCUCCCCCCAGCCCCUCCUCCCCUU

CCUGCACCCGUACCCCCGUGGUCUUUGAAUAAAGUCUGAGUGGGCGGC hCMVUL130 trimer (SEQ ID NO: 24)

TCAAGCTTTTGGACCCTCGTACAGAAGCTAATACGACTCACTATAGGGTGGCTCTTATATTT

CTTCTTAGTCCGAATTCGAAGTACGGCTACATGCTGCGGCTTCTGCTTCGTCACCACTTTCA

CTGCCTGCTTCTGTGCGCGGTTTGGGCAACGCCCTGTCTGGCGTCTCCGTGGTCGACGCTAA

CAGCAAACCAGAATCCGTCCCCGCCATGGTCTAAACTGACGTATTCCAAACCGCATGACGCG

GCGACGTTTTACTGTCCTTTTCTCTATCCCTCGCCCCCACGATCCCCCTTGCAATTCTCGGG

GTTCCAGCGGGTATCAACGGGTCCCGAGTGTCGCAACGAGACCCTGTATCTGCTGTACAACC

GGGAAGGCCAGACCTTGGTGGAGAGAAGCTCCACCTGGGTGAAAAAGGTGATCTGGTACCTG

AGCGGTCGGAACCAAACCATCCTCCAACGGATGCCCCGAACGGCTTCGAAACCGAGCGACGG

AAACGTGCAGATCAGCGTGGAAGACGCCAAGATTTTTGGAGCGCACATGGTGCCCAAGCAGA

CCAAGCTGCTACGCTTCGTCGTCAACGATGGCACACGTTATCAGATGTGTGTGATGAAGCTG

GAGAGCTGGGCTCACGTCTTCCGGGACTACAGCGTGTCTTTTCAGGTGCGATTGACGTTCAC

CGAGGCCAATAACCAGACTTACACCTTCTGCACCCATCCCAATCTCATCGTTTGATAATAGG

CTGGAGCCTCGGTGGCCATGCTTCTTGCCCCTTGGGCCTCCCCCCAGCCCCTCCTCCCCTTC

CTGCACCCGTACCCCCGTGGTCTTTGAATAAAGTCTGAGTGGGCGGC hCMVUL130 trimer mRNA (SEQ ID NO: 181)

UCAAGCUUUUGGACCCUCGUACAGAAGCUAAUACGACUCACUAUAGGGUGGCUCUUAUAUUU

CUUCUUAGUCCGAAUUCGAAGUACGGCUACAUGCUGCGGCUUCUGCUUCGUCACCACUUUCA

CUGCCUGCUUCUGUGCGCGGUUUGGGCAACGCCCUGUCUGGCGUCUCCGUGGUCGACGCUAA

CAGCAAACCAGAAUCCGUCCCCGCCAUGGUCUAAACUGACGUAUUCCAAACCGCAUGACGCG

GCGACGUUUUACUGUCCUUUUCUCUAUCCCUCGCCCCCACGAUCCCCCUUGCAAUUCUCGGG

-continued

GUUCCAGCGGGUAUCAACGGGUCCCGAGUGUCGCAACGAGACCCUGUAUCUGCUGUACAACC

GGGAAGGCCAGACCUUGGUGGAGAGAAGCUCCACCUGGGUGAAAAAGGUGAUCUGGUACCUG

AGCGGUCGGAACCAAACCAUCCUCCAACGGAUGCCCCGAACGGCUUCGAAACCGAGCGACGG

AAACGUGCAGAUCAGCGUGGAAGACGCCAAGAUUUUUGGAGCGCACAUGGUGCCCAAGCAGA

CCAAGCUGCUACGCUUCGUCGUCAACGAUGGCACACGUUAUCAGAUGUGUGUGAUGAAGCUG

GAGAGCUGGGCUCACGUCUUCCGGGACUACAGCGUGUCUUUUCAGGUGCGAUUGACGUUCAC

CGAGGCCAAUAACCAGACUUACACCUUCUGCACCCAUCCCAAUCUCAUCGUUUGAUAAUAGG

CUGGAGCCUCGGUGGCCAUGCUUCUUGCCCCUUGGGCCUCCCCCCAGCCCCUCCUCCCCUUC

CUGCACCCGUACCCCCGUGGUCUUUGAAUAAAGUCUGAGUGGGCGGC hCMV-UL131A penta (SEQ ID NO: 25)

TCAAGCTTTTGGACCCTCGTACAGAAGCTAATACGACTCACTATAGGGTAGCCGTACTTCGA

ATTCGGACAAGCTTCTCTCTCGTCTGTCCATGCGGCTGTGTCGGGTGTGGCTGTCTGTTTGT

CTGTGCGCCGTGGTGCTGGGTCAGTGCCAGCGGGAAACCGCGGAAAAAAACGATTATTACCG

AGTACCGCATTACTGGGACGCGTGCTCTCGCGCGCTGCCCGACCAAACCCGTTACAAGTATG

TGGAACAGCTCGTGGACCTCACGTTGAACTACCACTACGATGCGAGCCACGGCTTGGACAAC

TTTGACGTGCTCAAGAGAATCAACGTGACCGAGGTGTCGTTGCTCATCAGCGACTTTAGACG

TCAGAACCGTCGCGGCGGCACCAACAAAAGGACCACGTTCAACGCCGCCGGTTCGCTGGCGC

CACACGCCCGGAGCCTCGAGTTCAGCGTGCGGCTCTTTGCCAACTGATAATAGGCTGGAGCC

TCGGTGGCCATGCTTCTTGCCCCTTGGGCCTCCCCCCAGCCCCTCCTCCCCTTCCTGCACCC

GTACCCCCGTGGTCTTTGAATAAAGTCTGAGTGGGCGGC hCMV-UL131A penta mRNA (SEQ ID NO: 182)

UCAAGCUUUUGGACCCUCGUACAGAAGCUAAUACGACUCACUAUAGGGUAGCCGUACUUCGA

AUUCGGACAAGCUUCUCUCUCGUCUGUCCAUGCGGCUGUGUCGGGUGUGGCUGUCUGUUUGU

CUGUGCGCCGUGGUGCUGGGUCAGUGCCAGCGGGAAACCGCGGAALAAAACGAUUAUUACCG

AGUACCGCAUUACUGGGACGCGUGCUCUCGCGCGCUGCCCGACCAAACCCGUUACAAGUAUG

UGGAACAGCUCGUGGACCUCACGUUGAACUACCACUACGAUGCGAGCCACGGCUUGGACAAC

UUUGACGUGCUCAAGAGAAUCAACGUGACCGAGGUGUCGUUGCUCAUCAGCGACUUUAGACG

UCAGAACCGUCGCGGCGGCACCAACAAAAGGACCACGUUCAACGCCGCCGGUUCGCUGGCGC

CACACGCCCGGAGCCUCGAGUUCAGCGUGCGGCUCUUUGCCAACUGAUAAUAGGCUGGAGCC

UCGGUGGCCAUGCUUCUUGCCCCUUGGGCCUCCCCCCAGCCCCUCCUCCCCUUCCUGCACCC

GUACCCCCGUGGUCUUUGAAUAAAGUCUGAGUGGGCGGC hCMVUL131A trimer (SEQ TD NO: 26)

TCAAGCTTTTGGACCCTCGTACAGAAGCTAATACGACTCACTATAGGGTAGCCGTACTTCGA

ATTCGGACTTTCTTTTCTCTCTTATTTCCATGCGGCTGTGTCGGGTGTGGCTGTCTGTTTGT

CTGTGCGCCGTGGTGCTGGGTCAGTGCCAGCGGGAAACCGCGGAAAAAAACGATTATTACCG

AGTACCGCATTACTGGGACGCGTGCTCTCGCGCGCTGCCCGACCAAACCCGTTACAAGTATG

TGGAACAGCTCGTGGACCTCACGTTGAACTACCACTACGATGCGAGCCACGGCTTGGACAAC

TTTGACGTCCTCAAGACAATCAACCTGACCGAGGTGTCGTTGCTCATCAGCGACTTTAGACG

TCAGAACCGTCGCGGCGGCACCAACAAAAGGACCACGTTCAACGCCGCCGGTTCGCTGGCGC

CACACGCCCGGAGCCTCGAGTTCAGCGTGCGGCTCTTTGCCAACTGATAATAGGCTGGAGCC

-continued

TCGGTGGCCATGCTTCTTGCCCCTTGGGCCTCCCCCCAGCCCCTCCTCCCCTTCCTGCACCC

GTACCCCCGTGGTCTTTGAATAAAGTCTGAGTGGGCGGC hCMVUL131A trimer mRNA (SEQ ID NO: 183)

UCAAGCUUUUGGACCCUCGUACAGAAGCUAAUACGACUCACUAUAGGGUAGCCGUACUUCGA

AUUCGGACUUUCUUUUCUCUCUUAUUUCCAUGCGGCUGUGUCGGGUGUGGCUGUCUGUUUGU

CUGUGCGCCGUGGUGCUGGGUCAGUGCCAGCGGGAAACCGCGGAAAAAAACGAUUAUUACCG

AGUACCGCAUUACUGGGACGCGUGCUCUCGCGCGCUGCCCGACCAAACCCGUUACAAGUAUG

UGGAACAGCUCGUGGACCUCACGUUGAACUACCACUACGAUGCGAGCCACGGCUUGGACAAC

UUUGACGUGCUCAAGAGAAUCAACGUGACCGAGGUGUCGUUGCUCAUCAGCGACUUUAGACG

UCAGAACCGUCGCGGCGGCACCAACAAAAGGACCACGUUCAACGCCGCCGGUUCGCUGGCGC

CACACGCCCGGAGCCUCGAGUUCAGCGUGCGGCUCUUUGCCAACUGAUAAUAGGCUGGAGCC

UCGGUGGCCAUGCUUCUUGCCCCUUGGGCCUCCCCCCAGCCCCUCCUCCCCUUCCUGCACCC

GUACCCCCGUGGUCUUUGAAUAAAGUCUGAGUGGGCGGC

Example 16: hCMV Vaccine—hCMV UL Fusion Sequences

A hCMV vaccine may comprise, for example, at least one RNA polynucleotide encoded by at least one of the following sequences or by at least one fragment or epitope of the following sequences. In some embodiments, a hCMV vaccine may comprise at least one RNA polynucleotide comprising at least one of the mRNA sequences listed below or at least one fragment of the mRNA sequences listed below.

hCMV pp65-IE1, hCMV UL83-UL123 fusion (SEQ ID NO: 27)

TCAAGCTTTTGGACCCTCGTACAGAAGCTAATACGACTCACTATAGGGAAATAAGAGAGAAA

AGAAGAGTAAGAAGAAATATAAGAGCCACCATGGAGTCGCGCGGTCGCCGTTGTCCCGAAAT

GATATCCGTACTGGGTCCCATTTCGGGGCACGTGCTGAAAGCCGTGTTTAGTCGCGGCGATA

CGCCGGTGCTGCCGCACGAGACGCGACTCCTGCAGACGGGTATCCACGTACGCGTGAGCCAG

CCCTCGCTGATCCTGGTGTCGCAGTACACGCCCGACTCGACGCCATGCCACCGCGGCGACAA

TCAGCTGCAGGTGCAGCACACGTACTTTACGGGCAGCGAGGTGGAGAACGTGTCGGTCAACG

TGCACAACCCCACGGGCCGAAGCATCTGCCCCAGCCAAGAGCCCATGTCGATCTATGTGTAC

GCGCTGCCGCTCAAGATGCTGAACATCCCCAGCATCAACGTGCACCACTACCCGTCGGCGGC

CGAGCGCAAACACCGACACCTGCCCGTAGCCGACGCTGTTATTCACGCGTCGGGCAAGCAGA

TGTGGCAGGCGCGTCTCACGGTCTCGGGACTGGCCTGGACGCGTCAGCAGAACCAGTGGAAA

GAGCCCGACGTCTACTACACGTCAGCGTTCGTGTTTCCCACCAAGGACGTGGCACTGCGGCA

CGTGGTGTGCGCGCACGAGCTGGTTTGCTCCATGGAGAACACGCGCGCAACCAAGATGCAGG

TGATAGGTGACCAGTACGTCAAGGTGTACCTGGAGTCCTTCTGCGAGGACGTGCCCTCCGGC

AAGCTCTTTATGCACGTCACGCTGGGCTCTGACGTGGAAGAGGACCTAACGATGACCCGCAA

CCCGCAACCCTTCATGCGCCCCCACGAGCGCAACGGCTTTACGGTGTTGTGTCCCAAAAATA

TGATAATCAAACCGGGCAAGATCTCGCACATCATGCTGGATGTGGCTTTTACCTCACACGAG

CATTTTGGGCTGCTGTGTCCCAAGAGCATCCCGGGCCTGAGCATCTCAGGTAACCTGTTGAT

GAACGGGCAGCAAATCTTCCTGGAGGTACAAGCGATACGCGAGACCGTGGAACTGCGTCAGT

ACGATCCCGTGGCTGCGCTCTTCTTTTTCGATATCGACTTGTTGCTGCAGCGCGGGCCTCAG

TACAGCGAGCACCCCACCTTCACCAGCCAGTATCGCATCCAGGGCAAGCTTGAGTACCGACA

CACCTGGGACCGGCACGACGAGGGTGCCGCCCAGGGCGACGACGACGTCTGGACCAGCGGAT

CGGACTCCGACGAAGAACTCGTAACCACCGAGCGTAAGACGCCCCGCGTCACCGGCGGCGGC

-continued

GCCATGGCGAGCGCCTCCACTTCCGCGGGCCGCAAACGCAAATCAGCATCCTCGGCGACGGC

GTGCACGGCGGGCGTTATGACACGCGGCCGCCTTAAGGCCGAGTCCACCGTCGCGCCCGAAG

AGGACACCGACGAGGATTCCGACAACGAAATCCACAATCCGGCCGTGTTCACCTGGCCGCCC

TGGCAGGCCGGCATCCTGGCCCGCAACCTGGTGCCCATGGTGGCTACGGTTCAGGGTCAGAA

TCTGAAGTACCAGGAGTTCTTCTGGGACGCCAACGACATCTACCGCATCTTCGCCGAATTGG

AAGGCGTATGGCAGCCCGCTGCGCAACCCAAACGTCGCCGCCACCGGCAAGACGCCTTGCCC

GGGCCATGCATCGCCTCGACGCCCAAAAAGCACCGAGGTGAGTCCTCTGCCAAGAGAAAGAT

GGACCCTGATAATCCTGACGAGGGCCCTTCCTCCAAGGTGCCACGGCCCGAGACACCCGTGA

CCAAGGCCACGACGTTCCTGCAGACTATGTTAAGGAAGGAGGTTAACAGTCAGCTGAGCCTG

GGAGACCCGCTGTTCCCAGAATTGGCCGAAGAATCCCTCAAAACCTTTGAACAAGTGACCGA

GGATTGCAACGAGAACCCCGAAAAAGATGTCCTGACAGAACTCGTCAAACAGATTAAGGTTC

GAGTGGACATGGTGCGGCATAGAATCAAGGAGCACATGCTGAAAAAATATACCCAGACGGAA

GAAAAATTCACTGGCGCCTTTAATATGATGGGAGGATGTTTGCAGAATGCCTTAGATATCTT

AGATAAGGTTCATGAGCCTTTCGAGGACATGAAGTGTATTGGGCTAACTATGCAGAGCATGT

ATGAGAACTACATTGTACCTGAGGATAAGCGGGAGATGTGGATGGCTTGTATTAAGGAGCTG

CATGATGTGAGCAAGGGCGCCGCTAACAAGTTGGGGGGTGCACTGCAGGCTAAGGCCCGTGC

TAAAAAGGATGAACTTAGGAGAAAGATGATGTATATGTGCTACAGGAATATAGAGTTCTTTA

CCAAGAACTCAGCCTTCCCTAAGACCACCAATGGCTGCAGTCAGGCCATGGCGGCATTGCAG

AACTTGCCTCAGTGCTCTCCTGATGAGATTATGTCTTATGCCCAGAAAATCTTTAAGATTTT

GGATGAGGAGAGAGACAAGGTGCTCACGCACATTGATCACATATTTATGGATATCCTCACTA

CATGTGTGGAAACAATGTGTAATGAGTACAAGGTCACTAGTGACGCTTGTATGATGACCATG

TACGGGGGCATCTCTCTCTTAAGTGAGTTCTGTCGGGTGCTGTGCTGCTATGTCTTAGAGGA

GACTAGTGTGATGCTGGCCAAGCGGCCTCTGATAACCAAGCCTGAGGTTATCAGTGTAATGA

AGCGCCGCATTGAGGAGATCTGCATGAAGGTCTTTGCCCAGTACATTCTGGGGGCCGATCCT

TTGAGAGTCTGCTCTCCTAGTGTGGATGACCTACGGGCCATCGCCGAGGAGTCAGATGAGGA

AGAGGCTATTGTAGCCTACACTTTGGCCACCGCTGGTGCCAGCTCCTCTGATTCTCTGGTGT

CACCTCCAGAGTCCCCTGTACCCGCGACTATCCCTCTGTCCTCAGTAATTGTGGCTGAGAAC

AGTGATCAGGAAGAAAGTGAACAGAGTGATGAGGAACAGGAGGAGGGTGCTCAGGAGGAGCG

GGAGGACACTGTGTCTGTCAAGTCTGAGCCAGTGTCTGAGATAGAGGAAGTTGCCTCAGAGG

AAGAGGAGGATGGTGCTGAGGAACCCACCGCCTCTGGAGGCAAGAGCACCCACCCTATGGTG

ACTAGAAGCAAGGCTGACCAGTGATAATAGGCTGGAGCCTCGGTGGCCATGCTTCTTGCCCC

TTGGGCCTCCCCCCAGCCCCTCCTCCCCTTCCTGCACCCGTACCCCCGTGGTCTTTGAATAA

AGTCTGAGTGGGCGGC hCMV pp65-IE1, hCMV UL83-UL123 fusion mRNA (SEQ ID NO: 184)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGGAGUCGCGCGGUCGCCGUUGUCCCGAAAU

GAUAUCCGUACUGGGUCCCAUUUCGGGGCACGUGCUGAAAGCCGUGUUUAGUCGCGGCGAUA

CGCCGGUGCUGCCGCACGAGACGCGACUCCUGCAGACGGGUAUCCACGUACGCGUGAGCCAG

CCCUCGCUGAUCCUGGUGUCGCAGUACACGCCCGACUCGACGCCAUGCCACCGCGGCGACAA

UCAGCUGCAGGUGCAGCACACGUACUUUACGGGCAGCGAGGUGGAGAACGUGUCGGUCAACG

-continued

UGCACAACCCCACGGGCCGAAGCAUCUGCCCCAGCCAAGAGCCCAUGUCGAUCUAUGUGUAC

GCGCUGCCGCUCAAGAUGCUGAACAUCCCCAGCAUCAACGUGCACCACUACCCGUCGGCGGC

CGAGCGCAAACACCGACACCUGCCCGUAGCCGACGCUGUUAUUCACGCGUCGGGCAAGCAGA

UGUGGCAGGCGCGUCUCACGGUCUCGGGACUGGCCUGGACGCGUCAGCAGAACCAGUGGAAA

GAGCCCGACGUCUACUACACGUCAGCGUUCGUGUUUCCCACCAAGGACGUGGCACUGCGGCA

CGUGGUGUGCGCGCACGAGCUGGUUUGCUCCAUGGAGAACACGCGCGCAACCAAGAUGCAGG

UGAUAGGUGACCAGUACGUCAAGGUGUACCUGGAGUCCUUCUGCGAGGACGUGCCCUCCGGC

AAGCUCUUUAUGCACGUCACGCUGGGCUCUGACGUGGAAGAGGACCUAACGAUGACCCGCAA

CCCGCAACCCUUCAUGCGCCCCCACGAGCGCAACGGCUUUACGGUGUUGUGUCCCAAAAAUA

UGAUAAUCAAACCGGGCAAGAUCUCGCACAUCAUGCUGGAUGUGGCUUUUACCUCACACGAG

CAUUUUGGGCUGCUGUGUCCCAAGAGCAUCCCGGGCCUGAGCAUCUCAGGUAACCUGUUGAU

GAACGGGCAGCAAAUCUUCCUGGAGGUACAAGCGAUACGCGAGACCGUGGAACUGCGUCAGU

ACGAUCCCGUGGCUGCGCUCUUCUUUUUCGAUAUCGACUUGUUGCUGCAGCGCGGGCCUCAG

UACAGCGAGCACCCCACCUUCACCAGCCAGUAUCGCAUCCAGGGCAAGCUUGAGUACCGACA

CACCUGGGACCGGCACGACGAGGGUGCCGCCCAGGGCGACGACGACGUCUGGACCAGCGGAU

CGGACUCCGACGAAGAACUCGUAACCACCGAGCGUAAGACGCCCCGCGUCACCGGCGGCGGC

GCCAUGGCGAGCGCCUCCACUUCCGCGGGCCGCAAACGCAAAUCAGCAUCCUCGGCGACGGC

GUGCACGGCGGGCGUUAUGACACGCGGCCGCCUUAAGGCCGAGUCCACCGUCGCGCCCGAAG

AGGACACCGACGAGGAUUCCGACAACGAAAUCCACAAUCCGGCCGUGUUCACCUGGCCGCCC

UGGCAGGCCGGCAUCCUGGCCCGCAACCUGGUGCCCAUGGUGGCUACGGUUCAGGGUCAGAA

UCUGAAGUACCAGGAGUUCUUCUGGGACGCCAACGACAUCUACCGCAUCUUCGCCGAAUUGG

AAGGCGUAUGGCAGCCCGCUGCGCAACCCAAACGUCGCCGCCACCGGCAAGACGCCUUGCCC

GGGCCAUGCAUCGCCUCGACGCCCAAAAAGCACCGAGGUGAGUCCUCUGCCAAGAGAAAGAU

GGACCCUGAUAAUCCUGACGAGGGCCCUUCCUCCAAGGUGCCACGGCCCGAGACACCCGUGA

CCAAGGCCACGACGUUCCUGCAGACUAUGUUAAGGAAGGAGGUUAACAGUCAGCUGAGCCUG

GGAGACCCGCUGUUCCCAGAAUUGGCCGAAGAAUCCCUCAAAACCUUUGAACAAGUGACCGA

GGAUUGCAACGAGAACCCCGAAAAAGAUGUCCUGACAGAACUCGUCAAACAGAUUAAGGUUC

GAGUGGACAUGGUGCGGCAUAGAAUCAAGGAGCACAUGCUGAAAAAAUAUACCCAGACGGAA

GAAAAAUUCACUGGCGCCUUUAAUAUGAUGGGAGGAUGUUUGCAGAAUGCCUUAGAUAUCUU

AGAUAAGGUUCAUGAGCCUUUCGAGGACAUGAAGUGUAUUGGGCUAACUAUGCAGAGCAUGU

AUGAGAACUACAUUGUACCUGAGGAUAAGCGGGAGAUGUGGAUGGCUUGUAUUAAGGAGCUG

CAUGAUGUGAGCAAGGGCGCCGCUAACAAGUUGGGGGGUGCACUGCAGGCUAAGGCCCGUGC

UAAAAAGGAUGAACUUAGGAGAAAGAUGAUGUAUAUGUGCUACAGGAAUAUAGAGUUCUUUA

CCAAGAACUCAGCCUUCCCUAAGACCACCAAUGGCUGCAGUCAGGCCAUGGCGGCAUUGCAG

AACUUGCCUCAGUGCUCUCCUGAUGAGAUUAUGUCUUAUGCCCAGAAAAUCUUUAAGAUUUU

GGAUGAGGAGAGAGACAAGGUGCUCACGCACAUUGAUCACAUAUUUAUGGAUAUCCUCACUA

CAUGUGUGGAAACAAUGUGUAAUGAGUACAAGGUCACUAGUGACGCUUGUAUGAUGACCAUG

UACGGGGGCAUCUCUCUCUUAAGUGAGUUCUGUCGGGUGCUGUGCUGCUAUGUCUUAGAGGA

GACUAGUGUGAUGCUGGCCAAGCGGCCUCUGAUAACCAAGCCUGAGGUUAUCAGUGUAAUGA

AGCGCCGCAUUGAGGAGAUCUGCAUGAAGGUCUUUGCCCAGUACAUUCUGGGGGCCGAUCCU

UUGAGAGUCUGCUCUCCUAGUGUGGAUGACCUACGGGCCAUCGCCGAGGAGUCAGAUGAGGA

-continued

AGAGGCUAUUGUAGCCUACACUUUGGCCACCGCUGGUGCCAGCUCCUCUGAUUCUCUGGUGU

CACCUCCAGAGUCCCCUGUACCCGCGACUAUCCCUCUGUCCUCAGUAAUUGUGGCUGAGAAC

AGUGAUCAGGAAGAAAGUGAACAGAGUGAUGAGGAACAGGAGGAGGGUGCUCAGGAGGAGCG

GGAGGACACUGUGUCUGUCAAGUCUGAGCCAGUGUCUGAGAUAGAGGAAGUUGCCUCAGAGG

AAGAGGAGGAUGGUGCUGAGGAACCCACCGCCUCUGGAGGCAAGAGCACCCACCCUAUGGUG

ACUAGAAGCAAGGCUGACCAGUGAUAAUAGGCUGGAGCCUCGGUGGCCAUGCUUCUUGCCCC

UUGGGCCUCCCCCCAGCCCCUCCUCCCCUUCCUGCACCCGUACCCCCGUGGUCUUUGAAUAA

AGUCUGAGUGGGCGGC hCMV pp65-IE1FLAG, hCMV UL83-UL123 FLAG tag (SEQ ID NO: 28)

TCAAGCTTTTGGACCCTCGTACAGAAGCTAATACGACTCACTATAGGGAAATAAGAGAGAAA

AGAAGAGTAAGAAGAAATATAAGAGCCACCATGGAGTCGCGCGGTCGCCGTTGTCCCGAAAT

GATATCCGTACTGGGTCCCATTTCGGGGCACGTGCTGAAAGCCGTGTTTAGTCGCGGCGATA

CGCCGGTGCTGCCGCACGAGACGCGACTCCTGCAGACGGGTATCCACGTACGCGTGAGCCAG

CCCTCGCTGATCCTGGTGTCGCAGTACACGCCCGACTCGACGCCATGCCACCGCGGCGACAA

TCAGCTGCAGGTGCAGCACACGTACTTTACGGGCAGCGAGGTGGAGAACGTGTCGGTCAACG

TGCACAACCCCACGGGCCGAAGCATCTGCCCCAGCCAAGAGCCCATGTCGATCTATGTGTAC

GCGCTGCCGCTCAAGATGCTGAACATCCCCAGCATCAACGTGCACCACTACCCGTCGGCGGC

CGAGCGCAAACACCGACACCTGCCCGTAGCCGACGCTGTTATTCACGCGTCGGGCAAGCAGA

TGTGGCAGGCGCGTCTCACGGTCTCGGGACTGGCCTGGACGCGTCAGCAGAACCAGTGGAAA

GAGCCCGACGTCTACTACACGTCAGCGTTCGTGTTTCCCACCAAGGACGTGGCACTGCGGCA

CGTGGTGTGCGCGCACGAGCTGGTTTGCTCCATGGAGAACACGCGCGCAACCAAGATGCAGG

TGATAGGTGACCAGTACGTCAAGGTGTACCTGGAGTCCTTCTGCGAGGACGTGCCCTCCGGC

AAGCTCTTTATGCACGTCACGCTGGGCTCTGACGTGGAAGAGGACCTAACGATGACCCGCAA

CCCGCAACCCTTCATGCGCCCCCACGAGCGCAACGGCTTTACGGTGTTGTGTCCCAAAAATA

TGATAATCAAACCGGGCAAGATCTCGCACATCATGCTGGATGTGGCTTTTACCTCACACGAG

CATTTTGGGCTGCTGTGTCCCAAGAGCATCCCGGGCCTGAGCATCTCAGGTAACCTGTTGAT

GAACGGGCAGCAAATCTTCCTGGAGGTACAAGCGATACGCGAGACCGTGGAACTGCGTCAGT

ACGATCCCGTGGCTGCGCTCTTCTTTTTCGATATCGACTTGTTGCTGCAGCGCGGGCCTCAG

TACAGCGAGCACCCCACCTTCACCAGCCAGTATCGCATCCAGGGCAAGCTTGAGTACCGACA

CACCTGGGACCGGCACGACGAGGGTGCCGCCCAGGGCGACGACGACGTCTGGACCAGCGGAT

CGGACTCCGACGAAGAACTCGTAACCACCGAGCGTAAGACGCCCCGCGTCACCGGCGGCGGC

GCCATGGCGAGCGCCTCCACTTCCGCGGGCCGCAAACGCAAATCAGCATCCTCGGCGACGGC

GTGCACGGCGGGCGTTATGACACGCGGCCGCCTTAAGGCCGAGTCCACCGTCGCGCCCGAAG

AGGACACCGACGAGGATTCCGACAACGAAATCCACAATCCGGCCGTGTTCACCTGGCCGCCC

TGGCAGGCCGGCATCCTGGCCCGCAACCTGGTGCCCATGGTGGCTACGGTTCAGGGTCAGAA

TCTGAAGTACCAGGAGTTCTTCTGGGACGCCAACGACATCTACCGCATCTTCGCCGAATTGG

AAGGCGTATGGCAGCCCGCTGCGCAACCCAAACGTCGCCGCCACCGGCAAGACGCCTTGCCC

GGGCCATGCATCGCCTCGACGCCCAAAAAGCACCGAGGTGAGTCCTCTGCCAAGAGAAAGAT

GGACCCTGATAATCCTGACGAGGGCCCTTCCTCCAAGGTGCCACGGCCCGAGACACCCGTGA

CCAAGGCCACGACGTTCCTGCAGACTATGTTAAGGAAGGAGGTTAACAGTCAGCTGAGCCTG

-continued

GGAGACCCGCTGTTCCCAGAATTGGCCGAAGAATCCCTCAAAACCTTTGAACAAGTGACCGA

GGATTGCAACGAGAACCCCGAAAAAGATGTCCTGACAGAACTCGTCAAACAGATTAAGGTTC

GAGTGGACATGGTGCGGCATAGAATCAAGGAGCACATGCTGAAAAAATATACCCAGACGGAA

GAAAAATTCACTGGCGCCTTTAATATGATGGGAGGATGTTTGCAGAATGCCTTAGATATCTT

AGATAAGGTTCATGAGCCTTTCGAGGACATGAAGTGTATTGGGCTAACTATGCAGAGCATGT

ATGAGAACTACATTGTACCTGAGGATAAGCGGGAGATGTGGATGGCTTGTATTAAGGAGCTG

CATGATGTGAGCAAGGGCGCCGCTAACAAGTTGGGGGGTGCACTGCAGGCTAAGGCCCGTGC

TAAAAAGGATGAACTTAGGAGAAAGATGATGTATATGTGCTACAGGAATATAGAGTTCTTTA

CCAAGAACTCAGCCTTCCCTAAGACCACCAATGGCTGCAGTCAGGCCATGGCGGCATTGCAG

AACTTGCCTCAGTGCTCTCCTGATGAGATTATGTCTTATGCCCAGAAAATCTTTAAGATTTT

GGATGAGGAGAGAGACAAGGTGCTCACGCACATTGATCACATATTTATGGATATCCTCACTA

CATGTGTGGAAACAATGTGTAATGAGTACAAGGTCACTAGTGACGCTTGTATGATGACCATG

TACGGGGGCATCTCTCTCTTAAGTGAGTTCTGTCGGGTGCTGTGCTGCTATGTCTTAGAGGA

GACTAGTGTGATGCTGGCCAAGCGGCCTCTGATAACCAAGCCTGAGGTTATCAGTGTAATGA

AGCGCCGCATTGAGGAGATCTGCATGAAGGTCTTTGCCCAGTACATTCTGGGGGCCGATCCT

TTGAGAGTCTGCTCTCCTAGTGTGGATGACCTACGGGCCATCGCCGAGGAGTCAGATGAGGA

AGAGGCTATTGTAGCCTACACTTTGGCCACCGCTGGTGCCAGCTCCTCTGATTCTCTGGTGT

CACCTCCAGAGTCCCCTGTACCCGCGACTATCCCTCTGTCCTCAGTAATTGTGGCTGAGAAC

AGTGATCAGGAAGAAAGTGAACAGAGTGATGAGGAACAGGAGGAGGGTGCTCAGGAGGAGCG

GGAGGACACTGTGTCTGTCAAGTCTGAGCCAGTGTCTGAGATAGAGGAAGTTGCCTCAGAGG

AAGAGGAGGATGGTGCTGAGGAACCCACCGCCTCTGGAGGCAAGAGCACCCACCCTATGGTG

ACTAGAAGCAAGGCTGACCAGGATTACAAGGACGATGACGATAAGTGATAATAGGCTGGAGC

CTCGGTGGCCATGCTTCTTGCCCCTTGGGCCTCCCCCCAGCCCCTCCTCCCCTTCCTGCACC

CGTACCCCCGTGGTCTTTGAATAAAGTCTGAGTGGGCGGC hCMV pp65-IE1, hCMV UL83-UL123 fusion mRNA (SEQ ID NO: 185)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGGAGUCGCGCGGUCGCCGUUGUCCCGAAAU

GAUAUCCGUACUGGGUCCCAUUUCGGGGCACGUGCUGAAAGCCGUGUUUAGUCGCGGCGAUA

CGCCGGUGCUGCCGCACGAGACGCGACUCCUGCAGACGGGUAUCCACGUACGCGUGAGCCAG

CCCUCGCUGAUCCUGGUGUCGCAGUACACGCCCGACUCGACGCCAUGCCACCGCGGCGACAA

UCAGCUGCAGGUGCAGCACACGUACUUUACGGGCAGCGAGGUGGAGAACGUGUCGGUCAACG

UGCACAACCCCACGGGCCGAAGCAUCUGCCCCAGCCAAGAGCCCAUGUCGAUCUAUGUGUAC

GCGCUGCCGCUCAAGAUGCUGAACAUCCCCAGCAUCAACGUGCACCACUACCCGUCGGCGGC

CGAGCGCAAACACCGACACCUGCCCGUAGCCGACGCUGUUAUUCACGCGUCGGGCAAGCAGA

UGUGGCAGGCGCGUCUCACGGUCUCGGGACUGGCCUGGACGCGUCAGCAGAACCAGUGGAAA

GAGCCCGACGUCUACUACACGUCAGCGUUCGUGUUUCCCACCAAGGACGUGGCACUGCGGCA

CGUGGUGUGCGCGCACGAGCUGGUUUGCUCCAUGGAGAACACGCGCGCAACCAAGAUGCAGG

UGAUAGGUGACCAGUACGUCAAGGUGUACCUGGAGUCCUUCUGCGAGGACGUGCCCUCCGGC

AAGCUCUUUAUGCACGUCACGCUGGGCUCUGACGUGGAAGAGGACCUAACGAUGACCCGCAA

CCCGCAACCCUUCAUGCGCCCCCACGAGCGCAACGGCUUUACGGUGUUGUGUCCCAAAAAUA

UGAUAAUCAAACCGGGCAAGAUCUCGCACAUCAUGCUGGAUGUGGCUUUUACCUCACACGAG

-continued

CAUUUUGGGCUGCUGUGUCCCAAGAGCAUCCCGGGCCUGAGCAUCUCAGGUAACCUGUUGAU
GAACGGGCAGCAAAUCUUCCUGGAGGUACAAGCGAUACGCGAGACCGUGGAACUGCGUCAGU
ACGAUCCCGUGGCUGCGCUCUUCUUUUUCGAUAUCGACUUGUUGCUGCAGCGCGGGCCUCAG
UACAGCGAGCACCCCACCUUCACCAGCCAGUAUCGCAUCCAGGGCAAGCUUGAGUACCGACA
CACCUGGGACCGGCACGACGAGGGUGCCGCCCAGGGCGACGACGACGUCUGGACCAGCGGAU
CGGACUCCGACGAAGAACUCGUAACCACCGAGCGUAAGACGCCCCGCGUCACCGGCGGCGGC
GCCAUGGCGAGCGCCUCCACUUCCGCGGGCCGCAAACGCAAAUCAGCAUCCUCGGCGACGGC
GUGCACGGCGGGCGUUAUGACACGCGGCCGCCUUAAGGCCGAGUCCACCGUCGCGCCCGAAG
AGGACACCGACGAGGAUUCCGACAACGAAAUCCACAAUCCGGCCGUGUUCACCUGGCCGCCC
UGGCAGGCCGGCAUCCUGGCCCGCAACCUGGUGCCCAUGGUGGCUACGGUUCAGGGUCAGAA
UCUGAAGUACCAGGAGUUCUUCUGGGACGCCAACGACAUCUACCGCAUCUUCGCCGAAUUGG
AAGGCGUAUGGCAGCCCGCUGCGCAACCCAAACGUCGCCGCCACCGGCAAGACGCCUUGCCC
GGGCCAUGCAUCGCCUCGACGCCCAAAAAGCACCGAGGUGAGUCCUCUGCCAAGAGAAAGAU
GGACCCUGAUAAUCCUGACGAGGGCCCUUCCUCCAAGGUGCCACGGCCCGAGACACCCGUGA
CCAAGGCCACGACGUUCCUGCAGACUAUGUUAAGGAAGGAGGUUAACAGUCAGCUGAGCCUG
GGAGACCCGCUGUUCCCAGAAUUGGCCGAAGAAUCCCUCAAAACCUUUGAACAAGUGACCGA
GGAUUGCAACGAGAACCCCGAAAAAGAUGUCCUGACAGAACUCGUCAAACAGAUUAAGGUUC
GAGUGGACAUGGUGCGGCAUAGAAUCAAGGAGCACAUGCUGAAAAAAUAUACCCAGACGGAA
GAAAAAUUCACUGGCGCCUUUAAUAUGAUGGGAGGAUGUUUGCAGAAUGCCUUAGAUAUCUU
AGAUAAGGUUCAUGAGCCUUUCGAGGACAUGAAGUGUAUUGGGCUAACUAUGCAGAGCAUGU
AUGAGAACUACAUUGUACCUGAGGAUAAGCGGGAGAUGUGGAUGGCUUGUAUUAAGGAGCUG
CAUGAUGUGAGCAAGGGCGCCGCUAACAAGUUGGGGGGUGCACUGCAGGCUAAGGCCCGUGC
UAAAAAGGAUGAACUUAGGAGAAAGAUGAUGUAUAUGUGCUACAGGAAUAUAGAGUUCUUUA
CCAAGAACUCAGCCUUCCCUAAGACCACCAAUGGCUGCAGUCAGGCCAUGGCGGCAUUGCAG
AACUUGCCUCAGUGCUCUCCUGAUGAGAUUAUGUCUUAUGCCCAGAAAAUCUUUAAGAUUUU
GGAUGAGGAGAGAGACAAGGUGCUCACGCACAUUGAUCACAUAUUUAUGGAUAUCCUCACUA
CAUGUGUGGAAACAAUGUGUAAUGAGUACAAGGUCACUAGUGACGCUUGUAUGAUGACCAUG
UACGGGGGCAUCUCUCUCUUAAGUGAGUUCUGUCGGGUGCUGUGCUGCUAUGUCUUAGAGGA
GACUAGUGUGAUGCUGGCCAAGCGGCCUCUGAUAACCAAGCCUGAGGUUAUCAGUGUAAUGA
AGCGCCGCAUUGAGGAGAUCUGCAUGAAGGUCUUUGCCCAGUACAUUCUGGGGGCCGAUCCU
UUGAGAGUCUGCUCUCCUAGUGUGGAUGACCUACGGGCCAUCGCCGAGGAGUCAGAUGAGGA
AGAGGCUAUUGUAGCCUACACUUUGGCCACCGCUGGUGCCAGCUCCUCUGAUUCUCUGGUGU
CACCUCCAGAGUCCCCUGUACCCGCGACUAUCCCUCUGUCCUCAGUAAUUGUGGCUGAGAAC
AGUGAUCAGGAAGAAAGUGAACAGAGUGAUGAGGAACAGGAGGAGGGUGCUCAGGAGGAGCG
GGAGGACACUGUGUCUGUCAAGUCUGAGCCAGUGUCUGAGAUAGAGGAAGUUGCCUCAGAGG
AAGAGGAGGAUGGUGCUGAGGAACCCACCGCCUCUGGAGGCAAGAGCACCCACCCUAUGGUG
ACUAGAAGCAAGGCUGACCAGUGAUAAUAGGCUGGAGCCUCGGUGGCCAUGCUUCUUGCCCC
UUGGGCCUCCCCCCAGCCCCUCCUCCCCUUCCUGCACCCGUACCCCCGUGGUCUUUGAAUAA
AGUCUGAGUGGGCGGC

Example 17: hCMV Vaccine—hCMV Concatameric Sequences

A hCMV vaccine may comprise, for example, at least one RNA polynucleotide encoded by at least one of the following sequences or by at least one fragment or epitope of the following sequences. In some embodiments, a hCMV vaccine may comprise at least one RNA polynucleotide comprising at least one of the mRNA sequences listed below or at least one fragment of the mRNA sequences listed below.

hCMVgH-2A-gL (ORF-gH-*Furin*-*Linker*-P2A-gL)

(SEQ ID NO: 148)

*Furin*: *CCGCGCCAAGAGGAGC*

*Linker*: *GGAAGCGGA*

P2A peptide:

(SEQ ID NO: 149)

GCTACTAACTTCAGCCTGCTGAAGCAGGCTGGAGACGTGGAGGAGAACCCTGGACCT

5'-UTR: bold

3'-UTR: underline hCMVgH-2A-gL (ORF-gH-Furin-*Linker*-P2A-gL)

(SEQ ID NO: 29)

TCAAGCTTTTGGACCCTCGTACAGAAGCTAATACGACTCACTATAGGGAAATAAGAGAGAAA

AGAAGAGTAAGAAGAAATATAAGAGCCACCATGCGGCCAGGCCTCCCCTCCTACCTCATCAT

CCTCGCCGTCTGTCTCTTCAGCCACCTACTTTCGTCACGATATGGCGCAGAAGCCGTATCCG

AACCGCTGGACAAAGCGTTTCACCTACTGCTCAACACCTACGGGAGACCCATCCGCTTCCTG

CGTGAAAATACCACCCAGTGTACCTACAACAGCAGCCTCCGTAACAGCACGGTCGTCAGGGA

AAACGCCATCAGTTTCAACTTTTTCCAAAGCTATAATCAATACTATGTATTCCATATGCCTC

GATGTCTTTTTGCGGGTCCTCTGGCGGAGCAGTTTCTGAACCAGGTAGATCTGACCGAAACC

CTGGAAAGATACCAACAGAGACTTAACACTTACGCGCTGGTATCCAAAGACCTGGCCAGCTA

CCGATCTTTTTCGCAGCAGCTAAAGGCACAAGACAGCCTAGGTGAACAGCCCACCACTGTGC

CACCGCCCATTGACCTGTCAATACCTCACGTTTGGATGCCACCGCAAACCACTCCACACGGC

TGGACAGAATCACATACCACCTCAGGACTACACCGACCACACTTTAACCAGACCTGTATCCT

CTTTGATGGACACGATCTACTATTCAGCACCGTCACACCTTGTTTGCACCAAGGCTTTTACC

TCATCGACGAACTACGTTACGTTAAAATAACACTGACCGAGGACTTCTTCGTAGTTACGGTG

TCCATAGACGACGACACACCCATGCTGCTTATCTTCGGCCATCTTCCACGCGTACTTTTCAA

AGCGCCCTATCAACGCGACAACTTTATACTACGACAAACTGAAAAACACGAGCTCCTGGTGC

TAGTTAAGAAAGATCAACTGAACCGTCACTCTTATCTCAAAGACCCGGACTTTCTTGACGCC

GCACTTGACTTCAACTACCTAGACCTCAGCGCACTACTACGTAACAGCTTTCACCGTTACGC

CGTGGATGTACTCAAGAGCGGTCGATGTCAGATGCTGGACCGCCGCACGGTAGAAATGGCCT

TCGCCTACGCATTAGCACTGTTCGCAGCAGCCCGACAAGAAGAGGCCGGCGCCCAAGTCTCC

GTCCCACGGGCCCTAGACCGCCAGGCCGCACTCTTACAAATACAAGAATTTATGATCACCTG

CCTCTCACAAACACCACCACGCACCACGTTGCTGCTGTATCCCACGGCCGTGGACCTGGCCA

AACGAGCCCTTTGGACACCGAATCAGATCACCGACATCACCAGCCTCGTACGCCTGGTCTAC

ATACTCTCTAAACAGAATCAGCAACATCTCATCCCCCAATGGGCACTACGACAGATCGCCGA

CTTTGCCCTAAAACTACACAAAACGCACCTGGCCTCTTTTCTTTCAGCCTTCGCACGCCAAG

AACTCTACCTCATGGGCAGCCTCGTCCACTCCATGCTGGTACATACGACGGAGAGACGCGAA

ATCTTCATCGTAGAAACGGGCCTCTGTTCATTGGCCGAGCTATCACACTTTACGCAGTTGTT

AGCTCATCCACACCACGAATACCTCAGCGACCTGTACACACCCTGTTCCAGTAGCGGGCGAC

GCGATCACTCGCTCGAACGCCTCACGCGTCTCTTCCCCGATGCCACCGTCCCCGCTACCGTT

CCCGCCGCCCTCTCCATCCTATCTACCATGCAACCAAGCACGCTGGAAACCTTCCCCGACCT

GTTTTGCTTGCCGCTCGGCGAATCCTTCTCCGCGCTGACCGTCTCCGAACACGTCAGTTATA

-continued

TCGTAACAAACCAGTACCTGATCAAAGGTATCTCCTACCCTGTCTCCACCACCGTCGTAGGC

CAGAGCCTCATCATCACCCAGACGGACAGTCAAACTAAATGCGAACTGACGCGCAACATGCA

TACCACACACAGCATCACAGTGGCGCTCAACATTTCGCTAGAAAACTGCGCCTTTTGCCAAA

GCGCCCTGCTAGAATACGACGACACGCAAGGCGTCATCAACATCATGTACATGCACGACTCG

GACGACGTCCTTTTCGCCCTGGATCCCTACAACGAAGTGGTGGTCTCATCTCCGCGAACTCA

CTACCTCATGCTTTTGAAAAACGGTACGGTACTAGAAGTAACTGACGTCGTCGTGGACGCCA

CCGACAGTCGTCTCCTCATGATGTCCGTCTACGCGCTATCGGCCATCATCGGCATCTATCTG

CTCTACCGCATGCTCAAGACATG*CCGCGCCAAGAGGAGCGGAAGCGGA*GCTACTAACTTCAG

CCTGCTGAAGCAGGCTGGAGACGTGGAGGAGAACCCTGGACCTATGTGCCGCCGCCCGGATT

GCGGCTTCTCTTTCTCACCTGGACCGGTGATACTGCTGTGGTGTTGCCTTCTGCTGCCCATT

GTTTCCTCAGCCGCCGTCAGCGTCGCTCCTACCGCCGCCGAGAAAGTCCCCGCGGAGTGCCC

CGAACTAACGCGCCGATGCTTGTTGGGTGAGGTGTTTGAGGGTGACAAGTATGAAAGTTGGC

TGCGCCCGTTGGTGAATGTTACCGGGCGCGATGGCCCGCTATCGCAACTTATCCGTTACCGT

CCCGTTACGCCGGAGGCCGCCAACTCCGTGCTGTTGGACGAGGCTTTCCTGGACACTCTGGC

CCTGCTGTACAACAATCCGGATCAATTGCGGGCCCTGCTGACGCTGTTGAGCTCGGACACAG

CGCCGCGCTGGATGACGGTGATGCGCGGCTACAGCGAGTGCGGCGATGGCTCGCCGGCCGTG

TACACGTGCGTGGACGACCTGTGCCGCGGCTACGACCTCACGCGACTGTCATACGGGCGCAG

CATCTTCACGGAACACGTGTTAGGCTTCGAGCTGGTGCCACCGTCTCTCTTTAACGTGGTGG

TGGCCATACGCAACGAAGCCACGCGTACCAACCGCGCCGTGCGTCTGCCCGTGAGCACCGCT

GCCGCGCCCGAGGGCATCACGCTCTTTTACGGCCTGTACAACGCAGTGAAGGAATTCTGCCT

GCGTCACCAGCTGGACCCGCCGCTGCTACGCCACCTAGATAAATACTACGCCGGACTGCCGC

CCGAGCTGAAGCAGACGCGCGTCAACCTGCCGGCTCACTCGCGCTATGGCCCTCAAGCAGTG

GATGCTCGCTGATAATAGGCTGGAGCCTCGGTGGCCATGCTTCTTGCCCCTTGGGCCTCCCC

CCAGCCCCTCCTCCCCTTCCTGCACCCGTACCCCCGTGGTCTTTGAATAAAGTCTGAGTGGG

CGGC hCMVgH-2A-gL (ORF-gH-Furin-*Linker*-P2A-gL)mRNA (SEQ ID NO: 186)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGCGGCCAGGCCUCCCCUCCUACCUCAUCAU

CCUCGCCGUCUGUCUCUUCAGCCACCUACUUUCGUCACGAUAUGGCGCAGAAGCCGUAUCCG

AACCGCUGGACAAAGCGUUUCACCUACUGCUCAACACCUACGGGAGACCCAUCCGCUUCCUG

CGUGAAAAUACCACCCAGUGUACCUACAACAGCAGCCUCCGUAACAGCACGGUCGUCAGGGA

AAACGCCAUCAGUUUCAACUUUUUCCAAAGCUAUAAUCAAUACUAUGUAUUCCAUAUGCCUC

GAUGUCUUUUUGCGGGUCCUCUGGCGGAGCAGUUUCUGAACCAGGUAGAUCUGACCGAAACC

CUGGAAAGAUACCAACAGAGACUUAACACUUACGCGCUGGUAUCCAAAGACCUGGCCAGCUA

CCGAUCUUUUUCGCAGCAGCUAAAGGCACAAGACAGCCUAGGUGAACAGCCCACCACUGUGC

CACCGCCCAUUGACCUGUCAAUACCUCACGUUUGGAUGCCACCGCAAACCACUCCACACGGC

UGGACAGAAUCACAUACCACCUCAGGACUACACCGACCACACUUUAACCAGACCUGUAUCCU

CUUUGAUGGACACGAUCUACUAUUCAGCACCGUCACACCUUGUUUGCACCAAGGCUUUUACC

UCAUCGACGAACUACGUUACGUUAAAAUAACACUGACCGAGGACUUCUUCGUAGUUACGGUG

UCCAUAGACGACGACACACCCAUGCUGCUUAUCUUCGGCCAUCUUCCACGCGUACUUUUCAA

-continued

AGCGCCCUAUCAACGCGACAACUUUAUACUACGACAAACUGAAAAACACGAGCUCCUGGUGC

UAGUUAAGAAAGAUCAACUGAACCGUCACUCUUAUCUCAAAGACCCGGACUUUCUUGACGCC

GCACUUGACUUCAACUACCUAGACCUCAGCGCACUACUACGUAACAGCUUUCACCGUUACGC

CGUGGAUGUACUCAAGAGCGGUCGAUGUCAGAUGCUGGACCGCCGCACGGUAGAAAUGGCCU

UCGCCUACGCAUUAGCACUGUUCGCAGCAGCCCGACAAGAAGAGGCCGGCGCCCAAGUCUCC

GUCCCACGGGCCCUAGACCGCCAGGCCGCACUCUUACAAAUACAAGAAUUUAUGAUCACCUG

CCUCUCACAAACACCACCACGCACCACGUUGCUGCUGUAUCCCACGGCCGUGGACCUGGCCA

AACGAGCCCUUUGGACACCGAAUCAGAUCACCGACAUCACCAGCCUCGUACGCCUGGUCUAC

AUACUCUCUAAACAGAAUCAGCAACAUCUCAUCCCCCAAUGGGCACUACGACAGAUCGCCGA

CUUUGCCCUAAAACUACACAAAACGCACCUGGCCUCUUUUCUUUCAGCCUUCGCACGCCAAG

AACUCUACCUCAUGGGCAGCCUCGUCCACUCCAUGCUGGUACAUACGACGGAGAGACGCGAA

AUCUUCAUCGUAGAAACGGGCCUCUGUUCAUUGGCCGAGCUAUCACACUUUACGCAGUUGUU

AGCUCAUCCACACCACGAAUACCUCAGCGACCUGUACACACCCUGUUCCAGUAGCGGGCGAC

GCGAUCACUCGCUCGAACGCCUCACGCGUCUCUUCCCCGAUGCCACCGUCCCCGCUACCGUU

CCCGCCGCCCUCUCCAUCCUAUCUACCAUGCAACCAAGCACGCUGGAAACCUUCCCCGACCU

GUUUUGCUUGCCGCUCGGCGAAUCCUUCUCCGCGCUGACCGUCUCCGAACACGUCAGUUAUA

UCGUAACAAACCAGUACCUGAUCAAAGGUAUCUCCUACCCUGUCUCCACCACCGUCGUAGGC

CAGAGCCUCAUCAUCACCCAGACGGACAGUCAAACUAAAUGCGAACUGACGCGCAACAUGCA

UACCACACACAGCAUCACAGUGGCGCUCAACAUUUCGCUAGAAAACUGCGCCUUUUGCCAAA

GCGCCCUGCUAGAAUACGACGACACGCAAGGCGUCAUCAACAUCAUGUACAUGCACGACUCG

GACGACGUCCUUUUCGCCCUGGAUCCCUACAACGAAGUGGUGGUCUCAUCUCCGCGAACUCA

CUACCUCAUGCUUUUGAAAAACGGUACGGUACUAGAAGUAACUGACGUCGUCGUGGACGCCA

CCGACAGUCGUCUCCUCAUGAUGUCCGUCUACGCGCUAUCGGCCAUCAUCGGCAUCUAUCUG

CUCUACCGCAUGCUCAAGACAUG*CCGCGCCAAGAGGAGCGGAAGCGGA*GCUACUAACUUCAG

CCUGCUGAAGCAGGCUGGAGACGUGGAGGAGAACCCUGGACCUAUGUGCCGCCGCCCGGAUU

GCGGCUUCUCUUUCUCACCUGGACCGGUGAUACUGCUGUGGUGUUGCCUUCUGCUGCCCAUU

GUUUCCUCAGCCGCCGUCAGCGUCGCUCCUACCGCCGCCGAGAAAGUCCCCGCGGAGUGCCC

CGAACUAACGCGCCGAUGCUUGUUGGGUGAGGUGUUUGAGGGUGACAAGUAUGAAAGUUGGC

UGCGCCCGUUGGUGAAUGUUACCGGGCGCGAUGGCCCGCUAUCGCAACUUAUCCGUUACCGU

CCCGUUACGCCGGAGGCCGCCAACUCCGUGCUGUUGGACGAGGCUUUCCUGGACACUCUGGC

CCUGCUGUACAACAAUCCGGAUCAAUUGCGGGCCCUGCUGACGCUGUUGAGCUCGGACACAG

CGCCGCGCUGGAUGACGGUGAUGCGCGGCUACAGCGAGUGCGGCGAUGGCUCGCCGGCCGUG

UACACGUGCGUGGACGACCUGUGCCGCGGCUACGACCUCACGCGACUGUCAUACGGGCGCAG

CAUCUUCACGGAACACGUGUUAGGCUUCGAGCUGGUGCCACCGUCUCUCUUUAACGUGGUGG

UGGCCAUACGCAACGAAGCCACGCGUACCAACCGCGCCGUGCGUCUGCCCGUGAGCACCGCU

GCCGCGCCCGAGGGCAUCACGCUCUUUUACGGCCUGUACAACGCAGUGAAGGAAUUCUGCCU

GCGUCACCAGCUGGACCCGCCGCUGCUACGCCACCUAGAUAAAUACUACGCCGGACUGCCGC

CCGAGCUGAAGCAGACGCGCGUCAACCUGCCGGCUCACUCGCGCUAUGGCCCUCAAGCAGUG

GAUGCUCGCUGAUAAUAGGCUGGAGCCUCGGUGGCCAUGCUUCUUGCCCCUUGGGCCUCCCC

CCAGCCCCUCCUCCCCUUCCUGCACCCGUACCCCCGUGGUCUUUGAAUAAAGUCUGAGUGGG

CGGC

-continued

<u>hCMVUL128-2A-UL131</u> (ORF- UL128- *Furin*-*<u>Linker</u>*-<u>P2A</u>-UL130 *Furin*-*<u>Linker</u>*-*F2A*-UL131A)

(SEQ ID NO: 148)

*Furin*: *CCGCGCCAAGAGGAGC*

<u>Linker</u>: <u>GGAAGCGGA</u>

<u>P2A peptide</u>:

(SEQ ID NO: 149)

<u>GCTACTAACTTCAGCCTGCTGAAGCAGGCTGGAGACGTGGAGGAGAACCCTGGACCT</u>

*F2A peptide*:

(SEQ ID NO: 150)

*GTGAAACAGACTTTGAATTTTGACCTTCTCAAGTTGGCGGGAGACGTGGAGTCCAACCCTGGACCT*

5′-UTR: bold
<u>3′-UTR</u>: <u>underline</u>

<u>hCMVUL128-2A-UL131</u> (ORF- UL128- *Furin*-*<u>Linker</u>*-<u>P2A</u>-UL130 *Furin*-*<u>Linker</u>*-*F2A*-UL131A)

(SEQ ID NO: 30)

TCAAGCTTTTGGACCCTCGTACAGAAGCTAATACGACTCACTATAGGGAAATAAGAGAGAAA

AGAAGAGTAAGAAGAAATATAAGAGCCACCATGAGTCCCAAAGATCTGACGCCGTTCTTGAC

GGCGTTGTGGCTGCTATTGGGTCACAGCCGCGTGCCGCGGGTGCGCGCAGAAGAATGTTGCG

AATTCATAAACGTCAACCACCCGCCGGAACGCTGTTACGATTTCAAAATGTGCAATCGCTTC

ACCGTCGCGCTGCGGTGTCCGGACGGCGAAGTCTGCTACAGTCCCGAGAAAACGGCTGAGAT

TCGCGGGATCGTCACCACCATGACCCATTCATTGACACGCCAGGTCGTACACAACAAACTGA

CGAGCTGCAACTACAATCCGTTATACCTCGAAGCTGACGGGCGAATACGCTGCGGCAAAGTA

AACGACAAGGCGCAGTACCTGCTGGGCGCCGCTGGCAGCGTTCCCTATCGATGGATCAATCT

GGAATACGACAAGATAACCCGGATCGTGGGCCTGGATCAGTACCTGGAGAGCGTTAAGAAAC

ACAAACGGCTGGATGTGTGCCGCGCTAAAATGGGCTATATGCTGCAG*CGCGCCAAGAGGAGC*

*<u>GGAAGCGG</u>*<u>AGCTACTAACTTCAGCCTGCTGAAGCAGGCTGGAGACGTGGAGGAGAACCCTGG</u>

<u>ACCT</u>ATGCTGCGGCTTCTGCTTCGTCACCACTTTCACTGCCTGCTTCTGTGCGCGGTTTGGG

CAACGCCCTGTCTGGCGTCTCCGTGGTCGACGCTAACAGCAAACCAGAATCCGTCCCCGCCA

TGGTCTAAACTGACGTATTCCAAACCGCATGACGCGGCGACGTTTTACTGTCCTTTTCTCTA

TCCCTCGCCCCCACGATCCCCCTTGCAATTCTCGGGGTTCCAGCGGGTATCAACGGGTCCCG

AGTGTCGCAACGAGACCCTGTATCTGCTGTACAACCGGGAAGGCCAGACCTTGGTGGAGAGA

AGCTCCACCTGGGTGAAAAAGGTGATCTGGTACCTGAGCGGTCGGAACCAAACCATCCTCCA

ACGGATGCCCCGAACGGCTTCGAAACCGAGCGACGGAAACGTGCAGATCAGCGTGGAAGACG

CCAAGATTTTTGGAGCGCACATGGTGCCCAAGCAGACCAAGCTGCTACGCTTCGTCGTCAAC

GATGGCACACGTTATCAGATGTGTGTGATGAAGCTGGAGAGCTGGGCTCACGTCTTCCGGGA

CTACAGCGTGTCTTTTCAGGTGCGATTGACGTTCACCGAGGCCAATAACCAGACTTACACCT

TCTGCACCCATCCCAATCTCATCGTTCGCGCCAA*GAGGAGC<u>GGAAGCGGA</u>**GTGAAACAGACT*

*TTGAATTTTGACCTTCTCAAGTTGGCGGGAGACGTGGAGTCCAACCCTGGACCT*ATGCGGCT

GTGTCGGGTGTGGCTGTCTGTTTGTCTGTGCGCCGTGGTGCTGGGTCAGTGCCAGCGGGAAA

CCGCGGAAAAAAACGATTATTACCGAGTACCGCATTACTGGGACGCGTGCTCTCGCGCGCTG

CCCGACCAAACCCGTTACAAGTATGTGGAACAGCTCGTGGACCTCACGTTGAACTACCACTA

CGATGCGAGCCACGGCTTGGACAACTTTGACGTGCTCAAGAGAATCAACGTGACCGAGGTGT

CGTTGCTCATCAGCGACTTTAGACGTCAGAACCGTCGCGGCGGCACCAACAAAAGGACCACG

TTCAACGCCGCCGGTTCGCTGGCGCCACACGCCCGGAGCCTCGAGTTCAGCGTGCGGCTCTT

TGCCAAC<u>TGATAATAGGCTGGAGCCTCGGTGGCCATGCTTCTTGCCCCTTGGGCCTCCCCCC</u>

-continued

AGCCCCTCCTCCCCTTCCTGCACCCGTACCCCCGTGGTCTTTGAATAAAGTCTGAGTGGGCG

GC hCMVUL128-2A-UL131 (ORF- UL128- *Furin-Linker*-P2A-UL130 *Furin-Linker*-*F2A*-UL131A)mRNA (SEQ ID NO: 187)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGAGUCCCAAAGAUCUGACGCCGUUCUUGAC

GGCGUUGUGGCUGCUAUUGGGUCACAGCCGCGUGCCGCGGGUGCGCGCAGAAGAAUGUUGCG

AAUUCAUAAACGUCAACCACCCGCCGGAACGCUGUUACGAUUUCAAAAUGUGCAAUCGCUUC

ACCGUCGCGCUGCGGUGUCCGGACGGCGAAGUCUGCUACAGUCCCGAGAAAACGGCUGAGAU

UCGCGGGAUCGUCACCACCAUGACCCAUUCAUUGACACGCCAGGUCGUACACAACAAACUGA

CGAGCUGCAACUACAAUCCGUUAUACCUCGAAGCUGACGGGCGAAUACGCUGCGGCAAAGUA

AACGACAAGGCGCAGUACCUGCUGGGCGCCGCUGGCAGCGUUCCCUAUCGAUGGAUCAAUCU

GGAAUACGACAAGAUAACCCGGAUCGUGGGCCUGGAUCAGUACCUGGAGAGCGUUAAGAAAC

ACAAACGGCUGGAUGUGUGCCGCGCUAAAAUGGGCUAUAUGCUGCAG*CGCGCCAAGAGGAGC*

*GGAAGCGG*AGCUACUAACUUCAGCCUGCUGAAGCAGGCUGGAGACGUGGAGGAGAACCCUGG

ACCUAUGCUGCGGCUUCUGCUUCGUCACCACUUUCACUGCCUGCUUCUGUGCGCGGUUUGGG

CAACGCCCUGUCUGGCGUCUCCGUGGUCGACGCUAACAGCAAACCAGAAUCCGUCCCCGCCA

UGGUCUAAACUGACGUAUUCCAAACCGCAUGACGCGGCGACGUUUUACUGUCCUUUUCUCUA

UCCCUCGCCCCCACGAUCCCCCUUGCAAUUCUCGGGGUUCCAGCGGGUAUCAACGGGUCCCG

AGUGUCGCAACGAGACCCUGUAUCUGCUGUACAACCGGGAAGGCCAGACCUUGGUGGAGAGA

AGCUCCACCUGGGUGAAAAAGGUGAUCUGGUACCUGAGCGGUCGGAACCAAACCAUCCUCCA

ACGGAUGCCCCGAACGGCUUCGAAACCGAGCGACGGAAACGUGCAGAUCAGCGUGGAAGACG

CCAAGAUUUUUGGAGCGCACAUGGUGCCCAAGCAGACCAAGCUGCUACGCUUCGUCGUCAAC

GAUGGCACACGUUAUCAGAUGUGUGUGAUGAAGCUGGAGAGCUGGGCUCACGUCUUCCGGGA

CUACAGCGUGUCUUUUCAGGUGCGAUUGACGUUCACCGAGGCCAAUAACCAGACUUACACCU

UCUGCACCCAUCCCAAUCUCAUCGUU*CGCGCCAAGAGGAGCGGAAGCGGA**GUGAAACAGACU*

*UUGAAUUUUGACCUUCUCAAGUUGGCGGGAGACGUGGAGUCCAACCCUGGACCU*AUGCGGCU

GUGUCGGGUGUGGCUGUCUGUUUGUCUGUGCGCCGUGGUGCUGGGUCAGUGCCAGCGGGAAA

CCGCGGAAAAAAACGAUUAUUACCGAGUACCGCAUUACUGGGACGCGUGCUCUCGCGCGCUG

CCCGACCAAACCCGUUACAAGUAUGUGGAACAGCUCGUGGACCUCACGUUGAACUACCACUA

CGAUGCGAGCCACGGCUUGGACAACUUUGACGUGCUCAAGAGAAUCAACGUGACCGAGGUGU

CGUUGCUCAUCAGCGACUUUAGACGUCAGAACCGUCGCGGCGGCACCAACAAAAGGACCACG

UUCAACGCCGCCGGUUCGCUGGCGCCACACGCCCGGAGCCUCGAGUUCAGCGUGCGGCUCUU

UGCCAACUGAUAAUAGGCUGGAGCCUCGGUGGCCAUGCUUCUUGCCCCUUGGGCCUCCCCCC

AGCCCCUCCUCCCCUUCCUGCACCCGUACCCCCGUGGUCUUUGAAUAAAGUCUGAGUGGGCG

GC

-continued hCMVgH-gL-UL128-UL130-UL131A 2a (SEQ ID NO: 148)

*Furin-CCGCGCCAAGAGGAGC*

*Linker-GGAAGCGGA*

P2A peptide-

(SEQ ID NO: 149)

GCTACTAACTTCAGCCTGCTGAAGCAGGCTGGAGACGTGGAGGAGAACCCTGGACCT

*F2A peptide-*

(SEQ ID NO: 150)

*GTCAAACAGACTTTGAATTTTGACCTTCTCAAGTTGGCGGGAGACGTGGAGTCCAACCCTGGACCT* e2a peptide-

(SEQ ID NO: 151)

cagtgtactaattatgctctcttgaaattggctggagatgttgagagcaaccctggacct t2a-

(SEQ ID NO: 152)

gagggcagaggaagtctgctaacatgcggtgacgtcgaggagaatcctggacct

ORF- gH- *Furin-Linker*-P2A-gL *Furin-Linker*-*F2A*-UL128- *Furin-Linker*-e2a-UL130-*Furin-Linker*-t2a-UL131A (SEQ ID NO: 31)

TCAAGCTTTTGGACCCTCGTACAGAAGCTAATACGACTCACTATAGGGAAATAAGAGAGAAA

AGAAGAGTAAGAAGAAATATAAGAGCCACCATGCGGCCAGGCCTCCCCTCCTACCTCATCAT

CCTCGCCGTCTGTCTCTTCAGCCACCTACTTTCGTCACGATATGGCGCAGAAGCCGTATCCG

AACCGCTGGACAAAGCGTTTCACCTACTGCTCAACACCTACGGGAGACCCATCCGCTTCCTG

CGTGAAAATACCACCCAGTGTACCTACAACAGCAGCCTCCGTAACAGCACGGTCGTCAGGGA

AAACGCCATCAGTTTCAACTTTTTCCAAAGCTATAATCAATACTATGTATTCCATATGCCTC

GATGTCTTTTTGCGGGTCCTCTGGCGGAGCAGTTTCTGAACCAGGTAGATCTGACCGAAACC

CTGGAAAGATACCAACAGAGACTTAACACTTACGCGCTGGTATCCAAAGACCTGGCCAGCTA

CCGATCTTTTTCGCAGCAGCTAAAGGCACAAGACAGCCTAGGTGAACAGCCCACCACTGTGC

CACCGCCCATTGACCTGTCAATACCTCACGTTTGGATGCCACCGCAAACCACTCCACACGGC

TGGACAGAATCACATACCACCTCAGGACTACACCGACCACACTTTAACCAGACCTGTATCCT

CTTTGATGGACACGATCTACTATTCAGCACCGTCACACCTTGTTTGCACCAAGGCTTTTACC

TCATCGACGAACTACGTTACGTTAAAATAACACTGACCGAGGACTTCTTCGTAGTTACGGTG

TCCATAGACGACGACACACCCATGCTGCTTATCTTCGGCCATCTTCCACGCGTACTTTTCAA

AGCGCCCTATCAACGCGACAACTTTATACTACGACAAACTGAAAAACACGAGCTCCTGGTGC

TAGTTAAGAAAGATCAACTGAACCGTCACTCTTATCTCAAAGACCCGGACTTTCTTGACGCC

GCACTTGACTTCAACTACCTAGACCTCAGCGCACTACTACGTAACAGCTTTCACCGTTACGC

CGTGGATGTACTCAAGAGCGGTCGATGTCAGATGCTGGACCGCCGCACGGTAGAAATGGCCT

TCGCCTACGCATTAGCACTGTTCGCAGCAGCCCGACAAGAAGAGGCCGGCGCCCAAGTCTCC

GTCCCACGGGCCCTAGACCGCCAGGCCGCACTCTTACAAATACAAGAATTTATGATCACCTG

CCTCTCACAAACACCACCACGCACCACGTTGCTGCTGTATCCCACGGCCGTGGACCTGGCCA

AACGAGCCCTTTGGACACCGAATCAGATCACCGACATCACCAGCCTCGTACGCCTGGTCTAC

ATACTCTCTAAACAGAATCAGCAACATCTCATCCCCCAATGGGCACTACGACAGATCGCCGA

CTTTGCCCTAAAACTACACAAAACGCACCTGGCCTCTTTTCTTTCAGCCTTCGCACGCCAAG

AACTCTACCTCATGGGCAGCCTCGTCCACTCCATGCTGGTACATACGACGGAGAGACGCGAA

ATCTTCATCGTAGAAACGGGCCTCTGTTCATTGGCCGAGCTATCACACTTTACGCAGTTGTT

AGCTCATCCACACCACGAATACCTCAGCGACCTGTACACACCCTGTTCCAGTAGCGGGCGAC

-continued

GCGATCACTCGCTCGAACGCCTCACGCGTCTCTTCCCCGATGCCACCGTCCCCGCTACCGTT

CCCGCCGCCCTCTCCATCCTATCTACCATGCAACCAAGCACGCTGGAAACCTTCCCCGACCT

GTTTTGCTTGCCGCTCGGCGAATCCTTCTCCGCGCTGACCGTCTCCGAACACGTCAGTTATA

TCGTAACAAACCAGTACCTGATCAAAGGTATCTCCTACCCTGTCTCCACCACCGTCGTAGGC

CAGAGCCTCATCATCACCCAGACGGACAGTCAAACTAAATGCGAACTGACGCGCAACATGCA

TACCACACACAGCATCACAGTGGCGCTCAACATTTCGCTAGAAAACTGCGCCTTTTGCCAAA

GCGCCCTGCTAGAATACGACGACACGCAAGGCGTCATCAACATCATGTACATGCACGACTCG

GACGACGTCCTTTTCGCCCTGGATCCCTACAACGAAGTGGTGGTCTCATCTCCGCGAACTCA

CTACCTCATGCTTTTGAAAAACGGTACGGTACTAGAAGTAACTGACGTCGTCGTGGACGCCA

CCGACAGTCGTCTCCTCATGATGTCCGTCTACGCGCTATCGGCCATCATCGGCATCTATCTG

CTCTACCGCATGCTCAAGACATGC*CGCGCCAAGAGGAGCGGAAGCGGA*GCTACTAACTTCAG

CCTGCTGAAGCAGGCTGGAGACGTGGAGGAGAACCCTGGACCTATGTGCCGCCGCCCGGATT

GCGGCTTCTCTTTCTCACCTGGACCGGTGATACTGCTGTGGTGTTGCCTTCTGCTGCCCATT

GTTTCCTCAGCCGCCGTCAGCGTCGCTCCTACCGCCGCCGAGAAAGTCCCCGCGGAGTGCCC

CGAACTAACGCGCCGATGCTTGTTGGGTGAGGTGTTTGAGGGTGACAAGTATGAAAGTTGGC

TGCGCCCGTTGGTGAATGTTACCGGGCGCGATGGCCCGCTATCGCAACTTATCCGTTACCGT

CCCGTTACGCCGGAGGCCGCCAACTCCGTGCTGTTGGACGAGGCTTTCCTGGACACTCTGGC

CCTGCTGTACAACAATCCGGATCAATTGCGGGCCCTGCTGACGCTGTTGAGCTCGGACACAG

CGCCGCGCTGGATGACGGTGATGCGCGGCTACAGCGAGTGCGGCGATGGCTCGCCGGCCGTG

TACACGTGCGTGGACGACCTGTGCCGCGGCTACGACCTCACGCGACTGTCATACGGGCGCAG

CATCTTCACGGAACACGTGTTAGGCTTCGAGCTGGTGCCACCGTCTCTCTTTAACGTGGTGG

TGGCCATACGCAACGAAGCCACGCGTACCAACCGCGCCGTGCGTCTGCCCGTGAGCACCGCT

GCCGCGCCCGAGGGCATCACGCTCTTTTACGGCCTGTACAACGCAGTGAAGGAATTCTGCCT

GCGTCACCAGCTGGACCCGCCGCTGCTACGCCACCTAGATAAATACTACGCCGGACTGCCGC

CCGAGCTGAAGCAGACGCGCGTCAACCTGCCGGCTCACTCGCGCTATGGCCCTCAAGCAGTG

GATGCTCGC*CGCGCCAAGAGGAGCGGAAGCGGA**GTGAAACAGACTTTGAATTTTGACCTTCT*

*CAAGTTGGCGGGAGACGTGGAGTCCAACCCTGGACCT*ATGAGTCCCAAAGATCTGACGCCGT

TCTTGACGGCGTTGTGGCTGCTATTGGGTCACAGCCGCGTGCCGCGGGTGCGCGCAGAAGAA

TGTTGCGAATTCATAAACGTCAACCACCCGCCGGAACGCTGTTACGATTTCAAAATGTGCAA

TCGCTTCACCGTCGCGCTGCGGTGTCCGGACGGCGAAGTCTGCTACAGTCCCGAGAAAACGG

CTGAGATTCGCGGGATCGTCACCACCATGACCCATTCATTGACACGCCAGGTCGTACACAAC

AAACTGACGAGCTGCAACTACAATCCGTTATACCTCGAAGCTGACGGGCGAATACGCTGCGG

CAAAGTAAACGACAAGGCGCAGTACCTGCTGGGCGCCGCTGGCAGCGTTCCCTATCGATGGA

TCAATCTGGAATACGACAAGATAACCCGGATCGTGGGCCTGGATCAGTACCTGGAGAGCGTT

AAGAAACACAAACGGCTGGATGTGTGCCGCGCTAAAATGGGCTATATGCTGCAG*CGCGCCAA*

*GAGGAGCGGAAGCGGA*cagtgtactaattatgctctcttgaaattggctggagatgttgaga gcaaccctggacctATGCTGCGGCTTCTGCTTCGTCACCACTTTCACTGCCTGCTTCTGTGC

GCGGTTTGGGCAACGCCCTGTCTGGCGTCTCCGTGGTCGACGCTAACAGCAAACCAGAATCC

GTCCCCGCCATGGTCTAAACTGACGTATTCCAAACCGCATGACGCGGCGACGTTTTACTGTC

CTTTTCTCTATCCCTCGCCCCCACGATCCCCCTTGCAATTCTCGGGGTTCCAGCGGGTATCA

ACGGGTCCCGAGTGTCGCAACGAGACCCTGTATCTGCTGTACAACCGGGAAGGCCAGACCTT

-continued

GGTGGAGAGAAGCTCCACCTGGGTGAAAAAGGTGATCTGGTACCTGAGCGGTCGGAACCAAA

CCATCCTCCAACGGATGCCCCGAACGGCTTCGAAACCGAGCGACGGAAACGTGCAGATCAGC

GTGGAAGACGCCAAGATTTTTGGAGCGCACATGGTGCCCAAGCAGACCAAGCTGCTACGCTT

CGTCGTCAACGATGGCACACGTTATCAGATGTGTGTGATGAAGCTGGAGAGCTGGGCTCACG

TCTICCGGGACTACAGCGTGTCTTTICAGGTGCGATTGACGTTCACCGAGGCCAATAACCAG

ACTTACACCTTCTGCACCCATCCCAATCTCATCGTT*CGCGCCAAGAGGAGCGGAAGCGGA*ga gggcagaggaagtctgctaacatgcggtgacgtcgaggagaatcctggacctATGCGGCTGT

GTCGGGTGTGGCTGTCTGTTTGTCTGTGCGCCGTGGTGCTGGGTCAGTGCCAGCGGGAAACC

GCGGAAAAAAACGATTATTACCGAGTACCGCATTACTGGGACGCGTGCTCTCGCGCGCTGCC

CGACCAAACCCGTTACAAGTATGTGGAACAGCTCGTGGACCTCACGTTGAACTACCACTACG

ATGCGAGCCACGGCTTGGACAACTTTGACGTGCTCAAGAGAATCAACGTGACCGAGGTGTCG

TTGCTCATCAGCGACTTTAGACGTCAGAACCGTCGCGGCGGCACCAACAAAAGGACCACGTT

CAACGCCGCCGGTTCGCTGGCGCCACACGCCCGGAGCCTCGAGTTCAGCGTGCGGCTCTTTG

CCAACTGATAATAGGCTGGAGCCTCGGTGGCCATGCTTCTTGCCCCTTGGGCCTCCCCCCAG

CCCCTCCTCCCCTTCCTGCACCCGTACCCCCGTGGTCTTTGAATAAAGTCTGAGTGGGCGGC

ORF- gH- *Furin*-*Linker*-P2A-gL *Furin*-*Linker*-*F2A*-UL128- *Furin*-*Linker*-e2a-UL130-*Furin*-*Linker*-t2a-UL131A mRNA (SEQ ID NO: 188)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGCGGCCAGGCCUCCCCUCCUACCUCAUCAU

CCUCGCCGUCUGUCUCUUCAGCCACCUACUUUCGUCACGAUAUGGCGCAGAAGCCGUAUCCG

AACCGCUGGACAAAGCGUUUCACCUACUGCUCAACACCUACGGGAGACCCAUCCGCUUCCUG

CGUGAAAAUACCACCCAGUGUACCUACAACAGCAGCCUCCGUAACAGCACGGUCGUCAGGGA

AAACGCCAUCAGUUUCAACUUUUUCCAAAGCUAUAAUCAAUACUAUGUAUUCCAUAUGCCUC

GAUGUCUUUUUGCGGGUCCUCUGGCGGAGCAGUUUCUGAACCAGGUAGAUCUGACCGAAACC

CUGGAAAGAUACCAACAGAGACUUAACACUUACGCGCUGGUAUCCAAAGACCUGGCCAGCUA

CCGAUCUUUUUCGCAGCAGCUAAAGGCACAAGACAGCCUAGGUGAACAGCCCACCACUGUGC

CACCGCCCAUUGACCUGUCAAUACCUCACGUUUGGAUGCCACCGCAAACCACUCCACACGGC

UGGACAGAAUCACAUACCACCUCAGGACUACACCGACCACACUUUAACCAGACCUGUAUCCU

CUUUGAUGGACACGAUCUACUAUUCAGCACCGUCACACCUUGUUUGCACCAAGGCUUUUACC

UCAUCGACGAACUACGUUACGUUAAAAUAACACUGACCGAGGACUUCUUCGUAGUUACGGUG

UCCAUAGACGACGACACACCCAUGCUGCUUAUCUUCGGCCAUCUUCCACGCGUACUUUUCAA

AGCGCCCUAUCAACGCGACAACUUUAUACUACGACAAACUGAAAAACACGAGCUCCUGGUGC

UAGUUAAGAAAGAUCAACUGAACCGUCACUCUUAUCUCAAAGACCCGGACUUUCUUGACGCC

GCACUUGACUUCAACUACCUAGACCUCAGCGCACUACUACGUAACAGCUUUCACCGUUACGC

CGUGGAUGUACUCAAGAGCGGUCGAUGUCAGAUGCUGGACCGCCGCACGGUAGAAAUGGCCU

UCGCCUACGCAUUAGCACUGUUCGCAGCAGCCCGACAAGAAGAGGCCGGCGCCCAAGUCUCC

GUCCCACGGGCCCUAGACCGCCAGGCCGCACUCUUACAAAUACAAGAAUUUAUGAUCACCUG

CCUCUCACAAACACCACCACGCACCACGUUGCUGCUGUAUCCCACGGCCGUGGACCUGGCCA

AACGAGCCCUUUGGACACCGAAUCAGAUCACCGACAUCACCAGCCUCGUACGCCUGGUCUAC

AUACUCUCUAAACAGAAUCAGCAACAUCUCAUCCCCCAAUGGGCACUACGACAGAUCGCCGA

CUUUGCCCUAAAACUACACAAAACGCACCUGGCCUCUUUUCUUUCAGCCUUCGCACGCCAAG

-continued

AACUCUACCUCAUGGGCAGCCUCGUCCACUCCAUGCUGGUACAUACGACGGAGAGACGCGAA
AUCUUCAUCGUAGAAACGGGCCUCUGUUCAUUGGCCGAGCUAUCACACUUUACGCAGUUGUU
AGCUCAUCCACACCACGAAUACCUCAGCGACCUGUACACACCCUGUUCCAGUAGCGGGCGAC
GCGAUCACUCGCUCGAACGCCUCACGCGUCUCUUCCCCGAUGCCACCGUCCCCGCUACCGUU
CCCGCCGCCCUCUCCAUCCUAUCUACCAUGCAACCAAGCACGCUGGAAACCUUCCCCGACCU
GUUUUGCUUGCCGCUCGGCGAAUCCUUCUCCGCGCUGACCGUCUCCGAACACGUCAGUUAUA
UCGUAACAAACCAGUACCUGAUCAAAGGUAUCUCCUACCCUGUCUCCACCACCGUCGUAGGC
CAGAGCCUCAUCAUCACCCAGACGGACAGUCAAACUAAAUGCGAACUGACGCGCAACAUGCA
UACCACACACAGCAUCACAGUGGCGCUCAACAUUUCGCUAGAAAACUGCGCCUUUUGCCAAA
GCGCCCUGCUAGAAUACGACGACACGCAAGGCGUCAUCAACAUCAUGUACAUGCACGACUCG
GACGACGUCCUUUUCGCCCUGGAUCCCUACAACGAAGUGGUGGUCUCAUCUCCGCGAACUCA
CUACCUCAUGCUUUUGAAAAACGGUACGGUACUAGAAGUAACUGACGUCGUCGUGGACGCCA
CCGACAGUCGUCUCCUCAUGAUGUCCGUCUACGCGCUAUCGGCCAUCAUCGGCAUCUAUCUG
CUCUACCGCAUGCUCAAGACAUGC*CGCGCCAAGAGGAGC<u>GGAAGCGGA</u>*<u>GCUACUAACUUCAG</u>
<u>CCUGCUGAAGCAGGCUGGAGACGUGGAGGAGAACCCUGGACCU</u>AUGUGCCGCCGCCCGGAUU
GCGGCUUCUCUUUCUCACCUGGACCGGUGAUACUGCUGUGGUGUUGCCUUCUGCUGCCCAUU
GUUUCCUCAGCCGCCGUCAGCGUCGCUCCUACCGCCGCCGAGAAAGUCCCCGCGGAGUGCCC
CGAACUAACGCGCCGAUGCUUGUUGGGUGAGGUGUUUGAGGGUGACAAGUAUGAAAGUUGGC
UGCGCCCGUUGGUGAAUGUUACCGGGCGCGAUGGCCCGCUAUCGCAACUUAUCCGUUACCGU
CCCGUUACGCCGGAGGCCGCCAACUCCGUGCUGUUGGACGAGGCUUUCCUGGACACUCUGGC
CCUGCUGUACAACAAUCCGGAUCAAUUGCGGGCCCUGCUGACGCUGUUGAGCUCGGACACAG
CGCCGCGCUGGAUGACGGUGAUGCGCGGCUACAGCGAGUGCGGCGAUGGCUCGCCGGCCGUG
UACACGUGCGUGGACGACCUGUGCCGCGGCUACGACCUCACGCGACUGUCAUACGGGCGCAG
CAUCUUCACGGAACACGUGUUAGGCUUCGAGCUGGUGCCACCGUCUCUCUUUAACGUGGUGG
UGGCCAUACGCAACGAAGCCACGCGUACCAACCGCGCCGUGCGUCUGCCCGUGAGCACCGCU
GCCGCGCCCGAGGGCAUCACGCUCUUUUACGGCCUGUACAACGCAGUGAAGGAAUUCUGCCU
GCGUCACCAGCUGGACCCGCCGCUGCUACGCCACCUAGAUAAAUACUACGCCGGACUGCCGC
CCGAGCUGAAGCAGACGCGCGUCAACCUGCCGGCUCACUCGCGCUAUGGCCCUCAAGCAGUG
GAUGCUCGC*CGCGCCAAGAGGAGC<u>GGAAGCGGA</u>**GUGAAACAGACUUUGAAUUUUGACCUUCU*
*CAAGUUGGCGGGAGACGUGGAGUCCAACCCUGGACCU*AUGAGUCCCAAAGAUCUGACGCCGU
UCUUGACGGCGUUGUGGCUGCUAUUGGGUCACAGCCGCGUGCCGCGGGUGCGCGCAGAAGAA
UGUUGCGAAUUCAUAAACGUCAACCACCCGCCGGAACGCUGUUACGAUUUCAAAAUGUGCAA
UCGCUUCACCGUCGCGCUGCGGUGUCCGGACGGCGAAGUCUGCUACAGUCCCGAGAAAACGG
CUGAGAUUCGCGGGAUCGUCACCACCAUGACCCAUUCAUUGACACGCCAGGUCGUACACAAC
AAACUGACGAGCUGCAACUACAAUCCGUUAUACCUCGAAGCUGACGGGCGAAUACGCUGCGG
CAAAGUAAACGACAAGGCGCAGUACCUGCUGGGCGCCGCUGGCAGCGUUCCCCUAUCGAUGGA
UCAAUCUGGAAUACGACAAGAUAACCCGGAUCGUGGGCCUGGAUCAGUACCUGGAGAGCGUU
AAGAAACACAAACGGCUGGAUGUGUGCCGCGCUAAAAUGGGCUAUAUGCUGCAG*CGCGCCAA*
*GAGGAGC<u>GGAAGCGGA</u>*caguguacuaauuaugcucucuugaaauuggcuggagauguugaga
gcaacccuggaccuAUGCUGCGGCUUCUGCUUCGUCACCACUUUCACUGCCUGCUUCUGUGC -continued

GCGGUUUGGGCAACGCCCUGUCUGGCGUCUCCGUGGUCGACGCUAACAGCAAACCAGAAUCC

GUCCCCGCCAUGGUCUAAACUGACGUAUUCCAAACCGCAUGACGCGGCGACGUUUUACUGUC

CUUUUCUCUAUCCCUCGCCCCCACGAUCCCCCUUGCAAUUCUCGGGGUUCCAGCGGGUAUCA

ACGGGUCCCGAGUGUCGCAACGAGACCCUGUAUCUGCUGUACAACCGGGAAGGCCAGACCUU

GGUGGAGAGAAGCUCCACCUGGGUGAAAAAGGUGAUCUGGUACCUGAGCGGUCGGAACCAAA

CCAUCCUCCAACGGAUGCCCCGAACGGCUUCGAAACCGAGCGACGGAAACGUGCAGAUCAGC

GUGGAAGACGCCAAGAUUUUGGAGCGCACAUGGUGCCCAAGCAGACCAAGCUGCUACGCUU

CGUCGUCAACGAUGGCACACGUUAUCAGAUGUGUGUGAUGAAGCUGGAGAGCUGGGCUCACG

UCUUCCGGGACUACAGCGUGUCUUUUCAGGUGCGAUUGACGUUCACCGAGGCCAAUAACCAG

ACUUACACCUUCUGCACCCAUCCCAAUCUCAUCGUU*CGCGCCAAGAGGAGCGGAAGCGGA*ga gggcagaggaagucugcuaacaugcggugacgucgaggagaauccuggaccuAUGCGGCUGU

GUCGGGUGUGGCUGUCUGUUUGUCUGUGCGCCGUGGUGCUGGGUCAGUGCCAGCGGGAAACC

GCGGAAAAAAACGAUUAUUACCGAGUACCGCAUUACUGGGACGCGUGCUCUCGCGCGCUGCC

CGACCAAACCCGUUACAAGUAUGUGGAACAGCUCGUGGACCUCACGUUGAACUACCACUACG

AUGCGAGCCACGGCUUGGACAACUUUGACGUGCUCAAGAGAAUCAACGUGACCGAGGUGUCG

UUGCUCAUCAGCGACUUUAGACGUCAGAACCGUCGCGGCGGCACCAACAAAAGGACCACGUU

CAACGCCGCCGGUUCGCUGGCGCCACACGCCCGGAGCCUCGAGUUCAGCGUGCGGCUCUUUG

CCAACUGAUAAUAGGCUGGAGCCUCGGUGGCCAUGCUUCUUGCCCCUUGGGCCUCCCCCCAG

CCCCUCCUCCCCUUCCUGCACCCGUACCCCCGUGGUCUUUGAAUAAAGUCUGAGUGGGCGGC

Example 18: Immunogenicity Study

The instant study is designed to test the immunogenicity in mice of candidate CMV vaccines comprising an mRNA polynucleotide encoding the gH and gL glycoproteins or the UL128, UL130, and UL131A polypeptides obtained from MCMV.

Mice are vaccinated on week 0 and 4 via intramuscular (IM) or intradermal (ID) routes. One group remains unvaccinated and one is administered inactivated MCMV. Serum is collected from each mouse on weeks 1, 3 (pre-dose) and 5. Individual bleeds are tested for anti-gH and anti-gL activity or anti-UL128, anti-UL130, and anti-UL131A via ELISA assay from all three time points, and pooled samples from week 5 only are tested by Western blot using inactivated MCMV.

ELISA Immunoassays

Antibody production is measured in a sample by ELISA. Appropriately diluted samples were placed in 96-well plates precoated with a capture antibody directed against an epitope of the antibody. Serum samples typically were diluted 1:100 for the assay. Incubation and washing protocols were performed using routine methods. Data is read at 450 nm with wavelength. Data is reported and plotted.

Example 19: MCMV Challenge

The instant study is designed to test the efficacy in mice of candidate CMV vaccines against a lethal challenge using a mouse CMV vaccine comprising mRNAs encoding gH and gL or UL128, UL130, and UL131A. Due to the strict species specificity of CMV infection, there is no animal model available for study of HCMV infection and immunity. Murine cytomegalovirus (MCMV) infection is the most widely used mouse model simulating HCMV infection. In the current study, the immunogenicity and protective efficacy of MCMV gH, gL, UL128, UL130, UL131A antigens are investigated.

BALB/c mice are randomly divided into groups. The groups are respectively immunized with (1) 10 μg gB (positive control), (2) 10 μg gH and gL mRNAs (combination of separate sequences), (3) 10 μg gH-gL concatamer mRNA (single sequence), (4) 10 μg UL128, UL130, UL131A mRNAs (combination of separate sequences), (5) 10 μg UL128-UL130-UL131A concatamer mRNA (single sequence), (6) 10 μg gH-gL-UL128-UL130-UL131A concatamer mRNA (single sequence) and (7) PBS. Mice are immunized two times (second dose at day 28) by injection into the right quadriceps muscle (IM) or by intradermal administration (ID), and are challenged with a lethal dose (5×LD50, 200 μl/mouse) of SG-MCMV (Smith strain, $10^5$ PFU) by intraperitoneal injection. This infection causes systemic virus replication in mice and death of all unvaccinated mice within one week after the challenge.

Endpoint is day 5 post infection, death or euthanasia. Animals displaying severe illness as determined by >30% weight loss, extreme lethargy or paralysis are euthanized. The protective effects of the DNA vaccines are evaluated comprehensively using infection symptoms of body temperature, weight loss, and survival. The mice are weighed and assessed daily in order to monitor weight loss, apparent physical condition (bristled hair and wounded skin), body temperature, and behaviour. The mice are humanely euthanized via cervical dislocation after chloroform (inhalation excess) in all cases in order to minimize or avoid animal suffering.

Example 20: MCMV Neutralization Assay

Mice are immunized according to the methods in Example 18. Mouse serum samples are collected 3 weeks after the second immunization. Serum samples are stored at −20° C. until use. Neutralizing antibody directed against MCMV are determined by a plaque reduction assay, for example, as described in Geoffroy F, et al., Murine cytomegalovirus inactivated by sodium periodate is innocuous and immunogenic in mice and protects them against death and infection. Vaccine. 1996; 14: 1686-1694. Decomplemented sera (30 μl) are serially diluted 2-fold with MEM. Each dilution is mixed with 100 PFU MCMV in 30 μl of MEM and then incubated 1 hour at 4° C. and 1 hour at 37° C. The mixture is layered onto 3T3 monolayers and PFU are calculated by the standard plaque assay. A neutralization titer is expressed as the highest serum dilution required to achieve a 50% reduction in the number of plaques.

Example 21: IFN-γ ELISPOT Assay

Mice are immunized with gH or gL, or co-immunized with gH/gL mRNAs twice (day 0 and day 28) at a dosage of 10 μg by IM. Two weeks after the second immunization, splenocytes are isolated for ELISPOT assays. Immunospot are coated with rat anti-mouse IFN-γ mAb in accordance with manufacturer instructions, incubated at 4° C. overnight and then blocked with 200 μl of blocking solution. Subsequently, $2\times10^5$ lymphocytes are added to the wells in triplicate, stimulated with 10 μg/ml of corresponding gH or gL peptides or a gH/gL polypeptide mixture (for co-immunization group). After 18 hours, the lymphocytes are discarded and biotin-labeled anti-mouse IFN-γ Ab antibody is added to each well and incubated at 37° C. for 1 h. Next, diluted Streptavidin-HRP conjugate solution is added and incubated at room temperature for 2 hours. Finally, the plates are treated with 100 μl of AEC substrate solution and incubated at room temperature for 20 min in the dark. The reaction is stopped by washing with dematerialized water. Spots are quantified by an ELISPOT reader.

TABLE 2

<table>
<tr><th colspan="3">Human Cytomegalovirus Sequences</th></tr>
<tr><th>SEQ ID NO: Protein Name</th><th>Protein Sequence</th><th>Nucleotide Sequence (SEQ ID NO:)</th></tr>
<tr><td>32 gi|52139248|ref|YP_081523.1| envelope glycoprotein H [Human herpesvirus 5]</td><td>MRPGLPSYLIILAVCLFSHLLSSRYGAEAVSE<br>PLDKAFHLLLNTYGRPIRFLRENTTQCTYNSS<br>LRNSTVVRENAISFNFFQSYNQYYVFHMPRC<br>LFAGPLAEQFLNQVDLTETLERYQQRLNTYA<br>LVSKDLASYRSFSQQLKAQDSLGEQPTTVPP<br>PIDLSIPHVWMPPQTTPHGWTESHTTSGLHR<br>PHFNQTCILFDGHDLLFSTVTPCLHQGFYLID<br>ELRYVKITLTEDFFVVTVSIDDDTPMLLIFGH<br>LPRVLFKAPYQRDNFILRQTEKHELLVLVKK<br>DQLNRHSYLKDPDFLDAALDFNYLDLSALL<br>RNSFHRYAVDVLKSGRCQMLDRRTVEMAF<br>AYALALFAAARQEEAGAQVSVPRALDRQAA<br>LLQIQEFMITCLSQTPPRTTLLLYPTAVDLAK<br>RALWTPNQITDITSLVRLVYILSKQNQQHLIP<br>QWALRQIADFALKLHKTHLASFLSAFARQEL<br>YLMGSLVHSMLVHTTERREIFIVETGLCSLA<br>ELSHFTQLLAHPHHEYLSDLYTPCSSSGRRD<br>HSLERLTRLFPDATVPATVPAALSILSTMQPS<br>TLETFPDLFCLPLGESFSALTVSEHVSYIVTN<br>QYLIKGISYPVSTTVVGQSLIITQTDSQTKCEL<br>TRNMHTTHSITVALNISLENCAFCQSALLEY<br>DDTQGVINIMYMHDSDDVLFALDPYNEVVV<br>SSPRTHYLMLLKNGTVLEVTDVVVDATDSR<br>LLMMSVYALSAIIGIYLLYRMLKTC</td><td>1</td></tr>
<tr><td>33 gi|822887470|gb|AKI08892.1| RL1 protein [Human herpesvirus 5]</td><td>MPATDTNSTHTTPLHPENQHTLPLHHSTTQP<br>HVQTSDKHADKQHRTQMELDAADYAACAQ<br>ARQHLYGQTQPQPHAYPNANPQESAHFCTE<br>NQHQLTNLLHNIGEGAALGYPVPRAEIRRGG<br>GDWADSASDFDADCWCMWGRFGTMGRQP<br>VVTLLLARQRDGLADWNVVRCRGTGFRAH<br>DSEDGVSVWRQHLVFLLGGHGRRVQLERPS<br>AGEAQARGLLPRIRITPISTSPRPKPPQPTTST<br>ASHPHATARPDHTLFPVPSTPSATVHNPRNY<br>AVQLHAETTRTWRWARRGERGAWMPAETF<br>TCPKDKRPW</td><td>3</td></tr>
<tr><td>34 gi|822888315|gb|AKI09732.1| RL1 protein [Human herpesvirus 5]</td><td>MPATDTNSTHTTPLHPEDQHTLPLQHNTTQP<br>HVQTSDKPADKQHRTQMELDAADYAACAQ<br>ARQHLYGQTQ<br>PQLHAYPNANPQESAHFCTDNQHRLTNLLH<br>NIGEGAALGYPVPRAEIRRGGGDWADSASD<br>FDADCWCMWG<br>RFGTMGRQPVVTLLLARQRDGLADWNVVR<br>CRGTGFRAHDSEDGVSVWRQHLVFLLGGHG<br>RRVQLERPSAGEAQARGLLPRIRITPVSTSPR<br>PKAPQPTTSTASHPHATARPDHTLFPVPSTPS<br>ATVHNPRNYAVQLHAETTRTWRWARRGER<br>GAWMPAETFTCPKDKRPW</td><td>6</td></tr>
</table>

TABLE 2-continued

Human Cytomegalovirus Sequences

| SEQ ID NO: | Protein Name | Protein Sequence | Nucleotide Sequence (SEQ ID NO:) |
|---|---|---|---|
| 35 | gi\|136968\|sp\|P16 750.1/GO_HCM VA RecName: Full = Glycoprotein O; Short = gO; Flags: Precursor | MGRKEMMVRDVPKMVFLISISFLLVSFINCK VMSKALYNRPWRGLVLSKIGKYKLDQLKLE ILRQLETTISTKYNVSKQPVKNLTMNMTEFP QYYILAGPIQNYSITYLWFDFYSTQLRKPAK YVYSQYNHTAKTITFRPPPCGTVPSMTCLSE MLNVSKRNDTGEQGCGNFTTFNPMFFNVPR WNTKLYVGPTKVNVDSQTIYFLGLTALLLR YAQRNCTHSFYLVNAMSRNLFRVPKYINGT KLKNTMRKLKRKQAPVKEQFEKKAKKTQST TTPYFSYTTSAALNVTTNVTYSITTAARRVST STIAYRPDSSFMKSIMATQLRDLATWVYTTL RYRQNPFCEPSRNRTAVSEFMKNTHVLIRNE TPYTIYGTLDMSSLYYNETMFVENKTASDSN KTTPTSPSMGFQRTFIDPLWDYLDSLLFLDEI RNFSLRSPTYVNLTPPEHRRAVNLSTLNSLW WWLQ | |
| 36 | gi\|583844649\|gb\| AHI58989.1\| envelope glycoprotein N [Human herpesvirus 5] | MECNTLVLGLLVLSVVASSNNTSTASTPRPS SSTHASTTVKATTVATTSTTTATSTSSTTSAK PGFTTHDPNVMRPHAHNDFYNAHCTSHMYE LSLSSFAAWWTMLNALILMGAFCIVLRHCCF QNFTATTTKGY | |
| 37 | gi\|136994\|sp\|P16 733.1\|GM_HCM VA RecName: Full = Envelope glycoprotein M; Short = gM | MAPSHVDKVNTRTWSASIVFMVLTFVNVSV HLVLSNFPHLGYPCVYYHVVDFERLNMSAY NVMHLHTPMLFLDSVQLVCYAVFMQLVFL AVTIYYLVCWIKISMRKDKGMSLNQSTRDIS YMGDSLTAFLFILSMDTFQLFTLTMSFRLPS MIAFMAAVHFFCLTIFNVSMVTQYRSYKRSL FFFSRLHPKLKGTVQFRTLIVNLVEVALGFNT TVVAMALCYGFGNNFFVRTGHMVLAVFVV YAIISIIYFLLIEAVFFQYVKVQFGYHLGAFFG LCGLIYPIVQYDTFLSNEYRTGISWSFGMLFFI WAMFTTCRAVRYFRGRGSGSVKYQALATA SGEEVAVLSHHDSLESRRLREEEDDDDDEDF EDA | |
| 38 | gi\|77455773\|gb\| ABA86616.1\| UL128 [Human herpesvirus 5] | MSPKDLTPFLTALWLLLGHSRVLRVRAEECC EFINVNHPPERCYDFKMCNRFTVALRCPDGE VCYSPEKTAEIRGIVTTMTHSLTRQVVHNKL TSCNYNPLYLEADGRIRCGKVNDKAQYLLG AAGSVPYRWINLEYDKITRIVGLDQYLESVK KHKRLDVCRAKMGYMLQ | 13 |
| 39 | gi\|77455773\|gb\| ABA86616.1\| UL128 [Human herpesvirus 5] | MSPKDLTPFLTALWLLLGHSRVLRVRAEECC EFINVNHPPERCYDFKMCNRFTVALRCPDGE VCYSPEKTAEIRGIVTTMTHSLTRQVVHNKL TSCNYNPLYLEADGRIRCGKVNDKAQYLLG AAGSVPYRWINLEYDKITRIVGLDQYLESVK KHKRLDVCRAKMGYMLQ | 14 |
| 40 | gi\|822891002\|gb\| AKI12403.1\| RL1 protein [Human herpesvirus 5] | MPATDTNSTHTTPLHPEHHHSTTQPHAQTSD KHADKQHRTQMELDAADYAACAQARQHL YGQTQPQLHAYPNANPQESAHFCTENQHQL TNLLHNIGEGAALGYPVPRAEIRRGGGDWA DSASDFDADCWCMWGRFGTMGRQPVVTLL LARQRDGLADWNVVRCRGTGFRAHDSEDG VSVWRQHLVFLLGGHGRRVQLERPSAGEAQ ARGLLPRIRITPISTSPRPKPPQPTTSTASHPHA TARPDHTLFPVPSTPSATVHNPRNYAVQLHA ETTRTWRWARRGERGAWMPAETFTCPKDK RPW | 15 |
| 41 | gi\|52139182\|ref\| YP_081455.1\| protein RL1 [Human herpesvirus 5] | MPATDTNSTHTTPLHPEDQHTLPLHHSTTQP HVQTSDKHADKQHRTQMELDAADYAACAQ ARQHLYGQTQPQLHAYPNANPQESAHFRTE NQHQLTNLLHNIGEGAALGYPVPRAEIRRGG GDWADSASDFDADCWCMWGRFGTMGRQP VVTLLLARQRDGLADWNVVRCRGTGFRAH DSEDGVSVWRQHLVFLLGGHGRRVQLERPS AGEAQARGLLPRIRITPISTSPRPKPPQPTTST ASHPHATARPDHTLFPVPSTPSATVHNPRNY | 16 |

TABLE 2-continued

Human Cytomegalovirus Sequences

| SEQ ID NO: | Protein Name | Protein Sequence | Nucleotide Sequence (SEQ ID NO:) |
|---|---|---|---|
| | | AVQLHAETTRTWRWARRGERGAWMPAETF TCPKDKRPW | |
| 42 | gi\|52139291\|ref\| YP_081566.1\| envelope protein UL131A [Human herpesvirus 5] | MRLCRVWLSVCLCAVVLGQCQRETAEKND YYRVPHYWDACSRALPDQTRYKYVEQLVD LTLNYHYDASHGLDNFDVLKRINVTEVSLLI SDFRRQNRRGGTNKRTTFNAAGSLAPHARS LEFSVRLFAN | 17 |
| 43 | gi\|52139291\|ref\| YP_081566.1\| envelope protein UL131A [Human herpesvirus 5] | MRLCRVWLSVCLCAVVLGQCQRETAEKND YYRVPHYWDACSRALPDQTRYKYVEQLVD LTLNYHYDASHGLDNFDVLKRINVTEVSLLI SDFRRQNRRGGTNKRTTFNAAGSLAPHARS LEFSVRLFAN | 18 |
| 44 | gi\|52139182\|ref\| YP_081455.1\| protein RL1 [Human herpesvirus 5] | MPATDTNSTHTTPLHPEDQHTLPLHHSTTQP HVQTSDKHADKQHRTQMELDAADYAACAQ ARQHLYGQTQPQLHAYPNANPQESAHFRTE NQHQLTNLLHNIGEGAALGYPVPRAEIRRGG GDWADSASDFDADCWCMWGRFGTMGRQP VVTLLLARQRDGLADWNVVRCRGTGFRAH DSEDGVSVWRQHLVFLLGGHGRRVQLERPS AGEAQARGLLPRIRITPISTSPRPKPPQPTTST ASHPHATARPDHTLFPVPSTPSATVHNPRNY AVQLHAETTRTWRWARRGERGAWMPAETF TCPKDKRPW | 2 |
| 45 | gi\|52139182\|ref\| YP_081455.1\| protein RL1 [Human herpesvirus 5] | MPATDTNSTHTTPLHPEDQHTLPLHHSTTQP HVQTSDKHADKQHRTQMELDAADYAACAQ ARQHLYGQTQPQLHAYPNANPQESAHFRTE NQHQLTNLLHNIGEGAALGYPVPRAEIRRGG GDWADSASDFDADCWCMWGRFGTMGRQP VVTLLLARQRDGLADWNVVRCRGTGFRAH DSEDGVSVWRQHLVFLLGGHGRRVQLERPS AGEAQARGLLPRIRITPISTSPRPKPPQPTTST ASHPHATARPDHTLFPVPSTPSATVHNPRNY AVQLHAETTRTWRWARRGERGAWMPAETF TCPKDKRPW | 4 |
| 46 | gi\|822888315\|gb\| AKI09732.1\| RL1 protein [Human herpesvirus 5] | MPATDTNSTHTTPLHPEDQHTLPLQHNTTQP HVQTSDKPADKQHRTQMELDAADYAACAQ ARQHLYGQTQPQLHAYPNANPQESAHFCTD NQHRLTNLLHNIGEGAALGYPVPRAEIRRGG GDWADSASDFDADCWCMWGRFGTMGRQP VVTLLLARQRDGLADWNVVRCRGTGFRAH DSEDGVSVWRQHLVFLLGGHGRRVQLERPS AGEAQARGLLPRIRITPVSTSPRPKAPQPTTST ASHPHATARPDHTLFPVPSTPSATVHNPRNY AVQLHAETTRTWRWARRGERGAWMPAETF TCPKDKRPW | 6 |
| 47 | gi\|52139182\|ref\| YP_081455.1\| protein RL1 [Human herpesvirus 5] | MPATDTNSTHTTPLHPEDQHTLPLHHSTTQP HVQTSDKHADKQHRTQMELDAADYAACAQ ARQHLYGQTQPQLHAYPNANPQESAHFRTE NQHQLTNLLHNIGEGAALGYPVPRAEIRRGG GDWADSASDFDADCWCMWGRFGTMGRQP VVTLLLARQRDGLADWNVVRCRGTGFRAH DSEDGVSVWRQHLVFLLGGHGRRVQLERPS AGEAQARGLLPRIRITPISTSPRPKPPQPTTST ASHPHATARPDHTLFPVPSTPSATVHNPRNY AVQLHAETTRTWRWARRGERGAWMPAETF TCPKDKRPW | 7 |
| 48 | hCMV-gHtruncFLAG, glycoprotein H Ectodomain | SSFWTLVQKLIRLTIGK-ERKEE-EEI- EPPCGQASPPTSSSSPSVSSATYFRHDMAQKP YPNRWTKRFTYCSTPTGDPSASCVKIPPSVPT TAASVTARSSGKTPSVSTFSKAIINTMY SICLDVFLRVLWRSSF-TR-I- PKPWKDTNRDLTLTRWYPKTWPATDLFRSS- RHKTA-V NSPPLCHRPLTCQYLTFGCHRKPLHTAGQNH IPPQDYTDHTLTRPVSSLMDTIYYSAPSHLVC | 8 |

TABLE 2-continued

Human Cytomegalovirus Sequences

| SEQ ID NO: | Protein Name | Protein Sequence | Nucleotide Sequence (SEQ ID NO:) |
|---|---|---|---|
| | | TKAFTSSTNYVTLK-H-PRTSS-LRCP<br>TTTHPCCLSSAIFHAYFSKRPINATTLYYDKL<br>KNTSSWC-LRKIN-VTLISKTRTFLTPHLTSTT-<br>TSAHYYVTAFTVTPWMYSRAVDVRCWTAA<br>R-KWPSPTH-HCSQQPDKKRPAPKSPSHGP-<br>TARPHSYKYKNL-SPASHKHHH<br>APRCCCIPRPWTWPNEPFGHRIRSPTSPASYA<br>WSTYSLNRISNISSPNGHYDRSPTLP-N<br>YTKRTWPLFFQPSHAKNSTSWAASSTPCWYI<br>RRRDAKSSS-KRASVHWPSYHTLRSC-LI<br>HTTNTSATCTHPVPVAGDAITRSNASRVSSP<br>MPPSPLPFPPPSPSYLPCNQARWKPSPTC<br>FACRSANPSPR-PSPNTSVIS-QTST-<br>SKVSPTLSPPPS-ARASSSPRRTVKLNAN-RAT<br>CIPHTASQWRSTFR-KTAPFAKAPC-<br>NTTTRKASSTSCTCTTRTTSFSPWIPTTKWWS<br>HLRELTTSCF-KTVRY-K-<br>LTSSWTPPTITRTMTISDDNRLEPRWPCFLPL<br>GPPPSPSSPSCTRTPVVFE-SLSGR | |
| 49 | hCMVgHtrunc6 XHis, glycoprotein H Ectodomain-6XHis tag | SSFWTLVQKLIRLTIGK-ERKEE-EEI-<br>EPPCGQASPPTSSSSPSVSSATYFRHDMAQKP<br>YPNRWTKRFTYCSTPTGDPSASCVKIPPSVPT<br>TAASVTARSSGKTPSVSTFSKAIINTMY<br>SICLDVFLRVLWRSSF-TR-I-<br>PKPWKDTNRDLTLTRWYPKTWPATDLFRSS-<br>RHKTA-VNSPPLCHRPLTCQYLTFG<br>CHRKPLHTAGQNHIPPQDYTDHTLTRPVSSL<br>MDTIYYSAPSHLVCTKAFTSSTNYVTLK-H-<br>PRTSS-LRCP-TTTHPCCLSSAIFHAYFSKR<br>PINATTLYYDKLKNTSSWC-LRKIN-<br>TVTLISKTRTFLTPHLTSTT-<br>TSAHYYVTAFTVTPWMYSRAVD<br>VRCWTAAR-KWPSPTH-<br>HCSQQPDKKRPAPKSPSHGP-<br>TARPHSYKYKNL-SPASHKHHH<br>APRCCCIPRPWTWPNEPFGHRIRSPTSPASYA<br>WSTYSLNRISNISSPNGHYDRSPTLP-N<br>YTKRTWPLFFQPSHAKNSTSWAASSTPCWYI<br>RRRDAKSSS-KRASVHWPSYHTLRSC-LI<br>HTTNTSATCTHPVPVAGDAITRSNASRVSSP<br>MPPSPLPFPPPSPSYLPCNQARWKPSPTC<br>FACRSANPSPR-PSPNTSVIS-QTST-<br>SKVSPTLSPPPS-ARASSSPRRTVKLNAN-RAT<br>CIPHTASQWRSTFR-KTAPFAKAPC-<br>NTTTRKASSTSCTCTTRTTSFSPWIPTTKWWS<br>HLRELTTSCF-KTVRY-K-LTSSWTPPTTITTIT<br>DDNRLEPRWPCFLPLGPPPSPSSPSCTR<br>TPVVFE-SLSGR | 9 |
| 50 | hCMV_TrgB, glycoprotein B (ectodomain) | SSFWTLVQKLIRLTIGK-ERKEE-EEI-<br>EPPWNPGSGAW-ALTCVSSVWVLRFPHLLLV<br>ELLLLTVTIPLIRRLLLTLDPVQSLNA-<br>LLPKRSAMVLTRPSTTLPSSTEMWWGSIPPST<br>PIACVLWPRVRILFALNVISSAPR-<br>SPSMKTWTRASWWSTNATSSRTPLRYESTR<br>RF-RFVVATLTSTPLICWAATRNTW<br>RLLCGRFII STATVSATVPTAAL-QARFS<br>WLIIGTAMKTKPCN-CPTIIPTPTVPVT-<br>RSRINGTAAAAPGSIVRPVI-IVW-<br>PSLLRAPNILIIFSPLPRVTWLTFLLSTTEPIA<br>MPATLEKTPTSFSFFRTTLSSPTLEDRILR-<br>RPTGWWLFLNVRTR-SPGIYRTKR<br>MSLVNSLSGKPRNAPFVPKPRTRITFLLPK-<br>PPLSYLRSKR-TCPTLRWTAYVMRL-<br>ISYSRFSILHTIKHMKNMETCPSLKPLVVW-<br>CSGKVSSKNLWWNSNVWPTAPV-<br>ILLIIEPKEVQMATMQLIYPTWNRCTIWSTPS<br>CSSPMTRCAVTSTGRWRKSQKPGVWI<br>NGAP-RSSRNSARSTRQPFSRP FTTN<br>RLPRVSWVMSWAWPAA-PSTKPASRCCVI-T-<br>RSRQDAATHDPWSSLISPTARTCSTVNWART<br>TKSCWATTALRNVSFPASRSSSPGTRPTSTW<br>TTSSNA-LTSAVSPPSTA-SPWISTRW | 10 |

TABLE 2-continued

| Human Cytomegalovirus Sequences | | | |
|---|---|---|---|
| SEQ ID NO: | Protein Name | Protein Sequence | Nucleotide Sequence (SEQ ID NO:) |
| | | KIPTSGYWNFTRRKSCVPATFLTSKRSCANS TRTSSDNRLEPRWPCFLPLGPPPSPSSPSCTRT PVVFE-SLSGR | |
| 51 | hCMV_TrgBFL AG, hCMV glycoproteinB ectodomain-FLAG | SSFWTLVQKLIRLTIGK-ERKEE-EEI-EPPWNPGSGAW-SALTCVSSVWVLR FPHLLLVELLLLTVTIPLIRRLLLTLDPVQSLN A-LLPKRSAMVLTRPSTTLPSSTEMWWG SIPPSTPIACVLWPRVRILFALNVISSAPR-SPSMKTWTRASWWSTNATSSRTPLRYESTR RF-RFVVATLTSTPLICWAATRNTWRLLCGR FIISTATVSATVPTAAL-QARFSWLII GTAMKTKPCN-CPTIIPTPTVPVT-RSRINGTAAAAPGSIVRPVI-IVW-PSLLRAPN ILIIFSPLPRVTWLTFLLSTTEPIAMPATLEKTP TSFSFFRTTLSSPTLEDRILR-RPTGWWLF LNVRTR-SPGIYRTKRMSLVNS LSGKPRNAPFVPKPRTRITFLLPK-PPLSYLRSKR-TCPTLRWTAYVMRL-ISYSRFSILHTIKHMKNMETCPSLKPLVVW-CSGKVSSKNLWWNSNVWPTAP V-ILLIIEPKEVQMATMQLIYPTWNRCTI WSTPSCSSPMTRCAVTSTGRWRKSQKPGVW INGAP-RSSRNSARSTRQPFSRPFTTNRL PRVSWVMSWAWPAA-PSTKPASRCCVI-T-RS RQDAATHDPWSSLISPTARTCSTVNWARTTK SCWATTALRNVSFPASRSSSPGTRPTSTW TTSSNA-LTSAVSPPSTA-SPWISTRW KIPTSGYWNFTRRKSCVPATFLTSKRSCANS TRTSRITRTMTISDNRLEPRWPCFLPLGPPPSP SSPSCTRTPVVFE-SLSGR | 11 |
| 52 | hCMV-TrgB6XHis, hCMV glycoprotein ectodomain-6XHis tag | SSFWTLVQKLIRLTIGK-ERKEE-EEI-EPPWNPGSGAW-SALTCVSSVWVLR FPHLLLVELLLLTVTIPLIRRLLLTLDPVQSLN A-LLPKRSAMVLTRPSTTLPSSTEMWWGSIP PSTPIACVLWPRVRILFALNVISSAPR-SPSMKTWTRASWWSTNATSSRTPLRYESTR RF-RFVVATLTSTPLICWAATRNTWRLLCGR FIISTATVSATVPTAAL-QARFSWLIIG TAMKTKPCN-CPTIIPTPTVPVT-RSRINGTAAAAPGSIVRPVI-IVW-PSLLRA PNILIIFSPLPRVTWLTFLLSTTEPIAMPATLEK TPTSFSFFRTTLSSPTLEDRILR-RPTGWWLF LNVRTR-SPGIYRTKRMSLVNSLSGKPRN APFVPKPRTRITFLLPK-PPLSYLRSKR-TCPTLRWTAYVMRL-ISYSRFSIL HTIKHMKNMETCPSLKPLVVW-CSGKVSSKNLWWNSNVWPTAP V-ILLIIEPKEVQMATMQLIYPTWNRCTIWST PSCSSPMTRCAVTSTGRWRKSQKPGVWI NGAP-RSSRNSARSTRQPFSRPFTTNRLPRVS WVMSWAWPAA-PSTKPASRCCVI-T-RS RQDAATHDPWSSLISPTARTCSTVNWARTTK SCWATTALRNVSFPASRSSSPGTRPTSTW TTSSNA-LTSAVSPPSTA-SPWISTRWKIP TSGYWNFTRRKSCVPATFLTSKRSCANSTR TSSTITTITDNRLEPRWPCFLPLGPPPSPSSPSC TRTPVVFE-SLSGR | 12 |
| 55 | hCMV glycoprotein L | MCRRPDCGFSFSPGPVILLWCCLLLPIVSSAA VSVAPTAAEKVPAECPELTRRCLLGEVFEGD KYESWLRPLVNVTGRDGPLSQLIRYRPVTPE AANSVLLDEAFLDTLALLYNNPDQLRALLTL LSSDTAPRWMTVMRGYSECGDGSPAVYTCV DDLCRGYDLTRLSYGRSIFTEHVLGFELVPPS LFNVVVAIRNEATRTNRAVRLPVSTAAAPEG ITLFYGLYNAVKEFCLRHQLDPPLLRHLDKY YAGLPPELKQTRVNLPAHSRYGPQAVDAR | 3 |
| 56 | hCMV glycoprotein B | MESRIWCLVVCVNLCIVCLGAAVSSSSTRGT SATHSHHSSHTTSAAHSRSGSVSQRVTSSQT VSHGVNETIYNTTLKYGDVVGVNTTKYPYR VCSMAQGTDLIRFERNIVCTSMKPINEDLDE | 5 |

TABLE 2-continued

Human Cytomegalovirus Sequences

| SEQ ID NO: | Protein Name | Protein Sequence | Nucleotide Sequence (SEQ ID NO:) |
|---|---|---|---|
| | | GIMVVYKRNIVAHTFKVRVYQKVLTFRRSY AYIHTTYLLGSNTEYVAPPMWEIHHINSHSQ CYSSYSRVIAGTVFVAYHRDSYENKTMQLM PDDYSNTHSTRYVTVKDQWHSRGSTWLYRE TCNLNCMVTITTARSKYPYHFFATSTGDVVD ISPFYNGTNRNASYFGENADKFFIFPNYTIVS DFGRPNSALETHRLVAFLERADSVISWDIQD EKNVTCQLTFWEASERTIRSEAEDSYHFSSA KMTATFLSKKQEVNMSDSALDCVRDEAINK LQQIFNTSYNQTYEKYGNVSVFETTGGLVVF WQGIKQKSLVELERLANRSSLNLTHNRTKRS TDGNNATHLSNMESVHNLVYAQLQFTYDTL RGYINRALAQIAEAWCVDQRRTLEVFKELSK INPSAILSAIYNKPIAARFMGDVLGLASCVTI NQTSVKVLRDMNVKESPGRCYSRPVVIFNFA NSSYVQYGQLGEDNEILLGNHRTEECQLPSL KIFIAGNSAYEYVDYLFKRMIDLSSISTVDSM IALDIDPLENTDFRVLELYSQKELRSSNVFDL EEIMREFNSYKQRVKYVEDKVVDPLPPYLK GLDDLMSGLGAAGKAVGVAIGAVGGAVAS VVEGVATFLKNPFGAFTIILVAIAVVIITYLIY TRQRRLCTQPLQNLFPYLVSADGTTVTSGST KDTSLQAPPSYEESVYNSGRKGPGPPSSDAS TAAPPYTNEQAYQMLLALARLDAEQRAQQ NGTDSLDGRTGTQDKGQKPNLLDRLRHRKN GYRHLKDSDEEENV | |
| 57 | hCMV UL130 | MLRLLLRHHFHCLLLCAVWATPCLASPWST LTANQNPSPPWSKLTYSKPHDAATFYCPFLY PSPPRSPLQFSGFQRVSTGPECRNETLYLLYN REGQTLVERSSTWVKKVIWYLSGRNQTILQR MPRTASKPSDGNVQISVEDAKIFGAHMVPK QTKLLRFVVNDGTRYQMCVMKLESWAHVF RDYSVSFQVRLTFTEANNQTYTFCTHPNLIV | 15 |
| 53 | Ig heavy chain epsilon-1 signal peptide (IgE HC SP) | MDWTWILFLVAAATRVHS | |
| 54 | IgGk chain V-III region HAH signal peptide (IgGk SP) | METPAQLLFLLLLWLPDTTG | |

- represents a stop sequence

TABLE 3

CMV (Human herpesvirus 5) Amino Acid Sequences

| Protein | Name | GenBank Accession |
|---|---|---|
| Glycoprotein H | envelope glycoprotein H [Human herpesvirus 5] | ACZ79986.1 |
| Glycoprotein H | envelope glycoprotein H [Human herpesvirus 5] | AAA45918.1 |
| Glycoprotein H | envelope glycoprotein H [Human herpesvirus 5] | ACS93310.2 |
| Glycoprotein H | envelope glycoprotein H [Human herpesvirus 5] | AAA45911.1 |
| Glycoprotein H | envelope glycoprotein H [Human herpesvirus 5] | AAA98521.1 |
| Glycoprotein H | glycoprotein H [Human herpesvirus 5] | BAF44184.1 |
| Glycoprotein H | envelope glycoprotein H [Human herpesvirus 5] | AAA45912.1 |
| Glycoprotein H | envelope glycoprotein H [Human herpesvirus 5] | AKI21335.1 |
| Glycoprotein H | envelope glycoprotein H [Human herpesvirus 5] | AIC80661.1 |
| Glycoprotein H | envelope glycoprotein H [Human herpesvirus 5] | AKI11476.1 |
| Glycoprotein H | envelope glycoprotein H [Human herpesvirus 5] | ACZ80151.1 |
| Glycoprotein H | envelope glycoprotein H [Human herpesvirus 5] | AHV84023.1 |
| Glycoprotein H | envelope glycoprotein H [Human herpesvirus 5] | AAA45917.1 |
| Glycoprotein H | envelope glycoprotein H [Human herpesvirus 5] | AAA45915.1 |
| Glycoprotein H | envelope glycoprotein H [Human herpesvirus 5] | AFR55394.1 |
| Glycoprotein H | envelope glycoprotein H [Human herpesvirus 5] | AKI14309.1 |
| Glycoprotein H | envelope glycoprotein H [Human herpesvirus 5] | AKI11640.1 |
| Glycoprotein H | glycoprotein H [Human herpesvirus 5] | BAF44187.1 |

TABLE 3-continued

| CMV (Human herpesvirus 5) Amino Acid Sequences | | |
|---|---|---|
| Protein | Name | GenBank Accession |
| Glycoprotein H | envelope glycoprotein H [Human herpesvirus 5] | AKI18318.1 |
| Glycoprotein H | envelope glycoprotein H [Human herpesvirus 5] | AHB20043.1 |
| Glycoprotein H | envelope glycoprotein H [Human herpesvirus 5] | AAA45909.1 |
| Glycoprotein H | glycoprotein H [Human herpesvirus 5] | BAF44190.1 |
| Glycoprotein H | RecName: Full = Envelope glycoprotein H; Short = gH; Flags: Precursor | P12824.1 |
| Glycoprotein H | envelope glycoprotein H [Human herpesvirus 5] | AKI07789.1 |
| Glycoprotein H | glycoprotein H [Human herpesvirus 5] | BAF44183.1 |
| Glycoprotein H | envelope glycoprotein H [Human herpesvirus 5] | AGL96664.1 |
| Glycoprotein H | glycoprotein H [Human herpesvirus 5] | BAF44189.1 |
| Glycoprotein H | envelope glycoprotein H [Human herpesvirus 5] | AKI08793.1 |
| Glycoprotein H | glycoprotein H [Human herpesvirus 5] | BAF44185.1 |
| Glycoprotein H | envelope glycoprotein H [Human herpesvirus 5] | ADV04392.1 |
| Glycoprotein H | envelope glycoprotein H [Human herpesvirus 5] | AFR56062.1 |
| Glycoprotein H | envelope glycoprotein H [Human herpesvirus 5] | ACS92000.1 |
| Glycoprotein H | envelope glycoprotein H [Human herpesvirus 5] | AKI15316.1 |
| Glycoprotein H | envelope glycoprotein H [Human herpesvirus 5] | AFR54893.1 |
| Glycoprotein H | envelope glycoprotein H [Human herpesvirus 5] | AHJ86162.1 |
| Glycoprotein H | envelope glycoprotein H [Human herpesvirus 5] | ACS92165.1 |
| Glycoprotein H | envelope glycoprotein H [Human herpesvirus 5] | ACT81746.1 |
| Glycoprotein H | envelope glycoprotein H [Human herpesvirus 5] | AKI12305.1 |
| Glycoprotein H | envelope glycoprotein H [Human herpesvirus 5] | AKI09634.1 |
| Glycoprotein H | glycoprotein H [Human herpesvirus 5] | BAF44191.1 |
| Glycoprotein H | RecName: Full = Envelope glycoprotein H; Short = gH; AltName: Full = Glycoprotein P86; Flags: Precursor [Human herpesvirus 5 strain Towne] | P17176.1 |
| Glycoprotein H | envelope glycoprotein H [Human herpesvirus 5] | AKI13641.1 |
| Glycoprotein H | envelope glycoprotein H [Human herpesvirus 5] | AKI20832.1 |
| Glycoprotein H | envelope glycoprotein H [Human herpesvirus 5] | AKI09465.1 |
| Glycoprotein H | envelope glycoprotein H [Human herpesvirus 5] | ACS93407.1 |
| Glycoprotein H | envelope glycoprotein H [Human herpesvirus 5] | AKI07621.1 |
| Glycoprotein H | glycoprotein H [Human herpesvirus 5] | BAF44186.1 |
| Glycoprotein H | envelope glycoprotein H [Human herpesvirus 5] | AKI22834.1 |
| Glycoprotein H | envelope glycoprotein H [Human herpesvirus 5] | AKI14981.1 |
| Glycoprotein H | envelope glycoprotein H [Human herpesvirus 5] | AKI10139.1 |
| Glycoprotein H | envelope glycoprotein H [Human herpesvirus 5] | ACZ79822.1 |
| Glycoprotein H | envelope glycoprotein H [Human herpesvirus 5] | AAA45910.1 |
| Glycoprotein H | envelope glycoprotein H [Human herpesvirus 5] | AAA45913.1 |
| Glycoprotein H | glycoprotein H [Human herpesvirus 5] | BAF44188.1 |
| Glycoprotein H | envelope glycoprotein H [Human herpesvirus 5] | AKI18822.1 |
| Glycoprotein H | envelope glycoprotein H [Human herpesvirus 5] | AFR56229.1 |
| Glycoprotein H | envelope glycoprotein H [Human herpesvirus 5] | YP_081523.1 |
| Glycoprotein H | envelope glycoprotein H [Human herpesvirus 5] | AKI19826.1 |
| Glycoprotein H | envelope glycoprotein H [Human herpesvirus 5] | AAA45914.1 |
| Glycoprotein H | envelope glycoprotein H [Human herpesvirus 5] | AKI23334.1 |
| Glycoprotein H | envelope glycoprotein H [Human herpesvirus 5] | AKI14141.1 |
| Glycoprotein H | envelope glycoprotein H [Human herpesvirus 5] | AHB19545.1 |
| Glycoprotein H | envelope glycoprotein H [Human herpesvirus 5] | ACU83725.1 |
| Glycoprotein H | envelope glycoprotein H [Human herpesvirus 5] | AKI17318.1 |
| Glycoprotein H | envelope glycoprotein H [Human herpesvirus 5] | AKI13975.1 |
| Glycoprotein L | RecName: Full = Envelope glycoprotein L; Flags: Precursor [Human herpesvirus 5 (strain 5040)] | Q68672.1 |
| Glycoprotein L | RecName: Full = Envelope glycoprotein L; Flags: Precursor [Human herpesvirus 5 (strain 2387)] | Q68669.1 |
| Glycoprotein L | envelope glycoprotein L [Human herpesvirus 5] | AKI08825.1 |
| Glycoprotein L | envelope glycoprotein L [Human herpesvirus 5] | ACS92032.1 |
| Glycoprotein L | envelope glycoprotein L [Human herpesvirus 5] | AHJ86194.1 |
| Glycoprotein L | RecName: Full = Envelope glycoprotein L; Flags: Precursor | P16832.2 |
| Glycoprotein L | RecName: Full = Envelope glycoprotein L; Flags: Precursor [Human herpesvirus 5 (strain 5035)] | Q68671.1 |
| Glycoprotein L | envelope glycoprotein L [Human herpesvirus 5] | AHB20074.1 |
| Glycoprotein L | envelope glycoprotein L [Human herpesvirus 5] | AKI12337.1 |
| Glycoprotein L | RecName: Full = Envelope glycoprotein L; Flags: Precursor [Human herpesvirus 5 (strain 1042)] | Q68668.1 |
| Glycoprotein L | envelope glycoprotein L [Human herpesvirus 5] | AKI23365.1 |
| Glycoprotein L | envelope glycoprotein L [Human herpesvirus 5] | AKI21032.1 |
| Glycoprotein L | envelope glycoprotein L [Human herpesvirus 5] | YP_081555.1 |
| Glycoprotein L | RecName: Full = Envelope glycoprotein L; Flags: Precursor [Human herpesvirus 5 (strain 4654)] | Q68670.1 |
| Glycoprotein L | envelope glycoprotein L [Human herpesvirus 5] | AKI17850.1 |
| Glycoprotein L | envelope glycoprotein L [Human herpesvirus 5] | ACZ80183.1 |
| Glycoprotein L | envelope glycoprotein L [Human herpesvirus 5] | AKI11508.1 |
| Glycoprotein L | envelope glycoprotein L [Human herpesvirus 5] | AKI10171.1 |
| Glycoprotein L | RecName: Full = Envelope glycoprotein L; Flags: Precursor [Human herpesvirus 5 (strain 5160)] | Q68673.1 |

TABLE 3-continued

CMV (Human herpesvirus 5) Amino Acid Sequences

| Protein | Name | GenBank Accession |
|---|---|---|
| Glycoprotein L | RecName: Full = Envelope glycoprotein L; Flags: Precursor [Human herpesvirus 5 strain PT] | Q68666.1 |
| Glycoprotein L | envelope glycoprotein L [Human herpesvirus 5] | AKI18350.1 |
| Glycoprotein L | envelope glycoprotein L [Human herpesvirus 5] | AIC80693.1 |
| Glycoprotein L | envelope glycoprotein L [Human herpesvirus 5] | AKI12003.1 |
| Glycoprotein L | envelope glycoprotein L [Human herpesvirus 5] | AKI15849.1 |
| Glycoprotein L | envelope glycoprotein L [Human herpesvirus 5] | AKI13336.1 |
| Glycoprotein L | envelope glycoprotein L [Human herpesvirus 5] | AKI10840.1 |
| Glycoprotein L | RecName: Full = Envelope glycoprotein L; Flags: Precursor | Q68667.1 |
| Glycoprotein L | envelope glycoprotein L [Human herpesvirus 5] | AHV84055.1 |
| Glycoprotein L | envelope glycoprotein L [Human herpesvirus 5] | AKI07653.1 |
| Glycoprotein L | envelope glycoprotein L [Human herpesvirus 5] | AFR55425.1 |
| Glycoprotein L | envelope glycoprotein L [Human herpesvirus 5] | AKI15013.1 |
| Glycoprotein L | envelope glycoprotein L [Human herpesvirus 5] | ACT81943.1 |
| Glycoprotein L | envelope glycoprotein L [Human herpesvirus 5] | AKI21367.1 |
| Glycoprotein L | envelope glycoprotein L [Panine herpesvirus 2] | NP_612739.1 |
| pp150 | tegument protein pp150 [Human herpesvirus 5] | ACZ79954.1 |
| pp150 | tegument protein pp150 [Human herpesvirus 5] | AFR56030.1 |
| pp150 | tegument protein pp150 [Human herpesvirus 5] | ACU83693.1 |
| pp150 | tegument protein pp150 [Human herpesvirus 5] | AKI12106.1 |
| pp150 | tegument protein pp150 [Human herpesvirus 5] | AKI19625.1 |
| pp150 | tegument protein pp150 [Human herpesvirus 5] | AFR55362.1 |
| pp150 | tegument protein pp150 [Human herpesvirus 5] | AKI14613.1 |
| pp150 | tegument protein pp150 [Human herpesvirus 5] | AKI07924.1 |
| pp150 | tegument protein pp150 [Human herpesvirus 5] | AIC80127.1 |
| pp150 | tegument protein pp150 [Human herpesvirus 5] | AHB19512.1 |
| pp150 | tegument protein pp150 [Human herpesvirus 5] | YP_081491.1 |
| pp150 | tegument protein pp150 [Human herpesvirus 5] | AKI16116.1 |
| pp150 | extended tegument protein pp150 [Human herpesvirus 5] | AII79810.1 |
| pp150 | tegument protein pp150 [Human herpesvirus 5] | AIC80629.1 |
| pp150 | tegument protein pp150 [Human herpesvirus 5] | AFR55862.1 |
| pp150 | tegument protein pp150 [Human herpesvirus 5] | AKI10942.1 |
| pp150 | tegument protein pp150 [Human herpesvirus 5] | ACS91968.1 |
| pp150 | tegument protein pp150 [Human herpesvirus 5] | AKI15451.1 |
| pp150 | tegument protein pp150 [Human herpesvirus 5] | ACS92133.1 |
| pp150 | tegument protein pp150 [Human herpesvirus 5] | AFR56364.1 |
| pp150 | tegument protein pp150 [Human herpesvirus 5] | AFR54694.1 |
| pp150 | tegument protein pp150 [Human herpesvirus 5] | AKI23468.1 |
| pp150 | tegument protein pp150 [Human herpesvirus 5] | AKI17619.1 |
| pp150 | tegument protein pp150 [Human herpesvirus 5] | AFR55527.1 |
| pp150 | tegument protein pp150 [Human herpesvirus 5] | AFR55193.1 |
| pp150 | tegument protein pp150 [Human herpesvirus 5] | AFR54534.1 |
| pp150 | tegument protein pp150 [Human herpesvirus 5] | AKI18789.1 |
| pp150 | tegument protein pp150 [Human herpesvirus 5] | AKI07588.1 |
| pp150 | tegument protein pp150 [Human herpesvirus 5] | AKI22466.1 |
| pp150 | tegument protein pp150 [Human herpesvirus 5] | AKI20463.1 |
| pp150 | tegument protein pp150 [Human herpesvirus 5] | AKI14780.1 |
| pp150 | tegument protein pp150 [Human herpesvirus 5] | AKI15116.1 |
| pp150 | tegument protein pp150 [Human herpesvirus 5] | AKI14445.1 |
| pp150 | tegument protein pp150 [Human herpesvirus 5] | AKI22633.1 |
| pp150 | tegument protein pp150 [Human herpesvirus 5] | AKI09096.1 |
| pp150 | tegument protein pp150 [Human herpesvirus 5] | AKI13271.1 |
| pp150 | tegument protein pp150 [Human herpesvirus 5] | AKI08760.1 |
| pp150 | tegument protein pp150 [Human herpesvirus 5] | AFR56197.1 |
| pp150 | tegument protein pp150 [Human herpesvirus 5] | AFR54861.1 |
| pp150 | tegument protein pp150 [Human herpesvirus 5] | ACZ80119.1 |
| pp150 | tegument protein pp150 [Human herpesvirus 5] | AKI19960.1 |
| pp150 | tegument protein pp150 [Human herpesvirus 5] | AKI21134.1 |
| pp150 | tegument protein pp150 [Human herpesvirus 5] | AKI11938.1 |
| pp150 | tegument protein pp150 [Human herpesvirus 5] | AKI20128.1 |
| pp150 | tegument protein pp150 [Human herpesvirus 5] | AKI08928.1 |
| pp150 | tegument protein pp150 [Human herpesvirus 5] | ACZ80284.1 |
| pp150 | tegument protein pp150 [Human herpesvirus 5] | AKI21302.1 |
| pp150 | tegument protein pp150 [Human herpesvirus 5] | AKI12272.1 |
| pp150 | tegument protein pp150 [Human herpesvirus 5] | AKI20967.1 |
| pp150 | tegument protein pp150 [Human herpesvirus 5] | AKI19793.1 |
| pp150 | tegument protein pp150 [Human herpesvirus 5] | AKI23136.1 |
| pp150 | tegument protein pp150 [Human herpesvirus 5] | AKI10106.1 |
| pp150 | tegument protein pp150 [Human herpesvirus 5] | AKI11772.1 |
| pp150 | tegument protein pp150 [Human herpesvirus 5] | AKI08591.1 |
| pp150 | tegument protein pp150 [Human herpesvirus 5] | AKI11443.1 |
| pp150 | tegument protein pp150 [Human herpesvirus 5] | AKI14948.1 |
| pp150 | tegument protein pp150 [Human herpesvirus 5] | ADE88040.1 |
| pp150 | tegument protein pp150 [Human herpesvirus 5] | AKI22969.1 |
| pp150 | tegument protein pp150 [Human herpesvirus 5] | AHJ86130.1 |

TABLE 3-continued

CMV (Human herpesvirus 5) Amino Acid Sequences

| Protein | Name | GenBank Accession |
|---|---|---|
| pp150 | tegument protein pp150 [Human herpesvirus 5] | ACT81879.1 |
| pp150 | tegument protein pp150 [Human herpesvirus 5] | AKI15950.1 |
| pp150 | tegument protein pp150 [Human herpesvirus 5] | AKI15617.1 |
| pp150 | tegument protein pp150 [Human herpesvirus 5] | AHB19679.1 |
| pp150 | tegument protein pp150 [Human herpesvirus 5] | AHB19344.1 |
| pp150 | tegument protein pp150 [Human herpesvirus 5] | ACT81714.1 |
| pp150 | tegument protein pp150 [Human herpesvirus 5] | AKI07756.1 |
| pp150 | tegument protein pp150 [Human herpesvirus 5] | AKI11607.1 |
| pp150 | tegument protein pp150 [Human herpesvirus 5] | AIC80295.1 |
| pp150 | tegument protein pp150 [Human herpesvirus 5] | AKI11275.1 |
| pp150 | tegument protein pp150 [Human herpesvirus 5] | AHB20010.1 |
| pp150 | tegument protein pp150 [Human herpesvirus 5] | AIC80463.1 |
| pp150 | tegument protein pp150 [Human herpesvirus 5] | AKI17952.1 |
| pp150 | tegument protein pp150 [Human herpesvirus 5] | ACM48022.1 |
| pp150 | tegument protein pp150 [Human herpesvirus 5] | AKI16285.1 |
| pp150 | tegument protein pp150 [Human herpesvirus 5] | AKI09601.1 |
| pp150 | tegument protein pp150 [Human herpesvirus 5] | AKI22299.1 |
| pp150 | tegument protein pp150 [Human herpesvirus 5] | AHV83990.1 |
| pp150 | tegument protein pp150 [Human herpesvirus 5] | AKI23301.1 |
| pp150 | tegument protein pp150 [Human herpesvirus 5] | AGL96632.1 |
| pp150 | tegument protein pp150 [Human herpesvirus 5] | AKI18285.1 |
| pp150 | tegument protein pp150 [Human herpesvirus 5] | ADV04360.1 |
| pp65 | tegument protein pp65 [Human herpesvirus 5] | ACZ79994.1 |
| pp65 | tegument protein pp65 [Human herpesvirus 5] | ACS92173.1 |
| pp65 | tegument protein pp65 [Human herpesvirus 5] | AKI09642.1 |
| pp65 | tegument protein pp65 [Human herpesvirus 5] | AKI16326.1 |
| pp65 | tegument protein pp65 [Human herpesvirus 5] | ADD39129.1 |
| pp65 | tegument protein pp65 [Human herpesvirus 5] | ACM48061.1 |
| pp65 | tegument protein pp65 [Human herpesvirus 5] | AKI20001.1 |
| pp65 | tegument protein pp65 [Human herpesvirus 5] | AKI14149.1 |
| pp65 | tegument protein pp65 [Human herpesvirus 5] | AHB19720.1 |
| pp65 | tegument protein pp65 [Human herpesvirus 5] | ADV04400.1 |
| pp65 | tegument protein pp65 [Human herpesvirus 5] | AKI21507.1 |
| pp65 | tegument protein pp65 [Human herpesvirus 5] | AKI15825.1 |
| pp65 | tegument protein pp65 [Human herpesvirus 5] | AKI08299.1 |
| pp65 | tegument protein pp65 [Human herpesvirus 5] | AKI07965.1 |
| pp65 | tegument protein pp65 [Human herpesvirus 5] | AKI22339.1 |
| pp65 | tegument protein pp65 [Human herpesvirus 5] | AKI12978.1 |
| pp65 | tegument protein pp65 [Human herpesvirus 5] | AKI11979.1 |
| pp65 | tegument protein pp65 [Human herpesvirus 5] | AHB19886.1 |
| pp65 | tegument protein pp65 [Human herpesvirus 5] | YP_081531.1 |
| pp65 | tegument protein pp65 [Human herpesvirus 5] | AKI23010.1 |
| pp65 | tegument protein pp65 [Human herpesvirus 5] | AKI10983.1 |
| pp65 | tegument protein pp65 [Human herpesvirus 5] | AKI10314.1 |
| pp65 | tegument protein pp65 [Human herpesvirus 5] | AFR56070.1 |
| pp65 | 65K lower matrix phosphoprotein - human cytomegalovirus (strain Towne) | WMBETW |
| pp65 | mutant UL83 [Human herpesvirus 5] | AAP59842.1 |
| pp65 | tegument protein pp65 [Human herpesvirus 5] | AKI14317.1 |
| pp65 | tegument protein pp65 [Human herpesvirus 5] | AFR54574.1 |
| pp65 | tegument protein pp65 [Human herpesvirus 5] | AFR56237.1 |
| pp65 | tegument protein pp65 [Human herpesvirus 5] | AKI18326.1 |
| pp65 | tegument protein pp65 [Human herpesvirus 5] | AKI22842.1 |
| pp65 | tegument protein PP65 [Human herpesvirus 5] | AHV84031.1 |
| pp65 | tegument protein [synthetic construct] | AAT68258.1 |
| pp65 | phosphorylated matrix protein (pp65) [Human herpesvirus 5] | AAA45996.1 |
| pp65 | tegument protein pp65 [Panine herpesvirus 2] | NP_612716.1 |
| pp65 | tegument protein pp65 [Human herpesvirus 5] | ADJ68256.1 |
| pp65 | tegument protein pp65 [Human herpesvirus 5] | ADJ68266.1 |
| UL100 (gM) | envelope glycoprotein M [Human herpesvirus 5] | ACT81935.1 |
| UL100 (gM) | envelope glycoprotein M [Human herpesvirus 5] | YP_081547.1 |
| UL100 (gM) | envelope glycoprotein M [Human herpesvirus 5] | ACM48077.1 |
| UL100 (gM) | RecName: Full = Envelope glycoprotein M; Short = gM | P16733.1 |
| UL100 (gM) | envelope glycoprotein M [Human herpesvirus 5] | AKI18175.1 |
| UL100 (gM) | envelope glycoprotein M [Human herpesvirus 5] | AFR54590.1 |
| UL100 (gM) | envelope glycoprotein M [Human herpesvirus 5] | AKI20017.1 |
| UL100 (gM) | envelope glycoprotein M [Human herpesvirus 5] | AKI09994.1 |
| UL100 (gM) | UL100 [Human herpesvirus 5] | AAS48986.1 |
| UL100 (gM) | envelope glycoprotein M [Human herpesvirus 5] | AKI20856.1 |
| UL100 (gM) | envelope glycoprotein M [Human herpesvirus 5] | AKI14333.1 |
| UL100 (gM) | envelope glycoprotein M [Human herpesvirus 5] | AHB19736.1 |
| UL100 (gM) | envelope glycoprotein M [Human herpesvirus 5] | AGT36389.1 |
| UL100 (gM) | envelope glycoprotein M [Human herpesvirus 5] | ACZ80175.1 |
| UL100 (gM) | envelope glycoprotein M [Human herpesvirus 5] | AKI18009.1 |
| UL100 (gM) | envelope glycoprotein M [Human herpesvirus 5] | AKI23358.1 |

TABLE 3-continued

CMV (Human herpesvirus 5) Amino Acid Sequences

| Protein | Name | GenBank Accession |
|---|---|---|
| UL100 (gM) | envelope glycoprotein M [Human herpesvirus 5] | AHV84047.1 |
| UL100 (gM) | envelope glycoprotein M [Human herpesvirus 5] | ACS92024.1 |
| UL100 (gM) | envelope glycoprotein M [Human herpesvirus 5] | AKI10999.1 |
| UL100 (gM) | envelope glycoprotein M [Human herpesvirus 5] | AKI16173.1 |
| UL100 (gM) | envelope glycoprotein M [Human herpesvirus 5] | AFR54917.1 |
| UL100 (gM) | UL100 [Human herpesvirus 5] | ABV71622.1 |
| UL100 (gM) | envelope glycoprotein M [Human herpesvirus 5] | AKI13999.1 |
| UL100 (gM) | envelope glycoprotein M [Human herpesvirus 5] | AKI12329.1 |
| UL100 (gM) | envelope glycoprotein M [Human herpesvirus 5] | AKI21523.1 |
| UL100 (gM) | envelope glycoprotein M [Human herpesvirus 5] | AKI18342.1 |
| UL100 (gM) | envelope glycoprotein M [Human herpesvirus 5] | AKI09658.1 |
| UL100 (gM) | envelope glycoprotein M [Human herpesvirus 5] | AKI07813.1 |
| UL100 (gM) | envelope glycoprotein M [Human herpesvirus 5] | AKI18846.1 |
| UL100 (gM) | envelope glycoprotein M [Human herpesvirus 5] | AFR55081.1 |
| UL100 (gM) | envelope glycoprotein M [Human herpesvirus 5] | AKI17342.1 |
| UL123 | regulatory protein IE1 [Human herpesvirus 5] | ACT81950.1 |
| UL123 | regulatory protein IE1 [Human herpesvirus 5] | AKI07996.1 |
| UL123 | regulatory protein IE1 [Human herpesvirus 5] | AAR31361.1 |
| UL123 | regulatory protein IE1 [Human herpesvirus 5] | AKI09840.1 |
| UL123 | regulatory protein IE1 [Human herpesvirus 5] | AKI12010.1 |
| UL123 | regulatory protein IE1 [Human herpesvirus 5] | AAR31390.1 |
| UL123 | regulatory protein IE1 [Human herpesvirus 5] | AFR55598.1 |
| UL123 | regulatory protein IE1 [Human herpesvirus 5] | AKI08832.1 |
| UL123 | immediate early transcriptional regulator [Human herpesvirus 5] | ACL27071.1 |
| UL123 | regulatory protein IE1 [Human herpesvirus 5] | AHB19584.1 |
| UL123 | regulatory protein IE1 [Human herpesvirus 5] | AKI18861.1 |
| UL123 | regulatory protein IE1 [Human herpesvirus 5] | AAR31419.1 |
| UL123 | regulatory protein IE1 [Human herpesvirus 5] | AKI23372.1 |
| UL123 | regulatory protein IE1 [Human herpesvirus 5] | AKI16357.1 |
| UL123 | regulatory protein IE1 [Human herpesvirus 5] | AKI10512.1 |
| UL123 | regulatory protein IE1 [Human herpesvirus 5] | AKI19028.1 |
| UL123 | regulatory protein IE1 [Human herpesvirus 5] | AKI11347.1 |
| UL123 | 72 kDa immediate-early 1 protein [Human herpesvirus 5] | ACT34667.1 |
| UL123 | regulatory protein IE1 [Human herpesvirus 5] | ADB84698.1 |
| UL123 | immediate early transcriptional regulator [Human herpesvirus 5] | ACL27072.1 |
| UL123 | regulatory protein IE1 [Human herpesvirus 5] | AKI22873.1 |
| UL123 | regulatory protein IE1 [Human herpesvirus 5] | AKI20200.1 |
| UL123 | regulatory protein IE1 [Human herpesvirus 5] | AKI12677.1 |
| UL123 | regulatory protein IE1 [Human herpesvirus 5] | AHV84062.1 |
| UL123 | regulatory protein IE1 [Human herpesvirus 5] | AFR55096.1 |
| UL123 | regulatory protein IE1 [Human herpesvirus 5] | AFR54932.1 |
| UL123 | regulatory protein IE1 [Human herpesvirus 5] | AKI22205.1 |
| UL123 | regulatory protein IE1 [Human herpesvirus 5] | AFR55264.1 |
| UL123 | regulatory protein IE1 [Human herpesvirus 5] | AKI18357.1 |
| UL123 | regulatory protein IE1 [Human herpesvirus 5] | AKI17188.1 |
| UL123 | regulatory protein IE1 [Human herpesvirus 5] | AKI12841.1 |
| UL123 | regulatory protein IE1 [Human herpesvirus 5] | AKI09673.1 |
| UL123 | regulatory protein IE1 [Human herpesvirus 5] | AKI21537.1 |
| UL123 | regulatory protein IE1 [Human herpesvirus 5] | AKI20871.1 |
| UL123 | regulatory protein IE1 [Human herpesvirus 5] | AGL96703.1 |
| UL123 | regulatory protein IE1 [Human herpesvirus 5] | AAR31477.1 |
| UL123 | regulatory protein IE1 [Human herpesvirus 5] | AKI21374.1 |
| UL123 | regulatory protein IE1 [Human herpesvirus 5] | ACZ80025.1 |
| UL123 | 72 kDa immediate-early 1 protein [Human herpesvirus 5] | ACT34666.1 |
| UL123 | regulatory protein IE1 [Human herpesvirus 5] | AKI20032.1 |
| UL123 | regulatory protein IE1 [Human herpesvirus 5] | AAR31303.1 |
| UL123 | regulatory protein IE1 [Human herpesvirus 5] | AIC80700.1 |
| UL123 | regulatory protein IE1 [Human herpesvirus 5] | ADB84746.1 |
| UL123 | immediate early transcriptional regulator [Human herpesvirus 5] | ACL27084.1 |
| UL123 | regulatory protein IE1 [Human herpesvirus 5] | ADV04431.1 |
| UL123 | regulatory protein IE1 [Human herpesvirus 5] | AKI11515.1 |
| UL123 | regulatory protein IE1 [Human herpesvirus 5] | AFR56435.1 |
| UL123 | immediate early transcriptional regulator [Human herpesvirus 5] | ACL27074.1 |
| UL123 | regulatory protein IE1 [Human herpesvirus 5] | AKI14180.1 |
| UL123 | regulatory protein IE1 [Human herpesvirus 5] | AKI07828.1 |
| UL123 | regulatory protein IE1 [Human herpesvirus 5] | AHB19751.1 |
| UL123 | regulatory protein IE1 [Human herpesvirus 5] | ADB84818.1 |
| UL123 | regulatory protein IE1 [Human herpesvirus 5] | AKI18526.1 |
| UL123 | regulatory protein IE1 [Human herpesvirus 5] | AKI14014.1 |
| UL123 | regulatory protein IE1 [Human herpesvirus 5] | ACT81785.1 |
| UL123 | regulatory protein IE1 [Human herpesvirus 5] | ADB44102.1 |
| UL123 | regulatory protein IE1 [Human herpesvirus 5] | AKI15187.1 |
| UL123 | immediate early transcriptional regulator [Human herpesvirus 5] | ACL27092.1 |
| UL123 | immediate early transcriptional regulator [Human herpesvirus 5] | ACL27056.1 |
| UL123 | regulatory protein IE1 [Human herpesvirus 5] | AKI18024.1 |

TABLE 3-continued

CMV (Human herpesvirus 5) Amino Acid Sequences

| Protein | Name | GenBank Accession |
|---|---|---|
| UL123 | regulatory protein IE1 [Human herpesvirus 5] | AKI14517.1 |
| UL123 | regulatory protein IE1 [Human herpesvirus 5] | ADE88106.1 |
| UL123 | regulatory protein IE1 [Human herpesvirus 5] | AKI15355.1 |
| UL123 | regulatory protein IE1 [Human herpesvirus 5] | AKI10178.1 |
| UL123 | regulatory protein IE1 [Human herpesvirus 5] | ADB84722.1 |
| UL123 | regulatory protein IE1 [Human herpesvirus 5] | ADB84650.1 |
| UL123 | regulatory protein IE1 [Human herpesvirus 5] | AFR56268.1 |
| UL123 | regulatory protein IE1 [Human herpesvirus 5] | YP_081562.1 |
| UL123 | regulatory protein IE1 [Human herpesvirus 5] | AKI22538.1 |
| UL123 | regulatory protein IE1 [Human herpesvirus 5] | AHB19917.1 |
| UL123 | regulatory protein IE1 [Human herpesvirus 5] | AAR31332.1 |
| UL123 | RecName: Full = 55 kDa immediate-early protein 1; Short = IE1 | P13202.1 |
| UL123 | regulatory protein IE1 [Human herpesvirus 5] | AAR31448.1 |
| UL123 | regulatory protein IE1 [Human herpesvirus 5] | AKI14852.1 |
| UL123 | regulatory protein IE1 [Human herpesvirus 5] | AKI14348.1 |
| UL123 | immediate early transcriptional regulator [Human herpesvirus 5] | ACL27066.1 |
| UL123 | immediate early transcriptional regulator [Human herpesvirus 5] | ACL27058.1 |
| UL123 | immediate early transcriptional regulator [Human herpesvirus 5] | ACL27086.1 |
| UL123 | regulatory protein IE1 [Human herpesvirus 5] | AKI16022.1 |
| UL123 | regulatory protein IE1 [Human herpesvirus 5] | AIC80534.1 |
| UL123 | immediate early transcriptional regulator [Human herpesvirus 5] | ACL27094.1 |
| UL123 | immediate early transcriptional regulator [Human herpesvirus 5] | ACL27093.1 |
| UL123 | immediate early transcriptional regulator [Human herpesvirus 5] | ACL27073.1 |
| UL123 | pp65/IE1 fusion protein [synthetic construct] | ABQ23593.1 |
| UL123 | regulatory protein IE1 [Human herpesvirus 5] | ACS92204.1 |
| UL123 | RecName: Full = 55 kDa immediate-early protein 1; Short = IE1 [Human herpesvirus 5 strain Towne] | P03169.1 |
| UL123 | regulatory protein IE1 [Human herpesvirus 5] | ADB84794.1 |
| UL123 | major immediate-early protein [Human herpesvirus 5] | AAA45979.1 |
| UL123 | immediate early transcriptional regulator [Human herpesvirus 5] | ACL27059.1 |
| UL123 | regulatory protein IE1 [Human herpesvirus 5] | AKI21039.1 |
| UL123 | immediate early transcriptional regulator [Human herpesvirus 5] | ACL27065.1 |
| UL123 | immediate early transcriptional regulator [Human herpesvirus 5] | ACL27087.1 |
| UL123 | regulatory protein IE1 [Human herpesvirus 5] | AAR31504.1 |
| UL123 | immediate early transcriptional regulator [Human herpesvirus 5] | ACL27082.1 |
| UL123 | immediate early transcriptional regulator [Human herpesvirus 5] | ACL27055.1 |
| UL123 | immediate early transcriptional regulator [Human herpesvirus 5] | ACL27081.1 |
| UL123 | regulatory protein IE1 [Human herpesvirus 5] | AKI12344.1 |
| UL123 | immediate early transcriptional regulator [Human herpesvirus 5] | ACL27089.1 |
| UL123 | immediate early transcriptional regulator [Human herpesvirus 5] | ACL27062.1 |
| UL123 | immediate early transcriptional regulator [Human herpesvirus 5] | ACL27057.1 |
| UL128 | envelope protein UL128 [Human herpesvirus 5] | AAR31451.1 |
| UL128 | UL128 [Human herpesvirus 5] | ABA86617.1 |
| UL128 | envelope protein UL128 [Human herpesvirus 5] | AAR31335.1 |
| UL128 | envelope protein UL128 [Human herpesvirus 5] | ADV04433.1 |
| UL128 | UL128 [Human herpesvirus 5] | ADF30829.1 |
| UL128 | envelope protein UL128 [Human herpesvirus 5] | ACS92206.1 |
| UL128 | envelope protein UL128 [Human herpesvirus 5] | ADB84652.1 |
| UL128 | envelope protein UL128 [Human herpesvirus 5] | AHJ86203.1 |
| UL128 | envelope protein UL128 [Human herpesvirus 5] | AAO11759.2 |
| UL128 | envelope protein UL128 [Human herpesvirus 5] | AKI07662.1 |
| UL128 | UL128 [Human herpesvirus 5] | ABA86608.1 |
| UL128 | envelope protein UL128 [Human herpesvirus 5] | AKI12512.1 |
| UL128 | envelope protein UL128 [Human herpesvirus 5] | AKI21705.1 |
| UL128 | envelope protein UL128 [Human herpesvirus 5] | AKI20034.1 |
| UL128 | RecName: Full = Uncharacterized protein UL128 | P16837.2 |
| UL128 | UL128 [Human herpesvirus 5] | ABA86623.1 |
| UL128 | envelope protein UL128 [Human herpesvirus 5] | AKI16857.1 |
| UL128 | envelope protein UL128 [Human herpesvirus 5] | AKI18528.1 |
| UL128 | envelope protein UL128 [Human herpesvirus 5] | ADB84820.1 |
| UL128 | envelope protein UL128 [Human herpesvirus 5] | AAR31422.1 |
| UL128 | envelope protein UL128 [Human herpesvirus 5] | AGL96705.1 |
| UL128 | envelope protein UL128 [Human herpesvirus 5] | ACT81952.1 |
| UL128 | envelope protein UL128 [Human herpesvirus 5] | AKI18359.1 |
| UL128 | UL128 [Human herpesvirus 5] | AAO11775.2 |
| UL128 | UL128 [Human herpesvirus 5] | ABA86605.1 |
| UL128 | UL128 [Human herpesvirus 5] | ADF30833.1 |
| UL128 | envelope protein UL128 [Human herpesvirus 5] | AKI11182.1 |
| UL128 | envelope protein UL128 [Human herpesvirus 5] | AKI15691.1 |
| UL128 | UL128 [Human herpesvirus 5] | ABA86622.1 |
| UL128 | UL128 [Human herpesvirus 5] | ADF30832.1 |
| UL128 | UL128 [Human herpesvirus 5] | ABA86616.1 |
| UL128 | envelope protein UL128 [Human herpesvirus 5] | AAO11755.2 |
| UL128 | envelope protein UL128 [Human herpesvirus 5] | AFR55266.1 |
| UL128 | UL128 [Human herpesvirus 5] | ABA86618.1 |

TABLE 3-continued

CMV (Human herpesvirus 5) Amino Acid Sequences

| Protein | Name | GenBank Accession |
|---|---|---|
| UL128 | envelope protein UL128 [Human herpesvirus 5] | ADB84700.1 |
| UL128 | UL128 [Human herpesvirus 5] | ADE62337.1 |
| UL128 | UL128 [Human herpesvirus 5] | ADF30837.1 |
| UL128 | UL128 [Human herpesvirus 5] | ABA86604.1 |
| UL128 | envelope protein UL128 [Human herpesvirus 5] | AKI21208.1 |
| UL128 | UL128 [Human herpesvirus 5] | ABA86609.1 |
| UL128 | envelope protein UL128 [Human herpesvirus 5] | AKI10514.1 |
| UL128 | truncated UL128 protein [Human herpesvirus 5] | ADG36331.1 |
| UL128 | HCMVUL128 [Human herpesvirus 5] | CAA35330.1 |
| UL130 | UL130 [Human herpesvirus 5] | ABA86653.1 |
| UL130 | UL130 [Human herpesvirus 5] | ABA86666.1 |
| UL130 | UL130 [Human herpesvirus 5] | ABA86652.1 |
| UL130 | envelope glycoprotein UL130 [Human herpesvirus 5] | YP_081565.1 |
| UL130 | envelope glycoprotein UL130 [Human herpesvirus 5] | AKI08835.1 |
| UL130 | UL130 [Human herpesvirus 5] | AAY33781.1 |
| UL130 | envelope glycoprotein UL130 [Human herpesvirus 5] | ACS92042.1 |
| UL130 | envelope glycoprotein UL130 [Human herpesvirus 5] | AKI10515.1 |
| UL130 | envelope glycoprotein UL130 [Human herpesvirus 5] | AKI07663.1 |
| UL130 | envelope glycoprotein UL130 [Human herpesvirus 5] | AHB19754.1 |
| UL130 | envelope glycoprotein UL130 [Human herpesvirus 5] | AFR55435.1 |
| UL130 | UL130 [Human herpesvirus 5] | AAY33778.1 |
| UL130 | envelope glycoprotein UL130 [Human herpesvirus 5] | AKI18864.1 |
| UL130 | envelope glycoprotein UL130 [Human herpesvirus 5] | AIC80537.1 |
| UL130 | envelope glycoprotein UL130 [Human herpesvirus 5] | ADB44105.1 |
| UL130 | envelope glycoprotein UL130 [Human herpesvirus 5] | ADB84797.1 |
| UL130 | envelope glycoprotein UL130 [Human herpesvirus 5] | AKI22373.1 |
| UL130 | envelope glycoprotein UL130 [Human herpesvirus 5] | AGL96706.1 |
| UL130 | envelope glycoprotein UL130 [Human herpesvirus 5] | AKI22042.1 |
| UL130 | envelope glycoprotein UL130 [Human herpesvirus 5] | AHJ86204.1 |
| UL130 | RecName: Full = Uncharacterized protein UL130 | P16772.1 |
| UL130 | envelope glycoprotein UL130 [Human herpesvirus 5] | AKI20706.1 |
| UL130 | UL130 [Human herpesvirus 5] | ABA86662.1 |
| UL130 | UL130 [Human herpesvirus 5] | ABA86665.1 |
| UL130 | UL130 [Human herpesvirus 5] | ABA86659.1 |
| UL130 | UL130 [Human herpesvirus 5] | ADF30831.1 |
| UL130 | orf UL130 [Human herpesvirus 5] | AAA85889.1 |
| UL130 | envelope glycoprotein UL130 [Human herpesvirus 5] | AKI11183.1 |
| UL130 | envelope glycoprotein UL130 [Human herpesvirus 5] | AKI19031.1 |
| UL130 | UL130 [Human herpesvirus 5] | ADE62342.1 |
| UL130 | envelope glycoprotein UL130 [Human herpesvirus 5] | AFR55099.1 |
| UL130 | envelope glycoprotein UL130 [Human herpesvirus 5] | AAR31336.1 |
| UL130 | UL130 [Human herpesvirus 5] | ABA86654.1 |
| UL130 | envelope glycoprotein UL130 [Human herpesvirus 5] | AKI17191.1 |
| UL130 | envelope glycoprotein UL130 [Human herpesvirus 5] | ADB84701.1 |
| UL130 | UL130 [Human herpesvirus 5] | ADF30838.1 |
| UL130 | envelope glycoprotein UL130 [Human herpesvirus 5] | AKI15859.1 |
| UL130 | UL130 [Human herpesvirus 5] | ABA86651.1 |
| UL130 | envelope glycoprotein UL130 [Human herpesvirus 5] | AFR55267.1 |
| UL130 | envelope glycoprotein UL130 [Human herpesvirus 5] | ACS92207.1 |
| UL130 | envelope glycoprotein UL130 [Human herpesvirus 5] | AAR31307.1 |
| UL130 | envelope glycoprotein UL130 [Human herpesvirus 5] | AKI15358.1 |
| UL130 | envelope glycoprotein UL130 [Human herpesvirus 5] | AKI21042.1 |
| UL130 | envelope glycoprotein UL130 [Human herpesvirus 5] | AKI16360.1 |
| UL130 | UL130 [Human herpesvirus 5] | ABA86661.1 |
| UL130 | envelope glycoprotein UL130 [Human herpesvirus 5] | AHB19920.1 |
| UL130 | UL130 [Human herpesvirus 5] | ABV71640.1 |
| UL130 | envelope glycoprotein UL130 [Human herpesvirus 5] | AKI23375.1 |
| UL130 | envelope glycoprotein UL130 [Human herpesvirus 5] | AKI08333.1 |
| UL130 | envelope glycoprotein UL130 [Human herpesvirus 5] | AKI21377.1 |
| UL130 | envelope glycoprotein UL130 [Human herpesvirus 5] | AKI16526.1 |
| UL130 | UL130 [Human herpesvirus 5] | ADE62336.1 |
| UL130 | envelope glycoprotein UL130 [Human herpesvirus 5] | AKI14017.1 |
| UL130 | envelope glycoprotein UL130 [Human herpesvirus 5] | AKI09843.1 |
| UL130 | mutant fusion protein [Human herpesvirus 5] | ADE62322.1 |
| UL130 | envelope glycoprotein UL130 [Human herpesvirus 5] | AKI12013.1 |
| UL130 | envelope glycoprotein UL130 [Human herpesvirus 5] | AKI20371.1 |
| UL130 | envelope glycoprotein UL130 [Human herpesvirus 5] | ACZ81666.1 |
| UL130 | envelope glycoprotein UL130 [Human herpesvirus 5] | AAR31365.1 |
| UL130 | envelope glycoprotein UL130 [Human herpesvirus 5] | AAO11754.1 |
| UL131A | envelope protein UL131A [Human herpesvirus 5] | YP_081566.1 |
| UL131A | envelope protein UL131A [Human herpesvirus 5] | AKI12514.1 |
| UL131A | envelope protein UL131A [Human herpesvirus 5] | AKI11683.1 |
| UL131A | envelope protein UL131A [Human herpesvirus 5] | AAO11766.1 |
| UL131A | UL131A [Human herpesvirus 5] | ABA86643.1 |
| UL131A | UL131A [Human herpesvirus 5] | ADE62341.1 |

TABLE 3-continued

CMV (Human herpesvirus 5) Amino Acid Sequences

| Protein | Name | GenBank Accession |
|---|---|---|
| UL131A | truncated envelope protein UL131A [Human herpesvirus 5] | ADV04435.1 |
| UL131A | envelope protein UL131A [Human herpesvirus 5] | AFR56272.1 |
| UL131A | envelope protein UL131A [Human herpesvirus 5] | AKI11018.1 |
| UL131A | envelope protein UL131A [Human herpesvirus 5] | AHB19755.1 |
| UL131A | envelope protein UL131A [Human herpesvirus 5] | AKI12348.1 |
| UL131A | UL131a protein [Human herpesvirus 5] | ADG36333.1 |
| UL131A | UL131A [Human herpesvirus 5] | ABA86640.1 |
| UL131A | envelope protein UL131A [Human herpesvirus 5] | AKI08836.1 |
| UL131A | UL131A [Human herpesvirus 5] | ABA86639.1 |
| UL131A | envelope protein UL131A [Human herpesvirus 5] | AKI10182.1 |
| UL131A | envelope protein UL131A [Human herpesvirus 5] | ADB84774.1 |
| UL131A | envelope protein UL131A [Human herpesvirus 5] | ADB84822.1 |
| UL131A | UL131A [Human herpesvirus 5] | ADF30839.1 |
| UL131A | UL131A [Human herpesvirus 5] | ABA86648.1 |
| UL131A | UL131A [Human herpesvirus 5] | ABA86635.1 |
| UL131A | envelope protein UL131A [Human herpesvirus 5] | AFR55436.1 |
| UL131A | UL131A [Human herpesvirus 5] | ABA86637.1 |
| UL131A | UL131A [Human herpesvirus 5] | ABA86644.1 |
| UL131A | UL131A [Human herpesvirus 5] | ABA86647.1 |
| UL131A | UL131A [Human herpesvirus 5] | ABA86629.1 |
| UL131A | UL131A [Human herpesvirus 5] | ABA86630.1 |
| UL131A | UL131A [Human herpesvirus 5] | ABA86646.1 |
| UL55 (gB) | envelope glycoprotein B [Human herpesvirus 5] | ACS91991.1 |
| UL55 (gB) | envelope glycoprotein B [Human herpesvirus 5] | AKI12129.1 |
| UL55 (gB) | envelope glycoprotein B [Human herpesvirus 5] | ACZ79977.1 |
| UL55 (gB) | envelope glycoprotein B [Human herpesvirus 5] | AFR55216.1 |
| UL55 (gB) | envelope glycoprotein B [Human herpesvirus 5] | AKI22656.1 |
| UL55 (gB) | glycoprotein B [Human herpesvirus 5] | AAA45934.1 |
| UL55 (gB) | envelope glycoprotein B [Human herpesvirus 5] | AFR54884.1 |
| UL55 (gB) | envelope glycoprotein B [Human herpesvirus 5] | AKI22156.1 |
| UL55 (gB) | envelope glycoprotein B [Human herpesvirus 5] | AKI14299.1 |
| UL55 (gB) | envelope glycoprotein B [Human herpesvirus 5] | ADV04383.1 |
| UL55 (gB) | envelope glycoprotein B [Human herpesvirus 5] | AKI20990.1 |
| UL55 (gB) | envelope glycoprotein B [Human herpesvirus 5] | AKI09624.1 |
| UL55 (gB) | envelope glycoprotein B [Human herpesvirus 5] | ADD39116.1 |
| UL55 (gB) | envelope glycoprotein B [Human herpesvirus 5] | ACT81737.1 |
| UL55 (gB) | envelope glycoprotein B [Human herpesvirus 5] | AKI11131.1 |
| UL55 (gB) | envelope glycoprotein B [Human herpesvirus 5] | AKI17642.1 |
| UL55 (gB) | envelope glycoprotein B [Human herpesvirus 5] | AIC80652.1 |
| UL55 (gB) | envelope glycoprotein B [Human herpesvirus 5] | AFR55719.1 |
| UL55 (gB) | envelope glycoprotein B [Human herpesvirus 5] | AKI09288.1 |
| UL55 (gB) | glycoprotein B [Human herpesvirus 5] | AAA45930.1 |
| UL55 (gB) | envelope glycoprotein B [Human herpesvirus 5] | AKI12960.1 |
| UL55 (gB) | glycoprotein B [Human herpesvirus 5] | AAA45926.1 |
| UL55 (gB) | glycoprotein B [Human herpesvirus 5] | AAA45925.1 |
| UL55 (gB) | envelope glycoprotein B [Human herpesvirus 5] | AII80437.1 |
| UL55 (gB) | envelope glycoprotein B [Human herpesvirus 5] | AKI22824.1 |
| UL55 (gB) | envelope glycoprotein B [Human herpesvirus 5] | AHV84013.1 |
| UL55 (gB) | envelope glycoprotein B [Human herpesvirus 5] | AKI07947.1 |
| UL55 (gB) | envelope glycoprotein B [Human herpesvirus 5] | AFR54557.1 |
| UL55 (gB) | envelope glycoprotein B [Human herpesvirus 5] | AHB19702.1 |
| UL55 (gB) | RecName: Full = Envelope glycoprotein B; Short = gB; Flags: Precursor | P06473.1 |
| UL55 (gB) | glycoprotein B [Human herpesvirus 5] | ADB92600.1 |
| UL55 (gB) | envelope glycoprotein B [Human herpesvirus 5] | ADE88063.1 |
| UL55 (gB) | envelope glycoprotein B [Human herpesvirus 5] | AHJ86153.1 |
| UL55 (gB) | envelope glycoprotein B [Human herpesvirus 5] | AFR55885.1 |
| UL55 (gB) | UL55 [Human herpesvirus 5] | ABV71586.1 |
| UL55 (gB) | envelope glycoprotein B [Human herpesvirus 5] | ACS92156.1 |
| UL55 (gB) | envelope glycoprotein B [Human herpesvirus 5] | AKI23491.1 |
| UL55 (gB) | RecName: Full = Envelope glycoprotein B; Short = gB; Contains: RecName: Full = Glycoprotein GP55; Flags: Precursor | P13201.1 |
| UL55 (gB) | glycoprotein B [Human herpesvirus 5] | ABQ23592.1 |
| UL55 (gB) | glycoprotein B [Human herpesvirus 5] | AAB07485.1 |
| UL55 (gB) | envelope glycoprotein B [Human herpesvirus 5] | ACM48044.1 |
| UL55 (gB) | glycoprotein B [Human herpesvirus 5] | AAA45928.1 |
| UL55 (gB) | envelope glycoprotein B [Human herpesvirus 5] | ACS32370.1 |
| UL55 (gB) | envelope glycoprotein B [Human herpesvirus 5] | AKI19983.1 |
| UL55 (gB) | envelope glycoprotein B [Human herpesvirus 5] | AKI13294.1 |
| UL55 (gB) | envelope glycoprotein B [Human herpesvirus 5] | AFR55048.1 |
| UL55 (gB) | envelope glycoprotein B [Human herpesvirus 5] | AKI19483.1 |
| UL55 (gB) | envelope glycoprotein B [Human herpesvirus 5] | YP_081514.1 |
| UL55 (gB) | envelope glycoprotein B [Human herpesvirus 5] | AKI20319.1 |
| UL55 (gB) | envelope glycoprotein B [Human herpesvirus 5] | AHB20033.1 |
| UL55 (gB) | envelope glycoprotein B [Human herpesvirus 5] | AKI23324.1 |
| UL55 (gB) | envelope glycoprotein B [Human herpesvirus 5] | AKI13965.1 |

TABLE 3-continued

CMV (Human herpesvirus 5) Amino Acid Sequences

| Protein | Name | GenBank Accession |
|---|---|---|
| UL55 (gB) | envelope glycoprotein B [Human herpesvirus 5] | ACS93398.1 |
| UL55 (gB) | envelope glycoprotein B [Human herpesvirus 5] | AKI08783.1 |
| UL55 (gB) | envelope glycoprotein B [Human herpesvirus 5] | AFR55550.1 |
| UL55 (gB) | envelope glycoprotein B [Human herpesvirus 5] | AKI19648.1 |
| UL55 (gB) | envelope glycoprotein B [Human herpesvirus 5] | AGL96655.1 |
| UL55 (gB) | glycoprotein B [Human herpesvirus 5] | AAA45932.1 |
| UL55 (gB) | glycoprotein B [Human herpesvirus 5] | AAA45933.1 |
| UL55 (gB) | glycoprotein B [Gorilla gorilla cytomegalovirus 2.1] | ACT68391.2 |
| UL55 (gB) | glycoprotein B [Human herpesvirus 5] | AAA45931.1 |
| UL55 (gB) | glycoprotein B [Human herpesvirus 5] | AAA45923.1 |
| UL55 (gB) | glycoprotein gB precursor [synthetic construct] | AAT68257.1 |
| UL55 (gB) | glycoprotein B [Human herpesvirus 5] | AAA45924.1 |
| UL55 (gB) | glycoprotein B [Human herpesvirus 5] | AAA45935.1 |
| UL73 (gN) | structural glycoprotein gpUL73 [Human herpesvirus 5] | AAM82374.1 |
| UL73 (gN) | structural glycoprotein gpUL73 [Human herpesvirus 5] | AAG23509.1 |
| UL73 (gN) | structural glycoprotein gpUL73 [Human herpesvirus 5] | AAM82416.1 |
| UL73 (gN) | envelope glycoprotein gpUL73 [Human herpesvirus 5] | AAO24877.1 |
| UL73 (gN) | envelope glycoprotein N [Human herpesvirus 5] | ADE20136.1 |
| UL73 (gN) | envelope glycoprotein N [Human herpesvirus 5] | YP_081521.1 |
| UL73 (gN) | glycoprotein N [Human herpesvirus 5] | ACI45834.1 |
| UL73 (gN) | envelope glycoprotein gpUL73 [Human herpesvirus 5] | AAO27562.1 |
| UL73 (gN) | glycoprotein N [Human herpesvirus 5] | ACI45816.1 |
| UL73 (gN) | envelope glycoprotein N [Human herpesvirus 5] | ACS93313.1 |
| UL73 (gN) | envelope glycoprotein N [Human herpesvirus 5] | AKI07618.1 |
| UL73 (gN) | glycoprotein N [Human herpesvirus 5] | ADC32373.1 |
| UL73 (gN) | structural glycoprotein gpUL73 [Human herpesvirus 5] | AAG23521.1 |
| UL73 (gN) | glycoprotein N [Human herpesvirus 5] | ADH42929.1 |
| UL73 (gN) | glycoprotein N [Human herpesvirus 5] | ADC32376.1 |
| UL73 (gN) | glycoprotein N [Human herpesvirus 5] | ADH42919.1 |
| UL73 (gN) | glycoprotein N [Human herpesvirus 5] | ACI45808.1 |
| UL73 (gN) | envelope glycoprotein gpUL73 [Human herpesvirus 5] | AAO24851.1 |
| UL73 (gN) | glycoprotein N [Human herpesvirus 5] | ABY48941.1 |
| UL73 (gN) | structural glycoprotein gpUL73 [Human herpesvirus 5] | AAG23512.1 |
| UL73 (gN) | structural glycoprotein gpUL73 [Human herpesvirus 5] | AAM82399.1 |
| UL73 (gN) | UL73 [Human herpesvirus 5] | ABZ04151.1 |
| UL73 (gN) | envelope glycoprotein gpUL73 [Human herpesvirus 5] | AAO24895.1 |
| UL73 (gN) | structural glycoprotein gpUL73 [Human herpesvirus 5] | AAM82420.1 |
| UL73 (gN) | structural glycoprotein UL73 [Human herpesvirus 5] | AAL77782.1 |
| UL73 (gN) | glycoprotein N [Human herpesvirus 5] | ADH42921.1 |
| UL73 (gN) | structural glycoprotein gpUL73 [Human herpesvirus 5] | AAM82396.1 |
| UL73 (gN) | envelope glycoprotein gpUL73 [Human herpesvirus 5] | AAO24881.1 |
| UL73 (gN) | envelope glycoprotein gpUL73 [Human herpesvirus 5] | AAO24889.1 |
| UL73 (gN) | envelope glycoprotein gpUL73 [Human herpesvirus 5] | AAO24892.1 |
| UL73 (gN) | glycoprotein N [Human herpesvirus 5] | ABY48942.1 |
| UL73 (gN) | glycoprotein N [Human herpesvirus 5] | ACI45800.1 |
| UL73 (gN) | envelope glycoprotein gpUL73 [Human herpesvirus 5] | AAO27565.1 |
| UL73 (gN) | glycoprotein N [Human herpesvirus 5] | ABY48936.1 |
| UL73 (gN) | glycoprotein N [Human herpesvirus 5] | ABY48935.1 |
| UL73 (gN) | structural glycoprotein gpUL73 [Human herpesvirus 5] | AAM82375.1 |
| UL73 (gN) | structural glycoprotein gpUL73 [Human herpesvirus 5] | AAM82403.1 |
| UL73 (gN) | envelope glycoprotein N [Human herpesvirus 5] | AHB19542.1 |
| UL73 (gN) | envelope glycoprotein N [Human herpesvirus 5] | AKI23166.1 |
| UL73 (gN) | structural glycoprotein gpUL73 [Human herpesvirus 5] | AAM82412.1 |
| UL73 (gN) | envelope glycoprotein gpUL73 [Human herpesvirus 5] | AAO24836.1 |
| UL73 (gN) | UL73 [Human herpesvirus 5] | ABZ04148.1 |
| UL73 (gN) | envelope glycoprotein N [Human herpesvirus 5] | ACS93153.1 |
| UL73 (gN) | envelope glycoprotein N [Human herpesvirus 5] | AGT36363.1 |
| UL73 (gN) | structural glycoprotein gpUL73 [Human herpesvirus 5] | AAG23511.1 |
| UL73 (gN) | glycoprotein N [Human herpesvirus 5] | ADH42925.1 |
| UL73 (gN) | glycoprotein N [Human herpesvirus 5] | ACI45830.1 |
| UL73 (gN) | structural glycoprotein gpUL73 [Human herpesvirus 5] | AAG23510.1 |
| UL73 (gN) | glycoprotein N [Human herpesvirus 5] | ACI45798.1 |
| UL73 (gN) | structural glycoprotein UL73 [Human herpesvirus 5] | AAL77762.1 |
| UL73 (gN) | glycoprotein N [Human herpesvirus 5] | ADH42926.1 |
| UL73 (gN) | structural glycoprotein UL73 [Human herpesvirus 5] | AAL77766.1 |
| UL73 (gN) | glycoprotein N [Human herpesvirus 5] | ACI45823.1 |
| UL73 (gN) | structural glycoprotein gpUL73 [Human herpesvirus 5] | AAM82378.1 |
| UL73 (gN) | structural glycoprotein gpUL73 [Human herpesvirus 5] | AAM82379.1 |
| UL73 (gN) | UL73 [Human herpesvirus 5] | ABZ04149.1 |
| UL73 (gN) | structural glycoprotein UL73 [Human herpesvirus 5] | AAL77764.1 |
| UL73 (gN) | glycoprotein N [Human herpesvirus 5] | ACI45835.1 |
| UL73 (gN) | glycoprotein N [Human herpesvirus 5] | ACI45825.1 |
| UL73 (gN) | glycoprotein N [Human herpesvirus 5] | ADH42931.1 |
| UL73 (gN) | envelope glycoprotein N [Human herpesvirus 5] | ACS93218.1 |
| UL73 (gN) | structural glycoprotein gpUL73 [Human herpesvirus 5] | AAM82408.1 |

TABLE 3-continued

CMV (Human herpesvirus 5) Amino Acid Sequences

| Protein | Name | GenBank Accession |
|---|---|---|
| UL73 (gN) | glycoprotein N [Human herpesvirus 5] | ACI45831.1 |
| UL73 (gN) | envelope glycoprotein gpUL73 [Human herpesvirus 5] | AAO27561.1 |
| UL73 (gN) | glycoprotein N [Human herpesvirus 5] | ACI45826.1 |
| UL74 (gO) | UL74 protein [Human herpesvirus 5] | AAN40064.1 |
| UL74 (gO) | envelope glycoprotein O [Human herpesvirus 5] | AKI16316.1 |
| UL74 (gO) | envelope glycoprotein O [Human herpesvirus 5] | ACS93259.1 |
| UL74 (gO) | UL74 protein [Human herpesvirus 5] | AAN40079.1 |
| UL74 (gO) | envelope glycoprotein O [Human herpesvirus 5] | AKI18316.1 |
| UL74 (gO) | glycoprotein O [Human herpesvirus 5] | ABY48961.1 |
| UL74 (gO) | glycoprotein O [Human herpesvirus 5] | ABY48960.1 |
| UL74 (gO) | glycoprotein O [Human herpesvirus 5] | ABY48959.1 |
| UL74 (gO) | envelope glycoprotein O [Human herpesvirus 5] | ACS93169.1 |
| UL74 (gO) | UL74 protein [Human herpesvirus 5] | AAN40044.1 |
| UL74 (gO) | envelope glycoprotein O [Human herpesvirus 5] | ACS93340.1 |
| UL74 (gO) | RecName: Full = Glycoprotein O; Short = gO; Flags: Precursor | P16750.1 |
| UL74 (gO) | UL74 protein [Human herpesvirus 5] | AAN40046.1 |
| UL74 (gO) | UL74 protein [Human herpesvirus 5] | AAN40054.1 |
| UL74 (gO) | envelope glycoprotein O [Human herpesvirus 5] | AKI08959.1 |
| UL74 (gO) | envelope glycoprotein O [Human herpesvirus 5] | AKI20327.1 |
| UL74 (gO) | UL74 protein [Human herpesvirus 5] | AAN40071.1 |
| UL74 (gO) | envelope glycoprotein O [Human herpesvirus 5] | AHB19710.1 |
| UL74 (gO) | envelope glycoprotein O [Human herpesvirus 5] | AKI07787.1 |
| UL74 (gO) | UL74 protein [Human herpesvirus 5] | AAN40043.1 |
| UL74 (gO) | UL74 protein [Human herpesvirus 5] | AAN40078.1 |
| UL74 (gO) | envelope glycoprotein O [Human herpesvirus 5] | ACS93309.1 |
| UL74 (gO) | envelope glycoprotein O [Human herpesvirus 5] | ACS93234.1 |
| UL74 (gO) | UL74 protein [Human herpesvirus 5] | AAN40040.1 |
| UL74 (gO) | envelope glycoprotein O [Human herpesvirus 5] | AKI19491.1 |
| UL74 (gO) | envelope glycoprotein O [Human herpesvirus 5] | AKI16979.1 |
| UL74 (gO) | envelope glycoprotein O [Human herpesvirus 5] | AKI20998.1 |
| UL74 (gO) | envelope glycoprotein O [Human herpesvirus 5] | AKI23000.1 |
| UL74 (gO) | envelope glycoprotein O [Human herpesvirus 5] | AKI10806.1 |
| UL74 (gO) | UL74 protein [Human herpesvirus 5] | AAN40073.1 |
| UL74 (gO) | UL74 protein [Human herpesvirus 5] | AAN40057.1 |
| UL74 (gO) | UL74 protein [Human herpesvirus 5] | AAN40050.1 |
| UL74 (gO) | glycoprotein O [Human herpesvirus 5] | ABY48952.1 |
| UL74 (gO) | envelope glycoprotein O [Human herpesvirus 5] | AKI09296.1 |
| UL74 (gO) | envelope glycoprotein O [Human herpesvirus 5] | ACS93149.1 |
| UL74 (gO) | envelope glycoprotein O [Human herpesvirus 5] | AKI14979.1 |
| UL74 (gO) | UL74 protein [Human herpesvirus 5] | AAN40060.1 |
| UL74 (gO) | glycoprotein O [Human herpesvirus 5] | ABY48954.1 |
| UL74 (gO) | glycoprotein O [Human herpesvirus 5] | ABY48955.1 |
| UL74 (gO) | envelope glycoprotein O [Human herpesvirus 5] | ACS93219.1 |
| UL74 (gO) | envelope glycoprotein O [Human herpesvirus 5] | ACS93164.1 |
| UL74 (gO) | envelope glycoprotein O [Human herpesvirus 5] | YP__081522.1 |
| UL74 (gO) | glycoprotein O [Human herpesvirus 5] | ABY48956.1 |
| UL74 (gO) | envelope glycoprotein O [Human herpesvirus 5] | AKI11474.1 |
| UL74 (gO) | UL74 protein [Human herpesvirus 5] | AAN40039.1 |
| UL74 (gO) | UL74 protein [Human herpesvirus 5] | AAN40041.1 |
| UL74 (gO) | envelope glycoprotein O [Human herpesvirus 5] | ACS93154.1 |
| UL74 (gO) | envelope glycoprotein O [Human herpesvirus 5] | ACT81745.1 |
| UL74 (gO) | envelope glycoprotein O [Human herpesvirus 5] | ACS92164.1 |
| UL74 (gO) | UL74 protein [Human herpesvirus 5] | AAN40052.1 |
| UL74 (gO) | envelope glycoprotein O [Human herpesvirus 5] | AHJ86161.1 |
| UL74 (gO) | envelope glycoprotein O [Human herpesvirus 5] | ACS93204.1 |
| UL74 (gO) | envelope glycoprotein O [Human herpesvirus 5] | AKI15314.1 |
| UL74 (gO) | envelope glycoprotein O [Human herpesvirus 5] | ACZ80315.1 |
| UL74 (gO) | envelope glycoprotein O [Human herpesvirus 5] | AKI23332.1 |
| UL74 (gO) | envelope glycoprotein O [Human herpesvirus 5] | ACU83724.1 |
| UL74 (gO) | UL74 protein [Human herpesvirus 5] | AAN40047.1 |
| UL74 (gO) | envelope glycoprotein O [Human herpesvirus 5] | AHV84021.1 |
| UL74 (gO) | UL74 protein [Human herpesvirus 5] | AAN40056.1 |
| UL74 (gO) | envelope glycoprotein O [Human herpesvirus 5] | AKI22164.1 |
| UL74 (gO) | envelope glycoprotein O [Human herpesvirus 5] | ACS93189.1 |
| UL74 (gO) | UL74 protein [Human herpesvirus 5] | AAN40074.1 |
| UL74 (gO) | envelope glycoprotein O [Human herpesvirus 5] | AKI18820.1 |
| UL74 (gO) | envelope glycoprotein O [Human herpesvirus 5] | AKI07619.1 |
| UL74 (gO) | UL74 protein [Human herpesvirus 5] | AAN40072.1 |
| UL74 (gO) | envelope glycoprotein O [Human herpesvirus 5] | AKI19991.1 |
| UL74 (gO) | UL74 protein [Human herpesvirus 5] | AAN40062.1 |
| UL74 (gO) | envelope glycoprotein O [Human herpesvirus 5] | AKI10471.1 |
| UL74 (gO) | UL74 protein [Human herpesvirus 5] | AAN40042.1 |
| UL74 (gO) | glycoprotein O [Human herpesvirus 5] | AAT91377.1 |
| UL74 (gO) | glycoprotein O [Human herpesvirus 5] | ACI45857.1 |
| UL74 (gO) | UL74 protein [Human herpesvirus 5] | AAP88253.1 |

TABLE 3-continued

| CMV (Human herpesvirus 5) Amino Acid Sequences | | |
|---|---|---|
| Protein | Name | GenBank Accession |
| | RecName: Full = Large structural phosphoprotein; AltName: Full = 150 kDa matrix phosphoprotein; AltName: Full = 150 kDa phosphoprotein; Short = pp150; AltName: Full = Basic phosphoprotein; Short = BPP; AltName: Full = Phosphoprotein UL32; AltName: Full = Tegument protein UL32 | P08318.1 |
| | UL32 [Human herpesvirus 5] | ABV71562.1 |
| | UL32 [Human herpesvirus 5] | AAG31644.1 |
| | UL32 [Human herpesvirus 5] | AAS48942.1 |
| | UL83 [Human herpesvirus 5] | ABV71605.1 |
| | RecName: Full = 65 kDa phosphoprotein; Short = pp65; AltName: Full = 65 kDa matrix phosphoprotein; AltName: Full = Phosphoprotein UL83; AltName: Full = Tegument protein UL83 | P06725.2 |
| | RecName: Full = 65 kDa phosphoprotein; Short = pp65; AltName: Full = 64 kDa matrix phosphoprotein; Short = pp64; AltName: Full = GP64; AltName: Full = Phosphoprotein UL83; AltName: Full = Tegument protein UL83 [Human herpesvirus 5 strain Towne] | P18139.2 |
| | HCMVUL115 [Human herpesvirus 5] | CAA35317.1 |
| | truncated UL115 protein [Human herpesvirus 5] | ADG34192.1 |

Figure 1A:
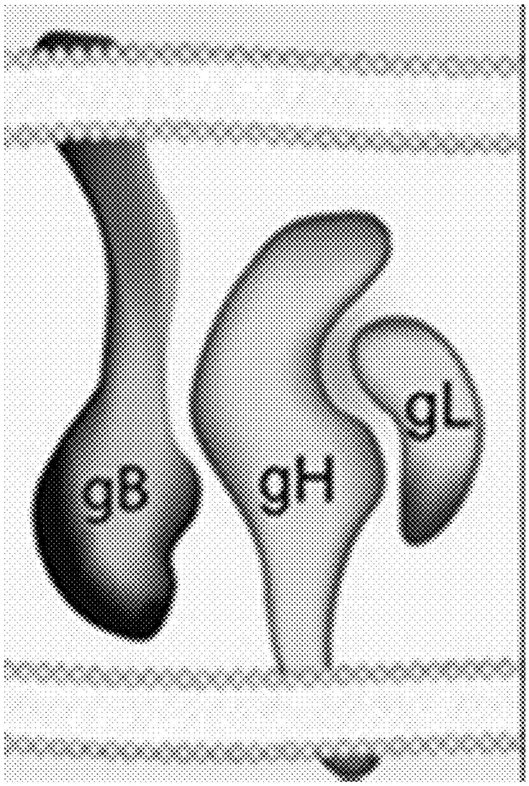
FIGS. 1A-1C depict different protein complexes formed by hCMV proteins. The tropism of hCMV is dictated by distinct protein complexes.
Figure 1B:
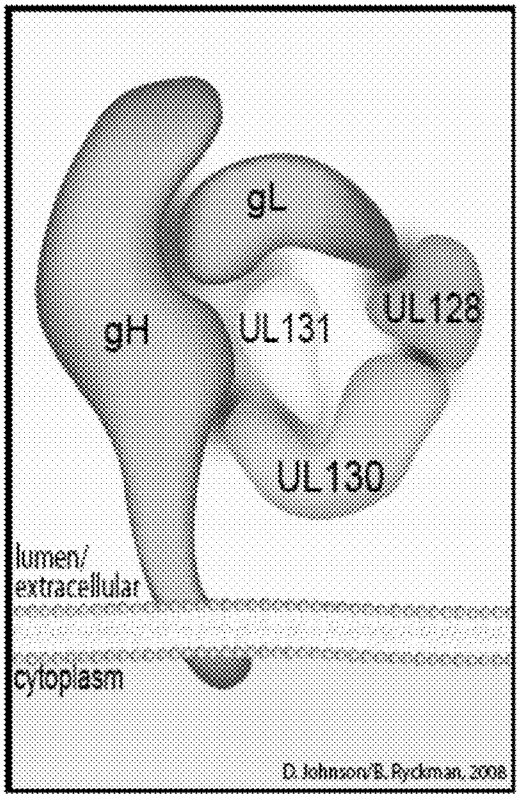
Figure 1C:
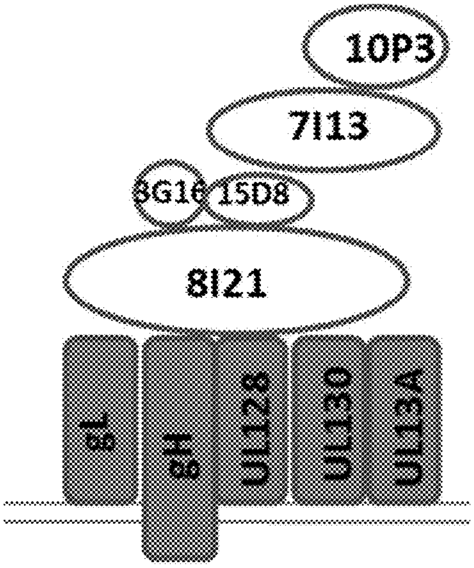
Figure 2A:
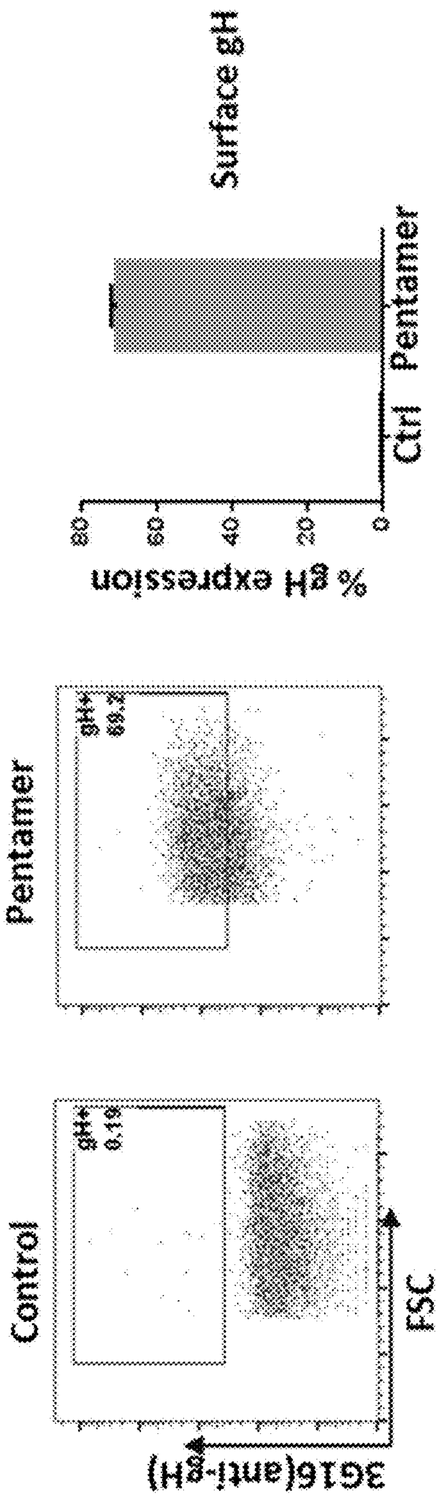
FIGS. 2A-2D show that delivery of pre-mixed mRNAs encoding the various subunits of hCMV pentamer leads to surface expression of the pentameric complex in HeLa cells.
Figure 2B:
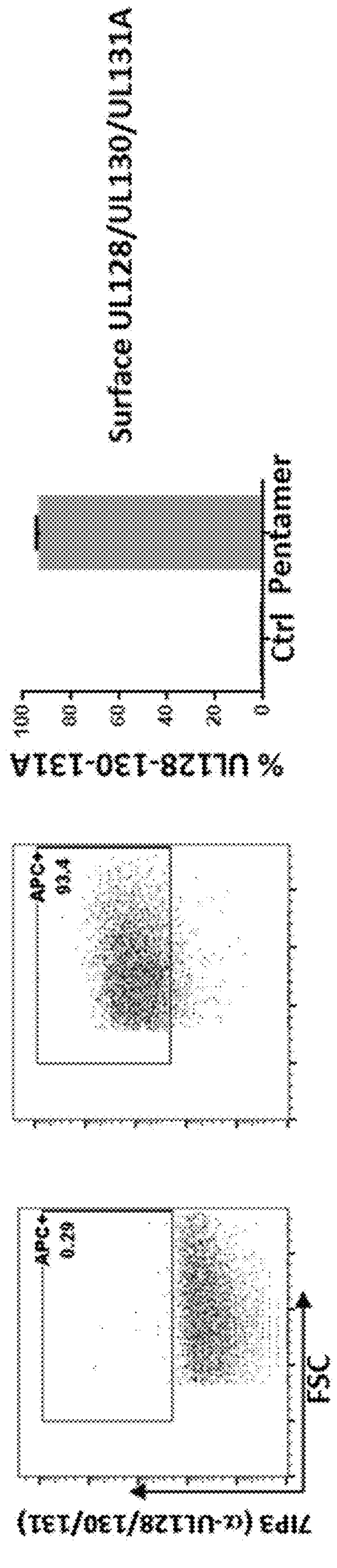
Figure 2C:
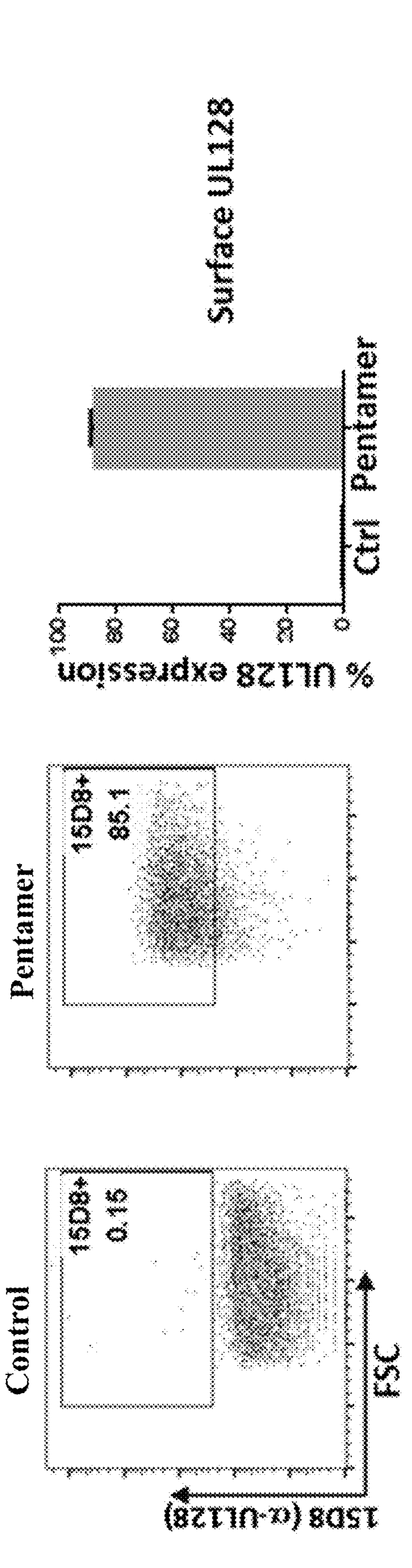
Figure 2D:
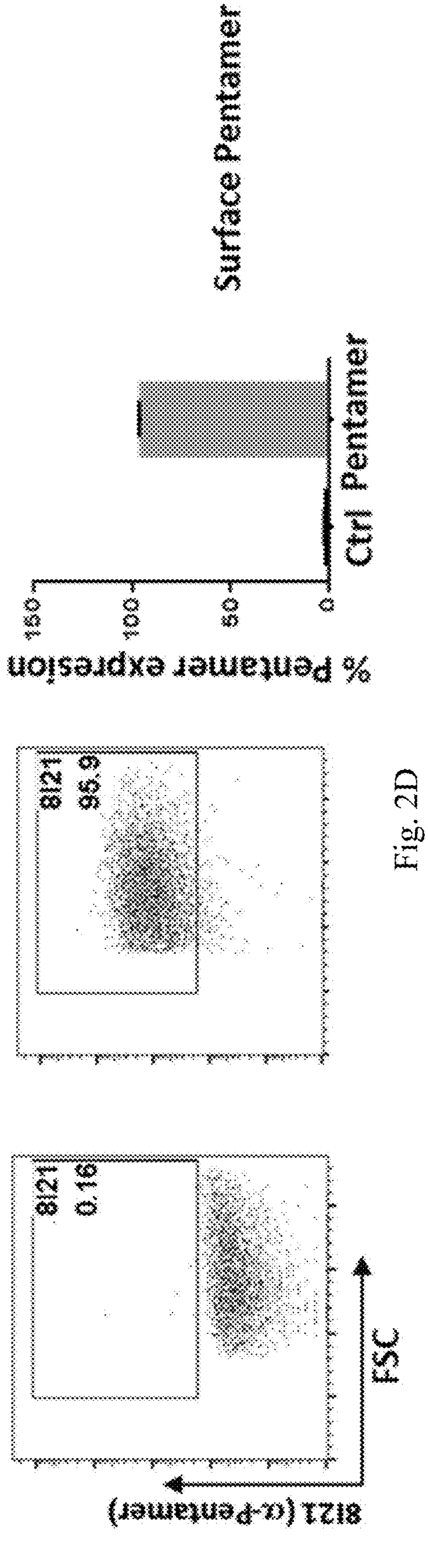

Example 22: Expression of mRNA Vaccine Constructs Encoding the hCMV Pentameric Complex in HeLa Cells Expression of mRNA vaccine constructs encoding the subunits of the hCMV pentameric complex, including gH, gL, UL128, UL130, and UL131A was tested (FIG. 1B). mRNAs encoding each subunit were mixed at a gH:gL:UL128:UL130:UL131A ratio of 4:2:1:1:1. The total amount of mRNA used for transfecting HeLa cells was 2 µg. The transfected HeLa cells were incubated for 24 hours before they were analyzed using fluorescence-activated cell sorting (FACS) on a flow cytometer for the surface expression of the pentameric complex subunits as well as the complete pentamer (FIGS. 2A-2D). Antibodies specific for gH, UL128, the UL128/130/131A complex, or the complete pentamer were used for the detection of surface expression of the proteins. Surface expression of gH, UL128, the UL128/130/131A complex, and the complete pentameric complex were detected in HeLa cells (FIGS. 2A-2D).

Similar results were observed when the pentameric components were transfected at equal mass ratios (FIGS. 43A-43B).

Figure 3A:
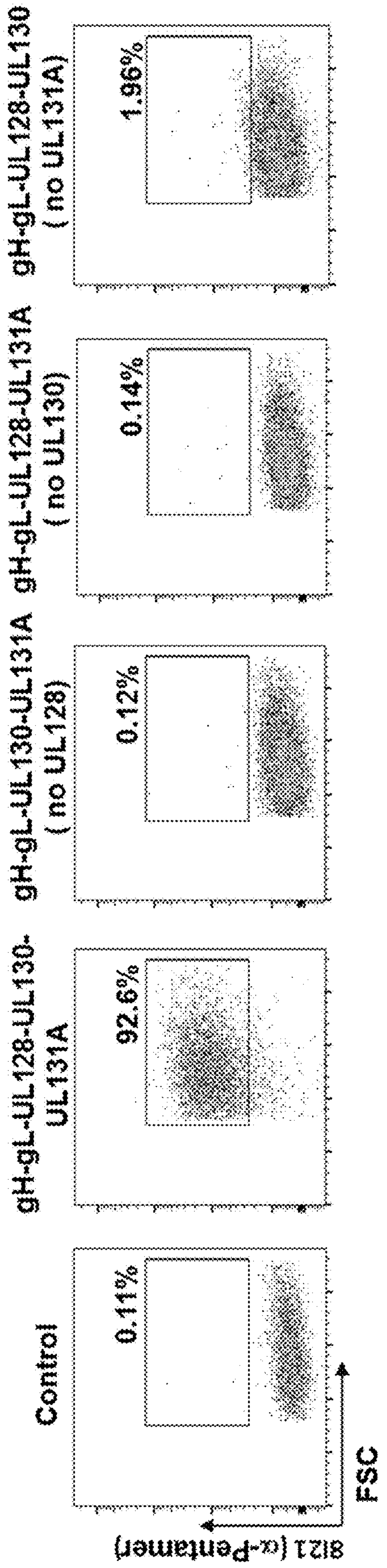
FIGS. 3A-3B show the surface expression of hCMV petameric complex (PC). Hela cells were transfected with mRNAs for all five subunits of the pentameric complex or lacking one of the subunits, as indicated. After 24 hr, cells were stained with anti-PC antibody 8121 and analyzed by flow cytometry. Representative flow cytometry plots (FIG. 3A) show PC surface expression. A bar graph (FIG. 3B) shows percent PC surface expression. hCMV pentameric complex was not observed to be expressed on the cell surface in the absence of one of the core subunits. Surface expression of the pentamer was only detected at high levels when all the core subunits were expressed.
Figure 3B:
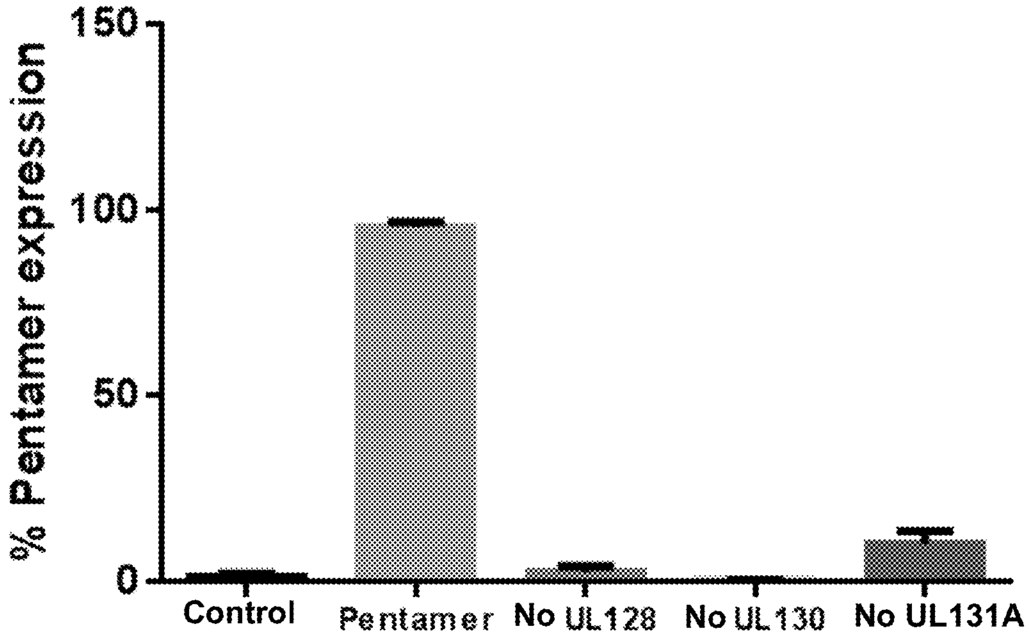

Different combinations of the mRNAs encoding the pentameric subunits were also tested to determine whether all of the core subunits were need for the surface expression of the complete pentameric complex (FIGS. 3A-3B). The experiments were carried out as described above with the indicated mRNA combinations. An antibody specific for the complete pentameric complex was used (8121). The results show that the pentameric complex does not express on the cell surface in the absence of any of UL128, UL130, or UL131A.

Figure 4A:
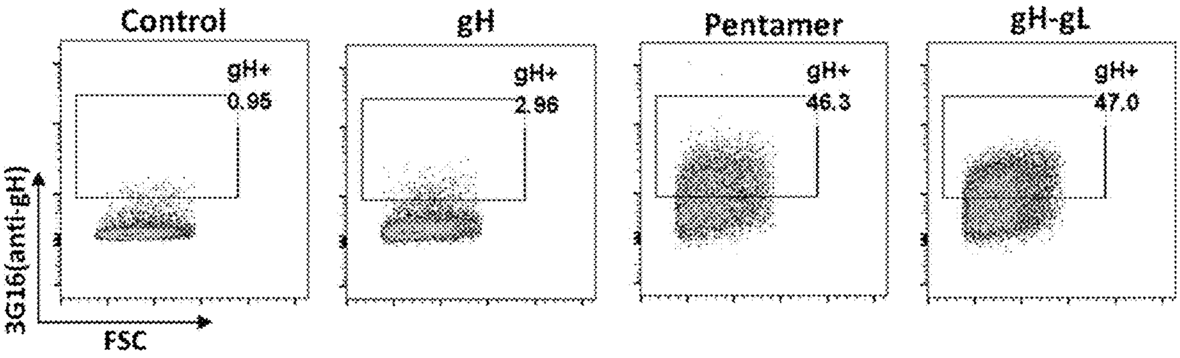
FIGS. 4A-4B shows the dimerization of gH-gL is sufficient to lead to surface expression of gH. The anti-gH antibody (3G16) was used for the detection of gH on the cell surface. When gH and gL were co-expressed, a similar level of gH was detected on the surface of HeLa cells as when all subunits in the pentameric complex were expressed. When gH was expressed alone, very little gH was detected on the surface of the transfected HeLa cells.
Figure 4B:
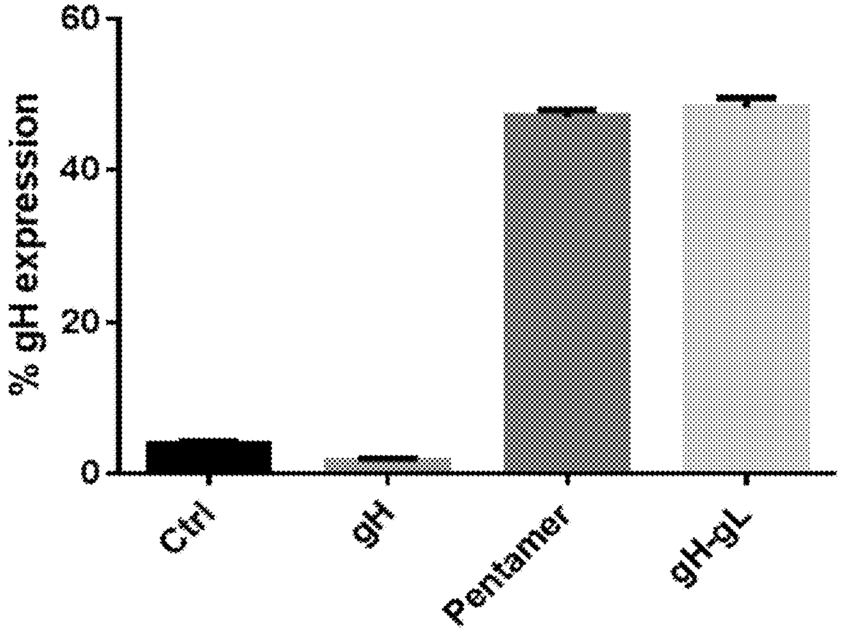

Next, the surface expression of the gH glycoprotein with or without gL was tested. The experiments were carried out as described above using mRNA constructs encoding gH, gH and gL, or constructs encoding the pentameric complex. An antibody specific for gH (3G16) was used. The results showed that expression of gH alone does not lead to gH expression on the cell surface. However, when gH was complexed with gL, a similar level of gH was detected on the surface of the HeLa cells as when all subunits in the pentameric complex were expressed (FIGS. 4A-4B).

Figure 5B:
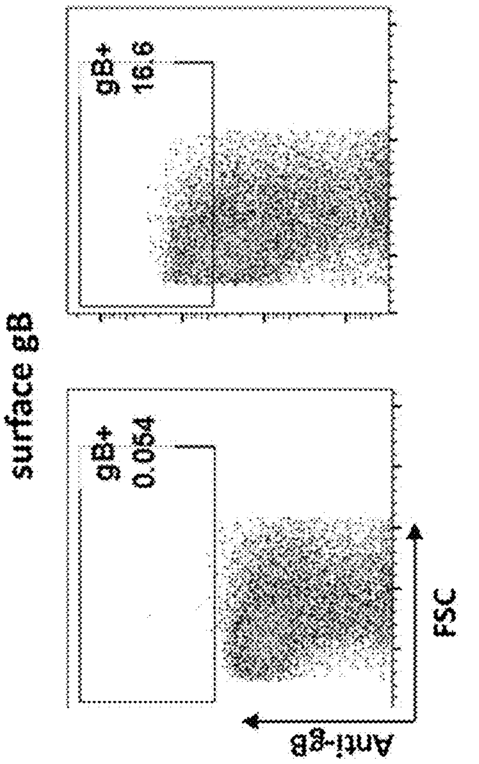
FIGS. 5A-5D show the intracellular and surface expression of hCMV antigen gB. The mRNA encoding gB was expressed both intracellularly and on the cell surface (FIGS. 5A-5C). Both gB precursor and the proteolytically processed, mature gB, were detected by anti-gB antibodies in an immunoblot (FIG. 5D). "*" indicates that the lane was overloaded.
Figure 5A:
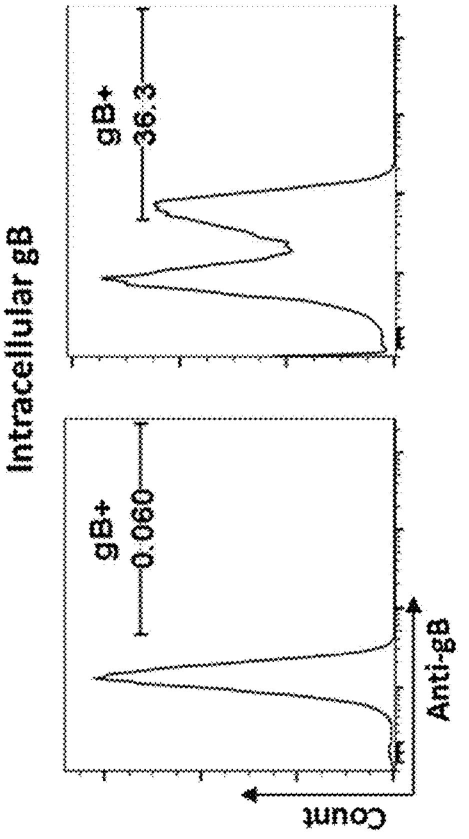
Figure 5C:
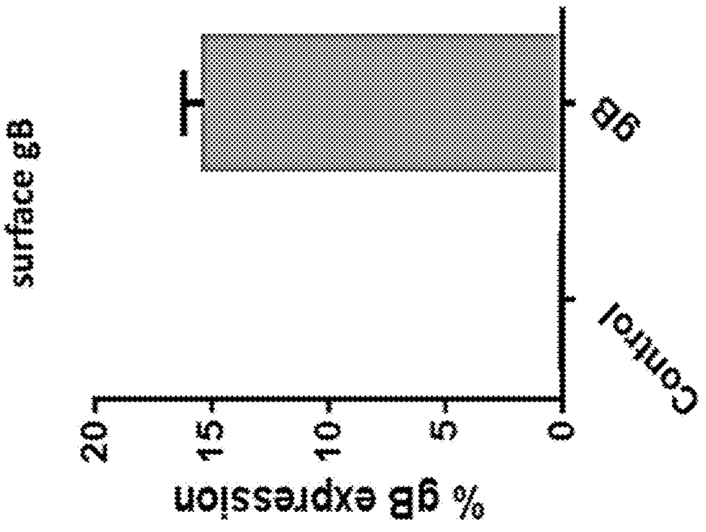
Figure 5D:
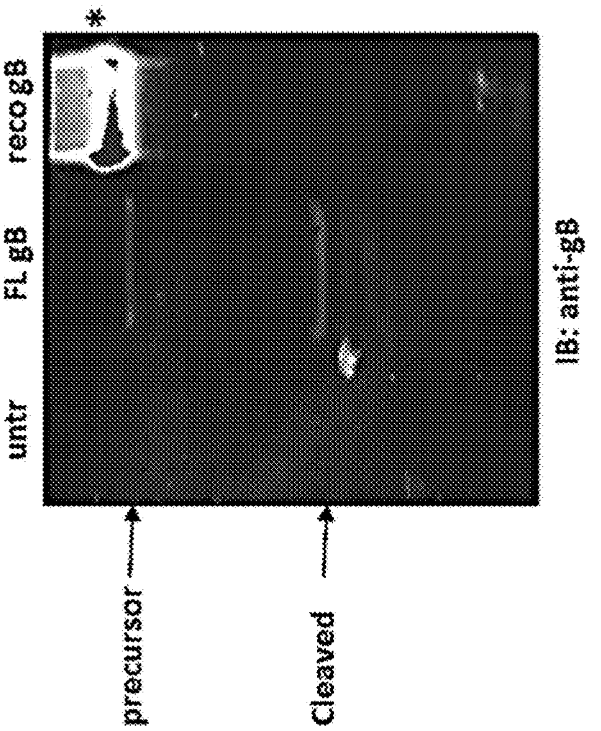

The intracellular and surface expression of gB was also tested using antibodies specific for gB. FIGS. 5A and 42A show intracellular gB expression. The surface expression of gB was measured by FACS on a flow cytometer and surface expression of gB was detected (FIGS. 5B and 42B). The quantification of gB surface expression is shown in FIGS. 5C, 42A and 42B. Further, an immunoblot conducted on cell lysates from HeLa cells transfected with mRNA constructs encoding gB is shown in FIGS. 5D and 42C. Untransfected HeLa cell lysates were used as a negative control and reconstituted full-length gB protein was used as a positive control. As shown in FIG. 5D, middle lane, or FIG. 42C, right lane, both full-length gB (the precursor) and the mature gB after proteolytic cleavage were detected.

Example 23: High Titers of Anti-Pentameric Antibodies Following Immunization with hCMV Pentameric Complex mRNA Vaccine Constructs The immunogenicity of candidate hCMV mRNA vaccine constructs encoding the pentameric complex subunits and/or the gB antigen was tested in mice. The immunization schedule and mRNA formulations areas shown in Table 4 below.

Mice were divided into groups (5 mice per group) and vaccinated on day 0, 21, and 42 via intramuscular (IM) routes. One group of mice was vaccinated with empty lipid nanoparticles (LNP) as a control. Other groups of mice received hCMV mRNA vaccine constructs encoding the pentameric complex, the gB antigen, both the pentameric complex and gB antigen, or either the pentameric protein complex or the gB protein antigen combined with MF59. When mRNA vaccine constructions were given, different preparation procedures were used. The "pre-mix" mRNAs were pre-mixed and then formulated, while the "post-mix" mRNAs were individually formulated and then mixed. The mRNAs encoding all the subunits of the pentameric complex were formulated with different ratios as shown in Table 4: gH-gL-UL128-UL130-UL131A was 4:2:1:1:1 or 1:1:1:1:1. gB+pentamer was formulated at 1:1:1:1:1:1. The dose schedules used are indicated in Table 4.

Figure 6:
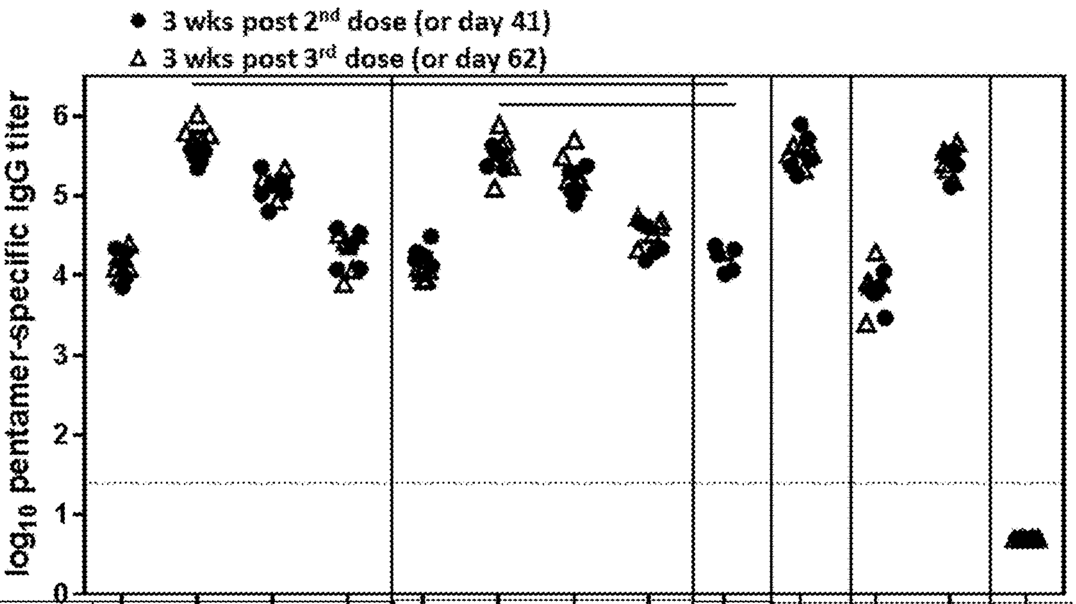
FIG. 6 shows an immunogenicity study of the hCMV pentameric complex mRNA vaccine constructs. Mice were vaccinated according to the vaccination schedule with indicated dosages of the mRNAs. High titers of anti-pentamer antibodies were detected in mice serum following the immunization. Different formulations of the pentamer mRNAs produced comparable levels of antibodies. A third immunization did not lead to boosting of antibody production.
Figure 7:
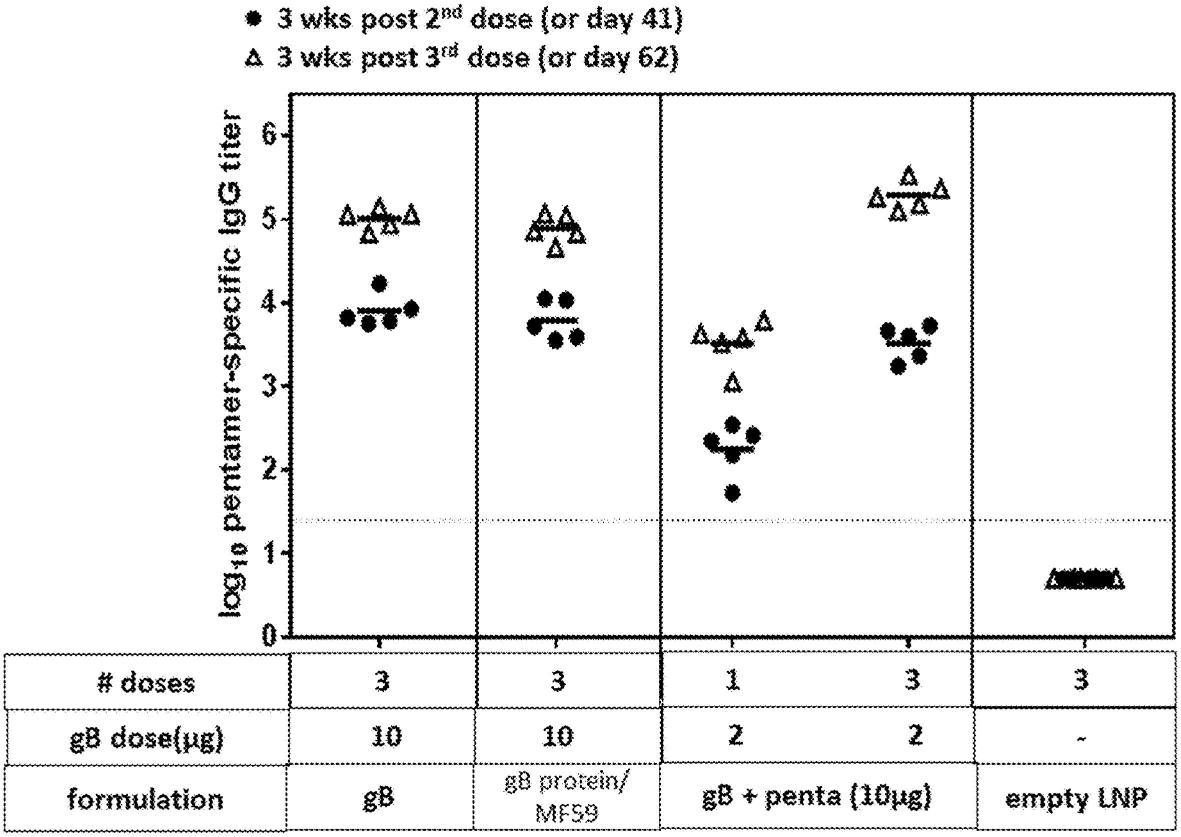
FIG. 7 shows an immunogenicity study of the hCMV gB mRNA vaccine construct, with or without the pentameric complex mRNA constructs. gB mRNA constructs produced similar IgG titers as the gB protein/MF59 antigens after 3 immunizations. A boost in IgG production was observed after the third immunization. Addition of pentameric mRNA constructs did not interefere with the induction of anti-gB IgG.

Mice sera were collected from each mouse on days −1 (pre-dos), 20, 41, 62, and 84. Individual bleeds from all time points were tested via ELISA assay carried out on plates coated with hCMV pentamers. Serum samples typically were diluted 1:100 for the assay. Incubation and washing protocols were performed using routine methods. Data was read at 450 nm wavelength. Data was reported and plotted (FIGS. 6 and 7). FIG. 6 shows that anti-pentamer-specific IgG were induced by hCMV mRNA vaccine constructs. However, little or no boosting was observed after the $3^{rd}$ immunization. IgG response was maintained from 6-9 weeks following a single immunization. Adding mRNAs encoding gB to mRNAs encoding the pentameric complex subunits did not interefere with anti-pentameric IgG production. Different molar ratios of the mRNAs encoding different pentameric complex subunits did not lead to different IgG induction levels. FIG. 7 shows that the mRNA vaccine constructs encoding gB induced anti-gB IgG response. IgG titers were similar for gB mRNA compared to gB protein/MF59 at 10 μg dose after three immunizations. A boost response was observed after the $3^{rd}$ immunization of gB mRNAs or antigens. Adding mRNAs encoding the pentameric complex subunits to mRNAs encoding gB did not interefere with anti-gB IgG production.

In one embodiment, mice were immunized using the regimen shown in FIG. 44A, and mice sera were collected according to the schedule in FIG. 44A. Antibody response to the pentameric complex (PC) and gB was evaluated by ELISA. Increases in antibody titers against both antigens were observed with increasing dose levels, which were boosted after a second or third dose of vaccine (FIGS. 45A-45B). Notably, the anti-PC and anti-gB antibody titers were not affected by the presence of the opposing antigen, indicating a lack of interference by combining two different antigens in the same LNP (FIGS. 45A-45B).

The ability of these antibodies to block CMV infection of epithelial and fibroblast cells in vitro was evaluated. Microneutralization assays showed potent and durable neutralizing antibodies against both cell types (FIGS. 44B and 44C). To evaluate the potency of the neutralizing antibodies elicited by CMV mRNA vaccine, Cytogam, which is used clinically for CMV infection prophylaxis, was used as a control. To enable direct comparison, Cytogam was diluted to approximate the maximum concentration in human sera after dosing. The results showed that the neutralizing antibody titers were higher than or similar to Cytogam for all vaccine groups tested at dose levels above 1 μg (FIGS. 44B and 44C).

To determine the specificity of antibodies that were generated with CMV mRNA vaccines, mouse immune sera were incubated with purified gB, gH/gL, or PC proteins prior to performing microneutralization assays on epithelial or fibroblast cells. The neutralization activity against epithelial cell infection was completely blocked by purified PC but not by the other human CMV antigens tested (FIG. 44D). In fibroblast cells, neutralization activity of sera from mice immunized with PC+gB was partially competed by gH/gL and PC proteins, but not by gB protein (FIG. 44E). This suggested that immunization with PC also generated anti-gH/gL antibodies and that the same neutralizing epitopes in gH/gL are also exposed when gH/gL is part of PC.

Figure 8:
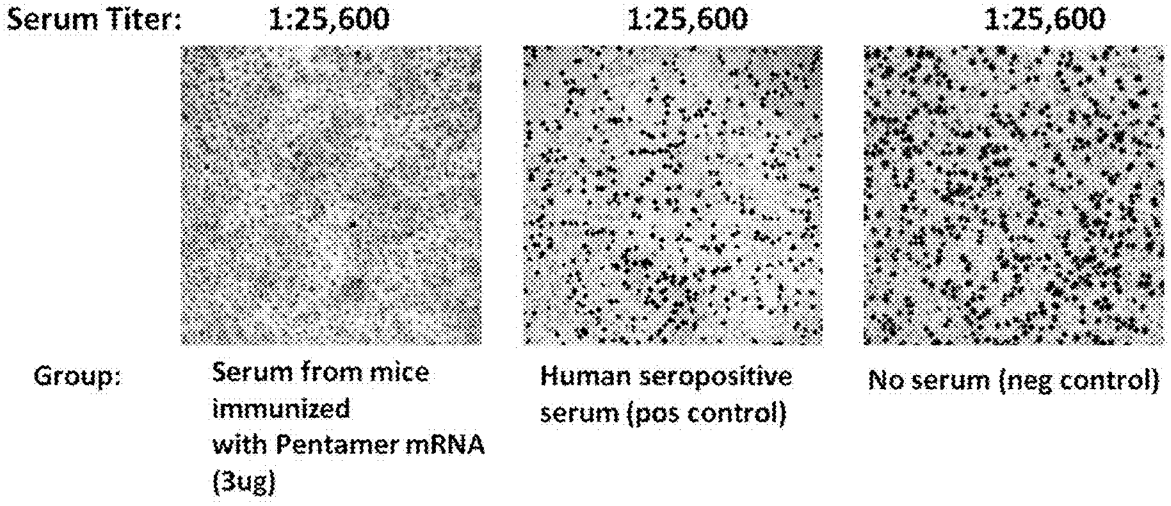
FIG. 8 shows a neutralization study of the hCMV pentameric complex mRNA vaccine constructs in the epithelial cell line ARPE-19. 1E1 staining in infected ARPE-19 cells is demonstrated. Immunization with hCMV pentameric complex mRNA vaccine constructs elicits highly potent neutralizing antibodies in mice. Neutralizing antiboey titer (1:25600) in mice serum at day 41 (3 weeks post second immunization) was able to neutrzalize the hCMV clinical isolate VR1814 in ARPE-19 cells.

Example 24: Immunization with hCMV Pentameric Complex mRNA Elicits Highly Potent Neutralizing Antibodies in Mice Neutralization assays were conducted in epithelial cell line ARPE-19 infected with hCMV clinical isolate VR1814 were conducted. Mice were immunized according to the methods in Example 23. Mouse serum samples were collected 3 weeks after the second immunization (on day 41). Mice sera collected from mice immunized with 3 μg of hCMV mRNA pentameric vaccine constructs were diluted (1:25600) and added to the infected cells. The cells were stained for hCMV 1E1 protein (as an indication of the presence of hCMV in the cells). Results showed that serum from mice immunized with 3 μg of hCMV pentameric mRNA vaccine constructs were able to neutralize the hCMV in ARPE-19 cells, while the controls of human seropositive serum or no serum did not neutralize the hCMV in ARPE-19 cells (FIG. 8).

Figure 9:
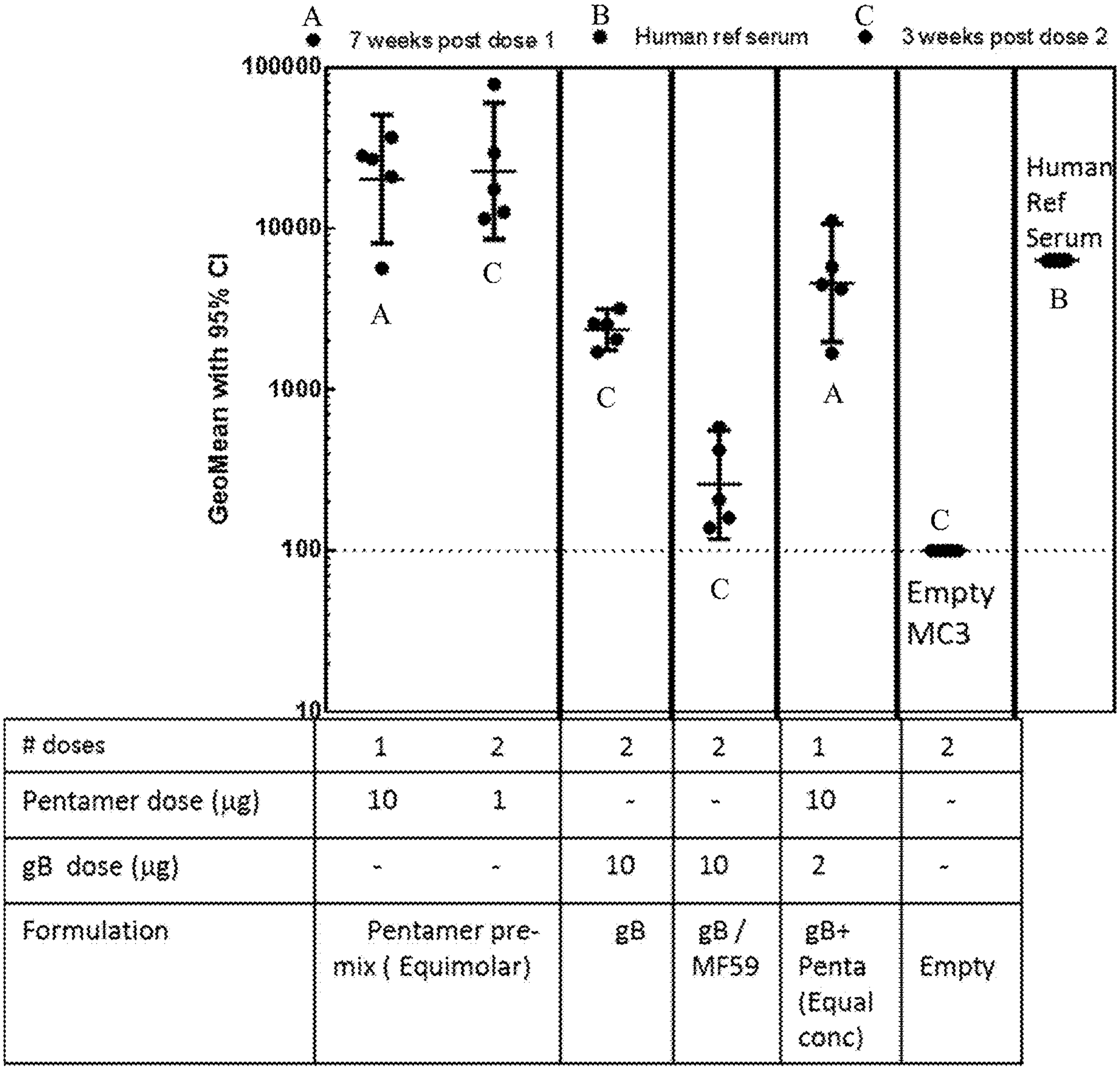
FIG. 9 shows a measurement of hCMV neutralization IgG tiers in ARPE-19 cells infected with the hCMV clinical isolate strain VR1814. See also Table 5.
Figure 10A:
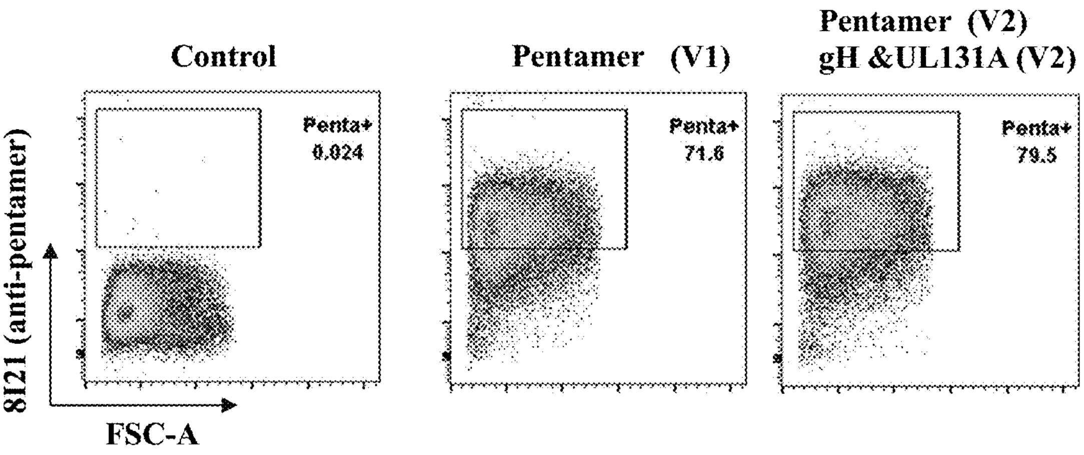
FIGS. 10A-10B show the surface expression in HeLa cells of the hCMV pentameric complex (gH-gL-UL128-UL130-UL131A) encoded by the first-generation pentameric constructs described herein (referred to as "version 1" or "V1") and second-generation pentameric constructs also described herein (referred to as "version 2" or "V2"). The sequences of the mRNAs within the second generation constructs are provided in Table 6, corresponding to SEQ ID NOs: 58-69.
Figure 10B:
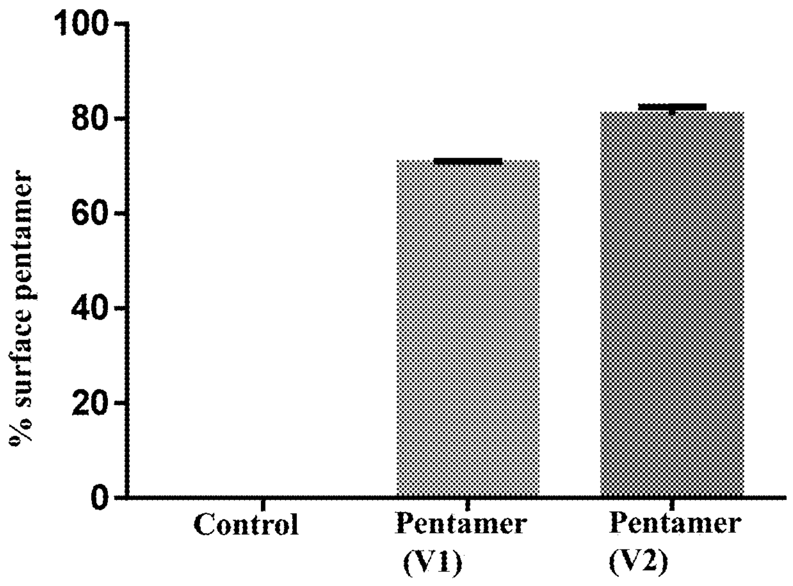
Figure 10C:
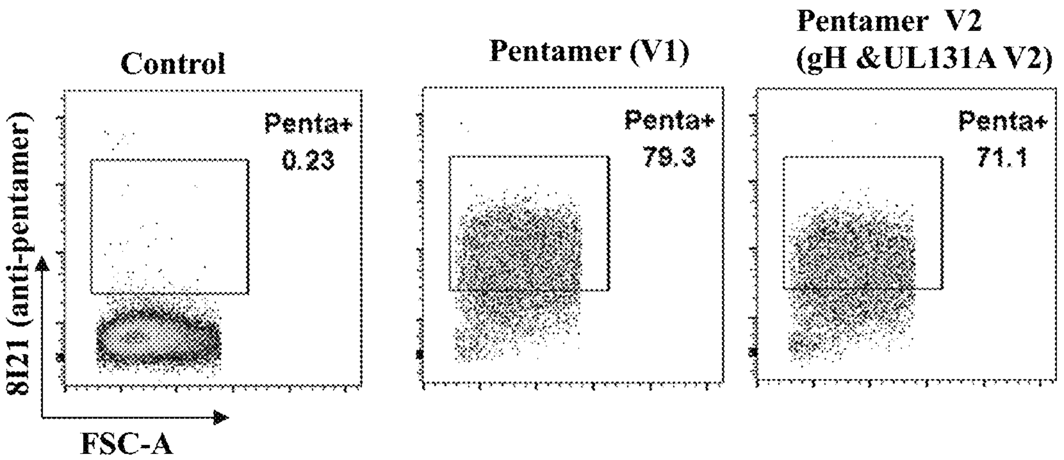
Figure 10D:
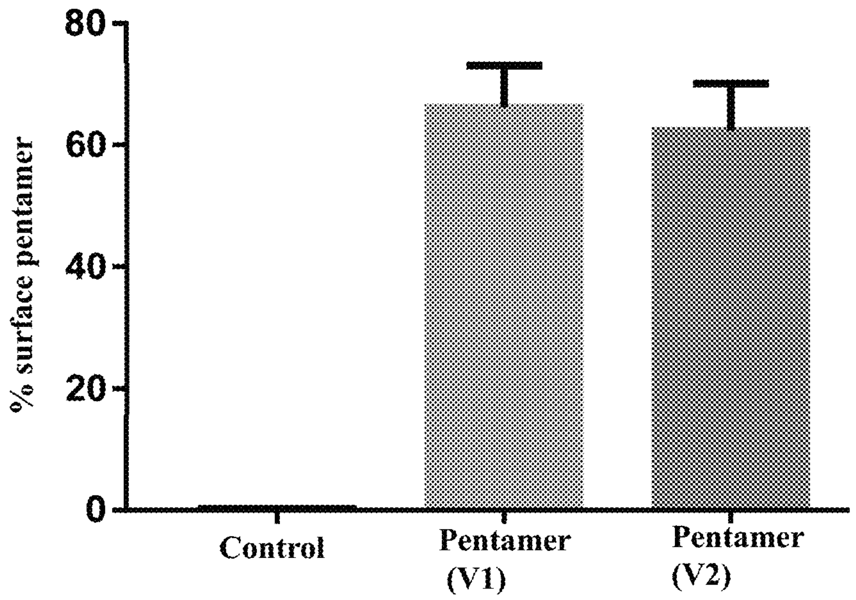
Figure 11A:
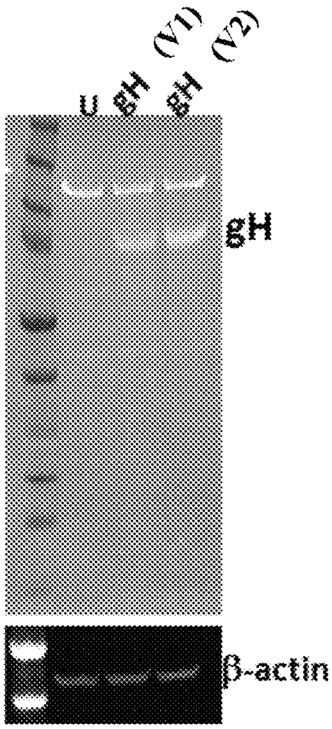
FIGS. 11A-11E depict Western blots showing the expression of the subunits of the hCMV pentameric complex (gH, gL, UL128, UL130, and UL131A) encoded by the first generation pentameric constructs described herein (referred to as "version 1" or "V1") and second-generation pentameric constructs also described herein (referred to as "version 2" or "V2"). Polyclonal antibodies against the various subunits were used for detection. β-actin serves as a loading control.
Figure 11B:
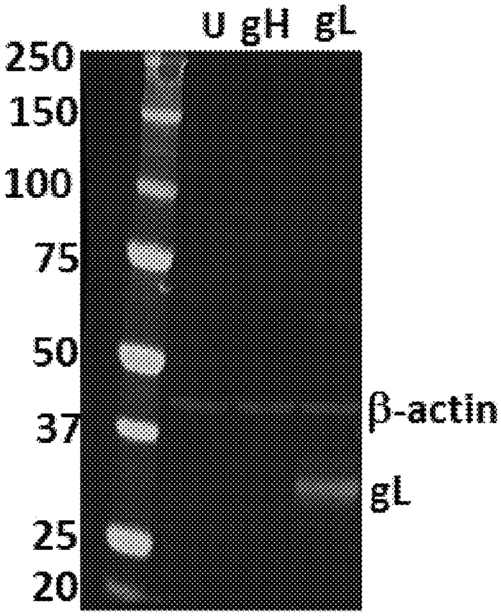
Figure 11C:
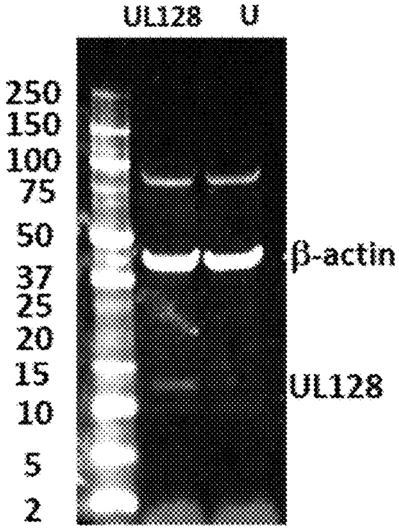
Figure 11D:
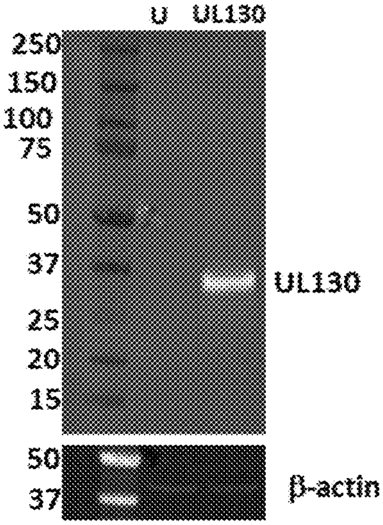
Figure 11E:
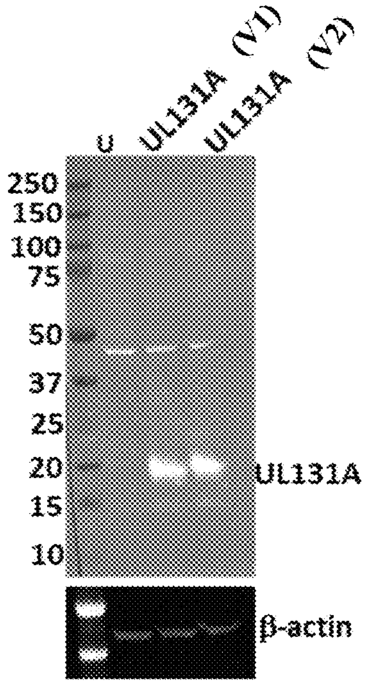
Figure 12:
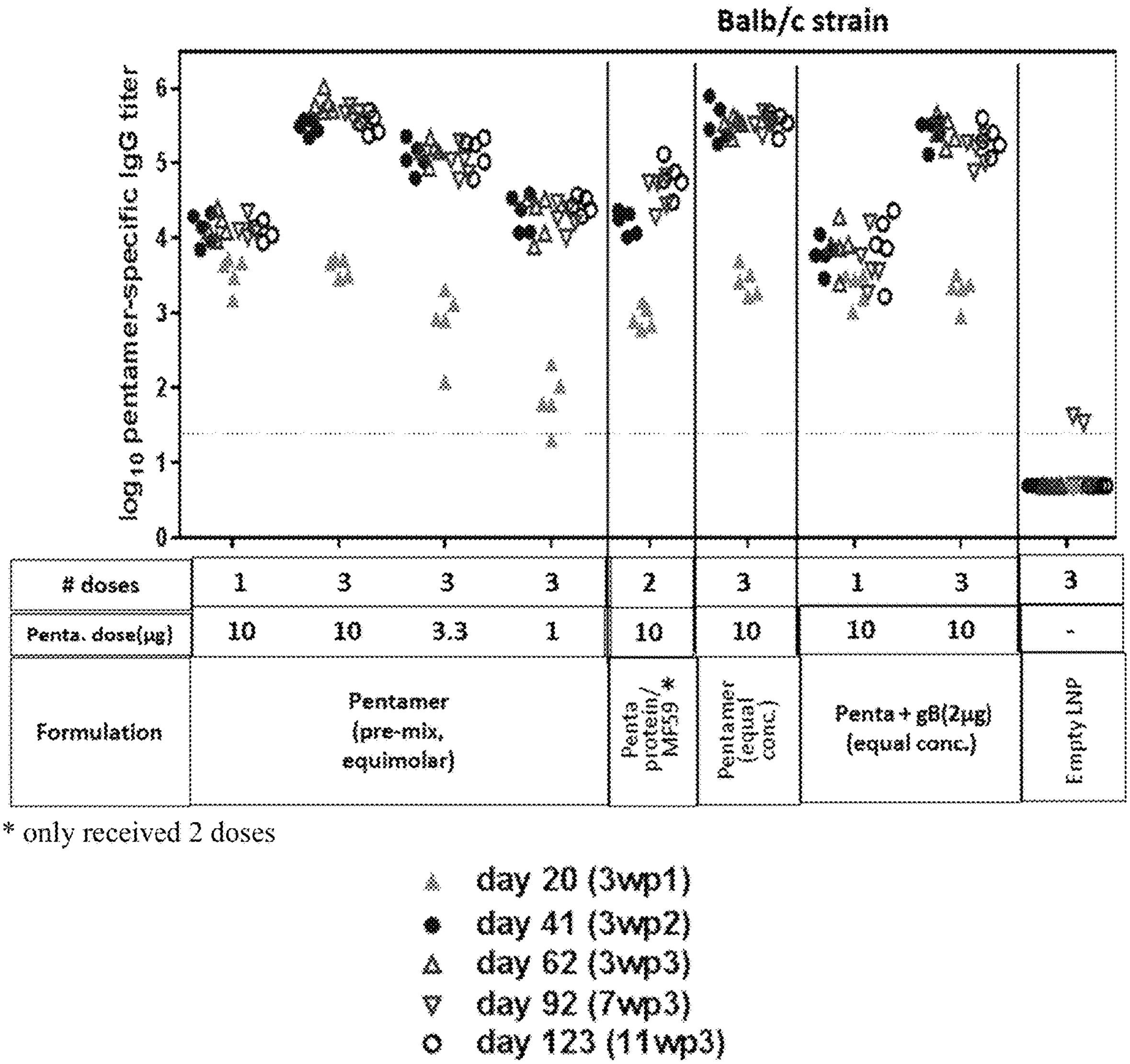
FIG. 12 shows that immunization with the pentameric mRNA complex elicits high titers of antibodies that are maintained up to several months. An immunogenicity study of the second generation hCMV pentameric complex mRNA vaccine constructs is shown. Balb/c mice were vaccinated according to the vaccination schedule with indicated dosages of the mRNAs (lower panel). Mice serum IgG titers were measured at days 20, 41, 62, 92, and 123 post immunization. hCMV pentamer coated plates were used to measure the serum IgG titer. High titers of anti-pentamer antibodies were detected in the serum of the immunized mice.
Figure 13:
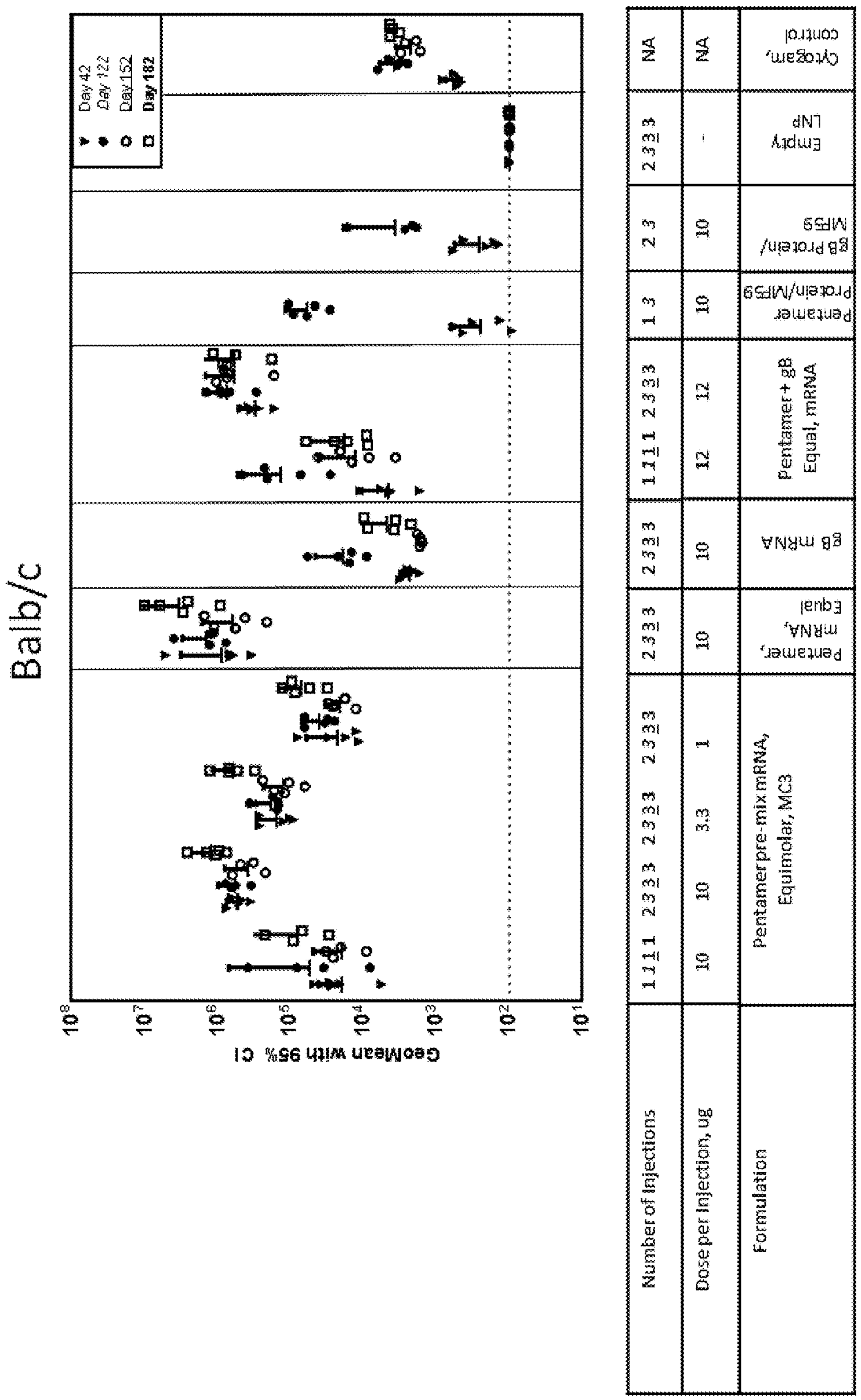
FIG. 13 shows that hCMV mRNA vaccines encoding the pentamer elicited higher neutralizing antibody titers in mice than CytoGam®, a hyperimmune serum used clinically for prophylaxis of hCMV. Balb/c mice were vaccinated according to the vaccination schedule with indicated dosages of the mRNAs (lower panel). Neutralizing antibody titers in mice serum were measured at days 42, 122, 152, and 182 post immunization, with ARPE-19 epithelial cells infected with the hCMV clinical isolate VR1814. High titers of neutralizing antibodies induced by the hCMV pentameric complex mRNA vaccine were maintained up to 6 months.
Figure 14:
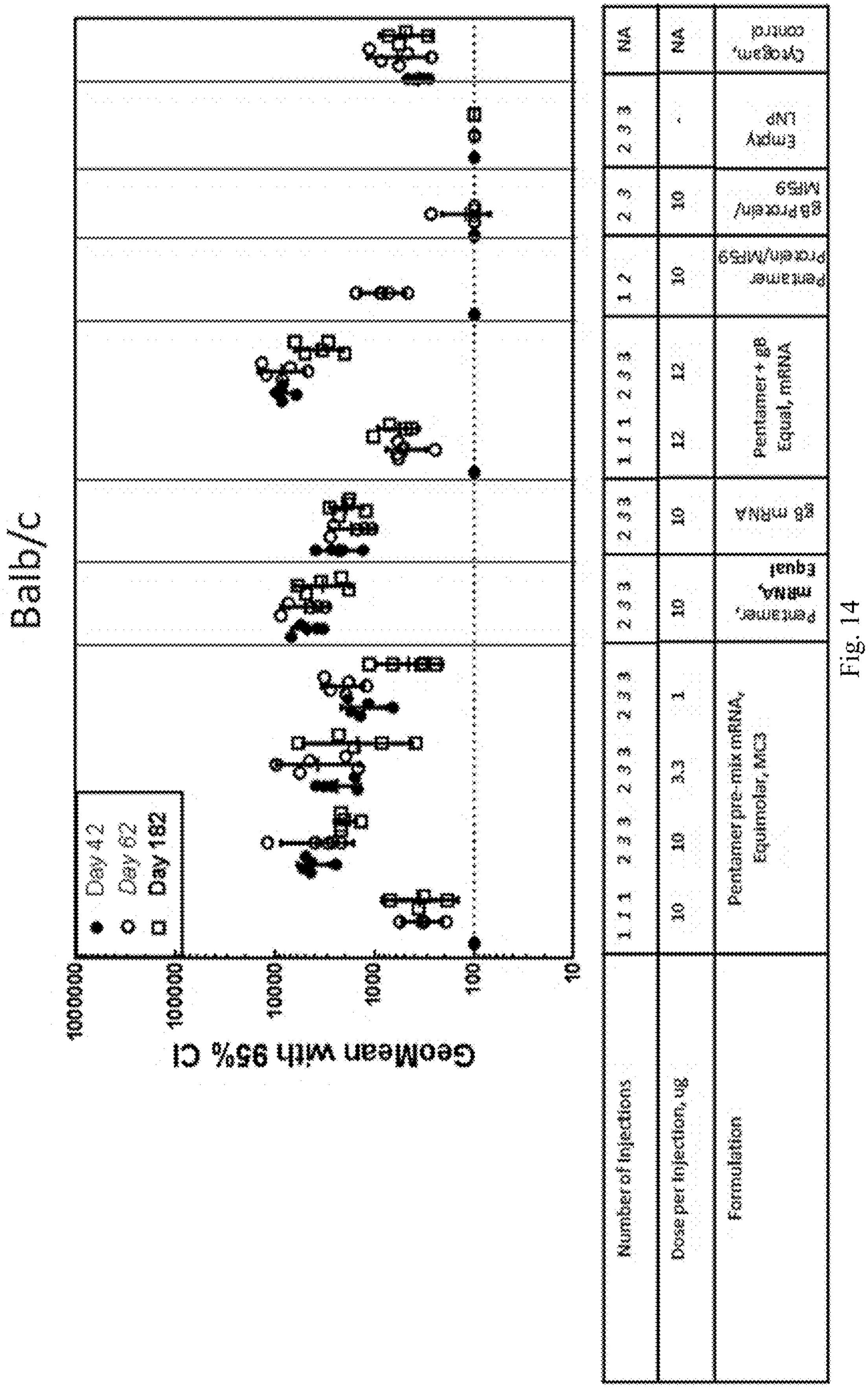
FIG. 14 is a graph showing the neutralizing antibody titers induced in mice by the hCMV pentameric complex mRNA vaccine constructs. Balb/c mice were vaccinated according to the vaccination schedule with indicated dosages of the mRNAs (lower panel). Neutralizing antibody titers in mice serum were measured at days 42, 62, and 182 post immunization, with HEL299 fibroblast cells infected with 500-2000 pfu of hCMV AD169 strain.

The hCMV neutralization titers of mouse serum measured in ARPE-19 cells infected with clinical hCMV isolate strain VR1814 are shown in FIG. 9 and Table 5.

TABLE 4

Immunization and bleed schedule

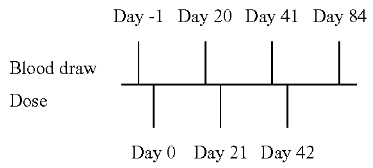

| Group | Vaccine | Route | Dose schedule | N |
|---|---|---|---|---|
| 1 | Pentamer (*4:2:1:1:1, pre-mix), Equimolar | IM | d0 (10 ug) | 5 |
| 2 | Pentamer (4:2:1:1:1, pre-mix) | IM | d0, d21, d42 (10 ug, 3 ug, 1 ug) | 5 |
| 3 | Pentamer (4:2:1:1:1), post-mix) | IM | d0 (10 ug) | 5 |
| 4 | Pentamer (4:2:1:1:1, post-mix) | IM | d0, d21, d42 (10 ug, 3 ug, 1 ug) | 5 |
| 5 | Pentamer (1:1:1:1:1, pre-mix), Equal conc | IM | d0, d21, d42 (10 ug) | 5 |
| 6 | gB | IM | d0, d21, d42 (10 ug) | 5 |
| 7 | gB + Pentamer (1:1:1:1:1:1, pre-mix) | IM | d0 (12 ug) | 5 |
| 8 | gB + Pentamer (1:1:1:1:1:1, pre-mix) | IM | d0, d21, d42 (12 ug) | 5 |
| 9 | Pentamer protein/MF59 | IM | d21, d42 (10 ug) | 5 |
| 10 | gB protein/MF59 | IM | d0, d21, d42 (10 ug) | 5 |
| 11 | Empty LNP | IM | d0, d21, d42 | 5 |

TABLE 5 hCMV neutralization titers of mouse serum measured in ARPE-19 cells infected with clinical isolate VR1814

| Formulation | # of doses | Dose (ug) | NT50 Titer |
|---|---|---|---|
| Pentamer, Pre-mix (Equimolar) | 2 | 10 | >2E4 |
| Pentamer, Pre-mix (Equimolar) | 2 | 3 | >2E4 |
| Pentamer, Post-mix (Equimolar) | 2 | 10 | >2E4 |
| Pentamer, Post-mix (Equimolar) | 2 | 3 | >2E4 |
| Pentamer + gB (Equal conc) | 2 | 12 | >2E4 |

Example 25: Second Generation hCMV Pentameric Complex mRNA Vaccine Constructs hCMV pentameric complex mRNA vaccine constructs were modified to produce second generation mRNA constructs. The nucleotide sequences of the second generation mRNA constructs and the encoded amino acid sequences are provided in Table 6. The expression of the second generation hCMV mRNA vaccine constructs was validated by western blot (FIGS. 11A-13E). Further, to test the surface expression of the hCMV pentamer using the second generation mRNA vaccine constructs, HeLa cells were transfected with 1.25 μg of each of the mRNA vaccine constructs (gH-gL-U1128-UL130-UL131A at 1:1:1:1:1). The transfected HeLa cells were then stained with pentamer-specific antibodies and analyzed with Fluorescence-activated cell sorting (FACS). The fluorescent cell population indicates surface expression of the hCMV pentamer (FIG. 10).

Figure 20A:
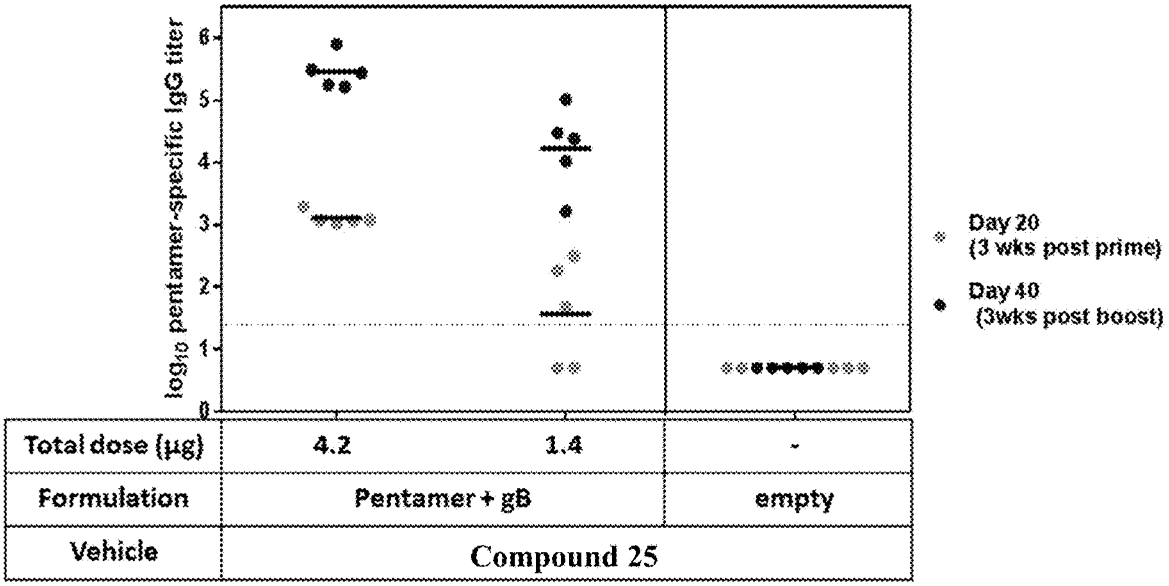
FIGS. 20A-20B are graphs showing the immunogenicity of second generation hCMV mRNA vaccine constructs formulated with Compound 25 lipids. The second generation mRNA constructs encoding the pentamer and gB induced pentamer-specific antibodies (FIG. 20A) and gB-specific antibodies (FIG. 20B) as early as 20 days post first immunization. The pentamer-specific and gB-specific antibody titers continue to increase in mice after the boost dose.
Figure 20B:
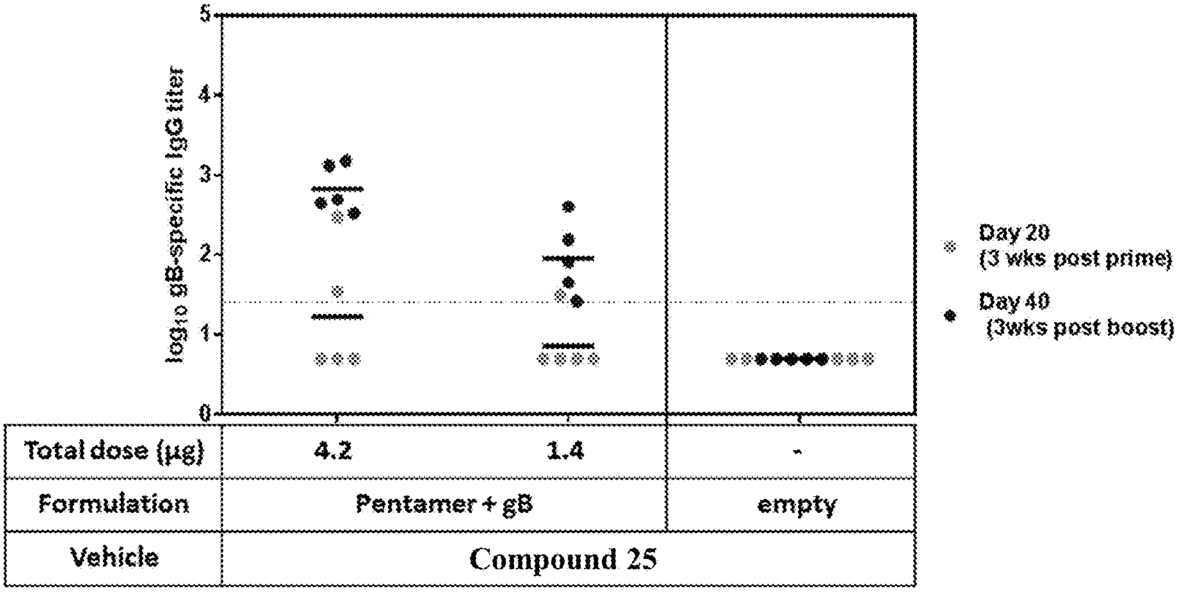

The second generation hCMV mRNA vaccines encoding the pentamer and gB were also formulated with Compound 25 lipids and the immunogenicity of the formulation was tested (FIGS. 20A-20B). Mice were immunized with a total dose of 4.2 μg or 1.4 μg of the mRNA vaccine. Mice serum samples were taken on day 20 and day 40 post immunization and the serum IgG titers were assessed on pentamer coated plates or gB coated plates. The second generation hCMV mRNA vaccines induced high levels of pentamer-specific (FIG. 20A) and gB-specific (FIG. 20B) antibodies.

An HCMV vaccine may comprise, for example, at least one RNA polynucleotide encoded by at least one of the following sequences or by at least one fragment or epitope of the following sequences:

Each of the sequences described herein encompasses a chemically modified sequence or an unmodified sequence which includes no nucleotide modifications.

The nucleotide sequences shown in Table 6 include open reading frame sequences linked to non-limiting examples of 5' and 3'UTRs. It should be appreciated that the same open reading frames can also be linked to different 5' and 3' UTR sequences.

Examples of UTR sequences include:

5' UTR coding sequence:
(SEQ ID NO: 145)
TCAAGCTTTTGGACCCTCGTACAGAAGCTAATACGACTCACTATAGG
GAAATAAGAGAGAAAAGAAGAGTAAGAAGAAATATAAGAGCCACC 5' UTR (without promoter) coding sequence:
(SEQ ID NO: 146)
GGGAAATAAGAGAGAAAAGAAGAGTAAGAAGAAATATAAGAGCCACC 3' UTR coding sequence:
(SEQ ID NO: 147)
TGATAATAGGCTGGAGCCTCGGTGGCCATGCTTCTTGCCCCTTGGGC
CTCCCCCCAGCCCCTCCTCCCCTTCCTGCACCCGTACCCCCGTGGTC
TTTGAATAAAGTCTGAGTGGGCGGC.

TABLE 6

Second Generation hCMV mRNA Vaccine Construct Sequences

| Name of mRNA Construct | ORF Sequence (5' UTR sequence is bolded and 3' UTR sequence is underlined) | SEQ ID NO |
|---|---|---|
| hCMV_gH dimer, nucleotide sequence | **TCAAGCTTTTGGACCCTCGTACAGAAGCTAATACGACTCACTATAGGGAA**<br>**ATAAGAGAGAAAAGAAGAGTAAGAAGAAATATAAGAGCCACC**ATGCGGCC<br>AGGCCTCCCCTCCTACCTCATCATCCTCGCCGTCTGTCTCTTCAGCCACCTACTT<br>TCGTCACGATATGGCGCAGAAGCCGTATCCGAACCGCTGGACAAAGCGTTTCA<br>CCTACTGCTCAACACCTACGGGAGACCCATCCGCTTCCTGCGTGAAAATACCA<br>CCCAGTGTACCTACAACAGCAGCCTCCGTAACAGCACGGTCGTCAGGGAAAAC<br>GCCATCAGTTTCAACTTCTTCCAAAGCTATAATCAATACTATGTATTCCATATG<br>CCTCGATGTCTCTTTGCGGGTCCTCTGGCGGAGCAGTTTCTGAACCAGGTAGAT<br>CTGACCGAAACCCTGGAAAGATACCAACAGAGACTTAACACTTACGCGCTGGT<br>ATCCAAAGACCTGGCCAGCTACCGATCTTTCTCGCAGCAGCTAAAGGCACAAG<br>ACAGCCTAGGTGAACAGCCCACCACTGTGCCACCGCCCATTGACCTGTCAATA<br>CCTCACGTTTGGATGCCACCGCAAACCACTCCACACGGCTGGACAGAATCACA<br>TACCACCTCAGGACTACACCGACCACACTTTAACCAGACCTGTATCCTCTTTGA<br>TGGACACGATCTACTATTCAGCACCGTCACACCTTGTTTGCACCAAGGCTTTTA<br>CCTCATCGACGAACTACGTTACGTTAAAATAACACTGACCGAGGACTTCTTCGT<br>AGTTACGGTGTCCATAGACGACGACACACCCATGCTGCTTATCTTCGGCCATCT<br>TCCACGCGTACTTTTCAAAGCGCCCTATCAACGCGACAACTTTATACTACGACA<br>AACTGAGAAACACGAGCTCCTGGTGCTAGTTAAGAAAGATCAACTGAACCGTC<br>ACTCTTATCTCAAAGACCCGGACTTTCTTGACGCCGCACTTGACTTCAACTACC<br>TAGACCTCAGCGCACTACTACGTAACAGCTTTCACCGTTACGCCGTGGATGTAC<br>TCAAGAGCGGTCGATGTCAGATGCTGGACCGCCGCACGGTAGAAATGGCCTTC<br>GCCTACGCATTAGCACTGTTCGCAGCAGCCCGACAAGAAGAGGCCGGCGCCCA<br>AGTCTCCGTCCCACGGGCCCTAGACCGCCAGGCCGCACTCTTACAAATACAAG<br>AATTTATGATCACCTGCCTCTCACAAACACCACCACGCACCACGTTGCTGCTGT<br>ATCCCACGGCCGTGGACCTGGCCAAACGAGCCCTTTGGACACCGAATCAGATC<br>ACCGACATCACCAGCCTCGTACGCCTGGTCTACATACTCTCTAAACAGAATCA<br>GCAACATCTCATCCCCCAATGGGCACTACGACAGATCGCCGACTTTGCCCTAA<br>AACTACACAAAACGCACCTGGCCTCTTTTCTTTCAGCCTTCGCACGCCAAGAAC<br>TCTACCTCATGGGCAGCCTCGTCCACTCCATGCTGGTACATACGACGGAGAGA<br>CGCGAAATCTTCATCGTAGAAACGGGCCTCTGTTCATTGGCCGAGCTATCACAC<br>TTTACGCAGTTGTTAGCTCATCCACACCACGAATACCTCAGCGACCTGTACACA<br>CCCTGTTCCAGTAGCGGGCGACGCGATCACTCGCTCGAACGCCTCACGCGTCTC<br>TTCCCCGATGCCACCGTCCCCGCTACCGTTCCCGCCGCCCTCTCCATCCTATCTA<br>CCATGCAACCAAGCACGCTGGAAACCTTCCCCGACCTGTTTTGCTTGCCGCTCG<br>GCGAATCCTTCTCCGCGCTGACCGTCTCCGAACACGTCAGTTATATCGTAACAA<br>ACCAGTACCTGATCAAAGGTATCTCCTACCCTGTCTCCACCACCGTCGTAGGCC<br>AGAGCCTCATCATCACCCAGACGGACAGTCAAACTAAATGCGAACTGACGCGC | 58 |

TABLE 6-continued

Second Generation hCMV mRNA Vaccine Construct Sequences

| Name of mRNA Construct | ORF Sequence (5' UTR sequence is bolded and 3' UTR sequence is underlined) | SEQ ID NO |
|---|---|---|
| | AACATGCATACCACACACAGCATCACAGTGGCGCTCAACATTTCGCTAGAAAA<br>CTGCGCCTTTTGCCAAAGCGCCCTGCTAGAATACGACGACACGCAAGGCGTCA<br>TCAACATCATGTACATGCACGACTCGGACGACGTCCTTTTCGCCCTGGATCCCT<br>ACAACGAAGTGGTGGTCTCATCTCCGCGAACTCACTACCTCATGCTTTTGAAGA<br>ACGGTACGGTACTAGAAGTAACTGACGTCGTCGTGGACGCCACCGACAGTCGT<br>CTCCTCATGATGTCCGTCTACGCGCTATCGGCCATCATCGGCATCTATCTGCTC<br>TACCGCATGCTCAAGACATGCTGATAATAGGCTGGAGCCTCGGTGGCCATGCT<br>TCTTGCCCCTTGGGCCTCCCCCCAGCCCCTCCTCCCCTTCCTGCACCCGTACCCC<br>CGTGGTCTTTGAATAAAGTCTGAGTGGGCGGC | |
| hCMV_gH dimer, nucleotide sequence mRNA | UCAAGCUUUUGGACCCUCGUACAGAAGCUAAUACGACUCACUAUAGGGAAA<br>UAAGAGAGAAAAGAAGAGUAAGAAGAAAUAUAAGAGCCACCAUGCGGCCAG<br>GCCUCCCCUCCUACCUCAUCAUCCUCGCCGUCUGUCUCUUCAGCCACCUACU<br>UUCGUCACGAUAUGGCGCAGAAGCCGUAUCCGAACCGCUGGACAAAGCGUU<br>UCACCUACUGCUCAACACCUACGGGAGACCCAUCCGCUUCCUGCGUGAAAAU<br>ACCACCCAGUGUACCUACAACAGCAGCCUCCGUAACAGCACGGUCGUCAGGG<br>AAAACGCCAUCAGUUUCAACUUCUUCCAAAGCUAUAAUCAAUACUAUGUAU<br>UCCAUAUGCCUCGAUGUCUCUUUGCGGGUCCUCUGGCGGAGCAGUUUCUGA<br>ACCAGGUAGAUCUGACCGAAACCCUGGAAAGAUACCAACAGAGACUUAACA<br>CUUACGCGCUGGUAUCCAAAGACCUGGCCAGCUACCGAUCUUUCUCGCAGCA<br>GCUAAAGGCACAAGACAGCCUAGGUGAACAGCCCACCACUGUGCCACCGCCC<br>AUUGACCUGUCAAUACCUCACGUUUGGAUGCCACCGCAAACCACUCCACACG<br>GCUGGACAGAAUCACAUACCACCUCAGGACUACACCGACCACACUUUAACCA<br>GACCUGUAUCCUCUUUGAUGGACACGAUCUACUAUUCAGCACCGUCACACCU<br>UGUUUGCACCAAGGCUUUUACCUCAUCGACGAACUACGUUACGUUAAAAUA<br>ACACUGACCGAGGACUUCUUCGUAGUUACGGUGUCCAUAGACGACGACACA<br>CCCAUGCUGCUUAUCUUCGGCCAUCUUCCACGCGUACUUUUCAAAGCGCCCU<br>AUCAACGCGACAACUUUAUACUACGACAAACUGAGAAACACGAGCUCCUGG<br>UGCUAGUUAAGAAAGAUCAACUGAACCGUCACUCUUAUCUCAAAGACCCGG<br>ACUUUCUUGACGCCGCACUUGACUUCAACUACCUAGACCUCAGCGCACUACU<br>ACGUAACAGCUUUCACCGUUACGCCGUGGAUGUACUCAAGAGCGGUCGAUG<br>UCAGAUGCUGGACCGCCGCACGGUAGAAAUGGCCUUCGCCUACGCAUUAGCA<br>CUGUUCGCAGCAGCCCGACAAGAAGAGGCCGGCGCCCAAGUCUCCGUCCCAC<br>GGGCCCUAGACCGCCAGGCCGCACUCUUACAAAUACAAGAAUUUAUGAUCAC<br>CUGCCUCUCACAAACACCACCACGCACCACGUUGCUGCUGUAUCCCACGGCC<br>GUGGACCUGGCCAAACGAGCCCUUUGGACACCGAAUCAGAUCACCGACAUCA<br>CCAGCCUCGUACGCCUGGUCUACAUACUCUCUAAACAGAAUCAGCAACAUCU<br>CAUCCCCCAAUGGGCACUACGACAGAUCGCCGACUUUGCCCUAAAACUACAC<br>AAAACGCACCUGGCCUCUUUUCUUUCAGCCUUCGCACGCCAAGAACUCUACC<br>UCAUGGGCAGCCUCGUCCACUCCAUGCUGGUACAUACGACGGAGAGACGCGA<br>AAUCUUCAUCGUAGAAACGGGCCUCUGUUCAUUGGCCGAGCUAUCACACUU<br>UACGCAGUUGUUAGCUCAUCCACACCACGAAUACCUCAGCGACCUGUACACA<br>CCCUGUUCCAGUAGCGGGCGACGCGAUCACUCGCUCGAACGCCUCACGCGUC<br>UCUUCCCCGAUGCCACCGUCCCCGCUACCGUUCCCGCCGCCCUCUCCAUCCUA<br>UCUACCAUGCAACCAAGCACGCUGGAAACCUUCCCCGACCUGUUUUGCUUGC<br>CGCUCGGCGAAUCCUUCUCCGCGCUGACCGUCUCCGAACACGUCAGUUAUAU<br>CGUAACAAACCAGUACCUGAUCAAAGGUAUCUCCUACCCUGUCUCCACCACC<br>GUCGUAGGCCAGAGCCUCAUCAUCACCCAGACGGACAGUCAAACUAAAUGCG<br>AACUGACGCGCAACAUGCAUACCACACACAGCAUCACAGUGGCGCUCAACAU<br>UUCGCUAGAAAACUGCGCCUUUUGCCAAAGCGCCCUGCUAGAAUACGACGAC<br>ACGCAAGGCGUCAUCAACAUCAUGUACAUGCACGACUCGGACGACGUCCUUU<br>UCGCCCUGGAUCCCUACAACGAAGUGGUGGUCUCAUCUCCGCGAACUCACUA<br>CCUCAUGCUUUUGAAGAACGGUACGGUACUAGAAGUAACUGACGUCGUCGU<br>GGACGCCACCGACAGUCGUCUCCUCAUGAUGUCCGUCUACGCGCUAUCGGCC<br>AUCAUCGGCAUCUAUCUGCUCUACCGCAUGCUCAAGACAUGCUGAUAAUAG<br>GCUGGAGCCUCGGUGGCCAUGCUUCUUGCCCCUUGGGCCUCCCCCCAGCCCC<br>UCCUCCCCUUCCUGCACCCGUACCCCCGUGGUCUUUGAAUAAAGUCUGAGUG<br>GGCGGC | 189 |
| hCMV_gH dimer, amino acid sequence | MRPGLPSYLIIILAVCLFSHLLSSRYGAEAVSEPLDKAFHLLLNTYGRPIRFLRENTTQ<br>CTYNSSLRNSTVVRENAISFNFFQSYNQYYVFHMPRCLFAGPLAEQFLNQVDLTET<br>LERYQQRLNTYALVSKDLASYRSFSQQLKAQDSLGEQPTTVPPPIDLSIPHVWMPP<br>QTTPHGWTESHTTSGLHRPHFNQTCILFDGHDLLFSTVTPCLHQGFYLIDELRYVKI<br>TLTEDFFVVTVSIDDDTPMLLIFGHLPRVLFKAPYQRDNFILRQTEKHELLVLVKKD<br>QLNRHSYLKDPDFLDAALDFNYLDLSALLRNSFHRYAVDVLKSGRCQMLDRRTV<br>EMAFAYALALFAAARQEEAGAQVSVPRALDRQAALLQIQEFMITCLSQTPPRTTLL<br>LYPTAVDLAKRALWTPNQITDITSLVRLVYILSKQNQQHLIPQWALRQIADFALKL<br>HKTHLASFLSAFARQELYLMGSLVHSMLVHTTERREIFIVETGLCSLAELSHFTQLL<br>AHPHHEYLSDLYTPCSSSGRRDHSLERLTRLFPDATVPATVPAALSILSTMQPSTLE<br>TFPDLFCLPLGESFSALTVSEHVSYIVTNQYLIKGISYPVSTTVVGQSLIITQTDSQTK<br>CELTRNMHTTHSITVALNISLENCAFCQSALLEYDDTQGVINIMYMHDSDDVLFAL<br>DPYNEVVVSSPRTHYLMLLKNGTVLEVTDVVVDATDSRLLMMSVYALSAIIGIYL<br>LYRMLKTC | 59 |

TABLE 6-continued

| Second Generation hCMV mRNA Vaccine Construct Sequences | | |
|---|---|---|
| Name of mRNA Construct | ORF Sequence (5' UTR sequence is bolded and 3' UTR sequence is underlined) | SEQ ID NO |
| hCMV-gL, nucleotide sequence | **TCAAGCTTTTGGACCCTCGTACAGAAGCTAATACGACTCACTATAGGGAA**<br>**ATAAGAGAGAAAAGAAGAGTAAGAAGAAATATAAGAGCCACC**ATGTGCCG<br>CCGCCCGGATTGCGGCTTCTCTTTCTCACCTGGACCGGTGATACTGCTGTGGTG<br>TTGCCTTCTGCTGCCCATTGTTTCCTCAGCCGCCGTCAGCGTCGCTCCTACCGCC<br>GCCGAGAAAGTCCCCGCGGAGTGCCCCGAACTAACGCGCCGATGCTTGTTGGG<br>TGAGGTGTTTGAGGGTGACAAGTATGAAAGTTGGCTGCGCCCGTTGGTGAATG<br>TTACCGGGCGCGATGGCCCGCTATCGCAACTTATCCGTTACCGTCCCGTTACGC<br>CGGAGGCCGCCAACTCCGTGCTGTTGGACGAGGCTTTCCTGGACACTCTGGCC<br>CTGCTGTACAACAATCCGGATCAATTGCGGGCCCTGCTGACGCTGTTGAGCTCG<br>GACACAGCGCCGCGCTGGATGACGGTGATGCGCGGCTACAGCGAGTGCGGCG<br>ATGGCTCGCCGGCCGTGTACACGTGCGTGGACGACCTGTGCCGCGGCTACGAC<br>CTCACGCGACTGTCATACGGGCGCAGCATCTTCACGGAACACGTGTTAGGCTT<br>CGAGCTGGTGCCACCGTCTCTCTTTAACGTGGTGGTGGCCATACGCAACGAAG<br>CCACGCGTACCAACCGCGCCGTGCGTCTGCCCGTGAGCACCGCTGCCGCGCCC<br>GAGGGCATCACGCTCTTTTACGGCCTGTACAACGCAGTGAAGGAATTCTGCCT<br>GCGTCACCAGCTGGACCCGCCGCTGCTACGCCACCTAGATAAATACTACGCCG<br>GACTGCCGCCCGAGCTGAAGCAGACGCGCGTCAACCTGCCGGCTCACTCGCGC<br>TATGGCCCTCAAGCAGTGGATGCTCGCTGATAATAGGCTGGAGCCTCGGTGGC<br>CATGCTTCTTGCCCCTTGGGCCTCCCCCCAGCCCCTCCTCCCCTTCCTGCACCCG<br>TACCCCCGTGGTCTTTGAATAAAGTCTGAGTGGGCGGC | 60 |
| hCMV-gL, nucleotide sequence mRNA | UCAAGCUUUUGGACCCUCGUACAGAAGCUAAUACGACUCACUAUAGGGAAA<br>UAAGAGAGAAAAGAAGAGUAAGAAGAAAUAUAAGAGCCACCAUGUGCCGCC<br>GCCCGGAUUGCGGCUUCUCUUUCUCACCUGGACCGGUGAUACUGCUGUGGU<br>GUUGCCUUCUGCUGCCCAUUGUUUCCUCAGCCGCCGUCAGCGUCGCUCCUAC<br>CGCCGCCGAGAAAGUCCCCGCGGAGUGCCCCGAACUAACGCGCCGAUGCUUG<br>UUGGGUGAGGUGUUUGAGGGUGACAAGUAUGAAAGUUGGCUGCGCCCGUUG<br>GUGAAUGUUACCGGGCGCGAUGGCCCGCUAUCGCAACUUAUCCGUUACCGUC<br>CCGUUACGCCGGAGGCCGCCAACUCCGUGCUGUUGGACGAGGCUUUCCUGGA<br>CACUCUGGCCCUGCUGUACAACAAUCCGGAUCAAUUGCGGGCCCUGCUGACG<br>CUGUUGAGCUCGGACACAGCGCCGCGCUGGAUGACGGUGAUGCGCGGCUAC<br>AGCGAGUGCGGCGAUGGCUCGCCGGCCGUGUACACGUGCGUGGACGACCUG<br>UGCCGCGGCUACGACCUCACGCGACUGUCAUACGGGCGCAGCAUCUUCACGG<br>AACACGUGUUAGGCUUCGAGCUGGUGCCACCGUCUCUCUUUAACGUGGUGG<br>UGGCCAUACGCAACGAAGCCACGCGUACCAACCGCGCCGUGCGUCUGCCCGU<br>GAGCACCGCUGCCGCGCCCGAGGGCAUCACGCUCUUUUACGGCCUGUACAAC<br>GCAGUGAAGGAAUUCUGCCUGCGUCACCAGCUGGACCCGCCGCUGCUACGCC<br>ACCUAGAUAAAUACUACGCCGGACUGCCGCCCGAGCUGAAGCAGACGCGCGU<br>CAACCUGCCGGCUCACUCGCGCUAUGGCCCUCAAGCAGUGGAUGCUCGCUGA<br>UAAUAGGCUGGAGCCUCGGUGGCCAUGCUUCUUGCCCCUUGGGCCUCCCCCC<br>AGCCCCUCCUCCCCUUCCUGCACCCGUACCCCCGUGGUCUUUGAAUAAAGUC<br>UGAGUGGGCGGC | 190 |
| hCMV-gL, amino acid sequence | MCRRPDCGFSFSPGPVILLWCCLLLPIVSSAAVSVAPTAAEKVPAECPELTRRCLLG<br>EVFEGDKYESWLRPLVNVTGRDGPLSQLIRYRPVTPEAANSVLLDEAFLDTLALLY<br>NNPDQLRALLTLLSSDTAPRWMTVMRGYSECGDGSPAVYTCVDDLCRGYDLTRL<br>SYGRSIFTEHVLGFELVPPSLFNVVVAIRNEATRTNRAVRLPVSTAAAPEGITLFYG<br>LYNAVKEFCLRHQLDPPLLRHLDKYYAGLPPELKQTRVNLPAHSRYGPQAVDAR | 61 |
| hCMV_UL 128, nucleotide sequence | **TCAAGCTTTTGGACCCTCGTACAGAAGCTAATACGACTCACTATAGGGAA**<br>**ATAAGAGAGAAAAGAAGAGTAAGAAGAAATATAAGAGCCACC**ATGAGTCC<br>CAAAGATCTGACGCCGTTCTTGACGGCGTTGTGGCTGCTATTGGGTCACAGCCG<br>CGTGCCGCGGGTGCGCGCAGAAGAATGTTGCGAATTCATAAACGTCAACCACC<br>CGCCGGAACGCTGTTACGATTTCAAAATGTGCAATCGCTTCACCGTCGCGCTGC<br>GGTGTCCGGACGGCGAAGTCTGCTACAGTCCCGAGAAAACGGCTGAGATTCGC<br>GGGATCGTCACCACCATGACCCATTCATTGACACGCCAGGTCGTACACAACAA<br>ACTGACGAGCTGCAACTACAATCCGTTATACCTCGAAGCTGACGGGCGAATAC<br>GCTGCGGCAAAGTAAACGACAAGGCGCAGTACCTGCTGGGCGCCGCTGGCAG<br>CGTTCCCTATCGATGGATCAATCTGGAATACGACAAGATAACCCGGATCGTGG<br>GCCTGGATCAGTACCTGGAGAGCGTTAAGAAACACAAACGGCTGGATGTGTGC<br>CGCGCTAAAATGGGCTATATGCTGCAGTGATAATAGGCTGGAGCCTCGGTGGC<br>CATGCTTCTTGCCCCTTGGGCCTCCCCCCAGCCCCTCCTCCCCTTCCTGCACCCG<br>TACCCCCGTGGTCTTTGAATAAAGTCTGAGTGGGCGGC | 62 |
| hCMV_UL 128, nucleotide sequence mRNA | UCAAGCUUUUGGACCCUCGUACAGAAGCUAAUACGACUCACUAUAGGGAAA<br>UAAGAGAGAAAAGAAGAGUAAGAAGAAAUAUAAGAGCCACCAUGAGUCCCA<br>AAGAUCUGACGCCGUUCUUGACGGCGUUGUGGCUGCUAUUGGGUCACAGCC<br>GCGUGCCGCGGGUGCGCGCAGAAGAAUGUUGCGAAUUCAUAAACGUCAACC<br>ACCCGCCGGAACGCUGUUACGAUUUCAAAAUGUGCAAUCGCUUCACCGUCGC<br>GCUGCGGUGUCCGGACGGCGAAGUCUGCUACAGUCCCGAGAAAACGGCUGA<br>GAUUCGCGGGAUCGUCACCACCAUGACCCAUUCAUUGACACGCCAGGUCGUA<br>CACAACAAACUGACGAGCUGCAACUACAAUCCGUUAUACCUCGAAGCUGACG<br>GGCGAAUACGCUGCGGCAAAGUAAACGACAAGGCGCAGUACCUGCUGGGCG<br>CCGCUGGCAGCGUUCCCUAUCGAUGGAUCAAUCUGGAAUACGACAAGAUAA | 191 |

TABLE 6-continued

Second Generation hCMV mRNA Vaccine Construct Sequences

| Name of mRNA Construct | ORF Sequence (5' UTR sequence is bolded and 3' UTR sequence is underlined) | SEQ ID NO |
|---|---|---|
| | CCCGGAUCGUGGGCCUGGAUCAGUACCUGGAGAGCGUUAAGAAACACAAAC<br>GGCUGGAUGUGUGCCGCGCUAAAAUGGGCUAUAUGCUGCAGUGAUAAUAGG<br>CUGGAGCCUCGGUGGCCAUGCUUCUUGCCCCUUGGGCCUCCCCCCAGCCCCU<br>CCUCCCCUUCCUGCACCCGUACCCCCGUGGUCUUUGAAUAAAGUCUGAGUGG<br>GCGGC | |
| hCMV_UL 128, amino acid sequence | MSPKDLTPFLTALWLLLGHSRVPRVRAEECCEFINVNHPPERCYDFKMCNRFTVA<br>LRCPDGEVCYSPEKTAEIRGIVTTMTHSLTRQVVHNKLTSCNYNPLYLEADGRIRC<br>GKVNDKAQYLLGAAGSVPYRWINLEYDKITRIVGLDQYLESVKKHKRLDVCRAK<br>MGYMLQ | 63 |
| hCMV-UL130, nucleotide sequence | **TCAAGCTTTTGGACCCTCGTACAGAAGCTAATACGACTCACTATAGGGAA**<br>**ATAAGAGAGAAAAGAAGAGTAAGAAGAAATATAAGAGCCACC**ATGCTGCG<br>GCTTCTGCTTCGTCACCACTTTCACTGCCTGCTTCTGTGCGCGGTTTGGGCAAC<br>GCCCTGTCTGGCGTCTCCGTGGTCGACGCTAACAGCAAACCAGAATCCGTCCC<br>CGCCATGGTCTAAACTGACGTATTCCAAACCGCATGACGCGGCGACGTTTTACT<br>GTCCTTTTCTCTATCCCTCGCCCCCACGATCCCCCTTGCAATTCTCGGGGTTCCA<br>GCGGGTATCAACGGGTCCCGAGTGTCGCAACGAGACCCTGTATCTGCTGTACA<br>ACCGGGAAGGCCAGACCTTGGTGGAGAGAAGCTCCACCTGGGTGAAAAAGGT<br>GATCTGGTACCTGAGCGGTCGGAACCAAACCATCCTCCAACGGATGCCCCGAA<br>CGGCTTCGAAACCGAGCGACGGAAACGTGCAGATCAGCGTGGAAGACGCCAA<br>GATTTTTGGAGCGCACATGGTGCCCAAGCGCTGCTACGCTTCGTCGTCAACGAT<br>GGCACACGTTATCAGATGTGTGTGATGAAGCTGGAGAGCTGGGCTCACGTCTT<br>CCGGGACTACAGCGTGTCTTTTCAGGTGCGATTGACGTTCACCGAGGCCAATA<br>ACCAGACTTACACCTTCTGCACCCATCCCAATCTCATCGTTTGATAATAGGCTG<br>GAGCCTCGGTGGCCATGCTTCTTGCCCCTTGGGCCTCCCCCCAGCCCCTCCTCC<br>CCTTCCTGCACCCGTACCCCCGTGGTCTTTGAATAAAGTCTGAGTGGGCGGC | 64 |
| hCMV-UL130, nucleotide sequence mRNA | UCAAGCUUUUGGACCCUCGUACAGAAGCUAAUACGACUCACUAUAGGGAAA<br>UAAGAGAGAAAAGAAGAGUAAGAAGAAAUAUAAGAGCCACCAUGCUGCGGC<br>UUCUGCUUCGUCACCACUUUCACUGCCUGCUUCUGUGCGCGGUUUGGGCAAC<br>GCCCUGUCUGGCGUCUCCGUGGUCGACGCUAACAGCAAACCAGAAUCCGUCC<br>CCGCCAUGGUCUAAACUGACGUAUUCCAAACCGCAUGACGCGGCGACGUUUU<br>ACUGUCCUUUUCUCUAUCCCUCGCCCCCACGAUCCCCCUUGCAAUUCUCGGG<br>GUUCCAGCGGGUAUCAACGGGUCCCGAGUGUCGCAACGAGACCCUGUAUCU<br>GCUGUACAACCGGGAAGGCCAGACCUUGGUGGAGAGAAGCUCCACCUGGGU<br>GAAAAAGGUGAUCUGGUACCUGAGCGGUCGGAACCAAACCAUCCUCCAACG<br>GAUGCCCCGAACGGCUUCGAAACCGAGCGACGGAAACGUGCAGAUCAGCGU<br>GGAAGACGCCAAGAUUUUUGGAGCGCACAUGGUGCCCAAGCGCUGCUACGC<br>UUCGUCGUCAACGAUGGCACACGUUAUCAGAUGUGUGUGAUGAAGCUGGAG<br>AGCUGGGCUCACGUCUUCCGGGACUACAGCGUGUCUUUUCAGGUGCGAUUG<br>ACGUUCACCGAGGCCAAUAACCAGACUUACACCUUCUGCACCCAUCCCAAUC<br>UCAUCGUUUGAUAAUAGGCUGGAGCCUCGGUGGCCAUGCUUCUUGCCCCUU<br>GGGCCUCCCCCCAGCCCCUCCUCCCCUUCCUGCACCCGUACCCCCGUGGUCUU<br>UGAAUAAAGUCUGAGUGGGCGGC | 192 |
| hCMV-UL130, amino acid sequence | MLRLLLRHHFHCLLLCAVWATPCLASPWSTLTANQNPSPPWSKLTYSKPHDAATF<br>YCPFLYPSPPRSPLQFSGFQRVSTGPECRNETLYLLYNREGQTLVERSSTWVKKVI<br>WYLSGRNQTILQRMPRTASKPSDGNVQISVEDAKIFGAHMVPKQTKLLRFVVNDG<br>TRYQMCVMKLESWAHVFRDYSVSFQVRLTFTEANNQTYTFCTHPNLIV | 65 |
| hCMV UL131A, nucleotide sequence | **TCAAGCTTTTGGACCCTCGTACAGAAGCTAATACGACTCACTATAGGGAA**<br>**ATAAGAGAGAAAAGAAGAGTAAGAAGAAATATAAGAGCCACC**ATGCGGCT<br>GTGTCGGGTGTGGCTGTCTGTTTGTCTGTGCGCCGTGGTGCTGGGTCAGTGCCA<br>GCGGGAAACCGCGGAAAAGAACGATTATTACCGAGTACCGCATTACTGGGAC<br>GCGTGCTCTCGCGCGCTGCCCGACCAAACCCGTTACAAGTATGTGGAACAGCT<br>CGTGGACCTCACGTTGAACTACCACTACGATGCGAGCCACGGCTTGGACAACT<br>TTGACGTGCTCAAGAGAATCAACGTGACCGAGGTGTCGTTGCTCATCAGCGAC<br>TTTAGACGTCAGAACCGTCGCGGCGGCACCAACAAAAGGACCACGTTCAACGC<br>CGCCGGTTCGCTGGCGCCACACGCCCGGAGCCTCGAGTTCAGCGTGCGGCTCT<br>TTGCCAACTGATAATAGGCTGGAGCCTCGGTGGCCATGCTTCTTGCCCCTTGGG<br>CCTCCCCCCAGCCCCTCCTCCCCTTCCTGCACCCGTACCCCCGTGGTCTTTGAAT<br>AAAGTCTGAGTGGGCGGC | 66 |
| hCMV UL131A, nucleotide sequence mRNA | UCAAGCUUUUGGACCCUCGUACAGAAGCUAAUACGACUCACUAUAGGGAAA<br>UAAGAGAGAAAAGAAGAGUAAGAAGAAAUAUAAGAGCCACCAUGCGGCUGU<br>GUCGGGUGUGGCUGUCUGUUUGUCUGUGCGCCGUGGUGCUGGGUCAGUGCC<br>AGCGGGAAACCGCGGAAAAGAACGAUUAUUACCGAGUACCGCAUUACUGGG<br>ACGCGUGCUCUCGCGCGCUGCCCGACCAAACCCGUUACAAGUAUGUGGAACA<br>GCUCGUGGACCUCACGUUGAACUACCACUACGAUGCGAGCCACGGCUUGGAC<br>AACUUUGACGUGCUCAAGAGAAUCAACGUGACCGAGGUGUCGUUGCUCAUC<br>AGCGACUUUAGACGUCAGAACCGUCGCGGCGGCACCAACAAAAGGACCACGU<br>UCAACGCCGCCGGUUCGCUGGCGCCACACGCCCGGAGCCUCGAGUUCAGCGU<br>GCGGCUCUUUGCCAACUGAUAAUAGGCUGGAGCCUCGGUGGCCAUGCUUCU | 193 |

TABLE 6-continued

Second Generation hCMV mRNA Vaccine Construct Sequences

| Name of mRNA Construct | ORF Sequence (5' UTR sequence is bolded and 3' UTR sequence is underlined) | SEQ ID NO |
|---|---|---|
| | UGCCCCUUGGGCCUCCCCCCAGCCCCUCCUCCCCUUCCUGCACCCGUACCCCC<br>GUGGUCUUUGAAUAAAGUCUGAGUGGGCGGC | |
| hCMV UL131A, amino acid sequence | MRLCRVWLSVCLCAVVLGQCQRETAEKNDYYRVPHYWDACSRALPDQTRYKYV<br>EQLVDLTLNYHYDASHGLDNFDVLKRINVTEVSLLISDFRRQNRRGGTNKRTTFN<br>AAGSLAPHARSLEFSVRLFAN | 67 |
| hCMV_gB, nucleotide sequence | **TCAAGCTTTTGGACCCTCGTACAGAAGCTAATACGACTCACTATAGGGAA**<br>**ATAAGAGAGAAAAGAAGAGTAAGAAGAAATATAAGAGCCACC**ATGGAATC<br>CAGGATCTGGTGCCTGGTAGTCTGCGTTAACTTGTGTATCGTCTGTCTGGGTGC<br>TGCGGTTTCCTCATCTTCTACTCGTGGAACTTCTGCTACTCACAGTCACCATTCC<br>TCTCATACGACGTCTGCTGCTCACTCTCGATCCGGTTCAGTCTCTCAACGCGTA<br>ACTTCTTCCCAAACGGTCAGCCATGGTGTTAACGAGACCATCTACAACACTACC<br>CTCAAGTACGGAGATGTGGTGGGGGTCAATACCACCAAGTACCCCTATCGCGT<br>GTGTTCTATGGCCCAGGGTACGGATCTTATTCGCTTTGAACGTAATATCGTCTG<br>CACCTCGATGAAGCCCATCAATGAAGACCTGGACGAGGGCATCATGGTGGTCT<br>ACAAACGCAACATCGTCGCGCACACCTTTAAGGTACGAGTCTACCAGAAGGTT<br>TTGACGTTTCGTCGTAGCTACGCTTACATCCACACCACTTATCTGCTGGGCAGC<br>AACACGGAATACGTGGCGCCTCCTATGTGGGAGATTCATCATATCAACAGCCA<br>CAGTCAGTGCTACAGTTCCTACAGCCGCGTTATAGCAGGCACGGTTTTCGTGGC<br>TTATCATAGGGACAGCTATGAAAACAAAACCATGCAATTAATGCCCGACGATT<br>ATTCCAACACCCACAGTACCCGTTACGTGACGGTCAAGGATCAATGGCACAGC<br>CGCGGCAGCACCTGGCTCTATCGTGAGACCTGTAATCTGAATTGTATGGTGACC<br>ATCACTACTGCGCGCTCCAAATATCCTTATCATTTTTTCGCCACTTCCACGGGT<br>GACGTGGTTGACATTTCTCCTTTCTACAACGGAACCAATCGCAATGCCAGCTAC<br>TTTGGAGAAAACGCCGACAAGTTTTTCATTTTTCCGAACTACACTATCGTCTCC<br>GACTTTGGAAGACCGAATTCTGCGTTAGAGACCCACAGGTTGGTGGCTTTTCTT<br>GAACGTGCGGACTCGGTGATCTCCTGGGATATACAGGACGAAAAGAATGTCAC<br>TTGTCAACTCACTTTCTGGGAAGCCTCGGAACGCACCATTCGTTCCGAAGCCGA<br>GGACTCGTATCACTTTTCTTCTGCCAAAATGACCGCCACTTTCTTATCTAAGAA<br>GCAAGAGGTGAACATGTCCGACTCTGCGCTGGACTGCGTACGTGATGAGGCTA<br>TAAATAAGTTACAGCAGATTTTCAATACTTCATACAATCAAACATATGAAAAA<br>TATGGAAACGTGTCCGTCTTTGAAACCACTGGTGGTTTGGTAGTGTTCTGGCAA<br>GGTATCAAGCAAAAATCTCTGGTGGAACTCGAACGTTTGGCCAACCGCTCCAG<br>TCTGAATCTTACTCATAATAGAACCAAAAGAAGTACAGATGGCAACAATGCAA<br>CTCATTTATCCAACATGGAATCGGTGCACAATCTGGTCTACGCCCAGCTGCAGT<br>TCACCTATGACACGTTGCGCGGTTACATCAACCGGGCGCTGGCGCAAATCGCA<br>GAAGCCTGGTGTGTGGATCAACGGCGCACCCTAGAGGTCTTCAAGGAACTCAG<br>CAAGATCAACCCGTCAGCCATTCTCTCGGCCATTTACAACAAACCGATTGCCGC<br>GCGTTTCATGGGTGATGTCTTGGGCCTGGCCAGCTGCGTGACCATCAACCAAA<br>CCAGCGTCAAGGTGCTGCGTGATATGAACGTGAAGGAGTCGCCAGGACGCTGC<br>TACTCACGACCCGTGGTCATCTTTAATTTCGCCAACAGCTCGTACGTGCAGTAC<br>GGTCAACTGGGCGAGGACAACGAAATCCTGTTGGGCAACCACCGCACTGAGG<br>AATGTCAGCTTCCCAGCCTCAAGATCTTCATCGCCGGGAACTCGGCCTACGAGT<br>ACGTGGACTACCTCTTCAAACGCATGATTGACCTCAGCAGTATCTCCACCGTCG<br>ACAGCATGATCGCCCTGGATATCGACCCGCTGGAAAATACCGACTTCAGGGTA<br>CTGGAACTTTACTCGCAGAAAGAGCTGCGTTCCAGCAACGTTTTTGACCTCGAA<br>GAGATCATGCGCGAATTCAACTCGTACAAGCAGCGGGTAAAGTACGTGGAGG<br>ACAAGGTAGTCGACCCGCTACCGCCCTACCTCAAGGGTCTGGACGACCTCATG<br>AGCGGCCTGGGCGCCGCGGGAAAGGCCGTTGGCGTAGCCATTGGGGCCGTGG<br>GTGGCGCGGTGGCCTCCGTGGTCGAAGGCGTTGCCACCTTCCTCAAAAACCCC<br>TTCGGAGCGTTCACCATCATCCTCGTGGCCATAGCTGTAGTCATTATCACTTAT<br>TTGATCTATACTCGACAGCGGCGTTTGTGCACGCAGCCGCTGCAGAACCTCTTT<br>CCCTATCTGGTGTCCGCCGACGGGACCACCGTGACGTCGGGCAGCACCAAAGA<br>CACGTCGTTACAGGCTCCGCCTTCCTACGAGGAAAGTGTTTATAATTCTGGTCG<br>CAAAGGACCGGGACCACCGTCGTCTGATGCATCCACGGCGGCTCCGCCTTACA<br>CCAACGAGCAGGCTTACCAGATGCTTCTGGCCCTGGCCCGTCTGGACGCAGAG<br>CAGCGAGCGCAGCAGAACGGTACAGATTCTTTGGACGGACGGACTGGCACGC<br>AGGACAAGGGACAGAAGCCCAACCTACTAGACCGACTGCGACATCGCAAAAA<br>CGGCTACCGACACTTGAAAGACTCTGACGAAGAAGAGAACGTCTTGATAATAG<br>GCTGGAGCCTCGGTGGCCATGCTTCTTGCCCCTTGGGCCTCCCCCCAGCCCCTC<br>CTCCCCTTCCTGCACCCGTACCCCCGTGGTCTTTGAATAAAGTCTGAGTGGGCG<br>GC | 68 |
| hCMV_gB, nucleotide sequence mRNA | UCAAGCUUUUGGACCCUCGUACAGAAGCUAAUACGACUCACUAUAGGGAAA<br>UAAGAGAGAAAAGAAGAGUAAGAAGAAAUAUAAGAGCCACCAUGGAAUCCA<br>GGAUCUGGUGCCUGGUAGUCUGCGUUAACUUGUGUAUCGUCUGUCUGGGUG<br>CUGCGGUUUCCUCAUCUUCUACUCGUGGAACUUCUGCUACUCACAGUCACCA<br>UUCCUCUCAUACGACGUCUGCUGCUCACUCUCGAUCCGGUUCAGUCUCUCAA<br>CGCGUAACUUCUUCCCAAACGGUCAGCCAUGGUGUUAACGAGACCAUCUACA<br>ACACUACCCUCAAGUACGGAGAUGUGGUGGGGGUCAAUACCACCAAGUACC<br>CCUAUCGCGUGUGUUCUAUGGCCCAGGGUACGGAUCUUAUUCGCUUUGAAC<br>GUAAUAUCGUCUGCACCUCGAUGAAGCCCAUCAAUGAAGACCUGGACGAGG | 194 |

TABLE 6-continued

| Second Generation hCMV mRNA Vaccine Construct Sequences | | |
|---|---|---|
| Name of mRNA Construct | ORF Sequence (5' UTR sequence is bolded and 3' UTR sequence is underlined) | SEQ ID NO |
| | GCAUCAUGGUGGUCUACAAACGCAACAUCGUCGCGCACACCUUUAAGGUAC<br>GAGUCUACCAGAAGGUUUUGACGUUUCGUCGUAGCUACGCUUACAUCCACA<br>CCACUUAUCUGCUGGGCAGCAACACGGAAUACGUGGCGCCUCCUAUGUGGG<br>AGAUUCAUCAUAUCAACAGCCACAGUCAGUGCUACAGUUCCUACAGCCGCGU<br>UAUAGCAGGCACGGUUUUCGUGGCUUAUCAUAGGGACAGCUAUGAAAACAA<br>AACCAUGCAAUUAAUGCCCGACGAUUAUUCCAACACCCACAGUACCCGUUAC<br>GUGACGGUCAAGGAUCAAUGGCACAGCCGCGGCAGCACCUGGCUCUAUCGU<br>GAGACCUGUAAUCUGAAUUGUAUGGUGACCAUCACUACUGCGCGCUCCAAA<br>UAUCCUUAUCAUUUUUUCGCCACUUCCACGGGUGACGUGGUUGACAUUUCU<br>CCUUUCUACAACGGAACCAAUCGCAAUGCCAGCUACUUUGGAGAAAACGCCG<br>ACAAGUUUUUCAUUUUUCCGAACUACACUAUCGUCUCCGACUUUGGAAGAC<br>CGAAUUCUGCGUUAGAGACCCACAGGUUGGUGGCUUUUCUUGAACGUGCGG<br>ACUCGGUGAUCUCCUGGGAUAUACAGGACGAAAAGAAUGUCACUUGUCAAC<br>UCACUUUCUGGGAAGCCUCGGAACGCACCAUUCGUUCCGAAGCCGAGGACUC<br>GUAUCACUUUUCUUCUGCCAAAAUGACCGCCACUUUCUUAUCUAAGAAGCA<br>AGAGGUGAACAUGUCCGACUCUGCGCUGGACUGCGUACGUGAUGAGGCUAU<br>AAAUAAGUUACAGCAGAUUUUCAAUACUUCAUACAAUCAAACAUAUGAAAA<br>AUAUGGAAACGUGUCCGUCUUUGAAACCACUGGUGGUUUGGUAGUGUUCUG<br>GCAAGGUAUCAAGCAAAAAUCUCUGGUGGAACUCGAACGUUUGGCCAACCG<br>CUCCAGUCUGAAUCUUACUCAUAAUAGAACCAAAAGAAGUACAGAUGGCAA<br>CAAUGCAACUCAUUUAUCCAACAUGGAAUCGGUGCACAAUCUGGUCUACGC<br>CCAGCUGCAGUUCACCUAUGACACGUUGCGCGGUUACAUCAACCGGGCGCUG<br>GCGCAAAUCGCAGAAGCCUGGUGUGUGGAUCAACGGCGCACCCUAGAGGUC<br>UUCAAGGAACUCAGCAAGAUCAACCCGUCAGCCAUUCUCUCGGCCAUUUACA<br>ACAAACCGAUUGCCGCGCGUUUCAUGGGUGAUGUCUUGGGCCUGGCCAGCU<br>GCGUGACCAUCAACCAAACCAGCGUCAAGGUGCUGCGUGAUAUGAACGUGA<br>AGGAGUCGCCAGGACGCUGCUACUCACGACCCGUGGUCAUCUUUAAUUUCGC<br>CAACAGCUCGUACGUGCAGUACGGUCAACUGGGCGAGGACAACGAAAUCCU<br>GUUGGGCAACCACCGCACUGAGGAAUGUCAGCUUCCCAGCCUCAAGAUCUUC<br>AUCGCCGGGAACUCGGCCUACGAGUACGUGGACUACCUCUUCAAACGCAUGA<br>UUGACCUCAGCAGUAUCUCCACCGUCGACAGCAUGAUCGCCCUGGAUAUCGA<br>CCCGCUGGAAAAUACCGACUUCAGGGUACUGGAACUUUACUCGCAGAAAGA<br>GCUGCGUUCCAGCAACGUUUUUGACCUCGAAGAGAUCAUGCGCGAAUUCAA<br>CUCGUACAAGCAGCGGGUAAAGUACGUGGAGGACAAGGUAGUCGACCCGCU<br>ACCGCCCUACCUCAAGGGUCUGGACGACCUCAUGAGCGGCCUGGGCGCCGCG<br>GGAAAGGCCGUUGGCGUAGCCAUUGGGGCCGUGGGUGGCGCGGUGGCCUCC<br>GUGGUCGAAGGCGUUGCCACCUUCCUCAAAAACCCCUUCGGAGCGUUCACCA<br>UCAUCCUCGUGGCCAUAGCUGUAGUCAUUAUCACUUAUUUGAUCUAUACUC<br>GACAGCGGCGUUUGUGCACGCAGCCGCUGCAGAACCUCUUUCCCUAUCUGGU<br>GUCCGCCGACGGGACCACCGUGACGUCGGGCAGCACCAAAGACACGUCGUUA<br>CAGGCUCCGCCUUCCUACGAGGAAAGUGUUUAUAAUUCUGGUCGCAAAGGA<br>CCGGGACCACCGUCGUCUGAUGCAUCCACGGCGGCUCCGCCUUACACCAACG<br>AGCAGGCUUACCAGAUGCUUCUGGCCCUGGCCCGUCUGGACGCAGAGCAGCG<br>AGCGCAGCAGAACGGUACAGAUUCUUUGGACGGACGGACUGGCACGCAGGA<br>CAAGGGACAGAAGCCCAACCUACUAGACCGACUGCGACAUCGCAAAAACGGC<br>UACCGACACUUGAAAGACUCUGACGAAGAAGAGAACGUCUUGAUAAUAGGC<br>UGGAGCCUCGGUGGCCAUGCUUCUUGCCCCUUGGGCCUCCCCCCAGCCCCUC<br>CUCCCCUUCCUGCACCCGUACCCCCGUGGUCUUUGAAUAAAGUCUGAGUGGG<br>CGGC | |
| hCMV_gB, amino acid sequence | MESRIWCLVVCVNLCIVCLGAAVSSSSTRGTSATHSHHSSHTTSAAHSRSGSVSQR<br>VTSSQTVSHGVNETIYNTTLKYGDVVGVNTTKYPYRVCSMAQGTDLIRFERNIVC<br>TSMKPINEDLDEGIMVVYKRNIVAHTFKVRVYQKVLTFRRSYAYIHTTYLLGSNTE<br>YVAPPMWEIHHINSHSQCYSSYSRVIAGTVFVAYHRDSYENKTMQLMPDDYSNTH<br>STRYVTVKDQWHSRGSTWLYRETCNLNCMVTITTARSKYPYHFFATSTGDVVDIS<br>PFYNGTNRNASYFGENADKFFIFPNYTIVSDFGRPNSALETHRLVAFLERADSVISW<br>DIQDEKNVTCQLTFWEASERTIRSEAEDSYHFSSAKMTATFLSKKQEVNMSDSALD<br>CVRDEAINKLQQIFNTSYNQTYEKYGNVSVFETTGGLVVFWQGIKQKSLVELERL<br>ANRSSLNLTHNRTKRSTDGNNATHLSNMESVHNLVYAQLQFTYDTLRGYINRALA<br>QIAEAWCVDQRRTLEVFKELSKINPSAILSAIYNKPIAARFMGDVLGLASCVTINQT<br>SVKVLRDMNVKESPGRCYSRPVVIFNFANSSYVQYGQLGEDNEILLGNHRTEECQ<br>LPSLKIFIAGNSAYEYVDYLFKRMIDLSSISTVDSMIALDIDPLENTDFRVLELYSQK<br>ELRSSNVFDLEEIMREFNSYKQRVKYVEDKVVDPLPPYLKGLDDLMSGLGAAGKA<br>VGVAIGAVGGAVASVVEGVATFLKNPFGAFTIILVAIAVVIITYLIYTRQRRLCTQP<br>LQNLFPYLVSADGTTVTSGSTKDTSLQAPPSYEESVYNSGRKGPGPPSSDASTAAPP<br>YTNEQAYQMLLALARLDAEQRAQQNGTDSLDGRTGTQDKGQKPNLLDRLRHRK<br>NGYRHLKDSDEEENV | 69 |

Example 26: 2A Peptide Linked Pentameric Subunits

Figure 15:
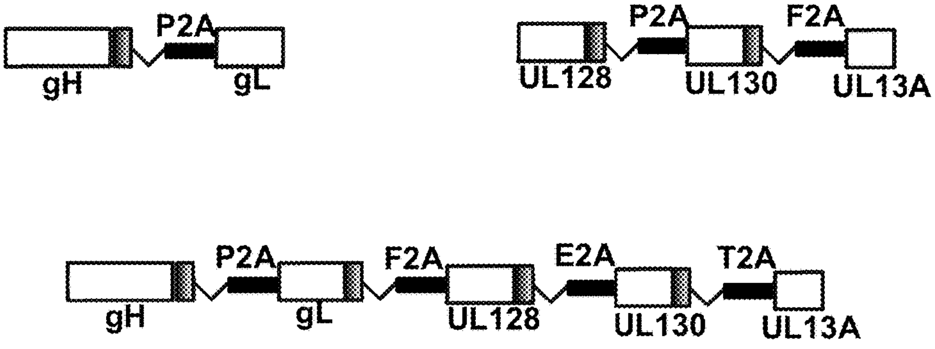
FIG. 15 is a schematic representation of pentametic subunits linked by a self-cleaving 2A peptide (e.g., as described in Kim et al., *PLoS ONE* 6(4): e18556, 2011).
Figure 16:
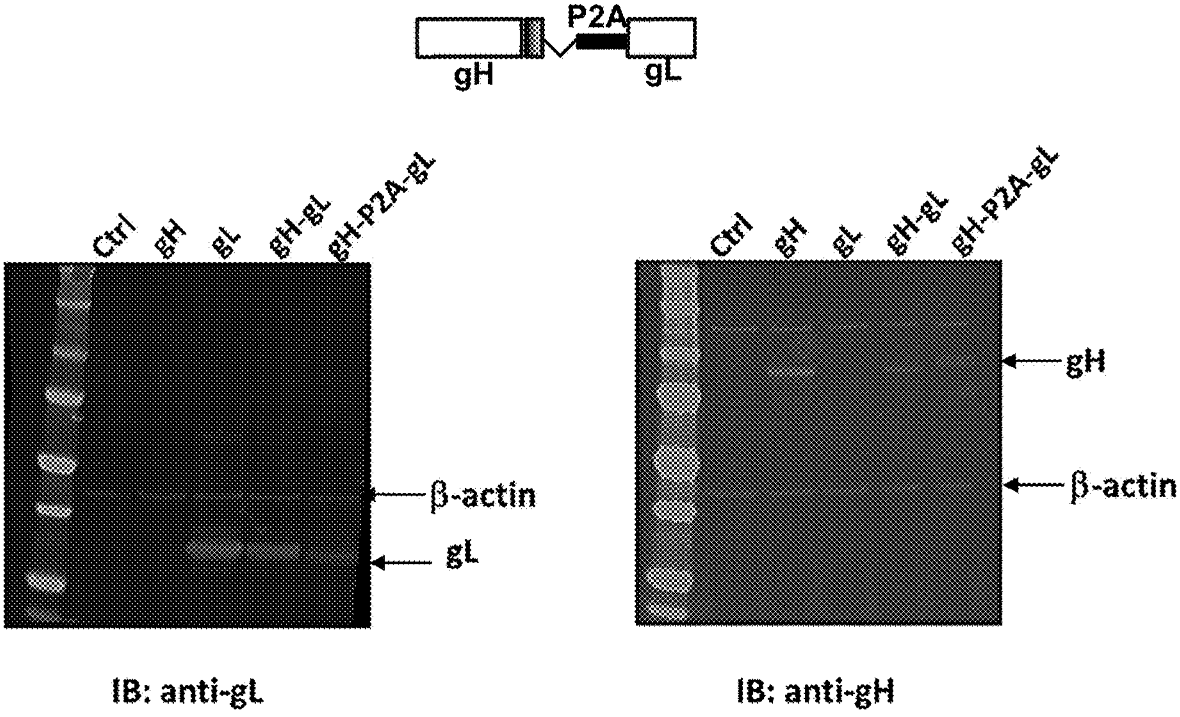
FIG. 16 is a Western blot showing that gH and gL linked by the 2A peptide underwent efficient self-cleavage to generate individual gH and gL subunits.
Figure 17:
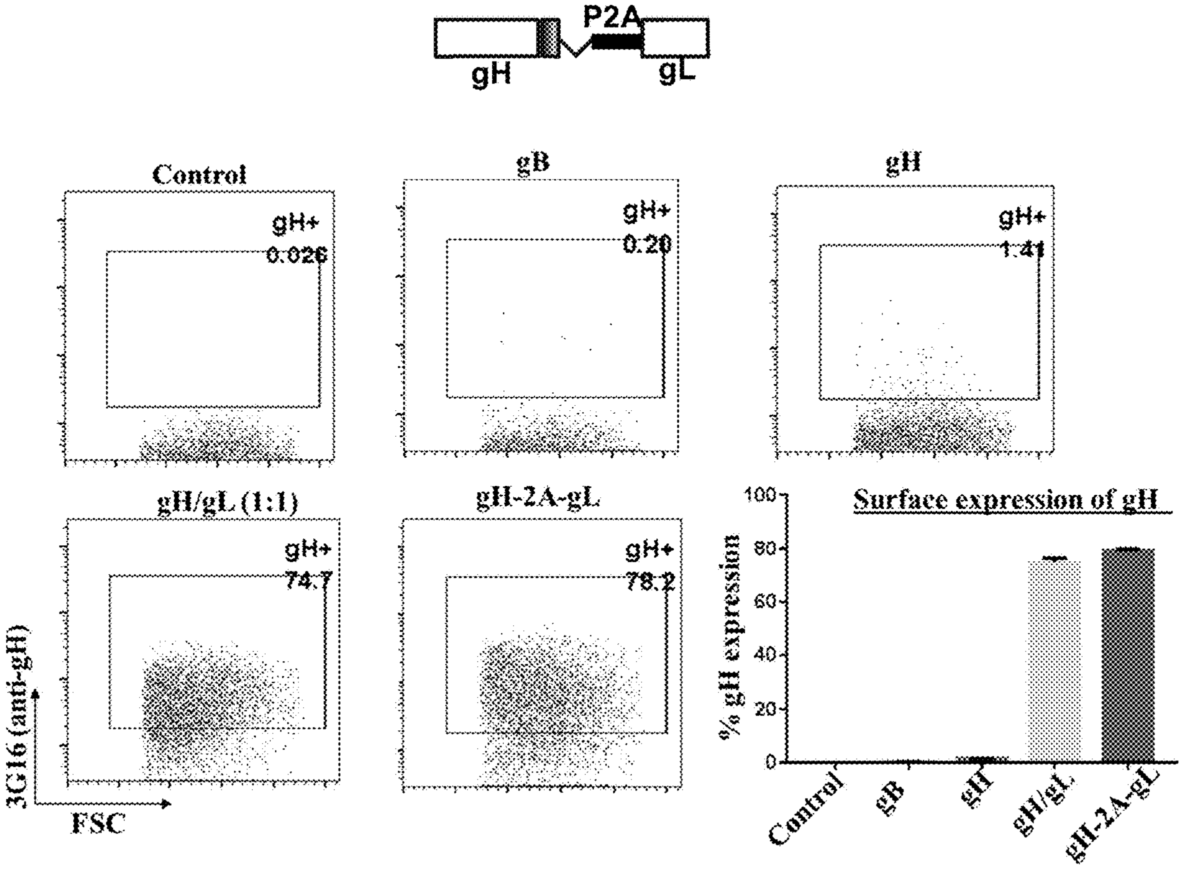
FIG. 17 shows that the individual gH and gL subunits generated from self-cleavage of the 2A peptide linked were able to dimerize and translocate to the cell surface.

Multivalent mRNA vaccine constructs encoding the subunits of the hCMV pentamer (gH, gL, UL128, UL130, and U1131A) were designed. The multivalent mRNA encoded pentamer subunits were linked with 2A self-cleaving peptides (FIG. 15), which allows the linked subunits to process into individual subunits. 1 μg of the mRNA vaccine constructs encoding a 2A peptide linked gH-gL were transfected into 293T cells. The cells were harvested 24 hours post transfection and the cleavage of the 2A peptide were analyzed by detecting individual gH or gL subunits using Western blotting. Individual gH and gL were detected, indicating successful expression of the construct and cleavage of the 2A peptide (FIG. 16). Further, processed gH or gL when expressed in HeLa cells, dimerized, and translocated to the cell surface 24 hours after the Hela cells were transfected with 0.5 μg of mRNA encoding the 2A linked gH-gL (FIG. 17).

Example 27: Comparison of Equimolar vs Equal Mass of Pentamer

Figure 18A:
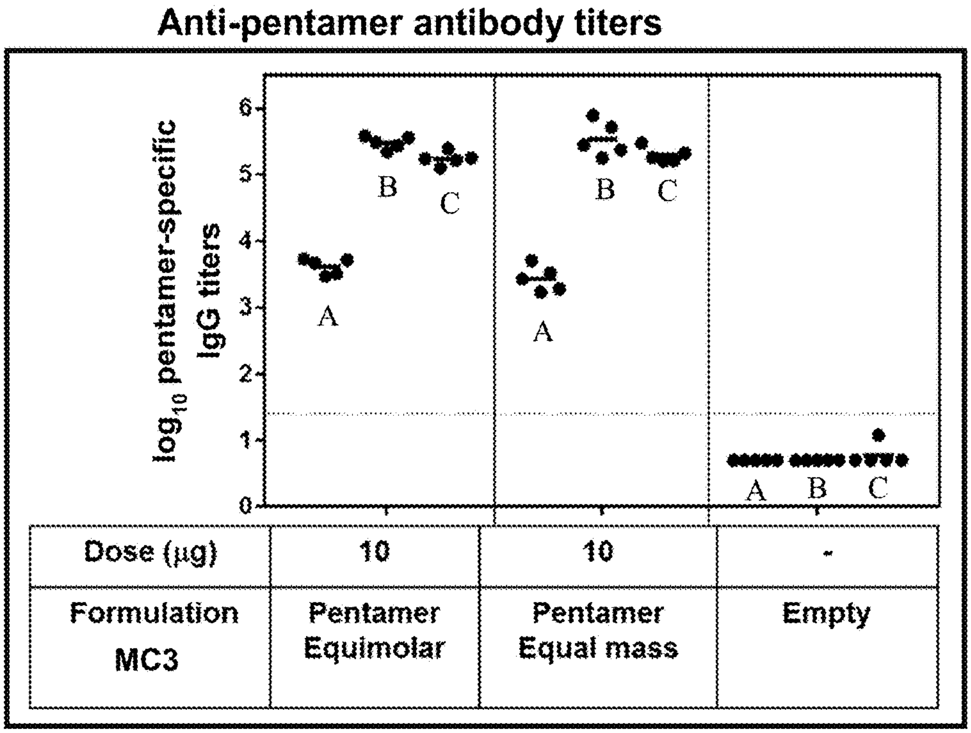
FIGS. 18A-B demonstrates high and sustained titers of anti-pentamer binding and neutralizing antibodies in mice.
Figure 18B:
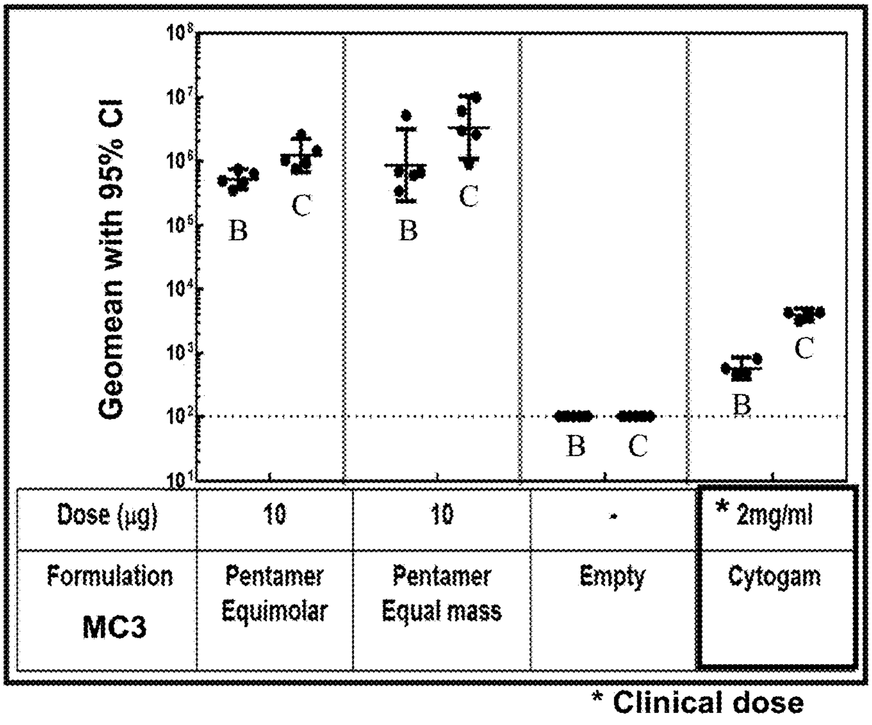

Pentameric formulations containing the pentameric subunit mRNAs at equimolar concentrations were compared to pentameric formulations containing the pentameric subunit mRNAs in equal mass. FIG. 18 demonstrates high and sustained titers of anti-pentamer binding and neutralizing antibodies in mice. FIG. 18A depicts a graph showing anti-pentamer antibody titers. Equimolar and equal mass formulations of the pentameric mRNAs were found to be equally effective. FIG. 18B depicts a graph showing neutralizing titers measured on ARPE19 epithelial cells infected with hCMV strain VR1814. Equimolar and equal mass formulations of the pentameric mRNAs were compared and were found to be equally effective. Neutralizing titers were found to be approximately 25 fold higher than CytoGam®.

Example 28: Neutralization Activity is Dependent on Anti-Pentamer Antibodies

Figure 19A:
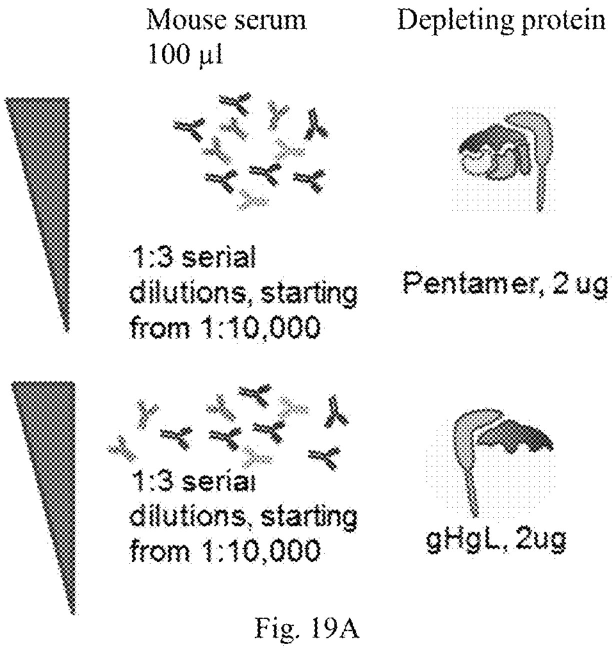
FIG. 19A-C demonstrate that neutralization activity against epithelial cell infection is dependent on anti-pentamer antibodies.
Figure 19B:
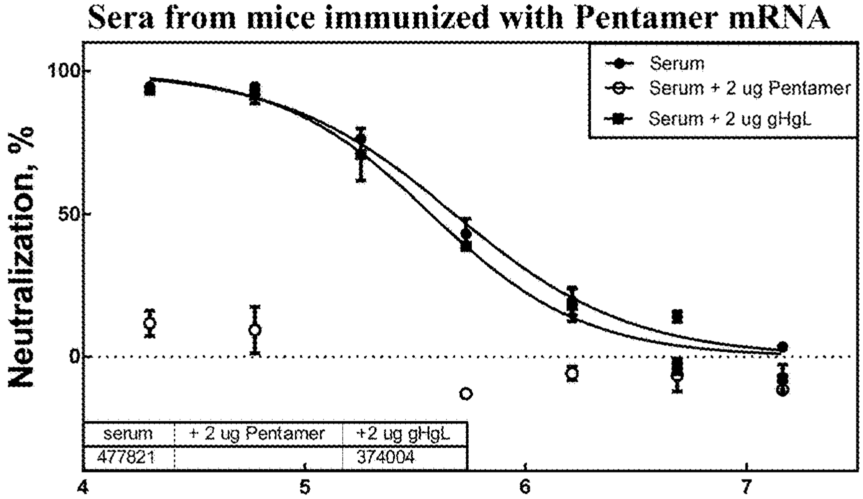
Figure 19C:
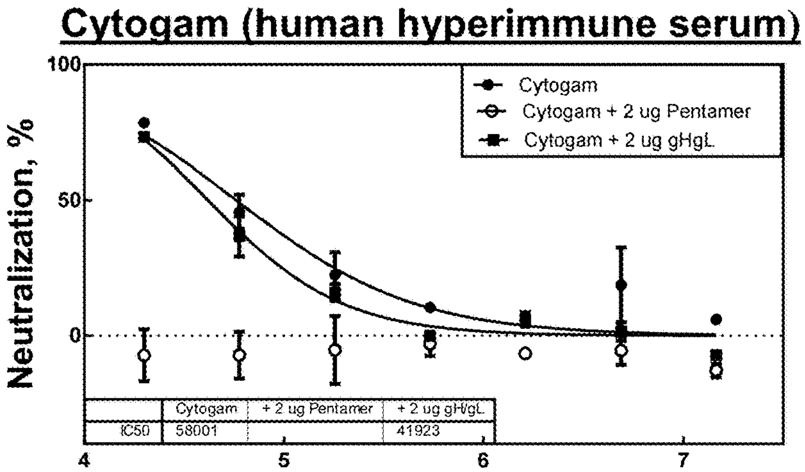

Neutralization data was assessed and compared against CytoGam®. FIG. 19 demonstrates that neutralization activity against epithelial cell infection is dependent on anti-pentamer antibodies. FIG. 19A shows that the depleting protein was either the pentamer or a gH/gL dimer. FIG. 19B and FIG. 19C depict graphs showing neutralization. FIG. 19B shows neutralization by sera from mice immunized with the pentamer or with a gH/gL dimer. FIG. 19C shows neutralization by CytoGam® combined with the pentamer or with a gH/gL.

Example 29:Phase 1 Clinical Trial

A phase 1 clinical trial is conducted to assess the safety of the hCMV mRNA vaccine encoding the pentameric complex (gH, gL, UL128, UL130, and UL131A)+gB in humans and to evaluate the ability of the hCMV mRNA vaccines to induce an immune response. One hundred and twenty (120) volunteers (both females and males) between ages 18-49 are enrolled in the clinical trial. The volunteers are tested for CMV prior to the start of the clinical trial. Sixty (60) of the healthy volunteers are $CMV^+$, while the other sixty (60) are $CMV^-$.

The healthy volunteers are divided into three dosage groups, each dosage group receiving a different dose of the hCMV mRNA vaccine (e.g., low, medium, or high). For each dosage group (n=40), the hCMV mRNA vaccine is administered intramuscularly (IM, n=20) or intravenously (IV, n=20). Thus, the 120 volunteers are placed into 6 groups (referred to as a "dose arm"): low dose-IM (n=20), low dose-IV (n=20), medium dose-IM (n=20), medium dose-IV (n=20), high dose-IM (n=20), high dose-IV (n=20). In each dose arm, the volunteers are separated into two cohorts: the safety cohort (n=4, 2 receiving vaccines and 2 receiving placebos); and the expansion cohort (n=16, 13 receiving vaccines and 3 receiving placebos). The immunization of the volunteers in the expansion cohort starts 7 days after the last healthy volunteer in the safety cohort has been immunized.

hCMV vaccines or placebos are given to the volunteers in the 6 dose arms on day 1, day 31, and day 61. It is a double blind clinical trial. The volunteers are followed up to a year. Blood samples are taken on day 1, day 8, day 22, day 30, day 44, 6 months, and 1 year after the first immunization.

Neutralizing hCMV antibody titers in the blood samples are measured using an Enzyme-linked ImmunoSpot (ELISPOT) assay or using a low cytometric intracellular cytokine staining (ICS) assay. Sustained neutralization antibody titers and strong anamnestic responses are expected in volunteers who received the hCMV mRNA vaccines by 12 months. The level of IgG induced by the hCMV mRNA vaccines are expected to be at least 4 times above the baseline (a clinical endpoint). The neutralization antibody titer in the blood samples of volunteers who received the hCMV mRNA vaccine, measured in a plaque reduction neutralization test (PRNT50) in both epithelial and fibroblast cells, is expected to be higher than that of CytoGam® (a clinical end point). Early signal of efficacy (ESOE) can also be indicated by measuring the viral load in urine and saliva of the volunteers by PCR on day 1, 6 months, and 12 months.

Parameters indicating safety of the vaccine are measured. Immunized volunteers are evaluated for clinical signs of hCMV infection (a clinical endpoint). Biochemical assays are performed to assess the coagulation parameters and the blood level of C-reactive proteins (CRP). The hCMV mRNA vaccine is expected to be safe.

Once safety and immunogenicity have been demonstrated, trials are conducted among target populations in phase 2 clinical trials. In some embodiments, suitable dose levels chosen from phase 1 trials will be used in phase 2 trials.

Example 30: Phase 2 Clinical Trial

The Phase 2 trial is designed to evaluate the hCMV mRNA vaccines in the target population, e.g., seronegative transplant patients that have received solid organ transplants (SOT, e.g., kidney transplant) from a seropositive donor; and/or seropositive patients who have received a hematopoietic stem cell transplant (HCT) from a seronegative donor; and/or seropositive transplant patients that have received solid organ transplants (SOT, e.g., kidney transplant) from a seropositive donor.

Four hundred (400) patients are enrolled in the Phase 2 clinical trial and are grouped as described in the phase 1 clinical trial described in Example 28. All patients are immunized with the same dosage of hCMV mRNA vaccine. Patients receive the first dose of the vaccine on day 1, which is 2-4 weeks prior to the initiation of immunosuppressive therapy, and receive boosts at 1, 3, and 6 months post transplant. It is a double blind clinical trial. The patients are followed up to a year. Blood samples are taken on day 1, day 8, day 22, day 30, day 44, 6 months, and 1 year after the first immunization.

The safety and immunogenicity of the vaccines are assessed using methods described in the phase 1 trial, described in Example 28. A vaccine efficacy of at least 70% is expected. One endpoint of the phase 2 trial is incidence of CMV viremia by central PCR assay. If the plasma viral load is over 1000 IU/ml within 12 months of trial initiation, the patient may be determined to have viremia and may be withdrawn from the trial. Other endpoints include: (i) incidence of CMV viremia by central PCR assay defined as plasma viral load ≥LLOQ (lower limit of quantification); (ii) incidence of CMV disease; (iii)incidence of adjudicated anitviral therapy of the treatment of CMV graft survival, and (iv) generation of pp65-specific DC4/CS8 responses.

The hCMV mRNA vaccine is expected to induce immune response and generate neutralizing antibodies. The safety profile is also expected to be high.

Example 31: Phase 3 Clinical Trial

The target population of the Phase 3 trial is patients receiving solid organ transplants (SOT) or hematopoietic stem cell transplant (HCT). No CMV screening is performed prior to enrollment.

Figure 21A:
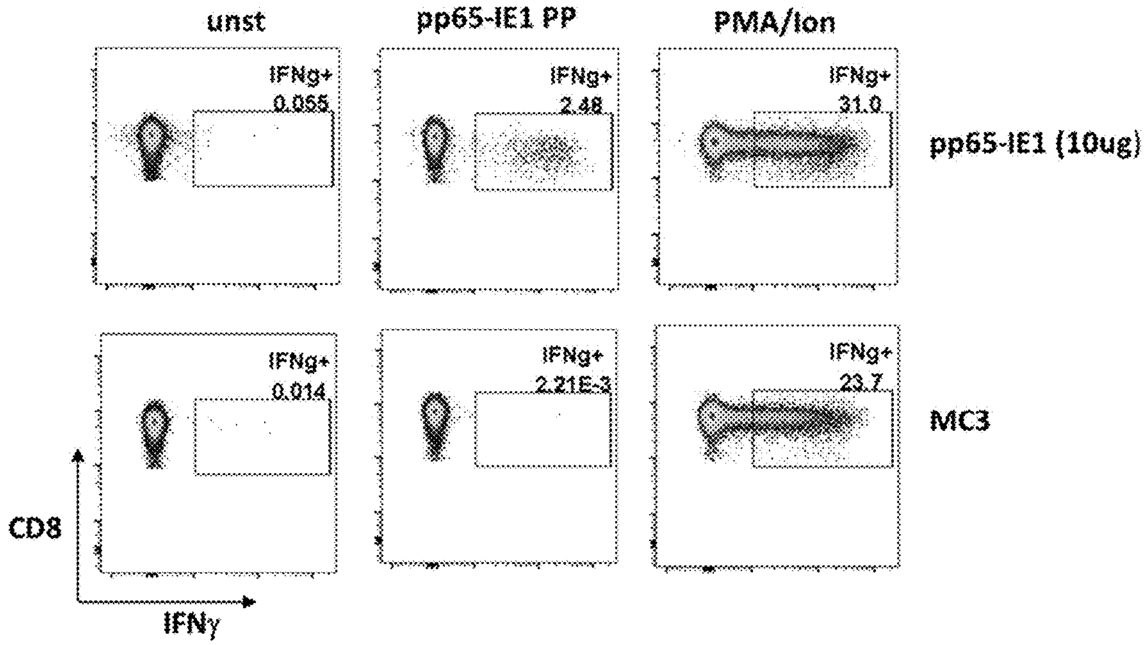
FIGS. 21A-21C show an analysis of the CD8 IFNγ responses in Balb/c mice splenic lymphocytes stimulated with a pp65-IE1 peptide pool. The mice were immunized with pp65-FE-1 or pp65-IE-1+gB mRNA vaccine constructs. pp65-IE1 mRNA induced specific CD8 IFNγ response.
Figure 21B:
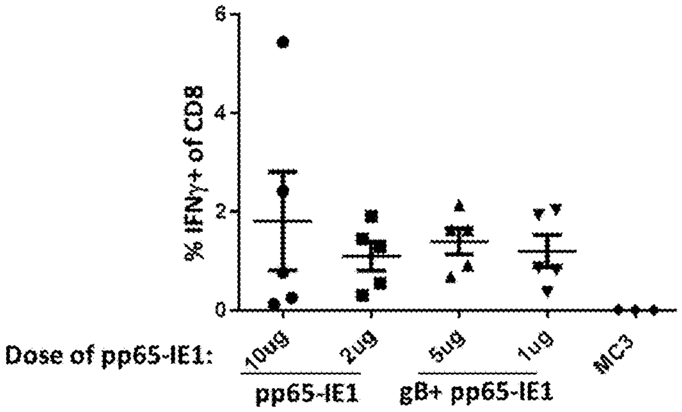
Figure 21C:
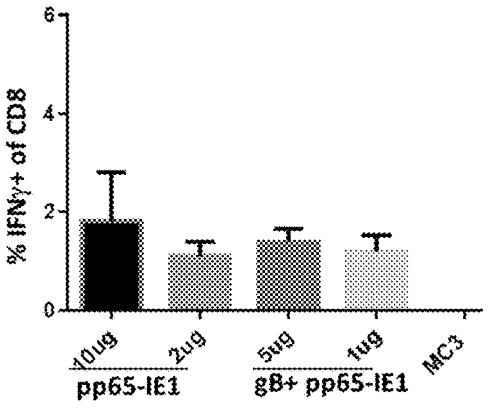

Example 32: Evaluation of Humoral and Cellular Immunity Following Intramuscular Vaccination Balb/c mice were immunized with pp65-IE1, or co-immunized with gB/pp65-IE1 mRNA vaccine constructs at the indicated time points with the indicated dosages by intramuscular administration, as described in Table 7. Splenocytes were isolated for T-cell (CD4 and CD8) IFNγ response analyses. Mice splenocytes were stimulated with pp65-IE1 peptide pools and the induction of INFγ was measured by FACS on a flow cytometer (FIGS. 21A and 22A). PMA+ionomycin was used to stimulate nonspecific T-cell IFNγ response (FIGS. 20A and 21A, right panels). The results showed that splenocytes from mice immunized with pp65-IE1 mRNA vaccines produced IFNγ upon pp65-IE1 peptide pool stimulation, while splenocytes from mice immunized with empty MC3 lipid nanoparticles did not produce IFNγ upon pp65-IE peptide pool stimulation, indicating that immunization with pp65-IE1 mRNAs afforded immunity against hCMV. The induction of IFNγ in splenocytes isolated from mice immunized with different formulations of mRNA vaccine constructs were plotted using the Kapil Bahl—ICS protocol (FIGS. 21B and 22B) or as a bar graph after background subtraction (FIGS. 21C and 22C).

TABLE 7

Evaluation of humoral and cellular immunity following intramuscular vaccination

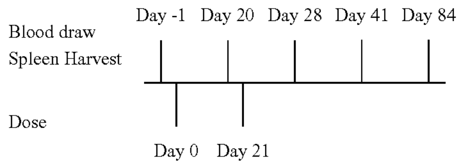

| Group | Vaccine | Route | Dose schedule | N |
|---|---|---|---|---|
| 1 | gB | IM | d0<br>10 ug | 5 |
| 2 | gB | IM | d0, d21<br>10 ug, 3 ug, 1 ug | 5 |
| 5 | gB<br>protein/MF59 | IM | d0, d21<br>10 ug | 5 |
| 6 | pp65-IE1 | IM | d0, d21<br>10 ug, 2 ug | 5 |
| 8 | gB + pp65 + IE1<br>(1:1), Equal conc | IM | d0, d21<br>10 ug, 2 ug | 5 |
| 11 | Empty LNP | IM | d0, d21, d42 | 5 |

Example 33: Combining hCMV Pentameric Complex mRNA Vaccine with mRNA Constructs Encoding Other Antigens The hCMV pentameric mRNA constructs were combined with mRNA constructs encoding gB and other hCMV antigens (e.g., pp65, and/or pp65-IE1, sequences shown in Tables 8 and 9) for immunization of Balb/c mice. Mice serum were taken at day 41 post immunization and assayed on pentamer coated plates for the assessment of pentamer-specific IgG titer. Addition of mRNA constructs encoding other antigens did not affect the induction of pentamer-specific IgG (FIG. 23 and FIG. 26). Similarly, when mice serum was assayed on gB-coated plates, the results showed that the addition of mRNAs encoding the pentamer and pp65-IE1 did not affect the induction of gB-specific IgG (FIG. 24 and FIG. 27). The level of neutralizing antibodies induced by mRNA vaccine constructs encoding hCMV pentamer, gB, and pp65-IE1 was also assessed, as shown in FIGS. 15-16. The combination of mRNA constructs encoding the pentamer, gB, and pp65-IE1 induced high neutralizing antibody titers against hCMV infection (FIG. 28). Different ratios of gB:pentamer were also tested (Table 10).

Next, antigen-specific T cell responses were assessed in the splenic lymphocytes of Balb/c mice immunized with hCMV mRNA vaccines encoding hCMV pentamer, gB, and pp65-IE1. The splenic lymphocytes were stimulated with a pentamer peptide library or a pp65-IE1 peptide pool. When the mRNA vaccine used to immunize the mice was pentamer (5 μg):gB (5 μg): pp65-IE1 (2 μg), robust CD8 response was stimulated by the pentamer peptide library (FIG. 25A). When the mRNA vaccine used to immunize the mice was pentamer (1 μg):gB (1 μg): pp65-IE1 (1 rig), CD8 (left panel) and CD4 (right panel) T cell responses were induced by a pp65-IE1 peptide pool (FIG. 25B). In summary, immunization with mRNA vaccine constructs encoding the hCMV pentamer elicited robust T cell responses. Equal concentrations of all mRNAs within the vaccine are likely to be effective as a prophylactic vaccine.

Each of the sequences described herein encompasses a chemically modified sequence or an unmodified sequence which includes no nucleotide modifications.

TABLE 8

| Second Generation hCMV pp65 mRNA Vaccine Constructs Sequences | | |
|---|---|---|
| Name of re-designed mRNA Construct | Sequence | SEQ ID NO |
| pp65 phos mut_DX, nucleotide sequence | TCAAGCTTTTGGACCCTCGTACAGAAGCTAATACGACTCACTATAGGGAAATA<br>AGAGAGAAAAGAAGAGTAAGAAGAAATATAAGAGCCACCATGGAGTCGCGCG<br>GTCGCCGTTGTCCCGAAATGATATCCGTACTGGGTCCCATTTCGGGGCACGTGC<br>TGAAAGCCGTGTTTAGTCGCGGCGATACGCCGGTGCTGCCGCACGAGACGAGA<br>CTCCTGCAGACGGGTATCCACGTACGCGTGAGCCAGCCCTCGCTGATCCTGGT<br>GTCGCAGTACACGCCCGACTCGACGCCATGCCACCGCGGCGACAATCAGCTGC<br>AGGTGCAGCACACGTACTTTACGGGCAGCGAGGTGGAGAACGTGTCGGTCAAC<br>GTGCACAACCCCACGGGCCGAAGCATCTGCCCCAGCCAAGAGCCCATGTCGAT<br>CTATGTGTACGCGCTGCCGCTCAAGATGCTGAACATCCCCAGCATCAACGTGC<br>ACCACTACCCGTCGGCGGCCGAGCGCAAACACCGACACCTGCCCGTAGCCGAC<br>GCTGTTATTCACGCGTCGGGCAAGCAGATGTGGCAGGCGCGTCTCACGGTCTC<br>GGGACTGGCCTGGACGCGTCAGCAGAACCAGTGGAAAGAGCCCGACGTCTACT<br>ACACGTCAGCGTTCGTGTTTCCCACCAAGGACGTGGCACTGCGGCACGTGGTG<br>TGCGCGCACGAGCTGGTTTGCTCCATGGAGAACACGCGCGCAACCAAGATGCA<br>GGTGATAGGTGACCAGTACGTCAAGGTGTACCTGGAGTCCTTCTGCGAGGACG<br>TGCCCTCCGGCAAGCTCTTTATGCACGTCACGCTGGGCTCTGACGTGGAAGAG<br>GACCTAACGATGACCCGCAACCCGCAACCCTTCATGCGCCCCCACGAGCGCAA<br>CGGCTTTACGGTGTTGTGTCCCAAAAATATGATAATCAAACCGGGCAAGATCT<br>CGCACATCATGCTGGATGTGGCTTTTACCTCACACGAGCATTTTGGGCTGCTGT<br>GTCCCAAGAGCATCCCGGGCCTGAGCATCTCAGGTAACCTGTTGATGAACGGG<br>CAGCAAATCTTCCTGGAGGTACAAGCGATACGCGAGACCGTGGAACTGCGTCA<br>GTACGATCCCGTGGCTGCGCTCTTCTTTTTCGATATCGACTTGTTGCTGCAGCG<br>CGGGCCTCAGTACAGCGAGCACCCCACCTTCACCAGCCAGTATCGCATCCAGG<br>GCAAGCTTGAGTACCGACACACCTGGGACCGGCACGACGAGGGTGCCGCCCA<br>GGGCGACGACGACGTCTGGACCAGCGGATCGGACTCCGACGAAGAACTCGTA<br>ACCACCGAGCGTAAGACGCCCCGCGTCACCGGCGGCGGAGCCATGGCGAGCG<br>CCTCCACTTCCGCGGGCTCAGCATCCTCGGCGACGGCGTGCACGGCGGGCGTT<br>ATGACACGCGGCCGCCTTAAGGCCGAGTCCACCGTCGCGCCCGAAGAGGACAC<br>CGACGAGGATTCCGACAACGAAATCCACAATCCGGCCGTGTTCACCTGGCCGC<br>CCTGGCAGGCCGGCATCCTGGCCCGCAACCTGGTGCCCATGGTGGCTACGGTT<br>CAGGGTCAGAATCTGAAGTACCAGGAGTTCTTCTGGGACGCCAACGACATCTA<br>CCGCATCTTCGCCGAATTGGAAGGCGTATGGCAGCCCGCTGCGCAACCCAAAC<br>GTCGCCGCCACCGGCAAGACGCCTTGCCCGGCCATGCATCGCCTCGACGCCC<br>AAAAAGCACCGAGGTTGATAATAGGCTGGAGCCTCGGTGGCCATGCTTCTTGC<br>CCCTTGGGCCTCCCCCCAGCCCCTCCTCCCCTTCCTGCACCCGTACCCCCGTGG<br>TCTTTGAATAAAGTCTGAGTGGGCGGC | 70 |
| pp65 phos mut_DX, amino acid sequence | MESRGRRCPEMISVLGPISGHVLKAVFSRGDTPVLPHETRLLQTGIHVRVSQPSLIL<br>VSQYTPDSTPCHRGDNQLQVQHTYFTGSEVENVSVNVHNPTGRSICPSQEPMSIYV<br>YALPLKMLNIPSINVHHYPSAAERKHRHLPVADAVIHASGKQMWQARLTVSGLA<br>WTRQQNQWKEPDVYYTSAFVFPTKDVALRHVVCAHELVCSMENTRATKMQVIG<br>DQYVKVYLESFCEDVPSGKLFMHVTLGSDVEEDLTMTRNPQPFMRPHERNGFTVL<br>CPKNMIIKPGKISHIMLDVAFTSHEHFGLLCPKSIPGLSISGNLLMNGQQIFLEVQAI<br>RETVELRQYDPVAALFFFDIDLLLQRGPQYSEHPTFTSQYRIQGKLEYRHTWDRHD<br>EGAAQGDDDVWTSGSDSDEELVTTERKTPRVTGGGAMASASTSAGSASSATACT<br>AGVMTRGRLKAESTVAPEEDTDEDSDNEIHNPAVFTWPPWQAGILARNLVPMVA<br>TVQGQNLKYQEFFWDANDIYRIFAELEGVWQPAAQPKRRRHRQDALPGPCIASTP<br>KKHRG | 71 |

TABLE 9

| hCMV pp65-IE1 Fusion Sequences | | | | |
|---|---|---|---|---|
| Construct Name | Sequence, NT (5' UTR, ORF, 3' UTR) | ORF Sequence, AA | ORF Sequence, NT | mRNA Sequence (assumes T100 tail) |
| hCMV_pp65-IE1 | TCAAGCTTTTGGACC<br>CTCGTACAGAAGCT<br>AATACGACTCACTAT<br>AGGGAAATAAGAGA<br>GAAAAGAAGAGTAA<br>GAAGAAATATAAGA<br>GCCACCATGGAGTC<br>GCGCGGTCGCCGTT<br>GTCCCGAAATGATA<br>TCCGTACTGGGTCCC<br>ATTTCGGGGCACGT<br>GCTGAAAGCCGTGT | MESRGRRCPE<br>MISVLGPISGH<br>VLKAVFSRGD<br>TPVLPHETRL<br>LQTGIHVRVS<br>QPSLILVSQYT<br>PDSTPCHRGD<br>NQLQVQHTYF<br>TGSEVENVSV<br>NVHNPTGRSI<br>CPSQEPMSIY<br>VYALPLKML | ATGGAGTCGCGCGGT<br>CGCCGTTGTCCCGAA<br>ATGATATCCGTACTG<br>GGTCCCATTTCGGGG<br>CACGTGCTGAAAGCC<br>GTGTTTAGTCGCGGC<br>GATACGCCGGTGCTG<br>CCGCACGAGACGCGA<br>CTCCTGCAGACGGGT<br>ATCCACGTACGCGTG<br>AGCCAGCCCTCGCTG<br>ATCCTGGTGTCGCAG | G*GGGAAATAAGAGA<br>GAAAAGAAGAGTAA<br>GAAGAAATATAAGA<br>GCCACCATGGAGTCG<br>CGCGGTCGCCGTTGT<br>CCCGAAATGATATCC<br>GTACTGGGTCCCATT<br>TCGGGGCACGTGCTG<br>AAAGCCGTGTTTAGT<br>CGCGGCGATACGCCG<br>GTGCTGCCGCACGAG<br>ACGCGACTCCTGCAG |

TABLE 9-continued

| hCMV pp65-IE1 Fusion Sequences | | | | |
|---|---|---|---|---|
| Construct Name | Sequence, NT (5' UTR, ORF, 3' UTR) | ORF Sequence, AA | ORF Sequence, NT | mRNA Sequence (assumes T100 tail) |
| | TTAGTCGCGGCGAT | NIPSINVHHYP | TACACGCCCGACTCG | ACGGGTATCCACGTA |
| | ACGCCGGTGCTGCC | SAAERKHRHL | ACGCCATGCCACCGC | CGCGTGAGCCAGCCC |
| | GCACGAGACGCGAC | PVADAVIHAS | GGCGACAATCAGCTG | TCGCTGATCCTGGTG |
| | TCCTGCAGACGGGT | GKQMWQARL | CAGGTGCAGCACACG | TCGCAGTACACGCCC |
| | ATCCACGTACGCGT | TVSGLAWTR | TACTTTACGGGCAGC | GACTCGACGCCATGC |
| | GAGCCAGCCCTCGC | QQNQWKEPD | GAGGTGGAGAACGT | CACCGCGGCGACAAT |
| | TGATCCTGGTGTCGC | VYYTSAFVFP | GTCGGTCAACGTGCA | CAGCTGCAGGTGCAG |
| | AGTACACGCCCGAC | TKDVALRHV | CAACCCCACGGGCCG | CACACGTACTTTACG |
| | TCGACGCCATGCCA | VCAHELVCS | AAGCATCTGCCCCAG | GGCAGCGAGGTGGA |
| | CCGCGGCGACAATC | MENTRATKM | CCAAGAGCCCATGTC | GAACGTGTCGGTCAA |
| | AGCTGCAGGTGCAG | QVIGDQYVKV | GATCTATGTGTACGC | CGTGCACAACCCCAC |
| | CACACGTACTTTACG | YLESFCEDVP | GCTGCCGCTCAAGAT | GGGCCGAAGCATCTG |
| | GGCAGCGAGGTGGA | SGKLFMHVTL | GCTGAACATCCCCAG | CCCCAGCCAAGAGCC |
| | GAACGTGTCGGTCA | GSDVEEDLTM | CATCAACGTGCACCA | CATGTCGATCTATGT |
| | ACGTGCACAACCCC | TRNPQPFMRP | CTACCCGTCGGCGGC | GTACGCGCTGCCGCT |
| | ACGGGCCGAAGCAT | HERNGFTVLC | CGAGCGCAAACACCG | CAAGATGCTGAACAT |
| | CTGCCCCAGCCAAG | PKNMIIKPGKI | ACACCTGCCCGTAGC | CCCCAGCATCAACGT |
| | AGCCCATGTCGATCT | SHIMLDVAFT | CGACGCTGTTATTCA | GCACCACTACCCGTC |
| | ATGTGTACGCGCTGC | SHEHFGLLCP | CGCGTCGGGCAAGCA | GGCGGCCGAGCGCA |
| | CGCTCAAGATGCTG | KSIPGLSISGN | GATGTGGCAGGCGCG | AACACCGACACCTGC |
| | AACATCCCCAGCAT | LLMNGQQIFL | TCTCACGGTCTCGGG | CCGTAGCCGACGCTG |
| | CAACGTGCACCACT | EVQAIRETVE | ACTGGCCTGGACGCG | TTATTCACGCGTCGG |
| | ACCCGTCGGCGGCC | LRQYDPVAAL | TCAGCAGAACCAGTG | GCAAGCAGATGTGGC |
| | GAGCGCAAACACCG | FFFDIDLLLQR | GAAAGAGCCCGACGT | AGGCGCGTCTCACGG |
| | ACACCTGCCCGTAG | GPQYSEHPTF | CTACTACACGTCAGC | TCTCGGGACTGGCCT |
| | CCGACGCTGTTATTC | TSQYRIQGKL | GTTCGTGTTTCCCAC | GGACGCGTCAGCAGA |
| | ACGCGTCGGGCAAG | EYRHTWDRH | CAAGGACGTGGCACT | ACCAGTGGAAAGAG |
| | CAGATGTGGCAGGC | DEGAAQGDD | GCGGCACGTGGTGTG | CCCGACGTCTACTAC |
| | GCGTCTCACGGTCTC | DVWTSGSDSD | CGCGCACGAGCTGGT | ACGTCAGCGTTCGTG |
| | GGGACTGGCCTGGA | EELVTTERKT | TTGCTCCATGGAGAA | TTTCCCACCAAGGAC |
| | CGCGTCAGCAGAAC | PRVTGGGAM | CACGCGCGCAACCAA | GTGGCACTGCGGCAC |
| | CAGTGGAAAGAGCC | ASASTSAGRK | GATGCAGGTGATAGG | GTGGTGTGCGCGCAC |
| | CGACGTCTACTACAC | RKSASSATAC | TGACCAGTACGTCAA | GAGCTGGTTTGCTCC |
| | GTCAGCGTTCGTGTT | TAGVMTRGR | GGTGTACCTGGAGTC | ATGGAGAACACGCGC |
| | TCCCACCAAGGACG | LKAESTVAPE | CTTCTGCGAGGACGT | GCAACCAAGATGCAG |
| | TGGCACTGCGGCAC | EDTDEDSDNE | GCCCTCCGGCAAGCT | GTGATAGGTGACCAG |
| | GTGGTGTGCGCGCA | IHNPAVFTWP | CTTTATGCACGTCAC | TACGTCAAGGTGTAC |
| | CGAGCTGGTTTGCTC | PWQAGILARN | GCTGGGCTCTGACGT | CTGGAGTCCTTCTGC |
| | CATGGAGAACACGC | LVPMVATVQ | GGAAGAGGACCTAA | GAGGACGTGCCCTCC |
| | GCGCAACCAAGATG | GQNLKYQEFF | CGATGACCCGCAACC | GGCAAGCTCTTTATG |
| | CAGGTGATAGGTGA | WDANDIYRIF | CGCAACCCTTCATGC | CACGTCACGCTGGGC |
| | CCAGTACGTCAAGG | AELEGVWQP | GCCCCCACGAGCGCA | TCTGACGTGGAAGAG |
| | TGTACCTGGAGTCCT | AAQPKRRRHR | ACGGCTTTACGGTGT | GACCTAACGATGACC |
| | TCTGCGAGGACGTG | QDALPGPCIA | TGTGTCCCAAAAATA | CGCAACCCGCAACCC |
| | CCCTCCGGCAAGCTC | STPKKHRGES | TGATAATCAAACCGG | TTCATGCGCCCCCAC |
| | TTTATGCACGTCACG | SAKRKMDPD | GCAAGATCTCGCACA | GAGCGCAACGGCTTT |
| | CTGGGCTCTGACGTG | NPDEGPSSKV | TCATGCTGGATGTGG | ACGGTGTTGTGTCCC |
| | GAAGAGGACCTAAC | PRPETPVTKA | CTTTTACCTCACACG | AAAAATATGATAATC |
| | GATGACCCGCAACC | TTFLQTMLRK | AGCATTTTGGGCTGC | AAACCGGGCAAGATC |
| | CGCAACCCTTCATGC | EVNSQLSLGD | TGTGTCCCAAGAGCA | TCGCACATCATGCTG |
| | GCCCCCACGAGCGC | PLFPELAEESL | TCCCGGGCCTGAGCA | GATGTGGCTTTTACC |
| | AACGGCTTTACGGT | KTFEQVTEDC | TCTCAGGTAACCTGT | TCACACGAGCATTTT |
| | GTTGTGTCCCAAAA | NENPEKDVLT | TGATGAACGGGCAGC | GGGCTGCTGTGTCCC |
| | ATATGATAATCAAA | ELVKQIKVRV | AAATCTTCCTGGAGG | AAGAGCATCCCGGGC |
| | CCGGGCAAGATCTC | DMVRHRIKEH | TACAAGCGATACGCG | CTGAGCATCTCAGGT |
| | GCACATCATGCTGG | MLKKYTQTEE | AGACCGTGGAACTGC | AACCTGTTGATGAAC |
| | ATGTGGCTTTTACCT | KFTGAFNMM | GTCAGTACGATCCCG | GGGCAGCAAATCTTC |
| | CACACGAGCATTTTG | GGCLQNALDI | TGGCTGCGCTCTTCTT | CTGGAGGTACAAGCG |
| | GGCTGCTGTGTCCCA | LDKVHEPFED | TTTCGATATCGACTT | ATACGCGAGACCGTG |
| | AGAGCATCCCGGGC | MKCIGLTMQS | GTTGCTGCAGCGCGG | GAACTGCGTCAGTAC |
| | CTGAGCATCTCAGGT | MYENYIVPED | GCCTCAGTACAGCGA | GATCCCGTGGCTGCG |
| | AACCTGTTGATGAA | KREMWMACI | GCACCCCACCTTCAC | CTCTTCTTTTTCGATA |
| | CGGGCAGCAAATCT | KELHDVSKGA | CAGCCAGTATCGCAT | TCGACTTGTTGCTGC |
| | TCCTGGAGGTACAA | ANKLGGALQ | CCAGGGCAAGCTTGA | AGCGCGGGCCTCAGT |
| | GCGATACGCGAGAC | AKARAKKDE | GTACCGACACACCTG | ACAGCGAGCACCCCA |
| | CGTGGAACTGCGTC | LRRKMMYMC | GGACCGGCACGACG | CCTTCACCAGCCAGT |
| | AGTACGATCCCGTG | YRNIEFFTKNS | AGGGTGCCGCCCAGG | ATCGCATCCAGGGCA |
| | GCTGCGCTCTTCTTT | AFPKTTNGCS | GCGACGACGACGTCT | AGCTTGAGTACCGAC |
| | TTCGATATCGACTTG | QAMAALQNL | GGACCAGCGGATCGG | ACACCTGGGACCGGC |
| | TTGCTGCAGCGCGG | PQCSPDEIMS | ACTCCGACGAAGAAC | ACGACGAGGGTGCCG |
| | GCCTCAGTACAGCG | YAQKIFKILDE | TCGTAACCACCGAGC | CCCAGGGCGACGACG |
| | AGCACCCCACCTTCA | ERDKVLTHID | GTAAGACGCCCCGCG | ACGTCTGGACCAGCG |
| | CCAGCCAGTATCGC | HIFMDILTTCV | TCACCGGCGGCGGCG | GATCGGACTCCGACG |
| | ATCCAGGGCAAGCT | ETMCNEYKV | CCATGGCGAGCGCCT | AAGAACTCGTAACCA |

TABLE 9-continued hCMV pp65-IE1 Fusion Sequences

| Construct Name | Sequence, NT (5' UTR, ORF, 3' UTR) | ORF Sequence, AA | ORF Sequence, NT | mRNA Sequence (assumes T100 tail) |
|---|---|---|---|---|
| | TGAGTACCGACACA | TSDACMMTM | CCACTTCCGCGGGCC | CCGAGCGTAAGACGC |
| | CCTGGGACCGGCAC | YGGISLLSEFC | GCAAACGCAAATCAG | CCCGCGTCACCGGCG |
| | GACGAGGGTGCCGC | RVLCCYVLEE | CATCCTCGGCGACGG | GCGGCGCCATGGCGA |
| | CCAGGGCGACGACG | TSVMLAKRPL | CGTGCACGGCGGGCG | GCGCCTCCACTTCCG |
| | ACGTCTGGACCAGC | ITKPEVISVMK | TTATGACACGCGGCC | CGGGCCGCAAACGCA |
| | GGATCGGACTCCGA | RRIEEICMKVF | GCCTTAAGGCCGAGT | AATCAGCATCCTCGG |
| | CGAAGAACTCGTAA | AQYILGADPL | CCACCGTCGCGCCCG | CGACGGCGTGCACGG |
| | CCACCGAGCGTAAG | RVCSPSVDDL | AAGAGGACACCGAC | CGGGCGTTATGACAC |
| | ACGCCCCGCGTCAC | RAIAEESDEEE | GAGGATTCCGACAAC | GCGGCCGCCTTAAGG |
| | CGGCGGCGGCGCCA | AIVAYTLATA | GAAATCCACAATCCG | CCGAGTCCACCGTCG |
| | TGGCGAGCGCCTCC | GASSSDSLVSP | GCCGTGTTCACCTGG | CGCCCGAAGAGGAC |
| | ACTTCCGCGGGCCG | PESPVPATIPL | CCGCCCTGGCAGGCC | ACCGACGAGGATTCC |
| | CAAACGCAAATCAG | SSVIVAENSD | GGCATCCTGGCCCGC | GACAACGAAATCCAC |
| | CATCCTCGGCGACG | QEESEQSDEE | AACCTGGTGCCCATG | AATCCGGCCGTGTTC |
| | GCGTGCACGGCGGG | QEEGAQEERE | GTGGCTACGGTTCAG | ACCTGGCCGCCCTGG |
| | CGTTATGACACGCG | DTVSVKSEPV | GGTCAGAATCTGAAG | CAGGCCGGCATCCTG |
| | GCCGCCTTAAGGCC | SEIEEVASEEE | TACCAGGAGTTCTTC | GCCCGCAACCTGGTG |
| | GAGTCCACCGTCGC | EDGAEEPTAS | TGGGACGCCAACGAC | CCCATGGTGGCTACG |
| | GCCCGAAGAGGACA | GGKSTHPMVT | ATCTACCGCATCTTC | GTTCAGGGTCAGAAT |
| | CCGACGAGGATTCC | RSKADQ | GCCGAATTGGAAGGC | CTGAAGTACCAGGAG |
| | GACAACGAAATCCA | (SEQ ID NO: 73) | GTATGGCAGCCCGCT | TTCTTCTGGGACGCC |
| | CAATCCGGCCGTGTT | | GCGCAACCCAAACGT | AACGACATCTACCGC |
| | CACCTGGCCGCCCTG | | CGCCGCCACCGGCAA | ATCTTCGCCGAATTG |
| | GCAGGCCGGCATCC | | GACGCCTTGCCCGGG | GAAGGCGTATGGCAG |
| | TGGCCCGCAACCTG | | CCATGCATCGCCTCG | CCCGCTGCGCAACCC |
| | GTGCCCATGGTGGCT | | ACGCCCAAAAAGCAC | AAACGTCGCCGCCAC |
| | ACGGTTCAGGGTCA | | CGAGGTGAGTCCTCT | CGGCAAGACGCCTTG |
| | GAATCTGAAGTACC | | GCCAAGAGAAAGAT | CCCGGGCCATGCATC |
| | AGGAGTTCTTCTGGG | | GGACCCTGATAATCC | GCCTCGACGCCCAAA |
| | ACGCCAACGACATC | | TGACGAGGGCCCTTC | AAGCACCGAGGTGA |
| | TACCGCATCTTCGCC | | CTCCAAGGTGCCACG | GTCCTCTGCCAAGAG |
| | GAATTGGAAGGCGT | | GCCCGAGACACCCGT | AAAGATGGACCCTGA |
| | ATGGCAGCCCGCTG | | GACCAAGGCCACGAC | TAATCCTGACGAGGG |
| | CGCAACCCAAACGT | | GTTCCTGCAGACTAT | CCCTTCCTCCAAGGT |
| | CGCCGCCACCGGCA | | GTTAAGGAAGGAGGT | GCCACGGCCCGAGAC |
| | AGACGCCTTGCCCG | | TAACAGTCAGCTGAG | ACCCGTGACCAAGGC |
| | GGCCATGCATCGCCT | | CCTGGGAGACCCGCT | CACGACGTTCCTGCA |
| | CGACGCCCAAAAAG | | GTTCCCAGAATTGGC | GACTATGTTAAGGAA |
| | CACCGAGGTGAGTC | | CGAAGAATCCCTCAA | GGAGGTTAACAGTCA |
| | CTCTGCCAAGAGAA | | AACCTTTGAACAAGT | GCTGAGCCTGGGAGA |
| | AGATGGACCCTGAT | | GACCGAGGATTGCAA | CCCGCTGTTCCCAGA |
| | AATCCTGACGAGGG | | CGAGAACCCCGAAA | ATTGGCCGAAGAATC |
| | CCCTTCCTCCAAGGT | | AAGATGTCCTGACAG | CCTCAAAACCTTTGA |
| | GCCACGGCCCGAGA | | AACTCGTCAAACAGA | ACAAGTGACCGAGG |
| | CACCCGTGACCAAG | | TTAAGGTTCGAGTGG | ATTGCAACGAGAACC |
| | GCCACGACGTTCCTG | | ACATGGTGCGGCATA | CCGAAAAAGATGTCC |
| | CAGACTATGTTAAG | | GAATCAAGGAGCAC | TGACAGAACTCGTCA |
| | GAAGGAGGTTAACA | | ATGCTGAAAAAATAT | AACAGATTAAGGTTC |
| | GTCAGCTGAGCCTG | | ACCCAGACGGAAGA | GAGTGGACATGGTGC |
| | GGAGACCCGCTGTT | | AAAATTCACTGGCGC | GGCATAGAATCAAGG |
| | CCCAGAATTGGCCG | | CTTTAATATGATGGG | AGCACATGCTGAAAA |
| | AAGAATCCCTCAAA | | AGGATGTTTGCAGAA | AATATACCCAGACGG |
| | ACCTTTGAACAAGT | | TGCCTTAGATATCTT | AAGAAAAATTCACTG |
| | GACCGAGGATTGCA | | AGATAAGGTTCATGA | GCGCCTTTAATATGA |
| | ACGAGAACCCCGAA | | GCCTTTCGAGGACAT | TGGGAGGATGTTTGC |
| | AAAGATGTCCTGAC | | GAAGTGTATTGGGCT | AGAATGCCTTAGATA |
| | AGAACTCGTCAAAC | | AACTATGCAGAGCAT | TCTTAGATAAGGTTC |
| | AGATTAAGGTTCGA | | GTATGAGAACTACAT | ATGAGCCTTTCGAGG |
| | GTGGACATGGTGCG | | TGTACCTGAGGATAA | ACATGAAGTGTATTG |
| | GCATAGAATCAAGG | | GCGGGAGATGTGGAT | GGCTAACTATGCAGA |
| | AGCACATGCTGAAA | | GGCTTGTATTAAGGA | GCATGTATGAGAACT |
| | AAATATACCCAGAC | | GCTGCATGATGTGAG | ACATTGTACCTGAGG |
| | GGAAGAAAAATTCA | | CAAGGGCGCCGCTAA | ATAAGCGGGAGATGT |
| | CTGGCGCCTTTAATA | | CAAGTTGGGGGGTGC | GGATGGCTTGTATTA |
| | TGATGGGAGGATGT | | ACTGCAGGCTAAGGC | AGGAGCTGCATGATG |
| | TTGCAGAATGCCTTA | | CCGTGCTAAAAAGGA | TGAGCAAGGGCGCCG |
| | GATATCTTAGATAA | | TGAACTTAGGAGAAA | CTAACAAGTTGGGGG |
| | GGTTCATGAGCCTTT | | GATGATGTATATGTG | GTGCACTGCAGGCTA |
| | CGAGGACATGAAGT | | CTACAGGAATATAGA | AGGCCCGTGCTAAAA |
| | GTATTGGGCTAACTA | | GTTCTTTACCAAGAA | AGGATGAACTTAGGA |
| | TGCAGAGCATGTAT | | CTCAGCCTTCCCTAA | GAAAGATGATGTATA |
| | GAGAACTACATTGT | | GACCACCAATGGCTG | TGTGCTACAGGAATA |
| | ACCTGAGGATAAGC | | CAGTCAGGCCATGGC | TAGAGTTCTTTACCA |
| | GGGAGATGTGGATG | | GGCATTGCAGAACTT | AGAACTCAGCCTTCC |

TABLE 9-continued hCMV pp65-IE1 Fusion Sequences

| Construct Name | Sequence, NT (5' UTR, ORF, 3' UTR) | ORF Sequence, AA | ORF Sequence, NT | mRNA Sequence (assumes T100 tail) |
|---|---|---|---|---|
| | GCTTGTATTAAGGA | | GCCTCAGTGCTCTCC | CTAAGACCACCAATG |
| | GCTGCATGATGTGA | | TGATGAGATTATGTC | GCTGCAGTCAGGCCA |
| | GCAAGGGCGCCGCT | | TTATGCCCAGAAAAT | TGGCGGCATTGCAGA |
| | AACAAGTTGGGGGG | | CTTTAAGATTTTGGA | ACTTGCCTCAGTGCT |
| | TGCACTGCAGGCTA | | TGAGGAGAGAGACA | CTCCTGATGAGATTA |
| | AGGCCCGTGCTAAA | | AGGTGCTCACGCACA | TGTCTTATGCCCAGA |
| | AAGGATGAACTTAG | | TTGATCACATATTTA | AAATCTTTAAGATTT |
| | GAGAAAGATGATGT | | TGGATATCCTCACTA | TGGATGAGGAGAGA |
| | ATATGTGCTACAGG | | CATGTGTGGAAACAA | GACAAGGTGCTCACG |
| | AATATAGAGTTCTTT | | TGTGTAATGAGTACA | CACATTGATCACATA |
| | ACCAAGAACTCAGC | | AGGTCACTAGTGACG | TTTATGGATATCCTC |
| | CTTCCCTAAGACCAC | | CTTGTATGATGACCA | ACTACATGTGTGGAA |
| | CAATGGCTGCAGTC | | TGTACGGGGGCATCT | ACAATGTGTAATGAG |
| | AGGCCATGGCGGCA | | CTCTCTTAAGTGAGT | TACAAGGTCACTAGT |
| | TTGCAGAACTTGCCT | | TCTGTCGGGTGCTGT | GACGCTTGTATGATG |
| | CAGTGCTCTCCTGAT | | GCTGCTATGTCTTAG | ACCATGTACGGGGGC |
| | GAGATTATGTCTTAT | | AGGAGACTAGTGTGA | ATCTCTCTCTTAAGT |
| | GCCCAGAAAATCTTT | | TGCTGGCCAAGCGGC | GAGTTCTGTCGGGTG |
| | AAGATTTTGGATGA | | CTCTGATAACCAAGC | CTGTGCTGCTATGTC |
| | GGAGAGAGACAAGG | | CTGAGGTTATCAGTG | TTAGAGGAGACTAGT |
| | TGCTCACGCACATTG | | TAATGAAGCGCCGCA | GTGATGCTGGCCAAG |
| | ATCACATATTTATGG | | TTGAGGAGATCTGCA | CGGCCTCTGATAACC |
| | ATATCCTCACTACAT | | TGAAGGTCTTTGCCC | AAGCCTGAGGTTATC |
| | GTGTGGAAACAATG | | AGTACATTCTGGGGG | AGTGTAATGAAGCGC |
| | TGTAATGAGTACAA | | CCGATCCTTTGAGAG | CGCATTGAGGAGATC |
| | GGTCACTAGTGACG | | TCTGCTCTCCTAGTGT | TGCATGAAGGTCTTT |
| | CTTGTATGATGACCA | | GGATGACCTACGGGC | GCCCAGTACATTCTG |
| | TGTACGGGGGCATC | | CATCGCCGAGGAGTC | GGGGCCGATCCTTTG |
| | TCTCTCTTAAGTGAG | | AGATGAGGAAGAGG | AGAGTCTGCTCTCCT |
| | TTCTGTCGGGTGCTG | | CTATTGTAGCCTACA | AGTGTGGATGACCTA |
| | TGCTGCTATGTCTTA | | CTTTGGCCACCGCTG | CGGGCCATCGCCGAG |
| | GAGGAGACTAGTGT | | GTGCCAGCTCCTCTG | GAGTCAGATGAGGA |
| | GATGCTGGCCAAGC | | ATTCTCTGGTGTCAC | AGAGGCTATTGTAGC |
| | GGCCTCTGATAACC | | CTCCAGAGTCCCCTG | CTACACTTTGGCCAC |
| | AAGCCTGAGGTTAT | | TACCCGCGACTATCC | CGCTGGTGCCAGCTC |
| | CAGTGTAATGAAGC | | CTCTGTCCTCAGTAA | CTCTGATTCTCTGGT |
| | GCCGCATTGAGGAG | | TTGTGGCTGAGAACA | GTCACCTCCAGAGTC |
| | ATCTGCATGAAGGT | | GTGATCAGGAAGAA | CCCTGTACCCGCGAC |
| | CTTTGCCCAGTACAT | | AGTGAACAGAGTGAT | TATCCCTCTGTCCTCA |
| | TCTGGGGGCCGATC | | GAGGAACAGGAGGA | GTAATTGTGGCTGAG |
| | CTTTGAGAGTCTGCT | | GGGTGCTCAGGAGGA | AACAGTGATCAGGAA |
| | CTCCTAGTGTGGATG | | GCGGGAGGACACTGT | GAAAGTGAACAGAG |
| | ACCTACGGGCCATC | | GTCTGTCAAGTCTGA | TGATGAGGAACAGG |
| | GCCGAGGAGTCAGA | | GCCAGTGTCTGAGAT | AGGAGGGTGCTCAGG |
| | TGAGGAAGAGGCTA | | AGAGGAAGTTGCCTC | AGGAGCGGGAGGAC |
| | TTGTAGCCTACACTT | | AGAGGAAGAGGAGG | ACTGTGTCTGTCAAG |
| | TGGCCACCGCTGGT | | ATGGTGCTGAGGAAC | TCTGAGCCAGTGTCT |
| | GCCAGCTCCTCTGAT | | CCACCGCCTCTGGAG | GAGATAGAGGAAGTT |
| | TCTCTGGTGTCACCT | | GCAAGAGCACCCACC | GCCTCAGAGGAAGA |
| | CCAGAGTCCCCTGTA | | CTATGGTGACTAGAA | GGAGGATGGTGCTGA |
| | CCCGCGACTATCCCT | | GCAAGGCTGACCAG | GGAACCCACCGCCTC |
| | CTGTCCTCAGTAATT | | (SEQ ID NO: 74) | TGGAGGCAAGAGCA |
| | GTGGCTGAGAACAG | | | CCCACCCTATGGTGA |
| | TGATCAGGAAGAAA | | | CTAGAAGCAAGGCTG |
| | GTGAACAGAGTGAT | | | ACCAGTGATAATAGG |
| | GAGGAACAGGAGGA | | | CTGGAGCCTCGGTGG |
| | GGGTGCTCAGGAGG | | | CCATGCTTCTTGCCC |
| | AGCGGGAGGACACT | | | CTTGGGCCTCCCCCC |
| | GTGTCTGTCAAGTCT | | | AGCCCCTCCTCCCCT |
| | GAGCCAGTGTCTGA | | | TCCTGCACCCGTACC |
| | GATAGAGGAAGTTG | | | CCCGTGGTCTTTGAA |
| | CCTCAGAGGAAGAG | | | TAAAGTCTGAGTGGG |
| | GAGGATGGTGCTGA | | | CGGCAAAAAAAAAA |
| | GGAACCCACCGCCT | | | AAAAAAAAAAAAAA |
| | CTGGAGGCAAGAGC | | | AAAAAAAAAAAAAA |
| | ACCCACCCTATGGTG | | | AAAAAAAAAAAAAA |
| | ACTAGAAGCAAGGC | | | AAAAAAAAAAAAAA |
| | TGACCAGTGATAAT | | | AAAAAAAAAAAAAA |
| | AGGCTGGAGCCTCG | | | AAAAAAAAAAAAAA |
| | GTGGCCATGCTTCTT | | | AAAAAATCTAG |
| | GCCCCTTGGGCCTCC | | | (SEQ ID NO: 75) |
| | CCCCAGCCCCTCCTC | | | |
| | CCCTTCCTGCACCCG | | | |
| | TACCCCCGTGGTCTT | | | |

TABLE 9-continued

| hCMV pp65-IE1 Fusion Sequences | | | | |
|---|---|---|---|---|
| Construct Name | Sequence, NT (5' UTR, ORF, 3' UTR) | ORF Sequence, AA | ORF Sequence, NT | mRNA Sequence (assumes T100 tail) |
| | TGAATAAAGTCTGA GTGGGCGGC (SEQ ID NO: 72) | | | |
| pp65-IE1 mut_DX | TCAAGCTTTTGGACC CTCGTACAGAAGCT AATACGACTCACTAT AGGGAAATAAGAGA GAAAAGAAGAGTAA GAAGAAATATAAGA GCCACCATGGAGTC GCGCGGTCGCCGTT GTCCCGAAATGATA TCCGTACTGGGTCCC ATTTCGGGTCATGTG CTGAAAGCGGTGTTT AGTCGCGGCGATAC GCCAGTACTGCCGC ACGAGACGCGACTC CTGCAGACAGGTAT CCACGTACGCGTGA GCCAGCCCTCGCTCA TCCTGGTGTCGCAGT ACACGCCCGACTCG ACGCCATGCCACCG CGGCGACAATCAGC TGCAGGTGCAGCAC ACGTACTTTACGGGC AGCGAGGTGGAGAA CGTGTCGGTCAACGT CCACAACCCCACGG GTCGAAGCATCTGC CCCTCTCAAGAGCCC ATGTCGATCTATGTG TACGCGCTGCCGCTC AAGATGCTGAACAT CCCGAGCATCAACG TGCACCACTACCCG AGCGCGGCCGAGCG CAAACACCGACACC TGCCCGTAGCCGAC GCTGTTATTCACGCG TCGGGCAAGCAGAT GTGGCAAGCGCGCC TCACGGTCTCGGGA CTAGCCTGGACGCG TCAGCAGAACCAGT GGAAAGAGCCCGAC GTCTACTACACGTCA GCGTTCGTGTTTCCC ACCAAGGACGTGGC ACTGCGCCACGTGG TGTGTGCGCACGAG CTGGTTTGCTCCATG GAGAATACGCGCGC AACCAAGATGCAGG TGATAGGTGATCAA TACGTCAAGGTGTA CCTGGAGTCCTTCTG CGAGGATGTGCCCT CCGGTAAGCTCTTTA TGCACGTCACGCTG GGCTCTGACGTGGA AGAGGACCTAACGA TGACCCGCAATCCG CAACCCTTCATGCGC CCCCACGAGCGCAA CGGCTTTACGGTGTT GTGTCCTAAAAATAT GATAATCAAACCAG GCAAGATCTCGCAC ATCATGCTGGATGTG GCTTTTACCTCACAC GAGCATTTTGGGCTG | MESRGRRCPE MISVLGPISGH VLKAVFSRGD TPVLPHETRL LQTGIHVRVS QPSLILVSQYT PDSTPCHRGD NQLQVQHTYF TGSEVENVSV NVHNPTGRSI CPSQEPMSIY VYALPLKML NIPSINVHHYP SAAERKHRHL PVADAVIHAS GKQMWQARL TVSGLAWTR QQNQWKEPD VYYTSAFVFP TKDVALRHV VCAHELVCS MENTRATKM QVIGDQYVKV YLESFCEDVP SGKLFMHVTL GSDVEEDLTM TRNPQPFMRP HERNGFTVLC PKNMIIKPGKI SHIMLDVAFT SHEHFGLLCP KSIPGLSISGN LLMNGQQIFL EVQAIRETVE LRQYDPVAAL FFFDIDLLLQR GPQYSEHPTF TSQYRIQGKL EYRHTWDRH DEGAAQGDD DVWTSGSDSD EELVTTERKT PRVTGGGAM ASASTSAGSA SSATACTAGV MTRGRLKAES TVAPEEDTDE DSDNEIHNPA VFTWPPWQA GILARNLVPM VATVQGQNL KYQEFFWDA NDIYRIFAELE GVWQPAAQP KRRRHRQDA LPGPCIASTPK KHRGESSAKR KMDPDNPDE GPSSKVPRPET PVTKATTFLQ TMLRKEVNSQ LSLGDPLFPEL AEESLKTFEQ VTEDCNENPE KDVLTELVKQ IKVRVDMVR HRIKEHMLKK YTQTEEKFTG AFNMMGGCL QNALDILDKV | ATGGAGTCGCGCGGT CGCCGTTGTCCCGAA ATGATATCCGTACTG GGTCCCATTTCGGGT CATGTGCTGAAAGCG GTGTTTAGTCGCGGC GATACGCCAGTACTG CCGCACGAGACGCGA CTCCTGCAGACAGGT ATCCACGTACGCGTG AGCCAGCCCTCGCTC ATCCTGGTGTCGCAG TACACGCCCGACTCG ACGCCATGCCACCGC GGCGACAATCAGCTG CAGGTGCAGCACACG TACTTTACGGGCAGC GAGGTGGAGAACGT GTCGGTCAACGTCCA CAACCCCACGGGTCG AAGCATCTGCCCCTC TCAAGAGCCCATGTC GATCTATGTGTACGC GCTGCCGCTCAAGAT GCTGAACATCCCGAG CATCAACGTGCACCA CTACCCGAGCGCGGC CGAGCGCAAACACCG ACACCTGCCCGTAGC CGACGCTGTTATTCA CGCGTCGGGCAAGCA GATGTGGCAAGCGCG CCTCACGGTCTCGGG ACTAGCCTGGACGCG TCAGCAGAACCAGTG GAAAGAGCCCGACGT CTACTACACGTCAGC GTTCGTGTTTCCCAC CAAGGACGTGGCACT GCGCCACGTGGTGTG TGCGCACGAGCTGGT TTGCTCCATGGAGAA TACGCGCGCAACCAA GATGCAGGTGATAGG TGATCAATACGTCAA GGTGTACCTGGAGTC CTTCTGCGAGGATGT GCCCTCCGGTAAGCT CTTTATGCACGTCAC GCTGGGCTCTGACGT GGAAGAGGACCTAA CGATGACCCGCAATC CGCAACCCTTCATGC GCCCCCACGAGCGCA ACGGCTTTACGGTGT TGTGTCCTAAAAATA TGATAATCAAACCAG GCAAGATCTCGCACA TCATGCTGGATGTGG CTTTTACCTCACACG AGCATTTTGGGCTGC AACCAGGCAAGATCT TGTGTCCCAAGAGCA TCCCGGGCCTGAGCA TCTCAGGTAACCTGT TGATGAACGGGCAGC AAATCTTTCTCGAGG TGCAAGCTATACGCG AGACCGTCGAACTGC GTCAGTACGATCCCG TGGCTGCGCTGTTCT | G*GGGAAATAAGAGA GAAAAGAAGAGTAA GAAGAAATATAAGA GCCACCATGGAGTCG CGCGGTCGCCGTTGT CCCGAAATGATATCC GTACTGGGTCCCATT TCGGGTCATGTGCTG AAAGCGGTGTTTAGT CGCGGCGATACGCCA GTACTGCCGCACGAG ACGCGACTCCTGCAG ACAGGTATCCACGTA CGCGTGAGCCAGCCC TCGCTCATCCTGGTG TCGCAGTACACGCCC GACTCGACGCCATGC CACCGCGGCGACAAT CAGCTGCAGGTGCAG CACACGTACTTTACG GGCAGCGAGGTGGA GAACGTGTCGGTCAA CGTCCACAACCCCAC GGGTCGAAGCATCTG CCCCTCTCAAGAGCC CATGTCGATCTATGT GTACGCGCTGCCGCT CAAGATGCTGAACAT CCCGAGCATCAACGT GCACCACTACCCGAG CGCGGCCGAGCGCAA ACACCGACACCTGCC CGTAGCCGACGCTGT TATTCACGCGTCGGG CAAGCAGATGTGGCA AGCGCGCCTCACGGT CTCGGGACTAGCCTG GACGCGTCAGCAGAA CCAGTGGAAAGAGCC CGACGTCTACTACAC GTCAGCGTTCGTGTT TCCCACCAAGGACGT GGCACTGCGCCACGT GGTGTGTGCGCACGA GCTGGTTTGCTCCAT GGAGAATACGCGCGC AACCAAGATGCAGGT GATAGGTGATCAATA CGTCAAGGTGTACCT GGAGTCCTTCTGCGA GGATGTGCCCTCCGG TAAGCTCTTTATGCA CGTCACGCTGGGCTC TGACGTGGAAGAGG ACCTAACGATGACCC GCAATCCGCAACCCT TCATGCGCCCCCACG AGCGCAACGGCTTTA CGGTGTTGTGTCCTA AAAATATGATAATCA AACCAGGCAAGATCT CGCACATCATGCTGG ATGTGGCTTTTACCT CACACGAGCATTTTG GGCTGCTGTGTCCCA AGAGCATCCCGGGCC TGAGCATCTCAGGTA ACCTGTTGATGAACG GGCAGCAAATCTTTC TCGAGGTGCAAGCTA |

TABLE 9-continued hCMV pp65-IE1 Fusion Sequences

| Construct Name | Sequence, NT (5' UTR, ORF, 3' UTR) | ORF Sequence, AA | ORF Sequence, NT | mRNA Sequence (assumes T100 tail) |
|---|---|---|---|---|
| | CTGTGTCCCAAGAG | HEPFEDMKCI | TTTTCGATATCGACTT | TACGCGAGACCGTCG |
| | CATCCCGGGCCTGA | GLTMQSMYE | GTTGCTGCAGCGCGG | AACTGCGTCAGTACG |
| | GCATCTCAGGTAAC | NYIVPEDKRE | GCCTCAGTACAGCGA | ATCCCGTGGCTGCGC |
| | CTGTTGATGAACGG | MWMACIKEL | GCACCCCACCTTCAC | TGTTCTTTTTCGATAT |
| | GCAGCAAATCTTTCT | HDVSKGAAN | CAGCCAGTATCGCAT | CGACTTGTTGCTGCA |
| | CGAGGTGCAAGCTA | KLGGALQAK | CCAGGGCAAGCTTGA | GCGCGGGCCTCAGTA |
| | TACGCGAGACCGTC | ARAKKDELRR | GTACCGACACACCTG | CAGCGAGCACCCCAC |
| | GAACTGCGTCAGTA | KMMYMCYR | GGACCGGCACGACG | CTTCACCAGCCAGTA |
| | CGATCCCGTGGCTGC | NIEFFTKNSAF | AGGGAGCCGCCCAG | TCGCATCCAGGGCAA |
| | GCTGTTCTTTTTCGA | PKTTNGCSQA | GGCGACGACGACGTC | GCTTGAGTACCGACA |
| | TATCGACTTGTTGCT | MAALQNLPQ | TGGACCTCTGGATCG | CACCTGGGACCGGCA |
| | GCAGCGCGGGCCTC | CSPDEIMSYA | GACTCCGACGAAGAA | CGACGAGGGAGCCG |
| | AGTACAGCGAGCAC | QKIFKILDEER | CTCGTAACGACCGAG | CCCAGGGCGACGACG |
| | CCCACCTTCACCAGC | DKVLTHIDHIF | CGTAAGACCCCCCGC | ACGTCTGGACCTCTG |
| | CAGTATCGCATCCA | MDILTTCVET | GTCACCGGCGGCGGC | GATCGGACTCCGACG |
| | GGGCAAGCTTGAGT | MCNEYKVTS | GCCATGGCGTCCGCC | AAGAACTCGTAACGA |
| | ACCGACACACCTGG | DACMMTMYG | TCAACTTCCGCGGGC | CCGAGCGTAAGACCC |
| | GACCGGCACGACGA | GISLLSEFCRV | TCAGCATCCTCGGCT | CCCGCGTCACCGGCG |
| | GGGAGCCGCCCAGG | LCCYVLEETS | ACGGCGTGCACGGCG | GCGGCGCCATGGCGT |
| | GCGACGACGACGTC | VMLAKRPLIT | GGCGTTATGACACGT | CCGCCTCAACTTCCG |
| | TGGACCTCTGGATCG | KPEVISVMKR | GGCAGACTTAAGGCC | CGGGCTCAGCATCCT |
| | GACTCCGACGAAGA | RIEEICMKVFA | GAGTCCACCGTCGCG | CGGCTACGGCGTGCA |
| | ACTCGTAACGACCG | QYILGADPLR | CCCGAAGAGGACACC | CGGCGGGCGTTATGA |
| | AGCGTAAGACCCCC | VCSPSVDDLR | GACGAGGATTCCGAC | CACGTGGCAGACTTA |
| | CGCGTCACCGGCGG | AIAEESDEEEA | AACGAAATCCACAAT | AGGCCGAGTCCACCG |
| | CGGCGCCATGGCGT | IVAYTLATAG | CCGGCCGTGTTCACC | TCGCGCCCGAAGAGG |
| | CCGCCTCAACTTCCG | ASSSDSLVSPP | TGGCCGCCCTGGCAG | ACACCGACGAGGATT |
| | CGGGCTCAGCATCCT | ESPVPATIPLS | GCCGGCATCCTGGCC | CCGACAACGAAATCC |
| | CGGCTACGGCGTGC | SVIVAENSDQ | CGCAACCTGGTGCCC | ACAATCCGGCCGTGT |
| | ACGGCGGGCGTTAT | EESEQSDEEQ | ATGGTGGCTACGGTT | TCACCTGGCCGCCCT |
| | GACACGTGGCAGAC | EEGAQEERED | CAGGGTCAGAATCTG | GGCAGGCCGGCATCC |
| | TTAAGGCCGAGTCC | TVSVKSEPVS | AAGTACCAGGAGTTC | TGGCCCGCAACCTGG |
| | ACCGTCGCGCCCGA | EIEEVASEEEE | TTCTGGGACGCCAAC | TGCCCATGGTGGCTA |
| | AGAGGACACCGACG | DGAEEPTASG | GACATCTACCGCATC | CGGTTCAGGGTCAGA |
| | AGGATTCCGACAAC | GKSTHPMVTR | TTCGCCGAATTGGAA | ATCTGAAGTACCAGG |
| | GAAATCCACAATCC | SKADQ | GGCGTATGGCAGCCC | AGTTCTTCTGGGACG |
| | GGCCGTGTTCACCTG | (SEQ ID NO: 77) | GCTGCGCAACCCAAA | CCAACGACATCTACC |
| | GCCGCCCTGGCAGG | | CGTCGCCGCCACCGG | GCATCTTCGCCGAAT |
| | CCGGCATCCTGGCCC | | CAAGACGCCTTGCCC | TGGAAGGCGTATGGC |
| | GCAACCTGGTGCCC | | GGGCCATGCATCGCC | AGCCCGCTGCGCAAC |
| | ATGGTGGCTACGGTT | | TCGACGCCCAAAAAG | CCAAACGTCGCCGCC |
| | CAGGGTCAGAATCT | | CACCGAGGTGAGTCC | ACCGGCAAGACGCCT |
| | GAAGTACCAGGAGT | | TCTGCCAAGAGAAAG | TGCCCGGGCCATGCA |
| | TCTTCTGGGACGCCA | | ATGGACCCTGATAAT | TCGCCTCGACGCCCA |
| | ACGACATCTACCGC | | CCTGACGAGGGCCCT | AAAAGCACCGAGGT |
| | ATCTTCGCCGAATTG | | TCCTCCAAGGTGCCA | GAGTCCTCTGCCAAG |
| | GAAGGCGTATGGCA | | CGGCCCGAGACACCC | AGAAAGATGGACCCT |
| | GCCCGCTGCGCAAC | | GTGACCAAGGCCACG | GATAATCCTGACGAG |
| | CCAAACGTCGCCGC | | ACGTTCCTGCAGACT | GGCCCTTCCTCCAAG |
| | CACCGGCAAGACGC | | ATGTTAAGGAAGGAG | GTGCCACGGCCCGAG |
| | CTTGCCCGGGCCATG | | GTTAACAGTCAGCTG | ACACCCGTGACCAAG |
| | CATCGCCTCGACGCC | | AGCCTGGGAGACCCG | GCCACGACGTTCCTG |
| | CAAAAAGCACCGAG | | CTGTTCCCAGAATTG | CAGACTATGTTAAGG |
| | GTGAGTCCTCTGCCA | | GCCGAAGAATCCCTC | AAGGAGGTTAACAGT |
| | AGAGAAAGATGGAC | | AAAACCTTTGAACAA | CAGCTGAGCCTGGGA |
| | CCTGATAATCCTGAC | | GTGACCGAGGATTGC | GACCCGCTGTTCCCA |
| | GAGGGCCCTTCCTCC | | AACGAGAACCCCGA | GAATTGGCCGAAGAA |
| | AAGGTGCCACGGCC | | AAAAGATGTCCTGAC | TCCCTCAAAACCTTT |
| | CGAGACACCCGTGA | | AGAACTCGTCAAACA | GAACAAGTGACCGA |
| | CCAAGGCCACGACG | | GATTAAGGTTCGAGT | GGATTGCAACGAGAA |
| | TTCCTGCAGACTATG | | GGACATGGTGCGGCA | CCCCGAAAAAGATGT |
| | TTAAGGAAGGAGGT | | TAGAATCAAGGAGCA | CCTGACAGAACTCGT |
| | TAACAGTCAGCTGA | | CATGCTGAAAAAATA | CAAACAGATTAAGGT |
| | GCCTGGGAGACCCG | | TACCCAGACGGAAGA | TCGAGTGGACATGGT |
| | CTGTTCCCAGAATTG | | AAAATTCACTGGCGC | GCGGCATAGAATCAA |
| | GCCGAAGAATCCCT | | CTTTAATATGATGGG | GGAGCACATGCTGAA |
| | CAAAACCTTTGAAC | | AGGATGTTTGCAGAA | AAAATATACCCAGAC |
| | AAGTGACCGAGGAT | | TGCCTTAGATATCTT | GGAAGAAAAATTCAC |
| | TGCAACGAGAACCC | | AGATAAGGTTCATGA | TGGCGCCTTTAATAT |
| | CGAAAAAGATGTCC | | GCCTTTCGAGGACAT | GATGGGAGGATGTTT |
| | TGACAGAACTCGTC | | GAAGTGTATTGGGCT | GCAGAATGCCTTAGA |
| | AAACAGATTAAGGT | | AACTATGCAGAGCAT | TATCTTAGATAAGGT |
| | TCGAGTGGACATGG | | GTATGAGAACTACAT | TCATGAGCCTTTCGA |
| | TGCGGCATAGAATC | | TGTACCTGAGGATAA | GGACATGAAGTGTAT |

TABLE 9-continued hCMV pp65-IE1 Fusion Sequences

| Construct Name | Sequence, NT (5' UTR, ORF, 3' UTR) | ORF Sequence, AA | ORF Sequence, NT | mRNA Sequence (assumes T100 tail) |
|---|---|---|---|---|
| | AAGGAGCACATGCT<br>GAAAAAATATACCC<br>AGACGGAAGAAAAA<br>TTCACTGGCGCCTTT<br>AATATGATGGGAGG<br>ATGTTTGCAGAATGC<br>CTTAGATATCTTAGA<br>TAAGGTTCATGAGC<br>CTTTCGAGGACATG<br>AAGTGTATTGGGCT<br>AACTATGCAGAGCA<br>TGTATGAGAACTAC<br>ATTGTACCTGAGGAT<br>AAGCGGGAGATGTG<br>GATGGCTTGTATTAA<br>GGAGCTGCATGATG<br>TGAGCAAGGGCGCC<br>GCTAACAAGTTGGG<br>GGGTGCACTGCAGG<br>CTAAGGCCCGTGCT<br>AAAAAGGATGAACT<br>TAGGAGAAAGATGA<br>TGTATATGTGCTACA<br>GGAATATAGAGTTC<br>TTTACCAAGAACTCA<br>GCCTTCCCTAAGACC<br>ACCAATGGCTGCTC<br>GCAGGCCATGGCGG<br>CATTGCAGAACTTGC<br>CTCAGTGCTCTCCTG<br>ATGAGATTATGTCTT<br>ATGCCCAGAAAATC<br>TTTAAGATTTTGGAT<br>GAGGAGCGAGACAA<br>GGTGCTTACGCACAT<br>TGATCACATATTTAT<br>GGATATCCTCACTAC<br>ATGTGTTGAAACGA<br>TGTGCAATGAGTAC<br>AAGGTCACTAGTGA<br>CGCTTGTATGATGAC<br>CATGTACGGGGGCA<br>TATCTCTCTTAAGTG<br>AATTCTGTCGGGTGC<br>TGTGCTGCTACGTCT<br>TAGAGGAGACTAGT<br>GTGATGCTGGCCAA<br>GCGGCCTCTGATAA<br>CCAAGCCTGAGGTC<br>ATCAGTGTAATGAA<br>GCGCCGCATTGAGG<br>AGATCTGCATGAAG<br>GTCTTTGCCCAGTAC<br>ATTCTGGGGGCCGA<br>TCCTTTGAGAGTCTG<br>CTCTCCAAGTGTGGA<br>TGACCTACGGGCCA<br>TCGCCGAGGAGTCA<br>GACGAGGAAGAGGC<br>TATTGTAGCCTACAC<br>TTTGGCCACCGCTGG<br>TGCCAGCTCCTCTGA<br>CTCTCTGGTGTCACC<br>TCCAGAATCCCCTGT<br>GCCCGCGACAATCC<br>CTCTGTCCTCAGTAA<br>TTGTGGCTGAGAAC<br>AGTGATCAGGAAGA<br>AAGTGAACAGAGTG<br>ATGAGGAACAGGAG<br>GAGGGTGCTCAGGA<br>GGAGCGGGAGGATA<br>CTGTGTCTGTCAAGT<br>CTGAGCCAGTGTCTG | | GCGGGAGATGTGGAT<br>GGCTTGTATTAAGGA<br>GCTGCATGATGTGAG<br>CAAGGGCGCCGCTAA<br>CAAGTTGGGGGGTGC<br>ACTGCAGGCTAAGGC<br>CCGTGCTAAAAAGGA<br>TGAACTTAGGAGAAA<br>GATGATGTATATGTG<br>CTACAGGAATATAGA<br>GTTCTTTACCAAGAA<br>CTCAGCCTTCCCTAA<br>GACCACCAATGGCTG<br>CTCGCAGGCCATGGC<br>GGCATTGCAGAACTT<br>GCCTCAGTGCTCTCC<br>TGATGAGATTATGTC<br>TTATGCCCAGAAAAT<br>CTTTAAGATTTTGGA<br>TGAGGAGCGAGACA<br>AGGTGCTTACGCACA<br>TTGATCACATATTTA<br>TGGATATCCTCACTA<br>CATGTGTTGAAACGA<br>TGTGCAATGAGTACA<br>AGGTCACTAGTGACG<br>CTTGTATGATGACCA<br>TGTACGGGGGCATAT<br>CTCTCTTAAGTGAAT<br>TCTGTCGGGTGCTGT<br>GCTGCTACGTCTTAG<br>AGGAGACTAGTGTGA<br>TGCTGGCCAAGCGGC<br>CTCTGATAACCAAGC<br>CTGAGGTCATCAGTG<br>TAATGAAGCGCCGCA<br>TTGAGGAGATCTGCA<br>TGAAGGTCTTTGCCC<br>AGTACATTCTGGGGG<br>CCGATCCTTTGAGAG<br>TCTGCTCTCCAAGTG<br>TGGATGACCTACGGG<br>CCATCGCCGAGGAGT<br>CAGACGAGGAAGAG<br>GCTATTGTAGCCTAC<br>ACTTTGGCCACCGCT<br>GGTGCCAGCTCCTCT<br>GACTCTCTGGTGTCA<br>CCTCCAGAATCCCCT<br>GTGCCCGCGACAATC<br>CCTCTGTCCTCAGTA<br>ATTGTGGCTGAGAAC<br>AGTGATCAGGAAGA<br>AAGTGAACAGAGTG<br>ATGAGGAACAGGAG<br>GAGGGTGCTCAGGAG<br>GAGCGGGAGGATACT<br>GTGTCTGTCAAGTCT<br>GAGCCAGTGTCTGAA<br>ATTGAGGAAGTTGCC<br>TCAGAGGAAGAGGA<br>GGATGGTGCTGAGGA<br>ACCCACCGCCTCTGG<br>AGGCAAGTCCACCCA<br>CCCTATGGTAACTAG<br>ATCAAAGGCTGACCAG<br>(SEQ ID NO: 78) | TGGGCTAACTATGCA<br>GAGCATGTATGAGAA<br>CTACATTGTACCTGA<br>GGATAAGCGGGAGA<br>TGTGGATGGCTTGTA<br>TTAAGGAGCTGCATG<br>ATGTGAGCAAGGGCG<br>CCGCTAACAAGTTGG<br>GGGGTGCACTGCAGG<br>CTAAGGCCCGTGCTA<br>AAAAGGATGAACTTA<br>GGAGAAAGATGATGT<br>ATATGTGCTACAGGA<br>ATATAGAGTTCTTTA<br>CCAAGAACTCAGCCT<br>TCCCTAAGACCACCA<br>ATGGCTGCTCGCAGG<br>CCATGGCGGCATTGC<br>AGAACTTGCCTCAGT<br>GCTCTCCTGATGAGA<br>TTATGTCTTATGCCC<br>AGAAAATCTTTAAGA<br>TTTTGGATGAGGAGC<br>GAGACAAGGTGCTTA<br>CGCACATTGATCACA<br>TATTTATGGATATCC<br>TCACTACATGTGTTG<br>AAACGATGTGCAATG<br>AGTACAAGGTCACTA<br>GTGACGCTTGTATGA<br>TGACCATGTACGGGG<br>GCATATCTCTCTTAA<br>GTGAATTCTGTCGGG<br>TGCTGTGCTGCTACG<br>TCTTAGAGGAGACTA<br>GTGTGATGCTGGCCA<br>AGCGGCCTCTGATAA<br>CCAAGCCTGAGGTCA<br>TCAGTGTAATGAAGC<br>GCCGCATTGAGGAGA<br>TCTGCATGAAGGTCT<br>TTGCCCAGTACATTC<br>TGGGGGCCGATCCTT<br>TGAGAGTCTGCTCTC<br>CAAGTGTGGATGACC<br>TACGGGCCATCGCCG<br>AGGAGTCAGACGAG<br>GAAGAGGCTATTGTA<br>GCCTACACTTTGGCC<br>ACCGCTGGTGCCAGC<br>TCCTCTGACTCTCTG<br>GTGTCACCTCCAGAA<br>TCCCCTGTGCCCGCG<br>ACAATCCCTCTGTCC<br>TCAGTAATTGTGGCT<br>GAGAACAGTGATCAG<br>GAAGAAAGTGAACA<br>GAGTGATGAGGAAC<br>AGGAGGAGGGTGCTC<br>AGGAGGAGCGGGAG<br>GATACTGTGTCTGTC<br>AAGTCTGAGCCAGTG<br>TCTGAAATTGAGGAA<br>GTTGCCTCAGAGGAA<br>GAGGAGGATGGTGCT<br>GAGGAACCCACCGCC<br>TCTGGAGGCAAGTCC<br>ACCCACCCTATGGTA<br>ACTAGATCAAAGGCT<br>GACCAGTGATAATAG<br>GCTGGAGCCTCGGTG<br>GCCATGCTTCTTGCC<br>CCTTGGGCCTCCCCC<br>CAGCCCCTCCTCCCC |

TABLE 9-continued

| hCMV pp65-IE1 Fusion Sequences | | | | |
|---|---|---|---|---|
| Construct Name | Sequence, NT (5' UTR, ORF, 3' UTR) | ORF Sequence, AA | ORF Sequence, NT | mRNA Sequence (assumes T100 tail) |
| | AAATTGAGGAAGTT GCCTCAGAGGAAGA GGAGGATGGTGCTG AGGAACCCACCGCC TCTGGAGGCAAGTC CACCCACCCTATGGT AACTAGATCAAAGG CTGACCAGTGATAA TAGGCTGGAGCCTC GGTGGCCATGCTTCT TGCCCCTTGGGCCTC CCCCCAGCCCCTCCT CCCCTTCCTGCACCC GTACCCCCGTGGTCT TTGAATAAAGTCTG AGTGGGCGGC (SEQ ID NO: 76) | | | TTCCTGCACCCGTAC CCCCGTGGTCTTTGA ATAAAGTCTGAGTGG GCGGCAAAAAAAAA AAAAAAAAAAAAAA AAAAAAAAAAAAAA AAAAAAAAAAAAAA AAAAAAAAAAAAAA AAAAAAAAAAAAAA AAAAAAAAAAAAAA AAAAAAATCTAG (SEQ ID NO: 79) |

TABLE 10

| Ratios of gB:Pentamer | | | | | | | | | | | | |
|---|---|---|---|---|---|---|---|---|---|---|---|---|
| Test/Control Material | Vehicle | Formulation | Route | Dosing Regimen | # of Doses | # of males | # of females | Dose Level (mg/kg) | Dose Vol (mL) | Dose Conc. (mg/ mL) | Total Vol Req (mL) | Total Min Mass Req (mg) |
| Pentamer (3) + gB (7) + pp65-IE1 (2) | MC3 | 50:10:38:5:1.5; 72 ± 1 nm | IM | d0, d21, d141 | 3 | | 5 | 0.6 | 0.05 | 0.24 | 1.05 | 0.252 |
| Pentamer (5) + gB (5) + pp65-IE1 (2) | MC3 | 50:10:38:5:1.5; 72 ± 1 nm | IM | d0, d21, d141 | 3 | | 25 | 0.6 | 0.05 | 0.24 | 5.25 | 1.26 |
| Pentamer (8)-gB (2) + pp65-IE1 (2) | MC3 | 50:10:38:5:1.5; 72 ± 1 nm | IM | d0, d21, d141 | 3 | | 5 | 0.6 | 0.05 | 0.24 | 1.05 | 0.252 |
| Pentamer (10) + gB (2) | MC3 | 50:10:38:5:1.5; 72 ± 1 nm | IM | d0, d21, d141 | 3 | | 5 | 0.6 | 0.05 | 0.24 | 1.05 | 0.252 |
| empty LNP | MC3 | 50:10:38:5:1.5; 72 ± 1 nm | IM | d0, d21, d141 | 3 | | 25 | | 0.05 | | | |
| pp65-IE1 (2) | MC3 | 50:10:38:5:1.5; 72 ± 1 nm | IM | d0, d21 | 3 | | 20 | 0.1 | 0.05 | 0.04 | 4.2 | 0.168 |

Example 34: Immunogenicity Study of hCMV mRNA Vaccines Formulated in Compound 25 Lipid Nanoparticles Different lipid nanoparticle formulations (e.g., cationic lipid formulations) were tested for the delivery of the hCMV mRNA vaccines. hCMV mRNA vaccine constructs encoding the pentamer, gB, and pp65-IE1 were formulated in Compound 25 or MC3 lipid nanoparticles for immunizing *Cynomolgus macaques*. The dosages and immunization regimen were as indicated in Table 11. All animals in the study were naturally infected with *Cynomolgus* CMV and had low but varying titers of anti-cyno CMV antibodies. Upon immunization with the hCMV mRNA vaccines, no injection site interactions (Draize score 0) were observed in either Compound 25 or MC3 formulations for all doses. *Cynomolgus macaques* received 100 μg of total mRNA vaccines in either formulation were monitored for 6 months to evaluate the immunogenicity of the mRNA vaccines and the duration of antibody response.

Serum samples were taken from the immunized animals on days 0, 21, and 42 post immunization. Serum pentamer-specific IgG titers were assayed on pentamer coated plates. Compound 25 and MC3 formulations induced comparable IgG titers at high doses (FIG. 24). The hCMV mRNA vaccines formulated in different lipids were also tested for their ability to induce neutralizing antibodies against hCMV in *Cynomolgus*. Serum samples were taken on days 0 and 42 for analysis in neutralization assays. The neutralization assays were performed on ARPE-19 epithelial cells infected with hCMV clinical isolate VR1814 strain (FIG. 25A), or HEL299 fibroblast cells infected with hCMV AS169 strain (FIG. 25B). The results showed that a 100 μg total dose of the hCMV pentamer mRNA vaccines formulated in either lipids induced comparable neutralizing antibody titers as CytoGam®, a hyperimmune serum used clinically for hCMV prevention.

Further, different configurations of the multivalent hCMV mRNA vaccine formulations were tested using the Compound 25 lipids (FIGS. 36A-36B). The results showed that different formulations elicited similar T cell response against pp65 or the pentamer in mice. FIG. 36 shows that the multivalent mRNA vaccine induced robust T cell response to the pentamer.

Figure 46B:
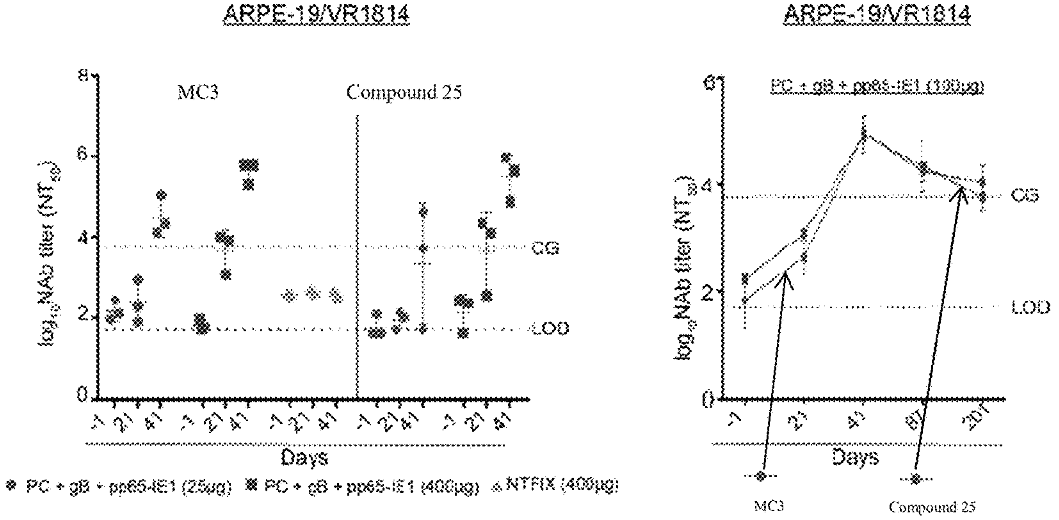
Figure 46C:
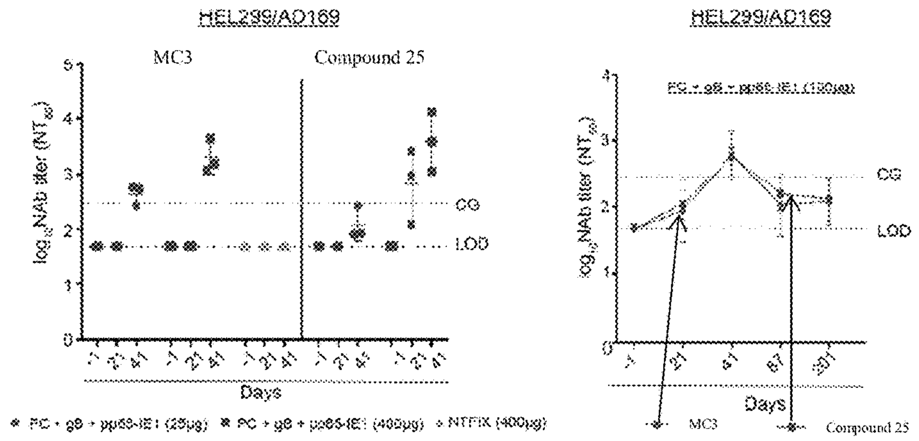
Figure 46D:
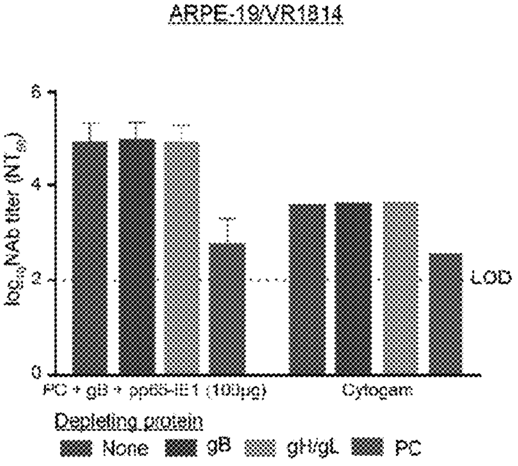
Figure 46E:
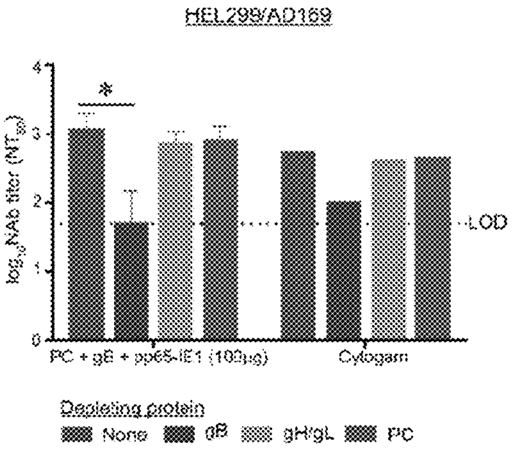

In one embodiment, cynomolgus macaques (cynos) were vaccinated according to the dosing regimen in FIG. 46A with the indicated doses of two different LNPs (MC3 and Compound 25) formulations containing the mRNA constructs, encoding the pentameric complex, gB, and fusion of pp65 and IE1 (referred to as pp65-IE1) or a nontranslating Factor IX mRNA (NTFIX) as a control (FIG. 46B). All monkeys used in this study had been naturally exposed to cyno CMV (cyCMV), and the majority had extremely low neutralizing titers against epithelial (NT50<500) but not fibroblast infection by CMV prior to immunization. ELISA results showed high titers of anti-PC and -gB antibodies after vaccination (FIGS. 47A and 47B). A dose-dependent increase in neutralizing antibodies was observed three weeks following the second vaccination. The neutralizing titers were higher than or equivalent to Cytogam in epithelial and fibroblast cells, respectively, at all doses of vaccine (FIG. 46B and 46C).

Cynos that received a 100 μg dose were monitored for an additional six months following the second dose vaccination. After the second dose, the neutralizing titers against epithelial and fibroblast infection initially dropped three- and eightfold, respectively, but thereafter were sustained for an additional four months (FIGS. 46B and 46C). Overall, vaccination with mRNA formulated in MC3 and Compound 25 elicited equivalent neutralizing titers and therefore further studies utilized Compound 25.

The specificity of these antibodies was further evaluated by performing antibody depletion experiments similar to those done with mouse immune sera. Purified PC and gB protein competed with neutralizing activity of NHP immune sera and Cytogam, in epithelial and fibroblast cells, respectively (FIGS. 46D and 46E), consistent with previous observations (Chandramouli et al., 2015). The results demonstrate that vaccination with CMV mRNA antigens elicits antibody specificities similar to those observed in CMV-seropositive individuals.

TABLE 11

Lipid Formulation Test

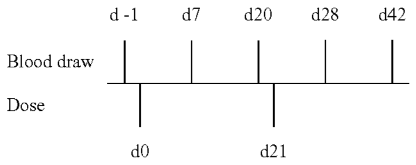

| Group | Test/Control group | vehicle | Route | Dosing Regimen | N | # of doses | Dose (ug) |
|---|---|---|---|---|---|---|---|
| 1 | Pentamer + gB + pp65-IE1 | Compound 25 | IM | d0, d21 | 3 | 2 | 400 |
| 2 | Pentamer + gB + pp65-IE1 | Compound 25 | IM | d0, d21 | 3 | 2 | 100 |
| 3 | Pentamer + gB + pp65-IE1 | Compound 25 | IM | d0, d21 | 3 | 2 | 25 |
| 4 | NTFIX (non translating RNA) | Compound 25 | IM | d0, d21 | 3 | 2 | 400 |
| 5 | Pentamer + gB + pp65-IE1 | MC3 | IM | d0, d21 | 3 | 2 | 400 |
| 6 | Pentamer + gB + pp65-IE1 | MC3 | IM | d0, d21 | 3 | 2 | 100 |
| 7 | Pentamer + gB + pp65-IE1 | MC3 | IM | d0, d21 | 3 | 2 | 25 |

Example 35: Evaluation of Immunogenicity of hCMV mRNA Vaccine Constructs with or without Chemical Modification and in Different Lipid Formulations The immunogenicity of hCMV mRNA vaccine constructs with or without chemical modification and in different lipid formulations was evaluated. hCMV mRNA vaccines encoding hCMV pentamer (5 μg) and gB (1 μg), or constructs encoding the hCMV pentamer (5 μg), gB (1 μg), and pp65mut (2 μg) were formulated in either MC3 lipid particles or compound 25 lipid particles. Balb/C mice were immunized with two doses (one primary dose and one booster dose 21 days after the primary dose) of the hCMV mRNA vaccines and sera were collected at days 21 and 43 post primary dose.

The sera were analyzed for antibody titers against hCMV pentamer and gB (FIGS. 37A, 37B, 38A, and 38B) and for neutralizing antibody titers against hCMV infection in fibroblast cells (FIG. 39A) or epithelial cells (FIG. 39B). The hCMV mRNA vaccine constructs with (C2,) or without (C1) N1-methylpseudouridine chemical modification were able to elicit antibodies against the pentamer, or gB. Neutralizing antibodies against hCMV infection were also elicited.

For mice immunized with hCMV mRNA vaccine constructs encoding hCMV pentamer, gB, and pp65mut, T-cell responses (CD4+ and CD8+ T-cell responses as indicated by cytokine secretion) were also evaluated. The results show hCMV mRNA constructs containing the N1-methylpseudouridine (C2) chemical modification formulated in MC3 lipid particles elicited CD4+ and CD8+ T-cell responses against pp65 (FIG. 40B), while the unmodified mRNA constructs formulated in compound 25 lipid particles elicited CD4+ and CD8+ T-cell responses against pp65 (FIG. 41B). Both unmodified hCMV mRNA constructs or mRNA constructs containing the N1-methylpseudouridine (C2) chemical modification formulated in either MC3 or compound 25 lipid particles elicited T-cell responses against the pentamer (FIG. 40A and FIG. 41A).

Example 36 Maintaining Strong T Cell Response to Pp65 by Sequential Immunization The CMV proteins pp65 and 1E1 have emerged as attractive vaccine antigens due to high antigen-specific T cell precursor frequencies in CMV-seropositive individuals. T cell responses to pp65-IE1 in mice were evaluated using intracellular staining assay (ICS). Splenocytes were stimulated with peptide pools comprising select immunodominant peptides for pp65 and IE1 (Reap et al., 2007), and IFNγ-producing T cells were measured by flow cytometry. In mice that were immunized only with pp65-IE1, IFNγ production was detected in both CD4 and CD8 T cells (FIGS. 48A and 48B). A reduction in pp65-IE1-specific T cell responses was observed when it was coformulated with PC and gB mRNAs (FIGS. 48A and 48B). An mRNA construct encoding a phosphorylation mutant of pp65 (pp65$^{\Delta P}$) that has been reported to retain immunogenicity but exhibit reduced biologic activity was synthesized (Zaia et al., 2009). T cell responses to pp65$^{\Delta P}$ were evaluated and compared to pp65-IE1 immunization harboring the same mutation. Splenocytes were stimulated with overlapping peptide library for pp65 and IFNγ producing CD4 and CD8 T cells evaluated by flow cytometry. In this embodiment, the overall T cell responses were higher in mice receiving pp65$^{\Delta P}$ as compared to pp65$^{\Delta P}$-IE1 (FIGS. 50A and 50B). Therefore, pp65$^{\Delta P}$ was used in the vaccine formulations.

Next, it was evaluated whether T cell responses to pp65 were repressed in the presence of other CMV antigens. Mice were immunized either with LNP encapsulating pp65 alone or pp65+PC+gB. Splenocytes were stimulated with overlapping peptide libraries for pp65, and antigen-specific polyfunctional T cell responses were analyzed by ICS. Robust T cell responses were seen in mice immunized with pp65 alone; the majority of the T cells produced IFNγ and TNF-α (FIGS. 48C and 48D) and, to a lesser extent, IL-2 (FIG. 51A). However, in this embodiment, the pp65-specific T cell responses were reduced in the presence of other CMV antigens (FIGS. 48C and 48D).

To determine whether pp65-specific T cell responses were repressed by other dominant antigens present in the multivalent vaccine, antigen-specific T cell responses to PC and gB were evaluated by ICS. Strong polyfunctional T cell responses to PC (FIGS. 48E and 48D) and little to modest gB-specific T cell responses (FIGS. 51C and 51D) were observed. The majority of these PC-specific T cells secreted IFNγ and TNFα (FIGS. 5E-5F) and, to a minor extent, IL-2 (FIG. 51B). These results suggest that the inhibition of T cell responses to pp65 stems from epitope competition due to dominating epitopes present in PC.

Figure 49B:
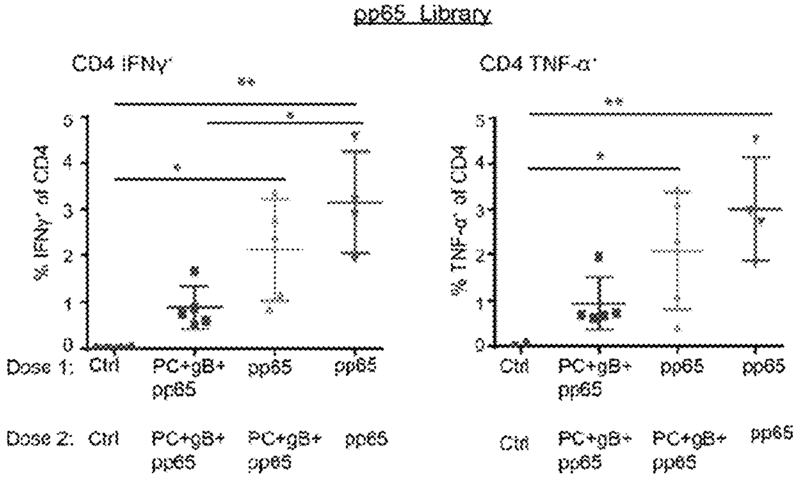
Figure 49C:
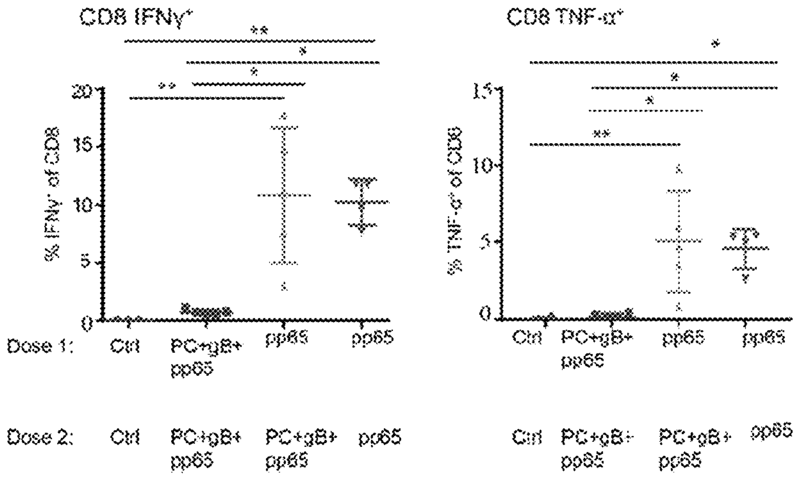
Figure 49D:
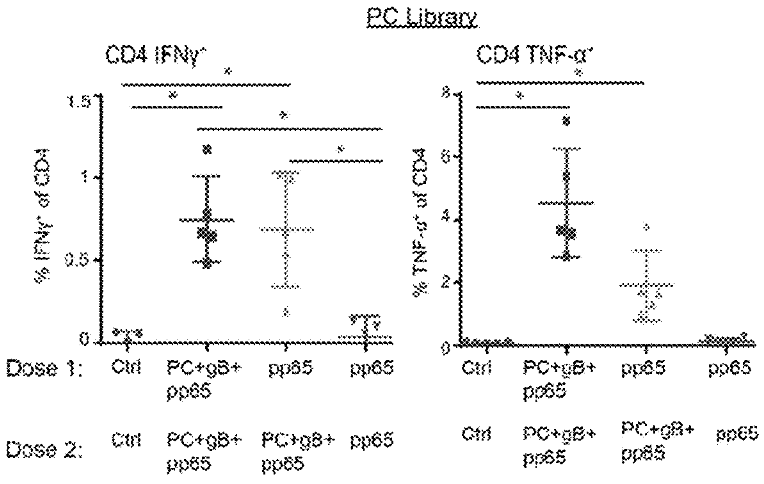
Figure 49E:
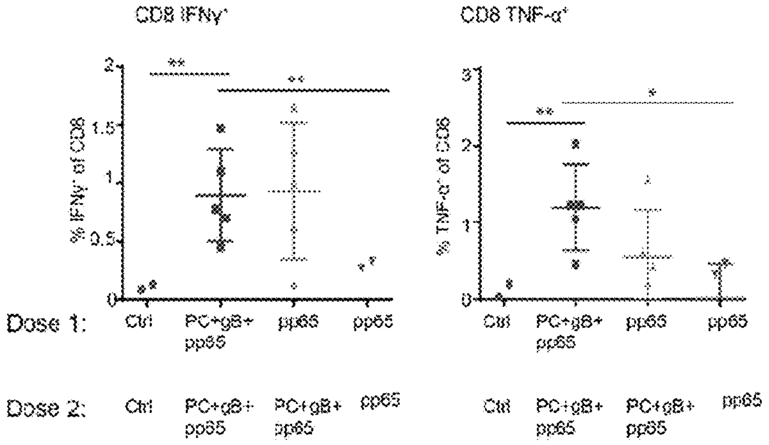

Epitope competition was found to be resolved by a heterologous prime/boost regimen of a dose of LNP (pp65) followed by a dose of LNP (PC+gB+pp65). Control mice were immunized with a homologous prime/boost regimen of LNP (PC+gB+pp65) or a homologous prime/boost regimen of LNP (pp65) according to the dosing regimen shown in FIG. 49A. In mice that received a first dose of pp65 alone followed by all three antigens, T cell responses were restored to levels comparable with those of mice receiving two doses of pp65 alone (FIGS. 49B and 49C). As expected, mice that received two doses of LNP (PC+gB+pp65) showed robust PC-specific T cell responses and negligible responses to pp65 (FIGS. 49D and 49E). These results demonstrate that epitope competition can be resolved by a heterologous and sequential prime/boost vaccine regimen.

Example 37 Materials and Methods for Examples 22-28, 31-33, 35, and 38

Animal Studies

Eight to ten week old female BALB/c mice (Charles River Laboratories International, Inc.; Wilmington, Mass.) were immunized by intramuscular injection with 50 μl of the indicated LNP/mRNA formulations or empty LNP. All mouse studies were approved by the Animal Care and Use Committee at Moderna Therapeutics, Cambridge, Mass.

Non-Human Primate Experiments

NHP studies were carried out at Southern Research Institute, Frederick, Md. Cynos 2-5 years old weighing 3 kg-6 kg were immunized twice with varying doses of two different LNP formulations (MC3 and Compound 25) containing the mRNA constructs encoding CMV pentamer, gB, and pp65-IE1 antigens. Injections were given intramuscularly in a volume of 0.5 ml. All monkeys were screened for cyCMV and included in the study based on neutralization titers to CMV. The animal protocol was approved by the Institutional Animal Care and Use Committee (IACUC) at Southern Research Institute.

Cells and Virus

HEK293, HeLa, HEL 299, and ARPE-19 cells were obtained from American Type Culture Collection (ATCC). All cells were cultured in Dulbecco's Modified Eagle's Medium (DMEM) with 10% fetal bovine serum (FBS) and 1% penicillin and streptomycin. HUVEC cells (ATCC) were cultured in endothelial cell growth medium. CMV strain AD169 (ATCC) was propagated on MRC-5 cells and VR1814 (G. Gerna, Fondazione IRCCS Policlinico San Matteo; Pavia, Italy) on HUVEC cells. Clarified supernatants were collected 10 days after 90% of cells showed cytopathic effect. Viral stocks were generated by adding FBS to a final concentration of 20%.

Western Blot and Immunoprecipitations

HEK293 cells were transiently transfected with mRNA encoding gH, gL, UL128, UL130, UL131A, or gB using Trans IT®-mRNA Transfection Kit (Mirus Bio LLC) per the manufacturer's recommendations. At 24 hr post-transfection, cells were lysed in RIPA buffer (Boston BioProducts) supplemented with complete mini-EDTA free protease inhibitor cocktail tablets (ThermoFisher Scientific). Precleared lysates were resolved on Novex 4%-12% Bis-Tris gels (Invitrogen) and blotted with rabbit polyclonal antibodies for gH, gL, UL128, UL130, or UL131A. (D. Johnson, OHSU; Portland, Oreg.) and mouse anti-n actin (Cell Signaling Technology). Alexa Fluor 488 goat antirabbit IgG or Alexa Fluor 680 goat antimouse IgG (ThermoFisher Scientific) were used as secondary antibodies. All images were captured on a ChemiDoc MP Imaging System (Bio-Rad Laboratories). For immunoprecipitations, lysates were first precleared with Protein G agarose beads (ThermoFisher Scientific), and gB was immunoprecipitated using an anti-gB monoclonal antibody (clone $CH_{28}$, Santa Cruz Biotechnology). Immunoprecipitates were resolved on Novex 4%-12% Bis-Tris gels (Invitrogen) and probed with mouse anti-gB antibody followed by incubation with HRP-conjugated rat antimouse IgG that recognizes native mouse IgG (Mouse TrueBlot® Western Blot Kit, Rockland Inc). Immunoblots were developed using TrueBlot substrate (Rockland Inc.) and visualized on a ChemiDoc MP Imaging System (Bio-Rad Laboratories, Inc.).

Flow Cytometry

HeLa cells were transiently transfected with mRNA for the various subunits of CMV PC (gH/gL/UL128/UL130/UL131A) or combinations lacking one of the subunits or gB. After 24 hr, the cells were harvested and resuspended in FACS buffer (1×PBS, 3% FBS, 0.05% sodium azide). To detect surface PC expression or components of PC, the cells were stained with human monoclonal antibodies 8121 (PC), 3G16 (gH), 15D8var1 (UL128), and 7113 (UL128/UL130/UL131A) (Macagno et al., 2010). All the above human monoclonal antibodies were custom synthesized by ThermoFisher from Expi293 cells that were transfected with expression plasmids encoding codon-optimized sequences for the respective heavy and light chain antibody. Surface gB was detected by mouse monoclonal anti-gB (Santa Cruz Biotechnology, Inc.). To detect intracellular gB, cells were permeabilized with 1x Cytofix/Cytoperm™ (BD Biosciences) and stained with mouse monoclonal anti-gB (Santa Cruz Biotechnology, Inc.). Alexaflour 647 goat antihuman IgG (SouthernBiotech) or Alexafluor 647 goat antimouse IgG (SouthernBiotech) were used as secondary antibodies. Cells were acquired on a BD LSRII Fortessa instrument (BD Biosciences) and analyzed by FlowJo software v10 (Tree Star, Inc.), Intracellular Cytokine Staining Overlapping peptide libraries for gH, gL, UL128, UL130, UL131A (15 mer overlapping by 5 amino acids) and gB (15 mer overlapping by 11 amino acids) were synthesized by Genscript (Piscataway, N.J.). A peptide library for PC was generated by pre-mixing the peptide pools for the five different components of the complex. The pp65 peptide library (15 mer overlapping by 11 amino acids) was from JPT Inc. Splenocytes were stimulated with peptides pools for PC, gB, and pp65 at 10 μg/ml for 5 hr at 37° C. in the presence of BD GolgiStop™ and GolgiPlug™ (BD Biosciences). Unstimulated or PMA/Ionomycin (Cell Stimulation Cocktail, eBioscience) were used as negative and positive controls, respectively. Following stimulation, cells were surface stained in FACS buffer in the presence of FcR blocking antibody 2.4G2 and eFluor™ 506 (eBioscience) as viability dye. Antibody clones used for surface staining were: anti-CD4 (GK1.5), anti-CD8 (53.6.7), anti-CD44 (IM7), anti-CD62L (MEL14), and anti-TCRβ (H57-59). Intracellular staining was carried out with BD Cytofix/Cytoperm and BD Perm/Wash™ buffers (BD Biosciences). Antibody clones used for intracellular staining were: anti-IFNγ (XMG1.2), anti-IL2 (JES6-5H4) and anti-TNFα (MP6-XT22). Samples were acquired on BD LSRII Fortessa (BD Biosciences) and analyzed by FlowJo software (Tree-Star, Inc.). Cytokine secreting T cells were plotted after background subtraction.

Generation of Modified CMV mRNA Vaccine Constructs and Formulations

Generation of mRNA encoding CMV antigens gH, gL, UL128, UL130, UL131A, and gB from strain Merlin was done by in vitro transcription using T7 polymerase from a linear DNA template that included 5' and 3' untranslated regions (UTRs) and a poly (A) tail as previously described (Richner et al., 2017b). mRNA encoding a phosphorylation mutant of pp65 (pp65$^{\Delta P}$) was generated by deleting a.a 435-438 (RKRK). A pp65/IE1 fusion mRNA was constructed by assembling in tandem the sequences of pp65 gene lacking the stop codon with IE1 gene without the start codon to generate an in-frame fusion gene. S-adenosylmethionine was added to the methylated capped RNA (cap1) for increased mRNA translation efficiency. Similarly, a pp65$^{\Delta P}$-IE1 mRNA construct lacking a.a 435-438 of pp665 was also generated. LNPs were formulated as previously described (Chen et al., 2016). Briefly, lipids were dissolved in ethanol at molar ratios of 50:10:38.5:1.5 (ionizable lipid: DSPC:cholesterol:PEG lipid). Two different LNPs having different ionizable lipids, referred to as MC3 and Compound 25, respectively, were developed. mRNA was combined with the lipid mixture, dialyzed and concentrated as previously described (Richner et al., 2017b). Empty LNPs lacking mRNA were also generated as controls. All formulations had particle sizes ranging from 80 nm to 100 nm, with greater than 90% encapsulation and <1 EU/ml of endotoxin.

ELISA

Overnight, 96-well microtiter plates were coated with 1 μg/ml of PC (Native Antigen Company) or gB (Sino Biological) protein. Serial dilutions of serum were added and bound antibody detected with HRP-conjugated goat anti-mouse IgG (Southern Biotech), followed by incubation with TMB substrate (KPL). The absorbance was measured at OD (450 nm). Titers were determined using a four parameter logistic curve fit in GraphPad Prism (GraphPad Software, Inc.) and defined as the reciprocal serum dilution at approximately OD (450 nm)=0.6 (normalized to a standard on each plate).

Neutralization Assays

Serum samples were heat inactivated at 56° C. for 30 min and diluted 1:50 in complete medium. Cytogam was diluted to 10 mg/ml. Thereafter, samples were serially diluted in 2-fold steps and mixed with an equal volume of VR1814 or AD169 virus in serum-free media supplemented with 10% guinea pig complement (Cedarlane Laboratories Ltd) and incubated for 4 hr at 37° C., 5% $CO_2$. The virus/serum mixture was then added to ARPE-19 or MRC-5 cells in 96-well tissue culture plates and incubated for 17-20 hr at 37° C., 5% $CO_2$. Cells were fixed with 200 proof ethanol, blocked with superblock (Sigma-Aldrich), washed with PBS/0.05% Tween-20, and stained with mouse monoclonal antibody to CMV 1E1 (Millipore), followed by Peroxidase AffiniPure Goat Anti-Mouse IgG (Jackson ImmunoResearch Laboratories) and developed with HistoMark® TrueBlue™ Peroxidase Substrate (SeraCare). CMV IE1-positive cells were counted using the CTL ImmunoSpot® Analyzer (Cellular Technology Limited). Neutralization titers (NT50) were determined using a four parameter logistic curve fit in GraphPad Prism (GraphPad Software, Inc.) and were defined as the reciprocal of the serum dilution resulting in 50% reduction in infected-cell count. In all experiments, the titers of Cytogam (CSL Behring) are shown for an approximate maximum concentration (2 mg/ml) in human sera after dosing, which was calculated based on an average body weight of 70 kg.

Statistical Analysis

Data were analyzed with Prism 7 (GraphPad Software) using the Kruskal-Wallis test and Dunn's multiple comparison test or by two-tailed Mann-Whitney U test. A p value of <0.05 indicated statistically significant differences.

TABLE 12

Table of Materials

| REAGENT or RESOURCE | SOURCE | IDENTIFIER |
|---|---|---|
| Antibodies | | |
| Rabbit anti-gH | Johnson Laboratory | N/A |
| Rabbit anti-gL | Johnson Laboratory | N/A |
| Rabbit anti-UL128 | Johnson Laboratory | N/A |
| Rabbit anti-UL130 | Johnson Laboratory | N/A |
| Rabbit anti-UL131A | Johnson Laboratory | N/A |
| 8I21 | Thermofisher | N/A |
| 3G16 | Thermofisher | N/A |
| 15D8Var1 | Thermofisher | N/A |

TABLE 12-continued

| Table of Materials | | |
|---|---|---|
| REAGENT or RESOURCE | SOURCE | IDENTIFIER |
| 7I13 | Thermofisher | N/A |
| Anti-mouse CD16/32 (2.4G2) | BD Biosciences | Cat# 553141 |
| Anti-mouse CD4 (GK1.5) | Biolegend | Cat# 100437 |
| Anti-mouse CD8 (53.6.7) | Biolegend | Cat# 100705 |
| Anti-mouse CD44 (IM7) | Biolegend | Cat# 103030 |
| Anti-mouse CD62L (MEL14) | Biolegend | Cat# 104428 |
| Anti-mouse TCRβ (H57-59) | Biolegend | Cat# 109224 |
| Anti-mouse IFNα (XMG 1.2) | Thermofisher | Cat# 17-7311-82 |
| Anti-mouse IL2 (JES6-5H4) | Biolegend | Cat# 503829 |
| Anti-mouse TNFα (MP6-XT22) | Thermofisher | Cat# 12-7321-41 |
| Mouse anti-β actin | Cell Signaling Technology | Cat# 3700S |
| Alexa Fluor 488 goat anti-rabbit IgG | Thermofisher | Cat# A21109 |
| Alexa Fluor 680 goat anti-mouse IgG | Thermofisher | Cat# A21057 |
| Alexa Fluor 647 goat anti-human IgG | Southern Biotech | Cat# 2016-31 |
| Alexa Fluor 647 goat anti-mouse IgG | Southern Biotech | Cat# 1031-31 |
| HRP-conjugated rat anti-mouse IgG | Rockland Inc | Cat# 18-8817-31 |
| HRP-conjugated goat anti-mouse IgG | Southern Biotech | Cat# 1030-05 |
| Peroxidase AffiniPure Goat Anti-mouse IgG | Jackson ImmunoResearch | 115-035-166 |
| Mouse anti-gB (clone CH28) | Santa Cruz Biotechnology | sc-69742 |
| Mouse anti-CMV IE1 | Millipore | MAB810 |
| Bacterial and Virus Strains | | |
| AD169 | ATCC | VR-538 |
| VR1814 | Gerna lab | N/A |
| Chemicals, Peptides, and Recombinant Proteins | | |
| RIPA Lysis Buffer | Boston Bio Products | BP-115 |
| Complete mini-EDTA free protease inhibitor tablets | Thermofisher | Cat# 88266 |
| Cytofix/Cytoperm | BD Biosciences | Cat# 554714 |
| GolgiStop | BD Biosciences | Cat# 554724 |
| GolgiPlug | BD Biosciences | Cat# 555029 |
| eFluor ™ 506 Fixable Viability Dye | Thermofisher | Cat# 65-0866-14 |
| PC peptide library | Genscript | N/A |

TABLE 13

| Additional hCMV Vaccine Constructs | | | |
|---|---|---|---|
| Antigen Name | Protein Sequence | Nucleotide Sequence (Open Reading Frames) | Tested Chemistry mRNA Chemistry/ Cap/ Tail |
| CMV IE1 (UL122) | MESSAKRKMDPD<br>NPDEGPSSKVPRPE<br>TPVTKATTFLQTM<br>LRKEVNSQLSLGD<br>PLFPELAEESLKTF<br>EQVTEDCNENPEK<br>DVLTELVKQIKVR<br>VDMVRHRIKEHML<br>KKYTQTEEKFTGA<br>FNMMGGCLQNAL<br>DILDKVHEPFEDM<br>KCIGLTMQSMYEN<br>YIVPEDKREMWM<br>ACIKELHDVSKGA<br>ANKLGGALQAKA<br>RAKKDELRRKMM<br>YMCYRNIEFFTKN<br>SAFPKTTNGCSQA<br>MAALQNLPQCSPD<br>EIMSYAQKIFKILD<br>EERDKVLTHIDHIF<br>MDILTTCVETMCN<br>EYKVTSDACMMT<br>MYGGISLLSEFCRV<br>LCCYVLEETSVML | ATGGAGTCCTCTGCCAAGAGAAAGATGGACCCTGATAA<br>TCCTGACGAGGGCCCTTCCTCCAAGGTGCCACGGCCCG<br>AGACACCCGTGACCAAGGCCACGACGTTCCTGCAGACT<br>ATGTTAAGGAAGGAGGTTAACAGTCAGCTGAGCCTGGG<br>AGACCCGCTGTTCCCAGAATTGGCCGAAGAATCCCTCA<br>AGACCTTTGAACAAGTGACCGAGGATTGCAACGAGAAC<br>CCCGAGAAAGATGTCCTGACAGAACTCGTCAAACAGAT<br>TAAGGTTCGAGTGGACATGGTGCGGCATAGAATCAAGG<br>AGCACATGCTGAAGAAATATACCCAGACGGAAGAGAA<br>ATTCACTGGCGCCTTTAATATGATGGGAGGATGTTTGCA<br>GAATGCCTTAGATATCTTAGATAAGGTTCATGAGCCTTT<br>CGAGGACATGAAGTGTATTGGGCTAACTATGCAGAGCA<br>TGTATGAGAACTACATTGTACCTGAGGATAAGCGGGAG<br>ATGTGGATGGCTTGTATTAAGGAGCTGCATGATGTGAG<br>CAAGGGCGCCGCTAACAAGTTGGGCGGTGCACTGCAGG<br>CTAAGGCCCGTGCTAAGAAGGATGAACTTAGGAGAAAG<br>ATGATGTATATGTGCTACAGGAATATAGAGTTCTTTACC<br>AAGAACTCAGCCTTCCCTAAGACCACCAATGGCTGCAG<br>TCAGGCCATGGCGGCATTGCAGAACTTGCCTCAGTGCTC<br>TCCTGATGAGATTATGTCTTATGCCCAGAAGATCTTTAA<br>GATTTTGGATGAGGAGAGAGACAAGGTGCTCACGCACA<br>TTGATCACATATTTATGGATATCCTCACTACATGTGTGG<br>AAACAATGTGTAATGAGTACAAGGTCACTAGTGACGCT<br>TGTATGATGACCATGTACGGCGGCATCTCTCTCTTAAGT<br>GAGTTCTGTCGGGTGCTGTGCTGCTATGTCTTAGAGGAG | C2/<br>CAP1/<br>T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | AKRPLITKPEVISV MKRRIEEICMKVF AQYILGADPLRVC SPSVDDLRAIAEES DEEEAIVAYTLAT AGASSSDSLVSPPE SPVPATIPLSSVIVA ENSDQEESEQSDEE QEEGAQEEREDTV SVKSEPVSEIEEVA SEEEEDGAEEPTAS GGKSTHPMVTRSK ADQ (SEQ ID NO: 80) | ACTAGTGTGATGCTGGCCAAGCGGCCTCTGATAACCAA GCCTGAGGTTATCAGTGTAATGAAGCGCCGCATTGAGG AGATCTGCATGAAGGTCTTTGCCCAGTACATTCTGGGAG CCGATCCTTTGAGAGTCTGCTCTCCTAGTGTGGATGACC TACGGGCCATCGCCGAGGAGTCAGATGAGGAAGAGGCT ATTGTAGCCTACACTTTGGCCACCGCTGGTGCCAGCTCC TCTGATTCTCTGGTGTCACCTCCAGAGTCCCCTGTACCC GCGACTATCCCTCTGTCCTCAGTAATTGTGGCTGAGAAC AGTGATCAGGAAGAAAGTGAACAGAGTGATGAGGAAC AGGAGGAGGGTGCTCAGGAGGAGCGGGAGGACACTGT GTCTGTCAAGTCTGAGCCAGTGTCTGAGATAGAGGAAG TTGCCTCAGAGGAAGAGGAGGATGGTGCTGAGGAACCC ACCGCCTCTGGAGGCAAGAGCACCCACCCTATGGTGAC TAGAAGCAAGGCTGACCAG (SEQ ID NO: 84) | |
| CMV IE2 | MESSAKRKMDPD NPDEGPSSKVPRPE TPVTKATTFLQTM LRKEVNSQLSLGD PLFPELAEESLKTF EQVTEDCNENPEK DVLTELGDILAQA VNHAGIDSSSTGPT LTTHSCSVSSAPLN KPTPTSVAVTNTPL PGASATPELSPRKK PRKTTRPFKVIIKPP VPPAPIMLPLIKQE DIKPEPDFTIQYRN KIIDTAGCIVISDSE EEQGEEVETRGAT ASSPSTGSGTPRVT SPTHPLSQMNHPPL PDPLGRPDEDSSSS SSSSCSSASDSESES EEMKCSSGGGASV TSSHHGRGGFGGA ASSSLLSCGHQSSG GASTGPRKKKSKRI SELDNEKVRNIMK DKNTPFCTPNVQT RRGRVKIDEVSRM FRHTNRSLEYKNL PFMIPSMHQVLEE AIKVCKTMQVNNK GIQIIYTRNHEVKN EVDQVRCRLGSMC NLALSTPFLMEHT MPVTHPPDVAQRT ADACNDGVKAVW NLKELHTHQLCPR SSDYRNMIIHAATP VDLLGALNLCLPL MQKFPKQVMVRIF STNQGGFMLPIYET AAKAYAVGQFEKP TETPPEDLDTLSLA IEAAIQDLRNKSQ (SEQ ID NO: 81) | ATGGAGTCCTCTGCCAAGAGAAAGATGGACCCTGATAA TCCTGACGAGGGCCCTTCCTCCAAGGTGCCACGGCCCG AGACACCCGTGACCAAGGCCACGACGTTCCTGCAGACT ATGTTAAGGAAGGAGGTTAACAGTCAGCTGAGCCTGGG AGACCCGCTGTTCCCAGAATTGGCCGAAGAATCCCTCA AGACCTTTGAACAAGTGACCGAGGATTGCAACGAGAAC CCCGAGAAAGATGTCCTGACAGAACTCGGTGACATCCT CGCCCAGGCTGTCAATCATGCCGGTATCGATTCCAGTAG CACCGGCCCCACGCTGACAACCCACTCTTGCAGCGTTAG CAGCGCCCCTCTTAACAAGCCGACGCCCACCAGCGTCG CGGTTACTAACACTCCTCTCCCCGGGGCATCCGCTACTC CCGAGCTCAGCCCGCGTAAGAAACCGCGCAAGACCACG CGTCCTTTCAAGGTGATTATTAAACCGCCCGTGCCTCCC GCGCCTATCATGCTGCCCCTCATCAAACAGGAAGACAT CAAGCCCGAGCCCGACTTTACCATCCAGTACCGCAACA AGATTATCGATACCGCCGGCTGTATCGTGATCTCTGATA GCGAGGAAGAACAGGGTGAAGAAGTCGAGACCCGCGG TGCTACCGCGTCTTCCCCTTCCACCGGCAGCGGCACGCC GCGAGTGACCTCTCCCACGCACCCGCTCTCCCAGATGAA CCACCCTCCTCTTCCCGATCCTTTGGGCCGGCCCGATGA AGATAGTTCCTCTTCGTCTTCCTCCTCCTGCAGTTCGGCT TCGGACAGCGAGAGTGAGTCCGAGGAGATGAAATGCAG CAGTGGCGGAGGAGCATCCGTGACCTCGAGCCACCATG GGCGCGGCGGTTTTGGTGGCGCGGCCTCCTCCTCTCTGC TGAGCTGCGGACATCAGAGCAGCGGCGGGGCGAGCACC GGACCTCGCAAGAAGAAGAGCAAACGCATCTCCGAGTT GGACAACGAGAAGGTGCGCAATATCATGAAAGATAAG AACACGCCCTTCTGCACACCCAACGTGCAGACTCGGCG GGGTCGCGTCAAGATTGACGAGGTGAGCCGCATGTTCC GTCACACCAATCGTTCTCTTGAGTACAAGAATCTGCCAT TCATGATCCCTAGTATGCACCAAGTGTTAGAAGAGGCC ATCAAAGTTTGCAAGACCATGCAGGTGAACAACAAGGG CATTCAGATCATCTACACCCGCAATCATGAAGTGAAGA ATGAGGTGGATCAGGTACGGTGTCGCCTGGGTAGCATG TGCAACCTGGCCCTCTCCACTCCCTTCCTCATGGAGCAC ACTATGCCTGTGACACACCCTCCTGATGTGGCGCAGCGC ACGGCCGATGCTTGTAACGACGGTGTCAAGGCCGTGTG GAACCTCAAAGAACTGCACACCCACCAATTGTGCCCGC GCTCTTCTGATTACCGCAACATGATTATCCACGCTGCCA CGCCCGTGGACCTGTTGGGCGCTCTCAACCTGTGCCTGC CCCTGATGCAGAAGTTTCCCAAACAGGTCATGGTGCGC ATCTTCTCCACCAACCAGGGTGGGTTCATGCTGCCTATC TACGAGACGGCCGCGAAGGCCTACGCCGTGGGGCAGTT TGAGAAGCCCACCGAGACCCCTCCCGAAGACCTGGACA CCCTGAGCCTGGCCATCGAGGCAGCCATCCAGGACCTG AGGAACAAATCTCAG (SEQ ID NO: 85) | C2/ CAP1/ T100 |
| hCMV_gB | MESRIWCLVVCVN LCIVCLGAAVSSSS TRGTSATHSHHSS HTTSAAHSRSGSVS QRVTSSQTVSHGV NETIYNTTLKYGD VVGVNTTKYPYRV CSMAQGTDLIRFE RNIVCTSMKPINED | ATGGAATCCAGGATCTGGTGCCTGGTAGTCTGCGTTAAC TTGTGTATCGTCTGTCTGGGTGCTGCGGTTTCCTCATCTT CTACTCGTGGAACTTCTGCTACTCACAGTCACCATTCCT CTCATACGACGTCTGCTGCTCACTCTCGATCCGGTTCAG TCTCTCAACGCGTAACTTCTTCCCAAACGGTCAGCCATG GTGTTAACGAGACCATCTACAACACTACCCTCAAGTAC GGAGATGTGGTGGGGGTCAATACCACCAAGTACCCCTA TCGCGTGTGTTCTATGGCCCAGGGTACGGATCTTATTCG CTTTGAACGTAATATCGTCTGCACCTCGATGAAGCCCAT | C2/ Cap1/ Tailless C2/no cap/T100 C1/cap1/ T100 |

TABLE 13-continued

| Antigen Name | Protein Sequence | Nucleotide Sequence (Open Reading Frames) | Tested Chemistry mRNA Chemistry/ Cap/ Tail |
|---|---|---|---|
| | LDEGIMVVYKRNI VAHTFKVRVYQK VLTFRRSYAYIHTT YLLGSNTEYVAPP MWEIHHINSHSQC YSSYSRVIAGTVFV AYHRDSYENKTM QLMPDDYSNTHST RYVTVKDQWHSR GSTWLYRETCNLN CMVTITTARSKYP YHFFATSTGDVVDI SPFYNGTNRNASY FGENADKFFIFPNY TIVSDFGRPNSALE THRLVAFLERADS VISWDIQDEKNVT CQLTFWEASERTIR SEAEDSYHFSSAK MTATFLSKKQEVN MSDSALDCVRDEA INKLQQIFNTSYNQ TYEKYGNVSVFET TGGLVVFWQGIKQ KSLVELERLANRSS LNLTHNRTKRSTD GNNATHLSNMESV HNLVYAQLQFTYD TLRGYINRALAQIA EAWCVDQRRTLEV FKELSKINPSAILSA IYNKPIAARFMGD VLGLASCVTINQTS VKVLRDMNVKESP GRCYSRPVVIFNFA NSSYVQYGQLGED NEILLGNHRTEECQ LPSLKIFIAGNSAY EYVDYLFKRMIDL SSISTVDSMIALDID PLENTDFRVLELYS QKELRSSNVFDLEE IMREFNSYKQRVK YVEDKVVDPLPPY LKGLDDLMSGLGA AGKAVGVAIGAVG GAVASVVEGVATF LKNPFGAFTIILVAI AVVIITYLIYTRQR RLCTQPLQNLFPYL VSADGTTVTSGST KDTSLQAPPSYEES VYNSGRKGPGPPS SDASTAAPPYTNE QAYQMLLALARL DAEQRAQQNGTDS LDGRTGTQDKGQK PNLLDRLRHRKNG YRHLKDSDEENV (SEQ ID NO: 69) | CAATGAAGACCTGGACGAGGGCATCATGGTGGTCTACA AACGCAACATCGTCGCGCACACCTTTAAGGTACGAGTC TACCAGAAGGTTTTGACGTTTCGTCGTAGCTACGCTTAC ATCCACACCACTTATCTGCTGGGCAGCAACACGGAATA CGTGGCGCCTCCTATGTGGGAGATTCATCATATCAACAG CCACAGTCAGTGCTACAGTTCCTACAGCCGCGTTATAGC AGGCACGGTTTTCGTGGCTTATCATAGGGACAGCTATGA AAACAAAACCATGCAATTAATGCCCGACGATTATTCCA ACACCCACAGTACCCGTTACGTGACGGTCAAGGATCAA TGGCACAGCCGCGGCAGCACCTGGCTCTATCGTGAGAC CTGTAATCTGAATTGTATGGTGACCATCACTACTGCGCG CTCCAAATATCCTTATCATTTTTTCGCCACTTCCACGGGT GACGTGGTTGACATTTCTCCTTTCTACAACGGAACCAAT CGCAATGCCAGCTACTTTGGAGAAAACGCCGACAAGTT TTTCATTTTTCCGAACTACACTATCGTCTCCGACTTTGGA AGACCGAATTCTGCGTTAGAGACCCACAGGTTGGTGGC TTTTCTTGAACGTGCGGACTCGGTGATCTCCTGGGATAT ACAGGACGAAAAGAATGTCACTTGTCAACTCACTTTCTG GGAAGCCTCGGAACGCACCATTCGTTCCGAAGCCGAGG ACTCGTATCACTTTTCTTCTGCCAAAATGACCGCCACTT TCTTATCTAAGAAGCAAGAGGTGAACATGTCCGACTCT GCGCTGGACTGCGTACGTGATGAGGCTATAAATAAGTT ACAGCAGATTTTCAATACTTCATACAATCAAACATATGA AAAATATGGAAACGTGTCCGTCTTTGAAACCACTGGTG GTTTGGTAGTGTTCTGGCAAGGTATCAAGCAAAAATCTC TGGTGGAACTCGAACGTTTGGCCAACCGCTCCAGTCTGA ATCTTACTCATAATAGAACCAAAAGAAGTACAGATGGC AACAATGCAACTCATTTATCCAACATGGAATCGGTGCA CAATCTGGTCTACGCCCAGCTGCAGTTCACCTATGACAC GTTGCGCGGTTACATCAACCGGGCGCTGGCGCAAATCG CAGAAGCCTGGTGTGTGGATCAACGGCGCACCCTAGAG GTCTTCAAGGAACTCAGCAAGATCAACCCGTCAGCCAT TCTCTCGGCCATTTACAACAAACCGATTGCCGCGCGTTT CATGGGTGATGTCTTGGGCCTGGCCAGCTGCGTGACCAT CAACCAAACCAGCGTCAAGGTGCTGCGTGATATGAACG TGAAGGAGTCGCCAGGACGCTGCTACTCACGACCCGTG GTCATCTTTAATTTCGCCAACAGCTCGTACGTGCAGTAC GGTCAACTGGGCGAGGACAACGAAATCCTGTTGGGCAA CCACCGCACTGAGGAATGTCAGCTTCCCAGCCTCAAGA TCTTCATCGCCGGGAACTCGGCCTACGAGTACGTGGACT ACCTCTTCAAACGCATGATTGACCTCAGCAGTATCTCCA CCGTCGACAGCATGATCGCCCTGGATATCGACCCGCTG GAAAATACCGACTTCAGGGTACTGGAACTTTACTCGCA GAAAGAGCTGCGTTCCAGCAACGTTTTTGACCTCGAAG AGATCATGCGCGAATTCAACTCGTACAAGCAGCGGGTA AAGTACGTGGAGGACAAGGTAGTCGACCCGCTACCGCC CTACCTCAAGGGTCTGGACGACCTCATGAGCGGCCTGG GCGCCGCGGGAAAGGCCGTTGGCGTAGCCATTGGGGCC GTGGGTGGCGCGGTGGCCTCCGTGGTCGAAGGCGTTGC CACCTTCCTCAAAAACCCCTTCGGAGCGTTCACCATCAT CCTCGTGGCCATAGCTGTAGTCATTATCACTTATTTGAT CTATACTCGACAGCGGCGTTTGTGCACGCAGCCGCTGCA GAACCTCTTTCCCTATCTGGTGTCCGCCGACGGGACCAC CGTGACGTCGGGCAGCACCAAAGACACGTCGTTACAGG CTCCGCCTTCCTACGAGGAAAGTGTTTATAATTCTGGTC GCAAAGGACCGGGACCACCGTCGTCTGATGCATCCACG GCGGCTCCGCCTTACACCAACGAGCAGGCTTACCAGAT GCTTCTGGCCCTGGCCCGTCTGGACGCAGAGCAGCGAG CGCAGCAGAACGGTACAGATTCTTTGGACGGACGGACT GGCACGCAGGACAAGGGACAGAAGCCCAACCTACTAG ACCGACTGCGACATCGCAAAAACGGCTACCGACACTTG AAAGACTCTGACGAAGAAGAGAACGTC (SEQ ID NO: 86) | |
| hCMV_gH dimer_v2 | MRPGLPSYLIILAV CLFSHLLSSRYGAE AVSEPLDKAFHLL LNTYGRPIRFLREN TTQCTYNSSLRNST VVRENAISFNFFQS YNQYYVFHMPRCL FAGPLAEQFLNQV | ATGCGGCCAGGCCTCCCCTCCTACCTCATCATCCTCGCC GTCTGTCTCTTCAGCCACCTACTTTCGTCACGATATGGC GCAGAAGCCGTATCCGAACCGCTGGACAAAGCGTTTCA CCTACTGCTCAACACCTACGGGAGACCCATCCGCTTCCT GCGTGAAAATACCACCCAGTGTACCTACAACAGCAGCC TCCGTAACAGCACGGTCGTCAGGGAAAACGCCATCAGT TTCAACTTCTTCCAAAGCTATAATCAATACTATGTATTC CATATGCCTCGATGTCTCTTTGCGGGTCCTCTGGCGGAG | C2/ Cap1/ Tailless C1/Cap1/ T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | DLTETLERYQQRL<br>NTYALVSKDLASY<br>RSFSQQLKAQDSL<br>GEQPTTVPPPIDLSI<br>PHVWMPPQTTPHG<br>WTESHTTSGLHRP<br>HFNQTCILFDGHDL<br>LFSTVTPCLHQGFY<br>LIDELRYVKITLTE<br>DFFVVTVSIDDDTP<br>MLLIFGHLPRVLFK<br>APYQRDNFILRQTE<br>KHELLVLVKKDQL<br>NRHSYLKDPDFLD<br>AALDFNYLDLSAL<br>LRNSFHRYAVDVL<br>KSGRCQMLDRRTV<br>EMAFAYALALFAA<br>ARQEEAGAQVSVP<br>RALDRQAALLQIQ<br>EFMITCLSQTPPRT<br>TLLLYPTAVDLAK<br>RALWTPNQITDITS<br>LVRLVYILSKQNQ<br>QHLIPQWALRQIA<br>DFALKLHKTHLAS<br>FLSAFARQELYLM<br>GSLVHSMLVHTTE<br>RREIFIVETGLCSLA<br>ELSHFTQLLAHPH<br>HEYLSDLYTPCSSS<br>GRRDHSLERLTRLF<br>PDATVPATVPAAL<br>SILSTMQPSTLETFP<br>DLFCLPLGESFSAL<br>TVSEHVSYIVTNQ<br>YLIKGISYPVSTTV<br>VGQSLIITQTDSQT<br>KCELTRNMHTTHS<br>ITVALNISLENCAF<br>CQSALLEYDDTQG<br>VINIMYMHDSDDV<br>LFALDPYNEVVVS<br>SPRTHYLMLLKNG<br>TVLEVTDVVVDAT<br>DSRLLMMSVYALS<br>AIIGIYLLYRMLKT<br>C (SEQ ID NO: 59) | CAGTTTCTGAACCAGGTAGATCTGACCGAAACCCTGGA<br>AAGATACCAACAGAGACTTAACACTTACGCGCTGGTAT<br>CCAAAGACCTGGCCAGCTACCGATCTTTCTCGCAGCAGC<br>TAAAGGCACAAGACAGCCTAGGTGAACAGCCCACCACT<br>GTGCCACCGCCCATTGACCTGTCAATACCTCACGTTTGG<br>ATGCCACCGCAAACCACTCCACACGGCTGGACAGAATC<br>ACATACCACCTCAGGACTACACCGACCACACTTTAACC<br>AGACCTGTATCCTCTTTGATGGACACGATCTACTATTCA<br>GCACCGTCACACCTTGTTTGCACCAAGGCTTTTACCTCA<br>TCGACGAACTACGTTACGTTAAAATAACACTGACCGAG<br>GACTTCTTCGTAGTTACGGTGTCCATAGACGACGACACA<br>CCCATGCTGCTTATCTTCGGCCATCTTCCACGCGTACTTT<br>TCAAAGCGCCCTATCAACGCGACAACTTTATACTACGAC<br>AAACTGAGAAACACGAGCTCCTGGTGCTAGTTAAGAAA<br>GATCAACTGAACCGTCACTCTTATCTCAAAGACCCGGAC<br>TTTCTTGACGCCGCACTTGACTTCAACTACCTAGACCTC<br>AGCGCACTACTACGTAACAGCTTTCACCGTTACGCCGTG<br>GATGTACTCAAGAGCGGTCGATGTCAGATGCTGGACCG<br>CCGCACGGTAGAAATGGCCTTCGCCTACGCATTAGCACT<br>GTTCGCAGCAGCCCGACAAGAAGAGGCCGGCGCCCAAG<br>TCTCCGTCCCACGGGCCCTAGACCGCCAGGCCGCACTCT<br>TACAAATACAAGAATTTATGATCACCTGCCTCTCACAAA<br>CACCACCACGCACCACGTTGCTGCTGTATCCCACGGCCG<br>TGGACCTGGCCAAACGAGCCCTTTGGACACCGAATCAG<br>ATCACCGACATCACCAGCCTCGTACGCCTGGTCTACATA<br>CTCTCTAAACAGAATCAGCAACATCTCATCCCCCAATGG<br>GCACTACGACAGATCGCCGACTTTGCCCTAAAACTACA<br>CAAAACGCACCTGGCCTCTTTTCTTTCAGCCTTCGCACG<br>CCAAGAACTCTACCTCATGGGCAGCCTCGTCCACTCCAT<br>GCTGGTACATACGACGGAGAGACGCGAAATCTTCATCG<br>TAGAAACGGGCCTCTGTTCATTGGCCGAGCTATCACACT<br>TTACGCAGTTGTTAGCTCATCCACACCACGAATACCTCA<br>GCGACCTGTACACACCCTGTTCCAGTAGCGGGCGACGC<br>GATCACTCGCTCGAACGCCTCACGCGTCTCTTCCCCGAT<br>GCCACCGTCCCCGCTACCGTTCCCGCCGCCCTCTCCATC<br>CTATCTACCATGCAACCAAGCACGCTGGAAACCTTCCCC<br>GACCTGTTTTGCTTGCCGCTCGGCGAATCCTTCTCCGCG<br>CTGACCGTCTCCGAACACGTCAGTTATATCGTAACAAAC<br>CAGTACCTGATCAAAGGTATCTCCTACCCTGTCTCCACC<br>ACCGTCGTAGGCCAGAGCCTCATCATCACCCAGACGGA<br>CAGTCAAACTAAATGCGAACTGACGCGCAACATGCATA<br>CCACACACAGCATCACAGTGGCGCTCAACATTTCGCTA<br>GAAAACTGCGCCTTTTGCCAAAGCGCCCTGCTAGAATA<br>CGACGACACGCAAGGCGTCATCAACATCATGTACATGC<br>ACGACTCGGACGACGTCCTTTTCGCCCTGGATCCCTACA<br>ACGAAGTGGTGGTCTCATCTCCGCGAACTCACTACCTCA<br>TGCTTTTGAAGAACGGTACGGTACTAGAAGTAACTGAC<br>GTCGTCGTGGACGCCACCGACAGTCGTCTCCTCATGATG<br>TCCGTCTACGCGCTATCGGCCATCATCGGCATCTATCTG<br>CTCTACCGCATGCTCAAGACATGC (SEQ ID NO: 87) | |
| hCMV_gH dimer_v2 | MRPGLPSYLIILAV<br>CLFSHLLSSRYGAE<br>AVSEPLDKAFHLL<br>LNTYGRPIRFLREN<br>TTQCTYNSSLRNST<br>VVRENAISFNFFQS<br>YNQYYVFHMPRCL<br>FAGPLAEQFLNQV<br>DLTETLERYQQRL<br>NTYALVSKDLASY<br>RSFSQQLKAQDSL<br>GEQPTTVPPPIDLSI<br>PHVWMPPQTTPHG<br>WTESHTTSGLHRP<br>HFNQTCILFDGHDL<br>LFSTVTPCLHQGFY<br>LIDELRYVKITLTE<br>DFFVVTVSIDDDTP<br>MLLIFGHLPRVLFK<br>APYQRDNFILRQTE | ATGCGGCCAGGCCTCCCCTCCTACCTCATCATCCTCGCC<br>GTCTGTCTCTTCAGCCACCTACTTTCGTCACGATATGGC<br>GCAGAAGCCGTATCCGAACCGCTGGACAAAGCGTTTCA<br>CCTACTGCTCAACACCTACGGGAGACCCATCCGCTTCCT<br>GCGTGAAAATACCACCCAGTGTACCTACAACAGCAGCC<br>TCCGTAACAGCACGGTCGTCAGGGAAAACGCCATCAGT<br>TTCAACTTCTTCCAAAGCTATAATCAATACTATGTATTC<br>CATATGCCTCGATGTCTCTTTGCGGGTCCTCTGGCGGAG<br>CAGTTTCTGAACCAGGTAGATCTGACCGAAACCCTGGA<br>AAGATACCAACAGAGACTTAACACTTACGCGCTGGTAT<br>CCAAAGACCTGGCCAGCTACCGATCTTTCTCGCAGCAGC<br>TAAAGGCACAAGACAGCCTAGGTGAACAGCCCACCACT<br>GTGCCACCGCCCATTGACCTGTCAATACCTCACGTTTGG<br>ATGCCACCGCAAACCACTCCACACGGCTGGACAGAATC<br>ACATACCACCTCAGGACTACACCGACCACACTTTAACC<br>AGACCTGTATCCTCTTTGATGGACACGATCTACTATTCA<br>GCACCGTCACACCTTGTTTGCACCAAGGCTTTTACCTCA<br>TCGACGAACTACGTTACGTTAAAATAACACTGACCGAG<br>GACTTCTTCGTAGTTACGGTGTCCATAGACGACGACACA<br>CCCATGCTGCTTATCTTCGGCCATCTTCCACGCGTACTTT | C2/<br>no cap/<br>T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | KHELLVLVKKDQL NRHSYLKDPDFLD AALDFNYLDLSAL LRNSFHRYAVDVL KSGRCQMLDRRTV EMAFAYALALFAA ARQEEAGAQVSVP RALDRQAALLQIQ EFMITCLSQTPPRT TLLLYPTAVDLAK RALWTPNQITDITS LVRLVYILSKQNQ QHLIPQWALRQIA DFALKLHKTHLAS FLSAFARQELYLM GSLVHSMLVHTTE RREIFIVETGLCSLA ELSHFTQLLAHPH HEYLSDLYTPCSSS GRRDHSLERLTRLF PDATVPATVPAAL SILSTMQPSTLETFP DLFCLPLGESFSAL TVSEHVSYIVTNQ YLIKGISYPVSTTV VGQSLIITQTDSQT KCELTRNMHTTHS ITVALNISLENCAF CQSALLEYDDTQG VINIMYMHDSDDV LFALDPYNEVVVS SPRTHYLMLLKNG TVLEVTDVVVDAT DSRLLMMSVYALS AIIGIYLLYRMLKT C (SEQ ID NO: 1)SEQ ID NO: 59) | TCAAAGCGCCCTATCAACGCGACAACTTTATACTACGAC AAACTGAGAAACACGAGCTCCTGGTGCTAGTTAAGAAA GATCAACTGAACCGTCACTCTTATCTCAAAGACCCGGAC TTTCTTGACGCCGCACTTGACTTCAACTACCTAGACCTC AGCGCACTACTACGTAACAGCTTTCACCGTTACGCCGTG GATGTACTCAAGAGCGGTCGATGTCAGATGCTGGACCG CCGCACGGTAGAAATGGCCTTCGCCTACGCATTAGCACT GTTCGCAGCAGCCCGACAAGAAGAGGCCGGCGCCCAAG TCTCCGTCCCACGGGCCCTAGACCGCCAGGCCGCACTCT TACAAATACAAGAATTTATGATCACCTGCCTCTCACAAA CACCACCACGCACCACGTTGCTGCTGTATCCCACGGCCG TGGACCTGGCCAAACGAGCCCTTTGGACACCGAATCAG ATCACCGACATCACCAGCCTCGTACGCCTGGTCTACATA CTCTCTAAACAGAATCAGCAACATCTCATCCCCCAATGG GCACTACGACAGATCGCCGACTTTGCCCTAAAACTACA CAAAACGCACCTGGCCTCTTTTCTTTCAGCCTTCGCACG CCAAGAACTCTACCTCATGGGCAGCCTCGTCCACTCCAT GCTGGTACATACGACGGAGAGACGCGAAATCTTCATCG TAGAAACGGGCCTCTGTTCATTGGCCGAGCTATCACACT TTACGCAGTTGTTAGCTCATCCACACCACGAATACCTCA GCGACCTGTACACACCCTGTTCCAGTAGCGGGCGACGC GATCACTCGCTCGAACGCCTCACGCGTCTCTTCCCCGAT GCCACCGTCCCCGCTACCGTTCCCGCCGCCCTCTCCATC CTATCTACCATGCAACCAAGCACGCTGGAAACCTTCCCC GACCTGTTTTGCTTGCCGCTCGGCGAATCCTTCTCCGCG CTGACCGTCTCCGAACACGTCAGTTATATCGTAACAAAC CAGTACCTGATCAAAGGTATCTCCTACCCTGTCTCCACC ACCGTCGTAGGCCAGAGCCTCATCATCACCCAGACGGA CAGTCAAACTAAATGCGAACTGACGCGCAACATGCATA CCACACACAGCATCACAGTGGCGCTCAACATTTCGCTA GAAAACTGCGCCTTTTGCCAAAGCGCCCTGCTAGAATA CGACGACACGCAAGGCGTCATCAACATCATGTACATGC ACGACTCGGACGACGTCCTTTTCGCCCTGGATCCCTACA ACGAAGTGGTGGTCTCATCTCCGCGAACTCACTACCTCA TGCTTTTGAAGAACGGTACGGTACTAGAAGTAACTGAC GTCGTCGTGGACGCCACCGACAGTCGTCTCCTCATGATG TCCGTCTACGCGCTATCGGCCATCATCGGCATCTATCTG CTCTACCGCATGCTCAAGACATGC (SEQ ID NO: 88) | |
| hCMV_UL128 | MSPKDLTPFLTAL WLLLGHSRVPRVR AEECCEFINVNHPP ERCYDFKMCNRFT VALRCPDGEVCYS PEKTAEIRGIVTTM THSLTRQVVHNKL TSCNYNPLYLEAD GRIRCGKVNDKAQ YLLGAAGSVPYRW INLEYDKITRIVGL DQYLESVKKHKRL DVCRAKMGYMLQ (SEQ ID NO: 63) | ATGAGTCCCAAAGATCTGACGCCGTTCTTGACGGCGTTG TGGCTGCTATTGGGTCACAGCCGCGTGCCGCGGGTGCG CGCAGAAGAATGTTGCGAATTCATAAACGTCAACCACC CGCCGGAACGCTGTTACGATTTCAAAATGTGCAATCGCT TCACCGTCGCGCTGCGGTGTCCGGACGGCGAAGTCTGCT ACAGTCCCGAGAAAACGGCTGAGATTCGCGGGATCGTC ACCACCATGACCCATTCATTGACACGCCAGGTCGTACAC AACAAACTGACGAGCTGCAACTACAATCCGTTATACCT CGAAGCTGACGGGCGAATACGCTGCGGCAAAGTAAACG ACAAGGCGCAGTACCTGCTGGGCGCCGCTGGCAGCGTT CCCTATCGATGGATCAATCTGGAATACGACAAGATAAC CCGGATCGTGGGCCTGGATCAGTACCTGGAGAGCGTTA AGAAACACAAACGGCTGGATGTGTGCCGCGCTAAAATG GGCTATATGCTGCAG (SEQ ID NO: 89) | C2/ Cap1/ Tailless C2/no cap/T100 C1/cap1/ T100 |
| hCMV-gL | MCRRPDCGFSFSP GPVILLWCCLLLPI VSSAAVSVAPTAA EKVPAECPELTRRC LLGEVFEGDKYES WLRPLVNVTGRDG PLSQLIRYRPVTPE AANSVLLDEAFLD TLALLYNNPDQLR ALLTLLSSDTAPR WMTVMRGYSECG DGSPAVYTCVDDL CRGYDLTRLSYGR SIFTEHVLGFELVP PSLFNVVVAIRNEA TRTNRAVRLPVST AAAPEGITLFYGLY | ATGTGCCGCCGCCCGGATTGCGGCTTCTCTTTCTCACCT GGACCGGTGATACTGCTGTGGTGTTGCCTTCTGCTGCCC ATTGTTTCCTCAGCCGCCGTCAGCGTCGCTCCTACCGCC GCCGAGAAAGTCCCCGCGGAGTGCCCCGAACTAACGCG CCGATGCTTGTTGGGTGAGGTGTTTGAGGGTGACAAGT ATGAAAGTTGGCTGCGCCCGTTGGTGAATGTTACCGGG CGCGATGGCCCGCTATCGCAACTTATCCGTTACCGTCCC GTTACGCCGGAGGCCGCCAACTCCGTGCTGTTGGACGA GGCTTTCCTGGACACTCTGGCCCTGCTGTACAACAATCC GGATCAATTGCGGGCCCTGCTGACGCTGTTGAGCTCGG ACACAGCGCCGCGCTGGATGACGGTGATGCGCGGCTAC AGCGAGTGCGGCGATGGCTCGCCGGCCGTGTACACGTG CGTGGACGACCTGTGCCGCGGCTACGACCTCACGCGAC TGTCATACGGGCGCAGCATCTTCACGGAACACGTGTTA GGCTTCGAGCTGGTGCCACCGTCTCTCTTTAACGTGGTG GTGGCCATACGCAACGAAGCCACGCGTACCAACCGCGC CGTGCGTCTGCCCGTGAGCACCGCTGCCGCGCCCGAGG | C2/ Cap1/ Tailless C2/no cap/T100 C1/cap1/ T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | NAVKEFCLRHQLD PPLLRHLDKYYAG LPPELKQTRVNLPA HSRYGPQAVDAR (SEQ ID NO: 3) | GCATCACGCTCTTTTACGGCCTGTACAACGCAGTGAAGG AATTCTGCCTGCGTCACCAGCTGGACCCGCCGCTGCTAC GCCACCTAGATAAATACTACGCCGGACTGCCGCCCGAG CTGAAGCAGACGCGCGTCAACCTGCCGGCTCACTCGCG CTATGGCCCTCAAGCAGTGGATGCTCGC (SEQ ID NO: 90) | |
| hCMV-UL130 | MLRLLLRHHFHCL LLCAVWATPCLAS PWSTLTANQNPSPP WSKLTYSKPHDAA TFYCPFLYPSPPRSP LQFSGFQRVSTGPE CRNETLYLLYNRE GQTLVERSSTWVK KVIWYLSGRNQTIL QRMPRTASKPSDG NVQISVEDAKIFGA HMVPKQTKLLRFV VNDGTRYQMCVM KLESWAHVFRDYS VSFQVRLTFTEAN NQTYTFCTHPNLIV (SEQ ID NO: 65) | ATGCTGCGGCTTCTGCTTCGTCACCACTTTCACTGCCTG CTTCTGTGCGCGGTTTGGGCAACGCCCTGTCTGGCGTCT CCGTGGTCGACGCTAACAGCAAACCAGAATCCGTCCCC GCCATGGTCTAAACTGACGTATTCCAAACCGCATGACG CGGCGACGTTTTACTGTCCTTTTCTCTATCCCTCGCCCCC ACGATCCCCCTTGCAATTCTCGGGGTTCCAGCGGGTATC AACGGGTCCCGAGTGTCGCAACGAGACCCTGTATCTGC TGTACAACCGGGAAGGCCAGACCTTGGTGGAGAGAAGC TCCACCTGGGTGAAAAAGGTGATCTGGTACCTGAGCGG TCGGAACCAAACCATCCTCCAACGGATGCCCCGAACGG CTTCGAAACCGAGCGACGGAAACGTGCAGATCAGCGTG GAAGACGCCAAGATTTTTGGAGCGCACATGGTGCCCAA GCAGACCAAGCTGCTACGCTTCGTCGTCAACGATGGCA CACGTTATCAGATGTGTGTGATGAAGCTGGAGAGCTGG GCTCACGTCTTCCGGGACTACAGCGTGTCTTTTCAGGTG CGATTGACGTTCACCGAGGCCAATAACCAGACTTACAC CTTCTGCACCCATCCCAATCTCATCGTT (SEQ ID NO: 91) | C2/ Cap1/ Tailless C2/no cap/T100 C1/Cap1/ T100 |
| pp65 phos mut_DX | MESRGRRCPEMIS VLGPISGHVLKAVF SRGDTPVLPHETRL LQTGIHVRVSQPSL ILVSQYTPDSTPCH RGDNQLQVQHTYF TGSEVENVSVNVH NPTGRSICPSQEPM SIYVYALPLKMLNI PSINVHHYPSAAER KHRHLPVADAVIH ASGKQMWQARLT VSGLAWTRQQNQ WKEPDVYYTSAFV FPTKDVALRHVVC AHELVCSMENTRA TKMQVIGDQYVK VYLESFCEDVPSG KLFMHVTLGSDVE EDLTMTRNPQPFM RPHERNGFTVLCP KNMIIKPGKISHIM LDVAFTSHEHFGL LCPKSIPGLSISGNL LMNGQQIFLEVQAI RETVELRQYDPVA ALFFFDIDLLLQRG PQYSEHPTFTSQYR IQGKLEYRHTWDR HDEGAAQGDDDV WTSGSDSDEELVT TERKTPRVTGGGA MASASTSAGSASS ATACTAGVMTRG RLKAESTVAPEED TDEDSDNEIHNPA VFTWPPWQAGILA RNLVPMVATVQG QNLKYQEFFWDA NDIYRIFAELEGVW QPAAQPKRRRHRQ DALPGPCIASTPKK HRG (SEQ ID NO: 71) | ATGGAGTCGCGCGGTCGCCGTTGTCCCGAAATGATATCC GTACTGGGTCCCATTTCGGGGCACGTGCTGAAAGCCGT GTTTAGTCGCGGCGATACGCCGGTGCTGCCGCACGAGA CGAGACTCCTGCAGACGGGTATCCACGTACGCGTGAGC CAGCCCTCGCTGATCCTGGTGTCGCAGTACACGCCCGAC TCGACGCCATGCCACCGCGGCGACAATCAGCTGCAGGT GCAGCACACGTACTTTACGGGCAGCGAGGTGGAGAACG TGTCGGTCAACGTGCACAACCCCACGGGCCGAAGCATC TGCCCCAGCCAAGAGCCCATGTCGATCTATGTGTACGCG CTGCCGCTCAAGATGCTGAACATCCCCAGCATCAACGT GCACCACTACCCGTCGGCGGCCGAGCGCAAACACCGAC ACCTGCCCGTAGCCGACGCTGTTATTCACGCGTCGGGCA AGCAGATGTGGCAGGCGCGTCTCACGGTCTCGGGACTG GCCTGGACGCGTCAGCAGAACCAGTGGAAAGAGCCCGA CGTCTACTACACGTCAGCGTTCGTGTTTCCCACCAAGGA CGTGGCACTGCGGCACGTGGTGTGCGCGCACGAGCTGG TTTGCTCCATGGAGAACACGCGCGCAACCAAGATGCAG GTGATAGGTGACCAGTACGTCAAGGTGTACCTGGAGTC CTTCTGCGAGGACGTGCCCTCCGGCAAGCTCTTTATGCA CGTCACGCTGGGCTCTGACGTGGAAGAGGACCTAACGA TGACCCGCAACCCGCAACCCTTCATGCGCCCCCACGAG CGCAACGGCTTTACGGTGTTGTGTCCCAAAAATATGATA ATCAAACCGGGCAAGATCTCGCACATCATGCTGGATGT GGCTTTTACCTCACACGAGCATTTTGGGCTGCTGTGTCC CAAGAGCATCCCGGGCCTGAGCATCTCAGGTAACCTGT TGATGAACGGGCAGCAAATCTTCCTGGAGGTACAAGCG ATACGCGAGACCGTGGAACTGCGTCAGTACGATCCCGT GGCTGCGCTCTTCTTTTTCGATATCGACTTGTTGCTGCAG CGCGGGCCTCAGTACAGCGAGCACCCCACCTTCACCAG CCAGTATCGCATCCAGGGCAAGCTTGAGTACCGACACA CCTGGGACCGGCACGACGAGGGTGCCGCCCAGGGCGAC GACGACGTCTGGACCAGCGGATCGGACTCCGACGAAGA ACTCGTAACCACCGAGCGTAAGACGCCCCGCGTCACCG GCGGCGGAGCCATGGCGAGCGCCTCCACTTCCGCGGGC TCAGCATCCTCGGCGACGGCGTGCACGGCGGGCGTTAT GACACGCGGCCGCCTTAAGGCCGAGTCCACCGTCGCGC CCGAAGAGGACACCGACGAGGATTCCGACAACGAAATC CACAATCCGGCCGTGTTCACCTGGCCGCCCTGGCAGGCC GGCATCCTGGCCCGCAACCTGGTGCCCATGGTGGCTAC GGTTCAGGGTCAGAATCTGAAGTACCAGGAGTTCTTCTG GGACGCCAACGACATCTACCGCATCTTCGCCGAATTGG AAGGCGTATGGCAGCCCGCTGCGCAACCCAAACGTCGC CGCCACCGGCAAGACGCCTTGCCCGGGCCATGCATCGC CTCGACGCCCAAAAAGCACCGAGGT (SEQ ID NO: 92) | C2/ Cap1/ Tailless C2/no cap/T100 C1/Cap1/ T100 |
| pp65 WT | MESRGRRCPEMIS VLGPISGHVLKAVF | ATGGAGTCGCGCGGTCGCCGTTGTCCCGAAATGATATCC GTACTGGGTCCCATTTCGGGGCACGTGCTGAAAGCCGT | C2/ CAP1/ |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | SRGDTPVLPHETRL LQTGIHVRVSQPSL ILVSQYTPDSTPCH RGDNQLQVQHTYF TGSEVENVSVNVH NPTGRSICPSQEPM SIYVYALPLKMLNI PSINVHHYPSAAER KHRHLPVADAVIH ASGKQMWQARLT VSGLAWTRQQNQ WKEPDVYYTSAFV FPTKDVALRHVVC AHELVCSMENTRA TKMQVIGDQYVK VYLESFCEDVPSG KLFMHVTLGSDVE EDLTMTRNPQPFM RPHERNGFTVLCP KNMIIKPGKISHIM LDVAFTSHEHFGL LCPKSIPGLSISGNL LMNGQQIFLEVQAI RETVELRQYDPVA ALFFFDIDLLLQRG PQYSEHPTFTSQYR IQGKLEYRHTWDR HDEGAAQGDDDV WTSGSDSDEELVT TERKTPRVTGGGA MASASTSAGRKRK SASSATACTAGVM TRGRLKAESTVAP EEDTDEDSDNEIHN PAVFTWPPWQAGI LARNLVPMVATVQ GQNLKYQEFFWD ANDIYRIFAELEGV WQPAAQPKRRRH RQDALPGPCIASTP KKHRG (SEQ ID NO: 82) | GTTTAGTCGCGGCGATACGCCGGTGCTGCCGCACGAGA CGCGACTCCTGCAGACGGGTATCCACGTACGCGTGAGC CAGCCCTCGCTGATCCTGGTGTCGCAGTACACGCCCGAC TCGACGCCATGCCACCGCGGCGACAATCAGCTGCAGGT GCAGCACACGTACTTTACGGGCAGCGAGGTGGAGAACG TGTCGGTCAACGTGCACAACCCCACGGGCCGAAGCATC TGCCCCAGCCAAGAGCCCATGTCGATCTATGTGTACGCG CTGCCGCTCAAGATGCTGAACATCCCCAGCATCAACGT GCACCACTACCCGTCGGCGGCCGAGCGCAAACACCGAC ACCTGCCCGTAGCCGACGCTGTTATTCACGCGTCGGGCA AGCAGATGTGGCAGGCGCGTCTCACGGTCTCGGGACTG GCCTGGACGCGTCAGCAGAACCAGTGGAAAGAGCCCGA CGTCTACTACACGTCAGCGTTCGTGTTTCCCACCAAGGA CGTGGCACTGCGGCACGTGGTGTGCGCGCACGAGCTGG TTTGCTCCATGGAGAACACGCGCGCAACCAAGATGCAG GTGATAGGTGACCAGTACGTCAAGGTGTACCTGGAGTC CTTCTGCGAGGACGTGCCCTCCGGCAAGCTCTTTATGCA CGTCACGCTGGGCTCTGACGTGGAAGAGGACCTAACGA TGACCCGCAACCCGCAACCCTTCATGCGCCCCCACGAG CGCAACGGCTTTACGGTGTTGTGTCCCAAGAATATGATA ATCAAACCGGGCAAGATCTCGCACATCATGCTGGATGT GGCTTTTACCTCACACGAGCATTTTGGGCTGCTGTGTCC CAAGAGCATCCCGGGCCTGAGCATCTCAGGTAACCTGT TGATGAACGGGCAGCAAATCTTCCTGGAGGTACAAGCG ATACGCGAGACCGTGGAACTGCGTCAGTACGATCCCGT GGCTGCGCTCTTCTTTTTCGATATCGACTTGTTGCTGCAG CGCGGGCCTCAGTACAGCGAGCACCCCACCTTCACCAG CCAGTATCGCATCCAGGGCAAGCTTGAGTACCGACACA CCTGGGACCGGCACGACGAGGGTGCCGCCCAGGGCGAC GACGACGTCTGGACCAGCGGATCGGACTCCGACGAAGA ACTCGTAACCACCGAGCGTAAGACGCCCCGCGTCACCG GCGGCGGCGCCATGGCGAGCGCCTCCACTTCCGCGGGC CGCAAACGCAAATCAGCATCCTCGGCGACGGCGTGCAC GGCGGGCGTTATGACACGCGGCCGCCTTAAGGCCGAGT CCACCGTCGCGCCCGAAGAGGACACCGACGAGGATTCC GACAACGAAATCCACAATCCGGCCGTGTTCACCTGGCC GCCCTGGCAGGCCGGCATCCTGGCCCGCAACCTGGTGC CCATGGTGGCTACGGTTCAGGGTCAGAATCTGAAGTAC CAGGAGTTCTTCTGGGACGCCAACGACATCTACCGCATC TTCGCCGAATTGGAAGGCGTATGGCAGCCCGCTGCGCA ACCCAAACGTCGCCGCCACCGGCAAGACGCCTTGCCCG GGCCATGCATCGCCTCGACGCCCAAGAAGCACCGAGGT (SEQ ID NO: 93) | T100 |
| SE_CMV_gB_ FL_061 | MESRIWCLVVCVN LCIVCLGAAVSSSS TRGTSATHSHHSS HTTSAAHSRSGSVS QRVTSSQTVSHGV NETIYNTTLKYGD VVGVNTTKYPYRV CSMAQGTDLIRFE RNIVCTSMKPINED LDEGIMVVYKRNI VAHTFKVRVYQK VLTFRRSYAYIHTT YLLGSNTEYVAPP MWEIHHINSHSQC YSSYSRVIAGTVFV AYHRDSYENKTM QLMPDDYSNTHST RYVTVKDQWHSR GSTWLYRETCNLN CMVTITTARSKYP YHFFATSTGDVVDI SPFYNGTNRNASY FGENADKFFIFPNY TIVSDFGRPNSALE THRLVAFLERADS VISWDIQDEKNVT CQLTFWEASERTIR | ATGGAAAGCCGGATCTGGTGTCTTGTGGTGTGCGTGAAT CTTTGCATCGTGTGCTTGGGTGCCGCCGTGTCATCTAGC AGCACAAGAGGCACCTCCGCCACTCACTCACACCACAG CAGCCACACGACCAGCGCCGCTCACTCCAGAAGCGGCT CTGTAAGCCAGAGAGTGACCAGTTCTCAAACCGTCAGC CACGGCGTCAATGAGACGATATATAATACAACCCTGAA GTATGGAGACGTGGTGGGTGTCAATACCACCAAGTACC CTTATCGCGTGTGCAGCATGGCCCAGGGCACTGACCTG ATCAGATTCGAGAGAAATATCGTCTGCACCTCCATGAA GCCTATCAACGAGGACCTTGACGAGGGCATCATGGTTG TCTACAAGAGAAACATTGTGGCTCACACCTTCAAGGTG AGAGTGTATCAGAAAGTACTGACCTTTAGGAGATCCTA CGCTTACATCCACACCACGTACCTGCTCGGCTCCAACAC CGAGTATGTGGCTCCACCCATGTGGGAGATTCATCACAT CAATTCCCACAGCCAATGTTACAGTTCCTATAGCAGAGT CATTGCTGGTACCGTGTTCGTCGCTTACCACAGAGACAG CTATGAGAACAAGACCATGCAGTTGATGCCCGATGACT ACTCCAATACACACTCTACAAGGTATGTGACAGTCAAA GATCAGTGGCACAGCCGGGGCAGCACCTGGCTGTACCG AGAGACATGTAATCTGAATTGTATGGTGACTATCACTAC AGCCAGGAGCAAATATCCATACCACTTCTTCGCCACTAG CACCGGGGACGTCGTGGACATTTCCCCATTCTACAATGG CACAAACAGAAACGCCAGCTACTTCGGCGAGAATGCCG ACAAGTTCTTTATATTCCCCAACTATACCATCGTGAGCG ACTTCGGCCGCCCCAACAGCGCCCTGGAAACCCACCGG CTCGTGGCCTTTCTCGAGCGGGCCGATAGCGTCATATCC TGGGACATCCAGGACGAGAAGAATGTGACATGCCAGCT | C2/ CAP1/ T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | SEAEDSYHFSSAK | GACCTTCTGGGAGGCCTCCGAGCGTACCATCCGGTCCG | |
| | MTATFLSKKQEVN | AGGCAGAGGACAGCTACCATTTCAGCAGCGCCAAGATG | |
| | MSDSALDCVRDEA | ACCGCAACCTTCCTCAGTAAGAAACAGGAGGTTAACAT | |
| | INKLQQIFNTSYNQ | GTCTGATTCTGCCCTGGACTGCGTGCGCGATGAGGCAAT | |
| | TYEKYGNVSVFET | CAACAAGCTGCAGCAGATCTTCAACACATCTTACAACC | |
| | TGGLVVFWQGIKQ | AAACTTACGAGAAGTACGGCAACGTCAGCGTGTTCGAG | |
| | KSLVELERLANRSS | ACAACAGGAGGCCTGGTAGTGTTCTGGCAAGGTATCAA | |
| | LNLTHNRTKRSTD | GCAGAAGAGTCTGGTGGAGCTCGAGCGACTGGCTAACC | |
| | GNNATHLSNMESV | GCAGCTCCCTCAACCTGACCCATAATAGGACAAAGAGA | |
| | HNLVYAQLQFTYD | AGCACCGACGGCAACAACGCTACTCATTTGAGCAACAT | |
| | TLRGYINRALAQIA | GGAATCCGTGCACAACCTGGTGTATGCCCAGCTGCAGTT | |
| | EAWCVDQRRTLEV | CACTTACGACACCCTGAGAGGCTACATCAATAGAGCCT | |
| | FKELSKINPSAILSA | TAGCTCAGATCGCAGAGGCTTGGTGTGTGGACCAGCGA | |
| | IYNKPIAARFMGD | AGAACTCTGGAGGTGTTCAAGGAGTTAAGTAAGATCAA | |
| | VLGLASCVTINQTS | TCCATCCGCCATCCTGTCTGCTATCTACAACAAGCCCAT | |
| | VKVLRDMNVKESP | TGCCGCCAGGTTCATGGGAGATGTGCTCGGCCTGGCTA | |
| | GRCYSRPVVIFNFA | GTTGTGTCACCATCAACCAGACCTCCGTGAAGGTGCTGC | |
| | NSSYVQYGQLGED | GGGACATGAATGTGAAGGAGAGCCCCGGTCGGTGTTAC | |
| | NEILLGNHRTEECQ | TCCAGACCAGTGGTGATTTTCAACTTCGCCAACAGCTCC | |
| | LPSLKIFIAGNSAY | TATGTGCAGTACGGACAGCTCGGAGAGGATAACGAGAT | |
| | EYVDYLFKRMIDL | CTTGCTCGGCAATCACAGAACTGAGGAGTGTCAGCTGC | |
| | SSISTVDSMIALDID | CATCACTGAAGATATTTATTGCCGGGAATTCCGCCTACG | |
| | PLENTDFRVLELYS | AATACGTTGACTACCTTTTCAAGAGAATGATCGACCTGA | |
| | QKELRSSNVFDLEE | GCAGCATCAGCACCGTCGACAGCATGATTGCTCTCGAT | |
| | IMREFNSYKQRVK | ATCGACCCTCTGGAGAACACCGACTTTAGAGTCCTTGAG | |
| | YVEDKVVDPLPPY | CTGTATTCACAGAAGGAGCTGAGGAGCTCCAATGTGTT | |
| | LKGLDDLMSGLGA | CGACCTGGAGGAAATCATGAGAGAGTTCAACTCTTACA | |
| | AGKAVGVAIGAVG | AGCAGCGGGTGAAGTACGTGGAGGATAAGGTAGTGGAC | |
| | GAVASVVEGVATF | CCACTCCCACCATACCTGAAAGGACTCGACGATCTCATG | |
| | LKNPFGAFTIILVAI | AGCGGACTGGGCGCAGCCGGGAAGGCTGTTGGCGTCGC | |
| | AVVIITYLIYTRQR | CATCGGAGCGGTCGGAGGAGCAGTGGCTAGCGTGGTGG | |
| | RLCTQPLQNLFPYL | AGGGCGTGGCCACCTTCCTGAAGAACCCTTTCGGCGCCT | |
| | VSADGTTVTSGST | TTACCATCATCCTGGTGGCCATCGCCGTGGTCATCATTA | |
| | KDTSLQAPPSYEES | CATATCTGATTTATACAAGACAGAGAAGGCTCTGCACC | |
| | VYNSGRKGPGPPS | CAGCCCTTGCAGAACCTGTTCCCCTACCTGGTCAGTGCC | |
| | SDASTAAPPYTNE | GACGGTACAACCGTGACCAGCGGTAGCACCAAGGACAC | |
| | QAYQMLLALARL | CTCCCTGCAGGCACCGCCGAGCTACGAGGAGTCCGTGT | |
| | DAEQRAQQNGTDS | ATAACAGTGGAAGAAAGGGCCCCGGACCGCCCAGCAGC | |
| | LDGRTGTQDKGQK | GACGCATCCACCGCCGCTCCTCCCTACACAAATGAGCA | |
| | PNLLDRLRHRKNG | GGCCTATCAGATGTTGCTGGCTCTGGCACGCCTGGACGC | |
| | YRHLKDSDEEENV | CGAGCAGCGAGCTCAGCAGAACGGCACCGATTCCCTGG | |
| | (SEQ ID NO: 69) | ATGGACGCACAGGCACACAGGACAAGGGGCAGAAGCC | |
| | | CAACCTCCTCGACAGACTGAGACACCGGAAGAACGGAT | |
| | | ACAGGCATCTGAAGGACTCCGATGAGGAGGAGAACGTT | |
| | | (SEQ ID NO: 94) | |
| SE_CMV_gB_ | MESRIWCLVVCVN | ATGGAAAGCAGAATTTGGTGCCTCGTGGTCTGCGTGAACCTCTGTAT | C2/ |
| FL_062 | LCIVCLGAAVSSSS | CGTGTGCTTAGGCGCCGCAGTTTCAAGCAGCTCCACCAGAGGTACGT | CAP1/ |
| | TRGTSATHSHHSS | CGGCTACCCACAGCCATCATCACTCAAGTCACACTACAAGCGCCGCTCAC | T100 |
| | HTTSAAHSRSGSVS | AGCAGAAGCGGATCTGTGAGCCAGAGGGTGACCAGCTCCCAGACCG | |
| | QRVTSSQTVSHGV | TGAGCCACGGAGTAAATGAAACCATCTACAATACCACATTGAAGTAT | |
| | NETIYNTTLKYGD | GGCGACGTCGTGGGCGTGAACACGACCAAATACCCCTACAGGGTCT | |
| | VVGVNTTKYPYRV | GCTCTATGGCTCAGGGCACTGACCTGATTCGGTTTGAGAGAAATATC | |
| | CSMAQGTDLIRFE | GTCTGCACCAGCATGAAGCCCATTAACGAGGACCTGGATGAGGGCA | |
| | RNIVCTSMKPINED | TCATGGTGGTATATAAACGTAACATTGTGGCCCACACCTTCAAAGTG | |
| | LDEGIMVVYKRNI | AGAGTTTACCAGAAAGTGCTGACCTTCAGAAGATCCTACGCTTACATT | |
| | VAHTFKVRVYQK | CACACAACCTACCTGCTGGGCTCAAACACCGAATACGTGGCCCCTCC | |
| | VLTFRRSYAYIHTT | CATGTGGGAAATCCACCACATCAACTCTCACAGCCAGTGCTACAGCT | |
| | YLLGSNTEYVAPP | CTTACAGCAGGGTTATTGCCGGCACCGTCTTCGTGGCCTACCACCGC | |
| | MWEIHHINSHSQC | GACAGTTATGAGAACAAGACCATGCAGCTGATGCCTGACGACTACA | |
| | YSSYSRVIAGTVFV | GCAACACCCACTCTACCAGATACGTGACCGTTAAGGACCAGTGGCAC | |
| | AYHRDSYENKTM | AGCCGGGGCTCAACCTGGCTGTATCGGGAAACTTGTAACCTGAATTG | |
| | QLMPDDYSNTHST | CATGGTGACCATCACAACTGCCAGAAGCAAGTACCCCTATCACTTCTT | |
| | RYVTVKDQWHSR | CGCCACCAGCACTGGCGATGTGGTGGATATCTCTCCCTTCTACAACG | |
| | GSTWLYRETCNLN | GAACCAATCGCAACGCTTCTTACTTTGGCGAGAACGCCGACAAGTTC | |
| | CMVTITTARSKYP | TTTATCTTTCCCAACTACACCATCGTCAGCGACTTCGGTAGACCCAATT | |
| | YHFFATSTGDVVDI | CTGCCCTGGAAACTCATCGACTTGTGGCATTCCTGGAAAGGGCCGAT | |
| | SPFYNGTNRNASY | TCCGTGATCAGCTGGGACATTCAGGACGAGAAGAACGTTACCTGCCA | |
| | FGENADKFFIFPNY | GCTCACATTTTGGGAGGCCAGCGAGAGGACCATTAGGAGCGAGGCC | |
| | TIVSDFGRPNSALE | GAGGACAGCTACCACTTTTCCAGTGCCAAGATGACAGCCACATTTCTC | |
| | THRLVAFLERADS | TCTAAGAAGCAGGAGGTTAACATGTCCGACAGCGCCCTGGACTGTGT | |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | VISWDIQDEKNVT | CAGAGACGAGGCCATCAATAAGCTGCAGCAGATCTTCAACACCAGCT | |
| | CQLTFWEASERTIR | ACAATCAGACATATGAGAAGTACGGCAACGTCAGCGTCTTCGAGACA | |
| | SEAEDSYHFSSAK | ACAGGCGGGCTGGTCGTGTTCTGGCAGGGAATCAAACAGAAGTCCC | |
| | MTATFLSKKQEVN | TGGTTGAGCTGGAGAGACTGGCGAACAGGAGCTCTCTGAATTTGAC | |
| | MSDSALDCVRDEA | TCATAACAGGACGAAGAGATCCACCGATGGAAACAACGCCACCCAC | |
| | INKLQQIFNTSYNQ | CTGAGCAATATGGAGAGCGTCCACAATCTCGTCTACGCCCAGCTCCA | |
| | TYEKYGNVSVFET | ATTCACCTACGACACCCTGAGGGGCTATATCAACCGGGCCCTGGCCC | |
| | TGGLVVFWQGIKQ | AGATCGCCGAGGCATGGTGCGTGGACCAGAGACGGACCCTGGAAGT | |
| | KSLVELERLANRSS | GTTCAAGGAGCTGTCAAAGATCAACCCTTCCGCCATCCTCTCCGCCAT | |
| | LNLTHNRTKRSTD | ATATAATAAGCCCATCGCCGCAAGATTCATGGGAGATGTCCTGGGTC | |
| | GNNATHLSNMESV | TGGCTAGCTGCGTTACCATCAACCAGACATCAGTGAAGGTTTTGCGA | |
| | HNLVYAQLQFTYD | GACATGAATGTGAAGGAGTCACCCGGCCGATGTTACAGCCGCCCAG | |
| | TLRGYINRALAQIA | TCGTGATCTTTAACTTCGCCAATTCCAGCTACGTCCAATACGGCCAGC | |
| | EAWCVDQRRTLEV | TGGGCGAGGACAATGAAATTCTCCTGGGTAATCATAGAACCGAGGA | |
| | FKELSKINPSAILSA | GTGCCAACTCCCCTCCCTTAAGATTTTCATCGCAGGCAATAGCGCTA | |
| | IYNKPIAARFMGD | TGAGTACGTTGACTACTTGTTTAAGAGAATGATCGATCTGAGCAGCA | |
| | VLGLASCVTINQTS | TCAGCACAGTGGACTCCATGATTGCCCTTGATATCGATCCCCTGGAG | |
| | VKVLRDMNVKESP | AATACCGACTTTAGAGTGCTGGAGTTATACAGCCAGAAAGAGCTGCG | |
| | GRCYSRPVVIFNFA | AAGCTCCAACGTGTTCGATCTGGAGGAAATTATGAGGGAGTTTAACT | |
| | NSSYVQYGQLGED | CCTACAAGCAGAGAGTGAAGTACGTCGAAGACAAAGTGGTGGATCC | |
| | NEILLGNHRTEECQ | ACTGCCGCCTTATCTTAAAGGCCTCGACGATCTGATGAGCGGACTGG | |
| | LPSLKIFIAGNSAY | GTGCCGCCGGCAAAGCTGTGGGCGTTGCCATCGGAGCCGTGGGCGG | |
| | EYVDYLFKRMIDL | GGCCGTGGCCTCCGTGGTGGAAGGCGTGGCTACCTTTCTGAAGAAC | |
| | SSISTVDSMIALDID | CCATTCGGCGCCTTTACCATTATCCTGGTGGCCATTGCCGTGGTGATC | |
| | PLENTDFRVLELYS | ATTACCTATCTCATCTACACTAGGCAGCGGAGGCTGTGTACGCAGCC | |
| | QKELRSSNVFDLEE | TCTGCAGAACCTGTTTCCCTACCTGGTTAGCGCCGACGGAACAACAG | |
| | IMREFNSYKQRVK | TGACATCTGGCTCTACCAAGGATACCTCTCTGCAGGCACCTCCTTCTT | |
| | YVEDKVVDPLPPY | ACGAGGAATCCGTGTACAACTCGGGAAGGAAAGGCCCCGGGCCACC | |
| | LKGLDDLMSGLGA | TTCATCCGACGCCTCCACAGCTGCCCCGCCATACACTAACGAGCAGG | |
| | AGKAVGVAIGAVG | CTTACCAGATGCTTCTCGCCCTGGCTAGATTGGATGCCGAGCAGCGC | |
| | GAVASVVEGVATF | GCCCAACAGAACGGCACCGACAGCCTGGACGGCCGGACAGGCACCC | |
| | LKNPFGAFTIILVAI | AGGACAAAGGGCAGAAGCCCAATCTGCTTGATAGACTGAGGCACCG | |
| | AVVIITYLIYTRQR | GAAGAACGGGTACAGGCATCTTAAGGACAGCGACGAGGAGGAGAA | |
| | RLCTQPLQNLFPYL | CGTC (SEQ ID NO: 157) | |
| | VSADGTTVTSGST | | |
| | KDTSLQAPPSYEES | | |
| | VYNSGRKGPGPPS | | |
| | SDASTAAPPYTNE | | |
| | QAYQMLLALARL | | |
| | DAEQRAQQNGTDS | | |
| | LDGRTGTQDKGQK | | |
| | PNLLDRLRHRKNG | | |
| | YRHLKDSDEEENV | | |
| | (SEQ ID NO: 69) | | |
| SE_CMV_gB_ | MESRIWCLVVCVN | ATGGAATCCAGGATCTGGTGCCTCGTGGTCTGTGTGAAC | C2/ |
| FL_063 | LCIVCLGAAVSSSS | TTGTGCATCGTGTGCTTGGGTGCCGCCGTGAGCAGTAGC | CAP1/ |
| | TRGTSATHSHHSS | AGCACCAGAGGCACCAGCGCAACACACTCACACCACAG | T100 |
| | HTTSAAHSRSGSVS | CTCCCATACCACTTCCGCCGCCCACTCCAGATCGGGCTC | |
| | QRVTSSQTVSHGV | CGTGAGCCAGAGGGTCACCAGCAGCCAGACGGTGTCCC | |
| | NETIYNTTLKYGD | ACGGAGTGAATGAAACCATCTACAACACTACTCTGAAG | |
| | VVGVNTTKYPYRV | TACGGAGACGTCGTCGGCGTGAATACCACTAAGTACCC | |
| | CSMAQGTDLIRFE | CTACAGGGTCTGCTCTATGGCCCAAGGCACAGACCTGA | |
| | RNIVCTSMKPINED | TCAGATTTGAAAGAAATATCGTCTGTACCTCCATGAAGC | |
| | LDEGIMVVYKRNI | CCATCAATGAGGACTTAGACGAGGGCATTATGGTGGTG | |
| | VAHTFKVRVYQK | TATAAACGCAACATTGTGGCCCACACTTTCAAGGTCAG | |
| | VLTFRRSYAYIHTT | AGTGTATCAGAAAGTGCTCACCTTCAGGCGTAGCTATGC | |
| | YLLGSNTEYVAPP | CTATATCCACACCACTTATCTCCTCGGCAGCAACACCGA | |
| | MWEIHHINSHSQC | GTATGTTGCCCCGCCTATGTGGGAGATTCACCATATAAA | |
| | YSSYSRVIAGTVFV | TAGCCATAGCCAGTGCTACAGCTCCTATTCGAGAGTAAT | |
| | AYHRDSYENKTM | CGCCGGAACCGTTTTCGTCGCCTACCACAGAGACTCGTA | |
| | QLMPDDYSNTHST | CGAGAACAAGACAATGCAGCTGATGCCAGATGACTATT | |
| | RYVTVKDQWHSR | CGAACACCCACAGCACGAGATATGTCACCGTGAAAGAT | |
| | GSTWLYRETCNLN | CAGTGGCACAGCAGGGGTAGTACATGGTTGTATAGGGA | |
| | CMVTITTARSKYP | AACCTGCAATCTCAATTGCATGGTGACCATCACCACCGC | |
| | YHFFATSTGDVVDI | CAGAAGCAAATACCCCTATCATTTCTTCGCTACCTCGAC | |
| | SPFYNGTNRNASY | AGGAGACGTGGTGGACATATCTCCCTTTTATAATGGCAC | |
| | FGENADKFFIFPNY | AAATAGAAATGCTAGCTACTTTGGAGAGAACGCCGACA | |
| | TIVSDFGRPNSALE | AATTCTTCATCTTCCCTAACTATACCATCGTGAGCGACT | |
| | THRLVAFLERADS | TTGGGCGACCTAACAGCGCCCTCGAGACTCACAGGCTG | |
| | VISWDIQDEKNVT | GTGGCTTTCTTAGAGAGGGCTGATAGTGTTATCTCTTGG | |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | CQLTFWEASERTIR | GACATTCAGGATGAGAAGAACGTGACATGCCAGCTGAC | |
| | SEAEDSYHFSSAK | ATTTTGGGAGGCTAGCGAGCGAACCATCAGGTCCGAGG | |
| | MTATFLSKKQEVN | CCGAGGACAGCTACCATTTCTCTAGTGCCAAGATGACC | |
| | MSDSALDCVRDEA | GCCACCTTCTTGTCAAAGAAGCAAGAGGTGAACATGTC | |
| | INKLQQIFNTSYNQ | CGACTCTGCGCTGGACTGTGTCCGCGACGAGGCAATTA | |
| | TYEKYGNVSVFET | ATAAACTGCAGCAGATCTTTAATACCAGCTACAACCAG | |
| | TGGLVVFWQGIKQ | ACATACGAGAAGTATGGCAACGTGAGCGTCTTCGAAAC | |
| | KSLVELERLANRSS | CACAGGCGGCCTTGTCGTCTTTTGGCAAGGCATCAAGCA | |
| | LNLTHNRTKRSTD | GAAGAGTCTGGTGGAGCTGGAAAGACTCGCCAACCGGT | |
| | GNNATHLSNMESV | CATCCCTGAATCTGACCCACAATAGGACAAAGCGCAGC | |
| | HNLVYAQLQFTYD | ACCGATGGGAACAACGCCACCCACCTGTCGAACATGGA | |
| | TLRGYINRALAQIA | GTCAGTGCACAACCTGGTGTACGCCCAGCTGCAGTTCAC | |
| | EAWCVDQRRTLEV | TTATGATACCCTCAGAGGCTACATTAACCGCGCACTGGC | |
| | FKELSKINPSAILSA | TCAGATCGCCGAAGCATGGTGCGTGGACCAGCGGCGAA | |
| | IYNKPIAARFMGD | CCCTGGAAGTGTTTAAAGAGCTCTCCAAGATTAATCCTA | |
| | VLGLASCVTINQTS | GCGCCATCCTGAGTGCTATCTACAATAAGCCTATCGCCG | |
| | VKVLRDMNVKESP | CAAGATTTATGGGCGACGTGCTGGGACTGGCTTCCTGCG | |
| | GRCYSRPVVIFNFA | TGACAATTAACCAGACCTCCGTCAAGGTGCTGAGGGAC | |
| | NSSYVQYGQLGED | ATGAACGTGAAGGAGAGCCCCGGCAGATGCTATAGCCG | |
| | NEILLGNHRTEECQ | GCCAGTGGTGATCTTCAATTTCGCCAACAGCTCATACGT | |
| | LPSLKIFIAGNSAY | GCAGTACGGCCAGCTCGGGGAGGATAATGAAATCCTGC | |
| | EYVDYLFKRMIDL | TGGGAAATCACAGAACCGAGGAGTGTCAGCTGCCCAGT | |
| | SSISTVDSMIALDID | CTGAAGATTTTCATCGCAGGCAACAGTGCCTATGAATAC | |
| | PLENTDFRVLELYS | GTGGACTATCTGTTCAAACGCATGATCGATCTGAGCTCT | |
| | QKELRSSNVFDLEE | ATCTCCACCGTGGACTCCATGATTGCCTTGGATATCGAC | |
| | IMREFNSYKQRVK | CCACTGGAGAACACCGATTTCAGAGTGCTGGAGCTGTA | |
| | YVEDKVVDPLPPY | CAGCCAGAAGGAGCTCAGGTCCAGCAATGTGTTCGACC | |
| | LKGLDDLMSGLGA | TGGAGGAAATCATGAGAGAGTTCAACTCCTACAAACAG | |
| | AGKAVGVAIGAVG | AGAGTCAAGTACGTGGAGGACAAGGTGGTGGATCCCCT | |
| | GAVASVVEGVATF | GCCTCCCTACCTGAAGGGGCTGGACGACCTGATGAGTG | |
| | LKNPFGAFTIILVAI | GCCTGGGAGCCGCCGGCAAAGCTGTGGGAGTGGCCATC | |
| | AVVIITYLIYTRQR | GGTGCCGTCGGAGGGGCTGTGGCCAGCGTCGTCGAGGG | |
| | RLCTQPLQNLFPYL | AGTTGCCACATTCCTGAAGAACCCCTTCGGGGCCTTCAC | |
| | VSADGTTVTSGST | CATTATCCTAGTCGCCATTGCCGTGGTCATCATTACCTA | |
| | KDTSLQAPPSYEES | TCTGATCTACACGCGGCAGAGACGGCTGTGCACCCAGC | |
| | VYNSGRKGPGPPS | CTTTGCAGAACCTGTTCCCCTATTTAGTGTCCGCTGACG | |
| | SDASTAAPPYTNE | GGACCACTGTGACAAGCGGAAGCACCAAGGACACATCC | |
| | QAYQMLLALARL | CTGCAGGCCCCACCCAGCTACGAGGAGTCTGTTTACAAT | |
| | DAEQRAQQNGTDS | TCTGGCCGGAAGGGCCCCGGCCCTCCCTCTTCTGACGCC | |
| | LDGRTGTQDKGQK | TCCACCGCAGCCCCTCCTTACACAAACGAGCAGGCTTAC | |
| | PNLLDRLRHRKNG | CAGATGCTGTTGGCTTTGGCCCGTCTGGACGCCGAACAG | |
| | YRHLKDSDEEENV | AGGGCCCAGCAGAATGGCACCGACTCCTTGGACGGCCG | |
| | (SEQ ID NO: 69) | GACAGGGACCCAGGATAAGGGTCAGAAGCCTAACCTAC | |
| | | TGGATCGGCTCCGCCATCGCAAGAATGGCTACAGACAT | |
| | | CTCAAGGACAGCGACGAAGAAGAGAATGTG (SEQ ID NO: 95) | |
| SE_CMV_gB_ FL_064 | MESRIWCLVVCVN | ATGGAATCAAGAATCTGGTGTCTCGTGGTGTGCGTGAA | C2/ |
| | LCIVCLGAAVSSSS | CCTGTGTATCGTCTGTCTTGGCGCCGCCGTCTCTTCCTCA | CAP1/ |
| | TRGTSATHSHHSS | AGCACCCGGGGTACCAGTGCCACCCACTCACATCACTC | T100 |
| | HTTSAAHSRSGSVS | CTCCCACACTACCAGCGCCGCCCACAGCAGATCCGGCT | |
| | QRVTSSQTVSHGV | CCGTGTCCCAGCGGGTGACCAGCAGCCAGACCGTGTCA | |
| | NETIYNTTLKYGD | CACGGCGTTAATGAAACCATTTACAACACCACACTGAA | |
| | VVGVNTTKYPYRV | GTACGGGGACGTGGTGGGCGTGAACACCACCAAGTATC | |
| | CSMAQGTDLIRFE | CCTACAGGGTGTGCAGCATGGCCCAGGGCACCGACCTG | |
| | RNIVCTSMKPINED | ATTCGGTTCGAGAGAAACATCGTGTGCACATCCATGAA | |
| | LDEGIMVVYKRNI | GCCTATCAATGAGGACCTCGACGAGGGCATCATGGTGG | |
| | VAHTFKVRVYQK | TTTACAAGAGGAACATTGTCGCACACACATTTAAGGTG | |
| | VLTFRRSYAYIHTT | CGAGTGTACCAGAAGGTGTTAACCTTCAGAAGGTCCTA | |
| | YLLGSNTEYVAPP | CGCATACATCCACACCACCTACCTCCTGGGCTCTAACAC | |
| | MWEIHHINSHSQC | AGAATACGTCGCCCCTCCCATGTGGGAGATTCACCACAT | |
| | YSSYSRVIAGTVFV | CAACAGTCACAGCCAGTGCTACAGCTCGTATAGCAGAG | |
| | AYHRDSYENKTM | TTATCGCTGGCACCGTGTTCGTGGCTTATCACCGCGACA | |
| | QLMPDDYSNTHST | GCTACGAGAACAAGACGATGCAACTTATGCCCGACGAT | |
| | RYVTVKDQWHSR | TACTCAAACACGCACTCCACTAGATACGTGACTGTGAA | |
| | GSTWLYRETCNLN | GGACCAGTGGCACAGTAGAGGCAGCACCTGGCTGTACC | |
| | CMVTITTARSKYP | GGGAAACATGCAATCTCAATTGTATGGTCACCATTACCA | |
| | YHFFATSTGDVVDI | CCGCCAGGTCCAAGTACCCTTACCACTTCTTCGCCACCT | |
| | SPFYNGTNRNASY | CCACTGGCGACGTGGTCGACATCAGCCCCTTCTACAATG | |
| | FGENADKFFIFPNY | GCACCAACAGGAACGCCTCTTACTTTGGGGAGAACGCC | |
| | TIVSDFGRPNSALE | GATAAATTCTTTATTTTCCCCAACTACACTATTGTCTCCG | |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | THRLVAFLERADS VISWDIQDEKNVT CQLTFWEASERTIR SEAEDSYHFSSAK MTATFLSKKQEVN MSDSALDCVRDEA INKLQQIFNTSYNQ TYEKYGNVSVFET TGGLVVFWQGIKQ KSLVELERLANRSS LNLTHNRTKRSTD GNNATHLSNMESV HNLVYAQLQFTYD TLRGYINRALAQIA EAWCVDQRRTLEV FKELSKINPSAILSA IYNKPIAARFMGD VLGLASCVTINQTS VKVLRDMNVKESP GRCYSRPVVIFNFA NSSYVQYGQLGED NEILLGNHRTEECQ LPSLKIFIAGNSAY EYVDYLFKRMIDL SSISTVDSMIALDID PLENTDFRVLELYS QKELRSSNVFDLEE IMREFNSYKQRVK YVEDKVVDPLPPY LKGLDDLMSGLGA AGKAVGVAIGAVG GAVASVVEGVATF LKNPFGAFTIILVAI AVVIITYLIYTRQR RLCTQPLQNLFPYL VSADGTTVTSGST KDTSLQAPPSYEES VYNSGRKGPGPPS SDASTAAPPYTNE QAYQMLLALARL DAEQRAQQNGTDS LDGRTGTQDKGQK PNLLDRLRHRKNG YRHLKDSDEEENV (SEQ ID NO: 69) | ACTTTGGCAGACCCAACTCAGCATTGGAAACCCACAGG CTCGTGGCCTTCCTGGAGCGGGCCGATAGTGTGATCAGC TGGGACATCCAGGATGAGAAGAACGTGACATGCCAGCT GACCTTCTGGGAGGCCAGCGAACGAACCATCCGGTCCG AGGCCGAGGACTCTTATCACTTCTCTAGCGCAAAGATG ACCGCCACCTTCCTGTCTAAGAAACAGGAGGTGAACAT GAGCGACAGCGCCCTGGACTGCGTCAGAGACGAGGCAA TCAACAAGCTGCAGCAAATCTTCAACACCAGCTACAAC CAAACCTACGAGAAATACGGCAACGTCAGCGTCTTCGA GACTACCGGAGGGCTCGTTGTTTTCTGGCAGGGCATTAA GCAGAAGTCTCTGGTCGAGCTGGAAAGGCTGGCCAATA GAAGCTCCCTAAACCTCACTCACAACAGAACTAAGAGA AGCACCGATGGCAATAACGCCACTCATCTGAGTAACAT GGAGTCTGTTCACAACCTGGTGTATGCCCAGCTGCAGTT TACTTATGACACACTGAGGGGCTACATCAATCGAGCCCT GGCCCAGATCGCCGAGGCTTGGTGCGTCGACCAGAGAA GAACACTGGAAGTGTTCAAGGAGCTGAGTAAGATTAAT CCCAGCGCCATTCTGTCCGCCATCTACAATAAGCCAATC GCCGCAAGATTCATGGGTGACGTGCTGGGCCTGGCCTC CTGCGTGACAATCAACCAGACAAGCGTGAAAGTCCTCA GAGACATGAACGTCAAGGAGTCTCCTGGCAGGTGTTAC TCCCGGCCCGTGGTGATATTTAATTTCGCCAACAGCAGT TACGTGCAGTACGGACAGCTGGGCGAGGATAACGAGAT ACTGCTCGGAAACCATAGAACAGAGGAGTGCCAACTGC CCTCCCTGAAGATTTTCATCGCCGGGAACAGCGCCTATG AGTATGTTGACTATCTGTTCAAGCGGATGATCGACCTGA GTTCTATCAGCACCGTTGACTCCATGATTGCTCTCGATA TCGATCCTCTGGAGAACACCGATTTCAGAGTGCTGGAA CTCTACTCTCAGAAAGAGCTAAGAAGCTCGAACGTGTT CGACCTGGAAGAAATCATGAGAGAGTTCAACTCCTACA AACAGAGGGTTAAGTACGTAGAGGATAAGGTCGTGGAC CCTCTGCCTCCATACCTTAAGGGATTAGATGATCTGATG AGCGGCCTGGGCGCTGCCGGAAAGGCCGTGGGAGTGGC CATCGGCGCAGTGGGTGGTGCCGTGGCTAGCGTCGTGG AAGGCGTTGCCACATTCTTGAAGAACCCATTCGGGGCCT TCACAATCATCCTGGTGGCTATCGCCGTTGTGATTATCA CATATCTGATCTACACTCGCCAGCGGAGGCTCTGCACCC AGCCTCTGCAGAACCTTTTCCCCTACCTAGTGTCCGCTG ATGGGACTACAGTCACTAGCGGCAGCACTAAGGACACA TCCCTGCAGGCTCCTCCATCTTACGAGGAGAGCGTGTAT AACTCCGGGCGCAAGGGACCTGGCCCTCCCAGCAGCGA CGCCAGCACGGCGGCTCCTCCCTACACCAACGAGCAGG CATACCAGATGTTGCTTGCACTGGCCCGTCTGGACGCTG AGCAGAGGGCCCAGCAGAATGGGACTGATTCCCTGGAC GGCAGAACCGGCACACAGGATAAAGGACAGAAACCGA ATCTGCTCGACAGGCTGAGGCACCGGAAGAATGGATAC AGGCATCTGAAGGACAGTGACGAGGAGGAGAACGTG (SEQ ID NO: 96) | |
| SE_CMV_gB_ FL_065 | MESRIWCLVVCVN LCIVCLGAAVSSSS TRGTSATHSHHSS HTTSAAHSRSGSVS QRVTSSQTVSHGV NETIYNTTLKYGD VVGVNTTKYPYRV CSMAQGTDLIRFE RNIVCTSMKPINED LDEGIMVVYKRNI VAHTFKVRVYQK VLTFRRSYAYIHTT YLLGSNTEYVAPP MWEIHHINSHSQC YSSYSRVIAGTVFV AYHRDSYENKTM QLMPDDYSNTHST RYVTVKDQWHSR GSTWLYRETCNLN CMVTITTARSKYP YHFFATSTGDVVDI SPFYNGTNRNASY | ATGGAGTCAAGAATCTGGTGCTTGGTGGTGTGTGTGAA CTTGTGTATCGTGTGCCTTGGAGCCGCCGTGAGCAGCAG CTCCACCAGAGGCACCAGCGCCACCCACAGCCATCACT CTTCCCACACCACAAGCGCCGCCCACTCGCGGAGCGGG AGTGTTTCCCAACGGGTGACAAGCAGCCAGACTGTGAG CCACGGCGTTAACGAGACAATCTACAACACAACACTGA AGTACGGCGACGTGGTGGGTGTAAATACTACCAAGTAT CCTTACAGGGTGTGCTCTATGGCCCAGGGTACCGACCTG ATCAGGTTTGAGAGAAACATTGTTTGCACAAGCATGAA GCCCATCAATGAGGACTTGGATGAGGGCATCATGGTGG TTTACAAGAGAAATATCGTGGCCCACACCTTCAAAGTG AGGGTGTATCAGAAGGTGCTGACCTTTAGAAGGAGCTA CGCTTATATCCACACAACCTACCTTCTGGGCAGCAACAC CGAGTACGTCGCACCACCCATGTGGGAAATTCACCACA TCAACTCTCACTCCCAGTGCTATTCCAGCTACAGCAGAG TGATAGCCGGCACAGTCTTCGTGGCCTACCACAGGGAT AGTTACGAGAATAAGACGATGCAACTGATGCCTGACGA TTACTCCAACACACACAGCACCCGGTACGTCACCGTGA AGGACCAGTGGCACTCCAGAGGTAGTACTTGGCTGTAC CGGGAGACTTGTAACCTGAACTGCATGGTGACAATTAC CACTGCTCGAAGCAAGTACCCTTACCACTTCTTTGCCAC CTCTACCGGCGATGTCGTAGACATATCTCCTTTCTATAA | C2/ CAP1/ T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | FGENADKFFIFPNY TIVSDFGRPNSALE THRLVAFLERADS VISWDIQDEKNVT CQLTFWEASERTIR SEAEDSYHFSSAK MTATFLSKKQEVN MSDSALDCVRDEA INKLQQIFNTSYNQ TYEKYGNVSVFET TGGLVVFWQGIKQ KSLVELERLANRSS LNLTHNRTKRSTD GNNATHLSNMESV HNLVYAQLQFTYD TLRGYINRALAQIA EAWCVDQRRTLEV FKELSKINPSAILSA IYNKPIAARFMGD VLGLASCVTINQTS VKVLRDMNVKESP GRCYSRPVVIFNFA NSSYVQYGQLGED NEILLGNHRTEECQ LPSLKIFIAGNSAY EYVDYLFKRMIDL SSISTVDSMIALDID PLENTDFRVLELYS QKELRSSNVFDLEE IMREFNSYKQRVK YVEDKVVDPLPPY LKGLDDLMSGLGA AGKAVGVAIGAVG GAVASVVEGVATF LKNPFGAFTIILVAI AVVIITYLIYTRQR RLCTQPLQNLFPYL VSADGTTVTSGST KDTSLQAPPSYEES VYNSGRKGPGPPS SDASTAAPPYTNE QAYQMLLALARL DAEQRAQQNGTDS LDGRTGTQDKGQK PNLLDRLRHRKNG YRHLKDSDEEENV (SEQ ID NO: 69) | CGGGACCAACAGAAACGCTTCGTACTTCGGCGAGAACG CTGACAAGTTCTTCATCTTCCCGAACTACACTATAGTTA GCGACTTTGGTAGGCCGAACAGCGCCCTGGAGACACAC CGACTTGTGGCCTTCCTCGAGAGAGCTGACAGCGTGATC TCCTGGGACATCCAGGACGAGAAGAACGTCACCTGCCA GCTGACATTCTGGGAGGCCTCTGAGAGGACCATCAGAT CCGAGGCCGAGGATTCATACCACTTTAGCAGCGCTAAG ATGACCGCTACCTTCCTGAGTAAGAAGCAGGAAGTGAA CATGTCCGACTCAGCCCTCGACTGCGTGAGGGACGAGG CCATCAACAAGCTGCAGCAGATCTTCAACACCTCCTACA ACCAGACATATGAGAAGTATGGTAACGTGAGCGTGTTC GAGACAACCGGCGGACTGGTCGTGTTTTGGCAGGGCAT AAAGCAGAAGTCTCTGGTCGAGCTGGAGAGGCTGGCGA ACAGGAGCAGCCTCAACCTGACCCATAACAGAACCAAA CGCAGCACCGACGGCAACAATGCTACCCACCTGTCAAA CATGGAGAGCGTCCACAACCTGGTGTATGCCCAGCTGC AATTTACATACGACACGCTGCGCGGCTACATCAATAGA GCCCTGGCCCAGATCGCCGAGGCTTGGTGCGTTGACCA GCGGCGTACTCTGGAAGTCTTCAAGGAGCTGAGCAAGA TCAATCCCAGCGCTATCCTGAGCGCGATCTACAATAAAC CTATTGCTGCCAGATTCATGGGAGACGTGTTGGGGCTGG CCAGCTGCGTGACAATCAATCAGACCAGCGTGAAAGTG CTGAGAGACATGAATGTGAAGGAGTCTCCTGGTAGGTG CTACTCAAGGCCCGTCGTAATTTTCAATTTCGCCAACAG TTCCTACGTGCAGTACGGACAGCTGGGCGAAGACAATG AGATCCTCCTGGGCAACCATCGGACGGAGGAGTGTCAA CTCCCATCACTGAAGATCTTTATCGCAGGCAATTCCGCC TATGAGTATGTGGACTATCTGTTCAAGAGGATGATCGAC CTGTCCAGCATCAGCACAGTGGATTCAATGATTGCCCTT GACATCGACCCTCTTGAGAATACCGACTTTAGAGTGCTG GAGCTTTATAGCCAGAAAGAGCTCAGGAGCTCCAATGT GTTCGACCTGGAAGAGATCATGCGGGAGTTTAACAGCT ACAAGCAGAGGGTTAAATATGTGGAGGACAAGGTTGTG GATCCACTGCCGCCCTACCTGAAAGGGCTGGACGACCT CATGTCCGGCCTAGGAGCCGCAGGGAAAGCCGTGGGCG TGGCCATCGGCGCAGTTGGAGGCGCCGTCGCCTCTGTG GTTGAAGGCGTTGCGACCTTTCTGAAGAACCCATTCGGC GCCTTCACCATTATCCTGGTGGCCATTGCCGTGGTCATC ATCACCTATCTGATCTACACCAGGCAACGACGCCTGTGC ACCCAGCCCCTGCAGAACCTGTTCCCTTACCTGGTCAGC GCCGATGGGACCACAGTGACCTCTGGTTCTACTAAAGA CACCAGCCTTCAGGCCCCTCCATCCTACGAGGAGTCTGT GTACAATAGCGGCAGAAAGGGCCCCGGCCCGCCCAGCA GCGATGCCAGCACCGCCGCTCCTCCATACACGAACGAG CAGGCCTATCAGATGCTGCTGGCCCTTGCCCGCCTGGAC GCCGAGCAGCGTGCTCAGCAGAATGGCACCGATTCTCT GGACGGCCGAACTGGAACGCAAGACAAGGGACAGAAG CCAAACCTGCTGGACAGACTGAGACACAGGAAGAATGG CTACAGGCATCTGAAGGATTCAGACGAGGAGGAGAACG TG (SEQ ID NO: 97) | |
| SE_CMV_gB_ FL_066 | MESRIWCLVVCVN LCIVCLGAAVSSSS TRGTSATHSHHSS HTTSAAHSRSGSVS QRVTSSQTVSHGV NETIYNTTLKYGD VVGVNTTKYPYRV CSMAQGTDLIRFE RNIVCTSMKPINED LDEGIMVVYKRNI VAHTFKVRVYQK VLTFRRSYAYIHTT YLLGSNTEYVAPP MWEIHHINSHSQC YSSYSRVIAGTVFV AYHRDSYENKTM QLMPDDYSNTHST RYVTVKDQWHSR GSTWLYRETCNLN CMVTITTARSKYP | ATGGAGAGCCGGATCTGGTGCCTTGTGGTGTGCGTGAA CCTTTGCATCGTGTGCCTCGGCGCCGCCGTGAGCTCATC GAGCACCCGGGGCACCAGCGCCACCCACAGCCACCACA GCAGCCACACCACCAGCGCGGCCCACAGTCGGAGCGGC AGCGTGAGCCAGCGGGTGACCTCCTCCCAGACCGTCTC CCACGGCGTGAACGAAACCATCTACAACACCACCCTGA AGTACGGCGACGTGGTTGGGGTAAATACCACTAAGTAC CCCTACCGGGTGTGCAGCATGGCCCAGGGCACCGACCT GATCCGGTTCGAGCGGAACATCGTCTGTACCAGCATGA AGCCCATCAACGAGGACCTGGACGAGGGCATCATGGTT GTCTACAAGCGGAATATCGTAGCCCACACCTTCAAGGT GCGGGTGTACCAGAAGGTGCTGACCTTCCGGCGGAGCT ACGCCTACATTCACACGACTTACCTGCTGGGCAGCAAC ACCGAGTACGTGGCGCCGCCCATGTGGGAGATCCACCA CATCAACTCTCACTCTCAGTGCTACAGCAGCTACAGCCG GGTGATCGCCGGCACCGTGTTCGTGGCCTACCACCGGG ACAGCTACGAGAACAAGACCATGCAGCTGATGCCCGAC GACTATTCTAACACACACTCCACTAGGTACGTGACCGTG AAGGACCAGTGGCACTCCAGAGGCAGCACCTGGCTGTA CCGGGAGACGTGCAACCTGAACTGCATGGTGACCATCA | C2/ CAP1/ T100 |

TABLE 13-continued

| Additional hCMV Vaccine Constructs | | | |
|---|---|---|---|
| Antigen Name | Protein Sequence | Nucleotide Sequence (Open Reading Frames) | Tested Chemistry mRNA Chemistry/ Cap/ Tail |
| | YHFFATSTGDVVDI SPFYNGTNRNASY FGENADKFFIFPNY TIVSDFGRPNSALE THRLVAFLERADS VISWDIQDEKNVT CQLTFWEASERTIR SEAEDSYHFSSAK MTATFLSKKQEVN MSDSALDCVRDEA INKLQQIFNTSYNQ TYEKYGNVSVFET TGGLVVFWQGIKQ KSLVELERLANRSS LNLTHNRTKRSTD GNNATHLSNMESV HNLVYAQLQFTYD TLRGYINRALAQIA EAWCVDQRRTLEV FKELSKINPSAILSA IYNKPIAARFMGD VLGLASCVTINQTS VKVLRDMNVKESP GRCYSRPVVIFNFA NSSYVQYGQLGED NEILLGNHRTEECQ LPSLKIFIAGNSAY EYVDYLFKRMIDL SSISTVDSMIALDID PLENTDFRVLELYS QKELRSSNVFDLEE IMREFNSYKQRVK YVEDKVVDPLPPY LKGLDDLMSGLGA AGKAVGVAIGAVG GAVASVVEGVATF LKNPFGAFTIILVAI AVVIITYLIYTRQR RLCTQPLQNLFPYL VSADGTTVTSGST KDTSLQAPPSYEES VYNSGRKGPGPPS SDASTAAPPYTNE QAYQMLLALARL DAEQRAQQNGTDS LDGRTGTQDKGQK PNLLDRLRHRKNG YRHLKDSDEENV (SEQ ID NO: 69) | CCACCGCCCGGTCAAAGTACCCTTACCACTTCTTCGCCA CCAGCACTGGGGATGTGGTTGACATCAGCCCCTTCTACA ACGGCACCAACCGGAACGCCAGCTACTTCGGCGAGAAC GCCGACAAGTTCTTCATCTTCCCCAACTACACCATCGTG AGCGACTTCGGCCGGCCCAACAGCGCCCTGGAAACACA CCGGCTGGTGGCCTTCCTGGAGCGGGCCGACAGCGTGA TCAGCTGGGACATCCAGGACGAGAAGAACGTGACCTGC CAACTCACATTTTGGGAGGCCAGCGAGCGGACCATCCG GAGCGAGGCCGAGGACTCCTATCACTTCAGCAGCGCCA AGATGACCGCCACCTTCCTGAGCAAGAAGCAGGAGGTG AACATGAGCGATTCGGCATTGGACTGCGTGCGGGACGA GGCCATCAACAAGCTGCAGCAGATCTTCAACACCAGCT ACAACCAGACCTATGAGAAATACGGCAACGTGAGCGTG TTCGAAACCACCGGCGGACTGGTTGTTTTCTGGCAGGGT ATCAAGCAGAAGAGTTTGGTGGAGCTCGAGCGCCTGGC AAACAGGAGCAGCCTGAACCTGACCCACAACCGGACCA AGCGGAGCACCGACGGCAACAATGCAACGCACCTATCC AACATGGAGTCCGTGCACAACCTGGTGTACGCCCAGCT GCAGTTCACCTACGACACCCTGCGGGGCTACATCAACC GGGCCCTGGCCCAGATCGCCGAGGCATGGTGCGTGGAC CAGCGGCGGACCCTGGAGGTGTTCAAGGAGCTTTCCAA GATCAACCCCTCTGCCATCCTGTCTGCTATCTACAATAA GCCAATCGCGGCACGCTTCATGGGAGACGTACTGGGCC TGGCCAGCTGCGTGACTATTAATCAGACTAGCGTCAAA GTGCTACGGGACATGAACGTAAAGGAGAGCCCCGGCCG GTGCTATTCTCGGCCCGTGGTCATTTTCAACTTCGCCAA CAGTTCCTACGTGCAGTACGGACAGTTAGGCGAGGACA ACGAGATTCTGCTGGGTAACCACCGGACCGAGGAGTGC CAACTTCCCAGTCTAAAGATATTTATCGCCGGGAATTCC GCTTATGAGTATGTCGACTACCTGTTCAAGCGGATGATC GACCTGTCCAGTATCAGCACCGTGGACAGCATGATTGC ACTGGATATCGACCCTCTCGAGAACACCGACTTCCGGGT GCTGGAGCTGTACAGCCAGAAAGAGCTGAGATCAAGTA ATGTCTTTGACCTGGAGGAGATCATGCGGGAGTTCAAT AGCTACAAGCAGAGGGTGAAATATGTCGAAGACAAGGT AGTAGACCCGCTGCCTCCCTACCTGAAGGGGCTTGACG ACCTCATGTCAGGGTTAGGGGCAGCTGGCAAGGCCGTT GGCGTCGCCATCGGCGCGGTGGGCGGTGCCGTTGCCTC CGTGGTCGAAGGCGTCGCTACCTTCCTCAAGAACCCCTT CGGCGCCTTCACCATCATCCTGGTGGCTATTGCAGTTGT CATCATTACCTACCTCATCTACACCCGGCAGCGGAGGCT GTGCACCCAGCCCCTGCAGAACCTGTTTCCATACCTGGT GAGCGCAGACGGAACTACCGTGACGAGCGGATCCACTA AGGACACCAGCCTGCAGGCGCCTCCTTCATACGAAGAG AGTGTGTACAACAGCGGCCGGAAGGGCCCCGGACCTCC GAGTAGCGACGCAAGTACCGCCGCCCCACCCTATACCA ACGAGCAAGCTTACCAGATGCTGCTGGCACTTGCTCGG CTGGACGCCGAACAACGCGCCCAGCAGAACGGAACTGA TTCTCTGGACGGCCGGACCGGCACCCAGGACAAGGGCC AGAAGCCCAACCTGTTGGACCGGCTGCGGCACCGGAAG AACGGCTATCGTCACCTGAAAGACAGCGACGAGGAGGA GAACGTG (SEQ ID NO: 98) | |
| SE_CMV_gB_ FL_067 | MESRIWCLVVCVN LCIVCLGAAVSSSS TRGTSATHSHHSS HTTSAAHSRSGSVS QRVTSSQTVSHGV NETIYNTTLKYGD VVGVNTTKYPYRV CSMAQGTDLIRFE RNIVCTSMKPINED LDEGIMVVYKRNI VAHTFKVRVYQK VLTFRRSYAYIHTT YLLGSNTEYVAPP MWEIHHINSHSQC YSSYSRVIAGTVFV AYHRDSYENKTM QLMPDDYSNTHST RYVTVKDQWHSR | ATGGAGAGCCGGATCTGGTGCCTAGTGGTGTGCGTGAA CCTCTGCATCGTGTGCCTAGGCGCCGCCGTGAGCAGTTC TAGTACCCGGGGCACCAGCGCCACCCACAGCCACCACA GCAGCCACACTACGTCAGCAGCGCATAGTCGGAGCGGC AGCGTGAGCCAGCGGGTGACGTCTTCCCAGACAGTGTC CCACGGCGTGAACGAAACCATCTACAACACCACCCTGA AGTACGGCGACGTGGTGGGTGTCAATACAACTAAGTAC CCCTACCGGGTGTGCAGCATGGCCCAGGGCACCGACCT GATCCGGTTCGAGCGGAATATTGTGTGTACCAGCATGA AGCCCATCAACGAGGACCTGGACGAGGGCATCATGGTG GTATACAAGAGAAACATTGTCGCCCACACCTTCAAGGT GCGGGTGTATCAGAAGGTGCTGACCTTCCGGCGGAGCT ACGCCTACATTCATACGACTTACCTGCTGGGCAGCAACA CCGAGTACGTGGCCCCGCCCATGTGGGAGATCCACCAC ATCAACAGCCACTCCCAGTGCTACAGCAGCTACAGCCG GGTGATCGCCGGCACCGTGTTCGTGGCCTACCACCGGG ACAGCTACGAGAACAAGACCATGCAGCTGATGCCCGAC GACTATAGCAATACTCACAGCACACGGTACGTGACCGT | C2/ CAP1/ T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | GSTWLYRETCNLN CMVTITTARSKYP YHFFATSTGDVVDI SPFYNGTNRNASY FGENADKFFIFPNY TIVSDFGRPNSALE THRLVAFLERADS VISWDIQDEKNVT CQLTFWEASERTIR SEAEDSYHFSSAK MTATFLSKKQEVN MSDSALDCVRDEA INKLQQIFNTSYNQ TYEKYGNVSVFET TGGLVVFWQGIKQ KSLVELERLANRSS LNLTHNRTKRSTD GNNATHLSNMESV HNLVYAQLQFTYD TLRGYINRALAQIA EAWCVDQRRTLEV FKELSKINPSAILSA IYNKPIAARFMGD VLGLASCVTINQTS VKVLRDMNVKESP GRCYSRPVVIFNFA NSSYVQYGQLGED NEILLGNHRTEECQ LPSLKIFIAGNSAY EYVDYLFKRMIDL SSISTVDSMIALDID PLENTDFRVLELYS QKELRSSNVFDLEE IMREFNSYKQRVK YVEDKVVDPLPPY LKGLDDLMSGLGA AGKAVGVAIGAVG GAVASVVEGVATF LKNPFGAFTIILVAI AVVIITYLIYTRQR RLCTQPLQNLFPYL VSADGTTVTSGST KDTSLQAPPSYEES VYNSGRKGPGPPS SDASTAAPPYTNE QAYQMLLALARL DAEQRAQQNGTDS LDGRTGTQDKGQK PNLLDRLRHRKNG YRHLKDSDEEENV (SEQ ID NO: 69) | GAAGGACCAGTGGCACAGCCGCGGCAGCACCTGGCTGT ACCGGGAAACGTGCAACCTGAACTGCATGGTGACCATC ACCACCGCCCGGTCGAAGTATCCCTATCACTTCTTCGCC ACCAGCACGGGCGATGTGGTTGACATCAGCCCCTTCTAC AACGGCACCAACCGGAACGCCAGCTACTTCGGCGAGAA CGCCGACAAGTTCTTCATCTTCCCCAACTACACCATCGT GAGCGACTTCGGCCGGCCCAACAGCGCCCTGGAAACCC ACCGGCTGGTGGCCTTCCTGGAGCGGGCCGACAGCGTG ATCAGCTGGGACATCCAGGACGAGAAGAACGTGACCTG CCAGCTTACATTCTGGGAGGCCAGCGAGCGGACCATCC GGAGCGAGGCCGAGGACAGTTACCACTTCTCGAGCGCC AAGATGACCGCCACCTTCCTGAGCAAGAAGCAGGAGGT GAACATGAGCGACAGTGCTCTGGACTGCGTGCGGGACG AGGCCATCAACAAGCTGCAGCAGATCTTCAACACCAGC TACAACCAGACCTATGAGAAATACGGGAACGTGAGCGT GTTCGAGACAACCGGCGGCTTAGTAGTGTTCTGGCAGG GGATCAAGCAGAAGAGTTTGGTGGAGCTCGAGCGGCTG GCGAACAGAAGCAGCCTGAACCTGACCCACAACCGGAC CAAGCGGAGCACCGACGGCAACAACGCAACGCACTTAT CAAACATGGAAAGTGTGCACAACCTGGTGTACGCCCAG CTGCAGTTCACCTACGACACCCTGCGGGGCTACATCAAC CGGGCCCTGGCCCAGATCGCCGAGGCGTGGTGCGTGGA CCAGCGGCGGACCCTGGAGGTGTTCAAGGAGTTGTCGA AGATCAACCCCTTCTGCCATCCTGTCAGCAATTTACAATA AACCTATTGCCGCAAGGTTCATGGGAGATGTCCTGGGC CTGGCCAGCTGCGTGACCATAAACCAGACAAGCGTCAA AGTCCTCCGGGACATGAATGTGAAAGAGAGCCCCGGCC GGTGTTACAGTCGACCCGTGGTGATCTTTAACTTCGCCA ATTCTTCTTATGTGCAGTACGGACAGCTCGGCGAGGACA ACGAGATCCTGCTCGGTAACCACCGGACCGAGGAGTGT CAGCTTCCCTCACTGAAGATTTTCATTGCGGGGAACAGT GCATACGAGTATGTTGACTACCTGTTCAAGCGGATGATC GATCTGTCTAGTATCAGCACCGTGGACAGCATGATCGCT CTGGATATCGACCCATTGGAGAACACCGACTTCCGGGT GCTGGAGCTGTACAGCCAGAAGGAGCTTCGCAGCAGTA ATGTGTTTGACCTGGAGGAGATCATGCGGGAGTTCAATT CTTACAAGCAGCGCGTGAAATACGTTGAGGACAAGGTG GTCGATCCGCTGCCTCCCTACCTGAAGGGCCTGGATGAT CTCATGAGCGGGTTAGGGGCTGCCGGCAAGGCCGTCGG CGTTGCCATCGGCGCAGTGGGCGGAGCCGTCGCCAGCG TGGTGGAGGGTGTTGCAACGTTCCTGAAGAACCCCTTCG GCGCCTTCACCATCATCTTGGTTGCAATCGCGGTTGTTA TCATTACCTACCTTATCTACACCCGGCAACGGCGGCTGT GCACCCAGCCCCTGCAGAACCTGTTTCCATACTTGGTGA GCGCGGATGGGACCACCGTGACTTCAGGTTCCACCAAG GACACCAGCCTGCAGGCGCCTCCCTCATACGAGGAGTC CGTATACAACAGCGGCCGGAAGGGGCCAGGTCCTCCTA GCTCGGACGCAAGTACTGCCGCACCGCCTTATACCAAC GAGCAGGCATATCAGATGCTGCTTGCCCTGGCTCGGCTG GACGCCGAACAGCGCGCCCAGCAGAACGGAACAGATTC CCTGGACGGCCGGACCGGCACCCAGGATAAGGGCCAGA AGCCCAACTTGCTGGACCGGCTGCGGCACCGGAAGAAC GGCTATAGGCATCTGAAGGACAGCGACGAGGAGGAGA ACGTG (SEQ ID NO: 99) | |
| SE_CMV_gB_ FL_068 | MESRIWCLVVCVN LCIVCLGAAVSSSS TRGTSATHSHHSS HTTSAAHSRSGSVS QRVTSSQTVSHGV NETIYNTTLKYGD VVGVNTTKYPYRV CSMAQGTDLIRFE RNIVCTSMKPINED LDEGIMVVYKRNI VAHTFKVRVYQK VLTFRRSYAYIHTT YLLGSNTEYVAPP MWEIHHINSHSQC YSSYSRVIAGTVFV AYHRDSYENKTM | ATGGAGAGCCGGATCTGGTGCCTAGTGGTGTGCGTGAA CCTATGCATCGTGTGCTTAGGCGCCGCCGTGAGCTCATC GTCCACCCGGGGCACCAGCGCCACCCACAGCCACCACA GCAGCCACACGACAAGCGCCGCCCACTCCCGGAGCGGC AGCGTGAGCCAGCGGGTGACTTCTTCCCAGACAGTGAG CCACGGCGTGAACGAGACTATCTACAACACCACCCTGA AGTACGGCGACGTGGTGGGCGTCAACACTACCAAGTAC CCCTACCGGGTGTGCAGCATGGCCCAGGGCACCGACCT GATCCGGTTCGAGCGGAACATTGTGTGCACCAGCATGA AGCCCATCAACGAGGACCTGGACGAGGGCATCATGGTT GTGTACAAGCGTAATATCGTCGCCCACACCTTCAAGGTG CGGGTGTACCAGAAGGTGCTGACCTTCCGGCGGAGCTA CGCCTACATCCATACTACGTACCTGCTGGGCAGCAACAC CGAGTACGTGGCTCCTCCCATGTGGGAGATCCACCACAT CAACTCCCATAGCCAGTGCTACAGCAGCTACAGCCGGG TGATCGCCGGCACCGTGTTCGTGGCCTACCACCGGGAC | C2/ CAP1/ T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | QLMPDDYSNTHST RYVTVKDQWHSR GSTWLYRETCNLN CMVTITTARSKYP YHFFATSTGDVVDI SPFYNGTNRNASY FGENADKFFIFPNY TIVSDFGRPNSALE THRLVAFLERADS VISWDIQDEKNVT CQLTFWEASERTIR SEAEDSYHFSSAK MTATFLSKKQEVN MSDSALDCVRDEA INKLQQIFNTSYNQ TYEKYGNVSVFET TGGLVVFWQGIKQ KSLVELERLANRSS LNLTHNRTKRSTD GNNATHLSNMESV HNLVYAQLQFTYD TLRGYINRALAQIA EAWCVDQRRTLEV FKELSKINPSAILSA IYNKPIAARFMGD VLGLASCVTINQTS VKVLRDMNVKESP GRCYSRPVVIFNFA NSSYVQYGQLGED NEILLGNHRTEECQ LPSLKIFIAGNSAY EYVDYLFKRMIDL SSISTVDSMIALDID PLENTDFRVLELYS QKELRSSNVFDLEE IMREFNSYKQRVK YVEDKVVDPLPPY LKGLDDLMSGLGA AGKAVGVAIGAVG GAVASVVEGVATF LKNPFGAFTIILVAI AVVIITYLIYTRQR RLCTQPLQNLFPYL VSADGTTVTSGST KDTSLQAPPSYEES VYNSGRKGPGPPS SDASTAAPPYTNE QAYQMLLALARL DAEQRAQQNGTDS LDGRTGTQDKGQK PNLLDRLRHRKNG YRHLKDSDEEENV (SEQ ID NO: 69) | AGCTACGAGAACAAGACCATGCAGCTGATGCCCGACGA CTATTCGAACACCCACTCAACCAGATACGTGACCGTGA AGGACCAGTGGCATTCACGGGGCAGCACCTGGCTGTAC CGGGAAACATGCAACCTGAACTGCATGGTGACCATCAC CACCGCCCGGAGTAAATACCCTTATCACTTCTTCGCCAC CAGCACGGGCGACGTCGTAGACATCAGCCCCTTCTACA ACGGCACCAACCGGAACGCCAGCTACTTCGGCGAGAAC GCCGACAAGTTCTTCATCTTCCCCAACTACACCATCGTG AGCGACTTCGGCCGGCCCAACAGCGCCCTGGAGACACA CCGGCTGGTGGCCTTCCTGGAGCGGGCCGACAGCGTGA TCAGCTGGGACATCCAGGACGAGAAGAACGTGACCTGC CAGCTGACGTTTTGGGAGGCCAGCGAGCGGACCATCCG GAGCGAGGCCGAAGATTCCTATCACTTTAGCAGCGCCA AGATGACCGCCACCTTCCTGAGCAAGAAGCAGGAGGTG AACATGTCTGATTCCGCGCTGGACTGCGTGCGGGACGA GGCCATCAACAAGCTGCAGCAGATCTTCAACACCAGCT ACAACCAGACCTATGAGAAGTATGGGAACGTGAGCGTG TTCGAGACAACCGGCGGGCTGGTCGTCTTCTGGCAAGG CATTAAGCAGAAGTCCCTCGTGGAGCTGGAACGGCTGG CCAACCGTAGCAGCCTGAACCTGACCCACAACCGGACC AAGCGGAGCACCGACGGCAACAATGCTACTCATCTATC AAACATGGAAAGCGTGCACAACCTGGTGTACGCCCAGC TGCAGTTCACCTACGACACCCTGCGGGGCTACATCAACC GGGCCCTGGCCCAGATCGCCGAGGCCTGGTGCGTGGAC CAGCGGCGGACCCTGGAGGTGTTCAAGGAGCTAAGTAA GATCAACCCCTCCGCAATCCTGAGCGCCATCTATAACAA GCCTATCGCCGCCCGGTTCATGGGCGATGTGCTGGGCCT GGCCAGCTGCGTCACCATCAATCAAACTAGCGTGAAGG TCCTACGGGACATGAACGTGAAAGAGAGCCCCGGCCGG TGCTACTCCCGGCCCGTGGTCATCTTCAATTTCGCCAAC TCTTCCTATGTGCAGTACGGGCAGCTGGGCGAGGACAA CGAGATTCTGCTGGGTAACCACCGGACCGAGGAGTGCC AGCTTCCCTCCCTCAAGATTTTCATAGCAGGCAATTCTG CCTATGAATACGTTGACTACCTGTTCAAGCGGATGATCG ATCTCTCTAGTATCAGCACCGTGGACAGCATGATTGCGT TGGACATCGACCCGTTAGAGAACACCGACTTCCGGGTG CTGGAGCTGTACAGCCAGAAAGAACTGCGTTCAAGCAA CGTTTTCGACCTGGAGGAGATCATGCGGGAGTTCAACTC TTACAAGCAGCGGGTCAAGTACGTCGAGGATAAGGTCG TGGACCCGCTGCCGCCCTACCTGAAGGGACTGGACGAT CTGATGTCCGGATTGGGAGCTGCAGGAAAGGCCGTGGG AGTAGCCATCGGCGCTGTTGGAGGGGCAGTGGCCAGCG TGGTCGAAGGCGTCGCGACGTTCCTGAAGAACCCCTTC GGCGCCTTCACAATAATCTTGGTTGCCATTGCTGTCGTC ATTATTACATATCTTATCTACACCCGGCAGAGAAGACTG TGCACCCAGCCCCTGCAGAACCTGTTCCCTTATTTGGTG AGCGCCGACGGGACAACCGTCACCTCCGGCTCAACGAA GGACACCAGCCTGCAGGCTCCGCCTTCATATGAAGAGT CAGTATATAACAGCGGCCGGAAGGGGCCAGGTCCTCCA TCTAGCGACGCATCAACTGCCGCACCTCCGTACACCAAC GAGCAGGCATACCAGATGCTGTTGGCCCTCGCACGGCT GGACGCCGAGCAACGCGCCCAGCAGAACGGGACGGAC TCTTTGGATGGCCGGACCGGCACCCAAGACAAGGGCCA GAAGCCCAATTTGCTGGACCGGCTGCGGCACCGGAAGA ACGGCTATAGACATCTGAAGGACAGCGACGAGGAGGA GAACGTG (SEQ ID NO: 100) | |
| SE_CMV_gB_ FL_069 | MESRIWCLVVCVN LCIVCLGAAVSSSS TRGTSATHSHHSS HTTSAAHSRSGSVS QRVTSSQTVSHGV NETIYNTTLKYGD VVGVNTTKYPYRV CSMAQGTDLIRFE RNIVCTSMKPINED LDEGIMVVYKRNI VAHTFKVRVYQK VLTFRRSYAYIHTT YLLGSNTEYVAPP MWEIHHINSHSQC | ATGGAGAGCCGGATCTGGTGCCTAGTGGTGTGCGTGAA CCTATGCATCGTGTGCCTTGGCGCCGCCGTGAGCTCGTC CAGTACCCGGGGCACCTCCGCCACCCACTCCCACCACTC CTCCCACACTACAAGCGCCGCCCACTCGCGCTCCGGCTC CGTCTCCCAGCGCGTCACCAGTTCCCAGACCGTGAGTCA CGGCGTCAACGAAACCATCTACAACACCACCCTCAAGT ACGGCGACGTCGTGGGCGTGAATACAACCAAGTACCCC TACCGCGTCTGCTCCATGGCCCAGGGCACCGACCTCATC CGCTTCGAGCGCAACATCGTCTGCACCTCCATGAAGCCC ATCAACGAGGACCTCGACGAGGGCATCATGGTCGTGTA TAAGCGAAATATTGTGGCCCACACCTTCAAGGTCCGCGT CTACCAGAAGGTCCTCACCTTCCGCCGCTCCTACGCCTA CATTCACACAACCTACCTCCTCGGCTCCAACACCGAGTA CGTCGCCCCTCCCATGTGGGAGATCCACCACATCAACA | C2/ CAP1/ T100 |

TABLE 13-continued

| Antigen Name | Protein Sequence | Nucleotide Sequence (Open Reading Frames) | Tested Chemistry mRNA Chemistry/ Cap/ Tail |
|---|---|---|---|
| | YSSYSRVIAGTVFV AYHRDSYENKTM QLMPDDYSNTHST RYVTVKDQWHSR GSTWLYRETCNLN CMVTITTARSKYP YHFFATSTGDVVDI SPFYNGTNRNASY FGENADKFFIFPNY TIVSDFGRPNSALE THRLVAFLERADS VISWDIQDEKNVT CQLTFWEASERTIR SEAEDSYHFSSAK MTATFLSKKQEVN MSDSALDCVRDEA INKLQQIFNTSYNQ TYEKYGNVSVFET TGGLVVFWQGIKQ KSLVELERLANRSS LNLTHNRTKRSTD GNNATHLSNMESV HNLVYAQLQFTYD TLRGYINRALAQIA EAWCVDQRRTLEV FKELSKINPSAILSA IYNKPIAARFMGD VLGLASCVTINQTS VKVLRDMNVKESP GRCYSRPVVIFNFA NSSYVQYGQLGED NEILLGNHRTEECQ LPSLKIFIAGNSAY EYVDYLFKRMIDL SSISTVDSMIALDID PLENTDFRVLELYS QKELRSSNVFDLEE IMREFNSYKQRVK YVEDKVVDPLPPY LKGLDDLMSGLGA AGKAVGVAIGAVG GAVASVVEGVATF LKNPFGAFTIILVAI AVVIITYLIYTRQR RLCTQPLQNLFPYL VSADGTTVTSGST KDTSLQAPPSYEES VYNSGRKGPGPPS SDASTAAPPYTNE QAYQMLLALARL DAEQRAQQNGTDS LDGRTGTQDKGQK PNLLDRLRHRKNG YRHLKDSDEEENV (SEQ ID NO: 69) | GTCACAGCCAGTGCTACTCCTCCTACTCCCGCGTCATCG CCGGCACCGTCTTCGTCGCCTACCACCGCGACTCCTACG AGAACAAGACCATGCAGCTCATGCCCGACGACTATAGC AATACACATAGTACCCGCTACGTCACCGTCAAGGACCA GTGGCACAGCAGGGGCTCCACCTGGCTCTACCGCGAGA CTTGCAACCTCAACTGCATGGTCACCATCACCACCGCCC GCTCAAAGTACCCGTATCACTTCTTCGCCACCTCCACGG GAGACGTGGTGGACATCTCCCCTTTCTACAACGGCACCA ACCGCAACGCTAGCTATTTCGGCGAGAACGCCGACAAG TTCTTCATCTTCCCCAACTACACCATCGTCTCCGACTTCG GCCGCCCCAACTCCGCCCTCGAAACCCACAGGCTTGTG GCCTTCCTCGAGCGCGCCGACTCCGTCATCTCCTGGGAC ATCCAGGACGAGAAGAACGTCACCTGCCAGCTCACATT CTGGGAGGCCTCCGAGCGCACCATCCGCTCCGAGGCCG AGGATTCGTACCACTTTAGCTCAGCAAAGATGACCGCC ACCTTCCTCTCCAAGAAGCAGGAGGTCAACATGAGCGA CTCTGCTTTGGACTGCGTCCGCGACGAGGCCATCAACAA GCTCCAGCAGATCTTCAACACCTCCTACAACCAGACTTA TGAGAAGTATGGCAACGTCTCGGTGTTCGAGACTACGG GCGGTCTGGTGGTCTTCTGGCAGGGGATTAAGCAGAAG TCCCTCGTCGAGTTGGAGAGACTCGCCAACCGCTCCTCC CTCAACCTCACCCACAACCGCACCAAGCGCTCCACCGA CGGCAACAACGCCACGCACCTCTCAAACATGGAGTCCG TCCACAACCTCGTCTACGCCCAGCTCCAGTTCACCTACG ACACCCTCCGCGGCTACATCAACCGCGCCCTCGCCCAG ATCGCCGAGGCCTGGTGCGTCGACCAGCGCCGCACCCT CGAGGTCTTCAAGGAGCTCAGTAAGATCAACCCCAAGTG CGATCCTGTCGGCCATTTACAATAAACCGATTGCAGCCC GCTTCATGGGTGACGTACTCGGCCTCGCCTCCTGCGTGA CGATTAATCAGACCAGCGTCAAGGTGCTTCGCGACATG AATGTGAAGGAGAGCCCAGGCCGCTGTTACAGTCGGCC CGTCGTCATTTTCAATTTCGCCAATAGCAGCTATGTCCA GTACGGCCAGCTCGGCGAGGACAACGAGATACTCCTTG GCAACCACCGCACCGAGGAGTGCCAGCTGCCGTCTCTG AAGATATTCATAGCCGGCAACAGCGCTTATGAATACGT GGACTACCTCTTCAAGCGCATGATCGACCTCTCCTCCAT CTCCACCGTCGACTCCATGATCGCACTTGATATCGACCC ACTGGAGAACACCGACTTCCGCGTTCTGGAACTCTACTC CCAGAAGGAGCTACGGTCCTCCAATGTTTTCGACCTCGA GGAGATCATGCGCGAGTTCAATTCATACAAGCAACGGG TGAAGTATGTGGAGGACAAGGTCGTCGATCCTCTGCCTC CCTACCTCAAGGGTCTTGATGATCTCATGTCCGGCCTCG GCGCTGCCGGGAAGGCAGTGGGAGTCGCCATCGGCGCC GTTGGAGGGGCCGTCGCCTCTGTGGTGGAGGGCGTGGC TACCTTCCTGAAGAACCCCTTCGGCGCCTTCACCATTAT TCTGGTGGCCATCGCAGTGGTTATCATCACGTACCTTAT CTACACCCGGCAGAGAAGGCTCTGCACCCAGCCCCTCC AGAACCTCTTTCCTTATCTCGTCAGCGCAGACGGTACAA CAGTTACTAGTGGAAGTACCAAGGACACCTCCCTCCAG GCCCCGCCAAGCTACGAGGAAAGTGTTTACAACTCCGG CCGCAAGGGCCCCGGCCCACCTTCTTCCGACGCTTCCAC CGCTGCTCCACCATACACCAACGAGCAGGCCTACCAGA TGCTCCTGGCACTGGCTCGGCTGGATGCCGAGCAGAGG GCCCAGCAGAACGGTACCGATTCCCTCGACGGCCGCAC CGGCACCCAGGATAAGGGCCAGAAGCCCAATTTACTAG ACAGACTGCGCCACCGGAAGAACGGCTACCGCCATCTG AAGGACTCCGACGAGGAGGAGAACGTC (SEQ ID NO: 101) | |
| SE_CMV_gB_ FL_070 | MESRIWCLVVCVN LCIVCLGAAVSSSS TRGTSATHSHHSS HTTSAAHSRSGSVS QRVTSSQTVSHGV NETIYNTTLKYGD VVGVNTTKYPYRV CSMAQGTDLIRFE RNIVCTSMKPINED LDEGIMVVYKRNI VAHTFKVRVYQK VLTFRRSYAYIHTT | ATGGAGAGCCGGATCTGGTGCCTAGTGGTGTGCGTGAA CCTCTGCATCGTGTGCTTGGGCGCCGCCGTGAGTAGTTC CAGTACCCGGGGCACCTCCGCCACCCACTCCCACCACTC CTCCCACACTACGAGTGCCGCCCACTCACGCTCCGGCTC CGTCTCCCAGCGCGTCACTAGTTCTCAGACAGTGTCTCA CGGCGTCAACGAGACAATCTACAACACCACCCTCAAGT ACGGCGACGTCGTGGGTGTGAATACTACTAAGTACCCC TACCGCGTCTGCTCCATGGCCCAGGGCACCGACCTCATC CGCTTCGAGCGCAACATCGTCTGCACCTCCATGAAGCCC ATCAACGAGGACCTCGACGAGGGCATCATGGTCGTCTA CAAGAGAAATATAGTGGCCCACACCTTCAAGGTCCGCG TCTACCAGAAGGTCCTCACCTTCCGCCGCTCCTACGCCT | C2/ CAP1/ T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | YLLGSNTEYVAPP | ACATTCACACTACCTACCTCCTCGGCTCCAACACCGAGT | |
| | MWEIHHINSHSQC | ACGTCGCCCCACCCATGTGGGAGATCCACCACATCAAC | |
| | YSSYSRVIAGTVFV | TCTCACAGTCAGTGCTACTCCTCCTACTCCCGCGTCATC | |
| | AYHRDSYENKTM | GCCGGCACCGTCTTCGTCGCCTACCACCGCGACTCCTAC | |
| | QLMPDDYSNTHST | GAGAACAAGACCATGCAGCTCATGCCCGACGACTACTC | |
| | RYVTVKDQWHSR | AAACACTCACAGCACCCGCTACGTCACCGTCAAGGACC | |
| | GSTWLYRETCNLN | AGTGGCACAGCCGCGGCTCCACCTGGCTCTACCGCGAG | |
| | CMVTITTARSKYP | ACTTGCAACCTCAACTGCATGGTCACCATCACCACCGCC | |
| | YHFFATSTGDVVDI | CGCTCGAAGTATCCGTACCACTTCTTCGCCACCTCCACG | |
| | SPFYNGTNRNASY | GGCGATGTGGTCGACATCAGTCCATTCTACAACGGCAC | |
| | FGENADKFFIFPNY | CAACCGCAACGCTTCATACTTCGGCGAGAACGCCGACA | |
| | TIVSDFGRPNSALE | AGTTCTTCATCTTCCCCAACTACACCATCGTCTCCGACTT | |
| | THRLVAFLERADS | CGGCCGCCCCAACTCCGCCCTCGAGACACACCGCCTGG | |
| | VISWDIQDEKNVT | TCGCCTTCCTCGAGCGCGCCGACTCCGTCATCTCCTGGG | |
| | CQLTFWEASERTIR | ACATCCAGGACGAGAAGAACGTCACCTGCCAGTTGACC | |
| | SEAEDSYHFSSAK | TTCTGGGAGGCCTCCGAGCGCACCATCCGCTCCGAGGC | |
| | MTATFLSKKQEVN | CGAGGACAGTTACCATTTCAGTAGTGCCAAGATGACCG | |
| | MSDSALDCVRDEA | CCACCTTCCTCTCCAAGAAGCAGGAGGTCAACATGTCG | |
| | INKLQQIFNTSYNQ | GACTCTGCTCTTGACTGCGTCCGCGACGAGGCCATCAAC | |
| | TYEKYGNVSVFET | AAGCTCCAGCAGATCTTCAACACCTCCTACAACCAGACT | |
| | TGGLVVFWQGIKQ | TATGAGAAGTATGGTAACGTCTCTGTGTTTGAGACTACA | |
| | KSLVELERLANRSS | GGCGGTCTTGTCGTCTTCTGGCAGGGTATCAAGCAGAA | |
| | LNLTHNRTKRSTD | GTCCCTCGTCGAGCTGGAACGCCTCGCCAACCGCTCCTC | |
| | GNNATHLSNMESV | CCTCAACCTCACCCACAACCGCACCAAGCGCTCCACCG | |
| | HNLVYAQLQFTYD | ACGGCAACAACGCAACACATCTTAGCAACATGGAGTCC | |
| | TLRGYINRALAQIA | GTCCACAACCTCGTCTACGCCCAGCTCCAGTTCACCTAC | |
| | EAWCVDQRRTLEV | GACACCCTCCGCGGCTACATCAACCGCGCCCTCGCCCA | |
| | FKELSKINPSAILSA | GATCGCCGAGGCCTGGTGCGTCGACCAGCGCCGCACCC | |
| | IYNKPIAARFMGD | TCGAGGTCTTCAAGGAGCTGAGTAAGATCAACCCAAGT | |
| | VLGLASCVTINQTS | GCAATCCTAAGCGCTATTTACAACAAACCTATCGCAGCC | |
| | VKVLRDMNVKESP | AGGTTCATGGGAGACGTCCTCGGCCTCGCCTCCTGCGTC | |
| | GRCYSRPVVIFNFA | ACCATTAATCAGACGTCTGTTAAGGTTCTCCGCGACATG | |
| | NSSYVQYGQLGED | AACGTGAAAGAGTCTCCGGGCCGCTGCTACAGCAGGCC | |
| | NEILLGNHRTEECQ | CGTCGTCATCTTCAATTTCGCCAATTCTTCATATGTCCAG | |
| | LPSLKIFIAGNSAY | TACGGCCAGCTCGGCGAGGACAACGAGATTCTCTTAGG | |
| | EYVDYLFKRMIDL | GAACCACCGCACCGAGGAGTGTCAGCTACCCAGCCTGA | |
| | SSISTVDSMIALDID | AGATCTTTATTGCCGGCAATAGCGCTTATGAGTATGTTG | |
| | PLENTDFRVLELYS | ACTACCTCTTCAAGCGCATGATCGACCTCTCCTCCATCT | |
| | QKELRSSNVFDLEE | CCACCGTCGACTCCATGATCGCTCTGGATATCGACCCTC | |
| | IMREFNSYKQRVK | TGGAGAACACCGACTTCCGCGTGCTTGAGCTCTACTCCC | |
| | YVEDKVVDPLPPY | AGAAAGAGCTTAGGTCAAGCAACGTTTTCGACCTCGAG | |
| | LKGLDDLMSGLGA | GAGATCATGCGCGAGTTCAACTCATATAAGCAACGCGT | |
| | AGKAVGVAIGAVG | TAAATATGTAGAGGATAAGGTGGTTGATCCACTTCCTCC | |
| | GAVASVVEGVATF | CTACCTCAAGGGTCTGGATGACCTCATGTCCGGCCTCGG | |
| | LKNPFGAFTIILVAI | GGCAGCAGGCAAGGCCGTCGGCGTTGCCATCGGCGCCG | |
| | AVVIITYLIYTRQR | TGGGAGGTGCTGTGGCCAGTGTTGTCGAGGGCGTAGCC | |
| | RLCTQPLQNLFPYL | ACCTTCTTAAAGAACCCCTTCGGCGCCTTTACAATAATC | |
| | VSADGTTVTSGST | CTGGTGGCCATCGCTGTGGTTATCATTACCTATCTTATCT | |
| | KDTSLQAPPSYEES | ACACCAGGCAGCGGAGGCTCTGCACCCAGCCCCTCCAG | |
| | VYNSGRKGPGPPS | AACCTCTTCCCTTACCTCGTGAGCGCGGACGGGACGACC | |
| | SDASTAAPPYTNE | GTCACATCTGGCAGTACAAAGGACACCTCCCTCCAGGC | |
| | QAYQMLLALARL | CCCGCCTAGTTATGAAGAGAGCGTTTACAACTCCGGCC | |
| | DAEQRAQQNGTDS | GCAAGGGCCCCGGTCCTCCCTCCTCCGACGCCAGCACC | |
| | LDGRTGTQDKGQK | GCAGCGCCTCCATACACCAACGAGCAGGCCTACCAGAT | |
| | PNLLDRLRHRKNG | GCTCTTGGCCCTGGCCCGACTGGATGCCGAGCAGCGCG | |
| | YRHLKDSDEEENV | CCCAGCAGAACGGAACCGACTCCCTCGACGGCCGCACC | |
| | (SEQ ID NO: 69) | GGCACCCAGGACAAAGGCCAGAAGCCCAATCTGCTCGA | |
| | | CCGCCTGCGACACCGCAAGAACGGCTATCGGCACCTTA | |
| | | AAGACTCCGACGAGGAGGAGAACGTC (SEQ ID NO: 102) | |
| SE_CMV_gH_ | MRPGLPSYLIILAV | ATGCGGCCAGGACTTCCTAGCTACCTAATCATCCTTGCC | C2/ |
| 031 | CLFSHLLSSRYGAE | GTGTGTCTTTTCTCACACCTCCTCTCTAGTAGGTACGGC | CAP1/ |
| | AVSEPLDKAFHLL | GCAGAGGCCGTGTCCGAGCCACTCGACAAGGCCTTCCA | T100 |
| | LNTYGRPIRFLREN | CCTTTTGTTAAACACCTACGGTCGGCCAATCAGATTCCT | |
| | TTQCTYNSSLRNST | CCGCGAGAACACCACCCAGTGCACGTACAATTCGTCTCT | |
| | VVRENAISFNFFQS | CCGCAACAGCACAGTCGTGAGGGAGAACGCTATATCAT | |
| | YNQYYVFHMPRCL | TCAACTTCTTCCAGTCTTACAACCAGTATTACGTGTTCC | |
| | FAGPLAEQFLNQV | ACATGCCAAGATGCCTGTTCGCTGGCCCACTGGCCGAG | |
| | DLTETLERYQQRL | CAGTTCCTTAACCAGGTGGATCTGACAGAGACTCTGGA | |
| | NTYALVSKDLASY | GAGATACCAACAGAGGCTGAACACCTACGCACTGGTGA | |
| | RSFSQQLKAQDSL | GCAAGGATCTGGCCTCCTACAGGAGCTTCAGCCAACAG | |

TABLE 13-continued

| Additional hCMV Vaccine Constructs | | | |
|---|---|---|---|
| Antigen Name | Protein Sequence | Nucleotide Sequence (Open Reading Frames) | Tested Chemistry mRNA Chemistry/ Cap/ Tail |
| | GEQPTTVPPPIDLSI PHVWMPPQTTPHG WTESHTTSGLHRP HFNQTCILFDGHDL LFSTVTPCLHQGFY LIDELRYVKITLTE DFFVVTVSIDDDTP MLLIFGHLPRVLFK APYQRDNFILRQTE KHELLVLVKKDQL NRHSYLKDPDFLD AALDFNYLDLSAL LRNSFHRYAVDVL KSGRCQMLDRRTV EMAFAYALALFAA ARQEEAGAQVSVP RALDRQAALLQIQ EFMITCLSQTPPRT TLLLYPTAVDLAK RALWTPNQITDITS LVRLVYILSKQNQ QHLIPQWALRQIA DFALKLHKTHLAS FLSAFARQELYLM GSLVHSMLVHTTE RREIFIVETGLCSLA ELSHFTQLLAHPH HEYLSDLYTPCSSS GRRDHSLERLTRLF PDATVPATVPAAL SILSTMQPSTLETFP DLFCLPLGESFSAL TVSEHVSYIVTNQ YLIKGISYPVSTTV VGQSLIITQTDSQT KCELTRNMHTTHS ITVALNISLENCAF CQSALLEYDDTQG VINIMYMHDSDDV LFALDPYNEVVVS SPRTHYLMLLKNG TVLEVTDVVVDAT DSRLLMMSVYALS AIIGIYLLYRMLKT C (SEQ ID NO: 59) | CTGAAGGCCCAGGACAGTCTGGGCGAGCAACCAACCAC CGTACCTCCACCTATTGACTTATCAATACCTCACGTGTG GATGCCTCCTCAGACCACTCCTCACGGCTGGACCGAATC CCACACCACCTCCGGCCTGCACAGGCCTCATTTCAACCA GACCTGTATTCTCTTCGACGGACACGACCTGCTTTTCAG CACCGTCACGCCATGCTTGCACCAGGGCTTCTACCTGAT CGACGAGCTCAGGTATGTGAAGATCACTCTGACCGAGG ACTTCTTCGTGGTTACTGTGAGCATCGATGACGATACCC CAATGTTACTGATCTTCGGCCACCTGCCTAGGGTGCTGT TCAAGGCACCATACCAGAGAGACAATTTCATCCTGAGA CAAACCGAGAAGCACGAGCTGCTGGTGCTGGTCAAGAA GGACCAGCTGAATAGGCACTCATACCTGAAGGACCCAG ATTTCCTGGACGCTGCCCTTGATTTCAATTACCTGGACC TGTCCGCCCTGCTGAGAAACAGCTTCCACAGATACGCC GTGGATGTGCTGAAGTCAGGCAGATGTCAGATGTTGGA CCGCCGAACCGTTGAGATGGCCTTCGCCTACGCGCTGGC CCTGTTCGCCGCCGCTCGGCAGGAGGAAGCTGGCGCAC AGGTGAGCGTGCCGAGGGCTCTGGACCGACAGGCTGCT CTGCTACAGATTCAGGAATTCATGATCACCTGCCTGTCA CAGACTCCGCCTCGGACTACCCTGCTGCTGTATCCTACA GCAGTGGACCTGGCAAAGAGAGCTCTTTGGACCCCTAA CCAGATCACCGATATCACCAGCCTCGTCCGGCTGGTCTA CATTCTGTCTAAGCAGAATCAGCAGCACCTGATCCCTCA GTGGGCTCTCAGACAGATCGCCGATTTCGCCCTGAAGCT GCACAAGACCCACCTGGCTTCTTTCCTGAGCGCTTTCGC CAGACAGGAACTGTACCTGATGGGATCGCTTGTGCACA GCATGCTGGTGCACACAACTGAGAGGAGAGAGATTTTC ATTGTGGAGACTGGCCTGTGCAGCCTGGCCGAGCTGTCC CATTTCACCCAGCTCCTCGCTCATCCGCACCACGAGTAC CTCTCCGACCTCTATACCCCTTGCTCCTCTTCCGGCCGGC GCGATCACAGCCTGGAAAGACTCACTAGACTGTTCCCA GACGCTACCGTGCCGGCTACTGTCCCGGCAGCACTGAG CATCCTGAGCACTATGCAGCCTTCTACGCTGGAAACCTT CCCGGACCTGTTCTGCCTGCCACTCGGAGAAAGCTTCTC TGCCCTGACGGTGAGTGAGCACGTGTCGTACATCGTGA CAAACCAGTACCTGATCAAGGGTATCAGCTACCCAGTG TCCACAACTGTGGTGGGCCAGAGCCTGATCATCACCCA GACCGATAGCCAAACAAAGTGCGAACTGACAAGAAAC ATGCATACCACTCATTCCATCACTGTGGCCTTAAACATC TCCCTGGAGAACTGCGCCTTCTGTCAGTCCGCCCTGCTG GAGTACGATGATACCCAGGGCGTTATTAATATCATGTAC ATGCATGATAGCGACGATGTGCTTTTCGCCCTGGACCCA TACAACGAGGTGGTGGTGTCCAGCCCTAGAACCCACTA CCTCATGCTGCTGAAGAACGGCACAGTGCTGGAGGTGA CCGACGTGGTGGTGGACGCTACGGACAGCAGGCTGCTG ATGATGAGCGTGTACGCCCTGAGCGCCATTATCGGAAT ATACCTGCTGTACAGGATGTTGAAGACCTGT (SEQ ID NO: 103) | |
| SE_CMV_gH_ 032 | MRPGLPSYLIILAV CLFSHLLSSRYGAE AVSEPLDKAFHLL LNTYGRPIRFLREN TTQCTYNSSLRNST VVRENAISFNFFQS YNQYYVFHMPRCL FAGPLAEQFLNQV DLTETLERYQQRL NTYALVSKDLASY RSFSQQLKAQDSL GEQPTTVPPPIDLSI PHVWMPPQTTPHG WTESHTTSGLHRP HFNQTCILFDGHDL LFSTVTPCLHQGFY LIDELRYVKITLTE DFFVVTVSIDDDTP MLLIFGHLPRVLFK APYQRDNFILRQTE KHELLVLVKKDQL NRHSYLKDPDFLD | ATGCGGCCGGGACTCCCTAGCTACCTCATCATCCTCGCC GTGTGCCTTTTCTCTCACCTTTTGAGCTCCAGATACGGC GCCGAAGCGGTGTCCGAGCCTCTCGACAAGGCCTTCCA CCTCCTTCTCAACACATACGGCAGACCGATCCGGTTCTT GAGGGAGAACACTACCCAATGCACATATAACAGTAGCC TGCGGAATAGCACTGTGGTGCGGGAGAACGCCATCAGC TTCAATTTCTTCCAGAGCTACAATCAGTATTACGTGTTC CACATGCCTAGATGTCTGTTCGCGGGCCCTCTGGCAGAG CAGTTCCTGAACCAGGTTGATCTCACAGAGACACTGGA GAGATACCAGCAAAGACTGAACACCTACGCTCTCGTCT CCAAGGACCTGGCCAGCTATAGGAGCTTCAGCCAGCAG CTGAAGGCCCAGGATTCCCTGGGAGAGCAGCCAACCAC CGTCCCGCCGCCAATCGACCTCTCTATCCCACACGTGTG GATGCCTCCACAAACCACACCACACGGATGGACTGAGT CCCATACCACCAGCGGACTGCACAGGCCTCACTTCAATC AGACCTGCATTTTGTTCGACGGCCACGACCTCCTGTTCA GCACTGTGACCCCGTGTCTGCATCAGGGCTTCTACCTGA TTGACGAGCTGAGGTACGTCAAGATTACGCTCACCGAA GACTTCTTCGTGGTCACAGTGAGTATCGATGACGACACC CCTATGCTGCTCATCTTCGGCCATCTGCCTAGGGTGCTG TTCAAGGCCCCTTACCAGAGAGATAATTTCATCTTGCGG CAGACTGAGAAGCACGAACTGCTGGTACTCGTGAAGAA | C2/ CAP1/ T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | AALDFNYLDLSAL LRNSFHRYAVDVL KSGRCQMLDRRTV EMAFAYALALFAA ARQEEAGAQVSVP RALDRQAALLQIQ EFMITCLSQTPPRT TLLLYPTAVDLAK RALWTPNQITDITS LVRLVYILSKQNQ QHLIPQWALRQIA DFALKLHKTHLAS FLSAFARQELYLM GSLVHSMLVHTTE RREIFIVETGLCSLA ELSHFTQLLAHPH HEYLSDLYTPCSSS GRRDHSLERLTRLF PDATVPATVPAAL SILSTMQPSTLETFP DLFCLPLGESFSAL TVSEHVSYIVTNQ YLIKGISYPVSTTV VGQSLIITQTDSQT KCELTRNMHTTHS ITVALNISLENCAF CQSALLEYDDTQG VINIMYMHDSDDV LFALDPYNEVVVS SPRTHYLMLLKNG TVLEVTDVVVDAT DSRLLMMSVYALS AIIGIYLLYRMLKT C (SEQ ID NO: 59) | GGACCAGCTGAACCGCCACTCTTACTTAAAGGATCCAG ACTTCCTGGATGCAGCACTTGACTTCAACTATCTCGACC TCTCTGCCCTGCTGAGGAACAGCTTCCACCGGTATGCCG TGGACGTGCTGAAGAGTGGACGGTGTCAGATGCTGGAC CGCAGAACAGTGGAAATGGCGTTCGCGTATGCTCTGGC CCTATTCGCGGCCGCAAGACAGGAGGAGGCCGGCGCTC AGGTGTCCGTCCCTAGAGCTCTGGACAGGCAGGCCGCC CTGCTGCAAATTCAGGAGTTCATGATAACTTGCCTGAGC CAAACCCCTCCGAGAACAACACTGCTGCTGTATCCAAC AGCCGTAGATCTGGCCAAGCGGGCCCTTTGGACTCCTA ACCAGATCACCGATATTACCTCCCTGGTGAGACTGGTGT ACATTCTGTCCAAGCAGAACCAGCAGCACCTGATCCCG CAGTGGGCCCTGAGACAGATCGCTGATTTCGCCTTGAA GCTGCACAAGACTCATCTGGCCTCCTTCCTGAGTGCTTT CGCCCGCCAGGAACTGTATCTGATGGGCTCTCTTGTCCA TTCCATGCTGGTTCATACCACGGAGAGAAGGGAGATCT TCATCGTGGAAACCGGCCTTTGCTCCCTCGCTGAGCTGA GCCATTTCACTCAGCTGCTCGCCCACCCGCACCACGAGT ACCTGTCAGACCTTTATACTCCGTGCTCCTCCAGCGGCA GGAGGGACCACAGCCTGGAACGGCTCACAAGACTGTTC CCGGATGCTACCGTGCCTGCTACTGTGCCAGCCGCCCTG AGCATCCTTTCCACCATGCAGCCTTCCACACTGGAGACT TTCCCTGACCTGTTCTGCCTGCCACTTGGCGAAAGTTTC AGCGCCCTGACCGTGTCCGAACATGTGAGCTACATCGT GACTAACCAGTACCTGATCAAGGGCATCAGCTACCCGG TTAGCACCACTGTCGTCGGACAGTCACTGATCATCACTC AGACCGACTCCCAGACCAAGTGCGAACTGACCAGAAAT ATGCACACAACCCATAGCATCACCGTGGCCCTGAACAT TAGCCTGGAGAACTGTGCCTTCTGCCAGAGCGCCCTCCT CGAGTACGACGATACCCAGGGTGTGATAAACATTATGT ATATGCACGACAGTGACGACGTTCTGTTCGCACTGGACC CTTACAACGAAGTGGTCGTTTCCTCTCCTCGGACCCATT ACCTGATGCTGCTGAAGAACGGCACCGTGCTAGAGGTT ACTGATGTGGTAGTGGACGCCACAGACAGCAGACTGCT GATGATGAGCGTGTACGCCCTGAGCGCCATTATTGGCAT CTACCTGCTGTACAGGATGCTGAAGACATGT (SEQ ID NO: 104) | |
| SE_CMV_gH_ 033 | MRPGLPSYLIILAV CLFSHLLSSRYGAE AVSEPLDKAFHLL LNTYGRPIRFLREN TTQCTYNSSLRNST VVRENAISFNFFQS YNQYYVFHMPRCL FAGPLAEQFLNQV DLTETLERYQQRL NTYALVSKDLASY RSFSQQLKAQDSL GEQPTTVPPPIDLSI PHVWMPPQTTPHG WTESHTTSGLHRP HFNQTCILFDGHDL LFSTVTPCLHQGFY LIDELRYVKITLTE DFFVVTVSIDDDTP MLLIFGHLPRVLFK APYQRDNFILRQTE KHELLVLVKKDQL NRHSYLKDPDFLD AALDFNYLDLSAL LRNSFHRYAVDVL KSGRCQMLDRRTV EMAFAYALALFAA ARQEEAGAQVSVP RALDRQAALLQIQ EFMITCLSQTPPRT TLLLYPTAVDLAK RALWTPNQITDITS LVRLVYILSKQNQ QHLIPQWALRQIA | ATGCGGCCGGGACTCCCTTCCTACCTCATCATCCTTGCC GTGTGTCTTTTCTCACACCTCCTCAGCAGCCGCTACGGC GCCGAGGCCGTGTCAGAGCCACTTGACAAGGCCTTCCA TCTTTTGTTGAACACCTACGGCAGACCTATTCGGTTCCT GAGAGAGAACACAACCCAGTGCACCTATAACAGCTCTC TGCGCAACTCCACAGTGGTTAGAGAGAATGCCATCAGC TTCAACTTCTTCCAGAGTTACAACCAGTATTACGTGTTC CATATGCCTAGGTGCCTGTTCGCTGGCCCGTTAGCCGAA CAGTTCCTCAACCAGGTGGATCTGACCGAAACACTGGA AAGGTACCAGCAGCGGCTGAATACATACGCCTTGGTGT CAAAGGATCTTGCTTCCTACAGAAGCTTCAGCCAGCAG CTGAAGGCCCAGGACAGCCTTGGAGAGCAGCCAACCAC CGTGCCTCCTCCTATTGACCTGAGCATCCCTCATGTGTG GATGCCTCCTCAGACCACCCCTCACGGCTGGACTGAGA GCCATACCACGTCCGGCCTGCACAGGCCTCACTTCAATC AGACCTGCATCCTGTTCGACGGCCACGATCTGCTTTTCA GCACCGTCACCCCTTGCCTGCACCAGGGATTCTACCTGA TCGACGAGCTCCGGTATGTGAAGATTACACTGACCGAG GACTTCTTCGTGGTGACCGTGTCCATCGACGATGACACC CCAATGCTGCTGATCTTCGGCCACCTGCCGAGAGTCCTG TTCAAGGCCCCATACCAGAGAGACAACTTCATCCTGCG GCAGACCGAGAAGCACGAACTGCTAGTGCTGGTGAAGA AGGATCAGCTGAACCGGCACTCCTACCTGAAGGACCCT GACTTCCTTGACGCCGCACTCGACTTCAACTACCTGGAC CTCAGTGCTCTACTGAGGAACTCTTTCCACCGGTACGCC GTGGACGTGCTGAAGTCTGGAAGATGCCAGATGCTGGA TAGGAGGACAGTGGAGATGGCGTTCGCGTACGCCCTGG CCCTGTTCGCCGCCGCCAGACAGGAGGAGGCCGGCGCA CAGGTCAGCGTCCCAAGGGCCCTGGACCGCCAGGCTGC CCTGCTGCAGATTCAGGAATTCATGATCACCTGTCTCAG CCAGACCCCTCCGAGAACAACCCTGCTGTTGTACCCGAC CGCAGTGGATCTGGCTAAGAGGGCCCTGTGGACCCCAA ACCAGATTACCGACATCACCTCTCTGGTGAGACTGGTGT | C2/ CAP1/ T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | DFALKLHKTHLAS FLSAFARQELYLM GSLVHSMLVHTTE RREIFIVETGLCSLA ELSHFTQLLAHPH HEYLSDLYTPCSSS GRRDHSLERLTRLF PDATVPATVPAAL SILSTMQPSTLETFP DLFCLPLGESFSAL TVSEHVSYIVTNQ YLIKGISYPVSTTV VGQSLIITQTDSQT KCELTRNMHTTHS ITVALNISLENCAF CQSALLEYDDTQG VINIMYMHDSDDV LFALDPYNEVVVS SPRTHYLMLLKNG TVLEVTDVVVDAT DSRLLMMSVYALS AIIGIYLLYRMLKT C (SEQ ID NO: 59) | ACATCCTGTCCAAGCAGAACCAACAGCACCTCATTCCA CAATGGGCCCTGAGGCAAATCGCCGATTTCGCTCTCAA GTTGCATAAGACCCATCTGGCCTCATTCCTCAGCGCCTT CGCAAGACAGGAGTTGTATCTCATGGGCTCCCTCGTGCA TAGCATGCTGGTGCACACAACCGAGCGCAGAGAAATTT TCATCGTTGAAACCGGACTGTGCAGCCTCGCCGAGTTGT CTCATTTCACCCAGCTGCTGGCTCATCCTCACCATGAGT ATCTTTCCGACCTGTACACCCCGTGCAGCAGCAGCGGCC GCAGGGATCACAGCCTCGAGAGACTGACAAGACTGTTC CCAGACGCCACCGTGCCTGCCACAGTGCCAGCCGCGCT GTCCATCCTGAGCACAATGCAGCCTAGCACACTGGAGA CTTTCCCAGATCTGTTCTGTCTTCCACTGGGCGAGAGCT TCAGCGCCCTGACCGTGAGCGAGCACGTGAGCTACATA GTGACCAACCAATATTTGATTAAGGGCATCTCCTACCCT GTGAGCACCACAGTGGTGGGCCAGTCTCTGATCATCAC ACAAACCGACAGTCAGACGAAGTGCGAGCTGACTAGAA ACATGCACACGACCCACAGCATAACCGTGGCACTCAAC ATCTCCCTGGAGAATTGCGCCTTCTGCCAGAGCGCCCTC CTGGAGTACGACGACACTCAAGGAGTGATCAACATCAT GTACATGCACGATAGCGATGACGTGCTGTTCGCCCTGG ACCCATACAATGAAGTGGTGGTGTCCAGCCCACGGACC CACTACCTGATGCTCCTCAAGAACGGCACAGTGCTGGA GGTTACAGACGTGGTGGTCGACGCTACCGATAGCAGAC TTCTTATGATGTCCGTGTACGCCCTGAGCGCCATCATCG GAATCTATCTGCTTTACAGGATGCTGAAGACTTGC (SEQ ID NO: 105) | |
| SE_CMV_gH_ 034 | MRPGLPSYLIILAV CLFSHLLSSRYGAE AVSEPLDKAFHLL LNTYGRPIRFLREN TTQCTYNSSLRNST VVRENAISFNFFQS YNQYYVFHMPRCL FAGPLAEQFLNQV DLTETLERYQQRL NTYALVSKDLASY RSFSQQLKAQDSL GEQPTTVPPPIDLSI PHVWMPPQTTPHG WTESHTTSGLHRP HFNQTCILFDGHDL LFSTVTPCLHQGFY LIDELRYVKITLTE DFFVVTVSIDDDTP MLLIFGHLPRVLFK APYQRDNFILRQTE KHELLVLVKKDQL NRHSYLKDPDFLD AALDFNYLDLSAL LRNSFHRYAVDVL KSGRCQMLDRRTV EMAFAYALALFAA ARQEEAGAQVSVP RALDRQAALLQIQ EFMITCLSQTPPRT TLLLYPTAVDLAK RALWTPNQITDITS LVRLVYILSKQNQ QHLIPQWALRQIA DFALKLHKTHLAS FLSAFARQELYLM GSLVHSMLVHTTE RREIFIVETGLCSLA ELSHFTQLLAHPH HEYLSDLYTPCSSS GRRDHSLERLTRLF PDATVPATVPAAL SILSTMQPSTLETFP DLFCLPLGESFSAL TVSEHVSYIVTNQ | ATGCGGCCAGGCCTCCCTTCGTACCTTATCATCTTGGCC GTGTGTCTTTTCTCTCACCTACTCTCCTCAAGGTACGGC GCCGAGGCCGTGAGTGAGCCGCTAGACAAGGCCTTCCA CCTATTACTTAACACCTACGGCCGGCCTATCCGATTCCT CCGGGAGAATACCACACAGTGTACATACAACTCTAGCC TGCGCAACAGCACTGTGGTCAGGGAGAACGCCATCAGC TTCAATTTCTTCCAGAGTTATAACCAGTACTACGTGTTC CACATGCCAAGATGCCTGTTCGCCGGACCTCTTGCCGAG CAGTTCCTGAACCAGGTGGATCTGACCGAGACACTGGA GAGATACCAGCAAAGGCTCAATACCTACGCTTTAGTGA GCAAGGACCTTGCTTCTTACAGATCTTTCTCACAACAGC TTAAGGCGCAGGACAGCCTCGGCGAGCAGCCTACCACC GTGCCTCCTCCTATTGACTTGAGCATCCCACACGTATGG ATGCCTCCACAGACGACACCACACGGCTGGACCGAATC CCATACAACCAGCGGACTCCACCGGCCTCATTTCAATCA GACCTGCATCCTTTTCGACGGCCATGACCTGCTATTCTC TACCGTCACCCCGTGCCTGCACCAGGGCTTCTACCTTAT CGACGAACTGAGATACGTCAAGATCACGCTGACCGAAG ACTTCTTCGTCGTTACAGTCAGCATCGACGACGATACCC CTATGCTGCTGATATTCGGCCACCTTCCTAGAGTCCTGT TCAAGGCACCGTACCAGAGGGACAACTTCATCCTGAGA CAGACAGAGAAGCACGAGCTCCTGGTGCTGGTGAAGAA GGATCAGCTGAATAGACACAGTTACCTGAAGGATCCAG ACTTCCTGGACGCCGCACTGGACTTCAACTATCTGGATC TGAGCGCCCTGCTTCGCAATAGCTTCCATAGATACGCTG TGGACGTGCTGAAGTCTGGCCGGTGTCAGATGCTGGAT CGTAGGACCGTGGAGATGGCCTTCGCCTACGCACTCGCT CTGTTCGCCGCCGCTAGACAGGAGGAGGCCGGAGCCCA AGTGAGTGTGCCTCGGGCACTGGACAGACAGGCAGCCT TACTGCAGATCCAGGAGTTCATGATTACCTGCCTGTCTC AGACTCCACCACGGACCACCCTTCTGCTGTATCCTACCG CGGTTGATCTGGCTAAGAGGGCCCTGTGGACCCCTAAC CAGATCACTGACATCACCAGCCTCGTGAGGCTGGTGTA CATTCTTAGCAAGCAGAACCAGCAGCACCTAATACCTC AGTGGGCCCTGCGGCAGATCGCCGACTTCGCCCTGAAG CTGCACAAGACCCACCTGGCAAGCTTCCTGTCCGCCTTC GCCCGCCAGGAGCTGTACCTCATGGGAAGTCTGGTACA CTCCATGCTGGTGCACACCACCGAGAGAAGAGAGATCT TCATCGTAGAAACCGGACTCTGCTCACTGGCCGAATTGT CACACTTCACCCAGCTGCTGGCCCATCCTCATCACGAGT ATCTGTCCGACCTGTACACCCCTTGCAGCTCTAGCGGCA GGCGGGACCATTCCTTGGAGAGGCTGACCAGGCTGTTC CCGGATGCCACCGTTCCAGCAACAGTGCCTGCAGCCCT GAGCATTCTGTCAACAATGCAGCCTAGCACCCTCGAAA | C2/ CAP1/ T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | YLIKGISYPVSTTV VGQSLIITQTDSQT KCELTRNMHTTHS ITVALNISLENCAF CQSALLEYDDTQG VINIMYMHDSDDV LFALDPYNEVVVS SPRTHYLMLLKNG TVLEVTDVVVDAT DSRLLMMSVYALS AIIGIYLLYRMLKT C (SEQ ID NO: 59) | CTTTCCCGGATCTGTTCTGCCTGCCTCTTGGTGAGAGCTT CAGCGCCCTGACCGTGTCCGAGCATGTGTCTTATATCGT AACCAATCAGTACCTGATCAAGGGCATCAGCTACCCTG TGTCCACAACTGTCGTGGGCCAAAGCCTCATCATAACCC AGACCGATTCCCAGACAAAGTGTGAACTGACCCGCAAC ATGCACACCACTCACAGCATTACTGTGGCCCTGAACATC TCCCTGGAGAACTGTGCCTTCTGTCAGAGCGCGCTTCTG GAGTATGATGACACCCAGGGTGTGATTAATATCATGTA CATGCACGACAGCGACGATGTGCTGTTCGCGCTGGATC CTTACAATGAGGTGGTCGTGAGCTCCCCTAGAACCCACT ATCTCATGCTGTTAAAGAACGGCACCGTCCTGGAGGTG ACAGACGTGGTGGTTGATGCCACCGACAGCAGGCTGCT GATGATGAGCGTTTATGCCCTGAGCGCCATCATCGGCAT TTACCTCCTGTACAGGATGTTAAAGACTTGT (SEQ ID NO: 106) | |
| SE_CMV_gH_ 035 | MRPGLPSYLIILAV CLFSHLLSSRYGAE AVSEPLDKAFHLL LNTYGRPIRFLREN TTQCTYNSSLRNST VVRENAISFNFFQS YNQYYVFHMPRCL FAGPLAEQFLNQV DLTETLERYQQRL NTYALVSKDLASY RSFSQQLKAQDSL GEQPTTVPPPIDLSI PHVWMPPQTTPHG WTESHTTSGLHRP HFNQTCILFDGHDL LFSTVTPCLHQGFY LIDELRYVKITLTE DFFVVTVSIDDDTP MLLIFGHLPRVLFK APYQRDNFILRQTE KHELLVLVKKDQL NRHSYLKDPDFLD AALDFNYLDLSAL LRNSFHRYAVDVL KSGRCQMLDRRTV EMAFAYALALFAA ARQEEAGAQVSVP RALDRQAALLQIQ EFMITCLSQTPPRT TLLLYPTAVDLAK RALWTPNQITDITS LVRLVYILSKQNQ QHLIPQWALRQIA DFALKLHKTHLAS FLSAFARQELYLM GSLVHSMLVHTTE RREIFIVETGLCSLA ELSHFTQLLAHPH HEYLSDLYTPCSSS GRRDHSLERLTRLF PDATVPATVPAAL SILSTMQPSTLETFP DLFCLPLGESFSAL TVSEHVSYIVTNQ YLIKGISYPVSTTV VGQSLIITQTDSQT KCELTRNMHTTHS ITVALNISLENCAF CQSALLEYDDTQG VINIMYMHDSDDV LFALDPYNEVVVS SPRTHYLMLLKNG TVLEVTDVVVDAT DSRLLMMSVYALS | ATGCGGCCAGGACTCCCTAGCTACCTCATTATCCTCGCC GTGTGCCTTTTCTCTCACCTCTTAAGCTCCCGGTACGGC GCCGAAGCCGTGAGCGAGCCGCTTGACAAGGCTTTCCA CCTCCTCCTTAACACCTACGGCAGACCTATTAGATTCCT GAGAGAGAACACCACCCAGTGTACATATAATTCTAGCC TGCGGAACTCCACCGTAGTGAGGGAGAATGCCATTAGC TTCAACTTCTTCCAGAGCTACAACCAGTACTATGTGTTC CATATGCCGAGATGTCTGTTCGCTGGACCTCTCGCAGAA CAGTTCTTGAACCAGGTGGATCTGACTGAAACTCTCGAG CGGTACCAGCAAAGACTGAATACCTATGCCTTGGTAAG CAAGGATCTGGCTAGCTACAGGAGCTTCTCCCAGCAGC TCAAGGCCCAGGACTCCCTTGGCGAACAGCCTACCACC GTCCCTCCTCCAATTGACCTGAGCATTCCGCACGTGTGG ATGCCTCCTCAGACCACCCCACACGGCTGGACAGAGTC TCATACCACCAGCGGACTGCATAGACCGCATTTCAACC AGACTTGCATCCTGTTCGATGGACATGATCTCCTGTTCT CTACAGTGACTCCATGCCTGCACCAGGGCTTCTACCTGA TCGATGAGCTCAGATACGTCAAGATCACCTTGACCGAA GATTTCTTCGTGGTCACAGTGAGCATTGACGACGACACC CCAATGCTTCTGATATTCGGTCACCTGCCTAGGGTCCTC TTCAAGGCTCCATACCAGAGAGACAATTTCATCCTTAGA CAGACCGAGAAGCACGAGCTGCTCGTGCTGGTGAAGAA GGATCAACTGAACAGACATAGCTACCTAAAGGATCCGG ATTTCCTGGACGCCGCTCTGGACTTCAACTACCTCGACC TCAGCGCCCTGCTGAGGAACAGCTTCCACCGGTATGCA GTCGATGTTCTCAAGTCCGGCAGATGCCAGATGCTGGA CCGTAGAACTGTGGAGATGGCCTTCGCCTATGCTCTGGC CCTGTTCGCCGCCGCACGCCAGGAAGAGGCTGGAGCCC AGGTGAGCGTCCCACGGGCTCTGGACAGACAGGCTGCT CTGCTGCAGATCCAAGAGTTCATGATTACCTGTCTGAGC CAGACCCCTCCTAGAACCACCCTCCTCCTCTATCCGACC GCTGTGGACCTGGCCAAGAGAGCCTTGTGGACCCCTAA TCAGATTACTGACATCACAAGCCTGGTCAGACTGGTGTA TATCCTGAGCAAGCAGAATCAGCAGCACCTCATTCCAC AGTGGGCGCTGCGGCAGATCGCTGATTTCGCCCTGAAG CTGCACAAGACCCACCTGGCCAGCTTCTTGAGCGCATTC GCACGGCAGGAACTCTACCTGATGGGCTCTCTGGTGCA CAGCATGCTCGTCCACACCACAGAACGGCGAGAGATAT TCATCGTTGAGACAGGCCTGTGCTCTCTGGCCGAGTTGT CCCACTTCACCCAACTGCTGGCTCACCCTCATCACGAGT ACCTCAGCGACCTGTACACCCCTTGCTCCTCCAGCGGTA GACGGGATCACAGCCTGGAAAGACTGACCAGACTGTTC CCAGACGCCACGGTCCCTGCAACCGTGCCTGCCGCTCTT TCAATCTTGTCCACCATGCAGCCTAGTACACTGGAAACA TTCCCTGACCTCTTCTGCCTGCCTCTCGGAGAGTCCTTCT CAGCCCTGACCGTGAGCGAACACGTGTCCTACATCGTG ACCAACCAGTACCTGATCAAGGGCATCTCCTACCCTGTG TCGACCACCGTCGTGGGCCAGAGCCTGATCATTACACA GACGGACTCTCAGACCAAGTGCGAGTTGACACGGAACA TGCACACCACACACAGCATCACTGTGGCCCTGAATATTA GCCTCGAGAACTGCGCCTTCTGCCAGAGTGCCCTGCTAG AGTATGATGATACACAGGGCGTGATTAATATCATGTAT ATGCACGACTCTGATGACGTCCTGTTCGCCCTGGACCCA TACAACGAGGTGGTTGTGAGCTCCCCTCGGACCCACTAT | C2/ CAP1/ T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | AIIGIYLLYRMLKT C (SEQ ID NO: 59) | CTGATGCTGCTCAAGAACGGCACTGTTCTCGAGGTGAC AGATGTGGTGGTCGATGCCACAGATTCTCGGCTGCTGAT GATGAGCGTGTACGCTCTTAGCGCCATCATCGGAATCTA CCTCCTGTACAGGATGCTGAAGACTTGT (SEQ ID NO: 107) | |
| SE_CMV_gH_ 036 | MRPGLPSYLIILAV CLFSHLLSSRYGAE AVSEPLDKAFHLL LNTYGRPIRFLREN TTQCTYNSSLRNST VVRENAISFNFFQS YNQYYVFHMPRCL FAGPLAEQFLNQV DLTETLERYQQRL NTYALVSKDLASY RSFSQQLKAQDSL GEQPTTVPPPIDLSI PHVWMPPQTTPHG WTESHTTSGLHRP HFNQTCILFDGHDL LFSTVTPCLHQGFY LIDELRYVKITLTE DFFVVTVSIDDDTP MLLIFGHLPRVLFK APYQRDNFILRQTE KHELLVLVKKDQL NRHSYLKDPDFLD AALDFNYLDLSAL LRNSFHRYAVDVL KSGRCQMLDRRTV EMAFAYALALFAA ARQEEAGAQVSVP RALDRQAALLQIQ EFMITCLSQTPPRT TLLLYPTAVDLAK RALWTPNQITDITS LVRLVYILSKQNQ QHLIPQWALRQIA DFALKLHKTHLAS FLSAFARQELYLM GSLVHSMLVHTTE RREIFIVETGLCSLA ELSHFTQLLAHPH HEYLSDLYTPCSSS GRRDHSLERLTRLF PDATVPATVPAAL SILSTMQPSTLETFP DLFCLPLGESFSAL TVSEHVSYIVTNQ YLIKGISYPVSTTV VGQSLIITQTDSQT KCELTRNMHTTHS ITVALNISLENCAF CQSALLEYDDTQG VINIMYMHDSDDV LFALDPYNEVVVS SPRTHYLMLLKNG TVLEVTDVVVDAT DSRLLMMSVYALS AIIGIYLLYRMLKT C (SEQ ID NO: 59) | ATGCGGCCGGGCCTCCCGTCTTACCTCATCATCTTGGCC GTGTGCCTCTTCTCCCACCTCTTGAGCTCCCGGTACGGC GCAGAGGCCGTGTCAGAGCCTCTCGACAAGGCCTTCCA TTTGCTCCTTAACACATACGGCAGGCCAATCAGGTTCCT GCGAGAGAATACCACACAATGCACCTACAACTCCAGCT TGAGGAATAGCACCGTGGTGCGGGAGAACGCCATCTCC TTCAATTTCTTCCAGTCCTACAATCAGTATTATGTGTTCC ATATGCCTAGGTGTCTCTTCGCAGGCCCACTTGCCGAAC AATTCCTGAACCAAGTGGACCTGACAGAGACACTGGAG AGATACCAGCAACGGCTGAATACCTACGCCTTGGTGAG CAAGGATCTCGCCAGCTACAGATCTTTCTCACAACAACT GAAGGCCCAGGATTCTCTCGGTGAGCAGCCAACGACTG TGCCTCCTCCAATTGACCTGTCTATCCCACATGTGTGGA TGCCACCTCAGACTACCCCTCACGGATGGACAGAGTCTC ATACCACTAGCGGCCTGCACAGGCCTCACTTCAATCAG ACCTGTATCCTCTTCGACGGTCACGATCTGTTGTTCAGC ACCGTGACCCCATGCCTGCATCAGGGCTTCTACCTGATT GACGAGCTGAGATATGTGAAGATAACACTGACCGAGGA TTTCTTCGTGGTCACCGTGAGCATAGACGACGACACACC GATGCTCCTGATCTTCGGCCATCTGCCACGAGTTCTGTT CAAGGCACCTTATCAGAGAGACAACTTCATCTTGAGGC AAACAGAGAAGCACGAGCTTCTCGTGCTGGTTAAGAAG GACCAGCTCAACAGGCATAGCTACCTGAAGGACCCAGA TTTCCTGGACGCCGCTCTGGATTTCAATTATCTGGACCT TTCTGCTCTGCTGAGAAACAGCTTCCATAGATACGCCGT GGACGTCCTTAAGTCTGGCCGCTGCCAGATGCTGGATA GACGGACTGTCGAGATGGCATTCGCCTACGCTCTGGCTC TGTTCGCCGCCGCCAGGCAGGAGGAGGCTGGAGCCCAA GTGTCAGTGCCTAGGGCTCTGGATAGACAAGCCGCCTT GCTCCAGATCCAGGAGTTCATGATTACCTGTCTGAGCCA GACCCCACCAAGAACCACGTTACTGCTGTACCCTACCGC TGTGGACCTGGCTAAGCGAGCCCTCTGGACGCCTAATC AAATCACCGACATCACCAGCTTAGTCAGACTGGTGTAC ATTCTGTCTAAGCAGAACCAGCAGCACTTGATTCCACAG TGGGCCCTGAGACAGATTGCCGACTTCGCCCTGAAGCTC CATAAGACCCATCTGGCGTCCTTCCTGAGCGCCTTCGCC AGACAGGAGCTCTACCTGATGGGCAGCCTGGTTCATTCC ATGCTGGTCCATACAACGGAGAGAAGAGAGATCTTCAT CGTGGAGACAGGACTGTGCTCTTTGGCCGAACTTTCCCA CTTCACTCAGCTGCTGGCGCACCCTCATCACGAGTACTT ATCGGACCTGTACACCCCTTGCAGCAGCAGCGGAAGGA GGGACCATTCTCTCGAAAGGCTGACAAGACTGTTCCCTG ACGCCACCGTCCCAGCCACAGTGCCTGCCGCACTGAGC ATCCTCAGCACAATGCAGCCAAGCACTCTGGAGACTTTC CCGGACTTGTTCTGCCTGCCGCTGGGCGAGTCCTTCAGC GCCCTTACAGTGTCAGAGCATGTGTCCTACATCGTGACC AATCAGTACCTGATCAAGGGAATCAGCTACCCTGTGTCT ACAACCGTGGTTGGCCAGTCCCTCATCATCACCCAGACA GATAGCCAAACTAAGTGCGAACTGACTAGAAACATGCA CACAACCCACTCCATCACAGTGGCCCTGAACATCAGCCT CGAGAATTGCGCCTTCTGCCAGAGCGCACTGTTGGAGT ACGACGATACTCAGGGCGTGATTAACATCATGTACATG CATGATAGCGACGATGTGCTGTTCGCCCTGGACCCTTAT AACGAGGTGGTGGTGAGTAGTCCTAGGACCCATTACCT TATGCTGCTGAAGAACGGAACTGTTCTGGAGGTTACCG ACGTCGTCGTTGACGCTACCGACTCACGCCTGCTCATGA TGTCTGTGTATGCCCTGTCTGCCATCATCGGCATCTACC TGCTGTATAGGATGCTGAAGACTTGC (SEQ ID NO: 108) | C2/ CAP1/ T100 |
| SE_CMV_gH_ 037 | MRPGLPSYLIILAV CLFSHLLSSRYGAE AVSEPLDKAFHLL LNTYGRPIRFLREN TTQCTYNSSLRNST VVRENAISFNFFQS | ATGCGGCCCGGCCTTCCCAGCTACCTCATCATCCTCGCC GTGTGCTTGTTCAGCCACCTTCTAAGCAGCCGGTACGGC GCCGAGGCCGTGAGCGAGCCCCTCGACAAGGCCTTCCA CTTGTTATTGAACACCTACGGCCGGCCCATCCGGTTCCT GCGGGAGAACACCACCCAGTGCACCTACAACAGCAGCC TGCGGAACAGCACCGTGGTTCGGGAGAATGCCATCAGC | C2/ CAP1/ T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | YNQYYVFHMPRCL<br>FAGPLAEQFLNQV<br>DLTETLERYQQRL<br>NTYALVSKDLASY<br>RSFSQQLKAQDSL<br>GEQPTTVPPPIDLSI<br>PHVWMPPQTTPHG<br>WTESHTTSGLHRP<br>HFNQTCILFDGHDL<br>LFSTVTPCLHQGFY<br>LIDELRYVKITLTE<br>DFFVVTVSIDDDTP<br>MLLIFGHLPRVLFK<br>APYQRDNFILRQTE<br>KHELLVLVKKDQL<br>NRHSYLKDPDFLD<br>AALDFNYLDLSAL<br>LRNSFHRYAVDVL<br>KSGRCQMLDRRTV<br>EMAFAYALALFAA<br>ARQEEAGAQVSVP<br>RALDRQAALLQIQ<br>EFMITCLSQTPPRT<br>TLLLYPTAVDLAK<br>RALWTPNQITDITS<br>LVRLVYILSKQNQ<br>QHLIPQWALRQIA<br>DFALKLHKTHLAS<br>FLSAFARQELYLM<br>GSLVHSMLVHTTE<br>RREIFIVETGLCSLA<br>ELSHFTQLLAHPH<br>HEYLSDLYTPCSSS<br>GRRDHSLERLTRLF<br>PDATVPATVPAAL<br>SILSTMQPSTLETFP<br>DLFCLPLGESFSAL<br>TVSEHVSYIVTNQ<br>YLIKGISYPVSTTV<br>VGQSLIITQTDSQT<br>KCELTRNMHTTHS<br>ITVALNISLENCAF<br>CQSALLEYDDTQG<br>VINIMYMHDSDDV<br>LFALDPYNEVVVS<br>SPRTHYLMLLKNG<br>TVLEVTDVVVDAT<br>DSRLLMMSVYALS<br>AIIGIYLLYRMLKT<br>C (SEQ ID NO: 59) | TTCAACTTCTTCCAGAGCTACAACCAGTACTACGTGTTC<br>CACATGCCCCGGTGTCTTTTCGCCGGACCGCTGGCCGAG<br>CAGTTCCTGAACCAGGTGGACCTGACCGAAACTCTGGA<br>GCGGTACCAGCAGCGGCTGAATACCTATGCCCTGGTGA<br>GCAAGGACCTGGCCTCATACCGGAGCTTCAGCCAGCAG<br>CTGAAGGCCCAGGACAGCCTGGGCGAGCAGCCCACCAC<br>CGTGCCTCCACCCATCGACCTGAGCATCCCGCACGTGTG<br>GATGCCTCCACAGACCACACCTCACGGCTGGACCGAGA<br>GCCACACCACCAGCGGCCTGCACCGGCCCCACTTCAAC<br>CAGACCTGCATCCTGTTCGACGGCCACGACCTGCTGTTC<br>AGCACAGTTACCCCTTGCCTTCATCAGGGCTTCTATCTT<br>ATAGACGAGCTGCGGTACGTGAAGATCACACTCACCGA<br>GGACTTCTTCGTGGTGACCGTGAGCATCGACGACGACA<br>CTCCTATGCTCCTCATCTTCGGCCATCTTCCCCGGGTTCT<br>GTTCAAGGCTCCATACCAGCGGGACAACTTCATCCTGCG<br>GCAGACCGAGAAGCACGAGTTGCTGGTGCTGGTGAAGA<br>AGGACCAGCTGAACCGGCATTCGTACCTTAAGGACCCC<br>GACTTCCTGGACGCCGCCCTGGACTTCAACTACCTAGAT<br>CTCAGCGCCCTGTTGAGGAATAGCTTCCACCGGTACGCC<br>GTGGACGTGTTAAAGAGCGGCCGGTGCCAGATGCTGGA<br>TCGGCGGACCGTGGAGATGGCCTTCGCCTACGCGCTGG<br>CCTTGTTCGCTGCCGCCCGGCAGGAGGAGGCCGGCGCC<br>CAGGTGAGCGTACCGCGGGCACTCGATCGGCAGGCCGC<br>TCTGCTGCAGATCCAGGAGTTCATGATCACCTGCCTGAG<br>CCAGACCCCTCCGCGGACCACCTTACTGCTTTACCCCAC<br>TGCAGTTGACCTGGCTAAGCGCGCACTCTGGACCCCTAA<br>CCAGATCACCGACATCACCAGCCTGGTGCGGCTGGTGT<br>ACATCCTGAGCAAGCAGAACCAGCAACACCTGATACCA<br>CAGTGGGCTCTGAGACAGATCGCCGACTTCGCCCTGAA<br>GCTGCACAAGACCCATCTGGCCAGCTTCCTGTCCGCTTT<br>CGCACGACAGGAGCTGTACCTGATGGGATCACTCGTGC<br>ACAGCATGCTCGTGCATACCACCGAGCGGCGGGAGATC<br>TTCATCGTGGAAACAGGCCTGTGTTCACTAGCCGAACTG<br>AGCCACTTCACCCAACTTTTGGCCCATCCACACCACGAG<br>TATTTGTCGGACCTGTACACCCCTTGTTCCTCTTCCGGA<br>AGGCGGGACCACTCCCTGGAACGGCTGACCCGGCTGTT<br>CCCCGACGCAACCGTACCGGCCACGGTTCCAGCTGCCTT<br>AAGCATCTTAAGTACCATGCAGCCCAGCACACTGGAAA<br>CCTTCCCAGATCTGTTCTGCCTGCCGCTGGGTGAGTCTT<br>TCAGCGCTCTCACCGTGTCCGAGCACGTGAGCTACATCG<br>TGACAAATCAATATCTGATTAAGGGCATCAGCTACCCA<br>GTGTCAACTACGGTGGTTGGCCAGAGCTTGATTATAACC<br>CAGACCGACTCGCAGACTAAGTGCGAGCTTACGAGAAA<br>CATGCACACAACCCACAGCATCACCGTGGCCCTGAACA<br>TAAGTCTGGAGAACTGCGCCTTCTGCCAGTCTGCCTTGC<br>TCGAGTATGATGACACCCAGGGCGTGATCAACATCATG<br>TACATGCATGACAGCGACGATGTTCTCTTCGCGTTGGAT<br>CCATACAACGAGGTGGTGGTGTCCAGTCCGAGAACTCA<br>CTATCTGATGCTCCTAAAGAACGGCACCGTGCTGGAGG<br>TGACCGACGTCGTGGTCGATGCCACGGACTCCAGACTG<br>CTTATGATGAGCGTGTACGCCCTAAGCGCCATCATCGGC<br>ATCTATCTCCTGTATCGGATGCTTAAGACCTGC (SEQ ID NO: 109) | |
| SE_CMV_gH_038 | MRPGLPSYLIILAV<br>CLFSHLLSSRYGAE<br>AVSEPLDKAFHLL<br>LNTYGRPIRFLREN<br>TTQCTYNSSLRNST<br>VVRENAISFNFFQS<br>YNQYYVFHMPRCL<br>FAGPLAEQFLNQV<br>DLTETLERYQQRL<br>NTYALVSKDLASY<br>RSFSQQLKAQDSL<br>GEQPTTVPPPIDLSI<br>PHVWMPPQTTPHG<br>WTESHTTSGLHRP<br>HFNQTCILFDGHDL<br>LFSTVTPCLHQGFY<br>LIDELRYVKITLTE<br>DFFVVTVSIDDDTP | ATGCGGCCCGGCCTTCCCAGCTACCTCATCATCCTCGCC<br>GTGTGCTTGTTCAGCCACTTGCTTAGCAGCCGGTACGGC<br>GCCGAGGCCGTGAGCGAGCCCTTGGACAAGGCCTTCCA<br>CTTACTCCTCAACACCTACGGCCGGCCCATCCGGTTCCT<br>GCGGGAGAACACCACCCAGTGCACCTACAACAGCAGCC<br>TGCGGAACAGCACCGTGGTGCGTGAGAACGCCATCAGC<br>TTCAACTTCTTCCAGAGCTACAACCAGTACTACGTGTTC<br>CACATGCCCAGGTGCCTTTTCGCCGGACCACTGGCCGAG<br>CAGTTCCTGAACCAGGTGGACCTGACCGAAACACTGGA<br>GCGGTACCAGCAGAGGCTGAACACATACGCCCTGGTGA<br>GCAAGGACCTGGCCTCCTACCGGAGCTTCAGCCAGCAG<br>CTGAAGGCCCAGGACAGCCTGGGCGAGCAGCCCACCAC<br>CGTGCCGCCACCCATCGACCTGAGCATCCCACACGTGTG<br>GATGCCACCACAGACCACCCCTCACGGCTGGACCGAGA<br>GCCACACCACCAGCGGCCTGCACCGGCCCCACTTCAAC<br>CAGACCTGCATCCTGTTCGACGGCCACGACCTGCTGTTC<br>TCGACCGTCACCCCTTGCTTGCACCAGGGCTTCTATCTG<br>ATAGACGAGCTGCGGTACGTGAAGATCACCTTGACCGA | C2/<br>CAP1/<br>T100 |

TABLE 13-continued

| Additional hCMV Vaccine Constructs | | | |
|---|---|---|---|
| Antigen Name | Protein Sequence | Nucleotide Sequence (Open Reading Frames) | Tested Chemistry mRNA Chemistry/ Cap/ Tail |
| | MLLIFGHLPRVLFK APYQRDNFILRQTE KHELLVLVKKDQL NRHSYLKDPDFLD AALDFNYLDLSAL LRNSFHRYAVDVL KSGRCQMLDRRTV EMAFAYALALFAA ARQEEAGAQVSVP RALDRQAALLQIQ EFMITCLSQTPPRT TLLLYPTAVDLAK RALWTPNQITDITS LVRLVYILSKQNQ QHLIPQWALRQIA DFALKLHKTHLAS FLSAFARQELYLM GSLVHSMLVHTTE RREIFIVETGLCSLA ELSHFTQLLAHPH HEYLSDLYTPCSSS GRRDHSLERLTRLF PDATVPATVPAAL SILSTMQPSTLETFP DLFCLPLGESFSAL TVSEHVSYIVTNQ YLIKGISYPVSTTV VGQSLIITQTDSQT KCELTRNMHTTHS ITVALNISLENCAF CQSALLEYDDTQG VINIMYMHDSDDV LFALDPYNEVVVS SPRTHYLMLLKNG TVLEVTDVVVDAT DSRLLMMSVYALS AIIGIYLLYRMLKT C (SEQ ID NO: 59) | GGACTTCTTCGTGGTGACCGTGAGCATCGACGACGACA CACCTATGCTGCTCATCTTCGGCCATTTACCCCGGGTTC TGTTCAAGGCACCATACCAGCGGGACAACTTCATCCTGC GGCAGACCGAGAAGCATGAGCTTCTGGTGCTGGTGAAG AAGGACCAGCTGAACCGGCACTCATATCTGAAGGACCC CGACTTCCTGGACGCCGCCCTGGACTTCAACTACCTGGA TTTAAGCGCCCTGCTCCGTAACTCTTTCCACCGGTACGC CGTGGACGTGTTAAAGTCAGGCCGGTGCCAGATGTTGG ACCGGCGGACCGTGGAGATGGCCTTCGCTTACGCATTA GCCCTCTTCGCAGCCGCCCGGCAGGAGGAGGCCGGCGC GCAGGTGAGCGTGCCTAGAGCGTTGGATAGACAGGCGG CCTTGCTGCAGATCCAGGAGTTCATGATCACCTGCCTGA GCCAGACTCCTCCACGGACCACATTGCTGCTCTACCCCA CCGCCGTTGACCTGGCAAAGCGGGCGCTCTGGACTCCG AACCAGATCACCGACATCACCAGCCTGGTGCGGCTGGT GTACATCCTGAGCAAGCAGAATCAGCAGCACCTGATAC CACAGTGGGCACTACGCCAGATCGCCGACTTCGCCCTG AAGCTGCACAAGACCCACCTGGCCAGCTTCCTGTCTGCT TTCGCAAGGCAGGAACTGTACCTGATGGGCTCTCTAGTG CACAGCATGCTCGTCCATACCACAGAGCGGCGGGAGAT CTTCATCGTGGAGACTGGCCTGTGCTCTCTTGCGGAACT GAGCCACTTCACCCAGCTCCTAGCCCACCCACACCACG AGTACCTTTCTGACCTGTACACCCCGTGCTCATCAAGTG GACGGCGGGACCACTCGCTGGAAAGACTCACCCGGCTG TTCCCCGACGCTACTGTGCCGGCAACTGTGCCTGCGGCT CTCTCTATATTATCTACCATGCAGCCCAGCACACTCGAA ACCTTCCCTGATCTGTTCTGCCTGCCTCTAGGAGAGAGC TTCTCTGCCCTTACAGTGTCCGAGCACGTGAGCTACATC GTGACAAACCAATACCTCATTAAGGGCATCAGCTACCC TGTTAGTACTACCGTCGTAGGCCAGAGCCTAATTATCAC CCAGACCGACTCCCAGACAAAGTGCGAATTAACGCGCA ACATGCACACAACCCACAGCATCACCGTGGCCCTGAAC ATTAGCCTCGAGAACTGCGCCTTCTGCCAGAGTGCCTTG CTTGAGTATGATGATACCCAGGGCGTGATCAACATCAT GTACATGCACGACAGCGACGATGTGCTGTTCGCACTCG ACCCCTACAACGAGGTGGTCGTAAGCAGTCCAAGGACC CATTATTTGATGCTGCTTAAGAACGGCACCGTGCTGGAG GTGACCGACGTGGTGGTAGACGCTACAGACTCCCGGCT GCTTATGATGAGCGTGTACGCGCTCAGTGCGATCATCGG CATCTACCTGCTTTATCGGATGCTAAAGACCTGC (SEQ ID NO: 110) | |
| SE_CMV_gH_ 039 | MRPGLPSYLIILAV CLFSHLLSSRYGAE AVSEPLDKAFHLL LNTYGRPIRFLREN TTQCTYNSSLRNST VVRENAISFNFFQS YNQYYVFHMPRCL FAGPLAEQFLNQV DLTETLERYQQRL NTYALVSKDLASY RSFSQQLKAQDSL GEQPTTVPPPIDLSI PHVWMPPQTTPHG WTESHTTSGLHRP HFNQTCILFDGHDL LFSTVTPCLHQGFY LIDELRYVKITLTE DFFVVTVSIDDDTP MLLIFGHLPRVLFK APYQRDNFILRQTE KHELLVLVKKDQL NRHSYLKDPDFLD AALDFNYLDLSAL LRNSFHRYAVDVL KSGRCQMLDRRTV EMAFAYALALFAA ARQEEAGAQVSVP RALDRQAALLQIQ EFMITCLSQTPPRT | ATGCGGCCCGGCTTGCCCAGCTACTTGATCATCTTGGCC GTGTGCTTGTTCAGCCACTTACTTAGCAGCCGGTACGGC GCCGAGGCCGTGTCCGAGCCCCTCGACAAGGCCTTCCA CCTCCTCCTCAACACCTACGGCCGCCCCATCCGCTTCCT CCGCGAGAACACCACCCAGTGCACCTACAACTCCTCCCT CCGCAACTCCACCGTCGTGCGGGAGAATGCCATCTCCTT CAACTTCTTCCAGTCCTACAACCAGTACTACGTCTTCCA CATGCCCCGCTGCCTCTTCGCCGGACCTCTCGCCGAGCA GTTCCTCAACCAGGTCGACCTCACCGAGACGCTCGAGC GCTACCAGCAGAGGTTGAATACCTATGCCCTCGTCTCCA AGGACCTCGCCTCCTACCGCTCCTTCTCCCAGCAGCTCA AGGCCCAGGACTCCCTCGGCGAGCAGCCCACCACCGTG CCTCCACCAATCGACCTCTCCATCCCGCACGTCTGGATG CCTCCCCAGACCACTCCGCACGGCTGGACCGAGTCCCA CACCACCTCCGGACTGCATCGCCCTCACTTCAACCAGAC CTGCATCCTCTTCGACGGCCACGACCTCCTCTTCAGTAC CGTGACGCCATGCCTGCACCAGGGCTTCTACCTCATCGA CGAGCTCCGCTACGTCAAGATCACCCTTACCGAGGACTT CTTCGTCGTCACCGTCTCGATTGACGACGACACACCAAT GCTCCTCATCTTCGGCCACCTCCCGCGCGTGCTGTTCAA GGCGCCCTACCAGCGCGACAACTTCATCCTGAGGCAGA CCGAGAAGCACGAGCTGCTCGTCCTCGTCAAGAAGGAC CAGCTCAACCGCCACTCCTACCTCAAGGACCCCGACTTC CTCGACGCCGCCCTCGACTTCAACTACCTCGATCTGAGT GCTCTGCTGAGGAATTCATTCCACCGCTACGCCGTCGAC GTCCTCAAGTCCGGCCGCTGCCAGATGCTCGACCGCCGC ACCGTCGAGATGGCCTTCGCTTACGCGCTGGCACTCTTC GCTGCCGCCCGCCAGGAGGAGGCCGGCGCCCAGGTCAG TGTGCCAAGAGCACTGGATAGACAGGCCGCACTTTTGC | C2/ CAP1/ T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | TLLLYPTAVDLAK | AGATCCAGGAGTTCATGATCACCTGCCTCTCCCAGACTC | |
| | RALWTPNQITDITS | CGCCTCGCACCACGTTGTTGTGTACCCCACAGCAGTCG | |
| | LVRLVYILSKQNQ | ATCTGGCTAAGAGAGCCTTATGGACACCTAACCAGATC | |
| | QHLIPQWALRQIA | ACCGACATCACCTCCCTCGTTCGGCTGGTCTACATCCTC | |
| | DFALKLHKTHLAS | TCCAAGCAGAATCAGCAGCACCTGATCCCTCAGTGGGC | |
| | FLSAFARQELYLM | ACTCCGTCAAATCGCCGACTTCGCCCTCAAGCTCCACAA | |
| | GSLVHSMLVHTTE | GACCCACCTGGCGTCTTTCCTCAGTGCATTCGCTAGGCA | |
| | RREIFIVETGLCSLA | GGAGCTGTACCTGATGGGCAGTCTCGTCCACTCCATGCT | |
| | ELSHFTQLLAHPH | GGTGCACACCACGGAGCGCCGCGAGATCTTCATCGTCG | |
| | HEYLSDLYTPCSSS | AGACTGGCCTCTGTAGTTTAGCCGAGCTCAGTCACTTCA | |
| | GRRDHSLERLTRLF | CCCAACTGCTCGCCCACCCTCACCACGAGTACCTTAGTG | |
| | PDATVPATVPAAL | ACCTCTATACCCCTTGCTCTAGTTCCGGTCGCCGCGACC | |
| | SILSTMQPSTLETFP | ACAGCCTGGAACGTCTGACCCGCCTCTTCCCCGACGCTA | |
| | DLFCLPLGESFSAL | CAGTACCAGCAACCGTGCCAGCGGCCCTGTCTATCCTGT | |
| | TVSEHVSYIVTNQ | CTACCATGCAGCCCTCCACCTTGGAGACGTTCCCAGATC | |
| | YLIKGISYPVSTTV | TGTTCTGCCTCCCTCTAGGCGAATCGTTCTCTGCACTCA | |
| | VGQSLIITQTDSQT | CGGTCAGCGAACACGTCTCCTACATCGTCACAAACCAG | |
| | KCELTRNMHTTHS | TATCTGATAAAGGGCATCTCCTACCCAGTGTCGACCACT | |
| | ITVALNISLENCAF | GTTGTCGGCCAGTCCCTCATCATCACACAGACTGATTCT | |
| | CQSALLEYDDTQG | CAGACTAAGTGCGAGTTGACACGGAACATGCATACTAC | |
| | VINIMYMHDSDDV | ACATTCTATCACCGTTGCTTTAAACATAAGCCTGGAGAA | |
| | LFALDPYNEVVVS | CTGCGCCTTCTGCCAGTCCGCTCTGCTCGAGTACGACGA | |
| | SPRTHYLMLLKNG | TACGCAGGGCGTCATCAACATCATGTACATGCACGACT | |
| | TVLEVTDVVVDAT | CCGATGACGTTCTGTTCGCACTGGACCCCTACAACGAGG | |
| | DSRLLMMSVYALS | TCGTCGTCTCCTCTCCTAGGACTCACTACTTAATGCTGTT | |
| | AIIGIYLLYRMLKT | GAAGAACGGCACCGTCCTCGAGGTCACCGACGTGGTCG | |
| | C (SEQ ID NO: 59) | TCGATGCTACAGACAGCCGACTGCTCATGATGTCCGTGT | |
| | | ACGCTCTCTCCGCCATCATCGGCATCTACCTGCTCTACC | |
| | | GCATGCTCAAGACCTGC (SEQ ID NO: 111) | |
| SE_CMV_gH_ | MRPGLPSYLIILAV | ATGCGGCCCGGCCTACCCAGCTACCTTATCATCTTAGCC | C2/ |
| 040 | CLFSHLLSSRYGAE | GTGTGCTTGTTCAGCCACTTGCTCAGCAGCCGGTACGGC | CAP1/ |
| | AVSEPLDKAFHLL | GCCGAGGCCGTGTCCGAGCCCCTCGACAAGGCCTTCCA | T100 |
| | LNTYGRPIRFLREN | CCTCCTCCTCAACACCTACGGCCGCCCCATCCGCTTCCT | |
| | TTQCTYNSSLRNST | CCGCGAGAACACCACCCAGTGCACCTACAACTCCTCCCT | |
| | VVRENAISFNFFQS | CCGCAACTCCACCGTCGTCAGAGAGAATGCCATCTCCTT | |
| | YNQYYVFHMPRCL | CAACTTCTTCCAGTCCTACAACCAGTACTACGTCTTCCA | |
| | FAGPLAEQFLNQV | CATGCCCCGCTGCCTCTTCGCCGGCCCACTCGCCGAGCA | |
| | DLTETLERYQQRL | GTTCCTCAACCAGGTCGACCTCACCGAAACTCTCGAGCG | |
| | NTYALVSKDLASY | CTACCAGCAGCGGCTGAATACGTATGCCCTCGTCTCCAA | |
| | RSFSQQLKAQDSL | GGACCTCGCCTCCTACCGCTCCTTCTCCCAGCAGCTCAA | |
| | GEQPTTVPPPIDLSI | GGCCCAGGACTCCCTCGGCGAGCAGCCCACCACCGTCC | |
| | PHVWMPPQTTPHG | CTCCTCCAATCGACCTCTCCATCCCACACGTCTGGATGC | |
| | WTESHTTSGLHRP | CTCCCCAGACCACTCCTCACGGCTGGACCGAGTCCCACA | |
| | HFNQTCILFDGHDL | CCACCTCCGGCCTCCACAGGCCACACTTCAACCAGACCT | |
| | LFSTVTPCLHQGFY | GCATCCTCTTCGACGGCCACGACCTCCTCTTCAGCACAG | |
| | LIDELRYVKITLTE | TGACGCCATGTCTGCATCAGGGCTTCTACCTCATCGACG | |
| | DFFVVTVSIDDDTP | AGCTCCGCTACGTCAAGATCACTCTGACGGAGGACTTCT | |
| | MLLIFGHLPRVLFK | TCGTCGTCACCGTCTCTATAGATGACGACACCCCAATGC | |
| | APYQRDNFILRQTE | TCCTCATCTTCGGCCACTTGCCTCGCGTGCTGTTCAAGG | |
| | KHELLVLVKKDQL | CTCCCTACCAGCGCGACAACTTCATCCTCCGCCAGACCG | |
| | NRHSYLKDPDFLD | AGAAGCATGAATTACTCGTCCTCGTCAAGAAGGACCAG | |
| | AALDFNYLDLSAL | CTCAACCGCCACTCCTACCTCAAGGACCCCGACTTCCTC | |
| | LRNSFHRYAVDVL | GACGCCGCCCTCGACTTCAACTACCTGGATCTTAGCGCC | |
| | KSGRCQMLDRRTV | CTGCTGCGTAACAGCTTCCACCGCTACGCCGTCGACGTC | |
| | EMAFAYALALFAA | CTCAAGTCCGGCCGCTGCCAGATGCTCGACCGCCGCAC | |
| | ARQEEAGAQVSVP | CGTCGAGATGGCCTTCGCCTATGCTCTGGCCCTGTTCGC | |
| | RALDRQAALLQIQ | TGCCGCCCGCCAGGAGGAGGCCGGCGCCCAGGTTTCCG | |
| | EFMITCLSQTPPRT | TTCCTCGGGCTTTAGACAGACAGGCTGCCCTGCTTCAGA | |
| | TLLLYPTAVDLAK | TCCAGGAGTTCATGATCACCTGCCTCTCCCAGACGCCAC | |
| | RALWTPNQITDITS | CACGCACCACACTGTTGCTGTACCCGACAGCAGTGGAC | |
| | LVRLVYILSKQNQ | CTGGCAAAGAGGGCACTCTGGACTCCAAACCAGATCAC | |
| | QHLIPQWALRQIA | CGACATCACCTCCCTCGTCCGCCTCGTCTACATCCTCTC | |
| | DFALKLHKTHLAS | CAAGCAGAACCAGCAACACCTGATACCTCAGTGGGCTC | |
| | FLSAFARQELYLM | TGCGGCAGATCGCCGACTTCGCCCTCAAGCTCCACAAG | |
| | GSLVHSMLVHTTE | ACCCATTTGGCCTCCTTCCTGAGTGCCTTCGCTAGACAG | |
| | RREIFIVETGLCSLA | GAGCTGTACCTGATGGGCTCCCTGGTGCACTCCATGCTG | |
| | ELSHFTQLLAHPH | GTTCACACCACAGAGCGCCGCGAGATCTTCATCGTCGA | |
| | HEYLSDLYTPCSSS | GACAGGCCTCTGTTCATTGGCAGAACTCTCGCATTTCAC | |
| | GRRDHSLERLTRLF | CCAGCTGCTGGCCCACCCGCACCACGAGTATCTGAGTG | |
| | PDATVPATVPAAL | ACCTCTACACACCATGCAGTTCGTCAGGAAGGCGCGAC | |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | SILSTMQPSTLETFP DLFCLPLGESFSAL TVSEHVSYIVTNQ YLIKGISYPVSTTV VGQSLIITQTDSQT KCELTRNMHTTHS ITVALNISLENCAF CQSALLEYDDTQG VINIMYMHDSDDV LFALDPYNEVVVS SPRTHYLMLLKNG TVLEVTDVVVDAT DSRLLMMSVYALS AIIGIYLLYRMLKT C (SEQ ID NO: 59) | CACAGCCTGGAGCGACTGACCCGCCTCTTCCCCGACGC AACAGTCCCTGCTACTGTCCCTGCCGCGCTGAGTATTTT ATCAACGATGCAGCCCTCCACGCTCGAAACCTTCCCTGA CTTGTTCTGCCTCCCTCTTGGAGAGAGTTTCAGTGCCCT GACCGTGTCAGAGCACGTCTCCTACATCGTCACGAACC AGTATCTTATCAAGGGCATCTCCTACCCAGTATCGACTA CAGTGGTTGGCCAGTCCCTCATCATCACCCAGACTGACA GTCAAACTAAGTGCGAGCTTACTAGAAACATGCACACA ACCCACTCCATCACCGTTGCATTAAACATCAGCCTCGAG AACTGCGCCTTCTGCCAGAGCGCTCTGCTGGAGTACGAC GACACACAGGGCGTCATCAACATCATGTACATGCACGA CTCCGACGACGTCCTGTTCGCGCTTGATCCCTACAACGA GGTCGTCGTGTCCAGTCCACGAACTCATTACCTCATGCT GCTTAAGAACGGCACCGTCCTCGAGGTCACCGACGTGG TCGTCGATGCTACCGACTCCCGCCTCCTCATGATGTCCG TTTACGCACTCTCTGCGATCATCGGCATCTACTTACTAT ATCGCATGCTCAAGACCTGC (SEQ ID NO: 112) | |
| SE_CMV_gL_ 041 | MCRRPDCGFSFSP GPVILLWCCLLLPI VSSAAVSVAPTAA EKVPAECPELTRRC LLGEVFEGDKYES WLRPLVNVTGRDG PLSQLIRYRPVTPE AANSVLLDEAFLD TLALLYNNPDQLR ALLTLLSSDTAPR WMTVMRGYSECG DGSPAVYTCVDDL CRGYDLTRLSYGR SIFTEHVLGFELVP PSLFNVVVAIRNEA TRTNRAVRLPVST AAAPEGITLFYGLY NAVKEFCLRHQLD PPLLRHLDKYYAG LPPELKQTRVNLPA HSRYGPQAVDAR (SEQ ID NO: 61) | ATGTGCAGAAGACCAGACTGCGGATTCAGCTTCTCCCC AGGCCCAGTGATCTTACTTTGGTGCTGCCTCCTCCTTCC GATTGTGAGCAGTGCCGCCGTGAGCGTGGCTCCTACCG CGGCCGAGAAGGTGCCGGCCGAGTGCCCAGAGCTCACC CGAAGGTGCCTTCTGGGCGAGGTTTTCGAGGGAGACAA GTACGAGTCTTGGCTCCGGCCTCTGGTCAACGTGACGGG CAGAGACGGCCCTTTGAGCCAGCTCATCAGATACAGAC CAGTAACACCTGAGGCCGCCAATTCCGTCCTGCTGGATG AGGCCTTCCTGGACACCCTCGCCCTCCTTTACAATAACC CAGACCAGCTGAGAGCCCTGTTGACCCTTCTCAGCAGC GACACCGCTCCACGGTGGATGACCGTCATGAGAGGCTA TAGCGAGTGCGGAGATGGCAGCCCTGCCGTCTATACCT GCGTTGACGACCTGTGCAGGGGCTACGATTTGACAAGG CTCAGCTACGGCAGATCTATATTCACAGAGCATGTGCTG GGCTTCGAGCTGGTGCCGCCATCCCTGTTCAACGTGGTG GTCGCTATAAGGAACGAGGCCACCAGAACAAATCGCGC CGTGAGACTGCCGGTGTCCACGGCAGCCGCACCTGAGG GCATTACACTGTTCTATGGCCTCTACAACGCCGTGAAGG AGTTCTGTTTGCGGCACCAGCTGGACCCACCACTGCTCA GACACCTGGATAAGTACTACGCTGGCCTGCCTCCGGAG CTGAAGCAAACACGTGTGAATCTGCCAGCCCACTCTCG GTACGGACCGCAGGCCGTGGACGCCCGG (SEQ ID NO: 113) | C2/ CAP1/ T100 |
| SE_CMV_gL_ 042 | MCRRPDCGFSFSP GPVILLWCCLLLPI VSSAAVSVAPTAA EKVPAECPELTRRC LLGEVFEGDKYES WLRPLVNVTGRDG PLSQLIRYRPVTPE AANSVLLDEAFLD TLALLYNNPDQLR ALLTLLSSDTAPR WMTVMRGYSECG DGSPAVYTCVDDL CRGYDLTRLSYGR SIFTEHVLGFELVP PSLFNVVVAIRNEA TRTNRAVRLPVST AAAPEGITLFYGLY NAVKEFCLRHQLD PPLLRHLDKYYAG LPPELKQTRVNLPA HSRYGPQAVDAR (SEQ ID NO: 61) | ATGTGCAGGAGGCCAGACTGCGGCTTCTCATTCAGCCC AGGCCCAGTCATCCTCCTTTGGTGTTGCCTCCTTCTCCCT ATAGTTAGCAGTGCCGCCGTGAGCGTGGCCCCTACAGC CGCGGAGAAGGTGCCAGCGGAGTGCCCGGAGTTAACCA GACGTTGCCTCTTGGGCGAGGTGTTCGAGGGCGATAAG TATGAGTCCTGGCTGCGGCCTCTGGTGAACGTGACCGGC AGAGACGGACCTCTGTCCCAGCTGATCAGATACAGACC AGTGACCCCTGAAGCCGCAAACAGCGTGCTGCTGGACG AGGCCTTCCTGGACACCCTGGCCCTGTTATACAACAACC CTGACCAGCTTCGCGCGCTGCTTACACTGCTGAGCAGCG ATACCGCCCCAAGATGGATGACTGTGATGAGGGGATAT AGCGAGTGTGGCGACGGCAGCCCTGCCGTCTACACCTG TGTGGACGACCTCTGCAGAGGCTATGACCTGACCAGAC TGTCATACGGCCGAAGCATCTTCACCGAGCACGTCTTAG GATTCGAGCTGGTGCCTCCAAGCCTCTTCAATGTGGTGG TGGCCATTCGGAACGAGGCTACCAGAACCAACCGGGCG GTGCGTCTTCCAGTTTCTACAGCCGCCGCCCCGGAAGGA ATTACCCTGTTCTACGGCCTGTACAACGCTGTCAAGGAG TTCTGCCTGAGACACCAGCTGGATCCACCGCTGCTGCGC CACTTGGACAAGTACTATGCGGGCCTCCCTCCTGAGCTC AAGCAGACGAGGGTGAACCTCCCTGCTCACTCACGTTA TGGACCACAGGCCGTGGACGCTAGA (SEQ ID NO: 114) | C2/ CAP1/ T100 |
| SE_CMV_gL_ 043 | MCRRPDCGFSFSP GPVILLWCCLLLPI VSSAAVSVAPTAA EKVPAECPELTRRC LLGEVFEGDKYES WLRPLVNVTGRDG | ATGTGCAGAAGGCCAGACTGCGGCTTCAGCTTCTCTCCA GGACCAGTGATCCTCCTCTGGTGCTGCCTTCTCCTCCCT ATTGTGTCCTCCGCCGCCGTGTCCGTGGCCCCAACCGCC GCCGAGAAGGTGCCAGCGGAGTGCCCAGAGCTCACCAG GCGCTGTCTGCTGGGCGAGGTGTTCGAGGGCGATAAGT ACGAGAGTTGGCTGAGGCCGTTGGTGAACGTGACGGGC | C2/ CAP1/ T100 |

TABLE 13-continued

| Additional hCMV Vaccine Constructs | | | |
|---|---|---|---|
| Antigen Name | Protein Sequence | Nucleotide Sequence (Open Reading Frames) | Tested Chemistry mRNA Chemistry/ Cap/ Tail |
| | PLSQLIRYRPVTPE<br>AANSVLLDEAFLD<br>TLALLYNNPDQLR<br>ALLTLLSSDTAPR<br>WMTVMRGYSECG<br>DGSPAVYTCVDDL<br>CRGYDLTRLSYGR<br>SIFTEHVLGFELVP<br>PSLFNVVVAIRNEA<br>TRTNRAVRLPVST<br>AAAPEGITLFYGLY<br>NAVKEFCLRHQLD<br>PPLLRHLDKYYAG<br>LPPELKQTRVNLPA<br>HSRYGPQAVDAR<br>(SEQ ID NO: 61) | AGGGACGGCCCGCTAAGTCAGTTAATAAGGTACCGGCC<br>AGTGACCCCGGAGGCCGCCAACAGCGTGCTGCTGGATG<br>AGGCCTTCTTGGACACCCTGGCCCTGTTGTACAACAACC<br>CAGACCAGCTGAGAGCCCTGCTGACTCTGTTGAGCAGC<br>GACACCGCCCCAAGATGGATGACCGTGATGAGAGGCTA<br>TAGCGAGTGCGGCGATGGCAGCCCTGCCGTGTACACGT<br>GCGTGGACGATTTGTGTAGAGGCTACGACCTCACCAGA<br>CTGAGCTACGGCAGAAGCATCTTCACTGAGCATGTGCT<br>GGGATTCGAGCTGGTGCCTCCTAGCCTGTTCAATGTTGT<br>GGTGGCTATACGCAACGAGGCCACAAGAACAAACAGG<br>GCCGTAAGACTCCCAGTGAGCACCGCTGCAGCCCCTGA<br>GGGAATCACGCTGTTCTACGGCCTCTACAACGCTGTGAA<br>GGAGTTCTGTCTGAGGCACCAACTGGACCCACCTCTGCT<br>TAGACACCTGGATAAGTACTACGCCGGCCTCCCACCTG<br>AACTGAAGCAGACCAGGGTGAATCTTCCTGCACACTCA<br>AGGTATGGCCCACAGGCCGTGGATGCCAGG (SEQ ID NO: 115) | |
| SE_CMV_gL_044 | MCRRPDCGFSFSP<br>GPVILLWCCLLLPI<br>VSSAAVSVAPTAA<br>EKVPAECPELTRRC<br>LLGEVFEGDKYES<br>WLRPLVNVTGRDG<br>PLSQLIRYRPVTPE<br>AANSVLLDEAFLD<br>TLALLYNNPDQLR<br>ALLTLLSSDTAPR<br>WMTVMRGYSECG<br>DGSPAVYTCVDDL<br>CRGYDLTRLSYGR<br>SIFTEHVLGFELVP<br>PSLFNVVVAIRNEA<br>TRTNRAVRLPVST<br>AAAPEGITLFYGLY<br>NAVKEFCLRHQLD<br>PPLLRHLDKYYAG<br>LPPELKQTRVNLPA<br>HSRYGPQAVDAR<br>(SEQ ID NO: 61) | ATGTGCAGGCGGCCAGACTGCGGCTTCAGCTTCTCACCG<br>GGCCCAGTCATCTTGTTGTGGTGCTGCCTCCTCCTCCCT<br>ATCGTAAGCTCGGCAGCCGTCAGTGTGGCCCCAACCGC<br>CGCCGAGAAGGTTCCAGCCGAGTGTCCAGAACTCACAA<br>GGCGGTGCCTGCTGGGCGAGGTCTTCGAGGGCGACAAG<br>TATGAAAGCTGGCTCAGGCCACTTGTCAATGTGACAGG<br>CAGAGACGGCCCACTGAGCCAGCTTATCCGGTATAGAC<br>CTGTCACTCCTGAGGCCGCTAACAGCGTGCTTCTGGACG<br>AGGCTTTCCTGGACACTCTGGCTCTGCTTTACAACAACC<br>CAGACCAGCTGAGAGCCCTGCTGACCCTGCTGAGCAGC<br>GATACAGCCCCAAGGTGGATGACAGTTATGAGGGGATA<br>CAGCGAGTGTGGCGACGGAAGCCCAGCCGTGTATACCT<br>GCGTGGATGACCTGTGCAGAGGCTACGACCTGACCCGC<br>CTCTCCTACGGAAGATCCATCTTCACCGAGCACGTGCTA<br>GGATTCGAGCTCGTCCCTCCTAGCCTGTTCAATGTGGTG<br>GTGGCCATCAGAAACGAGGCCACTCGGACCAATAGAGC<br>AGTGAGACTGCCAGTGAGCACCGCGGCCGCACCAGAGG<br>GTATCACACTGTTCTACGGCCTGTACAACGCCGTGAAGG<br>AGTTCTGTCTGCGTCACCAGCTGGACCCACCTCTGCTTA<br>GACATCTGGATAAGTACTATGCCGGCCTGCCTCCTGAAC<br>TCAAGCAGACCCGTGTGAATCTGCCTGCCCACTCCAGAT<br>ACGGCCCTCAGGCCGTGGACGCAAGG (SEQ ID NO: 116) | C2/<br>CAP1/<br>T100 |
| SE_CMV_gL_045 | MCRRPDCGFSFSP<br>GPVILLWCCLLLPI<br>VSSAAVSVAPTAA<br>EKVPAECPELTRRC<br>LLGEVFEGDKYES<br>WLRPLVNVTGRDG<br>PLSQLIRYRPVTPE<br>AANSVLLDEAFLD<br>TLALLYNNPDQLR<br>ALLTLLSSDTAPR<br>WMTVMRGYSECG<br>DGSPAVYTCVDDL<br>CRGYDLTRLSYGR<br>SIFTEHVLGFELVP<br>PSLFNVVVAIRNEA<br>TRTNRAVRLPVST<br>AAAPEGITLFYGLY<br>NAVKEFCLRHQLD<br>PPLLRHLDKYYAG<br>LPPELKQTRVNLPA<br>HSRYGPQAVDAR<br>(SEQ ID NO: 61) | ATGTGTAGACGACCAGACTGCGGCTTCTCTTTCTCTCCA<br>GGCCCGGTGATCTTACTCTGGTGTTGTTTGCTCCTTCCTA<br>TCGTTAGTAGCGCCGCCGTGAGCGTGGCTCCGACAGCC<br>GCCGAGAAGGTGCCAGCCGAGTGCCCAGAGCTCACCAG<br>AAGATGTCTGCTGGGCGAGGTCTTCGAAGGCGACAAGT<br>ACGAGTCTTGGCTGAGGCCTCTCGTGAATGTTACCGGCA<br>GGGACGGCCCACTGAGCCAGCTGATTAGGTACCGGCCA<br>GTGACCCCGGAAGCCGCCAACAGCGTGCTGCTGGATGA<br>AGCCTTCCTGGACACCCTGGCCCTGCTGTACAACAATCC<br>TGACCAGCTCCGGGCCCTGCTGACCCTCCTCAGCAGCGA<br>CACTGCCCCTCGGTGGATGACAGTCATGAGAGGCTACT<br>CCGAATGTGGAGACGGCAGCCCTGCCGTCTACACCTGT<br>GTGGACGACCTCTGTAGGGGCTACGACCTGACAAGACT<br>GTCCTATGGCAGAAGCATTTTCACCGAGCATGTGCTTGG<br>CTTCGAGCTGGTGCCTCCATCCCTGTTCAACGTGGTTGT<br>GGCCATTAGAAACGAGGCCACCAGAACCAACAGGGCCG<br>TGCGGCTGCCAGTGAGTACAGCCGCTGCTCCAGAGGGC<br>ATTACCCTGTTCTACGGCCTTTACAATGCCGTGAAGGAG<br>TTCTGTCTGCGCCATCAGCTGGACCCTCCTCTGCTGAGA<br>CACCTGGATAAGTATTACGCGGGCCTGCCTCCAGAACT<br>GAAGCAGACCCGCGTCAACCTGCCAGCTCATAGCCGTT<br>ACGGCCCGCAAGCAGTGGACGCCCGA (SEQ ID NO: 117) | C2/<br>CAP1/<br>T100 |
| SE_CMV_gL_046 | MCRRPDCGFSFSP<br>GPVILLWCCLLLPI<br>VSSAAVSVAPTAA<br>EKVPAECPELTRRC<br>LLGEVFEGDKYES<br>WLRPLVNVTGRDG<br>PLSQLIRYRPVTPE | ATGTGCCGAAGACCGGACTGCGGCTTCAGCTTCAGCCC<br>AGGCCCGGTTATCCTCCTCTGGTGCTGCCTCCTTCTCCC<br>AATCGTGAGCAGCGCCGCCGTGAGCGTGGCGCCTACCG<br>CCGCGGAGAAGGTCCCAGCCGAGTGCCCAGAATTGACG<br>AGGAGATGCTTGCTGGGCGAAGTGTTCGAGGGCGATAA<br>GTATGAGAGCTGGCTGCGGCCTCTGGTCAACGTGACCG<br>GCCGCGACGGCCCACTGTCCCAGCTGATCAGGTACAGA | C2/<br>CAP1/<br>T100 |

TABLE 13-continued

| Additional hCMV Vaccine Constructs | | | |
|---|---|---|---|
| Antigen Name | Protein Sequence | Nucleotide Sequence (Open Reading Frames) | Tested Chemistry mRNA Chemistry/ Cap/ Tail |
| | AANSVLLDEAFLD TLALLYNNPDQLR ALLTLLSSDTAPR WMTVMRGYSECG DGSPAVYTCVDDL CRGYDLTRLSYGR SIFTEHVLGFELVP PSLFNVVVAIRNEA TRTNRAVRLPVST AAAPEGITLFYGLY NAVKEFCLRHQLD PPLLRHLDKYYAG LPPELKQTRVNLPA HSRYGPQAVDAR (SEQ ID NO: 61) | CCAGTGACCCCAGAGGCTGCTAACAGCGTGCTGCTGGA TGAGGCTTTCCTCGACACGCTGGCTCTCCTGTACAACAA TCCGGATCAGCTCAGAGCCCTGCTCACACTGCTGTCCAG CGACACCGCTCCAAGGTGGATGACAGTGATGCGGGGCT ACTCAGAGTGCGGCGACGGTAGCCCTGCGGTGTATACA TGTGTGGACGACCTGTGCAGAGGCTACGACTTAACCAG GCTGTCCTACGGTAGATCCATCTTCACTGAGCACGTGCT GGGCTTCGAGCTGGTGCCACCTAGCCTGTTCAATGTCGT GGTAGCCATCCGGAACGAGGCTACCAGAACAAATCGGG CCGTGAGGCTCCCAGTGAGCACCGCCGCCGCTCCTGAG GGCATCACTCTGTTCTACGGACTTTACAACGCCGTCAAG GAGTTCTGCCTGCGGCACCAGCTCGATCCACCTCTGCTG AGACACCTGGACAAGTACTACGCCGGCCTTCCGCCTGA GCTGAAGCAGACCAGAGTCAACCTGCCTGCCCATAGCA GATACGGCCCACAGGCTGTGGATGCCAGA (SEQ ID NO: 118) | |
| SE_CMV_gL_ 047 | MCRRPDCGFSFSP GPVILLWCCLLLPI VSSAAVSVAPTAA EKVPAECPELTRRC LLGEVFEGDKYES WLRPLVNVTGRDG PLSQLIRYRPVTPE AANSVLLDEAFLD TLALLYNNPDQLR ALLTLLSSDTAPR WMTVMRGYSECG DGSPAVYTCVDDL CRGYDLTRLSYGR SIFTEHVLGFELVP PSLFNVVVAIRNEA TRTNRAVRLPVST AAAPEGITLFYGLY NAVKEFCLRHQLD PPLLRHLDKYYAG LPPELKQTRVNLPA HSRYGPQAVDAR (SEQ ID NO: 61) | ATGTGCCGGCGGCCCGACTGCGGCTTCAGCTTCAGCCCC GGCCCCGTGATCCTATTGTGGTGCTGCCTACTTTTGCCC ATCGTGAGCAGCGCCGCCGTGAGCGTGGCTCCTACCGC CGCCGAGAAGGTGCCCGCCGAGTGCCCCGAGCTAACCC GGCGGTGCCTTCTTGGCGAGGTGTTCGAGGGCGACAAG TACGAGAGCTGGCTGCGGCCCCTGGTGAACGTGACCGG CCGGGACGGCCCTCTGAGCCAGCTGATCCGGTACCGGC CCGTGACACCAGAGGCCGCCAACAGCGTGCTGCTGGAC GAGGCCTTCCTGGACACCCTGGCCCTGCTGTACAACAAC CCCGACCAGCTGAGAGCTCTGCTGACGCTGCTGTCAAG CGACACCGCGCCACGGTGGATGACCGTGATGCGGGGCT ACAGCGAGTGCGGCGACGGCAGCCCCGCCGTGTACACC TGCGTGGACGACCTGTGCAGGGGCTATGACCTGACCCG TCTGAGCTACGGCCGGAGCATCTTCACCGAGCACGTGCT GGGCTTCGAGCTGGTGCCTCCCAGCCTGTTCAACGTGGT GGTGGCCATCCGGAACGAGGCCACCCGGACCAACCGGG CCGTGCGGCTGCCCGTGAGCACCGCAGCAGCCCCAGAA GGCATCACCCTGTTCTACGGCCTGTACAATGCCGTGAAG GAGTTCTGCCTGCGGCACCAGCTGGACCCACCTCTTCTC AGGCACCTGGATAAGTACTACGCCGGCCTGCCTCCTGA ACTGAAGCAGACCCGGGTGAACCTGCCCGCCCACAGCC GGTATGGCCCACAGGCCGTGGACGCCCGG (SEQ ID NO: 119) | C2/ CAP1/ T100 |
| SE_CMV_gL_ 048 | MCRRPDCGFSFSP GPVILLWCCLLLPI VSSAAVSVAPTAA EKVPAECPELTRRC LLGEVFEGDKYES WLRPLVNVTGRDG PLSQLIRYRPVTPE AANSVLLDEAFLD TLALLYNNPDQLR ALLTLLSSDTAPR WMTVMRGYSECG DGSPAVYTCVDDL CRGYDLTRLSYGR SIFTEHVLGFELVP PSLFNVVVAIRNEA TRTNRAVRLPVST AAAPEGITLFYGLY NAVKEFCLRHQLD PPLLRHLDKYYAG LPPELKQTRVNLPA HSRYGPQAVDAR (SEQ ID NO: 61) | ATGTGCCGGCGGCCCGACTGCGGCTTCAGCTTCAGCCCC GGCCCCGTGATCCTCCTCTGGTGCTGCCTCTTGTTGCCC ATCGTGAGCAGCGCCGCCGTGAGCGTGGCTCCTACCGC CGCCGAGAAGGTGCCCGCCGAGTGCCCCGAGCTCACCC GGCGGTGCCTTCTGGGCGAGGTGTTCGAGGGCGACAAG TACGAGAGCTGGCTGCGGCCCCTGGTGAACGTGACCGG CCGGGACGGCCCTCTGAGCCAGCTGATCCGGTACCGGC CCGTGACTCCAGAGGCCGCCAACAGCGTGCTGCTGGAC GAGGCCTTCCTGGACACCCTGGCCCTGCTGTACAACAAC CCCGACCAGCTGAGGGCCCTTCTGACCCTGCTCAGCAGC GACACCGCCCCACGGTGGATGACCGTGATGCGGGGCTA CAGCGAGTGCGGCGACGGCAGCCCCGCCGTGTACACCT GCGTGGACGACCTGTGCAGGGGCTACGACCTGACCAGG CTGAGCTACGGCCGGAGCATCTTCACCGAGCACGTGCT GGGCTTCGAGCTGGTGCCGCCCAGCCTGTTCAACGTGGT GGTGGCCATCCGGAACGAGGCCACCCGGACCAACCGGG CCGTGCGGCTGCCCGTGTCGACAGCCGCCGCCCCTGAG GGCATCACCCTGTTCTACGGCCTATATAACGCCGTGAAG GAGTTCTGCCTGCGGCACCAGCTGGACCCGCCCCTGCTT CGCCACCTGGACAAGTATTACGCCGGCCTGCCTCCGGA GCTGAAGCAGACCCGGGTGAACCTGCCCGCCCACAGCC GGTACGGCCCTCAGGCCGTGGACGCCCGG (SEQ ID NO: 120) | C2/ CAP1/ T100 |
| SE_CMV_gL_ 049 | MCRRPDCGFSFSP GPVILLWCCLLLPI VSSAAVSVAPTAA EKVPAECPELTRRC LLGEVFEGDKYES WLRPLVNVTGRDG | ATGTGCCGGCGGCCCGACTGCGGCTTCAGCTTCAGCCCC GGCCCCGTGATCCTCCTTTGGTGCTGCTTGCTCTTGCCC ATCGTGAGCAGCGCCGCCGTCTCCGTCGCTCCTACCGCC GCCGAGAAGGTCCCCGCCGAGTGCCCCGAGCTCACCCG CCGCTGCCTCCTCGGCGAGGTCTTCGAGGGCGACAAGT ACGAGTCCTGGCTCAGACCTCTCGTCAACGTCACCGGCC | C2/ CAP1/ T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | PLSQLIRYRPVTPE<br>AANSVLLDEAFLD<br>TLALLYNNPDQLR<br>ALLTLLSSDTAPR<br>WMTVMRGYSECG<br>DGSPAVYTCVDDL<br>CRGYDLTRLSYGR<br>SIFTEHVLGFELVP<br>PSLFNVVVAIRNEA<br>TRTNRAVRLPVST<br>AAAPEGITLFYGLY<br>NAVKEFCLRHQLD<br>PPLLRHLDKYYAG<br>LPPELKQTRVNLPA<br>HSRYGPQAVDAR<br>(SEQ ID NO: 61) | GCGACGGCCCACTCTCCCAGCTCATCCGCTACCGCCCCG<br>TCACACCGGAGGCCGCCAACTCCGTCCTCCTCGACGAG<br>GCCTTCCTCGACACCCTCGCCCTCCTCTACAACAACCCC<br>GACCAGCTCCGAGCCCTGCTGACCCTGCTGTCCTCCGAC<br>ACCGCTCCTCGCTGGATGACCGTCATGCGCGGCTACTCC<br>GAGTGCGGCGACGGCTCCCCAGCTGTGTACACCTGCGT<br>CGACGACCTCTGCAGAGGCTACGACCTGACGCGCCTCT<br>CCTACGGCCGCTCCATCTTCACCGAGCACGTCCTCGGCT<br>TCGAGCTCGTGCCTCCCTCCCTCTTCAACGTCGTCGTCG<br>CCATCCGCAACGAGGCCACCCGCACCAACCGCGCCGTC<br>CGCCTCCCCGTCAGCACAGCCGCTGCACCAGAGGGCAT<br>CACCCTCTTCTACGGACTGTACAACGCCGTCAAGGAGTT<br>CTGCCTCCGCCACCAGCTCGACCCACCTCTGCTGAGGCA<br>TCTGGACAAGTATTACGCCGGCCTCCCACCAGAGCTGA<br>AGCAGACCCGCGTCAACCTCCCCGCCCACTCCCGCTACG<br>GACCACAGGCCGTCGACGCCCGC (SEQ ID NO: 121) | |
| SE_CMV_gL_<br>050 | MCRRPDCGFSFSP<br>GPVILLWCCLLLPI<br>VSSAAVSVAPTAA<br>EKVPAECPELTRRC<br>LLGEVFEGDKYES<br>WLRPLVNVTGRDG<br>PLSQLIRYRPVTPE<br>AANSVLLDEAFLD<br>TLALLYNNPDQLR<br>ALLTLLSSDTAPR<br>WMTVMRGYSECG<br>DGSPAVYTCVDDL<br>CRGYDLTRLSYGR<br>SIFTEHVLGFELVP<br>PSLFNVVVAIRNEA<br>TRTNRAVRLPVST<br>AAAPEGITLFYGLY<br>NAVKEFCLRHQLD<br>PPLLRHLDKYYAG<br>LPPELKQTRVNLPA<br>HSRYGPQAVDAR<br>(SEQ ID NO: 61) | ATGTGCCGGCGGCCCGACTGCGGCTTCAGCTTCAGCCCC<br>GGCCCCGTGATCCTCCTCTGGTGCTGCCTTTTGCTCCCC<br>ATCGTGAGCAGCGCCGCCGTCTCCGTCGCTCCTACCGCC<br>GCCGAGAAGGTCCCCGCCGAGTGCCCCGAGCTCACCCG<br>CCGCTGCCTCCTCGGCGAGGTCTTCGAGGGCGACAAGT<br>ACGAGTCCTGGCTCAGACCTCTCGTCAACGTCACCGGCC<br>GCGACGGCCCACTCTCCCAGCTCATCCGCTACCGCCCCG<br>TCACCCCAGAGGCCGCCAACTCCGTCCTCCTCGACGAG<br>GCCTTCCTCGACACCCTCGCCCTCCTCTACAACAACCCC<br>GACCAGCTCAGGGCCCTTCTAACCCTGCTGTCCTCCGAC<br>ACCGCCCCTCGCTGGATGACCGTCATGCGCGGCTACTCC<br>GAGTGCGGCGACGGCTCCCCGGCCGTGTACACCTGCGT<br>CGACGACCTCTGCAGAGGATACGACCTCACCCGGCTCT<br>CCTACGGCCGCTCCATCTTCACCGAGCACGTCCTCGGCT<br>TCGAGCTCGTCCCACCCTCCCTCTTCAACGTCGTCGTCG<br>CCATCCGCAACGAGGCCACCCGCACCAACCGCGCCGTC<br>CGCCTCCCCGTCAGCACAGCCGCAGCCCCAGAGGGCAT<br>CACCCTCTTCTACGGCCTGTATAACGCCGTCAAGGAGTT<br>CTGCCTCCGCCACCAGCTCGACCCGCCTCTGCTGAGGCA<br>CCTGGACAAGTATTACGCCGGCCTCCCTCCTGAGCTGAA<br>GCAGACCCGCGTCAACCTCCCCGCCCACTCCCGCTATGG<br>ACCACAGGCCGTCGACGCCCGC (SEQ ID NO: 122) | C2/<br>CAP1/<br>T100 |
| SE_CMV_Trg<br>B6XHis_051<br>(truncated gB<br>with his6, all<br>aa sequence<br>the same) | MESRIWCLVVCVN<br>LCIVCLGAAVSSSS<br>TRGTSATHSHHSS<br>HTTSAAHSRSGSVS<br>QRVTSSQTVSHGV<br>NETIYNTTLKYGD<br>VVGVNTTKYPYRV<br>CSMAQGTDLIRFE<br>RNIVCTSMKPINED<br>LDEGIMVVYKRNI<br>VAHTFKVRVYQK<br>VLTFRRSYAYIHTT<br>YLLGSNTEYVAPP<br>MWEIHHINSHSQC<br>YSSYSRVIAGTVFV<br>AYHRDSYENKTM<br>QLMPDDYSNTHST<br>RYVTVKDQWHSR<br>GSTWLYRETCNLN<br>CMVTITTARSKYP<br>YHFFATSTGDVVDI<br>SPFYNGTNRNASY<br>FGENADKFFIFPNY<br>TIVSDFGRPNSALE<br>THRLVAFLERADS<br>VISWDIQDEKNVT<br>CQLTFWEASERTIR<br>SEAEDSYHFSSAK<br>MTATFLSKKQEVN<br>MSDSALDCVRDEA<br>INKLQQIFNTSYNQ | ATGGAGAGCAGAATTTGGTGCTTGGTGGTGTGTGTTAAC<br>CTCTGCATTGTTTGCCTCGGCGCAGCAGTGTCTAGCAGC<br>TCTACTCGGGGAACATCCGCAACCCACAGCCACCATAG<br>CTCACACACCACCAGCGCCGCCCACTCCAGATCCGGTA<br>GCGTGAGCCAGCGGGTGACTAGCAGCCAGACTGTGTCC<br>CATGGCGTCAACGAGACAATCTACAACACCACCCTGAA<br>GTACGGCGACGTCGTGGGCGTGAACACAACGAAGTACC<br>CTTACAGGGTGTGTAGCATGGCTCAGGGCACCGACTTG<br>ATCCGGTTCGAGAGAAATATTGTATGCACCAGCATGAA<br>GCCAATTAACGAGGATCTGGACGAAGGCATCATGGTAG<br>TGTATAAGAGAAACATAGTTGCACACACTTTCAAGGTG<br>AGGGTCTACCAGAAGGTGCTGACCTTCCGCCGAAGCTA<br>TGCTTACATCCATACTACCTACCTGCTCGGTTCTAACAC<br>CGAGTATGTGGCACCTCCAATGTGGGAGATCCACCACA<br>TCAATTCTCATAGCCAGTGTTACAGCTCTTACAGCCGGG<br>TGATAGCCGGCACCGTCTTCGTGGCCTACCATAGAGATT<br>CATACGAGAACAAGACCATGCAGCTGATGCCAGACGAC<br>TACAGCAACACCCATTCCACCAGGTATGTGACAGTCAA<br>GGACCAATGGCACTCACGCGGCTCCACCTGGCTGTACA<br>GGGAGACTTGCAACCTCAATTGCATGGTGACCATCACC<br>ACCGCCCGCAGCAAGTACCCGTACCACTTCTTCGCCACC<br>AGCACCGGAGATGTCGTGGACATCAGCCCTTTCTATAAC<br>GGCACTAACAGAAACGCCAGTTACTTCGGAGAGAATGC<br>CGACAAGTTCTTCATCTTCCCGAACTACACTATTGTGAG<br>CGATTTCGGTCGCCCTAACTCCGCCCTGGAGACACACCG<br>CCTGGTTGCCTTCCTGGAGAGAGCCGATTCCGTGATCAG<br>CTGGGACATCCAGGACGAGAAGAATGTGACCTGTCAGC<br>TCACTTTCTGGGAGGCCTCCGAGAGGACTATCCGGAGC<br>GAGGCCGAGGACTCATACCATTTCAGCAGCGCCAAGAT<br>GACCGCCACCTTCCTGTCAAAGAAGCAGGAGGTGAACA<br>TGTCAGATAGCGCTCTGGACTGTGTGCGCGACGAGGCT | C2/<br>CAP1/<br>T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | TYEKYGNVSVFET TGGLVVFWQGIKQ KSLVELERLANRSS LNLTHNRTKRSTD GNNATHLSNMESV HNLVYAQLQFTYD TLRGYINRALAQIA EAWCVDQRRTLEV FKELSKINPSAILSA IYNKPIAARFMGD VLGLASCVTINQTS VKVLRDMNVKESP GRCYSRPVVIFNFA NSSYVQYGQLGED NEILLGNHRTEECQ LPSLKIFIAGNSAY EYVDYLFKRMIDL SSISTVDSMIALDID PLENTDFRVLELYS QKELRSSNVFDLEE IMREFNSYKQHHH HHH (SEQ ID NO: 83) | ATTAACAAGCTGCAGCAGATCTTCAATACCTCCTACAAT CAGACCTACGAGAAGTATGGTAACGTGTCAGTATTCGA GACAACTGGCGGCCTCGTGGTGTTCTGGCAGGGAATCA AGCAGAAGTCCCTGGTGGAGCTTGAAAGACTCGCCAAC CGGAGCAGCCTGAACCTGACCCACAACAGGACAAAGAG ATCTACAGATGGTAACAACGCCACCCATCTGAGCAACA TGGAGTCCGTGCACAACCTGGTGTACGCCCAGCTCCAGT TCACATACGACACCCTGAGAGGCTACATTAATAGAGCC CTCGCCCAAATCGCAGAGGCCTGGTGCGTGGACCAGAG GCGAACCCTGGAGGTGTTCAAGGAATTGAGCAAGATCA ATCCAAGCGCCATCTTGAGCGCAATCTATAACAAGCCG ATTGCGGCCAGATTCATGGGCGACGTGTTGGGCCTGGC CTCCTGCGTCACTATCAACCAGACCTCTGTCAAGGTGCT CAGAGATATGAACGTTAAGGAGTCCCCAGGCAGATGCT ATAGCAGACCTGTCGTGATTTTCAATTTCGCCAACTCAA GCTACGTGCAGTACGGCCAGCTCGGCGAAGATAACGAG ATCCTGCTGGGCAACCACAGAACCGAAGAGTGCCAGCT GCCTTCCCTGAAGATTTTCATCGCTGGCAACTCCGCTTA CGAGTACGTGGATTACCTGTTCAAGAGAATGATCGACC TCAGCAGCATCAGCACCGTGGACAGCATGATCGCCTTA GACATTGACCCTCTGGAGAACACAGATTTCAGGGTGCT GGAACTATACTCTCAGAAGGAGCTCCGGTCTAGCAACG TGTTCGATCTGGAGGAGATCATGCGGGAGTTCAATTCCT ACAAGCAGCACCACCACCATCATCAC (SEQ ID NO: 123) | |
| SE_CMV_Trg B6XHis_052 | MESRIWCLVVCVN LCIVCLGAAVSSSS TRGTSATHSHHSS HTTSAAHSRSGSVS QRVTSSQTVSHGV NETIYNTTLKYGD VVGVNTTKYPYRV CSMAQGTDLIRFE RNIVCTSMKPINED LDEGIMVVYKRNI VAHTFKVRVYQK VLTFRRSYAYIHTT YLLGSNTEYVAPP MWEIHHINSHSQC YSSYSRVIAGTVFV AYHRDSYENKTM QLMPDDYSNTHST RYVTVKDQWHSR GSTWLYRETCNLN CMVTITTARSKYP YHFFATSTGDVVDI SPFYNGTNRNASY FGENADKFFIFPNY TIVSDFGRPNSALE THRLVAFLERADS VISWDIQDEKNVT CQLTFWEASERTIR SEAEDSYHFSSAK MTATFLSKKQEVN MSDSALDCVRDEA INKLQQIFNTSYNQ TYEKYGNVSVFET TGGLVVFWQGIKQ KSLVELERLANRSS LNLTHNRTKRSTD GNNATHLSNMESV HNLVYAQLQFTYD TLRGYINRALAQIA EAWCVDQRRTLEV FKELSKINPSAILSA IYNKPIAARFMGD VLGLASCVTINQTS VKVLRDMNVKESP GRCYSRPVVIFNFA NSSYVQYGQLGED NEILLGNHRTEECQ | ATGGAGTCAAGAATCTGGTGTCTTGTGGTGTGCGTGAAC TTGTGTATCGTGTGTTTGGGCGCAGCCGTGTCCTCAAGC AGCACTAGAGGCACTAGCGCCACCCACTCCCATCATAG CTCACACACCACAAGCGCCGCCCACTCTAGGTCAGGCA GCGTGTCTCAGCGCGTGACCTCTAGCCAGACTGTGAGTC ACGGAGTCAATGAAACCATCTACAACACAACACTGAAG TACGGAGACGTCGTGGGCGTGAATACAACCAAGTACCC ATACAGGGTGTGCAGCATGGCTCAGGGCACTGACCTCA TCAGATTCGAGCGGAACATTGTGTGCACCTCAATGAAG CCTATCAACGAGGATTTGGATGAAGGCATCATGGTCGT GTACAAGAGAAACATCGTCGCTCATACCTTCAAGGTGA GAGTGTATCAGAAGGTGCTGACCTTCAGACGTAGCTAC GCTTACATTCACACCACCTACCTGCTGGGCAGCAACACC GAGTATGTGGCTCCTCCTATGTGGGAGATACATCACATC AACAGCCATTCTCAGTGCTATAGTTCTTATAGCAGGGTC ATCGCCGGCACCGTCTTCGTGGCCTACCATAGAGATAGC TACGAGAACAAGACCATGCAGTTGATGCCGGACGATTA CAGCAATACCCATAGCACTAGGTACGTGACTGTGAAGG ACCAGTGGCACTCCCGGGGTAGCACCTGGCTTTACAGG GAAACCTGCAATCTGAACTGCATGGTGACTATTACCACC GCCAGGAGCAAGTATCCTTACCACTTCTTCGCTACATCT ACTGGAGACGTGGTCGATATCTCTCCTTTCTACAATGGC ACAAACAGAAATGCTTCATATTTCGGCGAGAATGCCGA CAAGTTCTTCATCTTCCCAAACTACACCATTGTGTCCGA CTTCGGAAGACCTAATTCCGCCCTGGAAACCCATAGACT GGTCGCATTCCTGGAAAGGGCCGACTCCGTCATTTCATG GGACATCCAGGATGAGAAGAACGTCACCTGTCAGCTCA CATTCTGGGAAGCGAGCGAAAGAACAATTCGCAGCGAA GCCGAGGACAGCTATCATTTCAGCAGTGCTAAGATGAC CGCCACTTTCCTGTCTAAGAAGCAGGAGGTGAACATGT CCGACAGCGCCTTGGATTGCGTGAGAGACGAAGCTATT AACAAGCTGCAGCAGATCTTCAACACCTCCTACAACCA GACTTACGAGAAGTATGGCAATGTGAGTGTGTTCGAGA CAACCGGCGGCCTGGTAGTATTCTGGCAGGGCATCAAG CAGAAGTCACTGGTGGAGCTTGAGAGGCTGGCCAATAG ATCCAGCCTGAACCTGACCCACAACCGGACAAAGAGAT CTACCGACGGAAACAACGCCACTCATCTTTCCAATATGG AGAGCGTGCACAACCTGGTGTACGCGCAGCTCCAGTTC ACCTACGACACACTGAGGGGCTACATAAACAGGGCCCT GGCACAGATCGCCGAAGCCTGGTGCGTGGACCAGAGAA GGACCCTGGAGGTTTTCAAGGAGCTGAGCAAGATTAAT CCGTCCGCTATCCTGAGCGCAATATACAATAAGCCAATC GCCGCCAGATTCATGGGCGACGTGTTGGGACTGGCCAG TTGCGTCACAATAAACCAGACCTCTGTAAAGGTCCTGA GGGACATGAATGTCAAGGAGAGCCCGGGCAGGTGCTAC AGCCGTCCTGTGGTGATTTTCAACTTCGCTAATTCATCTT | C2/ CAP1/ T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | LPSLKIFIAGNSAY | ACGTCCAGTACGGCCAGCTGGGCGAAGACAATGAGATC | |
| | EYVDYLFKRMIDL | TTACTGGGCAACCATAGGACTGAGGAGTGCCAGCTGCC | |
| | SSISTVDSMIALDID | GAGTCTGAAGATTTTCATAGCCGGCAATAGCGCATATG | |
| | PLENTDFRVLELYS | AATATGTAGACTACCTGTTCAAGAGGATGATTGACCTCT | |
| | QKELRSSNVFDLEE | CTAGCATCTCGACCGTGGACAGCATGATCGCCCTCGAC | |
| | IMREFNSYKQHHH | ATCGACCCTCTGGAGAACACAGACTTCCGGGTCCTCGA | |
| | HHH (SEQ ID NO: | ACTGTACAGCCAGAAGGAGCTTAGGAGCTCCAACGTGT | |
| | 83) | TCGATCTTGAGGAGATCATGAGGGAGTTCAATAGCTAT | |
| | | AAGCAACATCACCACCATCATCAC (SEQ ID NO: 124) | |
| SE_CMV_Trg | MESRIWCLVVCVN | ATGGAGAGCAGAATTTGGTGTCTCGTGGTGTGTGTTAAT | C2/ |
| B6XHis_053 | LCIVCLGAAVSSSS | CTCTGCATCGTGTGCCTTGGCGCCGCCGTGTCCAGCAGC | CAP1/ |
| | TRGTSATHSHHSS | TCCACCAGGGGCACCAGCGCAACACACAGCCACCACTC | T100 |
| | HTTSAAHSRSGSVS | TAGCCACACAACCAGCGCCGCCCACTCTCGTTCAGGCTC | |
| | QRVTSSQTVSHGV | CGTTTCACAGAGGGTGACCTCCTCTCAAACCGTGTCTCA | |
| | NETIYNTTLKYGD | TGGAGTGAATGAAACCATTTATAACACAACACTGAAGT | |
| | VVGVNTTKYPYRV | ATGGCGACGTGGTGGGCGTCAACACCACCAAGTATCCT | |
| | CSMAQGTDLIRFE | TACCGGGTTTGTTCAATGGCCCAGGGCACCGATCTCATC | |
| | RNIVCTSMKPINED | AGATTCGAGCGAAATATCGTGTGTACATCCATGAAGCC | |
| | LDEGIMVVYKRNI | TATCAACGAAGACCTGGACGAGGGAATTATGGTCGTGT | |
| | VAHTFKVRVYQK | ACAAGAGAAATATTGTGGCCCACACTTTCAAGGTGAGA | |
| | VLTFRRSYAYIHTT | GTGTACCAGAAGGTGTTGACATTCAGGCGGTCCTACGC | |
| | YLLGSNTEYVAPP | CTACATCCACACCACTTATCTGTTGGGATCCAACACAGA | |
| | MWEIHHINSHSQC | GTACGTCGCACCGCCTATGTGGGAAATACATCACATCA | |
| | YSSYSRVIAGTVFV | ATTCCCATTCTCAGTGCTATTCTAGCTACTCCAGAGTGA | |
| | AYHRDSYENKTM | TCGCCGGCACCGTGTTCGTGGCCTACCACCGCGATAGCT | |
| | QLMPDDYSNTHST | ACGAGAATAAGACCATGCAGCTGATGCCTGACGATTAC | |
| | RYVTVKDQWHSR | AGCAACACTCATTCCACACGCTACGTGACCGTGAAGGA | |
| | GSTWLYRETCNLN | TCAGTGGCACAGCCGCGGCAGCACCTGGCTGTACCGGG | |
| | CMVTITTARSKYP | AAACCTGCAACCTGAACTGCATGGTGACAATAACAACC | |
| | YHFFATSTGDVVDI | GCACGTAGCAAGTACCCATACCACTTCTTCGCCACCTCC | |
| | SPFYNGTNRNASY | ACCGGTGACGTGGTCGACATCAGCCCTTTCTACAATGGC | |
| | FGENADKFFIFPNY | ACCAACAGAAATGCCTCCTACTTCGGCGAGAACGCCGA | |
| | TIVSDFGRPNSALE | CAAGTTCTTCATCTTCCCTAATTATACAATTGTGAGCGA | |
| | THRLVAFLERADS | CTTCGGCAGGCCTAACAGCGCCCTGGAGACTCATCGCTT | |
| | VISWDIQDEKNVT | GGTGGCTTTCCTGGAACGCGCTGACAGCGTCATCTCTTG | |
| | CQLTFWEASERTIR | GGATATCCAAGATGAGAAGAACGTGACCTGCCAGCTGA | |
| | SEAEDSYHFSSAK | CCTTCTGGGAGGCCAGCGAGAGGACAATCAGAAGCGAA | |
| | MTATFLSKKQEVN | GCCGAGGACTCTTACCATTTCAGTTCAGCTAAGATGACC | |
| | MSDSALDCVRDEA | GCCACCTTCCTGAGCAAGAAGCAGGAAGTGAATATGTC | |
| | INKLQQIFNTSYNQ | CGATTCCGCTCTTGACTGCGTCAGGGACGAAGCCATCA | |
| | TYEKYGNVSVFET | ACAAGCTCCAGCAGATTTTCAATACTTCTTATAATCAGA | |
| | TGGLVVFWQGIKQ | CCTATGAGAAGTACGGCAATGTCAGCGTCTTCGAGACG | |
| | KSLVELERLANRSS | ACCGGCGGCCTGGTTGTGTTCTGGCAAGGAATCAAGCA | |
| | LNLTHNRTKRSTD | GAAGTCACTGGTGGAGCTTGAGCGGCTGGCCAACAGAT | |
| | GNNATHLSNMESV | CCAGCTTGAACCTGACCCATAATCGCACCAAGCGGAGT | |
| | HNLVYAQLQFTYD | ACCGATGGCAACAACGCCACACACCTCAGCAATATGGA | |
| | TLRGYINRALAQIA | AAGCGTGCACAACCTTGTGTACGCTCAGCTGCAGTTCAC | |
| | EAWCVDQRRTLEV | CTACGATACCCTTAGAGGCTACATCAACAGAGCCCTGG | |
| | FKELSKINPSAILSA | CCCAGATCGCAGAGGCATGGTGCGTGGACCAGCGGCGG | |
| | IYNKPIAARFMGD | ACCCTGGAGGTGTTCAAGGAGCTCTCCAAGATCAACCC | |
| | VLGLASCVTINQTS | ATCCGCCATTCTCTCCGCCATCTACAACAAGCCTATTGC | |
| | VKVLRDMNVKESP | CGCTCGGTTCATGGGCGATGTGCTGGGACTGGCCAGCT | |
| | GRCYSRPVVIFNFA | GCGTGACCATCAACCAAACCTCAGTGAAGGTGCTCAGA | |
| | NSSYVQYGQLGED | GACATGAACGTCAAGGAGTCTCCAGGCAGATGTTACAG | |
| | NEILLGNHRTEECQ | CAGACCTGTGGTGATCTTCAACTTCGCCAATTCTTCCTA | |
| | LPSLKIFIAGNSAY | CGTGCAGTACGGCCAACTGGGTGAAGACAACGAGATTC | |
| | EYVDYLFKRMIDL | TGTTAGGCAACCACAGGACTGAGGAGTGTCAGCTGCCG | |
| | SSISTVDSMIALDID | AGCCTGAAGATCTTCATCGCTGGAAACAGCGCATACGA | |
| | PLENTDFRVLELYS | GTACGTGGACTACCTCTTCAAGAGGATGATCGACTTGTC | |
| | QKELRSSNVFDLEE | ATCTATCTCCACGGTTGATTCCATGATCGCCTTGGACAT | |
| | IMREFNSYKQHHH | CGATCCTCTGGAGAATACCGACTTCAGAGTGCTGGAGC | |
| | HHH (SEQ ID NO: | TCTACAGCCAGAAGGAGCTTAGGTCTAGCAATGTGTTC | |
| | 83) | GACCTGGAGGAGATCATGAGGGAGTTCAATAGCTATAA | |
| | | GCAGCATCACCACCACCATCAC (SEQ ID NO: 125) | |
| SE_CMV_Trg | MESRIWCLVVCVN | ATGGAGAGCAGAATCTGGTGCCTCGTGGTGTGCGTGAA | C2/ |
| B6XHis_054 | LCIVCLGAAVSSSS | CCTCTGTATCGTCTGCTTAGGAGCCGCCGTGAGCAGTAG | CAP1/ |
| | TRGTSATHSHHSSCT | CTACCAGAGGCACATCCGCCACCCACAGCCACCACT | T100 |
| | HTTSAAHSRSGSVS | CTTCACACACCACCAGCGCCGCCCACTCCAGATCAGGC | |
| | QRVTSSQTVSHGV | AGCGTATCCCAGAGAGTGACCAGCAGCCAGACCGTGTC | |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | NETIYNTTLKYGD VVGVNTTKYPYRV CSMAQGTDLIRFE RNIVCTSMKPINED LDEGIMVVYKRNI VAHTFKVRVYQK VLTFRRSYAYIHTT YLLGSNTEYVAPP MWEIHHINSHSQC YSSYSRVIAGTVFV AYHRDSYENKTM QLMPDDYSNTHST RYVTVKDQWHSR GSTWLYRETCNLN CMVTITTARSKYP YHFFATSTGDVVDI SPFYNGTNRNASY FGENADKFFIFPNY TIVSDFGRPNSALE THRLVAFLERADS VISWDIQDEKNVT CQLTFWEASERTIR SEAEDSYHFSSAK MTATFLSKKQEVN MSDSALDCVRDEA INKLQQIFNTSYNQ TYEKYGNVSVFET TGGLVVFWQGIKQ KSLVELERLANRSS LNLTHNRTKRSTD GNNATHLSNMESV HNLVYAQLQFTYD TLRGYINRALAQIA EAWCVDQRRTLEV FKELSKINPSAILSA IYNKPIAARFMGD VLGLASCVTINQTS VKVLRDMNVKESP GRCYSRPVVIFNFA NSSYVQYGQLGED NEILLGNHRTEECQ LPSLKIFIAGNSAY EYVDYLFKRMIDL SSISTVDSMIALDID PLENTDFRVLELYS QKELRSSNVFDLEE IMREFNSYKQHHH HHH (SEQ ID NO: 83) | ACATGGAGTGAATGAAACAATTTACAACACCACCCTCA AGTACGGCGACGTAGTGGGAGTGAACACTACTAAGTAC CCATACCGCGTGTGTAGCATGGCCCAGGGCACCGATCT GATCCGATTCGAGAGAAACATCGTTTGCACCAGCATGA AGCCTATCAACGAGGACCTGGATGAGGGCATCATGGTG GTGTACAAGAGGAACATCGTGGCCCACACGTTCAAGGT TAGGGTGTACCAGAAGGTGCTGACTTTCCGAAGAAGCT ATGCCTACATTCACACTACATACCTGCTCGGCAGTAACA CCGAGTACGTGGCGCCACCGATGTGGGAAATACACCAT ATTAATTCTCATAGTCAGTGCTATTCCAGCTACAGCAGG GTGATCGCCGGAACCGTTTTCGTGGCTTATCATAGAGAT TCCTACGAGAACAAGACCATGCAGCTGATGCCAGACGA CTATAGCAACACGCATAGCACCCGCTACGTGACCGTGA AGGACCAGTGGCATTCAAGAGGATCCACCTGGCTCTAC AGAGAGACATGCAATCTGAACTGCATGGTGACCATCAC CACCGCCCGGTCCAAGTACCCTTATCACTTCTTCGCCAC AAGCACCGGCGATGTGGTGGACATTTCCCCATTCTACAA CGGAACCAACCGGAACGCCTCTTACTTCGGCGAGAACG CCGACAAGTTCTTCATCTTCCCAAATTATACCATCGTGA GCGACTTCGGAAGACCTAACAGCGCCCTGGAGACACAC AGACTGGTGGCCTTCCTCGAGCGCGCCGACTCCGTGATC TCCTGGGACATCCAGGACGAGAAGAACGTGACTTGTCA GCTGACATTCTGGGAGGCCAGCGAACGGACCATCAGAA GCGAGGCTGAAGACTCCTACCACTTCAGCTCCGCCAAG ATGACCGCCACTTTCCTGTCAAAGAAGCAGGAGGTGAA CATGAGCGACAGCGCCTTGGATTGCGTGAGAGATGAGG CCATCAACAAGCTTCAACAGATCTTCAACACATCCTACA ACCAGACGTACGAGAAGTACGGAAACGTGAGCGTGTTC GAAACCACCGGCGGCTTAGTGGTGTTCTGGCAGGGAAT CAAGCAGAAGTCTCTGGTGGAGCTGGAGAGACTGGCTA ACAGATCCTCTCTAAACCTGACACACAACAGAACCAAG CGGAGCACAGACGGCAATAATGCCACACACCTGAGCAA CATGGAAAGCGTCCACAACCTCGTCTATGCCCAACTGC AGTTCACCTACGACACCCTCCGAGGCTACATCAACAGA GCCCTGGCCCAGATCGCCGAGGCTTGGTGTGTGGATCA GAGACGGACCCTGGAGGTGTTCAAGGAGTTGAGCAAGA TCAACCCGTCCGCCATCTTGAGCGCTATATACAACAAGC CAATTGCTGCGCGGTTCATGGGCGACGTGCTGGGCCTCG CCTCATGTGTGACCATTAATCAAACAAGCGTCAAGGTCC TGAGGGATATGAACGTTAAGGAGAGCCCAGGCAGGTGC TATAGCAGACCTGTGGTGATTTTCAACTTCGCCAACAGC AGCTACGTGCAGTACGGCCAGCTGGGCGAGGACAACGA GATCCTGCTGGGCAACCACCGCACTGAGGAGTGCCAGC TGCCAAGTCTGAAGATATTCATCGCGGGAAATTCAGCTT ACGAGTATGTAGACTACCTGTTCAAGAGAATGATAGAT CTTAGCAGCATCTCCACTGTGGACAGTATGATAGCTCTT GATATTGACCCACTGGAGAATACCGACTTCAGAGTGTT GGAGCTGTACAGTCAGAAGGAGCTCAGGAGCTCCAATG TGTTCGACCTGGAGGAGATCATGAGGGAATTCAATAGC TACAAGCAGCACCACCACCATCATCAC (SEQ ID NO: 126) | |
| SE_CMV_Trg B6XHis_055 | MESRIWCLVVCVN LCIVCLGAAVSSSS TRGTSATHSHHSS HTTSAAHSRSGSVS QRVTSSQTVSHGV NETIYNTTLKYGD VVGVNTTKYPYRV CSMAQGTDLIRFE RNIVCTSMKPINED LDEGIMVVYKRNI VAHTFKVRVYQK VLTFRRSYAYIHTT YLLGSNTEYVAPP MWEIHHINSHSQC YSSYSRVIAGTVFV AYHRDSYENKTM QLMPDDYSNTHST RYVTVKDQWHSR GSTWLYRETCNLN CMVTITTARSKYP | ATGGAATCCCGAATCTGGTGCCTCGTTGTGTGCGTGAAT TTGTGCATCGTGTGTTTGGGCGCCGCCGTCTCTTCTTCCT CCACACGTGGTACCAGCGCAACACACTCCCACCACTCA AGCCACACCACGTCCGCGGCACACAGCAGAAGCGGCAG TGTGAGCCAAAGGGTGACCAGCAGCCAGACCGTGAGTC ACGGCGTGAACGAGACAATCTACAATACCACACTCAAG TACGGCGATGTGGTGGGCGTCAACACCACCAAGTATCC TTACAGAGTCTGTTCCATGGCCCAGGGCACTGACCTGAT CCGGTTCGAAAGAAACATAGTGTGCACCTCCATGAAGC CTATCAATGAGGACCTCGATGAAGGCATTATGGTGGTG TACAAGAGGAATATTGTGGCCCATACCTTCAAGGTGAG AGTGTACCAGAAGGTGCTGACCTTCAGACGGAGCTACG CCTACATCCATACAACCTACCTGCTGGGAAGCAACACC GAGTACGTGGCTCCTCCAATGTGGGAGATCCACCACAT CAATAGCCACAGCCAGTGCTACTCCAGCTACAGCAGAG TGATTGCTGGCACCGTCTTCGTGGCTTACCACAGAGACA GCTATGAGAACAAGACAATGCAGCTCATGCCAGACGAC TACTCTAACACACATTCAACCCGGTATGTGACCGTGAAG GACCAGTGGCACTCAAGAGGCAGCACATGGCTCTACCG AGAGACATGTAACCTGAACTGCATGGTTACAATCACCA | C2/ CAP1/ T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | YHFFATSTGDVVDI SPFYNGTNRNASY FGENADKFFIFPNY TIVSDFGRPNSALE THRLVAFLERADS VISWDIQDEKNVT CQLTFWEASERTIR SEAEDSYHFSSAK MTATFLSKKQEVN MSDSALDCVRDEA INKLQQIFNTSYNQ TYEKYGNVSVFET TGGLVVFWQGIKQ KSLVELERLANRSS LNLTHNRTKRSTD GNNATHLSNMESV HNLVYAQLQFTYD TLRGYINRALAQIA EAWCVDQRRTLEV FKELSKINPSAILSA IYNKPIAARFMGD VLGLASCVTINQTS VKVLRDMNVKESP GRCYSRPVVIFNFA NSSYVQYGQLGED NEILLGNHRTEECQ LPSLKIFIAGNSAY EYVDYLFKRMIDL SSISTVDSMIALDID PLENTDFRVLELYS QKELRSSNVFDLEE IMREFNSYKQHHH HHH (SEQ ID NO: 83) | CTGCAAGGTCTAAGTACCCATATCACTTCTTCGCCACCT CTACCGGAGACGTGGTGGACATCAGCCCATTCTACAAT GGCACCAATCGGAACGCAAGCTACTTCGGAGAGAACGC CGACAAGTTCTTCATCTTCCCGAACTACACCATCGTGTC CGATTTCGGCAGGCCAAACAGCGCCCTGGAGACACACC GGCTGGTGGCCTTCCTGGAGCGCGCTGACTCCGTTATCT CTTGGGACATCCAGGATGAGAAGAATGTGACCTGCCAA CTGACATTCTGGGAGGCATCCGAGCGGACTATCAGAAG CGAGGCCGAGGACAGCTACCACTTCAGCAGCGCTAAGA TGACTGCTACCTTCCTGTCCAAGAAGCAGGAGGTGAAC ATGTCTGATTCCGCTCTGGACTGCGTGAGGGACGAGGCT ATCAACAAGCTCCAGCAGATATTCAATACTTCCTACAAC CAGACCTACGAGAAGTACGGTAACGTCAGCGTTTTCGA AACCACCGGCGGCCTGGTCGTGTTCTGGCAGGGAATCA AGCAGAAGTCCCTTGTCGAGCTCGAGAGACTGGCCAAC CGGTCTAGCCTCAATCTGACACACAATAGGACCAAGAG ATCTACTGACGGCAATAACGCCACACACCTCTCCAACAT GGAGAGTGTTCATAACCTGGTTTACGCCCAGCTGCAGTT CACTTACGATACCCTCCGCGGCTACATCAACAGGGCCCT GGCGCAGATCGCCGAGGCCTGGTGCGTGGATCAAAGAA GGACCCTGGAGGTCTTCAAGGAACTCAGCAAGATCAAC CCATCTGCTATCCTGAGCGCCATCTACAACAAGCCAATC GCCGCCCGGTTCATGGGCGACGTCCTGGGCTTGGCTAGC TGCGTGACCATCAATCAGACCAGCGTCAAGGTGCTTCG CGACATGAACGTCAAGGAGTCACCTGGCCGCTGTTACT CAAGGCCAGTCGTGATCTTCAATTTCGCCAATAGCTCCT ACGTGCAGTACGGACAGTTGGGCGAGGACAATGAAATA CTCCTGGGCAACCACCGCACCGAGGAGTGTCAGCTGCC AAGCCTGAAGATCTTCATCGCGGGAAACTCCGCTTACG AGTATGTGGACTACCTGTTCAAGAGAATGATTGATCTGA GCAGCATCTCCACCGTGGACAGCATGATTGCTCTGGATA TTGATCCTCTGGAGAACACCGATTTCCGCGTGCTGGAGC TGTACAGCCAGAAGGAATTAAGGAGCAGTAATGTGTTC GACCTGGAGGAGATCATGAGGGAGTTCAACAGTTACAA GCAGCACCACCATCACCACCAC (SEQ ID NO: 127) | |
| SE_CMV_Trg B6XHis_056 | MESRIWCLVVCVN LCIVCLGAAVSSSS TRGTSATHSHSS HTTSAAHSRSGSVS QRVTSSQTVSHGV NETIYNTTLKYGD VVGVNTTKYPYRV CSMAQGTDLIRFE RNIVCTSMKPINED LDEGIMVVYKRNI VAHTFKVRVYQK VLTFRRSYAYIHTT YLLGSNTEYVAPP MWEIHHINSHSQC YSSYSRVIAGTVFV AYHRDSYENKTM QLMPDDYSNTHST RYVTVKDQWHSR GSTWLYRETCNLN CMVTITTARSKYP YHFFATSTGDVVDI SPFYNGTNRNASY FGENADKFFIFPNY TIVSDFGRPNSALE THRLVAFLERADS VISWDIQDEKNVT CQLTFWEASERTIR SEAEDSYHFSSAK MTATFLSKKQEVN MSDSALDCVRDEA INKLQQIFNTSYNQ TYEKYGNVSVFET TGGLVVFWQGIKQ KSLVELERLANRSS LNLTHNRTKRSTD | ATGGAGTCCAGAATCTGGTGCTTGGTGGTGTGCGTGAAT CTTTGCATTGTGTGCCTCGGCGCCGCCGTGAGCAGCAGC AGTACTAGAGGTACCTCCGCTACCCACAGCCACCACTCT TCCCATACAACCAGCGCCGCCCACTCACGTAGCGGCTCT GTGAGCCAGAGGGTGACAAGCTCACAGACCGTGAGCCA CGGCGTGAACGAGACTATCTACAACACTACCCTGAAGT ACGGCGATGTGGTGGGAGTGAATACCACAAAGTACCCG TACAGGGTGTGTTCCATGGCCCAGGGCACCGACCTGATT CGCTTCGAAAGAAACATCGTCTGCACCAGCATGAAGCC TATCAACGAGGATTTGGATGAGGGTATTATGGTGGTCTA CAAGAGAAATATTGTGGCCCACACCTTCAAGGTCAGAG TGTACCAGAAGGTCCTGACGTTCAGGAGATCTTACGCTT ACATCCACACCACCTACCTTCTGGGCTCCAACACCGAGT ATGTGGCCCCGCCTATGTGGGAGATCCACCACATTAATT CCCACTCTCAATGCTACAGCTCCTATTCCAGAGTGATCG CCGGCACAGTCTTCGTGGCCTACCACCGGGACAGCTAT GAGAACAAGACTATGCAGCTCATGCCAGACGACTATAG CAATACTCATAGCACTAGATATGTGACTGTGAAGGACC AGTGGCATAGCAGAGGCAGCACTTGGCTGTACCGGGAA ACATGCAATCTTAATTGCATGGTCACCATAACCACCGCG AGATCCAAGTACCCTTACCACTTCTTCGCCACCTCCACT GGTGACGTCGTGGACATCTCCCCTTTCTATAACGGAACA AATAGAAACGCCAGCTACTTCGGTGAGAACGCCGACAA GTTCTTCATCTTCCCTAACTACACCATAGTGAGCGATTT CGGCAGACCGAACTCCGCTCTGGAGACACACCGGCTGG TGGCCTTCCTGGAACGGGCCGATAGTGTTATCTCTTGGG ATATTCAAGACGAGAAGAACGTCACCTGTCAGCTGACT TTCTGGGAAGCCAGCGAGAGGACCATCAGAAGTGAAGC TGAGGATAGCTACCATTTCTCTAGTGCCAAGATGACTGC CACCTTCCTGTCCAAGAAGCAGGAGGTCAACATGTCCG ACAGCGCCCTCGACTGTGTGAGAGACGAGGCTATTAAC AAGCTGCAGCAGATTTTCAACACTAGCTACAATCAGAC ATACGAGAAGTATGGAAACGTGAGCGTGTTCGAAACTA CCGGTGGCCTGGTGGTATTCTGGCAGGGCATCAAGCAG AAGTCCCTGGTGGAATTGGAGAGACTGGCTAACAGGTC | C2/ CAP1/ T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | GNNATHLSNMESV HNLVYAQLQFTYD TLRGYINRALAQIA EAWCVDQRRTLEV FKELSKINPSAILSA IYNKPIAARFMGD VLGLASCVTINQTS VKVLRDMNVKESP GRCYSRPVVIFNFA NSSYVQYGQLGED NEILLGNHRTEECQ LPSLKIFIAGNSAY EYVDYLFKRMIDL SSISTVDSMIALDID PLENTDFRVLELYS QKELRSSNVFDLEE IMREFNSYKQHHH HHH (SEQ ID NO: 83) | GTCCCTGAACCTGACTCACAATAGAACGAAGAGGAGCA CAGACGGCAATAATGCCACCCATCTGTCCAATATGGAG AGTGTGCACAATTTGGTGTATGCCCAGCTGCAGTTCACC TACGACACCCTCAGGGGCTACATCAACAGAGCCCTCGC CCAGATCGCTGAAGCCTGGTGCGTGGATCAGAGGAGGA CCCTGGAGGTCTTCAAGGAACTGAGCAAGATAAACCCA TCCGCCATCCTCAGTGCCATTTATAACAAGCCTATTGCC GCCAGGTTCATGGGCGACGTGCTGGGCCTGGCTTCCTGT GTCACGATTAATCAGACCTCCGTGAAGGTGCTGAGGGA CATGAACGTGAAGGAAAGCCCTGGACGGTGTTACAGCC GACCAGTAGTGATCTTCAACTTCGCCAACTCCTCATACG TGCAGTATGGCCAGCTGGGCGAGGACAATGAAATTCTG CTGGGCAACCACAGGACCGAAGAGTGCCAGCTGCCTAG CCTGAAGATATTCATCGCCGGTAATAGCGCCTACGAGT ACGTCGACTATCTTTTCAAGAGAATGATCGATCTGTCTA GCATTTCTACCGTGGATTCCATGATCGCTCTTGACATTG ACCCACTGGAGAACACAGACTTCAGGGTGCTCGAGCTG TATTCCCAGAAGGAACTCAGGTCTAGCAACGTTTTCGAC CTCGAGGAAATTATGAGAGAGTTCAACTCGTACAAGCA ACACCATCACCACCATCAC (SEQ ID NO: 128) | |
| SE_CMV_Trg B6XHis_057 | MESRIWCLVVCVN LCIVCLGAAVSSSS TRGTSATHSHHSSCT HTTSAAHSRSGSVS QRVTSSQTVSHGV NETIYNTTLKYGD VVGVNTTKYPYRV CSMAQGTDLIRFE RNIVCTSMKPINED LDEGIMVVYKRNI VAHTFKVRVYQK VLTFRRSYAYIHTT YLLGSNTEYVAPP MWEIHHINSHSQC YSSYSRVIAGTVFV AYHRDSYENKTM QLMPDDYSNTHST RYVTVKDQWHSR GSTWLYRETCNLN CMVTITTARSKYP YHFFATSTGDVVDI SPFYNGTNRNASY FGENADKFFIFPNY TIVSDFGRPNSALE THRLVAFLERADS VISWDIQDEKNVT CQLTFWEASERTIR SEAEDSYHFSSAK MTATFLSKKQEVN MSDSALDCVRDEA INKLQQIFNTSYNQ TYEKYGNVSVFET TGGLVVFWQGIKQ KSLVELERLANRSS LNLTHNRTKRSTD GNNATHLSNMESV HNLVYAQLQFTYD TLRGYINRALAQIA EAWCVDQRRTLEV FKELSKINPSAILSA IYNKPIAARFMGD VLGLASCVTINQTS VKVLRDMNVKESP GRCYSRPVVIFNFA NSSYVQYGQLGED NEILLGNHRTEECQ LPSLKIFIAGNSAY EYVDYLFKRMIDL SSISTVDSMIALDID PLENTDFRVLELYS | ATGGAGAGCCGGATCTGGTGCCTCGTGGTGTGCGTGAA CTTATGCATCGTGTGCCTCGGCGCCGCCGTGAGCTCTAG CTACCCGGGGCACCAGCGCCACCCCACAGCCACCACA GCAGCCACACCACCTCGGCCGCTCACAGCCGGAGCGGC AGCGTGAGCCAGCGGGTGACCTCCAGCCAGACCGTGTC CCACGGCGTGAACGAGACGATCTACAACACCACCCTGA AGTACGGCGACGTGGTGGGAGTGAACACGACCAAGTAC CCCTACCGGGTGTGCAGCATGGCCCAGGGCACCGACCT GATCCGGTTCGAGCGGAACATTGTGTGCACCAGCATGA AGCCCATCAACGAGGACCTGGACGAGGGCATCATGGTA GTGTACAAGAGAAACATCGTGGCCCACACCTTCAAGGT GCGGGTGTACCAGAAGGTGCTGACCTTCCGGCGGAGCT ACGCCTACATTCACACAACATACCTGCTGGGCAGCAAC ACCGAGTACGTGGCTCCTCCCATGTGGGAGATCCACCA CATCAACTCTCATAGCCAGTGCTACAGCAGCTACAGCC GGGTGATCGCCGGCACCGTGTTCGTGGCCTACCACCGG GACAGCTACGAGAACAAGACCATGCAGCTGATGCCCGA CGACTATAGCAACACACACTCCACTCGGTACGTGACCG TGAAGGACCAGTGGCACAGCAGAGGCAGCACCTGGCTG TACCGGGAGACTTGCAACCTGAACTGCATGGTGACCAT CACCACCGCCCGGTCTAAGTACCCTTACCACTTCTTCGC CACCAGCACCGGCGATGTGGTGGACATCAGCCCCTTCT ACAACGGCACCAACCGGAACGCCAGCTACTTCGGCGAG AACGCCGACAAGTTCTTCATCTTCCCCAACTACACCATC GTGAGCGACTTCGGCCGGCCCAACAGCGCCCTGGAAAC TCACCGGCTGGTGGCCTTCCTGGAGCGGGCCGACAGCG TGATCAGCTGGGACATCCAGGACGAGAAGAACGTGACC TGCCAGCTGACATTCTGGGAGGCCAGCGAGCGGACCAT CCGGAGCGAGGCCGAGGATAGCTATCACTTCAGCAGCG CCAAGATGACCGCCACCTTCCTGAGCAAGAAGCAGGAG GTGAACATGAGCGATTCTGCACTGGACTGCGTGCGGGA CGAGGCCATCAACAAGCTGCAGCAGATCTTCAACACCA GCTACAACCAGACCTACGAGAAGTACGGAAACGTGAGC GTGTTCGAGACTACCGGCGGCCTTGTCGTGTTCTGGCAG GGAATCAAGCAGAAGTCCCTGGTCGAGCTCGAGCGACT GGCCAACAGAAGCAGCCTGAACCTGACCCACAACCGGA CCAAGCGGAGCACCGACGGCAACAACGCCACACACCTG TCTAACATGGAGTCTGTGCACAACCTGGTGTACGCCCAG CTGCAGTTCACCTACGACACCCTGCGGGGCTACATCAAC CGGGCCCTGGCCCAGATCGCCGAGGCATGGTGCGTGGA CCAGCGGCGGACCCTGGAGGTGTTCAAGGAGCTCTCTA AGATCAACCCCGTCTGCCATCCTGAGCGCCATTTACAACA AGCCTATCGCCGCAAGATTCATGGGCGACGTCCTGGGC CTGGCCAGCTGCGTGACGATCAATCAGACCAGCGTGAA GGTCCTGCGGGACATGAACGTCAAGGAGAGCCCCGGCA GGTGCTATAGCCGGCCCGTGGTGATTTTCAACTTCGCCA ATAGCTCTTACGTGCAGTACGGTCAGTTAGGCGAGGAC AACGAGATCTTACTGGGCAACCACCGGACCGAGGAGTG CCAACTCCCGAGCCTCAAGATTTTCATTGCCGGCAATAG CGCATACGAATATGTGGACTACCTGTTCAAGCGGATGA | C2/ CAP1/ T100 |

TABLE 13-continued

| Additional hCMV Vaccine Constructs | | | |
|---|---|---|---|
| Antigen Name | Protein Sequence | Nucleotide Sequence (Open Reading Frames) | Tested Chemistry mRNA Chemistry/ Cap/ Tail |
| | QKELRSSNVFDLEE IMREFNSYKQHHH HHH (SEQ ID NO: 83) | TCGACCTGAGCAGCATCAGCACCGTGGACAGCATGATT GCTCTGGACATCGACCCTCTGGAGAACACCGACTTCCG GGTGCTGGAGCTGTACAGCCAGAAGGAGCTGCGGAGCT CTAATGTGTTCGACCTGGAGGAGATCATGCGGGAGTTC AACTCATATAAGCAGCACCACCACCATCATCAC (SEQ ID NO: 129) | |
| SE_CMV_Trg B6XHis_058 | MESRIWCLVVCVN LCIVCLGAAVSSSS TRGTSATHSHHSSCT HTTSAAHSRSGSVS QRVTSSQTVSHGV NETIYNTTLKYGD VVGVNTTKYPYRV CSMAQGTDLIRFE RNIVCTSMKPINED LDEGIMVVYKRNI VAHTFKVRVYQK VLTFRRSYAYIHTT YLLGSNTEYVAPP MWEIHHINSHSQC YSSYSRVIAGTVFV AYHRDSYENKTM QLMPDDYSNTHST RYVTVKDQWHSR GSTWLYRETCNLN CMVTITTARSKYP YHFFATSTGDVVDI SPFYNGTNRNASY FGENADKFFIFPNY TIVSDFGRPNSALE THRLVAFLERADS VISWDIQDEKNVT CQLTFWEASERTIR SEAEDSYHFSSAK MTATFLSKKQEVN MSDSALDCVRDEA INKLQQIFNTSYNQ TYEKYGNVSVFET TGGLVVFWQGIKQ KSLVELERLANRSS LNLTHNRTKRSTD GNNATHLSNMESV HNLVYAQLQFTYD TLRGYINRALAQIA EAWCVDQRRTLEV FKELSKINPSAILSA IYNKPIAARFMGD VLGLASCVTINQTS VKVLRDMNVKESP GRCYSRPVVIFNFA NSSYVQYGQLGED NEILLGNHRTEECQ LPSLKIFIAGNSAY EYVDYLFKRMIDL SSISTVDSMIALDID PLENTDFRVLELYS QKELRSSNVFDLEE IMREFNSYKQHHH HHH (SEQ ID NO: 83) | ATGGAGAGCCGGATCTGGTGCCTCGTGGTGTGCGTGAA CCTTTGCATCGTGTGCTTGGGCGCCGCCGTGAGCAGCAG CCACCCGGGGCACCTCCGCCACCCACTCCCACCACTC CTCCCACACCACCTCAGCCGCCCACTCTCGCTCCGGCTC CGTCTCCCAGCGCGTCACCTCCAGCCAGACCGTTAGCCA CGGCGTCAACGAAACCATCTACAACACCACCCTCAAGT ACGGCGACGTCGTCGGCGTAAACACAACCAAGTACCCC TACCGCGTCTGCTCCATGGCCCAGGGCACCGACCTCATC CGCTTCGAGCGCAACATCGTCTGCACCTCCATGAAGCCC ATCAACGAGGACCTCGACGAGGGCATCATGGTCGTCTA CAAGCGCAATATTGTGGCCCACACCTTCAAGGTCCGCGT CTACCAGAAGGTCCTCACCTTCCGCCGCTCCTACGCCTA CATCCACACAACCTACCTCCTCGGCTCCAACACCGAGTA CGTCGCCCCTCCCATGTGGGAGATCCACCACATCAACA GCCACAGCCAGTGCTACTCCTCCTACTCCCGCGTCATCG CCGGCACCGTCTTCGTCGCCTACCACCGCGACTCCTACG AGAACAAGACCATGCAGCTCATGCCCGACGACTACAGC AATACCCACAGCACCCGCTACGTCACCGTCAAGGACCA GTGGCACAGCAGAGGCTCCACCTGGCTCTACCGCGAGA CATGCAACCTCAACTGCATGGTCACCATCACCACCGCCC GCTCCAAGTATCCTTACCACTTCTTCGCCACCTCCACCG GCGATGTCGTGGACATCTCACCATTCTACAACGGCACCA ACCGCAACGCCAGTTACTTCGGCGAGAACGCCGACAAG TTCTTCATCTTCCCCAACTACACCATCGTCTCCGACTTCG GCCGCCCCAACTCCGCCCTCGAGACACACAGACTGGTG GCCTTCCTCGAGCGCGCCGACTCCGTCATCTCCTGGGAC ATCCAGGACGAGAAGAACGTCACCTGCCAGCTCACATT CTGGGAGGCCTCCGAGCGCACCATCCGCTCCGAGGCCG AGGACTCATACCATTTCTCCAGCGCCAAGATGACCGCC ACCTTCCTCTCCAAGAAGCAGGAGGTCAACATGAGCGA CAGCGCTCTCGACTGCGTCCGCGACGAGGCCATCAACA AGCTCCAGCAGATCTTCAACACCTCCTACAACCAGACGT ACGAGAAGTATGGAAACGTCAGTGTCTTCGAAACCACG GGCGGCCTGGTTGTATTCTGGCAGGGAATAAAGCAGAA GTCCCTCGTCGAGCTTGAGCGCCTCGCCAACCGCTCCTC CCTCAACCTCACCCACAACCGCACCAAGCGCTCCACCG ACGGCAACAACGCTACCCACCTGTCCAACATGGAGTCC GTCCACAACCTCGTCTACGCCCAGCTCCAGTTCACCTAC GACACCCTCCGCGGCTACATCAACCGCGCCCTCGCCCA GATCGCCGAGGCCTGGTGCGTCGACCAGCGCCGCACCC TCGAGGTCTTCAAGGAGCTGAGTAAGATCAACCCTAGC GCGATCCTCAGCGCTATCTATAACAAGCCAATCGCTGCT AGGTTCATGGGAGACGTGCTCGGCCTCGCCTCCTGCGTG ACCATCAATCAGACATCCGTGAAGGTGCTGCGCGACAT GAATGTCAAGGAGAGCCCAGGCCGCTGTTATTCCCGGC CCGTCGTCATTTTCAATTTCGCCAATAGCTCTTACGTCC AGTACGGCCAGCTCGGCGAGGACAACGAGATCCTGCTG GGCAACCACCGCACCGAGGAGTGCCAGCTGCCTAGCCT CAAGATTTTCATTGCCGGCAATTCCGCTTACGAATACGT GGACTACCTCTTCAAGCGCATGATCGACCTCTCCTCCAT CTCCACCGTCGACTCCATGATCGCCCTGGATATCGACCC TCTCGAGAACACCGACTTCCGCGTGTTGGAGCTCTACTC CCAGAAGGAGCTCAGATCCAGCAACGTATTCGACCTCG AGGAGATCATGCGCGAGTTCAACTCCTATAAGCAGCAC CACCACCATCATCAC (SEQ ID NO: 130) | C2/ CAP1/ T100 |
| SE_CMV_Trg B6XHis_059 | MESRIWCLVVCVN LCIVCLGAAVSSSS TRGTSATHSHHSS HTTSAAHSRSGSVS QRVTSSQTVSHGV NETIYNTTLKYGD VVGVNTTKYPYRV CSMAQGTDLIRFE | ATGGAGAGCCGGATCTGGTGCTTGGTGGTGTGCGTGAA CTTGTGCATCGTGTGCTTGGGCGCCGCCGTGAGCAGCTC TAGCACCCGGGGCACCAGCGCCACCCACAGCCACCACA GCAGCCACACGACCTCCGCCGCCCACTCACGGAGCGGC AGCGTGAGCCAGCGGGTGACCAGCTCACAGACCGTGTC CCACGGCGTGAACGAGACGATCTACAACACCACCCTGA AGTACGGCGACGTGGTGGGCGTCAACACTACCAAGTAC CCCTACCGGGTGTGCAGCATGGCCCAGGGCACCGACCT | C2/ CAP1/ T100 |

TABLE 13-continued

| Additional hCMV Vaccine Constructs | | | |
|---|---|---|---|
| Antigen Name | Protein Sequence | Nucleotide Sequence (Open Reading Frames) | Tested Chemistry mRNA Chemistry/ Cap/ Tail |
| | RNIVCTSMKPINED LDEGIMVVYKRNI VAHTFKVRVYQK VLTFRRSYAYIHTT YLLGSNTEYVAPP MWEIHHINSHSQC YSSYSRVIAGTVFV AYHRDSYENKTM QLMPDDYSNTHST RYVTVKDQWHSR GSTWLYRETCNLN CMVTITTARSKYP YHFFATSTGDVVDI SPFYNGTNRNASY FGENADKFFIFPNY TIVSDFGRPNSALE THRLVAFLERADS VISWDIQDEKNVT CQLTFWEASERTIR SEAEDSYHFSSAK MTATFLSKKQEVN MSDSALDCVRDEA INKLQQIFNTSYNQ TYEKYGNVSVFET TGGLVVFWQGIKQ KSLVELERLANRSS LNLTHNRTKRSTD GNNATHLSNMESV HNLVYAQLQFTYD TLRGYINRALAQIA EAWCVDQRRTLEV FKELSKINPSAILSA IYNKPIAARFMGD VLGLASCVTINQTS VKVLRDMNVKESP GRCYSRPVVIFNFA NSSYVQYGQLGED NEILLGNHRTEECQ LPSLKIFIAGNSAY EYVDYLFKRMIDL SSISTVDSMIALDID PLENTDFRVLELYS QKELRSSNVFDLEE IMREFNSYKQHHH HHH (SEQ ID NO: 83) | GATCCGGTTCGAGCGGAATATTGTGTGTACCAGCATGA AGCCCATCAACGAGGACCTGGACGAGGGCATCATGGTG GTCTACAAGAGAAACATTGTGGCCCACACCTTCAAGGT GCGGGTGTACCAGAAGGTGCTGACCTTCCGGCGGAGCT ACGCCTACATCCATACAACCTACCTGCTGGGCAGCAAC ACCGAGTACGTGGCGCCTCCCATGTGGGAGATCCACCA CATCAACTCTCACTCGCAGTGCTACAGCAGCTACAGCCG GGTGATCGCCGGCACCGTGTTCGTGGCCTACCACCGGG ACAGCTACGAGAACAAGACCATGCAGCTGATGCCCGAC GACTATTCTAACACCCACTCCACCAGATACGTGACCGTG AAGGACCAGTGGCACAGCAGGGGCAGCACCTGGCTGTA CCGGGAGACTTGCAACCTGAACTGCATGGTGACCATCA CCACCGCCCGGAGTAAGTATCCATATCACTTCTTCGCCA CCAGCACGGGCGACGTTGTGGACATCAGCCCCTTCTAC AACGGCACCAACCGGAACGCCAGCTACTTCGGCGAGAA CGCCGACAAGTTCTTCATCTTCCCCAACTACACCATCGT GAGCGACTTCGGCCGGCCCAACAGCGCCCTGGAAACCC ACCGGCTGGTGGCCTTCCTGGAGCGGGCCGACAGCGTG ATCAGCTGGGACATCCAGGACGAGAAGAACGTGACCTG CCAGCTGACTTTCTGGGAGGCCAGCGAGCGGACCATCC GGAGCGAGGCCGAAGACTCCTACCACTTCAGCAGCGCC AAGATGACCGCCACCTTCCTGAGCAAGAAGCAGGAGGT GAACATGAGCGATTCAGCTCTGGACTGCGTGCGGGACG AGGCCATCAACAAGCTGCAGCAGATCTTCAACACCAGC TACAACCAGACTTACGAGAAGTATGGAAACGTGAGCGT GTTCGAGACAACCGGCGGCCTCGTGGTGTTCTGGCAGG GTATCAAGCAGAAGTCTCTCGTGGAGCTGGAGAGACTG GCCAACAGAAGCAGCCTGAACCTGACCCACAACCGGAC CAAGCGGAGCACCGACGGCAACAACGCTACCCATCTGT CTAACATGGAGTCAGTGCACAACCTGGTGTACGCCCAG CTGCAGTTCACCTACGACACCCTGCGGGGCTACATCAAC CGGGCCCTGGCCCAGATCGCCGAGGCCTGGTGCGTGGA CCAGCGGCGGACCCTGGAGGTGTTCAAGGAGCTGTCCA AGATCAACCCTTCCGCCATCCTGAGCGCCATTTATAATA AGCCGATCGCCGCCCGGTTCATGGGCGATGTTCTGGGCC TGGCCAGCTGCGTCACCATTAATCAGACCAGCGTTAAG GTCCTGCGGGACATGAATGTCAAGGAGAGCCCCGGCAG GTGCTACTCCCGCCCCGTGGTGATATTCAACTTCGCCAA CTCTAGCTACGTGCAGTACGGCCAACTAGGCGAGGACA ACGAGATCTTGCTCGGTAACCACCGGACCGAGGAGTGC CAGTTACCTTCCCTGAAGATTTTCATCGCGGGCAACTCC GCCTACGAGTATGTGGACTACCTGTTCAAGCGGATGATC GATCTTTCTAGCATCAGCACCGTGGACAGCATGATAGCC CTGGACATCGACCCACTGGAGAACACCGACTTCCGGGT GCTGGAGCTGTACAGCCAGAAGGAGCTTCGGAGCAGCA ATGTGTTCGACCTGGAGGAGATCATGCGGGAGTTCAAT TCTTACAAGCAGCACCACCACCATCATCAC (SEQ ID NO: 131) | |
| SE_CMV_Trg B6XHis_060 | MESRIWCLVVCVN LCIVCLGAAVSSSS TRGTSATHSHHSSCT HTTSAAHSRSGSVS QRVTSSQTVSHGV NETIYNTTLKYGD VVGVNTTKYPYRV CSMAQGTDLIRFE RNIVCTSMKPINED LDEGIMVVYKRNI VAHTFKVRVYQK VLTFRRSYAYIHTT YLLGSNTEYVAPP MWEIHHINSHSQC YSSYSRVIAGTVFV AYHRDSYENKTM QLMPDDYSNTHST RYVTVKDQWHSR GSTWLYRETCNLN CMVTITTARSKYP YHFFATSTGDVVDI SPFYNGTNRNASY FGENADKFFIFPNY | ATGGAGAGCCGGATCTGGTGCCTCGTGGTGTGCGTGAA CCTCTGCATCGTGTGCCTCGGCGCCGCCGTGTCTTCATC CCACCCGGGGCACCTCCGCCACCCACTCCCACCACTC CTCCCACACCACTAGTGCCGCCCACTCACGCTCCGGCTC CGTCTCCCAGCGCGTCACCTCATCCCAGACAGTGAGCCA CGGCGTCAACGAAACCATCTACAACACCACCCTCAAGT ACGGCGACGTCGTGGGCGTGAACACTACAAAGTACCCC TACCGCGTCTGCTCCATGGCCCAGGGCACCGACCTGATC CGCTTCGAGCGCAACATCGTCTGCACCTCCATGAAGCCC ATCAACGAGGACCTCGACGAGGGCATCATGGTCGTCTA CAAGAGGAACATTGTGGCCCACACCTTCAAGGTCCGCG TCTACCAGAAGGTCCTCACCTTCCGCCGCTCCTACGCCT ACATCCACACTACGTACCTCCTCGGCTCCAACACCGAGT ACGTCGCCCCTCCCATGTGGGAGATCCACCACATCAACT CGCACAGCCAGTGCTACTCCTCCTACTCCCGCGTCATCG CCGGCACCGTCTTCGTCGCCTACCACCGCGACTCCTACG AGAACAAGACCATGCAGCTCATGCCCGACGACTATAGC AACACACATAGCACCCGCTACGTCACCGTCAAGGACCA GTGGCATAGCAGAGGCTCCACCTGGCTCTACCGCGAGA CGTGCAACCTCAACTGCATGGTCACCATCACCACCGCCC GCAGCAAGTATCCATATCACTTCTTCGCCACCTCCACAG GAGACGTGGTCGACATCTCGCCTTTCTACAACGGCACCA ACCGCAACGCTAGCTACTTCGGCGAGAACGCCGACAAG | C2/ CAP1/ T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | TIVSDFGRPNSALE THRLVAFLERADS VISWDIQDEKNVT CQLTFWEASERTIR SEAEDSYHFSSAK MTATFLSKKQEVN MSDSALDCVRDEA INKLQQIFNTSYNQ TYEKYGNVSVFET TGGLVVFWQGIKQ KSLVELERLANRSS LNLTHNRTKRSTD GNNATHLSNMESV HNLVYAQLQFTYD TLRGYINRALAQIA EAWCVDQRRTLEV FKELSKINPSAILSA IYNKPIAARFMGD VLGLASCVTINQTS VKVLRDMNVKESP GRCYSRPVVIFNFA NSSYVQYGQLGED NEILLGNHRTEECQ LPSLKIFIAGNSAY EYVDYLFKRMIDL SSISTVDSMIALDID PLENTDFRVLELYS QKELRSSNVFDLEE IMREFNSYKQHHH HHH (SEQ ID NO: 83) | TTCTTCATCTTCCCCAACTACACCATCGTCTCCGACTTCG GCCGCCCCAACTCCGCCCTCGAGACTCACCGCTTGGTGG CCTTCCTCGAGCGCGCCGACTCCGTCATCTCCTGGGACA TCCAGGACGAGAAGAACGTCACCTGCCAGCTGACCTTC TGGGAGGCCTCCGAGCGCACCATCCGCTCCGAGGCCGA GGACAGCTACCACTTCAGCAGCGCCAAGATGACCGCCA CCTTCCTCTCCAAGAAGCAGGAGGTCAACATGAGCGAC AGCGCCCTTGACTGCGTCCGCGACGAGGCCATCAACAA GCTCCAGCAGATCTTCAACACCTCCTACAACCAGACTTA TGAGAAGTACGGAAACGTCTCCGTTTTCGAGACAACAG GAGGCCTGGTTGTCTTCTGGCAGGGCATTAAGCAGAAG TCCCTCGTCGAGCTGGAGAGACTCGCCAACCGCTCCTCC CTCAACCTCACCCACAACCGCACCAAGCGCTCCACCGA CGGCAACAATGCTACACACCTGAGCAACATGGAGTCCG TCCACAACCTCGTCTACGCCCAGCTCCAGTTCACCTACG ACACCCTCCGCGGCTACATCAACCGCGCCCTCGCCCAG ATCGCCGAGGCGTGGTGCGTCGACCAGCGCCGCACCCT CGAGGTCTTCAAGGAGCTGTCCAAGATCAACCCTAGCG CCATCCTGTCCGCAATCTATAACAAGCCTATCGCGGCTA GGTTCATGGGCGATGTGCTCGGCCTCGCCTCCTGCGTGA CTATTAATCAGACCAGCGTCAAGGTGCTGCGCGACATG AACGTGAAGGAGAGCCCTGGCCGCTGCTATTCCAGGCC CGTCGTCATCTTCAATTTCGCCAATTCCAGCTATGTCCA GTACGGCCAGCTCGGCGAGGACAACGAGATCCTGCTTG GCAACCACCGCACCGAGGAGTGTCAGCTCCCTAGCCTG AAGATTTTCATTGCCGGCAATAGCGCTTATGAGTATGTG GACTACCTCTTCAAGCGCATGATCGACCTCTCCTCCATC TCCACCGTCGACTCCATGATCGCCCTGGACATCGACCCA CTGGAGAACACCGACTTCCGCGTGCTCGAACTCTACTCC CAGAAGGAACTGAGATCAAGCAACGTGTTCGACCTCGA GGAGATCATGCGCGAGTTCAACTCTTATAAGCAGCACC ACCACCATCATCAC (SEQ ID NO: 132) | |
| SE_CMV_ UL130_021 | MLRLLLRHHFHCL LLCAVWATPCLAS PWSTLTANQNPSPP WSKLTYSKPHDAA TFYCPFLYPSPPRSP LQFSGFQRVSTGPE CRNETLYLLYNRE GQTLVERSSTWVK KVIWYLSGRNQTIL QRMPRTASKPSDG NVQISVEDAKIFGA HMVPKQTKLLRFV VNDGTRYQMCVM KLESWAHVFRDYS VSFQVRLTFTEAN NQTYTFCTHPNLIV (SEQ ID NO: 65) | ATGCTCAGACTTCTCCTCAGACACCACTTCCACTGCCTC TTGCTTTGTGCCGTCTGGGCCACACCTTGCCTCGCCAGC CCTTGGAGCACCTTGACAGCCAACCAGAACCCTTCCCCT CCTTGGTCAAAGTTGACCTACAGCAAGCCTCACGACGCT GCTACCTTCTACTGTCCATTCCTGTACCCTAGCCCTCCA AGATCTCCGCTGCAGTTCAGCGGCTTCCAGAGGGTGTCT ACCGGACCTGAGTGCAGGAATGAGACGCTGTACCTGCT GTACAACAGAGAGGGCCAGACCCTGGTGGAAAGAAGCT CCACCTGGGTCAAGAAGGTAATCTGGTACCTGAGCGGC AGAAACCAGACAATACTCCAGAGAATGCCACGGACCGC TAGCAAGCCTAGCGATGGAAACGTGCAGATTAGCGTGG AGGACGCAAAGATTTTCGGCGCCCACATGGTGCCAAAG CAGACAAAGCTGCTGCGGTTCGTGGTCAACGACGGCAC CCGGTACCAGATGTGCGTGATGAAGCTGGAGAGCTGGG CTCACGTGTTCAGAGATTACTCTGTGAGCTTCCAAGTGC GGCTCACCTTCACCGAAGCCAACAATCAGACCTACACTT TCTGTACTCACCCTAACCTGATCGTG (SEQ ID NO: 133) | C2/ CAP1/ T100 |
| SE_CMV_ UL130_022 | MLRLLLRHHFHCL LLCAVWATPCLAS PWSTLTANQNPSPP WSKLTYSKPHDAA TFYCPFLYPSPPRSP LQFSGFQRVSTGPE CRNETLYLLYNRE GQTLVERSSTWVK KVIWYLSGRNQTIL QRMPRTASKPSDG NVQISVEDAKIFGA HMVPKQTKLLRFV VNDGTRYQMCVM KLESWAHVFRDYS VSFQVRLTFTEAN NQTYTFCTHPNLIV (SEQ ID NO: 65) | ATGCTTAGACTCCTCCTCAGACACCACTTCCATTGTCTC CTTTTGTGCGCCGTGTGGGCCACCCCTTGCCTTGCATCA CCTTGGTCTACCCTCACCGCCAACCAGAACCCTAGCCCT CCTTGGAGTAAGTTAACATACTCTAAGCCGCACGACGC CGCCACCTTCTACTGTCCTTTCCTCTACCCAAGCCCACCT CGTAGCCCACTTCAGTTCTCTGGATTCCAGAGAGTTTCA ACAGGCCCTGAGTGTCGGAACGAGACTCTGTACCTGTT GTATAACAGAGAGGGACAGACCCTGGTGGAGCGGTCCT CCACCTGGGTGAAGAAGGTGATCTGGTATCTGAGCGGC AGAAACCAGACCATCCTGCAGCGGATGCCAAGGACCGC TAGCAAGCCAAGCGACGGCAATGTGCAGATTAGCGTGG AGGATGCTAAGATTTTCGGCGCACACATGGTTCCTAAGC AGACCAAGCTGTTACGGTTCGTGGTGAACGATGGAACT CGGTACCAAATGTGCGTGATGAAGCTGGAGTCATGGGC ACATGTGTTCCGTGACTACTCTGTTTCTTTCCAGGTGCG CCTGACCTTCACCGAGGCCAATAACCAGACATACACCTT CTGTACGCACCCAAATCTGATCGTA (SEQ ID NO: 134) | C2/ CAP1/ T100 |
| SE_CMV_ UL130_023 | MLRLLLRHHFHCL LLCAVWATPCLAS | ATGCTCAGACTTTTGCTCAGACACCACTTCCACTGTTTG TTGTTATGTGCCGTGTGGGCTACCCCTTGCCTCGCATCT | C2/ CAP1/ |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | PWSTLTANQNPSPP WSKLTYSKPHDAA TFYCPFLYPSPPRSP LQFSGFQRVSTGPE CRNETLYLLYNRE GQTLVERSSTWVK KVIWYLSGRNQTIL QRMPRTASKPSDG NVQISVEDAKIFGA HMVPKQTKLLRFV VNDGTRYQMCVM KLESWAHVFRDYS VSFQVRLTFTEAN NQTYTFCTHPNLIV (SEQ ID NO: 65) | CCGTGGTCCACACTCACAGCCAACCAGAATCCTTCTCCT CCTTGGAGCAAGCTCACATATAGCAAGCCTCACGACGC GGCAACCTTCTACTGCCCATTCCTGTATCCTTCTCCTCCG CGGAGCCCTCTGCAGTTCTCCGGATTCCAGAGAGTGTCC ACCGGTCCTGAGTGCAGAAATGAAACACTGTATCTTCTC TACAACAGAGAGGGCCAGACCCTTGTGGAGAGAAGCAG CACCTGGGTGAAGAAGGTCATTTGGTATCTGTCTGGCAG AAACCAGACCATACTGCAGCGGATGCCAAGAACAGCCT CCAAGCCATCCGACGGTAACGTGCAGATCTCCGTGGAG GACGCCAAGATTTTCGGCGCCCACATGGTGCCAAAGCA GACCAAGCTGCTGAGATTCGTGGTGAACGATGGCACCA GGTACCAGATGTGCGTTATGAAGCTTGAGTCCTGGGCTC ACGTGTTCAGAGACTACTCTGTGAGCTTCCAGGTGAGAC TGACATTCACAGAGGCCAACAACCAGACTTACACCTTCT GCACGCATCCTAATCTGATCGTG (SEQ ID NO: 135) | T100 |
| SE_CMV_ UL130_024 | MLRLLLRHHFHCL LLCAVWATPCLAS PWSTLTANQNPSPP WSKLTYSKPHDAA TFYCPFLYPSPPRSP LQFSGFQRVSTGPE CRNETLYLLYNRE GQTLVERSSTWVK KVIWYLSGRNQTIL QRMPRTASKPSDG NVQISVEDAKIFGA HMVPKQTKLLRFV VNDGTRYQMCVM KLESWAHVFRDYS VSFQVRLTFTEAN NQTYTFCTHPNLIV (SEQ ID NO: 65) | ATGCTCAGACTTCTTCTCAGACACCACTTCCACTGTTTG CTTCTCTGCGCAGTGTGGGCAACCCCTTGCCTTGCTTCC CCTTGGTCGCTCTCACCGCCAACCAGAATCCAAGCCCT CCTTGGAGCAAGCTCACTTACAGCAAGCCGCACGACGC CGCCACCTTCTACTGTCCTTTCCTGTACCCTAGCCCTCCA AGATCTCCTCTGCAATTCTCTGGATTCCAGAGAGTGAGC ACCGGCCCAGAGTGCCGGAACGAGACTCTGTATCTGCT GTACAATAGGGAGGGACAAACCCTGGTGGAGAGGAGC AGCACATGGGTGAAGAAGGTGATCTGGTACCTGAGCGG CAGAAACCAGACCATCCTGCAGAGAATGCCACGGACCG CCAGCAAGCCAAGCGATGGCAACGTCCAGATTAGCGTG GAAGACGCCAAGATCTTCGGAGCCCACATGGTGCCTAA GCAGACCAAGCTTCTGCGATTCGTGGTGAACGACGGTA CCCGCTACCAAATGTGCGTGATGAAGCTGGAGTCATGG GCCCACGTCTTCCGCGACTACAGCGTATCCTTCCAGGTG AGGCTTACCTTCACCGAGGCCAACAACCAAACCTACAC ATTCTGCACCCATCCAAATTTGATTGTG (SEQ ID NO: 136) | C2/ CAP1/ T100 |
| SE_CMV_ UL130_025 | MLRLLLRHHFHCL LLCAVWATPCLAS PWSTLTANQNPSPP WSKLTYSKPHDAA TFYCPFLYPSPPRSP LQFSGFQRVSTGPE CRNETLYLLYNRE GQTLVERSSTWVK KVIWYLSGRNQTIL QRMPRTASKPSDG NVQISVEDAKIFGA HMVPKQTKLLRFV VNDGTRYQMCVM KLESWAHVFRDYS VSFQVRLTFTEAN NQTYTFCTHPNLIV (SEQ ID NO: 65) | ATGCTCAGACTATTGTTGAGACATCACTTCCATTGCCTC CTTTTGTGCGCCGTGTGGGCTACCCCTTGCCTCGCCTCA CCTTGGAGCACCTTGACCGCCAACCAGAACCCGAGCCC TCCGTGGTCAAAGCTCACCTACAGCAAGCCTCACGACG CCGCAACCTTCTATTGTCCATTCCTGTACCCTTCTCCGCC GAGGTCCCCTCTTCAGTTCAGCGGATTCCAGAGAGTGTC TACCGGACCAGAATGCAGAAACGAAACACTGTATCTGC TGTACAACCGGGAGGGCCAGACCCTGGTCGAGCGGAGC TCTACCTGGGTCAAGAAGGTTATATGGTATCTGAGCGGC AGGAACCAGACCATCCTGCAGCGCATGCCTAGAACCGC TAGCAAGCCAAGCGACGGCAACGTTCAGATCTCCGTGG AGGACGCTAAGATCTTCGGCGCCCATATGGTGCCAAAG CAGACTAAGCTGCTGAGATTCGTGGTAAACGACGGCAC AAGATATCAGATGTGCGTGATGAAGCTGGAGAGCTGGG CTCATGTGTTCAGGGACTACTCCGTGAGTTTCCAGGTGA GGCTGACATTCACCGAGGCTAATAATCAGACCTACACC TTCTGCACTCACCCAAATCTGATCGTG (SEQ ID NO: 137) | C2/ CAP1/ T100 |
| SE_CMV_ UL130_026 | MLRLLLRHHFHCL LLCAVWATPCLAS PWSTLTANQNPSPP WSKLTYSKPHDAA TFYCPFLYPSPPRSP LQFSGFQRVSTGPE CRNETLYLLYNRE GQTLVERSSTWVK KVIWYLSGRNQTIL QRMPRTASKPSDG NVQISVEDAKIFGA HMVPKQTKLLRFV VNDGTRYQMCVM KLESWAHVFRDYS VSFQVRLTFTEAN NQTYTFCTHPNLIV (SEQ ID NO: 65) | ATGCTCAGATTATTGCTCAGACACCACTTCCACTGCCTC CTCTTGTGCGCCGTGTGGGCGACACCGTGTCTCGCAAGC CCTTGGTCCACACTAACGGCCAACCAGAACCCTAGCCCT CCTTGGAGCAAGCTCACTTATAGCAAGCCACACGATGC GGCCACTTTCTACTGTCCTTTCCTGTATCCATCCCCTCCT AGATCTCCTCTGCAGTTCAGCGGATTCCAGAGAGTATCT ACTGGCCCTGAGTGCAGAAATGAAACCCTCTATCTCCTG TACAATCGGGAGGGCCAGACTTTGGTGGAGCGCAGCTC CACCTGGGTGAAGAAGGTGATCTGGTACCTGAGCGGCA GAAACCAGACCATCCTACAGAGGATGCCAAGGACCGCC AGCAAGCCATCTGACGGCAACGTGCAGATCTCTGTGGA GGACGCCAAGATCTTCGGAGCCCATATGGTGCCTAAGC AGACAAAGCTGTTGAGGTTCGTCGTGAATGACGGCACA AGATACCAGATGTGTGTGATGAAGCTGGAGAGCTGGGC TCACGTGTTCCGAGACTACAGCGTCTCGTTCCAGGTGAG ACTGACATTCACCGAGGCAAACAACCAGACCTACACCT TCTGTACGCACCCTAACCTGATCGTT (SEQ ID NO: 138) | C2/ CAP1/ T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| SE_CMV_ UL130_027 | MLRLLLRHHFHCL LLCAVWATPCLAS PWSTLTANQNPSPP WSKLTYSKPHDAA TFYCPFLYPSPPRSP LQFSGFQRVSTGPE CRNETLYLLYNRE GQTLVERSSTWVK KVIWYLSGRNQTIL QRMPRTASKPSDG NVQISVEDAKIFGA HMVPKQTKLLRFV VNDGTRYQMCVM KLESWAHVFRDYS VSFQVRLTFTEAN NQTYTFCTHPNLIV (SEQ ID NO: 65) | ATGCTTCGGCTCCTCCTTCGGCACCACTTCCACTGCCTC CTCCTCTGCGCCGTGTGGGCCACACCTTGCCTCGCCAGC CCCTGGAGCACCCTCACCGCCAACCAGAACCCCAGCCC TCCGTGGTCTAAGTTAACCTACAGCAAGCCCCACGACG CCGCCACCTTCTACTGCCCCTTCCTGTACCCTTCACCGCC GCGGAGCCCGCTGCAGTTCAGCGGCTTCCAGCGGGTGA GCACCGGCCCCGAGTGCCGGAACGAGACGCTGTACCTG CTGTACAACCGGGAGGGCCAGACCCTGGTGGAGCGGAG CAGCACCTGGGTGAAGAAGGTGATCTGGTACCTGAGCG GCCGGAACCAGACCATCCTGCAGCGGATGCCCCGGACC GCCTCAAAGCCAAGCGACGGCAACGTGCAGATCAGCGT GGAGGACGCCAAGATCTTCGGCGCCCACATGGTGCCCA AGCAGACCAAGTTGCTGCGCTTCGTGGTGAACGACGGC ACCCGGTACCAGATGTGCGTGATGAAGCTGGAGAGCTG GGCCCACGTGTTCCGGGACTACAGCGTGAGCTTCCAGG TGCGGCTGACATTCACCGAGGCCAACAATCAGACCTAC ACCTTCTGCACCCACCCCAACCTGATCGTG (SEQ ID NO: 139) | C2/ CAP1/ T100 |
| SE_CMV_ UL130_028 | MLRLLLRHHFHCL LLCAVWATPCLAS PWSTLTANQNPSPP WSKLTYSKPHDAA TFYCPFLYPSPPRSP LQFSGFQRVSTGPE CRNETLYLLYNRE GQTLVERSSTWVK KVIWYLSGRNQTIL QRMPRTASKPSDG NVQISVEDAKIFGA HMVPKQTKLLRFV VNDGTRYQMCVM KLESWAHVFRDYS VSFQVRLTFTEAN NQTYTFCTHPNLIV (SEQ ID NO: 65) | ATGTTACGGCTCCTTCTCCGCCACCACTTCCACTGCCTCT TACTCTGCGCCGTGTGGGCCACTCCATGCCTTGCCAGCC CCTGGAGCACCTTGACCGCCAACCAGAACCCCAGCCCA CCTTGGAGTAAGCTCACCTACAGCAAGCCCCACGACGC CGCCACCTTCTACTGCCCCTTCCTGTATCCGAGCCCACC GCGGAGCCCGCTGCAGTTCAGCGGCTTCCAGCGGGTGA GCACCGGCCCCGAGTGCCGGAACGAAACCCTGTACCTG CTGTACAACCGGGAGGGCCAGACCCTGGTGGAGCGGAG CAGCACCTGGGTGAAGAAGGTGATCTGGTACCTGAGCG GCCGGAACCAGACCATCCTGCAGCGGATGCCCCGGACC GCTAGTAAGCCTAGCGACGGCAACGTGCAGATCAGCGT GGAGGACGCCAAGATCTTCGGCGCCCACATGGTGCCCA AGCAGACCAAGCTGCTTAGGTTCGTGGTGAACGACGGC ACCCGGTACCAGATGTGCGTGATGAAGCTGGAGAGCTG GGCCCACGTGTTCCGGGACTACAGCGTGAGCTTCCAGG TGCGGCTGACCTTCACCGAGGCCAACAACCAGACATAC ACCTTCTGCACCCACCCCAACCTGATCGTG (SEQ ID NO: 140) | C2/ CAP1/ T100 |
| SE_CMV_ UL130_029 | MLRLLLRHHFHCL LLCAVWATPCLAS PWSTLTANQNPSPP WSKLTYSKPHDAA TFYCPFLYPSPPRSP LQFSGFQRVSTGPE CRNETLYLLYNRE GQTLVERSSTWVK KVIWYLSGRNQTIL QRMPRTASKPSDG NVQISVEDAKIFGA HMVPKQTKLLRFV VNDGTRYQMCVM KLESWAHVFRDYS VSFQVRLTFTEAN NQTYTFCTHPNLIV (SEQ ID NO: 65) | ATGCTACGGCTCCTACTCCGCCACCACTTCCACTGCTTA CTTTTGTGCGCCGTGTGGGCCACACCATGCTTGGCCAGC CCCTGGAGCACCCTCACCGCCAACCAGAACCCCTCACCT CCCTGGTCCAAGCTCACCTACTCCAAGCCCCACGACGCC GCCACCTTCTACTGCCCCTTCCTCTATCCATCTCCTCCAC GCAGCCCACTCCAGTTCTCCGGCTTCCAGCGCGTCTCCA CCGGCCCCGAGTGCCGCAACGAGACGCTCTACCTCCTCT ACAACCGCGAGGGCCAGACCCTCGTCGAGAGGTCATCC ACCTGGGTCAAGAAGGTCATCTGGTACCTCTCCGGCCGC AACCAGACCATCCTCCAGCGCATGCCCCGCACCGCGTCT AAGCCGTCCGACGGCAACGTCCAGATCTCCGTCGAGGA CGCCAAGATCTTCGGCGCCCACATGGTCCCCAAGCAGA CCAAGCTCCTCCGCTTCGTCGTCAACGACGGCACCCGCT ACCAGATGTGCGTCATGAAGCTCGAGTCCTGGGCCCAC GTCTTCCGCGACTACTCCGTCTCCTTCCAGGTCCGCCTC ACCTTCACCGAGGCCAATAACCAGACTTACACCTTCTGC ACCCACCCCAACCTCATCGTC (SEQ ID NO: 141) | C2/ CAP1/ T100 |
| SE_CMV_ UL130_029 | MLRLLLRHHFHCL LLCAVWATPCLAS PWSTLTANQNPSPP WSKLTYSKPHDAA TFYCPFLYPSPPRSP LQFSGFQRVSTGPE CRNETLYLLYNRE GQTLVERSSTWVK KVIWYLSGRNQTIL QRMPRTASKPSDG NVQISVEDAKIFGA HMVPKQTKLLRFV VNDGTRYQMCVM KLESWAHVFRDYS | ATGCTACGGCTCCTACTCCGCCACCACTTCCACTGCTTA CTTTTGTGCGCCGTGTGGGCCACACCATGCTTGGCCAGC CCCTGGAGCACCCTCACCGCCAACCAGAACCCCTCACCT CCCTGGTCCAAGCTCACCTACTCCAAGCCCCACGACGCC GCCACCTTCTACTGCCCCTTCCTCTATCCATCTCCTCCAC GCAGCCCACTCCAGTTCTCCGGCTTCCAGCGCGTCTCCA CCGGCCCCGAGTGCCGCAACGAGACGCTCTACCTCCTCT ACAACCGCGAGGGCCAGACCCTCGTCGAGAGGTCATCC ACCTGGGTCAAGAAGGTCATCTGGTACCTCTCCGGCCGC AACCAGACCATCCTCCAGCGCATGCCCCGCACCGCGTCT AAGCCGTCCGACGGCAACGTCCAGATCTCCGTCGAGGA CGCCAAGATCTTCGGCGCCCACATGGTCCCCAAGCAGA CCAAGCTCCTCCGCTTCGTCGTCAACGACGGCACCCGCT ACCAGATGTGCGTCATGAAGCTCGAGTCCTGGGCCCAC | C2/ CAP1/ T100 |

TABLE 13-continued

Additional hCMV Vaccine Constructs

| Antigen Name | Protein Sequence | Nucleotide Sequence (Open Reading Frames) | Tested Chemistry mRNA Chemistry/ Cap/ Tail |
|---|---|---|---|
| | VSFQVRLTFTEAN NQTYTFCTHPNLIV (SEQ ID NO: 65) | GTCTTCCGCGACTACTCCGTCTCCTTCCAGGTCCGCCTC ACCTTCACCGAGGCCAATAACCAGACTTACACCTTCTGC ACCCACCCCAACCTCATCGTC (SEQ ID NO: 142) | |
| SE_CMV_ UL130_030 | MLRLLLRHHFHCL LLCAVWATPCLAS PWSTLTANQNPSPP WSKLTYSKPHDAA TFYCPFLYPSPPRSP LQFSGFQRVSTGPE CRNETLYLLYNRE GQTLVERSSTWVK KVIWYLSGRNQTIL QRMPRTASKPSDG NVQISVEDAKIFGA HMVPKQTKLLRFV VNDGTRYQMCVM KLESWAHVFRDYS VSFQVRLTFTEAN NQTYTFCTHPNLIV (SEQ ID NO: 65) | ATGCTTCGGCTCCTCCTAAGGCACCACTTCCACTGCCTT TTGCTTTGCGCCGTGTGGGCCACCCCTTGCTTGGCCAGC CCCTGGAGCACCCTCACCGCCAACCAGAACCCCTCCCCT CCCTGGTCCAAGCTCACCTACTCCAAGCCCCACGACGCC GCCACCTTCTACTGCCCCTTCCTCTACCCGTCCCCTCCAC GCAGCCCACTCCAGTTCTCCGGCTTCCAGCGCGTCTCCA CCGGCCCCGAGTGCCGCAACGAAACACTCTACCTCCTCT ACAACCGCGAGGGCCAGACCCTCGTCGAGCGCTCCTCC ACCTGGGTCAAGAAGGTCATCTGGTACCTCTCCGGCCGC AACCAGACCATCCTCCAGCGCATGCCCCGCACCGCAAG CAAGCCATCCGACGGCAACGTCCAGATCTCCGTCGAGG ACGCCAAGATCTTCGGCGCCCACATGGTCCCCAAGCAG ACCAAGCTCCTCCGCTTCGTCGTCAACGACGGCACCCGC TACCAGATGTGCGTCATGAAGCTCGAGTCCTGGGCCCA CGTCTTCCGCGACTACTCCGTCTCCTTCCAGGTCCGCCT CACCTTCACCGAGGCCAATAATCAGACATACACCTTCTG CACCCACCCCAACCTCATCGTC (SEQ ID NO: 143) | C2/ CAP1/ T100 |
| UL131A | MRLCRVWLSVCLC AVVLGQCQRETAE KNDYYRVPHYWD ACSRALPDQTRYK YVEQLVDLTLNYH YDASHGLDNFDVL KRINVTEVSLLISD FRRQNRRGGTNKR TTFNAAGSLAPHA RSLEFSVRLFAN (SEQ ID NO: 67) | ATGCGGCTGTGTCGGGTGTGGCTGTCTGTTTGTCTGTGC GCCGTGGTGCTGGGTCAGTGCCAGCGGGAAACCGCGGA AAAGAACGATTATTACCGAGTACCGCATTACTGGGACG CGTGCTCTCGCGCGCTGCCCGACCAAACCCGTTACAAGT ATGTGGAACAGCTCGTGGACCTCACGTTGAACTACCACT ACGATGCGAGCCACGGCTTGGACAACTTTGACGTGCTC AAGAGAATCAACGTGACCGAGGTGTCGTTGCTCATCAG CGACTTTAGACGTCAGAACCGTCGCGGCGGCACCAACA AAAGGACCACGTTCAACGCCGCCGGTTCGCTGGCGCCA CACGCCCGGAGCCTCGAGTTCAGCGTGCGGCTCTTTGCC AAC (SEQ ID NO: 144) | C2/ Cap1/ tailless |
| UL131A | MRLCRVWLSVCLC AVVLGQCQRETAE KNDYYRVPHYWD ACSRALPDQTRYK YVEQLVDLTLNYH YDASHGLDNFDVL KRINVTEVSLLISD FRRQNRRGGTNKR TTFNAAGSLAPHA RSLEFSVRLFAN (SEQ ID NO: 67) | ATGCGGCTGTGTCGGGTGTGGCTGTCTGTTTGTCTGTGC GCCGTGGTGCTGGGTCAGTGCCAGCGGGAAACCGCGGA AAAGAACGATTATTACCGAGTACCGCATTACTGGGACG CGTGCTCTCGCGCGCTGCCCGACCAAACCCGTTACAAGT ATGTGGAACAGCTCGTGGACCTCACGTTGAACTACCACT ACGATGCGAGCCACGGCTTGGACAACTTTGACGTGCTC AAGAGAATCAACGTGACCGAGGTGTCGTTGCTCATCAG CGACTTTAGACGTCAGAACCGTCGCGGCGGCACCAACA AAAGGACCACGTTCAACGCCGCCGGTTCGCTGGCGCCA CACGCCCGGAGCCTCGAGTTCAGCGTGCGGCTCTTTGCC AAC (SEQ ID NO: 144) | C2/ no cap/ T100 |
| UL131A | MRLCRVWLSVCLC AVVLGQCQRETAE KNDYYRVPHYWD ACSRALPDQTRYK YVEQLVDLTLNYH YDASHGLDNFDVL KRINVTEVSLLISD FRRQNRRGGTNKR TTFNAAGSLAPHA RSLEFSVRLFAN (SEQ ID NO: 67) | ATGCGGCTGTGTCGGGTGTGGCTGTCTGTTTGTCTGTGC GCCGTGGTGCTGGGTCAGTGCCAGCGGGAAACCGCGGA AAAGAACGATTATTACCGAGTACCGCATTACTGGGACG CGTGCTCTCGCGCGCTGCCCGACCAAACCCGTTACAAGT ATGTGGAACAGCTCGTGGACCTCACGTTGAACTACCACT ACGATGCGAGCCACGGCTTGGACAACTTTGACGTGCTC AAGAGAATCAACGTGACCGAGGTGTCGTTGCTCATCAG CGACTTTAGACGTCAGAACCGTCGCGGCGGCACCAACA AAAGGACCACGTTCAACGCCGCCGGTTCGCTGGCGCCA CACGCCCGGAGCCTCGAGTTCAGCGTGCGGCTCTTTGCC AAC (SEQ ID NO: 144) | C1/ CAP1/ T100 |

* The nucleotide sequences shown in Table 13 are open reading frame sequences, which can be linked to sequences encoding a 5'UTR and a 3'UTR.

5' UTR coding sequence:
(SEQ ID NO: 145)
TCAAGCTTTTGGACCCTCGTACAGAAGCTAATACGACTCACTATAGGGA

AATAAGAGAGAAAAGAAGAGTAAGAAGAAATATAAGAGCCACC

5' UTR (without promoter) coding sequence:
(SEQ ID NO: 146)
GGGAAATAAGAGAGAAAAGAAGAGTAAGAAGAAATATAAGAGCCACC 3' UTR coding sequence:
(SEQ ID NO: 147)
TGATAATAGGCTGGAGCCTCGGTGGCCATGCTTCTTGCCCCTTGGGCCT

CCCCCCAGCCCCTCCTCCCCTTCCTGCACCCGTACCCCCGTGGTCTTTG

AATAAAGTCTGAGTGGGCGGC

C1: No chemical modification

C2: N1-methylpseudouridine chemical modification

Example 38 Expression of gB from Codon-Optimized mRNA Variant Constructs

HCMV glycoprotein B (gB) expression level in HEK 293 cells or on the cell surface was tested for codon-optimized gB mRNA variants (Var #1-Var #10, SEQ ID NOs: 94, 157, and 95-102, respectively, see Table 13). HEK293 cells were transiently transfected with mRNA encoding the codon-optimized gB mRNA variants using Trans 1T®-mRNA Transfection Kit (Mirus Bio LLC) per the manufacturer's recommendations. At 24 hr post-transfection, cells were lysed in 1% Digitonin buffer supplemented with complete mini-EDTA free protease inhibitor cocktail tablets (ThermoFisher Scientific). Precleared lysates were resolved on Novex 4-12% Bis-Tris gels (Invitrogen) and blotted with anti-gB mouse monoclonal antibody (clone CH28, Santa Cruz Biotechnology) and mouse anti-β actin (Cell Signaling Technology). Alexa Fluor 680 goat anti-mouse IgG (ThermoFisher Scientific) was used as secondary antibody. All images were captured on a ChemiDoc MP Imaging System (Bio-Rad Laboratories).

The result shows that all of the codon-optimized variants were expressed. Compared to the wild type gB mRNA, several of the codon-optimized variants (Var #1-Var #4, Var #9, and Var #10) showed enhanced expression in HEK293 cells, among which Var #4 showed the highest expression level (FIG. 52).

EQUIVALENTS

Those skilled in the art will recognize, or be able to ascertain using no more than routine experimentation, many equivalents to the specific embodiments of the disclosure described herein. Such equivalents are intended to be encompassed by the following claims.

All references, including patent documents, disclosed herein are incorporated by reference in their entirety. This application incorporates by reference the entire contents, including all the drawings and all parts of the specification (including sequence listing or amino acid/polynucleotide sequences) of PCT Application No. PCT/US2016/058310, filed on Oct. 21, 2016, and entitled "HUMAN CYTOMEGALOVIRUS VACCINE."

What is claimed is:

1. A human cytomegalovirus (hCMV) vaccine comprising:

i) at least one RNA polynucleotide having one or more open reading frames encoding hCMV antigenic polypeptides gH, gL, UL128, UL130, and UL131A;

ii) an RNA polynucleotide having an open reading frame encoding hCMV antigenic polypeptide gB;

iii) an RNA polynucleotide having an open reading frame encoding hCMV antigenic polypeptide pp65, and iv) a pharmaceutically acceptable carrier or excipient, wherein the RNA polynucleotides of (i)-(iii) are formulated in at least one lipid nanoparticle that comprises a molar ratio of 20-60% ionizable cationic lipid, 5-25% non-cationic lipid, 25-55% sterol, and 0.5-15% PEG-modified lipid, in an effective amount to induce an immune response in a subject administered at least one dose of the vaccine.

2. The hCMV vaccine of claim 1, wherein the RNA polynucleotide of (i)-(iii) further encode a 5' terminal cap, 7mG(5')ppp(5')NlmpNp.

3. The hCMV vaccine of claim 1, wherein at least 80% of the uracil in the open reading frame of (i)-(iii) have a chemical modification selected from 1-methyl-pseudouridine or 1-ethyl-pseudouridine.

4. The hCMV vaccine of claim 3, wherein the chemical modification is in the carbon-5 position of the uracil.

5. The hCMV vaccine of claim 1, wherein the efficacy of the vaccine in vaccinated subjects is at least 60%, relative to unvaccinated subjects, following a single dose of the vaccine.

6. The hCMV vaccine of claim 5, wherein the efficacy of the vaccine in vaccinated subjects is at least 70%, relative to unvaccinated subjects, following a single dose of the vaccine.

7. The hCMV vaccine of claim 6, wherein the efficacy of the vaccine in vaccinated subjects is at least 80%, relative to unvaccinated subjects, following a single dose of the vaccine.

8. The hCMV vaccine of claim 7, wherein the efficacy of the vaccine in vaccinated subjects is at least 90%, relative to unvaccinated subjects, following a single dose of the vaccine.

9. The hCMV vaccine of claim 1, wherein the effective amount is sufficient to produce detectable levels of hCMV gH, gL, UL128, UL130, UL13 1A, gB and/or pp65 polypeptide as measured in serum of a subject vaccinated with a dose of the vaccine at 1-72 hours post administration.

10. The hCMV vaccine of claim 1, wherein the effective amount is sufficient to produce a 1,000-10,000 neutralization titer produced by neutralizing antibody against the hCMV gH, gL, UL128, UL130, UL131A, gB and/or pp65 polypeptide as measured in serum of a subject vaccinated with a dose of the vaccine at 1-72 hours post administration.

11. The hCMV vaccine of claim 1, wherein an anti-hCMV gH, gL, UL128, UL130, UL131A, gB and/or pp65 polypeptide antibody titer produced in a subject vaccinated with a dose of the vaccine is increased by at least 1 log relative to a control, wherein the control is an anti-hCMV gH, gL, UL128, UL130, UL131A, gB and/or pp65 polypeptide antibody titer produced in a subject who has not been administered a vaccine against hCMV.

12. The hCMV vaccine of claim 1, wherein the anti-hCMV gH, gL, UL128, UL130, UL131A, gB and/or pp65 polypeptide antibody titer produced in a subject vaccinated with a dose of the vaccine is increased at least 2 times relative to a control, wherein the control is an anti-hCMV gH, gL, UL128, UL130, UL131A, gB and/or pp65 polypeptide antibody titer produced in a subject who has not been administered a vaccine against hCMV.

13. The hCMV vaccine of claim 1, wherein the effective amount is a total dose of 25 μg-200 μg.

14. The hCMV vaccine of claim 13, wherein the effective amount is a total dose of 25 μg-100 μg.

15. The hCMV vaccine of claim 1, wherein the ionizable cationic lipid comprises the following compound:

wherein each of the RNA polynucleotides of (a)-(f) further comprises a polyA tail, and wherein the polynucleotide of (g) further comprises a 5'UTR encoded by SEQ ID NO: 146, a 3'UTR encoded by SEQ ID NO: 147, and a polyA tail.

19. The hCMV vaccine of claim 18, wherein the polyA tail is 100 nucleotides in length.

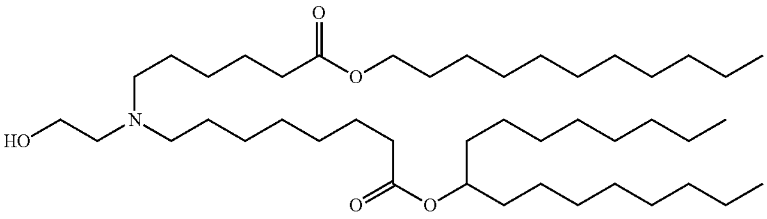

(Compound 25)

16. The hCMV vaccine of claim 1, wherein the hCMV vaccine comprises: (a) an RNA polynucleotide having an open reading frame encoding hCMV antigenic polypeptide gH; (b) an RNA polynucleotide having an open reading frame encoding hCMV antigenic polypeptide gL; (c) an RNA polynucleotide having an open reading frame encoding hCMV antigenic polypeptide UL128; (d) an RNA polynucleotide having an open reading frame encoding hCMV antigenic polypeptide UL130; (e) an RNA polynucleotide having an open reading frame encoding hCMV antigenic polypeptide UL131A; (f) an RNA polynucleotide having an open reading frame encoding hCMV antigenic polypeptide gB; and (g) an RNA polynucleotide having an open reading frame encoding hCMV antigenic polypeptide pp65.

17. The hCMV vaccine of claim 16, wherein the RNA polynucleotide of (a) comprises a sequence that has at least 90% identity to the nucleotide sequence of SEQ ID NO: 189, the RNA polynucleotide of (b) comprises a sequence that has at least 90% identity to the nucleotide sequence of SEQ ID NO: 190, the RNA polynucleotide of (c) comprises a sequence that has at least 90% identity to the nucleotide sequence of SEQ ID NO: 191, the RNA polynucleotide of (d) comprises a sequence that has at least 90% identity to the nucleotide sequence of SEQ ID NO: 172, the RNA polynucleotide of (e) comprises a sequence that has at least 90% identity to the nucleotide sequence of SEQ ID NO: 193, the RNA polynucleotide of (f) comprises a sequence that has at least 90% identity to the nucleotide sequence of SEQ ID NO: 162, and or the RNA polynucleotide of (g) comprises a sequence that has at least 90% identity to a RNA polynucleotide sequence encoded by SEQ ID NO: 92.

18. A human cytomegalovirus (hCMV) vaccine comprising: (a) at least one RNA polynucleotide comprising nucleotides 46-2437 of SEQ ID NO: 189, (b) at least one RNA polynucleotide comprising nucleotides 46-1045 of SEQ ID NO: 190, (c) at least one RNA polynucleotide comprising nucleotides 46-724 of SEQ ID NO: 191, (d) at least one RNA polynucleotide comprising an nucleotides 46-853 of SEQ ID NO: 172, (e) at least one RNA polynucleotide comprising nucleotides 46-598 of SEQ ID NO: 193, (f) at least one RNA polynucleotide comprising nucleotides 46-2932 of SEQ ID NO: 162, and (g) at least one RNA polynucleotide encoded by SEQ ID NO: 92, wherein each of the RNA polynucleotides of (a)-(g) are mRNA polynucleotides,

20. A human cytomegalovirus (hCMV) vaccine comprising: (a) at least one RNA polynucleotide encoded by a DNA polynucleotide of SEQ ID NO: 58, (b) at least one RNA polynucleotide encoded by a DNA polynucleotide of SEQ ID NO: 62, (c) at least one RNA polynucleotide encoded by a DNA polynucleotide of SEQ ID NO: 60, (d) at least one RNA polynucleotide encoded by a DNA polynucleotide of SEQ ID NO: 15, (e) at least one RNA polynucleotide encoded by a DNA polynucleotide of SEQ ID NO: 66, (f) at least one RNA polynucleotide encoded by a DNA polynucleotide of SEQ ID NO: 86, and (g) at least one RNA polynucleotide encoded by a DNA polynucleotide of SEQ ID NO: 92, wherein each of the RNA polynucleotides of (a)-(g) are mRNA polynucleotides, wherein each of the RNA polynucleotides of (a)-(f) comprises a polyA tail, and wherein the polynucleotide of (g) comprises a polyA tail and further comprises a 5'UTR encoded by SEQ ID NO: 146 and a 3'UTR encoded by SEQ ID NO: 147.

21. The hCMV vaccine of claim 20, wherein the polyA tail is 100 nucleotides in length.

22. The hCMV vaccine of claim 16, wherein the hCMV gH polypeptide comprises an amino acid sequence that has at least 90% identity to the amino acid sequence of SEQ ID NO: 59, the hCMV gL polypeptide comprises an amino acid sequence that has at least 90% identity to the amino acid sequence of SEQ ID NO: 61, the hCMV UL128 polypeptide comprises an amino acid sequence that has at least 90% identity to the amino acid sequence of SEQ ID NO: 63, the hCMV UL130 polypeptide comprises an amino acid sequence that has at least 90% identity to the amino acid sequence of SEQ ID NO: 65, the hCMV UL131A polypeptide comprises an amino acid sequence that has at least 90% identity to the amino acid sequence of SEQ ID NO: 67, the hCMV gB protein comprises an amino acid sequence that has at least 90% identity to the amino acid sequence of SEQ ID NO: 69; and/or the pp65 protein comprises an amino acid sequence that has at least 90% identity to the amino acid sequence of SEQ ID NO: 82.

23. The hCMV vaccine of claim 22, wherein the hCMV gH polypeptide comprises the amino acid sequence of SEQ ID NO: 59, the hCMV gL polypeptide comprises the amino acid sequence of SEQ ID NO: 61, the hCMV UL128 polypeptide comprises the amino acid sequence of SEQ ID NO: 63, the hCMV UL130 polypeptide comprises the amino acid sequence of SEQ ID NO: 65, the hCMV UL131A polypeptide comprises the amino acid sequence of SEQ ID NO: 67, the hCMV gB protein comprises the amino acid sequence of SEQ ID NO: 69; and the pp65 protein comprises the amino acid sequence of SEQ ID NO: 82.

24. The hCMV vaccine of claim 1, wherein the RNA polynucleotides are not self-replicating RNA.

* * * * *

SEQUENCE LISTING

```
<160> NUMBER OF SEQ ID NOS: 194

<210> SEQ ID NO 1
<211> LENGTH: 742
<212> TYPE: PRT
<213> ORGANISM: Artificial Sequence
<220> FEATURE:
<223> OTHER INFORMATION: Synthetic polypeptide

<400> SEQUENCE: 1

Met Arg Pro Gly Leu Pro Ser Tyr Leu Ile Ile Leu Ala Val Cys Leu
1               5                   10                  15

Phe Ser His Leu Leu Ser Ser Arg Tyr Gly Ala Glu Ala Val Ser Glu
            20                  25                  30

Pro Leu Asp Lys Ala Phe His Leu Leu Leu Asn Thr Tyr Gly Arg Pro
        35                  40                  45

Ile Arg Phe Leu Arg Glu Asn Thr Thr Gln Cys Thr Tyr Asn Ser Ser
    50                  55                  60

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
        115                 120                 125

Ser Lys Asp Leu Ala Ser Tyr Arg Ser Phe Ser Gln Gln Leu Lys Ala
    130                 135                 140
```

-continued

```
Gln Asp Ser Leu Gly Glu Gln Pro Thr Thr Val Pro Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
        195                 200                 205

Thr Pro Cys Leu His Gln Gly Phe Tyr Leu Ile Asp Glu Leu Arg Tyr
    210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
    290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
        355                 360                 365

Arg Gln Ala Ala Leu Leu Gln Ile Gln Glu Phe Met Ile Thr Cys Leu
    370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
            420                 425                 430

His Leu Ile Pro Gln Trp Ala Leu Arg Gln Ile Ala Asp Phe Ala Leu
        435                 440                 445

Lys Leu His Lys Thr His Leu Ala Ser Phe Leu Ser Ala Phe Ala Arg
    450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
            500                 505                 510

Glu Tyr Leu Ser Asp Leu Tyr Thr Pro Cys Ser Ser Ser Gly Arg Arg
        515                 520                 525

Asp His Ser Leu Glu Arg Leu Thr Arg Leu Phe Pro Asp Ala Thr Val
    530                 535                 540

Pro Ala Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
```

```
                565                 570                 575

Ser Phe Ser Ala Leu Thr Val Ser Glu His Val Ser Tyr Ile Val Thr
            580                 585                 590

Asn Gln Tyr Leu Ile Lys Gly Ile Ser Tyr Pro Val Ser Thr Thr Val
        595                 600                 605

Val Gly Gln Ser Leu Ile Ile Thr Gln Thr Asp Ser Gln Thr Lys Cys
    610                 615                 620

Glu Leu Thr Arg Asn Met His Thr Thr His Ser Ile Thr Val Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
            660                 665                 670

Asp Asp Val Leu Phe Ala Leu Asp Pro Tyr Asn Glu Val Val Val Ser
        675                 680                 685

Ser Pro Arg Thr His Tyr Leu Met Leu Leu Lys Asn Gly Thr Val Leu
    690                 695                 700

Glu Val Thr Asp Val Val Val Asp Ala Thr Asp Ser Arg Leu Leu Met
705                 710                 715                 720

Met Ser Val Tyr Ala Leu Ser Ala Ile Ile Gly Ile Tyr Leu Leu Tyr
                725                 730                 735

Arg Met Leu Lys Thr Cys
            740


<210> SEQ ID NO 2
<211> LENGTH: 2464
<212> TYPE: DNA
<213> ORGANISM: Artificial Sequence
<220> FEATURE:
<223> OTHER INFORMATION: Synthetic polynucleotide

<400> SEQUENCE: 2

tcaagctttt ggaccctcgt acagaagcta atacgactca ctatagggaa ataagagaga     60

aaagaagagt aagaagaaat ataagagcca ccatgcggcc aggcctcccc tcctacctca    120

tcatcctcgc cgtctgtctc ttcagccacc tactttcgtc acgatatggc gcagaagccg    180

tatccgaacc gctggacaaa gcgtttcacc tactgctcaa cacctacggg agacccatcc    240

gcttcctgcg tgaaaatacc acccagtgta cctacaacag cagcctccgt aacagcacgg    300

tcgtcaggga aaacgccatc agtttcaact ttttccaaag ctataatcaa tactatgtat    360

tccatatgcc tcgatgtctt tttgcgggtc ctctggcgga gcagtttctg aaccaggtag    420

atctgaccga aaccctggaa agataccaac agagacttaa cacttacgcg ctggtatcca    480

aagacctggc cagctaccga tctttttcgc agcagctaaa ggcacaagac agcctaggtg    540

aacagcccac cactgtgcca ccgcccattg acctgtcaat acctcacgtt tggatgccac    600

cgcaaaccac tccacacggc tggacagaat cacataccac ctcaggacta caccgaccac    660

actttaacca gacctgtatc ctctttgatg gacacgatct actattcagc accgtcacac    720

cttgtttgca ccaaggcttt tacctcatcg acgaactacg ttacgttaaa ataacactga    780

ccgaggactt cttcgtagtt acggtgtcca tagacgacga cacacccatg ctgcttatct    840

tcggccatct tccacgcgta cttttcaaag cgccctatca acgcgacaac tttatactac    900

gacaaactga aaaacacgag ctcctggtgc tagttaagaa agatcaactg aaccgtcact    960

cttatctcaa agacccggac tttcttgacg ccgcacttga cttcaactac ctagacctca   1020
```

gcgcactact acgtaacagc tttcaccgtt acgccgtgga tgtactcaag agcggtcgat 1080
gtcagatgct ggaccgccgc acggtagaaa tggccttcgc ctacgcatta gcactgttcg 1140
cagcagcccg acaagaagag gccggcgccc aagtctccgt cccacgggcc ctagaccgcc 1200
aggccgcact cttacaaata caagaattta tgatcacctg cctctcacaa acaccaccac 1260
gcaccacgtt gctgctgtat cccacggccg tggacctggc caaacgagcc ctttggacac 1320
cgaatcagat caccgacatc accagcctcg tacgcctggt ctacatactc tctaaacaga 1380
atcagcaaca tctcatcccc caatgggcac tacgacagat cgccgacttt gccctaaaac 1440
tacacaaaac gcacctggcc tcttttcttt cagccttcgc acgccaagaa ctctacctca 1500
tgggcagcct cgtccactcc atgctggtac atacgacgga gagacgcgaa atcttcatcg 1560
tagaaacggg cctctgttca ttggccgagc tatcacactt tacgcagttg ttagctcatc 1620
cacaccacga atacctcagc gacctgtaca caccctgttc cagtagcggg cgacgcgatc 1680
actcgctcga acgcctcacg cgtctcttcc ccgatgccac cgtccccgct accgttcccg 1740
ccgccctctc catcctatct accatgcaac caagcacgct ggaaaccttc cccgacctgt 1800
tttgcttgcc gctcggcgaa tccttctccg cgctgaccgt ctccgaacac gtcagttata 1860
tcgtaacaaa ccagtacctg atcaaaggta tctcctaccc tgtctccacc accgtcgtag 1920
gccagagcct catcatcacc cagacggaca gtcaaactaa atgcgaactg acgcgcaaca 1980
tgcataccac acacagcatc acagtggcgc tcaacatttc gctagaaaac tgcgcctttt 2040
gccaaagcgc cctgctagaa tacgacgaca cgcaaggcgt catcaacatc atgtacatgc 2100
acgactcgga cgacgtcctt ttcgccctgg atccctacaa cgaagtggtg gtctcatctc 2160
cgcgaactca ctacctcatg cttttgaaaa acggtacggt actagaagta actgacgtcg 2220
tcgtggacgc caccgacagt cgtctcctca tgatgtccgt ctacgcgcta tcggccatca 2280
tcggcatcta tctgctctac cgcatgctca agacatgcga ttacaaggac gatgacgata 2340
agtgatgata ataggctgga gcctcggtgg ccatgcttct tgccccttgg gcctcccccc 2400
agcccctcct ccccttcctg cacccgtacc cccgtggtct ttgaataaag tctgagtggg 2460
cggc 2464

<210> SEQ ID NO 3
<211> LENGTH: 1045
<212> TYPE: DNA
<213> ORGANISM: Artificial Sequence
<220> FEATURE:
<223> OTHER INFORMATION: Synthetic polynucleotide

<400> SEQUENCE: 3
tcaagctttt ggaccctcgt acagaagcta atacgactca ctatagggaa ataagagaga 60
aaagaagagt aagaagaaat ataagagcca ccatgtgccg ccgcccggat tgcggcttct 120
ctttctcacc tggaccggtg atactgctgt ggtgttgcct tctgctgccc attgtttcct 180
cagccgccgt cagcgtcgct cctaccgccg ccgagaaagt ccccgcggag tgccccgaac 240
taacgcgccg atgcttgttg ggtgaggtgt ttgagggtga caagtatgaa agttggctgc 300
gcccgttggt gaatgttacc gggcgcgatg gcccgctatc gcaacttatc cgttaccgtc 360
ccgttacgcc ggaggccgcc aactccgtgc tgttggacga ggctttcctg gacactctgg 420
ccctgctgta caacaatccg gatcaattgc gggccctgct gacgctgttg agctcggaca 480
cagcgccgcg ctggatgacg gtgatgcgcg gctacagcga gtgcggcgat ggctcgccgg 540
ccgtgtacac gtgcgtggac gacctgtgcc gcggctacga cctcacgcga ctgtcatacg 600

```
ggcgcagcat cttcacggaa cacgtgttag gcttcgagct ggtgccaccg tctctcttta    660

acgtggtggt ggccatacgc aacgaagcca cgcgtaccaa ccgcgccgtg cgtctgcccg    720

tgagcaccgc tgccgcgccc gagggcatca cgctctttta cggcctgtac aacgcagtga    780

aggaattctg cctgcgtcac cagctggacc cgccgctgct acgccaccta gataaatact    840

acgccggact gccgcccgag ctgaagcaga cgcgcgtcaa cctgccggct cactcgcgct    900

atggccctca agcagtggat gctcgctgat aataggctgg agcctcggtg gccatgcttc    960

ttgccccttg ggcctccccc cagcccctcc tccccttcct gcacccgtac cccgtggtc   1020

tttgaataaa gtctgagtgg gcggc                                         1045
```

<210> SEQ ID NO 4
<211> LENGTH: 1072
<212> TYPE: DNA
<213> ORGANISM: Artificial Sequence
<220> FEATURE:
<223> OTHER INFORMATION: Synthetic polynucleotide

<400> SEQUENCE: 4

```
tcaagctttt ggaccctcgt acagaagcta atacgactca ctatagggaa ataagagaga     60

aaagaagagt aagaagaaat ataagagcca ccatgtgccg ccgcccggat tgcggcttct    120

ctttctcacc tggaccggtg atactgctgt ggtgttgcct tctgctgccc attgtttcct    180

cagccgccgt cagcgtcgct cctaccgccg ccgagaaagt ccccgcggag tgccccgaac    240

taacgcgccg atgcttgttg ggtgaggtgt ttgagggtga caagtatgaa agttggctgc    300

gcccgttggt gaatgttacc gggcgcgatg gcccgctatc gcaacttatc cgttaccgtc    360

ccgttacgcc ggaggccgcc aactccgtgc tgttggacga ggctttcctg gacactctgg    420

ccctgctgta caacaatccg gatcaattgc gggccctgct gacgctgttg agctcggaca    480

cagcgccgcg ctggatgacg gtgatgcgcg gctacagcga gtgcggcgat ggctcgccgg    540

ccgtgtacac gtgcgtggac gacctgtgcc gcggctacga cctcacgcga ctgtcatacg    600

ggcgcagcat cttcacggaa cacgtgttag gcttcgagct ggtgccaccg tctctcttta    660

acgtggtggt ggccatacgc aacgaagcca cgcgtaccaa ccgcgccgtg cgtctgcccg    720

tgagcaccgc tgccgcgccc gagggcatca cgctctttta cggcctgtac aacgcagtga    780

aggaattctg cctgcgtcac cagctggacc cgccgctgct acgccaccta gataaatact    840

acgccggact gccgcccgag ctgaagcaga cgcgcgtcaa cctgccggct cactcgcgct    900

atggccctca agcagtggat gctcgcgatt acaaggacga tgacgataag tgatgataat    960

aggctggagc ctcggtggcc atgcttcttg ccccttgggc ctccccccag cccctcctcc   1020

ccttcctgca cccgtacccc cgtggtcttt gaataaagtc tgagtgggcg gc           1072
```

<210> SEQ ID NO 5
<211> LENGTH: 2932
<212> TYPE: DNA
<213> ORGANISM: Artificial Sequence
<220> FEATURE:
<223> OTHER INFORMATION: Synthetic polynucleotide

<400> SEQUENCE: 5

```
tcaagctttt ggaccctcgt acagaagcta atacgactca ctatagggaa ataagagaga     60

aaagaagagt aagaagaaat ataagagcca ccatggaatc caggatctgg tgcctggtag    120

tctgcgttaa cttgtgtatc gtctgtctgg gtgctgcggt ttcctcatct tctactcgtg    180
```

```
gaacttctgc tactcacagt caccattcct ctcatacgac gtctgctgct cactctcgat    240
ccggttcagt ctctcaacgc gtaacttctt cccaaacggt cagccatggt gttaacgaga    300
ccatctacaa cactaccctc aagtacggag atgtggtggg ggtcaatacc accaagtacc    360
cctatcgcgt gtgttctatg gcccagggta cggatcttat tcgctttgaa cgtaatatcg    420
tctgcacctc gatgaagccc atcaatgaag acctggacga gggcatcatg gtggtctaca    480
aacgcaacat cgtcgcgcac acctttaagg tacgagtcta ccagaaggtt ttgacgtttc    540
gtcgtagcta cgcttacatc cacaccactt atctgctggg cagcaacacg gaatacgtgg    600
cgcctcctat gtgggagatt catcatatca acagccacag tcagtgctac agttcctaca    660
gccgcgttat agcaggcacg gttttcgtgg cttatcatag ggacagctat gaaaacaaaa    720
ccatgcaatt aatgcccgac gattattcca acacccacag tacccgttac gtgacggtca    780
aggatcaatg gcacagccgc ggcagcacct ggctctatcg tgagacctgt aatctgaatt    840
gtatggtgac catcactact gcgcgctcca aatatcctta tcattttttc gccacttcca    900
cgggtgacgt ggttgacatt tctcctttct acaacggaac caatcgcaat gccagctact    960
ttggagaaaa cgccgacaag tttttcattt ttccgaacta cactatcgtc tccgactttg   1020
gaagaccgaa ttctgcgtta gagacccaca ggttggtggc ttttcttgaa cgtgcggact   1080
cggtgatctc ctgggatata caggacgaaa agaatgtcac ttgtcaactc actttctggg   1140
aagcctcgga acgcaccatt cgttccgaag ccgaggactc gtatcacttt tcttctgcca   1200
aaatgaccgc cactttctta tctaagaagc aagaggtgaa catgtccgac tctgcgctgg   1260
actgcgtacg tgatgaggct ataaataagt tacagcagat tttcaatact tcatacaatc   1320
aaacatatga aaaatatgga aacgtgtccg tctttgaaac cactggtggt ttggtagtgt   1380
tctggcaagg tatcaagcaa aaatctctgg tggaactcga acgtttggcc aaccgctcca   1440
gtctgaatct tactcataat agaaccaaaa gaagtacaga tggcaacaat gcaactcatt   1500
tatccaacat ggaatcggtg cacaatctgg tctacgccca gctgcagttc acctatgaca   1560
cgttgcgcgg ttacatcaac cgggcgctgg cgcaaatcgc agaagcctgg tgtgtggatc   1620
aacggcgcac cctagaggtc ttcaaggaac tcagcaagat caacccgtca gccattctct   1680
cggccattta caacaaaccg attgccgcgc gtttcatggg tgatgtcttg ggcctggcca   1740
gctgcgtgac catcaaccaa accagcgtca aggtgctgcg tgatatgaac gtgaaggagt   1800
cgccaggacg ctgctactca cgacccgtgg tcatctttaa tttcgccaac agctcgtacg   1860
tgcagtacgg tcaactgggc gaggacaacg aaatcctgtt gggcaaccac cgcactgagg   1920
aatgtcagct tcccagcctc aagatcttca tcgccgggaa ctcggcctac gagtacgtgg   1980
actacctctt caaacgcatg attgacctca gcagtatctc caccgtcgac agcatgatcg   2040
ccctggatat cgacccgctg gaaaataccg acttcagggt actggaactt tactcgcaga   2100
aagagctgcg ttccagcaac gtttttgacc tcgaagagat catgcgcgaa ttcaactcgt   2160
acaagcagcg ggtaaagtac gtggaggaca aggtagtcga cccgctaccg ccctacctca   2220
agggtctgga cgacctcatg agcggcctgg gcgccgcggg aaaggccgtt ggcgtagcca   2280
ttggggccgt gggtggcgcg gtggcctccg tggtcgaagg cgttgccacc ttcctcaaaa   2340
acccctcgg  agcgttcacc atcatcctcg tggccatagc tgtagtcatt atcacttatt   2400
tgatctatac tcgacagcgg cgtttgtgca cgcagccgct gcagaacctc tttccctatc   2460
tggtgtccgc cgacgggacc accgtgacgt cgggcagcac caaagacacg tcgttacagg   2520
ctccgccttc ctacgaggaa agtgtttata attctggtcg caaaggaccg ggaccaccgt   2580
```

cgtctgatgc atccacggcg gctccgcctt acaccaacga gcaggcttac cagatgcttc 2640
tggccctggc ccgtctggac gcagagcagc gagcgcagca gaacggtaca gattctttgg 2700
acggacggac tggcacgcag gacaagggac agaagcccaa cctactagac cgactgcgac 2760
atcgcaaaaa cggctaccga cacttgaaag actctgacga agaagagaac gtctgataat 2820
aggctggagc ctcggtggcc atgcttcttg ccccttgggc ctccccccag cccctcctcc 2880
ccttcctgca cccgtacccc cgtggtcttt gaataaagtc tgagtgggcg gc 2932

<210> SEQ ID NO 6
<211> LENGTH: 2956
<212> TYPE: DNA
<213> ORGANISM: Artificial Sequence
<220> FEATURE:
<223> OTHER INFORMATION: Synthetic polynucleotide

<400> SEQUENCE: 6
tcaagctttt ggaccctcgt acagaagcta atacgactca ctatagggaa ataagagaga 60
aaagaagagt aagaagaaat ataagagcca ccatggaatc caggatctgg tgcctggtag 120
tctgcgttaa cttgtgtatc gtctgtctgg gtgctgcggt ttcctcatct tctactcgtg 180
gaacttctgc tactcacagt caccattcct ctcatacgac gtctgctgct cactctcgat 240
ccggttcagt ctctcaacgc gtaacttctt cccaaacggt cagccatggt gttaacgaga 300
ccatctacaa cactaccctc aagtacggag atgtggtggg ggtcaatacc accaagtacc 360
cctatcgcgt gtgttctatg gcccagggta cggatcttat tcgctttgaa cgtaatatcg 420
tctgcacctc gatgaagccc atcaatgaag acctggacga gggcatcatg gtggtctaca 480
aacgcaacat cgtcgcgcac acctttaagg tacgagtcta ccagaaggtt ttgacgtttc 540
gtcgtagcta cgcttacatc cacaccactt atctgctggg cagcaacacg gaatacgtgg 600
cgcctcctat gtgggagatt catcatatca acagccacag tcagtgctac agttcctaca 660
gccgcgttat agcaggcacg gttttcgtgg cttatcatag ggacagctat gaaaacaaaa 720
ccatgcaatt aatgcccgac gattattcca acacccacag tacccgttac gtgacggtca 780
aggatcaatg gcacagccgc ggcagcacct ggctctatcg tgagacctgt aatctgaatt 840
gtatggtgac catcactact gcgcgctcca aatatcctta tcattttttc gccacttcca 900
cgggtgacgt ggttgacatt tctccttttct acaacggaac caatcgcaat gccagctact 960
ttggagaaaa cgccgacaag tttttcattt ttccgaacta cactatcgtc tccgactttg 1020
gaagaccgaa ttctgcgtta gagacccaca ggttggtggc ttttcttgaa cgtgcggact 1080
cggtgatctc ctgggatata caggacgaaa agaatgtcac ttgtcaactc actttctggg 1140
aagcctcgga acgcaccatt cgttccgaag ccgaggactc gtatcacttt tcttctgcca 1200
aaatgaccgc cactttctta tctaagaagc aagaggtgaa catgtccgac tctgcgctgg 1260
actgcgtacg tgatgaggct ataaataagt tacagcagat tttcaatact tcatacaatc 1320
aaacatatga aaaatatgga aacgtgtccg tctttgaaac cactggtggt ttggtagtgt 1380
tctggcaagg tatcaagcaa aaatctctgg tggaactcga acgtttggcc aaccgctcca 1440
gtctgaatct tactcataat agaaccaaaa gaagtacaga tggcaacaat gcaactcatt 1500
tatccaacat ggaatcggtg cacaatctgg tctacgccca gctgcagttc acctatgaca 1560
cgttgcgcgg ttacatcaac cgggcgctgg cgcaaatcgc agaagcctgg tgtgtggatc 1620
aacggcgcac cctagaggtc ttcaaggaac tcagcaagat caacccgtca gccattctct 1680

-continued

```
cggccattta caacaaaccg attgccgcgc gtttcatggg tgatgtcttg ggcctggcca   1740

gctgcgtgac catcaaccaa accagcgtca aggtgctgcg tgatatgaac gtgaaggagt   1800

cgccaggacg ctgctactca cgacccgtgg tcatctttaa tttcgccaac agctcgtacg   1860

tgcagtacgg tcaactgggc gaggacaacg aaatcctgtt gggcaaccac cgcactgagg   1920

aatgtcagct tcccagcctc aagatcttca tcgccgggaa ctcggcctac gagtacgtgg   1980

actacctctt caaacgcatg attgacctca gcagtatctc caccgtcgac agcatgatcg   2040

ccctggatat cgacccgctg gaaaataccg acttcagggt actggaactt tactcgcaga   2100

aagagctgcg ttccagcaac gtttttgacc tcgaagagat catgcgcgaa ttcaactcgt   2160

acaagcagcg ggtaaagtac gtggaggaca aggtagtcga cccgctaccg ccctacctca   2220

agggtctgga cgacctcatg agcggcctgg gcgccgcggg aaaggccgtt ggcgtagcca   2280

ttggggccgt gggtggcgcg gtggcctccg tggtcgaagg cgttgccacc ttcctcaaaa   2340

accccttcgg agcgttcacc atcatcctcg tggccatagc tgtagtcatt atcacttatt   2400

tgatctatac tcgacagcgg cgtttgtgca cgcagccgct gcagaacctc tttccctatc   2460

tggtgtccgc cgacgggacc accgtgacgt cgggcagcac caaagacacg tcgttacagg   2520

ctccgccttc ctacgaggaa agtgtttata attctggtcg caaaggaccg ggaccaccgt   2580

cgtctgatgc atccacggcg gctccgcctt acaccaacga gcaggcttac cagatgcttc   2640

tggccctggc ccgtctggac gcagagcagc gagcgcagca gaacggtaca gattctttgg   2700

acggacggac tggcacgcag gacaagggac agaagcccaa cctactagac cgactgcgac   2760

atcgcaaaaa cggctaccga cacttgaaag actctgacga agaagagaac gtcgattaca   2820

aggacgatga cgataagtga taataggctg gagcctcggt ggccatgctt cttgcccctt   2880

gggcctcccc ccagcccctc ctccccttcc tgcacccgta cccccgtggt ctttgaataa   2940

agtctgagtg ggcggc                                                   2956
```

<210> SEQ ID NO 7
<211> LENGTH: 2356
<212> TYPE: DNA
<213> ORGANISM: Artificial Sequence
<220> FEATURE:
<223> OTHER INFORMATION: Synthetic polynucleotide

<400> SEQUENCE: 7

```
tcaagctttt ggaccctcgt acagaagcta atacgactca ctatagggaa ataagagaga     60

aaagaagagt aagaagaaat ataagagcca ccatgcggcc aggcctcccc tcctacctca    120

tcatcctcgc cgtctgtctc ttcagccacc tactttcgtc acgatatggc gcagaagccg    180

tatccgaacc gctggacaaa gcgtttcacc tactgctcaa cacctacggg agacccatcc    240

gcttcctgcg tgaaaatacc acccagtgta cctacaacag cagcctccgt aacagcacgg    300

tcgtcaggga aaacgccatc agtttcaact tttccaaag ctataatcaa tactatgtat    360

tccatatgcc tcgatgtctt tttgcgggtc ctctggcgga gcagtttctg aaccaggtag    420

atctgaccga aaccctggaa agataccaac agagacttaa cacttacgcg ctggtatcca    480

aagacctggc cagctaccga tctttttcgc agcagctaaa ggcacaagac agcctaggtg    540

aacagcccac cactgtgcca ccgcccattg acctgtcaat acctcacgtt tggatgccac    600

cgcaaaccac tccacacggc tggacagaat cacataccac ctcaggacta caccgaccac    660

actttaacca gacctgtatc ctctttgatg gacacgatct actattcagc accgtcacac    720

cttgtttgca ccaaggcttt tacctcatcg acgaactacg ttacgttaaa ataacactga    780
```

ccgaggactt cttcgtagtt acggtgtcca tagacgacga cacacccatg ctgcttatct 840
tcggccatct tccacgcgta cttttcaaag cgccctatca acgcgacaac tttatactac 900
gacaaactga aaaacacgag ctcctggtgc tagttaagaa agatcaactg aaccgtcact 960
cttatctcaa agacccggac tttcttgacg ccgcacttga cttcaactac ctagacctca 1020
gcgcactact acgtaacagc tttcaccgtt acgccgtgga tgtactcaag agcggtcgat 1080
gtcagatgct ggaccgccgc acggtagaaa tggccttcgc ctacgcatta gcactgttcg 1140
cagcagcccg acaagaagag gccggcgccc aagtctccgt cccacgggcc ctagaccgcc 1200
aggccgcact cttacaaata caagaattta tgatcacctg cctctcacaa acaccaccac 1260
gcaccacgtt gctgctgtat cccacggccg tggacctggc caaacgagcc ctttggacac 1320
cgaatcagat caccgacatc accagcctcg tacgcctggt ctacatactc tctaaacaga 1380
atcagcaaca tctcatcccc caatgggcac tacgacagat cgccgacttt gccctaaaac 1440
tacacaaaac gcacctggcc tcttttcttt cagccttcgc acgccaagaa ctctacctca 1500
tgggcagcct cgtccactcc atgctggtac atacgacgga gagacgcgaa atcttcatcg 1560
tagaaacggg cctctgttca ttggccgagc tatcacactt tacgcagttg ttagctcatc 1620
cacaccacga atacctcagc gacctgtaca caccctgttc cagtagcggg cgacgcgatc 1680
actcgctcga acgcctcacg cgtctcttcc ccgatgccac cgtccccgct accgttcccg 1740
ccgccctctc catcctatct accatgcaac caagcacgct ggaaaccttc cccgacctgt 1800
tttgcttgcc gctcggcgaa tccttctccg cgctgaccgt ctccgaacac gtcagttata 1860
tcgtaacaaa ccagtacctg atcaaaggta tctcctaccc tgtctccacc accgtcgtag 1920
gccagagcct catcatcacc cagacggaca gtcaaactaa atgcgaactg acgcgcaaca 1980
tgcataccac acacagcatc acagtggcgc tcaacatttc gctagaaaac tgcgcctttt 2040
gccaaagcgc cctgctagaa tacgacgaca cgcaaggcgt catcaacatc atgtacatgc 2100
acgactcgga cgacgtcctt ttcgccctgg atccctacaa cgaagtggtg gtctcatctc 2160
cgcgaactca ctacctcatg cttttgaaaa acggtacggt actagaagta actgacgtcg 2220
tcgtggacgc caccgactga taataggctg gagcctcggt ggccatgctt cttgcccctt 2280
gggcctcccc ccagcccctc ctccccttcc tgcacccgta cccccgtggt ctttgaataa 2340
agtctgagtg ggcggc 2356

<210> SEQ ID NO 8
<211> LENGTH: 2383
<212> TYPE: DNA
<213> ORGANISM: Artificial Sequence
<220> FEATURE:
<223> OTHER INFORMATION: Synthetic polynucleotide

<400> SEQUENCE: 8
tcaagctttt ggaccctcgt acagaagcta atacgactca ctatagggaa ataagagaga 60
aaagaagagt aagaagaaat ataagagcca ccatgcggcc aggcctcccc tcctacctca 120
tcatcctcgc cgtctgtctc ttcagccacc tactttcgtc acgatatggc gcagaagccg 180
tatccgaacc gctggacaaa gcgtttcacc tactgctcaa cacctacggg agacccatcc 240
gcttcctgcg tgaaaatacc acccagtgta cctacaacag cagcctccgt aacagcacgg 300
tcgtcaggga aaacgccatc agtttcaact tttccaaag ctataatcaa tactatgtat 360
tccatatgcc tcgatgtctt tttgcgggtc ctctggcgga gcagtttctg aaccaggtag 420
atctgaccga aaccctggaa agataccaac agagacttaa cacttacgcg ctggtatcca 480
aagacctggc cagctaccga tctttttcgc agcagctaaa ggcacaagac agcctaggtg 540
aacagcccac cactgtgcca ccgcccattg acctgtcaat acctcacgtt tggatgccac 600
cgcaaaccac tccacacggc tggacagaat cacataccac ctcaggacta caccgaccac 660
actttaacca gacctgtatc ctctttgatg gacacgatct actattcagc accgtcacac 720
cttgtttgca ccaaggcttt tacctcatcg acgaactacg ttacgttaaa ataacactga 780
ccgaggactt cttcgtagtt acggtgtcca tagacgacga cacacccatg ctgcttatct 840
tcggccatct tccacgcgta cttttcaaag cgccctatca acgcgacaac tttatactac 900
gacaaactga aaaacacgag ctcctggtgc tagttaagaa agatcaactg aaccgtcact 960
cttatctcaa agacccggac tttcttgacg ccgcacttga cttcaactac ctagacctca 1020
gcgcactact acgtaacagc tttcaccgtt acgccgtgga tgtactcaag agcggtcgat 1080
gtcagatgct ggaccgccgc acggtagaaa tggccttcgc ctacgcatta gcactgttcg 1140
cagcagcccg acaagaagag gccggcgccc aagtctccgt cccacgggcc ctagaccgcc 1200
aggccgcact cttacaaata caagaattta tgatcacctg cctctcacaa acaccaccac 1260
gcaccacgtt gctgctgtat cccacggccg tggacctggc caaacgagcc ctttggacac 1320
cgaatcagat caccgacatc accagcctcg tacgcctggt ctacatactc tctaaacaga 1380
atcagcaaca tctcatcccc caatgggcac tacgacagat cgccgacttt gccctaaaac 1440
tacacaaaac gcacctggcc tctttttcttt cagccttcgc acgccaagaa ctctacctca 1500
tgggcagcct cgtccactcc atgctggtac atacgacgga gagacgcgaa atcttcatcg 1560
tagaaacggg cctctgttca ttggccgagc tatcacactt tacgcagttg ttagctcatc 1620
cacaccacga atacctcagc gacctgtaca caccctgttc cagtagcggg cgacgcgatc 1680
actcgctcga acgcctcacg cgtctcttcc ccgatgccac cgtccccgct accgttcccg 1740
ccgccctctc catcctatct accatgcaac caagcacgct ggaaaccttc cccgacctgt 1800
tttgcttgcc gctcggcgaa tccttctccg cgctgaccgt ctccgaacac gtcagttata 1860
tcgtaacaaa ccagtacctg atcaaaggta tctcctaccc tgtctccacc accgtcgtag 1920
gccagagcct catcatcacc cagacggaca gtcaaactaa atgcgaactg acgcgcaaca 1980
tgcataccac acacagcatc acagtggcgc tcaacatttc gctagaaaac tgcgcctttt 2040
gccaaagcgc cctgctagaa tacgacgaca cgcaaggcgt catcaacatc atgtacatgc 2100
acgactcgga cgacgtcctt ttcgccctgg atccctacaa cgaagtggtg gtctcatctc 2160
cgcgaactca ctacctcatg cttttgaaaa acggtacggt actagaagta actgacgtcg 2220
tcgtggacgc caccgacgat tacaaggacg atgacgataa gtgatgataa taggctggag 2280
cctcggtggc catgcttctt gccccttggg cctcccccca gcccctcctc cccttcctgc 2340
acccgtaccc ccgtggtctt tgaataaagt ctgagtgggc ggc 2383

<210> SEQ ID NO 9
<211> LENGTH: 2377
<212> TYPE: DNA
<213> ORGANISM: Artificial Sequence
<220> FEATURE:
<223> OTHER INFORMATION: Synthetic polynucleotide

<400> SEQUENCE: 9
tcaagctttt ggaccctcgt acagaagcta atacgactca ctatagggaa ataagagaga 60
aaagaagagt aagaagaaat ataagagcca ccatgcggcc aggcctcccc tcctacctca 120

```
tcatcctcgc cgtctgtctc ttcagccacc tactttcgtc acgatatggc gcagaagccg    180
tatccgaacc gctggacaaa gcgtttcacc tactgctcaa cacctacggg agacccatcc    240
gcttcctgcg tgaaaatacc acccagtgta cctacaacag cagcctccgt aacagcacgg    300
tcgtcaggga aaacgccatc agtttcaact ttttccaaag ctataatcaa tactatgtat    360
tccatatgcc tcgatgtctt tttgcgggtc ctctggcgga gcagtttctg aaccaggtag    420
atctgaccga aaccctggaa agataccaac agagacttaa cacttacgcg ctggtatcca    480
aagacctggc cagctaccga tctttttcgc agcagctaaa ggcacaagac agcctaggtg    540
aacagcccac cactgtgcca ccgcccattg acctgtcaat acctcacgtt tggatgccac    600
cgcaaaccac tccacacggc tggacagaat cacataccac ctcaggacta caccgaccac    660
actttaacca gacctgtatc ctctttgatg gacacgatct actattcagc accgtcacac    720
cttgtttgca ccaaggcttt tacctcatcg acgaactacg ttacgttaaa ataacactga    780
ccgaggactt cttcgtagtt acggtgtcca tagacgacga cacacccatg ctgcttatct    840
tcggccatct tccacgcgta cttttcaaag cgccctatca acgcgacaac tttatactac    900
gacaaactga aaaacacgag ctcctggtgc tagttaagaa agatcaactg aaccgtcact    960
cttatctcaa agacccggac tttcttgacg ccgcacttga cttcaactac ctagacctca   1020
gcgcactact acgtaacagc tttcaccgtt acgccgtgga tgtactcaag agcggtcgat   1080
gtcagatgct ggaccgccgc acggtagaaa tggccttcgc ctacgcatta gcactgttcg   1140
cagcagcccg acaagaagag gccggcgccc aagtctccgt cccacgggcc ctagaccgcc   1200
aggccgcact cttacaaata caagaattta tgatcacctg cctctcacaa acaccaccac   1260
gcaccacgtt gctgctgtat cccacggccg tggacctggc caaacgagcc ctttggacac   1320
cgaatcagat caccgacatc accagcctcg tacgcctggt ctacatactc tctaaacaga   1380
atcagcaaca tctcatcccc caatgggcac tacgacagat cgccgacttt gccctaaaac   1440
tacacaaaac gcacctggcc tcttttcttt cagccttcgc acgccaagaa ctctacctca   1500
tgggcagcct cgtccactcc atgctggtac atacgacgga gagacgcgaa atcttcatcg   1560
tagaaacggg cctctgttca ttggccgagc tatcacactt tacgcagttg ttagctcatc   1620
cacaccacga atacctcagc gacctgtaca caccctgttc cagtagcggg cgacgcgatc   1680
actcgctcga acgcctcacg cgtctcttcc ccgatgccac cgtccccgct accgttcccg   1740
ccgccctctc catcctatct accatgcaac caagcacgct ggaaaccttc cccgacctgt   1800
tttgcttgcc gctcggcgaa tccttctccg cgctgaccgt ctccgaacac gtcagttata   1860
tcgtaacaaa ccagtacctg atcaaaggta tctcctaccc tgtctccacc accgtcgtag   1920
gccagagcct catcatcacc cagacggaca gtcaaactaa atgcgaactg acgcgcaaca   1980
tgcataccac acacagcatc acagtggcgc tcaacatttc gctagaaaac tgcgcctttt   2040
gccaaagcgc cctgctagaa tacgacgaca cgcaaggcgt catcaacatc atgtacatgc   2100
acgactcgga cgacgtcctt ttcgccctgg atccctacaa cgaagtggtg gtctcatctc   2160
cgcgaactca ctacctcatg cttttgaaaa acggtacggt actagaagta actgacgtcg   2220
tcgtggacgc caccgaccac catcaccacc atcactgatg ataataggct ggagcctcgg   2280
tggccatgct tcttgcccct tgggcctccc cccagcccct cctccccttc ctgcacccgt   2340
acccccgtgg tctttgaata aagtctgagt gggcggc                            2377
```

<210> SEQ ID NO 10

<211> LENGTH: 2287
<212> TYPE: DNA
<213> ORGANISM: Artificial Sequence
<220> FEATURE:
<223> OTHER INFORMATION: Synthetic polynucleotide

<400> SEQUENCE: 10

```
tcaagctttt ggaccctcgt acagaagcta atacgactca ctatagggaa ataagagaga     60
aaagaagagt aagaagaaat ataagagcca ccatggaatc caggatctgg tgcctggtag    120
tctgcgttaa cttgtgtatc gtctgtctgg gtgctgcggt ttcctcatct tctactcgtg    180
gaacttctgc tactcacagt caccattcct ctcatacgac gtctgctgct cactctcgat    240
ccggttcagt ctctcaacgc gtaacttctt cccaaacggt cagccatggt gttaacgaga    300
ccatctacaa cactaccctc aagtacggag atgtggtggg ggtcaatacc accaagtacc    360
cctatcgcgt gtgttctatg gcccagggta cggatcttat tcgctttgaa cgtaatatcg    420
tctgcacctc gatgaagccc atcaatgaag acctggacga gggcatcatg gtggtctaca    480
aacgcaacat cgtcgcgcac acctttaagg tacgagtcta ccagaaggtt ttgacgtttc    540
gtcgtagcta cgcttacatc cacaccactt atctgctggg cagcaacacg gaatacgtgg    600
cgcctcctat gtgggagatt catcatatca acagccacag tcagtgctac agttcctaca    660
gccgcgttat agcaggcacg gttttcgtgg cttatcatag ggacagctat gaaaacaaaa    720
ccatgcaatt aatgcccgac gattattcca acacccacag tacccgttac gtgacggtca    780
aggatcaatg gcacagccgc ggcagcacct ggctctatcg tgagacctgt aatctgaatt    840
gtatggtgac catcactact gcgcgctcca aatatcctta tcattttttc gccacttcca    900
cgggtgacgt ggttgacatt tctcctttct acaacggaac caatcgcaat gccagctact    960
ttggagaaaa cgccgacaag tttttcattt ttccgaacta cactatcgtc tccgactttg   1020
gaagaccgaa ttctgcgtta gagacccaca ggttggtggc ttttcttgaa cgtgcggact   1080
cggtgatctc ctgggatata caggacgaaa agaatgtcac ttgtcaactc actttctggg   1140
aagcctcgga acgcaccatt cgttccgaag ccgaggactc gtatcacttt tcttctgcca   1200
aaatgaccgc cactttctta tctaagaagc aagaggtgaa catgtccgac tctgcgctgg   1260
actgcgtacg tgatgaggct ataaataagt tacagcagat tttcaatact tcatacaatc   1320
aaacatatga aaaatatgga aacgtgtccg tctttgaaac cactggtggt ttggtagtgt   1380
tctggcaagg tatcaagcaa aaatctctgg tggaactcga acgtttggcc aaccgctcca   1440
gtctgaatct tactcataat agaaccaaaa gaagtacaga tggcaacaat gcaactcatt   1500
tatccaacat ggaatcggtg cacaatctgg tctacgccca gctgcagttc acctatgaca   1560
cgttgcgcgg ttacatcaac cgggcgctgg cgcaaatcgc agaagcctgg tgtgtggatc   1620
aacggcgcac cctagaggtc ttcaaggaac tcagcaagat caacccgtca gccattctct   1680
cggccattta caacaaaccg attgccgcgc gtttcatggg tgatgtcttg ggcctggcca   1740
gctgcgtgac catcaaccaa accagcgtca aggtgctgcg tgatatgaac gtgaaggagt   1800
cgccaggacg ctgctactca cgacccgtgg tcatctttaa tttcgccaac agctcgtacg   1860
tgcagtacgg tcaactgggc gaggacaacg aaatcctgtt gggcaaccac cgcactgagg   1920
aatgtcagct tcccagcctc aagatcttca tcgccgggaa ctcggcctac gagtacgtgg   1980
actacctctt caaacgcatg attgacctca gcagtatctc caccgtcgac agcatgatcg   2040
ccctggatat cgacccgctg gaaaataccg acttcagggt actggaactt tactcgcaga   2100
aagagctgcg ttccagcaac gtttttgacc tcgaagagat catgcgcgaa ttcaactcgt   2160
```

acaagcagtg ataataggct ggagcctcgg tggccatgct tcttgcccct tgggcctccc 2220
cccagcccct cctccccttc ctgcacccgt acccccgtgg tctttgaata aagtctgagt 2280
gggcggc 2287

<210> SEQ ID NO 11
<211> LENGTH: 2311
<212> TYPE: DNA
<213> ORGANISM: Artificial Sequence
<220> FEATURE:
<223> OTHER INFORMATION: Synthetic polynucleotide

<400> SEQUENCE: 11
tcaagctttt ggaccctcgt acagaagcta atacgactca ctatagggaa ataagagaga 60
aaagaagagt aagaagaaat ataagagcca ccatggaatc caggatctgg tgcctggtag 120
tctgcgttaa cttgtgtatc gtctgtctgg gtgctgcggt ttcctcatct tctactcgtg 180
gaacttctgc tactcacagt caccattcct ctcatacgac gtctgctgct cactctcgat 240
ccggttcagt ctctcaacgc gtaacttctt cccaaacggt cagccatggt gttaacgaga 300
ccatctacaa cactaccctc aagtacggag atgtggtggg ggtcaatacc accaagtacc 360
cctatcgcgt gtgttctatg gcccagggta cggatcttat tcgctttgaa cgtaatatcg 420
tctgcacctc gatgaagccc atcaatgaag acctggacga gggcatcatg gtggtctaca 480
aacgcaacat cgtcgcgcac acctttaagg tacgagtcta ccagaaggtt ttgacgtttc 540
gtcgtagcta cgcttacatc cacaccactt atctgctggg cagcaacacg gaatacgtgg 600
cgcctcctat gtgggagatt catcatatca acagccacag tcagtgctac agttcctaca 660
gccgcgttat agcaggcacg gttttcgtgg cttatcatag ggacagctat gaaaacaaaa 720
ccatgcaatt aatgcccgac gattattcca acacccacag tacccgttac gtgacggtca 780
aggatcaatg gcacagccgc ggcagcacct ggctctatcg tgagacctgt aatctgaatt 840
gtatggtgac catcactact gcgcgctcca aatatcctta tcattttttc gccacttcca 900
cgggtgacgt ggttgacatt tctcctttct acaacggaac caatcgcaat gccagctact 960
ttggagaaaa cgccgacaag tttttcattt ttccgaacta cactatcgtc tccgactttg 1020
gaagaccgaa ttctgcgtta gagacccaca ggttggtggc ttttcttgaa cgtgcggact 1080
cggtgatctc ctgggatata caggacgaaa agaatgtcac ttgtcaactc actttctggg 1140
aagcctcgga acgcaccatt cgttccgaag ccgaggactc gtatcacttt tcttctgcca 1200
aaatgaccgc cactttctta tctaagaagc aagaggtgaa catgtccgac tctgcgctgg 1260
actgcgtacg tgatgaggct ataaataagt tacagcagat tttcaatact tcatacaatc 1320
aaacatatga aaaatatgga aacgtgtccg tctttgaaac cactggtggt ttggtagtgt 1380
tctggcaagg tatcaagcaa aaatctctgg tggaactcga acgtttggcc aaccgctcca 1440
gtctgaatct tactcataat agaaccaaaa gaagtacaga tggcaacaat gcaactcatt 1500
tatccaacat ggaatcggtg cacaatctgg tctacgccca gctgcagttc acctatgaca 1560
cgttgcgcgg ttacatcaac cgggcgctgg cgcaaatcgc agaagcctgg tgtgtggatc 1620
aacggcgcac cctagaggtc ttcaaggaac tcagcaagat caacccgtca gccattctct 1680
cggccattta caacaaaccg attgccgcgc gtttcatggg tgatgtcttg ggcctggcca 1740
gctgcgtgac catcaaccaa accagcgtca aggtgctgcg tgatatgaac gtgaaggagt 1800
cgccaggacg ctgctactca cgacccgtgg tcatctttaa tttcgccaac agctcgtacg 1860
tgcagtacgg tcaactgggc gaggacaacg aaatcctgtt gggcaaccac cgcactgagg 1920
aatgtcagct tcccagcctc aagatcttca tcgccgggaa ctcggcctac gagtacgtgg 1980
actacctctt caaacgcatg attgacctca gcagtatctc caccgtcgac agcatgatcg 2040
ccctggatat cgacccgctg gaaaataccg acttcagggt actggaactt tactcgcaga 2100
aagagctgcg ttccagcaac gtttttgacc tcgaagagat catgcgcgaa ttcaactcgt 2160
acaagcagga ttacaaggac gatgacgata agtgataata ggctggagcc tcggtggcca 2220
tgcttcttgc cccttgggcc tccccccagc ccctcctccc cttcctgcac ccgtaccccc 2280
gtggtctttg aataaagtct gagtgggcgg c 2311

<210> SEQ ID NO 12
<211> LENGTH: 2305
<212> TYPE: DNA
<213> ORGANISM: Artificial Sequence
<220> FEATURE:
<223> OTHER INFORMATION: Synthetic polynucleotide

<400> SEQUENCE: 12
tcaagctttt ggaccctcgt acagaagcta atacgactca ctatagggaa ataagagaga 60
aaagaagagt aagaagaaat ataagagcca ccatggaatc caggatctgg tgcctggtag 120
tctgcgttaa cttgtgtatc gtctgtctgg gtgctgcggt ttcctcatct tctactcgtg 180
gaacttctgc tactcacagt caccattcct ctcatacgac gtctgctgct cactctcgat 240
ccggttcagt ctctcaacgc gtaacttctt cccaaacggt cagccatggt gttaacgaga 300
ccatctacaa cactaccctc aagtacggag atgtggtggg ggtcaatacc accaagtacc 360
cctatcgcgt gtgttctatg gcccagggta cggatcttat tcgctttgaa cgtaatatcg 420
tctgcacctc gatgaagccc atcaatgaag acctggacga gggcatcatg gtggtctaca 480
aacgcaacat cgtcgcgcac acctttaagg tacgagtcta ccagaaggtt ttgacgtttc 540
gtcgtagcta cgcttacatc cacaccactt atctgctggg cagcaacacg gaatacgtgg 600
cgcctcctat gtgggagatt catcatatca acagccacag tcagtgctac agttcctaca 660
gccgcgttat agcaggcacg gttttcgtgg cttatcatag ggacagctat gaaaacaaaa 720
ccatgcaatt aatgcccgac gattattcca acacccacag tacccgttac gtgacggtca 780
aggatcaatg gcacagccgc ggcagcacct ggctctatcg tgagacctgt aatctgaatt 840
gtatggtgac catcactact gcgcgctcca aatatcctta tcattttttc gccacttcca 900
cgggtgacgt ggttgacatt tctcctttct acaacggaac caatcgcaat gccagctact 960
ttggagaaaa cgccgacaag tttttcattt ttccgaacta cactatcgtc tccgactttg 1020
gaagaccgaa ttctgcgtta gagacccaca ggttggtggc ttttcttgaa cgtgcggact 1080
cggtgatctc ctgggatata caggacgaaa agaatgtcac ttgtcaactc actttctggg 1140
aagcctcgga acgcaccatt cgttccgaag ccgaggactc gtatcacttt tcttctgcca 1200
aaatgaccgc cactttctta tctaagaagc aagaggtgaa catgtccgac tctgcgctgg 1260
actgcgtacg tgatgaggct ataaataagt tacagcagat tttcaatact tcatacaatc 1320
aaacatatga aaaatatgga aacgtgtccg tctttgaaac cactggtggt ttggtagtgt 1380
tctggcaagg tatcaagcaa aaatctctgg tggaactcga acgtttggcc aaccgctcca 1440
gtctgaatct tactcataat agaaccaaaa gaagtacaga tggcaacaat gcaactcatt 1500
tatccaacat ggaatcggtg cacaatctgg tctacgccca gctgcagttc acctatgaca 1560
cgttgcgcgg ttacatcaac cgggcgctgg cgcaaatcgc agaagcctgg tgtgtggatc 1620
aacggcgcac cctagaggtc ttcaaggaac tcagcaagat caacccgtca gccattctct 1680
cggccattta caacaaaccg attgccgcgc gtttcatggg tgatgtcttg ggcctggcca 1740
gctgcgtgac catcaaccaa accagcgtca aggtgctgcg tgatatgaac gtgaaggagt 1800
cgccaggacg ctgctactca cgacccgtgg tcatctttaa tttcgccaac agctcgtacg 1860
tgcagtacgg tcaactgggc gaggacaacg aaatcctgtt gggcaaccac cgcactgagg 1920
aatgtcagct tcccagcctc aagatcttca tcgccgggaa ctcggcctac gagtacgtgg 1980
actacctctt caaacgcatg attgacctca gcagtatctc caccgtcgac agcatgatcg 2040
ccctggatat cgacccgctg gaaaataccg acttcagggt actggaactt tactcgcaga 2100
aagagctgcg ttccagcaac gtttttgacc tcgaagagat catgcgcgaa ttcaactcgt 2160
acaagcagca ccatcaccac catcactgat aataggctgg agcctcggtg gccatgcttc 2220
ttgccccttg ggcctccccc cagcccctcc tccccttcct gcacccgtac ccccgtggtc 2280
tttgaataaa gtctgagtgg gcggc 2305

<210> SEQ ID NO 13
<211> LENGTH: 724
<212> TYPE: DNA
<213> ORGANISM: Artificial Sequence
<220> FEATURE:
<223> OTHER INFORMATION: Synthetic polynucleotide

<400> SEQUENCE: 13
tcaagctttt ggaccctcgt acagaagcta atacgactca ctatagggaa ataagagaga 60
aaagaagagt aagaagaaat ataagagcca ccatgagtcc caaagatctg acgccgttct 120
tgacggcgtt gtggctgcta ttgggtcaca gccgcgtgcc gcgggtgcgc gcagaagaat 180
gttgcgaatt cataaacgtc aaccacccgc cggaacgctg ttacgatttc aaaatgtgca 240
atcgcttcac cgtcgcgctg cggtgtccgg acggcgaagt ctgctacagt cccgagaaaa 300
cggctgagat tcgcgggatc gtcaccacca tgacccattc attgacacgc caggtcgtac 360
acaacaaact gacgagctgc aactacaatc cgttatacct cgaagctgac gggcgaatac 420
gctgcggcaa agtaaacgac aaggcgcagt acctgctggg cgccgctggc agcgttccct 480
atcgatggat caatctggaa tacgacaaga taacccggat cgtgggcctg gatcagtacc 540
tggagagcgt taagaaacac aaacggctgg atgtgtgccg cgctaaaatg ggctatatgc 600
tgcagtgata ataggctgga gcctcggtgg ccatgcttct tgccccttgg gcctcccccc 660
agcccctcct ccccttcctg cacccgtacc cccgtggtct ttgaataaag tctgagtggg 720
cggc 724

<210> SEQ ID NO 14
<211> LENGTH: 748
<212> TYPE: DNA
<213> ORGANISM: Artificial Sequence
<220> FEATURE:
<223> OTHER INFORMATION: Synthetic polynucleotide

<400> SEQUENCE: 14
tcaagctttt ggaccctcgt acagaagcta atacgactca ctatagggaa ataagagaga 60
aaagaagagt aagaagaaat ataagagcca ccatgagtcc caaagatctg acgccgttct 120
tgacggcgtt gtggctgcta ttgggtcaca gccgcgtgcc gcgggtgcgc gcagaagaat 180
gttgcgaatt cataaacgtc aaccacccgc cggaacgctg ttacgatttc aaaatgtgca 240

-continued

```
atcgcttcac cgtcgcgctg cggtgtccgg acggcgaagt ctgctacagt cccgagaaaa    300

cggctgagat tcgcgggatc gtcaccacca tgacccattc attgacacgc caggtcgtac    360

acaacaaact gacgagctgc aactacaatc cgttatacct cgaagctgac gggcgaatac    420

gctgcggcaa agtaaacgac aaggcgcagt acctgctggg cgccgctggc agcgttccct    480

atcgatggat caatctggaa tacgacaaga taacccggat cgtgggcctg gatcagtacc    540

tggagagcgt taagaaacac aaacggctgg atgtgtgccg cgctaaaatg ggctatatgc    600

tgcaggatta caaggacgat gacgataagt gataataggc tggagcctcg gtggccatgc    660

ttcttgcccc ttgggcctcc ccccagcccc tcctcccctt cctgcacccg tacccccgtg    720

gtctttgaat aaagtctgag tgggcggc                                       748
```

<210> SEQ ID NO 15
<211> LENGTH: 853
<212> TYPE: DNA
<213> ORGANISM: Artificial Sequence
<220> FEATURE:
<223> OTHER INFORMATION: Synthetic polynucleotide

<400> SEQUENCE: 15

```
tcaagctttt ggaccctcgt acagaagcta atacgactca ctatagggaa ataagagaga     60

aaagaagagt aagaagaaat ataagagcca ccatgctgcg gcttctgctt cgtcaccact    120

ttcactgcct gcttctgtgc gcggtttggg caacgccctg tctggcgtct ccgtggtcga    180

cgctaacagc aaaccagaat ccgtccccgc catggtctaa actgacgtat tccaaaccgc    240

atgacgcggc gacgttttac tgtccttttc tctatccctc gcccccacga tccccccttgc    300

aattctcggg gttccagcgg gtatcaacgg gtcccgagtg tcgcaacgag accctgtatc    360

tgctgtacaa ccgggaaggc cagaccttgg tggagagaag ctccacctgg gtgaaaaagg    420

tgatctggta cctgagcggt cggaaccaaa ccatcctcca acggatgccc cgaacggctt    480

cgaaaccgag cgacggaaac gtgcagatca gcgtggaaga cgccaagatt tttggagcgc    540

acatggtgcc caagcagacc aagctgctac gcttcgtcgt caacgatggc acacgttatc    600

agatgtgtgt gatgaagctg gagagctggg ctcacgtctt ccgggactac agcgtgtctt    660

ttcaggtgcg attgacgttc accgaggcca ataaccagac ttacaccttc tgcacccatc    720

ccaatctcat cgtttgataa taggctggag cctcggtggc catgcttctt gccccttggg    780

cctcccccca gcccctcctc cccttcctgc acccgtaccc ccgtggtctt tgaataaagt    840

ctgagtgggc ggc                                                       853
```

<210> SEQ ID NO 16
<211> LENGTH: 880
<212> TYPE: DNA
<213> ORGANISM: Artificial Sequence
<220> FEATURE:
<223> OTHER INFORMATION: Synthetic polynucleotide

<400> SEQUENCE: 16

```
tcaagctttt ggaccctcgt acagaagcta atacgactca ctatagggaa ataagagaga     60

aaagaagagt aagaagaaat ataagagcca ccatgctgcg gcttctgctt cgtcaccact    120

ttcactgcct gcttctgtgc gcggtttggg caacgccctg tctggcgtct ccgtggtcga    180

cgctaacagc aaaccagaat ccgtccccgc catggtctaa actgacgtat tccaaaccgc    240

atgacgcggc gacgttttac tgtccttttc tctatccctc gcccccacga tcccccttgc    300

aattctcggg gttccagcgg gtatcaacgg gtcccgagtg tcgcaacgag accctgtatc    360
```

tgctgtacaa ccgggaaggc cagaccttgg tggagagaag ctccacctgg gtgaaaaagg 420
tgatctggta cctgagcggt cggaaccaaa ccatcctcca acggatgccc cgaacggctt 480
cgaaaccgag cgacggaaac gtgcagatca gcgtggaaga cgccaagatt tttggagcgc 540
acatggtgcc caagcagacc aagctgctac gcttcgtcgt caacgatggc acacgttatc 600
agatgtgtgt gatgaagctg gagagctggg ctcacgtctt ccgggactac agcgtgtctt 660
ttcaggtgcg attgacgttc accgaggcca ataaccagac ttacaccttc tgcacccatc 720
ccaatctcat cgttgattac aaggacgatg acgataagtg atgataatag gctggagcct 780
cggtggccat gcttcttgcc ccttgggcct ccccccagcc cctcctcccc ttcctgcacc 840
cgtacccccg tggtctttga ataaagtctg agtgggcggc 880

<210> SEQ ID NO 17
<211> LENGTH: 598
<212> TYPE: DNA
<213> ORGANISM: Artificial Sequence
<220> FEATURE:
<223> OTHER INFORMATION: Synthetic polynucleotide

<400> SEQUENCE: 17
tcaagctttt ggaccctcgt acagaagcta atacgactca ctatagggaa ataagagaga 60
aaagaagagt aagaagaaat ataagagcca ccatgcggct gtgtcgggtg tggctgtctg 120
tttgtctgtg cgccgtggtg ctgggtcagt gccagcggga aaccgcggaa aaaaacgatt 180
attaccgagt accgcattac tgggacgcgt gctctcgcgc gctgcccgac caaacccgtt 240
acaagtatgt ggaacagctc gtggacctca cgttgaacta ccactacgat gcgagccacg 300
gcttggacaa ctttgacgtg ctcaagagaa tcaacgtgac cgaggtgtcg ttgctcatca 360
gcgactttag acgtcagaac cgtcgcggcg gcaccaacaa aaggaccacg ttcaacgccg 420
ccggttcgct ggcgccacac gcccggagcc tcgagttcag cgtgcggctc tttgccaact 480
gataataggc tggagcctcg gtggccatgc ttcttgcccc ttgggcctcc ccccagcccc 540
tcctcccctt cctgcacccg tacccccgtg gtctttgaat aaagtctgag tgggcggc 598

<210> SEQ ID NO 18
<211> LENGTH: 625
<212> TYPE: DNA
<213> ORGANISM: Artificial Sequence
<220> FEATURE:
<223> OTHER INFORMATION: Synthetic polynucleotide

<400> SEQUENCE: 18
tcaagctttt ggaccctcgt acagaagcta atacgactca ctatagggaa ataagagaga 60
aaagaagagt aagaagaaat ataagagcca ccatgcggct gtgtcgggtg tggctgtctg 120
tttgtctgtg cgccgtggtg ctgggtcagt gccagcggga aaccgcggaa aaaaacgatt 180
attaccgagt accgcattac tgggacgcgt gctctcgcgc gctgcccgac caaacccgtt 240
acaagtatgt ggaacagctc gtggacctca cgttgaacta ccactacgat gcgagccacg 300
gcttggacaa ctttgacgtg ctcaagagaa tcaacgtgac cgaggtgtcg ttgctcatca 360
gcgactttag acgtcagaac cgtcgcggcg gcaccaacaa aaggaccacg ttcaacgccg 420
ccggttcgct ggcgccacac gcccggagcc tcgagttcag cgtgcggctc tttgccaacg 480
attacaagga cgatgacgat aagtgatgat aataggctgg agcctcggtg gccatgcttc 540
ttgccccttg ggcctccccc cagcccctcc tccccttcct gcacccgtac ccccgtggtc 600
tttgaataaa gtctgagtgg gcggc 625

<210> SEQ ID NO 19
<211> LENGTH: 2434
<212> TYPE: DNA
<213> ORGANISM: Artificial Sequence
<220> FEATURE:
<223> OTHER INFORMATION: Synthetic polynucleotide

<400> SEQUENCE: 19
tcaagctttt ggaccctcgt acagaagcta atacgactca ctatagggac agacgagaga 60
gaagcacgcc aattctgcct gcttaagcca tgcggccagg cctcccctcc tacctcatca 120
tcctcgccgt ctgtctcttc agccacctac tttcgtcacg atatggcgca gaagccgtat 180
ccgaaccgct ggacaaagcg tttcacctac tgctcaacac ctacgggaga cccatccgct 240
tcctgcgtga aaataccacc cagtgtacct acaacagcag cctccgtaac agcacggtcg 300
tcagggaaaa cgccatcagt ttcaactttt tccaaagcta taatcaatac tatgtattcc 360
atatgcctcg atgtcttttt gcgggtcctc tggcggagca gtttctgaac caggtagatc 420
tgaccgaaac cctggaaaga taccaacaga gacttaacac ttacgcgctg gtatccaaag 480
acctggccag ctaccgatct tttcgcagc agctaaaggc acaagacagc ctaggtgaac 540
agcccaccac tgtgccaccg cccattgacc tgtcaatacc tcacgtttgg atgccaccgc 600
aaaccactcc acacggctgg acagaatcac ataccacctc aggactacac cgaccacact 660
ttaaccagac ctgtatcctc tttgatggac acgatctact attcagcacc gtcacacctt 720
gtttgcacca aggcttttac ctcatcgacg aactacgtta cgttaaaata acactgaccg 780
aggacttctt cgtagttacg gtgtccatag acgacgacac acccatgctg cttatcttcg 840
gccatcttcc acgcgtactt ttcaaagcgc cctatcaacg cgacaacttt atactacgac 900
aaactgaaaa acacgagctc ctggtgctag ttaagaaaga tcaactgaac cgtcactctt 960
atctcaaaga cccggacttt cttgacgccg cacttgactt caactaccta gacctcagcg 1020
cactactacg taacagcttt caccgttacg ccgtggatgt actcaagagc ggtcgatgtc 1080
agatgctgga ccgccgcacg gtagaaatgg ccttcgccta cgcattagca ctgttcgcag 1140
cagcccgaca agaagaggcc ggcgcccaag tctccgtccc acgggcccta gaccgccagg 1200
ccgcactctt acaaatacaa gaatttatga tcacctgcct ctcacaaaca ccaccacgca 1260
ccacgttgct gctgtatccc acggccgtgg acctggccaa acgagccctt tggacaccga 1320
atcagatcac cgacatcacc agcctcgtac gcctggtcta catactctct aaacagaatc 1380
agcaacatct catcccccaa tgggcactac gacagatcgc cgactttgcc ctaaaactac 1440
acaaaacgca cctggcctct ttctttcag ccttcgcacg ccaagaactc tacctcatgg 1500
gcagcctcgt ccactccatg ctggtacata cgacggagag acgcgaaatc ttcatcgtag 1560
aaacgggcct ctgttcattg gccgagctat cacactttac gcagttgtta gctcatccac 1620
accacgaata cctcagcgac ctgtacacac cctgttccag tagcgggcga cgcgatcact 1680
cgctcgaacg cctcacgcgt ctcttccccg atgccaccgt ccccgctacc gttcccgccg 1740
ccctctccat cctatctacc atgcaaccaa gcacgctgga aaccttcccc gacctgtttt 1800
gcttgccgct cggcgaatcc ttctccgcgc tgaccgtctc cgaacacgtc agttatatcg 1860
taacaaacca gtacctgatc aaaggtatct cctaccctgt ctccaccacc gtcgtaggcc 1920
agagcctcat catcacccag acggacagtc aaactaaatg cgaactgacg cgcaacatgc 1980
ataccacaca cagcatcaca gtggcgctca acatttcgct agaaaactgc gccttttgcc 2040
aaagcgccct gctagaatac gacgacacgc aaggcgtcat caacatcatg tacatgcacg 2100
actcggacga cgtccttttc gccctggatc cctacaacga agtggtggtc tcatctccgc 2160
gaactcacta cctcatgctt ttgaaaaacg gtacggtact agaagtaact gacgtcgtcg 2220
tggacgccac cgacagtcgt ctcctcatga tgtccgtcta cgcgctatcg gccatcatcg 2280
gcatctatct gctctaccgc atgctcaaga catgctgata ataggctgga gcctcggtgg 2340
ccatgcttct tgccccttgg gcctcccccc agcccctcct ccccttcctg cacccgtacc 2400
cccgtggtct ttgaataaag tctgagtggg cggc 2434

<210> SEQ ID NO 20
<211> LENGTH: 1044
<212> TYPE: DNA
<213> ORGANISM: Artificial Sequence
<220> FEATURE:
<223> OTHER INFORMATION: Synthetic polynucleotide

<400> SEQUENCE: 20
tcaagctttt ggaccctcgt acagaagcta atacgactca ctatagggct taagcaggca 60
gaattggccc ttagcctgta ccagccgaac catgtgccgc cgcccggatt gcggcttctc 120
tttctcacct ggaccggtga tactgctgtg gtgttgcctt ctgctgccca ttgtttcctc 180
agccgccgtc agcgtcgctc ctaccgccgc cgagaaagtc cccgcggagt gccccgaact 240
aacgcgccga tgcttgttgg gtgaggtgtt tgagggtgac aagtatgaaa gttggctgcg 300
cccgttggtg aatgttaccg ggcgcgatgg cccgctatcg caacttatcc gttaccgtcc 360
cgttacgccg gaggccgcca actccgtgct gttggacgag gctttcctgg acactctggc 420
cctgctgtac aacaatccgg atcaattgcg ggccctgctg acgctgttga gctcggacac 480
agcgccgcgc tggatgacgg tgatgcgcgg ctacagcgag tgcggcgatg gctcgccggc 540
cgtgtacacg tgcgtggacg acctgtgccg cggctacgac ctcacgcgac tgtcatacgg 600
gcgcagcatc ttcacggaac acgtgttagg cttcgagctg gtgccaccgt ctctctttaa 660
cgtggtggtg gccatacgca acgaagccac gcgtaccaac cgcgccgtgc gtctgcccgt 720
gagcaccgct gccgcgcccg agggcatcac gctcttttac ggcctgtaca acgcagtgaa 780
ggaattctgc ctgcgtcacc agctggaccc gccgctgcta cgccacctag ataaatacta 840
cgccggactg ccgcccgagc tgaagcagac gcgcgtcaac ctgccggctc actcgcgcta 900
tggccctcaa gcagtggatg ctcgctgata ataggctgga gcctcggtgg ccatgcttct 960
tgccccttgg gcctcccccc agcccctcct ccccttcctg cacccgtacc cccgtggtct 1020
ttgaataaag tctgagtggg cggc 1044

<210> SEQ ID NO 21
<211> LENGTH: 1045
<212> TYPE: DNA
<213> ORGANISM: Artificial Sequence
<220> FEATURE:
<223> OTHER INFORMATION: Synthetic polynucleotide

<400> SEQUENCE: 21
tcaagctttt ggaccctcgt acagaagcta atacgactca ctatagggtg gctcttatat 60
ttcttcttac tcttcttttc tctcttattt ccatgtgccg ccgcccggat tgcggcttct 120
ctttctcacc tggaccggtg atactgctgt ggtgttgcct tctgctgccc attgtttcct 180
cagccgccgt cagcgtcgct cctaccgccg ccgagaaagt ccccgcggag tgccccgaac 240

```
taacgcgccg atgcttgttg ggtgaggtgt ttgagggtga caagtatgaa agttggctgc    300

gcccgttggt gaatgttacc gggcgcgatg gcccgctatc gcaacttatc cgttaccgtc    360

ccgttacgcc ggaggccgcc aactccgtgc tgttggacga ggctttcctg gacactctgg    420

ccctgctgta caacaatccg gatcaattgc gggccctgct gacgctgttg agctcggaca    480

cagcgccgcg ctggatgacg gtgatgcgcg gctacagcga gtgcggcgat ggctcgccgg    540

ccgtgtacac gtgcgtggac gacctgtgcc gcggctacga cctcacgcga ctgtcatacg    600

ggcgcagcat cttcacggaa cacgtgttag gcttcgagct ggtgccaccg tctctcttta    660

acgtggtggt ggccatacgc aacgaagcca cgcgtaccaa ccgcgccgtg cgtctgcccg    720

tgagcaccgc tgccgcgccc gagggcatca cgctctttta cggcctgtac aacgcagtga    780

aggaattctg cctgcgtcac cagctggacc cgccgctgct acgccaccta gataaatact    840

acgccggact gccgcccgag ctgaagcaga cgcgcgtcaa cctgccggct cactcgcgct    900

atggccctca agcagtggat gctcgctgat aataggctgg agcctcggtg gccatgcttc    960

ttgccccttg ggcctccccc cagcccctcc tccccttcct gcacccgtac ccccgtggtc   1020

tttgaataaa gtctgagtgg gcggc                                         1045
```

<210> SEQ ID NO 22
<211> LENGTH: 722
<212> TYPE: DNA
<213> ORGANISM: Artificial Sequence
<220> FEATURE:
<223> OTHER INFORMATION: Synthetic polynucleotide

<400> SEQUENCE: 22

```
tcaagctttt ggaccctcgt acagaagcta atacgactca ctatagggtt cggctggtac     60

aggctaacca gaagacagat aagagcctcc atgagtccca aagatctgac gccgttcttg    120

acggcgttgt ggctgctatt gggtcacagc cgcgtgccgc gggtgcgcgc agaagaatgt    180

tgcgaattca taaacgtcaa ccacccgccg gaacgctgtt acgatttcaa aatgtgcaat    240

cgcttcaccg tcgcgctgcg gtgtccggac ggcgaagtct gctacagtcc cgagaaaacg    300

gctgagattc gcgggatcgt caccaccatg acccattcat tgacacgcca ggtcgtacac    360

aacaaactga cgagctgcaa ctacaatccg ttatacctcg aagctgacgg gcgaatacgc    420

tgcggcaaag taaacgacaa ggcgcagtac ctgctgggcg ccgctggcag cgttccctat    480

cgatggatca atctggaata cgacaagata acccggatcg tgggcctgga tcagtacctg    540

gagagcgtta agaaacacaa acggctggat gtgtgccgcg ctaaaatggg ctatatgctg    600

cagtgataat aggctggagc ctcggtggcc atgcttcttg ccccttgggc ctccccccag    660

cccctcctcc ccttcctgca cccgtacccc cgtggtcttt gaataaagtc tgagtgggcg    720

gc                                                                   722
```

<210> SEQ ID NO 23
<211> LENGTH: 854
<212> TYPE: DNA
<213> ORGANISM: Artificial Sequence
<220> FEATURE:
<223> OTHER INFORMATION: Synthetic polynucleotide

<400> SEQUENCE: 23

```
tcaagctttt ggaccctcgt acagaagcta atacgactca ctatagggag gctcttatct     60

gtcttctcag tccgaattcg aagtacggct accatgctgc ggcttctgct tcgtcaccac    120

tttcactgcc tgcttctgtg cgcggtttgg gcaacgccct gtctggcgtc tccgtggtcg    180
```

```
acgctaacag caaaccagaa tccgtccccg ccatggtcta aactgacgta ttccaaaccg    240

catgacgcgg cgacgtttta ctgtcctttt ctctatccct cgcccccacg atccccccttg   300

caattctcgg ggttccagcg ggtatcaacg ggtcccgagt gtcgcaacga gaccctgtat    360

ctgctgtaca accgggaagg ccagaccttg gtggagagaa gctccacctg ggtgaaaaag    420

gtgatctggt acctgagcgg tcggaaccaa accatcctcc aacggatgcc ccgaacggct    480

tcgaaaccga gcgacggaaa cgtgcagatc agcgtggaag acgccaagat ttttggagcg    540

cacatggtgc ccaagcagac caagctgcta cgcttcgtcg tcaacgatgg cacacgttat    600

cagatgtgtg tgatgaagct ggagagctgg gctcacgtct tccgggacta cagcgtgtct    660

tttcaggtgc gattgacgtt caccgaggcc aataaccaga cttacacctt ctgcacccat    720

cccaatctca tcgtttgata ataggctgga gcctcggtgg ccatgcttct tgccccttgg    780

gcctcccccc agcccctcct ccccttcctg cacccgtacc cccgtggtct ttgaataaag    840

tctgagtggg cggc                                                      854
```

<210> SEQ ID NO 24
<211> LENGTH: 853
<212> TYPE: DNA
<213> ORGANISM: Artificial Sequence
<220> FEATURE:
<223> OTHER INFORMATION: Synthetic polynucleotide

<400> SEQUENCE: 24

```
tcaagctttt ggaccctcgt acagaagcta atacgactca ctatagggtg gctcttatat     60

ttcttcttag tccgaattcg aagtacggct acatgctgcg gcttctgctt cgtcaccact    120

ttcactgcct gcttctgtgc gcggtttggg caacgccctg tctggcgtct ccgtggtcga    180

cgctaacagc aaaccagaat ccgtccccgc catggtctaa actgacgtat tccaaaccgc    240

atgacgcggc gacgttttac tgtccttttc tctatccctc gcccccacga tcccccttgc    300

aattctcggg gttccagcgg gtatcaacgg gtcccgagtg tcgcaacgag accctgtatc    360

tgctgtacaa ccgggaaggc cagaccttgg tggagagaag ctccacctgg gtgaaaaagg    420

tgatctggta cctgagcggt cggaaccaaa ccatcctcca acggatgccc cgaacggctt    480

cgaaaccgag cgacggaaac gtgcagatca gcgtggaaga cgccaagatt tttggagcgc    540

acatggtgcc caagcagacc aagctgctac gcttcgtcgt caacgatggc acacgttatc    600

agatgtgtgt gatgaagctg gagagctggg ctcacgtctt ccgggactac agcgtgtctt    660

ttcaggtgcg attgacgttc accgaggcca ataaccagac ttacaccttc tgcacccatc    720

ccaatctcat cgtttgataa taggctggag cctcggtggc catgcttctt gccccttggg    780

cctcccccca gcccctcctc cccttcctgc acccgtaccc ccgtggtctt tgaataaagt    840

ctgagtgggc ggc                                                       853
```

<210> SEQ ID NO 25
<211> LENGTH: 597
<212> TYPE: DNA
<213> ORGANISM: Artificial Sequence
<220> FEATURE:
<223> OTHER INFORMATION: Synthetic polynucleotide

<400> SEQUENCE: 25

```
tcaagctttt ggaccctcgt acagaagcta atacgactca ctatagggta gccgtacttc     60

gaattcggac aagcttctct ctcgtctgtc catgcggctg tgtcgggtgt ggctgtctgt    120
```

```
ttgtctgtgc gccgtggtgc tgggtcagtg ccagcgggaa accgcggaaa aaaacgatta    180

ttaccgagta ccgcattact gggacgcgtg ctctcgcgcg ctgcccgacc aaacccgtta    240

caagtatgtg gaacagctcg tggacctcac gttgaactac cactacgatg cgagccacgg    300

cttggacaac tttgacgtgc tcaagagaat caacgtgacc gaggtgtcgt tgctcatcag    360

cgactttaga cgtcagaacc gtcgcggcgg caccaacaaa aggaccacgt tcaacgccgc    420

cggttcgctg gcgccacacg cccggagcct cgagttcagc gtgcggctct ttgccaactg    480

ataataggct ggagcctcgg tggccatgct tcttgcccct tgggcctccc cccagcccct    540

cctccccttc ctgcacccgt acccccgtgg tctttgaata aagtctgagt gggcggc       597
```

<210> SEQ ID NO 26
<211> LENGTH: 597
<212> TYPE: DNA
<213> ORGANISM: Artificial Sequence
<220> FEATURE:
<223> OTHER INFORMATION: Synthetic polynucleotide

<400> SEQUENCE: 26

```
tcaagctttt ggaccctcgt acagaagcta atacgactca ctatagggta gccgtacttc     60

gaattcggac tttcttttct ctcttatttc catgcggctg tgtcgggtgt ggctgtctgt    120

ttgtctgtgc gccgtggtgc tgggtcagtg ccagcgggaa accgcggaaa aaaacgatta    180

ttaccgagta ccgcattact gggacgcgtg ctctcgcgcg ctgcccgacc aaacccgtta    240

caagtatgtg gaacagctcg tggacctcac gttgaactac cactacgatg cgagccacgg    300

cttggacaac tttgacgtgc tcaagagaat caacgtgacc gaggtgtcgt tgctcatcag    360

cgactttaga cgtcagaacc gtcgcggcgg caccaacaaa aggaccacgt tcaacgccgc    420

cggttcgctg gcgccacacg cccggagcct cgagttcagc gtgcggctct ttgccaactg    480

ataataggct ggagcctcgg tggccatgct tcttgcccct tgggcctccc cccagcccct    540

cctccccttc ctgcacccgt acccccgtgg tctttgaata aagtctgagt gggcggc       597
```

<210> SEQ ID NO 27
<211> LENGTH: 3364
<212> TYPE: DNA
<213> ORGANISM: Artificial Sequence
<220> FEATURE:
<223> OTHER INFORMATION: Synthetic polynucleotide

<400> SEQUENCE: 27

```
tcaagctttt ggaccctcgt acagaagcta atacgactca ctatagggaa ataagagaga     60

aaagaagagt aagaagaaat ataagagcca ccatggagtc gcgcggtcgc cgttgtcccg    120

aaatgatatc cgtactgggt cccatttcgg ggcacgtgct gaaagccgtg tttagtcgcg    180

gcgatacgcc ggtgctgccg cacgagacgc gactcctgca gacgggtatc cacgtacgcg    240

tgagccagcc ctcgctgatc ctggtgtcgc agtacacgcc cgactcgacg ccatgccacc    300

gcggcgacaa tcagctgcag gtgcagcaca cgtactttac gggcagcgag gtggagaacg    360

tgtcggtcaa cgtgcacaac cccacgggcc gaagcatctg ccccagccaa gagcccatgt    420

cgatctatgt gtacgcgctg ccgctcaaga tgctgaacat ccccagcatc aacgtgcacc    480

actacccgtc ggcggccgag cgcaaacacc gacacctgcc cgtagccgac gctgttattc    540

acgcgtcggg caagcagatg tggcaggcgc gtctcacggt ctcgggactg gcctggacgc    600

gtcagcagaa ccagtggaaa gagcccgacg tctactacac gtcagcgttc gtgtttccca    660

ccaaggacgt ggcactgcgg cacgtggtgt gcgcgcacga gctggtttgc tccatggaga    720
```

acacgcgcgc aaccaagatg caggtgatag gtgaccagta cgtcaaggtg tacctggagt 780
ccttctgcga ggacgtgccc tccggcaagc tctttatgca cgtcacgctg ggctctgacg 840
tggaagagga cctaacgatg acccgcaacc cgcaaccctt catgcgcccc cacgagcgca 900
acggctttac ggtgttgtgt cccaaaaata tgataatcaa accgggcaag atctcgcaca 960
tcatgctgga tgtggctttt acctcacacg agcattttgg gctgctgtgt cccaagagca 1020
tcccgggcct gagcatctca ggtaacctgt tgatgaacgg gcagcaaatc ttcctggagg 1080
tacaagcgat acgcgagacc gtggaactgc gtcagtacga tcccgtggct gcgctcttct 1140
ttttcgatat cgacttgttg ctgcagcgcg ggcctcagta cagcgagcac cccaccttca 1200
ccagccagta tcgcatccag ggcaagcttg agtaccgaca cacctgggac cggcacgacg 1260
agggtgccgc ccagggcgac gacgacgtct ggaccagcgg atcggactcc gacgaagaac 1320
tcgtaaccac cgagcgtaag acgccccgcg tcaccggcgg cggcgccatg gcgagcgcct 1380
ccacttccgc gggccgcaaa cgcaaatcag catcctcggc gacggcgtgc acggcgggcg 1440
ttatgacacg cggccgcctt aaggccgagt ccaccgtcgc gcccgaagag gacaccgacg 1500
aggattccga caacgaaatc cacaatccgg ccgtgttcac ctggccgccc tggcaggccg 1560
gcatcctggc ccgcaacctg gtgcccatgg tggctacggt tcagggtcag aatctgaagt 1620
accaggagtt cttctgggac gccaacgaca tctaccgcat cttcgccgaa ttggaaggcg 1680
tatggcagcc cgctgcgcaa cccaaacgtc gccgccaccg gcaagacgcc ttgcccgggc 1740
catgcatcgc ctcgacgccc aaaaagcacc gaggtgagtc ctctgccaag agaaagatgg 1800
accctgataa tcctgacgag ggcccttcct ccaaggtgcc acggcccgag acacccgtga 1860
ccaaggccac gacgttcctg cagactatgt taaggaagga ggttaacagt cagctgagcc 1920
tgggagaccc gctgttccca gaattggccg aagaatccct caaaaccttt gaacaagtga 1980
ccgaggattg caacgagaac cccgaaaaag atgtcctgac agaactcgtc aaacagatta 2040
aggttcgagt ggacatggtg cggcatagaa tcaaggagca catgctgaaa aaatataccc 2100
agacggaaga aaaattcact ggcgccttta atatgatggg aggatgtttg cagaatgcct 2160
tagatatctt agataaggtt catgagcctt tcgaggacat gaagtgtatt gggctaacta 2220
tgcagagcat gtatgagaac tacattgtac ctgaggataa gcgggagatg tggatggctt 2280
gtattaagga gctgcatgat gtgagcaagg gcgccgctaa caagttgggg ggtgcactgc 2340
aggctaaggc ccgtgctaaa aaggatgaac ttaggagaaa gatgatgtat atgtgctaca 2400
ggaatataga gttctttacc aagaactcag ccttccctaa gaccaccaat ggctgcagtc 2460
aggccatggc ggcattgcag aacttgcctc agtgctctcc tgatgagatt atgtcttatg 2520
cccagaaaat ctttaagatt ttggatgagg agagagacaa ggtgctcacg cacattgatc 2580
acatatttat ggatatcctc actacatgtg tggaaacaat gtgtaatgag tacaaggtca 2640
ctagtgacgc ttgtatgatg accatgtacg ggggcatctc tctcttaagt gagttctgtc 2700
gggtgctgtg ctgctatgtc ttagaggaga ctagtgtgat gctggccaag cggcctctga 2760
taaccaagcc tgaggttatc agtgtaatga agcgccgcat tgaggagatc tgcatgaagg 2820
tctttgccca gtacattctg ggggccgatc ctttgagagt ctgctctcct agtgtggatg 2880
acctacgggc catcgccgag gagtcagatg aggaagaggc tattgtagcc tacactttgg 2940
ccaccgctgg tgccagctcc tctgattctc tggtgtcacc tccagagtcc cctgtacccg 3000
cgactatccc tctgtcctca gtaattgtgg ctgagaacag tgatcaggaa gaaagtgaac 3060
agagtgatga ggaacaggag gagggtgctc aggaggagcg ggaggacact gtgtctgtca 3120
agtctgagcc agtgtctgag atagaggaag ttgcctcaga ggaagaggag gatggtgctg 3180
aggaacccac cgcctctgga ggcaagagca cccaccctat ggtgactaga agcaaggctg 3240
accagtgata ataggctgga gcctcggtgg ccatgcttct tgccccttgg gcctcccccc 3300
agcccctcct ccccttcctg cacccgtacc cccgtggtct ttgaataaag tctgagtggg 3360
cggc 3364

<210> SEQ ID NO 28
<211> LENGTH: 3388
<212> TYPE: DNA
<213> ORGANISM: Artificial Sequence
<220> FEATURE:
<223> OTHER INFORMATION: Synthetic polynucleotide

<400> SEQUENCE: 28
tcaagctttt ggaccctcgt acagaagcta atacgactca ctatagggaa ataagagaga 60
aaagaagagt aagaagaaat ataagagcca ccatggagtc gcgcggtcgc cgttgtcccg 120
aaatgatatc cgtactgggt cccatttcgg ggcacgtgct gaaagccgtg tttagtcgcg 180
gcgatacgcc ggtgctgccg cacgagacgc gactcctgca gacgggtatc cacgtacgcg 240
tgagccagcc ctcgctgatc ctggtgtcgc agtacacgcc cgactcgacg ccatgccacc 300
gcggcgacaa tcagctgcag gtgcagcaca cgtactttac gggcagcgag gtggagaacg 360
tgtcggtcaa cgtgcacaac cccacgggcc gaagcatctg ccccagccaa gagcccatgt 420
cgatctatgt gtacgcgctg ccgctcaaga tgctgaacat ccccagcatc aacgtgcacc 480
actacccgtc ggcggccgag cgcaaacacc gacacctgcc cgtagccgac gctgttattc 540
acgcgtcggg caagcagatg tggcaggcgc gtctcacggt ctcgggactg gcctggacgc 600
gtcagcagaa ccagtggaaa gagcccgacg tctactacac gtcagcgttc gtgtttccca 660
ccaaggacgt ggcactgcgg cacgtggtgt gcgcgcacga gctggtttgc tccatggaga 720
acacgcgcgc aaccaagatg caggtgatag gtgaccagta cgtcaaggtg tacctggagt 780
ccttctgcga ggacgtgccc tccggcaagc tctttatgca cgtcacgctg ggctctgacg 840
tggaagagga cctaacgatg acccgcaacc cgcaaccctt catgcgcccc cacgagcgca 900
acggctttac ggtgttgtgt cccaaaaata tgataatcaa accgggcaag atctcgcaca 960
tcatgctgga tgtggctttt acctcacacg agcattttgg gctgctgtgt cccaagagca 1020
tcccgggcct gagcatctca ggtaacctgt tgatgaacgg gcagcaaatc ttcctggagg 1080
tacaagcgat acgcgagacc gtggaactgc gtcagtacga tcccgtggct gcgctcttct 1140
ttttcgatat cgacttgttg ctgcagcgcg ggcctcagta cagcgagcac cccaccttca 1200
ccagccagta tcgcatccag ggcaagcttg agtaccgaca cacctgggac cggcacgacg 1260
agggtgccgc ccagggcgac gacgacgtct ggaccagcgg atcggactcc gacgaagaac 1320
tcgtaaccac cgagcgtaag acgccccgcg tcaccggcgg cggcgccatg gcgagcgcct 1380
ccacttccgc gggccgcaaa cgcaaatcag catcctcggc gacggcgtgc acggcgggcg 1440
ttatgacacg cggccgcctt aaggccgagt ccaccgtcgc gcccgaagag gacaccgacg 1500
aggattccga caacgaaatc cacaatccgg ccgtgttcac ctggccgccc tggcaggccg 1560
gcatcctggc ccgcaacctg gtgcccatgg tggctacggt tcagggtcag aatctgaagt 1620
accaggagtt cttctgggac gccaacgaca tctaccgcat cttcgccgaa ttggaaggcg 1680
tatggcagcc cgctgcgcaa cccaaacgtc gccgccaccg gcaagacgcc ttgcccgggc 1740

```
catgcatcgc ctcgacgccc aaaaagcacc gaggtgagtc ctctgccaag agaaagatgg   1800
accctgataa tcctgacgag ggcccttcct ccaaggtgcc acggcccgag acacccgtga   1860
ccaaggccac gacgttcctg cagactatgt taaggaagga ggttaacagt cagctgagcc   1920
tgggagaccc gctgttccca gaattggccg aagaatccct caaaaccttt gaacaagtga   1980
ccgaggattg caacgagaac cccgaaaaag atgtcctgac agaactcgtc aaacagatta   2040
aggttcgagt ggacatggtg cggcatagaa tcaaggagca catgctgaaa aaatataccc   2100
agacggaaga aaaattcact ggcgccttta atatgatggg aggatgtttg cagaatgcct   2160
tagatatctt agataaggtt catgagcctt tcgaggacat gaagtgtatt gggctaacta   2220
tgcagagcat gtatgagaac tacattgtac ctgaggataa gcgggagatg tggatggctt   2280
gtattaagga gctgcatgat gtgagcaagg gcgccgctaa caagttgggg ggtgcactgc   2340
aggctaaggc ccgtgctaaa aaggatgaac ttaggagaaa gatgatgtat atgtgctaca   2400
ggaatataga gttctttacc aagaactcag ccttccctaa gaccaccaat ggctgcagtc   2460
aggccatggc ggcattgcag aacttgcctc agtgctctcc tgatgagatt atgtcttatg   2520
cccagaaaat ctttaagatt ttggatgagg agagagacaa ggtgctcacg cacattgatc   2580
acatatttat ggatatcctc actacatgtg tggaaacaat gtgtaatgag tacaaggtca   2640
ctagtgacgc ttgtatgatg accatgtacg gggcatctc tctcttaagt gagttctgtc   2700
gggtgctgtg ctgctatgtc ttagaggaga ctagtgtgat gctggccaag cggcctctga   2760
taaccaagcc tgaggttatc agtgtaatga agcgccgcat tgaggagatc tgcatgaagg   2820
tctttgccca gtacattctg gggccgatc ctttgagagt ctgctctcct agtgtggatg   2880
acctacgggc catcgccgag gagtcagatg aggaagaggc tattgtagcc tacactttgg   2940
ccaccgctgg tgccagctcc tctgattctc tggtgtcacc tccagagtcc cctgtacccg   3000
cgactatccc tctgtcctca gtaattgtgg ctgagaacag tgatcaggaa gaaagtgaac   3060
agagtgatga ggaacaggag gagggtgctc aggaggagcg ggaggacact gtgtctgtca   3120
agtctgagcc agtgtctgag atagaggaag ttgcctcaga ggaagaggag gatggtgctg   3180
aggaacccac cgcctctgga ggcaagagca cccaccctat ggtgactaga agcaaggctg   3240
accaggatta caaggacgat gacgataagt gataataggc tggagcctcg gtggccatgc   3300
ttcttgcccc ttgggcctcc ccccagcccc tcctcccctt cctgcacccg tacccccgtg   3360
gtctttgaat aaagtctgag tgggcggc                                      3388
```

<210> SEQ ID NO 29
<211> LENGTH: 3352
<212> TYPE: DNA
<213> ORGANISM: Artificial Sequence
<220> FEATURE:
<223> OTHER INFORMATION: Synthetic polynucleotide

<400> SEQUENCE: 29

```
tcaagctttt ggaccctcgt acagaagcta atacgactca ctatagggaa ataagagaga     60
aaagaagagt aagaagaaat ataagagcca ccatgcggcc aggcctcccc tcctacctca    120
tcatcctcgc cgtctgtctc ttcagccacc tactttcgtc acgatatggc gcagaagccg    180
tatccgaacc gctggacaaa gcgtttcacc tactgctcaa cacctacggg agacccatcc    240
gcttcctgcg tgaaaatacc acccagtgta cctacaacag cagcctccgt aacagcacgg    300
tcgtcaggga aaacgccatc agtttcaact ttttccaaag ctataatcaa tactatgtat    360
```

-continued

```
tccatatgcc tcgatgtctt tttgcgggtc ctctggcgga gcagtttctg aaccaggtag    420
atctgaccga aaccctggaa agataccaac agagacttaa cacttacgcg ctggtatcca    480
aagacctggc cagctaccga tctttttcgc agcagctaaa ggcacaagac agcctaggtg    540
aacagcccac cactgtgcca ccgcccattg acctgtcaat acctcacgtt tggatgccac    600
cgcaaaccac tccacacggc tggacagaat cacataccac ctcaggacta caccgaccac    660
actttaacca gacctgtatc ctctttgatg gacacgatct actattcagc accgtcacac    720
cttgtttgca ccaaggcttt tacctcatcg acgaactacg ttacgttaaa ataacactga    780
ccgaggactt cttcgtagtt acggtgtcca tagacgacga cacacccatg ctgcttatct    840
tcggccatct tccacgcgta cttttcaaag cgccctatca acgcgacaac tttatactac    900
gacaaactga aaaacacgag ctcctggtgc tagttaagaa agatcaactg aaccgtcact    960
cttatctcaa agacccggac tttcttgacg ccgcacttga cttcaactac ctagacctca   1020
gcgcactact acgtaacagc tttcaccgtt acgccgtgga tgtactcaag agcggtcgat   1080
gtcagatgct ggaccgccgc acggtagaaa tggccttcgc ctacgcatta gcactgttcg   1140
cagcagcccg acaagaagag gccggcgccc aagtctccgt cccacgggcc ctagaccgcc   1200
aggccgcact cttacaaata caagaattta tgatcacctg cctctcacaa acaccaccac   1260
gcaccacgtt gctgctgtat cccacggccg tggacctggc caaacgagcc ctttggacac   1320
cgaatcagat caccgacatc accagcctcg tacgcctggt ctacatactc tctaaacaga   1380
atcagcaaca tctcatcccc caatgggcac tacgacagat cgccgacttt gccctaaaac   1440
tacacaaaac gcacctggcc tcttttcttt cagccttcgc acgccaagaa ctctacctca   1500
tgggcagcct cgtccactcc atgctggtac atacgacgga gagacgcgaa atcttcatcg   1560
tagaaacggg cctctgttca ttggccgagc tatcacactt tacgcagttg ttagctcatc   1620
cacaccacga atacctcagc gacctgtaca caccctgttc cagtagcggg cgacgcgatc   1680
actcgctcga acgcctcacg cgtctcttcc ccgatgccac cgtccccgct accgttcccg   1740
ccgccctctc catcctatct accatgcaac caagcacgct ggaaaccttc cccgacctgt   1800
tttgcttgcc gctcggcgaa tccttctccg cgctgaccgt ctccgaacac gtcagttata   1860
tcgtaacaaa ccagtacctg atcaaaggta tctcctaccc tgtctccacc accgtcgtag   1920
gccagagcct catcatcacc cagacggaca gtcaaactaa atgcgaactg acgcgcaaca   1980
tgcataccac acacagcatc acagtggcgc tcaacatttc gctagaaaac tgcgcctttt   2040
gccaaagcgc cctgctagaa tacgacgaca cgcaaggcgt catcaacatc atgtacatgc   2100
acgactcgga cgacgtcctt ttcgccctgg atccctacaa cgaagtggtg gtctcatctc   2160
cgcgaactca ctacctcatg cttttgaaaa acggtacggt actagaagta actgacgtcg   2220
tcgtggacgc caccgacagt cgtctcctca tgatgtccgt ctacgcgcta tcggccatca   2280
tcggcatcta tctgctctac cgcatgctca agacatgccg cgccaagagg agcggaagcg   2340
gagctactaa cttcagcctg ctgaagcagg ctggagacgt ggaggagaac cctggaccta   2400
tgtgccgccg cccggattgc ggcttctctt tctcacctgg accggtgata ctgctgtggt   2460
gttgccttct gctgcccatt gtttcctcag ccgccgtcag cgtcgctcct accgccgccg   2520
agaaagtccc cgcggagtgc cccgaactaa cgcgccgatg cttgttgggt gaggtgtttg   2580
agggtgacaa gtatgaaagt tggctgcgcc cgttggtgaa tgttaccggg cgcgatggcc   2640
cgctatcgca acttatccgt taccgtcccg ttacgccgga ggccgccaac tccgtgctgt   2700
tggacgaggc tttcctggac actctggccc tgctgtacaa caatccggat caattgcggg   2760
```

ccctgctgac gctgttgagc tcggacacag cgccgcgctg gatgacggtg atgcgcggct 2820
acagcgagtg cggcgatggc tcgccggccg tgtacacgtg cgtggacgac ctgtgccgcg 2880
gctacgacct cacgcgactg tcatacgggc gcagcatctt cacggaacac gtgttaggct 2940
tcgagctggt gccaccgtct ctctttaacg tggtggtggc catacgcaac gaagccacgc 3000
gtaccaaccg cgccgtgcgt ctgcccgtga gcaccgctgc cgcgcccgag ggcatcacgc 3060
tcttttacgg cctgtacaac gcagtgaagg aattctgcct gcgtcaccag ctggacccgc 3120
cgctgctacg ccacctagat aaatactacg ccggactgcc gcccgagctg aagcagacgc 3180
gcgtcaacct gccggctcac tcgcgctatg gccctcaagc agtggatgct cgctgataat 3240
aggctggagc ctcggtggcc atgcttcttg ccccttgggc ctccccccag cccctcctcc 3300
ccttcctgca cccgtacccc cgtggtcttt gaataaagtc tgagtgggcg gc 3352

<210> SEQ ID NO 30
<211> LENGTH: 1924
<212> TYPE: DNA
<213> ORGANISM: Artificial Sequence
<220> FEATURE:
<223> OTHER INFORMATION: Synthetic polynucleotide

<400> SEQUENCE: 30
tcaagctttt ggaccctcgt acagaagcta atacgactca ctatagggaa ataagagaga 60
aaagaagagt aagaagaaat ataagagcca ccatgagtcc caaagatctg acgccgttct 120
tgacggcgtt gtggctgcta ttgggtcaca gccgcgtgcc gcgggtgcgc gcagaagaat 180
gttgcgaatt cataaacgtc aaccacccgc cggaacgctg ttacgatttc aaaatgtgca 240
atcgcttcac cgtcgcgctg cggtgtccgg acggcgaagt ctgctacagt cccgagaaaa 300
cggctgagat tcgcgggatc gtcaccacca tgacccattc attgacacgc caggtcgtac 360
acaacaaact gacgagctgc aactacaatc cgttatacct cgaagctgac gggcgaatac 420
gctgcggcaa agtaaacgac aaggcgcagt acctgctggg cgccgctggc agcgttccct 480
atcgatggat caatctggaa tacgacaaga taacccggat cgtgggcctg gatcagtacc 540
tggagagcgt taagaaacac aaacggctgg atgtgtgccg cgctaaaatg ggctatatgc 600
tgcagcgcgc caagaggagc ggaagcggag ctactaactt cagcctgctg aagcaggctg 660
gagacgtgga ggagaaccct ggacctatgc tgcggcttct gcttcgtcac cactttcact 720
gcctgcttct gtgcgcggtt tggcaacgc cctgtctggc gtctccgtgg tcgacgctaa 780
cagcaaacca gaatccgtcc ccgccatggt ctaaactgac gtattccaaa ccgcatgacg 840
cggcgacgtt ttactgtcct tttctctatc cctcgccccc acgatccccc ttgcaattct 900
cggggttcca gcgggtatca acgggtcccg agtgtcgcaa cgagaccctg tatctgctgt 960
acaaccggga aggccagacc ttggtggaga gaagctccac ctgggtgaaa aaggtgatct 1020
ggtacctgag cggtcggaac caaaccatcc tccaacggat gccccgaacg gcttcgaaac 1080
cgagcgacgg aaacgtgcag atcagcgtgg aagacgccaa gatttttgga gcgcacatgg 1140
tgcccaagca gaccaagctg ctacgcttcg tcgtcaacga tggcacacgt tatcagatgt 1200
gtgtgatgaa gctggagagc tgggctcacg tcttccggga ctacagcgtg tcttttcagg 1260
tgcgattgac gttcaccgag gccaataacc agacttacac cttctgcacc catcccaatc 1320
tcatcgttcg cgccaagagg agcggaagcg gagtgaaaca gactttgaat tttgaccttc 1380
tcaagttggc gggagacgtg gagtccaacc ctggacctat gcggctgtgt cgggtgtggc 1440

-continued tgtctgtttg tctgtgcgcc gtggtgctgg gtcagtgcca gcgggaaacc gcggaaaaaa 1500
acgattatta ccgagtaccg cattactggg acgcgtgctc tcgcgcgctg cccgaccaaa 1560
cccgttacaa gtatgtggaa cagctcgtgg acctcacgtt gaactaccac tacgatgcga 1620
gccacggctt ggacaacttt gacgtgctca agagaatcaa cgtgaccgag gtgtcgttgc 1680
tcatcagcga ctttagacgt cagaaccgtc gcggcggcac caacaaaagg accacgttca 1740
acgccgccgg ttcgctggcg ccacacgccc ggagcctcga gttcagcgtg cggctctttg 1800
ccaactgata ataggctgga gcctcggtgg ccatgcttct tgccccttgg gcctcccccc 1860
agcccctcct ccccttcctg cacccgtacc cccgtggtct ttgaataaag tctgagtggg 1920
cggc 1924

<210> SEQ ID NO 31
<211> LENGTH: 5146
<212> TYPE: DNA
<213> ORGANISM: Artificial Sequence
<220> FEATURE:
<223> OTHER INFORMATION: Synthetic polynucleotide

<400> SEQUENCE: 31
tcaagctttt ggaccctcgt acagaagcta atacgactca ctatagggaa ataagagaga 60
aaagaagagt aagaagaaat ataagagcca ccatgcggcc aggcctcccc tcctacctca 120
tcatcctcgc cgtctgtctc ttcagccacc tactttcgtc acgatatggc gcagaagccg 180
tatccgaacc gctggacaaa gcgtttcacc tactgctcaa cacctacggg agacccatcc 240
gcttcctgcg tgaaaatacc acccagtgta cctacaacag cagcctccgt aacagcacgg 300
tcgtcaggga aaacgccatc agtttcaact tttccaaag ctataatcaa tactatgtat 360
tccatatgcc tcgatgtctt tttgcgggtc ctctggcgga gcagtttctg aaccaggtag 420
atctgaccga aaccctggaa agataccaac agagacttaa cacttacgcg ctggtatcca 480
aagacctggc cagctaccga tctttttcgc agcagctaaa ggcacaagac agcctaggtg 540
aacagcccac cactgtgcca ccgcccattg acctgtcaat acctcacgtt tggatgccac 600
cgcaaaccac tccacacggc tggacagaat cacataccac ctcaggacta caccgaccac 660
actttaacca gacctgtatc ctctttgatg gacacgatct actattcagc accgtcacac 720
cttgtttgca ccaaggcttt tacctcatcg acgaactacg ttacgttaaa ataacactga 780
ccgaggactt cttcgtagtt acggtgtcca tagacgacga cacacccatg ctgcttatct 840
tcggccatct tccacgcgta cttttcaaag cgccctatca acgcgacaac tttatactac 900
gacaaactga aaaacacgag ctcctggtgc tagttaagaa agatcaactg aaccgtcact 960
cttatctcaa agacccggac tttcttgacg ccgcacttga cttcaactac ctagacctca 1020
gcgcactact acgtaacagc tttcaccgtt acgccgtgga tgtactcaag agcggtcgat 1080
gtcagatgct ggaccgccgc acggtagaaa tggccttcgc ctacgcatta gcactgttcg 1140
cagcagcccg acaagaagag gccggcgccc aagtctccgt cccacgggcc ctagaccgcc 1200
aggccgcact cttacaaata caagaattta tgatcacctg cctctcacaa acaccaccac 1260
gcaccacgtt gctgctgtat cccacggccg tggacctggc caaacgagcc ctttggacac 1320
cgaatcagat caccgacatc accagcctcg tacgcctggt ctacatactc tctaaacaga 1380
atcagcaaca tctcatcccc caatgggcac tacgacagat cgccgacttt gccctaaaac 1440
tacacaaaac gcacctggcc tcttttcttt cagccttcgc acgccaagaa ctctacctca 1500
tgggcagcct cgtccactcc atgctggtac atacgacgga gagacgcgaa atcttcatcg 1560

```
tagaaacggg cctctgttca ttggccgagc tatcacactt tacgcagttg ttagctcatc   1620
cacaccacga atacctcagc gacctgtaca caccctgttc cagtagcggg cgacgcgatc   1680
actcgctcga acgcctcacg cgtctcttcc ccgatgccac cgtccccgct accgttcccg   1740
ccgccctctc catcctatct accatgcaac caagcacgct ggaaaccttc cccgacctgt   1800
tttgcttgcc gctcggcgaa tccttctccg cgctgaccgt ctccgaacac gtcagttata   1860
tcgtaacaaa ccagtacctg atcaaaggta tctcctaccc tgtctccacc accgtcgtag   1920
gccagagcct catcatcacc cagacggaca gtcaaactaa atgcgaactg acgcgcaaca   1980
tgcataccac acacagcatc acagtggcgc tcaacatttc gctagaaaac tgcgcctttt   2040
gccaaagcgc cctgctagaa tacgacgaca cgcaaggcgt catcaacatc atgtacatgc   2100
acgactcgga cgacgtcctt ttcgccctgg atccctacaa cgaagtggtg gtctcatctc   2160
cgcgaactca ctacctcatg cttttgaaaa acggtacggt actagaagta actgacgtcg   2220
tcgtggacgc caccgacagt cgtctcctca tgatgtccgt ctacgcgcta tcggccatca   2280
tcggcatcta tctgctctac cgcatgctca agacatgccg cgccaagagg agcggaagcg   2340
gagctactaa cttcagcctg ctgaagcagg ctggagacgt ggaggagaac cctggaccta   2400
tgtgccgccg cccggattgc ggcttctctt tctcacctgg accggtgata ctgctgtggt   2460
gttgccttct gctgcccatt gtttcctcag ccgccgtcag cgtcgctcct accgccgccg   2520
agaaagtccc cgcggagtgc cccgaactaa cgcgccgatg cttgttgggt gaggtgtttg   2580
agggtgacaa gtatgaaagt tggctgcgcc cgttggtgaa tgttaccggg cgcgatggcc   2640
cgctatcgca acttatccgt taccgtcccg ttacgccgga ggccgccaac tccgtgctgt   2700
tggacgaggc tttcctggac actctggccc tgctgtacaa caatccggat caattgcggg   2760
ccctgctgac gctgttgagc tcggacacag cgccgcgctg gatgacggtg atgcgcggct   2820
acagcgagtg cggcgatggc tcgccggccg tgtacacgtg cgtggacgac ctgtgccgcg   2880
gctacgacct cacgcgactg tcatacgggc gcagcatctt cacggaacac gtgttaggct   2940
tcgagctggt gccaccgtct ctctttaacg tggtggtggc catacgcaac gaagccacgc   3000
gtaccaaccg cgccgtgcgt ctgcccgtga gcaccgctgc cgcgcccgag ggcatcacgc   3060
tcttttacgg cctgtacaac gcagtgaagg aattctgcct gcgtcaccag ctggacccgc   3120
cgctgctacg ccacctagat aaatactacg ccggactgcc gcccgagctg aagcagacgc   3180
gcgtcaacct gccggctcac tcgcgctatg gccctcaagc agtggatgct cgccgcgcca   3240
agaggagcgg aagcggagtg aaacagactt tgaattttga ccttctcaag ttggcgggag   3300
acgtggagtc caaccctgga cctatgagtc ccaaagatct gacgccgttc ttgacggcgt   3360
tgtggctgct attgggtcac agccgcgtgc cgcgggtgcg cgcagaagaa tgttgcgaat   3420
tcataaacgt caaccacccg ccggaacgct gttacgattt caaaatgtgc aatcgcttca   3480
ccgtcgcgct gcggtgtccg gacggcgaag tctgctacag tcccgagaaa acggctgaga   3540
ttcgcgggat cgtcaccacc atgacccatt cattgacacg ccaggtcgta cacaacaaac   3600
tgacgagctg caactacaat ccgttatacc tcgaagctga cgggcgaata cgctgcggca   3660
aagtaaacga caaggcgcag tacctgctgg gcgccgctgg cagcgttccc tatcgatgga   3720
tcaatctgga atacgacaag ataacccgga tcgtgggcct ggatcagtac ctggagagcg   3780
ttaagaaaca caaacggctg gatgtgtgcc gcgctaaaat gggctatatg ctgcagcgcg   3840
ccaagaggag cggaagcgga cagtgtacta attatgctct cttgaaattg gctggagatg   3900
```

```
ttgagagcaa ccctggacct atgctgcggc ttctgcttcg tcaccacttt cactgcctgc   3960

ttctgtgcgc ggtttgggca acgccctgtc tggcgtctcc gtggtcgacg ctaacagcaa   4020

accagaatcc gtccccgcca tggtctaaac tgacgtattc caaaccgcat gacgcggcga   4080

cgttttactg tccttttctc tatccctcgc cccacgatc ccccttgcaa ttctcggggt    4140

tccagcgggt atcaacgggt cccgagtgtc gcaacgagac cctgtatctg ctgtacaacc   4200

gggaaggcca gaccttggtg gagagaagct ccacctgggt gaaaaaggtg atctggtacc   4260

tgagcggtcg gaaccaaacc atcctccaac ggatgccccg aacggcttcg aaaccgagcg   4320

acggaaacgt gcagatcagc gtggaagacg ccaagatttt tggagcgcac atggtgccca   4380

agcagaccaa gctgctacgc ttcgtcgtca acgatggcac acgttatcag atgtgtgtga   4440

tgaagctgga gagctgggct cacgtcttcc gggactacag cgtgtctttt caggtgcgat   4500

tgacgttcac cgaggccaat aaccagactt acaccttctg cacccatccc aatctcatcg   4560

ttcgcgccaa gaggagcgga agcggagagg gcagaggaag tctgctaaca tgcggtgacg   4620

tcgaggagaa tcctggacct atgcggctgt gtcgggtgtg gctgtctgtt tgtctgtgcg   4680

ccgtggtgct gggtcagtgc cagcgggaaa ccgcggaaaa aaacgattat taccgagtac   4740

cgcattactg ggacgcgtgc tctcgcgcgc tgcccgacca aacccgttac aagtatgtgg   4800

aacagctcgt ggacctcacg ttgaactacc actacgatgc gagccacggc ttggacaact   4860

ttgacgtgct caagagaatc aacgtgaccg aggtgtcgtt gctcatcagc gactttagac   4920

gtcagaaccg tcgcggcggc accaacaaaa ggaccacgtt caacgccgcc ggttcgctgg   4980

cgccacacgc ccggagcctc gagttcagcg tgcggctctt tgccaactga taataggctg   5040

gagcctcggt ggccatgctt cttgcccctt gggcctcccc ccagcccctc ctccccttcc   5100

tgcacccgta cccccgtggt ctttgaataa agtctgagtg ggcggc                  5146
```

<210> SEQ ID NO 32
<211> LENGTH: 742
<212> TYPE: PRT
<213> ORGANISM: Artificial Sequence
<220> FEATURE:
<223> OTHER INFORMATION: Synthetic polypeptide

<400> SEQUENCE: 32

```
Met Arg Pro Gly Leu Pro Ser Tyr Leu Ile Ile Leu Ala Val Cys Leu
1               5                   10                  15

Phe Ser His Leu Leu Ser Ser Arg Tyr Gly Ala Glu Ala Val Ser Glu
            20                  25                  30

Pro Leu Asp Lys Ala Phe His Leu Leu Leu Asn Thr Tyr Gly Arg Pro
        35                  40                  45

Ile Arg Phe Leu Arg Glu Asn Thr Thr Gln Cys Thr Tyr Asn Ser Ser
    50                  55                  60

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
        115                 120                 125

Ser Lys Asp Leu Ala Ser Tyr Arg Ser Phe Ser Gln Gln Leu Lys Ala
    130                 135                 140
```

-continued

```
Gln Asp Ser Leu Gly Glu Gln Pro Thr Thr Val Pro Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
        195                 200                 205

Thr Pro Cys Leu His Gln Gly Phe Tyr Leu Ile Asp Glu Leu Arg Tyr
    210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
    290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
        355                 360                 365

Arg Gln Ala Ala Leu Leu Gln Ile Gln Glu Phe Met Ile Thr Cys Leu
    370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
            420                 425                 430

His Leu Ile Pro Gln Trp Ala Leu Arg Gln Ile Ala Asp Phe Ala Leu
        435                 440                 445

Lys Leu His Lys Thr His Leu Ala Ser Phe Leu Ser Ala Phe Ala Arg
    450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
            500                 505                 510

Glu Tyr Leu Ser Asp Leu Tyr Thr Pro Cys Ser Ser Ser Gly Arg Arg
        515                 520                 525

Asp His Ser Leu Glu Arg Leu Thr Arg Leu Phe Pro Asp Ala Thr Val
    530                 535                 540

Pro Ala Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
```

565 570 575

Ser Phe Ser Ala Leu Thr Val Ser Glu His Val Ser Tyr Ile Val Thr
580 585 590

Asn Gln Tyr Leu Ile Lys Gly Ile Ser Tyr Pro Val Ser Thr Thr Val
595 600 605

Val Gly Gln Ser Leu Ile Ile Thr Gln Thr Asp Ser Gln Thr Lys Cys
610 615 620

Glu Leu Thr Arg Asn Met His Thr Thr His Ser Ile Thr Val Ala Leu
625 630 635 640

Asn Ile Ser Leu Glu Asn Cys Ala Phe Cys Gln Ser Ala Leu Leu Glu
645 650 655

Tyr Asp Asp Thr Gln Gly Val Ile Asn Ile Met Tyr Met His Asp Ser
660 665 670

Asp Asp Val Leu Phe Ala Leu Asp Pro Tyr Asn Glu Val Val Val Ser
675 680 685

Ser Pro Arg Thr His Tyr Leu Met Leu Leu Lys Asn Gly Thr Val Leu
690 695 700

Glu Val Thr Asp Val Val Val Asp Ala Thr Asp Ser Arg Leu Leu Met
705 710 715 720

Met Ser Val Tyr Ala Leu Ser Ala Ile Ile Gly Ile Tyr Leu Leu Tyr
725 730 735

Arg Met Leu Lys Thr Cys
740

<210> SEQ ID NO 33
<211> LENGTH: 310
<212> TYPE: PRT
<213> ORGANISM: Artificial Sequence
<220> FEATURE:
<223> OTHER INFORMATION: Synthetic polypeptide

<400> SEQUENCE: 33

Met Pro Ala Thr Asp Thr Asn Ser Thr His Thr Thr Pro Leu His Pro
1 5 10 15

Glu Asn Gln His Thr Leu Pro Leu His His Ser Thr Thr Gln Pro His
20 25 30

Val Gln Thr Ser Asp Lys His Ala Asp Lys Gln His Arg Thr Gln Met
35 40 45

Glu Leu Asp Ala Ala Asp Tyr Ala Ala Cys Ala Gln Ala Arg Gln His
50 55 60

Leu Tyr Gly Gln Thr Gln Pro Gln Pro His Ala Tyr Pro Asn Ala Asn
65 70 75 80

Pro Gln Glu Ser Ala His Phe Cys Thr Glu Asn Gln His Gln Leu Thr
85 90 95

Asn Leu Leu His Asn Ile Gly Glu Gly Ala Ala Leu Gly Tyr Pro Val
100 105 110

Pro Arg Ala Glu Ile Arg Arg Gly Gly Gly Asp Trp Ala Asp Ser Ala
115 120 125

Ser Asp Phe Asp Ala Asp Cys Trp Cys Met Trp Gly Arg Phe Gly Thr
130 135 140

Met Gly Arg Gln Pro Val Val Thr Leu Leu Leu Ala Arg Gln Arg Asp
145 150 155 160

Gly Leu Ala Asp Trp Asn Val Val Arg Cys Arg Gly Thr Gly Phe Arg
165 170 175

Ala His Asp Ser Glu Asp Gly Val Ser Val Trp Arg Gln His Leu Val

```
            180                 185                 190

Phe Leu Leu Gly Gly His Gly Arg Arg Val Gln Leu Glu Arg Pro Ser
        195                 200                 205

Ala Gly Glu Ala Gln Ala Arg Gly Leu Leu Pro Arg Ile Arg Ile Thr
    210                 215                 220

Pro Ile Ser Thr Ser Pro Arg Pro Lys Pro Pro Gln Pro Thr Thr Ser
225                 230                 235                 240

Thr Ala Ser His Pro His Ala Thr Ala Arg Pro Asp His Thr Leu Phe
                245                 250                 255

Pro Val Pro Ser Thr Pro Ser Ala Thr Val His Asn Pro Arg Asn Tyr
            260                 265                 270

Ala Val Gln Leu His Ala Glu Thr Thr Arg Thr Trp Arg Trp Ala Arg
        275                 280                 285

Arg Gly Glu Arg Gly Ala Trp Met Pro Ala Glu Thr Phe Thr Cys Pro
    290                 295                 300

Lys Asp Lys Arg Pro Trp
305                 310


<210> SEQ ID NO 34
<211> LENGTH: 310
<212> TYPE: PRT
<213> ORGANISM: Artificial Sequence
<220> FEATURE:
<223> OTHER INFORMATION: Synthetic polypeptide

<400> SEQUENCE: 34

Met Pro Ala Thr Asp Thr Asn Ser Thr His Thr Thr Pro Leu His Pro
1               5                   10                  15

Glu Asp Gln His Thr Leu Pro Leu Gln His Asn Thr Thr Gln Pro His
            20                  25                  30

Val Gln Thr Ser Asp Lys Pro Ala Asp Lys Gln His Arg Thr Gln Met
        35                  40                  45

Glu Leu Asp Ala Ala Asp Tyr Ala Ala Cys Ala Gln Ala Arg Gln His
    50                  55                  60

Leu Tyr Gly Gln Thr Gln Pro Gln Leu His Ala Tyr Pro Asn Ala Asn
65                  70                  75                  80

Pro Gln Glu Ser Ala His Phe Cys Thr Asp Asn Gln His Arg Leu Thr
                85                  90                  95

Asn Leu Leu His Asn Ile Gly Glu Gly Ala Ala Leu Gly Tyr Pro Val
            100                 105                 110

Pro Arg Ala Glu Ile Arg Arg Gly Gly Gly Asp Trp Ala Asp Ser Ala
        115                 120                 125

Ser Asp Phe Asp Ala Asp Cys Trp Cys Met Trp Gly Arg Phe Gly Thr
    130                 135                 140

Met Gly Arg Gln Pro Val Val Thr Leu Leu Leu Ala Arg Gln Arg Asp
145                 150                 155                 160

Gly Leu Ala Asp Trp Asn Val Val Arg Cys Arg Gly Thr Gly Phe Arg
                165                 170                 175

Ala His Asp Ser Glu Asp Gly Val Ser Val Trp Arg Gln His Leu Val
            180                 185                 190

Phe Leu Leu Gly Gly His Gly Arg Arg Val Gln Leu Glu Arg Pro Ser
        195                 200                 205

Ala Gly Glu Ala Gln Ala Arg Gly Leu Leu Pro Arg Ile Arg Ile Thr
    210                 215                 220

Pro Val Ser Thr Ser Pro Arg Pro Lys Ala Pro Gln Pro Thr Thr Ser
```

225 230 235 240

Thr Ala Ser His Pro His Ala Thr Ala Arg Pro Asp His Thr Leu Phe
245 250 255

Pro Val Pro Ser Thr Pro Ser Ala Thr Val His Asn Pro Arg Asn Tyr
260 265 270

Ala Val Gln Leu His Ala Glu Thr Thr Arg Thr Trp Arg Trp Ala Arg
275 280 285

Arg Gly Glu Arg Gly Ala Trp Met Pro Ala Glu Thr Phe Thr Cys Pro
290 295 300

Lys Asp Lys Arg Pro Trp
305 310

<210> SEQ ID NO 35
<211> LENGTH: 466
<212> TYPE: PRT
<213> ORGANISM: Artificial Sequence
<220> FEATURE:
<223> OTHER INFORMATION: Synthetic polypeptide

<400> SEQUENCE: 35

Met Gly Arg Lys Glu Met Met Val Arg Asp Val Pro Lys Met Val Phe
1 5 10 15

Leu Ile Ser Ile Ser Phe Leu Leu Val Ser Phe Ile Asn Cys Lys Val
20 25 30

Met Ser Lys Ala Leu Tyr Asn Arg Pro Trp Arg Gly Leu Val Leu Ser
35 40 45

Lys Ile Gly Lys Tyr Lys Leu Asp Gln Leu Lys Leu Glu Ile Leu Arg
50 55 60

Gln Leu Glu Thr Thr Ile Ser Thr Lys Tyr Asn Val Ser Lys Gln Pro
65 70 75 80

Val Lys Asn Leu Thr Met Asn Met Thr Glu Phe Pro Gln Tyr Tyr Ile
85 90 95

Leu Ala Gly Pro Ile Gln Asn Tyr Ser Ile Thr Tyr Leu Trp Phe Asp
100 105 110

Phe Tyr Ser Thr Gln Leu Arg Lys Pro Ala Lys Tyr Val Tyr Ser Gln
115 120 125

Tyr Asn His Thr Ala Lys Thr Ile Thr Phe Arg Pro Pro Pro Cys Gly
130 135 140

Thr Val Pro Ser Met Thr Cys Leu Ser Glu Met Leu Asn Val Ser Lys
145 150 155 160

Arg Asn Asp Thr Gly Glu Gln Gly Cys Gly Asn Phe Thr Thr Phe Asn
165 170 175

Pro Met Phe Phe Asn Val Pro Arg Trp Asn Thr Lys Leu Tyr Val Gly
180 185 190

Pro Thr Lys Val Asn Val Asp Ser Gln Thr Ile Tyr Phe Leu Gly Leu
195 200 205

Thr Ala Leu Leu Leu Arg Tyr Ala Gln Arg Asn Cys Thr His Ser Phe
210 215 220

Tyr Leu Val Asn Ala Met Ser Arg Asn Leu Phe Arg Val Pro Lys Tyr
225 230 235 240

Ile Asn Gly Thr Lys Leu Lys Asn Thr Met Arg Lys Leu Lys Arg Lys
245 250 255

Gln Ala Pro Val Lys Glu Gln Phe Glu Lys Lys Ala Lys Lys Thr Gln
260 265 270

Ser Thr Thr Thr Pro Tyr Phe Ser Tyr Thr Thr Ser Ala Ala Leu Asn

```
        275                 280                 285

Val Thr Thr Asn Val Thr Tyr Ser Ile Thr Thr Ala Ala Arg Arg Val
    290                 295                 300

Ser Thr Ser Thr Ile Ala Tyr Arg Pro Asp Ser Ser Phe Met Lys Ser
305                 310                 315                 320

Ile Met Ala Thr Gln Leu Arg Asp Leu Ala Thr Trp Val Tyr Thr Thr
                325                 330                 335

Leu Arg Tyr Arg Gln Asn Pro Phe Cys Glu Pro Ser Arg Asn Arg Thr
            340                 345                 350

Ala Val Ser Glu Phe Met Lys Asn Thr His Val Leu Ile Arg Asn Glu
        355                 360                 365

Thr Pro Tyr Thr Ile Tyr Gly Thr Leu Asp Met Ser Ser Leu Tyr Tyr
    370                 375                 380

Asn Glu Thr Met Phe Val Glu Asn Lys Thr Ala Ser Asp Ser Asn Lys
385                 390                 395                 400

Thr Thr Pro Thr Ser Pro Ser Met Gly Phe Gln Arg Thr Phe Ile Asp
                405                 410                 415

Pro Leu Trp Asp Tyr Leu Asp Ser Leu Leu Phe Leu Asp Glu Ile Arg
            420                 425                 430

Asn Phe Ser Leu Arg Ser Pro Thr Tyr Val Asn Leu Thr Pro Pro Glu
        435                 440                 445

His Arg Arg Ala Val Asn Leu Ser Thr Leu Asn Ser Leu Trp Trp Trp
    450                 455                 460

Leu Gln
465


<210> SEQ ID NO 36
<211> LENGTH: 135
<212> TYPE: PRT
<213> ORGANISM: Artificial Sequence
<220> FEATURE:
<223> OTHER INFORMATION: Synthetic polypeptide

<400> SEQUENCE: 36

Met Glu Cys Asn Thr Leu Val Leu Gly Leu Leu Val Leu Ser Val Val
1               5                   10                  15

Ala Ser Ser Asn Asn Thr Ser Thr Ala Ser Thr Pro Arg Pro Ser Ser
            20                  25                  30

Ser Thr His Ala Ser Thr Thr Val Lys Ala Thr Thr Val Ala Thr Thr
        35                  40                  45

Ser Thr Thr Thr Ala Thr Ser Thr Ser Ser Thr Thr Ser Ala Lys Pro
    50                  55                  60

Gly Phe Thr Thr His Asp Pro Asn Val Met Arg Pro His Ala His Asn
65                  70                  75                  80

Asp Phe Tyr Asn Ala His Cys Thr Ser His Met Tyr Glu Leu Ser Leu
                85                  90                  95

Ser Ser Phe Ala Ala Trp Trp Thr Met Leu Asn Ala Leu Ile Leu Met
            100                 105                 110

Gly Ala Phe Cys Ile Val Leu Arg His Cys Cys Phe Gln Asn Phe Thr
        115                 120                 125

Ala Thr Thr Thr Lys Gly Tyr
    130                 135


<210> SEQ ID NO 37
<211> LENGTH: 372
<212> TYPE: PRT
```

<213> ORGANISM: Artificial Sequence
<220> FEATURE:
<223> OTHER INFORMATION: Synthetic polypeptide

<400> SEQUENCE: 37

```
Met Ala Pro Ser His Val Asp Lys Val Asn Thr Arg Thr Trp Ser Ala
1               5                   10                  15

Ser Ile Val Phe Met Val Leu Thr Phe Val Asn Val Ser Val His Leu
            20                  25                  30

Val Leu Ser Asn Phe Pro His Leu Gly Tyr Pro Cys Val Tyr Tyr His
        35                  40                  45

Val Val Asp Phe Glu Arg Leu Asn Met Ser Ala Tyr Asn Val Met His
    50                  55                  60

Leu His Thr Pro Met Leu Phe Leu Asp Ser Val Gln Leu Val Cys Tyr
65                  70                  75                  80

Ala Val Phe Met Gln Leu Val Phe Leu Ala Val Thr Ile Tyr Tyr Leu
                85                  90                  95

Val Cys Trp Ile Lys Ile Ser Met Arg Lys Asp Lys Gly Met Ser Leu
            100                 105                 110

Asn Gln Ser Thr Arg Asp Ile Ser Tyr Met Gly Asp Ser Leu Thr Ala
        115                 120                 125

Phe Leu Phe Ile Leu Ser Met Asp Thr Phe Gln Leu Phe Thr Leu Thr
    130                 135                 140

Met Ser Phe Arg Leu Pro Ser Met Ile Ala Phe Met Ala Ala Val His
145                 150                 155                 160

Phe Phe Cys Leu Thr Ile Phe Asn Val Ser Met Val Thr Gln Tyr Arg
                165                 170                 175

Ser Tyr Lys Arg Ser Leu Phe Phe Phe Ser Arg Leu His Pro Lys Leu
            180                 185                 190

Lys Gly Thr Val Gln Phe Arg Thr Leu Ile Val Asn Leu Val Glu Val
        195                 200                 205

Ala Leu Gly Phe Asn Thr Thr Val Val Ala Met Ala Leu Cys Tyr Gly
    210                 215                 220

Phe Gly Asn Asn Phe Phe Val Arg Thr Gly His Met Val Leu Ala Val
225                 230                 235                 240

Phe Val Val Tyr Ala Ile Ile Ser Ile Ile Tyr Phe Leu Leu Ile Glu
                245                 250                 255

Ala Val Phe Phe Gln Tyr Val Lys Val Gln Phe Gly Tyr His Leu Gly
            260                 265                 270

Ala Phe Phe Gly Leu Cys Gly Leu Ile Tyr Pro Ile Val Gln Tyr Asp
        275                 280                 285

Thr Phe Leu Ser Asn Glu Tyr Arg Thr Gly Ile Ser Trp Ser Phe Gly
    290                 295                 300

Met Leu Phe Phe Ile Trp Ala Met Phe Thr Thr Cys Arg Ala Val Arg
305                 310                 315                 320

Tyr Phe Arg Gly Arg Gly Ser Gly Ser Val Lys Tyr Gln Ala Leu Ala
                325                 330                 335

Thr Ala Ser Gly Glu Glu Val Ala Val Leu Ser His His Asp Ser Leu
            340                 345                 350

Glu Ser Arg Arg Leu Arg Glu Glu Glu Asp Asp Asp Asp Asp Glu Asp
        355                 360                 365

Phe Glu Asp Ala
    370
```

<210> SEQ ID NO 38
<211> LENGTH: 171
<212> TYPE: PRT
<213> ORGANISM: Artificial Sequence
<220> FEATURE:
<223> OTHER INFORMATION: Synthetic polypeptide

<400> SEQUENCE: 38

```
Met Ser Pro Lys Asp Leu Thr Pro Phe Leu Thr Ala Leu Trp Leu Leu
1               5                   10                  15

Leu Gly His Ser Arg Val Leu Arg Val Arg Ala Glu Glu Cys Cys Glu
            20                  25                  30

Phe Ile Asn Val Asn His Pro Pro Glu Arg Cys Tyr Asp Phe Lys Met
        35                  40                  45

Cys Asn Arg Phe Thr Val Ala Leu Arg Cys Pro Asp Gly Glu Val Cys
    50                  55                  60

Tyr Ser Pro Glu Lys Thr Ala Glu Ile Arg Gly Ile Val Thr Thr Met
65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Arg Ile Val
    130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170
```

<210> SEQ ID NO 39
<211> LENGTH: 171
<212> TYPE: PRT
<213> ORGANISM: Artificial Sequence
<220> FEATURE:
<223> OTHER INFORMATION: Synthetic polypeptide

<400> SEQUENCE: 39

```
Met Ser Pro Lys Asp Leu Thr Pro Phe Leu Thr Ala Leu Trp Leu Leu
1               5                   10                  15

Leu Gly His Ser Arg Val Leu Arg Val Arg Ala Glu Glu Cys Cys Glu
            20                  25                  30

Phe Ile Asn Val Asn His Pro Pro Glu Arg Cys Tyr Asp Phe Lys Met
        35                  40                  45

Cys Asn Arg Phe Thr Val Ala Leu Arg Cys Pro Asp Gly Glu Val Cys
    50                  55                  60

Tyr Ser Pro Glu Lys Thr Ala Glu Ile Arg Gly Ile Val Thr Thr Met
65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Arg Ile Val
    130                 135                 140
```

```
Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170


<210> SEQ ID NO 40
<211> LENGTH: 304
<212> TYPE: PRT
<213> ORGANISM: Artificial Sequence
<220> FEATURE:
<223> OTHER INFORMATION: Synthetic polypeptide

<400> SEQUENCE: 40

Met Pro Ala Thr Asp Thr Asn Ser Thr His Thr Thr Pro Leu His Pro
1               5                   10                  15

Glu His His His Ser Thr Thr Gln Pro His Ala Gln Thr Ser Asp Lys
            20                  25                  30

His Ala Asp Lys Gln His Arg Thr Gln Met Glu Leu Asp Ala Ala Asp
        35                  40                  45

Tyr Ala Ala Cys Ala Gln Ala Arg Gln His Leu Tyr Gly Gln Thr Gln
    50                  55                  60

Pro Gln Leu His Ala Tyr Pro Asn Ala Asn Pro Gln Glu Ser Ala His
65                  70                  75                  80

Phe Cys Thr Glu Asn Gln His Gln Leu Thr Asn Leu Leu His Asn Ile
                85                  90                  95

Gly Glu Gly Ala Ala Leu Gly Tyr Pro Val Pro Arg Ala Glu Ile Arg
            100                 105                 110

Arg Gly Gly Gly Asp Trp Ala Asp Ser Ala Ser Asp Phe Asp Ala Asp
        115                 120                 125

Cys Trp Cys Met Trp Gly Arg Phe Gly Thr Met Gly Arg Gln Pro Val
    130                 135                 140

Val Thr Leu Leu Leu Ala Arg Gln Arg Asp Gly Leu Ala Asp Trp Asn
145                 150                 155                 160

Val Val Arg Cys Arg Gly Thr Gly Phe Arg Ala His Asp Ser Glu Asp
                165                 170                 175

Gly Val Ser Val Trp Arg Gln His Leu Val Phe Leu Leu Gly Gly His
            180                 185                 190

Gly Arg Arg Val Gln Leu Glu Arg Pro Ser Ala Gly Glu Ala Gln Ala
        195                 200                 205

Arg Gly Leu Leu Pro Arg Ile Arg Ile Thr Pro Ile Ser Thr Ser Pro
    210                 215                 220

Arg Pro Lys Pro Pro Gln Pro Thr Thr Ser Thr Ala Ser His Pro His
225                 230                 235                 240

Ala Thr Ala Arg Pro Asp His Thr Leu Phe Pro Val Pro Ser Thr Pro
                245                 250                 255

Ser Ala Thr Val His Asn Pro Arg Asn Tyr Ala Val Gln Leu His Ala
            260                 265                 270

Glu Thr Thr Arg Thr Trp Arg Trp Ala Arg Arg Gly Glu Arg Gly Ala
        275                 280                 285

Trp Met Pro Ala Glu Thr Phe Thr Cys Pro Lys Asp Lys Arg Pro Trp
    290                 295                 300


<210> SEQ ID NO 41
<211> LENGTH: 310
<212> TYPE: PRT
<213> ORGANISM: Artificial Sequence
<220> FEATURE:
```

<223> OTHER INFORMATION: Synthetic polypeptide

<400> SEQUENCE: 41

Met Pro Ala Thr Asp Thr Asn Ser Thr His Thr Thr Pro Leu His Pro
1 5 10 15

Glu Asp Gln His Thr Leu Pro Leu His His Ser Thr Thr Gln Pro His
20 25 30

Val Gln Thr Ser Asp Lys His Ala Asp Lys Gln His Arg Thr Gln Met
35 40 45

Glu Leu Asp Ala Ala Asp Tyr Ala Ala Cys Ala Gln Ala Arg Gln His
50 55 60

Leu Tyr Gly Gln Thr Gln Pro Gln Leu His Ala Tyr Pro Asn Ala Asn
65 70 75 80

Pro Gln Glu Ser Ala His Phe Arg Thr Glu Asn Gln His Gln Leu Thr
85 90 95

Asn Leu Leu His Asn Ile Gly Glu Gly Ala Ala Leu Gly Tyr Pro Val
100 105 110

Pro Arg Ala Glu Ile Arg Arg Gly Gly Gly Asp Trp Ala Asp Ser Ala
115 120 125

Ser Asp Phe Asp Ala Asp Cys Trp Cys Met Trp Gly Arg Phe Gly Thr
130 135 140

Met Gly Arg Gln Pro Val Val Thr Leu Leu Leu Ala Arg Gln Arg Asp
145 150 155 160

Gly Leu Ala Asp Trp Asn Val Val Arg Cys Arg Gly Thr Gly Phe Arg
165 170 175

Ala His Asp Ser Glu Asp Gly Val Ser Val Trp Arg Gln His Leu Val
180 185 190

Phe Leu Leu Gly Gly His Gly Arg Arg Val Gln Leu Glu Arg Pro Ser
195 200 205

Ala Gly Glu Ala Gln Ala Arg Gly Leu Leu Pro Arg Ile Arg Ile Thr
210 215 220

Pro Ile Ser Thr Ser Pro Arg Pro Lys Pro Pro Gln Pro Thr Thr Ser
225 230 235 240

Thr Ala Ser His Pro His Ala Thr Ala Arg Pro Asp His Thr Leu Phe
245 250 255

Pro Val Pro Ser Thr Pro Ser Ala Thr Val His Asn Pro Arg Asn Tyr
260 265 270

Ala Val Gln Leu His Ala Glu Thr Thr Arg Thr Trp Arg Trp Ala Arg
275 280 285

Arg Gly Glu Arg Gly Ala Trp Met Pro Ala Glu Thr Phe Thr Cys Pro
290 295 300

Lys Asp Lys Arg Pro Trp
305 310

<210> SEQ ID NO 42
<211> LENGTH: 129
<212> TYPE: PRT
<213> ORGANISM: Artificial Sequence
<220> FEATURE:
<223> OTHER INFORMATION: Synthetic polypeptide

<400> SEQUENCE: 42

Met Arg Leu Cys Arg Val Trp Leu Ser Val Cys Leu Cys Ala Val Val
1 5 10 15

Leu Gly Gln Cys Gln Arg Glu Thr Ala Glu Lys Asn Asp Tyr Tyr Arg
20 25 30

```
Val Pro His Tyr Trp Asp Ala Cys Ser Arg Ala Leu Pro Asp Gln Thr
        35                  40                  45

Arg Tyr Lys Tyr Val Glu Gln Leu Val Asp Leu Thr Leu Asn Tyr His
    50                  55                  60

Tyr Asp Ala Ser His Gly Leu Asp Asn Phe Asp Val Leu Lys Arg Ile
65                  70                  75                  80

Asn Val Thr Glu Val Ser Leu Leu Ile Ser Asp Phe Arg Arg Gln Asn
                85                  90                  95

Arg Arg Gly Gly Thr Asn Lys Arg Thr Thr Phe Asn Ala Ala Gly Ser
            100                 105                 110

Leu Ala Pro His Ala Arg Ser Leu Glu Phe Ser Val Arg Leu Phe Ala
        115                 120                 125

Asn


<210> SEQ ID NO 43
<211> LENGTH: 129
<212> TYPE: PRT
<213> ORGANISM: Artificial Sequence
<220> FEATURE:
<223> OTHER INFORMATION: Synthetic polypeptide

<400> SEQUENCE: 43

Met Arg Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr Tyr Arg
            20                  25                  30

Val Pro His Tyr Trp Asp Ala Cys Ser Arg Ala Leu Pro Asp Gln Thr
        35                  40                  45

Arg Tyr Lys Tyr Val Glu Gln Leu Val Asp Leu Thr Leu Asn Tyr His
    50                  55                  60

Tyr Asp Ala Ser His Gly Leu Asp Asn Phe Asp Val Leu Lys Arg Ile
65                  70                  75                  80

Asn Val Thr Glu Val Ser Leu Leu Ile Ser Asp Phe Arg Arg Gln Asn
                85                  90                  95

Arg Arg Gly Gly Thr Asn Lys Arg Thr Thr Phe Asn Ala Ala Gly Ser
            100                 105                 110

Leu Ala Pro His Ala Arg Ser Leu Glu Phe Ser Val Arg Leu Phe Ala
        115                 120                 125

Asn


<210> SEQ ID NO 44
<211> LENGTH: 310
<212> TYPE: PRT
<213> ORGANISM: Artificial Sequence
<220> FEATURE:
<223> OTHER INFORMATION: Synthetic polypeptide

<400> SEQUENCE: 44

Met Pro Ala Thr Asp Thr Asn Ser Thr His Thr Thr Pro Leu His Pro
1               5                   10                  15

Glu Asp Gln His Thr Leu Pro Leu His His Ser Thr Thr Gln Pro His
            20                  25                  30

Val Gln Thr Ser Asp Lys His Ala Asp Lys Gln His Arg Thr Gln Met
        35                  40                  45

Glu Leu Asp Ala Ala Asp Tyr Ala Ala Cys Ala Gln Ala Arg Gln His
    50                  55                  60
```

-continued

```
Leu Tyr Gly Gln Thr Gln Pro Gln Leu His Ala Tyr Pro Asn Ala Asn
65                  70                  75                  80

Pro Gln Glu Ser Ala His Phe Arg Thr Glu Asn Gln His Gln Leu Thr
                85                  90                  95

Asn Leu Leu His Asn Ile Gly Glu Gly Ala Ala Leu Gly Tyr Pro Val
            100                 105                 110

Pro Arg Ala Glu Ile Arg Arg Gly Gly Gly Asp Trp Ala Asp Ser Ala
        115                 120                 125

Ser Asp Phe Asp Ala Asp Cys Trp Cys Met Trp Gly Arg Phe Gly Thr
    130                 135                 140

Met Gly Arg Gln Pro Val Val Thr Leu Leu Leu Ala Arg Gln Arg Asp
145                 150                 155                 160

Gly Leu Ala Asp Trp Asn Val Val Arg Cys Arg Gly Thr Gly Phe Arg
                165                 170                 175

Ala His Asp Ser Glu Asp Gly Val Ser Val Trp Arg Gln His Leu Val
            180                 185                 190

Phe Leu Leu Gly Gly His Gly Arg Arg Val Gln Leu Glu Arg Pro Ser
        195                 200                 205

Ala Gly Glu Ala Gln Ala Arg Gly Leu Leu Pro Arg Ile Arg Ile Thr
    210                 215                 220

Pro Ile Ser Thr Ser Pro Arg Pro Lys Pro Pro Gln Pro Thr Thr Ser
225                 230                 235                 240

Thr Ala Ser His Pro His Ala Thr Ala Arg Pro Asp His Thr Leu Phe
                245                 250                 255

Pro Val Pro Ser Thr Pro Ser Ala Thr Val His Asn Pro Arg Asn Tyr
            260                 265                 270

Ala Val Gln Leu His Ala Glu Thr Thr Arg Thr Trp Arg Trp Ala Arg
        275                 280                 285

Arg Gly Glu Arg Gly Ala Trp Met Pro Ala Glu Thr Phe Thr Cys Pro
    290                 295                 300

Lys Asp Lys Arg Pro Trp
305                 310
```

<210> SEQ ID NO 45
<211> LENGTH: 310
<212> TYPE: PRT
<213> ORGANISM: Artificial Sequence
<220> FEATURE:
<223> OTHER INFORMATION: Synthetic polypeptide

<400> SEQUENCE: 45

```
Met Pro Ala Thr Asp Thr Asn Ser Thr His Thr Thr Pro Leu His Pro
1               5                   10                  15

Glu Asp Gln His Thr Leu Pro Leu His His Ser Thr Thr Gln Pro His
            20                  25                  30

Val Gln Thr Ser Asp Lys His Ala Asp Lys Gln His Arg Thr Gln Met
        35                  40                  45

Glu Leu Asp Ala Ala Asp Tyr Ala Ala Cys Ala Gln Ala Arg Gln His
    50                  55                  60

Leu Tyr Gly Gln Thr Gln Pro Gln Leu His Ala Tyr Pro Asn Ala Asn
65                  70                  75                  80

Pro Gln Glu Ser Ala His Phe Arg Thr Glu Asn Gln His Gln Leu Thr
                85                  90                  95

Asn Leu Leu His Asn Ile Gly Glu Gly Ala Ala Leu Gly Tyr Pro Val
            100                 105                 110
```

```
Pro Arg Ala Glu Ile Arg Arg Gly Gly Gly Asp Trp Ala Asp Ser Ala
        115                 120                 125

Ser Asp Phe Asp Ala Asp Cys Trp Cys Met Trp Gly Arg Phe Gly Thr
    130                 135                 140

Met Gly Arg Gln Pro Val Val Thr Leu Leu Leu Ala Arg Gln Arg Asp
145                 150                 155                 160

Gly Leu Ala Asp Trp Asn Val Val Arg Cys Arg Gly Thr Gly Phe Arg
                165                 170                 175

Ala His Asp Ser Glu Asp Gly Val Ser Val Trp Arg Gln His Leu Val
            180                 185                 190

Phe Leu Leu Gly Gly His Gly Arg Arg Val Gln Leu Glu Arg Pro Ser
        195                 200                 205

Ala Gly Glu Ala Gln Ala Arg Gly Leu Leu Pro Arg Ile Arg Ile Thr
    210                 215                 220

Pro Ile Ser Thr Ser Pro Arg Pro Lys Pro Pro Gln Pro Thr Thr Ser
225                 230                 235                 240

Thr Ala Ser His Pro His Ala Thr Ala Arg Pro Asp His Thr Leu Phe
                245                 250                 255

Pro Val Pro Ser Thr Pro Ser Ala Thr Val His Asn Pro Arg Asn Tyr
            260                 265                 270

Ala Val Gln Leu His Ala Glu Thr Thr Arg Thr Trp Arg Trp Ala Arg
        275                 280                 285

Arg Gly Glu Arg Gly Ala Trp Met Pro Ala Glu Thr Phe Thr Cys Pro
    290                 295                 300

Lys Asp Lys Arg Pro Trp
305                 310


<210> SEQ ID NO 46
<211> LENGTH: 310
<212> TYPE: PRT
<213> ORGANISM: Artificial Sequence
<220> FEATURE:
<223> OTHER INFORMATION: Synthetic polypeptide

<400> SEQUENCE: 46

Met Pro Ala Thr Asp Thr Asn Ser Thr His Thr Thr Pro Leu His Pro
1               5                   10                  15

Glu Asp Gln His Thr Leu Pro Leu Gln His Asn Thr Thr Gln Pro His
            20                  25                  30

Val Gln Thr Ser Asp Lys Pro Ala Asp Lys Gln His Arg Thr Gln Met
        35                  40                  45

Glu Leu Asp Ala Ala Asp Tyr Ala Ala Cys Ala Gln Ala Arg Gln His
    50                  55                  60

Leu Tyr Gly Gln Thr Gln Pro Gln Leu His Ala Tyr Pro Asn Ala Asn
65                  70                  75                  80

Pro Gln Glu Ser Ala His Phe Cys Thr Asp Asn Gln His Arg Leu Thr
                85                  90                  95

Asn Leu Leu His Asn Ile Gly Glu Gly Ala Ala Leu Gly Tyr Pro Val
            100                 105                 110

Pro Arg Ala Glu Ile Arg Arg Gly Gly Gly Asp Trp Ala Asp Ser Ala
        115                 120                 125

Ser Asp Phe Asp Ala Asp Cys Trp Cys Met Trp Gly Arg Phe Gly Thr
    130                 135                 140

Met Gly Arg Gln Pro Val Val Thr Leu Leu Leu Ala Arg Gln Arg Asp
145                 150                 155                 160
```

Gly Leu Ala Asp Trp Asn Val Val Arg Cys Arg Gly Thr Gly Phe Arg
165 170 175

Ala His Asp Ser Glu Asp Gly Val Ser Val Trp Arg Gln His Leu Val
180 185 190

Phe Leu Leu Gly Gly His Gly Arg Arg Val Gln Leu Glu Arg Pro Ser
195 200 205

Ala Gly Glu Ala Gln Ala Arg Gly Leu Leu Pro Arg Ile Arg Ile Thr
210 215 220

Pro Val Ser Thr Ser Pro Arg Pro Lys Ala Pro Gln Pro Thr Thr Ser
225 230 235 240

Thr Ala Ser His Pro His Ala Thr Ala Arg Pro Asp His Thr Leu Phe
245 250 255

Pro Val Pro Ser Thr Pro Ser Ala Thr Val His Asn Pro Arg Asn Tyr
260 265 270

Ala Val Gln Leu His Ala Glu Thr Thr Arg Thr Trp Arg Trp Ala Arg
275 280 285

Arg Gly Glu Arg Gly Ala Trp Met Pro Ala Glu Thr Phe Thr Cys Pro
290 295 300

Lys Asp Lys Arg Pro Trp
305 310

<210> SEQ ID NO 47
<211> LENGTH: 310
<212> TYPE: PRT
<213> ORGANISM: Artificial Sequence
<220> FEATURE:
<223> OTHER INFORMATION: Synthetic polypeptide

<400> SEQUENCE: 47

Met Pro Ala Thr Asp Thr Asn Ser Thr His Thr Thr Pro Leu His Pro
1 5 10 15

Glu Asp Gln His Thr Leu Pro Leu His His Ser Thr Thr Gln Pro His
20 25 30

Val Gln Thr Ser Asp Lys His Ala Asp Lys Gln His Arg Thr Gln Met
35 40 45

Glu Leu Asp Ala Ala Asp Tyr Ala Ala Cys Ala Gln Ala Arg Gln His
50 55 60

Leu Tyr Gly Gln Thr Gln Pro Gln Leu His Ala Tyr Pro Asn Ala Asn
65 70 75 80

Pro Gln Glu Ser Ala His Phe Arg Thr Glu Asn Gln His Gln Leu Thr
85 90 95

Asn Leu Leu His Asn Ile Gly Glu Gly Ala Ala Leu Gly Tyr Pro Val
100 105 110

Pro Arg Ala Glu Ile Arg Arg Gly Gly Gly Asp Trp Ala Asp Ser Ala
115 120 125

Ser Asp Phe Asp Ala Asp Cys Trp Cys Met Trp Gly Arg Phe Gly Thr
130 135 140

Met Gly Arg Gln Pro Val Val Thr Leu Leu Leu Ala Arg Gln Arg Asp
145 150 155 160

Gly Leu Ala Asp Trp Asn Val Val Arg Cys Arg Gly Thr Gly Phe Arg
165 170 175

Ala His Asp Ser Glu Asp Gly Val Ser Val Trp Arg Gln His Leu Val
180 185 190

Phe Leu Leu Gly Gly His Gly Arg Arg Val Gln Leu Glu Arg Pro Ser
195 200 205

```
Ala Gly Glu Ala Gln Ala Arg Gly Leu Leu Pro Arg Ile Arg Ile Thr
    210                 215                 220

Pro Ile Ser Thr Ser Pro Arg Pro Lys Pro Pro Gln Pro Thr Thr Ser
225                 230                 235                 240

Thr Ala Ser His Pro His Ala Thr Ala Arg Pro Asp His Thr Leu Phe
                245                 250                 255

Pro Val Pro Ser Thr Pro Ser Ala Thr Val His Asn Pro Arg Asn Tyr
            260                 265                 270

Ala Val Gln Leu His Ala Glu Thr Thr Arg Thr Trp Arg Trp Ala Arg
        275                 280                 285

Arg Gly Glu Arg Gly Ala Trp Met Pro Ala Glu Thr Phe Thr Cys Pro
    290                 295                 300

Lys Asp Lys Arg Pro Trp
305                 310


<210> SEQ ID NO 48
<211> LENGTH: 760
<212> TYPE: PRT
<213> ORGANISM: Artificial Sequence
<220> FEATURE:
<223> OTHER INFORMATION: Synthetic polypeptide

<400> SEQUENCE: 48

Ser Ser Phe Trp Thr Leu Val Gln Lys Leu Ile Arg Leu Thr Ile Gly
1               5                   10                  15

Lys Glu Arg Lys Glu Glu Glu Glu Ile Glu Pro Pro Cys Gly Gln Ala
            20                  25                  30

Ser Pro Pro Thr Ser Ser Ser Ser Pro Ser Val Ser Ser Ala Thr Tyr
        35                  40                  45

Phe Arg His Asp Met Ala Gln Lys Pro Tyr Pro Asn Arg Trp Thr Lys
    50                  55                  60

Arg Phe Thr Tyr Cys Ser Thr Pro Thr Gly Asp Pro Ser Ala Ser Cys
65                  70                  75                  80

Val Lys Ile Pro Pro Ser Val Pro Thr Thr Ala Ala Ser Val Thr Ala
                85                  90                  95

Arg Ser Ser Gly Lys Thr Pro Ser Val Ser Thr Phe Ser Lys Ala Ile
            100                 105                 110

Ile Asn Thr Met Tyr Ser Ile Cys Leu Asp Val Phe Leu Arg Val Leu
        115                 120                 125

Trp Arg Ser Ser Phe Thr Arg Ile Pro Lys Pro Trp Lys Asp Thr Asn
    130                 135                 140

Arg Asp Leu Thr Leu Thr Arg Trp Tyr Pro Lys Thr Trp Pro Ala Thr
145                 150                 155                 160

Asp Leu Phe Arg Ser Ser Arg His Lys Thr Ala Val Asn Ser Pro Pro
                165                 170                 175

Leu Cys His Arg Pro Leu Thr Cys Gln Tyr Leu Thr Phe Gly Cys His
            180                 185                 190

Arg Lys Pro Leu His Thr Ala Gly Gln Asn His Ile Pro Pro Gln Asp
        195                 200                 205

Tyr Thr Asp His Thr Leu Thr Arg Pro Val Ser Ser Leu Met Asp Thr
    210                 215                 220

Ile Tyr Tyr Ser Ala Pro Ser His Leu Val Cys Thr Lys Ala Phe Thr
225                 230                 235                 240

Ser Ser Thr Asn Tyr Val Thr Leu Lys His Pro Arg Thr Ser Ser Leu
                245                 250                 255
```

-continued

```
Arg Cys Pro Thr Thr Thr His Pro Cys Cys Leu Ser Ser Ala Ile Phe
            260                 265                 270

His Ala Tyr Phe Ser Lys Arg Pro Ile Asn Ala Thr Thr Leu Tyr Tyr
        275                 280                 285

Asp Lys Leu Lys Asn Thr Ser Ser Trp Cys Leu Arg Lys Ile Asn Val
    290                 295                 300

Thr Leu Ile Ser Lys Thr Arg Thr Phe Leu Thr Pro His Leu Thr Ser
305                 310                 315                 320

Thr Thr Thr Ser Ala His Tyr Tyr Val Thr Ala Phe Thr Val Thr Pro
                325                 330                 335

Trp Met Tyr Ser Arg Ala Val Asp Val Arg Cys Trp Thr Ala Ala Arg
            340                 345                 350

Lys Trp Pro Ser Pro Thr His His Cys Ser Gln Gln Pro Asp Lys Lys
        355                 360                 365

Arg Pro Ala Pro Lys Ser Pro Ser His Gly Pro Thr Ala Arg Pro His
    370                 375                 380

Ser Tyr Lys Tyr Lys Asn Leu Ser Pro Ala Ser His Lys His His His
385                 390                 395                 400

Ala Pro Arg Cys Cys Cys Ile Pro Arg Pro Trp Thr Trp Pro Asn Glu
                405                 410                 415

Pro Phe Gly His Arg Ile Arg Ser Pro Thr Ser Pro Ala Ser Tyr Ala
            420                 425                 430

Trp Ser Thr Tyr Ser Leu Asn Arg Ile Ser Asn Ile Ser Ser Pro Asn
        435                 440                 445

Gly His Tyr Asp Arg Ser Pro Thr Leu Pro Asn Tyr Thr Lys Arg Thr
    450                 455                 460

Trp Pro Leu Phe Phe Gln Pro Ser His Ala Lys Asn Ser Thr Ser Trp
465                 470                 475                 480

Ala Ala Ser Ser Thr Pro Cys Trp Tyr Ile Arg Arg Arg Asp Ala Lys
                485                 490                 495

Ser Ser Ser Lys Arg Ala Ser Val His Trp Pro Ser Tyr His Thr Leu
            500                 505                 510

Arg Ser Cys Leu Ile His Thr Thr Asn Thr Ser Ala Thr Cys Thr His
        515                 520                 525

Pro Val Pro Val Ala Gly Asp Ala Ile Thr Arg Ser Asn Ala Ser Arg
    530                 535                 540

Val Ser Ser Pro Met Pro Pro Ser Pro Leu Pro Phe Pro Pro Pro Ser
545                 550                 555                 560

Pro Ser Tyr Leu Pro Cys Asn Gln Ala Arg Trp Lys Pro Ser Pro Thr
                565                 570                 575

Cys Phe Ala Cys Arg Ser Ala Asn Pro Ser Pro Arg Pro Ser Pro Asn
            580                 585                 590

Thr Ser Val Ile Ser Gln Thr Ser Thr Ser Lys Val Ser Pro Thr Leu
        595                 600                 605

Ser Pro Pro Pro Ser Ala Arg Ala Ser Ser Ser Pro Arg Arg Thr Val
    610                 615                 620

Lys Leu Asn Ala Asn Arg Ala Thr Cys Ile Pro His Thr Ala Ser Gln
625                 630                 635                 640

Trp Arg Ser Thr Phe Arg Lys Thr Ala Pro Phe Ala Lys Ala Pro Cys
                645                 650                 655

Asn Thr Thr Thr Arg Lys Ala Ser Ser Thr Ser Cys Thr Cys Thr Thr
            660                 665                 670

Arg Thr Thr Ser Phe Ser Pro Trp Ile Pro Thr Thr Lys Trp Trp Ser
```

-continued

```
        675                 680                 685

His Leu Arg Glu Leu Thr Thr Ser Cys Phe Lys Thr Val Arg Tyr Lys
    690                 695                 700

Leu Thr Ser Ser Trp Thr Pro Pro Thr Ile Thr Arg Thr Met Thr Ile
705                 710                 715                 720

Ser Asp Asp Asn Arg Leu Glu Pro Arg Trp Pro Cys Phe Leu Pro Leu
                725                 730                 735

Gly Pro Pro Pro Ser Pro Ser Ser Pro Ser Cys Thr Arg Thr Pro Val
            740                 745                 750

Val Phe Glu Ser Leu Ser Gly Arg
        755                 760


<210> SEQ ID NO 49
<211> LENGTH: 759
<212> TYPE: PRT
<213> ORGANISM: Artificial Sequence
<220> FEATURE:
<223> OTHER INFORMATION: Synthetic polypeptide

<400> SEQUENCE: 49

Ser Ser Phe Trp Thr Leu Val Gln Lys Leu Ile Arg Leu Thr Ile Gly
1               5                   10                  15

Lys Glu Arg Lys Glu Glu Glu Glu Ile Glu Pro Pro Cys Gly Gln Ala
            20                  25                  30

Ser Pro Pro Thr Ser Ser Ser Ser Pro Ser Val Ser Ser Ala Thr Tyr
        35                  40                  45

Phe Arg His Asp Met Ala Gln Lys Pro Tyr Pro Asn Arg Trp Thr Lys
    50                  55                  60

Arg Phe Thr Tyr Cys Ser Thr Pro Thr Gly Asp Pro Ser Ala Ser Cys
65                  70                  75                  80

Val Lys Ile Pro Pro Ser Val Pro Thr Thr Ala Ala Ser Val Thr Ala
                85                  90                  95

Arg Ser Ser Gly Lys Thr Pro Ser Val Ser Thr Phe Ser Lys Ala Ile
            100                 105                 110

Ile Asn Thr Met Tyr Ser Ile Cys Leu Asp Val Phe Leu Arg Val Leu
        115                 120                 125

Trp Arg Ser Ser Phe Thr Arg Ile Pro Lys Pro Trp Lys Asp Thr Asn
    130                 135                 140

Arg Asp Leu Thr Leu Thr Arg Trp Tyr Pro Lys Thr Trp Pro Ala Thr
145                 150                 155                 160

Asp Leu Phe Arg Ser Ser Arg His Lys Thr Ala Val Asn Ser Pro Pro
                165                 170                 175

Leu Cys His Arg Pro Leu Thr Cys Gln Tyr Leu Thr Phe Gly Cys His
            180                 185                 190

Arg Lys Pro Leu His Thr Ala Gly Gln Asn His Ile Pro Pro Gln Asp
        195                 200                 205

Tyr Thr Asp His Thr Leu Thr Arg Pro Val Ser Ser Leu Met Asp Thr
    210                 215                 220

Ile Tyr Tyr Ser Ala Pro Ser His Leu Val Cys Thr Lys Ala Phe Thr
225                 230                 235                 240

Ser Ser Thr Asn Tyr Val Thr Leu Lys His Pro Arg Thr Ser Ser Leu
                245                 250                 255

Arg Cys Pro Thr Thr Thr His Pro Cys Cys Leu Ser Ser Ala Ile Phe
            260                 265                 270

His Ala Tyr Phe Ser Lys Arg Pro Ile Asn Ala Thr Thr Leu Tyr Tyr
```

```
        275                 280                 285

Asp Lys Leu Lys Asn Thr Ser Ser Trp Cys Leu Arg Lys Ile Asn Thr
    290                 295                 300

Val Thr Leu Ile Ser Lys Thr Arg Thr Phe Leu Thr Pro His Leu Thr
305                 310                 315                 320

Ser Thr Thr Thr Ser Ala His Tyr Tyr Val Thr Ala Phe Thr Val Thr
                325                 330                 335

Pro Trp Met Tyr Ser Arg Ala Val Asp Val Arg Cys Trp Thr Ala Ala
            340                 345                 350

Arg Lys Trp Pro Ser Pro Thr His His Cys Ser Gln Gln Pro Asp Lys
        355                 360                 365

Lys Arg Pro Ala Pro Lys Ser Pro Ser His Gly Pro Thr Ala Arg Pro
    370                 375                 380

His Ser Tyr Lys Tyr Lys Asn Leu Ser Pro Ala Ser His Lys His His
385                 390                 395                 400

His Ala Pro Arg Cys Cys Cys Ile Pro Arg Pro Trp Thr Trp Pro Asn
                405                 410                 415

Glu Pro Phe Gly His Arg Ile Arg Ser Pro Thr Ser Pro Ala Ser Tyr
            420                 425                 430

Ala Trp Ser Thr Tyr Ser Leu Asn Arg Ile Ser Asn Ile Ser Ser Pro
        435                 440                 445

Asn Gly His Tyr Asp Arg Ser Pro Thr Leu Pro Asn Tyr Thr Lys Arg
    450                 455                 460

Thr Trp Pro Leu Phe Phe Gln Pro Ser His Ala Lys Asn Ser Thr Ser
465                 470                 475                 480

Trp Ala Ala Ser Ser Thr Pro Cys Trp Tyr Ile Arg Arg Arg Asp Ala
                485                 490                 495

Lys Ser Ser Ser Lys Arg Ala Ser Val His Trp Pro Ser Tyr His Thr
            500                 505                 510

Leu Arg Ser Cys Leu Ile His Thr Thr Asn Thr Ser Ala Thr Cys Thr
        515                 520                 525

His Pro Val Pro Val Ala Gly Asp Ala Ile Thr Arg Ser Asn Ala Ser
    530                 535                 540

Arg Val Ser Ser Pro Met Pro Pro Ser Pro Leu Pro Phe Pro Pro Pro
545                 550                 555                 560

Ser Pro Ser Tyr Leu Pro Cys Asn Gln Ala Arg Trp Lys Pro Ser Pro
                565                 570                 575

Thr Cys Phe Ala Cys Arg Ser Ala Asn Pro Ser Pro Arg Pro Ser Pro
            580                 585                 590

Asn Thr Ser Val Ile Ser Gln Thr Ser Thr Ser Lys Val Ser Pro Thr
        595                 600                 605

Leu Ser Pro Pro Pro Ser Ala Arg Ala Ser Ser Ser Pro Arg Arg Thr
    610                 615                 620

Val Lys Leu Asn Ala Asn Arg Ala Thr Cys Ile Pro His Thr Ala Ser
625                 630                 635                 640

Gln Trp Arg Ser Thr Phe Arg Lys Thr Ala Pro Phe Ala Lys Ala Pro
                645                 650                 655

Cys Asn Thr Thr Thr Arg Lys Ala Ser Ser Thr Ser Cys Thr Cys Thr
            660                 665                 670

Thr Arg Thr Thr Ser Phe Ser Pro Trp Ile Pro Thr Thr Lys Trp Trp
        675                 680                 685

Ser His Leu Arg Glu Leu Thr Thr Ser Cys Phe Lys Thr Val Arg Tyr
    690                 695                 700
```

Lys Leu Thr Ser Ser Trp Thr Pro Pro Thr Thr Ile Thr Thr Ile Thr
705 710 715 720

Asp Asp Asn Arg Leu Glu Pro Arg Trp Pro Cys Phe Leu Pro Leu Gly
725 730 735

Pro Pro Pro Ser Pro Ser Ser Pro Ser Cys Thr Arg Thr Pro Val Val
740 745 750

Phe Glu Ser Leu Ser Gly Arg
755

<210> SEQ ID NO 50
<211> LENGTH: 735
<212> TYPE: PRT
<213> ORGANISM: Artificial Sequence
<220> FEATURE:
<223> OTHER INFORMATION: Synthetic polypeptide

<400> SEQUENCE: 50

Ser Ser Phe Trp Thr Leu Val Gln Lys Leu Ile Arg Leu Thr Ile Gly
1 5 10 15

Lys Glu Arg Lys Glu Glu Glu Glu Ile Glu Pro Pro Trp Asn Pro Gly
20 25 30

Ser Gly Ala Trp Ala Leu Thr Cys Val Ser Ser Val Trp Val Leu Arg
35 40 45

Phe Pro His Leu Leu Leu Val Glu Leu Leu Leu Leu Thr Val Thr Ile
50 55 60

Pro Leu Ile Arg Arg Leu Leu Leu Thr Leu Asp Pro Val Gln Ser Leu
65 70 75 80

Asn Ala Leu Leu Pro Lys Arg Ser Ala Met Val Leu Thr Arg Pro Ser
85 90 95

Thr Thr Leu Pro Ser Ser Thr Glu Met Trp Trp Gly Ser Ile Pro Pro
100 105 110

Ser Thr Pro Ile Ala Cys Val Leu Trp Pro Arg Val Arg Ile Leu Phe
115 120 125

Ala Leu Asn Val Ile Ser Ser Ala Pro Arg Ser Pro Ser Met Lys Thr
130 135 140

Trp Thr Arg Ala Ser Trp Trp Ser Thr Asn Ala Thr Ser Ser Arg Thr
145 150 155 160

Pro Leu Arg Tyr Glu Ser Thr Arg Arg Phe Arg Phe Val Val Ala Thr
165 170 175

Leu Thr Ser Thr Pro Leu Ile Cys Trp Ala Ala Thr Arg Asn Thr Trp
180 185 190

Arg Leu Leu Cys Gly Arg Phe Ile Ile Ser Thr Ala Thr Val Ser Ala
195 200 205

Thr Val Pro Thr Ala Ala Leu Gln Ala Arg Phe Ser Trp Leu Ile Ile
210 215 220

Gly Thr Ala Met Lys Thr Lys Pro Cys Asn Cys Pro Thr Ile Ile Pro
225 230 235 240

Thr Pro Thr Val Pro Val Thr Arg Ser Arg Ile Asn Gly Thr Ala Ala
245 250 255

Ala Ala Pro Gly Ser Ile Val Arg Pro Val Ile Ile Val Trp Pro Ser
260 265 270

Leu Leu Arg Ala Pro Asn Ile Leu Ile Ile Phe Ser Pro Leu Pro Arg
275 280 285

Val Thr Trp Leu Thr Phe Leu Leu Ser Thr Thr Glu Pro Ile Ala Met
290 295 300

-continued

```
Pro Ala Thr Leu Glu Lys Thr Pro Thr Ser Phe Ser Phe Phe Arg Thr
305                 310                 315                 320

Thr Leu Ser Ser Pro Thr Leu Glu Asp Arg Ile Leu Arg Arg Pro Thr
                325                 330                 335

Gly Trp Trp Leu Phe Leu Asn Val Arg Thr Arg Ser Pro Gly Ile Tyr
            340                 345                 350

Arg Thr Lys Arg Met Ser Leu Val Asn Ser Leu Ser Gly Lys Pro Arg
        355                 360                 365

Asn Ala Pro Phe Val Pro Lys Pro Arg Thr Arg Ile Thr Phe Leu Leu
    370                 375                 380

Pro Lys Pro Pro Leu Ser Tyr Leu Arg Ser Lys Arg Thr Cys Pro Thr
385                 390                 395                 400

Leu Arg Trp Thr Ala Tyr Val Met Arg Leu Ile Ser Tyr Ser Arg Phe
                405                 410                 415

Ser Ile Leu His Thr Ile Lys His Met Lys Asn Met Glu Thr Cys Pro
            420                 425                 430

Ser Leu Lys Pro Leu Val Val Trp Cys Ser Gly Lys Val Ser Ser Lys
        435                 440                 445

Asn Leu Trp Trp Asn Ser Asn Val Trp Pro Thr Ala Pro Val Ile Leu
    450                 455                 460

Leu Ile Ile Glu Pro Lys Glu Val Gln Met Ala Thr Met Gln Leu Ile
465                 470                 475                 480

Tyr Pro Thr Trp Asn Arg Cys Thr Ile Trp Ser Thr Pro Ser Cys Ser
                485                 490                 495

Ser Pro Met Thr Arg Cys Ala Val Thr Ser Thr Gly Arg Trp Arg Lys
            500                 505                 510

Ser Gln Lys Pro Gly Val Trp Ile Asn Gly Ala Pro Arg Ser Ser Arg
        515                 520                 525

Asn Ser Ala Arg Ser Thr Arg Gln Pro Phe Ser Arg Pro Phe Thr Thr
    530                 535                 540

Asn Arg Leu Pro Arg Val Ser Trp Val Met Ser Trp Ala Trp Pro Ala
545                 550                 555                 560

Ala Pro Ser Thr Lys Pro Ala Ser Arg Cys Cys Val Ile Thr Arg Ser
                565                 570                 575

Arg Gln Asp Ala Ala Thr His Asp Pro Trp Ser Ser Leu Ile Ser Pro
            580                 585                 590

Thr Ala Arg Thr Cys Ser Thr Val Asn Trp Ala Arg Thr Thr Lys Ser
        595                 600                 605

Cys Trp Ala Thr Thr Ala Leu Arg Asn Val Ser Phe Pro Ala Ser Arg
    610                 615                 620

Ser Ser Ser Pro Gly Thr Arg Pro Thr Ser Thr Trp Thr Thr Ser Ser
625                 630                 635                 640

Asn Ala Leu Thr Ser Ala Val Ser Pro Pro Ser Thr Ala Ser Pro Trp
                645                 650                 655

Ile Ser Thr Arg Trp Lys Ile Pro Thr Ser Gly Tyr Trp Asn Phe Thr
            660                 665                 670

Arg Arg Lys Ser Cys Val Pro Ala Thr Phe Leu Thr Ser Lys Arg Ser
        675                 680                 685

Cys Ala Asn Ser Thr Arg Thr Ser Ser Asp Asn Arg Leu Glu Pro Arg
    690                 695                 700

Trp Pro Cys Phe Leu Pro Leu Gly Pro Pro Pro Ser Pro Ser Ser Pro
705                 710                 715                 720
```

```
Ser Cys Thr Arg Thr Pro Val Val Phe Glu Ser Leu Ser Gly Arg
                725                 730                 735


<210> SEQ ID NO 51
<211> LENGTH: 744
<212> TYPE: PRT
<213> ORGANISM: Artificial Sequence
<220> FEATURE:
<223> OTHER INFORMATION: Synthetic polypeptide

<400> SEQUENCE: 51

Ser Ser Phe Trp Thr Leu Val Gln Lys Leu Ile Arg Leu Thr Ile Gly
1               5                   10                  15

Lys Glu Arg Lys Glu Glu Glu Glu Ile Glu Pro Pro Trp Asn Pro Gly
            20                  25                  30

Ser Gly Ala Trp Ser Ala Leu Thr Cys Val Ser Ser Val Trp Val Leu
        35                  40                  45

Arg Phe Pro His Leu Leu Leu Val Glu Leu Leu Leu Leu Thr Val Thr
    50                  55                  60

Ile Pro Leu Ile Arg Arg Leu Leu Leu Thr Leu Asp Pro Val Gln Ser
65                  70                  75                  80

Leu Asn Ala Leu Leu Pro Lys Arg Ser Ala Met Val Leu Thr Arg Pro
                85                  90                  95

Ser Thr Thr Leu Pro Ser Ser Thr Glu Met Trp Trp Gly Ser Ile Pro
            100                 105                 110

Pro Ser Thr Pro Ile Ala Cys Val Leu Trp Pro Arg Val Arg Ile Leu
        115                 120                 125

Phe Ala Leu Asn Val Ile Ser Ser Ala Pro Arg Ser Pro Ser Met Lys
    130                 135                 140

Thr Trp Thr Arg Ala Ser Trp Trp Ser Thr Asn Ala Thr Ser Ser Arg
145                 150                 155                 160

Thr Pro Leu Arg Tyr Glu Ser Thr Arg Arg Phe Arg Phe Val Val Ala
                165                 170                 175

Thr Leu Thr Ser Thr Pro Leu Ile Cys Trp Ala Ala Thr Arg Asn Thr
            180                 185                 190

Trp Arg Leu Leu Cys Gly Arg Phe Ile Ile Ser Thr Ala Thr Val Ser
        195                 200                 205

Ala Thr Val Pro Thr Ala Ala Leu Gln Ala Arg Phe Ser Trp Leu Ile
    210                 215                 220

Ile Gly Thr Ala Met Lys Thr Lys Pro Cys Asn Cys Pro Thr Ile Ile
225                 230                 235                 240

Pro Thr Pro Thr Val Pro Val Thr Arg Ser Arg Ile Asn Gly Thr Ala
                245                 250                 255

Ala Ala Ala Pro Gly Ser Ile Val Arg Pro Val Ile Ile Val Trp Pro
            260                 265                 270

Ser Leu Leu Arg Ala Pro Asn Ile Leu Ile Ile Phe Ser Pro Leu Pro
        275                 280                 285

Arg Val Thr Trp Leu Thr Phe Leu Leu Ser Thr Thr Glu Pro Ile Ala
    290                 295                 300

Met Pro Ala Thr Leu Glu Lys Thr Pro Thr Ser Phe Ser Phe Phe Arg
305                 310                 315                 320

Thr Thr Leu Ser Ser Pro Thr Leu Glu Asp Arg Ile Leu Arg Arg Pro
                325                 330                 335

Thr Gly Trp Trp Leu Phe Leu Asn Val Arg Thr Arg Ser Pro Gly Ile
            340                 345                 350
```

-continued

```
Tyr Arg Thr Lys Arg Met Ser Leu Val Asn Ser Leu Ser Gly Lys Pro
        355                 360                 365

Arg Asn Ala Pro Phe Val Pro Lys Pro Arg Thr Arg Ile Thr Phe Leu
    370                 375                 380

Leu Pro Lys Pro Pro Leu Ser Tyr Leu Arg Ser Lys Arg Thr Cys Pro
385                 390                 395                 400

Thr Leu Arg Trp Thr Ala Tyr Val Met Arg Leu Ile Ser Tyr Ser Arg
                405                 410                 415

Phe Ser Ile Leu His Thr Ile Lys His Met Lys Asn Met Glu Thr Cys
            420                 425                 430

Pro Ser Leu Lys Pro Leu Val Val Trp Cys Ser Gly Lys Val Ser Ser
        435                 440                 445

Lys Asn Leu Trp Trp Asn Ser Asn Val Trp Pro Thr Ala Pro Val Ile
    450                 455                 460

Leu Leu Ile Ile Glu Pro Lys Glu Val Gln Met Ala Thr Met Gln Leu
465                 470                 475                 480

Ile Tyr Pro Thr Trp Asn Arg Cys Thr Ile Trp Ser Thr Pro Ser Cys
                485                 490                 495

Ser Ser Pro Met Thr Arg Cys Ala Val Thr Ser Thr Gly Arg Trp Arg
            500                 505                 510

Lys Ser Gln Lys Pro Gly Val Trp Ile Asn Gly Ala Pro Arg Ser Ser
        515                 520                 525

Arg Asn Ser Ala Arg Ser Thr Arg Gln Pro Phe Ser Arg Pro Phe Thr
    530                 535                 540

Thr Asn Arg Leu Pro Arg Val Ser Trp Val Met Ser Trp Ala Trp Pro
545                 550                 555                 560

Ala Ala Pro Ser Thr Lys Pro Ala Ser Arg Cys Cys Val Ile Thr Arg
                565                 570                 575

Ser Arg Gln Asp Ala Ala Thr His Asp Pro Trp Ser Ser Leu Ile Ser
            580                 585                 590

Pro Thr Ala Arg Thr Cys Ser Thr Val Asn Trp Ala Arg Thr Thr Lys
        595                 600                 605

Ser Cys Trp Ala Thr Thr Ala Leu Arg Asn Val Ser Phe Pro Ala Ser
    610                 615                 620

Arg Ser Ser Ser Pro Gly Thr Arg Pro Thr Ser Thr Trp Thr Thr Ser
625                 630                 635                 640

Ser Asn Ala Leu Thr Ser Ala Val Ser Pro Pro Ser Thr Ala Ser Pro
                645                 650                 655

Trp Ile Ser Thr Arg Trp Lys Ile Pro Thr Ser Gly Tyr Trp Asn Phe
            660                 665                 670

Thr Arg Arg Lys Ser Cys Val Pro Ala Thr Phe Leu Thr Ser Lys Arg
        675                 680                 685

Ser Cys Ala Asn Ser Thr Arg Thr Ser Arg Ile Thr Arg Thr Met Thr
    690                 695                 700

Ile Ser Asp Asn Arg Leu Glu Pro Arg Trp Pro Cys Phe Leu Pro Leu
705                 710                 715                 720

Gly Pro Pro Pro Ser Pro Ser Ser Pro Ser Cys Thr Arg Thr Pro Val
                725                 730                 735

Val Phe Glu Ser Leu Ser Gly Arg
            740
```

<210> SEQ ID NO 52
<211> LENGTH: 742
<212> TYPE: PRT

<213> ORGANISM: Artificial Sequence
<220> FEATURE:
<223> OTHER INFORMATION: Synthetic polypeptide

<400> SEQUENCE: 52

```
Ser Ser Phe Trp Thr Leu Val Gln Lys Leu Ile Arg Leu Thr Ile Gly
1               5                   10                  15

Lys Glu Arg Lys Glu Glu Glu Glu Ile Glu Pro Pro Trp Asn Pro Gly
            20                  25                  30

Ser Gly Ala Trp Ser Ala Leu Thr Cys Val Ser Ser Val Trp Val Leu
        35                  40                  45

Arg Phe Pro His Leu Leu Leu Val Glu Leu Leu Leu Leu Thr Val Thr
    50                  55                  60

Ile Pro Leu Ile Arg Arg Leu Leu Leu Thr Leu Asp Pro Val Gln Ser
65                  70                  75                  80

Leu Asn Ala Leu Leu Pro Lys Arg Ser Ala Met Val Leu Thr Arg Pro
                85                  90                  95

Ser Thr Thr Leu Pro Ser Ser Thr Glu Met Trp Trp Gly Ser Ile Pro
            100                 105                 110

Pro Ser Thr Pro Ile Ala Cys Val Leu Trp Pro Arg Val Arg Ile Leu
        115                 120                 125

Phe Ala Leu Asn Val Ile Ser Ser Ala Pro Arg Ser Pro Ser Met Lys
    130                 135                 140

Thr Trp Thr Arg Ala Ser Trp Trp Ser Thr Asn Ala Thr Ser Ser Arg
145                 150                 155                 160

Thr Pro Leu Arg Tyr Glu Ser Thr Arg Arg Phe Arg Phe Val Val Ala
                165                 170                 175

Thr Leu Thr Ser Thr Pro Leu Ile Cys Trp Ala Ala Thr Arg Asn Thr
            180                 185                 190

Trp Arg Leu Leu Cys Gly Arg Phe Ile Ile Ser Thr Ala Thr Val Ser
        195                 200                 205

Ala Thr Val Pro Thr Ala Ala Leu Gln Ala Arg Phe Ser Trp Leu Ile
    210                 215                 220

Ile Gly Thr Ala Met Lys Thr Lys Pro Cys Asn Cys Pro Thr Ile Ile
225                 230                 235                 240

Pro Thr Pro Thr Val Pro Val Thr Arg Ser Arg Ile Asn Gly Thr Ala
                245                 250                 255

Ala Ala Ala Pro Gly Ser Ile Val Arg Pro Val Ile Ile Val Trp Pro
            260                 265                 270

Ser Leu Leu Arg Ala Pro Asn Ile Leu Ile Ile Phe Ser Pro Leu Pro
        275                 280                 285

Arg Val Thr Trp Leu Thr Phe Leu Leu Ser Thr Thr Glu Pro Ile Ala
    290                 295                 300

Met Pro Ala Thr Leu Glu Lys Thr Pro Thr Ser Phe Ser Phe Phe Arg
305                 310                 315                 320

Thr Thr Leu Ser Ser Pro Thr Leu Glu Asp Arg Ile Leu Arg Arg Pro
                325                 330                 335

Thr Gly Trp Trp Leu Phe Leu Asn Val Arg Thr Arg Ser Pro Gly Ile
            340                 345                 350

Tyr Arg Thr Lys Arg Met Ser Leu Val Asn Ser Leu Ser Gly Lys Pro
        355                 360                 365

Arg Asn Ala Pro Phe Val Pro Lys Pro Arg Thr Arg Ile Thr Phe Leu
    370                 375                 380

Leu Pro Lys Pro Pro Leu Ser Tyr Leu Arg Ser Lys Arg Thr Cys Pro
```

385 390 395 400

Thr Leu Arg Trp Thr Ala Tyr Val Met Arg Leu Ile Ser Tyr Ser Arg
405 410 415

Phe Ser Ile Leu His Thr Ile Lys His Met Lys Asn Met Glu Thr Cys
420 425 430

Pro Ser Leu Lys Pro Leu Val Val Trp Cys Ser Gly Lys Val Ser Ser
435 440 445

Lys Asn Leu Trp Trp Asn Ser Asn Val Trp Pro Thr Ala Pro Val Ile
450 455 460

Leu Leu Ile Ile Glu Pro Lys Glu Val Gln Met Ala Thr Met Gln Leu
465 470 475 480

Ile Tyr Pro Thr Trp Asn Arg Cys Thr Ile Trp Ser Thr Pro Ser Cys
485 490 495

Ser Ser Pro Met Thr Arg Cys Ala Val Thr Ser Thr Gly Arg Trp Arg
500 505 510

Lys Ser Gln Lys Pro Gly Val Trp Ile Asn Gly Ala Pro Arg Ser Ser
515 520 525

Arg Asn Ser Ala Arg Ser Thr Arg Gln Pro Phe Ser Arg Pro Phe Thr
530 535 540

Thr Asn Arg Leu Pro Arg Val Ser Trp Val Met Ser Trp Ala Trp Pro
545 550 555 560

Ala Ala Pro Ser Thr Lys Pro Ala Ser Arg Cys Cys Val Ile Thr Arg
565 570 575

Ser Arg Gln Asp Ala Ala Thr His Asp Pro Trp Ser Ser Leu Ile Ser
580 585 590

Pro Thr Ala Arg Thr Cys Ser Thr Val Asn Trp Ala Arg Thr Thr Lys
595 600 605

Ser Cys Trp Ala Thr Thr Ala Leu Arg Asn Val Ser Phe Pro Ala Ser
610 615 620

Arg Ser Ser Ser Pro Gly Thr Arg Pro Thr Ser Thr Trp Thr Thr Ser
625 630 635 640

Ser Asn Ala Leu Thr Ser Ala Val Ser Pro Pro Ser Thr Ala Ser Pro
645 650 655

Trp Ile Ser Thr Arg Trp Lys Ile Pro Thr Ser Gly Tyr Trp Asn Phe
660 665 670

Thr Arg Arg Lys Ser Cys Val Pro Ala Thr Phe Leu Thr Ser Lys Arg
675 680 685

Ser Cys Ala Asn Ser Thr Arg Thr Ser Ser Thr Ile Thr Thr Ile Thr
690 695 700

Asp Asn Arg Leu Glu Pro Arg Trp Pro Cys Phe Leu Pro Leu Gly Pro
705 710 715 720

Pro Pro Ser Pro Ser Ser Pro Ser Cys Thr Arg Thr Pro Val Val Phe
725 730 735

Glu Ser Leu Ser Gly Arg
740

<210> SEQ ID NO 53
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 53

Met Asp Trp Thr Trp Ile Leu Phe Leu Val Ala Ala Ala Thr Arg Val 1 5 10 15

His Ser

<210> SEQ ID NO 54
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 54

Met Glu Thr Pro Ala Gln Leu Leu Phe Leu Leu Leu Leu Trp Leu Pro
1 5 10 15

Asp Thr Thr Gly
20

<210> SEQ ID NO 55
<211> LENGTH: 278
<212> TYPE: PRT
<213> ORGANISM: Artificial Sequence
<220> FEATURE:
<223> OTHER INFORMATION: Synthetic polypeptide

<400> SEQUENCE: 55

Met Cys Arg Arg Pro Asp Cys Gly Phe Ser Phe Ser Pro Gly Pro Val
1 5 10 15

Ile Leu Leu Trp Cys Cys Leu Leu Leu Pro Ile Val Ser Ser Ala Ala
20 25 30

Val Ser Val Ala Pro Thr Ala Ala Glu Lys Val Pro Ala Glu Cys Pro
35 40 45

Glu Leu Thr Arg Arg Cys Leu Leu Gly Glu Val Phe Glu Gly Asp Lys
50 55 60

Tyr Glu Ser Trp Leu Arg Pro Leu Val Asn Val Thr Gly Arg Asp Gly
65 70 75 80

Pro Leu Ser Gln Leu Ile Arg Tyr Arg Pro Val Thr Pro Glu Ala Ala
85 90 95

Asn Ser Val Leu Leu Asp Glu Ala Phe Leu Asp Thr Leu Ala Leu Leu
100 105 110

Tyr Asn Asn Pro Asp Gln Leu Arg Ala Leu Leu Thr Leu Leu Ser Ser
115 120 125

Asp Thr Ala Pro Arg Trp Met Thr Val Met Arg Gly Tyr Ser Glu Cys
130 135 140

Gly Asp Gly Ser Pro Ala Val Tyr Thr Cys Val Asp Asp Leu Cys Arg
145 150 155 160

Gly Tyr Asp Leu Thr Arg Leu Ser Tyr Gly Arg Ser Ile Phe Thr Glu
165 170 175

His Val Leu Gly Phe Glu Leu Val Pro Pro Ser Leu Phe Asn Val Val
180 185 190

Val Ala Ile Arg Asn Glu Ala Thr Arg Thr Asn Arg Ala Val Arg Leu
195 200 205

Pro Val Ser Thr Ala Ala Ala Pro Glu Gly Ile Thr Leu Phe Tyr Gly
210 215 220

Leu Tyr Asn Ala Val Lys Glu Phe Cys Leu Arg His Gln Leu Asp Pro
225 230 235 240

Pro Leu Leu Arg His Leu Asp Lys Tyr Tyr Ala Gly Leu Pro Pro Glu
245 250 255

Leu Lys Gln Thr Arg Val Asn Leu Pro Ala His Ser Arg Tyr Gly Pro 260 265 270

Gln Ala Val Asp Ala Arg
275

<210> SEQ ID NO 56
<211> LENGTH: 907
<212> TYPE: PRT
<213> ORGANISM: Artificial Sequence
<220> FEATURE:
<223> OTHER INFORMATION: Synthetic polypeptide

<400> SEQUENCE: 56

Met Glu Ser Arg Ile Trp Cys Leu Val Val Cys Val Asn Leu Cys Ile
1 5 10 15

Val Cys Leu Gly Ala Ala Val Ser Ser Ser Ser Thr Arg Gly Thr Ser
20 25 30

Ala Thr His Ser His His Ser Ser His Thr Thr Ser Ala Ala His Ser
35 40 45

Arg Ser Gly Ser Val Ser Gln Arg Val Thr Ser Ser Gln Thr Val Ser
50 55 60

His Gly Val Asn Glu Thr Ile Tyr Asn Thr Thr Leu Lys Tyr Gly Asp
65 70 75 80

Val Val Gly Val Asn Thr Thr Lys Tyr Pro Tyr Arg Val Cys Ser Met
85 90 95

Ala Gln Gly Thr Asp Leu Ile Arg Phe Glu Arg Asn Ile Val Cys Thr
100 105 110

Ser Met Lys Pro Ile Asn Glu Asp Leu Asp Glu Gly Ile Met Val Val
115 120 125

Tyr Lys Arg Asn Ile Val Ala His Thr Phe Lys Val Arg Val Tyr Gln
130 135 140

Lys Val Leu Thr Phe Arg Arg Ser Tyr Ala Tyr Ile His Thr Thr Tyr
145 150 155 160

Leu Leu Gly Ser Asn Thr Glu Tyr Val Ala Pro Pro Met Trp Glu Ile
165 170 175

His His Ile Asn Ser His Ser Gln Cys Tyr Ser Ser Tyr Ser Arg Val
180 185 190

Ile Ala Gly Thr Val Phe Val Ala Tyr His Arg Asp Ser Tyr Glu Asn
195 200 205

Lys Thr Met Gln Leu Met Pro Asp Asp Tyr Ser Asn Thr His Ser Thr
210 215 220

Arg Tyr Val Thr Val Lys Asp Gln Trp His Ser Arg Gly Ser Thr Trp
225 230 235 240

Leu Tyr Arg Glu Thr Cys Asn Leu Asn Cys Met Val Thr Ile Thr Thr
245 250 255

Ala Arg Ser Lys Tyr Pro Tyr His Phe Phe Ala Thr Ser Thr Gly Asp
260 265 270

Val Val Asp Ile Ser Pro Phe Tyr Asn Gly Thr Asn Arg Asn Ala Ser
275 280 285

Tyr Phe Gly Glu Asn Ala Asp Lys Phe Phe Ile Phe Pro Asn Tyr Thr
290 295 300

Ile Val Ser Asp Phe Gly Arg Pro Asn Ser Ala Leu Glu Thr His Arg
305 310 315 320

Leu Val Ala Phe Leu Glu Arg Ala Asp Ser Val Ile Ser Trp Asp Ile
325 330 335

Gln Asp Glu Lys Asn Val Thr Cys Gln Leu Thr Phe Trp Glu Ala Ser

-continued

```
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Leu Thr His Asn Arg Thr Lys Arg Ser Thr Asp Gly
    450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile
        515                 520                 525

Leu Ser Ala Ile Tyr Asn Lys Pro Ile Ala Ala Arg Phe Met Gly Asp
    530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605

Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
        675                 680                 685

Ser Tyr Lys Gln Arg Val Lys Tyr Val Glu Asp Lys Val Val Asp Pro
    690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn Pro Phe
            740                 745                 750

Gly Ala Phe Thr Ile Ile Leu Val Ala Ile Ala Val Val Ile Ile Thr
        755                 760                 765
```

Tyr Leu Ile Tyr Thr Arg Gln Arg Arg Leu Cys Thr Gln Pro Leu Gln
770 775 780

Asn Leu Phe Pro Tyr Leu Val Ser Ala Asp Gly Thr Thr Val Thr Ser
785 790 795 800

Gly Ser Thr Lys Asp Thr Ser Leu Gln Ala Pro Pro Ser Tyr Glu Glu
805 810 815

Ser Val Tyr Asn Ser Gly Arg Lys Gly Pro Gly Pro Pro Ser Ser Asp
820 825 830

Ala Ser Thr Ala Ala Pro Pro Tyr Thr Asn Glu Gln Ala Tyr Gln Met
835 840 845

Leu Leu Ala Leu Ala Arg Leu Asp Ala Glu Gln Arg Ala Gln Gln Asn
850 855 860

Gly Thr Asp Ser Leu Asp Gly Arg Thr Gly Thr Gln Asp Lys Gly Gln
865 870 875 880

Lys Pro Asn Leu Leu Asp Arg Leu Arg His Arg Lys Asn Gly Tyr Arg
885 890 895

His Leu Lys Asp Ser Asp Glu Glu Glu Asn Val
900 905

<210> SEQ ID NO 57
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 57

Met Leu Arg Leu Leu Leu Arg His His Phe His Cys Leu Leu Leu Cys
1 5 10 15

Ala Val Trp Ala Thr Pro Cys Leu Ala Ser Pro Trp Ser Thr Leu Thr
20 25 30

Ala Asn Gln Asn Pro Ser Pro Pro Trp Ser Lys Leu Thr Tyr Ser Lys
35 40 45

Pro His Asp Ala Ala Thr Phe Tyr Cys Pro Phe Leu Tyr Pro Ser Pro
50 55 60

Pro Arg Ser Pro Leu Gln Phe Ser Gly Phe Gln Arg Val Ser Thr Gly
65 70 75 80

Pro Glu Cys Arg Asn Glu Thr Leu Tyr Leu Leu Tyr Asn Arg Glu Gly
85 90 95

Gln Thr Leu Val Glu Arg Ser Ser Thr Trp Val Lys Lys Val Ile Trp
100 105 110

Tyr Leu Ser Gly Arg Asn Gln Thr Ile Leu Gln Arg Met Pro Arg Thr
115 120 125

Ala Ser Lys Pro Ser Asp Gly Asn Val Gln Ile Ser Val Glu Asp Ala
130 135 140

Lys Ile Phe Gly Ala His Met Val Pro Lys Gln Thr Lys Leu Leu Arg
145 150 155 160

Phe Val Val Asn Asp Gly Thr Arg Tyr Gln Met Cys Val Met Lys Leu
165 170 175

Glu Ser Trp Ala His Val Phe Arg Asp Tyr Ser Val Ser Phe Gln Val
180 185 190

Arg Leu Thr Phe Thr Glu Ala Asn Asn Gln Thr Tyr Thr Phe Cys Thr
195 200 205

His Pro Asn Leu Ile Val
210

<210> SEQ ID NO 58
<211> LENGTH: 2437
<212> TYPE: DNA
<213> ORGANISM: Artificial Sequence
<220> FEATURE:
<223> OTHER INFORMATION: Synthetic polynucleotide

<400> SEQUENCE: 58
tcaagctttt ggaccctcgt acagaagcta atacgactca ctatagggaa ataagagaga 60
aaagaagagt aagaagaaat ataagagcca ccatgcggcc aggcctcccc tcctacctca 120
tcatcctcgc cgtctgtctc ttcagccacc tactttcgtc acgatatggc gcagaagccg 180
tatccgaacc gctggacaaa gcgtttcacc tactgctcaa cacctacggg agacccatcc 240
gcttcctgcg tgaaaatacc acccagtgta cctacaacag cagcctccgt aacagcacgg 300
tcgtcaggga aaacgccatc agtttcaact tcttccaaag ctataatcaa tactatgtat 360
tccatatgcc tcgatgtctc tttgcgggtc ctctggcgga gcagtttctg aaccaggtag 420
atctgaccga aaccctggaa agataccaac agagacttaa cacttacgcg ctggtatcca 480
aagacctggc cagctaccga tctttctcgc agcagctaaa ggcacaagac agcctaggtg 540
aacagcccac cactgtgcca ccgcccattg acctgtcaat acctcacgtt tggatgccac 600
cgcaaaccac tccacacggc tggacagaat cacataccac ctcaggacta caccgaccac 660
actttaacca gacctgtatc ctctttgatg gacacgatct actattcagc accgtcacac 720
cttgtttgca ccaaggcttt tacctcatcg acgaactacg ttacgttaaa ataacactga 780
ccgaggactt cttcgtagtt acggtgtcca tagacgacga cacacccatg ctgcttatct 840
tcggccatct tccacgcgta cttttcaaag cgccctatca acgcgacaac tttatactac 900
gacaaactga gaaacacgag ctcctggtgc tagttaagaa agatcaactg aaccgtcact 960
cttatctcaa agacccggac tttcttgacg ccgcacttga cttcaactac ctagacctca 1020
gcgcactact acgtaacagc tttcaccgtt acgccgtgga tgtactcaag agcggtcgat 1080
gtcagatgct ggaccgccgc acggtagaaa tggccttcgc ctacgcatta gcactgttcg 1140
cagcagcccg acaagaagag gccggcgccc aagtctccgt cccacgggcc ctagaccgcc 1200
aggccgcact cttacaaata caagaattta tgatcacctg cctctcacaa acaccaccac 1260
gcaccacgtt gctgctgtat cccacggccg tggacctggc caaacgagcc ctttggacac 1320
cgaatcagat caccgacatc accagcctcg tacgcctggt ctacatactc tctaaacaga 1380
atcagcaaca tctcatcccc caatgggcac tacgacagat cgccgacttt gccctaaaac 1440
tacacaaaac gcacctggcc tcttttcttt cagccttcgc acgccaagaa ctctacctca 1500
tgggcagcct cgtccactcc atgctggtac atacgacgga gagacgcgaa atcttcatcg 1560
tagaaacggg cctctgttca ttggccgagc tatcacactt tacgcagttg ttagctcatc 1620
cacaccacga atacctcagc gacctgtaca caccctgttc cagtagcggg cgacgcgatc 1680
actcgctcga acgcctcacg cgtctcttcc ccgatgccac cgtccccgct accgttcccg 1740
ccgccctctc catcctatct accatgcaac caagcacgct ggaaaccttc cccgacctgt 1800
tttgcttgcc gctcggcgaa tccttctccg cgctgaccgt ctccgaacac gtcagttata 1860
tcgtaacaaa ccagtacctg atcaaaggta tctcctaccc tgtctccacc accgtcgtag 1920
gccagagcct catcatcacc cagacggaca gtcaaactaa atgcgaactg acgcgcaaca 1980
tgcataccac acacagcatc acagtggcgc tcaacatttc gctagaaaac tgcgcctttt 2040

```
gccaaagcgc cctgctagaa tacgacgaca cgcaaggcgt catcaacatc atgtacatgc   2100

acgactcgga cgacgtcctt ttcgccctgg atccctacaa cgaagtggtg gtctcatctc   2160

cgcgaactca ctacctcatg cttttgaaga acggtacggt actagaagta actgacgtcg   2220

tcgtggacgc caccgacagt cgtctcctca tgatgtccgt ctacgcgcta tcggccatca   2280

tcggcatcta tctgctctac cgcatgctca agacatgctg ataataggct ggagcctcgg   2340

tggccatgct tcttgcccct tgggcctccc cccagcccct cctccccttc ctgcacccgt   2400

acccccgtgg tctttgaata aagtctgagt gggcggc                            2437
```

<210> SEQ ID NO 59
<211> LENGTH: 742
<212> TYPE: PRT
<213> ORGANISM: Artificial Sequence
<220> FEATURE:
<223> OTHER INFORMATION: Synthetic polypeptide

<400> SEQUENCE: 59

```
Met Arg Pro Gly Leu Pro Ser Tyr Leu Ile Ile Leu Ala Val Cys Leu
1               5                   10                  15

Phe Ser His Leu Leu Ser Ser Arg Tyr Gly Ala Glu Ala Val Ser Glu
            20                  25                  30

Pro Leu Asp Lys Ala Phe His Leu Leu Leu Asn Thr Tyr Gly Arg Pro
        35                  40                  45

Ile Arg Phe Leu Arg Glu Asn Thr Thr Gln Cys Thr Tyr Asn Ser Ser
    50                  55                  60

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
        115                 120                 125

Ser Lys Asp Leu Ala Ser Tyr Arg Ser Phe Ser Gln Gln Leu Lys Ala
    130                 135                 140

Gln Asp Ser Leu Gly Glu Gln Pro Thr Thr Val Pro Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
        195                 200                 205

Thr Pro Cys Leu His Gln Gly Phe Tyr Leu Ile Asp Glu Leu Arg Tyr
    210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
```

-continued

```
    290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
        355                 360                 365

Arg Gln Ala Ala Leu Leu Gln Ile Gln Glu Phe Met Ile Thr Cys Leu
    370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
            420                 425                 430

His Leu Ile Pro Gln Trp Ala Leu Arg Gln Ile Ala Asp Phe Ala Leu
        435                 440                 445

Lys Leu His Lys Thr His Leu Ala Ser Phe Leu Ser Ala Phe Ala Arg
    450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
            500                 505                 510

Glu Tyr Leu Ser Asp Leu Tyr Thr Pro Cys Ser Ser Ser Gly Arg Arg
        515                 520                 525

Asp His Ser Leu Glu Arg Leu Thr Arg Leu Phe Pro Asp Ala Thr Val
    530                 535                 540

Pro Ala Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                565                 570                 575

Ser Phe Ser Ala Leu Thr Val Ser Glu His Val Ser Tyr Ile Val Thr
            580                 585                 590

Asn Gln Tyr Leu Ile Lys Gly Ile Ser Tyr Pro Val Ser Thr Thr Val
        595                 600                 605

Val Gly Gln Ser Leu Ile Ile Thr Gln Thr Asp Ser Gln Thr Lys Cys
    610                 615                 620

Glu Leu Thr Arg Asn Met His Thr Thr His Ser Ile Thr Val Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
            660                 665                 670

Asp Asp Val Leu Phe Ala Leu Asp Pro Tyr Asn Glu Val Val Val Ser
        675                 680                 685

Ser Pro Arg Thr His Tyr Leu Met Leu Leu Lys Asn Gly Thr Val Leu
    690                 695                 700

Glu Val Thr Asp Val Val Val Asp Ala Thr Asp Ser Arg Leu Leu Met
705                 710                 715                 720
```

```
Met Ser Val Tyr Ala Leu Ser Ala Ile Ile Gly Ile Tyr Leu Leu Tyr
                725                 730                 735

Arg Met Leu Lys Thr Cys
            740


<210> SEQ ID NO 60
<211> LENGTH: 1045
<212> TYPE: DNA
<213> ORGANISM: Artificial Sequence
<220> FEATURE:
<223> OTHER INFORMATION: Synthetic polynucleotide

<400> SEQUENCE: 60

tcaagctttt ggaccctcgt acagaagcta atacgactca ctatagggaa ataagagaga     60

aaagaagagt aagaagaaat ataagagcca ccatgtgccg ccgcccggat tgcggcttct    120

ctttctcacc tggaccggtg atactgctgt ggtgttgcct tctgctgccc attgtttcct    180

cagccgccgt cagcgtcgct cctaccgccg ccgagaaagt ccccgcggag tgccccgaac    240

taacgcgccg atgcttgttg ggtgaggtgt ttgagggtga caagtatgaa agttggctgc    300

gcccgttggt gaatgttacc gggcgcgatg gcccgctatc gcaacttatc cgttaccgtc    360

ccgttacgcc ggaggccgcc aactccgtgc tgttggacga ggctttcctg gacactctgg    420

ccctgctgta caacaatccg gatcaattgc gggccctgct gacgctgttg agctcggaca    480

cagcgccgcg ctggatgacg gtgatgcgcg gctacagcga gtgcggcgat ggctcgccgg    540

ccgtgtacac gtgcgtggac gacctgtgcc gcggctacga cctcacgcga ctgtcatacg    600

ggcgcagcat cttcacggaa cacgtgttag gcttcgagct ggtgccaccg tctctcttta    660

acgtggtggt ggccatacgc aacgaagcca cgcgtaccaa ccgcgccgtg cgtctgcccg    720

tgagcaccgc tgccgcgccc gagggcatca cgctctttta cggcctgtac aacgcagtga    780

aggaattctg cctgcgtcac cagctggacc cgccgctgct acgccaccta gataaatact    840

acgccggact gccgcccgag ctgaagcaga cgcgcgtcaa cctgccggct cactcgcgct    900

atggccctca agcagtggat gctcgctgat aataggctgg agcctcggtg gccatgcttc    960

ttgccccttg ggcctccccc cagcccctcc tccccttcct gcacccgtac cccgtggtc    1020

tttgaataaa gtctgagtgg gcggc                                          1045


<210> SEQ ID NO 61
<211> LENGTH: 278
<212> TYPE: PRT
<213> ORGANISM: Artificial Sequence
<220> FEATURE:
<223> OTHER INFORMATION: Synthetic polypeptide

<400> SEQUENCE: 61

Met Cys Arg Arg Pro Asp Cys Gly Phe Ser Phe Ser Pro Gly Pro Val
1               5                   10                  15

Ile Leu Leu Trp Cys Cys Leu Leu Leu Pro Ile Val Ser Ser Ala Ala
            20                  25                  30

Val Ser Val Ala Pro Thr Ala Ala Glu Lys Val Pro Ala Glu Cys Pro
        35                  40                  45

Glu Leu Thr Arg Arg Cys Leu Leu Gly Glu Val Phe Glu Gly Asp Lys
    50                  55                  60

Tyr Glu Ser Trp Leu Arg Pro Leu Val Asn Val Thr Gly Arg Asp Gly
65                  70                  75                  80

Pro Leu Ser Gln Leu Ile Arg Tyr Arg Pro Val Thr Pro Glu Ala Ala
```

-continued

```
                85                  90                  95

Asn Ser Val Leu Leu Asp Glu Ala Phe Leu Asp Thr Leu Ala Leu Leu
            100                 105                 110

Tyr Asn Asn Pro Asp Gln Leu Arg Ala Leu Leu Thr Leu Leu Ser Ser
        115                 120                 125

Asp Thr Ala Pro Arg Trp Met Thr Val Met Arg Gly Tyr Ser Glu Cys
    130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
        195                 200                 205

Pro Val Ser Thr Ala Ala Ala Pro Glu Gly Ile Thr Leu Phe Tyr Gly
    210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
        275
```

<210> SEQ ID NO 62
<211> LENGTH: 724
<212> TYPE: DNA
<213> ORGANISM: Artificial Sequence
<220> FEATURE:
<223> OTHER INFORMATION: Synthetic polynucleotide

<400> SEQUENCE: 62

```
tcaagctttt ggaccctcgt acagaagcta atacgactca ctatagggaa ataagagaga     60

aaagaagagt aagaagaaat ataagagcca ccatgagtcc caaagatctg acgccgttct    120

tgacggcgtt gtggctgcta ttgggtcaca gccgcgtgcc gcgggtgcgc gcagaagaat    180

gttgcgaatt cataaacgtc aaccacccgc cggaacgctg ttacgatttc aaaatgtgca    240

atcgcttcac cgtcgcgctg cggtgtccgg acggcgaagt ctgctacagt cccgagaaaa    300

cggctgagat tcgcgggatc gtcaccacca tgacccattc attgacacgc caggtcgtac    360

acaacaaact gacgagctgc aactacaatc cgttatacct cgaagctgac gggcgaatac    420

gctgcggcaa agtaaacgac aaggcgcagt acctgctggg cgccgctggc agcgttccct    480

atcgatggat caatctggaa tacgacaaga taacccggat cgtgggcctg gatcagtacc    540

tggagagcgt taagaaacac aaacggctgg atgtgtgccg cgctaaaatg ggctatatgc    600

tgcagtgata ataggctgga gcctcggtgg ccatgcttct tgccccttgg gcctcccccc    660

agcccctcct ccccttcctg cacccgtacc cccgtggtct ttgaataaag tctgagtggg    720

cggc                                                                 724
```

<210> SEQ ID NO 63
<211> LENGTH: 171
<212> TYPE: PRT
<213> ORGANISM: Artificial Sequence
<220> FEATURE:
<223> OTHER INFORMATION: Synthetic polypeptide

<400> SEQUENCE: 63

```
Met Ser Pro Lys Asp Leu Thr Pro Phe Leu Thr Ala Leu Trp Leu Leu
1               5                   10                  15

Leu Gly His Ser Arg Val Pro Arg Val Arg Ala Glu Glu Cys Cys Glu
            20                  25                  30

Phe Ile Asn Val Asn His Pro Pro Glu Arg Cys Tyr Asp Phe Lys Met
        35                  40                  45

Cys Asn Arg Phe Thr Val Ala Leu Arg Cys Pro Asp Gly Glu Val Cys
    50                  55                  60

Tyr Ser Pro Glu Lys Thr Ala Glu Ile Arg Gly Ile Val Thr Thr Met
65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Arg Ile Val
    130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170
```

<210> SEQ ID NO 64
<211> LENGTH: 846
<212> TYPE: DNA
<213> ORGANISM: Artificial Sequence
<220> FEATURE:
<223> OTHER INFORMATION: Synthetic polynucleotide

<400> SEQUENCE: 64

```
tcaagctttt ggaccctcgt acagaagcta atacgactca ctatagggaa ataagagaga     60

aaagaagagt aagaagaaat ataagagcca ccatgctgcg gcttctgctt cgtcaccact    120

ttcactgcct gcttctgtgc gcggtttggg caacgccctg tctggcgtct ccgtggtcga    180

cgctaacagc aaaccagaat ccgtccccgc catggtctaa actgacgtat tccaaaccgc    240

atgacgcggc gacgttttac tgtccttttc tctatccctc gcccccacga tccccccttgc    300

aattctcggg gttccagcgg gtatcaacgg gtcccgagtg tcgcaacgag accctgtatc    360

tgctgtacaa ccgggaaggc cagaccttgg tggagagaag ctccacctgg gtgaaaaagg    420

tgatctggta cctgagcggt cggaaccaaa ccatcctcca acggatgccc cgaacggctt    480

cgaaaccgag cgacggaaac gtgcagatca gcgtggaaga cgccaagatt tttggagcgc    540

acatggtgcc caagcgctgc tacgcttcgt cgtcaacgat ggcacacgtt atcagatgtg    600

tgtgatgaag ctggagagct gggctcacgt cttccgggac tacagcgtgt cttttcaggt    660

gcgattgacg ttcaccgagg ccaataacca gacttacacc ttctgcaccc atcccaatct    720

catcgtttga taataggctg gagcctcggt ggccatgctt cttgcccctt gggcctcccc    780

ccagcccctc ctccccttcc tgcacccgta cccccgtggt ctttgaataa agtctgagtg    840

ggcggc                                                               846
```

<210> SEQ ID NO 65
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 65

```
Met Leu Arg Leu Leu Leu Arg His His Phe His Cys Leu Leu Leu Cys
1               5                   10                  15

Ala Val Trp Ala Thr Pro Cys Leu Ala Ser Pro Trp Ser Thr Leu Thr
            20                  25                  30

Ala Asn Gln Asn Pro Ser Pro Pro Trp Ser Lys Leu Thr Tyr Ser Lys
        35                  40                  45

Pro His Asp Ala Ala Thr Phe Tyr Cys Pro Phe Leu Tyr Pro Ser Pro
    50                  55                  60

Pro Arg Ser Pro Leu Gln Phe Ser Gly Phe Gln Arg Val Ser Thr Gly
65                  70                  75                  80

Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Lys Val Ile Trp
            100                 105                 110

Tyr Leu Ser Gly Arg Asn Gln Thr Ile Leu Gln Arg Met Pro Arg Thr
        115                 120                 125

Ala Ser Lys Pro Ser Asp Gly Asn Val Gln Ile Ser Val Glu Asp Ala
    130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
        195                 200                 205

His Pro Asn Leu Ile Val
    210
```

<210> SEQ ID NO 66
<211> LENGTH: 598
<212> TYPE: DNA
<213> ORGANISM: Artificial Sequence
<220> FEATURE:
<223> OTHER INFORMATION: Synthetic polynucleotide

<400> SEQUENCE: 66

```
tcaagctttt ggaccctcgt acagaagcta atacgactca ctatagggaa ataagagaga      60

aaagaagagt aagaagaaat ataagagcca ccatgcggct gtgtcgggtg tggctgtctg     120

tttgtctgtg cgccgtggtg ctgggtcagt gccagcggga aaccgcggaa aagaacgatt     180

attaccgagt accgcattac tggacgcgt gctctcgcgc gctgcccgac caaacccgtt     240

acaagtatgt ggaacagctc gtggacctca cgttgaacta ccactacgat gcgagccacg     300

gcttggacaa ctttgacgtg ctcaagagaa tcaacgtgac cgaggtgtcg ttgctcatca     360

gcgactttag acgtcagaac cgtcgcggcg gcaccaacaa aaggaccacg ttcaacgccg     420

ccggttcgct ggcgccacac gcccggagcc tcgagttcag cgtgcggctc tttgccaact     480

gataataggc tggagcctcg gtggccatgc ttcttgcccc ttgggcctcc ccccagcccc     540
```

tcctcccctt cctgcacccg tacccccgtg gtctttgaat aaagtctgag tgggcggc 598

<210> SEQ ID NO 67
<211> LENGTH: 129
<212> TYPE: PRT
<213> ORGANISM: Artificial Sequence
<220> FEATURE:
<223> OTHER INFORMATION: Synthetic polypeptide

<400> SEQUENCE: 67

```
Met Arg Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr Tyr Arg
            20                  25                  30

Val Pro His Tyr Trp Asp Ala Cys Ser Arg Ala Leu Pro Asp Gln Thr
        35                  40                  45

Arg Tyr Lys Tyr Val Glu Gln Leu Val Asp Leu Thr Leu Asn Tyr His
    50                  55                  60

Tyr Asp Ala Ser His Gly Leu Asp Asn Phe Asp Val Leu Lys Arg Ile
65                  70                  75                  80

Asn Val Thr Glu Val Ser Leu Leu Ile Ser Asp Phe Arg Arg Gln Asn
                85                  90                  95

Arg Arg Gly Gly Thr Asn Lys Arg Thr Thr Phe Asn Ala Ala Gly Ser
            100                 105                 110

Leu Ala Pro His Ala Arg Ser Leu Glu Phe Ser Val Arg Leu Phe Ala
        115                 120                 125

Asn
```

<210> SEQ ID NO 68
<211> LENGTH: 2933
<212> TYPE: DNA
<213> ORGANISM: Artificial Sequence
<220> FEATURE:
<223> OTHER INFORMATION: Synthetic polynucleotide

<400> SEQUENCE: 68

```
tcaagctttt ggaccctcgt acagaagcta atacgactca ctatagggaa ataagagaga     60

aaagaagagt aagaagaaat ataagagcca ccatggaatc caggatctgg tgcctggtag    120

tctgcgttaa cttgtgtatc gtctgtctgg gtgctgcggt ttcctcatct tctactcgtg    180

gaacttctgc tactcacagt caccattcct ctcatacgac gtctgctgct cactctcgat    240

ccggttcagt ctctcaacgc gtaacttctt cccaaacggt cagccatggt gttaacgaga    300

ccatctacaa cactaccctc aagtacggag atgtggtggg ggtcaatacc accaagtacc    360

cctatcgcgt gtgttctatg gcccagggta cggatcttat tcgctttgaa cgtaatatcg    420

tctgcacctc gatgaagccc atcaatgaag acctggacga gggcatcatg gtggtctaca    480

aacgcaacat cgtcgcgcac acctttaagg tacgagtcta ccagaaggtt ttgacgtttc    540

gtcgtagcta cgcttacatc cacaccactt atctgctggg cagcaacacg gaatacgtgg    600

cgcctcctat gtgggagatt catcatatca acagccacag tcagtgctac agttcctaca    660

gccgcgttat agcaggcacg gttttcgtgg cttatcatag ggacagctat gaaaacaaaa    720

ccatgcaatt aatgcccgac gattattcca acacccacag tacccgttac gtgacggtca    780

aggatcaatg gcacagccgc ggcagcacct ggctctatcg tgagacctgt aatctgaatt    840

gtatggtgac catcactact gcgcgctcca aatatcctta tcattttttc gccacttcca    900

cgggtgacgt ggttgacatt tctcctttct acaacggaac caatcgcaat gccagctact    960
```

```
ttggagaaaa cgccgacaag tttttcattt ttccgaacta cactatcgtc tccgactttg   1020

gaagaccgaa ttctgcgtta gagacccaca ggttggtggc ttttcttgaa cgtgcggact   1080

cggtgatctc ctgggatata caggacgaaa agaatgtcac ttgtcaactc actttctggg   1140

aagcctcgga acgcaccatt cgttccgaag ccgaggactc gtatcacttt tcttctgcca   1200

aaatgaccgc cactttctta tctaagaagc aagaggtgaa catgtccgac tctgcgctgg   1260

actgcgtacg tgatgaggct ataaataagt tacagcagat tttcaatact tcatacaatc   1320

aaacatatga aaaatatgga aacgtgtccg tctttgaaac cactggtggt ttggtagtgt   1380

tctggcaagg tatcaagcaa aaatctctgg tggaactcga acgtttggcc aaccgctcca   1440

gtctgaatct tactcataat agaaccaaaa gaagtacaga tggcaacaat gcaactcatt   1500

tatccaacat ggaatcggtg cacaatctgg tctacgccca gctgcagttc acctatgaca   1560

cgttgcgcgg ttacatcaac cgggcgctgg cgcaaatcgc agaagcctgg tgtgtggatc   1620

aacggcgcac cctagaggtc ttcaaggaac tcagcaagat caacccgtca gccattctct   1680

cggccattta caacaaaccg attgccgcgc gtttcatggg tgatgtcttg ggcctggcca   1740

gctgcgtgac catcaaccaa accagcgtca aggtgctgcg tgatatgaac gtgaaggagt   1800

cgccaggacg ctgctactca cgacccgtgg tcatctttaa tttcgccaac agctcgtacg   1860

tgcagtacgg tcaactgggc gaggacaacg aaatcctgtt gggcaaccac cgcactgagg   1920

aatgtcagct tcccagcctc aagatcttca tcgccgggaa ctcggcctac gagtacgtgg   1980

actacctctt caaacgcatg attgacctca gcagtatctc caccgtcgac agcatgatcg   2040

ccctggatat cgacccgctg gaaaataccg acttcagggt actggaactt tactcgcaga   2100

aagagctgcg ttccagcaac gtttttgacc tcgaagagat catgcgcgaa ttcaactcgt   2160

acaagcagcg ggtaaagtac gtggaggaca aggtagtcga cccgctaccg ccctacctca   2220

agggtctgga cgacctcatg agcggcctgg gcgccgcggg aaaggccgtt ggcgtagcca   2280

ttggggccgt gggtggcgcg gtggcctccg tggtcgaagg cgttgccacc ttcctcaaaa   2340

acccctt cgg agcgttcacc atcatcctcg tggccatagc tgtagtcatt atcacttatt   2400

tgatctatac tcgacagcgg cgtttgtgca cgcagccgct gcagaacctc tttccctatc   2460

tggtgtccgc cgacgggacc accgtgacgt cgggcagcac caaagacacg tcgttacagg   2520

ctccgccttc ctacgaggaa agtgtttata attctggtcg caaaggaccg ggaccaccgt   2580

cgtctgatgc atccacggcg gctccgcctt acaccaacga gcaggcttac cagatgcttc   2640

tggccctggc ccgtctggac gcagagcagc gagcgcagca gaacggtaca gattctttgg   2700

acggacggac tggcacgcag gacaagggac agaagcccaa cctactagac cgactgcgac   2760

atcgcaaaaa cggctaccga cacttgaaag actctgacga agaagagaac gtcttgataa   2820

taggctggag cctcggtggc catgcttctt gccccttggg cctccccccca gcccctcctc   2880

cccttcctgc acccgtaccc ccgtggtctt tgaataaagt ctgagtgggc ggc          2933
```

<210> SEQ ID NO 69
<211> LENGTH: 907
<212> TYPE: PRT
<213> ORGANISM: Artificial Sequence
<220> FEATURE:
<223> OTHER INFORMATION: Synthetic polypeptide

<400> SEQUENCE: 69

```
Met Glu Ser Arg Ile Trp Cys Leu Val Val Cys Val Asn Leu Cys Ile
1               5                   10                  15
```

-continued

```
Val Cys Leu Gly Ala Ala Val Ser Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430
```

-continued

```
Gly Ile Lys Gln Lys Ser Leu Val Glu Leu Glu Arg Leu Ala Asn Arg
        435                 440                 445

Ser Ser Leu Asn Leu Thr His Asn Arg Thr Lys Arg Ser Thr Asp Gly
    450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile
        515                 520                 525

Leu Ser Ala Ile Tyr Asn Lys Pro Ile Ala Ala Arg Phe Met Gly Asp
    530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605

Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
        675                 680                 685

Ser Tyr Lys Gln Arg Val Lys Tyr Val Glu Asp Lys Val Val Asp Pro
    690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn Pro Phe
            740                 745                 750

Gly Ala Phe Thr Ile Ile Leu Val Ala Ile Ala Val Val Ile Ile Thr
        755                 760                 765

Tyr Leu Ile Tyr Thr Arg Gln Arg Arg Leu Cys Thr Gln Pro Leu Gln
    770                 775                 780

Asn Leu Phe Pro Tyr Leu Val Ser Ala Asp Gly Thr Thr Val Thr Ser
785                 790                 795                 800

Gly Ser Thr Lys Asp Thr Ser Leu Gln Ala Pro Pro Ser Tyr Glu Glu
                805                 810                 815

Ser Val Tyr Asn Ser Gly Arg Lys Gly Pro Gly Pro Pro Ser Ser Asp
            820                 825                 830

Ala Ser Thr Ala Ala Pro Pro Tyr Thr Asn Glu Gln Ala Tyr Gln Met
        835                 840                 845

Leu Leu Ala Leu Ala Arg Leu Asp Ala Glu Gln Arg Ala Gln Gln Asn
```

850 855 860

Gly Thr Asp Ser Leu Asp Gly Arg Thr Gly Thr Gln Asp Lys Gly Gln
865 870 875 880

Lys Pro Asn Leu Leu Asp Arg Leu Arg His Arg Lys Asn Gly Tyr Arg
885 890 895

His Leu Lys Asp Ser Asp Glu Glu Glu Asn Val
900 905

<210> SEQ ID NO 70
<211> LENGTH: 1882
<212> TYPE: DNA
<213> ORGANISM: Artificial Sequence
<220> FEATURE:
<223> OTHER INFORMATION: Synthetic polynucleotide

<400> SEQUENCE: 70
tcaagctttt ggaccctcgt acagaagcta atacgactca ctatagggaa ataagagaga 60
aaagaagagt aagaagaaat ataagagcca ccatggagtc gcgcggtcgc cgttgtcccg 120
aaatgatatc cgtactgggt cccatttcgg ggcacgtgct gaaagccgtg tttagtcgcg 180
gcgatacgcc ggtgctgccg cacgagacga gactcctgca gacgggtatc cacgtacgcg 240
tgagccagcc ctcgctgatc ctggtgtcgc agtacacgcc cgactcgacg ccatgccacc 300
gcggcgacaa tcagctgcag gtgcagcaca cgtactttac gggcagcgag gtggagaacg 360
tgtcggtcaa cgtgcacaac cccacgggcc gaagcatctg ccccagccaa gagcccatgt 420
cgatctatgt gtacgcgctg ccgctcaaga tgctgaacat ccccagcatc aacgtgcacc 480
actacccgtc ggcggccgag cgcaaacacc gacacctgcc cgtagccgac gctgttattc 540
acgcgtcggg caagcagatg tggcaggcgc gtctcacggt ctcgggactg gcctggacgc 600
gtcagcagaa ccagtggaaa gagcccgacg tctactacac gtcagcgttc gtgtttccca 660
ccaaggacgt ggcactgcgg cacgtggtgt gcgcgcacga gctggtttgc tccatggaga 720
acacgcgcgc aaccaagatg caggtgatag gtgaccagta cgtcaaggtg tacctggagt 780
ccttctgcga ggacgtgccc tccggcaagc tctttatgca cgtcacgctg ggctctgacg 840
tggaagagga cctaacgatg acccgcaacc cgcaaccctt catgcgcccc cacgagcgca 900
acggctttac ggtgttgtgt cccaaaaata tgataatcaa accgggcaag atctcgcaca 960
tcatgctgga tgtggctttt acctcacacg agcattttgg gctgctgtgt cccaagagca 1020
tcccgggcct gagcatctca ggtaacctgt tgatgaacgg gcagcaaatc ttcctggagg 1080
tacaagcgat acgcgagacc gtggaactgc gtcagtacga tcccgtggct gcgctcttct 1140
ttttcgatat cgacttgttg ctgcagcgcg ggcctcagta cagcgagcac cccaccttca 1200
ccagccagta tcgcatccag ggcaagcttg agtaccgaca cacctgggac cggcacgacg 1260
agggtgccgc ccagggcgac gacgacgtct ggaccagcgg atcggactcc gacgaagaac 1320
tcgtaaccac cgagcgtaag acgccccgcg tcaccggcgg cggagccatg gcgagcgcct 1380
ccacttccgc gggctcagca tcctcggcga cggcgtgcac ggcgggcgtt atgacacgcg 1440
gccgccttaa ggccgagtcc accgtcgcgc ccgaagagga caccgacgag gattccgaca 1500
acgaaatcca caatccggcc gtgttcacct ggccgccctg gcaggccggc atcctggccc 1560
gcaacctggt gcccatggtg gctacggttc agggtcagaa tctgaagtac caggagttct 1620
tctgggacgc caacgacatc taccgcatct tcgccgaatt ggaaggcgta tggcagcccg 1680
ctgcgcaacc caaacgtcgc cgccaccggc aagacgcctt gcccgggcca tgcatcgcct 1740

```
cgacgcccaa aaagcaccga ggttgataat aggctggagc ctcggtggcc atgcttcttg   1800

ccccttgggc ctccccccag cccctcctcc ccttcctgca cccgtacccc cgtggtcttt   1860

gaataaagtc tgagtgggcg gc                                            1882


<210> SEQ ID NO 71
<211> LENGTH: 557
<212> TYPE: PRT
<213> ORGANISM: Artificial Sequence
<220> FEATURE:
<223> OTHER INFORMATION: Synthetic polypeptide

<400> SEQUENCE: 71

Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
        195                 200                 205

Glu Asn Thr Arg Ala Thr Lys Met Gln Val Ile Gly Asp Gln Tyr Val
    210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
        275                 280                 285

His Ile Met Leu Asp Val Ala Phe Thr Ser His Glu His Phe Gly Leu
    290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335
```

-continued

```
Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365

Phe Thr Ser Gln Tyr Arg Ile Gln Gly Lys Leu Glu Tyr Arg His Thr
    370                 375                 380

Trp Asp Arg His Asp Glu Gly Ala Ala Gln Gly Asp Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Gly Ala Met Ala Ser Ala Ser Thr Ser
            420                 425                 430

Ala Gly Ser Ala Ser Ser Ala Thr Ala Cys Thr Ala Gly Val Met Thr
        435                 440                 445

Arg Gly Arg Leu Lys Ala Glu Ser Thr Val Ala Pro Glu Glu Asp Thr
    450                 455                 460

Asp Glu Asp Ser Asp Asn Glu Ile His Asn Pro Ala Val Phe Thr Trp
465                 470                 475                 480

Pro Pro Trp Gln Ala Gly Ile Leu Ala Arg Asn Leu Val Pro Met Val
                485                 490                 495

Ala Thr Val Gln Gly Gln Asn Leu Lys Tyr Gln Glu Phe Phe Trp Asp
            500                 505                 510

Ala Asn Asp Ile Tyr Arg Ile Phe Ala Glu Leu Glu Gly Val Trp Gln
        515                 520                 525

Pro Ala Ala Gln Pro Lys Arg Arg Arg His Arg Gln Asp Ala Leu Pro
    530                 535                 540

Gly Pro Cys Ile Ala Ser Thr Pro Lys Lys His Arg Gly
545                 550                 555
```

<210> SEQ ID NO 72
<211> LENGTH: 3364
<212> TYPE: DNA
<213> ORGANISM: Artificial Sequence
<220> FEATURE:
<223> OTHER INFORMATION: Synthetic polynucleotide

<400> SEQUENCE: 72

```
tcaagctttt ggaccctcgt acagaagcta atacgactca ctatagggaa ataagagaga      60

aaagaagagt aagaagaaat ataagagcca ccatggagtc gcgcggtcgc cgttgtcccg     120

aaatgatatc cgtactgggt cccatttcgg ggcacgtgct gaaagccgtg tttagtcgcg     180

gcgatacgcc ggtgctgccg cacgagacgc gactcctgca gacgggtatc cacgtacgcg     240

tgagccagcc ctcgctgatc ctggtgtcgc agtacacgcc cgactcgacg ccatgccacc     300

gcggcgacaa tcagctgcag gtgcagcaca cgtactttac gggcagcgag gtggagaacg     360

tgtcggtcaa cgtgcacaac cccacgggcc gaagcatctg ccccagccaa gagcccatgt     420

cgatctatgt gtacgcgctg ccgctcaaga tgctgaacat ccccagcatc aacgtgcacc     480

actacccgtc ggcggccgag cgcaaacacc gacacctgcc cgtagccgac gctgttattc     540

acgcgtcggg caagcagatg tggcaggcgc gtctcacggt ctcgggactg gcctggacgc     600

gtcagcagaa ccagtggaaa gagcccgacg tctactacac gtcagcgttc gtgtttccca     660

ccaaggacgt ggcactgcgg cacgtggtgt gcgcgcacga gctggtttgc tccatggaga     720

acacgcgcgc aaccaagatg caggtgatag gtgaccagta cgtcaaggtg tacctggagt     780

ccttctgcga ggacgtgccc tccggcaagc tctttatgca cgtcacgctg ggctctgacg     840
```

```
tggaagagga cctaacgatg acccgcaacc cgcaaccctt catgcgcccc cacgagcgca    900
acggctttac ggtgttgtgt cccaaaaata tgataatcaa accgggcaag atctcgcaca    960
tcatgctgga tgtggctttt acctcacacg agcattttgg gctgctgtgt cccaagagca   1020
tcccgggcct gagcatctca ggtaacctgt tgatgaacgg gcagcaaatc ttcctggagg   1080
tacaagcgat acgcgagacc gtggaactgc gtcagtacga tcccgtggct gcgctcttct   1140
ttttcgatat cgacttgttg ctgcagcgcg ggcctcagta cagcgagcac cccaccttca   1200
ccagccagta tcgcatccag ggcaagcttg agtaccgaca cacctgggac cggcacgacg   1260
agggtgccgc ccagggcgac gacgacgtct ggaccagcgg atcggactcc gacgaagaac   1320
tcgtaaccac cgagcgtaag acgccccgcg tcaccggcgg cggcgccatg gcgagcgcct   1380
ccacttccgc gggccgcaaa cgcaaatcag catcctcggc gacggcgtgc acggcgggcg   1440
ttatgacacg cggccgcctt aaggccgagt ccaccgtcgc gcccgaagag gacaccgacg   1500
aggattccga caacgaaatc cacaatccgg ccgtgttcac ctggccgccc tggcaggccg   1560
gcatcctggc ccgcaacctg gtgcccatgg tggctacggt tcagggtcag aatctgaagt   1620
accaggagtt cttctgggac gccaacgaca tctaccgcat cttcgccgaa ttggaaggcg   1680
tatggcagcc cgctgcgcaa cccaaacgtc gccgccaccg gcaagacgcc ttgcccgggc   1740
catgcatcgc ctcgacgccc aaaaagcacc gaggtgagtc ctctgccaag agaaagatgg   1800
accctgataa tcctgacgag ggcccttcct ccaaggtgcc acggcccgag acacccgtga   1860
ccaaggccac gacgttcctg cagactatgt taaggaagga ggttaacagt cagctgagcc   1920
tgggagaccc gctgttccca gaattggccg aagaatccct caaaaccttt gaacaagtga   1980
ccgaggattg caacgagaac cccgaaaaag atgtcctgac agaactcgtc aaacagatta   2040
aggttcgagt ggacatggtg cggcatagaa tcaaggagca catgctgaaa aaatataccc   2100
agacggaaga aaaattcact ggcgccttta atatgatggg aggatgtttg cagaatgcct   2160
tagatatctt agataaggtt catgagcctt tcgaggacat gaagtgtatt gggctaacta   2220
tgcagagcat gtatgagaac tacattgtac ctgaggataa gcgggagatg tggatggctt   2280
gtattaagga gctgcatgat gtgagcaagg gcgccgctaa caagttgggg ggtgcactgc   2340
aggctaaggc ccgtgctaaa aaggatgaac ttaggagaaa gatgatgtat atgtgctaca   2400
ggaatataga gttctttacc aagaactcag ccttccctaa gaccaccaat ggctgcagtc   2460
aggccatggc ggcattgcag aacttgcctc agtgctctcc tgatgagatt atgtcttatg   2520
cccagaaaat ctttaagatt ttggatgagg agagagacaa ggtgctcacg cacattgatc   2580
acatatttat ggatatcctc actacatgtg tggaaacaat gtgtaatgag tacaaggtca   2640
ctagtgacgc ttgtatgatg accatgtacg ggggcatctc tctcttaagt gagttctgtc   2700
gggtgctgtg ctgctatgtc ttagaggaga ctagtgtgat gctggccaag cggcctctga   2760
taaccaagcc tgaggttatc agtgtaatga agcgccgcat tgaggagatc tgcatgaagg   2820
tctttgccca gtacattctg ggggccgatc ctttgagagt ctgctctcct agtgtggatg   2880
acctacgggc catcgccgag gagtcagatg aggaagaggc tattgtagcc tacactttgg   2940
ccaccgctgg tgccagctcc tctgattctc tggtgtcacc tccagagtcc cctgtacccg   3000
cgactatccc tctgtcctca gtaattgtgg ctgagaacag tgatcaggaa gaaagtgaac   3060
agagtgatga ggaacaggag gagggtgctc aggaggagcg ggaggacact gtgtctgtca   3120
agtctgagcc agtgtctgag atagaggaag ttgcctcaga ggaagaggag gatggtgctg   3180
```

aggaacccac cgcctctgga ggcaagagca cccaccctat ggtgactaga agcaaggctg 3240
accagtgata ataggctgga gcctcggtgg ccatgcttct tgccccttgg gcctccccc 3300 agcccctcct ccccttcctg cacccgtacc cccgtggtct ttgaataaag tctgagtggg 3360
cggc 3364

<210> SEQ ID NO 73
<211> LENGTH: 1051
<212> TYPE: PRT
<213> ORGANISM: Artificial Sequence
<220> FEATURE:
<223> OTHER INFORMATION: Synthetic polypeptide

<400> SEQUENCE: 73

Met Glu Ser Arg Gly Arg Arg Cys Pro Glu Met Ile Ser Val Leu Gly
1 5 10 15

Pro Ile Ser Gly His Val Leu Lys Ala Val Phe Ser Arg Gly Asp Thr
20 25 30

Pro Val Leu Pro His Glu Thr Arg Leu Leu Gln Thr Gly Ile His Val
35 40 45

Arg Val Ser Gln Pro Ser Leu Ile Leu Val Ser Gln Tyr Thr Pro Asp
50 55 60

Ser Thr Pro Cys His Arg Gly Asp Asn Gln Leu Gln Val Gln His Thr
65 70 75 80

Tyr Phe Thr Gly Ser Glu Val Glu Asn Val Ser Val Asn Val His Asn
85 90 95

Pro Thr Gly Arg Ser Ile Cys Pro Ser Gln Glu Pro Met Ser Ile Tyr
100 105 110

Val Tyr Ala Leu Pro Leu Lys Met Leu Asn Ile Pro Ser Ile Asn Val
115 120 125

His His Tyr Pro Ser Ala Ala Glu Arg Lys His Arg His Leu Pro Val
130 135 140

Ala Asp Ala Val Ile His Ala Ser Gly Lys Gln Met Trp Gln Ala Arg
145 150 155 160

Leu Thr Val Ser Gly Leu Ala Trp Thr Arg Gln Gln Asn Gln Trp Lys
165 170 175

Glu Pro Asp Val Tyr Tyr Thr Ser Ala Phe Val Phe Pro Thr Lys Asp
180 185 190

Val Ala Leu Arg His Val Val Cys Ala His Glu Leu Val Cys Ser Met
195 200 205

Glu Asn Thr Arg Ala Thr Lys Met Gln Val Ile Gly Asp Gln Tyr Val
210 215 220

Lys Val Tyr Leu Glu Ser Phe Cys Glu Asp Val Pro Ser Gly Lys Leu
225 230 235 240

Phe Met His Val Thr Leu Gly Ser Asp Val Glu Glu Asp Leu Thr Met
245 250 255

Thr Arg Asn Pro Gln Pro Phe Met Arg Pro His Glu Arg Asn Gly Phe
260 265 270

Thr Val Leu Cys Pro Lys Asn Met Ile Ile Lys Pro Gly Lys Ile Ser
275 280 285

His Ile Met Leu Asp Val Ala Phe Thr Ser His Glu His Phe Gly Leu
290 295 300

Leu Cys Pro Lys Ser Ile Pro Gly Leu Ser Ile Ser Gly Asn Leu Leu
305 310 315 320

Met Asn Gly Gln Gln Ile Phe Leu Glu Val Gln Ala Ile Arg Glu Thr

-continued

```
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365

Phe Thr Ser Gln Tyr Arg Ile Gln Gly Lys Leu Glu Tyr Arg His Thr
    370                 375                 380

Trp Asp Arg His Asp Glu Gly Ala Ala Gln Gly Asp Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Gly Ala Met Ala Ser Ala Ser Thr Ser
            420                 425                 430

Ala Gly Arg Lys Arg Lys Ser Ala Ser Ser Ala Thr Ala Cys Thr Ala
        435                 440                 445

Gly Val Met Thr Arg Gly Arg Leu Lys Ala Glu Ser Thr Val Ala Pro
    450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
            500                 505                 510

Phe Phe Trp Asp Ala Asn Asp Ile Tyr Arg Ile Phe Ala Glu Leu Glu
        515                 520                 525

Gly Val Trp Gln Pro Ala Ala Gln Pro Lys Arg Arg Arg His Arg Gln
    530                 535                 540

Asp Ala Leu Pro Gly Pro Cys Ile Ala Ser Thr Pro Lys Lys His Arg
545                 550                 555                 560

Gly Glu Ser Ser Ala Lys Arg Lys Met Asp Pro Asp Asn Pro Asp Glu
                565                 570                 575

Gly Pro Ser Ser Lys Val Pro Arg Pro Glu Thr Pro Val Thr Lys Ala
            580                 585                 590

Thr Thr Phe Leu Gln Thr Met Leu Arg Lys Glu Val Asn Ser Gln Leu
        595                 600                 605

Ser Leu Gly Asp Pro Leu Phe Pro Glu Leu Ala Glu Glu Ser Leu Lys
    610                 615                 620

Thr Phe Glu Gln Val Thr Glu Asp Cys Asn Glu Asn Pro Glu Lys Asp
625                 630                 635                 640

Val Leu Thr Glu Leu Val Lys Gln Ile Lys Val Arg Val Asp Met Val
                645                 650                 655

Arg His Arg Ile Lys Glu His Met Leu Lys Lys Tyr Thr Gln Thr Glu
            660                 665                 670

Glu Lys Phe Thr Gly Ala Phe Asn Met Met Gly Gly Cys Leu Gln Asn
        675                 680                 685

Ala Leu Asp Ile Leu Asp Lys Val His Glu Pro Phe Glu Asp Met Lys
    690                 695                 700

Cys Ile Gly Leu Thr Met Gln Ser Met Tyr Glu Asn Tyr Ile Val Pro
705                 710                 715                 720

Glu Asp Lys Arg Glu Met Trp Met Ala Cys Ile Lys Glu Leu His Asp
                725                 730                 735

Val Ser Lys Gly Ala Ala Asn Lys Leu Gly Gly Ala Leu Gln Ala Lys
            740                 745                 750
```

```
Ala Arg Ala Lys Lys Asp Glu Leu Arg Arg Lys Met Met Tyr Met Cys
        755                 760                 765

Tyr Arg Asn Ile Glu Phe Phe Thr Lys Asn Ser Ala Phe Pro Lys Thr
    770                 775                 780

Thr Asn Gly Cys Ser Gln Ala Met Ala Ala Leu Gln Asn Leu Pro Gln
785                 790                 795                 800

Cys Ser Pro Asp Glu Ile Met Ser Tyr Ala Gln Lys Ile Phe Lys Ile
                805                 810                 815

Leu Asp Glu Glu Arg Asp Lys Val Leu Thr His Ile Asp His Ile Phe
            820                 825                 830

Met Asp Ile Leu Thr Thr Cys Val Glu Thr Met Cys Asn Glu Tyr Lys
        835                 840                 845

Val Thr Ser Asp Ala Cys Met Met Thr Met Tyr Gly Gly Ile Ser Leu
    850                 855                 860

Leu Ser Glu Phe Cys Arg Val Leu Cys Cys Tyr Val Leu Glu Glu Thr
865                 870                 875                 880

Ser Val Met Leu Ala Lys Arg Pro Leu Ile Thr Lys Pro Glu Val Ile
                885                 890                 895

Ser Val Met Lys Arg Arg Ile Glu Glu Ile Cys Met Lys Val Phe Ala
            900                 905                 910

Gln Tyr Ile Leu Gly Ala Asp Pro Leu Arg Val Cys Ser Pro Ser Val
        915                 920                 925

Asp Asp Leu Arg Ala Ile Ala Glu Glu Ser Asp Glu Glu Glu Ala Ile
    930                 935                 940

Val Ala Tyr Thr Leu Ala Thr Ala Gly Ala Ser Ser Ser Asp Ser Leu
945                 950                 955                 960

Val Ser Pro Pro Glu Ser Pro Val Pro Ala Thr Ile Pro Leu Ser Ser
                965                 970                 975

Val Ile Val Ala Glu Asn Ser Asp Gln Glu Glu Ser Glu Gln Ser Asp
            980                 985                 990

Glu Glu Gln Glu Glu Gly Ala Gln  Glu Glu Arg Glu Asp  Thr Val Ser
        995                 1000                 1005

Val Lys  Ser Glu Pro Val Ser  Glu Ile Glu Glu Val  Ala Ser Glu
    1010                 1015                 1020

Glu Glu  Glu Asp Gly Ala Glu  Glu Pro Thr Ala Ser  Gly Gly Lys
    1025                 1030                 1035

Ser Thr  His Pro Met Val Thr  Arg Ser Lys Ala Asp  Gln
    1040                 1045                 1050
```

<210> SEQ ID NO 74
<211> LENGTH: 3153
<212> TYPE: DNA
<213> ORGANISM: Artificial Sequence
<220> FEATURE:
<223> OTHER INFORMATION: Synthetic polynucleotide

<400> SEQUENCE: 74

```
atggagtcgc gcggtcgccg ttgtcccgaa atgatatccg tactgggtcc catttcgggg      60

cacgtgctga aagccgtgtt tagtcgcggc gatacgccgg tgctgccgca cgagacgcga     120

ctcctgcaga cgggtatcca cgtacgcgtg agccagccct cgctgatcct ggtgtcgcag     180

tacacgcccg actcgacgcc atgccaccgc ggcgacaatc agctgcaggt gcagcacacg     240

tactttacgg gcagcgaggt ggagaacgtg tcggtcaacg tgcacaaccc cacgggccga     300

agcatctgcc ccagccaaga gcccatgtcg atctatgtgt acgcgctgcc gctcaagatg     360
```

-continued

```
ctgaacatcc ccagcatcaa cgtgcaccac tacccgtcgg cggccgagcg caaacaccga    420
cacctgcccg tagccgacgc tgttattcac gcgtcgggca agcagatgtg gcaggcgcgt    480
ctcacggtct cgggactggc ctggacgcgt cagcagaacc agtggaaaga gcccgacgtc    540
tactacacgt cagcgttcgt gtttcccacc aaggacgtgg cactgcggca cgtggtgtgc    600
gcgcacgagc tggtttgctc catggagaac acgcgcgcaa ccaagatgca ggtgataggt    660
gaccagtacg tcaaggtgta cctggagtcc ttctgcgagg acgtgccctc cggcaagctc    720
tttatgcacg tcacgctggg ctctgacgtg gaagaggacc taacgatgac ccgcaacccg    780
caacccttca tgcgccccca cgagcgcaac ggctttacgg tgttgtgtcc caaaaatatg    840
ataatcaaac cgggcaagat ctcgcacatc atgctggatg tggcttttac ctcacacgag    900
cattttgggc tgctgtgtcc caagagcatc ccgggcctga gcatctcagg taacctgttg    960
atgaacgggc agcaaatctt cctggaggta caagcgatac gcgagaccgt ggaactgcgt   1020
cagtacgatc ccgtggctgc gctcttcttt ttcgatatcg acttgttgct gcagcgcggg   1080
cctcagtaca gcgagcaccc caccttcacc agccagtatc gcatccaggg caagcttgag   1140
taccgacaca cctgggaccg gcacgacgag ggtgccgccc agggcgacga cgacgtctgg   1200
accagcggat cggactccga cgaagaactc gtaaccaccg agcgtaagac gccccgcgtc   1260
accggcggcg gcgccatggc gagcgcctcc acttccgcgg gccgcaaacg caaatcagca   1320
tcctcggcga cggcgtgcac ggcgggcgtt atgacacgcg gccgccttaa ggccgagtcc   1380
accgtcgcgc ccgaagagga caccgacgag gattccgaca acgaaatcca caatccggcc   1440
gtgttcacct ggccgccctg gcaggccggc atcctggccc gcaacctggt gcccatggtg   1500
gctacggttc agggtcagaa tctgaagtac caggagttct tctgggacgc caacgacatc   1560
taccgcatct tcgccgaatt ggaaggcgta tggcagcccg ctgcgcaacc caaacgtcgc   1620
cgccaccggc aagacgcctt gcccgggcca tgcatcgcct cgacgcccaa aaagcaccga   1680
ggtgagtcct ctgccaagag aaagatggac cctgataatc ctgacgaggg cccttcctcc   1740
aaggtgccac ggcccgagac acccgtgacc aaggccacga cgttcctgca gactatgtta   1800
aggaaggagg ttaacagtca gctgagcctg ggagacccgc tgttcccaga attggccgaa   1860
gaatccctca aaacctttga acaagtgacc gaggattgca acgagaaccc cgaaaaagat   1920
gtcctgacag aactcgtcaa acagattaag gttcgagtgg acatggtgcg gcatagaatc   1980
aaggagcaca tgctgaaaaa atatacccag acggaagaaa aattcactgg cgcctttaat   2040
atgatgggag gatgtttgca gaatgcctta gatatcttag ataaggttca tgagcctttc   2100
gaggacatga agtgtattgg gctaactatg cagagcatgt atgagaacta cattgtacct   2160
gaggataagc gggagatgtg gatggcttgt attaaggagc tgcatgatgt gagcaagggc   2220
gccgctaaca agttgggggg tgcactgcag gctaaggccc gtgctaaaaa ggatgaactt   2280
aggagaaaga tgatgtatat gtgctacagg aatatagagt tctttaccaa gaactcagcc   2340
ttccctaaga ccaccaatgg ctgcagtcag gccatggcgg cattgcagaa cttgcctcag   2400
tgctctcctg atgagattat gtcttatgcc cagaaaatct ttaagatttt ggatgaggag   2460
agagacaagg tgctcacgca cattgatcac atatttatgg atatcctcac tacatgtgtg   2520
gaaacaatgt gtaatgagta caaggtcact agtgacgctt gtatgatgac catgtacggg   2580
ggcatctctc tcttaagtga gttctgtcgg gtgctgtgct gctatgtctt agaggagact   2640
agtgtgatgc tggccaagcg gcctctgata accaagcctg aggttatcag tgtaatgaag   2700
```

cgccgcattg aggagatctg catgaaggtc tttgcccagt acattctggg ggccgatcct 2760
ttgagagtct gctctcctag tgtggatgac ctacgggcca tcgccgagga gtcagatgag 2820
gaagaggcta ttgtagccta cactttggcc accgctggtg ccagctcctc tgattctctg 2880
gtgtcacctc cagagtcccc tgtacccgcg actatccctc tgtcctcagt aattgtggct 2940
gagaacagtg atcaggaaga aagtgaacag agtgatgagg aacaggagga gggtgctcag 3000
gaggagcggg aggacactgt gtctgtcaag tctgagccag tgtctgagat agaggaagtt 3060
gcctcagagg aagaggagga tggtgctgag gaacccaccg cctctggagg caagagcacc 3120
caccctatgg tgactagaag caaggctgac cag 3153

<210> SEQ ID NO 75
<211> LENGTH: 3424
<212> TYPE: DNA
<213> ORGANISM: Artificial Sequence
<220> FEATURE:
<223> OTHER INFORMATION: Synthetic polynucleotide

<400> SEQUENCE: 75
gggaaataag agagaaaaga agagtaagaa gaaatataag agccaccatg gagtcgcgcg 60
gtcgccgttg tcccgaaatg atatccgtac tgggtcccat ttcggggcac gtgctgaaag 120
ccgtgtttag tcgcggcgat acgccggtgc tgccgcacga gacgcgactc ctgcagacgg 180
gtatccacgt acgcgtgagc cagccctcgc tgatcctggt gtcgcagtac acgcccgact 240
cgacgccatg ccaccgcggc gacaatcagc tgcaggtgca gcacacgtac tttacgggca 300
gcgaggtgga gaacgtgtcg gtcaacgtgc acaaccccac gggccgaagc atctgcccca 360
gccaagagcc catgtcgatc tatgtgtacg cgctgccgct caagatgctg aacatcccca 420
gcatcaacgt gcaccactac ccgtcggcgg ccgagcgcaa acaccgacac ctgcccgtag 480
ccgacgctgt tattcacgcg tcgggcaagc agatgtggca ggcgcgtctc acggtctcgg 540
gactggcctg gacgcgtcag cagaaccagt ggaaagagcc cgacgtctac tacacgtcag 600
cgttcgtgtt tcccaccaag gacgtggcac tgcggcacgt ggtgtgcgcg cacgagctgg 660
tttgctccat ggagaacacg cgcgcaacca agatgcaggt gataggtgac cagtacgtca 720
aggtgtacct ggagtccttc tgcgaggacg tgccctccgg caagctcttt atgcacgtca 780
cgctgggctc tgacgtggaa gaggacctaa cgatgacccg caacccgcaa cccttcatgc 840
gcccccacga gcgcaacggc tttacggtgt tgtgtcccaa aaatatgata atcaaaccgg 900
gcaagatctc gcacatcatg ctggatgtgg cttttacctc acacgagcat tttgggctgc 960
tgtgtcccaa gagcatcccg ggcctgagca tctcaggtaa cctgttgatg aacgggcagc 1020
aaatcttcct ggaggtacaa gcgatacgcg agaccgtgga actgcgtcag tacgatcccg 1080
tggctgcgct cttctttttc gatatcgact tgttgctgca gcgcgggcct cagtacagcg 1140
agcaccccac cttcaccagc cagtatcgca tccagggcaa gcttgagtac cgacacacct 1200
gggaccggca cgacgagggt gccgcccagg gcgacgacga cgtctggacc agcggatcgg 1260
actccgacga agaactcgta accaccgagc gtaagacgcc ccgcgtcacc ggcggcggcg 1320
ccatggcgag cgcctccact tccgcgggcc gcaaacgcaa atcagcatcc tcggcgacgg 1380
cgtgcacggc gggcgttatg acacgcggcc gccttaaggc cgagtccacc gtcgcgcccg 1440
aagaggacac cgacgaggat tccgacaacg aaatccacaa tccggccgtg ttcacctggc 1500
cgccctggca ggccggcatc ctggcccgca acctggtgcc catggtggct acggttcagg 1560
gtcagaatct gaagtaccag gagttcttct gggacgccaa cgacatctac cgcatcttcg 1620
ccgaattgga aggcgtatgg cagcccgctg cgcaacccaa acgtcgccgc caccggcaag 1680
acgccttgcc cgggccatgc atcgcctcga cgcccaaaaa gcaccgaggt gagtcctctg 1740
ccaagagaaa gatggaccct gataatcctg acgagggccc ttcctccaag gtgccacggc 1800
ccgagacacc cgtgaccaag gccacgacgt tcctgcagac tatgttaagg aaggaggtta 1860
acagtcagct gagcctggga gacccgctgt tcccagaatt ggccgaagaa tccctcaaaa 1920
cctttgaaca agtgaccgag gattgcaacg agaaccccga aaaagatgtc ctgacagaac 1980
tcgtcaaaca gattaaggtt cgagtggaca tggtgcggca tagaatcaag gagcacatgc 2040
tgaaaaaata tacccagacg gaagaaaaat tcactggcgc ctttaatatg atgggaggat 2100
gtttgcagaa tgccttagat atcttagata aggttcatga gcctttcgag gacatgaagt 2160
gtattgggct aactatgcag agcatgtatg agaactacat tgtacctgag gataagcggg 2220
agatgtggat ggcttgtatt aaggagctgc atgatgtgag caagggcgcc gctaacaagt 2280
tggggggtgc actgcaggct aaggcccgtg ctaaaaagga tgaacttagg agaaagatga 2340
tgtatatgtg ctacaggaat atagagttct ttaccaagaa ctcagccttc cctaagacca 2400
ccaatggctg cagtcaggcc atggcggcat tgcagaactt gcctcagtgc tctcctgatg 2460
agattatgtc ttatgcccag aaaatcttta agattttgga tgaggagaga gacaaggtgc 2520
tcacgcacat tgatcacata tttatggata tcctcactac atgtgtggaa acaatgtgta 2580
atgagtacaa ggtcactagt gacgcttgta tgatgaccat gtacgggggc atctctctct 2640
taagtgagtt ctgtcgggtg ctgtgctgct atgtcttaga ggagactagt gtgatgctgg 2700
ccaagcggcc tctgataacc aagcctgagg ttatcagtgt aatgaagcgc cgcattgagg 2760
agatctgcat gaaggtcttt gcccagtaca ttctgggggc cgatcctttg agagtctgct 2820
ctcctagtgt ggatgaccta cggccatcg ccgaggagtc agatgaggaa gaggctattg 2880
tagcctacac tttggccacc gctggtgcca gctcctctga ttctctggtg tcacctccag 2940
agtcccctgt acccgcgact atccctctgt cctcagtaat tgtggctgag aacagtgatc 3000
aggaagaaag tgaacagagt gatgaggaac aggaggaggg tgctcaggag gagcgggagg 3060
acactgtgtc tgtcaagtct gagccagtgt ctgagataga ggaagttgcc tcagaggaag 3120
aggaggatgg tgctgaggaa cccaccgcct ctggaggcaa gagcacccac cctatggtga 3180
ctagaagcaa ggctgaccag tgataatagg ctggagcctc ggtggccatg cttcttgccc 3240
cttgggcctc cccccagccc ctcctcccct tcctgcaccc gtacccccgt ggtctttgaa 3300
taaagtctga gtgggcggca aaaaaaaaaa aaaaaaaaaa aaaaaaaaaa aaaaaaaaaa 3360
aaaaaaaaaa aaaaaaaaaa aaaaaaaaaa aaaaaaaaaa aaaaaaaaaa aaaaaaaaat 3420
ctag 3424

<210> SEQ ID NO 76
<211> LENGTH: 3352
<212> TYPE: DNA
<213> ORGANISM: Artificial Sequence
<220> FEATURE:
<223> OTHER INFORMATION: Synthetic polynucleotide

<400> SEQUENCE: 76
tcaagctttt ggaccctcgt acagaagcta atacgactca ctatagggaa ataagagaga 60
aaagaagagt aagaagaaat ataagagcca ccatggagtc gcgcggtcgc cgttgtcccg 120
aaatgatatc cgtactgggt cccatttcgg gtcatgtgct gaaagcggtg tttagtcgcg 180

-continued

```
gcgatacgcc agtactgccg cacgagacgc gactcctgca gacaggtatc cacgtacgcg    240
tgagccagcc ctcgctcatc ctggtgtcgc agtacacgcc cgactcgacg ccatgccacc    300
gcggcgacaa tcagctgcag gtgcagcaca cgtactttac gggcagcgag gtggagaacg    360
tgtcggtcaa cgtccacaac cccacgggtc gaagcatctg cccctctcaa gagcccatgt    420
cgatctatgt gtacgcgctg ccgctcaaga tgctgaacat cccgagcatc aacgtgcacc    480
actacccgag cgcggccgag cgcaaacacc gacacctgcc cgtagccgac gctgttattc    540
acgcgtcggg caagcagatg tggcaagcgc gcctcacggt ctcgggacta gcctggacgc    600
gtcagcagaa ccagtggaaa gagcccgacg tctactacac gtcagcgttc gtgtttccca    660
ccaaggacgt ggcactgcgc cacgtggtgt gtgcgcacga gctggtttgc tccatggaga    720
atacgcgcgc aaccaagatg caggtgatag gtgatcaata cgtcaaggtg tacctggagt    780
ccttctgcga ggatgtgccc tccggtaagc tctttatgca cgtcacgctg ggctctgacg    840
tggaagagga cctaacgatg acccgcaatc cgcaaccctt catgcgcccc cacgagcgca    900
acggctttac ggtgttgtgt cctaaaaata tgataatcaa accaggcaag atctcgcaca    960
tcatgctgga tgtggctttt acctcacacg agcattttgg gctgctgtgt cccaagagca   1020
tcccgggcct gagcatctca ggtaacctgt tgatgaacgg gcagcaaatc tttctcgagg   1080
tgcaagctat acgcgagacc gtcgaactgc gtcagtacga tcccgtggct gcgctgttct   1140
ttttcgatat cgacttgttg ctgcagcgcg ggcctcagta cagcgagcac cccaccttca   1200
ccagccagta tcgcatccag ggcaagcttg agtaccgaca cacctgggac cggcacgacg   1260
agggagccgc ccagggcgac gacgacgtct ggacctctgg atcggactcc gacgaagaac   1320
tcgtaacgac cgagcgtaag accccccgcg tcaccggcgg cggcgccatg gcgtccgcct   1380
caacttccgc gggctcagca tcctcggcta cggcgtgcac ggcgggcgtt atgacacgtg   1440
gcagacttaa ggccgagtcc accgtcgcgc ccgaagagga caccgacgag gattccgaca   1500
acgaaatcca caatccggcc gtgttcacct ggccgccctg gcaggccggc atcctggccc   1560
gcaacctggt gcccatggtg gctacggttc agggtcagaa tctgaagtac caggagttct   1620
tctgggacgc caacgacatc taccgcatct tcgccgaatt ggaaggcgta tggcagcccg   1680
ctgcgcaacc caaacgtcgc cgccaccggc aagacgcctt gcccgggcca tgcatcgcct   1740
cgacgcccaa aaagcaccga ggtgagtcct ctgccaagag aaagatggac cctgataatc   1800
ctgacgaggg cccttcctcc aaggtgccac ggcccgagac acccgtgacc aaggccacga   1860
cgttcctgca gactatgtta aggaaggagg ttaacagtca gctgagcctg ggagacccgc   1920
tgttcccaga attggccgaa gaatccctca aaacctttga acaagtgacc gaggattgca   1980
acgagaaccc cgaaaaagat gtcctgacag aactcgtcaa acagattaag gttcgagtgg   2040
acatggtgcg gcatagaatc aaggagcaca tgctgaaaaa atatacccag acggaagaaa   2100
aattcactgg cgcctttaat atgatgggag gatgtttgca gaatgcctta gatatcttag   2160
ataaggttca tgagcctttc gaggacatga agtgtattgg gctaactatg cagagcatgt   2220
atgagaacta cattgtacct gaggataagc gggagatgtg gatggcttgt attaaggagc   2280
tgcatgatgt gagcaagggc gccgctaaca agttgggggg tgcactgcag gctaaggccc   2340
gtgctaaaaa ggatgaactt aggagaaaga tgatgtatat gtgctacagg aatatagagt   2400
tctttaccaa gaactcagcc ttccctaaga ccaccaatgg ctgctcgcag gccatggcgg   2460
cattgcagaa cttgcctcag tgctctcctg atgagattat gtcttatgcc cagaaaatct   2520
ttaagatttt ggatgaggag cgagacaagg tgcttacgca cattgatcac atatttatgg   2580
```

atatcctcac tacatgtgtt gaaacgatgt gcaatgagta caaggtcact agtgacgctt 2640
gtatgatgac catgtacggg ggcatatctc tcttaagtga attctgtcgg gtgctgtgct 2700
gctacgtctt agaggagact agtgtgatgc tggccaagcg gcctctgata accaagcctg 2760
aggtcatcag tgtaatgaag cgccgcattg aggagatctg catgaaggtc tttgcccagt 2820
acattctggg ggccgatcct ttgagagtct gctctccaag tgtggatgac ctacgggcca 2880
tcgccgagga gtcagacgag gaagaggcta ttgtagccta cactttggcc accgctggtg 2940
ccagctcctc tgactctctg gtgtcacctc cagaatcccc tgtgcccgcg acaatccctc 3000
tgtcctcagt aattgtggct gagaacagtg atcaggaaga aagtgaacag agtgatgagg 3060
aacaggagga gggtgctcag gaggagcggg aggatactgt gtctgtcaag tctgagccag 3120
tgtctgaaat tgaggaagtt gcctcagagg aagaggagga tggtgctgag gaacccaccg 3180
cctctggagg caagtccacc caccctatgg taactagatc aaaggctgac cagtgataat 3240
aggctggagc ctcggtggcc atgcttcttg ccccttgggc ctccccccag cccctcctcc 3300
ccttcctgca cccgtacccc cgtggtcttt gaataaagtc tgagtgggcg gc 3352

<210> SEQ ID NO 77
<211> LENGTH: 1047
<212> TYPE: PRT
<213> ORGANISM: Artificial Sequence
<220> FEATURE:
<223> OTHER INFORMATION: Synthetic polypeptide

<400> SEQUENCE: 77

Met Glu Ser Arg Gly Arg Arg Cys Pro Glu Met Ile Ser Val Leu Gly
1 5 10 15

Pro Ile Ser Gly His Val Leu Lys Ala Val Phe Ser Arg Gly Asp Thr
20 25 30

Pro Val Leu Pro His Glu Thr Arg Leu Leu Gln Thr Gly Ile His Val
35 40 45

Arg Val Ser Gln Pro Ser Leu Ile Leu Val Ser Gln Tyr Thr Pro Asp
50 55 60

Ser Thr Pro Cys His Arg Gly Asp Asn Gln Leu Gln Val Gln His Thr
65 70 75 80

Tyr Phe Thr Gly Ser Glu Val Glu Asn Val Ser Val Asn Val His Asn
85 90 95

Pro Thr Gly Arg Ser Ile Cys Pro Ser Gln Glu Pro Met Ser Ile Tyr
100 105 110

Val Tyr Ala Leu Pro Leu Lys Met Leu Asn Ile Pro Ser Ile Asn Val
115 120 125

His His Tyr Pro Ser Ala Ala Glu Arg Lys His Arg His Leu Pro Val
130 135 140

Ala Asp Ala Val Ile His Ala Ser Gly Lys Gln Met Trp Gln Ala Arg
145 150 155 160

Leu Thr Val Ser Gly Leu Ala Trp Thr Arg Gln Gln Asn Gln Trp Lys
165 170 175

Glu Pro Asp Val Tyr Tyr Thr Ser Ala Phe Val Phe Pro Thr Lys Asp
180 185 190

Val Ala Leu Arg His Val Val Cys Ala His Glu Leu Val Cys Ser Met
195 200 205

Glu Asn Thr Arg Ala Thr Lys Met Gln Val Ile Gly Asp Gln Tyr Val
210 215 220

```
Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
        275                 280                 285

His Ile Met Leu Asp Val Ala Phe Thr Ser His Glu His Phe Gly Leu
    290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365

Phe Thr Ser Gln Tyr Arg Ile Gln Gly Lys Leu Glu Tyr Arg His Thr
    370                 375                 380

Trp Asp Arg His Asp Glu Gly Ala Ala Gln Gly Asp Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Gly Ala Met Ala Ser Ala Ser Thr Ser
            420                 425                 430

Ala Gly Ser Ala Ser Ser Ala Thr Ala Cys Thr Ala Gly Val Met Thr
        435                 440                 445

Arg Gly Arg Leu Lys Ala Glu Ser Thr Val Ala Pro Glu Glu Asp Thr
    450                 455                 460

Asp Glu Asp Ser Asp Asn Glu Ile His Asn Pro Ala Val Phe Thr Trp
465                 470                 475                 480

Pro Pro Trp Gln Ala Gly Ile Leu Ala Arg Asn Leu Val Pro Met Val
                485                 490                 495

Ala Thr Val Gln Gly Gln Asn Leu Lys Tyr Gln Glu Phe Phe Trp Asp
            500                 505                 510

Ala Asn Asp Ile Tyr Arg Ile Phe Ala Glu Leu Glu Gly Val Trp Gln
        515                 520                 525

Pro Ala Ala Gln Pro Lys Arg Arg Arg His Arg Gln Asp Ala Leu Pro
    530                 535                 540

Gly Pro Cys Ile Ala Ser Thr Pro Lys Lys His Arg Gly Glu Ser Ser
545                 550                 555                 560

Ala Lys Arg Lys Met Asp Pro Asp Asn Pro Asp Glu Gly Pro Ser Ser
                565                 570                 575

Lys Val Pro Arg Pro Glu Thr Pro Val Thr Lys Ala Thr Thr Phe Leu
            580                 585                 590

Gln Thr Met Leu Arg Lys Glu Val Asn Ser Gln Leu Ser Leu Gly Asp
        595                 600                 605

Pro Leu Phe Pro Glu Leu Ala Glu Glu Ser Leu Lys Thr Phe Glu Gln
    610                 615                 620

Val Thr Glu Asp Cys Asn Glu Asn Pro Glu Lys Asp Val Leu Thr Glu
625                 630                 635                 640

Leu Val Lys Gln Ile Lys Val Arg Val Asp Met Val Arg His Arg Ile
```

-continued

```
                645                 650                 655

Lys Glu His Met Leu Lys Lys Tyr Thr Gln Thr Glu Glu Lys Phe Thr
            660                 665                 670

Gly Ala Phe Asn Met Met Gly Gly Cys Leu Gln Asn Ala Leu Asp Ile
        675                 680                 685

Leu Asp Lys Val His Glu Pro Phe Glu Asp Met Lys Cys Ile Gly Leu
    690                 695                 700

Thr Met Gln Ser Met Tyr Glu Asn Tyr Ile Val Pro Glu Asp Lys Arg
705                 710                 715                 720

Glu Met Trp Met Ala Cys Ile Lys Glu Leu His Asp Val Ser Lys Gly
                725                 730                 735

Ala Ala Asn Lys Leu Gly Gly Ala Leu Gln Ala Lys Ala Arg Ala Lys
            740                 745                 750

Lys Asp Glu Leu Arg Arg Lys Met Met Tyr Met Cys Tyr Arg Asn Ile
        755                 760                 765

Glu Phe Phe Thr Lys Asn Ser Ala Phe Pro Lys Thr Thr Asn Gly Cys
    770                 775                 780

Ser Gln Ala Met Ala Ala Leu Gln Asn Leu Pro Gln Cys Ser Pro Asp
785                 790                 795                 800

Glu Ile Met Ser Tyr Ala Gln Lys Ile Phe Lys Ile Leu Asp Glu Glu
                805                 810                 815

Arg Asp Lys Val Leu Thr His Ile Asp His Ile Phe Met Asp Ile Leu
            820                 825                 830

Thr Thr Cys Val Glu Thr Met Cys Asn Glu Tyr Lys Val Thr Ser Asp
        835                 840                 845

Ala Cys Met Met Thr Met Tyr Gly Gly Ile Ser Leu Leu Ser Glu Phe
    850                 855                 860

Cys Arg Val Leu Cys Cys Tyr Val Leu Glu Glu Thr Ser Val Met Leu
865                 870                 875                 880

Ala Lys Arg Pro Leu Ile Thr Lys Pro Glu Val Ile Ser Val Met Lys
                885                 890                 895

Arg Arg Ile Glu Glu Ile Cys Met Lys Val Phe Ala Gln Tyr Ile Leu
            900                 905                 910

Gly Ala Asp Pro Leu Arg Val Cys Ser Pro Ser Val Asp Asp Leu Arg
        915                 920                 925

Ala Ile Ala Glu Glu Ser Asp Glu Glu Glu Ala Ile Val Ala Tyr Thr
    930                 935                 940

Leu Ala Thr Ala Gly Ala Ser Ser Ser Asp Ser Leu Val Ser Pro Pro
945                 950                 955                 960

Glu Ser Pro Val Pro Ala Thr Ile Pro Leu Ser Ser Val Ile Val Ala
                965                 970                 975

Glu Asn Ser Asp Gln Glu Glu Ser Glu Gln Ser Asp Glu Glu Gln Glu
            980                 985                 990

Glu Gly Ala Gln Glu Glu Arg Glu  Asp Thr Val Ser Val  Lys Ser Glu
        995                 1000                 1005

Pro Val  Ser Glu Ile Glu Glu  Val Ala Ser Glu Glu  Glu Glu Asp
    1010                 1015                 1020

Gly Ala  Glu Glu Pro Thr Ala  Ser Gly Gly Lys Ser  Thr His Pro
    1025                 1030                 1035

Met Val  Thr Arg Ser Lys Ala  Asp Gln
    1040                 1045
```

<210> SEQ ID NO 78

<211> LENGTH: 3141
<212> TYPE: DNA
<213> ORGANISM: Artificial Sequence
<220> FEATURE:
<223> OTHER INFORMATION: Synthetic polynucleotide

<400> SEQUENCE: 78
atggagtcgc gcggtcgccg ttgtcccgaa atgatatccg tactgggtcc catttcgggt 60
catgtgctga aagcggtgtt tagtcgcggc gatacgccag tactgccgca cgagacgcga 120
ctcctgcaga caggtatcca cgtacgcgtg agccagccct cgctcatcct ggtgtcgcag 180
tacacgcccg actcgacgcc atgccaccgc ggcgacaatc agctgcaggt gcagcacacg 240
tactttacgg gcagcgaggt ggagaacgtg tcggtcaacg tccacaaccc cacgggtcga 300
agcatctgcc cctctcaaga gcccatgtcg atctatgtgt acgcgctgcc gctcaagatg 360
ctgaacatcc cgagcatcaa cgtgcaccac tacccgagcg cggccgagcg caaacaccga 420
cacctgcccg tagccgacgc tgttattcac gcgtcgggca agcagatgtg gcaagcgcgc 480
ctcacggtct cgggactagc ctggacgcgt cagcagaacc agtggaaaga gcccgacgtc 540
tactacacgt cagcgttcgt gtttcccacc aaggacgtgg cactgcgcca cgtggtgtgt 600
gcgcacgagc tggtttgctc catggagaat acgcgcgcaa ccaagatgca ggtgataggt 660
gatcaatacg tcaaggtgta cctggagtcc ttctgcgagg atgtgccctc cggtaagctc 720
tttatgcacg tcacgctggg ctctgacgtg gaagaggacc taacgatgac ccgcaatccg 780
caacccttca tgcgccccca cgagcgcaac ggctttacgg tgttgtgtcc taaaaatatg 840
ataatcaaac caggcaagat ctcgcacatc atgctggatg tggcttttac ctcacacgag 900
cattttgggc tgctgtgtcc caagagcatc ccgggcctga gcatctcagg taacctgttg 960
atgaacgggc agcaaatctt tctcgaggtg caagctatac gcgagaccgt cgaactgcgt 1020
cagtacgatc ccgtggctgc gctgttcttt ttcgatatcg acttgttgct gcagcgcggg 1080
cctcagtaca gcgagcaccc caccttcacc agccagtatc gcatccaggg caagcttgag 1140
taccgacaca cctgggaccg gcacgacgag ggagccgccc agggcgacga cgacgtctgg 1200
acctctggat cggactccga cgaagaactc gtaacgaccg agcgtaagac cccccgcgtc 1260
accggcggcg gcgccatggc gtccgcctca acttccgcgg gctcagcatc ctcggctacg 1320
gcgtgcacgg cgggcgttat gacacgtggc agacttaagg ccgagtccac cgtcgcgccc 1380
gaagaggaca ccgacgagga ttccgacaac gaaatccaca atccggccgt gttcacctgg 1440
ccgccctggc aggccggcat cctggcccgc aacctggtgc ccatggtggc tacggttcag 1500
ggtcagaatc tgaagtacca ggagttcttc tgggacgcca acgacatcta ccgcatcttc 1560
gccgaattgg aaggcgtatg gcagcccgct gcgcaaccca aacgtcgccg ccaccggcaa 1620
gacgccttgc ccgggccatg catcgcctcg acgcccaaaa agcaccgagg tgagtcctct 1680
gccaagagaa agatggaccc tgataatcct gacgagggcc cttcctccaa ggtgccacgg 1740
cccgagacac ccgtgaccaa ggccacgacg ttcctgcaga ctatgttaag gaaggaggtt 1800
aacagtcagc tgagcctggg agacccgctg ttcccagaat tggccgaaga atccctcaaa 1860
acctttgaac aagtgaccga ggattgcaac gagaaccccg aaaaagatgt cctgacagaa 1920
ctcgtcaaac agattaaggt tcgagtggac atggtgcggc atagaatcaa ggagcacatg 1980
ctgaaaaaat atacccagac ggaagaaaaa ttcactggcg cctttaatat gatgggagga 2040
tgtttgcaga atgccttaga tatcttagat aaggttcatg agcctttcga ggacatgaag 2100
tgtattgggc taactatgca gagcatgtat gagaactaca ttgtacctga ggataagcgg 2160
gagatgtgga tggcttgtat taaggagctg catgatgtga gcaagggcgc cgctaacaag 2220
ttggggggtg cactgcaggc taaggcccgt gctaaaaagg atgaacttag gagaaagatg 2280
atgtatatgt gctacaggaa tatagagttc tttaccaaga actcagcctt ccctaagacc 2340
accaatggct gctcgcaggc catggcggca ttgcagaact tgcctcagtg ctctcctgat 2400
gagattatgt cttatgccca gaaaatcttt aagattttgg atgaggagcg agacaaggtg 2460
cttacgcaca ttgatcacat atttatggat atcctcacta catgtgttga aacgatgtgc 2520
aatgagtaca aggtcactag tgacgcttgt atgatgacca tgtacggggg catatctctc 2580
ttaagtgaat tctgtcgggt gctgtgctgc tacgtcttag aggagactag tgtgatgctg 2640
gccaagcggc ctctgataac caagcctgag gtcatcagtg taatgaagcg ccgcattgag 2700
gagatctgca tgaaggtctt tgcccagtac attctggggg ccgatccttt gagagtctgc 2760
tctccaagtg tggatgacct acgggccatc gccgaggagt cagacgagga agaggctatt 2820
gtagcctaca ctttggccac cgctggtgcc agctcctctg actctctggt gtcacctcca 2880
gaatcccctg tgcccgcgac aatccctctg tcctcagtaa ttgtggctga gaacagtgat 2940
caggaagaaa gtgaacagag tgatgaggaa caggaggagg gtgctcagga ggagcgggag 3000
gatactgtgt ctgtcaagtc tgagccagtg tctgaaattg aggaagttgc ctcagaggaa 3060
gaggaggatg gtgctgagga acccaccgcc tctggaggca agtccaccca ccctatggta 3120
actagatcaa aggctgacca g 3141

<210> SEQ ID NO 79
<211> LENGTH: 3412
<212> TYPE: DNA
<213> ORGANISM: Artificial Sequence
<220> FEATURE:
<223> OTHER INFORMATION: Synthetic polynucleotide

<400> SEQUENCE: 79
gggaaataag agagaaaaga agagtaagaa gaaatataag agccaccatg gagtcgcgcg 60
gtcgccgttg tcccgaaatg atatccgtac tgggtcccat ttcgggtcat gtgctgaaag 120
cggtgtttag tcgcggcgat acgccagtac tgccgcacga gacgcgactc ctgcagacag 180
gtatccacgt acgcgtgagc cagccctcgc tcatcctggt gtcgcagtac acgcccgact 240
cgacgccatg ccaccgcggc gacaatcagc tgcaggtgca gcacacgtac tttacgggca 300
gcgaggtgga gaacgtgtcg gtcaacgtcc acaaccccac gggtcgaagc atctgcccct 360
ctcaagagcc catgtcgatc tatgtgtacg cgctgccgct caagatgctg aacatcccga 420
gcatcaacgt gcaccactac ccgagcgcgg ccgagcgcaa acaccgacac ctgcccgtag 480
ccgacgctgt tattcacgcg tcgggcaagc agatgtggca agcgcgcctc acggtctcgg 540
gactagcctg gacgcgtcag cagaaccagt ggaaagagcc cgacgtctac tacacgtcag 600
cgttcgtgtt tcccaccaag gacgtggcac tgcgccacgt ggtgtgtgcg cacgagctgg 660
tttgctccat ggagaatacg cgcgcaacca agatgcaggt gataggtgat caatacgtca 720
aggtgtacct ggagtccttc tgcgaggatg tgccctccgg taagctcttt atgcacgtca 780
cgctgggctc tgacgtggaa gaggacctaa cgatgacccg caatccgcaa cccttcatgc 840
gcccccacga gcgcaacggc tttacggtgt tgtgtcctaa aaatatgata atcaaaccag 900
gcaagatctc gcacatcatg ctggatgtgg cttttacctc acacgagcat tttgggctgc 960
tgtgtcccaa gagcatcccg ggcctgagca tctcaggtaa cctgttgatg aacgggcagc 1020

-continued

```
aaatctttct cgaggtgcaa gctatacgcg agaccgtcga actgcgtcag tacgatcccg   1080
tggctgcgct gttctttttc gatatcgact tgttgctgca gcgcgggcct cagtacagcg   1140
agcaccccac cttcaccagc cagtatcgca tccagggcaa gcttgagtac cgacacacct   1200
gggaccggca cgacgaggga gccgcccagg gcgacgacga cgtctggacc tctggatcgg   1260
actccgacga agaactcgta acgaccgagc gtaagacccc ccgcgtcacc ggcggcggcg   1320
ccatggcgtc cgcctcaact tccgcgggct cagcatcctc ggctacggcg tgcacggcgg   1380
gcgttatgac acgtggcaga cttaaggccg agtccaccgt cgcgcccgaa gaggacaccg   1440
acgaggattc cgacaacgaa atccacaatc cggccgtgtt cacctggccg ccctggcagg   1500
ccggcatcct ggcccgcaac ctggtgccca tggtggctac ggttcagggt cagaatctga   1560
agtaccagga gttcttctgg gacgccaacg acatctaccg catcttcgcc gaattggaag   1620
gcgtatggca gcccgctgcg caacccaaac gtcgccgcca ccggcaagac gccttgcccg   1680
ggccatgcat cgcctcgacg cccaaaaagc accgaggtga gtcctctgcc aagagaaaga   1740
tggaccctga taatcctgac gagggccctt cctccaaggt gccacggccc gagacacccg   1800
tgaccaaggc cacgacgttc ctgcagacta tgttaaggaa ggaggttaac agtcagctga   1860
gcctgggaga cccgctgttc ccagaattgg ccgaagaatc cctcaaaacc tttgaacaag   1920
tgaccgagga ttgcaacgag aaccccgaaa aagatgtcct gacagaactc gtcaaacaga   1980
ttaaggttcg agtggacatg gtgcggcata gaatcaagga gcacatgctg aaaaaatata   2040
cccagacgga agaaaaattc actggcgcct ttaatatgat gggaggatgt ttgcagaatg   2100
ccttagatat cttagataag gttcatgagc ctttcgagga catgaagtgt attgggctaa   2160
ctatgcagag catgtatgag aactacattg tacctgagga taagcgggag atgtggatgg   2220
cttgtattaa ggagctgcat gatgtgagca agggcgccgc taacaagttg gggggtgcac   2280
tgcaggctaa ggcccgtgct aaaaaggatg aacttaggag aaagatgatg tatatgtgct   2340
acaggaatat agagttcttt accaagaact cagccttccc taagaccacc aatggctgct   2400
cgcaggccat ggcggcattg cagaacttgc ctcagtgctc tcctgatgag attatgtctt   2460
atgcccagaa aatctttaag attttggatg aggagcgaga caaggtgctt acgcacattg   2520
atcacatatt tatggatatc ctcactacat gtgttgaaac gatgtgcaat gagtacaagg   2580
tcactagtga cgcttgtatg atgaccatgt acgggggcat atctctctta agtgaattct   2640
gtcgggtgct gtgctgctac gtcttagagg agactagtgt gatgctggcc aagcggcctc   2700
tgataaccaa gcctgaggtc atcagtgtaa tgaagcgccg cattgaggag atctgcatga   2760
aggtctttgc ccagtacatt ctgggggccg atcctttgag agtctgctct ccaagtgtgg   2820
atgacctacg ggccatcgcc gaggagtcag acgaggaaga ggctattgta gcctacactt   2880
tggccaccgc tggtgccagc tcctctgact ctctggtgtc acctccagaa tcccctgtgc   2940
ccgcgacaat ccctctgtcc tcagtaattg tggctgagaa cagtgatcag gaagaaagtg   3000
aacagagtga tgaggaacag gaggagggtg ctcaggagga gcgggaggat actgtgtctg   3060
tcaagtctga gccagtgtct gaaattgagg aagttgcctc agaggaagag gaggatggtg   3120
ctgaggaacc caccgcctct ggaggcaagt ccacccaccc tatggtaact agatcaaagg   3180
ctgaccagtg ataataggct ggagcctcgg tggccatgct tcttgcccct tgggcctccc   3240
cccagcccct cctccccttc ctgcacccgt acccccgtgg tctttgaata aagtctgagt   3300
gggcggcaaa aaaaaaaaaa aaaaaaaaaa aaaaaaaaaa aaaaaaaaaa aaaaaaaaaa   3360
aaaaaaaaaa aaaaaaaaaa aaaaaaaaaa aaaaaaaaaa aaaaaaatct ag           3412
```

<210> SEQ ID NO 80
<211> LENGTH: 491
<212> TYPE: PRT
<213> ORGANISM: Artificial Sequence
<220> FEATURE:
<223> OTHER INFORMATION: Synthetic polypeptide

<400> SEQUENCE: 80

```
Met Glu Ser Ser Ala Lys Arg Lys Met Asp Pro Asp Asn Pro Asp Glu
1               5                   10                  15

Gly Pro Ser Ser Lys Val Pro Arg Pro Glu Thr Pro Val Thr Lys Ala
            20                  25                  30

Thr Thr Phe Leu Gln Thr Met Leu Arg Lys Glu Val Asn Ser Gln Leu
        35                  40                  45

Ser Leu Gly Asp Pro Leu Phe Pro Glu Leu Ala Glu Glu Ser Leu Lys
    50                  55                  60

Thr Phe Glu Gln Val Thr Glu Asp Cys Asn Glu Asn Pro Glu Lys Asp
65                  70                  75                  80

Val Leu Thr Glu Leu Val Lys Gln Ile Lys Val Arg Val Asp Met Val
                85                  90                  95

Arg His Arg Ile Lys Glu His Met Leu Lys Lys Tyr Thr Gln Thr Glu
            100                 105                 110

Glu Lys Phe Thr Gly Ala Phe Asn Met Met Gly Gly Cys Leu Gln Asn
        115                 120                 125

Ala Leu Asp Ile Leu Asp Lys Val His Glu Pro Phe Glu Asp Met Lys
    130                 135                 140

Cys Ile Gly Leu Thr Met Gln Ser Met Tyr Glu Asn Tyr Ile Val Pro
145                 150                 155                 160

Glu Asp Lys Arg Glu Met Trp Met Ala Cys Ile Lys Glu Leu His Asp
                165                 170                 175

Val Ser Lys Gly Ala Ala Asn Lys Leu Gly Gly Ala Leu Gln Ala Lys
            180                 185                 190

Ala Arg Ala Lys Lys Asp Glu Leu Arg Arg Lys Met Met Tyr Met Cys
        195                 200                 205

Tyr Arg Asn Ile Glu Phe Phe Thr Lys Asn Ser Ala Phe Pro Lys Thr
    210                 215                 220

Thr Asn Gly Cys Ser Gln Ala Met Ala Ala Leu Gln Asn Leu Pro Gln
225                 230                 235                 240

Cys Ser Pro Asp Glu Ile Met Ser Tyr Ala Gln Lys Ile Phe Lys Ile
                245                 250                 255

Leu Asp Glu Glu Arg Asp Lys Val Leu Thr His Ile Asp His Ile Phe
            260                 265                 270

Met Asp Ile Leu Thr Thr Cys Val Glu Thr Met Cys Asn Glu Tyr Lys
        275                 280                 285

Val Thr Ser Asp Ala Cys Met Met Thr Met Tyr Gly Gly Ile Ser Leu
    290                 295                 300

Leu Ser Glu Phe Cys Arg Val Leu Cys Cys Tyr Val Leu Glu Glu Thr
305                 310                 315                 320

Ser Val Met Leu Ala Lys Arg Pro Leu Ile Thr Lys Pro Glu Val Ile
                325                 330                 335

Ser Val Met Lys Arg Arg Ile Glu Glu Ile Cys Met Lys Val Phe Ala
            340                 345                 350

Gln Tyr Ile Leu Gly Ala Asp Pro Leu Arg Val Cys Ser Pro Ser Val
        355                 360                 365
```

```
Asp Asp Leu Arg Ala Ile Ala Glu Glu Ser Asp Glu Glu Glu Ala Ile
    370                 375                 380

Val Ala Tyr Thr Leu Ala Thr Ala Gly Ala Ser Ser Ser Asp Ser Leu
385                 390                 395                 400

Val Ser Pro Pro Glu Ser Pro Val Pro Ala Thr Ile Pro Leu Ser Ser
                405                 410                 415

Val Ile Val Ala Glu Asn Ser Asp Gln Glu Glu Ser Glu Gln Ser Asp
            420                 425                 430

Glu Glu Gln Glu Glu Gly Ala Gln Glu Glu Arg Glu Asp Thr Val Ser
        435                 440                 445

Val Lys Ser Glu Pro Val Ser Glu Ile Glu Glu Val Ala Ser Glu Glu
    450                 455                 460

Glu Glu Asp Gly Ala Glu Glu Pro Thr Ala Ser Gly Gly Lys Ser Thr
465                 470                 475                 480

His Pro Met Val Thr Arg Ser Lys Ala Asp Gln
                485                 490


<210> SEQ ID NO 81
<211> LENGTH: 580
<212> TYPE: PRT
<213> ORGANISM: Artificial Sequence
<220> FEATURE:
<223> OTHER INFORMATION: Synthetic polypeptide

<400> SEQUENCE: 81

Met Glu Ser Ser Ala Lys Arg Lys Met Asp Pro Asp Asn Pro Asp Glu
1               5                   10                  15

Gly Pro Ser Ser Lys Val Pro Arg Pro Glu Thr Pro Val Thr Lys Ala
            20                  25                  30

Thr Thr Phe Leu Gln Thr Met Leu Arg Lys Glu Val Asn Ser Gln Leu
        35                  40                  45

Ser Leu Gly Asp Pro Leu Phe Pro Glu Leu Ala Glu Glu Ser Leu Lys
    50                  55                  60

Thr Phe Glu Gln Val Thr Glu Asp Cys Asn Glu Asn Pro Glu Lys Asp
65                  70                  75                  80

Val Leu Thr Glu Leu Gly Asp Ile Leu Ala Gln Ala Val Asn His Ala
                85                  90                  95

Gly Ile Asp Ser Ser Ser Thr Gly Pro Thr Leu Thr Thr His Ser Cys
            100                 105                 110

Ser Val Ser Ser Ala Pro Leu Asn Lys Pro Thr Pro Thr Ser Val Ala
        115                 120                 125

Val Thr Asn Thr Pro Leu Pro Gly Ala Ser Ala Thr Pro Glu Leu Ser
    130                 135                 140

Pro Arg Lys Lys Pro Arg Lys Thr Thr Arg Pro Phe Lys Val Ile Ile
145                 150                 155                 160

Lys Pro Pro Val Pro Pro Ala Pro Ile Met Leu Pro Leu Ile Lys Gln
                165                 170                 175

Glu Asp Ile Lys Pro Glu Pro Asp Phe Thr Ile Gln Tyr Arg Asn Lys
            180                 185                 190

Ile Ile Asp Thr Ala Gly Cys Ile Val Ile Ser Asp Ser Glu Glu Glu
        195                 200                 205

Gln Gly Glu Glu Val Glu Thr Arg Gly Ala Thr Ala Ser Ser Pro Ser
    210                 215                 220

Thr Gly Ser Gly Thr Pro Arg Val Thr Ser Pro Thr His Pro Leu Ser
225                 230                 235                 240
```

-continued

```
Gln Met Asn His Pro Pro Leu Pro Asp Pro Leu Gly Arg Pro Asp Glu
                245                 250                 255

Asp Ser Ser Ser Ser Ser Ser Ser Ser Cys Ser Ser Ala Ser Asp Ser
            260                 265                 270

Glu Ser Glu Ser Glu Glu Met Lys Cys Ser Ser Gly Gly Gly Ala Ser
        275                 280                 285

Val Thr Ser Ser His His Gly Arg Gly Gly Phe Gly Gly Ala Ala Ser
    290                 295                 300

Ser Ser Leu Leu Ser Cys Gly His Gln Ser Ser Gly Gly Ala Ser Thr
305                 310                 315                 320

Gly Pro Arg Lys Lys Lys Ser Lys Arg Ile Ser Glu Leu Asp Asn Glu
                325                 330                 335

Lys Val Arg Asn Ile Met Lys Asp Lys Asn Thr Pro Phe Cys Thr Pro
            340                 345                 350

Asn Val Gln Thr Arg Arg Gly Arg Val Lys Ile Asp Glu Val Ser Arg
        355                 360                 365

Met Phe Arg His Thr Asn Arg Ser Leu Glu Tyr Lys Asn Leu Pro Phe
    370                 375                 380

Met Ile Pro Ser Met His Gln Val Leu Glu Glu Ala Ile Lys Val Cys
385                 390                 395                 400

Lys Thr Met Gln Val Asn Asn Lys Gly Ile Gln Ile Ile Tyr Thr Arg
                405                 410                 415

Asn His Glu Val Lys Asn Glu Val Asp Gln Val Arg Cys Arg Leu Gly
            420                 425                 430

Ser Met Cys Asn Leu Ala Leu Ser Thr Pro Phe Leu Met Glu His Thr
        435                 440                 445

Met Pro Val Thr His Pro Pro Asp Val Ala Gln Arg Thr Ala Asp Ala
    450                 455                 460

Cys Asn Asp Gly Val Lys Ala Val Trp Asn Leu Lys Glu Leu His Thr
465                 470                 475                 480

His Gln Leu Cys Pro Arg Ser Ser Asp Tyr Arg Asn Met Ile Ile His
                485                 490                 495

Ala Ala Thr Pro Val Asp Leu Leu Gly Ala Leu Asn Leu Cys Leu Pro
            500                 505                 510

Leu Met Gln Lys Phe Pro Lys Gln Val Met Val Arg Ile Phe Ser Thr
        515                 520                 525

Asn Gln Gly Gly Phe Met Leu Pro Ile Tyr Glu Thr Ala Ala Lys Ala
    530                 535                 540

Tyr Ala Val Gly Gln Phe Glu Lys Pro Thr Glu Thr Pro Pro Glu Asp
545                 550                 555                 560

Leu Asp Thr Leu Ser Leu Ala Ile Glu Ala Ala Ile Gln Asp Leu Arg
                565                 570                 575

Asn Lys Ser Gln
            580


<210> SEQ ID NO 82
<211> LENGTH: 561
<212> TYPE: PRT
<213> ORGANISM: Artificial Sequence
<220> FEATURE:
<223> OTHER INFORMATION: Synthetic polypeptide

<400> SEQUENCE: 82

Met Glu Ser Arg Gly Arg Arg Cys Pro Glu Met Ile Ser Val Leu Gly
1               5                   10                  15
```

-continued

```
Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
        195                 200                 205

Glu Asn Thr Arg Ala Thr Lys Met Gln Val Ile Gly Asp Gln Tyr Val
    210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
        275                 280                 285

His Ile Met Leu Asp Val Ala Phe Thr Ser His Glu His Phe Gly Leu
    290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365

Phe Thr Ser Gln Tyr Arg Ile Gln Gly Lys Leu Glu Tyr Arg His Thr
    370                 375                 380

Trp Asp Arg His Asp Glu Gly Ala Ala Gln Gly Asp Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Gly Ala Met Ala Ser Ala Ser Thr Ser
            420                 425                 430
```

```
Ala Gly Arg Lys Arg Lys Ser Ala Ser Ser Ala Thr Ala Cys Thr Ala
        435                 440                 445

Gly Val Met Thr Arg Gly Arg Leu Lys Ala Glu Ser Thr Val Ala Pro
    450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
            500                 505                 510

Phe Phe Trp Asp Ala Asn Asp Ile Tyr Arg Ile Phe Ala Glu Leu Glu
        515                 520                 525

Gly Val Trp Gln Pro Ala Ala Gln Pro Lys Arg Arg Arg His Arg Gln
    530                 535                 540

Asp Ala Leu Pro Gly Pro Cys Ile Ala Ser Thr Pro Lys Lys His Arg
545                 550                 555                 560

Gly
```

<210> SEQ ID NO 83
<211> LENGTH: 698
<212> TYPE: PRT
<213> ORGANISM: Artificial Sequence
<220> FEATURE:
<223> OTHER INFORMATION: Synthetic polypeptide

<400> SEQUENCE: 83

```
Met Glu Ser Arg Ile Trp Cys Leu Val Val Cys Val Asn Leu Cys Ile
1               5                   10                  15

Val Cys Leu Gly Ala Ala Val Ser Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Trp
```

-continued

```
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Leu Thr His Asn Arg Thr Lys Arg Ser Thr Asp Gly
    450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile
        515                 520                 525

Leu Ser Ala Ile Tyr Asn Lys Pro Ile Ala Ala Arg Phe Met Gly Asp
    530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605

Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655
```

```
Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
        675                 680                 685

Ser Tyr Lys Gln His His His His His His
    690                 695


<210> SEQ ID NO 84
<211> LENGTH: 1473
<212> TYPE: DNA
<213> ORGANISM: Artificial Sequence
<220> FEATURE:
<223> OTHER INFORMATION: Synthetic polynucleotide

<400> SEQUENCE: 84

atggagtcct ctgccaagag aaagatggac cctgataatc ctgacgaggg cccttcctcc     60

aaggtgccac ggcccgagac acccgtgacc aaggccacga cgttcctgca gactatgtta    120

aggaaggagg ttaacagtca gctgagcctg ggagacccgc tgttcccaga attggccgaa    180

gaatccctca agacctttga acaagtgacc gaggattgca acgagaaccc cgagaaagat    240

gtcctgacag aactcgtcaa acagattaag gttcgagtgg acatggtgcg gcatagaatc    300

aaggagcaca tgctgaagaa atatacccag acggaagaga aattcactgg cgcctttaat    360

atgatgggag gatgtttgca gaatgcctta gatatcttag ataaggttca tgagcctttc    420

gaggacatga agtgtattgg gctaactatg cagagcatgt atgagaacta cattgtacct    480

gaggataagc gggagatgtg gatggcttgt attaaggagc tgcatgatgt gagcaagggc    540

gccgctaaca agttgggcgg tgcactgcag gctaaggccc gtgctaagaa ggatgaactt    600

aggagaaaga tgatgtatat gtgctacagg aatatagagt tctttaccaa gaactcagcc    660

ttccctaaga ccaccaatgg ctgcagtcag gccatggcgg cattgcagaa cttgcctcag    720

tgctctcctg atgagattat gtcttatgcc cagaagatct ttaagatttt ggatgaggag    780

agagacaagg tgctcacgca cattgatcac atatttatgg atatcctcac tacatgtgtg    840

gaaacaatgt gtaatgagta caaggtcact agtgacgctt gtatgatgac catgtacggc    900

ggcatctctc tcttaagtga gttctgtcgg gtgctgtgct gctatgtctt agaggagact    960

agtgtgatgc tggccaagcg gcctctgata accaagcctg aggttatcag tgtaatgaag   1020

cgccgcattg aggagatctg catgaaggtc tttgcccagt acattctggg agccgatcct   1080

ttgagagtct gctctcctag tgtggatgac ctacgggcca tcgccgagga gtcagatgag   1140

gaagaggcta ttgtagccta cactttggcc accgctggtg ccagctcctc tgattctctg   1200

gtgtcacctc cagagtcccc tgtacccgcg actatccctc tgtcctcagt aattgtggct   1260

gagaacagtg atcaggaaga aagtgaacag agtgatgagg aacaggagga gggtgctcag   1320

gaggagcggg aggacactgt gtctgtcaag tctgagccag tgtctgagat agaggaagtt   1380

gcctcagagg aagaggagga tggtgctgag gaacccaccg cctctggagg caagagcacc   1440

caccctatgg tgactagaag caaggctgac cag                                1473


<210> SEQ ID NO 85
<211> LENGTH: 1740
<212> TYPE: DNA
<213> ORGANISM: Artificial Sequence
<220> FEATURE:
<223> OTHER INFORMATION: Synthetic polynucleotide

<400> SEQUENCE: 85
```

-continued

```
atggagtcct ctgccaagag aaagatggac cctgataatc ctgacgaggg cccttcctcc     60

aaggtgccac ggcccgagac acccgtgacc aaggccacga cgttcctgca gactatgtta    120

aggaaggagg ttaacagtca gctgagcctg ggagacccgc tgttcccaga attggccgaa    180

gaatccctca agacctttga acaagtgacc gaggattgca acgagaaccc cgagaaagat    240

gtcctgacag aactcggtga catcctcgcc caggctgtca atcatgccgg tatcgattcc    300

agtagcaccg gccccacgct gacaacccac tcttgcagcg ttagcagcgc ccctcttaac    360

aagccgacgc ccaccagcgt cgcggttact aacactcctc tccccggggc atccgctact    420

cccgagctca gcccgcgtaa gaaaccgcgc aagaccacgc gtcctttcaa ggtgattatt    480

aaaccgcccg tgcctcccgc gcctatcatg ctgcccctca tcaaacagga agacatcaag    540

cccgagcccg actttaccat ccagtaccgc aacaagatta tcgataccgc cggctgtatc    600

gtgatctctg atagcgagga agaacagggt gaagaagtcg agacccgcgg tgctaccgcg    660

tcttcccctt ccaccggcag cggcacgccg cgagtgacct ctcccacgca cccgctctcc    720

cagatgaacc accctcctct tcccgatcct ttgggccggc ccgatgaaga tagttcctct    780

tcgtcttcct cctcctgcag ttcggcttcg gacagcgaga gtgagtccga ggagatgaaa    840

tgcagcagtg gcggaggagc atccgtgacc tcgagccacc atgggcgcgg cggttttggt    900

ggcgcggcct cctcctctct gctgagctgc ggacatcaga gcagcggcgg ggcgagcacc    960

ggacctcgca agaagaagag caaacgcatc tccgagttgg acaacgagaa ggtgcgcaat   1020

atcatgaaag ataagaacac gcccttctgc acacccaacg tgcagactcg gcggggtcgc   1080

gtcaagattg acgaggtgag ccgcatgttc cgtcacacca atcgttctct tgagtacaag   1140

aatctgccat tcatgatccc tagtatgcac caagtgttag aagaggccat caaagtttgc   1200

aagaccatgc aggtgaacaa caagggcatt cagatcatct acacccgcaa tcatgaagtg   1260

aagaatgagg tggatcaggt acggtgtcgc ctgggtagca tgtgcaacct ggccctctcc   1320

actcccttcc tcatggagca cactatgcct gtgacacacc ctcctgatgt ggcgcagcgc   1380

acggccgatg cttgtaacga cggtgtcaag gccgtgtgga acctcaaaga actgcacacc   1440

caccaattgt gcccgcgctc ttctgattac cgcaacatga ttatccacgc tgccacgccc   1500

gtggacctgt tgggcgctct caacctgtgc ctgcccctga tgcagaagtt tcccaaacag   1560

gtcatggtgc gcatcttctc caccaaccag ggtgggttca tgctgcctat ctacgagacg   1620

gccgcgaagg cctacgccgt ggggcagttt gagaagccca ccgagacccc tcccgaagac   1680

ctggacaccc tgagcctggc catcgaggca gccatccagg acctgaggaa caaatctcag   1740
```

<210> SEQ ID NO 86
<211> LENGTH: 2721
<212> TYPE: DNA
<213> ORGANISM: Artificial Sequence
<220> FEATURE:
<223> OTHER INFORMATION: Synthetic polynucleotide

<400> SEQUENCE: 86

```
atggaatcca ggatctggtg cctggtagtc tgcgttaact tgtgtatcgt ctgtctgggt     60

gctgcggttt cctcatcttc tactcgtgga acttctgcta ctcacagtca ccattcctct    120

catacgacgt ctgctgctca ctctcgatcc ggttcagtct ctcaacgcgt aacttcttcc    180

caaacggtca gccatggtgt taacgagacc atctacaaca ctaccctcaa gtacggagat    240

gtggtggggg tcaataccac caagtacccc tatcgcgtgt gttctatggc ccagggtacg    300
```

-continued

```
gatcttattc gctttgaacg taatatcgtc tgcacctcga tgaagcccat caatgaagac    360
ctggacgagg gcatcatggt ggtctacaaa cgcaacatcg tcgcgcacac ctttaaggta    420
cgagtctacc agaaggtttt gacgtttcgt cgtagctacg cttacatcca caccacttat    480
ctgctgggca gcaacacgga atacgtggcg cctcctatgt gggagattca tcatatcaac    540
agccacagtc agtgctacag ttcctacagc cgcgttatag caggcacggt tttcgtggct    600
tatcataggg acagctatga aaacaaaacc atgcaattaa tgcccgacga ttattccaac    660
acccacagta cccgttacgt gacggtcaag gatcaatggc acagccgcgg cagcacctgg    720
ctctatcgtg agacctgtaa tctgaattgt atggtgacca tcactactgc gcgctccaaa    780
tatccttatc attttttcgc cacttccacg ggtgacgtgg ttgacatttc tcctttctac    840
aacggaacca atcgcaatgc cagctacttt ggagaaaacg ccgacaagtt tttcattttt    900
ccgaactaca ctatcgtctc cgactttgga agaccgaatt ctgcgttaga gacccacagg    960
ttggtggctt ttcttgaacg tgcggactcg gtgatctcct gggatataca ggacgaaaag   1020
aatgtcactt gtcaactcac tttctgggaa gcctcggaac gcaccattcg ttccgaagcc   1080
gaggactcgt atcacttttc ttctgccaaa atgaccgcca ctttcttatc taagaagcaa   1140
gaggtgaaca tgtccgactc tgcgctggac tgcgtacgtg atgaggctat aaataagtta   1200
cagcagattt tcaatacttc atacaatcaa acatatgaaa aatatggaaa cgtgtccgtc   1260
tttgaaacca ctggtggttt ggtagtgttc tggcaaggta tcaagcaaaa atctctggtg   1320
gaactcgaac gtttggccaa ccgctccagt ctgaatctta ctcataatag aaccaaaaga   1380
agtacagatg gcaacaatgc aactcattta tccaacatgg aatcggtgca caatctggtc   1440
tacgcccagc tgcagttcac ctatgacacg ttgcgcggtt acatcaaccg ggcgctggcg   1500
caaatcgcag aagcctggtg tgtggatcaa cggcgcaccc tagaggtctt caaggaactc   1560
agcaagatca acccgtcagc cattctctcg gccatttaca acaaaccgat tgccgcgcgt   1620
ttcatgggtg atgtcttggg cctggccagc tgcgtgacca tcaaccaaac cagcgtcaag   1680
gtgctgcgtg atatgaacgt gaaggagtcg ccaggacgct gctactcacg acccgtggtc   1740
atctttaatt tcgccaacag ctcgtacgtg cagtacggtc aactgggcga ggacaacgaa   1800
atcctgttgg gcaaccaccg cactgaggaa tgtcagcttc ccagcctcaa gatcttcatc   1860
gccgggaact cggcctacga gtacgtggac tacctcttca aacgcatgat tgacctcagc   1920
agtatctcca ccgtcgacag catgatcgcc ctggatatcg acccgctgga aaataccgac   1980
ttcagggtac tggaacttta ctcgcagaaa gagctgcgtt ccagcaacgt tttgacctc    2040
gaagagatca tgcgcgaatt caactcgtac aagcagcggg taaagtacgt ggaggacaag   2100
gtagtcgacc cgctaccgcc ctacctcaag ggtctggacg acctcatgag cggcctgggc   2160
gccgcgggaa aggccgttgg cgtagccatt ggggccgtgg gtggcgcggt ggcctccgtg   2220
gtcgaaggcg ttgccacctt cctcaaaaac cccttcggag cgttcaccat catcctcgtg   2280
gccatagctg tagtcattat cacttatttg atctatactc gacagcggcg tttgtgcacg   2340
cagccgctgc agaacctctt tccctatctg gtgtccgccg acgggaccac cgtgacgtcg   2400
ggcagcacca aagacacgtc gttacaggct ccgccttcct acgaggaaag tgtttataat   2460
tctggtcgca aaggaccggg accaccgtcg tctgatgcat ccacggcggc tccgccttac   2520
accaacgagc aggcttacca gatgcttctg gccctggccc gtctggacgc agagcagcga   2580
gcgcagcaga acggtacaga ttctttggac ggacggactg gcacgcagga caagggacag   2640
aagcccaacc tactagaccg actgcgacat cgcaaaaacg gctaccgaca cttgaaagac   2700
```

```
tctgacgaag aagagaacgt c                                          2721


<210> SEQ ID NO 87
<211> LENGTH: 2226
<212> TYPE: DNA
<213> ORGANISM: Artificial Sequence
<220> FEATURE:
<223> OTHER INFORMATION: Synthetic polynucleotide

<400> SEQUENCE: 87

atgcggccag gcctcccctc ctacctcatc atcctcgccg tctgtctctt cagccaccta     60

ctttcgtcac gatatggcgc agaagccgta tccgaaccgc tggacaaagc gtttcaccta    120

ctgctcaaca cctacgggag acccatccgc ttcctgcgtg aaaataccac ccagtgtacc    180

tacaacagca gcctccgtaa cagcacggtc gtcagggaaa acgccatcag tttcaacttc    240

ttccaaagct ataatcaata ctatgtattc catatgcctc gatgtctctt tgcgggtcct    300

ctggcggagc agtttctgaa ccaggtagat ctgaccgaaa ccctggaaag ataccaacag    360

agacttaaca cttacgcgct ggtatccaaa gacctggcca gctaccgatc tttctcgcag    420

cagctaaagg cacaagacag cctaggtgaa cagcccacca ctgtgccacc gcccattgac    480

ctgtcaatac ctcacgtttg gatgccaccg caaaccactc cacacggctg gacagaatca    540

cataccacct caggactaca ccgaccacac tttaaccaga cctgtatcct ctttgatgga    600

cacgatctac tattcagcac cgtcacacct tgtttgcacc aaggctttta cctcatcgac    660

gaactacgtt acgttaaaat aacactgacc gaggacttct tcgtagttac ggtgtccata    720

gacgacgaca cacccatgct gcttatcttc ggccatcttc cacgcgtact tttcaaagcg    780

ccctatcaac gcgacaactt tatactacga caaactgaga aacacgagct cctggtgcta    840

gttaagaaag atcaactgaa ccgtcactct tatctcaaag acccggactt tcttgacgcc    900

gcacttgact tcaactacct agacctcagc gcactactac gtaacagctt tcaccgttac    960

gccgtggatg tactcaagag cggtcgatgt cagatgctgg accgccgcac ggtagaaatg   1020

gccttcgcct acgcattagc actgttcgca gcagcccgac aagaagaggc cggcgcccaa   1080

gtctccgtcc cacgggccct agaccgccag gccgcactct tacaaataca agaatttatg   1140

atcacctgcc tctcacaaac accaccacgc accacgttgc tgctgtatcc cacggccgtg   1200

gacctggcca aacgagccct ttggacaccg aatcagatca ccgacatcac cagcctcgta   1260

cgcctggtct acatactctc taaacagaat cagcaacatc tcatccccca atgggcacta   1320

cgacagatcg ccgactttgc cctaaaacta cacaaaacgc acctggcctc ttttctttca   1380

gccttcgcac gccaagaact ctacctcatg ggcagcctcg tccactccat gctggtacat   1440

acgacggaga gacgcgaaat cttcatcgta gaaacgggcc tctgttcatt ggccgagcta   1500

tcacacttta cgcagttgtt agctcatcca caccacgaat acctcagcga cctgtacaca   1560

ccctgttcca gtagcgggcg acgcgatcac tcgctcgaac gcctcacgcg tctcttcccc   1620

gatgccaccg tccccgctac cgttcccgcc gccctctcca tcctatctac catgcaacca   1680

agcacgctgg aaaccttccc cgacctgttt tgcttgccgc tcggcgaatc cttctccgcg   1740

ctgaccgtct ccgaacacgt cagttatatc gtaacaaacc agtacctgat caaaggtatc   1800

tcctaccctg tctccaccac cgtcgtaggc cagagcctca tcatcaccca gacggacagt   1860

caaactaaat gcgaactgac gcgcaacatg cataccacac acagcatcac agtggcgctc   1920

aacatttcgc tagaaaactg cgccttttgc caaagcgccc tgctagaata cgacgacacg   1980
```

```
caaggcgtca tcaacatcat gtacatgcac gactcggacg acgtcctttt cgccctggat   2040

ccctacaacg aagtggtggt ctcatctccg cgaactcact acctcatgct tttgaagaac   2100

ggtacggtac tagaagtaac tgacgtcgtc gtggacgcca ccgacagtcg tctcctcatg   2160

atgtccgtct acgcgctatc ggccatcatc ggcatctatc tgctctaccg catgctcaag   2220

acatgc                                                              2226
```

<210> SEQ ID NO 88
<211> LENGTH: 2226
<212> TYPE: DNA
<213> ORGANISM: Artificial Sequence
<220> FEATURE:
<223> OTHER INFORMATION: Synthetic polynucleotide

<400> SEQUENCE: 88

```
atgcggccag gcctcccctc ctacctcatc atcctcgccg tctgtctctt cagccaccta     60

ctttcgtcac gatatggcgc agaagccgta tccgaaccgc tggacaaagc gtttcaccta    120

ctgctcaaca cctacgggag acccatccgc ttcctgcgtg aaaataccac ccagtgtacc    180

tacaacagca gcctccgtaa cagcacggtc gtcagggaaa acgccatcag tttcaacttc    240

ttccaaagct ataatcaata ctatgtattc catatgcctc gatgtctctt tgcgggtcct    300

ctggcggagc agtttctgaa ccaggtagat ctgaccgaaa ccctggaaag ataccaacag    360

agacttaaca cttacgcgct ggtatccaaa gacctggcca gctaccgatc tttctcgcag    420

cagctaaagg cacaagacag cctaggtgaa cagcccacca ctgtgccacc gcccattgac    480

ctgtcaatac ctcacgtttg gatgccaccg caaaccactc cacacggctg gacagaatca    540

cataccacct caggactaca ccgaccacac tttaaccaga cctgtatcct ctttgatgga    600

cacgatctac tattcagcac cgtcacacct tgtttgcacc aaggctttta cctcatcgac    660

gaactacgtt acgttaaaat aacactgacc gaggacttct tcgtagttac ggtgtccata    720

gacgacgaca cacccatgct gcttatcttc ggccatcttc cacgcgtact tttcaaagcg    780

ccctatcaac gcgacaactt tatactacga caaactgaga aacacgagct cctggtgcta    840

gttaagaaag atcaactgaa ccgtcactct tatctcaaag acccggactt tcttgacgcc    900

gcacttgact tcaactacct agacctcagc gcactactac gtaacagctt tcaccgttac    960

gccgtggatg tactcaagag cggtcgatgt cagatgctgg accgccgcac ggtagaaatg   1020

gccttcgcct acgcattagc actgttcgca gcagcccgac aagaagaggc cggcgcccaa   1080

gtctccgtcc cacgggccct agaccgccag gccgcactct tacaaataca agaatttatg   1140

atcacctgcc tctcacaaac accaccacgc accacgttgc tgctgtatcc cacggccgtg   1200

gacctggcca aacgagccct ttggacaccg aatcagatca ccgacatcac cagcctcgta   1260

cgcctggtct acatactctc taaacagaat cagcaacatc tcatccccca atgggcacta   1320

cgacagatcg ccgactttgc cctaaaacta cacaaaacgc acctggcctc ttttctttca   1380

gccttcgcac gccaagaact ctacctcatg ggcagcctcg tccactccat gctggtacat   1440

acgacggaga gacgcgaaat cttcatcgta gaaacgggcc tctgttcatt ggccgagcta   1500

tcacacttta cgcagttgtt agctcatcca caccacgaat acctcagcga cctgtacaca   1560

ccctgttcca gtagcgggcg acgcgatcac tcgctcgaac gcctcacgcg tctcttcccc   1620

gatgccaccg tccccgctac cgttcccgcc gccctctcca tcctatctac catgcaacca   1680

agcacgctgg aaaccttccc cgacctgttt tgcttgccgc tcggcgaatc cttctccgcg   1740

ctgaccgtct ccgaacacgt cagttatatc gtaacaaacc agtacctgat caaaggtatc   1800
```

-continued tcctaccctg tctccaccac cgtcgtaggc cagagcctca tcatcaccca gacggacagt 1860
caaactaaat gcgaactgac gcgcaacatg cataccacac acagcatcac agtggcgctc 1920
aacatttcgc tagaaaactg cgccttttgc caaagcgccc tgctagaata cgacgacacg 1980
caaggcgtca tcaacatcat gtacatgcac gactcggacg acgtcctttt cgccctggat 2040
ccctacaacg aagtggtggt ctcatctccg cgaactcact acctcatgct tttgaagaac 2100
ggtacggtac tagaagtaac tgacgtcgtc gtggacgcca ccgacagtcg tctcctcatg 2160
atgtccgtct acgcgctatc ggccatcatc ggcatctatc tgctctaccg catgctcaag 2220
acatgc 2226

<210> SEQ ID NO 89
<211> LENGTH: 513
<212> TYPE: DNA
<213> ORGANISM: Artificial Sequence
<220> FEATURE:
<223> OTHER INFORMATION: Synthetic polynucleotide

<400> SEQUENCE: 89
atgagtccca aagatctgac gccgttcttg acggcgttgt ggctgctatt gggtcacagc 60
cgcgtgccgc gggtgcgcgc agaagaatgt tgcgaattca taaacgtcaa ccacccgccg 120
gaacgctgtt acgatttcaa aatgtgcaat cgcttcaccg tcgcgctgcg gtgtccggac 180
ggcgaagtct gctacagtcc cgagaaaacg gctgagattc gcgggatcgt caccaccatg 240
acccattcat tgacacgcca ggtcgtacac aacaaactga cgagctgcaa ctacaatccg 300
ttatacctcg aagctgacgg gcgaatacgc tgcggcaaag taaacgacaa ggcgcagtac 360
ctgctgggcg ccgctggcag cgttccctat cgatggatca atctggaata cgacaagata 420
acccggatcg tgggcctgga tcagtacctg gagagcgtta agaaacacaa acggctggat 480
gtgtgccgcg ctaaaatggg ctatatgctg cag 513

<210> SEQ ID NO 90
<211> LENGTH: 834
<212> TYPE: DNA
<213> ORGANISM: Artificial Sequence
<220> FEATURE:
<223> OTHER INFORMATION: Synthetic polynucleotide

<400> SEQUENCE: 90
atgtgccgcc gcccggattg cggcttctct ttctcacctg gaccggtgat actgctgtgg 60
tgttgccttc tgctgcccat tgtttcctca gccgccgtca gcgtcgctcc taccgccgcc 120
gagaaagtcc ccgcggagtg ccccgaacta acgcgccgat gcttgttggg tgaggtgttt 180
gagggtgaca agtatgaaag ttggctgcgc ccgttggtga atgttaccgg gcgcgatggc 240
ccgctatcgc aacttatccg ttaccgtccc gttacgccgg aggccgccaa ctccgtgctg 300
ttggacgagg ctttcctgga cactctggcc ctgctgtaca acaatccgga tcaattgcgg 360
gccctgctga cgctgttgag ctcggacaca gcgccgcgct ggatgacggt gatgcgcggc 420
tacagcgagt gcggcgatgg ctcgccggcc gtgtacacgt gcgtggacga cctgtgccgc 480
ggctacgacc tcacgcgact gtcatacggg cgcagcatct tcacggaaca cgtgttaggc 540
ttcgagctgg tgccaccgtc tctctttaac gtggtggtgg ccatacgcaa cgaagccacg 600
cgtaccaacc gcgccgtgcg tctgcccgtg agcaccgctg ccgcgcccga gggcatcacg 660
ctcttttacg gcctgtacaa cgcagtgaag gaattctgcc tgcgtcacca gctggacccg 720

```
ccgctgctac gccacctaga taaatactac gccggactgc cgcccgagct gaagcagacg    780

cgcgtcaacc tgccggctca ctcgcgctat ggccctcaag cagtggatgc tcgc          834
```

```
<210> SEQ ID NO 91
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 91

atgctgcggc ttctgcttcg tcaccacttt cactgcctgc ttctgtgcgc ggtttgggca     60

acgccctgtc tggcgtctcc gtggtcgacg ctaacagcaa accagaatcc gtccccgcca    120

tggtctaaac tgacgtattc caaaccgcat gacgcggcga cgttttactg tccttttctc    180

tatccctcgc ccccacgatc ccccttgcaa ttctcggggt tccagcgggt atcaacgggt    240

cccgagtgtc gcaacgagac cctgtatctg ctgtacaacc gggaaggcca gaccttggtg    300

gagagaagct ccacctgggt gaaaaaggtg atctggtacc tgagcggtcg gaaccaaacc    360

atcctccaac ggatgccccg aacggcttcg aaaccgagcg acggaaacgt gcagatcagc    420

gtggaagacg ccaagatttt tggagcgcac atggtgccca agcagaccaa gctgctacgc    480

ttcgtcgtca acgatggcac acgttatcag atgtgtgtga tgaagctgga gagctgggct    540

cacgtcttcc gggactacag cgtgtctttt caggtgcgat tgacgttcac cgaggccaat    600

aaccagactt acaccttctg cacccatccc aatctcatcg tt                       642
```

```
<210> SEQ ID NO 92
<211> LENGTH: 1671
<212> TYPE: DNA
<213> ORGANISM: Artificial Sequence
<220> FEATURE:
<223> OTHER INFORMATION: Synthetic polynucleotide

<400> SEQUENCE: 92

atggagtcgc gcggtcgccg ttgtcccgaa atgatatccg tactgggtcc catttcgggg     60

cacgtgctga aagccgtgtt tagtcgcggc gatacgccgg tgctgccgca cgagacgaga    120

ctcctgcaga cgggtatcca cgtacgcgtg agccagccct cgctgatcct ggtgtcgcag    180

tacacgcccg actcgacgcc atgccaccgc ggcgacaatc agctgcaggt gcagcacacg    240

tactttacgg gcagcgaggt ggagaacgtg tcggtcaacg tgcacaaccc cacgggccga    300

agcatctgcc ccagccaaga gcccatgtcg atctatgtgt acgcgctgcc gctcaagatg    360

ctgaacatcc ccagcatcaa cgtgcaccac tacccgtcgg cggccgagcg caaacaccga    420

cacctgcccg tagccgacgc tgttattcac gcgtcgggca agcagatgtg gcaggcgcgt    480

ctcacggtct cgggactggc ctggacgcgt cagcagaacc agtggaaaga gcccgacgtc    540

tactacacgt cagcgttcgt gtttcccacc aaggacgtgg cactgcggca cgtggtgtgc    600

gcgcacgagc tggtttgctc catggagaac acgcgcgcaa ccaagatgca ggtgataggt    660

gaccagtacg tcaaggtgta cctggagtcc ttctgcgagg acgtgccctc cggcaagctc    720

tttatgcacg tcacgctggg ctctgacgtg gaagaggacc taacgatgac ccgcaacccg    780

caacccttca tgcgccccca cgagcgcaac ggctttacgg tgttgtgtcc caaaaaatatg   840

ataatcaaac cgggcaagat ctcgcacatc atgctggatg tggcttttac ctcacacgag    900

cattttgggc tgctgtgtcc caagagcatc ccgggcctga gcatctcagg taacctgttg    960

atgaacgggc agcaaatctt cctggaggta caagcgatac gcgagaccgt ggaactgcgt   1020
```

cagtacgatc ccgtggctgc gctcttcttt ttcgatatcg acttgttgct gcagcgcggg 1080
cctcagtaca gcgagcaccc caccttcacc agccagtatc gcatccaggg caagcttgag 1140
taccgacaca cctgggaccg gcacgacgag ggtgccgccc agggcgacga cgacgtctgg 1200
accagcggat cggactccga cgaagaactc gtaaccaccg agcgtaagac gccccgcgtc 1260
accggcggcg gagccatggc gagcgcctcc acttccgcgg gctcagcatc ctcggcgacg 1320
gcgtgcacgg cgggcgttat gacacgcggc cgccttaagg ccgagtccac cgtcgcgccc 1380
gaagaggaca ccgacgagga ttccgacaac gaaatccaca atccggccgt gttcacctgg 1440
ccgccctggc aggccggcat cctggcccgc aacctggtgc ccatggtggc tacggttcag 1500
ggtcagaatc tgaagtacca ggagttcttc tgggacgcca acgacatcta ccgcatcttc 1560
gccgaattgg aaggcgtatg gcagcccgct gcgcaaccca aacgtcgccg ccaccggcaa 1620
gacgccttgc ccgggccatg catcgcctcg acgcccaaaa agcaccgagg t 1671

<210> SEQ ID NO 93
<211> LENGTH: 1683
<212> TYPE: DNA
<213> ORGANISM: Artificial Sequence
<220> FEATURE:
<223> OTHER INFORMATION: Synthetic polynucleotide

<400> SEQUENCE: 93
atggagtcgc gcggtcgccg ttgtcccgaa atgatatccg tactgggtcc catttcgggg 60
cacgtgctga aagccgtgtt tagtcgcggc gatacgccgg tgctgccgca cgagacgcga 120
ctcctgcaga cgggtatcca cgtacgcgtg agccagccct cgctgatcct ggtgtcgcag 180
tacacgcccg actcgacgcc atgccaccgc ggcgacaatc agctgcaggt gcagcacacg 240
tactttacgg gcagcgaggt ggagaacgtg tcggtcaacg tgcacaaccc cacgggccga 300
agcatctgcc ccagccaaga gcccatgtcg atctatgtgt acgcgctgcc gctcaagatg 360
ctgaacatcc ccagcatcaa cgtgcaccac tacccgtcgg cggccgagcg caaacaccga 420
cacctgcccg tagccgacgc tgttattcac gcgtcgggca agcagatgtg gcaggcgcgt 480
ctcacggtct cgggactggc ctggacgcgt cagcagaacc agtggaaaga gcccgacgtc 540
tactacacgt cagcgttcgt gtttcccacc aaggacgtgg cactgcggca cgtggtgtgc 600
gcgcacgagc tggtttgctc catggagaac acgcgcgcaa ccaagatgca ggtgataggt 660
gaccagtacg tcaaggtgta cctggagtcc ttctgcgagg acgtgccctc cggcaagctc 720
tttatgcacg tcacgctggg ctctgacgtg gaagaggacc taacgatgac ccgcaacccg 780
caacccttca tgcgccccca cgagcgcaac ggctttacgg tgttgtgtcc caagaatatg 840
ataatcaaac cgggcaagat ctcgcacatc atgctggatg tggcttttac ctcacacgag 900
cattttgggc tgctgtgtcc caagagcatc ccgggcctga gcatctcagg taacctgttg 960
atgaacgggc agcaaatctt cctggaggta caagcgatac gcgagaccgt ggaactgcgt 1020
cagtacgatc ccgtggctgc gctcttcttt ttcgatatcg acttgttgct gcagcgcggg 1080
cctcagtaca gcgagcaccc caccttcacc agccagtatc gcatccaggg caagcttgag 1140
taccgacaca cctgggaccg gcacgacgag ggtgccgccc agggcgacga cgacgtctgg 1200
accagcggat cggactccga cgaagaactc gtaaccaccg agcgtaagac gccccgcgtc 1260
accggcggcg gcgccatggc gagcgcctcc acttccgcgg gccgcaaacg caaatcagca 1320
tcctcggcga cggcgtgcac ggcgggcgtt atgacacgcg gccgccttaa ggccgagtcc 1380
accgtcgcgc ccgaagagga caccgacgag gattccgaca acgaaatcca caatccggcc 1440
gtgttcacct ggccgccctg gcaggccggc atcctggccc gcaacctggt gcccatggtg 1500
gctacggttc agggtcagaa tctgaagtac caggagttct tctgggacgc caacgacatc 1560
taccgcatct tcgccgaatt ggaaggcgta tggcagcccg ctgcgcaacc caaacgtcgc 1620
cgccaccggc aagacgcctt gcccgggcca tgcatcgcct cgacgcccaa gaagcaccga 1680
ggt 1683

<210> SEQ ID NO 94
<211> LENGTH: 2721
<212> TYPE: DNA
<213> ORGANISM: Artificial Sequence
<220> FEATURE:
<223> OTHER INFORMATION: Synthetic polynucleotide

<400> SEQUENCE: 94
atggaaagcc ggatctggtg tcttgtggtg tgcgtgaatc tttgcatcgt gtgcttgggt 60
gccgccgtgt catctagcag cacaagaggc acctccgcca ctcactcaca ccacagcagc 120
cacacgacca gcgccgctca ctccagaagc ggctctgtaa gccagagagt gaccagttct 180
caaaccgtca gccacggcgt caatgagacg atatataata caaccctgaa gtatggagac 240
gtggtgggtg tcaataccac caagtaccct tatcgcgtgt gcagcatggc ccagggcact 300
gacctgatca gattcgagag aaatatcgtc tgcacctcca tgaagcctat caacgaggac 360
cttgacgagg gcatcatggt tgtctacaag agaaacattg tggctcacac cttcaaggtg 420
agagtgtatc agaaagtact gacctttagg agatcctacg cttacatcca caccacgtac 480
ctgctcggct ccaacaccga gtatgtggct ccacccatgt gggagattca tcacatcaat 540
tcccacagcc aatgttacag ttcctatagc agagtcattg ctggtaccgt gttcgtcgct 600
taccacagag acagctatga gaacaagacc atgcagttga tgcccgatga ctactccaat 660
acacactcta caaggtatgt gacagtcaaa gatcagtggc acagccgggg cagcacctgg 720
ctgtaccgag agacatgtaa tctgaattgt atggtgacta tcactacagc caggagcaaa 780
tatccatacc acttcttcgc cactagcacc ggggacgtcg tggacatttc cccattctac 840
aatggcacaa acagaaacgc cagctacttc ggcgagaatg ccgacaagtt ctttatattc 900
cccaactata ccatcgtgag cgacttcggc cgccccaaca gcgccctgga aacccaccgg 960
ctcgtggcct ttctcgagcg ggccgatagc gtcatatcct gggacatcca ggacgagaag 1020
aatgtgacat gccagctgac cttctgggag gcctccgagc gtaccatccg gtccgaggca 1080
gaggacagct accatttcag cagcgccaag atgaccgcaa ccttcctcag taagaaacag 1140
gaggttaaca tgtctgattc tgccctggac tgcgtgcgcg atgaggcaat caacaagctg 1200
cagcagatct tcaacacatc ttacaaccaa acttacgaga agtacggcaa cgtcagcgtg 1260
ttcgagacaa caggaggcct ggtagtgttc tggcaaggta tcaagcagaa gagtctggtg 1320
gagctcgagc gactggctaa ccgcagctcc ctcaacctga cccataatag gacaaagaga 1380
agcaccgacg gcaacaacgc tactcatttg agcaacatgg aatccgtgca caacctggtg 1440
tatgcccagc tgcagttcac ttacgacacc ctgagaggct acatcaatag agccttagct 1500
cagatcgcag aggcttggtg tgtggaccag cgaagaactc tggaggtgtt caaggagtta 1560
agtaagatca atccatccgc catcctgtct gctatctaca acaagcccat tgccgccagg 1620
ttcatgggag atgtgctcgg cctggctagt tgtgtcacca tcaaccagac ctccgtgaag 1680
gtgctgcggg acatgaatgt gaaggagagc cccggtcggt gttactccag accagtggtg 1740

```
attttcaact tcgccaacag ctcctatgtg cagtacggac agctcggaga ggataacgag   1800
atcttgctcg gcaatcacag aactgaggag tgtcagctgc catcactgaa gatatttatt   1860
gccgggaatt ccgcctacga atacgttgac taccttttca agagaatgat cgacctgagc   1920
agcatcagca ccgtcgacag catgattgct ctcgatatcg accctctgga gaacaccgac   1980
tttagagtcc ttgagctgta ttcacagaag gagctgagga gctccaatgt gttcgacctg   2040
gaggaaatca tgagagagtt caactcttac aagcagcggg tgaagtacgt ggaggataag   2100
gtagtggacc cactcccacc atacctgaaa ggactcgacg atctcatgag cggactgggc   2160
gcagccggga aggctgttgg cgtcgccatc ggagcggtcg gaggagcagt ggctagcgtg   2220
gtggagggcg tggccacctt cctgaagaac cctttcggcg cctttaccat catcctggtg   2280
gccatcgccg tggtcatcat tacatatctg atttatacaa gacagagaag gctctgcacc   2340
cagcccttgc agaacctgtt cccctacctg gtcagtgccg acggtacaac cgtgaccagc   2400
ggtagcacca aggacacctc cctgcaggca ccgccgagct acgaggagtc cgtgtataac   2460
agtggaagaa agggccccgg accgcccagc agcgacgcat ccaccgccgc tcctccctac   2520
acaaatgagc aggcctatca gatgttgctg gctctggcac gcctggacgc cgagcagcga   2580
gctcagcaga acggcaccga ttccctggat ggacgcacag gcacacagga caaggggcag   2640
aagcccaacc tcctcgacag actgagacac cggaagaacg gatacaggca tctgaaggac   2700
tccgatgagg aggagaacgt t                                             2721
```

<210> SEQ ID NO 95
<211> LENGTH: 2721
<212> TYPE: DNA
<213> ORGANISM: Artificial Sequence
<220> FEATURE:
<223> OTHER INFORMATION: Synthetic polynucleotide

<400> SEQUENCE: 95

```
atggaatcca ggatctggtg cctcgtggtc tgtgtgaact tgtgcatcgt gtgcttgggt     60
gccgccgtga gcagtagcag caccagaggc accagcgcaa cacactcaca ccacagctcc    120
cataccactt ccgccgccca ctccagatcg ggctccgtga gccagagggt caccagcagc    180
cagacggtgt cccacggagt gaatgaaacc atctacaaca ctactctgaa gtacggagac    240
gtcgtcggcg tgaataccac taagtacccc tacagggtct gctctatggc ccaaggcaca    300
gacctgatca gatttgaaag aaatatcgtc tgtacctcca tgaagcccat caatgaggac    360
ttagacgagg gcattatggt ggtgtataaa cgcaacattg tggcccacac tttcaaggtc    420
agagtgtatc agaaagtgct caccttcagg cgtagctatg cctatatcca caccacttat    480
ctcctcggca gcaacaccga gtatgttgcc ccgcctatgt gggagattca ccatataaat    540
agccatagcc agtgctacag ctcctattcg agagtaatcg ccggaaccgt tttcgtcgcc    600
taccacagag actcgtacga gaacaagaca atgcagctga tgccagatga ctattcgaac    660
acccacagca cgagatatgt caccgtgaaa gatcagtggc acagcagggg tagtacatgg    720
ttgtataggg aaacctgcaa tctcaattgc atggtgacca tcaccaccgc cagaagcaaa    780
taccccctatc atttcttcgc tacctcgaca ggagacgtgg tggacatatc tccctttttat    840
aatggcacaa atagaaatgc tagctacttt ggagagaacg ccgacaaatt cttcatcttc    900
cctaactata ccatcgtgag cgactttggg cgacctaaca gcgccctcga gactcacagg    960
ctggtggctt tcttagagag ggctgatagt gttatctctt gggacattca ggatgagaag   1020
```

```
aacgtgacat gccagctgac attttgggag gctagcgagc gaaccatcag gtccgaggcc   1080

gaggacagct accatttctc tagtgccaag atgaccgcca ccttcttgtc aaagaagcaa   1140

gaggtgaaca tgtccgactc tgcgctggac tgtgtccgcg acgaggcaat taataaactg   1200

cagcagatct ttaataccag ctacaaccag acatacgaga agtatggcaa cgtgagcgtc   1260

ttcgaaacca caggcggcct tgtcgtcttt tggcaaggca tcaagcagaa gagtctggtg   1320

gagctggaaa gactcgccaa ccggtcatcc ctgaatctga cccacaatag gacaaagcgc   1380

agcaccgatg ggaacaacgc cacccacctg tcgaacatgg agtcagtgca caacctggtg   1440

tacgcccagc tgcagttcac ttatgatacc ctcagaggct acattaaccg cgcactggct   1500

cagatcgccg aagcatggtg cgtggaccag cggcgaaccc tggaagtgtt taaagagctc   1560

tccaagatta atcctagcgc catcctgagt gctatctaca ataagcctat cgccgcaaga   1620

tttatgggcg acgtgctggg actggcttcc tgcgtgacaa ttaaccagac ctccgtcaag   1680

gtgctgaggg acatgaacgt gaaggagagc cccggcagat gctatagccg gccagtggtg   1740

atcttcaatt tcgccaacag ctcatacgtg cagtacggcc agctcgggga ggataatgaa   1800

atcctgctgg gaaatcacag aaccgaggag tgtcagctgc ccagtctgaa gattttcatc   1860

gcaggcaaca gtgcctatga atacgtggac tatctgttca aacgcatgat cgatctgagc   1920

tctatctcca ccgtggactc catgattgcc ttggatatcg acccactgga gaacaccgat   1980

ttcagagtgc tggagctgta cagccagaag gagctcaggt ccagcaatgt gttcgacctg   2040

gaggaaatca tgagagagtt caactcctac aaacagagag tcaagtacgt ggaggacaag   2100

gtggtggatc ccctgcctcc ctacctgaag gggctggacg acctgatgag tggcctggga   2160

gccgccggca aagctgtggg agtggccatc ggtgccgtcg gaggggctgt ggccagcgtc   2220

gtcgagggag ttgccacatt cctgaagaac cccttcgggg ccttcaccat tatcctagtc   2280

gccattgccg tggtcatcat tacctatctg atctacacgc ggcagagacg gctgtgcacc   2340

cagcctttgc agaacctgtt cccctattta gtgtccgctg acgggaccac tgtgacaagc   2400

ggaagcacca aggacacatc cctgcaggcc ccacccagct acgaggagtc tgtttacaat   2460

tctggccgga agggccccgg ccctccctct tctgacgcct ccaccgcagc ccctccttac   2520

acaaacgagc aggcttacca gatgctgttg gctttggccc gtctggacgc cgaacagagg   2580

gcccagcaga atggcaccga ctccttggac ggccggacag ggacccagga taagggtcag   2640

aagcctaacc tactggatcg gctccgccat cgcaagaatg gctacagaca tctcaaggac   2700

agcgacgaag aagagaatgt g                                             2721
```

<210> SEQ ID NO 96
<211> LENGTH: 2721
<212> TYPE: DNA
<213> ORGANISM: Artificial Sequence
<220> FEATURE:
<223> OTHER INFORMATION: Synthetic polynucleotide

<400> SEQUENCE: 96

```
atggaatcaa gaatctggtg tctcgtggtg tgcgtgaacc tgtgtatcgt ctgtcttggc     60

gccgccgtct cttcctcaag cacccggggt accagtgcca cccactcaca tcactcctcc    120

cacactacca gcgccgccca cagcagatcc ggctccgtgt cccagcgggt gaccagcagc    180

cagaccgtgt cacacggcgt taatgaaacc atttacaaca ccacactgaa gtacggggac    240

gtggtgggcg tgaacaccac caagtatccc tacagggtgt gcagcatggc ccagggcacc    300

gacctgattc ggttcgagag aaacatcgtg tgcacatcca tgaagcctat caatgaggac    360
```

-continued

```
ctcgacgagg gcatcatggt ggtttacaag aggaacattg tcgcacacac atttaaggtg    420
cgagtgtacc agaaggtgtt aaccttcaga aggtcctacg catacatcca caccacctac    480
ctcctgggct ctaacacaga atacgtcgcc cctcccatgt gggagattca ccacatcaac    540
agtcacagcc agtgctacag ctcgtatagc agagttatcg ctggcaccgt gttcgtggct    600
tatcaccgcg acagctacga gaacaagacg atgcaactta tgcccgacga ttactcaaac    660
acgcactcca ctagatacgt gactgtgaag gaccagtggc acagtagagg cagcacctgg    720
ctgtaccggg aaacatgcaa tctcaattgt atggtcacca ttaccaccgc caggtccaag    780
tacccttacc acttcttcgc cacctccact ggcgacgtgg tcgacatcag cccctctac    840
aatggcacca acaggaacgc ctcttacttt ggggagaacg ccgataaatt ctttattttc    900
cccaactaca ctattgtctc cgactttggc agacccaact cagcattgga aacccacagg    960
ctcgtggcct tcctggagcg ggccgatagt gtgatcagct gggacatcca ggatgagaag   1020
aacgtgacat gccagctgac cttctgggag gccagcgaac gaaccatccg gtccgaggcc   1080
gaggactctt atcacttctc tagcgcaaag atgaccgcca ccttcctgtc taagaaacag   1140
gaggtgaaca tgagcgacag cgccctggac tgcgtcagag acgaggcaat caacaagctg   1200
cagcaaatct tcaacaccag ctacaaccaa acctacgaga aatacggcaa cgtcagcgtc   1260
ttcgagacta ccggagggct cgttgttttc tggcagggca ttaagcagaa gtctctggtc   1320
gagctggaaa ggctggccaa tagaagctcc ctaaacctca ctcacaacag aactaagaga   1380
agcaccgatg gcaataacgc cactcatctg agtaacatgg agtctgttca caacctggtg   1440
tatgcccagc tgcagtttac ttatgacaca ctgaggggct acatcaatcg agccctggcc   1500
cagatcgccg aggcttggtg cgtcgaccag agaagaacac tggaagtgtt caaggagctg   1560
agtaagatta atcccagcgc cattctgtcc gccatctaca ataagccaat cgccgcaaga   1620
ttcatgggtg acgtgctggg cctggcctcc tgcgtgacaa tcaaccagac aagcgtgaaa   1680
gtcctcagag acatgaacgt caaggagtct cctggcaggt gttactcccg gcccgtggtg   1740
atatttaatt tcgccaacag cagttacgtg cagtacggac agctgggcga ggataacgag   1800
atactgctcg gaaaccatag aacagaggag tgccaactgc cctccctgaa gattttcatc   1860
gccgggaaca gcgcctatga gtatgttgac tatctgttca agcggatgat cgacctgagt   1920
tctatcagca ccgttgactc catgattgct ctcgatatcg atcctctgga gaacaccgat   1980
ttcagagtgc tggaactcta ctctcagaaa gagctaagaa gctcgaacgt gttcgacctg   2040
gaagaaatca tgagagagtt caactcctac aaacagaggg ttaagtacgt agaggataag   2100
gtcgtggacc ctctgcctcc ataccttaag ggattagatg atctgatgag cggcctgggc   2160
gctgccggaa aggccgtggg agtggccatc ggcgcagtgg gtggtgccgt ggctagcgtc   2220
gtggaaggcg ttgccacatt cttgaagaac ccattcgggg ccttcacaat catcctggtg   2280
gctatcgccg ttgtgattat cacatatctg atctacactc gccagcggag gctctgcacc   2340
cagcctctgc agaacctttt cccctaccta gtgtccgctg atgggactac agtcactagc   2400
ggcagcacta aggacacatc cctgcaggct cctccatctt acgaggagag cgtgtataac   2460
tccgggcgca agggacctgg ccctcccagc agcgacgcca gcacggcggc tcctccctac   2520
accaacgagc aggcatacca gatgttgctt gcactggccc gtctggacgc tgagcagagg   2580
gcccagcaga atgggactga ttccctggac ggcagaaccg gcacacagga taaaggacag   2640
aaaccgaatc tgctcgacag gctgaggcac cggaagaatg gatacaggca tctgaaggac   2700
```

agtgacgagg aggagaacgt g 2721

<210> SEQ ID NO 97
<211> LENGTH: 2721
<212> TYPE: DNA
<213> ORGANISM: Artificial Sequence
<220> FEATURE:
<223> OTHER INFORMATION: Synthetic polynucleotide

<400> SEQUENCE: 97
atggagtcaa gaatctggtg cttggtggtg tgtgtgaact tgtgtatcgt gtgccttgga 60
gccgccgtga gcagcagctc caccagaggc accagcgcca cccacagcca tcactcttcc 120
cacaccacaa gcgccgccca ctcgcggagc gggagtgttt cccaacgggt gacaagcagc 180
cagactgtga gccacggcgt taacgagaca atctacaaca caacactgaa gtacggcgac 240
gtggtgggtg taaatactac caagtatcct tacagggtgt gctctatggc ccagggtacc 300
gacctgatca ggtttgagag aaacattgtt tgcacaagca tgaagcccat caatgaggac 360
ttggatgagg gcatcatggt ggtttacaag agaaatatcg tggcccacac cttcaaagtg 420
agggtgtatc agaaggtgct gacctttaga aggagctacg cttatatcca cacaacctac 480
cttctgggca gcaacaccga gtacgtcgca ccacccatgt gggaaattca ccacatcaac 540
tctcactccc agtgctattc cagctacagc agagtgatag ccggcacagt cttcgtggcc 600
taccacaggg atagttacga gaataagacg atgcaactga tgcctgacga ttactccaac 660
acacacagca cccggtacgt caccgtgaag gaccagtggc actccagagg tagtacttgg 720
ctgtaccggg agacttgtaa cctgaactgc atggtgacaa ttaccactgc tcgaagcaag 780 taccccttacc acttctttgc cacctctacc ggcgatgtcg tagacatatc tcctttctat 840
aacgggacca acagaaacgc ttcgtacttc ggcgagaacg ctgacaagtt cttcatcttc 900
ccgaactaca ctatagttag cgactttggt aggccgaaca gcgccctgga gacacaccga 960
cttgtggcct tcctcgagag agctgacagc gtgatctcct gggacatcca ggacgagaag 1020
aacgtcacct gccagctgac attctgggag gcctctgaga ggaccatcag atccgaggcc 1080
gaggattcat accactttag cagcgctaag atgaccgcta ccttcctgag taagaagcag 1140
gaagtgaaca tgtccgactc agccctcgac tgcgtgaggg acgaggccat caacaagctg 1200
cagcagatct tcaacacctc ctacaaccag acatatgaga agtatggtaa cgtgagcgtg 1260
ttcgagacaa ccggcggact ggtcgtgttt tggcagggca taaagcagaa gtctctggtc 1320
gagctggaga ggctggcgaa caggagcagc ctcaacctga cccataacag aaccaaacgc 1380
agcaccgacg gcaacaatgc tacccacctg tcaaacatgg agagcgtcca caacctggtg 1440
tatgcccagc tgcaatttac atacgacacg ctgcgcggct acatcaatag agccctggcc 1500
cagatcgccg aggcttggtg cgttgaccag cggcgtactc tggaagtctt caaggagctg 1560
agcaagatca atcccagcgc tatcctgagc gcgatctaca ataaacctat tgctgccaga 1620
ttcatgggag acgtgttggg gctggccagc tgcgtgacaa tcaatcagac cagcgtgaaa 1680
gtgctgagag acatgaatgt gaaggagtct cctggtaggt gctactcaag gcccgtcgta 1740
attttcaatt tcgccaacag ttcctacgtg cagtacggac agctgggcga agacaatgag 1800
atcctcctgg gcaaccatcg gacggaggag tgtcaactcc catcactgaa gatctttatc 1860
gcaggcaatt ccgcctatga gtatgtggac tatctgttca agaggatgat cgacctgtcc 1920
agcatcagca cagtggattc aatgattgcc cttgacatcg accctcttga gaataccgac 1980
tttagagtgc tggagcttta tagccagaaa gagctcagga gctccaatgt gttcgacctg 2040
gaagagatca tgcgggagtt taacagctac aagcagaggg ttaaatatgt ggaggacaag 2100
gttgtggatc cactgccgcc ctacctgaaa gggctggacg acctcatgtc cggcctagga 2160
gccgcaggga aagccgtggg cgtggccatc ggcgcagttg gaggcgccgt cgcctctgtg 2220
gttgaaggcg ttgcgacctt tctgaagaac ccattcggcg ccttcaccat tatcctggtg 2280
gccattgccg tggtcatcat cacctatctg atctacacca ggcaacgacg cctgtgcacc 2340
cagcccctgc agaacctgtt cccttacctg gtcagcgccg atgggaccac agtgacctct 2400
ggttctacta aagacaccag ccttcaggcc cctccatcct acgaggagtc tgtgtacaat 2460
agcggcagaa agggccccgg cccgcccagc agcgatgcca gcaccgccgc tcctccatac 2520
acgaacgagc aggcctatca gatgctgctg gcccttgccc gcctggacgc cgagcagcgt 2580
gctcagcaga atggcaccga ttctctggac ggccgaactg gaacgcaaga caagggacag 2640
aagccaaacc tgctggacag actgagacac aggaagaatg gctacaggca tctgaaggat 2700
tcagacgagg aggagaacgt g 2721

<210> SEQ ID NO 98
<211> LENGTH: 2721
<212> TYPE: DNA
<213> ORGANISM: Artificial Sequence
<220> FEATURE:
<223> OTHER INFORMATION: Synthetic polynucleotide

<400> SEQUENCE: 98
atggagagcc ggatctggtg ccttgtggtg tgcgtgaacc tttgcatcgt gtgcctcggc 60
gccgccgtga gctcatcgag cacccggggc accagcgcca cccacagcca ccacagcagc 120
cacaccacca gcgcggccca cagtcggagc ggcagcgtga gccagcgggt gacctcctcc 180
cagaccgtct cccacggcgt gaacgaaacc atctacaaca ccaccctgaa gtacggcgac 240
gtggttgggg taaataccac taagtacccc taccgggtgt gcagcatggc ccagggcacc 300
gacctgatcc ggttcgagcg gaacatcgtc tgtaccagca tgaagcccat caacgaggac 360
ctggacgagg gcatcatggt tgtctacaag cggaatatcg tagcccacac cttcaaggtg 420
cgggtgtacc agaaggtgct gaccttccgg cggagctacg cctacattca cacgacttac 480
ctgctgggca gcaacaccga gtacgtggcg ccgcccatgt gggagatcca ccacatcaac 540
tctcactctc agtgctacag cagctacagc cgggtgatcg ccggcaccgt gttcgtggcc 600
taccaccggg acagctacga gaacaagacc atgcagctga tgcccgacga ctattctaac 660
acacactcca ctaggtacgt gaccgtgaag gaccagtggc actccagagg cagcacctgg 720
ctgtaccggg agacgtgcaa cctgaactgc atggtgacca tcaccaccgc ccggtcaaag 780 taccccttacc acttcttcgc caccagcact ggggatgtgg ttgacatcag ccccttctac 840
aacggcacca accggaacgc cagctacttc ggcgagaacg ccgacaagtt cttcatcttc 900
cccaactaca ccatcgtgag cgacttcggc cggcccaaca gcgccctgga aacacaccgg 960
ctggtggcct tcctggagcg ggccgacagc gtgatcagct gggacatcca ggacgagaag 1020
aacgtgacct gccaactcac attttgggag gccagcgagc ggaccatccg gagcgaggcc 1080
gaggactcct atcacttcag cagcgccaag atgaccgcca ccttcctgag caagaagcag 1140
gaggtgaaca tgagcgattc ggcattggac tgcgtgcggg acgaggccat caacaagctg 1200
cagcagatct tcaacaccag ctacaaccag acctatgaga aatacggcaa cgtgagcgtg 1260
ttcgaaacca ccggcggact ggttgttttc tggcagggta tcaagcagaa gagtttggtg 1320

-continued

```
gagctcgagc gcctggcaaa caggagcagc ctgaacctga cccacaaccg gaccaagcgg   1380

agcaccgacg gcaacaatgc aacgcaccta tccaacatgg agtccgtgca caacctggtg   1440

tacgcccagc tgcagttcac ctacgacacc ctgcggggct acatcaaccg ggccctggcc   1500

cagatcgccg aggcatggtg cgtggaccag cggcggaccc tggaggtgtt caaggagctt   1560

tccaagatca accccctctgc catcctgtct gctatctaca ataagccaat cgcggcacgc   1620

ttcatgggag acgtactggg cctggccagc tgcgtgacta ttaatcagac tagcgtcaaa   1680

gtgctacggg acatgaacgt aaaggagagc cccggccggt gctattctcg gcccgtggtc   1740

attttcaact tcgccaacag ttcctacgtg cagtacggac agttaggcga ggacaacgag   1800

attctgctgg gtaaccaccg gaccgaggag tgccaacttc ccagtctaaa gatatttatc   1860

gccgggaatt ccgcttatga gtatgtcgac tacctgttca agcggatgat cgacctgtcc   1920

agtatcagca ccgtggacag catgattgca ctggatatcg accctctcga gaacaccgac   1980

ttccgggtgc tggagctgta cagccagaaa gagctgagat caagtaatgt ctttgacctg   2040

gaggagatca tgcgggagtt caatagctac aagcagaggg tgaaatatgt cgaagacaag   2100

gtagtagacc cgctgcctcc ctacctgaag gggcttgacg acctcatgtc agggttaggg   2160

gcagctggca aggccgttgg cgtcgccatc ggcgcggtgg gcggtgccgt tgcctccgtg   2220

gtcgaaggcg tcgctacctt cctcaagaac cccttcggcg ccttcaccat catcctggtg   2280

gctattgcag ttgtcatcat tacctacctc atctacaccc ggcagcggag gctgtgcacc   2340

cagcccctgc agaacctgtt tccatacctg gtgagcgcag acggaactac cgtgacgagc   2400

ggatccacta aggacaccag cctgcaggcg cctccttcat acgaagagag tgtgtacaac   2460

agcggccgga agggccccgg acctccgagt agcgacgcaa gtaccgccgc cccaccctat   2520

accaacgagc aagcttacca gatgctgctg gcacttgctc ggctggacgc cgaacaacgc   2580

gcccagcaga acggaactga ttctctggac ggccggaccg gcacccagga caagggccag   2640

aagcccaacc tgttggaccg gctgcggcac cggaagaacg gctatcgtca cctgaaagac   2700

agcgacgagg aggagaacgt g                                             2721
```

<210> SEQ ID NO 99
<211> LENGTH: 2721
<212> TYPE: DNA
<213> ORGANISM: Artificial Sequence
<220> FEATURE:
<223> OTHER INFORMATION: Synthetic polynucleotide

<400> SEQUENCE: 99

```
atggagagcc ggatctggtg cctagtggtg tgcgtgaacc tctgcatcgt gtgcctaggc     60

gccgccgtga gcagttctag tacccggggc accagcgcca cccacagcca ccacagcagc    120

cacactacgt cagcagcgca tagtcggagc ggcagcgtga gccagcgggt gacgtcttcc    180

cagacagtgt cccacggcgt gaacgaaacc atctacaaca ccaccctgaa gtacggcgac    240

gtggtgggtg tcaatacaac taagtacccc taccgggtgt gcagcatggc ccagggcacc    300

gacctgatcc ggttcgagcg gaatattgtg tgtaccagca tgaagcccat caacgaggac    360

ctggacgagg gcatcatggt ggtatacaag agaaacattg tcgcccacac cttcaaggtg    420

cgggtgtatc agaaggtgct gaccttccgg cggagctacg cctacattca tacgacttac    480

ctgctgggca gcaacaccga gtacgtggcc ccgcccatgt gggagatcca ccacatcaac    540

agccactccc agtgctacag cagctacagc cgggtgatcg ccggcaccgt gttcgtggcc    600

taccaccggg acagctacga gaacaagacc atgcagctga tgcccgacga ctatagcaat    660
```

-continued actcacagca cacggtacgt gaccgtgaag gaccagtggc acagccgcgg cagcacctgg 720
ctgtaccggg aaacgtgcaa cctgaactgc atggtgacca tcaccaccgc ccggtcgaag 780
tatccctatc acttcttcgc caccagcacg ggcgatgtgg ttgacatcag ccccttctac 840
aacggcacca accggaacgc cagctacttc ggcgagaacg ccgacaagtt cttcatcttc 900
cccaactaca ccatcgtgag cgacttcggc cggcccaaca gcgccctgga aacccaccgg 960
ctggtggcct tcctggagcg ggccgacagc gtgatcagct gggacatcca ggacgagaag 1020
aacgtgacct gccagcttac attctgggag gccagcgagc ggaccatccg gagcgaggcc 1080
gaggacagtt accacttctc gagcgccaag atgaccgcca ccttcctgag caagaagcag 1140
gaggtgaaca tgagcgacag tgctctggac tgcgtgcggg acgaggccat caacaagctg 1200
cagcagatct tcaacaccag ctacaaccag acctatgaga aatacgggaa cgtgagcgtg 1260
ttcgagacaa ccggcggctt agtagtgttc tggcagggga tcaagcagaa gagtttggtg 1320
gagctcgagc ggctggcgaa cagaagcagc ctgaacctga cccacaaccg gaccaagcgg 1380
agcaccgacg gcaacaacgc aacgcactta tcaaacatgg aaagtgtgca caacctggtg 1440
tacgcccagc tgcagttcac ctacgacacc ctgcggggct acatcaaccg ggccctggcc 1500
cagatcgccg aggcgtggtg cgtggaccag cggcggaccc tggaggtgtt caaggagttg 1560
tcgaagatca acccttctgc catcctgtca gcaatttaca ataaacctat tgccgcaagg 1620
ttcatgggag atgtcctggg cctggccagc tgcgtgacca taaaccagac aagcgtcaaa 1680
gtcctccggg acatgaatgt gaaagagagc cccggccggt gttacagtcg acccgtggtg 1740
atctttaact tcgccaattc ttcttatgtg cagtacggac agctcggcga ggacaacgag 1800
atcctgctcg gtaaccaccg gaccgaggag tgtcagcttc cctcactgaa gattttcatt 1860
gcggggaaca gtgcatacga gtatgttgac tacctgttca agcggatgat cgatctgtct 1920
agtatcagca ccgtggacag catgatcgct ctggatatcg acccattgga gaacaccgac 1980
ttccgggtgc tggagctgta cagccagaag gagcttcgca gcagtaatgt gtttgacctg 2040
gaggagatca tgcgggagtt caattcttac aagcagcgcg tgaaatacgt tgaggacaag 2100
gtggtcgatc cgctgcctcc ctacctgaag ggcctggatg atctcatgag cgggttaggg 2160
gctgccggca aggccgtcgg cgttgccatc ggcgcagtgg gcggagccgt cgccagcgtg 2220
gtggagggtg ttgcaacgtt cctgaagaac cccttcggcg ccttcaccat catcttggtt 2280
gcaatcgcgg ttgttatcat tacctacctt atctacaccc ggcaacggcg gctgtgcacc 2340
cagcccctgc agaacctgtt tccatacttg gtgagcgcgg atgggaccac cgtgacttca 2400
ggttccacca aggacaccag cctgcaggcg cctccctcat acgaggagtc cgtatacaac 2460
agcggccgga aggggccagg tcctcctagc tcggacgcaa gtactgccgc accgccttat 2520
accaacgagc aggcatatca gatgctgctt gccctggctc ggctggacgc cgaacagcgc 2580
gcccagcaga acggaacaga ttccctggac ggccggaccg gcacccagga taagggccag 2640
aagcccaact tgctggaccg gctgcggcac cggaagaacg gctataggca tctgaaggac 2700
agcgacgagg aggagaacgt g 2721

<210> SEQ ID NO 100
<211> LENGTH: 2721
<212> TYPE: DNA
<213> ORGANISM: Artificial Sequence
<220> FEATURE:
<223> OTHER INFORMATION: Synthetic polynucleotide -continued

<400> SEQUENCE: 100

```
atggagagcc ggatctggtg cctagtggtg tgcgtgaacc tatgcatcgt gtgcttaggc     60
gccgccgtga gctcatcgtc cacccggggc accagcgcca cccacagcca ccacagcagc    120
cacacgacaa gcgccgccca ctcccggagc ggcagcgtga gccagcgggt gacttcttcc    180
cagacagtga gccacggcgt gaacgagact atctacaaca ccaccctgaa gtacggcgac    240
gtggtgggcg tcaacactac caagtacccc taccgggtgt gcagcatggc ccagggcacc    300
gacctgatcc ggttcgagcg gaacattgtg tgcaccagca tgaagcccat caacgaggac    360
ctggacgagg gcatcatggt tgtgtacaag cgtaatatcg tcgcccacac cttcaaggtg    420
cgggtgtacc agaaggtgct gaccttccgg cggagctacg cctacatcca tactacgtac    480
ctgctgggca gcaacaccga gtacgtggct cctcccatgt gggagatcca ccacatcaac    540
tcccatagcc agtgctacag cagctacagc cgggtgatcg ccggcaccgt gttcgtggcc    600
taccaccggg acagctacga gaacaagacc atgcagctga tgcccgacga ctattcgaac    660
acccactcaa ccagatacgt gaccgtgaag gaccagtggc attcacgggg cagcacctgg    720
ctgtaccggg aaacatgcaa cctgaactgc atggtgacca tcaccaccgc ccggagtaaa    780
tacccttatc acttcttcgc caccagcacg ggcgacgtcg tagacatcag ccccttctac    840
aacggcacca accggaacgc cagctacttc ggcgagaacg ccgacaagtt cttcatcttc    900
cccaactaca ccatcgtgag cgacttcggc cggcccaaca gcgccctgga gacacaccgg    960
ctggtggcct tcctggagcg ggccgacagc gtgatcagct gggacatcca ggacgagaag   1020
aacgtgacct gccagctgac gttttgggag gccagcgagc ggaccatccg gagcgaggcc   1080
gaagattcct atcactttag cagcgccaag atgaccgcca ccttcctgag caagaagcag   1140
gaggtgaaca tgtctgattc cgcgctggac tgcgtgcggg acgaggccat caacaagctg   1200
cagcagatct tcaacaccag ctacaaccag acctatgaga agtatgggaa cgtgagcgtg   1260
ttcgagacaa ccggcgggct ggtcgtcttc tggcaaggca ttaagcagaa gtccctcgtg   1320
gagctggaac ggctggccaa ccgtagcagc ctgaacctga cccacaaccg gaccaagcgg   1380
agcaccgacg gcaacaatgc tactcatcta tcaaacatgg aaagcgtgca caacctggtg   1440
tacgcccagc tgcagttcac ctacgacacc ctgcggggct acatcaaccg ggccctggcc   1500
cagatcgccg aggcctggtg cgtggaccag cggcggaccc tggaggtgtt caaggagcta   1560
agtaagatca acccctccgc aatcctgagc gccatctata acaagcctat cgccgcccgg   1620
ttcatgggcg atgtgctggg cctggccagc tgcgtcacca tcaatcaaac tagcgtgaag   1680
gtcctacggg acatgaacgt gaaagagagc cccggccggt gctactcccg gcccgtggtc   1740
atcttcaatt tcgccaactc ttcctatgtg cagtacgggc agctgggcga ggacaacgag   1800
attctgctgg gtaaccaccg gaccgaggag tgccagcttc cctccctcaa gattttcata   1860
gcaggcaatt ctgcctatga atacgttgac tacctgttca agcggatgat cgatctctct   1920
agtatcagca ccgtggacag catgattgcg ttggacatcg acccgttaga gaacaccgac   1980
ttccgggtgc tggagctgta cagccagaaa gaactgcgtt caagcaacgt tttcgacctg   2040
gaggagatca tgcgggagtt caactcttac aagcagcggg tcaagtacgt cgaggataag   2100
gtcgtggacc cgctgccgcc ctacctgaag ggactggacg atctgatgtc cggattggga   2160
gctgcaggaa aggccgtggg agtagccatc ggcgctgttg gaggggcagt ggccagcgtg   2220
gtcgaaggcg tcgcgacgtt cctgaagaac cccttcggcg ccttcacaat aatcttggtt   2280
gccattgctg tcgtcattat tacatatctt atctacaccc ggcagagaag actgtgcacc   2340
```

cagcccctgc agaacctgtt cccttatttg gtgagcgccg acgggacaac cgtcacctcc 2400
ggctcaacga aggacaccag cctgcaggct ccgccttcat atgaagagtc agtatataac 2460
agcggccgga aggggccagg tcctccatct agcgacgcat caactgccgc acctccgtac 2520
accaacgagc aggcatacca gatgctgttg gccctcgcac ggctggacgc cgagcaacgc 2580
gcccagcaga acgggacgga ctctttggat ggccggaccg gcacccaaga caagggccag 2640
aagcccaatt tgctggaccg gctgcggcac cggaagaacg gctatagaca tctgaaggac 2700
agcgacgagg aggagaacgt g 2721

<210> SEQ ID NO 101
<211> LENGTH: 2721
<212> TYPE: DNA
<213> ORGANISM: Artificial Sequence
<220> FEATURE:
<223> OTHER INFORMATION: Synthetic polynucleotide

<400> SEQUENCE: 101
atggagagcc ggatctggtg cctagtggtg tgcgtgaacc tatgcatcgt gtgccttggc 60
gccgccgtga gctcgtccag tacccggggc acctccgcca cccactccca ccactcctcc 120
cacactacaa gcgccgccca ctcgcgctcc ggctccgtct cccagcgcgt caccagttcc 180
cagaccgtga gtcacggcgt caacgaaacc atctacaaca ccaccctcaa gtacggcgac 240
gtcgtgggcg tgaatacaac caagtacccc taccgcgtct gctccatggc ccagggcacc 300
gacctcatcc gcttcgagcg caacatcgtc tgcacctcca tgaagcccat caacgaggac 360
ctcgacgagg gcatcatggt cgtgtataag cgaaatattg tggcccacac cttcaaggtc 420
cgcgtctacc agaaggtcct caccttccgc cgctcctacg cctacattca cacaacctac 480
ctcctcggct ccaacaccga gtacgtcgcc cctcccatgt gggagatcca ccacatcaac 540
agtcacagcc agtgctactc ctcctactcc cgcgtcatcg ccggcaccgt cttcgtcgcc 600
taccaccgcg actcctacga gaacaagacc atgcagctca tgcccgacga ctatagcaat 660
acacatagta cccgctacgt caccgtcaag gaccagtggc acagcagggg ctccacctgg 720
ctctaccgcg agacttgcaa cctcaactgc atggtcacca tcaccaccgc ccgctcaaag 780
tacccgtatc acttcttcgc cacctccacg ggagacgtgg tggacatctc ccctttctac 840
aacggcacca accgcaacgc tagctatttc ggcgagaacg ccgacaagtt cttcatcttc 900
cccaactaca ccatcgtctc cgacttcggc cgccccaact ccgccctcga aacccacagg 960
cttgtggcct tcctcgagcg cgccgactcc gtcatctcct gggacatcca ggacgagaag 1020
aacgtcacct gccagctcac attctgggag gcctccgagc gcaccatccg ctccgaggcc 1080
gaggattcgt accactttag ctcagcaaag atgaccgcca ccttcctctc caagaagcag 1140
gaggtcaaca tgagcgactc tgctttggac tgcgtccgcg acgaggccat caacaagctc 1200
cagcagatct tcaacacctc ctacaaccag acttatgaga agtatggcaa cgtctcggtg 1260
ttcgagacta cgggcggtct ggtggtcttc tggcagggga ttaagcagaa gtccctcgtc 1320
gagttggaga gactcgccaa ccgctcctcc ctcaacctca cccacaaccg caccaagcgc 1380
tccaccgacg gcaacaacgc cacgcacctc tcaaacatgg agtccgtcca caacctcgtc 1440
tacgcccagc tccagttcac ctacgacacc ctccgcggct acatcaaccg cgccctcgcc 1500
cagatcgccg aggcctggtg cgtcgaccag cgccgcaccc tcgaggtctt caaggagctc 1560
agtaagatca acccaagtgc gatcctgtcg gccatttaca ataaaccgat tgcagcccgc 1620

```
ttcatgggtg acgtactcgg cctcgcctcc tgcgtgacga ttaatcagac cagcgtcaag   1680

gtgcttcgcg acatgaatgt gaaggagagc ccaggccgct gttacagtcg gcccgtcgtc   1740

attttcaatt tcgccaatag cagctatgtc cagtacggcc agctcggcga ggacaacgag   1800

atactccttg gcaaccaccg caccgaggag tgccagctgc cgtctctgaa gatattcata   1860

gccggcaaca gcgcttatga atacgtggac tacctcttca agcgcatgat cgacctctcc   1920

tccatctcca ccgtcgactc catgatcgca cttgatatcg acccactgga gaacaccgac   1980

ttccgcgttc tggaactcta ctcccagaag gagctacggt cctccaatgt tttcgacctc   2040

gaggagatca tgcgcgagtt caattcatac aagcaacggg tgaagtatgt ggaggacaag   2100

gtcgtcgatc ctctgcctcc ctacctcaag ggtcttgatg atctcatgtc cggcctcggc   2160

gctgccggga aggcagtggg agtcgccatc ggcgccgttg gaggggccgt cgcctctgtg   2220

gtggagggcg tggctacctt cctgaagaac cccttcggcg ccttcaccat tattctggtg   2280

gccatcgcag tggttatcat cacgtacctt atctacaccc ggcagagaag gctctgcacc   2340

cagcccctcc agaacctctt tccttatctc gtcagcgcag acggtacaac agttactagt   2400

ggaagtacca aggacacctc cctccaggcc ccgccaagct acgaggaaag tgtttacaac   2460

tccggccgca agggccccgg cccaccttct tccgacgctt ccaccgctgc tccaccatac   2520

accaacgagc aggcctacca gatgctcctg gcactggctc ggctggatgc cgagcagagg   2580

gcccagcaga acggtaccga ttccctcgac ggccgcaccg gcacccagga taagggccag   2640

aagcccaatt tactagacag actgcgccac cggaagaacg gctaccgcca tctgaaggac   2700

tccgacgagg aggagaacgt c                                             2721
```

<210> SEQ ID NO 102
<211> LENGTH: 2721
<212> TYPE: DNA
<213> ORGANISM: Artificial Sequence
<220> FEATURE:
<223> OTHER INFORMATION: Synthetic polynucleotide

<400> SEQUENCE: 102

```
atggagagcc ggatctggtg cctagtggtg tgcgtgaacc tctgcatcgt gtgcttgggc     60

gccgccgtga gtagttccag tacccggggc acctccgcca cccactccca ccactcctcc    120

cacactacga gtgccgccca ctcacgctcc ggctccgtct cccagcgcgt cactagttct    180

cagacagtgt ctcacggcgt caacgagaca atctacaaca ccaccctcaa gtacggcgac    240

gtcgtgggtg tgaatactac taagtacccc taccgcgtct gctccatggc ccagggcacc    300

gacctcatcc gcttcgagcg caacatcgtc tgcacctcca tgaagcccat caacgaggac    360

ctcgacgagg gcatcatggt cgtctacaag agaaatatag tggcccacac cttcaaggtc    420

cgcgtctacc agaaggtcct caccttccgc cgctcctacg cctacattca cactacctac    480

ctcctcggct ccaacaccga gtacgtcgcc ccacccatgt gggagatcca ccacatcaac    540

tctcacagtc agtgctactc ctcctactcc cgcgtcatcg ccggcaccgt cttcgtcgcc    600

taccaccgcg actcctacga gaacaagacc atgcagctca tgcccgacga ctactcaaac    660

actcacagca cccgctacgt caccgtcaag gaccagtggc acagccgcgg ctccacctgg    720

ctctaccgcg agacttgcaa cctcaactgc atggtcacca tcaccaccgc ccgctcgaag    780

tatccgtacc acttcttcgc cacctccacg ggcgatgtgg tcgacatcag tccattctac    840

aacggcacca accgcaacgc ttcatacttc ggcgagaacg ccgacaagtt cttcatcttc    900

cccaactaca ccatcgtctc cgacttcggc cgccccaact ccgccctcga gacacaccgc    960
```

```
ctggtcgcct tcctcgagcg cgccgactcc gtcatctcct gggacatcca ggacgagaag   1020
aacgtcacct gccagttgac cttctgggag gcctccgagc gcaccatccg ctccgaggcc   1080
gaggacagtt accatttcag tagtgccaag atgaccgcca ccttcctctc caagaagcag   1140
gaggtcaaca tgtcggactc tgctcttgac tgcgtccgcg acgaggccat caacaagctc   1200
cagcagatct tcaacacctc ctacaaccag acttatgaga agtatggtaa cgtctctgtg   1260
tttgagacta caggcggtct tgtcgtcttc tggcagggta tcaagcagaa gtccctcgtc   1320
gagctggaac gcctcgccaa ccgctcctcc ctcaacctca cccacaaccg caccaagcgc   1380
tccaccgacg gcaacaacgc aacacatctt agcaacatgg agtccgtcca caacctcgtc   1440
tacgcccagc tccagttcac ctacgacacc ctccgcggct acatcaaccg cgccctcgcc   1500
cagatcgccg aggcctggtg cgtcgaccag cgccgcaccc tcgaggtctt caaggagctg   1560
agtaagatca acccaagtgc aatcctaagc gctatttaca acaaacctat cgcagccagg   1620
ttcatgggag acgtcctcgg cctcgcctcc tgcgtcacca ttaatcagac gtctgttaag   1680
gttctccgcg acatgaacgt gaaagagtct ccgggccgct gctacagcag gcccgtcgtc   1740
atcttcaatt tcgccaattc ttcatatgtc cagtacggcc agctcggcga ggacaacgag   1800
attctcttag ggaaccaccg caccgaggag tgtcagctac ccagcctgaa gatctttatt   1860
gccggcaata gcgcttatga gtatgttgac tacctcttca agcgcatgat cgacctctcc   1920
tccatctcca ccgtcgactc catgatcgct ctggatatcg accctctgga gaacaccgac   1980
ttccgcgtgc ttgagctcta ctcccagaaa gagcttaggt caagcaacgt tttcgacctc   2040
gaggagatca tgcgcgagtt caactcatat aagcaacgcg ttaaatatgt agaggataag   2100
gtggttgatc cacttcctcc ctacctcaag ggtctggatg acctcatgtc cggcctcggg   2160
gcagcaggca aggccgtcgg cgttgccatc ggcgccgtgg gaggtgctgt ggccagtgtt   2220
gtcgagggcg tagccacctt cttaaagaac cccttcggcg cctttacaat aatcctggtg   2280
gccatcgctg tggttatcat tacctatctt atctacacca ggcagcggag gctctgcacc   2340
cagcccctcc agaacctctt cccttacctc gtgagcgcgg acgggacgac cgtcacatct   2400
ggcagtacaa aggacacctc cctccaggcc ccgcctagtt atgaagagag cgtttacaac   2460
tccggccgca agggccccgg tcctccctcc tccgacgcca gcaccgcagc gcctccatac   2520
accaacgagc aggcctacca gatgctcttg gccctggccc gactggatgc cgagcagcgc   2580
gcccagcaga acggaaccga ctccctcgac ggccgcaccg gcacccagga caaaggccag   2640
aagcccaatc tgctcgaccg cctgcgacac cgcaagaacg gctatcggca ccttaaagac   2700
tccgacgagg aggagaacgt c                                           2721
```

<210> SEQ ID NO 103
<211> LENGTH: 2226
<212> TYPE: DNA
<213> ORGANISM: Artificial Sequence
<220> FEATURE:
<223> OTHER INFORMATION: Synthetic polynucleotide

<400> SEQUENCE: 103

```
atgcggccag gacttcctag ctacctaatc atccttgccg tgtgtctttt ctcacacctc     60
ctctctagta ggtacggcgc agaggccgtg tccgagccac tcgacaaggc cttccacctt    120
ttgttaaaca cctacggtcg gccaatcaga ttcctccgcg agaacaccac ccagtgcacg    180
tacaattcgt ctctccgcaa cagcacagtc gtgagggaga acgctatatc attcaacttc    240
```

```
ttccagtctt acaaccagta ttacgtgttc cacatgccaa gatgcctgtt cgctggccca    300

ctggccgagc agttccttaa ccaggtggat ctgacagaga ctctggagag ataccaacag    360

aggctgaaca cctacgcact ggtgagcaag gatctggcct cctacaggag cttcagccaa    420

cagctgaagg cccaggacag tctgggcgag caaccaacca ccgtacctcc acctattgac    480

ttatcaatac ctcacgtgtg gatgcctcct cagaccactc ctcacggctg gaccgaatcc    540

cacaccacct ccggcctgca caggcctcat ttcaaccaga cctgtattct cttcgacgga    600

cacgacctgc ttttcagcac cgtcacgcca tgcttgcacc agggcttcta cctgatcgac    660

gagctcaggt atgtgaagat cactctgacc gaggacttct tcgtggttac tgtgagcatc    720

gatgacgata ccccaatgtt actgatcttc ggccacctgc ctagggtgct gttcaaggca    780

ccataccaga gagacaattt catcctgaga caaaccgaga agcacgagct gctggtgctg    840

gtcaagaagg accagctgaa taggcactca tacctgaagg acccagattt cctggacgct    900

gcccttgatt tcaattacct ggacctgtcc gccctgctga gaaacagctt ccacagatac    960

gccgtggatg tgctgaagtc aggcagatgt cagatgttgg accgccgaac cgttgagatg   1020

gccttcgcct acgcgctggc cctgttcgcc gccgctcggc aggaggaagc tggcgcacag   1080

gtgagcgtgc cgagggctct ggaccgacag gctgctctgc tacagattca ggaattcatg   1140

atcacctgcc tgtcacagac tccgcctcgg actaccctgc tgctgtatcc tacagcagtg   1200

gacctggcaa agagagctct ttggacccct aaccagatca ccgatatcac cagcctcgtc   1260

cggctggtct acattctgtc taagcagaat cagcagcacc tgatccctca gtgggctctc   1320

agacagatcg ccgatttcgc cctgaagctg cacaagaccc acctggcttc tttcctgagc   1380

gctttcgcca gacaggaact gtacctgatg ggatcgcttg tgcacagcat gctggtgcac   1440

acaactgaga ggagagagat tttcattgtg gagactggcc tgtgcagcct ggccgagctg   1500

tcccatttca cccagctcct cgctcatccg caccacgagt acctctccga cctctatacc   1560

ccttgctcct cttccggccg gcgcgatcac agcctggaaa gactcactag actgttccca   1620

gacgctaccg tgccggctac tgtcccggca gcactgagca tcctgagcac tatgcagcct   1680

tctacgctgg aaaccttccc ggacctgttc tgcctgccac tcggagaaag cttctctgcc   1740

ctgacggtga gtgagcacgt gtcgtacatc gtgacaaacc agtacctgat caagggtatc   1800

agctacccag tgtccacaac tgtggtgggc cagagcctga tcatcaccca gaccgatagc   1860

caaacaaagt gcgaactgac aagaaacatg cataccactc attccatcac tgtggcctta   1920

aacatctccc tggagaactg cgccttctgt cagtccgccc tgctggagta cgatgatacc   1980

cagggcgtta ttaatatcat gtacatgcat gatagcgacg atgtgctttt cgccctggac   2040

ccatacaacg aggtggtggt gtccagccct agaacccact acctcatgct gctgaagaac   2100

ggcacagtgc tggaggtgac cgacgtggtg gtggacgcta cggacagcag gctgctgatg   2160

atgagcgtgt acgccctgag cgccattatc ggaatatacc tgctgtacag gatgttgaag   2220

acctgt                                                              2226
```

<210> SEQ ID NO 104
<211> LENGTH: 2226
<212> TYPE: DNA
<213> ORGANISM: Artificial Sequence
<220> FEATURE:
<223> OTHER INFORMATION: Synthetic polynucleotide

<400> SEQUENCE: 104

```
atgcggccgg gactccctag ctacctcatc atcctcgccg tgtgcctttt ctctcacctt     60
```

```
ttgagctcca gatacggcgc cgaagcggtg tccgagcctc tcgacaaggc cttccacctc    120
cttctcaaca catacggcag accgatccgg ttcttgaggg agaacactac ccaatgcaca    180
tataacagta gcctgcggaa tagcactgtg gtgcgggaga acgccatcag cttcaatttc    240
ttccagagct acaatcagta ttacgtgttc cacatgccta gatgtctgtt cgcgggccct    300
ctggcagagc agttcctgaa ccaggttgat ctcacagaga cactggagag ataccagcaa    360
agactgaaca cctacgctct cgtctccaag gacctggcca gctataggag cttcagccag    420
cagctgaagg cccaggattc cctgggagag cagccaacca ccgtcccgcc gccaatcgac    480
ctctctatcc cacacgtgtg gatgcctcca caaaccacac cacacggatg gactgagtcc    540
cataccacca gcggactgca caggcctcac ttcaatcaga cctgcatttt gttcgacggc    600
cacgacctcc tgttcagcac tgtgaccccg tgtctgcatc agggcttcta cctgattgac    660
gagctgaggt acgtcaagat tacgctcacc gaagacttct tcgtggtcac agtgagtatc    720
gatgacgaca cccctatgct gctcatcttc ggccatctgc ctagggtgct gttcaaggcc    780
ccttaccaga gagataattt catcttgcgg cagactgaga agcacgaact gctggtactc    840
gtgaagaagg accagctgaa ccgccactct tacttaaagg atccagactt cctggatgca    900
gcacttgact tcaactatct cgacctctct gccctgctga ggaacagctt ccaccggtat    960
gccgtggacg tgctgaagag tggacggtgt cagatgctgg accgcagaac agtggaaatg   1020
gcgttcgcgt atgctctggc cctattcgcg gccgcaagac aggaggaggc cggcgctcag   1080
gtgtccgtcc ctagagctct ggacaggcag gccgccctgc tgcaaattca ggagttcatg   1140
ataacttgcc tgagccaaac ccctccgaga acaacactgc tgctgtatcc aacagccgta   1200
gatctggcca agcgggccct ttggactcct aaccagatca ccgatattac ctccctggtg   1260
agactggtgt acattctgtc caagcagaac cagcagcacc tgatcccgca gtgggccctg   1320
agacagatcg ctgatttcgc cttgaagctg cacaagactc atctggcctc cttcctgagt   1380
gctttcgccc gccaggaact gtatctgatg ggctctcttg tccattccat gctggttcat   1440
accacggaga gaagggagat cttcatcgtg gaaaccggcc tttgctccct cgctgagctg   1500
agccatttca ctcagctgct cgcccacccg caccacgagt acctgtcaga cctttatact   1560
ccgtgctcct ccagcggcag gagggaccac agcctggaac ggctcacaag actgttcccg   1620
gatgctaccg tgcctgctac tgtgccagcc gccctgagca tcctttccac catgcagcct   1680
tccacactgg agactttccc tgacctgttc tgcctgccac ttggcgaaag tttcagcgcc   1740
ctgaccgtgt ccgaacatgt gagctacatc gtgactaacc agtacctgat caagggcatc   1800
agctacccgg ttagcaccac tgtcgtcgga cagtcactga tcatcactca gaccgactcc   1860
cagaccaagt gcgaactgac cagaaatatg cacacaaccc atagcatcac cgtggccctg   1920
aacattagcc tggagaactg tgccttctgc cagagcgccc tcctcgagta cgacgatacc   1980
cagggtgtga taaacattat gtatatgcac gacagtgacg acgttctgtt cgcactggac   2040
ccttacaacg aagtggtcgt ttcctctcct cggacccatt acctgatgct gctgaagaac   2100
ggcaccgtgc tagaggttac tgatgtggta gtggacgcca cagacagcag actgctgatg   2160
atgagcgtgt acgccctgag cgccattatt ggcatctacc tgctgtacag gatgctgaag   2220
acatgt                                                              2226
```

<210> SEQ ID NO 105
<211> LENGTH: 2226
<212> TYPE: DNA

```
<213> ORGANISM: Artificial Sequence
<220> FEATURE:
<223> OTHER INFORMATION: Synthetic polynucleotide

<400> SEQUENCE: 105

atgcggccgg gactcccttc ctacctcatc atccttgccg tgtgtctttt ctcacacctc     60

ctcagcagcc gctacggcgc cgaggccgtg tcagagccac ttgacaaggc cttccatctt    120

ttgttgaaca cctacggcag acctattcgg ttcctgagag agaacacaac ccagtgcacc    180

tataacagct ctctgcgcaa ctccacagtg gttagagaga atgccatcag cttcaacttc    240

ttccagagtt acaaccagta ttacgtgttc catatgccta ggtgcctgtt cgctggcccg    300

ttagccgaac agttcctcaa ccaggtggat ctgaccgaaa cactggaaag gtaccagcag    360

cggctgaata catacgcctt ggtgtcaaag gatcttgctt cctacagaag cttcagccag    420

cagctgaagg cccaggacag ccttggagag cagccaacca ccgtgcctcc tcctattgac    480

ctgagcatcc ctcatgtgtg gatgcctcct cagaccaccc ctcacggctg gactgagagc    540

cataccacgt ccggcctgca caggcctcac ttcaatcaga cctgcatcct gttcgacggc    600

cacgatctgc ttttcagcac cgtcacccct tgcctgcacc agggattcta cctgatcgac    660

gagctccggt atgtgaagat tacactgacc gaggacttct tcgtggtgac cgtgtccatc    720

gacgatgaca ccccaatgct gctgatcttc ggccacctgc cgagagtcct gttcaaggcc    780

ccataccaga gagacaactt catcctgcgg cagaccgaga agcacgaact gctagtgctg    840

gtgaagaagg atcagctgaa ccggcactcc tacctgaagg accctgactt ccttgacgcc    900

gcactcgact tcaactacct ggacctcagt gctctactga ggaactcttt ccaccggtac    960

gccgtggacg tgctgaagtc tggaagatgc cagatgctgg ataggaggac agtggagatg   1020

gcgttcgcgt acgccctggc cctgttcgcc gccgccagac aggaggaggc cggcgcacag   1080

gtcagcgtcc caagggccct ggaccgccag gctgccctgc tgcagattca ggaattcatg   1140

atcacctgtc tcagccagac ccctccgaga acaaccctgc tgttgtaccc gaccgcagtg   1200

gatctggcta agagggccct gtggacccca aaccagatta ccgacatcac ctctctggtg   1260

agactggtgt acatcctgtc caagcagaac caacagcacc tcattccaca atgggccctg   1320

aggcaaatcg ccgatttcgc tctcaagttg cataagaccc atctggcctc attcctcagc   1380

gccttcgcaa gacaggagtt gtatctcatg ggctccctcg tgcatagcat gctggtgcac   1440

acaaccgagc gcagagaaat tttcatcgtt gaaaccggac tgtgcagcct cgccgagttg   1500

tctcatttca cccagctgct ggctcatcct caccatgagt atctttccga cctgtacacc   1560

ccgtgcagca gcagcggccg cagggatcac agcctcgaga gactgacaag actgttccca   1620

gacgccaccg tgcctgccac agtgccagcc gcgctgtcca tcctgagcac aatgcagcct   1680

agcacactgg agactttccc agatctgttc tgtcttccac tgggcgagag cttcagcgcc   1740

ctgaccgtga gcgagcacgt gagctacata gtgaccaacc aatatttgat taagggcatc   1800

tcctaccctg tgagcaccac agtggtgggc cagtctctga tcatcacaca aaccgacagt   1860

cagacgaagt gcgagctgac tagaaacatg cacacgaccc acagcataac cgtggcactc   1920

aacatctccc tggagaattg cgccttctgc cagagcgccc tcctggagta cgacgacact   1980

caaggagtga tcaacatcat gtacatgcac gatagcgatg acgtgctgtt cgccctggac   2040

ccatacaatg aagtggtggt gtccagccca cggacccact acctgatgct cctcaagaac   2100

ggcacagtgc tggaggttac agacgtggtg gtcgacgcta ccgatagcag acttcttatg   2160

atgtccgtgt acgccctgag cgccatcatc ggaatctatc tgctttacag gatgctgaag   2220
```

acttgc 2226

<210> SEQ ID NO 106
<211> LENGTH: 2226
<212> TYPE: DNA
<213> ORGANISM: Artificial Sequence
<220> FEATURE:
<223> OTHER INFORMATION: Synthetic polynucleotide

<400> SEQUENCE: 106
atgcggccag gcctcccttc gtaccttatc atcttggccg tgtgtctttt ctctcaccta 60
ctctcctcaa ggtacggcgc cgaggccgtg agtgagccgc tagacaaggc cttccaccta 120
ttacttaaca cctacggccg gcctatccga ttcctccggg agaataccac acagtgtaca 180
tacaactcta gcctgcgcaa cagcactgtg gtcagggaga acgccatcag cttcaatttc 240
ttccagagtt ataaccagta ctacgtgttc cacatgccaa gatgcctgtt cgccggacct 300
cttgccgagc agttcctgaa ccaggtggat ctgaccgaga cactggagag ataccagcaa 360
aggctcaata cctacgcttt agtgagcaag gaccttgctt cttacagatc tttctcacaa 420
cagcttaagg cgcaggacag cctcggcgag cagcctacca ccgtgcctcc tcctattgac 480
ttgagcatcc cacacgtatg gatgcctcca cagacgacac cacacggctg gaccgaatcc 540
catacaacca gcggactcca ccggcctcat ttcaatcaga cctgcatcct tttcgacggc 600
catgacctgc tattctctac cgtcaccccg tgcctgcacc agggcttcta ccttatcgac 660
gaactgagat acgtcaagat cacgctgacc gaagacttct tcgtcgttac agtcagcatc 720
gacgacgata cccctatgct gctgatattc ggccaccttc ctagagtcct gttcaaggca 780
ccgtaccaga gggacaactt catcctgaga cagacagaga agcacgagct cctggtgctg 840
gtgaagaagg atcagctgaa tagacacagt tacctgaagg atccagactt cctggacgcc 900
gcactggact tcaactatct ggatctgagc gccctgcttc gcaatagctt ccatagatac 960
gctgtggacg tgctgaagtc tggccggtgt cagatgctgg atcgtaggac cgtggagatg 1020
gccttcgcct acgcactcgc tctgttcgcc gccgctagac aggaggaggc cggagcccaa 1080
gtgagtgtgc ctcgggcact ggacagacag gcagccttac tgcagatcca ggagttcatg 1140
attacctgcc tgtctcagac tccaccacgg accacccttc tgctgtatcc taccgcggtt 1200
gatctggcta agagggccct gtggacccct aaccagatca ctgacatcac cagcctcgtg 1260
aggctggtgt acattcttag caagcagaac cagcagcacc taatacctca gtgggccctg 1320
cggcagatcg ccgacttcgc cctgaagctg cacaagaccc acctggcaag cttcctgtcc 1380
gccttcgccc gccaggagct gtacctcatg ggaagtctgg tacactccat gctggtgcac 1440
accaccgaga gaagagagat cttcatcgta gaaaccggac tctgctcact ggccgaattg 1500
tcacacttca cccagctgct ggcccatcct catcacgagt atctgtccga cctgtacacc 1560
ccttgcagct ctagcggcag gcgggaccat tccttggaga ggctgaccag gctgttcccg 1620
gatgccaccg ttccagcaac agtgcctgca gccctgagca ttctgtcaac aatgcagcct 1680
agcaccctcg aaactttccc ggatctgttc tgcctgcctc ttggtgagag cttcagcgcc 1740
ctgaccgtgt ccgagcatgt gtcttatatc gtaaccaatc agtacctgat caagggcatc 1800
agctaccctg tgtccacaac tgtcgtgggc caaagcctca tcataaccca gaccgattcc 1860
cagacaaagt gtgaactgac ccgcaacatg cacaccactc acagcattac tgtggccctg 1920
aacatctccc tggagaactg tgccttctgt cagagcgcgc ttctggagta tgatgacacc 1980

-continued

```
cagggtgtga ttaatatcat gtacatgcac gacagcgacg atgtgctgtt cgcgctggat   2040

ccttacaatg aggtggtcgt gagctcccct agaacccact atctcatgct gttaaagaac   2100

ggcaccgtcc tggaggtgac agacgtggtg gttgatgcca ccgacagcag gctgctgatg   2160

atgagcgttt atgccctgag cgccatcatc ggcatttacc tcctgtacag gatgttaaag   2220

acttgt                                                              2226


<210> SEQ ID NO 107
<211> LENGTH: 2226
<212> TYPE: DNA
<213> ORGANISM: Artificial Sequence
<220> FEATURE:
<223> OTHER INFORMATION: Synthetic polynucleotide

<400> SEQUENCE: 107

atgcggccag gactccctag ctacctcatt atcctcgccg tgtgcctttt ctctcacctc     60

ttaagctccc ggtacggcgc cgaagccgtg agcgagccgc ttgacaaggc tttccacctc    120

ctccttaaca cctacggcag acctattaga ttcctgagag agaacaccac ccagtgtaca    180

tataattcta gcctgcggaa ctccaccgta gtgagggaga atgccattag cttcaacttc    240

ttccagagct acaaccagta ctatgtgttc catatgccga gatgtctgtt cgctggacct    300

ctcgcagaac agttcttgaa ccaggtggat ctgactgaaa ctctcgagcg gtaccagcaa    360

agactgaata cctatgcctt ggtaagcaag gatctggcta gctacaggag cttctcccag    420

cagctcaagg cccaggactc ccttggcgaa cagcctacca ccgtccctcc tccaattgac    480

ctgagcattc cgcacgtgtg gatgcctcct cagaccaccc cacacggctg gacagagtct    540

cataccacca gcggactgca tagaccgcat ttcaaccaga cttgcatcct gttcgatgga    600

catgatctcc tgttctctac agtgactcca tgcctgcacc agggcttcta cctgatcgat    660

gagctcagat acgtcaagat caccttgacc gaagatttct tcgtggtcac agtgagcatt    720

gacgacgaca ccccaatgct tctgatattc ggtcacctgc ctagggtcct cttcaaggct    780

ccataccaga gagacaattt catccttaga cagaccgaga agcacgagct gctcgtgctg    840

gtgaagaagg atcaactgaa cagacatagc tacctaaagg atccggattt cctggacgcc    900

gctctggact tcaactacct cgacctcagc gccctgctga ggaacagctt ccaccggtat    960

gcagtcgatg ttctcaagtc cggcagatgc cagatgctgg accgtagaac tgtggagatg   1020

gccttcgcct atgctctggc cctgttcgcc gccgcacgcc aggaagaggc tggagcccag   1080

gtgagcgtcc cacgggctct ggacagacag gctgctctgc tgcagatcca agagttcatg   1140

attacctgtc tgagccagac ccctcctaga accaccctcc tcctctatcc gaccgctgtg   1200

gacctggcca agagagcctt gtggacccct aatcagatta ctgacatcac aagcctggtc   1260

agactggtgt atatcctgag caagcagaat cagcagcacc tcattccaca gtgggcgctg   1320

cggcagatcg ctgatttcgc cctgaagctg cacaagaccc acctggccag cttcttgagc   1380

gcattcgcac ggcaggaact ctacctgatg ggctctctgg tgcacagcat gctcgtccac   1440

accacagaac ggcgagagat attcatcgtt gagacaggcc tgtgctctct ggccgagttg   1500

tcccacttca cccaactgct ggctcaccct catcacgagt acctcagcga cctgtacacc   1560

ccttgctcct ccagcggtag acgggatcac agcctggaaa gactgaccag actgttccca   1620

gacgccacgg tccctgcaac cgtgcctgcc gctctttcaa tcttgtccac catgcagcct   1680

agtacactgg aaacattccc tgacctcttc tgcctgcctc tcggagagtc cttctcagcc   1740

ctgaccgtga gcgaacacgt gtcctacatc gtgaccaacc agtacctgat caagggcatc   1800
```

tcctaccctg tgtcgaccac cgtcgtgggc cagagcctga tcattacaca gacggactct 1860
cagaccaagt gcgagttgac acggaacatg cacaccacac acagcatcac tgtggccctg 1920
aatattagcc tcgagaactg cgccttctgc cagagtgccc tgctagagta tgatgataca 1980
cagggcgtga ttaatatcat gtatatgcac gactctgatg acgtcctgtt cgccctggac 2040
ccatacaacg aggtggttgt gagctcccct cggacccact atctgatgct gctcaagaac 2100
ggcactgttc tcgaggtgac agatgtggtg gtcgatgcca cagattctcg gctgctgatg 2160
atgagcgtgt acgctcttag cgccatcatc ggaatctacc tcctgtacag gatgctgaag 2220
acttgt 2226

<210> SEQ ID NO 108
<211> LENGTH: 2226
<212> TYPE: DNA
<213> ORGANISM: Artificial Sequence
<220> FEATURE:
<223> OTHER INFORMATION: Synthetic polynucleotide

<400> SEQUENCE: 108
atgcggccgg gcctcccgtc ttacctcatc atcttggccg tgtgcctctt ctcccacctc 60
ttgagctccc ggtacggcgc agaggccgtg tcagagcctc tcgacaaggc cttccatttg 120
ctccttaaca catacggcag gccaatcagg ttcctgcgag agaataccac acaatgcacc 180
tacaactcca gcttgaggaa tagcaccgtg gtgcgggaga acgccatctc cttcaatttc 240
ttccagtcct acaatcagta ttatgtgttc catatgccta ggtgtctctt cgcaggccca 300
cttgccgaac aattcctgaa ccaagtggac ctgacagaga cactggagag ataccagcaa 360
cggctgaata cctacgcctt ggtgagcaag gatctcgcca gctacagatc tttctcacaa 420
caactgaagg cccaggattc tctcggtgag cagccaacga ctgtgcctcc tccaattgac 480
ctgtctatcc cacatgtgtg gatgccacct cagactaccc ctcacggatg gacagagtct 540
cataccacta gcggcctgca caggcctcac ttcaatcaga cctgtatcct cttcgacggt 600
cacgatctgt tgttcagcac cgtgacccca tgcctgcatc agggcttcta cctgattgac 660
gagctgagat atgtgaagat aacactgacc gaggatttct tcgtggtcac cgtgagcata 720
gacgacgaca caccgatgct cctgatcttc ggccatctgc cacgagttct gttcaaggca 780
ccttatcaga gagacaactt catcttgagg caaacagaga agcacgagct tctcgtgctg 840
gttaagaagg accagctcaa caggcatagc tacctgaagg acccagattt cctggacgcc 900
gctctggatt tcaattatct ggacctttct gctctgctga gaaacagctt ccatagatac 960
gccgtggacg tccttaagtc tggccgctgc cagatgctgg atagacggac tgtcgagatg 1020
gcattcgcct acgctctggc tctgttcgcc gccgccaggc aggaggaggc tggagcccaa 1080
gtgtcagtgc ctagggctct ggatagacaa gccgccttgc tccagatcca ggagttcatg 1140
attacctgtc tgagccagac ccccaccaaga accacgttac tgctgtaccc taccgctgtg 1200
gacctggcta agcgagccct ctggacgcct aatcaaatca ccgacatcac cagcttagtc 1260
agactggtgt acattctgtc taagcagaac cagcagcact tgattccaca gtgggccctg 1320
agacagattg ccgacttcgc cctgaagctc cataagaccc atctggcgtc cttcctgagc 1380
gccttcgcca gacaggagct ctacctgatg ggcagcctgg ttcattccat gctggtccat 1440
acaacggaga gaagagagat cttcatcgtg gagacaggac tgtgctcttt ggccgaactt 1500
tcccacttca ctcagctgct ggcgcaccct catcacgagt acttatcgga cctgtacacc 1560

```
ccttgcagca gcagcggaag gagggaccat tctctcgaaa ggctgacaag actgttccct   1620

gacgccaccg tcccagccac agtgcctgcc gcactgagca tcctcagcac aatgcagcca   1680

agcactctgg agactttccc ggacttgttc tgcctgccgc tgggcgagtc cttcagcgcc   1740

cttacagtgt cagagcatgt gtcctacatc gtgaccaatc agtacctgat caagggaatc   1800

agctaccctg tgtctacaac cgtggttggc cagtccctca tcatcaccca gacagatagc   1860

caaactaagt gcgaactgac tagaaacatg cacacaaccc actccatcac agtggccctg   1920

aacatcagcc tcgagaattg cgccttctgc cagagcgcac tgttggagta cgacgatact   1980

cagggcgtga ttaacatcat gtacatgcat gatagcgacg atgtgctgtt cgccctggac   2040

ccttataacg aggtggtggt gagtagtcct aggacccatt accttatgct gctgaagaac   2100

ggaactgttc tggaggttac cgacgtcgtc gttgacgcta ccgactcacg cctgctcatg   2160

atgtctgtgt atgccctgtc tgccatcatc ggcatctacc tgctgtatag gatgctgaag   2220

acttgc                                                               2226
```

```
<210> SEQ ID NO 109
<211> LENGTH: 2226
<212> TYPE: DNA
<213> ORGANISM: Artificial Sequence
<220> FEATURE:
<223> OTHER INFORMATION: Synthetic polynucleotide

<400> SEQUENCE: 109
```

```
atgcggcccg gccttcccag ctacctcatc atcctcgccg tgtgcttgtt cagccacctt     60

ctaagcagcc ggtacggcgc cgaggccgtg agcgagcccc tcgacaaggc cttccacttg    120

ttattgaaca cctacggccg gcccatccgg ttcctgcggg agaacaccac ccagtgcacc    180

tacaacagca gcctgcggaa cagcaccgtg gttcgggaga atgccatcag cttcaacttc    240

ttccagagct acaaccagta ctacgtgttc cacatgcccc ggtgtctttt cgccggaccg    300

ctggccgagc agttcctgaa ccaggtggac ctgaccgaaa ctctggagcg gtaccagcag    360

cggctgaata cctatgccct ggtgagcaag gacctggcct cataccggag cttcagccag    420

cagctgaagg cccaggacag cctgggcgag cagcccacca ccgtgcctcc acccatcgac    480

ctgagcatcc cgcacgtgtg gatgcctcca cagaccacac ctcacggctg gaccgagagc    540

cacaccacca gcggcctgca ccggccccac ttcaaccaga cctgcatcct gttcgacggc    600

cacgacctgc tgttcagcac agttacccct tgccttcatc agggcttcta tcttatagac    660

gagctgcggt acgtgaagat cacactcacc gaggacttct tcgtggtgac cgtgagcatc    720

gacgacgaca ctcctatgct cctcatcttc ggccatcttc cccgggttct gttcaaggct    780

ccataccagc gggacaactt catcctgcgg cagaccgaga agcacgagtt gctggtgctg    840

gtgaagaagg accagctgaa ccggcattcg taccttaagg accccgactt cctggacgcc    900

gccctggact tcaactacct agatctcagc gccctgttga ggaatagctt ccaccggtac    960

gccgtggacg tgttaaagag cggccggtgc cagatgctgg atcggcggac cgtggagatg   1020

gccttcgcct acgcgctggc cttgttcgct gccgcccggc aggaggaggc cggcgcccag   1080

gtgagcgtac cgcgggcact cgatcggcag gccgctctgc tgcagatcca ggagttcatg   1140

atcacctgcc tgagccagac ccctccgcgg accaccttac tgctttaccc cactgcagtt   1200

gacctggcta agcgcgcact ctggacccct aaccagatca ccgacatcac cagcctggtg   1260

cggctggtgt acatcctgag caagcagaac cagcaacacc tgataccaca gtgggctctg   1320

agacagatcg ccgacttcgc cctgaagctg cacaagaccc atctggccag cttcctgtcc   1380
```

gctttcgcac gacaggagct gtacctgatg ggatcactcg tgcacagcat gctcgtgcat 1440
accaccgagc ggcgggagat cttcatcgtg gaaacaggcc tgtgttcact agccgaactg 1500
agccacttca cccaactttt ggcccatcca caccacgagt atttgtcgga cctgtacacc 1560
ccttgttcct cttccggaag gcgggaccac tccctggaac ggctgacccg gctgttcccc 1620
gacgcaaccg taccggccac ggttccagct gccttaagca tcttaagtac catgcagccc 1680
agcacactgg aaaccttccc agatctgttc tgcctgccgc tgggtgagtc tttcagcgct 1740
ctcaccgtgt ccgagcacgt gagctacatc gtgacaaatc aatatctgat taagggcatc 1800
agctacccag tgtcaactac ggtggttggc cagagcttga ttataaccca gaccgactcg 1860
cagactaagt gcgagcttac gagaaacatg cacacaaccc acagcatcac cgtggccctg 1920
aacataagtc tggagaactg cgccttctgc cagtctgcct tgctcgagta tgatgacacc 1980
cagggcgtga tcaacatcat gtacatgcat gacagcgacg atgttctctt cgcgttggat 2040
ccatacaacg aggtggtggt gtccagtccg agaactcact atctgatgct cctaaagaac 2100
ggcaccgtgc tggaggtgac cgacgtcgtg gtcgatgcca cggactccag actgcttatg 2160
atgagcgtgt acgccctaag cgccatcatc ggcatctatc tcctgtatcg gatgcttaag 2220
acctgc 2226

<210> SEQ ID NO 110
<211> LENGTH: 2226
<212> TYPE: DNA
<213> ORGANISM: Artificial Sequence
<220> FEATURE:
<223> OTHER INFORMATION: Synthetic polynucleotide

<400> SEQUENCE: 110
atgcggcccg gccttcccag ctacctcatc atcctcgccg tgtgcttgtt cagccacttg 60
cttagcagcc ggtacggcgc cgaggccgtg agcgagccct tggacaaggc cttccactta 120
ctcctcaaca cctacggccg gcccatccgg ttcctgcggg agaacaccac ccagtgcacc 180
tacaacagca gcctgcggaa cagcaccgtg gtgcgtgaga acgccatcag cttcaacttc 240
ttccagagct acaaccagta ctacgtgttc cacatgccca ggtgcctttt cgccggacca 300
ctggccgagc agttcctgaa ccaggtggac ctgaccgaaa cactggagcg gtaccagcag 360
aggctgaaca catacgccct ggtgagcaag gacctggcct cctaccggag cttcagccag 420
cagctgaagg cccaggacag cctgggcgag cagcccacca ccgtgccgcc acccatcgac 480
ctgagcatcc cacacgtgtg gatgccacca cagaccaccc ctcacggctg gaccgagagc 540
cacaccacca gcggcctgca ccggccccac ttcaaccaga cctgcatcct gttcgacggc 600
cacgacctgc tgttctcgac cgtcacccct tgcttgcacc agggcttcta tctgatagac 660
gagctgcggt acgtgaagat caccttgacc gaggacttct tcgtggtgac cgtgagcatc 720
gacgacgaca cacctatgct gctcatcttc ggccatttac cccgggttct gttcaaggca 780
ccataccagc gggacaactt catcctgcgg cagaccgaga agcatgagct tctggtgctg 840
gtgaagaagg accagctgaa ccggcactca tatctgaagg accccgactt cctggacgcc 900
gccctggact tcaactacct ggatttaagc gccctgctcc gtaactcttt ccaccggtac 960
gccgtggacg tgttaaagtc aggccggtgc cagatgttgg accggcggac cgtggagatg 1020
gccttcgctt acgcattagc cctcttcgca gccgcccggc aggaggaggc cggcgcgcag 1080
gtgagcgtgc ctagagcgtt ggatagacag gcggccttgc tgcagatcca ggagttcatg 1140

```
atcacctgcc tgagccagac tcctccacgg accacattgc tgctctaccc caccgccgtt   1200

gacctggcaa agcgggcgct ctggactccg aaccagatca ccgacatcac cagcctggtg   1260

cggctggtgt acatcctgag caagcagaat cagcagcacc tgataccaca gtgggcacta   1320

cgccagatcg ccgacttcgc cctgaagctg cacaagaccc acctggccag cttcctgtct   1380

gctttcgcaa ggcaggaact gtacctgatg ggctctctag tgcacagcat gctcgtccat   1440

accacagagc ggcgggagat cttcatcgtg gagactggcc tgtgctctct tgcggaactg   1500

agccacttca cccagctcct agcccaccca caccacgagt acctttctga cctgtacacc   1560

ccgtgctcat caagtggacg gcgggaccac tcgctggaaa gactcacccg gctgttcccc   1620

gacgctactg tgccggcaac tgtgcctgcg gctctctcta tattatctac catgcagccc   1680

agcacactcg aaaccttccc tgatctgttc tgcctgcctc taggagagag cttctctgcc   1740

cttacagtgt ccgagcacgt gagctacatc gtgacaaacc aatacctcat taagggcatc   1800

agctaccctg ttagtactac cgtcgtaggc cagagcctaa ttatcaccca gaccgactcc   1860

cagacaaagt gcgaattaac gcgcaacatg cacacaaccc acagcatcac cgtggccctg   1920

aacattagcc tcgagaactg cgccttctgc cagagtgcct tgcttgagta tgatgatacc   1980

cagggcgtga tcaacatcat gtacatgcac gacagcgacg atgtgctgtt cgcactcgac   2040

ccctacaacg aggtggtcgt aagcagtcca aggacccatt atttgatgct gcttaagaac   2100

ggcaccgtgc tggaggtgac cgacgtggtg gtagacgcta cagactcccg gctgcttatg   2160

atgagcgtgt acgcgctcag tgcgatcatc ggcatctacc tgctttatcg gatgctaaag   2220

acctgc                                                              2226
```

```
<210> SEQ ID NO 111
<211> LENGTH: 2226
<212> TYPE: DNA
<213> ORGANISM: Artificial Sequence
<220> FEATURE:
<223> OTHER INFORMATION: Synthetic polynucleotide

<400> SEQUENCE: 111

atgcggcccg gcttgcccag ctacttgatc atcttggccg tgtgcttgtt cagccactta     60

cttagcagcc ggtacggcgc cgaggccgtg tccgagcccc tcgacaaggc cttccacctc    120

ctcctcaaca cctacggccg ccccatccgc ttcctccgcg agaacaccac ccagtgcacc    180

tacaactcct ccctccgcaa ctccaccgtc gtgcgggaga atgccatctc cttcaacttc    240

ttccagtcct acaaccagta ctacgtcttc cacatgcccc gctgcctctt cgccggacct    300

ctcgccgagc agttcctcaa ccaggtcgac ctcaccgaga cgctcgagcg ctaccagcag    360

aggttgaata cctatgccct cgtctccaag gacctcgcct cctaccgctc cttctcccag    420

cagctcaagg cccaggactc cctcggcgag cagcccacca ccgtgcctcc accaatcgac    480

ctctccatcc cgcacgtctg gatgcctccc cagaccactc cgcacggctg gaccgagtcc    540

cacaccacct ccggactgca tcgccctcac ttcaaccaga cctgcatcct cttcgacggc    600

cacgacctcc tcttcagtac cgtgacgcca tgcctgcacc agggcttcta cctcatcgac    660

gagctccgct acgtcaagat cacccttacc gaggacttct tcgtcgtcac cgtctcgatt    720

gacgacgaca caccaatgct cctcatcttc ggccacctcc cgcgcgtgct gttcaaggcg    780

ccctaccagc gcgacaactt catcctgagg cagaccgaga agcacgagct gctcgtcctc    840

gtcaagaagg accagctcaa ccgccactcc tacctcaagg accccgactt cctcgacgcc    900

gccctcgact tcaactacct cgatctgagt gctctgctga ggaattcatt ccaccgctac    960
```

```
gccgtcgacg tcctcaagtc cggccgctgc cagatgctcg accgccgcac cgtcgagatg   1020
gccttcgctt acgcgctggc actcttcgct gccgcccgcc aggaggaggc cggcgcccag   1080
gtcagtgtgc caagagcact ggatagacag gccgcacttt tgcagatcca ggagttcatg   1140
atcacctgcc tctcccagac tccgcctcgc accacgttgt tgttgtaccc cacagcagtc   1200
gatctggcta agagagcctt atggacacct aaccagatca ccgacatcac ctccctcgtt   1260
cggctggtct acatcctctc caagcagaat cagcagcacc tgatccctca gtgggcactc   1320
cgtcaaatcg ccgacttcgc cctcaagctc cacaagaccc acctggcgtc tttcctcagt   1380
gcattcgcta ggcaggagct gtacctgatg ggcagtctcg tccactccat gctggtgcac   1440
accacggagc gccgcgagat cttcatcgtc gagactggcc tctgtagttt agccgagctc   1500
agtcacttca cccaactgct cgcccaccct caccacgagt accttagtga cctctatacc   1560
ccttgctcta gttccggtcg ccgcgaccac agcctggaac gtctgacccg cctcttcccc   1620
gacgctacag taccagcaac cgtgccagcg gccctgtcta tcctgtctac catgcagccc   1680
tccaccttgg agacgttccc agatctgttc tgcctccctc taggcgaatc gttctctgca   1740
ctcacggtca gcgaacacgt ctcctacatc gtcacaaacc agtatctgat aaagggcatc   1800
tcctacccag tgtcgaccac tgttgtcggc cagtccctca tcatcacaca gactgattct   1860
cagactaagt gcgagttgac acggaacatg catactacac attctatcac cgttgcttta   1920
aacataagcc tggagaactg cgccttctgc cagtccgctc tgctcgagta cgacgatacg   1980
cagggcgtca tcaacatcat gtacatgcac gactccgatg acgttctgtt cgcactggac   2040
ccctacaacg aggtcgtcgt ctcctctcct aggactcact acttaatgct gttgaagaac   2100
ggcaccgtcc tcgaggtcac cgacgtggtc gtcgatgcta cagacagccg actgctcatg   2160
atgtccgtgt acgctctctc cgccatcatc ggcatctacc tgctctaccg catgctcaag   2220
acctgc                                                              2226
```

<210> SEQ ID NO 112
<211> LENGTH: 2226
<212> TYPE: DNA
<213> ORGANISM: Artificial Sequence
<220> FEATURE:
<223> OTHER INFORMATION: Synthetic polynucleotide

<400> SEQUENCE: 112

```
atgcggcccg gcctacccag ctaccttatc atcttagccg tgtgcttgtt cagccacttg     60
ctcagcagcc ggtacggcgc cgaggccgtg tccgagcccc tcgacaaggc cttccacctc    120
ctcctcaaca cctacggccg ccccatccgc ttcctccgcg agaacaccac ccagtgcacc    180
tacaactcct ccctccgcaa ctccaccgtc gtcagagaga atgccatctc cttcaacttc    240
ttccagtcct acaaccagta ctacgtcttc cacatgcccc gctgcctctt cgccggccca    300
ctcgccgagc agttcctcaa ccaggtcgac ctcaccgaaa ctctcgagcg ctaccagcag    360
cggctgaata cgtatgccct cgtctccaag gacctcgcct cctaccgctc cttctcccag    420
cagctcaagg cccaggactc cctcggcgag cagcccacca ccgtccctcc tccaatcgac    480
ctctccatcc cacacgtctg gatgcctccc cagaccactc ctcacggctg gaccgagtcc    540
cacaccacct ccggcctcca caggccacac ttcaaccaga cctgcatcct cttcgacggc    600
cacgacctcc tcttcagcac agtgacgcca tgtctgcatc agggcttcta cctcatcgac    660
gagctccgct acgtcaagat cactctgacg gaggacttct tcgtcgtcac cgtctctata    720
```

```
gatgacgaca ccccaatgct cctcatcttc ggccacttgc ctcgcgtgct gttcaaggct    780
ccctaccagc gcgacaactt catcctccgc cagaccgaga agcatgaatt actcgtcctc    840
gtcaagaagg accagctcaa ccgccactcc tacctcaagg accccgactt cctcgacgcc    900
gccctcgact tcaactacct ggatcttagc gccctgctgc gtaacagctt ccaccgctac    960
gccgtcgacg tcctcaagtc cggccgctgc cagatgctcg accgccgcac cgtcgagatg   1020
gccttcgcct atgctctggc cctgttcgct gccgcccgcc aggaggaggc cggcgcccag   1080
gtttccgttc ctcgggcttt agacagacag gctgccctgc ttcagatcca ggagttcatg   1140
atcacctgcc tctcccagac gccaccacgc accacactgt tgctgtaccc gacagcagtg   1200
gacctggcaa agagggcact ctggactcca aaccagatca ccgacatcac ctccctcgtc   1260
cgcctcgtct acatcctctc caagcagaac cagcaacacc tgatacctca gtgggctctg   1320
cggcagatcg ccgacttcgc cctcaagctc cacaagaccc atttggcctc cttcctgagt   1380
gccttcgcta gacaggagct gtacctgatg ggctccctgg tgcactccat gctggttcac   1440
accacagagc gccgcgagat cttcatcgtc gagacaggcc tctgttcatt ggcagaactc   1500
tcgcatttca cccagctgct ggcccacccg caccacgagt atctgagtga cctctacaca   1560
ccatgcagtt cgtcaggaag gcgcgaccac agcctggagc gactgacccg cctcttcccc   1620
gacgcaacag tccctgctac tgtccctgcc gcgctgagta ttttatcaac gatgcagccc   1680
tccacgctcg aaaccttccc tgacttgttc tgcctccctc ttggagagag tttcagtgcc   1740
ctgaccgtgt cagagcacgt ctcctacatc gtcacgaacc agtatcttat caagggcatc   1800
tcctacccag tatcgactac agtggttggc cagtccctca tcatcaccca gactgacagt   1860
caaactaagt gcgagcttac tagaaacatg cacacaaccc actccatcac cgttgcatta   1920
aacatcagcc tcgagaactg cgccttctgc cagagcgctc tgctggagta cgacgacaca   1980
cagggcgtca tcaacatcat gtacatgcac gactccgacg acgtcctgtt cgcgcttgat   2040
ccctacaacg aggtcgtcgt gtccagtcca cgaactcatt acctcatgct gcttaagaac   2100
ggcaccgtcc tcgaggtcac cgacgtggtc gtcgatgcta ccgactcccg cctcctcatg   2160
atgtccgttt acgcactctc tgcgatcatc ggcatctact tactatatcg catgctcaag   2220
acctgc                                                              2226
```

<210> SEQ ID NO 113
<211> LENGTH: 834
<212> TYPE: DNA
<213> ORGANISM: Artificial Sequence
<220> FEATURE:
<223> OTHER INFORMATION: Synthetic polynucleotide

<400> SEQUENCE: 113

```
atgtgcagaa gaccagactg cggattcagc ttctccccag gcccagtgat cttactttgg     60
tgctgcctcc tccttccgat tgtgagcagt gccgccgtga gcgtggctcc taccgcggcc    120
gagaaggtgc cggccgagtg cccagagctc acccgaaggt gccttctggg cgaggttttc    180
gagggagaca agtacgagtc ttggctccgg cctctggtca acgtgacggg cagagacggc    240
cctttgagcc agctcatcag atacagacca gtaacacctg aggccgccaa ttccgtcctg    300
ctggatgagg ccttcctgga caccctcgcc ctcctttaca ataacccaga ccagctgaga    360
gccctgttga cccttctcag cagcgacacc gctccacggt ggatgaccgt catgagaggc    420
tatagcgagt gcggagatgg cagccctgcc gtctatacct gcgttgacga cctgtgcagg    480
ggctacgatt tgacaaggct cagctacggc agatctatat tcacagagca tgtgctgggc    540
```

```
ttcgagctgg tgccgccatc cctgttcaac gtggtggtcg ctataaggaa cgaggccacc    600

agaacaaatc gcgccgtgag actgccggtg tccacggcag ccgcacctga gggcattaca    660

ctgttctatg gcctctacaa cgccgtgaag gagttctgtt tgcggcacca gctggaccca    720

ccactgctca gacacctgga taagtactac gctggcctgc ctccggagct gaagcaaaca    780

cgtgtgaatc tgccagccca ctctcggtac ggaccgcagg ccgtggacgc ccgg          834
```

<210> SEQ ID NO 114
<211> LENGTH: 834
<212> TYPE: DNA
<213> ORGANISM: Artificial Sequence
<220> FEATURE:
<223> OTHER INFORMATION: Synthetic polynucleotide

<400> SEQUENCE: 114

```
atgtgcagga ggccagactg cggcttctca ttcagcccag gcccagtcat cctcctttgg     60

tgttgcctcc ttctccctat agttagcagt gccgccgtga gcgtggcccc tacagccgcg    120

gagaaggtgc cagcggagtg cccggagtta accagacgtt gcctcttggg cgaggtgttc    180

gagggcgata agtatgagtc ctggctgcgg cctctggtga acgtgaccgg cagagacgga    240

cctctgtccc agctgatcag atacagacca gtgacccctg aagccgcaaa cagcgtgctg    300

ctggacgagg ccttcctgga caccctggcc ctgttataca acaaccctga ccagcttcgc    360

gcgctgctta cactgctgag cagcgatacc gccccaagat ggatgactgt gatgaggga     420

tatagcgagt gtggcgacgg cagccctgcc gtctacacct gtgtggacga cctctgcaga    480

ggctatgacc tgaccagact gtcatacggc cgaagcatct tcaccgagca cgtcttagga    540

ttcgagctgg tgcctccaag cctcttcaat gtggtggtgg ccattcggaa cgaggctacc    600

agaaccaacc gggcggtgcg tcttccagtt tctacagccg ccgccccgga aggaattacc    660

ctgttctacg gcctgtacaa cgctgtcaag gagttctgcc tgagacacca gctggatcca    720

ccgctgctgc gccacttgga caagtactat gcgggcctcc ctcctgagct caagcagacg    780

agggtgaacc tccctgctca ctcacgttat ggaccacagg ccgtggacgc taga          834
```

<210> SEQ ID NO 115
<211> LENGTH: 834
<212> TYPE: DNA
<213> ORGANISM: Artificial Sequence
<220> FEATURE:
<223> OTHER INFORMATION: Synthetic polynucleotide

<400> SEQUENCE: 115

```
atgtgcagaa ggccagactg cggcttcagc ttctctccag gaccagtgat cctcctctgg     60

tgctgccttc tcctccctat tgtgtcctcc gccgccgtgt ccgtggcccc aaccgccgcc    120

gagaaggtgc cagcggagtg cccagagctc accaggcgct gtctgctggg cgaggtgttc    180

gagggcgata agtacgagag ttggctgagg ccgttggtga acgtgacggg cagggacggc    240

ccgctaagtc agttaataag gtaccggcca gtgaccccgg aggccgccaa cagcgtgctg    300

ctggatgagg ccttcttgga caccctggcc ctgttgtaca acaacccaga ccagctgaga    360

gccctgctga ctctgttgag cagcgacacc gccccaagat ggatgaccgt gatgagaggc    420

tatagcgagt gcggcgatgg cagccctgcc gtgtacacgt gcgtggacga tttgtgtaga    480

ggctacgacc tcaccagact gagctacggc agaagcatct tcactgagca tgtgctggga    540

ttcgagctgg tgcctcctag cctgttcaat gttgtggtgg ctatacgcaa cgaggccaca    600
```

agaacaaaca gggccgtaag actcccagtg agcaccgctg cagcccctga gggaatcacg 660
ctgttctacg gcctctacaa cgctgtgaag gagttctgtc tgaggcacca actggaccca 720
cctctgctta gacacctgga taagtactac gccggcctcc cacctgaact gaagcagacc 780
agggtgaatc ttcctgcaca ctcaaggtat ggcccacagg ccgtggatgc cagg 834

<210> SEQ ID NO 116
<211> LENGTH: 834
<212> TYPE: DNA
<213> ORGANISM: Artificial Sequence
<220> FEATURE:
<223> OTHER INFORMATION: Synthetic polynucleotide

<400> SEQUENCE: 116
atgtgcaggc ggccagactg cggcttcagc ttctcaccgg gcccagtcat cttgttgtgg 60
tgctgcctcc tcctccctat cgtaagctcg gcagccgtca gtgtggcccc aaccgccgcc 120
gagaaggttc cagccgagtg tccagaactc acaaggcggt gcctgctggg cgaggtcttc 180
gagggcgaca agtatgaaag ctggctcagg ccacttgtca atgtgacagg cagagacggc 240
ccactgagcc agcttatccg gtatagacct gtcactcctg aggccgctaa cagcgtgctt 300
ctggacgagg ctttcctgga cactctggct ctgctttaca acaacccaga ccagctgaga 360
gccctgctga ccctgctgag cagcgataca gccccaaggt ggatgacagt tatgagggga 420
tacagcgagt gtggcgacgg aagcccagcc gtgtatacct gcgtggatga cctgtgcaga 480
ggctacgacc tgacccgcct ctcctacgga agatccatct tcaccgagca cgtgctagga 540
ttcgagctcg tccctcctag cctgttcaat gtggtggtgg ccatcagaaa cgaggccact 600
cggaccaata gagcagtgag actgccagtg agcaccgcgg ccgcaccaga gggtatcaca 660
ctgttctacg gcctgtacaa cgccgtgaag gagttctgtc tgcgtcacca gctggaccca 720
cctctgctta gacatctgga taagtactat gccggcctgc ctcctgaact caagcagacc 780
cgtgtgaatc tgcctgccca ctccagatac ggccctcagg ccgtggacgc aagg 834

<210> SEQ ID NO 117
<211> LENGTH: 834
<212> TYPE: DNA
<213> ORGANISM: Artificial Sequence
<220> FEATURE:
<223> OTHER INFORMATION: Synthetic polynucleotide

<400> SEQUENCE: 117
atgtgtagac gaccagactg cggcttctct ttctctccag gcccggtgat cttactctgg 60
tgttgtttgc tccttcctat cgttagtagc gccgccgtga gcgtggctcc gacagccgcc 120
gagaaggtgc cagccgagtg cccagagctc accagaagat gtctgctggg cgaggtcttc 180
gaaggcgaca agtacgagtc ttggctgagg cctctcgtga atgttaccgg cagggacggc 240
ccactgagcc agctgattag gtaccggcca gtgaccccgg aagccgccaa cagcgtgctg 300
ctggatgaag ccttcctgga caccctggcc ctgctgtaca acaatcctga ccagctccgg 360
gccctgctga ccctcctcag cagcgacact gccccctcggt ggatgacagt catgagaggc 420
tactccgaat gtggagacgg cagccctgcc gtctacacct gtgtggacga cctctgtagg 480
ggctacgacc tgacaagact gtcctatggc agaagcattt tcaccgagca tgtgcttggc 540
ttcgagctgg tgcctccatc cctgttcaac gtggttgtgg ccattagaaa cgaggccacc 600
agaaccaaca gggccgtgcg gctgccagtg agtacagccg ctgctccaga gggcattacc 660
ctgttctacg gcctttacaa tgccgtgaag gagttctgtc tgcgccatca gctggaccct 720
cctctgctga gacacctgga taagtattac gcgggcctgc ctccagaact gaagcagacc 780
cgcgtcaacc tgccagctca tagccgttac ggcccgcaag cagtggacgc ccga 834

<210> SEQ ID NO 118
<211> LENGTH: 834
<212> TYPE: DNA
<213> ORGANISM: Artificial Sequence
<220> FEATURE:
<223> OTHER INFORMATION: Synthetic polynucleotide

<400> SEQUENCE: 118
atgtgccgaa gaccggactg cggcttcagc ttcagcccag gcccggttat cctcctctgg 60
tgctgcctcc ttctcccaat cgtgagcagc gccgccgtga gcgtggcgcc taccgccgcg 120
gagaaggtcc cagccgagtg cccagaattg acgaggagat gcttgctggg cgaagtgttc 180
gagggcgata agtatgagag ctggctgcgg cctctggtca acgtgaccgg ccgcgacggc 240
ccactgtccc agctgatcag gtacagacca gtgaccccag aggctgctaa cagcgtgctg 300
ctggatgagg ctttcctcga cacgctggct ctcctgtaca acaatccgga tcagctcaga 360
gccctgctca cactgctgtc cagcgacacc gctccaaggt ggatgacagt gatgcggggc 420
tactcagagt gcggcgacgg tagccctgcg gtgtatacat gtgtggacga cctgtgcaga 480
ggctacgact taaccaggct gtcctacggt agatccatct tcactgagca cgtgctgggc 540
ttcgagctgg tgccacctag cctgttcaat gtcgtggtag ccatccggaa cgaggctacc 600
agaacaaatc gggccgtgag gctcccagtg agcaccgccg ccgctcctga gggcatcact 660
ctgttctacg gactttacaa cgccgtcaag gagttctgcc tgcggcacca gctcgatcca 720
cctctgctga gacacctgga caagtactac gccggccttc cgcctgagct gaagcagacc 780
agagtcaacc tgcctgccca tagcagatac ggcccacagg ctgtggatgc caga 834

<210> SEQ ID NO 119
<211> LENGTH: 834
<212> TYPE: DNA
<213> ORGANISM: Artificial Sequence
<220> FEATURE:
<223> OTHER INFORMATION: Synthetic polynucleotide

<400> SEQUENCE: 119
atgtgccggc ggcccgactg cggcttcagc ttcagccccg gccccgtgat cctattgtgg 60
tgctgcctac ttttgcccat cgtgagcagc gccgccgtga gcgtggctcc taccgccgcc 120
gagaaggtgc ccgccgagtg ccccgagcta acccggcggt gccttcttgg cgaggtgttc 180
gagggcgaca agtacgagag ctggctgcgg cccctggtga acgtgaccgg ccgggacggc 240
cctctgagcc agctgatccg gtaccggccc gtgacaccag aggccgccaa cagcgtgctg 300
ctggacgagg ccttcctgga caccctggcc ctgctgtaca acaaccccga ccagctgaga 360
gctctgctga cgctgctgtc aagcgacacc gcgccacggt ggatgaccgt gatgcggggc 420
tacagcgagt gcggcgacgg cagccccgcc gtgtacacct gcgtggacga cctgtgcagg 480
ggctatgacc tgacccgtct gagctacggc cggagcatct tcaccgagca cgtgctgggc 540
ttcgagctgg tgcctcccag cctgttcaac gtggtggtgg ccatccggaa cgaggccacc 600
cggaccaacc gggccgtgcg gctgcccgtg agcaccgcag cagccccaga aggcatcacc 660
ctgttctacg gcctgtacaa tgccgtgaag gagttctgcc tgcggcacca gctggaccca 720
cctcttctca ggcacctgga taagtactac gccggcctgc ctcctgaact gaagcagacc 780
cgggtgaacc tgcccgccca cagccggtat ggcccacagg ccgtggacgc ccgg 834

<210> SEQ ID NO 120
<211> LENGTH: 834
<212> TYPE: DNA
<213> ORGANISM: Artificial Sequence
<220> FEATURE:
<223> OTHER INFORMATION: Synthetic polynucleotide

<400> SEQUENCE: 120
atgtgccggc ggcccgactg cggcttcagc ttcagccccg gccccgtgat cctcctctgg 60
tgctgcctct tgttgcccat cgtgagcagc gccgccgtga gcgtggctcc taccgccgcc 120
gagaaggtgc ccgccgagtg ccccgagctc acccggcggt gccttctggg cgaggtgttc 180
gagggcgaca agtacgagag ctggctgcgg cccctggtga acgtgaccgg ccgggacggc 240
cctctgagcc agctgatccg gtaccggccc gtgactccag aggccgccaa cagcgtgctg 300
ctggacgagg ccttcctgga caccctggcc ctgctgtaca acaaccccga ccagctgagg 360
gcccttctga ccctgctcag cagcgacacc gccccacggt ggatgaccgt gatgcggggc 420
tacagcgagt gcggcgacgg cagccccgcc gtgtacacct gcgtggacga cctgtgcagg 480
ggctacgacc tgaccaggct gagctacggc cggagcatct tcaccgagca cgtgctgggc 540
ttcgagctgg tgccgcccag cctgttcaac gtggtggtgg ccatccggaa cgaggccacc 600
cggaccaacc gggccgtgcg gctgcccgtg tcgacagccg ccgcccctga gggcatcacc 660
ctgttctacg gcctatataa cgccgtgaag gagttctgcc tgcggcacca gctggacccg 720
cccctgcttc gccacctgga caagtattac gccggcctgc ctccggagct gaagcagacc 780
cgggtgaacc tgcccgccca cagccggtac ggccctcagg ccgtggacgc ccgg 834

<210> SEQ ID NO 121
<211> LENGTH: 834
<212> TYPE: DNA
<213> ORGANISM: Artificial Sequence
<220> FEATURE:
<223> OTHER INFORMATION: Synthetic polynucleotide

<400> SEQUENCE: 121
atgtgccggc ggcccgactg cggcttcagc ttcagccccg gccccgtgat cctcctttgg 60
tgctgcttgc tcttgcccat cgtgagcagc gccgccgtct ccgtcgctcc taccgccgcc 120
gagaaggtcc ccgccgagtg ccccgagctc acccgccgct gcctcctcgg cgaggtcttc 180
gagggcgaca agtacgagtc ctggctcaga cctctcgtca acgtcaccgg ccgcgacggc 240
ccactctccc agctcatccg ctaccgcccc gtcacaccgg aggccgccaa ctccgtcctc 300
ctcgacgagg ccttcctcga caccctcgcc ctcctctaca acaaccccga ccagctccga 360
gccctgctga ccctgctgtc ctccgacacc gctcctcgct ggatgaccgt catgcgcggc 420
tactccgagt gcggcgacgg ctccccagct gtgtacacct gcgtcgacga cctctgcaga 480
ggctacgacc tgacgcgcct ctcctacggc cgctccatct tcaccgagca cgtcctcggc 540
ttcgagctcg tgcctccctc cctcttcaac gtcgtcgtcg ccatccgcaa cgaggccacc 600
cgcaccaacc gcgccgtccg cctccccgtc agcacagccg ctgcaccaga gggcatcacc 660
ctcttctacg gactgtacaa cgccgtcaag gagttctgcc tccgccacca gctcgaccca 720
cctctgctga ggcatctgga caagtattac gccggcctcc caccagagct gaagcagacc 780
cgcgtcaacc tccccgccca ctcccgctac ggaccacagg ccgtcgacgc ccgc 834

<210> SEQ ID NO 122
<211> LENGTH: 834
<212> TYPE: DNA
<213> ORGANISM: Artificial Sequence
<220> FEATURE:
<223> OTHER INFORMATION: Synthetic polynucleotide

<400> SEQUENCE: 122
atgtgccggc ggcccgactg cggcttcagc ttcagccccg gccccgtgat cctcctctgg 60
tgctgccttt tgctccccat cgtgagcagc gccgccgtct ccgtcgctcc taccgccgcc 120
gagaaggtcc ccgccgagtg ccccgagctc acccgccgct gcctcctcgg cgaggtcttc 180
gagggcgaca agtacgagtc ctggctcaga cctctcgtca acgtcaccgg ccgcgacggc 240
ccactctccc agctcatccg ctaccgcccc gtcaccccag aggccgccaa ctccgtcctc 300
ctcgacgagg ccttcctcga caccctcgcc ctcctctaca acaaccccga ccagctcagg 360
gcccttctaa ccctgctgtc ctccgacacc gcccctcgct ggatgaccgt catgcgcggc 420
tactccgagt gcggcgacgg ctccccggcc gtgtacacct gcgtcgacga cctctgcaga 480
ggatacgacc tcacccggct ctcctacggc cgctccatct tcaccgagca cgtcctcggc 540
ttcgagctcg tcccaccctc cctcttcaac gtcgtcgtcg ccatccgcaa cgaggccacc 600
cgcaccaacc gcgccgtccg cctccccgtc agcacagccg cagccccaga gggcatcacc 660
ctcttctacg gcctgtataa cgccgtcaag gagttctgcc tccgccacca gctcgacccg 720
cctctgctga ggcacctgga caagtattac gccggcctcc ctcctgagct gaagcagacc 780
cgcgtcaacc tccccgccca ctcccgctat ggaccacagg ccgtcgacgc ccgc 834

<210> SEQ ID NO 123
<211> LENGTH: 2094
<212> TYPE: DNA
<213> ORGANISM: Artificial Sequence
<220> FEATURE:
<223> OTHER INFORMATION: Synthetic polynucleotide

<400> SEQUENCE: 123
atggagagca gaatttggtg cttggtggtg tgtgttaacc tctgcattgt ttgcctcggc 60
gcagcagtgt ctagcagctc tactcgggga acatccgcaa cccacagcca ccatagctca 120
cacaccacca gcgccgccca ctccagatcc ggtagcgtga gccagcgggt gactagcagc 180
cagactgtgt cccatggcgt caacgagaca atctacaaca ccaccctgaa gtacggcgac 240
gtcgtgggcg tgaacacaac gaagtaccct tacagggtgt gtagcatggc tcagggcacc 300
gacttgatcc ggttcgagag aaatattgta tgcaccagca tgaagccaat taacgaggat 360
ctggacgaag gcatcatggt agtgtataag agaaacatag ttgcacacac tttcaaggtg 420
agggtctacc agaaggtgct gaccttccgc cgaagctatg cttacatcca tactacctac 480
ctgctcggtt ctaacaccga gtatgtggca cctccaatgt gggagatcca ccacatcaat 540
tctcatagcc agtgttacag ctcttacagc cgggtgatag ccggcaccgt cttcgtggcc 600
taccatagag attcatacga gaacaagacc atgcagctga tgccagacga ctacagcaac 660
acccattcca ccaggtatgt gacagtcaag gaccaatggc actcacgcgg ctccacctgg 720
ctgtacaggg agacttgcaa cctcaattgc atggtgacca tcaccaccgc ccgcagcaag 780
tacccgtacc acttcttcgc caccagcacc ggagatgtcg tggacatcag ccctttctat 840
aacggcacta acagaaacgc cagttacttc ggagagaatg ccgacaagtt cttcatcttc 900
ccgaactaca ctattgtgag cgatttcggt cgccctaact ccgccctgga gacacaccgc 960
ctggttgcct tcctggagag agccgattcc gtgatcagct gggacatcca ggacgagaag 1020
aatgtgacct gtcagctcac tttctgggag gcctccgaga ggactatccg gagcgaggcc 1080
gaggactcat accatttcag cagcgccaag atgaccgcca ccttcctgtc aaagaagcag 1140
gaggtgaaca tgtcagatag cgctctggac tgtgtgcgcg acgaggctat taacaagctg 1200
cagcagatct tcaatacctc ctacaatcag acctacgaga agtatggtaa cgtgtcagta 1260
ttcgagacaa ctggcggcct cgtggtgttc tggcagggaa tcaagcagaa gtccctggtg 1320
gagcttgaaa gactcgccaa ccggagcagc ctgaacctga cccacaacag gacaaagaga 1380
tctacagatg gtaacaacgc cacccatctg agcaacatgg agtccgtgca caacctggtg 1440
tacgcccagc tccagttcac atacgacacc ctgagaggct acattaatag agccctcgcc 1500
caaatcgcag aggcctggtg cgtggaccag aggcgaaccc tggaggtgtt caaggaattg 1560
agcaagatca atccaagcgc catcttgagc gcaatctata acaagccgat tgcggccaga 1620
ttcatgggcg acgtgttggg cctggcctcc tgcgtcacta tcaaccagac ctctgtcaag 1680
gtgctcagag atatgaacgt taaggagtcc ccaggcagat gctatagcag acctgtcgtg 1740
attttcaatt tcgccaactc aagctacgtg cagtacggcc agctcggcga agataacgag 1800
atcctgctgg gcaaccacag aaccgaagag tgccagctgc cttccctgaa gatttttcatc 1860 gctggcaact ccgcttacga gtacgtggat tacctgttca agagaatgat cgacctcagc 1920
agcatcagca ccgtggacag catgatcgcc ttagacattg accctctgga gaacacagat 1980
ttcagggtgc tggaactata ctctcagaag gagctccggt ctagcaacgt gttcgatctg 2040
gaggagatca tgcgggagtt caattcctac aagcagcacc accaccatca tcac 2094

<210> SEQ ID NO 124
<211> LENGTH: 2094
<212> TYPE: DNA
<213> ORGANISM: Artificial Sequence
<220> FEATURE:
<223> OTHER INFORMATION: Synthetic polynucleotide

<400> SEQUENCE: 124
atggagtcaa gaatctggtg tcttgtggtg tgcgtgaact tgtgtatcgt gtgtttgggc 60
gcagccgtgt cctcaagcag cactagaggc actagcgcca cccactccca tcatagctca 120
cacaccacaa gcgccgccca ctctaggtca ggcagcgtgt ctcagcgcgt gacctctagc 180
cagactgtga gtcacggagt caatgaaacc atctacaaca caacactgaa gtacggagac 240
gtcgtgggcg tgaatacaac caagtaccca tacagggtgt gcagcatggc tcagggcact 300
gacctcatca gattcgagcg gaacattgtg tgcacctcaa tgaagcctat caacgaggat 360
ttggatgaag gcatcatggt cgtgtacaag agaaacatcg tcgctcatac cttcaaggtg 420
agagtgtatc agaaggtgct gaccttcaga cgtagctacg cttacattca caccacctac 480
ctgctgggca gcaacaccga gtatgtggct cctcctatgt gggagataca tcacatcaac 540
agccattctc agtgctatag ttcttatagc agggtcatcg ccggcaccgt cttcgtggcc 600
taccatagag atagctacga gaacaagacc atgcagttga tgccggacga ttacagcaat 660
acccatagca ctaggtacgt gactgtgaag gaccagtggc actcccgggg tagcacctgg 720
ctttacaggg aaacctgcaa tctgaactgc atggtgacta ttaccaccgc caggagcaag 780
tatccttacc acttcttcgc tacatctact ggagacgtgg tcgatatctc tcctttctac 840
aatggcacaa acagaaatgc ttcatatttc ggcgagaatg ccgacaagtt cttcatcttc 900
ccaaactaca ccattgtgtc cgacttcgga agacctaatt ccgccctgga aacccataga 960

```
ctggtcgcat tcctggaaag ggccgactcc gtcatttcat gggacatcca ggatgagaag   1020

aacgtcacct gtcagctcac attctgggaa gcgagcgaaa gaacaattcg cagcgaagcc   1080

gaggacagct atcatttcag cagtgctaag atgaccgcca ctttcctgtc taagaagcag   1140

gaggtgaaca tgtccgacag cgccttggat tgcgtgagag acgaagctat taacaagctg   1200

cagcagatct tcaacacctc ctacaaccag acttacgaga agtatggcaa tgtgagtgtg   1260

ttcgagacaa ccggcggcct ggtagtattc tggcagggca tcaagcagaa gtcactggtg   1320

gagcttgaga ggctggccaa tagatccagc ctgaacctga cccacaaccg gacaaagaga   1380

tctaccgacg gaaacaacgc cactcatctt tccaatatgg agagcgtgca caacctggtg   1440

tacgcgcagc tccagttcac ctacgacaca ctgaggggct acataaacag ggccctggca   1500

cagatcgccg aagcctggtg cgtggaccag agaaggaccc tggaggtttt caaggagctg   1560

agcaagatta atccgtccgc tatcctgagc gcaatataca ataagccaat cgccgccaga   1620

ttcatgggcg acgtgttggg actggccagt tgcgtcacaa taaaccagac ctctgtaaag   1680

gtcctgaggg acatgaatgt caaggagagc ccgggcaggt gctacagccg tcctgtggtg   1740

attttcaact tcgctaattc atcttacgtc cagtacggcc agctgggcga agacaatgag   1800

atcttactgg gcaaccatag gactgaggag tgccagctgc cgagtctgaa gattttcata   1860

gccggcaata gcgcatatga atatgtagac tacctgttca agaggatgat tgacctctct   1920

agcatctcga ccgtggacag catgatcgcc ctcgacatcg accctctgga gaacacagac   1980

ttccgggtcc tcgaactgta cagccagaag gagcttagga gctccaacgt gttcgatctt   2040

gaggagatca tgagggagtt caatagctat aagcaacatc accaccatca tcac         2094
```

```
<210> SEQ ID NO 125
<211> LENGTH: 2094
<212> TYPE: DNA
<213> ORGANISM: Artificial Sequence
<220> FEATURE:
<223> OTHER INFORMATION: Synthetic polynucleotide

<400> SEQUENCE: 125

atggagagca gaatttggtg tctcgtggtg tgtgttaatc tctgcatcgt gtgccttggc     60

gccgccgtgt ccagcagctc caccaggggc accagcgcaa cacacagcca ccactctagc    120

cacacaacca gcgccgccca ctctcgttca ggctccgttt cacagagggt gacctcctct    180

caaaccgtgt ctcatggagt gaatgaaacc atttataaca caacactgaa gtatggcgac    240

gtggtgggcg tcaacaccac caagtatcct taccgggttt gttcaatggc ccagggcacc    300

gatctcatca gattcgagcg aaatatcgtg tgtacatcca tgaagcctat caacgaagac    360

ctggacgagg gaattatggt cgtgtacaag agaaatattg tggcccacac tttcaaggtg    420

agagtgtacc agaaggtgtt gacattcagg cggtcctacg cctacatcca caccacttat    480

ctgttgggat ccaacacaga gtacgtcgca ccgcctatgt gggaaataca tcacatcaat    540

tcccattctc agtgctattc tagctactcc agagtgatcg ccggcaccgt gttcgtggcc    600

taccaccgcg atagctacga gaataagacc atgcagctga tgcctgacga ttacagcaac    660

actcattcca cacgctacgt gaccgtgaag gatcagtggc acagccgcgg cagcacctgg    720

ctgtaccggg aaacctgcaa cctgaactgc atggtgacaa taacaaccgc acgtagcaag    780

tacccatacc acttcttcgc cacctccacc ggtgacgtgg tcgacatcag ccctttctac    840

aatggcacca acagaaatgc ctcctacttc ggcgagaacg ccgacaagtt cttcatcttc    900
```

cctaattata caattgtgag cgacttcggc aggcctaaca gcgccctgga gactcatcgc 960
ttggtggctt tcctggaacg cgctgacagc gtcatctctt gggatatcca agatgagaag 1020
aacgtgacct gccagctgac cttctgggag gccagcgaga ggacaatcag aagcgaagcc 1080
gaggactctt accatttcag ttcagctaag atgaccgcca ccttcctgag caagaagcag 1140
gaagtgaata tgtccgattc cgctcttgac tgcgtcaggg acgaagccat caacaagctc 1200
cagcagattt tcaatacttc ttataatcag acctatgaga agtacggcaa tgtcagcgtc 1260
ttcgagacga ccggcggcct ggttgtgttc tggcaaggaa tcaagcagaa gtcactggtg 1320
gagcttgagc ggctggccaa cagatccagc ttgaacctga cccataatcg caccaagcgg 1380
agtaccgatg gcaacaacgc cacacacctc agcaatatgg aaagcgtgca caaccttgtg 1440
tacgctcagc tgcagttcac ctacgatacc cttagaggct acatcaacag agccctggcc 1500
cagatcgcag aggcatggtg cgtggaccag cggcggaccc tggaggtgtt caaggagctc 1560
tccaagatca acccatccgc cattctctcc gccatctaca acaagcctat tgccgctcgg 1620
ttcatgggcg atgtgctggg actggccagc tgcgtgacca tcaaccaaac ctcagtgaag 1680
gtgctcagag acatgaacgt caaggagtct ccaggcagat gttacagcag acctgtggtg 1740
atcttcaact tcgccaattc ttcctacgtg cagtacggcc aactgggtga agacaacgag 1800
attctgttag gcaaccacag gactgaggag tgtcagctgc cgagcctgaa gatcttcatc 1860
gctggaaaca gcgcatacga gtacgtggac tacctcttca agaggatgat cgacttgtca 1920
tctatctcca cggttgattc catgatcgcc ttggacatcg atcctctgga gaataccgac 1980
ttcagagtgc tggagctcta cagccagaag gagcttaggt ctagcaatgt gttcgacctg 2040
gaggagatca tgagggagtt caatagctat aagcagcatc accaccacca tcac 2094

<210> SEQ ID NO 126
<211> LENGTH: 2094
<212> TYPE: DNA
<213> ORGANISM: Artificial Sequence
<220> FEATURE:
<223> OTHER INFORMATION: Synthetic polynucleotide

<400> SEQUENCE: 126
atggagagca gaatctggtg cctcgtggtg tgcgtgaacc tctgtatcgt ctgcttagga 60
gccgccgtga gcagtagctc taccagaggc acatccgcca cccacagcca ccactcttca 120
cacaccacca gcgccgccca ctccagatca ggcagcgtat cccagagagt gaccagcagc 180
cagaccgtgt cacatggagt gaatgaaaca atttacaaca ccaccctcaa gtacggcgac 240
gtagtgggag tgaacactac taagtaccca taccgcgtgt gtagcatggc ccagggcacc 300
gatctgatcc gattcgagag aaacatcgtt tgcaccagca tgaagcctat caacgaggac 360
ctggatgagg gcatcatggt ggtgtacaag aggaacatcg tggcccacac gttcaaggtt 420
agggtgtacc agaaggtgct gactttccga agaagctatg cctacattca cactacatac 480
ctgctcggca gtaacaccga gtacgtggcg ccaccgatgt gggaaataca ccatattaat 540
tctcatagtc agtgctattc cagctacagc agggtgatcg ccggaaccgt tttcgtggct 600
tatcatagag attcctacga gaacaagacc atgcagctga tgccagacga ctatagcaac 660
acgcatagca cccgctacgt gaccgtgaag gaccagtggc attcaagagg atccacctgg 720
ctctacagag agacatgcaa tctgaactgc atggtgacca tcaccaccgc ccggtccaag 780
tacccttatc acttcttcgc cacaagcacc ggcgatgtgg tggacatttc cccattctac 840
aacggaacca accggaacgc ctcttacttc ggcgagaacg ccgacaagtt cttcatcttc 900
ccaaattata ccatcgtgag cgacttcgga agacctaaca gcgccctgga gacacacaga 960
ctggtggcct tcctcgagcg cgccgactcc gtgatctcct gggacatcca ggacgagaag 1020
aacgtgactt gtcagctgac attctgggag gccagcgaac ggaccatcag aagcgaggct 1080
gaagactcct accacttcag ctccgccaag atgaccgcca ctttcctgtc aaagaagcag 1140
gaggtgaaca tgagcgacag cgccttggat tgcgtgagag atgaggccat caacaagctt 1200
caacagatct tcaacacatc ctacaaccag acgtacgaga agtacggaaa cgtgagcgtg 1260
ttcgaaacca ccggcggctt agtggtgttc tggcagggaa tcaagcagaa gtctctggtg 1320
gagctggaga gactggctaa cagatcctct ctaaacctga cacacaacag aaccaagcgg 1380
agcacagacg gcaataatgc cacacacctg agcaacatgg aaagcgtcca caacctcgtc 1440
tatgcccaac tgcagttcac ctacgacacc ctccgaggct acatcaacag agccctggcc 1500
cagatcgccg aggcttggtg tgtggatcag agacggaccc tggaggtgtt caaggagttg 1560
agcaagatca acccgtccgc catcttgagc gctatataca acaagccaat tgctgcgcgg 1620
ttcatgggcg acgtgctggg cctcgcctca tgtgtgacca ttaatcaaac aagcgtcaag 1680
gtcctgaggg atatgaacgt taaggagagc ccaggcaggt gctatagcag acctgtggtg 1740
attttcaact tcgccaacag cagctacgtg cagtacggcc agctgggcga ggacaacgag 1800
atcctgctgg gcaaccaccg cactgaggag tgccagctgc caagtctgaa gatattcatc 1860
gcgggaaatt cagcttacga gtatgtagac tacctgttca agagaatgat agatcttagc 1920
agcatctcca ctgtggacag tatgatagct cttgatattg acccactgga gaataccgac 1980
ttcagagtgt tggagctgta cagtcagaag gagctcagga gctccaatgt gttcgacctg 2040
gaggagatca tgagggaatt caatagctac aagcagcacc accaccatca tcac 2094

<210> SEQ ID NO 127
<211> LENGTH: 2094
<212> TYPE: DNA
<213> ORGANISM: Artificial Sequence
<220> FEATURE:
<223> OTHER INFORMATION: Synthetic polynucleotide

<400> SEQUENCE: 127
atggaatccc gaatctggtg cctcgttgtg tgcgtgaatt tgtgcatcgt gtgtttgggc 60
gccgccgtct cttcttcctc cacacgtggt accagcgcaa cacactccca ccactcaagc 120
cacaccacgt ccgcggcaca cagcagaagc ggcagtgtga gccaaagggt gaccagcagc 180
cagaccgtga gtcacggcgt gaacgagaca atctacaata ccacactcaa gtacggcgat 240
gtggtgggcg tcaacaccac caagtatcct tacagagtct gttccatggc ccagggcact 300
gacctgatcc ggttcgaaag aaacatagtg tgcacctcca tgaagcctat caatgaggac 360
ctcgatgaag gcattatggt ggtgtacaag aggaatattg tggcccatac cttcaaggtg 420
agagtgtacc agaaggtgct gaccttcaga cggagctacg cctacatcca tacaacctac 480
ctgctgggaa gcaacaccga gtacgtggct cctccaatgt gggagatcca ccacatcaat 540
agccacagcc agtgctactc cagctacagc agagtgattg ctggcaccgt cttcgtggct 600
taccacagag acagctatga gaacaagaca atgcagctca tgccagacga ctactctaac 660
acacattcaa cccggtatgt gaccgtgaag gaccagtggc actcaagagg cagcacatgg 720
ctctaccgag agacatgtaa cctgaactgc atggttacaa tcaccactgc aaggtctaag 780
tacccatatc acttcttcgc cacctctacc ggagacgtgg tggacatcag cccattctac 840

```
aatggcacca atcggaacgc aagctacttc ggagagaacg ccgacaagtt cttcatcttc    900

ccgaactaca ccatcgtgtc cgatttcggc aggccaaaca gcgccctgga gacacaccgg    960

ctggtggcct tcctggagcg cgctgactcc gttatctctt gggacatcca ggatgagaag   1020

aatgtgacct gccaactgac attctgggag gcatccgagc ggactatcag aagcgaggcc   1080

gaggacagct accacttcag cagcgctaag atgactgcta ccttcctgtc caagaagcag   1140

gaggtgaaca tgtctgattc cgctctggac tgcgtgaggg acgaggctat caacaagctc   1200

cagcagatat tcaatacttc ctacaaccag acctacgaga agtacggtaa cgtcagcgtt   1260

ttcgaaacca ccggcggcct ggtcgtgttc tggcagggaa tcaagcagaa gtcccttgtc   1320

gagctcgaga gactggccaa ccggtctagc ctcaatctga cacacaatag gaccaagaga   1380

tctactgacg gcaataacgc cacacacctc tccaacatgg agagtgttca taacctggtt   1440

tacgcccagc tgcagttcac ttacgatacc ctccgcggct acatcaacag ggccctggcg   1500

cagatcgccg aggcctggtg cgtggatcaa agaaggaccc tggaggtctt caaggaactc   1560

agcaagatca acccatctgc tatcctgagc gccatctaca acaagccaat cgccgcccgg   1620

ttcatgggcg acgtcctggg cttggctagc tgcgtgacca tcaatcagac cagcgtcaag   1680

gtgcttcgcg acatgaacgt caaggagtca cctggccgct gttactcaag gccagtcgtg   1740

atcttcaatt tcgccaatag ctcctacgtg cagtacggac agttgggcga ggacaatgaa   1800

atactcctgg gcaaccaccg caccgaggag tgtcagctgc caagcctgaa gatcttcatc   1860

gcgggaaact ccgcttacga gtatgtggac tacctgttca agagaatgat tgatctgagc   1920

agcatctcca ccgtggacag catgattgct ctggatattg atcctctgga gaacaccgat   1980

ttccgcgtgc tggagctgta cagccagaag gaattaagga gcagtaatgt gttcgacctg   2040

gaggagatca tgagggagtt caacagttac aagcagcacc accatcacca ccac         2094
```

<210> SEQ ID NO 128
<211> LENGTH: 2094
<212> TYPE: DNA
<213> ORGANISM: Artificial Sequence
<220> FEATURE:
<223> OTHER INFORMATION: Synthetic polynucleotide

<400> SEQUENCE: 128

```
atggagtcca gaatctggtg cttggtggtg tgcgtgaatc tttgcattgt gtgcctcggc     60

gccgccgtga gcagcagcag tactagaggt acctccgcta cccacagcca ccactcttcc    120

catacaacca gcgccgccca ctcacgtagc ggctctgtga gccagagggt gacaagctca    180

cagaccgtga gccacggcgt gaacgagact atctacaaca ctaccctgaa gtacggcgat    240

gtggtgggag tgaataccac aaagtacccg tacagggtgt gttccatggc ccagggcacc    300

gacctgattc gcttcgaaag aaacatcgtc tgcaccagca tgaagcctat caacgaggat    360

ttggatgagg gtattatggt ggtctacaag agaaatattg tggcccacac cttcaaggtc    420

agagtgtacc agaaggtcct gacgttcagg agatcttacg cttacatcca caccacctac    480

cttctgggct ccaacaccga gtatgtggcc ccgcctatgt gggagatcca ccacattaat    540

tcccactctc aatgctacag ctcctattcc agagtgatcg ccggcacagt cttcgtggcc    600

taccaccggg acagctatga gaacaagact atgcagctca tgccagacga ctatagcaat    660

actcatagca ctagatatgt gactgtgaag gaccagtggc atagcagagg cagcacttgg    720

ctgtaccggg aaacatgcaa tcttaattgc atggtcacca taaccaccgc gagatccaag    780

taccettacc acttcttcgc cacctccact ggtgacgtcg tggacatctc cccttttctat    840
```

-continued aacggaacaa atagaaacgc cagctacttc ggtgagaacg ccgacaagtt cttcatcttc 900
cctaactaca ccatagtgag cgatttcggc agaccgaact ccgctctgga gacacaccgg 960
ctggtggcct tcctggaacg ggccgatagt gttatctctt gggatattca agacgagaag 1020
aacgtcacct gtcagctgac tttctgggaa gccagcgaga ggaccatcag aagtgaagct 1080
gaggatagct accatttctc tagtgccaag atgactgcca ccttcctgtc caagaagcag 1140
gaggtcaaca tgtccgacag cgccctcgac tgtgtgagag acgaggctat taacaagctg 1200
cagcagattt tcaacactag ctacaatcag acatacgaga agtatggaaa cgtgagcgtg 1260
ttcgaaacta ccggtggcct ggtggtattc tggcagggca tcaagcagaa gtccctggtg 1320
gaattggaga gactggctaa caggtcgtcc ctgaacctga ctcacaatag aacgaagagg 1380
agcacagacg gcaataatgc cacccatctg tccaatatgg agagtgtgca caatttggtg 1440
tatgcccagc tgcagttcac ctacgacacc ctcaggggct acatcaacag agccctcgcc 1500
cagatcgctg aagcctggtg cgtggatcag aggaggaccc tggaggtctt caaggaactg 1560
agcaagataa acccatccgc catcctcagt gccatttata acaagcctat tgccgccagg 1620
ttcatgggcg acgtgctggg cctggcttcc tgtgtcacga ttaatcagac ctccgtgaag 1680
gtgctgaggg acatgaacgt gaaggaaagc cctggacggt gttacagccg accagtagtg 1740
atcttcaact tcgccaactc ctcatacgtg cagtatggcc agctgggcga ggacaatgaa 1800
attctgctgg gcaaccacag gaccgaagag tgccagctgc ctagcctgaa gatattcatc 1860
gccggtaata gcgcctacga gtacgtcgac tatcttttca agagaatgat cgatctgtct 1920
agcatttcta ccgtggattc catgatcgct cttgacattg acccactgga gaacacagac 1980
ttcagggtgc tcgagctgta ttcccagaag gaactcaggt ctagcaacgt tttcgacctc 2040
gaggaaatta tgagagagtt caactcgtac aagcaacacc atcaccacca tcac 2094

<210> SEQ ID NO 129
<211> LENGTH: 2094
<212> TYPE: DNA
<213> ORGANISM: Artificial Sequence
<220> FEATURE:
<223> OTHER INFORMATION: Synthetic polynucleotide

<400> SEQUENCE: 129
atggagagcc ggatctggtg cctcgtggtg tgcgtgaact tatgcatcgt gtgcctcggc 60
gccgccgtga gctctagctc tacccggggc accagcgcca cccacagcca ccacagcagc 120
cacaccacct cggccgctca cagccggagc ggcagcgtga gccagcgggt gacctccagc 180
cagaccgtgt cccacggcgt gaacgagacg atctacaaca ccaccctgaa gtacggcgac 240
gtggtgggag tgaacacgac caagtacccc taccgggtgt gcagcatggc ccagggcacc 300
gacctgatcc ggttcgagcg gaacattgtg tgcaccagca tgaagcccat caacgaggac 360
ctggacgagg gcatcatggt agtgtacaag agaaacatcg tggcccacac cttcaaggtg 420
cgggtgtacc agaaggtgct gaccttccgg cggagctacg cctacattca cacaacatac 480
ctgctgggca gcaacaccga gtacgtggct cctcccatgt gggagatcca ccacatcaac 540
tctcatagcc agtgctacag cagctacagc cgggtgatcg ccggcaccgt gttcgtggcc 600
taccaccggg acagctacga gaacaagacc atgcagctga tgcccgacga ctatagcaac 660
acacactcca ctcggtacgt gaccgtgaag gaccagtggc acagcagagg cagcacctgg 720
ctgtaccggg agacttgcaa cctgaactgc atggtgacca tcaccaccgc ccggtctaag 780 taccccttacc acttcttcgc caccagcacc ggcgatgtgg tggacatcag cccccttctac 840 aacggcacca accggaacgc cagctacttc ggcgagaacg ccgacaagtt cttcatcttc 900
cccaactaca ccatcgtgag cgacttcggc cggcccaaca gcgccctgga aactcaccgg 960
ctggtggcct tcctggagcg ggccgacagc gtgatcagct gggacatcca ggacgagaag 1020
aacgtgacct gccagctgac attctgggag gccagcgagc ggaccatccg gagcgaggcc 1080
gaggatagct atcacttcag cagcgccaag atgaccgcca ccttcctgag caagaagcag 1140
gaggtgaaca tgagcgattc tgcactggac tgcgtgcggg acgaggccat caacaagctg 1200
cagcagatct tcaacaccag ctacaaccag acctacgaga agtacggaaa cgtgagcgtg 1260
ttcgagacta ccggcggcct tgtcgtgttc tggcagggaa tcaagcagaa gtccctggtc 1320
gagctcgagc gactggccaa cagaagcagc ctgaacctga cccacaaccg gaccaagcgg 1380
agcaccgacg gcaacaacgc cacacacctg tctaacatgg agtctgtgca caacctggtg 1440
tacgcccagc tgcagttcac ctacgacacc ctgcggggct acatcaaccg ggccctggcc 1500
cagatcgccg aggcatggtg cgtggaccag cggcggaccc tggaggtgtt caaggagctc 1560
tctaagatca acccgtctgc catcctgagc gccatttaca acaagcctat cgccgcaaga 1620
ttcatgggcg acgtcctggg cctggccagc tgcgtgacga tcaatcagac cagcgtgaag 1680
gtcctgcggg acatgaacgt caaggagagc cccggcaggt gctatagccg gcccgtggtg 1740
attttcaact tcgccaatag ctcttacgtg cagtacggtc agttaggcga ggacaacgag 1800
atcttactgg gcaaccaccg gaccgaggag tgccaactcc cgagcctcaa gattttcatt 1860
gccggcaata gcgcatacga atatgtggac tacctgttca agcggatgat cgacctgagc 1920
agcatcagca ccgtggacag catgattgct ctggacatcg accctctgga gaacaccgac 1980
ttccgggtgc tggagctgta cagccagaag gagctgcgga gctctaatgt gttcgacctg 2040
gaggagatca tgcgggagtt caactcatat aagcagcacc accaccatca tcac 2094

<210> SEQ ID NO 130
<211> LENGTH: 2094
<212> TYPE: DNA
<213> ORGANISM: Artificial Sequence
<220> FEATURE:
<223> OTHER INFORMATION: Synthetic polynucleotide

<400> SEQUENCE: 130
atggagagcc ggatctggtg cctcgtggtg tgcgtgaacc tttgcatcgt gtgcttgggc 60
gccgccgtga gcagcagctc cacccggggc acctccgcca cccactccca ccactcctcc 120
cacaccacct cagccgccca ctctcgctcc ggctccgtct cccagcgcgt cacctccagc 180
cagaccgtta gccacggcgt caacgaaacc atctacaaca ccaccctcaa gtacggcgac 240
gtcgtcggcg taaacacaac caagtacccc taccgcgtct gctccatggc ccagggcacc 300
gacctcatcc gcttcgagcg caacatcgtc tgcacctcca tgaagcccat caacgaggac 360
ctcgacgagg gcatcatggt cgtctacaag cgcaatattg tggcccacac cttcaaggtc 420
cgcgtctacc agaaggtcct caccttccgc cgctcctacg cctacatcca cacaacctac 480
ctcctcggct ccaacaccga gtacgtcgcc cctcccatgt gggagatcca ccacatcaac 540
agccacagcc agtgctactc ctcctactcc cgcgtcatcg ccggcaccgt cttcgtcgcc 600
taccaccgcg actcctacga gaacaagacc atgcagctca tgcccgacga ctacagcaat 660
acccacagca cccgctacgt caccgtcaag gaccagtggc acagcagagg ctccacctgg 720
ctctaccgcg agacatgcaa cctcaactgc atggtcacca tcaccaccgc ccgctccaag 780

```
tatccttacc acttcttcgc cacctccacc ggcgatgtcg tggacatctc accattctac    840

aacggcacca accgcaacgc cagttacttc ggcgagaacg ccgacaagtt cttcatcttc    900

cccaactaca ccatcgtctc cgacttcggc cgccccaact ccgccctcga gacacacaga    960

ctggtggcct tcctcgagcg cgccgactcc gtcatctcct gggacatcca ggacgagaag   1020

aacgtcacct gccagctcac attctgggag gcctccgagc gcaccatccg ctccgaggcc   1080

gaggactcat accatttctc cagcgccaag atgaccgcca ccttcctctc caagaagcag   1140

gaggtcaaca tgagcgacag cgctctcgac tgcgtccgcg acgaggccat caacaagctc   1200

cagcagatct tcaacacctc ctacaaccag acgtacgaga agtatggaaa cgtcagtgtc   1260

ttcgaaacca cgggcggcct ggttgtattc tggcagggaa taaagcagaa gtccctcgtc   1320

gagcttgagc gcctcgccaa ccgctcctcc ctcaacctca cccacaaccg caccaagcgc   1380

tccaccgacg gcaacaacgc tacccacctg tccaacatgg agtccgtcca caacctcgtc   1440

tacgcccagc tccagttcac ctacgacacc ctccgcggct acatcaaccg cgccctcgcc   1500

cagatcgccg aggcctggtg cgtcgaccag cgccgcaccc tcgaggtctt caaggagctg   1560

agtaagatca accctagcgc gatcctcagc gctatctata acaagccaat cgctgctagg   1620

ttcatgggag acgtgctcgg cctcgcctcc tgcgtgacca tcaatcagac atccgtgaag   1680

gtgctgcgcg acatgaatgt caaggagagc ccaggccgct gttattcccg gcccgtcgtc   1740

attttcaatt tcgccaatag ctcttacgtc cagtacggcc agctcggcga ggacaacgag   1800

atcctgctgg gcaaccaccg caccgaggag tgccagctgc ctagcctcaa gattttcatt   1860

gccggcaatt ccgcttacga atacgtggac tacctcttca agcgcatgat cgacctctcc   1920

tccatctcca ccgtcgactc catgatcgcc ctggatatcg accctctcga gaacaccgac   1980

ttccgcgtgt tggagctcta ctcccagaag gagctcagat ccagcaacgt attcgacctc   2040

gaggagatca tgcgcgagtt caactcctat aagcagcacc accaccatca tcac         2094
```

<210> SEQ ID NO 131
<211> LENGTH: 2094
<212> TYPE: DNA
<213> ORGANISM: Artificial Sequence
<220> FEATURE:
<223> OTHER INFORMATION: Synthetic polynucleotide

<400> SEQUENCE: 131

```
atggagagcc ggatctggtg cttggtggtg tgcgtgaact tgtgcatcgt gtgcttgggc     60

gccgccgtga gcagctctag cacccggggc accagcgcca cccacagcca ccacagcagc    120

cacacgacct ccgccgccca ctcacggagc ggcagcgtga gccagcgggt gaccagctca    180

cagaccgtgt cccacggcgt gaacgagacg atctacaaca ccaccctgaa gtacggcgac    240

gtggtgggcg tcaacactac caagtacccc taccgggtgt gcagcatggc ccagggcacc    300

gacctgatcc ggttcgagcg gaatattgtg tgtaccagca tgaagcccat caacgaggac    360

ctggacgagg gcatcatggt ggtctacaag agaaacattg tggcccacac cttcaaggtg    420

cgggtgtacc agaaggtgct gaccttccgg cggagctacg cctacatcca tacaacctac    480

ctgctgggca gcaacaccga gtacgtggcg cctcccatgt gggagatcca ccacatcaac    540

tctcactcgc agtgctacag cagctacagc cgggtgatcg ccggcaccgt gttcgtggcc    600

taccaccggg acagctacga gaacaagacc atgcagctga tgcccgacga ctattctaac    660

acccactcca ccagatacgt gaccgtgaag gaccagtggc acagcagggg cagcacctgg    720
```

-continued

```
ctgtaccggg agacttgcaa cctgaactgc atggtgacca tcaccaccgc ccggagtaag    780

tatccatatc acttcttcgc caccagcacg ggcgacgttg tggacatcag cccc ttctac    840

aacggcacca accggaacgc cagctacttc ggcgagaacg ccgacaagtt cttcatcttc    900

cccaactaca ccatcgtgag cgacttcggc cggcccaaca gcgccctgga aacccaccgg    960

ctggtggcct tcctggagcg ggccgacagc gtgatcagct gggacatcca ggacgagaag   1020

aacgtgacct gccagctgac tttctgggag gccagcgagc ggaccatccg gagcgaggcc   1080

gaagactcct accacttcag cagcgccaag atgaccgcca ccttcctgag caagaagcag   1140

gaggtgaaca tgagcgattc agctctggac tgcgtgcggg acgaggccat caacaagctg   1200

cagcagatct tcaacaccag ctacaaccag acttacgaga agtatggaaa cgtgagcgtg   1260

ttcgagacaa ccggcggcct cgtggtgttc tggcagggta tcaagcagaa gtctctcgtg   1320

gagctggaga gactggccaa cagaagcagc ctgaacctga cccacaaccg gaccaagcgg   1380

agcaccgacg gcaacaacgc tacccatctg tctaacatgg agtcagtgca caacctggtg   1440

tacgcccagc tgcagttcac ctacgacacc ctgcggggct acatcaaccg ggccctggcc   1500

cagatcgccg aggcctggtg cgtggaccag cggcggaccc tggaggtgtt caaggagctg   1560

tccaagatca acccttccgc catcctgagc gccatttata ataagccgat cgccgcccgg   1620

ttcatgggcg atgttctggg cctggccagc tgcgtcacca ttaatcagac cagcgttaag   1680

gtcctgcggg acatgaatgt caaggagagc cccggcaggt gctactcccg ccccgtggtg   1740

atattcaact tcgccaactc tagctacgtg cagtacggcc aactaggcga ggacaacgag   1800

atcttgctcg gtaaccaccg gaccgaggag tgccagttac cttccctgaa gattttcatc   1860

gcgggcaact ccgcctacga gtatgtggac tacctgttca agcggatgat cgatctttct   1920

agcatcagca ccgtggacag catgatagcc ctggacatcg acccactgga gaacaccgac   1980

ttccgggtgc tggagctgta cagccagaag gagcttcgga gcagcaatgt gttcgacctg   2040

gaggagatca tgcgggagtt caattcttac aagcagcacc accaccatca tcac         2094
```

<210> SEQ ID NO 132
<211> LENGTH: 2094
<212> TYPE: DNA
<213> ORGANISM: Artificial Sequence
<220> FEATURE:
<223> OTHER INFORMATION: Synthetic polynucleotide

<400> SEQUENCE: 132

```
atggagagcc ggatctggtg cctcgtggtg tgcgtgaacc tctgcatcgt gtgcctcggc     60

gccgccgtgt cttcatcctc cacccggggc acctccgcca cccactccca ccactcctcc    120

cacaccacta gtgccgccca ctcacgctcc ggctccgtct cccagcgcgt cacctcatcc    180

cagacagtga gccacggcgt caacgaaacc atctacaaca ccaccctcaa gtacggcgac    240

gtcgtgggcg tgaacactac aaagtacccc taccgcgtct gctccatggc ccagggcacc    300

gacctgatcc gcttcgagcg caacatcgtc tgcacctcca tgaagcccat caacgaggac    360

ctcgacgagg gcatcatggt cgtctacaag aggaacattg tggcccacac cttcaaggtc    420

cgcgtctacc agaaggtcct caccttccgc cgctcctacg cctacatcca cactacgtac    480

ctcctcggct ccaacaccga gtacgtcgcc cctcccatgt gggagatcca ccacatcaac    540

tcgcacagcc agtgctactc ctcctactcc cgcgtcatcg ccggcaccgt cttcgtcgcc    600

taccaccgcg actcctacga gaacaagacc atgcagctca tgcccgacga ctatagcaac    660

acacatagca cccgctacgt caccgtcaag gaccagtggc atagcagagg ctccacctgg    720
```

-continued

```
ctctaccgcg agacgtgcaa cctcaactgc atggtcacca tcaccaccgc ccgcagcaag    780
tatccatatc acttcttcgc cacctccaca ggagacgtgg tcgacatctc gcctttctac    840
aacggcacca accgcaacgc tagctacttc ggcgagaacg ccgacaagtt cttcatcttc    900
cccaactaca ccatcgtctc cgacttcggc cgccccaact ccgccctcga gactcaccgc    960
ttggtggcct tcctcgagcg cgccgactcc gtcatctcct gggacatcca ggacgagaag   1020
aacgtcacct gccagctgac cttctgggag gcctccgagc gcaccatccg ctccgaggcc   1080
gaggacagct accacttcag cagcgccaag atgaccgcca ccttcctctc caagaagcag   1140
gaggtcaaca tgagcgacag cgcccttgac tgcgtccgcg acgaggccat caacaagctc   1200
cagcagatct tcaacacctc ctacaaccag acttatgaga agtacggaaa cgtctccgtt   1260
ttcgagacaa caggaggcct ggttgtcttc tggcagggca ttaagcagaa gtccctcgtc   1320
gagctggaga gactcgccaa ccgctcctcc ctcaacctca cccacaaccg caccaagcgc   1380
tccaccgacg gcaacaatgc tacacacctg agcaacatgg agtccgtcca caacctcgtc   1440
tacgcccagc tccagttcac ctacgacacc ctccgcggct acatcaaccg cgccctcgcc   1500
cagatcgccg aggcgtggtg cgtcgaccag cgccgcaccc tcgaggtctt caaggagctg   1560
tccaagatca accctagcgc catcctgtcc gcaatctata acaagcctat cgcggctagg   1620
ttcatgggcg atgtgctcgg cctcgcctcc tgcgtgacta ttaatcagac cagcgtcaag   1680
gtgctgcgcg acatgaacgt gaaggagagc cctggccgct gctattccag gcccgtcgtc   1740
atcttcaatt tcgccaattc cagctatgtc cagtacggcc agctcggcga ggacaacgag   1800
atcctgcttg gcaaccaccg caccgaggag tgtcagctcc ctagcctgaa gattttcatt   1860
gccggcaata gcgcttatga gtatgtggac tacctcttca agcgcatgat cgacctctcc   1920
tccatctcca ccgtcgactc catgatcgcc ctggacatcg acccactgga gaacaccgac   1980
ttccgcgtgc tcgaactcta ctcccagaag gaactgagat caagcaacgt gttcgacctc   2040
gaggagatca tgcgcgagtt caactcttat aagcagcacc accaccatca tcac         2094
```

<210> SEQ ID NO 133
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 133

```
atgctcagac ttctcctcag acaccacttc cactgcctct tgctttgtgc cgtctgggcc     60
acaccttgcc tcgccagccc ttggagcacc ttgacagcca accagaaccc ttcccctcct    120
tggtcaaagt tgacctacag caagcctcac gacgctgcta ccttctactg tccattcctg    180
taccctagcc ctccaagatc tccgctgcag ttcagcggct tccagagggt gtctaccgga    240
cctgagtgca ggaatgagac gctgtacctg ctgtacaaca gagagggcca gaccctggtg    300
gaaagaagct ccacctgggt caagaaggta atctggtacc tgagcggcag aaaccagaca    360
atactccaga gaatgccacg gaccgctagc aagcctagcg atggaaacgt gcagattagc    420
gtggaggacg caaagatttt cggcgcccac atggtgccaa agcagacaaa gctgctgcgg    480
ttcgtggtca acgacggcac ccggtaccag atgtgcgtga tgaagctgga gagctgggct    540
cacgtgttca gagattactc tgtgagcttc caagtgcggc tcaccttcac cgaagccaac    600
aatcagacct acactttctg tactcaccct aacctgatcg tg                       642
```

<210> SEQ ID NO 134
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 134
atgcttagac tcctcctcag acaccacttc cattgtctcc ttttgtgcgc cgtgtgggcc 60 acccccttgcc ttgcatcacc ttggtctacc ctcaccgcca accagaaccc tagccctcct 120
tggagtaagt taacatactc taagccgcac gacgccgcca ccttctactg tcctttcctc 180
tacccaagcc cacctcgtag cccacttcag ttctctggat tccagagagt ttcaacaggc 240
cctgagtgtc ggaacgagac tctgtacctg ttgtataaca gagagggaca gaccctggtg 300
gagcggtcct ccacctgggt gaagaaggtg atctggtatc tgagcggcag aaaccagacc 360
atcctgcagc ggatgccaag gaccgctagc aagccaagcg acggcaatgt gcagattagc 420
gtggaggatg ctaagatttt cggcgcacac atggttccta agcagaccaa gctgttacgg 480
ttcgtggtga acgatggaac tcggtaccaa atgtgcgtga tgaagctgga gtcatgggca 540
catgtgttcc gtgactactc tgtttctttc caggtgcgcc tgaccttcac cgaggccaat 600
aaccagacat acaccttctg tacgcaccca aatctgatcg ta 642

<210> SEQ ID NO 135
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 135
atgctcagac ttttgctcag acaccacttc cactgtttgt tgttatgtgc cgtgtgggct 60 acccccttgcc tcgcatctcc gtggtccaca ctcacagcca accagaatcc ttctcctcct 120
tggagcaagc tcacatatag caagcctcac gacgcggcaa ccttctactg cccattcctg 180
tatccttctc ctccgcggag ccctctgcag ttctccggat tccagagagt gtccaccggt 240
cctgagtgca gaaatgaaac actgtatctt ctctacaaca gagagggcca gacccttgtg 300
gagagaagca gcacctgggt gaagaaggtc atttggtatc tgtctggcag aaaccagacc 360
atactgcagc ggatgccaag aacagcctcc aagccatccg acggtaacgt gcagatctcc 420
gtggaggacg ccaagatttt cggcgcccac atggtgccaa agcagaccaa gctgctgaga 480
ttcgtggtga acgatggcac caggtaccag atgtgcgtta tgaagcttga gtcctgggct 540
cacgtgttca gagactactc tgtgagcttc caggtgagac tgacattcac agaggccaac 600
aaccagactt acaccttctg cacgcatcct aatctgatcg tg 642

<210> SEQ ID NO 136
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 136
atgctcagac ttcttctcag acaccacttc cactgtttgc ttctctgcgc agtgtgggca 60 acccccttgcc ttgcttcccc ttggtcgact ctcaccgcca accagaatcc aagccctcct 120
tggagcaagc tcacttacag caagccgcac gacgccgcca ccttctactg tcctttcctg 180
taccctagcc ctccaagatc tcctctgcaa ttctctggat tccagagagt gagcaccggc 240
ccagagtgcc ggaacgagac tctgtatctg ctgtacaata gggagggaca aaccctggtg 300
gagaggagca gcacatgggt gaagaaggtg atctggtacc tgagcggcag aaaccagacc 360
atcctgcaga gaatgccacg gaccgccagc aagccaagcg atggcaacgt ccagattagc 420
gtggaagacg ccaagatctt cggagcccac atggtgccta agcagaccaa gcttctgcga 480
ttcgtggtga acgacggtac ccgctaccaa atgtgcgtga tgaagctgga gtcatgggcc 540
cacgtcttcc gcgactacag cgtatccttc caggtgaggc ttaccttcac cgaggccaac 600
aaccaaacct acacattctg cacccatcca aatttgattg tg 642

<210> SEQ ID NO 137
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 137
atgctcagac tattgttgag acatcacttc cattgcctcc ttttgtgcgc cgtgtgggct 60
accccttgcc tcgcctcacc ttggagcacc ttgaccgcca accagaaccc gagccctccg 120
tggtcaaagc tcacctacag caagcctcac gacgccgcaa ccttctattg tccattcctg 180
tacccttctc cgccgaggtc ccctcttcag ttcagcggat tccagagagt gtctaccgga 240
ccagaatgca gaaacgaaac actgtatctg ctgtacaacc gggagggcca gaccctggtc 300
gagcggagct ctacctgggt caagaaggtt atatggtatc tgagcggcag gaaccagacc 360
atcctgcagc gcatgcctag aaccgctagc aagccaagcg acggcaacgt tcagatctcc 420
gtggaggacg ctaagatctt cggcgcccat atggtgccaa agcagactaa gctgctgaga 480
ttcgtggtaa acgacggcac aagatatcag atgtgcgtga tgaagctgga gagctgggct 540
catgtgttca gggactactc cgtgagtttc caggtgaggc tgacattcac cgaggctaat 600
aatcagacct acaccttctg cactcaccca aatctgatcg tg 642

<210> SEQ ID NO 138
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 138
atgctcagat tattgctcag acaccacttc cactgcctcc tcttgtgcgc cgtgtgggcg 60
acaccgtgtc tcgcaagccc ttggtccaca ctaacggcca accagaaccc tagccctcct 120
tggagcaagc tcacttatag caagccacac gatgcggcca ctttctactg tcctttcctg 180
tatccatccc ctcctagatc tcctctgcag ttcagcggat tccagagagt atctactggc 240
cctgagtgca gaaatgaaac cctctatctc ctgtacaatc gggagggcca gactttggtg 300
gagcgcagct ccacctgggt gaagaaggtg atctggtacc tgagcggcag aaaccagacc 360
atcctacaga ggatgccaag gaccgccagc aagccatctg acggcaacgt gcagatctct 420
gtggaggacg ccaagatctt cggagcccat atggtgccta agcagacaaa gctgttgagg 480
ttcgtcgtga atgacggcac aagataccag atgtgtgtga tgaagctgga gagctgggct 540
cacgtgttcc gagactacag cgtctcgttc caggtgagac tgacattcac cgaggcaaac 600

-continued aaccagacct acaccttctg tacgcaccct aacctgatcg tt 642

<210> SEQ ID NO 139
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 139
atgcttcggc tcctccttcg gcaccacttc cactgcctcc tcctctgcgc cgtgtgggcc 60
acaccttgcc tcgccagccc ctggagcacc ctcaccgcca accagaaccc cagccctccg 120
tggtctaagt taacctacag caagccccac gacgccgcca ccttctactg ccccttcctg 180
tacccttcac cgccgcggag cccgctgcag ttcagcggct tccagcgggt gagcaccggc 240
cccgagtgcc ggaacgagac gctgtacctg ctgtacaacc gggagggcca gaccctggtg 300
gagcggagca gcacctgggt gaagaaggtg atctggtacc tgagcggccg gaaccagacc 360
atcctgcagc ggatgccccg gaccgcctca aagccaagcg acggcaacgt gcagatcagc 420
gtggaggacg ccaagatctt cggcgcccac atggtgccca agcagaccaa gttgctgcgc 480
ttcgtggtga acgacggcac ccggtaccag atgtgcgtga tgaagctgga gagctgggcc 540
cacgtgttcc gggactacag cgtgagcttc caggtgcggc tgacattcac cgaggccaac 600
aatcagacct acaccttctg cacccacccc aacctgatcg tg 642

<210> SEQ ID NO 140
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 140
atgttacggc tccttctccg ccaccacttc cactgcctct tactctgcgc cgtgtgggcc 60
actccatgcc ttgccagccc ctggagcacc ttgaccgcca accagaaccc cagcccacct 120
tggagtaagc tcacctacag caagccccac gacgccgcca ccttctactg ccccttcctg 180
tatccgagcc caccgcggag cccgctgcag ttcagcggct tccagcgggt gagcaccggc 240
cccgagtgcc ggaacgaaac cctgtacctg ctgtacaacc gggagggcca gaccctggtg 300
gagcggagca gcacctgggt gaagaaggtg atctggtacc tgagcggccg gaaccagacc 360
atcctgcagc ggatgccccg gaccgctagt aagcctagcg acggcaacgt gcagatcagc 420
gtggaggacg ccaagatctt cggcgcccac atggtgccca agcagaccaa gctgcttagg 480
ttcgtggtga acgacggcac ccggtaccag atgtgcgtga tgaagctgga gagctgggcc 540
cacgtgttcc gggactacag cgtgagcttc caggtgcggc tgaccttcac cgaggccaac 600
aaccagacat acaccttctg cacccacccc aacctgatcg tg 642

<210> SEQ ID NO 141
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 141
atgctacggc tcctactccg ccaccacttc cactgcttac ttttgtgcgc cgtgtgggcc 60
acaccatgct tggccagccc ctggagcacc ctcaccgcca accagaaccc ctcacctccc 120
tggtccaagc tcacctactc caagccccac gacgccgcca ccttctactg ccccttcctc 180
tatccatctc ctccacgcag cccactccag ttctccggct tccagcgcgt ctccaccggc 240
cccgagtgcc gcaacgagac gctctacctc ctctacaacc gcgagggcca gaccctcgtc 300
gagaggtcat ccacctgggt caagaaggtc atctggtacc tctccggccg caaccagacc 360
atcctccagc gcatgccccg caccgcgtct aagccgtccg acggcaacgt ccagatctcc 420
gtcgaggacg ccaagatctt cggcgcccac atggtcccca agcagaccaa gctcctccgc 480
ttcgtcgtca acgacggcac ccgctaccag atgtgcgtca tgaagctcga gtcctgggcc 540
cacgtcttcc gcgactactc cgtctccttc caggtccgcc tcaccttcac cgaggccaat 600
aaccagactt acaccttctg cacccacccc aacctcatcg tc 642

<210> SEQ ID NO 142
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 142
atgctacggc tcctactccg ccaccacttc cactgcttac ttttgtgcgc cgtgtgggcc 60
acaccatgct tggccagccc ctggagcacc ctcaccgcca accagaaccc ctcacctccc 120
tggtccaagc tcacctactc caagccccac gacgccgcca ccttctactg ccccttcctc 180
tatccatctc ctccacgcag cccactccag ttctccggct tccagcgcgt ctccaccggc 240
cccgagtgcc gcaacgagac gctctacctc ctctacaacc gcgagggcca gaccctcgtc 300
gagaggtcat ccacctgggt caagaaggtc atctggtacc tctccggccg caaccagacc 360
atcctccagc gcatgccccg caccgcgtct aagccgtccg acggcaacgt ccagatctcc 420
gtcgaggacg ccaagatctt cggcgcccac atggtcccca agcagaccaa gctcctccgc 480
ttcgtcgtca acgacggcac ccgctaccag atgtgcgtca tgaagctcga gtcctgggcc 540
cacgtcttcc gcgactactc cgtctccttc caggtccgcc tcaccttcac cgaggccaat 600
aaccagactt acaccttctg cacccacccc aacctcatcg tc 642

<210> SEQ ID NO 143
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 143
atgcttcggc tcctcctaag gcaccacttc cactgccttt tgctttgcgc cgtgtgggcc 60
accccttgct tggccagccc ctggagcacc ctcaccgcca accagaaccc ctcccctccc 120
tggtccaagc tcacctactc caagccccac gacgccgcca ccttctactg ccccttcctc 180
tacccgtccc ctccacgcag cccactccag ttctccggct tccagcgcgt ctccaccggc 240
cccgagtgcc gcaacgaaac actctacctc ctctacaacc gcgagggcca gaccctcgtc 300
gagcgctcct ccacctgggt caagaaggtc atctggtacc tctccggccg caaccagacc 360
atcctccagc gcatgccccg caccgcaagc aagccatccg acggcaacgt ccagatctcc 420
gtcgaggacg ccaagatctt cggcgcccac atggtcccca agcagaccaa gctcctccgc 480
ttcgtcgtca acgacggcac ccgctaccag atgtgcgtca tgaagctcga gtcctgggcc 540
cacgtcttcc gcgactactc cgtctccttc caggtccgcc tcaccttcac cgaggccaat 600
aatcagacat acaccttctg cacccacccc aacctcatcg tc 642

<210> SEQ ID NO 144
<211> LENGTH: 387
<212> TYPE: DNA
<213> ORGANISM: Artificial Sequence
<220> FEATURE:
<223> OTHER INFORMATION: Synthetic polynucleotide

<400> SEQUENCE: 144
atgcggctgt gtcgggtgtg gctgtctgtt tgtctgtgcg ccgtggtgct gggtcagtgc 60
cagcgggaaa ccgcggaaaa gaacgattat taccgagtac cgcattactg ggacgcgtgc 120
tctcgcgcgc tgcccgacca aacccgttac aagtatgtgg aacagctcgt ggacctcacg 180
ttgaactacc actacgatgc gagccacggc ttggacaact ttgacgtgct caagagaatc 240
aacgtgaccg aggtgtcgtt gctcatcagc gactttagac gtcagaaccg tcgcggcggc 300
accaacaaaa ggaccacgtt caacgccgcc ggttcgctgg cgccacacgc ccggagcctc 360
gagttcagcg tgcggctctt tgccaac 387

<210> SEQ ID NO 145
<211> LENGTH: 92
<212> TYPE: DNA
<213> ORGANISM: Artificial Sequence
<220> FEATURE:
<223> OTHER INFORMATION: Synthetic polynucleotide

<400> SEQUENCE: 145
tcaagctttt ggaccctcgt acagaagcta atacgactca ctatagggaa ataagagaga 60
aaagaagagt aagaagaaat ataagagcca cc 92

<210> SEQ ID NO 146
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 146
gggaaataag agagaaaaga agagtaagaa gaaatataag agccacc 47

<210> SEQ ID NO 147
<211> LENGTH: 119
<212> TYPE: DNA
<213> ORGANISM: Artificial Sequence
<220> FEATURE:
<223> OTHER INFORMATION: Synthetic polynucleotide

<400> SEQUENCE: 147
tgataatagg ctggagcctc ggtggccatg cttcttgccc cttgggcctc cccccagccc 60
ctcctcccct tcctgcaccc gtacccccgt ggtctttgaa taaagtctga gtgggcggc 119

<210> SEQ ID NO 148
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 148
ccgcgccaag aggagc 16

<210> SEQ ID NO 149
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 149
gctactaact tcagcctgct gaagcaggct ggagacgtgg aggagaaccc tggacct 57

<210> SEQ ID NO 150
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 150
gtgaaacaga ctttgaattt tgaccttctc aagttggcgg gagacgtgga gtccaaccct 60
ggacct 66

<210> SEQ ID NO 151
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 151
cagtgtacta attatgctct cttgaaattg gctggagatg ttgagagcaa ccctggacct 60

<210> SEQ ID NO 152
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 152
gagggcagag gaagtctgct aacatgcggt gacgtcgagg agaatcctgg acct 54

<210> SEQ ID NO 153
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 153

```
Gly Ser Gly Ala Thr Asn Phe Ser Leu Leu Lys Gln Ala Gly Asp Val
1               5                   10                  15

Glu Glu Asn Pro Gly Pro
            20
```

<210> SEQ ID NO 154
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 154

```
Gly Ser Gly Glu Gly Arg Gly Ser Leu Leu Thr Cys Gly Asp Val Glu
1               5                   10                  15
```

Glu Asn Pro Gly Pro
20

<210> SEQ ID NO 155
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 155

Gly Ser Gly Gln Cys Thr Asn Tyr Ala Leu Leu Lys Leu Ala Gly Asp
1 5 10 15

Val Glu Ser Asn Pro Gly Pro
20

<210> SEQ ID NO 156
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 156

Gly Ser Gly Val Lys Gln Thr Leu Asn Phe Asp Leu Leu Lys Leu Ala
1 5 10 15

Gly Asp Val Glu Ser Asn Pro Gly Pro
20 25

<210> SEQ ID NO 157
<211> LENGTH: 2721
<212> TYPE: DNA
<213> ORGANISM: Artificial Sequence
<220> FEATURE:
<223> OTHER INFORMATION: Synthetic polynucleotide

<400> SEQUENCE: 157
atggaaagca gaatttggtg cctcgtggtc tgcgtgaacc tctgtatcgt gtgcttaggc 60
gccgcagttt caagcagctc caccagaggt acgtcggcta cccacagcca tcactcaagt 120
cacactacaa gcgccgctca cagcagaagc ggatctgtga gccagagggt gaccagctcc 180
cagaccgtga gccacggagt aaatgaaacc atctacaata ccacattgaa gtatggcgac 240
gtcgtgggcg tgaacacgac caaataccec tacagggtct gctctatggc tcagggcact 300
gacctgattc ggtttgagag aaatatcgtc tgcaccagca tgaagcccat taacgaggac 360
ctggatgagg gcatcatggt ggtatataaa cgtaacattg tggcccacac cttcaaagtg 420
agagtttacc agaaagtgct gaccttcaga agatcctacg cttacattca cacaacctac 480
ctgctgggct caaacaccga atacgtggcc cctcccatgt gggaaatcca ccacatcaac 540
tctcacagcc agtgctacag ctcttacagc agggttattg ccggcaccgt cttcgtggcc 600
taccaccgcg acagttatga gaacaagacc atgcagctga tgcctgacga ctacagcaac 660
acccactcta ccagatacgt gaccgttaag gaccagtggc acagccgggg ctcaacctgg 720
ctgtatcggg aaacttgtaa cctgaattgc atggtgacca tcacaactgc cagaagcaag 780
tacccctatc acttcttcgc caccagcact ggcgatgtgg tggatatctc tcccttctac 840
aacggaacca atcgcaacgc ttcttacttt ggcgagaacg ccgacaagtt ctttatcttt 900
cccaactaca ccatcgtcag cgacttcggt agacccaatt ctgccctgga aactcatcga 960
cttgtggcat tcctggaaag ggccgattcc gtgatcagct gggacattca ggacgagaag 1020
aacgttacct gccagctcac attttgggag gccagcgaga ggaccattag gagcgaggcc 1080
gaggacagct accacttttc cagtgccaag atgacagcca catttctctc taagaagcag 1140
gaggttaaca tgtccgacag cgccctggac tgtgtcagag acgaggccat caataagctg 1200
cagcagatct tcaacaccag ctacaatcag acatatgaga agtacggcaa cgtcagcgtc 1260
ttcgagacaa caggcgggct ggtcgtgttc tggcagggaa tcaaacagaa gtccctggtt 1320
gagctggaga gactggcgaa caggagctct ctgaatttga ctcataacag gacgaagaga 1380
tccaccgatg gaaacaacgc cacccacctg agcaatatgg agagcgtcca caatctcgtc 1440
tacgcccagc tccaattcac ctacgacacc ctgaggggct atatcaaccg ggccctggcc 1500
cagatcgccg aggcatggtg cgtggaccag agacggaccc tggaagtgtt caaggagctg 1560
tcaaagatca acccttccgc catcctctcc gccatatata ataagcccat cgccgcaaga 1620
ttcatgggag atgtcctggg tctggctagc tgcgttacca tcaaccagac atcagtgaag 1680
gttttgcgag acatgaatgt gaaggagtca cccggccgat gttacagccg cccagtcgtg 1740
atctttaact tcgccaattc cagctacgtc caatacggcc agctgggcga ggacaatgaa 1800
attctcctgg gtaatcatag aaccgaggag tgccaactcc cctcccttaa gattttcatc 1860
gcaggcaata gcgcttatga gtacgttgac tacttgttta agagaatgat cgatctgagc 1920
agcatcagca cagtggactc catgattgcc cttgatatcg atcccctgga gaataccgac 1980
tttagagtgc tggagttata cagccagaaa gagctgcgaa gctccaacgt gttcgatctg 2040
gaggaaatta tgagggagtt taactcctac aagcagagag tgaagtacgt cgaagacaaa 2100
gtggtggatc cactgccgcc ttatcttaaa ggcctcgacg atctgatgag cggactgggt 2160
gccgccggca aagctgtggg cgttgccatc ggagccgtgg gcggggccgt ggcctccgtg 2220
gtggaaggcg tggctacctt tctgaagaac ccattcggcg cctttaccat tatcctggtg 2280
gccattgccg tggtgatcat tacctatctc atctacacta ggcagcggag gctgtgtacg 2340
cagcctctgc agaacctgtt tccctacctg gttagcgccg acggaacaac agtgacatct 2400
ggctctacca aggatacctc tctgcaggca cctccttctt acgaggaatc cgtgtacaac 2460
tcgggaagga aaggccccgg gccaccttca tccgacgcct ccacagctgc cccgccatac 2520
actaacgagc aggcttacca gatgcttctc gccctggcta gattggatgc cgagcagcgc 2580
gcccaacaga acggcaccga cagcctggac ggccggacag gcacccagga caaagggcag 2640
aagcccaatc tgcttgatag actgaggcac cggaagaacg ggtacaggca tcttaaggac 2700
agcgacgagg aggagaacgt c 2721

<210> SEQ ID NO 158
<211> LENGTH: 2437
<212> TYPE: RNA
<213> ORGANISM: Artificial Sequence
<220> FEATURE:
<223> OTHER INFORMATION: Synthetic polynucleotide

<400> SEQUENCE: 158
ucaagcuuuu ggacccucgu acagaagcua auacgacuca cuauagggaa auaagagaga 60
aaagaagagu aagaagaaau auaagagcca ccaugcggcc aggccucccc uccuaccuca 120
ucauccucgc cgucugucuc uucagccacc uacuuucguc acgauauggc gcagaagccg 180
uauccgaacc gcuggacaaa gcguuucacc uacugcucaa caccuacggg agacccaucc 240
gcuuccugcg ugaaaauacc acccagugua ccuacaacag cagccuccgu aacagcacgg 300

```
ucgucaggga aaacgccauc aguuucaacu uuuuccaaag cuauaaucaa uacuauguau    360
uccauaugcc ucgaugucuu uuugcggguc cucuggcgga gcaguuucug aaccagguag    420
aucugaccga aacccuggaa agauaccaac agagacuuaa cacuuacgcg cugguaucca    480
aagaccuggc cagcuaccga ucuuuuucgc agcagcuaaa ggcacaagac agccuaggug    540
aacagcccac cacugugcca ccgcccauug accugucaau accucacguu uggaugccac    600
cgcaaaccac uccacacggc uggacagaau cacauaccac cucaggacua caccgaccac    660
acuuuaacca gaccuguauc cucuuugaug gacacgaucu acuauucagc accgucacac    720
cuuguuugca ccaaggcuuu uaccucaucg acgaacuacg uuacguuaaa auaacacuga    780
ccgaggacuu cuucguaguu acggugucca uagacgacga cacacccaug cugcuuaucu    840
ucggccaucu uccacgcgua cuuuucaaag cgcccuauca acgcgacaac uuuauacuac    900
gacaaacuga aaaacacgag cuccuggugc uaguuaagaa agaucaacug aaccgucacu    960
cuuaucucaa agacccggac uuucuugacg ccgcacuuga cuucaacuac cuagaccuca   1020
gcgcacuacu acguaacagc uuucaccguu acgccgugga uguacucaag agcggucgau   1080
gucagaugcu ggaccgccgc acgguagaaa uggccuucgc cuacgcauua gcacuguucg   1140
cagcagcccg acaagaagag gccggcgccc aagucuccgu cccacgggcc cuagaccgcc   1200
aggccgcacu cuuacaaaua caagaauuua ugaucaccug ccucucacaa acaccaccac   1260
gcaccacguu gcugcuguau cccacggccg uggaccuggc caaacgagcc cuuuggacac   1320
cgaaucagau caccgacauc accagccucg uacgccuggu cuacauacuc ucuaaacaga   1380
aucagcaaca ucucaucccc caaugggcac uacgacagau cgccgacuuu gcccuaaaac   1440
uacacaaaac gcaccuggcc ucuuuucuuu cagccuucgc acgccaagaa cucuaccuca   1500
ugggcagccu cguccacucc augcugguac auacgacgga gagacgcgaa aucuucaucg   1560
uagaaacggg ccucuguuca uuggccgagc uaucacacuu uacgcaguug uuagcucauc   1620
cacaccacga auaccucagc gaccuguaca cacccuguuc caguagcggg cgacgcgauc   1680
acucgcucga acgccucacg cgucucuucc ccgaugccac cgucccccgcu accguucccg   1740
ccgcccucuc cauccuaucu accaugcaac caagcacgcu ggaaaccuuc cccgaccugu   1800
uuugcuugcc gcucggcgaa uccuucuccg cgcugaccgu cuccgaacac gucaguuaua   1860
ucguaacaaa ccaguaccug aucaaaggua ucuccuaccc ugucuccacc accgucguag   1920
gccagagccu caucaucacc cagacggaca gucaaacuaa augcgaacug acgcgcaaca   1980
ugcauaccac acacagcauc acaguggcgc ucaacauuuc gcuagaaaac ugcgccuuuu   2040
gccaaagcgc ccugcuagaa uacgacgaca cgcaaggcgu caucaacauc auguacaugc   2100
acgacucgga cgacguccuu uucgcccugg aucccuacaa cgaaguggug gucucaucuc   2160
cgcgaacuca cuaccucaug cuuuugaaaa acgguacggu acuagaagua acugacgucg   2220
ucguggacgc caccgacagu cgucuccuca ugauguccgu cuacgcgcua ucggccauca   2280
ucggcaucua ucugcucuac cgcaugcuca agacaugcug auaauaggcu ggagccucgg   2340
uggccaugcu ucuugccccu ugggccuccc cccagccccu ccucccccuuc cugcacccgu   2400
acccccgugg ucuuugaaua aagucugagu gggcggc                            2437
```

```
<210> SEQ ID NO 159
<211> LENGTH: 2464
<212> TYPE: RNA
<213> ORGANISM: Artificial Sequence
<220> FEATURE:
<223> OTHER INFORMATION: Synthetic polynucleotide
```

<400> SEQUENCE: 159
ucaagcuuuu ggacccucgu acagaagcua auacgacuca cuauagggaa auaagagaga 60
aaagaagagu aagaagaaau auaagagcca ccaugcggcc aggccucccc uccuaccuca 120
ucauccucgc cgucugucuc uucagccacc uacuuucguc acgauauggc gcagaagccg 180
uauccgaacc gcuggacaaa gcguuucacc uacugcucaa caccuacggg agacccaucc 240
gcuuccugcg ugaaaauacc acccagugua ccuacaacag cagccuccgu aacagcacgg 300
ucgucaggga aaacgccauc aguuucaacu uuuuccaaag cuauaaucaa uacuauguau 360
uccauaugcc ucgaugucuu uuugcgggua cucuggcgga gcaguuucug aaccagguag 420
aucugaccga aacccuggaa agauaccaac agagacuuaa cacuuacgcg cugguaucca 480
aagaccuggc cagcuaccga ucuuuuucgc agcagcuaaa ggcacaagac agccuaggug 540
aacagcccac cacugugcca ccgcccauug accugucaau accucacguu uggaugccac 600
cgcaaaccac uccacacggc uggacagaau cacauaccac cucaggacua caccgaccac 660
acuuuaacca gaccuguauc cucuuugaug gacacgaucu acuauucagc accgucacac 720
cuuguuugca ccaaggcuuu uaccucaucg acgaacuacg uuacguuaaa auaacacuga 780
ccgaggacuu cuucguaguu acggugucca uagacgacga cacacccaug cugcuuaucu 840
ucggccaucu uccacgcgua cuuuucaaag cgcccuauca acgcgacaac uuuauacuac 900
gacaaacuga aaaacacgag cuccuggugc uaguuaagaa agaucaacug aaccgucacu 960
cuuaucucaa agacccggac uuucuugacg ccgcacuuga cuucaacuac cuagaccuca 1020
gcgcacuacu acguaacagc uuucaccguu acgccgugga uguacucaag agcggucgau 1080
gucagaugcu ggaccgccgc acgguagaaa uggccuucgc cuacgcauua gcacuguucg 1140
cagcagcccg acaagaagag gccggcgccc aagucuccgu cccacgggcc cuagaccgcc 1200
aggccgcacu cuuacaaaua caagaauuua ugaucaccug ccucucacaa acaccaccac 1260
gcaccacguu gcugcuguau cccacggccg uggaccuggc caaacgagcc cuuuggacac 1320
cgaaucagau caccgacauc accagccucg uacgccuggu cuacauacuc ucuaaacaga 1380
aucagcaaca ucucaucccc caaugggcac uacgacagau cgccgacuuu gcccuaaaac 1440
uacacaaaac gcaccuggcc ucuuuucuuu cagccuucgc acgccaagaa cucuaccuca 1500
ugggcagccu cguccacucc augcugguac auacgacgga gagacgcgaa aucuucaucg 1560
uagaaacggg ccucuguuca uuggccgagc uaucacacuu uacgcaguug uuagcucauc 1620
cacaccacga auaccucagc gaccuguaca cacccuguuc caguagcggg cgacgcgauc 1680
acucgcucga acgccucacg cgucucuucc ccgaugccac cguccccgcu accguucccg 1740
ccgcccucuc cauccuaucu accaugcaac caagcacgcu ggaaaccuuc cccgaccugu 1800
uuugcuugcc gcucggcgaa uccuucuccg cgcugaccgu cuccgaacac gucaguuaua 1860
ucguaacaaa ccaguaccug aucaaaggua ucuccuaccc ugucuccacc accgucguag 1920
gccagagccu caucaucacc cagacggaca gucaaacuaa augcgaacug acgcgcaaca 1980
ugcauaccac acacagcauc acaguggcgc ucaacauuuc gcuagaaaac ugcgccuuuu 2040
gccaaagcgc ccugcuagaa uacgacgaca cgcaaggcgu caucaacauc auguacaugc 2100
acgacucgga cgacguccuu uucgcccugg aucccuacaa cgaaguggug gucucaucuc 2160
cgcgaacuca cuaccucaug cuuuugaaaa acgguacggu acuagaagua acugacgucg 2220
ucguggacgc caccgacagu cgucuccuca ugauguccgu cuacgcgcua ucggccauca 2280
ucggcaucua ucugcucuac cgcaugcuca agacaugcga uuacaaggac gaugacgaua 2340
agugaugaua auaggcugga gccucggugg ccaugcuucu ugccccuugg gccucccccc 2400
agccccuccu ccccuuccug cacccguacc cccguggucu uugaauaaag ucugaguggg 2460
cggc 2464

<210> SEQ ID NO 160
<211> LENGTH: 1045
<212> TYPE: RNA
<213> ORGANISM: Artificial Sequence
<220> FEATURE:
<223> OTHER INFORMATION: Synthetic polynuceotide

<400> SEQUENCE: 160
ucaagcuuuu ggacccucgu acagaagcua auacgacuca cuauagggaa auaagagaga 60
aaagaagagu aagaagaaau auaagagcca ccaugugccg ccgcccggau ugcggcuucu 120
cuuucucacc uggaccggug auacugcugu gguguugccu ucugcugccc auuguuuccu 180
cagccgccgu cagcgucgcu ccuaccgccg ccgagaaagu ccccgcggag ugccccgaac 240
uaacgcgccg augcuuguug ggugaggugu uugagggugu caaguaugaa aguuggcugc 300
gcccguuggu gaauguuacc gggcgcgaug gcccgcuauc gcaacuuauc cguuaccguc 360
ccguuacgcc ggaggccgcc aacuccgugc uguuggacga ggcuuuccug gacacucugg 420
cccugcugua caacaauccg gaucaauugc gggcccugcu gacgcuguug agcucggaca 480
cagcgccgcg cuggaugacg gugaugcgcg gcuacagcga gugcggcgau ggcucgccgg 540
ccguguacac gugcguggac gaccugugcc gcggcuacga ccucacgcga cugucauacg 600
ggcgcagcau cuucacggaa cacguguuag gcuucgagcu ggugccaccg ucucucuuua 660
acgugguggu ggccauacgc aacgaagcca cgcguaccaa ccgcgccgug cgucugcccg 720
ugagcaccgc ugccgcgccc gagggcauca cgcucuuuua cggccuguac aacgcaguga 780
aggaauucug ccugcgucac cagcuggacc cgccgcugcu acgccaccua gauaaauacu 840
acgccggacu gccgcccgag cugaagcaga cgcgcgucaa ccugccggcu cacucgcgcu 900
auggcccuca agcaguggau gcucgcugau aauaggcugg agccucggug gccaugcuuc 960
uugccccuug ggccuccccc cagccccucc uccccuuccu gcacccguac ccccgugguc 1020
uuugaauaaa gucugagugg gcggc 1045

<210> SEQ ID NO 161
<211> LENGTH: 1072
<212> TYPE: RNA
<213> ORGANISM: Artificial Sequence
<220> FEATURE:
<223> OTHER INFORMATION: Synthetic polynucleotide

<400> SEQUENCE: 161
ucaagcuuuu ggacccucgu acagaagcua auacgacuca cuauagggaa auaagagaga 60
aaagaagagu aagaagaaau auaagagcca ccaugugccg ccgcccggau ugcggcuucu 120
cuuucucacc uggaccggug auacugcugu gguguugccu ucugcugccc auuguuuccu 180
cagccgccgu cagcgucgcu ccuaccgccg ccgagaaagu ccccgcggag ugccccgaac 240
uaacgcgccg augcuuguug ggugaggugu uugagggugu caaguaugaa aguuggcugc 300
gcccguuggu gaauguuacc gggcgcgaug gcccgcuauc gcaacuuauc cguuaccguc 360
ccguuacgcc ggaggccgcc aacuccgugc uguuggacga ggcuuuccug gacacucugg 420
cccugcugua caacaauccg gaucaauugc gggcccugcu gacgcuguug agcucggaca 480
cagcgccgcg cuggaugacg gugaugcgcg gcuacagcga gugcggcgau ggcucgccgg 540
ccguguacac gugcguggac gaccugugcc gcggcuacga ccucacgcga cugucauacg 600
ggcgcagcau cuucacggaa cacguguuag gcuucgagcu ggugccaccg ucucucuuua 660
acgugguggu ggccauacgc aacgaagcca cgcguaccaa ccgcgccgug cgucugcccg 720
ugagcaccgc ugccgcgccc gagggcauca cgcucuuuua cggccuguac aacgcaguga 780
aggaauucug ccugcgucac cagcuggacc cgccgcugcu acgccaccua gauaaauacu 840
acgccggacu gccgcccgag cugaagcaga cgcgcgucaa ccugccggcu cacucgcgcu 900
auggcccuca agcaguggau gcucgcgauu acaaggacga ugacgauaag ugaugauaau 960
aggcuggagc cucgguggcc augcuucuug ccccuugggc cucccccag ccccuccucc 1020 ccuuccugca cccguacccc cgugggucuuu gaauaaaguc ugagugggcg gc 1072

<210> SEQ ID NO 162
<211> LENGTH: 2932
<212> TYPE: RNA
<213> ORGANISM: Artificial Sequence
<220> FEATURE:
<223> OTHER INFORMATION: Synthetic polynucleotide

<400> SEQUENCE: 162
ucaagcuuuu ggacccucgu acagaagcua auacgacuca cuauagggaa auaagagaga 60
aaagaagagu aagaagaaau auaagagcca ccauggaauc caggaucugg ugccugguag 120
ucugcguuaa cuuguguauc gucugucugg gugcugcggu uuccucaucu ucuacucgug 180
gaacuucugc uacucacagu caccauuccu cucauacgac gucugcugcu cacucucgau 240
ccgguucagu cucucaacgc guaacuucuu cccaaacggu cagccauggu guuaacgaga 300
ccaucuacaa cacuacccuc aaguacggag auguggugggg ggucaauacc accaaguacc 360
ccuaucgcgu guguucuaug gcccagggua cggaucuuau ucgcuuugaa cguaauaucg 420
ucugcaccuc gaugaagccc aucaaugaag accuggacga gggcaucaug guggucuaca 480
aacgcaacau cgucgcgcac accuuuaagg uacgagucua ccagaagguu uugacguuuc 540
gucguagcua cgcuuacauc cacaccacuu aucugcuggg cagcaacacg gaauacgugg 600
cgccuccuau gugggagauu caucauauca acagccacag ucagugcuac aguuccuaca 660
gccgcguuau agcaggcacg guuuucgugg cuuaucauag ggacagcuau gaaaacaaaa 720
ccaugcaauu aaugcccgac gauuauucca acacccacag uacccguuac gugacgguca 780
aggaucaaug gcacagccgc ggcagcaccu ggcucuaucg ugagaccugu aaucugaauu 840
guauggugac caucacuacu gcgcgcucca aauauccuua ucauuuuuuc gccacuucca 900
cgggugacgu gguugacauu ucuccuuucu acaacggaac caaucgcaau gccagcuacu 960
uuggagaaaa cgccgacaag uuuuucauuu uuccgaacua cacuaucguc uccgacuuug 1020
gaagaccgaa uucugcguua gagacccaca gguuggugggc uuuucuugaa cgugcggacu 1080
cggugaucuc cugggauaua caggacgaaa agaaugucac uugucaacuc acuuucuggg 1140
aagccucgga acgcaccauu cguuccgaag ccgaggacuc guaucacuuu ucuucugcca 1200
aaaugaccgc cacuuucuua ucuaagaagc aagaggugaa cauguccgac ucugcgcugg 1260
acugcguacg ugaugaggcu auaaauaagu uacagcagau uuucaauacu ucauacaauc 1320
aaacauauga aaaauaugga aacguguccg ucuuugaaac cacuggugggu uugguagugu 1380 ucuggcaagg uaucaagcaa aaaucucugg uggaacucga acguuuggcc aaccgcucca 1440

-continued gucugaaucu uacucauaau agaaccaaaa gaaguacaga uggcaacaau gcaacucauu 1500
uauccaacau ggaaucggug cacaaucugg ucuacgccca gcugcaguuc accuaugaca 1560
cguugcgcgg uuacaucaac cgggcgcugg cgcaaaucgc agaagccugg uguguggauc 1620
aacggcgcac ccuagagguc uucaaggaac ucagcaagau caacccguca gccauucucu 1680
cggccauuua caacaaaccg auugccgcgc guuucauggg ugaugucuug ggccuggcca 1740
gcugcgugac caucaaccaa accagcguca aggugcugcg ugauaugaac gugaaggagu 1800
cgccaggacg cugcuacuca cgacccgugg ucaucuuuaa uuucgccaac agcucguacg 1860
ugcaguacgg ucaacugggc gaggacaacg aaauccuguu gggcaaccac cgcacugagg 1920
aaugucagcu ucccagccuc aagaucuuca ucgccgggaa cucggccuac gaguacgugg 1980
acuaccucuu caaacgcaug auugaccuca gcaguaucuc caccgucgac agcaugaucg 2040
cccuggauau cgacccgcug gaaaauaccg acuucagggu acuggaacuu uacucgcaga 2100
aagagcugcg uuccagcaac guuuuugacc ucgaagagau caugcgcgaa uucaacucgu 2160
acaagcagcg gguaaaguac guggaggaca agguagucga cccgcuaccg cccuaccuca 2220
agggucugga cgaccucaug agcggccugg gcgccgcggg aaaggccguu ggcguagcca 2280
uuggggccgu ggguggcgcg guggccuccg uggucgaagg cguugccacc uuccucaaaa 2340
accccuucgg agcguucacc aucauccucg uggccauagc uguagucauu aucacuuauu 2400
ugaucuauac ucgacagcgg cguuugugca cgcagccgcu gcagaaccuc uuucccuauc 2460 uggugucegc cgacgggacc accgugacgu cgggcagcac caaagacacg ucguuacagg 2520
cuccgccuuc cuacgaggaa aguguuuaua auucuggucg caaaggaccg ggaccaccgu 2580
cgucugaugc auccacggcg gcuccgccuu acaccaacga gcaggcuuac cagaugcuuc 2640
uggcccuggc ccgucuggac gcagagcagc gagcgcagca gaacgguaca gauucuuugg 2700
acggacggac uggcacgcag gacaagggac agaagcccaa ccuacuagac cgacugcgac 2760
aucgcaaaaa cggcuaccga cacuugaaag acucugacga agaagagaac gucugauaau 2820
aggcuggagc cucgguggcc augcuucuug ccccuuggc cuccccccag ccccuccucc 2880
ccuuccugca cccguacccc cguggucuuu gaauaaaguc ugagugggcg gc 2932

<210> SEQ ID NO 163
<211> LENGTH: 2956
<212> TYPE: DNA
<213> ORGANISM: Artificial Sequence
<220> FEATURE:
<223> OTHER INFORMATION: Synthetic polynucleotide

<400> SEQUENCE: 163
tcaagcuuuu ggacccucgu acagaagcua auacgacuca cuauagggaa auaagagaga 60
aaagaagagu aagaagaaau auaagagcca ccauggaauc caggaucugg ugccugguag 120
ucugcguuaa cuuguguauc gucugucugg gugcugcggu uuccucaucu ucuacucgug 180
gaacuucugc uacucacagu caccauuccu cucauacgac gucugcugcu cacucucgau 240
ccgguucagu cucucaacgc guaacuucuu cccaaacggu cagccauggu guuaacgaga 300
ccaucuacaa cacuacccuc aaguacggag augugguggg ggucaauacc accaaguacc 360
ccuaucgcgu guguucuaug gcccagggua cggaucuuau ucgcuuugaa cguaaauaucg 420 ucugcaccuc gaugaagccc aucaaugaag accuggacga gggcaucaug guggucuaca 480
aacgcaacau cgucgcgcac accuuuaagg uacgagucua ccagaagguu uugacguuuc 540
gucguagcua cgcuuacauc cacaccacuu aucugcuggg cagcaacacg gaauacgugg 600

-continued

```
cgccuccuau gugggagauu caucauauca acagccacag ucagugcuac aguuccuaca    660
gccgcguuau agcaggcacg guuuucgugg cuuaucauag ggacagcuau gaaaacaaaa    720
ccaugcaauu aaugcccgac gauuauucca acacccacag uacccguuac gugacgguca    780
aggaucaaug gcacagccgc ggcagcaccu ggcucuaucg ugagaccugu aaucugaauu    840
guauggugac caucacuacu gcgcgcucca aauauccuua ucauuuuuuc gccacuucca    900
cgggugacgu gguugacauu ucuccuuucu acaacggaac caaucgcaau gccagcuacu    960
uuggagaaaa cgccgacaag uuuuucauuu uuccgaacua cacuaucguc uccgacuuug   1020
gaagaccgaa uucugcguua gagacccaca gguugguggc uuuucuugaa cgugcggacu   1080
cggugaucuc cugggauaua caggacgaaa agaaugucac uugucaacuc acuuucuggg   1140
aagccucgga acgcaccauu cguuccgaag ccgaggacuc guaucacuuu ucuucugcca   1200
aaaugaccgc cacuuucuua ucuaagaagc aagaggugaa cauguccgac ucugcgcugg   1260
acugcguacg ugaugaggcu auaaauaagu uacagcagau uucaauacu ucauacaauc    1320
aaacauauga aaaauaugga aacguguccg ucuuugaaac cacugguggu uugguagugu   1380
ucuggcaagg uaucaagcaa aaaucucugg uggaacucga acguuuggcc aaccgcucca   1440
gucugaaucu uacucauaau agaaccaaaa gaaguacaga uggcaacaau gcaacucauu   1500
uauccaacau ggaaucggug cacaaucugg ucuacgccca gcugcaguuc accuaugaca   1560
cguugcgcgg uuacaucaac cgggcgcugg cgcaaaucgc agaagccugg ugugguggauc   1620
aacggcgcac ccuagagguc uucaaggaac ucagcaagau caacccguca gccauucucu   1680
cggccauuua caacaaaccg auugccgcgc guuucauggg ugaugucuug ggccuggcca   1740
gcugcgugac caucaaccaa accagcguca aggugcugcg ugauaugaac gugaaggagu   1800
cgccaggacg cugcuacuca cgacccgugg ucaucuuuaa uuucgccaac agcucguacg   1860
ugcaguacgg ucaacugggc gaggacaacg aaauccuguu gggcaaccac cgcacugagg   1920
aaugucagcu ucccagccuc aagaucuuca ucgccgggaa cucggccuac gaguacgugg   1980
acuaccucuu caaacgcaug auugaccuca gcaguaucuc caccgucgac agcaugaucg   2040
cccuggauau cgacccgcug gaaaauaccg acuucagggu acuggaacuu uacucgcaga   2100
aagagcugcg uuccagcaac guuuuugacc ucgaagagau caugcgcgaa uucaacucgu   2160
acaagcagcg gguaaaguac guggaggaca agguagucga cccgcuaccg cccuaccuca   2220
agggucugga cgaccucaug agcggccugg gcgccgcggg aaaggccguu ggcguagcca   2280
uuggggccgu gggugggcgcg guggccuccg uggucgaagg cguugccacc uuccucaaaa   2340
accccuucgg agcguucacc aucauccucg uggccauagc uguagucauu aucacuuauu   2400
ugaucuauac ucgacagcgg cguuugugca cgcagccgcu gcagaaccuc uuucccuauc   2460
uggugucccgc cgacgggacc accgugacgu cgggcagcac caaagacacg ucguuacagg   2520
cuccgccuuc cuacgaggaa aguguuuaua auucuggucg caaaggaccg ggaccaccgu   2580
cgucugaugc auccacggcg gcuccgccuu acaccaacga gcaggcuuac cagaugcuuc   2640
uggcccuggc ccgucuggac gcagagcagc gagcgcagca gaacgguaca gauucuuugg   2700
acggacggac uggcacgcag gacaagggac agaagcccaa ccuacuagac cgacugcgac   2760
aucgcaaaaa cggcuaccga cacuugaaag acucugacga agaagagaac gucgauuaca   2820
aggacgauga cgauaaguga uaauaggcug gagccucggu ggccaugcuu cuugccccuu   2880
gggccucccc ccagccccuc cucccccuucc ugcacccgua cccccguggu cuuugaauaa   2940
```

agucugagug ggcggc 2956

<210> SEQ ID NO 164
<211> LENGTH: 2356
<212> TYPE: RNA
<213> ORGANISM: Artificial Sequence
<220> FEATURE:
<223> OTHER INFORMATION: Synthetic polynucleotide

<400> SEQUENCE: 164
ucaagcuuuu ggacccucgu acagaagcua auacgacuca cuauagggaa auaagagaga 60
aaagaagagu aagaagaaau auaagagcca ccaugcggcc aggccucccc uccuaccuca 120
ucauccucgc cgucugucuc uucagccacc uacuuucguc acgauauggc gcagaagccg 180
uauccgaacc gcuggacaaa gcguuucacc uacugcucaa caccuacggg agacccaucc 240
gcuuccugcg ugaaaauacc acccagugua ccuacaacag cagccuccgu aacagcacgg 300
ucgucaggga aaacgccauc aguuucaacu uuuuccaaag cuauaaucaa uacuauguau 360
uccauaugcc ucgaugucuu uuugcggguc cucuggcgga gcaguuucug aaccagguag 420
aucugaccga aacccuggaa agauaccaac agagacuuaa cacuuacgcg cugguaucca 480
aagaccuggc cagcuaccga ucuuuuucgc agcagcuaaa ggcacaagac agccuaggug 540
aacagcccac cacugugcca ccgcccauug accugucaau accucacguu uggaugccac 600
cgcaaaccac uccacacggc uggacagaau cacauaccac cucaggacua caccgaccac 660
acuuuaacca gaccuguauc cucuuugaug gacacgaucu acuauucagc accgucacac 720
cuuguuugca ccaaggcuuu uaccucaucg acgaacuacg uuacguuaaa auaacacuga 780
ccgaggacuu cuucguaguu acggugucca uagacgacga cacacccaug cugcuuaucu 840
ucggccaucu uccacgcgua cuuuucaaag cgcccuauca acgcgacaac uuuauacuac 900
gacaaacuga aaaacacgag cuccuggugc uaguuaagaa agaucaacug aaccgucacu 960
cuuaucucaa agacccggac uuucuugacg ccgcacuuga cuucaacuac cuagaccuca 1020
gcgcacuacu acguaacagc uuucaccguu acgccgugga uguacucaag agcggucgau 1080
gucagaugcu ggaccgccgc acgguagaaa uggccuucgc cuacgcauua gcacuguucg 1140
cagcagcccg acaagaagag gccggcgccc aagucuccgu cccacgggcc cuagaccgcc 1200
aggccgcacu cuuacaaaua caagaauuua ugaucaccug ccucucacaa acaccaccac 1260
gcaccacguu gcugcuguau cccacggccg uggaccuggc caaacgagcc cuuuggacac 1320
cgaaucagau caccgacauc accagccucg uacgccuggu cuacauacuc ucuaaacaga 1380
aucagcaaca ucucaucccc caaugggcac uacgacagau cgccgacuuu gcccuaaaac 1440
uacacaaaac gcaccuggcc ucuuuucuuu cagccuucgc acgccaagaa cucuaccuca 1500
ugggcagccu cguccacucc augcugguac auacgacgga gagacgcgaa aucuucaucg 1560
uagaaacggg ccucuguuca uuggccgagc uaucacacuu uacgcaguug uuagcucauc 1620
cacaccacga auaccucagc gaccuguaca cacccuguuc caguagcggg cgacgcgauc 1680
acucgcucga acgccucacg cgucucuucc ccgaugccac cgucccccgcu accguucccg 1740 ccgcccucuc cauccuaucu accaugcaac caagcacgcu ggaaaccuuc cccgaccugu 1800
uuugcuugcc gcucggcgaa uccuucuccg cgcugaccgu cuccgaacac gucaguuaua 1860
ucguaacaaa ccaguaccug aucaaaggua ucuccuaccc ugucuccacc accgucguag 1920
gccagagccu caucaucacc cagacggaca gucaaacuaa augcgaacug acgcgcaaca 1980
ugcauaccac acacagcauc acaguggcgc ucaacauuuc gcuagaaaac ugcgccuuuu 2040
gccaaagcgc ccugcuagaa uacgacgaca cgcaaggcgu caucaacauc auguacaugc 2100
acgacucgga cgacguccuu uucgcccugg aucccuacaa cgaaguggug gucucaucuc 2160
cgcgaacuca cuaccucaug cuuuugaaaa acgguacggu acuagaagua acugacgucg 2220
ucguggacgc caccgacuga uaauaggcug gagccucggu ggccaugcuu cuugccccuu 2280
gggccucccc ccagccccuc cuccccuucc ugcacccgua cccccguggu cuuugaauaa 2340
agucugagug ggcggc 2356

<210> SEQ ID NO 165
<211> LENGTH: 2383
<212> TYPE: RNA
<213> ORGANISM: Artificial Sequence
<220> FEATURE:
<223> OTHER INFORMATION: Synthetic polynucleotide

<400> SEQUENCE: 165
ucaagcuuuu ggacccucgu acagaagcua auacgacuca cuauagggaa auaagagaga 60
aaagaagagu aagaagaaau auaagagcca ccaugcggcc aggccucccc uccuaccuca 120
ucauccucgc cgucugucuc uucagccacc uacuuucguc acgauauggc gcagaagccg 180
uauccgaacc gcuggacaaa gcguuucacc uacugcucaa caccuacggg agacccaucc 240
gcuuccugcg ugaaaauacc acccagugua ccuacaacag cagccuccgu aacagcacgg 300
ucgucaggga aaacgccauc aguuucaacu uuuuccaaag cuauaaucaa uacuauguau 360
uccauaugcc ucgaugucuu uuugcggguc cucuggcgga gcaguuucug aaccagguag 420
aucugaccga aacccuggaa agauaccaac agagacuuaa cacuuacgcg cugguaucca 480
aagaccuggc cagcuaccga ucuuuuucgc agcagcuaaa ggcacaagac agccuaggug 540
aacagcccac cacugugcca ccgcccauug accugucaau accucacguu uggaugccac 600
cgcaaaccac uccacacggc uggacagaau cacauaccac cucaggacua caccgaccac 660
acuuuaacca gaccuguauc cucuuugaug gacacgaucu acuauucagc accgucacac 720
cuuguuugca ccaaggcuuu uaccucaucg acgaacuacg uuacguuaaa auaacacuga 780
ccgaggacuu cuucguaguu acggugucca uagacgacga cacacccaug cugcuuaucu 840
ucggccaucu uccacgcgua cuuuucaaag cgcccuauca acgcgacaac uuuauacuac 900
gacaaacuga aaaacacgag cuccuggugc uaguuaagaa agaucaacug aaccgucacu 960
cuuaucucaa agacccggac uuucuugacg ccgcacuuga cuucaacuac cuagaccuca 1020
gcgcacuacu acguaacagc uuucaccguu acgccgugga uguacucaag agcggucgau 1080
gucagaugcu ggaccgccgc acgguagaaa uggccuucgc cuacgcauua gcacuguucg 1140
cagcagcccg acaagaagag gccggcgccc aagucuccgu cccacgggcc cuagaccgcc 1200
aggccgcacu cuuacaaaua caagaauuua ugaucaccug ccucucacaa acaccaccac 1260
gcaccacguu gcugcuguau cccacggccg uggaccuggc caaacgagcc cuuuggacac 1320
cgaaucagau caccgacauc accagccucg uacgccuggu cuacauacuc ucuaaacaga 1380
aucagcaaca ucucaucccc caaugggcac uacgacagau cgccgacuuu gcccuaaaac 1440
uacacaaaac gcaccuggcc ucuuuucuuu cagccuucgc acgccaagaa cucuaccuca 1500
ugggcagccu cguccacucc augcugguac auacgacgga gagacgcgaa aucuucaucg 1560
uagaaacggg ccucuguuca uuggccgagc uaucacacuu uacgcaguug uuagcucauc 1620
cacaccacga auaccucagc gaccuguaca cacccuguuc caguagcggg cgacgcgauc 1680

```
acucgcucga acgccucacg cgucucuucc ccgaugccac cguccccgcu accguucccg   1740

ccgcccucuc cauccuaucu accaugcaac caagcacgcu ggaaaccuuc cccgaccugu   1800

uuugcuugcc gcucggcgaa uccuucuccg cgcugaccgu cuccgaacac gucaguuaua   1860

ucguaacaaa ccaguaccug aucaaaggua ucuccuaccc ugucuccacc accgucguag   1920

gccagagccu caucaucacc cagacggaca gucaaacuaa augcgaacug acgcgcaaca   1980

ugcauaccac acacagcauc acaguggcgc ucaacauuuc gcuagaaaac ugcgccuuuu   2040

gccaaagcgc ccugcuagaa uacgacgaca cgcaaggcgu caucaacauc auguacaugc   2100

acgacucgga cgacguccuu uucgcccugg aucccuacaa cgaagguggug gucucaucuc   2160

cgcgaacuca cuaccucaug cuuuugaaaa acgguacggu acuagaagua acugacgucg   2220

ucguggacgc caccgacgau uacaaggacg augacgauaa gugaugauaa uaggcuggag   2280

ccucgguggc caugcuucuu gccccuuggg ccucccccca gccccuccuc cccuuccugc   2340

acccguaccc ccguggucuu ugaauaaagu cugagugggc ggc                      2383
```

<210> SEQ ID NO 166
<211> LENGTH: 2377
<212> TYPE: RNA
<213> ORGANISM: Artificial Sequence
<220> FEATURE:
<223> OTHER INFORMATION: Synthetic polynucleotide

<400> SEQUENCE: 166

```
ucaagcuuuu ggacccucgu acagaagcua auacgacuca cuauagggaa auaagagaga     60

aaagaagagu aagaagaaau auaagagcca ccaugcggcc aggccucccc uccuaccuca    120

ucauccucgc cgucugucuc uucagccacc uacuuucguc acgauauggc gcagaagccg    180

uauccgaacc gcuggacaaa gcguuucacc uacugcucaa caccuacggg agacccaucc    240

gcuuccugcg ugaaaauacc acccagugua ccuacaacag cagccuccgu aacagcacgg    300

ucgucaggga aaacgccauc aguuucaacu uuuuccaaag cuauaaucaa uacuauguau    360

uccauaugcc ucgaugucuu uuugcggguc cucuggcgga gcaguuucug aaccagguag    420

aucugaccga aacccuggaa agauaccaac agagacuuaa cacuuacgcg cugguaucca    480

aagaccuggc cagcuaccga ucuuuuucgc agcagcuaaa ggcacaagac agccuaggug    540

aacagcccac cacugugcca ccgcccauug accugucaau accucacguu uggaugccac    600

cgcaaaccac uccacacggc uggacagaau cacauaccac cucaggacua caccgaccac    660

acuuuaacca gaccuguauc cucuuugaug gacacgaucu acuauucagc accgucacac    720

cuuguuugca ccaaggcuuu uaccucaucg acgaacuacg uuacguuaaa auaacacuga    780

ccgaggacuu cuucguaguu acggugucca uagacgacga cacacccaug cugcuuaucu    840

ucggccaucu uccacgcgua cuuuucaaag cgcccuauca acgcgacaac uuuauacuac    900

gacaaacuga aaaacacgag cuccuggugc uaguuaagaa agaucaacug aaccgucacu    960

cuuaucucaa agacccggac uuucuugacg ccgcacuuga cuucaacuac cuagaccuca   1020

gcgcacuacu acguaacagc uuucaccguu acgccgugga uguacucaag agcggucgau   1080

gucagaugcu ggaccgccgc acgguagaaa uggccuucgc cuacgcauua gcacuguucg   1140

cagcagcccg acaagaagag gccggcgccc aagucuccgu cccacgggcc cuagaccgcc   1200

aggccgcacu cuuacaaaua caagaauuua ugaucaccug ccucucacaa acaccaccac   1260

gcaccacguu gcugcuguau cccacggccg uggaccuggc caaacgagcc cuuuggacac   1320

cgaaucagau caccgacauc accagccucg uacgccuggu cuacauacuc ucuaaacaga   1380
```

-continued aucagcaaca ucucaucccc caaugggcac uacgacagau cgccgacuuu gcccuaaaac 1440
uacacaaaac gcaccuggcc ucuuuucuuu cagccuucgc acgccaagaa cucuaccuca 1500
ugggcagccu cguccacucc augcugguac auacgacgga gagacgcgaa aucuucaucg 1560
uagaaacggg ccucuguuca uuggccgagc uaucacacuu uacgcaguug uuagcucauc 1620
cacaccacga auaccucagc gaccuguaca cacccuguuc caguagcggg cgacgcgauc 1680
acucgcucga acgccucacg cgucucuucc ccgaugccac cguccccgcu accguucccg 1740
ccgcccucuc cauccuaucu accaugcaac caagcacgcu ggaaaccuuc cccgaccugu 1800
uuugcuugcc gcucggcgaa uccuucuccg cgcugaccgu cuccgaacac gucaguuaua 1860
ucguaacaaa ccaguaccug aucaaaggua ucuccuaccc ugucuccacc accgucguag 1920
gccagagccu caucaucacc cagacggaca gucaaacuaa augcgaacug acgcgcaaca 1980
ugcauaccac acacagcauc acaguggcgc ucaacauuuc gcuagaaaac ugcgccuuuu 2040
gccaaagcgc ccugcuagaa uacgacgaca cgcaaggcgu caucaacauc auguacaugc 2100
acgacucgga cgacguccuu uucgcccugg aucccuacaa cgaaguggug gucucaucuc 2160
cgcgaacuca cuaccucaug cuuuugaaaa acgguacggu acuagaagua acugacgucg 2220
ucguggacgc caccgaccac caucaccacc aucacugaug auaauaggcu ggagccucgg 2280
uggccaugcu ucuugccccu ugggccuccc cccagccccu ccuccccuuc cugcacccgu 2340
acccccgugg ucuuugaaua aagucugagu gggcggc 2377

<210> SEQ ID NO 167
<211> LENGTH: 2287
<212> TYPE: RNA
<213> ORGANISM: Artificial Sequence
<220> FEATURE:
<223> OTHER INFORMATION: Synthetic polynucleotide

<400> SEQUENCE: 167
ucaagcuuuu ggacccucgu acagaagcua auacgacuca cuauagggaa auaagagaga 60
aaagaagagu aagaagaaau auaagagcca ccauggaauc caggaucugg ugccugguag 120
ucugcguuaa cuuguguauc gucugucugg gugcugcggu uuccucaucu ucuacucgug 180
gaacuucugc uacucacagu caccauuccu cucauacgac gucugcugcu cacucucgau 240
ccgguucagu cucucaacgc guaacuucuu cccaaacggu cagccauggu guuaacgaga 300
ccaucuacaa cacuacccuc aaguacggag augugguggg ggucaauacc accaaguacc 360
ccuaucgcgu guguucuaug gcccagggua cggaucuuau ucgcuuugaa cguaauaucg 420
ucugcaccuc gaugaagccc aucaaugaag accuggacga gggcaucaug guggucuaca 480
aacgcaacau cgucgcgcac accuuuaagg uacgagucua ccagaagguu uugacguuuc 540
gucguagcua cgcuuacauc cacaccacuu aucugcuggg cagcaacacg gaauacgugg 600
cgccuccuau gugggagauu caucauauca acagccacag ucagugcuac aguuccuaca 660
gccgcguuau agcaggcacg guuuucgugg cuuaucauag ggacagcuau gaaaacaaaa 720
ccaugcaauu aaugcccgac gauuauucca acacccacag uacccguuac gugacgguca 780
aggaucaaug gcacagccgc ggcagcaccu ggcucuaucg ugagaccugu aaucugaauu 840
guauggugac caucacuacu gcgcgcucca aauauccuua ucauuuuuuc gccacuucca 900
cgggugacgu gguugacauu ucuccuuucu acaacggaac caaucgcaau gccagcuacu 960
uuggagaaaa cgccgacaag uuuuucauuu uuccgaacua cacuaucguc uccgacuuug 1020
gaagaccgaa uucugcguua gagacccaca gguuggugge uuuucuugaa cgugcggacu 1080
cggugaucuc cugggauaua caggacgaaa agaaugucac uugucaacuc acuuucuggg 1140
aagccucgga acgcaccauu cguuccgaag ccgaggacuc guaucacuuu ucuucugcca 1200
aaaugaccgc cacuuucuua ucuaagaagc aagaggugaa cauguccgac ucugcgcugg 1260
acugcguacg ugaugaggcu auaaauaagu uacagcagau uuucaauacu ucauacaauc 1320
aaacauauga aaaauaugga aacguguccg ucuuugaaac cacuggugu uugguagugu 1380 ucuggcaagg uaucaagcaa aaaucucugg uggaacucga acguuuggcc aaccgcucca 1440
gucugaaucu uacucauaau agaaccaaaa gaaguacaga uggcaacaau gcaacucauu 1500
uauccaacau ggaaucggug cacaaucugg ucuacgccca gcugcaguuc accuaugaca 1560
cguugcgcgg uuacaucaac cgggcgcugg cgcaaaucgc agaagccugg ugugugggauc 1620 aacggcgcac ccuagagguc uucaaggaac ucagcaagau caacccguca gccauucucu 1680
cggccauuua caacaaaccg auugccgcgc guuucauggg ugaugucuug ggccuggcca 1740
gcugcgugac caucaaccaa accagcguca aggugcugcg ugauaugaac gugaaggagu 1800
cgccaggacg cugcuacuca cgacccgugg ucaucuuuaa uuucgccaac agcucguacg 1860
ugcaguacgg ucaacugggc gaggacaacg aaauccuguu gggcaaccac cgcacugagg 1920
aaugucagcu ucccagccuc aagaucuuca ucgccgggaa cucggccuac gaguacgugg 1980
acuaccucuu caaacgcaug auugaccuca gcaguaucuc caccgucgac agcaugaucg 2040
cccuggauau cgacccgcug gaaaauaccg acuucagggu acuggaacuu uacucgcaga 2100
aagagcugcg uuccagcaac guuuuugacc ucgaagagau caugcgcgaa uucaacucgu 2160
acaagcagug auaauaggcu ggagccucgg uggccaugcu ucuugccccu ugggccuccc 2220
cccagccccu ccuccccuuc cugcacccgu acccccgugg ucuuugaaua aagucugagu 2280
gggcggc 2287

<210> SEQ ID NO 168
<211> LENGTH: 2311
<212> TYPE: RNA
<213> ORGANISM: Artificial Sequence
<220> FEATURE:
<223> OTHER INFORMATION: Synthetic polynucleotide

<400> SEQUENCE: 168
ucaagcuuuu ggacccucgu acagaagcua auacgacuca cuauagggaa auaagagaga 60
aaagaagagu aagaagaaau auaagagcca ccauggaauc caggaucugg ugccugguag 120
ucugcguuaa cuuguguauc gucugucugg gugcugcggu uuccucaucu ucuacucgug 180
gaacuucugc uacucacagu caccauuccu cucauacgac gucugcugcu cacucucgau 240
ccgguucagu cucucaacgc guaacuucuu cccaaacggu cagccauggu guuaacgaga 300
ccaucuacaa cacuacccuc aaguacggag augugguggg ggucaauacc accaaguacc 360
ccuaucgcgu guguucuaug gcccagggua cggaucuuau ucgcuuugaa cguaauaucg 420
ucugcaccuc gaugaagccc aucaaugaag accuggacga gggcaucaug guggucuaca 480
aacgcaacau cgucgcgcac accuuuaagg uacgagucua ccagaagguu uugacguuuc 540
gucguagcua cgcuuacauc cacaccacuu aucugcuggg cagcaacacg gaauacgugg 600
cgccuccuau gugggagauu caucauauca acagccacag ucagugcuac aguuccuaca 660
gccgcguuau agcaggcacg guuuucgugg cuuaucauag ggacagcuau gaaaacaaaa 720
ccaugcaauu aaugcccgac gauuauucca acacccacag uacccguuac gugacgguca 780
aggaucaaug gcacagccgc ggcagcaccu ggcucuaucg ugagaccugu aaucugaauu 840
guauggugac caucacuacu gcgcgcucca aauauccuua ucauuuuuuc gccacuucca 900
cgggugacgu gguugacauu ucuccuuucu acaacggaac caaucgcaau gccagcuacu 960
uuggagaaaa cgccgacaag uuuuucauuu uuccgaacua cacuaucguc uccgacuuug 1020
gaagaccgaa uucugcguua gagacccaca gguuggugggc uuuucuugaa cgugcggacu 1080
cggugaucuc cugggauaua caggacgaaa agaaugucac uugucaacuc acuuucuggg 1140
aagccucgga acgcaccauu cguuccgaag ccgaggacuc guaucacuuu ucuucugcca 1200
aaaugaccgc cacuuucuua ucuaagaagc aagaggugaa cauguccgac ucugcgcugg 1260
acugcguacg ugaugaggcu auaaaauaagu uacagcagau uuucaauacu ucauacaauc 1320
aaacauauga aaaauaugga aacguguccg ucuuugaaac cacugguggu uugguagugu 1380
ucuggcaagg uaucaagcaa aaaucucugg uggaacucga acguuuggcc aaccgcucca 1440
gucugaaucu uacucauaau agaaccaaaa gaaguacaga uggcaacaau gcaacucauu 1500
uauccaacau ggaaucggug cacaaucugg ucuacgccca gcugcaguuc accuaugaca 1560
cguugcgcgg uuacaucaac cgggcgcugg cgcaaaucgc agaagccugg ugugugggauc 1620 aacggcgcac ccuagagguc uucaaggaac ucagcaagau caacccguca gccauucucu 1680
cggccauuua caacaaaccg auugccgcgc guuucauggg ugaugucuug ggccuggcca 1740
gcugcgugac caucaaccaa accagcguca aggugcugcg ugauaugaac gugaaggagu 1800
cgccaggacg cugcuacuca cgacccgugg ucaucuuuaa uuucgccaac agcucguacg 1860
ugcaguacgg ucaacugggc gaggacaacg aaauccuguu gggcaaccac cgcacugagg 1920
aaugucagcu ucccagccuc aagaucuuca ucgccgggaa cucggccuac gaguacgugg 1980
acuaccucuu caaacgcaug auugaccuca gcaguaucuc caccgucgac agcaugaucg 2040
cccuggauau cgacccgcug gaaaauaccg acuucagggu acuggaacuu uacucgcaga 2100
aagagcugcg uuccagcaac guuuuugacc ucgaagagau caugcgcgaa uucaacucgu 2160
acaagcagga uuacaaggac gaugacgaua agugauaaua ggcuggagcc ucgguggcca 2220
ugcuucuugc cccuugggcc ucccccccagc cccuccuccc cuuccugcac ccguaccccc 2280
guggucuuug aauaaagucu gagugggcgg c 2311

<210> SEQ ID NO 169
<211> LENGTH: 2305
<212> TYPE: RNA
<213> ORGANISM: Artificial Sequence
<220> FEATURE:
<223> OTHER INFORMATION: Synthetic polynucleotide

<400> SEQUENCE: 169
ucaagcuuuu ggacccucgu acagaagcua auacgacuca cuauagggaa auaagagaga 60
aaagaagagu aagaagaaau auaagagcca ccauggaauc caggaucugg ugccugguag 120
ucugcguuaa cuuguguauc gucugucugg gugcugcggu uuccucaucu ucuacucgug 180
gaacuucugc uacucacagu caccauuccu cucauacgac gucugcugcu cacucucgau 240
ccgguucagu cucucaacgc guaacuucuu cccaaacggu cagccauggu guuaacgaga 300
ccaucuacaa cacuacccuc aaguacggag auguggugggg ggucaauacc accaaguacc 360
ccuaucgcgu guguucuaug gcccagggua cggaucuuau ucgcuuugaa cguaauaucg 420
ucugcaccuc gaugaagccc aucaaugaag accuggacga gggcaucaug guggucuaca 480
aacgcaacau cgucgcgcac accuuuaagg uacgagucua ccagaagguu uugacguuuc 540
gucguagcua cgcuuacauc cacaccacuu aucugcuggg cagcaacacg gaauacgugg 600
cgccuccuau gugggagauu caucauauca acagccacag ucagugcuac aguuccuaca 660
gccgcguuau agcaggcacg guuuucgugg cuuaucauag ggacagcuau gaaaacaaaa 720
ccaugcaauu aaugcccgac gauuauucca acacccacag uacccguuac gugacgguca 780
aggaucaaug gcacagccgc ggcagcaccu ggcucuaucg ugagaccugu aaucugaauu 840
guauggugac caucacuacu gcgcgcucca aauauccuua ucauuuuuuc gccacuucca 900
cgggugacgu gguugacauu ucuccuuucu acaacggaac caaucgcaau gccagcuacu 960
uuggagaaaa cgccgacaag uuuuucauuu uuccgaacua cacuaucguc uccgacuuug 1020
gaagaccgaa uucugcguua gagacccaca gguugguggc uuuucuugaa cgugcggacu 1080
cggugaucuc cugggauaua caggacgaaa agaaugucac uugucaacuc acuuucuggg 1140
aagccucgga acgcaccauu cguuccgaag ccgaggacuc guaucacuuu ucuucugcca 1200
aaaugaccgc cacuuucuua ucuaagaagc aagaggugaa cauguccgac ucugcgcugg 1260
acugcguacg ugaugaggcu auaaauaagu uacagcagau uuucaauacu ucauacaauc 1320
aaacauauga aaaauaugga aacguguccg ucuuugaaac cacugguggu uugguagugu 1380
ucuggcaagg uaucaagcaa aaaucucugg uggaacucga acguuuggcc aaccgcucca 1440
gucugaaucu uacucauaau agaaccaaaa gaaguacaga uggcaacaau gcaacucauu 1500
uauccaacau ggaaucggug cacaaucugg ucuacgccca gcugcaguuc accuaugaca 1560
cguugcgcgg uuacaucaac cgggcgcugg cgcaaaucgc agaagccugg ugugugggauc 1620 aacggcgcac ccuagagguc uucaaggaac ucagcaagau caacccguca gccauucucu 1680
cggccauuua caacaaaccg auugccgcgc guuucauggg ugaugucuug ggccuggcca 1740
gcugcgugac caucaaccaa accagcguca aggugcugcg ugauaugaac gugaaggagu 1800
cgccaggacg cugcuacuca cgacccgugg ucaucuuuaa uuucgccaac agcucguacg 1860
ugcaguacgg ucaacugggc gaggacaacg aaauccuguu gggcaaccac cgcacugagg 1920
aaugucagcu ucccagccuc aagaucuuca ucgccgggaa cucggccuac gaguacgugg 1980
acuaccucuu caaacgcaug auugaccuca gcaguaucuc caccgucgac agcaugaucg 2040
cccuggauau cgacccgcug gaaaauaccg acuucagggu acuggaacuu uacucgcaga 2100
aagagcugcg uuccagcaac guuuuugacc ucgaagagau caugcgcgaa uucaacucgu 2160
acaagcagca ccaucaccac caucacugau aauaggcugg agccucggug gccaugcuuc 2220
uugccccuug ggccuccccc cagccccucc uccccuuccu gcacccguac ccccgugguc 2280
uuugaauaaa gucugagugg gcggc 2305

<210> SEQ ID NO 170
<211> LENGTH: 724
<212> TYPE: RNA
<213> ORGANISM: Artificial Sequence
<220> FEATURE:
<223> OTHER INFORMATION: Synthetic polynucleotide

<400> SEQUENCE: 170
ucaagcuuuu ggacccucgu acagaagcua auacgacuca cuauagggaa auaagagaga 60
aaagaagagu aagaagaaau auaagagcca ccaugagucc caaagaucug acgccguucu 120
ugacggcguu guggcugcua uugggucaca gccgcgugcc gcgggugcgc gcagaagaau 180
guugcgaauu cauaaacguc aaccacccgc cggaacgcug uuacgauuuc aaaaugugca 240

```
aucgcuucac cgucgcgcug cggugucogg acggcgaagu cugcuacagu cccgagaaaa    300

cggcugagau ucgcgggauc gucaccacca ugacccauuc auugacacgc caggucguac    360

acaacaaacu gacgagcugc aacuacaauc cguuauaccu cgaagcugac gggcgaauac    420

gcugcggcaa aguaaacgac aaggcgcagu accugcuggg cgccgcuggc agcguucccu    480

aucgauggau caaucuggaa uacgacaaga uaacccggau cgugggccug gaucaguacc    540

uggagagcgu uaagaaacac aaacggcugg augugugccg cgcuaaaaug ggcuauaugc    600

ugcagugaua auaggcugga gccucggugg ccaugcuucu ugccccuugg gccucccccc    660

agccccuccu ccccuuccug cacccguacc cccguggucu uugaauaaag ucugaguggg    720

cggc                                                                 724
```

<210> SEQ ID NO 171
<211> LENGTH: 748
<212> TYPE: RNA
<213> ORGANISM: Artificial Sequence
<220> FEATURE:
<223> OTHER INFORMATION: Synthetic polynucleotide

<400> SEQUENCE: 171

```
ucaagcuuuu ggacccucgu acagaagcua auacgacuca cuauagggaa auaagagaga     60

aaagaagagu aagaagaaau auaagagcca ccaugagucc caaagaucug acgccguucu    120

ugacggcguu guggcugcua uugggucaca gccgcgugcc gcgggugcgc gcagaagaau    180

guugcgaauu cauaaacguc aaccacccgc cggaacgcug uuacgauuuc aaaaugugca    240

aucgcuucac cgucgcgcug cggugucogg acggcgaagu cugcuacagu cccgagaaaa    300

cggcugagau ucgcgggauc gucaccacca ugacccauuc auugacacgc caggucguac    360

acaacaaacu gacgagcugc aacuacaauc cguuauaccu cgaagcugac gggcgaauac    420

gcugcggcaa aguaaacgac aaggcgcagu accugcuggg cgccgcuggc agcguucccu    480

aucgauggau caaucuggaa uacgacaaga uaacccggau cgugggccug gaucaguacc    540

uggagagcgu uaagaaacac aaacggcugg augugugccg cgcuaaaaug ggcuauaugc    600

ugcaggauua caaggacgau gacgauaagu gauaauaggc uggagccucg guggccaugc    660

uucuugcccc uugggccucc ccccagcccc uccuccccuu ccugcacccg uacccccgug    720

gucuuugaau aaagucugag ugggcggc                                       748
```

<210> SEQ ID NO 172
<211> LENGTH: 853
<212> TYPE: RNA
<213> ORGANISM: Artificial Sequence
<220> FEATURE:
<223> OTHER INFORMATION: Synthetic polynucleotide

<400> SEQUENCE: 172

```
ucaagcuuuu ggacccucgu acagaagcua auacgacuca cuauagggaa auaagagaga     60

aaagaagagu aagaagaaau auaagagcca ccaugcugcg gcuucugcuu cgucaccacu    120

uucacugccu gcuucugugc gcgguuuggg caacgcccug ucuggcgucu ccguggucga    180

cgcuaacagc aaaccagaau ccguccccgc cauggucuaa acugacguau uccaaaccgc    240

augacgcggc gacguuuuac uguccuuuuc ucuaucccuc gcccccacga ucccccuugc    300

aauucucggg guuccagcgg guaucaacgg gucccgagug ucgcaacgag acccuguauc    360

ugcuguacaa ccgggaaggc cagaccuugg uggagagaag cuccaccugg gugaaaaagg    420
```

-continued

```
ugaucuggua ccugagcggu cggaaccaaa ccauccucca acggaugccc cgaacggcuu    480

cgaaaccgag cgacggaaac gugcagauca gcguggaaga cgccaagauu uuuggagcgc    540

acauggugcc caagcagacc aagcugcuac gcuucgucgu caacgauggc acacguuauc    600

agaugugugu gaugaagcug gagagcuggg cucacgucuu ccgggacuac agcgugucuu    660

uucaggugcg auugacguuc accgaggcca auaaccagac uuacaccuuc ugcacccauc    720

ccaaucucau cguuugauaa uaggcuggag ccucggugge caugcuucuu gccccuuggg    780

ccucccccca gccccuccuc cccuuccugc acccguaccc ccguggucuu ugaauaaagu    840

cugagugggc ggc                                                       853
```

<210> SEQ ID NO 173
<211> LENGTH: 880
<212> TYPE: RNA
<213> ORGANISM: Artificial Sequence
<220> FEATURE:
<223> OTHER INFORMATION: Synthetic polynucleotide

<400> SEQUENCE: 173

```
ucaagcuuuu ggacccucgu acagaagcua auacgacuca cuauagggaa auaagagaga     60

aaagaagagu aagaagaaau auaagagcca ccaugcugcg gcuucugcuu cgucaccacu    120

uucacugccu gcuucugugc gcgguuuggg caacgcccug ucuggcgucu ccguggucga    180

cgcuaacagc aaaccagaau ccguccccgc cauggucuaa acugacguau uccaaaccgc    240

augacgcggc gacguuuuac uguccuuuuc ucuaucccuc gcccccacga ucccccuugc    300

aauucucggg guuccagcgg guaucaacgg gucccgagug ucgcaacgag acccuguauc    360

ugcuguacaa ccgggaaggc cagaccuugg uggagagaag cuccaccugg gugaaaaagg    420

ugaucuggua ccugagcggu cggaaccaaa ccauccucca acggaugccc cgaacggcuu    480

cgaaaccgag cgacggaaac gugcagauca gcguggaaga cgccaagauu uuuggagcgc    540

acauggugcc caagcagacc aagcugcuac gcuucgucgu caacgauggc acacguuauc    600

agaugugugu gaugaagcug gagagcuggg cucacgucuu ccgggacuac agcgugucuu    660

uucaggugcg auugacguuc accgaggcca auaaccagac uuacaccuuc ugcacccauc    720

ccaaucucau cguugauuac aaggacgaug acgauaagug augauaauag gcuggagccu    780

cgguggccau gcuucuugcc ccuugggccu ccccccagcc ccuccucccc uuccugcacc    840

cguacccccg uggucuuuga auaaagucug agugggcggc                          880
```

<210> SEQ ID NO 174
<211> LENGTH: 598
<212> TYPE: RNA
<213> ORGANISM: Artificial Sequence
<220> FEATURE:
<223> OTHER INFORMATION: Synthetic polynucleotide

<400> SEQUENCE: 174

```
ucaagcuuuu ggacccucgu acagaagcua auacgacuca cuauagggaa auaagagaga     60

aaagaagagu aagaagaaau auaagagcca ccaugcggcu gugucgggug uggcugucug    120

uuugucugug cgccguggug cugggucagu gccagcggga aaccgcggaa aaaaacgauu    180

auuaccgagu accgcauuac ugggacgcgu gcucucgcgc gcugcccgac caaacccguu    240

acaaguaugu ggaacagcuc guggaccuca cguugaacua ccacuacgau gcgagccacg    300

gcuuggacaa cuuugacgug cucaagagaa ucaacgugac cgaggugucg uugcucauca    360

gcgacuuuag acgucagaac cgucgcggcg gcaccaacaa aaggaccacg uucaacgccg    420
```

ccgguucgcu ggcgccacac gcccggagcc ucgaguucag cgugcggcuc uuugccaacu 480
gauaauaggc uggagccucg guggccaugc uucuugcccc uugggccucc ccccagcccc 540
uccuccccuu ccugcacccg uacccccgug gucuuugaau aaagucugag ugggcggc 598

<210> SEQ ID NO 175
<211> LENGTH: 625
<212> TYPE: RNA
<213> ORGANISM: Artificial Sequence
<220> FEATURE:
<223> OTHER INFORMATION: Synthetic polynucleotide

<400> SEQUENCE: 175
ucaagcuuuu ggacccucgu acagaagcua auacgacuca cuauagggaa auaagagaga 60
aaagaagagu aagaagaaau auaagagcca ccaugcggcu gugucgggug uggcugucug 120
uuugucugug cgccguggug cugggucagu gccagcggga aaccgcggaa aaaaacgauu 180
auuaccgagu accgcauuac ugggacgcgu gcucucgcgc gcugcccgac caaacccguu 240
acaaguaugu ggaacagcuc guggaccuca cguugaacua ccacuacgau gcgagccacg 300
gcuuggacaa cuuugacgug cucaagagaa ucaacgugac cgaggugucg uugcucauca 360
gcgacuuuag acgucagaac cgucgcggcg gcaccaacaa aaggaccacg uucaacgccg 420
ccgguucgcu ggcgccacac gcccggagcc ucgaguucag cgugcggcuc uuugccaacg 480
auuacaagga cgaugacgau aagugaugau aauaggcugg agccucggug gccaugcuuc 540
uugccccuug ggccuccccc cagccccucc uccccuuccu gcacccguac ccccgugguc 600
uuugaauaaa gucugagugg gcggc 625

<210> SEQ ID NO 176
<211> LENGTH: 2434
<212> TYPE: RNA
<213> ORGANISM: Artificial Sequence
<220> FEATURE:
<223> OTHER INFORMATION: Synthetic polynucleotide

<400> SEQUENCE: 176
ucaagcuuuu ggacccucgu acagaagcua auacgacuca cuauagggac agacgagaga 60
gaagcacgcc aauucugccu gcuuaagcca ugcggccagg ccucccccuc uaccucauca 120
uccucgccgu cugucucuuc agccaccuac uuucgucacg auauggcgca gaagccguau 180
ccgaaccgcu ggacaaagcg uuucaccuac ugcucaacac cuacgggaga cccauccgcu 240
uccugcguga aaauaccacc caguguaccu acaacagcag ccuccguaac agcacggucg 300
ucagggaaaa cgccaucagu uucaacuuuu uccaaagcua uaaucaauac uauguauucc 360
auaugccucg augucuuuuu gcgggucuc uggcggagca guuucugaac cagguagauc 420
ugaccgaaac ccuggaaaga uaccaacaga gacuuaacac uuacgcgcug guauccaaag 480
accuggccag cuaccgaucu uuuucgcagc agcuaaaggc acaagacagc cuaggugaac 540
agcccaccac ugugccaccg cccauugacc ugucaauacc ucacguuugg augccaccgc 600
aaaccacucc acacggcugg acagaaucac auaccaccuc aggacuacac cgaccacacu 660
uuaaccagac cuguauccuc uuugauggac acgaucuacu auucagcacc gucacaccuu 720
guuugcacca aggcuuuuac cucaucgacg aacuacguua cguuaaaaua acacugaccg 780
aggacuucuu cguaguuacg guguccauag acgacgacac acccaugcug cuuaucuucg 840
gccaucuucc acgcguacuu uucaaagcgc ccuaucaacg cgacaacuuu auacuacgac 900
aaacugaaaa acacgagcuc cugguguag uuaagaaaga ucaacugaac cgucacucuu 960
aucucaaaga cccggacuuu cuugacgccg cacuugacuu caacuaccua gaccucagcg 1020
cacuacuacg uaacagcuuu caccguuacg ccguggaugu acucaagagc ggucgauguc 1080
agaugcugga ccgccgcacg guagaaaugg ccuucgccua cgcauuagca cuguucgcag 1140
cagcccgaca agaagaggcc ggcgcccaag ucuccguccc acgggcccua gaccgccagg 1200
ccgcacucuu acaaauacaa gaauuuauga ucaccugccu cucacaaaca ccaccacgca 1260
ccacguugcu gcuguauccc acggccgugg accuggccaa acgagcccuu uggacaccga 1320
aucagaucac cgacaucacc agccucguac gccuggucua cauacucucu aaacagaauc 1380
agcaacaucu caucccccaa ugggcacuac gacagaucgc cgacuuugcc cuaaaacuac 1440
acaaaacgca ccuggccucu uuucuuucag ccuucgcacg ccaagaacuc uaccucaugg 1500
gcagccucgu ccacuccaug cugguacaua cgacggagag acgcgaaauc uucaucguag 1560
aaacgggccu cuguucauug gccgagcuau cacacuuuac gcaguuguua gcucauccac 1620
accacgaaua ccucagcgac cuguacacac ccuguuccag uagcgggcga cgcgaucacu 1680
cgcucgaacg ccucacgcgu cucuuccccg augccaccgu ccccgcuacc guucccgccg 1740
cccucuccau ccuaucuacc augcaaccaa gcacgcugga aaccuucccc gaccuguuuu 1800
gcuugccgcu cggcgaaucc uucuccgcgc ugaccgucuc cgaacacguc aguuauaucg 1860
uaacaaacca guaccugauc aaagguaucu ccuacccugu cuccaccacc gucguaggcc 1920
agagccucau caucacccag acggacaguc aaacuaaaug cgaacugacg cgcaacaugc 1980
auaccacaca cagcaucaca guggcgcuca acauuucgcu agaaaacugc gccuuuugcc 2040
aaagcgcccu gcuagaauac gacgacacgc aaggcgucau caacaucaug uacaugcacg 2100
acucggacga cguccuuuuc gcccuggauc ccuacaacga agugguggguc ucaucuccgc 2160 gaacucacua ccucaugcuu uugaaaaacg guacgguacu agaaguaacu gacgucgucg 2220
uggacgccac cgacagucgu cuccucauga uguccgucua cgcgcuaucg gccaucaucg 2280
gcaucuaucu gcucuaccgc augcucaaga caugcugaua auaggcugga gccucggugg 2340
ccaugcuucu ugccccuugg gccucccccc agccccuccu ccccuuccug cacccguacc 2400
cccguggucu uugaauaaag ucugaguggg cggc 2434

<210> SEQ ID NO 177
<211> LENGTH: 1044
<212> TYPE: RNA
<213> ORGANISM: Artificial Sequence
<220> FEATURE:
<223> OTHER INFORMATION: Synthetic polynucleotide

<400> SEQUENCE: 177
ucaagcuuuu ggacccucgu acagaagcua auacgacuca cuauagggcu uaagcaggca 60
gaauuggccc uuagccugua ccagccgaac caugugccgc cgcccggauu gcggcuucuc 120
uuucucaccu ggaccgguga uacugcugug guguugccuu cugcugccca uuguuuccuc 180
agccgccguc agcgucgcuc cuaccgccgc cgagaaaguc cccgcggagu gccccgaacu 240
aacgcgccga ugcuuguugg gugagguguu ugagggugac aaguaugaaa guuggcugcg 300
cccguuggug aauguuaccg ggcgcgaugg cccgcuaucg caacuuaucc guuaccgucc 360
cguuacgccg gaggccgcca acuccgugcu guuggacgag gcuuuccugg acacucuggc 420
ccugcuguac aacaauccgg aucaauugcg ggcccugcug acgcuguuga gcucggacac 480
agcgccgcgc uggaugacgg ugaugcgcgg cuacagcgag ugcggcgaug gcucgccggc 540
cgugaucacg ugcguggacg accugugccg cggcuacgac cucacgcgac ugucauacgg 600
gcgcagcauc uucacggaac acguguuagg cuucgagcug gugccaccgu cucucuuuaa 660
cgugguggug gccauacgca acgaagccac gcguaccaac cgcgccgugc gucugcccgu 720
gagcaccgcu gccgcgcccg agggcaucac gcucuuuuac ggccuguaca acgcagugaa 780
ggaauucugc cugcgucacc agcuggaccc gccgcugcua cgccaccuag auaaauacua 840
cgccggacug ccgcccgagc ugaagcagac gcgcgucaac cugccggcuc acucgcgcua 900
uggcccucaa gcaguggaug cucgcugaua auaggcugga gccucggugg ccaugcuucu 960
ugccccuugg gccucccccc agccccuccu ccccuuccug cacccguacc cccgugggucu 1020 uugaauaaag ucugaguggg cggc 1044

<210> SEQ ID NO 178
<211> LENGTH: 1045
<212> TYPE: RNA
<213> ORGANISM: Artificial Sequence
<220> FEATURE:
<223> OTHER INFORMATION: Synthetic polynucleotide

<400> SEQUENCE: 178
ucaagcuuuu ggacccucgu acagaagcua auacgacuca cuauagggug gcucuuauau 60
uucuucuuac ucuucuuuuc ucucuuauuu ccaugugccg ccgcccggau ugcggcuucu 120
cuuucucacc uggaccggug auacugcugu gguguugccu ucugcugccc auuguuuccu 180
cagccgccgu cagcgucgcu ccuaccgccg ccgagaaagu ccccgcggag ugccccgaac 240
uaacgcgccg augcuuguug ggugaggugu uugaggguga caaguaugaa aguuggcugc 300
gcccguuggu gaauguuacc gggcgcgaug gcccgcuauc gcaacuuauc cguuaccguc 360
ccguuacgcc ggaggccgcc aacuccgugc uguuggacga ggcuuuccug gacacucugg 420
cccugcugua caacaauccg gaucaauugc gggcccugcu gacgcuguug agcucggaca 480
cagcgccgcg cuggaugacg gugaugcgcg gcuacagcga gugcggcgau ggcucgccgg 540
ccguguacac gugcguggac gaccugugcc gcggcuacga ccucacgcga cugucauacg 600
ggcgcagcau cuucacggaa cacguguuag gcuucgagcu ggugccaccg ucucucuuua 660
acgugguggu ggccauacgc aacgaagcca cgcguaccaa ccgcgccgug cgucugcccg 720
ugagcaccgc ugccgcgccc gagggcauca cgcucuuuua cggccuguac aacgcaguga 780
aggaauucug ccugcgucac cagcuggacc cgccgcugcu acgccaccua gauaaauacu 840
acgccggacu gccgcccgag cugaagcaga cgcgcgucaa ccugccggcu cacucgcgcu 900
auggcccuca agcaguggau gcucgcugau aauaggcugg agccucggug gccaugcuuc 960
uugccccuug ggccuccccc cagccccucc uccccuuccu gcacccguac ccccguggguc 1020 uuugaauaaa gucugagugg gcggc 1045

<210> SEQ ID NO 179
<211> LENGTH: 722
<212> TYPE: RNA
<213> ORGANISM: Artificial Sequence
<220> FEATURE:
<223> OTHER INFORMATION: Synthetic polynucleotide

<400> SEQUENCE: 179
ucaagcuuuu ggacccucgu acagaagcua auacgacuca cuauaggguu cggcugguac 60
aggcuaacca gaagacagau aagagccucc augaguccca aagaucugac gccguucuug 120

```
acggcguugu ggcugcuauu gggucacagc cgcgugccgc gggugcgcgc agaagaaugu    180

ugcgaauuca uaaacgucaa ccacccgccg gaacgcuguu acgauuucaa aaugugcaau    240

cgcuucaccg ucgcgcugcg guguccggac ggcgaagucu gcuacagucc cgagaaaacg    300

gcugagauuc gcgggaucgu caccaccaug acccauucau ugacacgcca ggucguacac    360

aacaaacuga cgagcugcaa cuacaauccg uuauaccucg aagcugacgg gcgaauacgc    420

ugcggcaaag uaaacgacaa ggcgcaguac cugcugggcg ccgcuggcag cguucccuau    480

cgauggauca aucuggaaua cgacaagaua acccggaucg ugggccugga ucaguaccug    540

gagagcguua agaaacacaa acggcuggau gugugccgcg cuaaaauggg cuauaugcug    600

cagugauaau aggcuggagc cucgguggcc augcuucuug ccccuugggc cuccccccag    660

ccccuccucc ccuuccugca cccguacccc cguggucuuu gaauaaaguc ugagugggcg    720

gc                                                                    722
```

```
<210> SEQ ID NO 180
<211> LENGTH: 854
<212> TYPE: RNA
<213> ORGANISM: Artificial Sequence
<220> FEATURE:
<223> OTHER INFORMATION: Synthetic polynucleotide

<400> SEQUENCE: 180

ucaagcuuuu ggacccucgu acagaagcua auacgacuca cuauagggag gcucuuaucu     60

gucuucucag uccgaauucg aaguacggcu accaugcugc ggcuucugcu ucgucaccac    120

uuucacugcc ugcuucugug cgcgguuugg gcaacgcccu gucuggcguc uccguggucg    180

acgcuaacag caaaccagaa uccguccccg ccauggucua aacugacgua uuccaaaccg    240

caugacgcgg cgacguuuua cuguccuuuu cucuaucccu cgccccccacg aucccccuug    300

caauucucgg gguuccagcg gguaucaacg ggucccgagu gucgcaacga gacccuguau    360

cugcuguaca accgggaagg ccagaccuug guggagagaa gcuccaccug ggugaaaaag    420

gugaucuggu accugagcgg ucggaaccaa accauccucc aacggaugcc ccgaacggcu    480

ucgaaaccga gcgacggaaa cgugcagauc agcguggaag acgccaagau uuuuggagcg    540

cacauggugc ccaagcagac caagcugcua cgcuucgucg ucaacgaugg cacacguuau    600

cagaugugug ugaugaagcu ggagagcugg gcucacgucu uccgggacua cagcgugucu    660

uuucaggugc gauugacguu caccgaggcc aauaaccaga cuuacaccuu cugcacccau    720

cccaaucuca ucguuugaua auaggcugga gccucggugg ccaugcuucu ugccccuugg    780

gccucccccc agccccuccu ccccuuccug cacccguacc cccguggucu uugaauaaag    840

ucugaguggg cggc                                                      854
```

```
<210> SEQ ID NO 181
<211> LENGTH: 853
<212> TYPE: RNA
<213> ORGANISM: Artificial Sequence
<220> FEATURE:
<223> OTHER INFORMATION: Synthetic polynucleotide

<400> SEQUENCE: 181

ucaagcuuuu ggacccucgu acagaagcua auacgacuca cuauagggug gcucuuauau     60

uucuucuuag uccgaauucg aaguacggcu acaugcugcg gcuucugcuu cgucaccacu    120

uucacugccu gcuucugugc gcgguuuggg caacgcccug ucuggcgucu ccguggucga    180

cgcuaacagc aaaccagaau ccguccccgc cauggucuaa acugacguau uccaaaccgc    240
```

augacgcggc gacguuuuac uguccuuuuc ucuaucccuc gcccccacga ucccccuugc 300
aauucucggg guuccagcgg guaucaacgg gucccgagug ucgcaacgag acccuguauc 360
ugcuguacaa ccgggaaggc cagaccuugg uggagagaag cuccaccugg gugaaaaagg 420
ugaucuggua ccugagcggu cggaaccaaa ccauccucca acggaugccc cgaacggcuu 480
cgaaaccgag cgacggaaac gugcagauca gcguggaaga cgccaagauu uuuggagcgc 540
acauggugcc caagcagacc aagcugcuac gcuucgucgu caacgauggc acacguuauc 600
agaugugugu gaugaagcug gagagcuggg cucacgucuu ccgggacuac agcgugucuu 660
uucaggugcg auugacguuc accgaggcca auaaccagac uuacaccuuc ugcacccauc 720
ccaaucucau cguuugauaa uaggcuggag ccucgguggc caugcuucuu gccccuuggg 780
ccucccccca gccccuccuc cccuuccugc acccguaccc ccguggucuu ugaauaaagu 840
cugagugggc ggc 853

<210> SEQ ID NO 182
<211> LENGTH: 597
<212> TYPE: RNA
<213> ORGANISM: Artificial Sequence
<220> FEATURE:
<223> OTHER INFORMATION: Synthetic polynucleotide

<400> SEQUENCE: 182
ucaagcuuuu ggacccucgu acagaagcua auacgacuca cuauagggua gccguacuuc 60
gaauucggac aagcuucucu cucgucuguc caugcggcug ugucgggugu ggcugucugu 120
uugucugugc gccguggugc ugggucagug ccagcgggaa accgcggaaa aaaacgauua 180
uuaccgagua ccgcauuacu gggacgcgug cucucgcgcg cugcccgacc aaacccguua 240
caaguaugug gaacagcucg uggaccucac guugaacuac cacuacgaug cgagccacgg 300
cuuggacaac uuugacgugc ucaagagaau caacgugacc gaggugucgu ugcucaucag 360
cgacuuuaga cgucagaacc gucgcggcgg caccaacaaa aggaccacgu ucaacgccgc 420
cgguucgcug gcgccacacg cccggagccu cgaguucagc gugcggcucu uugccaacug 480
auaauaggcu ggagccucgg uggccaugcu ucuugccccu ugggccuccc cccagccccu 540
ccuccccuuc cugcacccgu acccccgugg ucuuugaaua aagucugagu gggcggc 597

<210> SEQ ID NO 183
<211> LENGTH: 597
<212> TYPE: RNA
<213> ORGANISM: Artificial Sequence
<220> FEATURE:
<223> OTHER INFORMATION: Synthetic polynucleotide

<400> SEQUENCE: 183
ucaagcuuuu ggacccucgu acagaagcua auacgacuca cuauagggua gccguacuuc 60
gaauucggac uuucuuuucu cucuuauuuc caugcggcug ugucgggugu ggcugucugu 120
uugucugugc gccguggugc ugggucagug ccagcgggaa accgcggaaa aaaacgauua 180
uuaccgagua ccgcauuacu gggacgcgug cucucgcgcg cugcccgacc aaacccguua 240
caaguaugug gaacagcucg uggaccucac guugaacuac cacuacgaug cgagccacgg 300
cuuggacaac uuugacgugc ucaagagaau caacgugacc gaggugucgu ugcucaucag 360
cgacuuuaga cgucagaacc gucgcggcgg caccaacaaa aggaccacgu ucaacgccgc 420
cgguucgcug gcgccacacg cccggagccu cgaguucagc gugcggcucu uugccaacug 480
auaauaggcu ggagccucgg uggccaugcu ucuugccccu ugggccuccc cccagccccu 540
ccuccccuuc cugcacccgu accccc guggucuuugaaua aagucugagu gggcggc 597

<210> SEQ ID NO 184
<211> LENGTH: 3364
<212> TYPE: RNA
<213> ORGANISM: Artificial Sequence
<220> FEATURE:
<223> OTHER INFORMATION: Synthetic polynucleotide

<400> SEQUENCE: 184
ucaagcuuuu ggacccucgu acagaagcua auacgacuca cuauagggaa auaagagaga 60
aaagaagagu aagaagaaau auaagagcca ccauggaguc gcgcggucgc cguuguccc g 120 aaaugauauc cguacugggu cccauuucgg ggcacgugcu gaaagccgug uuuagucgcg 180
gcgauacgcc ggugcugccg cacgagacgc gacuccugca gacggguauc cacguacgcg 240
ugagccagcc cucgcugauc cuggugucgc aguacacgcc cgacucgacg ccaugccacc 300
gcggcgacaa ucagcugcag gugcagcaca cguacuuuac gggcagcgag guggagaacg 360
ugucggucaa cgugcacaac ccc acgggcc gaagcaucug ccccagccaa gagcccaugu 420
cgaucuaugu guacgcgcug ccgcucaaga ugcugaacau ccccagcauc aacgugcacc 480
acuacccguc ggcggccgag cgcaaacacc gacaccugcc cguagccgac gcuguuauuc 540
acgcgucggg caagcagaug uggcaggcgc gucucacggu cucgggacug gccuggacgc 600
gucagcagaa ccaguggaaa gagcccgacg ucuacuacac gucagcguuc guguuuccca 660
ccaaggacgu ggcacugcgg cacguggugu gcgcgcacga gcugguuugc uccauggaga 720
acacgcgcgc aaccaagaug caggugauag gugaccagua cgucaaggug uaccuggagu 780
ccuucugcga ggacgugccc uccggcaagc ucuuuaugca cgucacgcug ggcucugacg 840
uggaagagga ccuaacgaug acccgcaacc cgcaacccuu caugcgcccc cacgagcgca 900
acggcuuuac gguguugugu cccaaaaaua ugauaaucaa accgggcaag aucucgcaca 960
ucaugcugga uguggcuuuu accucacacg agcauuuugg gcugcugugu cccaagagca 1020
ucccgggccu gagcaucuca gguaaccugu ugaugaacgg gcagcaaauc uuccuggagg 1080
uacaagcgau acgcgagacc guggaacugc gucaguacga ucccguggcu gcgcucuucu 1140
uuuucgauau cgacuuguug cugcagcgcg ggccucagua cagcgagcac cccaccuuca 1200
ccagccagua ucgcauccag ggcaagcuug aguaccgaca caccugggac cggcacgacg 1260
agggugccgc ccagggcgac gacgacgucu ggaccagcgg aucggacucc gacgaagaac 1320
ucguaaccac cgagcguaag acgccccgcg ucaccggcgg cggcgccaug gcgagcgccu 1380
ccacuuccgc gggccgcaaa cgcaaaucag cauccucggc gacggcgugc acggcgggcg 1440
uuaugacacg cggccgccuu aaggccgagu ccaccgucgc gcccgaagag gacaccgacg 1500
aggauuccga caacgaaauc cacaauccgg ccguguucac cuggccgccc uggcaggccg 1560
gcauccuggc ccgcaaccug gugcccaugg uggcuacggu ucagggucag aaucugaagu 1620
accaggaguu cuucugggac gccaacgaca ucuaccgcau cuucgccgaa uuggaaggcg 1680
uauggcagcc cgcugcgcaa cccaaacguc gccgccaccg gcaagacgcc uugcccgggc 1740
caugcaucgc cucgacgccc aaaaagcacc gaggugaguc cucugccaag agaaagaugg 1800
acccugauaa uccugacgag ggcccuuccu ccaaggugcc acggcccgag acacccguga 1860
ccaaggccac gacguuccug cagacuaugu uaaggaagga gguuaacagu cagcugagcc 1920
ugggagaccc gcuguuccca gaauuggccg aagaaucccu caaaaccuuu gaacaaguga 1980
ccgaggauug caacgagaac cccgaaaaag auguccugac agaacucguc aaacagauua 2040
agguucgagu ggacauggug cggcauagaa ucaaggagca caugcugaaa aaauauaccc 2100
agacggaaga aaaauucacu ggcgccuuua auaugauggg aggauguuug cagaaugccu 2160
uagauaucuu agauaagguu caugagccuu ucgaggacau gaaguguauu gggcuaacua 2220
ugcagagcau guaugagaac uacauuguac cugaggauaa gcgggagaug uggauggcuu 2280
guauuaagga gcugcaugau gugagcaagg gcgccgcuaa caaguugggg ggugcacugc 2340
aggcuaaggc ccgugcuaaa aaggaugaac uuaggagaaa gaugauguau augugcuaca 2400
ggaauauaga guucuuuacc aagaacucag ccuucccuaa gaccaccaau ggcugcaguc 2460
aggccauggc ggcauugcag aacuugccuc agugcucucc ugaugagauu augucuuaug 2520
cccagaaaau cuuuaagauu uuggaugagg agagagacaa ggugcucacg cacauugauc 2580
acauauuuau ggauauccuc acuacaugug uggaaacaau guguaaugag uacaagguca 2640
cuagugacgc uuguaugaug accauguacg gggcaucuc ucucuuaagu gaguucuguc 2700
gggugcugug cugcuauguc uuagaggaga cuagugugau gcuggccaag cggccucuga 2760
uaaccaagcc ugagguuauc aguguaauga agcgccgcau ugaggagauc ugcaugaagg 2820
ucuuugccca guacauucug gggccgauc cuuugagagu cugcucuccu aguguggaug 2880
accuacgggc caucgccgag gagucagaug aggaagaggc uauuguagcc uacacuuugg 2940
ccaccgcugg ugccagcucc ucugauucuc uggugucacc uccagagucc ccuguacccg 3000
cgacuauccc ucuguccuca guaauugugg cugagaacag ugaucaggaa gaaagugaac 3060
agagugauga ggaacaggag gagggugcuc aggaggagcg ggaggacacu gugucuguca 3120
agucugagcc agugucugag auagaggaag uugccucaga ggaagaggag gauggugcug 3180
aggaacccac cgccucugga ggcaagagca cccacccuau ggugacuaga agcaaggcug 3240
accagugaua auaggcugga gccucggugg ccaugcuucu ugccccuugg gccucccccc 3300
agccccuccu ccccuuccug cacccguacc cccguggucu uugaauaaag ucugaguggg 3360
cggc 3364

<210> SEQ ID NO 185
<211> LENGTH: 3364
<212> TYPE: RNA
<213> ORGANISM: Artificial Sequence
<220> FEATURE:
<223> OTHER INFORMATION: Synthetic polynucleotide

<400> SEQUENCE: 185
ucaagcuuuu ggacccucgu acagaagcua auacgacuca cuauagggaa auaagagaga 60
aaagaagagu aagaagaaau auaagagcca ccauggaguc gcgcggucgc cguuguccccg 120 aaaugauauc cguacugggu cccauuucgg ggcacgugcu gaaagccgug uuuagucgcg 180
gcgauacgcc ggugcugccg cacgagacgc gacuccugca gacggguauc cacguacgcg 240
ugagccagcc cucgcugauc cuggugucgc aguacacgcc cgacucgacg ccaugccacc 300
gcggcgacaa ucagcugcag gugcagcaca cguacuuuac gggcagcgag guggagaacg 360
ugucggucaa cgugcacaac ccacgggcc gaagcaucug ccccagccaa gagcccaugu 420
cgaucuaugu guacgcgcug ccgcucaaga ugcugaacau ccccagcauc aacgugcacc 480
acuacccguc ggcggccgag cgcaaacacc gacaccugcc cguagccgac gcuguuauuc 540
acgcgucggg caagcagaug uggcaggcgc gucucacggu cucgggacug gccuggacgc 600

-continued

```
gucagcagaa ccaguggaaa gagcccgacg ucuacuacac gucagcguuc guguuuccca    660
ccaaggacgu ggcacugcgg cacguggugu gcgcgcacga gcugguuugc uccauggaga    720
acacgcgcgc aaccaagaug caggugauag gugaccagua cgucaaggug uaccuggagu    780
ccuucugcga ggacgugccc uccggcaagc ucuuuaugca cgucacgcug ggcucugacg    840
uggaagagga ccuaacgaug acccgcaacc cgcaacccuu caugcgcccc cacgagcgca    900
acggcuuuac gguguugugu cccaaaaaua ugauaaucaa accgggcaag aucucgcaca    960
ucaugcugga uguggcuuuu accucacacg agcauuuugg gcugcugugu cccaagagca   1020
ucccgggccu gagcaucuca gguaaccugu ugaugaacgg gcagcaaauc uuccuggagg   1080
uacaagcgau acgcgagacc guggaacugc gucaguacga ucccguggcu gcgcucuucu   1140
uuuucgauau cgacuuguug cugcagcgcg ggccucagua cagcgagcac ccccaccuuca   1200
ccagccagua ucgcauccag ggcaagcuug aguaccgaca caccugggac cggcacgacg   1260
agggugccgc ccagggcgac gacgacgucu ggaccagcgg aucggacucc gacgaagaac   1320
ucguaaccac cgagcguaag acgccccgcg ucaccggcgg cggcgccaug gcgagcgccu   1380
ccacuuccgc gggccgcaaa cgcaaaucag cauccucggc gacggcgugc acggcgggcg   1440
uuaugacacg cggccgccuu aaggccgagu ccaccgucgc gcccgaagag gacaccgacg   1500
aggauuccga caacgaaauc cacaauccgg ccguguucac cuggccgccc uggcaggccg   1560
gcauccuggc ccgcaaccug gugcccaugg uggcuacggu ucagggucag aaucugaagu   1620
accaggaguu cuucugggac gccaacgaca ucuaccgcau cuucgccgaa uuggaaggcg   1680
uauggcagcc cgcugcgcaa cccaaacguc gccgccaccg gcaagacgcc uugcccgggc   1740
caugcaucgc cucgacgccc aaaaagcacc gaggugaguc cucugccaag agaaagaugg   1800
acccugauaa uccugacgag ggcccuuccu ccaaggugcc acggcccgag acacccguga   1860
ccaaggccac gacguuccug cagacuaugu uaaggaagga gguuaacagu cagcugagcc   1920
ugggagaccc gcuguuccca gaauuggccg aagaaucccu caaaaccuuu gaacaaguga   1980
ccgaggauug caacgagaac cccgaaaaag auguccugac agaacucguc aaacagauua   2040
agguucgagu ggacauggug cggcauagaa ucaaggagca caugcugaaa aaauauaccc   2100
agacggaaga aaaauucacu ggcgccuuua auaugauggg aggauguuug cagaaugccu   2160
uagauaucuu agauaagguu caugagccuu ucgaggacau gaaguguauu gggcuaacua   2220
ugcagagcau guaugagaac uacauuguac cugaggauaa gcgggagaug uggauggcuu   2280
guauuaagga gcugcaugau gugagcaagg gcgccgcuaa caaguugggg ggugcacugc   2340
aggcuaaggc ccgugcuaaa aaggaugaac uuaggagaaa gaugauguau augugcuaca   2400
ggaauauaga guucuuuacc aagaacucag ccuucccuaa gaccaccaau ggcugcaguc   2460
aggccauggc ggcauugcag aacuugccuc agugcucucc ugaugagauu augucuuaug   2520
cccagaaaau cuuuaagauu uuggaugagg agagagacaa ggugcucacg cacauugauc   2580
acauauuuau ggauauccuc acuacaugug uggaaacaau guguaaugag uacaagguca   2640
cuagugacgc uuguaugaug accauguacg ggggcaucuc ucucuuaagu gaguucuguc   2700
gggugcugug cugcuauguc uuagaggaga cuagugugau gcuggccaag cggccucuga   2760
uaaccaagcc ugagguuauc aguguaauga agcgccgcau ugaggagauc ugcaugaagg   2820
ucuuugccca guacauucug gggggccgauc cuuugagagu cugcucuccu aguguggaug   2880
accuacgggc caucgccgag gagucagaug aggaagaggc uauuguagcc uacacuuugg   2940
ccaccgcugg ugccagcucc ucugauucuc uggugucacc uccagagucc ccuguacccg   3000
```

cgacuauccc ucuguccuca guaauugugg cugagaacag ugaucaggaa gaaagugaac 3060
agagugauga ggaacaggag gagggugcuc aggaggagcg ggaggacacu gugucuguca 3120
agucugagcc agugucugag auagaggaag uugccucaga ggaagaggag gauggugcug 3180
aggaacccac cgccucugga ggcaagagca cccacccuau ggugacuaga agcaaggcug 3240
accagugaua auaggcugga gccucggugg ccaugcuucu ugccccuugg gccucccccc 3300
agccccuccu ccccuuccug cacccguacc cccguggucu uugaauaaag ucugaguggg 3360
cggc 3364

<210> SEQ ID NO 186
<211> LENGTH: 3352
<212> TYPE: RNA
<213> ORGANISM: Artificial Sequence
<220> FEATURE:
<223> OTHER INFORMATION: Synthetic polynucleotide

<400> SEQUENCE: 186
ucaagcuuuu ggacccucgu acagaagcua auacgacuca cuauagggaa auaagagaga 60
aaagaagagu aagaagaaau auaagagcca ccaugcggcc aggccucccc uccuaccuca 120
ucauccucgc cgucugucuc uucagccacc uacuuucguc acgauauggc gcagaagccg 180
uauccgaacc gcuggacaaa gcguuucacc uacugcucaa caccuacggg agacccaucc 240
gcuuccugcg ugaaaauacc acccagugua ccuacaacag cagccuccgu aacagcacgg 300
ucgucaggga aaacgccauc aguuucaacu uuuuccaaag cuauaaucaa uacuauguau 360
uccauaugcc ucgaugucuu uuugcggguc cucuggcgga gcaguuucug aaccagguag 420
aucugaccga aacccuggaa agauaccaac agagacuuaa cacuuacgcg cugguaucca 480
aagaccuggc cagcuaccga ucuuuuucgc agcagcuaaa ggcacaagac agccuaggug 540
aacagcccac cacugugcca ccgcccauug accugucaau accucacguu uggaugccac 600
cgcaaaccac uccacacggc uggacagaau cacauaccac cucaggacua caccgaccac 660
acuuuaacca gaccuguauc cucuuugaug gacacgaucu acuauucagc accgucacac 720
cuuguuugca ccaaggcuuu uaccucaucg acgaacuacg uuacguuaaa auaacacuga 780
ccgaggacuu cuucguaguu acggugucca uagacgacga cacacccaug cugcuuaucu 840
ucggccaucu uccacgcgua cuuuucaaag cgcccuauca acgcgacaac uuuauacuac 900
gacaaacuga aaaacacgag cuccuggugc uaguuaagaa agaucaacug aaccgucacu 960
cuuaucucaa agacccggac uuucuugacg ccgcacuuga cuucaacuac cuagaccuca 1020
gcgcacuacu acguaacagc uuucaccguu acgccgugga uguacucaag agcggucgau 1080
gucagaugcu ggaccgccgc acgguagaaa uggccuucgc cuacgcauua gcacuguucg 1140
cagcagcccg acaagaagag gccggcgccc aagucuccgu cccacgggcc cuagaccgcc 1200
aggccgcacu cuuacaaaua caagaauuua ugaucaccug ccucucacaa acaccaccac 1260
gcaccacguu gcugcuguau cccacggccg uggaccuggc caaacgagcc cuuuggacac 1320
cgaaucagau caccgacauc accagccucg uacgccuggu cuacauacuc ucuaaacaga 1380
aucagcaaca ucucaucccc caaugggcac uacgacagau cgccgacuuu gcccuaaaac 1440
uacacaaaac gcaccuggcc ucuuuucuuu cagccuucgc acgccaagaa cucuaccuca 1500
ugggcagccu cguccacucc augcugguac auacgacgga gagacgcgaa aucuucaucg 1560
uagaaacggg ccucuguuca uuggccgagc uaucacacuu uacgcaguug uuagcucauc 1620

-continued

```
cacaccacga auaccucagc gaccuguaca cacccuguuc caguagcggg cgacgcgauc   1680

acucgcucga acgccucacg cgucucuucc ccgaugccac cgucccccgcu accguucccg   1740

ccgcccucuc cauccuaucu accaugcaac caagcacgcu ggaaaccuuc cccgaccugu   1800

uuugcuugcc gcucggcgaa uccuucuccg cgcugaccgu cuccgaacac gucaguuaua   1860

ucguaacaaa ccaguaccug aucaaaggua ucuccuaccc ugucuccacc accgucguag   1920

gccagagccu caucaucacc cagacggaca gucaaacuaa augcgaacug acgcgcaaca   1980

ugcauaccac acacagcauc acaguggcgc ucaacauuuc gcuagaaaac ugcgccuuuu   2040

gccaaagcgc ccugcuagaa uacgacgaca cgcaaggcgu caucaacauc auguacaugc   2100

acgacucgga cgacguccuu uucgcccugg aucccuacaa cgaaguggug gucucaucuc   2160

cgcgaacuca cuaccucaug cuuuugaaaa acgguacggu acuagaagua acugacgucg   2220

ucguggacgc caccgacagu cgucuccuca ugauguccgu cuacgcgcua ucggccauca   2280

ucggcaucua ucugcucuac cgcaugcuca agacaugccg cgccaagagg agcggaagcg   2340

gagcuacuaa cuucagccug cugaagcagg cuggagacgu ggaggagaac ccuggaccua   2400

ugugccgccg cccggauugc ggcuucucuu ucucaccugg accggugaua cugcuguggu   2460

guugccuucu gcugcccauu guuuccucag ccgccgucag cgucgcuccu accgccgccg   2520

agaaaguccc cgcggagugc cccgaacuaa cgcgccgaug cuuguugggu gagguguuug   2580

agggugacaa guaugaaagu uggcugcgcc cguuggugaa uguuaccggg cgcgauggcc   2640

cgcuaucgca acuuauccgu uaccgucccg uuacgccgga ggccgccaac uccgugcugu   2700

uggacgaggc uuuccuggac acucuggccc ugcuguacaa caauccggau caauugcggg   2760

cccugcugac gcuguugagc ucggacacag cgccgcgcug gaugacggug augcgcggcu   2820

acagcgagug cggcgauggc ucgccggccg uguacacgug cguggacgac cugugccgcg   2880

gcuacgaccu cacgcgacug ucauacgggc gcagcaucuu cacggaacac guguuaggcu   2940

ucgagcuggu gccaccgucu cucuuuaacg ugguggugcc cauacgcaac gaagccacgc   3000

guaccaaccg cgccgugcgu cugcccguga gcaccgcugc cgcgcccgag ggcaucacgc   3060

ucuuuuacgg ccuguacaac gcagugaagg aauucugccu gcgucaccag cuggacccgc   3120

cgcugcuacg ccaccuagau aaauacuacg ccggacugcc gcccgagcug aagcagacgc   3180

gcgucaaccu gccggcucac ucgcgcuaug gcccucaagc aguggaugcu cgcugauaau   3240

aggcuggagc cucgguggcc augcuucuug ccccuugggc cuccccccag ccccuccucc   3300

ccuuccugca cccguacccc cguggucuuu gaauaaaguc ugagugggcg gc           3352
```

<210> SEQ ID NO 187
<211> LENGTH: 1924
<212> TYPE: RNA
<213> ORGANISM: Artificial Sequence
<220> FEATURE:
<223> OTHER INFORMATION: Synthetic polynucleotide

<400> SEQUENCE: 187

```
ucaagcuuuu ggacccucgu acagaagcua auacgacuca cuauagggaa auaagagaga     60

aaagaagagu aagaagaaau auaagagcca ccaugagucc caaagaucug acgccguucu    120

ugacggcguu guggcugcua uugggucaca gccgcgugcc gcgggugcgc gcagaagaau    180

guugcgaauu cauaaacguc aaccacccgc cggaacgcug uuacgauuuc aaaaugugca    240

aucgcuucac cgucgcgcug cggugucegg acggcgaagu cugcuacagu cccgagaaaa    300

cggcugagau ucgcgggauc gucaccacca ugacccauuc auugacacgc caggucguac    360
```

-continued acaacaaacu gacgagcugc aacuacaauc cguuauaccu cgaagcugac gggcgaauac 420
gcugcggcaa aguaaacgac aaggcgcagu accugcuggg cgccgcuggc agcguucccu 480
aucgauggau caaucuggaa uacgacaaga uaacccggau cgugggccug gaucaguacc 540
uggagagcgu uaagaaacac aaacggcugg augugugccg cgcuaaaaug ggcuauaugc 600
ugcagcgcgc caagaggagc ggaagcggag cuacuaacuu cagccugcug aagcaggcug 660
gagacgugga ggagaacccu ggaccuaugc ugcggcuucu gcuucgucac cacuuucacu 720
gccugcuucu gugcgcgguu ugggcaacgc ccugucuggc gucuccgugg ucgacgcuaa 780
cagcaaacca gaauccgucc ccgccauggu cuaaacugac guauuccaaa ccgcaugacg 840
cggcgacguu uuacuguccu uuucucuauc ccucgccccc acgauccccc uugcaauucu 900 cggggguucca gcggguauca acgggucccg agugucgcaa cgagacccug uaucugcugu 960
acaaccggga aggccagacc uugguggaga gaagcuccac cugggugaaa aaggugaucu 1020
gguaccugag cggucggaac caaaccaucc uccaacggau gccccgaacg gcuucgaaac 1080
cgagcgacgg aaacgugcag aucagcgugg aagacgccaa gauuuuugga gcgcacaugg 1140
ugcccaagca gaccaagcug cuacgcuucg ucgucaacga uggcacacgu uaucagaugu 1200
gugugaugaa gcuggagagc ugggcucacg ucuuccggga cuacagcgug ucuuuucagg 1260
ugcgauugac guucaccgag gccaauaacc agacuuacac cuucugcacc caucccaauc 1320
ucaucguucg cgccaagagg agcggaagcg gagugaaaca gacuuugaau uuugaccuuc 1380
ucaaguuggc gggagacgug gaguccaacc cuggaccuau gcggcugugu cgggugugc 1440 ugucuguuug ucugugcgcc guggugcugg gucagugcca gcgggaaacc gcggaaaaaa 1500
acgauuauua ccgaguaccg cauuacuggg acgcgugcuc ucgcgcgcug cccgaccaaa 1560
cccguuacaa guauguggaa cagcucgugg accucacguu gaacuaccac uacgaugcga 1620
gccacggcuu ggacaacuuu gacgugcuca agagaaucaa cgugaccgag gugucguugc 1680
ucaucagcga cuuuagacgu cagaaccguc gcggcggcac caacaaaagg accacguuca 1740
acgccgccgg uucgcuggcg ccacacgccc ggagccucga guucagcgug cggcucuuug 1800
ccaacugaua auaggcugga gccucggugg ccaugcuucu ugccccuugg gccuccccc 1860 agccccuccu ccccuuccug cacccguacc cccguggucu uugaauaaag ucugaguggg 1920
cggc 1924

<210> SEQ ID NO 188
<211> LENGTH: 5146
<212> TYPE: RNA
<213> ORGANISM: Artificial Sequence
<220> FEATURE:
<223> OTHER INFORMATION: Synthetic polynucleotide

<400> SEQUENCE: 188
ucaagcuuuu ggacccucgu acagaagcua auacgacuca cuauagggaa auaagagaga 60
aaagaagagu aagaagaaau auaagagcca ccaugcggcc aggccucccc uccuaccuca 120
ucauccucgc cgucugucuc uucagccacc uacuuucguc acgauauggc gcagaagccg 180
uauccgaacc gcuggacaaa gcguuucacc uacugcucaa caccuacggg agacccaucc 240
gcuuccugcg ugaaaauacc acccagugua ccuacaacag cagccuccgu aacagcacgg 300
ucgucaggga aaacgccauc aguuucaacu uuuuccaaag cuauaaucaa uacuauguau 360
uccauaugcc ucgaugucuu uuugcggguc cucuggcgga gcaguuucug aaccagguag 420

-continued

```
aucugaccga aacccuggaa agauaccaac agagacuuaa cacuuacgcg cugguaucca    480
aagaccuggc cagcuaccga ucuuuuucgc agcagcuaaa ggcacaagac agccuaggug    540
aacagcccac cacugugcca ccgcccauug accugucaau accucacguu uggaugccac    600
cgcaaaccac uccacacggc uggacagaau cacauaccac cucaggacua caccgaccac    660
acuuuaacca gaccuguauc cucuuugaug gacacgaucu acuauucagc accgucacac    720
cuuguuugca ccaaggcuuu uaccucaucg acgaacuacg uuacguuaaa auaacacuga    780
ccgaggacuu cuucguaguu acggugucca uagacgacga cacacccaug cugcuuaucu    840
ucggccaucu uccacgcgua cuuuucaaag cgcccuauca acgcgacaac uuuauacuac    900
gacaaacuga aaaacacgag cuccuggugc uaguuaagaa agaucaacug aaccgucacu    960
cuuaucucaa agacccggac uuucuugacg ccgcacuuga cuucaacuac cuagaccuca   1020
gcgcacuacu acguaacagc uuucaccguu acgccgugga uguacucaag agcggucgau   1080
gucagaugcu ggaccgccgc acgguagaaa uggccuucgc cuacgcauua gcacuguucg   1140
cagcagcccg acaagaagag gccggcgccc aagucuccgu cccacgggcc cuagaccgcc   1200
aggccgcacu cuuacaaaua caagaauuua ugaucaccug ccucucacaa acaccaccac   1260
gcaccacguu gcugcuguau cccacggccg uggaccuggc caaacgagcc cuuuggacac   1320
cgaaucagau caccgacauc accagccucg uacgccuggu cuacauacuc ucuaaacaga   1380
aucagcaaca ucucaucccc caaugggcac uacgacagau cgccgacuuu gcccuaaaac   1440
uacacaaaac gcaccuggcc ucuuuucuuu cagccuucgc acgccaagaa cucuaccuca   1500
ugggcagccu cguccacucc augcugguac auacgacgga gagacgcgaa aucuucaucg   1560
uagaaacggg ccucuguuca uuggccgagc uaucacacuu uacgcaguug uuagcucauc   1620
cacaccacga auaccucagc gaccuguaca cacccuguuc caguagcggg cgacgcgauc   1680
acucgcucga acgccucacg cgucucuucc ccgaugccac cgucccccgcu accguucccg   1740
ccgcccucuc cauccuaucu accaugcaac caagcacgcu ggaaaccuuc cccgaccugu   1800
uuugcuugcc gcucggcgaa uccuucuccg cgcugaccgu cuccgaacac gucaguuaua   1860
ucguaacaaa ccaguaccug aucaaaggua ucuccuaccc ugucuccacc accgucguag   1920
gccagagccu caucaucacc cagacggaca gucaaacuaa augcgaacug acgcgcaaca   1980
ugcauaccac acacagcauc acaguggcgc ucaacauuuc gcuagaaaac ugcgccuuuu   2040
gccaaagcgc ccugcuagaa uacgacgaca cgcaaggcgu caucaacauc auguacaugc   2100
acgacucgga cgacguccuu uucgcccugg aucccuacaa cgaagugguug gucucaucuc   2160
cgcgaacuca cuaccucaug cuuuugaaaa acgguacggu acuagaagua acugacgucg   2220
ucguggacgc caccgacagu cgucuccuca ugauguccgu cuacgcgcua ucggccauca   2280
ucggcaucua ucugcucuac cgcaugcuca agacaugccg cgccaagagg agcggaagcg   2340
gagcuacuaa cuucagccug cugaagcagg cuggagacgu ggaggagaac ccuggaccua   2400
ugugccgccg cccggauugc ggcuucucuu ucucaccugg accggugaua cugcugguggu   2460
guugccuucu gcugcccauu guuuccucag ccgccgucag cgucgcuccu accgccgccg   2520
agaaaguccc cgcggagugc cccgaacuaa cgcgccgaug cuuguugggu gaggugguuug   2580
agggugacaa guaugaaagu uggcugcgcc cguuggugaa uguuaccggg cgcgauggcc   2640
cgcuaucgca acuuauccgu uaccgucccg uuacgccgga ggccgccaac uccgugcugu   2700
uggacgaggc uuuccuggac acucuggccc ugcuguacaa caauccggau caauugcggg   2760
cccugcugac gcuguugagc ucggacacag cgccgcgcug gaugacggug augcgcggcu   2820
```

-continued

```
acagcgagug cggcgauggc ucgccggccg uguacacgug cguggacgac cugugccgcg   2880
gcuacgaccu cacgcgacug ucauacgggc gcagcaucuu cacggaacac guguuaggcu   2940
ucgagcuggu gccaccgucu cucuuuaacg ugguggugge cauacgcaac gaagccacgc   3000
guaccaaccg cgccgugcgu cugcccguga gcaccgcugc cgcgcccgag ggcaucacgc   3060
ucuuuuacgg ccuguacaac gcagugaagg aauucugccu gcgucaccag cuggacccgc   3120
cgcugcuacg ccaccuagau aaauacuacg ccggacugcc gcccgagcug aagcagacgc   3180
gcgucaaccu gccggcucac ucgcgcuaug gcccucaagc aguggaugcu cgccgcgcca   3240
agaggagcgg aagcggagug aaacagacuu ugaauuuuga ccuucucaag uuggcgggag   3300
acguggaguc caacccugga ccuaugaguc ccaaagaucu gacgccguuc uugacggcgu   3360
uguggcugcu auugggucac agccgcgugc cgcgggugcg cgcagaagaa uguugcgaau   3420
ucauaaacgu caaccacccg ccggaacgcu guuacgauuu caaaaugugc aaucgcuuca   3480
ccgucgcgcu gcggugucccg gacggcgaag ucugcuacag ucccgagaaa acggcugaga   3540
uucgcgggau cgucaccacc augacccauu cauugacacg ccaggucgua cacaacaaac   3600
ugacgagcug caacuacaau ccguuauacc ucgaagcuga cgggcgaaua cgcugcggca   3660
aaguaaacga caaggcgcag uaccugcugg gcgccgcugg cagcguuccc uaucgaugga   3720
ucaaucugga auacgacaag auaacccgga ucgugggccu ggaucaguac cuggagagcg   3780
uuaagaaaca caaacggcug gaugugugcc gcgcuaaaau gggcuauaug cugcagcgcg   3840
ccaagaggag cggaagcgga caguguacua auuaugcucu cuugaaauug gcuggagaug   3900
uugagagcaa cccuggaccu augcugcggc uucugcuucg ucaccacuuu cacugccugc   3960
uucugugcgc gguuugggca acgcccuguc uggcgucucc guggucgacg cuaacagcaa   4020
accagaaucc gucccccgcca uggucuaaac ugacguauuc caaaccgcau gacgcggcga   4080
cguuuuacug uccuuuucuc uaucccucgc ccccacgauc ccccuugcaa uucucggggu   4140
uccagcgggu aucaacgggu cccgaguguc gcaacgagac ccuguaucug cuguacaacc   4200
gggaaggcca gaccuuggug gagagaagcu ccaccugggu gaaaaaggug aucugguacc   4260
ugagcggucg gaaccaaacc auccuccaac ggaugccccg aacggcuucg aaaccgagcg   4320
acggaaacgu gcagaucagc guggaagacg ccaagauuuu uggagcgcac auggugccca   4380
agcagaccaa gcugcuacgc uucgucguca acgauggcac acguuaucag auguguguga   4440
ugaagcugga gagcugggcu cacgucuucc gggacuacag cgugucuuuu caggugcgau   4500
ugacguucac cgaggccaau aaccagacuu acaccuucug cacccauccc aaucucaucg   4560
uucgcgccaa gaggagcgga agcggagagg gcagaggaag ucugcuaaca ugcggugacg   4620
ucgaggagaa uccuggaccu augcggcugu gucgggugug gcugucuguu ugucugugcg   4680
ccguggugcu gggucagugc cagcgggaaa ccgcggaaaa aaacgauuau uaccgaguac   4740
cgcauuacug ggacgcgugc ucucgcgcgc ugcccgacca aacccguuac aaguaugugg   4800
aacagcucgu ggaccucacg uugaacuacc acuacgaugc gagccacggc uuggacaacu   4860
uugacgugcu caagagaauc aacgugaccg aggugucguu gcucaucagc gacuuuagac   4920
gucagaaccg ucgcggcggc accaacaaaa ggaccacguu caacgccgcc gguucgcugg   4980
cgccacacgc ccggagccuc gaguucagcg ugcggcucuu ugccaacuga uaauaggcug   5040
gagccucggu ggccaugcuu cuugccccuu gggccucccc ccagccccuc cuccccuucc   5100
ugcacccgua cccccguggu cuuugaauaa agucugagug ggcggc                  5146
```

<210> SEQ ID NO 189
<211> LENGTH: 2437
<212> TYPE: RNA
<213> ORGANISM: Artificial Sequence
<220> FEATURE:
<223> OTHER INFORMATION: Synthetic polynucleotide

<400> SEQUENCE: 189
ucaagcuuuu ggacccucgu acagaagcua auacgacuca cuauagggaa auaagagaga 60
aaagaagagu aagaagaaau auaagagcca ccaugcggcc aggccucccc uccuaccuca 120
ucauccucgc cgucugucuc uucagccacc uacuuucguc acgauauggc gcagaagccg 180
uauccgaacc gcuggacaaa gcguuucacc uacugcucaa caccuacggg agacccaucc 240
gcuuccugcg ugaaaauacc acccagugua ccuacaacag cagccuccgu aacagcacgg 300
ucgucaggga aaacgccauc aguuucaacu ucuuccaaag cuauaaucaa uacuauguau 360
uccauaugcc ucgaugucuc uuugcggguc cucuggcgga gcaguuucug aaccagguag 420
aucugaccga aacccuggaa agauaccaac agagacuuaa cacuuacgcg cugguaucca 480
aagaccuggc cagcuaccga ucuuucucgc agcagcuaaa ggcacaagac agccuaggug 540
aacagcccac cacugugcca ccgcccauug accugucaau accucacguu uggaugccac 600
cgcaaaccac uccacacggc uggacagaau cacauaccac cucaggacua caccgaccac 660
acuuuaacca gaccuguauc cucuuugaug gacacgaucu acuauucagc accgucacac 720
cuuguuugca ccaaggcuuu uaccucaucg acgaacuacg uuacguuaaa auaacacuga 780
ccgaggacuu cuucguaguu acggugucca uagacgacga cacacccaug cugcuuaucu 840
ucggccaucu uccacgcgua cuuuucaaag cgcccuauca acgcgacaac uuuauacuac 900
gacaaacuga gaaacacgag cuccuggugc uaguuaagaa agaucaacug aaccgucacu 960
cuuaucucaa agacccggac uuucuugacg ccgcacuuga cuucaacuac cuagaccuca 1020
gcgcacuacu acguaacagc uuucaccguu acgccgugga uguacucaag agcggucgau 1080
gucagaugcu ggaccgccgc acgguagaaa uggccuucgc cuacgcauua gcacuguucg 1140
cagcagcccg acaagaagag gccggcgccc aagucuccgu cccacgggcc cuagaccgcc 1200
aggccgcacu cuuacaaaua caagaauuua ugaucaccug ccucucacaa acaccaccac 1260
gcaccacguu gcugcuguau cccacggccg uggaccuggc caaacgagcc cuuuggacac 1320
cgaaucagau caccgacauc accagccucg uacgccuggu cuacauacuc ucuaaacaga 1380
aucagcaaca ucucaucccc caaugggcac uacgacagau cgccgacuuu gcccuaaaac 1440
uacacaaaac gcaccuggcc ucuuucuuu cagccuucgc acgccaagaa cucuaccuca 1500
ugggcagccu cguccacucc augcugguac auacgacgga gagacgcgaa aucuucaucg 1560
uagaaacggg ccucuguuca uuggccgagc uaucacacuu uacgcaguug uuagcucauc 1620
cacaccacga auaccucagc gaccuguaca cacccuguuc caguagcggg cgacgcgauc 1680
acucgcucga acgccucacg cgucucuucc ccgaugccac cgucccccgcu accguucccg 1740 ccgcccucuc cauccuaucu accaugcaac caagcacgcu ggaaaccuuc cccgaccugu 1800
uuugcuugcc gcucggcgaa uccuucuccg cgcugaccgu cuccgaacac gucaguuaua 1860
ucguaacaaa ccaguaccug aucaaaggua ucuccuaccc ugucuccacc accgucguag 1920
gccagagccu caucaucacc cagacggaca gucaaacuaa augcgaacug acgcgcaaca 1980
ugcauaccac acacagcauc acaguggcgc ucaacauuuc gcuagaaaac ugcgccuuuu 2040
gccaaagcgc ccugcuagaa uacgacgaca cgcaaggcgu caucaacauc auguacaugc 2100

-continued acgacucgga cgacguccuu uucgcccugg aucccuacaa cgaagugqug gucucaucuc 2160 cgcgaacuca cuaccucaug cuuuugaaga acgguacggu acuagaagua acugacgucg 2220
ucguggacgc caccgacagu cgucuccuca ugauguccgu cuacgcgcua ucggccauca 2280
ucggcaucua ucugcucuac cgcaugcuca agacaugcug auaauaggcu ggagccucgg 2340
uggccaugcu ucuugccccu ugggccuccc cccagccccu ccucccccuuc cugcacccgu 2400 acccccgugg ucuuugaaua aagucugagu gggcggc 2437

<210> SEQ ID NO 190
<211> LENGTH: 1045
<212> TYPE: RNA
<213> ORGANISM: Artificial Sequence
<220> FEATURE:
<223> OTHER INFORMATION: Synthetic polynucleotide

<400> SEQUENCE: 190
ucaagcuuuu ggacccucgu acagaagcua auacgacuca cuauagggaa auaagagaga 60
aaagaagagu aagaagaaau auaagagcca ccaugugccg ccgcccggau ugcggcuucu 120
cuuucucacc uggaccggug auacugcugu gguguugccu ucugcugccc auuguuuccu 180
cagccgccgu cagcgucgcu ccuaccgccg ccgagaaagu ccccgcggag ugccccgaac 240
uaacgcgccg augcuuguug ggugaggugu uugaggguga caaguaugaa aguuggcugc 300
gcccguuggu gaauguuacc gggcgcgaug gcccgcuauc gcaacuuauc cguuaccguc 360
ccguuacgcc ggaggccgcc aacuccgugc uguuggacga ggcuuuccug gacacucugg 420
cccugcugua caacaauccg gaucaauugc gggcccugcu gacgcuguug agcucggaca 480
cagcgccgcg cuggaugacg gugaugcgcg gcuacagcga gugcggcgau ggcucgccgg 540
ccguguacac gugcguggac gaccugugcc gcggcuacga ccucacgcga cugucauacg 600
ggcgcagcau cuucacggaa cacguguuag gcuucgagcu ggugccaccg ucucucuuua 660
acgugguggu ggccauacgc aacgaagcca cgcguaccaa ccgcgccgug cgucugcccg 720
ugagcaccgc ugccgcgccc gagggcauca cgcucuuuua cggccuguac aacgcaguga 780
aggaauucug ccugcgucac cagcuggacc cgccgcugcu acgccaccua gauaaaauacu 840 acgccggacu gccgcccgag cugaagcaga cgcgcgucaa ccugccggcu cacucgcgcu 900
auggcccuca agcaguggau gcucgcugau aauaggcugg agccucggug gccaugcuuc 960
uugccccuug ggccuccccc cagccccucc uccccuuccu gcacccguac ccccguggucc 1020 uuugaauaaa gucugagugg gcggc 1045

<210> SEQ ID NO 191
<211> LENGTH: 724
<212> TYPE: RNA
<213> ORGANISM: Artificial Sequence
<220> FEATURE:
<223> OTHER INFORMATION: Synthetic polynucleotide

<400> SEQUENCE: 191
ucaagcuuuu ggacccucgu acagaagcua auacgacuca cuauagggaa auaagagaga 60
aaagaagagu aagaagaaau auaagagcca ccaugagucc caaagaucug acgccguucu 120
ugacggcguu guggcugcua uugggucaca gccgcgugcc gcgggugcgc gcagaagaau 180
guugcgaauu cauaaacguc aaccacccgc cggaacgcug uuacgauuuc aaaaugugca 240
aucgcuucac cgucgcgcug cggguguccgg acggcgaagu cugcuacagu cccgagaaaa 300

-continued cggcugagau ucgcgggauc gucaccacca ugacccauuc auugacacgc caggucguac 360
acaacaaacu gacgagcugc aacuacaauc cguuauaccu cgaagcugac gggcgaauac 420
gcugcggcaa aguaaacgac aaggcgcagu accugcuggg cgccgcuggc agcguucccu 480
aucgauggau caaucuggaa uacgacaaga uaacccggau cgugggccug gaucaguacc 540
uggagagcgu uaagaaacac aaacggcugg augugugccg cgcuaaaaug ggcuauaugc 600
ugcagugaua auaggcugga gccucggugg ccaugcuucu ugccccuugg gccucccccc 660
agccccuccu ccccuuccug cacccguacc cccguggucu uugaauaaag ucugaguggg 720
cggc 724

<210> SEQ ID NO 192
<211> LENGTH: 846
<212> TYPE: RNA
<213> ORGANISM: Artificial Sequence
<220> FEATURE:
<223> OTHER INFORMATION: Synthetic polynucleotide

<400> SEQUENCE: 192
ucaagcuuuu ggacccucgu acagaagcua auacgacuca cuauagggaa auaagagaga 60
aaagaagagu aagaagaaau auaagagcca ccaugcugcg gcuucugcuu cgucaccacu 120
uucacugccu gcuucugugc gcgguuuggg caacgcccug ucuggcgucu ccguggucga 180
cgcuaacagc aaaccagaau ccguccccgc cauggucuaa acugacguau uccaaaccgc 240
augacgcggc gacguuuuac uguccuuuuc ucuaucccuc gcccccacga ucccccuugc 300
aauucucggg guuccagcgg guaucaacgg gucccgagug ucgcaacgag acccuguauc 360
ugcuguacaa ccgggaaggc cagaccuugg uggagagaag cuccaccugg gugaaaaagg 420
ugaucuggua ccugagcggu cggaaccaaa ccauccucca acggaugccc cgaacggcuu 480
cgaaaccgag cgacggaaac gugcagauca gcguggaaga cgccaagauu uuuggagcgc 540
acauggugcc caagcgcugc uacgcuucgu cgucaacgau ggcacacguu aucagaugug 600
ugugaugaag cuggagagcu gggcucacgu cuuccgggac uacagcgugu cuuuucaggu 660
gcgauugacg uucaccgagg ccaauaacca gacuuacacc uucugcaccc aucccaaucu 720
caucguuuga uaauaggcug gagccucggu ggccaugcuu cuugccccuu gggccucccc 780
ccagccccuc cuccccuucc ugcacccgua cccccguggu cuuugaauaa agucugagug 840
ggcggc 846

<210> SEQ ID NO 193
<211> LENGTH: 598
<212> TYPE: RNA
<213> ORGANISM: Artificial Sequence
<220> FEATURE:
<223> OTHER INFORMATION: Synthetic polynucleotide

<400> SEQUENCE: 193
ucaagcuuuu ggacccucgu acagaagcua auacgacuca cuauagggaa auaagagaga 60
aaagaagagu aagaagaaau auaagagcca ccaugcggcu gugucgggug uggcugucug 120
uuugucugug cgccguggug cugggucagu gccagcggga aaccgcggaa aagaacgauu 180
auuaccgagu accgcauuac ugggacgcgu gcucucgcgc gcugcccgac caaacccguu 240
acaaguaugu ggaacagcuc guggaccuca cguugaacua ccacuacgau gcgagccacg 300
gcuuggacaa cuuugacgug cucaagagaa ucaacgugac cgaggugucg uugcucauca 360
gcgacuuuag acgucagaac cgucgcggcg gcaccaacaa aaggaccacg uucaacgccg 420
ccgguucgcu ggcgccacac gcccggagcc ucgaguucag cgugcggcuc uuugccaacu 480
gauaauaggc uggagccucg guggccaugc uucuugcccc uugggccucc ccccagcccc 540
uccuccccuu ccugcacccg uacccccgug gucuuugaau aaagucugag ugggcggc 598

<210> SEQ ID NO 194
<211> LENGTH: 2933
<212> TYPE: RNA
<213> ORGANISM: Artificial Sequence
<220> FEATURE:
<223> OTHER INFORMATION: Synthetic polynucleotide

<400> SEQUENCE: 194
ucaagcuuuu ggacccucgu acagaagcua auacgacuca cuauagggaa auaagagaga 60
aaagaagagu aagaagaaau auaagagcca ccauggaauc caggaucugg ugccugguag 120
ucugcguuaa cuuguguauc gucugucugg gugcugcggu uuccucaucu ucuacucgug 180
gaacuucugc uacucacagu caccauuccu cucauacgac gucugcugcu cacucucgau 240
ccgguucagu cucucaacgc guaacuucuu cccaaacggu cagccauggu guuaacgaga 300
ccaucuacaa cacuacccuc aaguacggag augugguggg ggucaauacc accaaguacc 360
ccuaucgcgu guguucuaug gcccagggua cggaucuuau ucgcuuugaa cguaauaucg 420
ucugcaccuc gaugaagccc aucaaugaag accuggacga gggcaucaug guggucuaca 480
aacgcaacau cgucgcgcac accuuuaagg uacgagucua ccagaagguu uugacguuuc 540
gucguagcua cgcuuacauc cacaccacuu aucugcuggg cagcaacacg gaauacgugg 600
cgccuccuau gugggagauu caucauauca acagccacag ucagugcuac aguuccuaca 660
gccgcguuau agcaggcacg guuuucgugg cuuaucauag ggacagcuau gaaaacaaaa 720
ccaugcaauu aaugcccgac gauuauucca acacccacag uacccguuac gugacgguca 780
aggaucaaug gcacagccgc ggcagcaccu ggcucuaucg ugagaccugu aaucugaauu 840
guauggugac caucacuacu gcgcgcucca aauauccuua ucauuuuuuc gccacuucca 900
cgggugacgu gguugacauu ucuccuuucu acaacggaac caaucgcaau gccagcuacu 960
uuggagaaaa cgccgacaag uuuuucauuu uuccgaacua cacuaucguc uccgacuuug 1020
gaagaccgaa uucugcguua gagacccaca gguugguggc uuuucuugaa cgugcggacu 1080
cggugaucuc cugggauaua caggacgaaa agaaugucac uugucaacuc acuuucuggg 1140
aagccucgga acgcaccauu cguuccgaag ccgaggacuc guaucacuuu ucuucugcca 1200
aaaugaccgc cacuuucuua ucuaagaagc aagaggugaa cauguccgac ucugcgcugg 1260
acugcguacg ugaugaggcu auaaauaagu uacagcagau uuucaauacu ucauacaauc 1320
aaacauauga aaaauaugga aacguguccg ucuuugaaac cacuggugga uugguagugu 1380
ucuggcaagg uaucaagcaa aaaucucugg uggaacucga acguuuggcc aaccgcucca 1440
gucugaaucu uacucauaau agaaccaaaa gaaguacaga uggcaacaau gcaacucauu 1500
uauccaacau ggaaucggug cacaaucugg ucuacgccca gcugcaguuc accuaugaca 1560
cguugcgcgg uuacaucaac cgggcgcugg cgcaaaucgc agaagccugg ugugguggauc 1620 aacggcgcac ccuagagguc uucaaggaac ucagcaagau caacccguca gccauucucu 1680
cggccauuua caacaaaccg auugccgcgc guuucauggg ugaugucuug ggccuggcca 1740
gcugcgugac caucaaccaa accagcguca aggugcugcg ugauaugaac gugaaggagu 1800
cgccaggacg cugcuacuca cgacccgugg ucaucuuuaa uuucgccaac agcucguacg 1860

-continued

```
ugcaguacgg ucaacugggc gaggacaacg aaauccuguu gggcaaccac cgcacugagg   1920
aaugucagcu ucccagccuc aagaucuuca ucgccgggaa cucggccuac gaguacgugg   1980
acuaccucuu caaacgcaug auugaccuca gcaguaucuc caccgucgac agcaugaucg   2040
cccuggauau cgacccgcug gaaaauaccg acuucagggu acuggaacuu uacucgcaga   2100
aagagcugcg uuccagcaac guuuuugacc ucgaagagau caugcgcgaa uucaacucgu   2160
acaagcagcg gguaaaguac guggaggaca agguagucga cccgcuaccg cccuaccuca   2220
agggucugga cgaccucaug agcggccugg gcgccgcggg aaaggccguu ggcguagcca   2280
uuggggccgu ggguggcgcg guggccuccg uggucgaagg cguugccacc uuccucaaaa   2340
accccuucgg agcguucacc aucauccucg uggccauagc uguagucauu aucacuuauu   2400
ugaucuauac ucgacagcgg cguuugugca cgcagccgcu gcagaaccuc uuucccuauc   2460
uggugucegc cgacgggacc accgugacgu cgggcagcac caaagacacg ucguuacagg   2520
cuccgccuuc cuacgaggaa aguguuuaua auucuggucg caaaggaccg ggaccaccgu   2580
cgucugaugc auccacggcg gcuccgccuu acaccaacga gcaggcuuac cagaugcuuc   2640
uggcccuggc ccgucuggac gcagagcagc gagcgcagca gaacgguaca gauucuuugg   2700
acggacggac uggcacgcag gacaagggac agaagcccaa ccuacuagac cgacugcgac   2760
aucgcaaaaa cggcuaccga cacuugaaag acucugacga agaagagaac gucuugauaa   2820
uaggcuggag ccucgguggc caugcuucuu gccccuuggg ccuccccca gccccuccuc   2880
cccuuccugc acccguaccc ccguggucuu ugaauaaagu cugagugggc ggc          2933
```